US010612086B2

(12) United States Patent
Ehrich et al.

(10) Patent No.: US 10,612,086 B2
(45) Date of Patent: Apr. 7, 2020

(54) PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES

(71) Applicant: SEQUENOM, INC., San Diego, CA (US)

(72) Inventors: Mathias Ehrich, San Diego, CA (US); Anders Olof Herman Nygren, San Diego, CA (US); Tyler Jacob Jensen, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 50 days.

(21) Appl. No.: 15/428,659

(22) Filed: Feb. 9, 2017

(65) Prior Publication Data

US 2017/0314071 A1 Nov. 2, 2017

Related U.S. Application Data

(60) Continuation of application No. 13/791,466, filed on Mar. 8, 2013, now abandoned, which is a division of application No. 12/727,198, filed on Mar. 18, 2010, now Pat. No. 8,962,247, which is a continuation-in-part of application No. 12/561,241, filed on Sep. 16, 2009, now Pat. No. 8,476,013.

(60) Provisional application No. 61/192,264, filed on Sep. 16, 2008.

(51) Int. Cl.

| | |
|---|---|
| ***C12Q 1/68*** | (2018.01) |
| ***C12Q 1/6869*** | (2018.01) |
| ***C12Q 1/6804*** | (2018.01) |
| ***C12Q 1/6806*** | (2018.01) |
| ***C12Q 1/6809*** | (2018.01) |
| ***C12Q 1/6888*** | (2018.01) |

(52) U.S. Cl.

CPC ......... *C12Q 1/6869* (2013.01); *C12Q 1/6804* (2013.01); *C12Q 1/6806* (2013.01); *C12Q 1/6809* (2013.01); *C12Q 1/6888* (2013.01); *C12Q 2600/16* (2013.01)

(58) Field of Classification Search

None

See application file for complete search history.

(56) References Cited

U.S. PATENT DOCUMENTS

| | | | |
|---|---|---|---|
| 4,109,496 | A | 8/1978 | Allemann et al. |
| 4,179,337 | A | 12/1979 | Davis et al. |
| 4,458,066 | A | 7/1984 | Caruthers et al. |
| 4,469,863 | A | 9/1984 | Ts'o et al. |
| 4,522,811 | A | 6/1985 | Eppstein et al. |
| 4,656,127 | A | 4/1987 | Mundy |
| 4,676,980 | A | 6/1987 | Segal et al. |
| 4,683,195 | A | 7/1987 | Mullis et al. |
| 4,683,202 | A | 7/1987 | Mullis |
| 4,851,331 | A | 7/1989 | Vary et al. |
| 4,868,103 | A | 9/1989 | Stavrianopoulos et al. |
| 4,873,316 | A | 10/1989 | Meade et al. |
| 4,965,188 | A | 10/1990 | Mullis et al. |
| 5,048,530 | A | 9/1991 | Hurwitz et al. |
| 5,075,212 | A | 12/1991 | Rotbart et al. |
| 5,118,937 | A | 6/1992 | Hillenkamp et al. |
| 5,210,015 | A | 5/1993 | Gelfand et al. |
| 5,272,071 | A | 12/1993 | Chappel et al. |
| 5,283,317 | A | 2/1994 | Saifer et al. |
| 5,487,972 | A | 1/1996 | Gelfand et al. |
| 5,492,806 | A | 2/1996 | Drmanac et al. |
| 5,525,464 | A | 6/1996 | Drmanac et al. |
| 5,536,821 | A | 7/1996 | Agrawal et al. |
| 5,541,306 | A | 7/1996 | Agrawal et al. |
| 5,547,835 | A | 8/1996 | Koster |
| 5,589,330 | A | 12/1996 | Shuber |
| 5,605,798 | A | 2/1997 | Koster |
| 5,614,622 | A | 3/1997 | Iyer et al. |
| 5,631,169 | A | 5/1997 | Lakowicz et al. |
| 5,637,683 | A | 6/1997 | Usher et al. |
| 5,637,684 | A | 6/1997 | Cook et al. |
| 5,656,493 | A | 8/1997 | Mullis et al. |
| 5,679,524 | A | 10/1997 | Nikiforov et al. |
| 5,691,141 | A | 11/1997 | Koester et al. |
| 5,695,940 | A | 12/1997 | Drmanac et al. |
| 5,700,922 | A | 12/1997 | Cook |
| 5,717,083 | A | 2/1998 | Cook et al. |
| 5,719,262 | A | 2/1998 | Buchardt et al. |
| 5,720,928 | A | 2/1998 | Schwartz |
| 5,739,308 | A | 4/1998 | Kandimalla et al. |

(Continued)

FOREIGN PATENT DOCUMENTS

| | | | |
|---|---|---|---|
| AU | 2009293232 | B2 | 5/2015 |
| AU | 2010295968 | B2 | 8/2015 |

(Continued)

OTHER PUBLICATIONS

AU 2013290102, "First Examination Report", dated Apr. 19, 2018, 3 pages.
EP 13739590.1, "Communication Pursuant to Article 94(3) EPC,", dated Jun. 18, 2018, 5 pages.
JP 2015-521823, "Office Action", dated Apr. 19, 2018, 10 pages.
JP 2016-199141, "Office Action", dated May 28, 2018, 18 pages.
Lo et al., "Maternal Plasma DNA Sequencing Reveals the Genome-Wide Genetic and Mutational Profile of the Fetus", Science Translation Medicine, vol. 2, No. 61, Dec. 8, 2010, pp. 1-13, plus 60 pages of "Supporting Online Material" (73 total pages).
Old et al., "Reproductive BioMedicine Online", vol. 15, No. 2, 2007, pp. 227-235.

(Continued)

*Primary Examiner* — Jehanne S Sitton

(74) *Attorney, Agent, or Firm* — Kilpatrick Townsend & Stockton LLP

(57) ABSTRACT

Provided are compositions and processes that utilize genomic regions that are differentially methylated between a mother and her fetus to separate, isolate or enrich fetal nucleic acid from a maternal sample. The compositions and processes described herein are particularly useful for non-invasive prenatal diagnostics, including the detection of chromosomal aneuploidies.

20 Claims, 32 Drawing Sheets

Specification includes a Sequence Listing.

(56) References Cited

U.S. PATENT DOCUMENTS

| | | | |
|---|---|---|---|
| 5,739,314 | A | 4/1998 | Roy et al. |
| 5,766,849 | A | 6/1998 | McDonough et al. |
| 5,773,601 | A | 6/1998 | Agrawal |
| 5,786,146 | A | 7/1998 | Herman et al. |
| 5,834,189 | A | 11/1998 | Stevens et al. |
| 5,849,483 | A | 12/1998 | Shuber |
| 5,849,497 | A | 12/1998 | Steinman |
| 5,849,542 | A | 12/1998 | Reeve et al. |
| 5,849,546 | A | 12/1998 | Sousa et al. |
| 5,851,770 | A | 12/1998 | Babon et al. |
| 5,869,242 | A | 2/1999 | Kamb |
| 5,876,934 | A | 3/1999 | Duthie et al. |
| 5,886,165 | A | 3/1999 | Kandimalla et al. |
| 5,891,625 | A | 4/1999 | Buchardt et al. |
| 5,908,755 | A | 6/1999 | Kumar et al. |
| 5,912,118 | A | 6/1999 | Ansorge et al. |
| 5,928,906 | A | 7/1999 | Koster et al. |
| 5,929,226 | A | 7/1999 | Padmapriya et al. |
| 5,952,174 | A | 9/1999 | Nikiforov et al. |
| 5,955,599 | A | 9/1999 | Iyer et al. |
| 5,958,692 | A | 9/1999 | Cotton et al. |
| 5,962,674 | A | 10/1999 | Iyer et al. |
| 5,976,802 | A | 11/1999 | Ansorge et al. |
| 5,977,296 | A | 11/1999 | Nielsen et al. |
| 5,981,186 | A | 11/1999 | Gabe et al. |
| 5,998,143 | A | 12/1999 | Ellis et al. |
| 6,004,744 | A | 12/1999 | Goelet et al. |
| 6,013,431 | A | 1/2000 | Soderlund et al. |
| 6,013,499 | A | 1/2000 | Narumiya et al. |
| 6,017,702 | A | 1/2000 | Lee et al. |
| 6,018,041 | A | 1/2000 | Drmanac et al. |
| 6,024,925 | A | 2/2000 | Little et al. |
| 6,043,031 | A | 3/2000 | Küster et al. |
| 6,045,996 | A | 4/2000 | Cronin et al. |
| 6,046,005 | A | 4/2000 | Ju et al. |
| 6,057,134 | A | 5/2000 | Lader et al. |
| 6,057,143 | A | 5/2000 | Meyer et al. |
| 6,087,095 | A | 7/2000 | Rosenthal et al. |
| 6,107,037 | A | 8/2000 | Sousa et al. |
| 6,110,684 | A | 8/2000 | Kemper et al. |
| 6,117,992 | A | 9/2000 | Iyer et al. |
| 6,136,541 | A | 10/2000 | Gulati |
| 6,140,053 | A | 10/2000 | Koester |
| 6,140,054 | A | 10/2000 | Wittwer et al. |
| 6,140,482 | A | 10/2000 | Iyer et al. |
| 6,142,681 | A | 11/2000 | Gulati |
| 6,143,496 | A | 11/2000 | Brown et al. |
| 6,156,501 | A | 12/2000 | McGall et al. |
| 6,183,958 | B1 | 2/2001 | Stanton et al. |
| 6,194,144 | B1 | 2/2001 | Köster |
| 6,194,180 | B1 | 2/2001 | Joyce et al. |
| 6,197,506 | B1 | 3/2001 | Fodor et al. |
| 6,210,574 | B1 | 4/2001 | Sammons et al. |
| 6,210,891 | B1 | 4/2001 | Nyren et al. |
| 6,214,556 | B1 | 4/2001 | Olek et al. |
| 6,214,560 | B1 | 4/2001 | Yguerabide et al. |
| 6,223,127 | B1 | 4/2001 | Berno et al. |
| 6,225,625 | B1 | 5/2001 | Pirrung et al. |
| 6,229,911 | B1 | 5/2001 | Balaban et al. |
| 6,239,273 | B1 | 5/2001 | Pease et al. |
| 6,251,638 | B1 | 6/2001 | Umansky et al. |
| 6,258,538 | B1 | 7/2001 | Küster et al. |
| 6,258,540 | B1 | 7/2001 | Lo et al. |
| 6,297,028 | B1 | 10/2001 | Taniguchi et al. |
| 6,326,174 | B1 | 12/2001 | Joyce et al. |
| 6,368,834 | B1 | 4/2002 | Senapathy et al. |
| 6,440,706 | B1 | 8/2002 | Vogelstein et al. |
| 6,468,748 | B1 | 10/2002 | Monforte et al. |
| 6,610,492 | B1 | 8/2003 | Stanton, Jr. et al. |
| 6,664,056 | B2 | 12/2003 | Lo et al. |
| 6,723,513 | B2 | 4/2004 | Lexow |
| 6,759,217 | B2 | 7/2004 | Kopreski |
| 6,818,394 | B1 | 11/2004 | O'Donnell-Maloney et al. |
| 6,884,586 | B2 | 4/2005 | Van Ness et al. |
| 6,916,634 | B2 | 7/2005 | Kopreski |
| 6,927,028 | B2 | 8/2005 | Dennis et al. |
| 6,929,911 | B2 | 8/2005 | Oefner et al. |
| 7,081,339 | B2 | 7/2006 | Slepnev et al. |
| 7,169,314 | B2 | 1/2007 | Unger et al. |
| 7,244,567 | B2 | 7/2007 | Chen et al. |
| 7,253,259 | B2 | 8/2007 | Otagiri et al. |
| 7,285,422 | B1 | 10/2007 | Little et al. |
| 7,468,249 | B2 | 12/2008 | Xie et al. |
| 7,655,399 | B2 | 2/2010 | Cantor et al. |
| 7,709,194 | B2 | 5/2010 | Lo et al. |
| 7,709,262 | B2 | 5/2010 | Cantor et al. |
| 7,754,428 | B2 | 7/2010 | Lo et al. |
| 7,785,798 | B2 | 8/2010 | Cantor et al. |
| 7,901,884 | B2 | 3/2011 | Lo et al. |
| 8,195,415 | B2 | 6/2012 | Fan et al. |
| 8,476,013 | B2 | 7/2013 | Ehrich et al. |
| 8,962,247 | B2 | 2/2015 | Ehrich et al. |
| 9,074,013 | B2 | 7/2015 | Rehli |
| 9,249,464 | B2 | 2/2016 | Rehli |
| 9,926,593 | B2 | 3/2018 | Ehrich et al. |
| 2001/0008615 | A1 | 7/2001 | Little et al. |
| 2001/0051341 | A1 | 12/2001 | Lo et al. |
| 2002/0006621 | A1 | 1/2002 | Bianchi et al. |
| 2003/0022207 | A1 | 1/2003 | Balasubramanian et al. |
| 2003/0082600 | A1 | 5/2003 | Olek et al. |
| 2003/0087276 | A1 | 5/2003 | Kopreski et al. |
| 2003/0096426 | A1 | 5/2003 | Little et al. |
| 2003/0180748 | A1 | 9/2003 | Braun et al. |
| 2003/0180779 | A1 | 9/2003 | Lofton-Day et al. |
| 2003/0211483 | A1 | 11/2003 | Schroeder et al. |
| 2003/0211522 | A1 | 11/2003 | Landes et al. |
| 2004/0014105 | A1 | 1/2004 | Schroeder et al. |
| 2004/0081993 | A1 | 4/2004 | Cantor et al. |
| 2004/0115684 | A1 | 6/2004 | Costa et al. |
| 2004/0137470 | A1 | 7/2004 | Dhallan |
| 2004/0203037 | A1 | 10/2004 | Lo et al. |
| 2005/0009059 | A1 | 1/2005 | Shapero et al. |
| 2005/0019762 | A1 | 1/2005 | Olek et al. |
| 2005/0037388 | A1 | 2/2005 | Antonarakis et al. |
| 2005/0059003 | A1 | 3/2005 | Enoki et al. |
| 2005/0064406 | A1 | 3/2005 | Zabarovsky et al. |
| 2005/0064428 | A1 | 3/2005 | Berlin et al. |
| 2005/0069879 | A1 | 3/2005 | Berlin et al. |
| 2005/0079521 | A1 | 4/2005 | Beaulieu et al. |
| 2005/0112590 | A1 | 5/2005 | Boom et al. |
| 2005/0153316 | A1 | 7/2005 | Jeddeloh et al. |
| 2005/0153347 | A1 | 7/2005 | Shapero et al. |
| 2005/0164241 | A1 | 7/2005 | Hahn |
| 2005/0266473 | A1 | 12/2005 | Zhang et al. |
| 2005/0272070 | A1 | 12/2005 | Ehrich et al. |
| 2005/0287592 | A1 | 12/2005 | Kless et al. |
| 2006/0019278 | A1 | 1/2006 | Lo et al. |
| 2006/0094039 | A1 | 5/2006 | Rosenfeld et al. |
| 2006/0136142 | A1 | 6/2006 | Berlin et al. |
| 2006/0160105 | A1 | 7/2006 | Dhallan et al. |
| 2006/0166228 | A1 | 7/2006 | Page et al. |
| 2006/0210992 | A1 | 9/2006 | van den Boom et al. |
| 2006/0252068 | A1 | 11/2006 | Lo |
| 2006/0252071 | A1 | 11/2006 | Lo et al. |
| 2007/0048755 | A1 | 3/2007 | Di Fiore et al. |
| 2007/0059707 | A1 | 3/2007 | Cantor et al. |
| 2007/0065823 | A1 | 3/2007 | Dressman et al. |
| 2007/0111233 | A1 | 5/2007 | Bianchi et al. |
| 2007/0202525 | A1 | 8/2007 | Quake et al. |
| 2007/0207466 | A1 | 9/2007 | Cantor et al. |
| 2007/0212689 | A1 | 9/2007 | Bianchi |
| 2007/0243549 | A1 | 10/2007 | Bischoff et al. |
| 2007/0275402 | A1 | 11/2007 | Lo |
| 2008/0020390 | A1 | 1/2008 | Mitchell |
| 2008/0070792 | A1 | 3/2008 | Stoughton et al. |
| 2008/0096766 | A1 | 4/2008 | Lee |
| 2008/0299562 | A1 | 12/2008 | Oeth et al. |
| 2008/0305479 | A1 | 12/2008 | Van et al. |
| 2009/0026082 | A1 | 1/2009 | Rothberg et al. |
| 2009/0029377 | A1 | 1/2009 | Lo et al. |
| 2009/0061425 | A1 | 3/2009 | Lo et al. |
| 2009/0111712 | A1 | 4/2009 | Van et al. |
| 2009/0142755 | A1 | 6/2009 | Albitar et al. |
| 2009/0202984 | A1 | 8/2009 | Cantor et al. |

(56) References Cited

U.S. PATENT DOCUMENTS

2009/0317817 A1 12/2009 Oeth et al.
2009/0317818 A1 12/2009 Ehrich et al.
2010/0105049 A1 4/2010 Ehrich et al.
2010/0184046 A1 7/2010 Klass et al.
2010/0203529 A1 8/2010 Kuslich et al.
2010/0216153 A1 8/2010 Lapidus et al.
2010/0227320 A1 9/2010 Fu et al.
2010/0240054 A1 9/2010 Bischoff et al.
2010/0273165 A1 10/2010 Ehrich et al.
2010/0279295 A1 11/2010 Roy et al.
2011/0033851 A1 2/2011 Rand et al.
2011/0039724 A1 2/2011 Lo et al.
2011/0105353 A1 5/2011 Lo et al.
2011/0151460 A1 6/2011 Klass et al.
2011/0177517 A1 7/2011 Rava et al.
2011/0178719 A1 7/2011 Rabinowitz et al.
2011/0201507 A1 8/2011 Rava et al.
2011/0212846 A1 9/2011 Spier et al.
2011/0224087 A1 9/2011 Quake et al.
2011/0244451 A1 10/2011 Cantor et al.
2011/0276277 A1 11/2011 Lo et al.
2011/0288780 A1 11/2011 Rabinowitz et al.
2012/0065076 A1 3/2012 Peters et al.
2012/0184449 A1 7/2012 Hixson et al.
2012/0264618 A1 10/2012 Nygren et al.
2012/0276542 A1 11/2012 Nygren et al.
2012/0277119 A1 11/2012 Ehrich et al.
2012/0282613 A1 11/2012 Patsalis et al.
2013/0012399 A1 1/2013 Myers et al.
2013/0085681 A1 4/2013 Deciu et al.
2013/0130923 A1 5/2013 Ehrich et al.
2013/0143211 A1 6/2013 Ehrich et al.
2013/0150249 A1 6/2013 Ehrich et al.
2013/0230858 A1 9/2013 Cantor et al.
2013/0295564 A1 11/2013 Ehrich et al.
2013/0296180 A1 11/2013 Ehrich et al.
2013/0310260 A1 11/2013 Kim et al.
2014/0093873 A1 4/2014 Tynan et al.
2015/0267263 A1 9/2015 Rehli
2015/0275304 A1 10/2015 Ehrich et al.
2016/0145685 A1 5/2016 Jensen et al.
2016/0201113 A1 7/2016 Rehli
2017/0058350 A1 3/2017 Tynan et al.

FOREIGN PATENT DOCUMENTS

AU 2015252141 A1 12/2015
AU 2013290102 B2 2/2019
CA 2737200 A1 3/2010
CA 2774342 C 1/2019
EP 264166 4/1988
EP 0401384 12/1990
EP 1373561 2/2009
EP 1524321 7/2009
EP 2271772 B1 7/2014
EP 2872648 A1 5/2015
EP 2329021 B1 8/2016
EP 3103871 A1 12/2016
EP 2478119 A1 3/2017
EP 2650666 1/2018
EP 3330382 A1 6/2018
GR 2329021 8/2016
HK 1229846 11/2017
JP 2005-514956 5/2005
JP 2006-508632 3/2006
JP 2007-505641 3/2007
JP 2007-508017 A 4/2007
JP 2008-518639 A 6/2008
JP 2008-521389 6/2008
JP 2009/529330 8/2009
JP 2010/534068 11/2010
JP 5727375 6/2015
JP 2015-126748 7/2015
JP 5923571 5/2016
JP 6039034 12/2016
JP 2017-000165 A 1/2017
JP 5873434 3/2017
JP 6447765 B1 3/2018
JP 2018038438 3/2018
JP 6513522 B2 5/2019
WO 1991/006667 5/1991
WO 1994/010300 5/1994
WO 1997/012058 4/1997
WO 1997/035589 10/1997
WO 1997/037041 10/1997
WO 1998/020020 5/1998
WO 1998/022489 5/1998
WO 1998/039352 9/1998
WO 1998/039474 9/1998
WO 1998/054364 12/1998
WO 1999/057318 11/1999
WO 2000/052625 9/2000
WO 2000/056746 9/2000
WO 2000/066771 11/2000
WO 2000/075372 12/2000
WO 2005/118852 12/2000
WO 2001/014398 3/2001
WO 2001/020039 3/2001
WO 2001/025485 4/2001
WO 2001/027326 4/2001
WO 2001/027327 4/2001
WO 2001027329 4/2001
WO 2001029259 4/2001
WO 2002018616 3/2002
WO 2002086163 10/2002
WO 2003000919 1/2003
WO 2003/020974 3/2003
WO 2003/057909 7/2003
WO 2003/062441 A1 7/2003
WO 03/074723 A2 9/2003
WO 2003/080863 10/2003
WO 2004/013284 10/2003
WO 2004/076653 9/2004
WO 2004/078999 9/2004
WO 2004/079011 9/2004
WO 2005/012578 2/2005
WO 2005/021793 3/2005
WO 2005/023091 3/2005
WO 2005/035725 4/2005
WO 2005/040399 5/2005
WO 2005/098050 10/2005
WO 2006/056480 6/2006
WO 2006/097049 9/2006
WO 2006/097051 9/2006
WO 2007/016668 2/2007
WO 2007/028155 3/2007
WO 2007/092473 8/2007
WO 2007/100911 9/2007
WO 2007/121276 10/2007
WO 2007/132166 11/2007
WO 2007/132167 11/2007
WO 2007/140417 12/2007
WO 2007/147063 12/2007
WO 2008/098142 8/2008
WO 2008/103761 8/2008
WO 2008/103763 8/2008
WO 2008/118988 10/2008
WO 2008/157264 12/2008
WO 2009/030100 3/2009
WO 2009/032779 3/2009
WO 2009/039507 3/2009
WO 2009032781 3/2009
WO 2009/046445 4/2009
WO 2009/091934 7/2009
WO 200/9114543 9/2009
WO 2010/004265 1/2010
WO 2010/065470 6/2010
WO 2010/115016 10/2010
WO 2010/033639 2/2011
WO 2011/018600 2/2011
WO 2011/034631 3/2011
WO 2011/054936 5/2011
WO 2011/057094 5/2011
WO 2011/087760 7/2011

(56) References Cited

FOREIGN PATENT DOCUMENTS

| | | | |
|---|---|---|---|
| WO | 2011/091063 | | 7/2011 |
| WO | 2011/092592 | | 8/2011 |
| WO | 2011/143659 | | 11/2011 |
| WO | 2011/142836 | | 1/2012 |
| WO | 2012/012703 | | 1/2012 |
| WO | 2012/118745 | | 9/2012 |
| WO | 2012/149339 | | 11/2012 |
| WO | 2013/052913 | | 4/2013 |
| WO | 2013/055817 | | 4/2013 |
| WO | 2013/176958 | A1 | 11/2013 |
| WO | 2013/177086 | A1 | 11/2013 |
| WO | 2014/011928 | | 1/2014 |
| WO | 2014/168711 | | 10/2014 |
| WO | 2015/138774 | | 9/2015 |
| WO | 2017/045654 | A1 | 3/2017 |

OTHER PUBLICATIONS

U.S. Appl. No. 12/561,241, "Non-Final Rejection", dated Jun. 15, 2012, 8 Pages.
U.S. Appl. No. 12/727,198, "Non-Final Rejection", dated Apr. 12, 2013, 5 Pages.
U.S. Appl. No. 12/727,198, "Non-Final Rejection," dated Dec. 31, 2013, 8 Pages.
U.S. Appl. No. 13/517,508, "Final Office Action," dated Jan. 7, 2014, 14 Pages.
U.S. Appl. No. 13/517,508, "Final Office Action," dated Feb. 5, 2014, 15 Pages.
U.S. Appl. No. 13/517,508 , "Non-Final Rejection," dated Aug. 13, 2013, 11 Pages.
U.S. Appl. No. 13/517,508, "Non-Final Rejection," dated Dec. 18, 2014, 7 Pages.
U.S. Appl. No. 13/517,532 , "Final Rejection," dated Sep. 20, 2013, 20 Pages.
U.S. Appl. No. 13/517,532 , "Non-Final Rejection," dated Apr. 5, 2013, 18 Pages.
U.S. Appl. No. 13/518,368, "Non-Final Rejection," dated Jan. 30, 2015, 16 Pages.
U.S. Appl. No. 13/782,857, "Non-Final Rejection," dated Jun. 26, 2014, 12 Pages.
U.S. Appl. No. 13/782,901, "Non-Final Rejection," dated Aug. 8, 2014.
U.S. Appl. No. 13/791,466 , "Final Office Action," dated Aug. 3, 2015, 10 Pages.
U.S. Appl. No. 13/791,466 , "Final Office Action," dated Aug. 12, 2016, 10 Pages.
U.S. Appl. No. 13/791,466 , "Non-Final Rejection", dated Nov. 7, 2014, 8 Pages.
U.S. Appl. No. 13/801,384, "Final Rejection", dated Dec. 22, 2014, 9 Pages.
U.S. Appl. No. 13/801,384, "Non-Final Rejection," dated Mar. 7, 2014, 11 Pages.
U.S. Appl. No. 13/940,162, "Final Office Action," dated Mar. 17, 2016, 17 Pages.
U.S. Appl. No. 13/940,162, "Non-Final Rejection," dated Aug. 20, 2015, 12 Pages.
U.S. Appl. No. 14/735,477 , "Final Office Action," dated Dec. 22, 2017, 10 pages.
U.S. Appl. No. 14/735,477, "Non Final Office Action," dated May 15, 2017, 8 pages.
Adinolfi , "Rapid detection of aneuploidies by micro satellite and the quantitative fluorescent polymerase chain reaction", Prenatal Diagnosis, vol. 17, No. 13, Dec. 1997, pp. 1299-1311.
Agresti , "Categorical Data Analysis", 2nd Edition, 2002, Wiley, 13 pages.
Altschul et al., "Basic local alignment search tool", J Mol Biol., vol. 215, No. 3, 1990, pp. 403-410.
Altschul et al., "Gapped BLAST and PSI-BLAST: a new generation of protein database search programs", 1997, Nucleic Acids Res., vol. 25, No. 17, pp. :3389-:3402.
Amicucci et al., Clin. Chemical, 2000, vol. 46 pp. 301-302.
Amir et al., "Rett syndrome is caused by mutations in X-linked MECP2, encoding methyl-CpG-binding protein 2", Nature Genetics; vol. 23, 1999, pp. 185-188.
Anantha et al., "Porphyrin binding to quadrupled T4G4", Biochemistry 37(9), Mar. 1998, vol. 37, No. 9, 2709-2714.
Anders et al., "Clin Chem", Oct. 2010, vol. 56, No. 10, pp. 1627-1635, Epub Aug. 20, 2010.
Anderson , "Shotgun DNA sequencing using cloned Dnase !-generated fragments", Nucl. Acids Res. 9, 1981, vol. 9, pp. 3015-3027.
Antonarakis et al., Am J Hum Genet, Mar. 1992, vol. 50, No. 3, pp. 544-550.
Antonarakis et al., "Nat Genet.", Feb. 1993, vol. 3, No. 2, pp. 146-150.
Aoki , "Methylation status of the p151NK4B gene in hematopoietic progenitors and peripheral blood cells in myelodysplastic syndromes", Leukemia, vol. 14, No. 4, pp. 2000, 586-593.
Armour et al., "Measurement of locus copy number by hybridization with amplifiable probes", Nucleic Acids Research, vol. 28, No. 2, Jan. 2000, pp. 605-609.
Armour et al., "The detection of large deletions or duplications in genomic DNA", Human Mutation vol. 20, No. 5, Nov. 2002, pp. 325-337.
Asimakopoulos et al., "ABL 1 methylation is a distinct molecular event associated with clonal evolution of chronic myeloid leukemia", Blood, vol. 94, No. 7, 1999, pp. 2452-2460.
Aston et al., Methods Enzymol, 1999, vol. 303, pp. 55-73.
Aston et al., Trends Biotechnol, 1999, vol. 17, No. 7, pp. 297-302.
AU 2015252141, "First Examination Report," dated Oct. 28, 2016, 4 pages.
AU 2015252141, "Second Examination Report," dated Oct. 3, 2017, 3 pages.
Ausubel et al., Current Protocols in Molecular Biology, 1994.
Banerji et al., "A lymphocyte-specific cellular enhancer is located downstream of the joining region in immunoglobulin heavy chain genes", Cell, vol. 33, No. 3, Jul. 1983, pp. 729-740.
Bartel et al., Biotechniques, 1993, vol. 14, pp. 920-924.
Batey et al., Nucl. Acids Res, 1992, vol. 20, pp. 4515-4523.
Batey et al., Nucl. Acids Res, 1996, vol. 24, pp. 4836-4837.
Batzer et al., Nucleic Acid Res, vol. 19, 1991, p. 5081.
Beaucage et al., Tetrahedron Lett., vol. 22, 1981, pp. 1859-1862.
Beaudet , "Progress toward noninvasive prenatal diagnosis," Clinical Chemistry, vol. 57, No. 6, Jun. 2011, pp. 802-804.
Benson , "Tandem repeats finder: a program to analyze DNA sequences," Nucleic Acids Research, vol. 27, No. 2, Jan. 15, 1999, pp. 573-580.
Bianchi , "Fetal cells in the mother: from genetic diagnosis to diseases associated with fetal cell microchimerism," European Journal of Obstetrics & Gynecology and Reproductive Biology, vol. 92, No. 1, Sep. 2000, pp. 103-108.
Bock et al., "CpG island methylation in human lymphocytes is highly correlated with DNA sequence, repeats, and predicted DNA structure," PLOS Genetics, vol. 2, No. 3, 2006, pp. e26.
Boguski et al., "Identification of a cytidine-specific ribonuclease from chicken liver," J. Biology Chemistry vol. 255, No. 5, Mar. 10, Mar. 1980, pp. 2160-2163.
Boom et al., "J. Clin. Microbial 28," vol. 28, 1990, pp. 495-503.
Boom et al., "J. Clin. Microbial 29," vol. 29, 1991, pp. 1804-1811.
Boyer et al., "Polycomb complexes repress developmental regulators in murine embryonic stem cells," Nature, 2006, vol. 441, pp. 349-353.
Braslavsky et al., "Sequence information can be obtained from single DNA molecules," Proc Natl Acad Sci US A., Apr. 1, vol. 100, No. 7, 2003, pp. 3960-3964, Epub Mar. 21, 2003.
Brizot et al., "Maternal serum hCG an fetal nuchal translucency thickness for the prediction of fetal trisomies in the first trimester of pregnancy", British Journal of Obstetrics Gynaecology, vol. 102, No. 2, Feb. 1995, pp. 127-132.
Bullinger et al., "Use of gene-expression profiling to identifying prognostic subclasses in adult acute myeloid leukemia", New England Journal of Medicine, vol. 350, No. 16, Apr. 15, 2004, pp. 1605-1616.
Burlingame et al., Anal. Chem., vol. 70, 1998, pp. 647R-716R.

(56) References Cited

OTHER PUBLICATIONS

Burnier et al., "Cell-derived microparticles in haemostasis and vascular medicine", Thromb Haemost, 2009, vol. 101, pp. 439-451.
Byrne et al., "Multiplex gene regulation: a two-tiered approach to transgene regulation in transgenic mice", Proc Natl Acad Sci U.S.A., Jul. 1989, vol. 86, No. 14, pp. 5473-5477.
CA 2,737,200, "Office Action", dated Dec. 11, 2017, 3 pages.
CA 2,774,342, "Office Action", dated Mar. 28, 2017.
Calame et al., "Transcriptional controlling elements in the immunoglobulin and T cell receptor loci", Adv Immunol., 1988, vol. 43, pp. 235-275.
Caliper LifeSciences, Products and Contract Services, LabChip Gx 2010, printed from the internet on Mar. 15, 2011 (http://www.caliperl.com/products/labchip-gx.htm).
Camper et al., "Postnatal repression of the alpha-fetoprotein gene is enhancer independent.", Genes Dev., Apr. 1989, vol. 3, No. 4, pp. 537-546.
Cell Death Detection ELISA PLUS Cat. No. 11 774 425 001 "Detection of Post-translational Modifications on Native Intact Nucleosomes by ELISA," Version 11.0, Roche, Content Version: Sep. 2010, pp. 1-19.
Chan et al., Clin. Chem., vol. 50, 2004, pp. 88-92.
Chan et al., "Hypermethylated RASSFIA in Maternal Plasma: A Universal Fetal DNA Marker that Improves the Reliability of Noninvasive Prenatal Diagnosis", Clin. Chem., 2006, 2211-2218.
Chan et al., Oncogene, vol. 22, 2003, pp. 924-934.
Chang et al., "LIBSVM: a library for Support Vector Machines", 2001.
Chen et al., "Fluorescence energy transfer detection as a homogeneous DNA diagnostic method", Proc Natl Acad Sci U.S.A., Sep. 30, 1997, vol. 94, No. 20, pp. 10756-10761.
Chen et al., "Template-directed dye-terminator incorporation (TDI) assay: a homogeneous DNA diagnostic method based on fluorescence resonance energy transfer", Nucleic Acids Res, Jan. 15, 1997, vol. 25, No. 2, pp. 347-353.
Cheson et al., "Report of the National Cancer Institute-sponsored workshop on definitions of diagnosis and response in acute myeloid leukemia", J Clin Oneal, vol. 8, 1990, pp. 813-819.
Cheung et al., J. Clin. Microbial, vol. 32, 1994, pp. 2593-2597.
Chirgwin et al., Biochem, vol. 18, 1979, pp. 5294-5299.
Chitty et al., Br Med Bull, vol. 54, 1998, pp. 839-856.
Chiu et al., "Effects of blood-processing protocols on fetal and total DNA quantification in maternal plasma", Clin Chem., Sep. 2001, vol. 47, No. 9, pp. 1607-1613.
Chiu et al., Lancet, vol. 360, 2002, pp. 998-1000.
Chomczynski et al., Anal. Biochem, vol. 225, 1995, pp. 163-164.
Chomczynski et al., Analytical Biochem, vol. 162, 1987, p. 156-159.
Chomczynski , Biotech, vol. 15, 1993, pp. 532-537.
Chomczynski et al., Biotechniques, Vlo. 19, 1995, pp. 942-945.
Chow et al., "Mass Spectrometric detection of a SNP panel as an internal positive control for fetal DNA analysis in maternal plasma". Clin. Chem., vol. 53, 2007, pp. 141-142.
Chu et al., "A novel approach toward the challenge of accurately quantifying fetal DNA in maternal plasma", Prenatal Diagnosis, vol. 30, 2010, pp. 1226-1229.
Colella et al., Biotechniques, vol. 35, Jul. 2003, pp. 146-150.
Costa et al., N. Engl. J. Med., vol. 346, 2002, p. 1502.
Costello et al., "Restriction Landmark Genomic Scanning (RLGS): Analysis of CpG Islands in genomes by 2D Gel Electrophoresis", Methods in Molecular Biology, DNA Methylation, 2 Methods and Protocols, vol. 507, 2nd eds, 2000, pp. 131-148.
Coulter , "Introduction to Capillary Electrophoresis", Beckman Coulter, 1991, 47 pages.
Craig et al., "Gen-Probe Transcription-Mediated Amplification: System Principles", httl://www.gen-probe.com/pdfs/tma whiteppr.pdf, Jan. 1996.
Cross et al., "Purification of CpG islands using a methylated DNA binding column", Nature Genetics, 1994, vol. 6, No. 3, pp. 236-244.
Cruikshank et al., "A lipidated anti-Tat antibody enters living cells and blocks HIV-1 viral replication", J. Acquired Immune Deficiency Syndromes and Human Retrovirology, Mar. 1, 1997, vol. 14, No. 3, pp. 193-203.
Dai et al., "Detection of Post-translational Modifications on Native Intact Nucleosomes by ELISA", Journal of Visualized Experiments, 2011, pp. 1-4.
D'Alton , "Prenatal diagnostic procedures", Semin Perinatal., Jun. 1994, vol. 18, No. 3, pp. 140-62.
Das et al., Proc Natl Acad Sci U S A, vol. 103, 2006, pp. 10713-10716.
Davison , "Sedimentation of deoxyribonucleic acid isolated under low hydrodynamic shear", Nature, Mar. 26, 1960, vol. 185, pp. 918-920.
Davison , "The Effect of Hydrodynamic Shear on the Deoxyribonucleic Acid From T(2) and T(4) Bacteriophages", Proc Natl Acad Sci USA vol. 45, No. 11, Nov. 1959, 1560-1568.
Dayie et al., J. Mag. Reson, vol. 130, pp. 1998, 97-101.
Dear , "One by one: Single molecule tools for genomics: Brief Funct Genomic Proteomic.", Jan. 2003, vol. 1, No. 4, pp. 397-416.
Deininger et al., "Random subcloning of sonicated DNA: application to shotgun DNA sequence analysis", Anal. Biochem, vol. 129, No. 1, 1983, 216-223.
Deininger et al., "Random subcloning of sonicated DNA: application to shotgun DNA sequence analysis", Anal. Biochem, vol. 129, No. 1, 1983, pp. 216-223.
Dembo et al., Ann. Prob vol. 22, 1994, pp. 2022-2039.
Ding et al., "A high-throughput gene expression analysis technique using competitive PCR and matrix-assisted laser desorption ionization time-of-flight", MS. Proc Natl Acad Sci USA, vol. 100, 2003, pp. 3059-3064.
Donis-Keller et al., Nucl. Acids Res., vol. 4, 1977, pp. 2527-2537.
Donis-Keller., "Phy M: an RNase activity specific for U and A residues useful in RNA sequence analysis." Nucleic Acids Res., Jul. 25, 1980, vol. 8, No. 14, pp. 3133-3142.
Dupont , et al., Anal Biochem, Oct 2004, vol. 333, No. 1. pp. 119-127.
Eads et al., Cancer Res., vol. 59, 1999, pp. 2302-2306.
Eckhardt et al., Nat Genet, vol. 38, 2006, pp. 1378-1385.
Eckstein , "Oligonucleotides and Analogues, A Practical Approach", IRL Press, Oxford, 1991.
Edlund et al., "Cell-specific expression of the rat insulin gene: evidence for role of two distinct 5' flanking elements", Science, Nov. 22, 1985, vol. 230, No. 4728, pp. 912-916.
Egger et al., "Reverse transcription multiplex PCR for differentiation between polio-and enteroviruses from clinical and environmental samples", J Clin Microbial, Jun. 1995, vol. 33, No. 6, pp. 1442-1447.
Ehrich et al., "A new method for accurate assessment of DNA quality after bisulfite treatment", Nucl. Acids Res., 2007, vol. 35, No. 5, pp. e29 1-8.
Ehrich et al., "Cytosine methylation profiling of cancer cell lines." Proc Natl Acad Sci, USA, vol. 105, 2008, pp. 4844-4848.
Ehrich et al., "Noninvasive detection of fetal trisomy 21 by sequencing of DNA in maternal blood: a study in a clinical setting", Reports of Major Impact, American Journal of Obstetrics and Gyenocology, Mar. 2011,pp. 205e1-205e11.
Ehrich et al., "Quantitative high-throughput analysis of DNA methylation patterns by base specific cleavage and mass spectrometry", Proc Natl Acad Sci USA, 2005, vol. 102, pp. 15785-15790.
Eiben et al., "First-trimester screening: an overview", J Histochem Cytochem, Mar. 2005, vol. 53, No. 3, pp. 281-283.
Elisa, "Detection of Posttranslational Modifications on Native Intact Nucleosomes", Cell Death Detection ELISA PLUS Cat. No. 11 774 425 001 Version 11.0, Roche, Content Version, Sep. 2010, pp. 1-19.
EP 09720284 , "Supplementary European Search Report dated", dated Jul. 14, 2011.
EP 09815148 , "Extended European Search Report dated", Apr. 19, 2012.
EP 10817598.5 , "Extended European Search Report dated", Jan. 4, 2012.
EP 10843520 , "Extended European Search Report dated", Apr. 22, 2013.

(56) References Cited

OTHER PUBLICATIONS

EP 13739590.1, "Office Action", dated Aug. 1, 2017, 4 pages.
EP16173137.7 , "Extended European Search Report", dated Nov. 14, 2016, 8 pages.
EP 17182863.5, "Extended European Search Report", dated Feb. 26, 2018, 9 pages.
Ernani et al., "Agilent's SureSelect Target Enrichment System: Bringing Cost and Process Efficiency to Next-Generation Sequencing Product Note", Agilent Technologies, Mar. 16, 2009.
Eva et al., Nature, vol. 316, 1985, pp. 273-275.
Fajkusova et al., "Detailed Mapping of Methylcytosine Positions at the CpG Island Surrounding the Pa Promoter at the bcr-abl Locus in CML Patients and in Two Cell Lines K562 and BV173", Blood Cells Mol. Dis. vol. 26, No. 3, 2000, pp. 193-204.
Fan et al., "Analysis of the size distributions of fetal and maternal cell-free DNA by paired end sequencing", Clinical Chemistry, vol. 56, No. 8, 2010, pp. 1279-1286.
Fan et al., "Molecular Counting: From Noninvasive Prenatal Diagnostics to Whole-Genome Haplotyping", Dissertation, Stanford University, Nov. 2010.
Fan et al., "Noninvasive diagnosis of fetal aneuploidy by shotgun sequencing DNA from maternal blood", Proc Natl Acad Sci USA, Oct. 21, 2008, vol. 105, No. 42, pp. 16266-16271.
Fan et al., "Working Set Selection Using the Second Order Information for Training SVM", Journal of Machine Learning Research, vol. 6, 2005, pp. 1889-1918.
Feinberg , "Methylation meets Genomics", Nat Genet., vol. 27, No. 1, Jan. 2001, pp. 9-10.
Ferguson et al., "Placental mRNA in maternal plasma: Prospects for fetal screening", PNAS, vol. 100, No. 8, Apr. 15, 2003, pp. 4360-4362.
Fournie et al., Anal. Biochem. 158, 1986, pp. 250-256.
Frommer et al., "Proc. Natl. Acad. Sci.", USA, vol. 89, 1992, pp. 1827-1831.
Futreal et al., "Nat Rev Cancer 4", vol. 4, 2004, pp. 177-183.
Gardiner et al., "CpG islands in vertebrate genomes", J Mol Bioi., vol. 196, No. 2, Jul. 20, 1987, pp. 261-282.
Gebhard et al., "Genomewide profiling of CpG methylation identifies novel targets of aberrant hypermethylation in myeloid leukemia", Cancer Res, vol. 66, 2006, pp. 6118-6128.
Gebhard et al., "Rapid and sensitive detection of CpG-methylation using methyl-binding (MB)-PCR", Nucleic Acids Res, vol. 34, 2006, p. e82.
Giles et al., "Acute myeloid leukemia", Hematology Am Soc Hematol Educ Program, 2002, pp. 73-110.
Go et al., "Clin Chem", vol. 53, No. 12, Dec. 2007, pp. 2223-2224.
Go et al., "Non-invasive aneuploidy detection using free fetal DNA and RNA in maternal plasma recent progress and future possibilities", Human Reproduction Update, vol. 17, No. 3, 2011, pp. 372-382.
Goeddel et al., "Gene Expression Technology: Methods in Enzymology 185", Academic Press, San Diego, California, 1990.
Gonzalgo et al., Nucleic Acids Res., vol. 25, 1997, pp. 2529-2531.
Gottesman , "Gene Expression Technology: Methods in Enzymology", Academic Press, San Diego, California, vol. 185, 1990, pp. 119-129.
Grompe et al., Proc. Natl. Acad. Sci USA, vol. 86, 1989, pp. 5855-5892.
Grompe , "The rapid detection of unknown mutations in nucleic acids", Nat Genet., vol. 5, No. 2, Oct. 1993, pp. 111-117.
Grunau et al., "Bisulfite genomic sequencing: systematic investigation of critical experimental parameters", Nucleic Acids Res., vol. 29, No. 13, Jul. 2001, pp. E65-E65.
Gupta et al., "Use of specific endonuclease cleavage in RNA sequencing", Nucleic Acids Res., vol. 4, No. 6, Jun. 1977, pp. 1957-1978.
Haase et al., Methods in Virology, 1984, pp. 189-226.
Haddow et al., "Screening of maternal serum for fetal Down's syndrome in the first trimester", The New England Journal of Medicine, vol. 338, No. 14, Apr. 2 1998, pp. 955-961.
Hage et al., J. Chromatogr. B Biomed. Sci. Appl., vol. 699, No. 1-2, Oct. 10, 1997, pp. 499-525.
Hahn et al., Placenta 32 Suppl, 2011, pp. S17-S20.
Hahner et al., "Matrix-assisted laser desorption/ionization mass spectrometry (MALDI) of endonuclease digests of RNA", Nucleic Acids Res., vol. 25, No. 10, May 15, 1997, pp. 1957-1964.
Hames et al., Nucleic Acid Hybridization: A Practical Approach, IRL Press, 1985.
Hannish et al., "Activity of DNA modification and restriction enzymes in KGB, a potassium glutamate buffer", Gene Anal. Tech, vol. 5, 1988, p. 105.
Harris et al., "Single-molecule DNA sequencing of a viral genome", Science. vol. 320, No. 5872, Apr. 4, 2008, pp. 106-109.
Hart et al., J.Bioi. Chem. 269, 1994, pp. 62-65.
Hasan et al., Nucl. Acids Res., vol. 24, 1996, pp. 2150-2157.
Health Screen Inc , "The Cancer Test, Cell Free DNA", http://www.thecancertest.com/science-of-cell-free-dna/, via the internet on Mar. 20, 2011.
Heegaard , J Mol. Recognit., Winter; vol. 11 No. 1-6, 1998, pp. 141-148.
Hennig et al., J. Am. Chem. Soc. 129, 2007, pp. 14911-14921.
Herman et al., Proc. Nat. Acad. Sci. USA, vol. 93, 1996, pp. 9821-9826.
Hershey, E. J. Mol. Bioi, vol. 2, 1960, pp. 143-152.
Homer et al., Prenat Diagn, vol. 23, 2003, pp. 566-571.
Hook , "E. B. Lancet 2", 1981, 169-172.
Hromandnikova et al., "Quantification of Fetal and Total Circulatory DNA in Maternal Plasma Samples Before and After Size Fractionation by Agarose Gel Electrophoresis", DNA and Cell Biology, vol. 25. No. 11, 2006, pp. 635-640.
Hu et al., "Aneuploidy detection in single cells using DNA array-based comparative genomic hybridization", Mol Hum Reprod, vol. 10, 2004, pp. 283-289.
Hua et al., "Quantitative methylation analysis of multiple genes using methylationsensitive restriction enzyme-based quantitative PCR for the detection of hepatocellular carcinoma", Experimental and Molecular Pathology, 2011, vol. 91, pp. 455-460.
Huang et al., "Mechanism of ribose 2'-group discrimination by an RNA polymerase", Biochemistry, vol. 36 No. 27, Jul 8, 1997, pp. 8231-8242.
Hulten et al., "Rapid and simple prenatal diagnosis of common chromosome disorders: advantages and disadvantages of the molecular methods FISH and QF-PCR Reproduction", Sep. 2003, 279-97.
Hunkapiller et al., "A microchemical facility for the analysis and synthesis of genes and proteins", Nature 310(5973), Jul. 12-18, 1984, 105-11.
Hyrup et al., "Peptide nucleic acids (PNA): synthesis, properties and potential applications", BioorQ Med Chem. 4 (1), 1996, 5-23.
Iliumina Inc , "Hi Seq 2000 Sequencing System Specification Sheet", 2010.
Imai et al., "J. Viral. Methods 36", 1992, 181-184.
Imamura et al., "Prenatal diagnosis of adrenoleukodystrophy by means of mutation analysis", Prenat Diagn 16(3), Mar. 1996, 259-61.
Innis et al., "PCR Protocols: A Guide to Methods and Applications", Academic Press, Inc., N.Y., 1990.
Iverson et al., "Prenat. Diagn 9", 1981, 31-48.
Jammes et al., "Anal Biochem 333(1)", Oct. 2004, 119-27.
Jensen et al., "Detection of microdeletion 22q11.2 in a fetus by next-generation sequencing of maternal plasma", Clim Chem vol. 58, 2012, pp. 1148-1151.
Jensen et al., "High-throughput massively parallel sequencing for fetal aneuploidy detection from maternal plasma", PloS One, 2013, 8:e57381.
Jing et al., Proc Natl Acad Sci, USA. , vol. 95, No.(14), 1998, 8046-51.
Johansen et al., "An investigation of methods for enriching trophoblast from maternal blood", Prenat Diagn. 15(10), Oct. 1995, 921-31.
JP 2015-076001, "Office Action", dated Oct. 2, 2017, 4 pages.
JP 2015-521823, "Office Action", dated Jun. 28, 2017, 15 pages.
JP 2016-199141, "Office Action", dated Jun. 16, 2017, 2 pages.

(56) References Cited

OTHER PUBLICATIONS

Jurinke et al., "MALDI-TOF mass spectrometry: a versatile tool for high-performance DNA analysis", Mol. Biotechnol.,vol. 26, 2004, pp. 147-164.
Kalinina et al., "Nanoliter scale PCR with TaqMan detection", Nucleic Acids Res., vol. 25 No, 10, May 15, 1997, pp. 1999-2004.
Kaneko et al., "Gut 52", 2003, pp. 641-646.
Karlin et al., "Methods for assessing the statistical significance of molecular sequence features by using general scoring schemes", Proc Natl Acad Sci USA 87(6), Mar. 1990, pp. 2264-2268.
Keller et al., "Nucl. Acids Res. 4", 1977, pp. 2527-2537.
Keller et al., "Phy M: an Rnase activity specific for U and A residues useful in RNA sequence analysis", Nucleic Acids Res., Jul. 25, 1980, pp. 3133-3142.
Kent, "BLAT-the BLAST-like alignment tool," Genome Res. 12(4), Apr. 2002, pp. 656-664.
Kessel et al., "Murine developmental control genes", Science.249 (4967), Jul. 27, 1990, pp. 374-379.
Kidd et al., "Mapping and sequencing of structural variation from eight human genomes nature", 453 (7191), May 1, 2008, pp. 56-64.
Kitzman et al., "Noninvasive Whole-Genome Sequencing of a Human Fetus", Science Translation Medicine 4(137-140), 2012, pp. 115-122.
Kriegier, "Gene Transfer and Expression: A Laboratory Manual", 1990.
Kristensen et al., "PCR-Based Methods for Detecting Single-Locus DNA Methylation Biomarkers in Cancer Diagnostics, Prognostics, and Response to Treatment", Clinical Chemistry, Washington DC, vol. 55, No. 8, Aug. 1, 2009, pp. 1471-1483.
Krueger et al., "Bismark: a flexible aligner and methylation caller for Bisulfite-Seq applications", Bioinformatics, 2011, vol. 27, pp. 1571-1572.
Kuchino et al., "Enzymatic RNA sequencing", Methods Enzymol, 1989, vol. 180, pp. 154-163.
Kuhn et al., "DNA Helicases", Cold Spring Harb Symp Quant Bioi, 1979, vol. 1, pp. 63-67.
Kulkarmi et al., "Global DNA methylation patterns in placenta and its association with maternal hypertension in pre-eclampsia", DNA Cell Bioi, vol. 30, No. 2, 2011, pp. 79-84.
Kumps et al., "Rmeseuarlcthi aprtilcelex Amplicon Quantification (MAO), a fast and efficient method for the simultaneous detection of copy number alterations in neuroblastoma", BMC Genomics 11 :298, 2010, pp. 1-10.
Labchip , "Caliper LifeSciences, Products and Contract Services", GX 2010 (http://www.caliperl.com/products/labchip-gx.htm), Mar. 15, 2011.
Lai et al., Nat Genet., vol. 23, No. 3, 1999, pp. 309-313.
Laird, "P. W. Nature Reviews Cancer 3", 2003, pp. 253-266.
Langmead et al., "Ultrafast and memory-efficient alignment of short DNA sequences to the human genome", Genome Bioi. vol. 10, No. 3, R25, 2009.
Larkin et al., "Ciustal W and Clustal X version 2.0", Bioinformatics, vol. 23, No. 21, Sep. 10, 2007, pp. 2947-2948.
Lee et al., "Control of developmental regulators by Polycomb in human embryonic stem cells", Cell, vol. 25, 2006, pp. 301-313.
Lee et al., "Fetal Nucleic Acids in Maternal Plasma", ln:Fetal and Maternal Medicine Review vol. 17, No. 2, 2006, pp. 125-137.
Leung et al., "An efficient algorithm for identifying matches with errors in multiple long molecular sequences", J Mol Bioi., vol. 221, No. 4, Oct. 20, 1991, pp. 1367-1378.
Li et al., "Dynamic Distribution of Linker Histone H1.5 in Cellular Differentiation, PLOS Genetics", vol. 8, No. 8, e 1002879, Aug. 2012, pp. 1-13.
Li et al., "Genotyping fetal paternally inherited SNPs by MALDI-TOF MS using cell-free fetal DNA in maternal plasma: Influence of size fractionation", Electrophoresis 27, 2006, pp. 3889-3896.
Li et al., "Mapping short DNA sequencing reads and calling variants using mapping quality scores", Genome Res. vol. 18, No. 11, 2008, pp. 1851-1858.
Li et al., Nucl. Acids Res. 23, 1995, pp. 4495-4501.
Li et al., "Size separation of circulatory DNA in maternal plasma permits ready detection of fetal DNA polymorphisms", Clin Chem, vol. 50, No. 6, Apr. 8, 2004, pp. 1002-1011.
Li et al., "Targeted mutation of the DNA methyltransferase gene results in embryonic lethality", Cell, vol. 69, No. 6, Jun. 1996, pp. 915-926.
Lingbeek et al., M. Cell, vol. 118, 2004, pp. 409-418.
Lingbeek et al., "Stem cells and cancer; the polycomb connection", Cell, vol. 118, No. 4, Aug. 20, 2004, pp. 409-418.
Little et al., Nat Med 3, 1997, pp. 1413-1416.
Litz et al., "Methylation status of the major breakpoint cluster region in Philadelphia chromosome negative leukemias", Leukemia, vol. 6, No. 1, 1992, pp. 35-41.
Liu et al., "Quantification of regional DNA methylation by liquid chromatography/tandem mass spectrometry", Analytical Biochemistry, Academic Press Inc, New York, vol. 391, No. 2, Aug. 15, 2009, pp. 106-113.
Liu et al., "The ribosomal small-subunit protein S28 gene from Helianthus annuus (asteraceae) is down-regulated in response to drought, high salinity, and abscisic acid", American Journal of Botany, vol. 90, No. 4, Apr. 1, 2003, pp. 526-531.
Lo et al., Clin. Chem. vol. 45, 1999, pp. 1747-1751.
Lo et al., Clin. Chem., vol. 45, 1999, pp. 184-188.
Lo et al., "Maternal Plasma DNA Sequencing Reveals the Genome-Wide Genetic and Mutational Profile of the Fetus", Prenatal Diagnosis, Science Translational Medicine vol. 2, No. 61, Dec. 8, 2010, pp. 1-13.
Lo et al., N. Engl. J. Med., vol. 339, 1998, pp. 1734-1738.
Lo et al., Nat Med, vol. 13, No. 2, 2007, pp. 218-223.
Lo et al., "Prenatal diagnosis: progress through plasma nucleic acids", Nature Reviews Genetics, 2007, vol. 8, pp. 71-77.
Lo et al., "Presence of fetal DNA in maternal plasma and serum", Lancet, vol. 350, No. 9076, Aug. 16, 1997, pp. 485-487.
Lo et al., "Quantitative analysis of fetal DNA in maternal plasma and serum: implications for noninvasive prenatal diagnosis", Am J Hum Genet, Apr. 1998, pp. 768-775.
Lo, "Recent advances in fetal nucleic acids in maternal plasma", J Histochem Cytochem, Mar. 2005, pp. 293-296.
Lssa, "CpG island methylator phenotype in cancer", Nat Rev Cancer, vol. 4, No. 12, Dec. 2004, pp. 988-993.
Lun et al., "Microfluidics digital PCR reveals a higher than expected fraction of fetal DNA in maternal plasma", Clin Chem., vol. 54, No. 10, Epub, Oct. 2008, pp. 1664-1672.
Lun et al., "Noninvasive prenatal diagnosis of monogenic diseases by digital size selection and relative mutation dosage on DNA in maternal plasma", PNAS, vol. 1 05, No. 50, Dec. 16, 2008, pp. 19920-19925.
Lun et al., "Noninvasive prenatal diagnosis of monogenic diseases by digital size selection and relative mutation dosage on DNA in maternal plasma", Available Online at:—http://www.pnas.org/content/105/50/19920.full.pdf PNAS, 2008, vol. 105, No. 50, Dec. 16, 2008, pp. 19920-19925.
Lwabuchi et al., Oncogene 8, 1993, pp. 1693-1696.
Madura et al., J. Bioi. Chem. 268, 1993, pp. 12046-12054.
Majlessi et al., Nucleic Acids Research. vol. 26, No. 9, 1998, pp. 2224-2229.
Malik et al., "Polyethylene glycol (PEG)-modified granulocyte-macrophage colonystimulating factor (GM-CSF) with conserved biological activity", Exp Hematol, Sep. 1998, pp. 1028-1035.
Mann et al., "Development and implementation of a new rapid aneuploidy diagnostic service within the UK National Health Service and implications for the future of prenatal diagnosis", Sep. 2001, pp. 1057-1061.
Mann , Methods Mol Med, vol. 9, 2004, pp. 141-156.
Mao et al., Nucl. Acids Res., vol. 27, 1999, pp. 4059-4070.
Marais et al., EMBO Journal, vol. 14, 1995, pp. 3136-3145.
Marais et al., J. Bioi. Chem., vol. 272, 1997, pp. 4378-4383.
Margulies et.., "Genome sequencing in microfabricated high-density picolitre reactors", Nature, vol. 437, No. 7057, Epub Jul. 31, 2005, Sep. 2005, pp. 376-380.
Mason et al., EMBO Journal, vol. 18, 1999, pp. 2137-2148.
McClelland et al., "A single buffer for all restriction endonucleases", Nucl. Acids Res, 1988, 16-364.

(56) References Cited

OTHER PUBLICATIONS

McConnell et al., Science, vol. 257, 1992, pp. 1906-1912.
Meller , Clin Chem , vol. 53, 2007, pp. 1996-2001.
Metzker , Nature Rev, vol. 11, 2010, pp. 31-46.
Meyers et al., Cabios, vol. 4, 1989, pp, 11-17.
Millipore, QIA25 Nucleosome ELISA Kit, Information Brochure Calbiochem, Feb. 26, 2013.
Mito et al., S. Nat Genet ., vol. 37, 2005, pp. 1090-1097.
Molecular Cloning of PCR Products Unit 15.4, Current Protocols in Molecular Biology, (2001 John Wiley & Sons, Inc.) Supplement 56, 2001, 15.4.1-15.4.11.
Moudrianakis et al., Proc Natl Acad Sci USA, Mar. 1965, vol. 53, pp. 564-571.
Mouliere et al., "High fragmentation characterizes tumour-derived circulating DNA", PLOS ONE, vol. 6, No. 9 e23418, Sep. 6, 2011, pp. 1-10.
Nakamaye et al., Nucl. Acids Res., vol. 23, 1988, pp. 9947-9959.
Nakano et al., "Single-molecule PCR using water-in-oil emulsion", Journal of Biotechnology, vol. 102, 2003, pp. 117-124.
"NCBI dbSNP cluster report record for rs16139", Sep. 16, 2013.
Needham et al., "Characterization of an adduct between CC-1065 and a defined oligodeoxynucleotide duplex", Nucleic Acids Res., vol. 12, No. 15, Aug. 10, 1984, pp. 6159-6168.
Needleman et al., "A general method applicable to the search for similarities in the amino acid sequence of two proteins", J Mol Bioi., vol. 48, No. 3, Mar. 1970, pp. 444-453.
Ng et al., Clin. Chem., vol. 48, 2002, pp. 1212-1217.
Ng et al., Proc. Natl. Acad. Sci. USA, vol. 100, 2003, pp. 4748-4753.
Nicolaides et al., "One-stop clinic for assessment of risk of chromosomal defects at 12 weeks of gestation", J Matern Fetal Neonatal Med., vol. 12, No. 1, Jul. 2002, pp. 9-18.
Nicolaides et al., Prenat Diagn, vol. 22, 2002, pp. 308-315.
Nicolaidis et al., "Origin and mechanisms of non-disjunction in human autosomal trisomies", Hum Reprod., vol. 13, No. 2, Feb. 1998, pp. 313-319.
Nishizuka et al., "Proteomic profiling of the NCI-60 cancer cell lines using new high-density reverse-phase lysate microarrays", Proc Natl Acad Sci USA, Nov. 25, 2003, Epub, Nov. 17, 2003, vol. 100, No. 24, pp. 14229-14234.
Nolte , "Branched DNA signal amplification for direct quantitation of nucleic acid sequences in clinical specimens", Adv Clin Chem, 1998, vol. 33, pp. 201-235.
Nosaka et al., "Increasing methylation of the CDKN2A gene is associated with the progression of adult T-cell leukemia", Cancer Res., vol. 60, No. 4, 2000, pp. 1043-1048.
Nygren et al., "Quantification of Fetal DNA by Use of Methylation-Based DNA Discrimination", Clinical Chemistry, vol. 56, No. 10, Sep. 2010, pp. 1627-1635.
Oefner et al., "Efficient random subcloning of DNA sheared in a recirculating pointsink flow system", Nucl. Acids Res., vol. 24, No. 20, 1996, pp. 3879-3886.
Oeth et al., "iPLEX™ Assay: Increased Plexing Efficiency and Flexibility for MassARRAY® System through single base primer extension with mass-modified Terminators", SEQUENOM Application Note, 2005.
Oeth et al., "Qualitative and quantitative genotyping using single base primer extension coupled with matrix-assisted laser desorption/ionization time-of-flight mass spectrometry", Methods Mol Bioi., 2009, vol. 578, pp. 307-343.
Ohm et al., "A stem cell-like chromatin pattern may predispose tumor suppressor genes to DNA hypermethylation and heritable silencing", Nat Genet., vol. 39, 2007, pp. 237-242.
Ohtsuka et al., J. Bioi. Chem., vol. 260,1985, pp. 2605-2608.
Okano et al., "DNA methyltransferases Dnmt3a and Dnmt3b are essential for de novo methylation and mammalian development", Oct. 1999, vol. 99, No. 3, pp. 247-257.
Old et al., "Candidate Epigenetic Biomarkers for Non-invasive Prenatal Diagnosis of Down Syndrome", Reprod Biomed., vol. 15, No. 2, Jan. 1, 2007, pp. 227-235.
Olek et al., "A modified and improved method for bisulphite based cytosine methylation analysis", Nucleic Acids Res., Dec. 1996, vol. 24, No. 24, pp. 5064-5066.
Oligonucleotides and Analogues, A Practical Approach, IRL Press, Oxford, 1991.
Orita et al., Proc. Natl. Acad. Sci. USA, vol. 86, 1989, pp. 27776-2770.
Osborne et al., Curr. Opin. Chem. Biol., vol. 1, No. 1, 1997, pp. 5-9.
Oudejans et al., Prenatal Diagnosis, vol. 23, 2003, pp. 111-116.
Padilla et al., "Efficient synthesis of nucleic acids heavily modified with non-canonical ribose 2'-groups using a mutantT7 RNA polymerase (RNAP)", Nucleic Acids Res, vol. 27, No. 6, Mar. 1999, pp. 1561-1563.
Palomaki et al., "DNA sequencing of maternal plasma to detect Down syndrome: an international clinical validation study", Expanded Methods Appendix A, Genet Med, 2011. vol. 13, No. 913-920, 2011, pp. 1-65.
Palomaki et al., "Maternal serum screening for Down syndrome in the United States: a 1995 survey", Am J Obstet Gynecol., vol. 176, No. 5, May 1997, pp. 1046-1051.
Pandya et al., "Screening for fetal trisomies by maternal age and fetal nuchal translucency thickness at 10 to 14 weeks of gestation", Br J Obstet Gynaecol., vol. 102, No. 12, Dec. 1995, pp. 957-962.
Papageorgiou et al., "Fetal-specific DNA methylation ratio permits noninvasive prenatal diagnosis of trisomy 21", Nature Medicine, 2011, vol. 17, pp. 510-513.
Papageorgiou et al., "Sites of differential DNA methylation between placenta and peripheral blood: molecular markers for noninvasive prenatal diagnosis of aneuploidies", The American Journal of Pathology, 2009, vol. 174, No. 5, pp. 1609-1618.
Patel et al., "Curr. Opin. Chem. Biol.", Jun. 1997, vol. 1, No. 1, pp. 32-46.
Paulin et al., Nucleic Acids Res., vol. 26, 1998, pp. 5009-5010.
PCT/US2008/054468 "International Preliminary Report on Patentability", dated Sep. 3, 2009.
PCT/US2008/066791 "International Preliminary Report on Patentability", dated Dec. 30, 2009.
PCT/US2008/066791 , "International Search Report and Written Opinion", dated Dec. 22, 2008.
PCT/US2008/54468 , "International Search Report and Written Opinion", dated Sep. 23, 2008.
PCT/US2008/54470 "International Preliminary Report on Patentability", dated Feb. 18, 2010.
PCT/US2008/54470 , "International Search Report and Written Opinion", dated Aug. 18, 2008.
PCT/US2009/036683 "International Preliminary Report on Patentability", dated Sep. 23, 2010.
PCT/US2009/036683 , "International Search Report and Written Opinion," dated Feb. 24, 2010.
PCT/US2009/036683 , "Invitation to Pay Additional Fees and Partial International Search Report," dated Dec. 28, 2009.
PCT/US2009/057215, "International Preliminary Report on Patentability," dated Mar. 31, 2011.
PCT/US2009/057215, "International Search Report and Written Opinion," dated Dec. 29, 2010.
PCT/US2010/027879, "International Preliminary Report on Patentability," dated Mar. 29, 2012.
PCT/US2010/027879, "International Search Report and Written Opinion," dated Dec. 30, 2010.
PCT/US2010/061319, "International Preliminary Report on Patentability," dated Jul. 5, 2012.
PCT/US2010/061319, "International Search Report and Written Opinion," dated Sep. 21, 2011.
PCT/US2012/035479, "International Preliminary Report on Patentability," dated Nov. 7, 2013.
PCT/US2012/035479, "International Search Report and Written Opinion," dated Jan. 10, 2012.
PCT/US2013/028699, "International Preliminary Report on Patentability," dated Sep. 12, 2014.
PCT/US2013/028699, "International Search Report and Written Opinion," dated Jul. 1, 2013.
PCT/US2013/041354, "International Search Report and Written Opinion", dated Aug. 14, 2013.

(56) References Cited

OTHER PUBLICATIONS

PCT/US2013/041906, "International Preliminary Report on Patentability," dated Dec. 4, 2014.
PCT/US2013/041906 , "International Search Report and Written Opinion," dated Jul. 16, 2013.
PCT/US2013/050145, "International Preliminary Report on Patentability," dated Jan. 22, 2015.
PCT/US2013/050145, "International Search Report and Written Opinion," dated Oct. 23, 2013.
PCT/US2014/025132, "International Preliminary Report on Patentability," dated Sep. 24, 2015.
PCT/US2014/025132, "International Search Report and Written Opinion\", dated Jul. 30, 2014.
PCT/US2015/020250 "International Preliminary Report on Patentability," dated Sep. 22, 2016.
Pearson et al., J. Chrom., vol. 255, 1983, pp. 137-149.
Pearson et al., Proc. Natl. Acad. Sci. USA, vol. 85, No. 5, 1998, pp. 2444-2448.
Perry-O'Keefe et al., "Peptide nucleic acid pre-gel hybridization: an alternative to southern hybridization", Proc Natl Acad Sci US A., Dec. 1996, vol. 93, No. 25, pp. 14670-14675.
Pertl et al., "Rapid molecular method for prenatal detection of Down's syndrome", Lancet., May 14, 1994, vol. 343, No. 8907, pp. 1197-1198.
Peters et al., "Noninvasive Prenatal Diagnosis of a Fetal Microdeletion Syndrome", New England Journal of Medicine, Nov. 10, 2011, pp. 1847-1848.
Petersen et al., Cytogenet Cell Genet., 2000, vol. 91, No. 1-4, pp. 199-203.
Pinkert et al., Genes Dev., 1987, vol. 1, pp. 268-277.
Poon et al., Clin. Chem., vol. 46, 2000, pp. 1832-1834.
Poon et al., "Differential DNA methylation between fetus and mother as a strategy for detecting fetal DNA in maternal plasma", Clin Chem., Jan. 2002', vol. 48, No. 1, pp. 35-41.
Porter et al., Biochemistry, vol. 34, 1995, pp. 11963-11969.
Qu et al., "Analysis of drug-DNA binding data", Methods Enzymol., 2000, vol. 321, pp. 353-369.
Queen et al., "Immunoglobulin gene transcription is activated by downstream sequence elements", Cell, Jul. 1983, vol. 33, No. 3, pp. 741-748.
Radding , "Homologous pairing and strand exchange in genetic recombination", Annu Rev Genet, 1982, vol. 16, pp. 405-437.
Randen et al., "Prenatal genotyping of RHO and SRY using maternal blood", Vox Sanguinis, vol. 85, No. 4, Nov. 2003, pp. 300-306.
Rashtchian, PCR Methods Applic 4, 1994, pp. S83-S91.
Rivas et al., Trends Biochem Sci, Aug. 1993, vol. 18, No. 8, pp. 284-287.
Roach et al., "Association between the abnormal expression of matrix-degrading enzymes by human osteoarthritic chondrocytes and demethylation of specific CpG sites in the promoter regions", Arthritis & Rheumatism, 2005, vol. 52, No. 10, pp. 3110-3124.
Robert et al., "Candidate Epigenetic 1-9 Biomarkers for Non-Invasive Prenatal Diagnosis of Down Syndrome", Reproductive Biomedicine Online, Reproductive Healthcare ltd,GB, vol. 15, No. 2, Jan. 1, 2007, pp. 227-235.
Robertson et al., Nature Rev. Genet., vol. 1, 2000, pp. 11-19.
Robinson et al., "A comparison of Affymetrix gene expression arrays", BMC Bioinformatics, 2007, vol. 8, p. 449.
Rojo et al., "Cusativin, a new cytidine-specific ribonuclease accumulated in seeds of *Cucumis sativus* L.", Planta., 1994, vol. 194, No. 3, pp. 328-338.
Rollins et al., "Large-scale structure of genomic methylation patterns", Genome Res., Feb. 2006, Epub Dec. 19, 2005, vol. 16, No. 2, pp. 157-163.
Romero et al., "Diagnostic Molecular Biology: Principles and Applications", Mayo Foundation, Rochester, Minn, 1993, pp. 401-406.
Roschke et al., "Karyotypic complexity of the NCI-60 drug-screening panel", Cancer Res., vol. 63, No. 24, Dec. 15, 2003, vol. 63, No. 24, pp. 8634-8647.
Rosenberg et al., A. J. Am. Chem. Soc., vol. 82, 1960, pp. 3198-3201.
Rossolini et al., Mol. Cell. Probes, vol. 8, 1994, pp. 91-98.
Sadri et al., Nucl. Acids Res., vol. 24, 1996, pp. 5058-5059.
Saito et al., Lancet, vol. 356, 2000, 1170.
Salgame et al., "An ELISA for detection of apoptosis", Nucleic Acids Research, vol. 25, No. 3, 1997, 680-681.
Sambrook et al., Molecular Biology: A laboratory Approach, Cold Spring Harbor, N.Y., 1989.
Sambrook et al., Molecular Cloning, A Laboratory Manual, 3rd edition, 2001.
Sanchez et al., "Effects of Sulpiride on Prolactin and mRNA Levels of Steroid 5areductase Isozymes in Adult Rat Brain", Neurochem Res., vol. 33, 2008, pp. 820-825.
Santoro et al., "A general purpose RNA-cleaving DNA enzyme", Proc. Natl. Acad. Sci. USA, Vo. 94, 1997, pp. 4262-4266.
Sargent et al., Meth. Enz., 1988, pp. 152:432.
Sayres et al., "Cell-free fetal nucleic acid testing: A review of the technology and its applications", Obstetrical and Gynecological Survey, vol. 66, No. 7, 2011, pp. 431-442.
Schlesinger et al., "Polycomb-mediated methylation on Lys27 of histone H3 pre-marks genes for de novo methylation in cancer", Nat Genet., vol. 39, No. 2, Epub Dec. 31, 2006, Feb. 2007, pp. 232-236.
Schouten et al., "Relative quantification of 40 nucleic acid sequences by multiplex ligationdependent probe amplification", Nucleic Acids Res., vol. 30, No. 12, Jun. 15, 2002, p. e57.
Schriefer et al., "Low pressure DNA shearing: a method for random DNA sequence analysis", Nucl. Acids Res. vol. 18, 1990, pp. 7455-7456.
Schroeder et al., "The human placenta methylome", PNAS USA, vol. 110, No. 15, 2013, pp. 6037-6042.
Schuler , "Sequence mapping by electronic PCR.", Genome Res., vol. 7, No. 5, May 1997, pp. 541-550.
Scott et al., J. Am. Chem. Soc., vol. 126, 2004, pp. 11776-11777.
Sekizawa et al., Clin. Chem., vol. 47, 2001, pp. 2164-2165.
Sharma et al., "Mass spectrometric based analysis, characterization and applications of circulating cell free DNA isolated from human body fluids", International Journal of Mass Spectrometry, vol. 304, 2011, pp. 172-183.
Sheffield et al., "Identification of novel rhodopsin mutations associated with retinitis pigmentosa by GC-clamped denaturing gradient gel electrophoresis", Am J Hum Genet., Oct. 1991, vol. 49, No. 4, pp. 699-706.
Silverman et al., "Methylation inhibitor therapy in the treatment of myelodysplastic syndrome", Nat Clin Pract Oneal. 2 Suppl 1, Dec. 2005, pp. S12-S23.
Simoncsits et al., "New rapid gel sequencing method for RNA", Nature. vol. 269, No. 5631, Oct. 27, 1977, pp. 833-866.
Singer et al., Biotechniques, vol. 4, 1986, p. 230.
Sjolander et al., Anal. Chem, vol. 63, 1991, pp. 2338-2345.
Slater et al., "Rapid, high throughput prenatal detection of aneuploidy using a novel quantitative method (MLPA)", J Med Genet., vol. 40, No. 12, Dec. 2003, pp. 907-912.
Smith et al., "Identification of common molecular subsequences", J Mol Bioi., vol. 147, No. 1, Mar. 25, 1981, pp. 195-197.
Smith et al., "Single-step purification of polypeptides expressed in *Escherichia coli* as fusions with Qlutathione S-transferase", Gene., vol. 67, No. 1, Jul. 15, 1988, pp. 31-40.
Snijders et al., "Assembly of microarrays for genome-wide measurement of DNA copy number", Nat Genet.,vol. 29, No. 3, Nov. 2001, pp. 263-264.
Snijders et al., "First-trimester ultrasound screening for chromosomal defects", Ultrasound Obstet Gynecol., vol. 7, No. 3, Mar. 1996, pp. 216-226.
Snijders et al., "UK 40ulticenter project on assessment of risk of trisomy 21 by maternal age and fetal nuchal-translucency thickness at 10-14 weeks of gestation. Fetal Medicine Foundation First Trimester Screening Group", Lancet. 352(9125) :X, Aug. 1, 1998, pp. 343-346.

(56) References Cited

OTHER PUBLICATIONS

Soni et al., "Progress toward ultrafast DNA sequencing using solid-state nanopores", Clin Chem., vol. 53, No. 11, Epub 2007, Sep. 21, Nov. 2007, pp. 1996-2001.
Sousa et al., "A mutant T7 RNA polymerase as a DNA polymerase", EMBO J., vol. 14, No. 18, Sep. 15, 1995, pp. 4609-4621.
Spetzler et al., "Enriching for Rare Subpopulations of Circulating Microvesicles by the Depletion of Endothelial-and Leukocyte-Derived Microvesicles", Caris Life Sciences, Carisome Posters, Papers, Abstracts and Presentations, American Academy of Cancer Research, AACR 2011.
Stanssens et al., "High-throughput MALDI-TOF discovery of genomic sequence polymorphisms", Genome Res. vol. 14, No. 1, Jan. 2004, pp. 126-133.
Staunton et al., "Chemosensitivity prediction by transcriptional profiling", Proc Natl Acad Sci USA, vol. 98, No. 19, Sep. 11, 2001, pp. 10787-10792.
Strachan, "The Human Genome", BIOS Scientific Publishers, 1992.
Strathdee et al., Am. J. Pathol., vol. 158, 2001, pp. 1121-1127.
Strohmeier et al., "A New High-Performance Capillary Electrophoresis Instrument", Hewlett-Packard Journal, Jun. 1995, pp. 10-19.
Szabo et al., Curr. Opin. Struct. Biol., vol. 5, 1995, pp. 699-705.
Tabor et al., "Non-Invasive Fetal Genome Sequencing: Opportunities and Challenges", American Journal of Medical Genetics Part A, vol. 158A, No. 10, 2012, pp. 2382-2384.
Takai et al., Proc. Natl. Acad. Sci. U.S.A., vol. 99, 2002, pp. 3740-3745.
Tang et al., Analytical Chemistry, vol. 74, 2002, pp. 226-331.
Terme et al., "Histone H1 Variants Are Differentially Expressed and Incorporated into Chromatin during Differentiation and Reprogramming to Pluripotency", The Journal of Clinical Chemistry, vol. 286, No. 41, Oct. 14, 2011, pp. 35347-35357.
Thorstenson et al., "An Automated Hydrodynamic Process for Controlled, Unbiased DNA Shearing", Genome Research, vol. 8, 1998, pp. 848-855.
Tolbert et al., J. Am. Chem. Soc. 118, 1996, pp. 7929-7940.
Tolbert et al., J. Am. Chem. Soc. 119, 1997, pp. 12100-12108.
Tong et al., "Noninvasive Prenatal Detection of Fetal Trisomy 18 by Epigenetic Allelic Ratio Analysis in Maternal Plasma: Theoretical and Empirical Considerations", Clinical Chemistry, vol. 52, No. 12, pp. 2149-2202.
Tooke et al., M. IVDT., Nov. 2004, p. 41.
Tost et al., Nucl. Acids Res. 37, 2003, p. e50.
Toyota et al., Cancer Res., vol. 59, 1999, pp. 2307-2312.
Toyota et al., "Methylation profiling in acute myeloid leukemia", Blood, May 1, 2001, vol. 97 No. 9, pp. 2823-2829.
Tsaliki et al., "MeDIP real-time qPCR of maternal peripheral blood reliably identifies trisomy 21", Prenat Diagn vol. 32, 2012, pp. 996-1001.
Tsui et al., "Systemic Identification of Placental Epigenetic Signatures for the Noninvasive Prenatal Detection of Edwards Syndrome", PLOS One, vol. 5, No. 11, 2010, p. e15069.
Tungwiwat et al., "Non-invasive fetal sex determination using a conventional nested PCR analysis of fetal DNA in maternal plasma", Clinica Chimica Acta, vol. 334, No. 1-2, Aug. 2003, pp. 173-177.
Tynan et al., "Fractional DNA quantification by massively parallel shotgun sequencing implications for fetal fraction measurement in maternal plasma", (Sequenom MME) ASHG Poster, 2011.
Uhlmann et al., Electrophoresis, vol. 23, 2002, pp. 4072-4079.
Valk et al., "Prognostically useful gene-expression profiles in acute myeloid leukemia", N Engl J Med., vol. 350, No. 16, Apr. 15, 2004, pp. 1617-1628.
Van Der Schoot et al., "Real-time PCR of bi-allelic insertion/deletion polymorphisms can serve as a reliable positive control for cell-free fetal DNA in non-invasive prenatal Qenotyping", abstract, Blood, vol. 102, 2003, p. 93a.
Veltman et al., "High-throughput analysis of subtelomeric chromosome rearrangements by use of array-based comparative genomic hybridization", Am J Hum Genet., vol. 70, No. 5, Epub Apr. 9, 2002, May 2002, pp. 1269-1276.
Venter et al., "The sequence of the human genome", Science, vol. 291, No. 5507, Feb. 16, 2001, pp. 1304-1351.
Verbeck et al., The Journal of Biomolecular Techniques, vol. 13, No. 2, 2002, pp. 56-61.
Verma et al., "Rapid and simple prenatal DNA diagnosis of Down's syndrome", Lancet, vol. 352, No. 9121, Jul. 4, 1998, pp. 9-12.
Vincenet et al., "Helicase-Dependent isothermal DNA Amplification", EMBO reports, vol. 5, No. 8, 2004, pp. 795-800.
Vire et al., "The Polycomb group protein EZH2 directly controls DNA methylation", Nature, vol. 439, No. 7078, Epub Dec. 14, 2005, Feb. 16, 2006, pp. 871-874.
Vogelstein et al., "Digital PCR", Proc Natl Acad Sci USA, vol. 96, No. 16, Aug. 3, 1999, pp. 9236-9241.
Volkerding et al., Clin Chem, vol. 55, 2009, pp. 641-658.
Vu et al., "Symmetric and asymmetric DNA methylation in the human IGF2-H19 imprinted region", Genomics, vol. 64, No. 2, Mar. 1, 2000, pp. 132-143.
Wada et al., "Codon usage tabulated from the GenBank genetic sequence data", Nucleic Acids Res., 20 Suppl., May 11, 1992, pp. 2111-2118.
Wald et al., Prenat Diagn, vol. 17, No. 9, 1997, pp. 821-829.
Wang et al., BMC Genomics 7, 2006, p. 166.
Wapner et al., "First-trimester screening for trisomies 21 and 18", N Engl J Med., vol. 349, No. 15, Oct. 9, 2003, pp. 1405-1413.
Waterman et al., J. Mol. Biol., vol. 147, 1980, pp. 195-197.
Weber et al., Oncogene, vol. 19, 2000, pp. 169-176.
Weisenberger et al., Nat Genet, vol. 38, 2006, pp. 787-793.
Weiss et al., "H1 variant-specific lysine methylation by G9a/KMT1 C and Glpl /KMT1 D", Epigenetics & Chromatin, Mar. 24, 2010, vol. 3, No. 7, pp. 1-13.
White et al., "Detecting single base substitutions as heteroduplex polymorphisms", Genomics, vol. 12, No. 2, Feb. 1992, pp. 301-306.
WHO, "The World Health Organization histological typing of lung tumours", Am J Clin Pathol., 1982, vol. 77, pp. 123-136.
Widschwendter et al., "Epigenetic stem cell signature in cancer", Nat Genet, vol. 39, 2007, pp. 157-158.
Wiley & Sons, "Current Protocols in Molecular Biology", 1989, 6.3.1-6.3.6.
Wilkinson, "In situ Hybridization", Wilkinson ed., IRL Press, Oxford University Press, Oxford, 1998.
Winoto et al., "A novel, inducible and T cell-specific enhancer located at the 3' end of the T cell receptor alpha locus", Embo J., vol. 8, No. 3, Mar. 1989, pp. 729-733.
Xiong et al., Nucleic Acids Res., vol. 25, 1997, pp. 2532-2534.
Yamada et al., Genome Research, vol. 14, 2004, pp. 247-266.
Yamada et al., "Suppressive effect of epigallocatechin gallate (EGCg) on DNA methylation in mice: Detection by methylation sensitive restriction endonuclease digestion and PCR", Journal of Food, Agriculture & Environment, 2005, vol. 3, No. 2, pp. 73-76.
Yan et al., "A novel diagnostic strategy for trisomy 21 using short tandem repeats", Electrophoresis, vol. 27, 2006, pp. 416-422.
Zahra et al., "Plasma microparticles are not elevated in fresh plasma from patients with gynaecologicalmalignancy—An observational study", Gynecol Onco, vol. 123, No. 1, Oct. 2011, pp. 152-156.
Zervos et al., Cell, vol. 72, 1993, pp. 223-232.
Zhang et al., "Histone H1 Depletion Impairs Embryonic Stem Cell Differentiation", PLOS Genetics, vol. 8, No. 5, e1 002691, May 2012, pp. 1-14.
Zhao et al., Pretat Diag, vol. 30, No. 8, 2010, pp. 778-782.
Zheng et al., "Nonhematopoietically Derived DNA Is Shorter than Hematopoietically Derived DNA in Plasma: A Transplantation Model", Clin Chem., vol. 58, No. 2, Nov. 3, 2011.
Zhong et al., Am. J. Obstet. Gynecol, 2001, vol. 184, pp. 414-419.
Zhong et al., Prenat. Diagn vol. 20, 2000, pp. 795-798.
Zimmermann et al., Clin Chem, Vo. 48, 2002, pp. 362-363.
Zimmermann et al., "Serum parameters and nuchal translucency in first trimester screening for fetal chromosomal abnormalities", In: BJOG: An International Journal of Obstetrics & Gynaecology, vol. 103, No. 10, 1996, pp. 1009-1014.
Zuker et al., "Mfold web server for nucleic acid folding and hybridization prediction", Nucleic Acids Res. vol. 31, No. 13, pp. 3406-3415.

(56) References Cited

OTHER PUBLICATIONS

U.S. Appl. No. 12/561,241, "Notice of Allowance," dated Feb. 27, 2013, 7 pages.
U.S. Appl. No. 12/727,198, "Notice of Allowance," dated Sep. 15, 2014, 7 pages.
U.S. Appl. No. 14/735,477, "Final Office Action," dated Mar. 21, 2019, 11 pages.
U.S. Appl. No. 15/261,457, "Non-Final Office Action," dated Oct. 23, 2018, 15 pages.
AU 2009293232, "First Examination Report," dated Mar. 11, 2014, 3 pages.
AU 2009293232, "Notice of Acceptance," dated Apr. 30, 2015, 2 pages.
AU 2010295968, "First Examination Report," dated Jul. 17, 2014, 4 pages.
AU 2010295968, "Notice of Acceptance," dated Aug. 10, 2015, 3 pages.
AU 2013290102, "Notice of Acceptance," dated Nov. 6, 2018, 3 pages.
AU 2017251674, "First Examination Report," dated Sep. 14, 2018, 6 pages.
CA 2,878,979, "Office Action," dated Feb. 7, 2019, 4 pages.
EP 09815148.3, "Notice of Decision to Grant," dated Jul. 14, 2016, 3 pages.
EP 09815148.3, "Office Action," dated Nov. 13, 2014, 4 pages.
EP 09815148.3, "Office Action," dated May 14, 2014, 5 pages.
EP 09815148.3, "Office Action," dated Jan. 3, 2013, 7 pages.
EP 10817598.5, "Notice of Decision to Grant," dated Jun. 29, 2017, 3 pages.
EP 10817598.5, "Office Action," dated Jan. 29, 2014, 5 pages.
EP 13739590.1, "Office Action," dated Feb. 1, 2016, 5 pages.
EP 13739590.1, "Office Action," dated Nov. 26, 2018, 5 pages.
EP 16173137.7, "Office Action," dated Oct. 1, 2018, 6 pages.
IN 3139/DELNP/2012, "First Examination Report," dated Oct. 25, 2017, 8 pages.
JP 2011-527069, "Notice of Decision to Grant," dated Mar. 4, 2015, 6 pages.
JP 2011-527069, "Office Action," dated Mar. 7, 2014, 14 pages.
JP 2012-529756, "Notice of Decision to Grant," dated Dec. 24, 2015, 5 pages.
JP 2012-529756, "Office Action," dated Jul. 14, 2014, 14 pages.
JP 2012-529756, "Office Action," dated Jun. 2, 2015, 17 pages.
JP 2014-180865, "Notice of Decision to Grant," dated Apr. 1, 2016, 6 pages.
JP 2014-180865, "Office Action," dated Oct. 9, 2015, 7 pages.
JP 2015-005024, "Office Action," dated Jan. 25, 2016, 5 pages.
JP 2015-076001, "Office Action," dated Feb. 10, 2016, 6 pages.
JP 2015-076001, "Office Action," dated Nov. 11, 2016, 9 pages.
JP 2015-195591, "Notice of Decision to Grant," dated Oct. 26, 2016, 6 pages.
JP 2015-195591, "Office Action," dated Jul. 15, 2016, 6 pages.
JP 2017-241844, "Office Action," dated Oct. 19, 2018, 4 pages.
JP 2018-17348, "Office Action," dated Feb. 6, 2019, 15 pages.
JP 2018-17349, "Office Action," dated Dec. 26, 2018, 4 pages.
EP 16173137.7, "Office Action," dated Jun. 26, 2019, 5 pages.
EP 17182863.5, "Office Action," dated Jul. 19, 2019, 4 pages.
U.S. Appl. No. 15/261,457, "Final Office Action," dated Jul. 15, 2019, 15 pages.

Fractionating DNA Based on Methylation

CORRELATION BETWEEN MICROARRAY AND EpiTYPER RESULTS

1. Selection of differentially methylated targets for specific DNA sequence capture 2. Distribution of CCF DNA after capture 3. Distribution of CCF DNA after digestion 4. Quantification of non-digested DNA molecules

FIGURE 14A-B
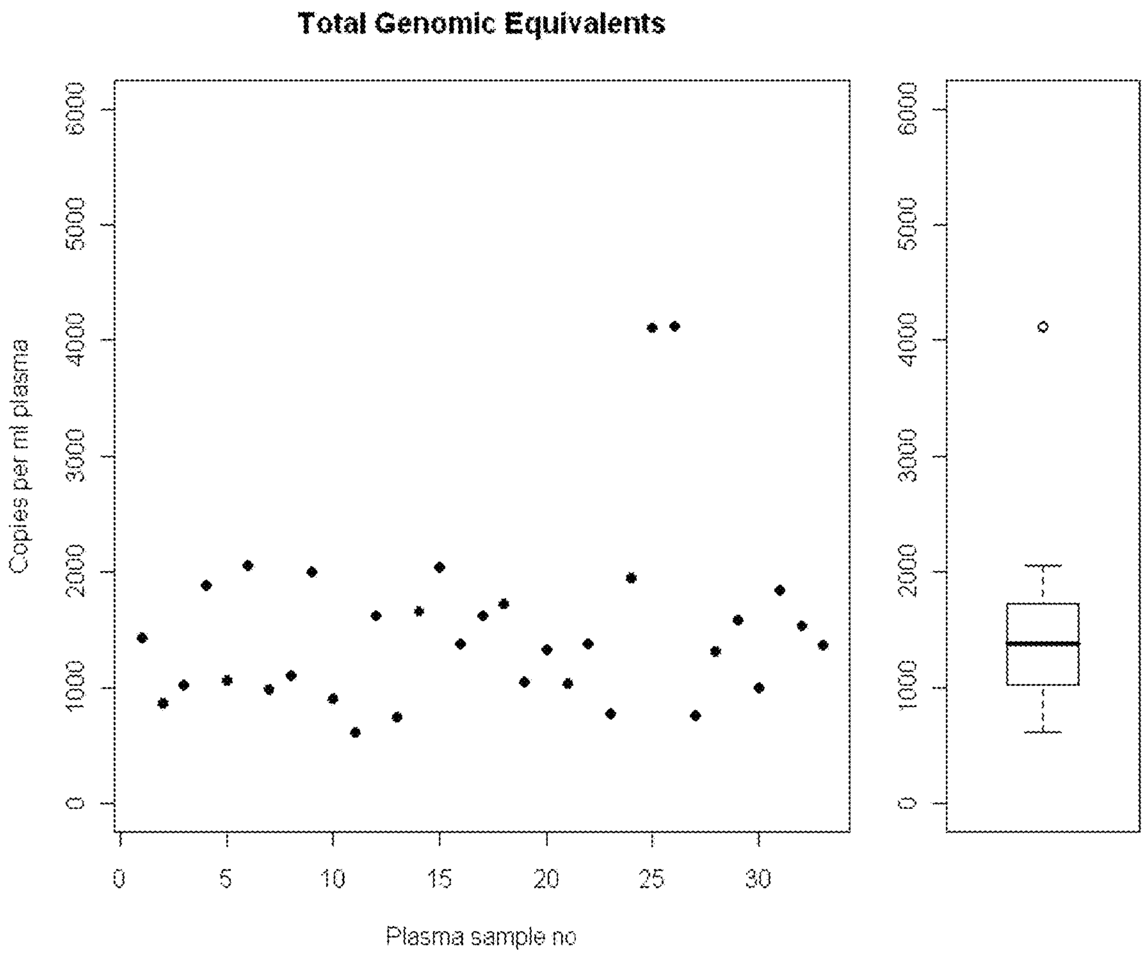

FIGURE 15A-B
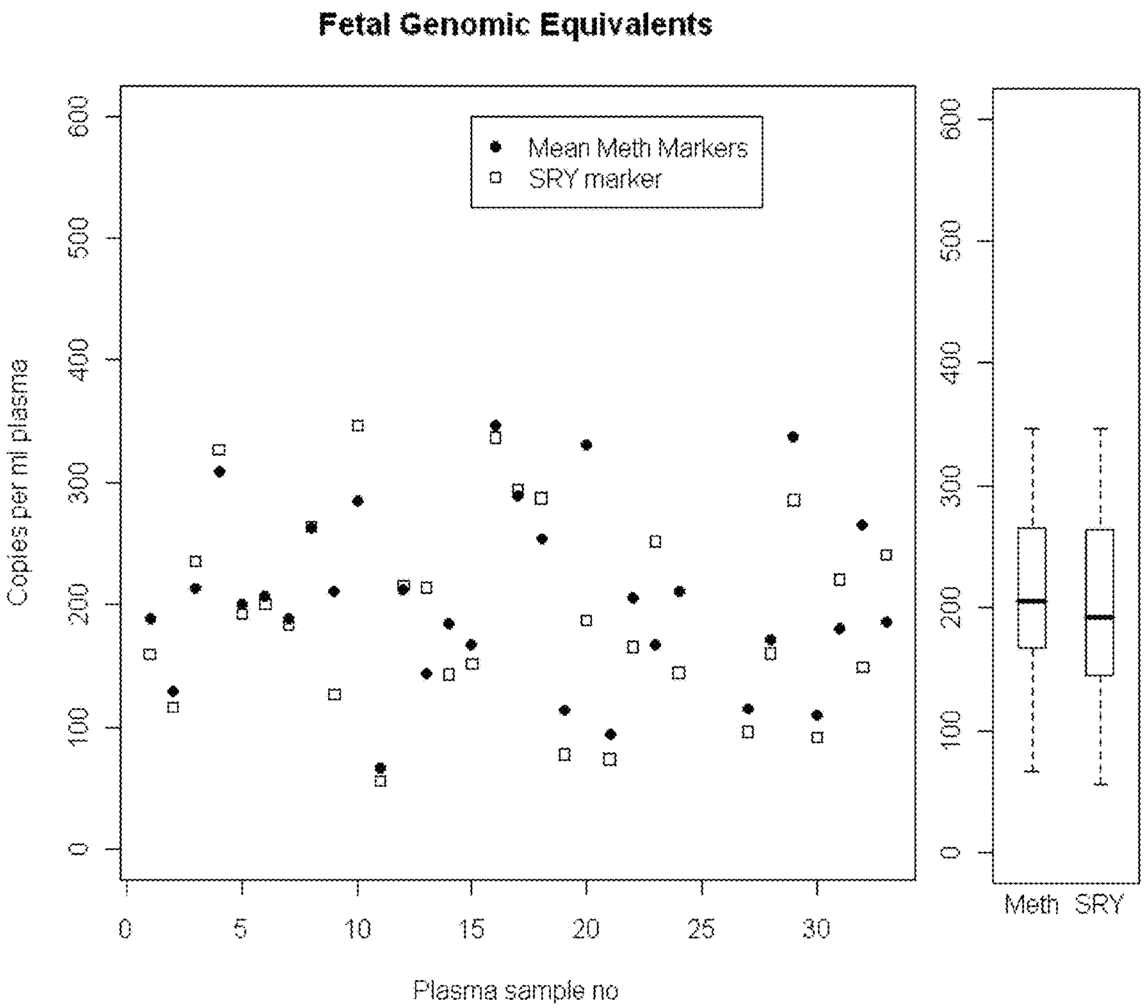

PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES

RELATED PATENT APPLICATIONS

This patent application is continuation of U.S. patent application Ser. No. 13/791,466, filed Mar. 8, 2013, having the same title as this application, which is a divisional of U.S. patent application Ser. No. 12/727,198, filed Mar. 18, 2010, now U.S. Pat. No. 8,962,247, having the same title as this application, which is a continuation-in-part of U.S. patent application Ser. No. 12/561,241, filed Sep. 16, 2009, now U.S. Pat. No. 8,476,013, having the same title as this application, which claims the benefit of U.S. Provisional Patent Application No. 61/192,264, filed Sep. 16, 2008. The entire content of the foregoing patent applications is incorporated by reference herein, including all text, drawings and tables.

FIELD

The technology in part relates to prenatal diagnostics and enrichment methods.

BACKGROUND

Non-invasive prenatal testing is becoming a field of rapidly growing interest. Early detection of pregnancy-related conditions, including complications during pregnancy and genetic defects of the fetus is of crucial importance, as it allows early medical intervention necessary for the safety of both the mother and the fetus. Prenatal diagnosis has been conducted using cells isolated from the fetus through procedures such as chorionic villus sampling (CVS) or amniocentesis. However, these conventional methods are invasive and present an appreciable risk to both the mother and the fetus. The National Health Service currently cites a miscarriage rate of between 1 and 2 percent following the invasive amniocentesis and chorionic villus sampling (CVS) tests.

An alternative to these invasive approaches has been developed for prenatal screening, e.g., to detecting fetal abnormalities, following the discovery that circulating cell-free fetal nucleic acid can be detected in maternal plasma and serum (Lo et al., Lancet 350:485-487, 1997; and U.S. Pat. No. 6,258,540). Circulating cell free fetal nucleic acid (cffNA) has several advantages making it more applicable for non-invasive prenatal testing. For example, cell free nucleic acid is present at higher levels than fetal cells and at concentrations sufficient for genetic analysis. Also, cffNA is cleared from the maternal bloodstream within hours after delivery, preventing contamination from previous pregnancies.

Examples of prenatal tests performed by detecting fetal DNA in maternal plasma or serum include fetal rhesus D (RhD) genotyping (Lo et al., N. Engl. J. Med. 339:1734-1738, 1998), fetal sex determination (Costa et al., N. Engl. J. Med. 346:1502, 2002), and diagnosis of several fetal disorders (Amicucci et al., Clin. Chem. 46:301-302, 2000; Saito et al., Lancet 356:1170, 2000; and Chiu et al., Lancet 360:998-1000, 2002). In addition, quantitative abnormalities of fetal DNA in maternal plasma/serum have been reported in preeclampsia (Lo et al., Clin. Chem. 45:184-188, 1999 and Zhong et al., Am. J. Obstet. Gynecol. 184:414-419, 2001), fetal trisomy 21 (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001).

SUMMARY

The invention provides inter alia human epigenetic biomarkers that are useful for the noninvasive detection of fetal genetic traits, including, but not limited to, the presence or absence of fetal nucleic acid, the absolute or relative amount of fetal nucleic acid, fetal sex, and fetal chromosomal abnormalities such as aneuploidy. The human epigenetic biomarkers of the invention represent genomic DNA that display differential CpG methylation patterns between the fetus and mother. The compositions and processes of the invention allow for the detection and quantification of fetal nucleic acid in a maternal sample based on the methylation status of the nucleic acid in said sample. More specifically, the amount of fetal nucleic acid from a maternal sample can be determined relative to the total amount of nucleic acid present, thereby providing the percentage of fetal nucleic acid in the sample. Further, the amount of fetal nucleic acid can be determined in a sequence-specific (or locus-specific) manner and with sufficient sensitivity to allow for accurate chromosomal dosage analysis (for example, to detect the presence or absence of a fetal aneuploidy).

In the first aspect of the invention, a method is provided for enriching fetal nucleic acids from a maternal biological sample, based on differential methylation between fetal and maternal nucleic acid comprising the steps of: (a) binding a target nucleic acid, from a sample, and a control nucleic acid, from the sample, to a methylation-specific binding protein; and (b) eluting the bound nucleic acid based on methylation status, wherein differentially methylated nucleic acids elute at least partly into separate fractions. In an embodiment, the nucleic acid sequence includes one or more of the polynucleotide sequences of SEQ ID NOs: 1-261. SEQ ID NOs: 1-261 are provided in Tables 4A-4C. The invention includes the sequences of SEQ ID NOs: 1-261, and variations thereto. In an embodiment, a control nucleic acid is not included in step (a).

In a related embodiment, a method is provided for enriching fetal nucleic acid from a maternal sample, which comprises the following steps: (a) obtaining a biological sample from a woman; (b) separating fetal and maternal nucleic acid based on the methylation status of a CpG-containing genomic sequence in the sample, wherein the genomic sequence from the fetus and the genomic sequence from the woman are differentially methylated, thereby distinguishing the genomic sequence from the woman and the genomic sequence from the fetus in the sample. In an embodiment, the genomic sequence is at least 15 nucleotides in length, comprising at least one cytosine, further wherein the region consists of (1) a genomic locus selected from Tables 1A-1C; and (2) a DNA sequence of no more than 10 kb upstream and/or downstream from the locus. For this aspect and all aspects of the invention, obtaining a biological sample from a woman is not meant to limit the scope of the invention. Said obtaining can refer to actually drawing a sample from a woman (e.g., a blood draw) or to receiving a sample from elsewhere (e.g., from a clinic or hospital) and performing the remaining steps of the method.

In a related embodiment, a method is provided for enriching fetal nucleic acid from a maternal sample, which comprises the following steps: (a) obtaining a biological sample from the woman; (b) digesting or removing maternal nucleic acid based on the methylation status of a CpG-containing genomic sequence in the sample, wherein the genomic sequence from the fetus and the genomic sequence from the woman are differentially methylated, thereby enriching for the genomic sequence from the fetus in the sample. Maternal nucleic acid may be digested using one or more methylation sensitive restriction enzymes that selectively digest or cleave maternal nucleic acid based on its methylation status. In an embodiment, the genomic sequence is at least 15 nucleotides in length, comprising at least one cytosine, further wherein the region consists of (1) a genomic locus selected from Tables 1A-1C; and (2) a DNA sequence of no more than 10 kb upstream and/or downstream from the locus.

In a second aspect of the invention, a method is provided for preparing nucleic acid having a nucleotide sequence of a fetal nucleic acid, which comprises the following steps: (a) providing a sample from a pregnant female; (b) separating fetal nucleic acid from maternal nucleic acid from the sample of the pregnant female according to a different methylation state between the fetal nucleic acid and the maternal nucleic acid counterpart, wherein the nucleotide sequence of the fetal nucleic acid comprises one or more CpG sites from one or more of the polynucleotide sequences of SEQ ID NOs: 1-261 within a polynucleotide sequence from a gene or locus that contains one of the polynucleotide sequences of SEQ ID NOs: 1-261; and (c) preparing nucleic acid comprising a nucleotide sequence of the fetal nucleic acid by an amplification process in which fetal nucleic acid separated in part (b) is utilized as a template. In an embodiment, a method is provided for preparing nucleic acid having a nucleotide sequence of a fetal nucleic acid, which comprises the following steps: (a) providing a sample from a pregnant female; (b) digesting or removing maternal nucleic acid from the sample of the pregnant female according to a different methylation state between the fetal nucleic acid and the maternal nucleic acid counterpart, wherein the nucleotide sequence of the fetal nucleic acid comprises one or more CpG sites from one or more of the polynucleotide sequences of SEQ ID NOs: 1-261 within a polynucleotide sequence from a gene that contains one of the polynucleotide sequences of SEQ ID NOs: 1-261; and (c) preparing nucleic acid comprising a nucleotide sequence of the fetal nucleic acid. The preparing process of step (c) may be a hybridization process, a capture process, or an amplification process in which fetal nucleic acid separated in part (b) is utilized as a template. Also, in the above embodiment wherein maternal nucleic acid is digested, the maternal nucleic acid may be digested using one or more methylation sensitive restriction enzymes that selectively digest or cleave maternal nucleic acid based on its methylation status. In either embodiment, the polynucleotide sequences of SEQ ID NOs: 1-261 may be within a polynucleotide sequence from a CpG island that contains one of the polynucleotide sequences of SEQ ID NOs: 1-261. The polynucleotide sequences of SEQ ID NOs: 1-261 are further characterized in Tables 1-3 herein, including the identification of CpG islands that overlap with the polynucleotide sequences provided in SEQ ID NOs: 1-261. In an embodiment, the nucleic acid prepared by part (c) is in solution. In yet an embodiment, the method further comprises quantifying the fetal nucleic acid from the amplification process of step (c).

In a third aspect of the invention, a method is provided for enriching fetal nucleic acid from a sample from a pregnant female with respect to maternal nucleic acid, which comprises the following steps: (a) providing a sample from a pregnant female; and (b) separating or capturing fetal nucleic acid from maternal nucleic acid from the sample of the pregnant female according to a different methylation state between the fetal nucleic acid and the maternal nucleic acid, wherein the nucleotide sequence of the fetal nucleic acid comprises one or more CpG sites from one or more of the polynucleotide sequences of SEQ ID NOs: 1-261 within a polynucleotide sequence from a gene that contains one of the polynucleotide sequences of SEQ ID NOs: 1-261. In an embodiment, the polynucleotide sequences of SEQ ID NOs: 1-261 may be within a polynucleotide sequence from a CpG island that contains one of the polynucleotide sequences of SEQ ID NOs: 1-261. The polynucleotide sequences of SEQ ID NOs: 1-261 are characterized in Tables 1A-1C herein. In an embodiment, the nucleic acid separated by part (b) is in solution. In yet an embodiment, the method further comprises amplifying and/or quantifying the fetal nucleic acid from the separation process of step (b).

In a fourth aspect of the invention, a composition is provided comprising an isolated nucleic acid from a fetus of a pregnant female, wherein the nucleotide sequence of the nucleic acid comprises one or more of the polynucleotide sequences of SEQ ID NOs: 1-261. In one embodiment, the nucleotide sequence consists essentially of a nucleotide sequence of a gene, or portion thereof. In an embodiment, the nucleotide sequence consists essentially of a nucleotide sequence of a CpG island, or portion thereof. The polynucleotide sequences of SEQ ID NOs: 1-261 are further characterized in Tables 1A-1C. In an embodiment, the nucleic acid is in solution. In an embodiment, the nucleic acid from the fetus is enriched relative to maternal nucleic acid. In an embodiment, the composition further comprises an agent that binds to methylated nucleotides. For example, the agent may be a methyl-CpG binding protein (MBD) or fragment thereof.

In a fifth aspect of the invention, a composition is provided comprising an isolated nucleic acid from a fetus of a pregnant female, wherein the nucleotide sequence of the nucleic acid comprises one or more CpG sites from one or more of the polynucleotide sequences of SEQ ID NOs: 1-261 within a polynucleotide sequence from a gene, or portion thereof, that contains one of the polynucleotide sequences of SEQ ID NOs: 1-261. In an embodiment, the nucleotide sequence of the nucleic acid comprises one or more CpG sites from one or more of the polynucleotide sequences of SEQ ID NOs: 1-261 within a polynucleotide sequence from a CpG island, or portion thereof, that contains one of the polynucleotide sequences of SEQ ID NOs: 1-261. The polynucleotide sequences of SEQ ID NOs: 1-261 are further characterized in Tables 1A-1C. In an embodiment, the nucleic acid is in solution. In an embodiment, the nucleic acid from the fetus is enriched relative to maternal nucleic acid. Hyper- and hypomethylated nucleic acid sequences of the invention are identified in Tables 1A-1C. In an embodiment, the composition further comprises an agent that binds to methylated nucleotides. For example, the agent may be a methyl-CpG binding protein (MBD) or fragment thereof.

In some embodiments, a nucleotide sequence of the invention includes three or more of the CpG sites. In an embodiment, the nucleotide sequence includes five or more of the CpG sites. In an embodiment, the nucleotide sequence is from a gene region that comprises a PRC2 domain (see Table 3). In an embodiment, the nucleotide sequence is from a gene region involved with development. For example, SOX14—which is an epigenetic marker of the present invention (See Table 1)—is a member of the SOX (SRY-related HMG-box) family of transcription factors involved in the regulation of embryonic development and in the determination of cell fate.

In some embodiments, the genomic sequence from the woman is methylated and the genomic sequence from the fetus is unmethylated. In other embodiments, the genomic sequence from the woman is unmethylated and the genomic sequence from the fetus is methylated. In an embodiment, the genomic sequence from the fetus is hypermethylated relative to the genomic sequence from the mother. Fetal genomic sequences found to be hypermethylated relative to maternal genomic sequence are provided in SEQ ID NOs: 1-59, 90-163, 176, 179, 180, 184, 188, 189, 190, 191, 193, 195, 198, 199, 200, 201, 202, 203, 205, 206, 207, 208, 209, 210, 211, 212, 213, 214, 221, 223, 225, 226, 231, 232, 233, 235, 239, 241, 257, 258, 259, and 261. Alternatively, the genomic sequence from the fetus is hypomethylated relative to the genomic sequence from the mother. Fetal genomic sequences found to be hypomethylated relative to maternal genomic sequence are provided in SEQ ID NOs: 60-85, 164, 165, 166, 167, 168, 169, 170, 171, 172, 173, 174, 175, 177, 178, 181, 182, 183, 185, 186, 187, 192, 194, 196, 197, 204, 215, 216, 217, 218, 219, 220, 222, 224, 227, 228, 229, 230, 234, 236, 237, 238, 240, 242, 243, 244, 245, 246, 247, 248, 249, 250, 251, 252, 253, 254, 255, 256, and 260. Methylation sensitive restriction enzymes of the invention may be sensitive to hypo- or hyper-methylated nucleic acid.

In an embodiment, the fetal nucleic acid is extracellular nucleic acid. Generally the extracellular fetal nucleic acid is about 500, 400, 300, 250, 200 or 150 (or any number there between) nucleotide bases or less. In an embodiment, the digested maternal nucleic acid is less than about 90, 100, 110, 120, 130, 140 or 150 base pairs. In a related embodiment, the fetal nucleic acid is selectively amplified, captured or separated from or relative to the digested maternal nucleic acid based on size. For example, PCR primers may be designed to amplify nucleic acid greater than about 75, 80, 85, 90, 95, 100, 105, 110, 115 or 120 (or any number there between) base pairs thereby amplifying fetal nucleic acid and not digested maternal nucleic acid. In an embodiment, the nucleic acid is subjected to fragmentation prior to the methods of the invention. Examples of methods of fragmenting nucleic acid, include but are not limited to sonication and restriction enzyme digestion. In some embodiments the fetal nucleic acid is derived from the placenta. In other embodiments the fetal nucleic acid is apoptotic.

In some embodiments, the present invention provides a method in which the sample is a member selected from the following: maternal whole blood, maternal plasma or serum, amniotic fluid, a chorionic villus sample, biopsy material from a pre-implantation embryo, fetal nucleated cells or fetal cellular remnants isolated from maternal blood, maternal urine, maternal saliva, washings of the female reproductive tract and a sample obtained by celocentesis or lung lavage. In certain embodiments, the biological sample is maternal blood. In some embodiments, the biological sample is a chorionic villus sample. In certain embodiments, the maternal sample is enriched for fetal nucleic acid prior to the methods of the present invention. Examples of fetal enrichment methods are provided in PCT Publication Nos. WO/2007140417A2, WO2009/032781A2 and US Publication No. 20050164241.

In some embodiments, all nucleated and a nucleated cell populations are removed from the sample prior to practicing the methods of the invention. In some embodiments, the sample is collected, stored or transported in a manner known to the person of ordinary skill in the art to minimize degradation or the quality of fetal nucleic acid present in the sample.

The sample can be from any animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable pregnancy-associated disorder or chromosomal abnormality.

In some embodiments, the sample is treated with a reagent that differentially modifies methylated and unmethylated DNA. For example, the reagent may comprise bisulfite; or the reagent may comprise one or more enzymes that preferentially cleave methylated DNA; or the reagent may comprise one or more enzymes that preferentially cleave unmethylated DNA. Examples of methylation sensitive restriction enzymes include, but are not limited to, HhaI and HpaII.

In one embodiment, the fetal nucleic acid is separated from the maternal nucleic acid by an agent that specifically binds to methylated nucleotides in the fetal nucleic acid. In an embodiment, the fetal nucleic acid is separated or removed from the maternal nucleic acid by an agent that specifically binds to methylated nucleotides in the maternal nucleic acid counterpart. In an embodiment, the agent that binds to methylated nucleotides is a methyl-CpG binding protein (MBD) or fragment thereof.

In a sixth aspect of the invention, a method is provided for determining the amount or copy number of fetal DNA in a maternal sample that comprises differentially methylated maternal and fetal DNA. The method is performed by a) distinguishing between the maternal and fetal DNA based on differential methylation status; and b) quantifying the fetal DNA of step a). In a specific embodiment, the method comprises a) digesting the maternal DNA in a maternal sample using one or more methylation sensitive restriction enzymes thereby enriching the fetal DNA; and b) determining the amount of fetal DNA from step a). The amount of fetal DNA can be used inter alia to confirm the presence or absence of fetal nucleic acid, determine fetal sex, diagnose fetal disease or a pregnancy-associated disorder, or be used in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. Bisulfite is known to degrade DNA, thereby, further reducing the already limited fetal nucleic acid present in maternal samples. In one embodiment, determining the amount of fetal DNA in step b) is done by introducing one or more competitors at known concentrations. In an embodiment, determining the amount of fetal DNA in step b) is done by RT-PCR, primer extension, sequencing or counting. In a related embodiment, the amount of nucleic acid is determined using BEAMing technology as described in US Patent Publication No. US20070065823. In a another related embodiment, the amount of nucleic acid is determined using the shotgun sequencing technology described in US Patent Publication No. US20090029377 (U.S. application Ser. No. 12/178,181), or variations thereof. In an embodiment, the restriction efficiency is determined and the efficiency rate is used to further determine the amount of fetal DNA. Exemplary differentially methylated nucleic acids are provided in SEQ ID NOs: 1-261.

In a seventh aspect of the invention, a method is provided for determining the concentration of fetal DNA in a maternal sample, wherein the maternal sample comprises differentially methylated maternal and fetal DNA, comprising a) determining the total amount of DNA present in the maternal sample; b) selectively digesting the maternal DNA in a maternal sample using one or more methylation sensitive restriction enzymes thereby enriching the fetal DNA; c) determining the amount of fetal DNA from step b); and d) comparing the amount of fetal DNA from step c) to the total amount of DNA from step a), thereby determining the concentration of fetal DNA in the maternal sample. The concentration of fetal DNA can be used inter alia in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. In one embodiment, determining the amount of fetal DNA in step b) is done by introducing one or more competitors at known concentrations. In an embodiment, determining the amount of fetal DNA in step b) is done by RT-PCR, sequencing or counting. In an embodiment, the restriction efficiency is determined and used to further determine the amount of total DNA and fetal DNA. Exemplary differentially methylated nucleic acids are provided in SEQ ID NOs: 1-261.

In an eighth aspect of the invention, a method is provided for determining the presence or absence of a fetal aneuploidy using fetal DNA from a maternal sample, wherein the maternal sample comprises differentially methylated maternal and fetal DNA, comprising a) selectively digesting the maternal DNA in a maternal sample using one or more methylation sensitive restriction enzymes thereby enriching the fetal DNA; b) determining the amount of fetal DNA from a target chromosome; c) determining the amount of fetal DNA from a reference chromosome; and d) comparing the amount of fetal DNA from step b) to step c), wherein a biologically or statistically significant difference between the amount of target and reference fetal DNA is indicative of the presence of a fetal aneuploidy. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. In one embodiment, determining the amount of fetal DNA in steps b) and c) is done by introducing one or more competitors at known concentrations. In an embodiment, determining the amount of fetal DNA in steps b) and c) is done by RT-PCR, sequencing or counting. In an embodiment, the amount of fetal DNA from a target chromosome determined in step b) is compared to a standard control, for example, the amount of fetal DNA from a target chromosome from euploid pregnancies. In an embodiment, the restriction efficiency is determined and used to further determine the amount of fetal DNA from a target chromosome and from a reference chromosome. Exemplary differentially methylated nucleic acids are provided in SEQ ID NOs: 1-261.

In a ninth aspect of the invention, a method is provided for detecting the presence or absence of a chromosomal abnormality by analyzing the amount or copy number of target nucleic acid and control nucleic acid from a sample of differentially methylated nucleic acids comprising the steps of: (a) enriching a target nucleic acid, from a sample, and a control nucleic acid, from the sample, based on its methylation state; (b) performing a copy number analysis of the enriched target nucleic acid in at least one of the fractions; (c) performing a copy number analysis of the enriched control nucleic acid in at least one of the fractions; (d) comparing the copy number from step (b) with the copy number from step (c); and (e) determining if a chromosomal abnormality exists based on the comparison in step (d), wherein the target nucleic acid and control nucleic acid have the same or substantially the same methylation status. In a related embodiment, a method is provided for detecting the presence or absence of a chromosomal abnormality by analyzing the amount or copy number of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, wherein differentially methylated nucleic acids elute at least partly into separate fractions; (c) performing a copy number analysis of the eluted target nucleic acid in at least one of the fractions; (d) performing a copy number analysis of the eluted control nucleic acid in at least one of the fractions; (e) comparing the copy number from step (c) with the copy number from step (d); and (f) determining if a chromosomal abnormality exists based on the comparison in step (e), wherein the target nucleic acid and control nucleic acid have the same or substantially the same methylation status. Differentially methylated nucleic acids are provided in SEQ ID NOs: 1-261.

In a tenth aspect of the invention, a method is provided for detecting the presence or absence of a chromosomal abnormality by analyzing the allelic ratio of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, wherein differentially methylated nucleic acids elute at least partly into separate fractions; (c) performing an allelic ratio analysis of the eluted target nucleic acid in at least one of the fractions; (d) performing an allelic ratio analysis of the eluted control nucleic acid in at least one of the fractions; (e) comparing the allelic ratio from step c with the all from step d; and (f) determining if a chromosomal abnormality exists based on the comparison in step (e), wherein the target nucleic acid and control nucleic acid have the same or substantially the same methylation status. Differentially methylated nucleic acids are provided in SEQ ID NOs: 1-261, and SNPs within the differentially methylated nucleic acids are provided in Table 2. The methods may also be useful for detecting a pregnancy-associated disorder.

In an eleventh aspect of the invention, the amount of maternal nucleic acid is determined using the methylation-based methods of the invention. For example, fetal nucleic acid can be separated (for example, digested using a methylation-sensitive enzyme) from the maternal nucleic acid in a sample, and the maternal nucleic acid can be quantified using the methods of the invention. Once the amount of maternal nucleic acid is determined, that amount can subtracted from the total amount of nucleic acid in a sample to determine the amount of fetal nucleic acid. The amount of fetal nucleic acid can be used to detect fetal traits, including fetal aneuploidy, as described herein.

For all aspects and embodiments of the invention described herein, the methods may also be useful for detecting a pregnancy-associated disorder. In some embodiments, the sample comprises fetal nucleic acid, or fetal nucleic acid and maternal nucleic acid. In the case when the sample comprises fetal and maternal nucleic acid, the fetal nucleic acid and the maternal nucleic acid may have a different methylation status. Nucleic acid species with a different methylation status can be differentiated by any method known in the art. In an embodiment, the fetal nucleic acid is enriched by the selective digestion of maternal nucleic acid by a methylation sensitive restriction enzyme. In an embodiment, the fetal nucleic acid is enriched by the selective digestion of maternal nucleic acid using two or more methylation sensitive restriction enzymes in the same assay. In an embodiment, the target nucleic acid and control nucleic acid are both from the fetus. In an embodiment, the average size of the fetal nucleic acid is about 100 bases to about 500 bases in length. In an embodiment the chromosomal abnormality is an aneuploidy, such as trisomy 21. In some embodiments, the target nucleic acid is at least a portion of a chromosome which may be abnormal and the control nucleic acid is at least a portion of a chromosome which is very rarely abnormal. For example, when the target nucleic acid is from chromosome 21, the control nucleic acid is from a chromosome other than chromosome 21—preferably another autosome. In an embodiment, the binding agent is a methylation-specific binding protein such as MBD-Fc. Also, the enriched or eluted nucleic acid is amplified and/or quantified by any method known in the art. In an embodiment, the fetal DNA is quantified using a method that does not require the use of a polymorphic sequence. For example, an allelic ratio is not used to quantify the fetal DNA. In an embodiment, the method for quantifying the amount of fetal DNA does not require the treatment of DNA with bisulfite to convert cytosine residues to uracil.

In some embodiments, the methods of the invention include the additional step of determining the amount of one or more Y-chromosome-specific sequences in a sample. In a related embodiment, the amount of fetal nucleic acid in a sample as determined by using the methylation-based methods of the invention is compared to the amount of Y-chromosome nucleic acid present.

Methods for differentiating nucleic acid based on methylation status include, but are not limited to, methylation sensitive capture, for example using, MBD2-Fc fragment; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes. Except where explicitly stated, any method for differentiating nucleic acid based on methylation status can be used with the compositions and methods of the invention.

In some embodiments, methods of the invention may further comprise an amplification step. The amplification step can be performed by PCR, such as methylation-specific PCR. In an embodiment, the amplification reaction is performed on single molecules, for example, by digital PCR, which is further described in U.S. Pat. Nos. 6,143,496 and 6,440,706, both of which are hereby incorporated by reference. In other embodiments, the method does not require amplification. For example, the amount of enriched fetal DNA may be determined by counting the fetal DNA (or sequence tags attached thereto) with a flow cytometer or by sequencing means that do not require amplification. In an embodiment, the amount of fetal DNA is determined by an amplification reaction that generates amplicons larger than the digested maternal nucleic acid, thereby further enriching the fetal nucleic acid.

In some embodiments, the fetal nucleic acid (alone or in combination with the maternal nucleic acid) comprises one or more detection moieties. In one embodiment, the detection moiety may be any one or more of a compomer, sugar, peptide, protein, antibody, chemical compound (e.g., biotin), mass tag (e.g., metal ions or chemical groups), fluorescent tag, charge tag (e.g., such as polyamines or charged dyes) and hydrophobic tag. In a related embodiment, the detection moiety is a mass-distinguishable product (MDP) or part of an MDP detected by mass spectrometry. In a specific embodiment, the detection moiety is a fluorescent tag or label that is detected by mass spectrometry. In some embodiments, the detection moiety is at the 5' end of a detector oligonucleotide, the detection moiety is attached to a non-complementary region of a detector oligonucleotide, or the detection moiety is at the 5' terminus of a non-complementary sequence. In certain embodiments, the detection moiety is incorporated into or linked to an internal nucleotide or to a nucleotide at the 3' end of a detector oligonucleotide. In some embodiments, one or more detection moieties are used either alone or in combination. See for example US Patent Applications US20080305479 and US20090111712. In certain embodiments, a detection moiety is cleaved by a restriction endonuclease, for example, as described in U.S. application Ser. No. 12/726,246. In some embodiments, a specific target chromosome is labeled with a specific detection moiety and one or more non-target chromosomes are labeled with a different detection moiety, whereby the amount target chromsome can be compared to the amount of non-target chromosome.

For embodiments that require sequence analysis, any one of the following sequencing technologies may be used: a primer extension method (e.g., iPLEX®; Sequenom, Inc.), direct DNA sequencing, restriction fragment length polymorphism (RFLP analysis), real-time PCR, for example using "STAR" (Scalable Transcription Analysis Routine) technology (see U.S. Pat. No. 7,081,339), or variations thereof, allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, fluorescence tagged dNTP/ddNTPs, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader™ assay, hybridization using at least one probe, hybridization using at least one fluorescently labeled probe, electrophoresis, cloning and sequencing, for example as performed on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, or nanopore-based sequencing (Soni G V and Meller A. 2007 Clin Chem 53: 1996-2001), for example, using an Ion Torrent ion sensor that measures an electrical charge associated with each individual base of DNA as each base passes through a tiny pore at the bottom of a sample well, or Oxford Nanopore device that uses a nanopore to measure the electrical charge associated with each individual unit of DNA, and combinations thereof. Nanopore-based methods may include sequencing nucleic acid using a nanopore, or counting nucleic acid molecules using a nanopore, for example, based on size wherein sequence information is not determined.

The absolute copy number of one or more nucleic acids can be determined, for example, using mass spectrometry, a system that uses a competitive PCR approach for absolute copy number measurements. See for example, Ding C, Cantor C R (2003) A high-throughput gene expression analysis technique using competitive PCR and matrix-assisted laser desorption ionization time-of-flight MS. Proc Natl Acad Sci USA 100:3059-3064, and U.S. patent application Ser. No. 10/655,762, which published as US Patent Publication No. 20040081993, both of which are hereby incorporated by reference.

In some embodiments, the amount of the genomic sequence is compared with a standard control, wherein an increase or decrease from the standard control indicates the presence or progression of a pregnancy-associated disorder. For example, the amount of fetal nucleic acid may be compared to the total amount of DNA present in the sample. Or when detecting the presence or absence of fetal aneuploidy, the amount of fetal nucleic acid from target chromosome may be compared to the amount of fetal nucleic acid from a reference chromosome. Preferably the reference chromosome is another autosome that has a low rate of aneuploidy. The ratio of target fetal nucleic acid to reference fetal nucleic acid may be compared to the same ratio from a normal, euploid pregnancy. For example, a control ratio may be determined from a DNA sample obtained from a female carrying a healthy fetus who does not have a chromosomal abnormality. Preferably, one uses a panel of control samples. Where certain chromosome anomalies are known, one can also have standards that are indicative of a specific disease or condition. Thus, for example, to screen for three different chromosomal aneuploidies in a maternal plasma of a pregnant female, one preferably uses a panel of control DNAs that have been isolated from mothers who are known to carry a fetus with, for example, chromosome 13, 18, or 21 trisomy, and a mother who is pregnant with a fetus who does not have a chromosomal abnormality.

In some embodiments, the present invention provides a method in which the alleles from the target nucleic acid and control nucleic acid are differentiated by sequence variation. The sequence variation may be a single nucleotide polymorphism (SNP) or an insertion/deletion polymorphism. In an embodiment, the fetal nucleic acid should comprise at least one high frequency heterozygous polymorphism (e.g., about 2%, 3%, 4%, 5%, 6%, 7%, 8%, 9%, 10%, 11%, 12%, 13%, 14%, 15%, 16%, 17%, 18%, 19%, 20%, 25% or more frequency rate), which allows the determination of the allelic-ratio of the nucleic acid in order to assess the presence or absence of the chromosomal abnormality. A list of exemplary SNPs is provided in Table 2, however, this does not represent a complete list of polymorphic alleles that can be used as part of the invention. Any SNP meeting the following criteria may also be considered: (a) the SNP has a heterozygosity frequency greater than about 2% (preferably across a range of different populations), (b) the SNP is a heterozygous locus; and (c)(i) the SNP is within nucleic acid sequence described herein, or (c)(iii) the SNP is within about 5 to about 2000 base pairs of a SNP described herein (e.g., within about 5, 10, 15, 20, 25, 30, 40, 50, 60, 70, 80, 90, 100, 200, 300, 400, 500, 600, 700, 800, 900, 1000, 1250, 1500, 1750 or 2000 base pairs of a SNP described herein).

In other embodiments, the sequence variation is a short tandem repeat (STR) polymorphism. In some embodiments, the sequence variation falls in a restriction site, whereby one allele is susceptible to digestion by a restriction enzyme and the one or more other alleles are not. In some embodiments, the sequence variation is a methylation site.

In some embodiments, performing an allelic ratio analysis comprises determining the ratio of alleles of the target nucleic acid and control nucleic acid from the fetus of a pregnant woman by obtaining an nucleic acid-containing biological sample from the pregnant woman, wherein the biological sample contains fetal nucleic acid, partially or wholly separating the fetal nucleic acid from the maternal nucleic acid based on differential methylation, discriminating the alleles from the target nucleic acid and the control nucleic acid, followed by determination of the ratio of the alleles, and detecting the presence or absence of a chromosomal disorder in the fetus based on the ratio of alleles, wherein a ratio above or below a normal, euploid ratio is indicative of a chromosomal disorder. In one embodiment, the target nucleic acid is from a suspected aneuploid chromosome (e.g., chromosome 21) and the control nucleic acid is from a euploid chromosome from the same fetus.

In some embodiments, the present invention is combined with other fetal markers to detect the presence or absence of multiple chromosomal abnormalities, wherein the chromosomal abnormalities are selected from the following: trisomy 21, trisomy 18 and trisomy 13, or combinations thereof. In some embodiments, the chromosomal disorder involves the X chromosome or the Y chromosome.

In some embodiments, the compositions or processes may be multiplexed in a single reaction. For example, the amount of fetal nucleic acid may be determined at multiple loci across the genome. Or when detecting the presence or absence of fetal aneuploidy, the amount of fetal nucleic acid may be determined at multiple loci on one or more target chromosomes (e.g., chromosomes 13, 18 or 21) and on one or more reference chromosomes. If an allelic ratio is being used, one or more alleles from Table 2 can be detected and discriminated simultaneously. When determining allelic ratios, multiplexing embodiments are particularly important when the genotype at a polymorphic locus is not known. In some instances, for example when the mother and child are homozygous at the polymorphic locus, the assay may not be informative. In one embodiment, greater than 1, 2, 3, 4, 5, 6, 7, 8, 9, 10, 11, 12, 13, 14, 15, 16, 17, 18, 19, 20, 25, 30, 35, 40, 50, 100, 200, 300 or 500, and any intermediate levels, polynucleotide sequences of the invention are enriched, separated and/or examined according the methods of the invention. When detecting a chromosomal abnormality by analyzing the copy number of target nucleic acid and control nucleic acid, less than 3, 4, 5, 6, 7, 8, 9, 10, 11, 12, 13, or 14 polynucleotide sequences may need to be analyzed to accurately detect the presence or absence of a chromosomal abnormality. In an embodiment, the compositions or processes of the invention may be used to assay samples that have been divided into 2, 3, 4, 5, 6, 7, 8, 9, 10, 11, 12, 13, 14, 15, 16, 17, 18, 19, 20, 25, 30, 35, 40, 50, 100 or more replicates, or into single molecule equivalents. Methods for analyzing fetal nucleic acids from a maternal sample in replicates, including single molecule analyses, are provided in U.S. application Ser. No. 11/364,294, which published as US Patent Publication No. US 2007-0207466 A1, which is hereby incorporated by reference.

In a further embodiment, the present invention provides a method wherein a comparison step shows an increased risk of a fetus having a chromosomal disorder if the ratio of the alleles or absolute copy number of the target nucleic acid is higher or lower by 1 standard deviation from the standard control sequence. In some embodiments, the comparison step shows an increased risk of a fetus having a chromosomal disorder if the ratio of the alleles or absolute copy number of the target nucleic acid is higher or lower by 2 standard deviation from the standard control sequence. In some other embodiments, the comparison step shows an increased risk of a fetus having a chromosomal disorder if the ratio of the alleles or absolute copy number of the target nucleic acid is higher or lower by 3 standard deviation from the standard control sequence. In some embodiments, the comparison step shows an increased risk of a fetus having a chromosomal disorder if the ratio of the alleles or absolute copy number of the target nucleic acid is higher or lower than a statistically significant standard deviation from the control. In one embodiment, the standard control is a maternal reference, and in an embodiment the standard control is a fetal reference chromosome (e.g., non-trisomic autosome).

In some embodiments, the methods of the invention may be combined with other methods for diagnosing a chromosomal abnormality. For example, a noninvasive diagnostic method may require confirmation of the presence or absence of fetal nucleic acid, such as a sex test for a female fetus or to confirm an RhD negative female fetus in an RhD negative mother. In an embodiment, the compositions and methods of the invention may be used to determine the percentage of fetal nucleic acid in a maternal sample in order to enable another diagnostic method that requires the percentage of fetal nucleic acid be known. For example, does a sample meet certain threshold concentration requirements? When determining an allelic ratio to diagnose a fetal aneuploidy from a maternal sample, the amount or concentration of fetal nucleic acid may be required to make a diagnose with a given sensitivity and specificity. In other embodiments, the compositions and methods of the invention for detecting a chromosomal abnormality can be combined with other known methods thereby improving the overall sensitivity and specificity of the detection method. For example, mathematical models have suggested that a combined first-trimester screening program utilizing maternal age (MA), nuchal translucency (NT) thickness, serum-free beta-hCG, and serum PAPP-A will detect more than 80% of fetuses with Down's syndrome for a 5% invasive testing rate (Wald and Hackshaw, Prenat Diagn 17(9):921-9 (1997)). However, the combination of commonly used aneuploidy detection methods combined with the non-invasive free fetal nucleic acid-based methods described herein may offer improved accuracy with a lower false positive rate. Examples of combined diagnostic methods are provided in PCT Publication Number WO2008157264A2 (assigned to the Applicant), which is hereby incorporated by reference. In some embodiments, the methods of the invention may be combined with cell-based methods, wherein fetal cells are procured invasively or non-invasively.

In certain embodiments, an increased risk for a chromosomal abnormality is based on the outcome or result(s) produced from the compositions or methods provided herein. An example of an outcome is a deviation from the euploid absolute copy number or allelic ratio, which indicates the presence of chromosomal aneuploidy. This increase or decrease in the absolute copy number or ratio from the standard control indicates an increased risk of having a fetus with a chromosomal abnormality (e.g., trisomy 21). Information pertaining to a method described herein, such as an outcome, result, or risk of trisomy or aneuploidy, for example, may be transfixed, renditioned, recorded and/or displayed in any suitable medium. For example, an outcome may be transfixed in a medium to save, store, share, communicate or otherwise analyze the outcome. A medium can be tangible (e.g., paper) or intangible (e.g., electronic medium), and examples of media include, but are not limited to, computer media, databases, charts, patient charts, records, patient records, graphs and tables, and any other medium of expression. The information sometimes is stored and/or renditioned in computer readable form and sometimes is stored and organized in a database. In certain embodiments, the information may be transferred from one location to another using a physical medium (e.g., paper) or a computer readable medium (e.g., optical and/or magnetic storage or transmission medium, floppy disk, hard disk, random access memory, computer processing unit, facsimile signal, satellite signal, transmission over an internet or transmission over the world-wide web).

In practicing the present invention within all aspects mentioned above, a CpG island may be used as the CpG-containing genomic sequence in some cases, whereas in other cases the CpG-containing genomic sequence may not be a CpG island.

In some embodiments, the present invention provides a kit for performing the methods of the invention. One component of the kit is a methylation-sensitive binding agent.

BRIEF DESCRIPTION OF THE DRAWINGS

FIG. 6 discloses SEQ ID NOS 350 and 351, respectively, in order of appearance.

FIGS. 14 A and B: Show the results of the total copy number assay from plasma samples. In FIG. 14A, the copy number for each sample is shown. Two samples (no 25 and 26) have a significantly higher total copy number than all the other samples. A mean of approximately 1300 amplifiable copies/ml plasma was obtained (range 766-2055). FIG. 14B shows a box-and-whisker plot of the given values, summarizing the results.

FIGS. 15A and B: The amount (or copy numbers) of fetal nucleic acid from 33 different plasma samples taken from pregnant women with male fetuses are plotted. The copy numbers obtained were calculated using the methylation markers and the Y-chromosome-specific markers using the assays provided in Table X. As can be seen in FIG. 15B, the box-and-whisker plot of the given values indicated minimal difference between the two different measurements, thus validating the accuracy and stability of the method.

DEFINITIONS

Figure 1:
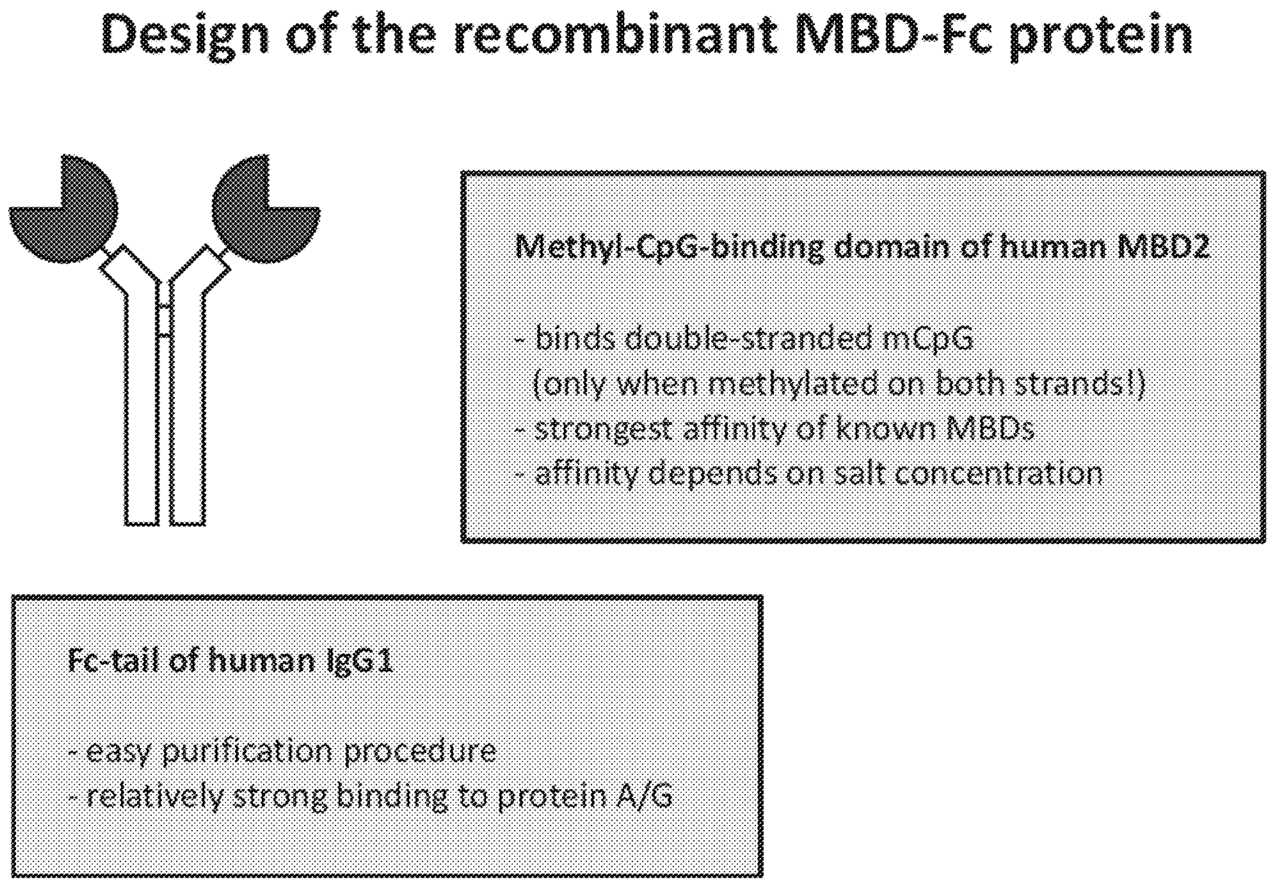
FIG. 1: Shows the design of the recombinant MBD-Fc protein used to separate differentially methylated DNA.

The term "pregnancy-associated disorder," as used in this application, refers to any condition or disease that may affect a pregnant woman, the fetus, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, RhD incompatibility, fetal chromosomal abnormalities such as trisomy 21, and genetically inherited fetal disorders such as cystic fibrosis, beta-thalassemia or other monogenic disorders. The compositions and processes described herein are particularly useful for diagnosis, prognosis and monitoring of pregnancy-associated disorders associated with quantitative abnormalities of fetal DNA in maternal plasma/serum, including but not limited to, preeclampsia (Lo et al., Clin. Chem. 45:184-188, 1999 and Zhong et al., Am. J. Obstet. Gynecol. 184:414-419, 2001), fetal trisomy (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001). For example, an elevated level of fetal nucleic acid in maternal blood (as compared to a normal pregnancy or pregnancies) may be indicative of a preeclamptic preganancy. Further, the ability to enrich fetal nucleic from a maternal sample may prove particularly useful for the noninvasive prenatal diagnosis of autosomal recessive diseases such as the case when a mother and father share an identical disease causing mutation, an occurrence previously perceived as a challenge for maternal plasma-based non-trisomy prenatal diagnosis.

The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (in humans, 46XX or 46XY). A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. Chromosomal abnormality may also refer to a state of chromosomal abnormality where a portion of one or more chromosomes is not an exact multiple of the usual haploid number due to, for example, chromosome translocation. Chromosomal translocation (e.g. translocation between chromosome 21 and 14 where some of the 14th chromosome is replaced by extra 21st chromosome) may cause partial trisomy 21. A chromosomal abnormality can be correlated with presence of a pathological condition or with a predisposition to develop a pathological condition. A chromosomal abnormality may be detected by quantitative analysis of nucleic acid.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. For example, the nucleic acids provided in SEQ ID NOs: 1-261 (see Tables 4A-4C) can be in any form useful for conducting processes herein (e.g., linear, circular, supercoiled, single-stranded, double-stranded and the like) or may include variations (e.g., insertions, deletions or substitutions) that do not alter their utility as part of the present invention. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

A "nucleic acid comprising one or more CpG sites" or a "CpG-containing genomic sequence" as used herein refers to a segment of DNA sequence at a defined location in the genome of an individual such as a human fetus or a pregnant woman. Typically, a "CpG-containing genomic sequence" is at least 15 nucleotides in length and contains at least one cytosine. Preferably, it can be at least 30, 50, 80, 100, 150, 200, 250, or 300 nucleotides in length and contains at least 2, 5, 10, 15, 20, 25, or 30 cytosines. For anyone "CpG-containing genomic sequence" at a given location, e.g., within a region centering around a given genetic locus (see Tables 1A-1C), nucleotide sequence variations may exist from individual to individual and from allele to allele even for the same individual. Typically, such a region centering around a defined genetic locus (e.g., a CpG island) contains the locus as well as upstream and/or downstream sequences. Each of the upstream or downstream sequence (counting from the 5' or 3' boundary of the genetic locus, respectively) can be as long as 10 kb, in other cases may be as long as 5 kb, 2 kb, 1 kb, 500 bp, 200 bp, or 100 bp. Furthermore, a "CpG-containing genomic sequence" may encompass a nucleotide sequence transcribed or not transcribed for protein production, and the nucleotide sequence can be an inter-gene sequence, intra-gene sequence, protein-coding sequence, a non protein-coding sequence (such as a transcription promoter), or a combination thereof.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" is the location in the target gene nucleic acid region where methylation has, or has the possibility of occurring. For example a location containing CpG is a methylation site wherein the cytosine may or may not be methylated.

As used herein, a "CpG site" or "methylation site" is a nucleotide within a nucleic acid that is susceptible to methylation either by natural occurring events in vivo or by an event instituted to chemically methylate the nucleotide in vitro.

As used herein, a "methylated nucleic acid molecule" refers to a nucleic acid molecule that contains one or more methylated nucleotides that is/are methylated.

A "CpG island" as used herein describes a segment of DNA sequence that comprises a functionally or structurally deviated CpG density. For example, Yamada et al. (Genome Research 14:247-266, 2004) have described a set of standards for determining a CpG island: it must be at least 400 nucleotides in length, has a greater than 50% GC content, and an OCF/ECF ratio greater than 0.6. Others (Takai et al., Proc. Natl. Acad. Sci. U.S.A. 99:3740-3745, 2002) have defined a CpG island less stringently as a sequence at least 200 nucleotides in length, having a greater than 50% GC content, and an OCF/ECF ratio greater than 0.6.

The term "epigenetic state" or "epigenetic status" as used herein refers to any structural feature at a molecular level of a nucleic acid (e.g., DNA or RNA) other than the primary nucleotide sequence. For instance, the epigenetic state of a genomic DNA may include its secondary or tertiary structure determined or influenced by, e.g., its methylation pattern or its association with cellular proteins.

The term "methylation profile" "methylation state" or "methylation status," as used herein to describe the state of methylation of a genomic sequence, refers to the characteristics of a DNA segment at a particular genomic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles. The term "methylation" profile" or "methylation status" also refers to the relative or absolute concentration of methylated C or unmethylated C at any particular stretch of residues in a biological sample. For example, if the cytosine (C) residue(s) within a DNA sequence are methylated it may be referred to as "hypermethylated"; whereas if the cytosine (C) residue(s) within a DNA sequence are not methylated it may be referred to as "hypomethylated". Likewise, if the cytosine (C) residue(s) within a DNA sequence (e.g., fetal nucleic acid) are methylated as compared to another sequence from a different region or from a different individual (e.g., relative to maternal nucleic acid), that sequence is considered hypermethylated compared to the other sequence. Alternatively, if the cytosine (C) residue(s) within a DNA sequence are not methylated as compared to another sequence from a different region or from a different individual (e.g., the mother), that sequence is considered hypomethylated compared to the other sequence. These sequences are said to be "differentially methylated", and more specifically, when the methylation status differs between mother and fetus, the sequences are considered "differentially methylated maternal and fetal nucleic acid".

Figure 2:
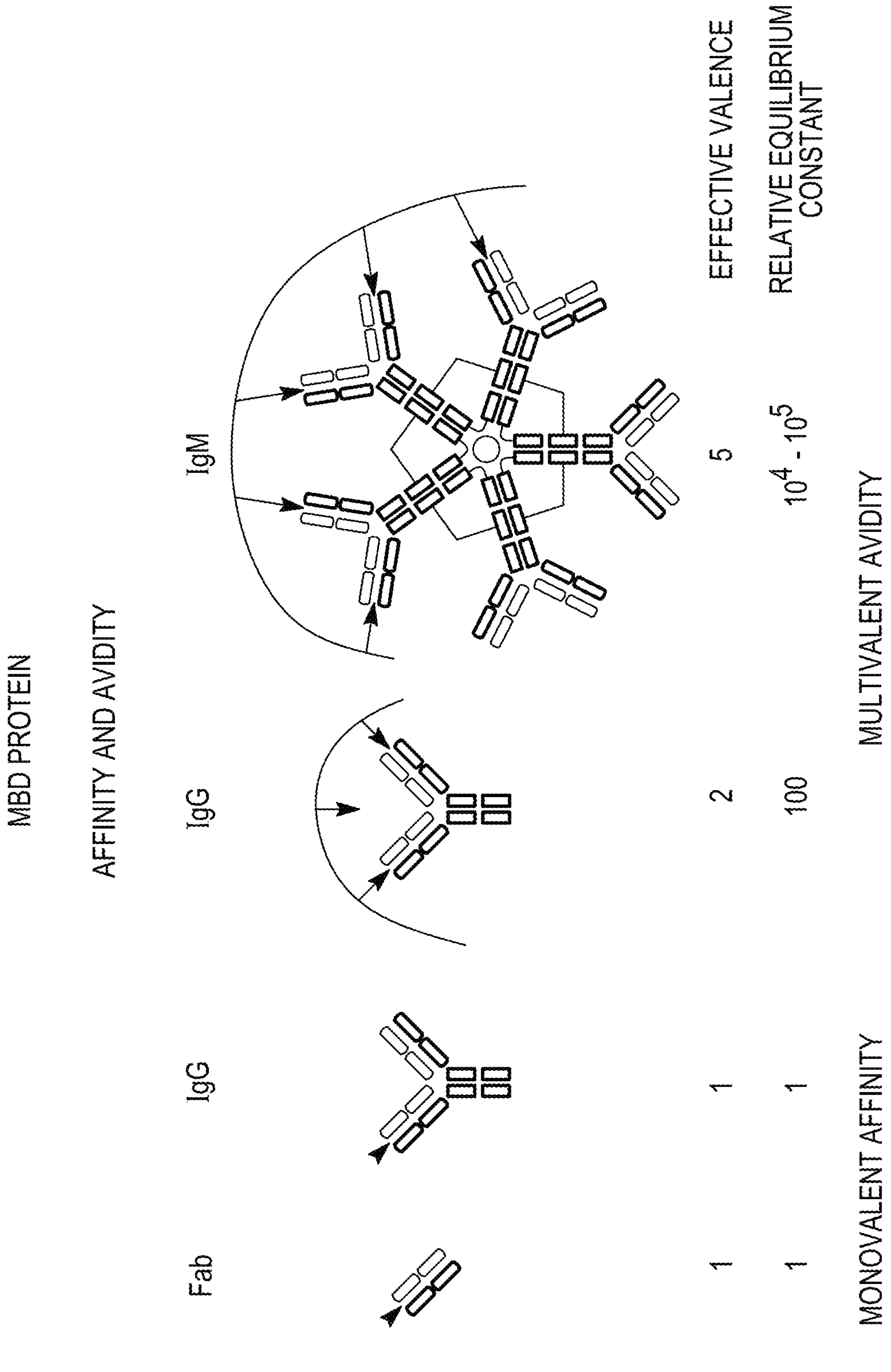
FIG. 2: Shows the methyl-CpG-binding, antibody-like protein has a high affinity and high avidity to its "antigen", which is preferably DNA that is methylated at CpG dinucleotides.

The term "agent that binds to methylated nucleotides" as used herein refers to a substance that is capable of binding to methylated nucleic acid. The agent may be naturally-occurring or synthetic, and may be modified or unmodified. In one embodiment, the agent allows for the separation of different nucleic acid species according to their respective methylation states. An example of an agent that binds to methylated nucleotides is described in PCT Patent Application No. PCT/EP2005/012707, which published as WO06056480A2 and is hereby incorporated by reference. The described agent is a bifunctional polypeptide comprising the DNA-binding domain of a protein belonging to the family of Methyl-CpG binding proteins (MBDs) and an Fc portion of an antibody (see FIG. 1). The recombinant methyl-CpG-binding, antibody-like protein can preferably bind CpG methylated DNA in an antibody-like manner. That means, the methyl-CpG-binding, antibody-like protein has a high affinity and high avidity to its "antigen", which is preferably DNA that is methylated at CpG dinucleotides. The agent may also be a multivalent MBD (see FIG. 2).

The term "polymorphism" as used herein refers to a sequence variation within different alleles of the same genomic sequence. A sequence that contains a polymorphism is considered "polymorphic sequence". Detection of one or more polymorphisms allows differentiation of different alleles of a single genomic sequence or between two or more individuals. As used herein, the term "polymorphic marker" or "polymorphic sequence" refers to segments of genomic DNA that exhibit heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), and the like. Polymorphic markers according to the present invention can be used to specifically differentiate between a maternal and paternal allele in the enriched fetal nucleic acid sample.

The terms "single nucleotide polymorphism" or "SNP" as used herein refer to the polynucleotide sequence variation present at a single nucleotide residue within different alleles of the same genomic sequence. This variation may occur within the coding region or non-coding region (i.e., in the promoter or intronic region) of a genomic sequence, if the genomic sequence is transcribed during protein production. Detection of one or more SNP allows differentiation of different alleles of a single genomic sequence or between two or more individuals.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

The terms "ratio of the alleles" or "allelic ratio" as used herein refer to the ratio of the population of one allele and the population of the other allele in a sample. In some trisomic cases, it is possible that a fetus may be tri-allelic for a particular locus. In such cases, the term "ratio of the alleles" refers to the ratio of the population of any one allele against one of the other alleles, or any one allele against the other two alleles.

The term "non-polymorphism-based quantitative method" as used herein refers to a method for determining the amount of an analyte (e.g., total nucleic acid, Y-chromosome nucleic acid, or fetal nucleic acid) that does not require the use of a polymorphic marker or sequence. Although a polymorphism may be present in the sequence, said polymorphism is not required to quantify the sequence. Examples of non-polymorphism-based quantitative methods include, but are not limited to, RT-PCR, digital PCR, array-based methods, sequencing methods, nanopore-based methods, nucleic acid-bound bead-based counting methods and competitor-based methods wherein one or more competitors are introduced at a known concentration(s) to determine the amount of one or more analytes. In some embodiments, some of the above exemplary methods (for example, sequencing) may need to be actively modified or designed such that one or more polymorphisms are not interrogated.

The terms "absolute amount" or "copy number" as used herein refers to the amount or quantity of an analyte (e.g., total nucleic acid or fetal nucleic acid). The present invention provides compositions and processes for determining the absolute amount of fetal nucleic acid in a mixed maternal sample. Absolute amount or copy number represents the number of molecules available for detection, and may be expressed as the genomic equivalents per unit. The term "concentration" refers to the amount or proportion of a substance in a mixture or solution (e.g., the amount of fetal nucleic acid in a maternal sample that comprises a mixture of maternal and fetal nucleic acid). The concentration may be expressed as a percentage, which is used to express how large/small one quantity is, relative to another quantity as a fraction of 100. Platforms for determining the quantity or amount of an analyte (e.g., target nucleic acid) include, but are not limited to, mass spectrometery, digital PCR, sequencing by synthesis platforms (e.g., pyrosequencing), fluorescence spectroscopy and flow cytometry.

The term "sample" as used herein refers to a specimen containing nucleic acid. Examples of samples include, but are not limited to, tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), umbilical cord blood, chorionic villi, amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

Fetal DNA can be obtained from sources including but not limited to maternal blood, maternal serum, maternal plasma, fetal cells, umbilical cord blood, chorionic villi, amniotic fluid, urine, saliva, lung lavage, cells or tissues.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C.fwdarw.U conversion by bisulfite) and enzymatic treatment (such as cleavage by a methylation-dependent endonuclease). Thus, an enzyme that preferentially cleaves or digests methylated DNA is one capable of cleaving or digesting a DNA molecule at a much higher efficiency when the DNA is methylated, whereas an enzyme that preferentially cleaves or digests unmethylated DNA exhibits a significantly higher efficiency when the DNA is not methylated.

The terms "non-bisulfite-based method" and "non-bisulfite-based quantitative method" as used herein refer to any method for quantifying methylated or non-methylated nucleic acid that does not require the use of bisulfite. The terms also refer to methods for preparing a nucleic acid to be quantified that do not require bisulfite treatment. Examples of non-bisulfite-based methods include, but are not limited to, methods for digesting nucleic acid using one or more methylation sensitive enzymes and methods for separating nucleic acid using agents that bind nucleic acid based on methylation status.

The terms "methyl-sensitive enzymes" and "methylation sensitive restriction enzymes" are DNA restriction endonucleases that are dependent on the methylation state of their DNA recognition site for activity. For example, there are methyl-sensitive enzymes that cleave or digest at their DNA recognition sequence only if it is not methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated. As used herein, the terms "cleave", "cut" and "digest" are used interchangeably.

The term "target nucleic acid" as used herein refers to a nucleic acid examined using the methods disclosed herein to determine if the nucleic acid is part of a pregnancy-related disorder or chromosomal abnormality. For example, a target nucleic acid from chromosome 21 could be examined using the methods of the invention to detect Down's Syndrome.

The term "control nucleic acid" as used herein refers to a nucleic acid used as a reference nucleic acid according to the methods disclosed herein to determine if the nucleic acid is part of a chromosomal abnormality. For example, a control nucleic acid from a chromosome other than chromosome 21 (herein referred to as a "reference chromosome") could be as a reference sequence to detect Down's Syndrome. In some embodiments, the control sequence has a known or predetermined quantity.

The term "sequence-specific" or "locus-specific method" as used herein refers to a method that interrogates (for example, quantifies) nucleic acid at a specific location (or locus) in the genome based on the sequence composition. Sequence-specific or locus-specific methods allow for the quantification of specific regions or chromosomes.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Primers" as used herein refer to oligonucleotides that can be used in an amplification method, such as a polymerase chain reaction (PCR), to amplify a nucleotide sequence based on the polynucleotide sequence corresponding to a particular genomic sequence, e.g., one located within the CpG island CG1137, PDE9A, or CGI009 on chromosome 21, in various methylation status. At least one of the PCR primers for amplification of a polynucleotide sequence is sequence-specific for the sequence. The term "template" refers to any nucleic acid molecule that can be used for amplification in the invention. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The term "amplification reaction" as used herein refers to a process for copying nucleic acid one or more times. In embodiments, the method of amplification includes but is not limited to polymerase chain reaction, self-sustained sequence reaction, ligase chain reaction, rapid amplification of cDNA ends, polymerase chain reaction and ligase chain reaction, Q-beta phage amplification, strand displacement amplification, or splice overlap extension polymerase chain reaction. In some embodiments, a single molecule of nucleic acid is amplified, for example, by digital PCR.

The term "sensitivity" as used herein refers to the number of true positives divided by the number of true positives plus the number of false negatives, where sensitivity (sens) may be within the range of 0≤sens≤1. Ideally, method embodiments herein have the number of false negatives equaling zero or close to equaling zero, so that no subject is wrongly identified as not having at least one chromosome abnormality or other genetic disorder when they indeed have at least one chromosome abnormality or other genetic disorder. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of 0≤spec≤1. Ideally, methods embodiments herein have the number of false positives equaling zero or close to equaling zero, so that no subject wrongly identified as having at least one chromosome abnormality other genetic disorder when they do not have the chromosome abnormality other genetic disorder being assessed. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the design of a set of amplified nucleic acid species, the number of sets of amplified nucleic acid species, percent fetal genetic contribution tested, percent maternal genetic contribution tested, type of chromosome abnormality assayed, type of genetic disorder assayed, type of sex-linked abnormalities assayed, the age of the mother and the like. The term "independent" as used herein refers to not being influenced or not being controlled by another. The term "dependent" as used herein refers to being influenced or controlled by another. For example, a particular chromosome and a trisomy event occurring for that particular chromosome that results in a viable being are variables that are dependent upon each other.

One of skill in the art may use any type of method or prediction algorithm to give significance to the data of the present invention within an acceptable sensitivity and/or specificity. For example, prediction algorithms such as Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present invention. And one or more methods or prediction algorithms may be determined not to give significance to the data having different independent and/or dependent variables of the present invention. One may design or change parameters of the different variables of methods described herein based on results of one or more prediction algorithms (e.g., number of sets analyzed, types of nucleotide species in each set). For example, applying the Chi-squared test to detection data may suggest that specific ranges of maternal age are correlated to a higher likelihood of having an offspring with a specific chromosome abnormality, hence the variable of maternal age may be weighed differently verses being weighed the same as other variables.

In certain embodiments, several algorithms may be chosen to be tested. These algorithms can be trained with raw data. For each new raw data sample, the trained algorithms will assign a classification to that sample (i.e. trisomy or normal). Based on the classifications of the new raw data samples, the trained algorithms' performance may be assessed based on sensitivity and specificity. Finally, an algorithm with the highest sensitivity and/or specificity or combination thereof may be identified.

DETAILED DESCRIPTION

Introduction

The presence of fetal nucleic acid in maternal plasma was first reported in 1997 and offers the possibility for non-invasive prenatal diagnosis simply through the analysis of a maternal blood sample (Lo et al., Lancet 350:485-487, 1997). To date, numerous potential clinical applications have been developed. In particular, quantitative abnormalities of fetal nucleic acid, for example DNA, concentrations in maternal plasma have been found to be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma represents a powerful mechanism for the monitoring of fetomaternal well-being.

However, fetal DNA co-exists with background maternal DNA in maternal plasma. Hence, most reported applications have relied on the detection of Y-chromosome sequences as these are most conveniently distinguishable from maternal DNA. Such an approach limits the applicability of the existing assays to only 50% of all pregnancies, namely those with male fetuses. Thus, there is much need for the development of sex-independent compositions and methods for enriching and analyzing fetal nucleic acid from a maternal sample. Also, methods that rely on polymorphic markers to quantify fetal nucleic acid may be susceptible to varying heterozygosity rates across different ethnicities thereby limiting their applicability (e.g., by increasing the number of markers that are needed).

It was previously demonstrated that fetal and maternal DNA can be distinguished by their differences in methylation status (U.S. Pat. No. 6,927,028, which is hereby incorporated by reference). Methylation is an epigenetic phenomenon, which refers to processes that alter a phenotype without involving changes in the DNA sequence. By exploiting the difference in the DNA methylation status between mother and fetus, one can successfully detect and analyze fetal nucleic acid in a background of maternal nucleic acid.

The present inventors provides novel genomic polynucleotides that are differentially methylated between the fetal DNA from the fetus (e.g., from the placenta) and the maternal DNA from the mother, for example from peripheral blood cells. This discovery thus provides a new approach for distinguishing fetal and maternal genomic DNA and new methods for accurately quantifying fetal nucleic which may be used for non-invasive prenatal diagnosis.

Methodology

Practicing the invention utilizes routine techniques in the field of molecular biology. Basic texts disclosing the general methods of use in the invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, Tetrahedron Lett. 22: 1859-1862 (1981), using an automated synthesizer, as described in Van Devanter et. al., Nucleic Acids Res. 12: 6159-6168 (1984). Purification of oligonucleotides is performed using any art-recognized strategy, e.g., native acrylamide gel electrophoresis or anion-exchange high performance liquid chromatography (HPLC) as described in Pearson & Reanier, J. Chrom. 255: 137-149 (1983).

Acquisition of Blood Samples and Extraction of DNA

The present invention relates to separating, enriching and analyzing fetal DNA found in maternal blood as a non-invasive means to detect the presence and/or to monitor the progress of a pregnancy-associated condition or disorder. Thus, the first steps of practicing the invention are to obtain a blood sample from a pregnant woman and extract DNA from the sample.

A. Acquisition of Blood Samples

A blood sample is obtained from a pregnant woman at a gestational age suitable for testing using a method of the present invention. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation. Blood samples may be collected, stored or transported in a manner known to the person of ordinary skill in the art to minimize degradation or the quality of nucleic acid present in the sample.

B. Preparation of Blood Samples

The analysis of fetal DNA found in maternal blood according to the present invention may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

C. Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present invention alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

Methylation Specific Separation of Nucleic Acid

The methods provided herein offer an alternative approach for the enrichment of fetal DNA based on the methylation-specific separation of differentially methylated DNA. It has recently been discovered that many genes involved in developmental regulation are controlled through epigenetics in embryonic stem cells. Consequently, multiple genes can be expected to show differential DNA methylation between nucleic acid of fetal origin and maternal origin. Once these regions are identified, a technique to capture methylated DNA can be used to specifically enrich fetal DNA. For identification of differentially methylated regions, a novel approach was used to capture methylated DNA. This approach uses a protein, in which the methyl binding domain of MBD2 is fused to the Fc fragment of an antibody (MBD-FC) (Gebhard C, Schwarzfischer L, Pham T H, Schilling E, Klug M, Andreesen R, Rehli M (2006) Genomewide profiling of CpG methylation identifies novel targets of aberrant hypermethylation in myeloid leukemia. Cancer Res 66:6118-6128). This fusion protein has several advantages over conventional methylation specific antibodies. The MBD-FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC on the other hand binds all DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard C, Schwarzfischer L, Pham T H, Andreesen R, Mackensen A, Rehli M (2006) Rapid and sensitive detection of CpG-methylation using methyl-binding (MB)-PCR. Nucleic Acids Res 34:e82). Consequently this method, called Methyl-CpG immunoprecipitation (MCIP), cannot only enrich, but also fractionate genomic DNA according to methylation level, which is particularly helpful when the unmethylated DNA fraction should be investigated as well.

Methylation Sensitive Restriction Enzyme Digestion

The invention also provides compositions and processes for determining the amount of fetal nucleic acid from a maternal sample. The invention allows for the enrichment of fetal nucleic acid regions in a maternal sample by selectively digesting nucleic acid from said maternal sample with an enzyme that selectively and completely or substantially digests the maternal nucleic acid to enrich the sample for at least one fetal nucleic acid region. Preferably, the digestion efficiency is greater than about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Following enrichment, the amount of fetal nucleic acid can be determined by quantitative methods that do not require polymorphic sequences or bisulfite treatment, thereby, offering a solution that works equally well for female fetuses and across different ethnicities and preserves the low copy number fetal nucleic acid present in the sample.

For example, there are methyl-sensitive enzymes that preferentially or substantially cleave or digest at their DNA recognition sequence if it is non-methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated.

Methyl-sensitive enzymes that digest unmethylated DNA suitable for use in methods of the invention include, but are not limited to, HpaII, HhaI, MaeII, BstUI and AciI. An enzyme that can be used is HpaII that cuts only the unmethylated sequence CCGG. Another enzyme that can be used is HhaI that cuts only the unmethylated sequence GCGC. Both enzymes are available from New England BioLabs®, Inc. Combinations of two or more methyl-sensitive enzymes that digest only unmethylated DNA can also be used. Suitable enzymes that digest only methylated DNA include, but are not limited to, DpnI, which cuts at a recognition sequence GATC, and McrBC, which belongs to the family of AAA.sup.+ proteins and cuts DNA containing modified cytosines and cuts at recognition site 5' . . . Pu.sup.mC (N.sub.40-3000) Pu.sup.mC . . . 3' (New England BioLabs, Inc., Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al., Molecular Biology: A laboratory Approach, Cold Spring Harbor, N.Y. 1989) provide a general description of methods for using restriction enzymes and other enzymes. Enzymes often are used under conditions that will enable cleavage of the maternal DNA with about 95%-100% efficiency, preferably with about 98%-100% efficiency.

Other Methods for Methylation Analysis

Various methylation analysis procedures are known in the art, and can be used in conjunction with the present invention. These assays allow for determination of the methylation state of one or a plurality of CpG islands within a DNA sequence. In addition, the methods maybe used to quantify methylated nucleic acid. Such assays involve, among other techniques, DNA sequencing of bisulfite-treated DNA, PCR (for sequence-specific amplification), Southern blot analysis, and use of methylation-sensitive restriction enzymes.

Genomic sequencing is a technique that has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA may be used, e.g., the method described by Sadri & Hornsby (Nucl. Acids Res. 24:5058-5059, 1996), or COBRA (Combined Bisulfite Restriction Analysis) (Xiong & Laird, Nucleic Acids Res. 25:2532-2534, 1997).

COBRA analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

The MethyLight™ assay is a high-throughput quantitative methylation assay that utilizes fluorescence-based real-time PCR (TaqMan™) technology that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can by used with a "Taq Man" probe in the amplification process. For example, double-stranded genomic DNA is treated with sodium bisulfite and subjected to one of two sets of PCR reactions using TaqMan™ probes; e.g., with either biased primers and TaqMan™ probe, or unbiased primers and TaqMan™ probe. The TaqMan™ probe is dual-labeled with fluorescent "reporter" and "quencher" molecules, and is designed to be specific for a relatively high GC content region so that it melts out at about 10.degree. C. higher temperature in the PCR cycle than the forward or reverse primers. This allows the TaqMan™ probe to remain fully hybridized during the PCR annealing/extension step. As the Taq polymerase enzymatically synthesizes a new strand during PCR, it will eventually reach the annealed TaqMan™ probe. The Taq polymerase 5' to 3' endonuclease activity will then displace the TaqMan™ probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific gene (or methylation-altered DNA sequence or CpG island); TaqMan™ probes; optimized PCR buffers and deoxynucleotides; and Taq polymerase.

The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997).

Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP (methylation-specific PCR) allows for assessing the methylation status of virtually any group of CpG sites within a CpG island, independent of the use of methylation-sensitive restriction enzymes (Herman et al. Proc. Nat. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Another method for analyzing methylation sites is a primer extension assay, including an optimized PCR amplification reaction that produces amplified targets for subsequent primer extension genotyping analysis using mass spectrometry. The assay can also be done in multiplex. This method (particularly as it relates to genotyping single nucleotide polymorphisms) is described in detail in PCT publication WO05012578A1 and US publication US20050079521A1. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Four additional methods for DNA methylation analysis include restriction landmark genomic scanning (RLGS, Costello et al., 2000), methylation-sensitive-representational difference analysis (MS-RDA), methylation-specific AP-PCR (MS-AP-PCR) and methyl-CpG binding domain column/segregation of partly melted molecules (MBD/SPM).

Additional methylation analysis methods that may be used in conjunction with the present invention are described in the following papers: Laird, P. W. Nature Reviews Cancer 3, 253-266 (2003); Biotechniques; Uhlmann, K. et al. Electrophoresis 23:4072-4079 (2002)—PyroMeth; Colella et al. Biotechniques. 2003 July; 35(1):146-50; Dupont J M, Tost J, Jammes H, and Gut I G. Anal Biochem, October 2004; 333(1): 119-27; and Tooke N and Pettersson M. IVDT. November 2004; 41.

Polynucleotide Sequence Amplification and Determination

Following separation of nucleic acid in a methylation-differential manner, the nucleic acid may be subjected to sequence-based analysis. Furthermore, once it is determined that one particular genomic sequence of fetal origin is hypermethylated or hypomethylated compared to the maternal counterpart, the amount of this fetal genomic sequence can be determined. Subsequently, this amount can be compared to a standard control value and serve as an indication for the potential of certain pregnancy-associated disorder.

A. Amplification of Nucleotide Sequences

In many instances, it is desirable to amplify a nucleic acid sequence of the invention using any of several nucleic acid amplification procedures which are well known in the art (listed above and described in greater detail below). Specifically, nucleic acid amplification is the enzymatic synthesis of nucleic acid amplicons (copies) which contain a sequence that is complementary to a nucleic acid sequence being amplified. Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence is typically used in practicing the present invention, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the invention, which represents a particular methylation pattern, or to quantitatively determine the amount of this particular genomic sequence in the maternal blood. For a review of branched-DNA signal amplification for direct quantitation of nucleic acid sequences in clinical samples, see Nolte, Adv. Clin. Chem. 33:201-235, 1998.

The compositions and processes of the invention are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US 20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

B. Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes in a polynucleotide sequence for practicing the methods of the present invention include but are not limited to mass spectrometry, primer extension, polynucleotide hybridization, real-time PCR, and electrophoresis.

Use of a primer extension reaction also can be applied in methods of the invention. A primer extension reaction operates, for example, by discriminating the SNP alleles by the incorporation of deoxynucleotides and/or dideoxynucleotides to a primer extension primer which hybridizes to a region adjacent to the SNP site. The primer is extended with a polymerase. The primer extended SNP can be detected physically by mass spectrometry or by a tagging moiety such as biotin. As the SNP site is only extended by a complementary deoxynucleotide or dideoxynucleotide that is either tagged by a specific label or generates a primer extension product with a specific mass, the SNP alleles can be discriminated and quantified.

Reverse transcribed and amplified nucleic acids may be modified nucleic acids. Modified nucleic acids can include nucleotide analogs, and in certain embodiments include a detectable label and/or a capture agent. Examples of detectable labels include without limitation fluorophores, radioisotopes, colormetric agents, light emitting agents, chemiluminescent agents, light scattering agents, enzymes and the like. Examples of capture agents include without limitation an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments Mass spectrometry is a particularly effective method for the detection of a polynucleotide of the invention, for example a PCR amplicon, a primer extension product or a detector probe that is cleaved from a target nucleic acid. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005), both of which are hereby incorporated by reference. For a review of detecting and quantifying target nucleic using cleavable detector probes that are cleaved during the amplification process and detected by mass spectrometry, see U.S. patent application Ser. No. 11/950,395, which was filed Dec. 4, 2007, and is hereby incorporated by reference.

Sequencing technologies are improving in terms of throughput and cost. Sequencing technologies, such as that achievable on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001), allow the sequencing of many nucleic acid molecules isolated from a specimen at high orders of multiplexing in a parallel fashion (Dear Brief Funct Genomic Proteomic 2003; 1: 397-416).

Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label (e.g., 1 fluorescent label, 2, 3, or 4 fluorescent labels).

An example of a system that can be used by a person of ordinary skill based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., “Single-molecule PCR using water-in-oil emulsion;” Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the “single pair”, in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer—released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the “primer only” reference image are discarded as non-specific fluorescence. Following immobilization of the primer—released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a “microreactor.” Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a nucleic acid for sequencing (“base nucleic acid,” e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components known to the person of ordinary skill in the art.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction.

In certain embodiments, the number of nucleic acid species multiplexed include, without limitation, about 1 to about 500 (e.g., about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays can include primer and oligonucleotide design methods and reaction design methods. See, for example, the multiplex schemes provided in Tables X and Y. For primer and oligonucleotide design in multiplexed assays, the same general guidelines for primer design applies for uniplexed reactions, such as avoiding false priming and primer dimers, only more primers are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced micro-reaction chambers or devices or arrays or chips may be used to facilitate multiplex analysis, and are commercially available.

Detection of Fetal Aneuploidy

For the detection of fetal aneuploidies, some methods rely on measuring the ratio between maternally and paternally inherited alleles. However, the ability to quantify chromosomal changes is impaired by the maternal contribution of cell free nucleic acids, which makes it necessary to deplete the sample from maternal DNA prior to measurement. Promising approaches take advantage of the different size distribution of fetal and maternal DNA or measure RNA that is exclusively expressed by the fetus (see for example, U.S. patent application Ser. No. 11/384,128, which published as US20060252071 and is hereby incorporated by reference). Assuming fetal DNA makes up only about 5% of all cell free DNA in the maternal plasma, there is a decrease of the ratio difference from 1.6% to only about 1.2% between a trisomy sample and a healthy control. Consequently, reliable detection of allele ratio changes requires enriching the fetal fraction of cell free DNA, for example, using the compositions and methods of the present invention.

Some methods rely on measuring the ratio of maternal to paternally inherited alleles to detect fetal chromosomal aneuploidies from maternal plasma. A diploid set yields a 1:1 ratio while trisomies can be detected as a 2:1 ratio. Detection of this difference is impaired by statistical sampling due to the low abundance of fetal DNA, presence of excess maternal DNA in the plasma sample and variability of the measurement technique. The latter is addressed by using methods with high measurement precision, like digital PCR or mass spectrometry. Enriching the fetal fraction of cell free DNA in a sample is currently achieved by either depleting maternal DNA through size exclusion or focusing on fetal-specific nucleic acids, like fetal-expressed RNA. Another differentiating feature of fetal DNA is its DNA methylation pattern. Thus, provided herein are novel compositions and methods for accurately quantifying fetal nucleic acid based on differential methylation between a fetus and mother. The methods rely on sensitive absolute copy number analysis to quantify the fetal nucleic acid portion of a maternal sample, thereby allowing for the prenatal detection of fetal traits. The methods of the invention have identified approximately 3000 CpG rich regions in the genome that are differentially methylated between maternal and fetal DNA. The selected regions showed highly conserved differential methylation across all measured samples. In addition the set of regions is enriched for genes important in developmental regulation, indicating that epigenetic regulation of these areas is a biologically relevant and consistent process (see Table 3). Enrichment of fetal DNA can now be achieved by using our MBD-FC protein to capture all cell free DNA and then elute the highly methylated DNA fraction with high salt concentrations. Using the low salt eluate fractions, the MBD-FC is equally capable of enriching non-methylated fetal DNA.

The present invention provides 63 confirmed genomic regions on chromosomes 13, 18 and 21 with low maternal and high fetal methylation levels. After capturing these regions, SNPs can be used to determine the aforementioned allele ratios. When high frequency SNPs are used around 10 markers have to be measured to achieve a high confidence of finding at least one SNP where the parents have opposite homozygote genotypes and the child has a heterozygote genotype.

In an embodiment, a method for chromosomal abnormality detection is provided that utilizes absolute copy number quantification. A diploid chromosome set will show the same number of copies for differentially methylated regions across all chromosomes, but, for example, a trisomy 21 sample would show 1.5 times more copies for differentially methylated regions on chromosome 21. Normalization of the genomic DNA amounts for a diploid chromosome set can be achieved by using unaltered autosomes as reference (also provided herein—see Table 1B). Comparable to other approaches, a single marker is less likely to be sufficient for detection of this difference, because the overall copy numbers are low. Typically there are approximately 100 to 200 copies of fetal DNA from 1 ml of maternal plasma at 10 to 12 weeks of gestation. However, the methods of the present invention offer a redundancy of detectable markers that enables highly reliable discrimination of diploid versus aneuploid chromosome sets.

Data Processing and Identifying Presence or Absence of a Chromosome Abnormality

The term "detection" of a chromosome abnormality as used herein refers to identification of an imbalance of chromosomes by processing data arising from detecting sets of amplified nucleic acid species, nucleotide sequence species, or a detectable product generated from the foregoing (collectively "detectable product"). Any suitable detection device and method can be used to distinguish one or more sets of detectable products, as addressed herein. An outcome pertaining to the presence or absence of a chromosome abnormality can be expressed in any suitable form, including, without limitation, probability (e.g., odds ratio, p-value), likelihood, percentage, value over a threshold, or risk factor, associated with the presence of a chromosome abnormality for a subject or sample. An outcome may be provided with one or more of sensitivity, specificity, standard deviation, coefficient of variation (CV) and/or confidence level, or combinations of the foregoing, in certain embodiments.

Detection of a chromosome abnormality based on one or more sets of detectable products may be identified based on one or more calculated variables, including, but not limited to, sensitivity, specificity, standard deviation, coefficient of variation (CV), a threshold, confidence level, score, probability and/or a combination thereof. In some embodiments, (i) the number of sets selected for a diagnostic method, and/or (ii) the particular nucleotide sequence species of each set selected for a diagnostic method, is determined in part or in full according to one or more of such calculated variables.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

For example, scoring or a score may refer to calculating the probability that a particular chromosome abnormality is actually present or absent in a subject/sample. The value of a score may be used to determine for example the variation, difference, or ratio of amplified nucleic detectable product that may correspond to the actual chromosome abnormality. For example, calculating a positive score from detectable products can lead to an identification of a chromosome abnormality, which is particularly relevant to analysis of single samples.

In certain embodiments, simulated (or simulation) data can aid data processing for example by training an algorithm or testing an algorithm. Simulated data may for instance involve hypothetical various samples of different concentrations of fetal and maternal nucleic acid in serum, plasma and the like. Simulated data may be based on what might be expected from a real population or may be skewed to test an algorithm and/or to assign a correct classification based on a simulated data set. Simulated data also is referred to herein as "virtual" data. Fetal/maternal contributions within a sample can be simulated as a table or array of numbers (for example, as a list of peaks corresponding to the mass signals of cleavage products of a reference biomolecule or amplified nucleic acid sequence), as a mass spectrum, as a pattern of bands on a gel, or as a representation of any technique that measures mass distribution. Simulations can be performed in most instances by a computer program. One possible step in using a simulated data set is to evaluate the confidence of the identified results, i.e. how well the selected positives/negatives match the sample and whether there are additional variations. A common approach is to calculate the probability value (p-value) which estimates the probability of a random sample having better score than the selected one. As p-value calculations can be prohibitive in certain circumstances, an empirical model may be assessed, in which it is assumed that at least one sample matches a reference sample (with or without resolved variations). Alternatively other distributions such as Poisson distribution can be used to describe the probability distribution.

In certain embodiments, an algorithm can assign a confidence value to the true positives, true negatives, false positives and false negatives calculated. The assignment of a likelihood of the occurrence of a chromosome abnormality can also be based on a certain probability model.

Simulated data often is generated in an in silico process. As used herein, the term "in silico" refers to research and experiments performed using a computer. In silico methods include, but are not limited to, molecular modeling studies, karyotyping, genetic calculations, biomolecular docking experiments, and virtual representations of molecular structures and/or processes, such as molecular interactions.

As used herein, a "data processing routine" refers to a process, that can be embodied in software, that determines the biological significance of acquired data (i.e., the ultimate results of an assay). For example, a data processing routine can determine the amount of each nucleotide sequence species based upon the data collected. A data processing routine also may control an instrument and/or a data collection routine based upon results determined. A data processing routine and a data collection routine often are integrated and provide feedback to operate data acquisition by the instrument, and hence provide assay-based judging methods provided herein.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

Different methods of predicting abnormality or normality can produce different types of results. For any given prediction, there are four possible types of outcomes: true positive, true negative, false positive, or false negative. The term "true positive" as used herein refers to a subject correctly diagnosed as having a chromosome abnormality. The term "false positive" as used herein refers to a subject wrongly identified as having a chromosome abnormality. The term "true negative" as used herein refers to a subject correctly identified as not having a chromosome abnormality. The term "false negative" as used herein refers to a subject wrongly identified as not having a chromosome abnormality. Two measures of performance for any given method can be calculated based on the ratios of these occurrences: (i) a sensitivity value, the fraction of predicted positives that are correctly identified as being positives (e.g., the fraction of nucleotide sequence sets correctly identified by level comparison detection/determination as indicative of chromosome abnormality, relative to all nucleotide sequence sets identified as such, correctly or incorrectly), thereby reflecting the accuracy of the results in detecting the chromosome abnormality; and (ii) a specificity value, the fraction of predicted negatives correctly identified as being negative (the fraction of nucleotide sequence sets correctly identified by level comparison detection/determination as indicative of chromosomal normality, relative to all nucleotide sequence sets identified as such, correctly or incorrectly), thereby reflecting accuracy of the results in detecting the chromosome abnormality.

EXAMPLES

The following examples are provided by way of illustration only and not by way of limitation. Those of skill in the art will readily recognize a variety of non-critical parameters that could be changed or modified to yield essentially the same or similar results.

In Example 1 below, the Applicants used a new fusion protein that captures methylated DNA in combination with CpG Island array to identify genomic regions that are differentially methylated between fetal placenta tissue and maternal blood. A stringent statistical approach was used to only select regions which show little variation between the samples, and hence suggest an underlying biological mechanism. Eighty-five differentially methylated genomic regions predominantly located on chromosomes 13, 18 and 21 were validated. For this validation, a quantitative mass spectrometry based approach was used that interrogated 261 PCR amplicons covering these 85 regions. The results are in very good concordance (95% confirmation), proving the feasibility of the approach.

Next, the Applicants provide an innovative approach for aneuploidy testing, which relies on the measurement of absolute copy numbers rather than allele ratios.

Example 1

Figure 3:
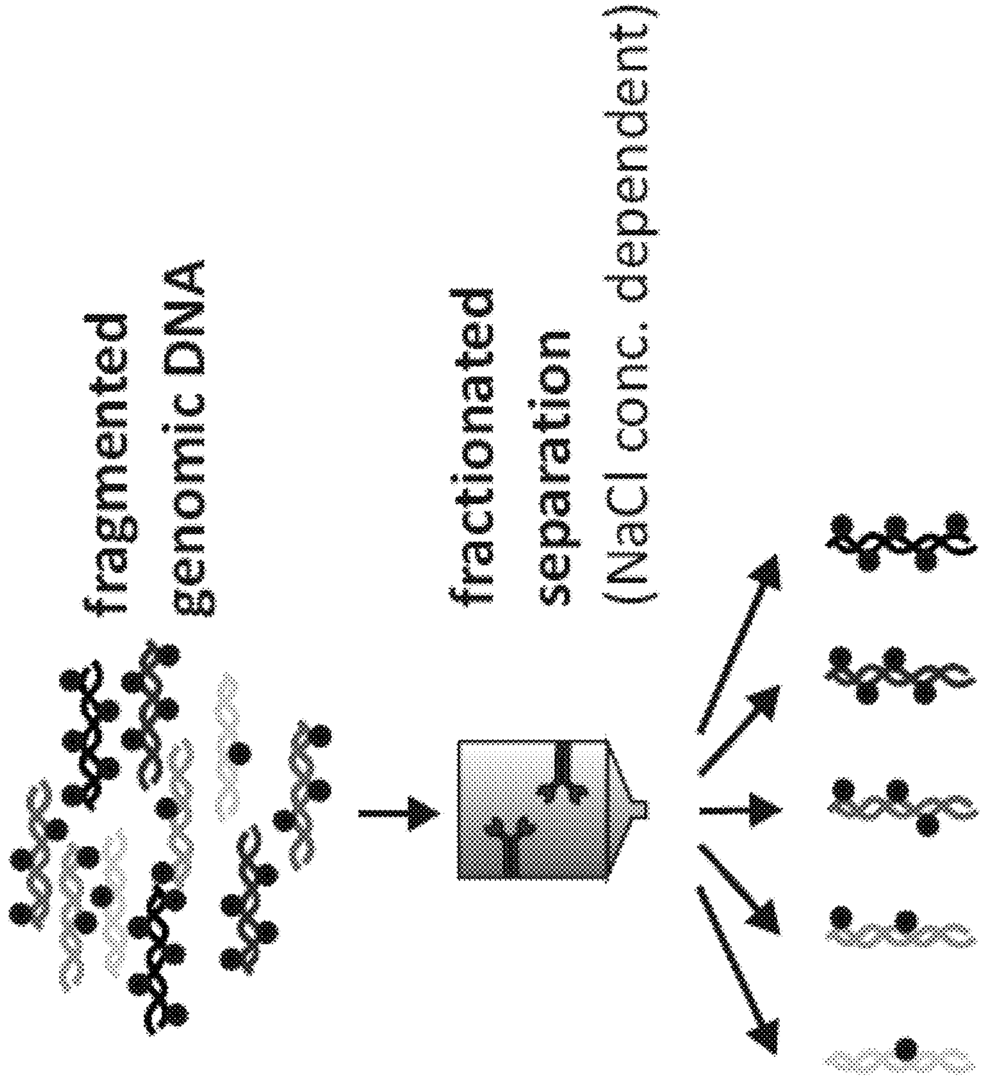
FIG. 3: Shows the methyl binding domain of MBD-FC binds all DNA molecules regardless of their methylation status. The strength of this protein/DNA interaction is defined by the level of DNA methylation. After binding genomic DNA, eluate solutions of increasing salt concentrations can be used to fractionate non-methylated and methylated DNA allowing for a controlled separation.
Figure 4:
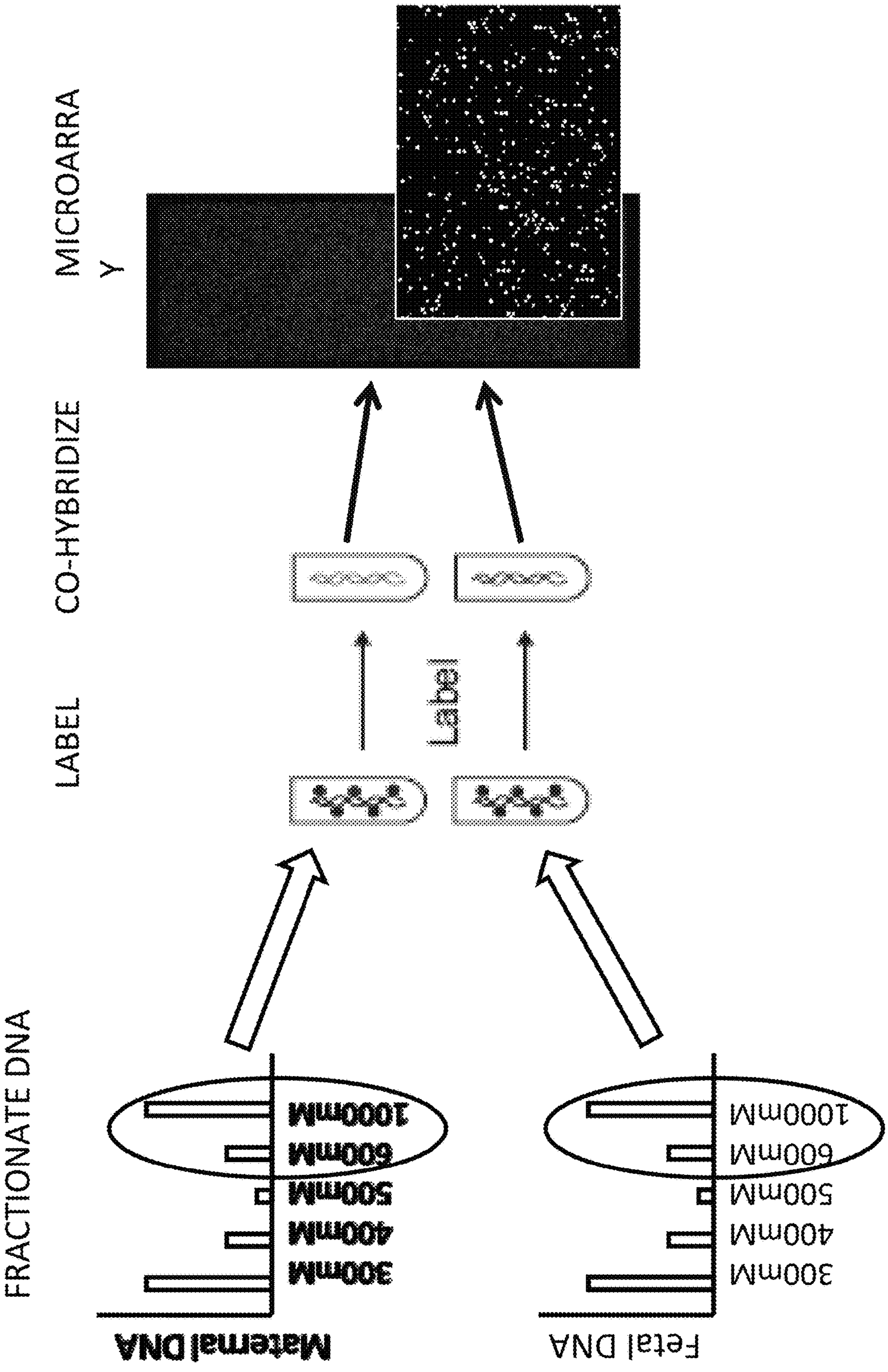
FIG. 4: Shows the experiment used to identify differentially methylated DNA from a fetus and mother using the recombinant MBD-Fc protein and a microarray.
Figure 5:
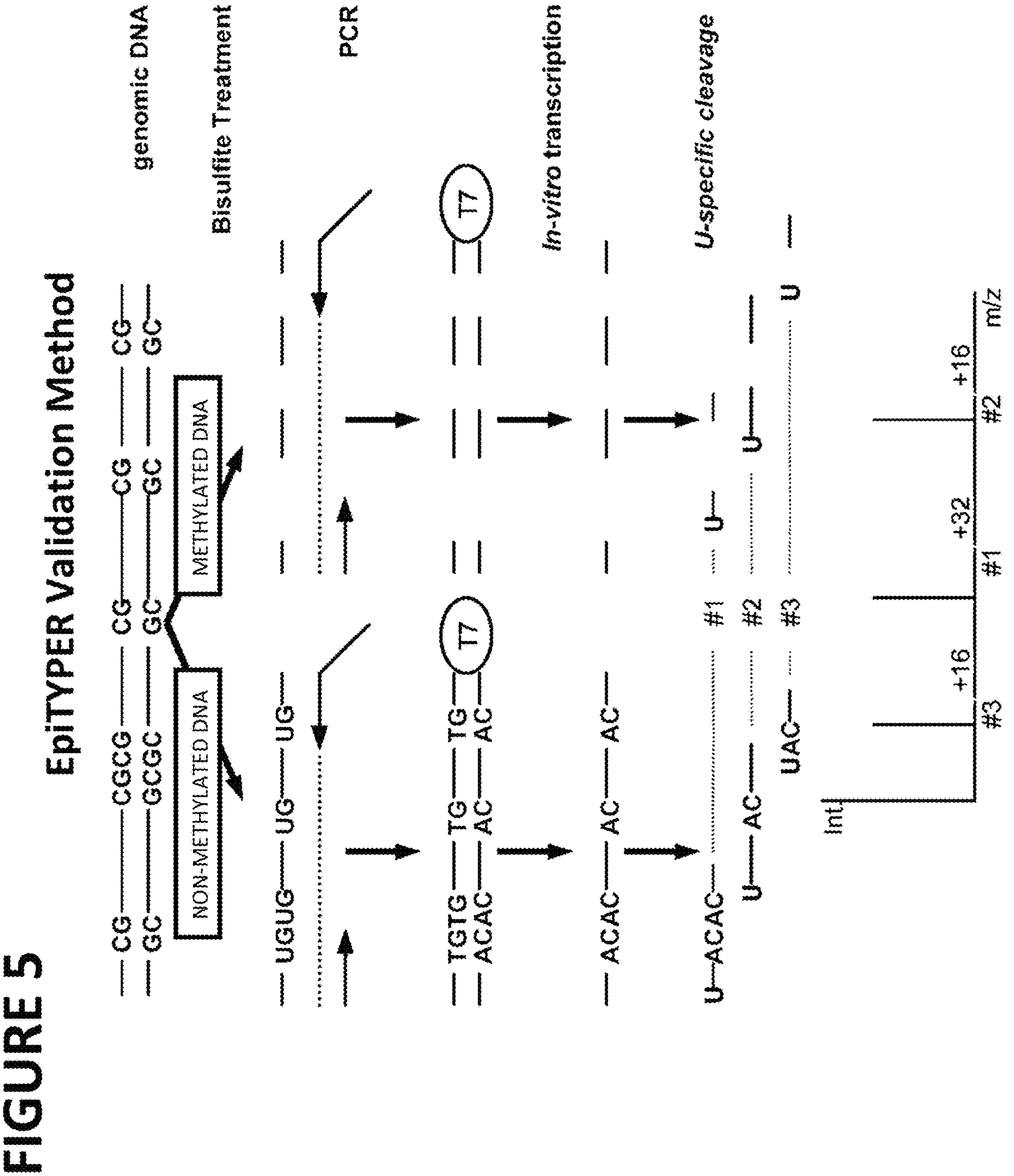
FIG. 5: Shows typical results generated by Sequenom® EpiTYPER™ method, which was used to validate the results generated from the experiment illustrated in FIG. 4.
Figure 6:
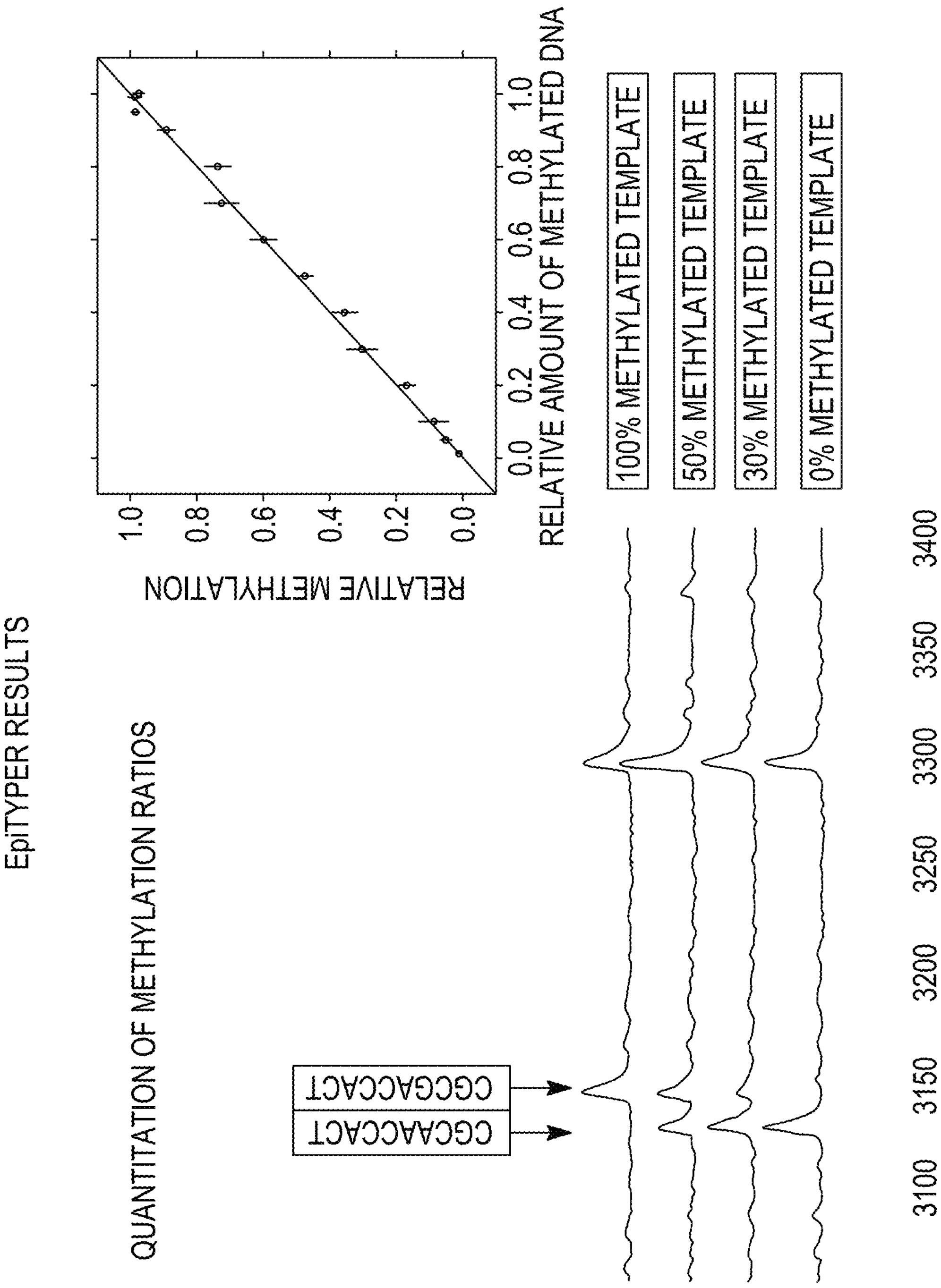
FIG. 6: Shows the correlation between the log ratios derived from microarray analysis (x axis) and methylation differences obtained by EpiTYPER analysis (y axis). Each data point represents the average for one region across all measured samples. The microarray analysis is comparative in nature because the highly methylated fraction of the maternal DNA is hybridized together with the highly methylated fraction of placenta DNA. Positive values indicate higher methylation of the placenta samples. In mass spectrometry each samples is measured individually. We first calculated difference in methylation by subtracting the maternal methylation values from the placenta methylation value. To compare the results with the microarray data we calculated the average of the differences for all maternal/placenta DNA pairs.

In the below Example, ten paired maternal and placental DNA samples were used to identify differentially methylated regions. These results were validated using a mass spectrometry-based quantitative methylation assay. First, genomic DNA from maternal buffy coat and corresponding placental tissue was first extracted. Next the MBD-FC was used to capture the methylated fraction of each DNA sample. See FIGS. 1-3. The two tissue fractions were labeled with different fluorescent dyes and hybridized to an Agilent® CpG Island microarray. See FIG. 4. This was done to identify differentially methylated regions that could be utilized for prenatal diagnoses. Therefore, two criteria were employed to select genomic regions as potential enrichment markers: the observed methylation difference had to be present in all tested sample pairs, and the region had to be more than 200 bp in length.

DNA Preparation and Fragmentation

Genomic DNA (gDNA) from maternal buffy coat and placental tissue was prepared using the QIAamp DNA Mini Kit™ and QIAamp DNA Blood Mini Kit™, respectively, from Qiagen® (Hilden, Germany). For MCIp, gDNA was quantified using the NanoDrop ND 1000™ spectrophotometer (Thermo Fisher®, Waltham, Mass., USA). Ultrasonication of 2.5 μg DNA in 500 μl TE buffer to a mean fragment size of 300-500 bp was carried out with the Branson Digital Sonifier 450™ (Danbury, Conn., USA) using the following settings: amplitude 20%, sonication time 110 seconds, pulse on/pulse off time 1.4/0.6 seconds. Fragment range was monitored using gel electrophoresis.

Methyl-CpG Immunoprecipitation

Per sample, 56 μg purified MBD-Fc protein and 150 μl of Protein A Sepharose 4 Fast Flow beads (Amersham Biosciences®, Piscataway, N.J., USA) were rotated in 15 ml TBS overnight at 4° C. Then, the MBD-Fc beads (150 μl/assay) were transferred and dispersed in to 2 ml Ultrafree-CL centrifugal filter devices (Millipore®, Billerica, Mass., USA) and spin-washed three times with Buffer A (20 mM Tris-HCl, pH8.0, 2 mM MgCl2, 0.5 mM EDTA 300 mM NaCl, 0.1% NP-40). Sonicated DNA (2 μg) was added to the washed MBD-Fc beads in 2 ml Buffer A and rotated for 3 hours at 4° C. Beads were centrifuged to recover unbound DNA fragments (300 mM fraction) and subsequently washed twice with 600 μl of buffers containing increasing NaCl concentrations (400, 500, 550, 600, and 1000 mM). The flow through of each wash step was collected in separate tubes and desalted using a MinElute PCR Purification Kit™ (Qiagen®). In parallel, 200 ng sonicated input DNA was processed as a control using the MinElute PCR Purification Kit™ (Qiagen®).

Microarray Handling and Analysis

To generate fluorescently labeled DNA for microarray hybridization, the 600 mM and 1M NaCl fractions (enriched methylated DNA) for each sample were combined and labeled with either Alexa Fluor 555-aha-dCTP (maternal) or Alexa Fluor 647-aha-dCTP (placental) using the BioPrime Total Genomic Labeling System™ (Invitrogen®, Carlsbad, Calif., USA). The labeling reaction was carried out according to the manufacturer's manual. The differently labeled genomic DNA fragments of matched maternal/placental pairs were combined to a final volume of 80 μl, supplemented with 50 μg Cot-1 DNA (Invitrogen®), 52 μl of Agilent 10× blocking reagent (Agilent Technologies®, Santa Clara, Calif., USA), 78 μl of deionized formamide, and 260 μl Agilent 2× hybridization buffer. The samples were heated to 95° C. for 3 min, mixed, and subsequently incubated at 37° C. for 30 min. Hybridization on Agilent CpG Island Microarray Kit™ was then carried out at 67° C. for 40 hours using an Agilent SureHyb™ chamber and an Agilent hybridization oven. Slides were washed in Wash I (6×SSPE, 0.005% N-lauroylsarcosine) at room temperature for 5 min and in Wash II (0.06×SSPE) at 37° C. for an additional 5 min. Next, the slides were submerged in acetonitrile and Agilent Ozone Protection Solution™, respectively, for 30 seconds. Images were scanned immediately and analyzed using an Agilent DNA Microarray Scanner™. Microarray images were processed using Feature Extraction Software v9.5 and the standard CGH protocol.

Bisulfite Treatment

Genomic DNA sodium bisulfite conversion was performed using EZ-96 DNA Methylation Kit™ (ZymoResearch, Orange County, Calif.). The manufacturer's protocol was followed using 1 ug of genomic DNA and the alternative conversion protocol (a two temperature DNA denaturation).

Quantitative Methylation Analysis

Sequenom's MassARRAY® System was used to perform quantitative methylation analysis. This system utilizes matrix-assisted laser desorption ionization time-of-flight (MALDI-TOF) mass spectrometry in combination with RNA base specific cleavage (Sequenom® MassCLEAVE™). A detectable pattern is then analyzed for methylation status. PCR primers were designed using Sequenom® EpiDESIGNER™ (www.epidesigner.com). A total of 261 amplicons, covering 85 target regions, were used for validation (median amplification length=367 bp, min=108, max=500; median number of CpG's per amplicon=23, min=4, max=65). For each reverse primer, an additional T7 promoter tag for in-vivo transcription was added, as well as a 10mer tag on the forward primer to adjust for melting temperature differences. The MassCLEAVE™ biochemistry was performed as previously described (Ehrich M, et al. (2005) Quantitative high-throughput analysis of DNA methylation patterns by base specific cleavage and mass spectrometry. Proc Natl Acad Sci USA 102:15785-15790). Mass spectra were acquired using a MassARRAY™ Compact MALDI-TOF (Sequenom®, San Diego) and methylation ratios were generated by the EpiTYPER™ software v1.0 (Sequenom®, San Diego).

Statistical Analysis

All statistical calculations were performed using the R statistical software package (www.r-project.org). First, the array probes were grouped based on their genomic location. Subsequent probes that were less than 1000 bp apart were grouped together. To identify differentially methylated regions, a control sample was used as reference. In the control sample, the methylated fraction of a blood derived control DNA was hybridized against itself. Ideally this sample should show log ratios of the two color channels around 0. However because of the variability in hybridization behavior, the probes show a mean log ratio of 0.02 and a standard deviation of 0.18. Next the log ratios observed in our samples were compared to the control sample. A two way, paired t-test was used to test the NULL hypothesis that the groups are identical. Groups that contained less than 4 probes were excluded from the analysis. For groups including four or five probes, all probes were used in a paired t-test. For Groups with six or more probes, a sliding window test consisting of five probes at a time was used, whereby the window was moved by one probe increments. Each test sample was compared to the control sample and the p-values were recorded. Genomic regions were selected as being differentially methylated if eight out of ten samples showed a p value<0.01, or if six out of ten samples showed a p value<0.001. The genomic regions were classified as being not differentially methylated when the group showed less than eight samples with a p value<0.01 and less than six samples with a p value<0.001. Samples that didn't fall in either category were excluded from the analysis. For a subset of genomic regions that have been identified as differentially methylated, the results were confirmed using quantitative methylation analysis.

The Go analysis was performed using the online GOstat tool (http://gostat.wehi.edu.au/cgibin/-goStat.pl). P values were calculated using Fisher's exact test.

Microarray-Based Marker Discovery Results

To identify differentially methylated regions a standard sample was used, in which the methylated DNA fraction of monocytes was hybridized against itself. This standard provided a reference for the variability of fluorescent measurements in a genomic region. Differentially methylated regions were then identified by comparing the log ratios of each of the ten placental/maternal samples against this standard. Because the goal of this study was to identify markers that allow the reliable separation of maternal and fetal DNA, the target selection was limited to genes that showed a stable, consistent methylation difference over a contiguous stretch of genomic DNA. This focused the analysis on genomic regions where multiple probes indicated differential methylation. The selection was also limited to target regions where all samples showed differential methylation, excluding those with strong inter-individual differences. Two of the samples showed generally lower log ratios in the microarray analysis. Because a paired test was used for target selection, this did not negatively impact the results. Based on these selection criteria, 3043 genomic regions were identified that were differentially methylated between maternal and fetal DNA. 21778 regions did not show a methylation difference. No inter-chromosomal bias in the distribution of differentially methylated regions was observed. The differentially methylated regions were located next to or within 2159 known genes. The majority of differentially methylated regions are located in the promoter area (18%) and inside the coding region (68%), while only few regions are located downstream of the gene (7%) or at the transition from promoter to coding region (7%). Regions that showed no differential methylation showed a similar distribution for promoter (13%) and downstream (5%) locations, but the fraction of regions located in the transition of promoter to coding region was higher (39%) and the fraction inside the coding region was lower (43%).

It has been shown in embryonic stem cells (ES) that genes targeted by the polycomb repressive complex2 (PRC2) are enriched for genes regulating development (Lee T I, et al. (2006) Control of developmental regulators by Polycomb in human embryonic stem cells. *Cell* 125:301-313). It has also been shown that differentially methylated genes are enriched for genes targeted by PRC2 in many cancer types (Ehrich M, et al. (2008) Cytosine methylation profiling of cancer cell lines. *Proc Natl Acad Sci USA* 105:4844-48). The set of genes identified as differentially methylated in this study is also enriched for genes targeted by PRC2 (p-value<0.001, odds ratio=3.6, 95% CI for odds ratio=3.1–4.2). A GO analysis of the set of differentially methylated genes reveals that this set is significantly enriched for functions important during development. Six out of the ten most enriched functions include developmental or morphogenic processes [anatomical structure morphogenesis (GO:0009653, p value=0), developmental process (GO:0032502, p value=0), multicellular organismal development (GO:0007275, p value=0), developmental of an organ (GO:0048513, p value=0), system development (GO:0048731, p value=0) and development of an anatomical structure (GO:0048856, p value=0)].

Validation using Sequenom® EpiTYPER™

Figure 7:
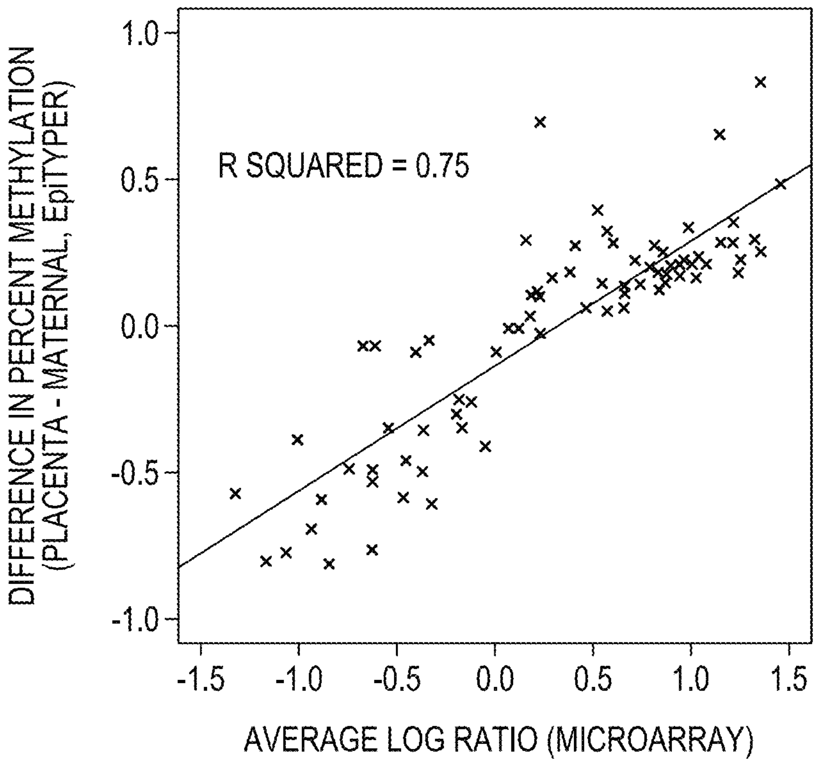
FIG. 7 shows a correlation between microarray and EpiTYPER™ results.

To validate the microarray findings, 63 regions from chromosomes 13, 18 and 21 and an additional 26 regions from other autosomes were selected for confirmation by a different technology. Sequenom EpiTYPER™ technology was used to quantitatively measure DNA methylation in maternal and placental samples. For an explanation of the EpiTYPER™ methods, see Ehrich M, Nelson M R, Stanssens P, Zabeau M, Liloglou T, Xinarianos G, Cantor C R, Field J K, van den Boom D (2005) Quantitative high-throughput analysis of DNA methylation patterns by base specific cleavage and mass spectrometry. Proc Natl Acad Sci USA 102:15785-15790). For each individual CpG site in a target region the average methylation value across all maternal DNA samples and across all placenta samples was calculated. The difference between average maternal and placenta methylation was then compared to the microarray results. The results from the two technologies were in good concordance (see FIG. 7). For 85 target regions the quantitative results confirm the microarray results (95% confirmation rate). For 4 target regions, all located on chromosome 18, the results could not be confirmed. The reason for this discrepancy is currently unclear.

In contrast to microarrays, which focus on identification of methylation differences, the quantitative measurement of DNA methylation allowed analysis of absolute methylation values. In the validation set of 85 confirmed differentially methylated regions, a subset of 26 regions is more methylated in the maternal DNA sample and 59 regions are more methylated in the placental sample (see Table 1A). Interestingly, genes that are hypomethylated in the placental samples tend to show larger methylation differences than genes that are hypermethylated in the placental sample (median methylation difference for hypomethylated genes=39%, for hypermethylated genes=20%).

Example 2

Figure 10:
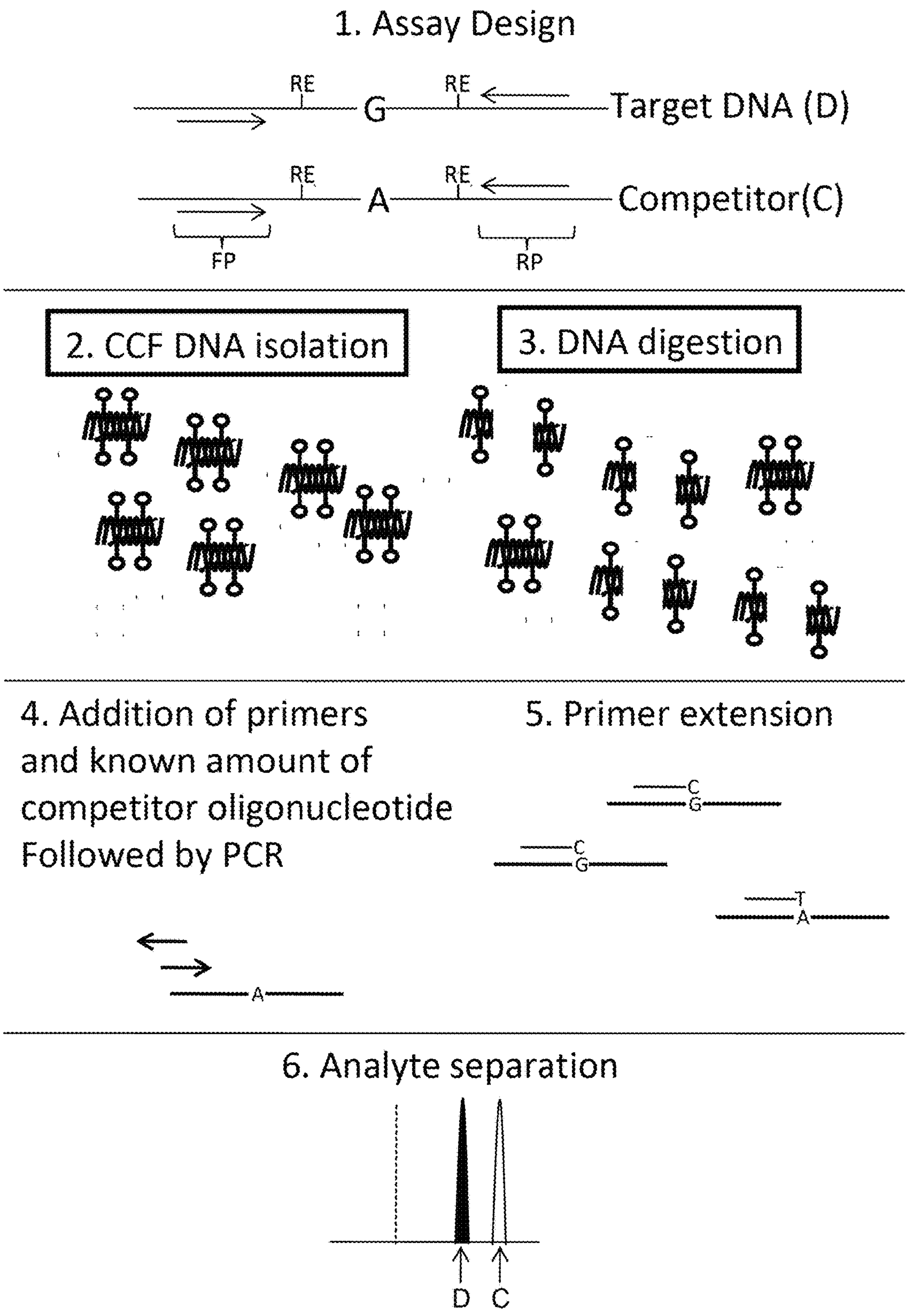
FIG. 10: Shows one embodiment of the Fetal Quantifier Method. Maternal nucleic acid is selectively digested and the remaining fetal nucleic acid is quantified using a competitor of known concentration. In this schema, the analyte is separated and quantified by a mass spectromter.
Figure 11:
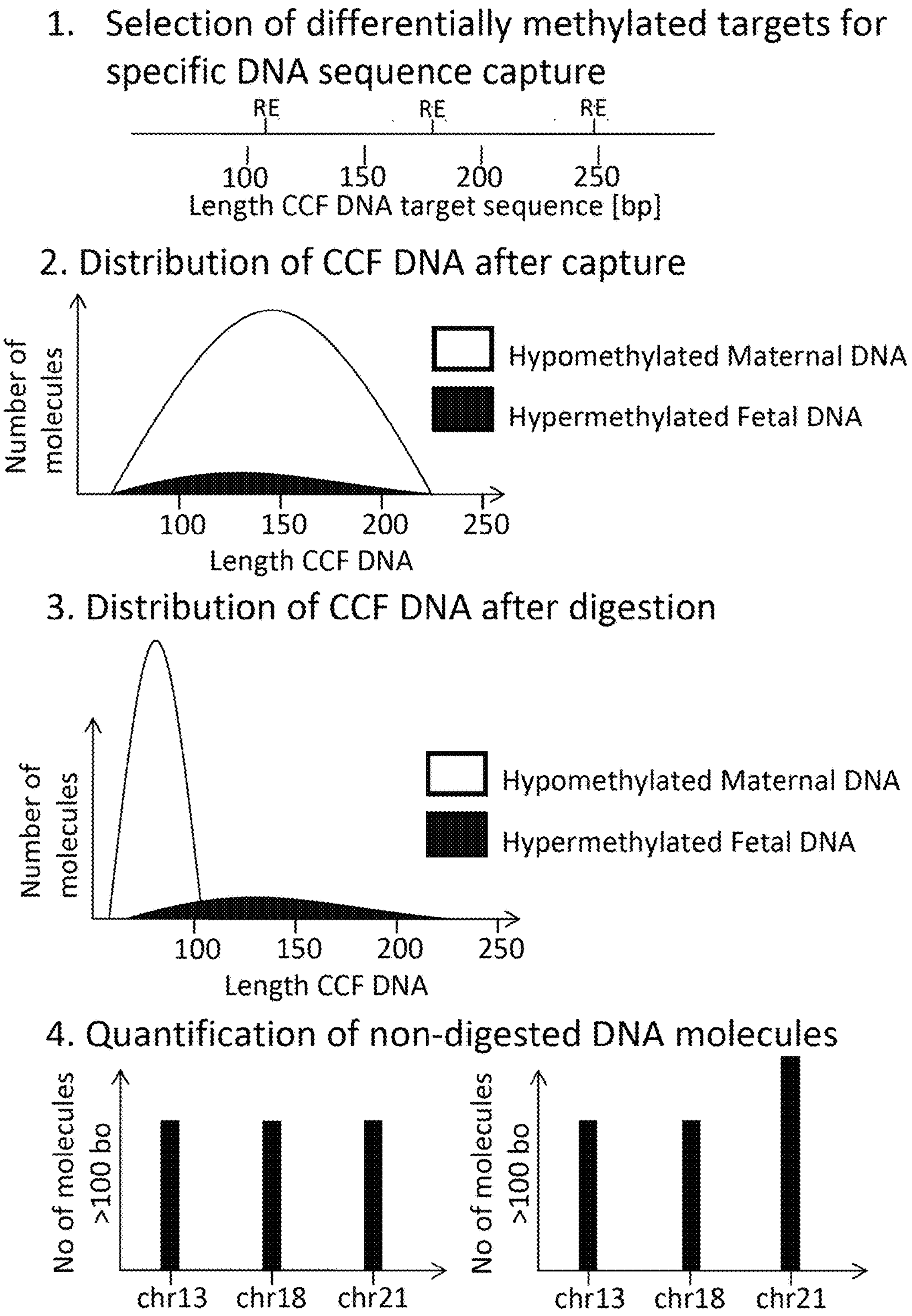
FIG. 11: Shows one embodiment of the Methylation-Based Fetal Diagnostic Method. Maternal nucleic acid is selectively digested and the remaining fetal nucleic acid is quantified for three different chromosomes (13, 18 and 21). Parts 2 and 3 of the Figure illustrate the size distribution of the nucleic acid in the sample before and after digestion. The amplification reactions can be size-specific (e.g., greater than 100 base pair amplicons) such that they favor the longer, non-digested fetal nucleic acid over the digested maternal nucleic acid, thereby further enriching the fetal nucleic acid. The spectra at the bottom of the Figure show an increased amount of chromosome 21 fetal nucleic acid indicative of trisomy 21.

Example 2 describes a non-invasive approach for detecting the amount of fetal nucleic acid present in a maternal sample (herein referred to as the "Fetal Quantifier Method"), which may be used to detect or confirm fetal traits (e.g., fetal sex of RhD compatibility), or diagnose chromosomal abnormalities such as Trisomy 21 (both of which are herein referred to as the "Methylation-Based Fetal Diagnostic Method"). FIG. 10 shows one embodiment of the Fetal Quantifier Method, and FIG. 11 shows one embodiment of the Methylation-Based Fetal Diagnostic Method. Both processes use fetal DNA obtained from a maternal sample. The sample comprises maternal and fetal nucleic acid that is differentially methylated. For example, the sample may be maternal plasma or serum. Fetal DNA comprises approximately 2-30% of the total DNA in maternal plasma. The actual amount of fetal contribution to the total nucleic acid present in a sample varies from pregnancy to pregnancy and can change based on a number of factors, including, but not limited to, gestational age, the mother's health and the fetus' health.

As described herein, the technical challenge posed by analysis of fetal DNA in maternal plasma lies in the need to be able to discriminate the fetal DNA from the co-existing background maternal DNA. The methods of the present invention exploit such differences, for example, the differential methylation that is observed between fetal and maternal DNA, as a means to enrich for the relatively small percentage of fetal DNA present in a sample from the mother. The non-invasive nature of the approach provides a major advantage over conventional methods of prenatal diagnosis such as, amniocentesis, chronic villus sampling and cordocentesis, which are associated with a small but finite risk of fetal loss. Also, because the method is not dependent on fetal cells being in any particular cell phase, the method provides a rapid detection means to determine the presence and also the nature of the chromosomal abnormality. Further, the approach is sex-independent (i.e., does not require the presence of a Y-chromosome) and polymorphic-independent (i.e., an allelic ratio is not determined). Thus, the compositions and methods of the invention represent improved universal, noninvasive approaches for accurately determining the amount of fetal nucleic acid present in a maternal sample.

Assay Design and Advantages

There is a need for accurate detection and quantification of fetal DNA isolated noninvasively from a maternal sample. The present invention takes advantage of the presence of circulating, cell free fetal nucleic acid (ccfDNA) in maternal plasma or serum. In order to be commercially and clinically practical, the methods of the invention should only consume a small portion of the limited available fetal DNA. For example, less than 50%, 40%, 30%, 25%, 20%, 15%, 10%, 5% or less of the sample. Further, the approach should preferably be developed in a multiplex assay format in which one or more (preferably all) of the following assays are included:

- Assays for the detection of total amount of genomic equivalents present in the sample, i.e., assays recognizing both maternal and fetal DNA species;
- Assays for the detection of fetal DNA isolated from a male pregnancy, i.e., sequences specific for chromosome Y;
- Assays specific for regions identified as differentially methylated between the fetus and mother; or
- Assays specific for regions known to be hypomethylated in all tissues to be investigated, which can serve as a control for restriction efficiency.

Other features of the assay may include one or more of the following:

- For each assay, a target-specific, competitor oligonucleotide that is identical, or substantially identical, to the target sequence apart from a distinguishable feature of the competitor, such as a difference in one or more nucleotides relative to the target sequence. This oligonucleotide when added into the PCR reaction will be co-amplified with the target and a ratio obtained between these two PCR amplicons will indicate the number of target specific DNA sequences (e.g., fetal DNA from a specific locus) present in the maternal sample.
- The amplicon lengths should preferably be of similar length in order not to skew the amplification towards the shorter fragments. However, as long as the amplification efficiency is about equal, different lengths may be used.
- Differentially methylated targets can be selected from Tables 1A-1C or from any other targets known to be differentially methylated between mother and fetus. These targets can be hypomethylated in DNA isolated from non-pregnant women and hypermethylated in samples obtained from fetal samples. These assays will serve as controls for the restriction efficiency.

The results obtained from the different assays can be used to quantify one or more of the following:

- Total number of amplifiable genomes present in the sample (total amount of genomic equivalents);
- The fetal fraction of the amplifiable genomes (fetal concentration or percentage); or
- Differences in copy number between fetally-derived DNA sequences (for example, between fetal chromosome 21 and a reference chromosome such as chromosome 3).

Examples of Assays Used in the Test

Below is an outline of the reaction steps used to perform a method of the invention, for example, as provided in FIG. 10. This outline is not intended to limit the scope of the invention. Rather it provides one embodiment of the invention using the Sequenom® MassARRAY® technology.

1) DNA isolation from plasma samples.
2) Digestion of the DNA targets using methylation sensitive restriction enzymes (for example, HhaI and HpaII).

For each reaction the available DNA was mixed with water to a final volume of 25 ul.

10 ul of a reaction mix consisting of 10 units HhaI, 10 units HpaII and a reaction buffer were added. The sample was incubated at an optimal temperature for the restriction enzymes. HhaI and HpaII digest non-methylated DNA (and will not digest hemi- or completely methylated DNA). Following digestion, the enzymes were denatured using a heating step.

3) Genomic Amplification—PCR was performed in a total volume of 50 ul by adding PCR reagents (Buffer, dNTPs, primers and polymerase). Exemplary PCR and extend primers are provided below. In addition, synthetic competitor oligonucleotide was added at known concentrations.
4) Replicates (optional)—Following PCR the 50 ul reaction was split into 5 ul parallel reactions (replicates) in order to minimize variation introduced during the post PCR steps of the test. Post PCR steps include SAP, primer extension (MassEXTEND® technology), resin treatment, dispensing of spectrochip and MassARRAY.
5) Quantification of the Amplifiable Genomes—Sequenom MassARRAY® technology was used to determine the amount of amplification product for each assay. Following PCR, a single base extension assay was used to interrogate the amplified regions (including the competitor oligonucleotides introduced in step 3). Specific extend primers designed to hybridize directly adjacent to the site of interest were introduced. See extend primers provided below. These DNA oligonucleotides are referred to as iPLEX® MassEXTEND® primers. In the extension reaction, the iPLEX primers were hybridized to the complementary DNA templates and extended with a DNA polymerase. Special termination mixtures that contain different combinations of deoxy- and dideoxynucleotide triphosphates along with enzyme and buffer, directed limited extension of the iPLEX primers. Primer extension occurs until a complementary dideoxynucleotide is incorporated.

The extension reaction generated primer products of varying length, each with a unique molecular weight. As a result, the primer extension products can be simultaneously separated and detected using Matrix Assisted Laser Desorption/Ionization, Time-Of-Flight (MALDI-TOF) mass spectrometry on the MassARRAY® Analyzer Compact. Following this separation and detection, SEQUENOM's proprietary software automatically analyzes the data.

Figure 18:
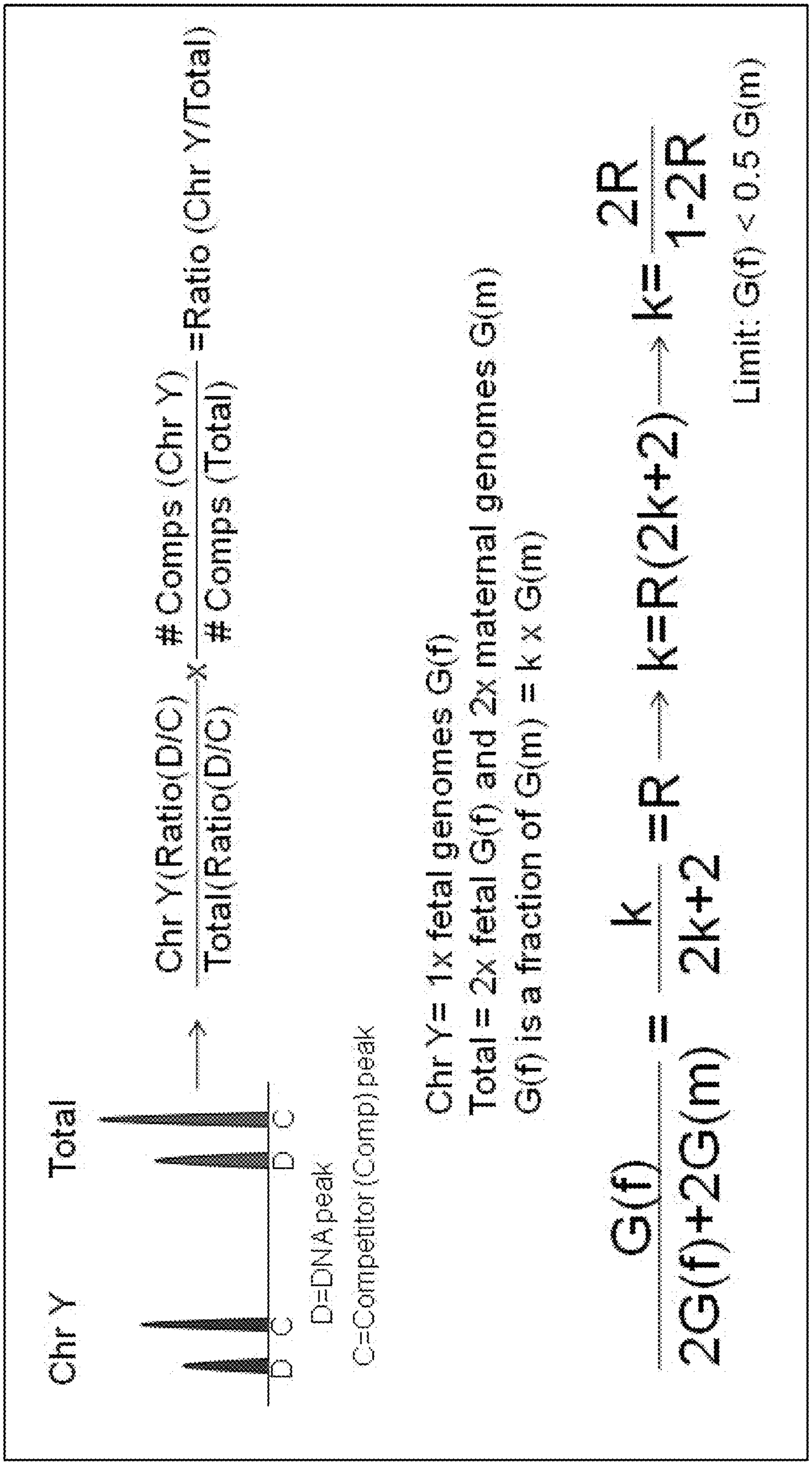
FIG. 18: Provides a specific method for calculating fetal DNA fraction (or concentration) in a sample using the Y-chromosome-specific markers for male pregnancies and the mean of the methylated fraction for all pregnancies (regardless of fetal sex).

6) Calculating the amount and concentration of fetal nucleic acid—Methods for calculating the total amount of genomic equivalents present in the sample, the amount (and concentration) of fetal nucleic acid isolated from a male pregnancy, and the amount (and concentration) of fetal nucleic based on differentially methylated targets are provided below and in FIGS. 18 and 19.

The above protocol can be used to perform one or more of the assays described below. In addition to the sequences provided immediately below, a multiplex scheme that interrogates multiple targets is provided in Table X below.

1) Assay for the Quantification of the Total Number of Amplifiable Genomic Equivalents in the Sample.

Targets were selected in housekeeping genes not located on the chromosomes 13, 18, 21, X or Y. The targets should be in a single copy gene and not contain any recognition sites for the methylation sensitive restriction enzymes.

Underlined sequences are PCR primer sites, italic is the site for the single base extend primer and bold letter (C) is the nucleotide extended on human DNA ApoE Chromosome 19:45409835-45409922 DNA target sequence with interrogated nucleotide C in bold. All of the chromosome positions provided in this section are from the February 2009 UCSC Genome Build.

(SEQ ID NO: 262)
GATTGACAGTTTCTCCTTCCCCAGACTGGCCAATCACAGGCAGGAAGATG
AAGGTTCTGTGGGCTGCGTTGCTGGTCACATTCCTGGC

ApoE Forward Primer:

(SEQ ID NO: 263)
5'-ACGTTGGATG-TTGACAGTTTCTCCTTCCCC
(Primer contains a 5' 10 bp MassTag separated by a dash)

ApoE Reverse Primer:

(SEQ ID NO: 264)
5'-ACGTTGGATG-GAATGTGACCAGCAACGCAG
(Primer contains a 5' 10 bp MassTag separated by a dash)

ApoE Extension Primer:

(SEQ ID NO: 265)
5'-GCAGGAAGATGAAGGTT[C/T]
Primer extends C on human DNA targets and T on synthetic DNA targets ApoE synthetic competitor oligonucleotide:

(SEQ ID NO: 266)
5'-GATTGACAGTTTCTCCTTCCCCAGACTGGCCAATCACAGGCAGGAAG
ATGAAGGTTTTGTGGGCTGCGTTGCTGGTCACATTCCTGGC
(Bold T at position 57 is different from human DNA)

2) Assay for the Quantification of the Total Number of Chromosome Y Sequences in the Sample.

Targets specific for the Y-chromosome were selected, with no similar or paralog sequences elsewhere in the genome. The targets should preferably be in a single copy gene and not contain any recognition sites for the methylation sensitive restriction enzyme(s).

Underlined sequences are PCR primer sites, and italic nucleotide(s) is the site for the single-base extend primer and bold letter (C) is the nucleotide extended on human DNA.

SRY on chrY:2655628-2655717 (reverse complement)

(SEQ ID NO: 267)
GAGTTTTGGATAGTAAAATAAGTTTCGAACTCTGGCACCTTTCAATTTTG
TCGCACTCTCCTTGTTTTTGACAATGCAATCATATGCTTC

SRY Forward Primer:

(SEQ ID NO: 268)
5'-ACG-TGGATAGTAAAATAAGTTTCGAACTCTG
(Primer contains a 5' 3 bp MassTag separated by a dash)

SRY Reverse Primer:

(SEQ ID NO: 269)
5'-GAAGCATATGATTGCATTGTCAAAAAC

SRY Extension Primer:

(SEQ ID NO: 270)
5'-aTTTCAATTTTGTCGCACT[C/T]
Primer extends C on human DNA targets and T on synthetic DNA targets. 5' Lower case "a" is a non-complementary nucleotide SRY synthetic competitor oligonucleotide:

(SEQ ID NO: 271)
5'-GAGTTTTGGATAGTAAAATAAGTTTCGAACTCTGGCACCTTTCAATT
TTGTCGCACTTTCCTTGTTTTTGACAATGCAATCATATGCTTC

3) Assay for the Quantification of Fetal Methylated DNA Sequences Present in the Sample.

Targets were selected in regions known to be differentially methylated between maternal and fetal DNA. Sequences were selected to contain several restriction sites for methylation sensitive enzymes. For this study the HhaI (GCGC) and HpaII (CCGG) enzymes were used.

Underlined sequences are PCR primer sites, italic is the site for the single base extend primer and bold letter (C) is the nucleotide extended on human DNA, lower case letter are recognition sites for the methylation sensitive restriction enzymes.

TBX3 on chr12:115124905-115125001

(SEQ ID NO: 272)
GAACTCCTCTTTGTCTCTGCGTGCccggcgcgcCCCCCTCccggTGGGTG
ATAAACCCACTCTGgcgccggCCATgcgcTGGGTGATTAATTTGCGA TBX3 Forward Primer:

(SEQ ID NO: 273)
5'-ACGTTGGATG-TCTTTGTCTCTGCGTGCCC
(Primer contains a 5' 10 bp MassTag separated by a dash)

TBX3 Reverse Primer:

(SEQ ID NO: 274)
5'-ACGTTGGATG-TTAATCACCCAGCGCATGGC
(Primer contains a 5' 10 bp MassTag separated by a dash)

TBX3 Extension Primer:

(SEQ ID NO: 275)
5'-CCCCTCCCGGTGGGTGATAAA[C/T]
Primer extends C on human DNA targets and T on synthetic DNA targets. 5' Lower case "a" is a non-complementary nucleotide TBX3 synthetic competitor oligonucleotide:

(SEQ ID NO: 276)
5'-GAACTCCTCTTTGTCTCTGCGTGCCCGGCGCGCCCCCCTCCCGGTGG
GTGATAAATCCACTCTGGCGCCGGCCATGCGCTGGGTGATTAATTTGCGA

4) Control Assay for the Enzyme Restriction Efficiency.

Targets were selected in regions known not to be methylated in any tissue to be investigated. Sequences were selected to contain no more than one site for each restriction enzyme to be used.

Underlined sequences are PCR primer sites, italic nucleotide(s) represent the site for the single-base extend primer and bold letter (G) is the reverse nucleotide extended on human DNA, lower case letter are recognition sites for the methylation sensitive restriction enzymes.

CACNA1G chr17:48637892-48637977 (reverse complement)

(SEQ ID NO: 277)

CCATTGGCCGTCCGCCGTGGCAGTGCGGGCGGGAgcgcAGG*GAGAGAACCA CAGCTGGAAT*CCGATTCCCACCCCAAAACCCAGGA HhaI Forward Primer:

(SEQ ID NO: 278)

5'-ACGTTGGATG-CCATTGGCCGTCCGCCGTG
(Primer contains a 5' 10 bp MassTag separated by a dash)

HhaI Reverse Primer:

(SEQ ID NO: 279)

5'-ACGTTGGATG-TCCTGGGTTTTGGGGTGGGAA
(Primer contains a 5' 10 bp MassTag separated by a dash)

HhaI Extension Primer:

(SEQ ID NO: 280)

5'-TTCCAGCTGTGGTTCTCTC

HhaI synthetic competitor oligonucleotide:

(SEQ ID NO: 281)

5'-CCATTGGCCGTCCGCCGTGGCAGTGCGGGCGGGAGCGCAGA*GAGAGAA CCACAGCTGGAAT*CCGATTCCCACCCCAAAACCCAGGA

Validation Experiments

The sensitivity and accuracy of the present invention was measured using both a model system and clinical samples. In the different samples, a multiplex assay was run that contains 2 assays for total copy number quantification, 3 assays for methylation quantification, 1 assay specific for chromosome Y and 1 digestion control assay. See Table X. Another multiplex scheme with additional assays is provided in Table Y.

TABLE X

PCR Primers and Extend Primers
Table X discloses 'First Primer' as SEQ ID NOS 282-288, 'Second Primer' as SEQ ID NOS 289-295, and 'Extend Primer' as SEQ ID NOS 296-302, respectively, in order of appearance.

| Gene ID | * | First Primer | Second Primer | Extend Primer |
|---|---|---|---|---|
| SOX14 | M | ACGTTGGATG ACATGGTCGG CCCCACGGAA T | ACGTTGGATG CTCCTTCCTA GTGTGAGAAC CG | CAGGTTCCGG GGCTTGGG |
| HhaI_CTRL | D | ACGTTGGATG ACCCATTGGC CGTCCGCCGT | ACGTTGGATG TTTTGGGGTG GGAATCGGAT T | CGCAGGGAGA GAACCACAG |
| TBX3 | M | ACGTTGGATG GAACTCCTCT TTGTCTCTGC G | ACGTTGGATG TGGCATGGCC GGCGCCAGA | CCCCTCCCGG TGGGTGATAA A |
| SRY | Y | ACGTTGGATG CGCAGCAACG GGACCGCTAC A | ACGTTGGCAT CTAGGTAGGT CTTTGTAGCC AA | AAAGCTGTAG GACAATCGGG T |
| ALB | T | ACGTTGCGTA GCAACCTGTT ACATATTAA | ACGTTGGATC TGAGCAAAGG CAATCAACAC CC | CATTTTTCTA CATCCTTTGT TT |

TABLE X-continued

PCR Primers and Extend Primers
Table X discloses 'First Primer' as SEQ ID NOS 282-288, 'Second Primer' as SEQ ID NOS 289-295, and 'Extend Primer' as SEQ ID NOS 296-302, respectively, in order of appearance.

| Gene ID | * | First Primer | Second Primer | Extend Primer |
|---|---|---|---|---|
| EDG6 | M | ACGTTGGATG CATAGAGGCC CATGATGGTG G | ACGTTGGATG ACCTTCTGCC CCTCTACTCC AA | agAAGATCAC CAGGCAGAAG AGG |
| RNaseP | T | ACGTTGGATG GTGTGGTCAG CTCTTCCCTT CAT | ACGTTGGCCC ACATGTAATG TGTTGAAAAA GCA | ACTTGGAGAA CAAAGGACAC CGTTA |

TABLE X

Competitor Oligonucleotide Sequence
Table X discloses SEQ ID NOS 303-309, respectively, in order of appearance.

| Gene ID | * | Competitor Oligonucleotide Sequence |
|---|---|---|
| SOX14 | M | GGTCGGCCCCACGGAATCCCGGCTCTGTGTGCGCC CAGGTTCCGGGGCTTGGGTGTTGCCGGTTCTCACA CTAGGAAGGAG |
| HhaI_CTRL | D | CCATTGGCCGTCCGCCGTGGCAGTGCGGGCGGGAG CGCAGAGAGAGAACCACAGCTGGAATCCGATTCCC ACCCCAAAA |
| TBX3 | M | GAACTCCTCTTTGTCTCTGCGTGCCCGGCGCGCCC CCCTCCCGGTGGGTGATAAATCCACTCTGGCGCCG GCCATGC |
| SRY | Y | GCAGCAACGGGACCGCTACAGCCACTGGACAAAGC CGTAGGACAATCGGGTAACATTGGCTACAAAGACC TACCTAGATGC |
| ALB | T | GCGTAGCAACCTGTTACATATTAAAGTTTTATTAT ACTACATTTTTCTACATCCTTTGTTTCAGAGTGTT GATTGCCTTTGCTCAGTATCTTCAG |
| EDG6 | M | CCTTCTGCCCCTCTACTCCAAGCGCTACACCCTCT TCTGCCTGGTGATCTTTGCCGGCGTCCTGGCCACC ATCATGGGCCTCTATG |
| RNaseP | T | GTGTGGTCAGCTCTTCCCTTCATCACATACTTGGA GAACAAAGGACACCGTTATCCATGCTTTTTCAACA CATTACATGTGGG |

TABLE Y

PCR Primers and Extend Primers
Table Y discloses 'First Primer' as SEQ ID NOS 310-319, 'Second Primer' as SEQ ID NOS 320-329, and 'Extend Primer' as SEQ ID NOS 330-339, respectively, in order of appearance.

| Gene ID | * | First Primer | Second Primer | Extend Primer |
|---|---|---|---|---|
| EDG6 | M | ACGTTGGATG TTCTGCCCCT CTACTCCAAG | ACGTTGGATG CATAGAGGCC CATGATGGTG | TTCTGCCTGG TGATCTT |
| RNAseP | T | ACGTTGGATG TCAGCTCTTC CCTTCATCAC | ACGTTGGATG CCTACCTCCC ACATGTAATG T | AACAAAGGAC ACCGTTA |

TABLE Y-continued

PCR Primers and Extend Primers
Table Y discloses 'First Primer' as SEQ ID NOS 310-319, 'Second Primer' as SEQ ID NOS 320-329, and 'Extend Primer' as SEQ ID NOS 330-339, respectively, in order of appearance.

| Gene ID | * | First Primer | Second Primer | Extend Primer |
|---|---|---|---|---|
| ApoE | T | ACGTTGGATG TTGACAGTTT CTCCTTCCCC | ACGTTGGATG GAATGTGACC AGCAACGCAG | GCAGGAAGAT GAAGGTT |
| SOX14 | M | ACGTTGGATG CGGTCGGCCC CACGGAAT | ACGTTGGATG CTCCTTCCTA GTGTGAGAAC CG | aAGGTTCCGG GGCTTGGG |
| SRY no2 | Y | ACGTGGATAG TAAAATAAGT TTCGAACTCT G | GAAGCATATG ATTGCATTGT CAAAAAC | aTTTCAATTT TGTCGCACT |
| SRY no1 | Y | ACGTTGGATG CACAGCTCAC CGCAGCAACG | ACGTTGGATG CTAGGTAGGT CTTTGTAGCC AA | AGCTGTAGGA CAATCGGGT |
| TBX3 | M | ACGTTGGATG TCTTTGTCTC TGCGTGCCC | ACGTTGGATG TTAATCACCC AGCGCATGGC | CCCTCCCGGT GGGTGATAAA |
| CACNA1G dig CTRL 1 | D | ACGTTGGATG GACTGAGCCC CAGAACTCG | ACGTTGGATG GTGGGTTTGT GCTTTCCACG | AGGGCCGGGG TCTGCGCGTG |
| DAPK1 dig CTRL 2 | D | ACGTTGGATG AAGCCAAGTT TCCCTCCGC | ACGTTGGATG CTTTTGCTTT CCCAGCCAGG | GAGGCACTGC CCGGACAAAC C |
| ALB | T | ACGTTAGCGT AGCAACCTGT TACATATTAA | ACGTTGGATG CTGAGCAAAG GCAATCAACA | CATTTTTCTA CATCCTTTGT TT |

TABLE Y

Competitor Oligonucleotide Sequence
Table Y discloses SEQ ID NOS 340-349, respectively, in order of appearance.

| Gene ID | * | Competitor |
|---|---|---|
| EDG6 | M | CCTTCTGCCCCTCTACTCCAAGCGCTACACCCTCTTCTGCCTGGTGATCTTTGCCGGCGTCCTGGCCACCATCATGGGCCTCTATG |
| RNAseP | T | GTGTGGTCAGCTCTTCCCTTCATCACATACTTGGAGAACAAAGGACACCGTTATCCATGCTTTTTCAACACATTACATGTGGGAGGTAGG |
| ApoE | T | GATTGACAGTTTCTCCTTCCCCAGACTGGCCAATCACAGGCAGGAAGATGAAGGTTTTGTGGGCTGCGTTGCTGGTCACATTCCTGGC |
| SOX14 | M | AAAACCAGAGATTCGCGGTCGGCCCCACGGAATCCCGGCTCTGTGTGCGCCCAGGTTCCGGGGCTTGGGTGTTGCCGGTTCTCACACTAGGAAGGAGC |
| SRY no2 | Y | GAGTTTTGGATAGTAAAATAAGTTTCGAACTCTGGCACCTTTCAATTTTGTCGCACTTTCCTTGTTTTTGACAATGCAATCATATGCTTC |
| SRY no1 | Y | GCAGCCAGCTCACCGCAGCAACGGGACCGCTACAGCCACTGGACAAAGCTGTAGGACAATCGGGTGACATTGGCTACAAAGACCTACCTAGATGC |

TABLE Y-continued

Competitor Oligonucleotide Sequence
Table Y discloses SEQ ID NOS 340-349, respectively, in order of appearance.

| Gene ID | * | Competitor |
|---|---|---|
| TBX3 | M | GAACTCCTCTTTGTCTCTGCGTGCCCGGCGCGCCCCCCTCCCGGTGGGTGATAAATCCACTCTGGCGCCGGCCATGCGCTGGGTGATTAATTTGCGA |
| CACNA1G dig CTRL 1 | D | GTGGGTTTGTGCTTTCCACGCGTGCACACACACGCGCAGACCCCGGCCCTTGCCCCGCCTACCTCCCCGAGTTCTGGGGCTCAGTC |
| DAPK1 dig CTRL 2 | D | GCGCCAGCTTTTGCTTTCCCAGCCAGGGCGCGGTGAGGTTTGTCCGGGCAGTGCCTCGAGCAACTGGGAAGGCCAAGGCGGAGGGAAAC |
| ALB | T | GCGTAGCAACCTGTTACATATTAAAGTTTTATTATACTACATTTTTCTACATCCTTTGTTTTAGGGTGTTGATTGCCTTTGCTCAGTATCTTCAGC |

Figure 12:
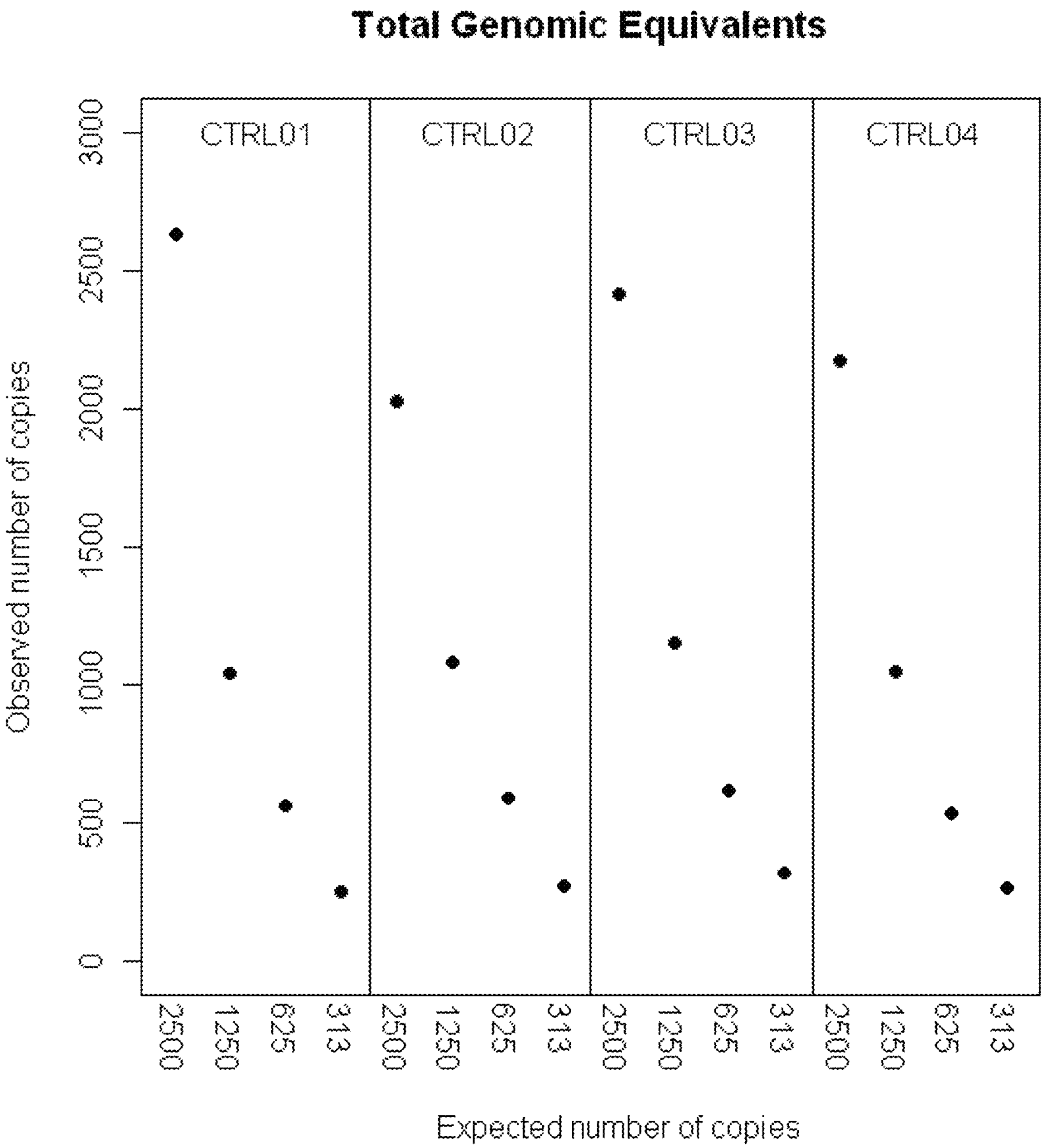
FIG. 12: Shows the total number of amplifiable genomic copies from four different DNA samples isolated from the blood of non-pregnant women. Each sample was diluted to contain approximately 2500, 1250, 625 or 313 copies per reaction. Each measurement was obtained by taking the mean DNA/competitor ratio obtained from two total copy number assays (ALB and RNAseP in Table X). As FIG. 12 shows, the total copy number is accurate and stable across the different samples, thus validating the usefulness of the competitor-based approach.

T = Assay for Total Amount
M = Assay for Methylation quantification
Y = Y-Chromosome Specific Assay
D = Digestion control Model System Using Genomic DNA In order to determine the sensitivity and accuracy of the method when determining the total number of amplifiable genomic copies in a sample, a subset of different DNA samples isolated from the blood of non-pregnant women was tested. Each sample was diluted to contain approximately 2500, 1250, 625 or 313 copies per reaction. The total number of amplifiable genomic copies was obtained by taking the mean DNA/competitor ratio obtained from the three total copy number assays. The results from the four different samples are shown in FIG. 12.

Figure 13A:
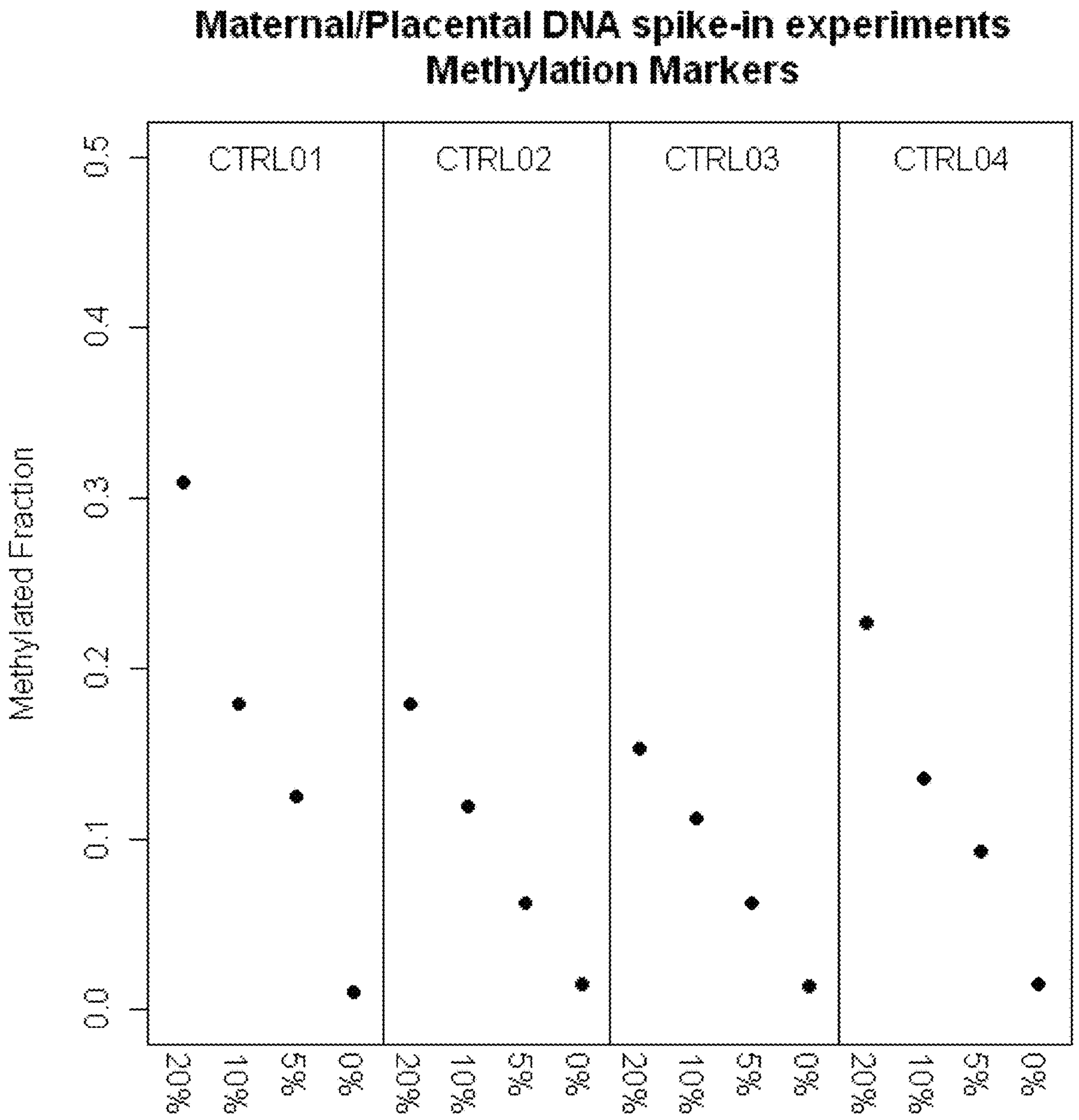
FIGS. 13A and B: A model system was created that contained a constant number of maternal non-methylated DNA with varying amounts of male placental methylated DNA spiked-in. The samples were spiked with male placental amounts ranging from approximately 0 to 25% relative to the maternal non-methylated DNA. The fraction of placental DNA was calculated using the ratios obtained from the methylation assays (FIG. 13A) and the Y-chromosome marker (FIG. 13B) as compared to the total copy number assay. The methylation and Y-chromosome markers are provided in Table X.
Figure 13B:
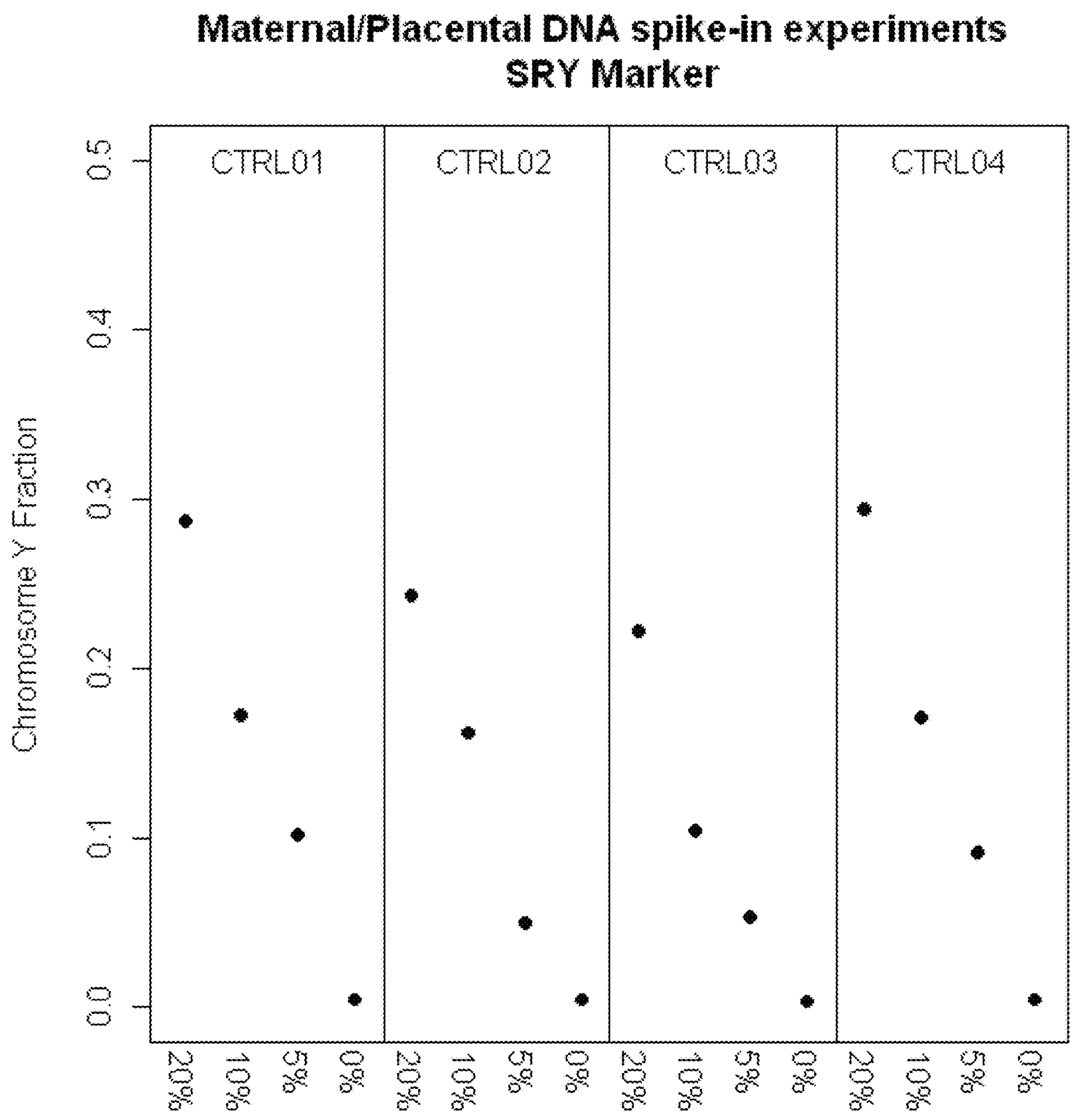

To optimize the reaction, a model system was developed to simulate DNA samples isolated from plasma. These samples contained a constant number of maternal non-methylated DNA and were spiked with different amounts of male placental methylated DNA. The samples were spiked with amounts ranging from approximately 0 to 25% relative to the maternal non-methylated DNA. The results are shown in FIGS. 13A and B. The fraction of placental DNA was calculated using the ratios obtained from the methylation assays (FIG. 13A), the SRY markers (FIG. 13B) and the total copy number assays. The primer sequences for the methylation assays (TBX), Y-chromosome assays (SRY) and total copy number (APOE) are provided above. The model system demonstrated that the methylation-based method performed equal to the Y-chromosome method (SRY markers), thus validating the methylation-based method as a sex-independent fetal quantifier.

Plasma Samples

To investigate the sensitivity and accuracy of the methods in clinical samples, 33 plasma samples obtained from women pregnant with a male fetus were investigated using the multiplex scheme from Table X. For each reaction, a quarter of the DNA obtained from a 4 ml extraction was used in order to meet the important requirement that only a portion of the total sample is used.

Total Copy Number Quantification

The results from the total copy number quantification can be seen in FIGS. 14A and B. In FIG. 14A, the copy number for each sample is shown. Two samples (nos. 25 and 26) have a significantly higher total copy number than all the other samples. In general, a mean of approximately 1300 amplifiable copies/ml plasma was obtained (range 766-

2055). FIG. 14B shows a box-and-whisker plot of the given values, summarizing the results.

Correlation Between Results Obtained from the Methylation Markers and the Y-Chromosome Marker In FIGS. 15A and B, the numbers of fetal copies for each sample are plotted. As all samples were from male pregnancies. The copy numbers obtained can be calculated using either the methylation or the Y-chromosome-specific markers. As can be seen in FIG. 15B, the box-and-whisker plot of the given values indicated minimal difference between the two different measurements.

Figure 16:
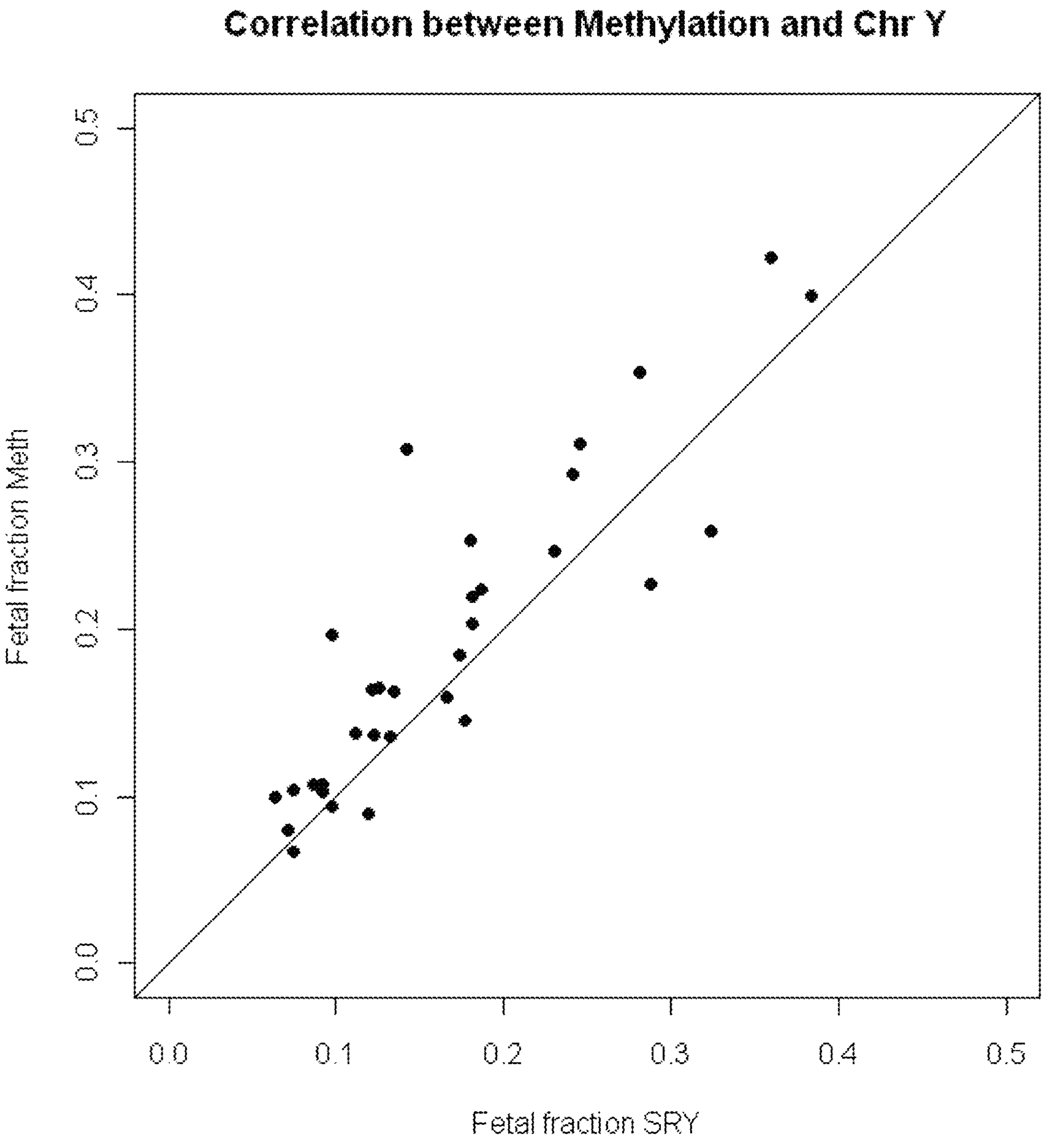
FIG. 16: Shows a paired correlation between the results obtained using the methylation markers versus the Y-chromosome marker from FIG. 15A.

The results showing the correlation between results obtained from the methylation markers and the Y-chromosome marker (SRY) is shown in FIG. 16. Again, the methylation-based method performed equal to the Y-chromosome method (SRY markers), further validating the methylation-based method as a sex-independent and polymorphism-independent fetal quantifier. The multiplexed assays disclosed in Table X were used to determine the amount fetal nucleic.

Figure 17:
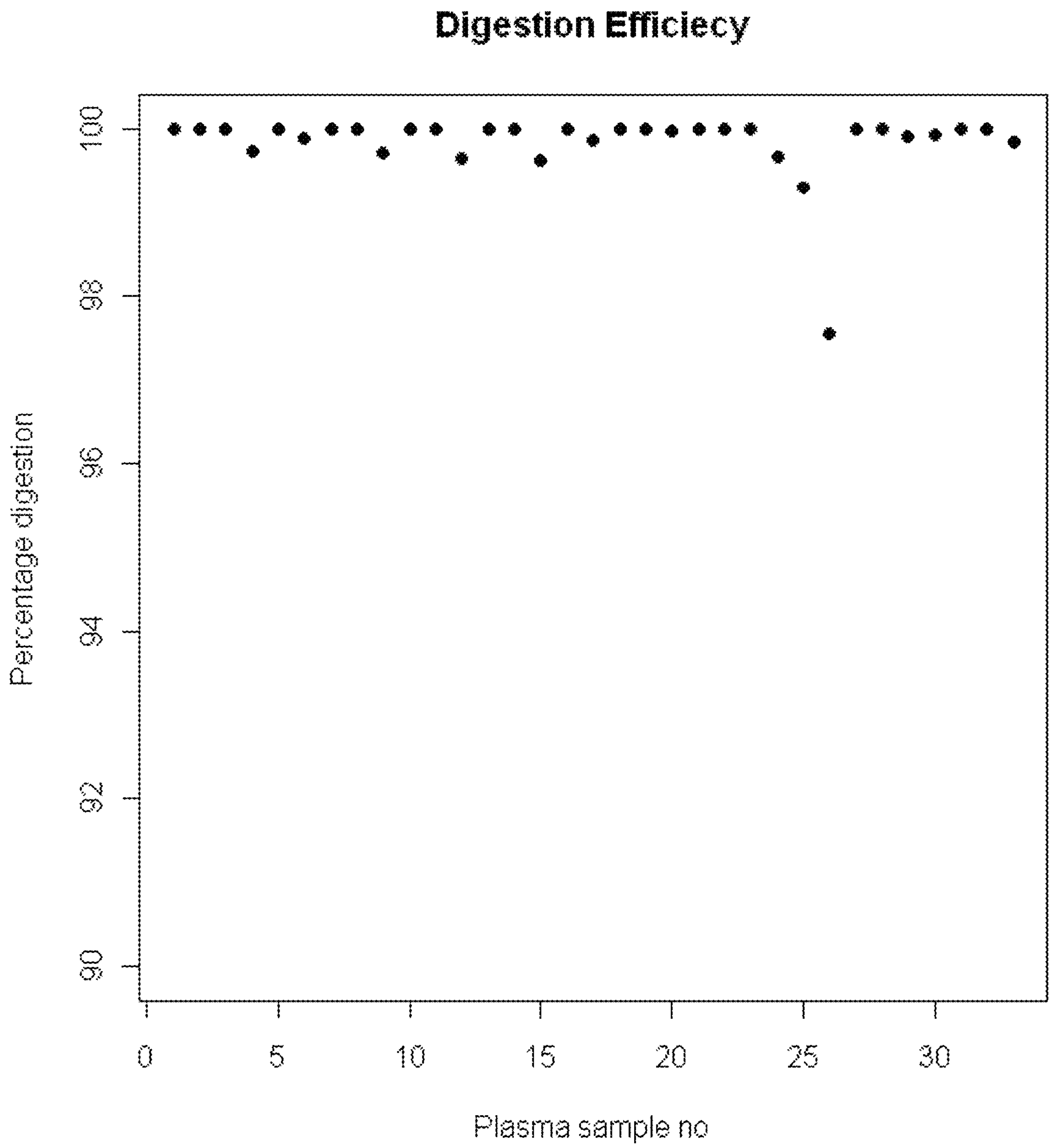
FIG. 17: Shows the digestion efficiency of the restriction enzymes using the ratio of digestion for the control versus the competitor and comparing this value to the mean total copy number assays. Apart from sample 26 all reactions indicate the efficiency to be above about 99%.

Finally, the digestion efficiency was determined by using the ratio of digestion for the control versus the competitor and comparing this value to the mean total copy number assays. See FIG. 17. Apart from sample 26 all reactions indicate the efficiency to be above 99%.

Data Analysis

Mass spectra analysis was done using Typer 4 (a Sequenom software product). The peak height (signal over noise) for each individual DNA analyte and competitor assay was determined and exported for further analysis.

The total number of molecules present for each amplicon was calculated by dividing the DNA specific peak by the competitor specific peak to give a ratio. (The "DNA" Peak in FIGS. 18 and 19 can be thought of as the analyte peak for a given assay). Since the number of competitor molecules added into the reaction is known, the total number of DNA molecules can be determined by multiplying the ratio by the number of added competitor molecules.

The fetal DNA fraction (or concentration) in each sample was calculated using the Y-chromosome-specific markers for male pregnancies and the mean of the methylated fraction for all pregnancies. In brief, for chromosome Y, the ratio was obtained by dividing the analyte (DNA) peak by the competitor peak and multiplying this ratio by the number of competitor molecules added into the reaction. This value was divided by a similar ratio obtained from the total number of amplifiable genome equivalents determination (using the Assay(s) for Total Amount). See FIG. 18. Since the total amount of nucleic acid present in a sample is a sum of maternal and fetal nucleic acid, the fetal contribution can be considered to be a fraction of the larger, background maternal contribution. Therefore, translating this into the equation shown in FIG. 18, the fetal fraction (k) of the total nucleic acid present in the sample is equal to the equation: $k=2\times R/(1-2R)$, where R is the ratio between the Y-chromosome amount and the total amount. Since the Y-chromosome is haploid and Assays for the Total Amount are determined using diploid targets, this calculation is limited to a fetal fraction smaller than 50% of the maternal fraction.

Figure 19:
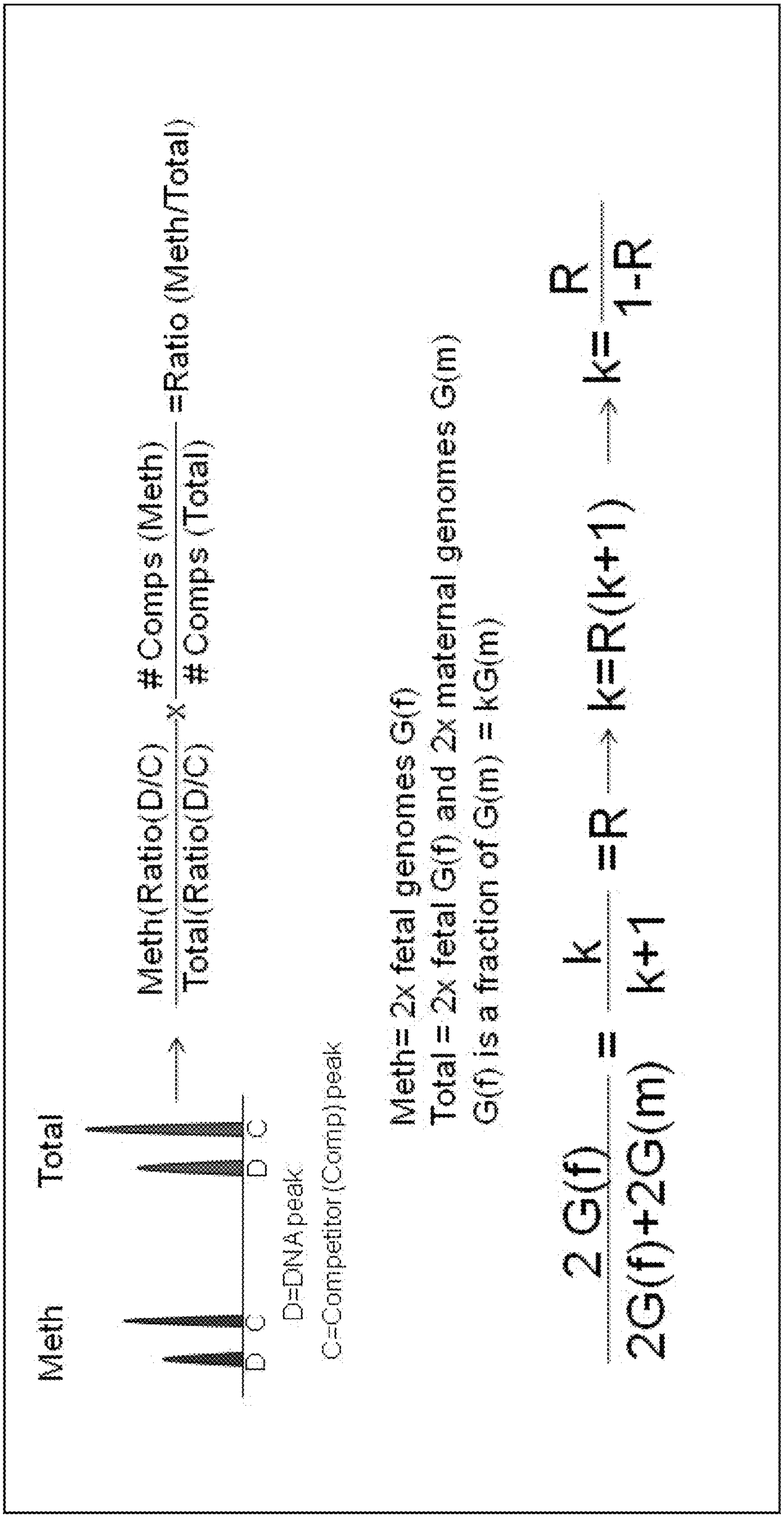
FIG. 19: Provides a specific method for calculating fetal DNA fraction (or concentration) in a sample without the Y-chromosome-specific markers. Instead, only the Assays for Methylation Quantification were used to determine the concentration of fetal DNA.

In FIG. 19, a similar calculation for the fetal concentration is shown by using the methylation specific markers (see Assays for Methylation Quantification). In contrast to Y-chromosome specific markers, these markers are from diploid targets, therefore, the limitations stated for the Y-Chromosome Specific Assay can be omitted. Thus, the fetal fraction (k) can be determined using the equation: $k=R(1-R)$, where R is the ratio between the methylation assay and the total assay.

Simulation

Figure 8:
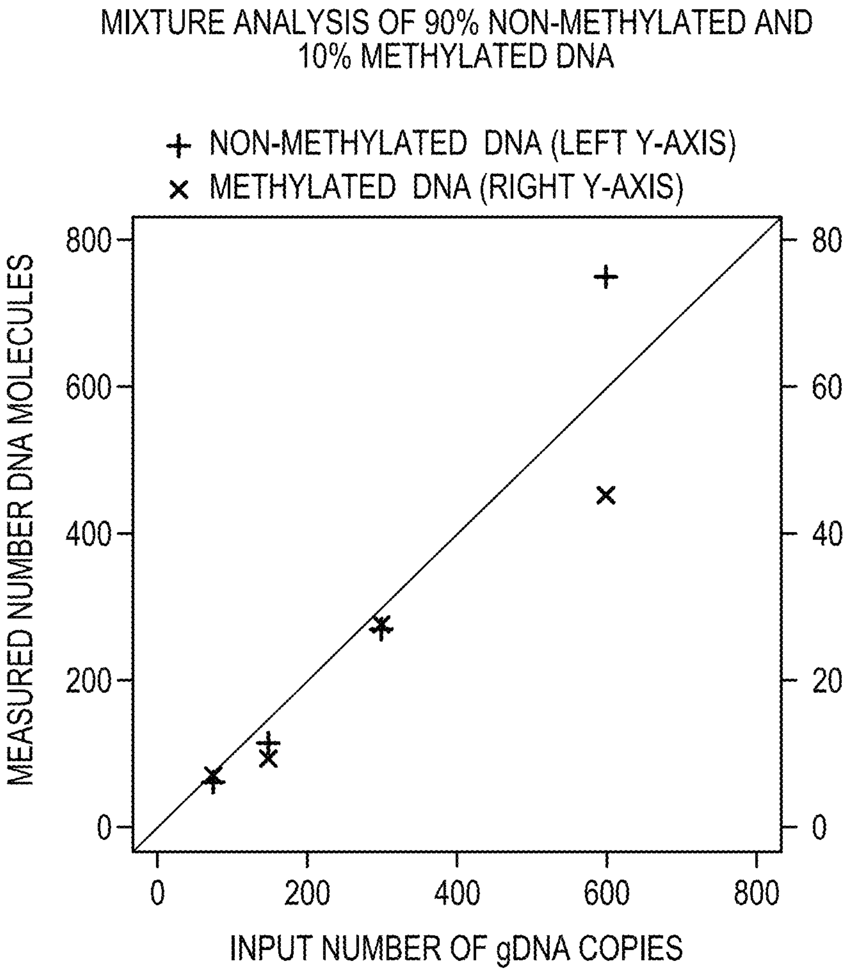
FIG. 8: Shown is the correlation between the number of gDNA molecules that were expected and the number of molecules measured by competitive PCR in combination with mass spectrometry analysis. In this experiment we used DNA derived from whole blood (black plus signs) and commercially available fully methylated DNA (red crosses) in a 90 to 10 ratio. We used the MBD-FC fusion protein to separate the non-methylated and the methylated fraction of DNA. Each fraction was subject to competitive PCR analysis with mass spectrometry readout. The method has been described earlier for the analysis of copy number variations and is commercially available for gene expression analysis. The approach allows absolute quantification of DNA molecules with the help of a synthetic oligonucleotides of know concentration. In this experiment we targeted the MGMT locus, which was not methylated in the whole blood sample used here. Using an input of 300 total gDNA copies we expect to see 270 copies of non-methylated DNA and 30 copies of methylated DNA. The measured copy numbers are largely in agreement with the expected values. The data point at 600 copies of input DNA indicates a bias in the reaction and shows that this initial proof of concept experiment needs to be followed up with more development work, before the assay can be used. However, this initial data indicates the feasibility of the approach for capturing and quantifying of a few copies of methylated DNA in the presence of an excess of unmethylated DNA species.
Figure 9A:
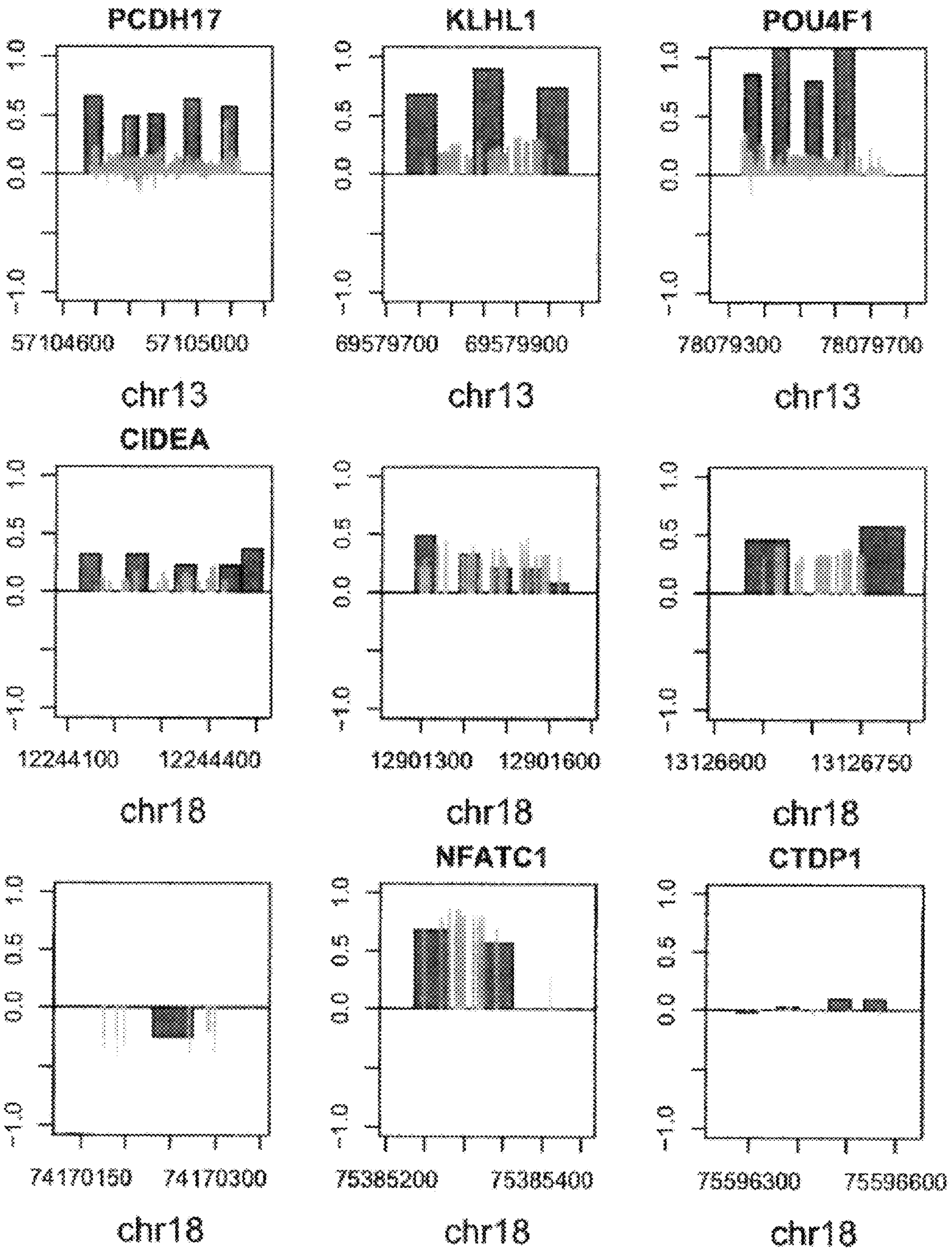
FIG. 9A-9L show bar graph plots of the methylation differences obtained from the microarray analysis (dark bars) and the mass spectrometry analysis (light grey bars) with respect to their genomic location. For each of the 85 region that were identified to be differentially methylated by microarray an individual plot is provided. The x axis for each plot shows the chromosomal position of the region. The y axis depicts the log ration (in case of the microarrays) and the methylation differences (in case of the mass spectrometry results). For the microarrays each hybridization probe in the area is shown as a single black (or dark grey) bar. For the mass spectrometry results each CpG site, is shown as a light grey bar. Bars showing values greater than zero indicate higher DNA methylation in the placenta samples compared to the maternal DNA. For some genes the differences are small (i.e. RB1 or DSCR6) but still statistically significant. Those regions would be less suitable for a fetal DNA enrichment strategy.
Figure 9B:
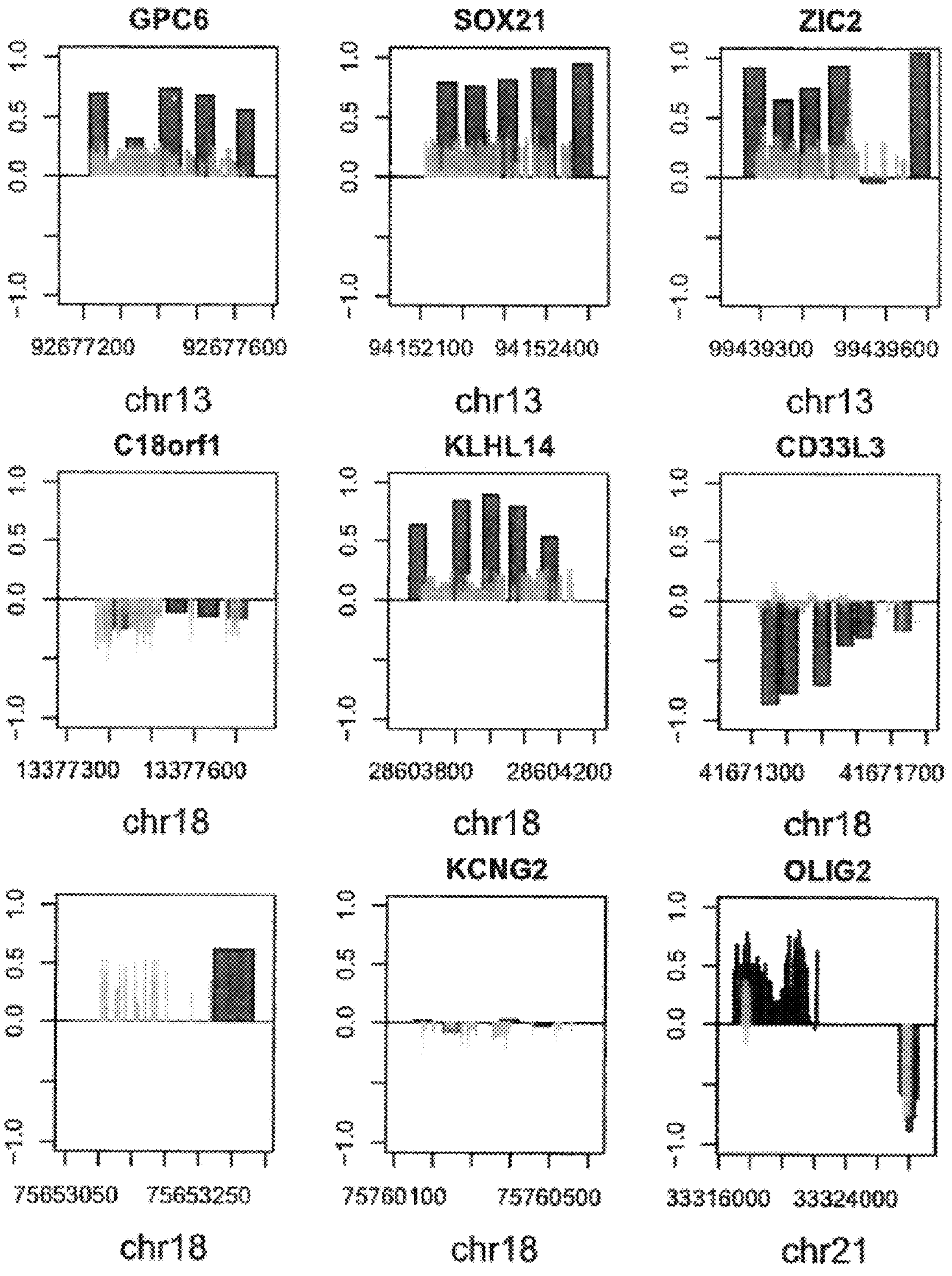
Figure 9C:
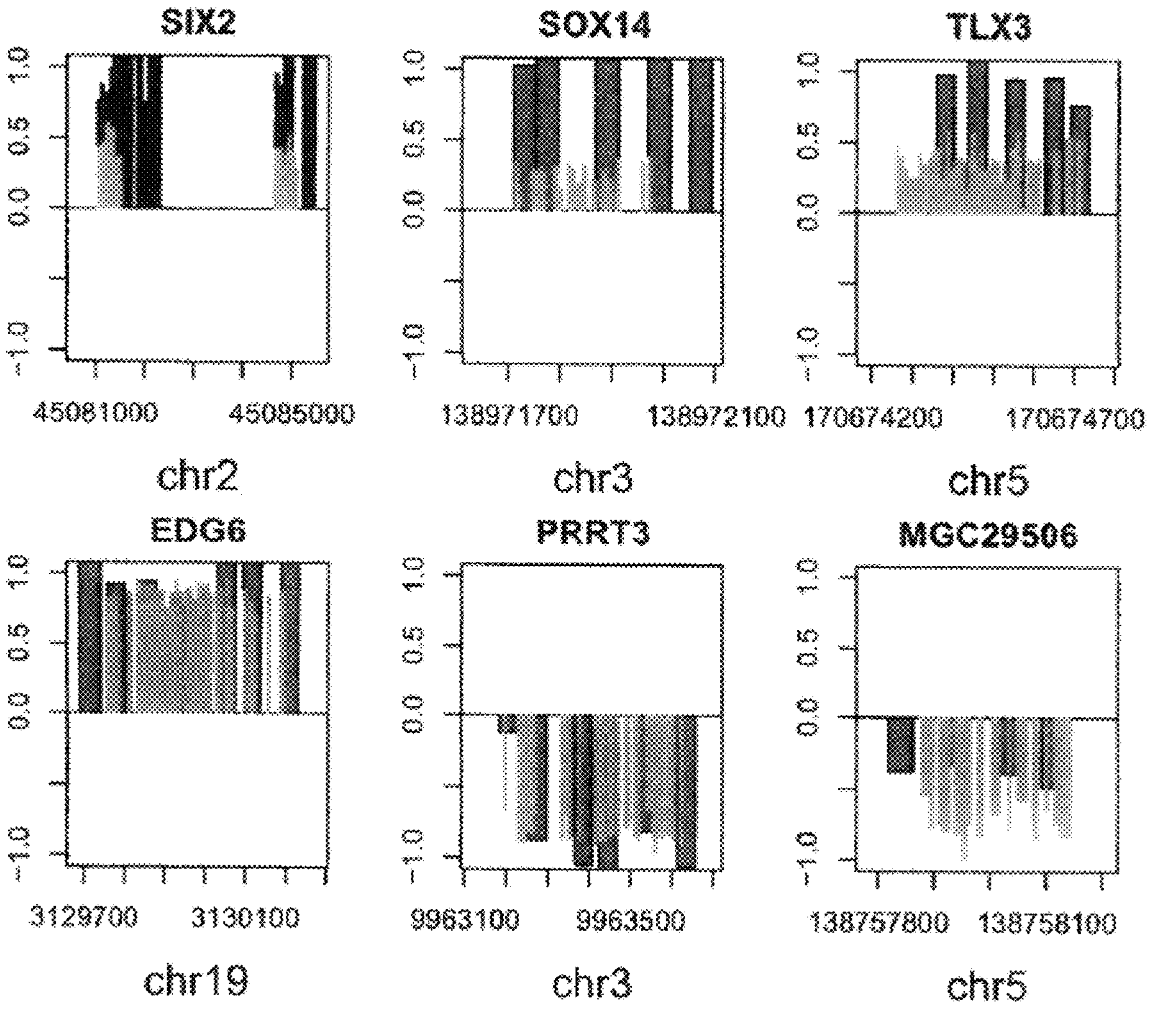
Figure 9D:
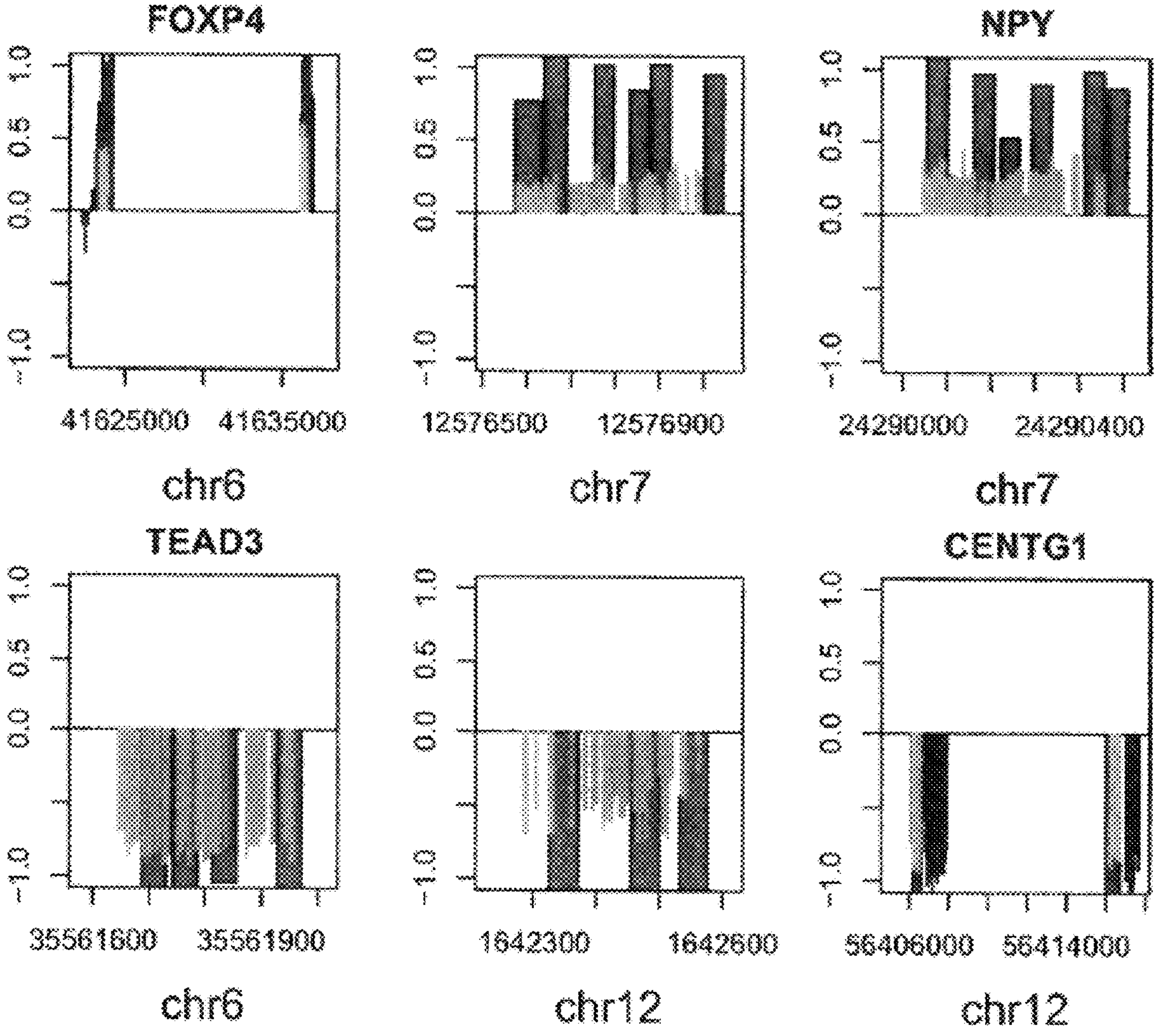
Figure 9E:
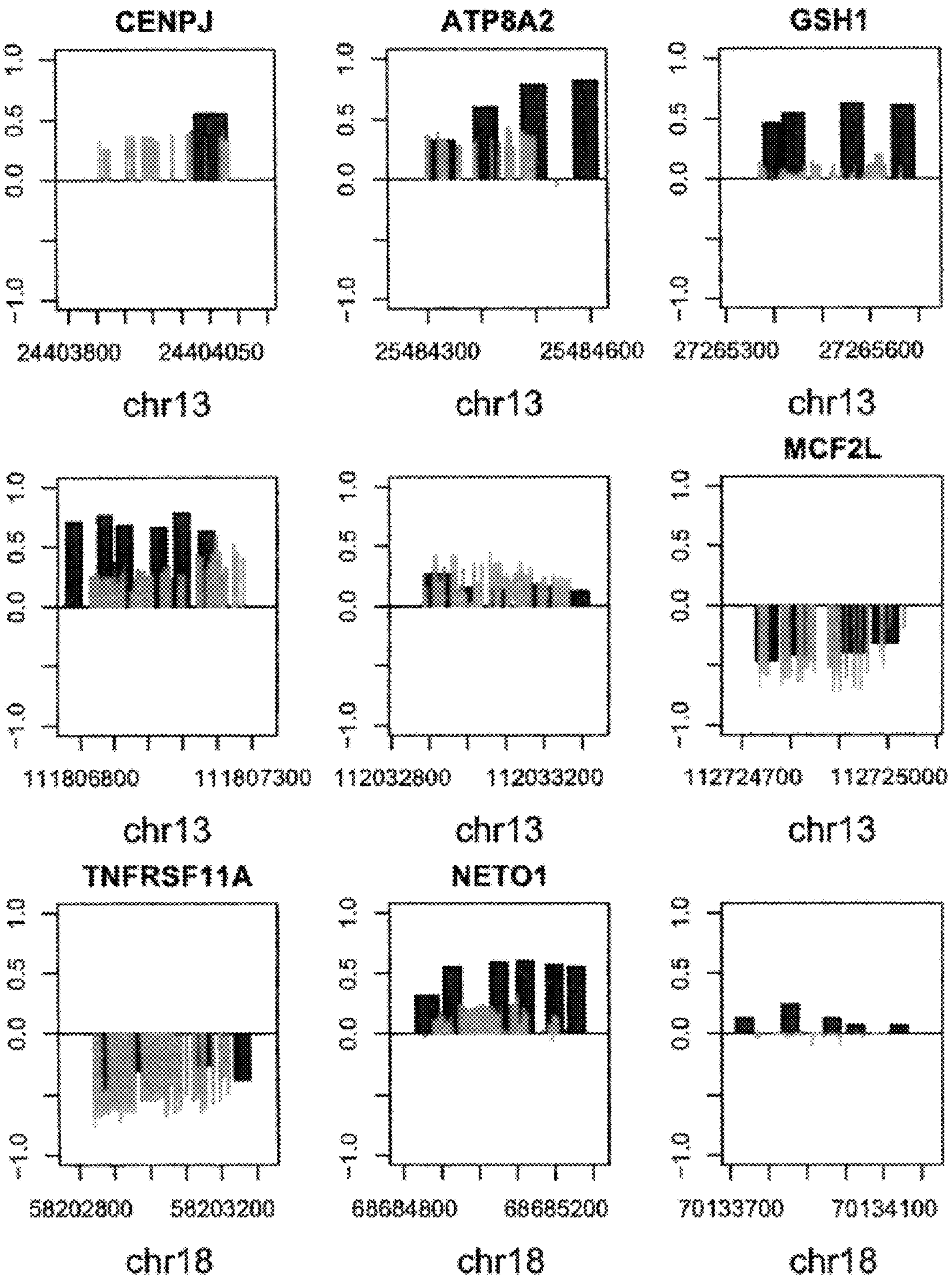
Figure 9F:
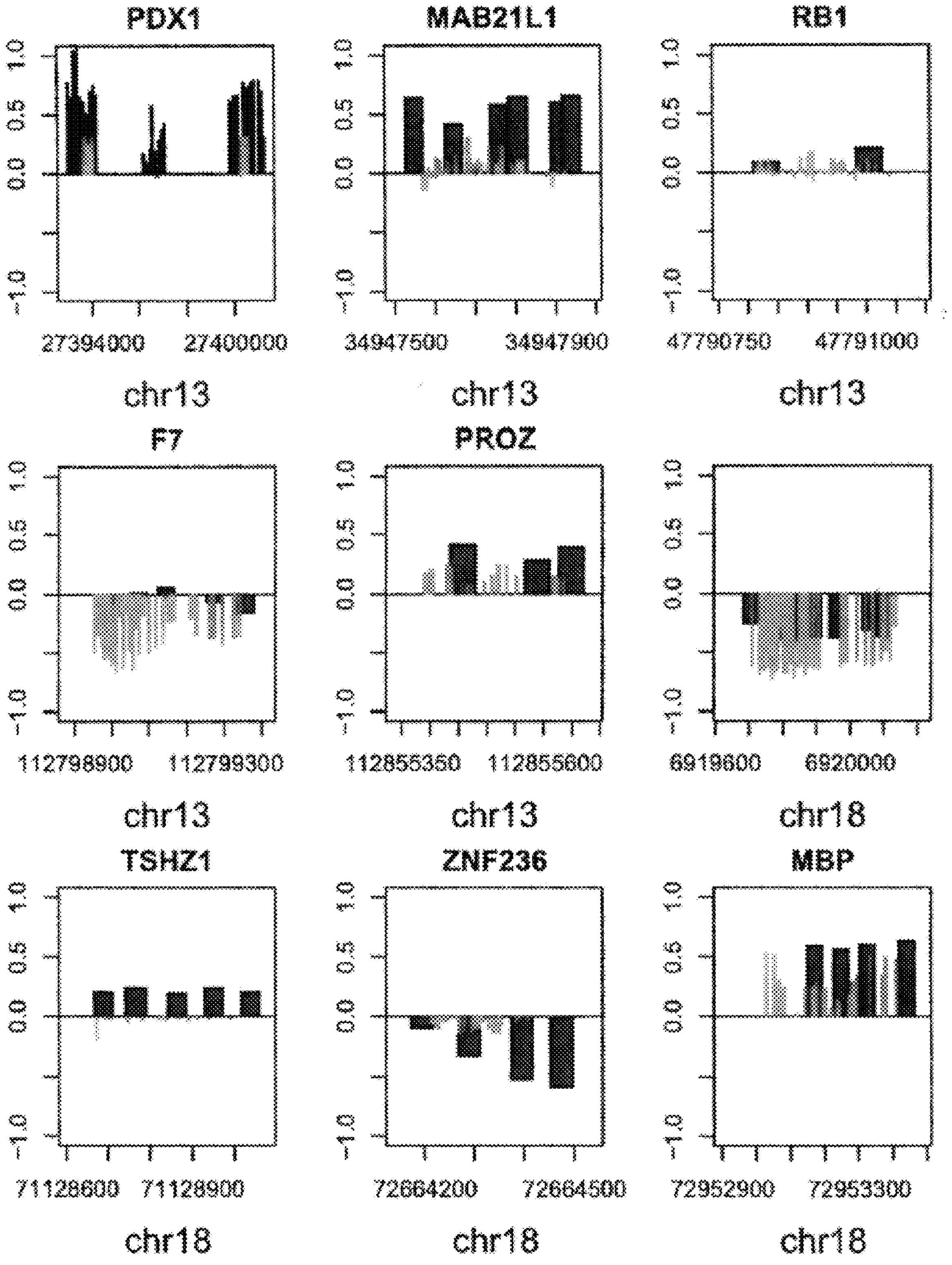
Figure 9G:
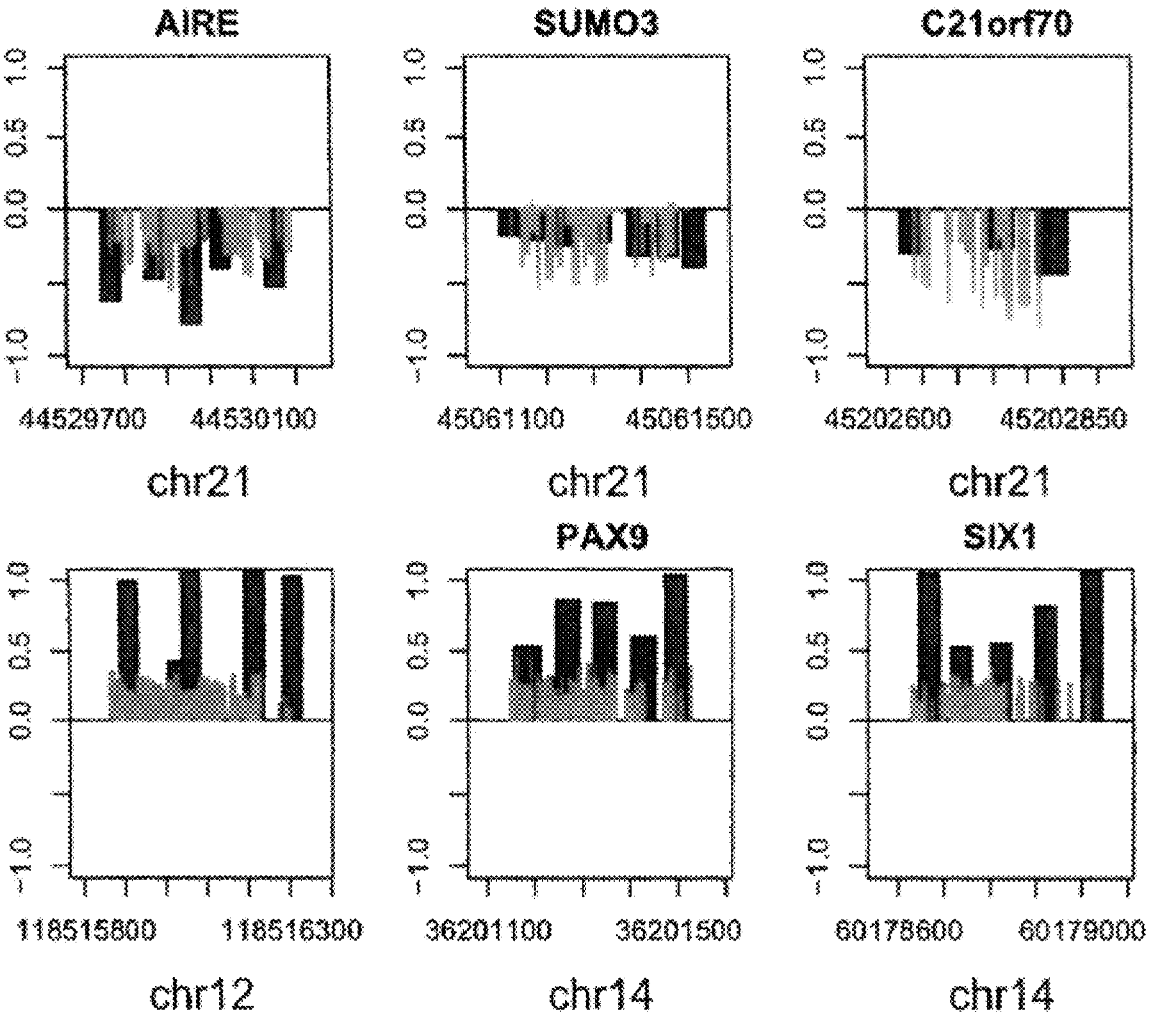
Figure 9H:
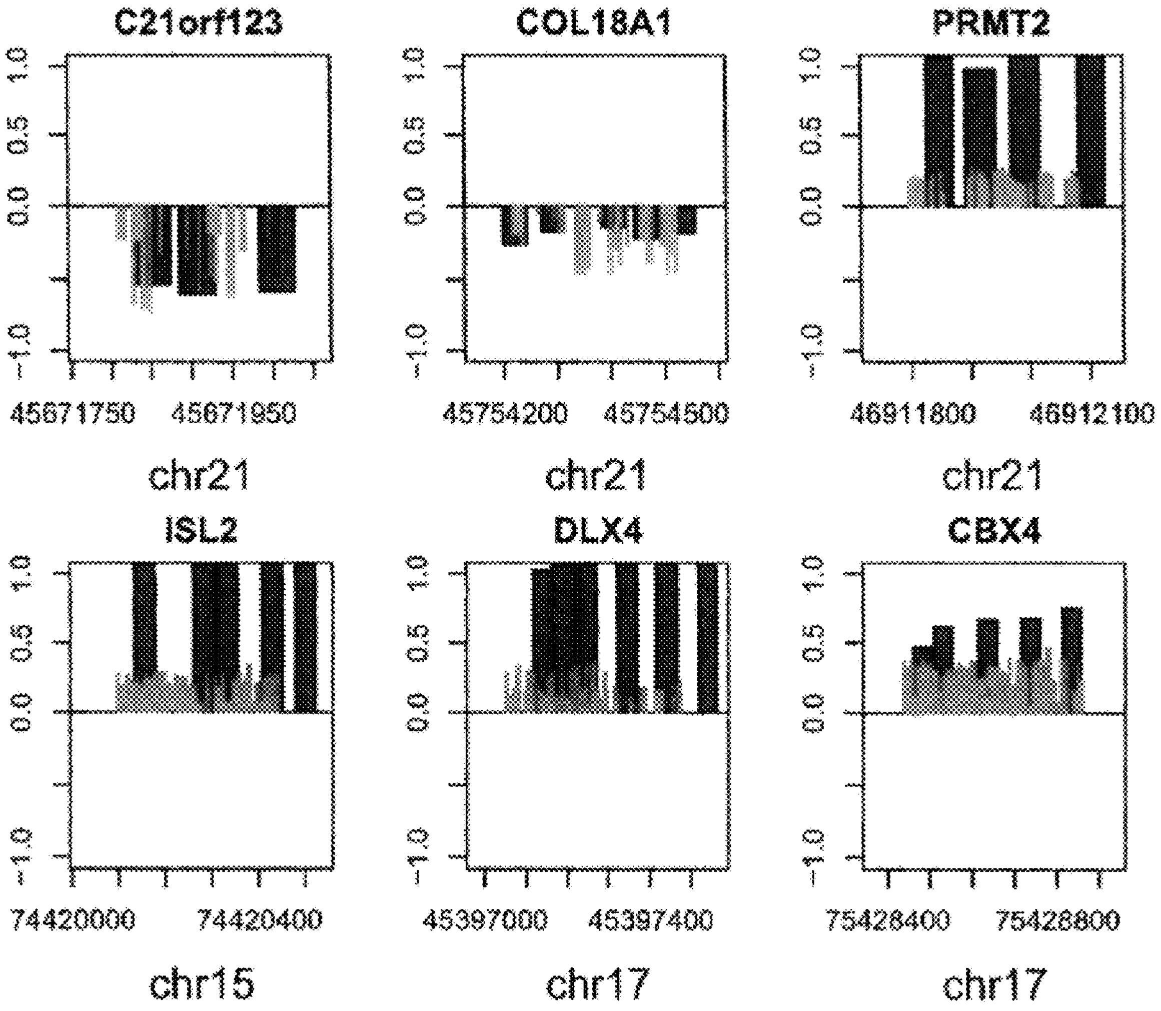
Figure 9I:
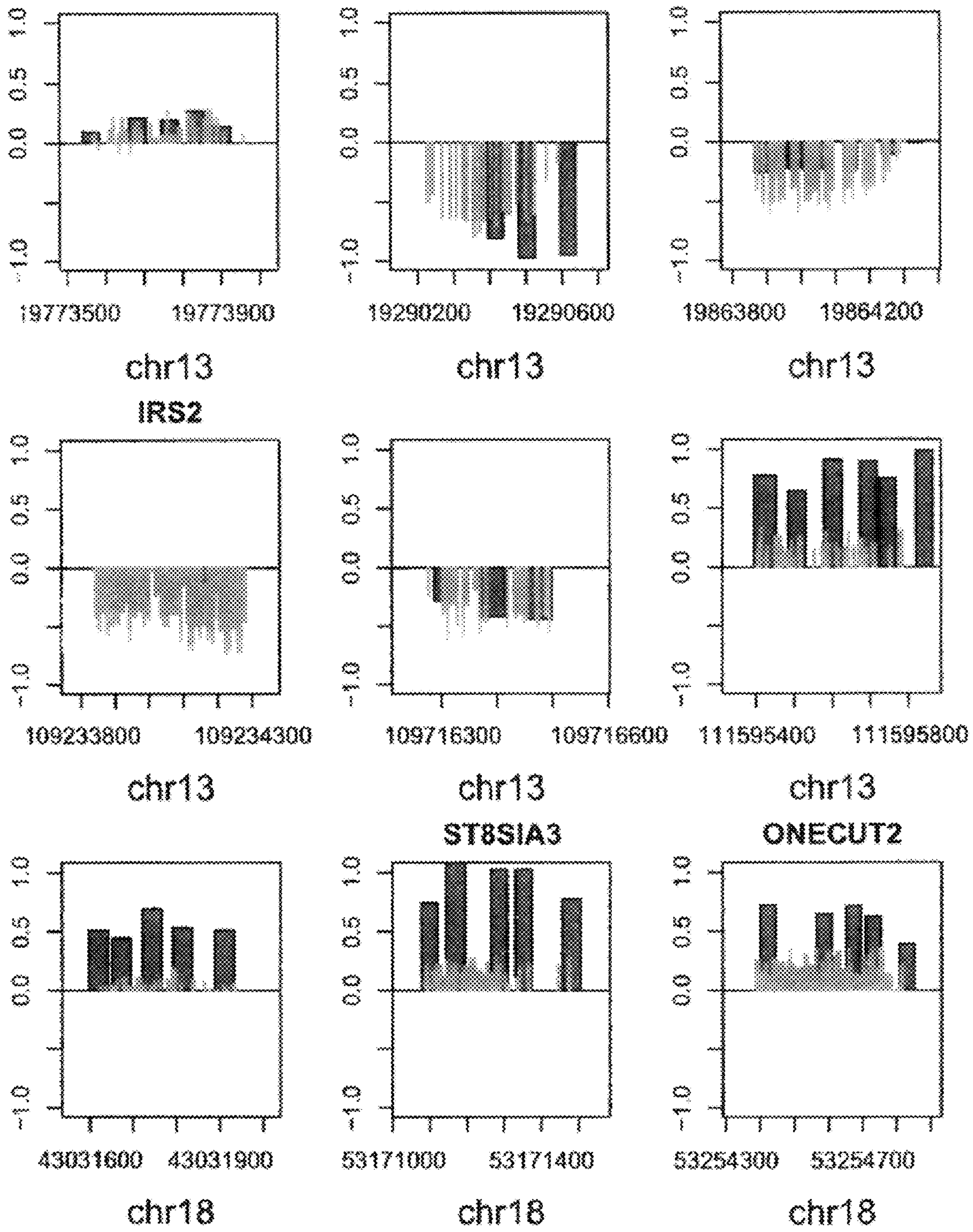
Figure 9J:
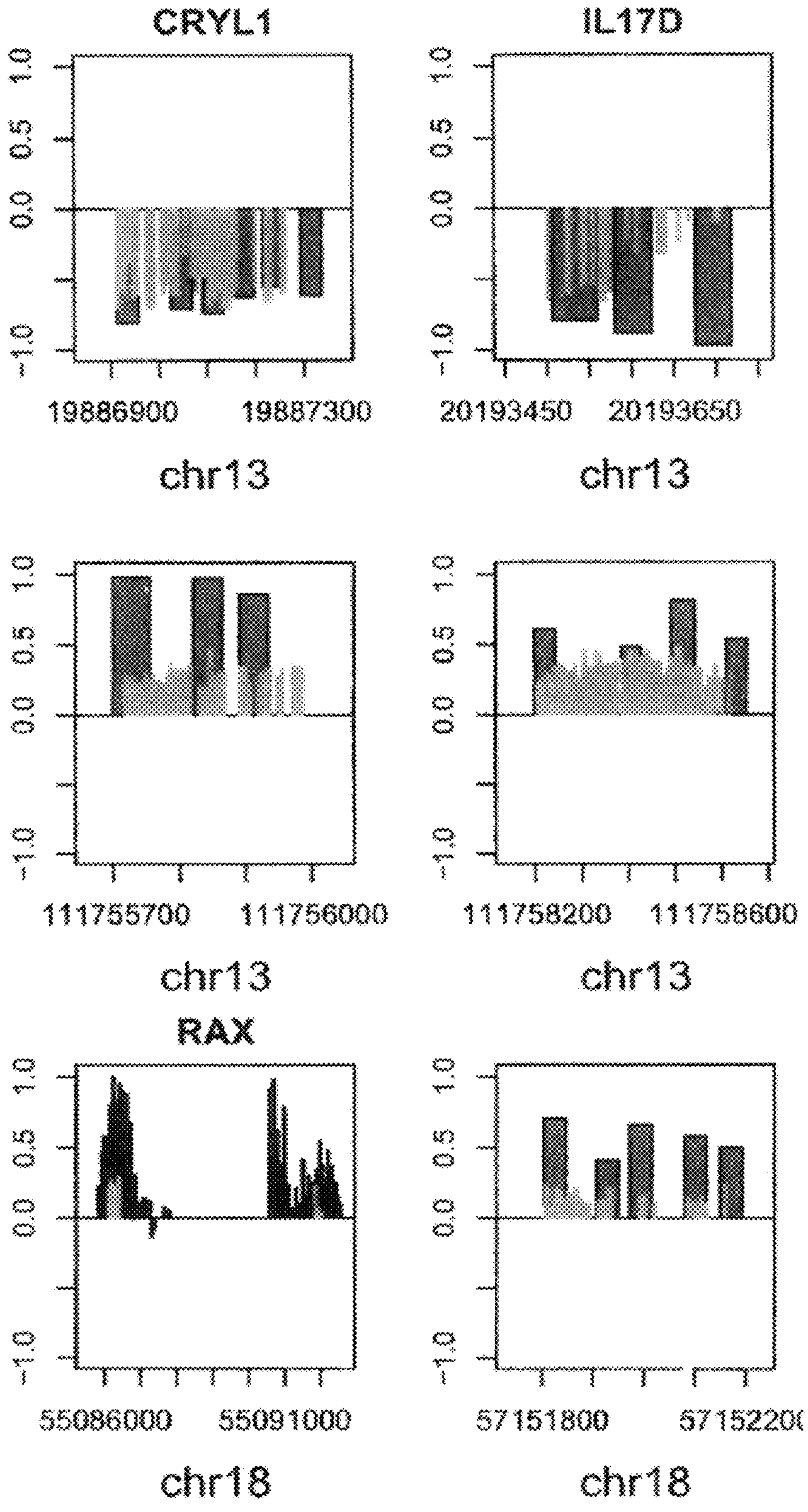
Figure 9K:
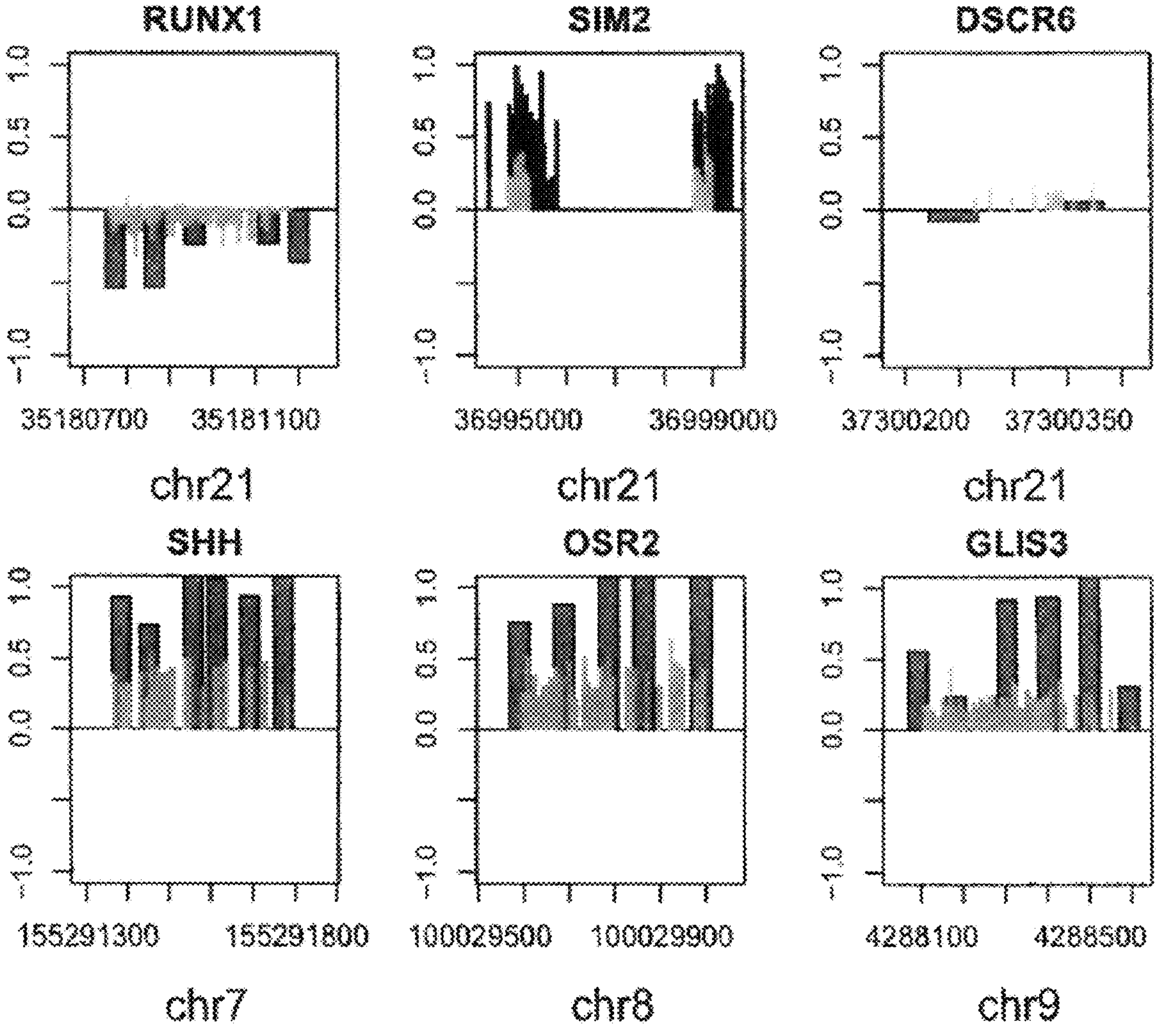
Figure 9L:
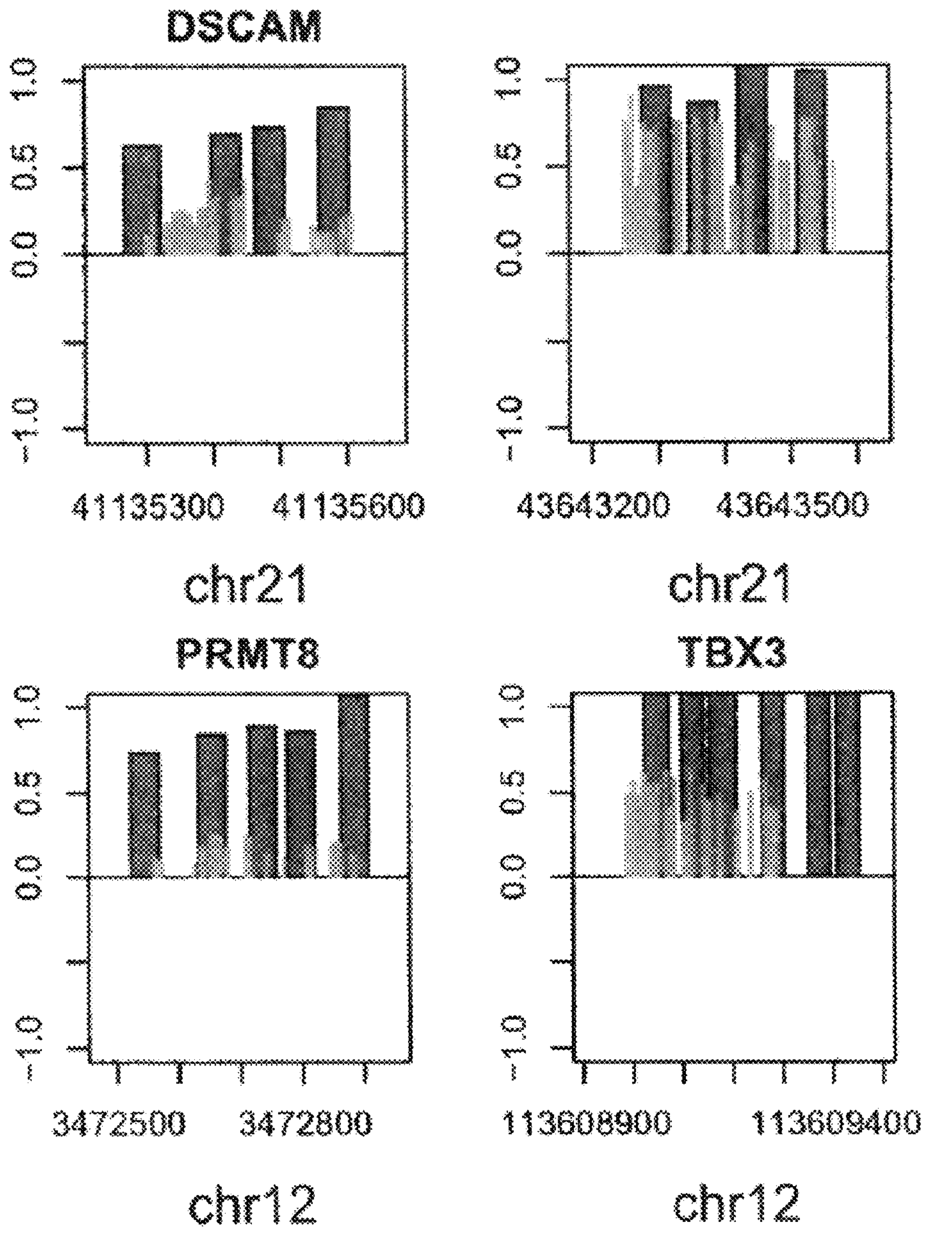

A first simple power calculation was performed that assumes a measurement system that uses 20 markers from chromosome 21, and 20 markers from one or more other autosomes. Starting with 100 copies of fetal DNA, a measurement standard deviation of 25 copies and the probability for a type I error to be lower than 0.001, it was found that the methods of the invention will be able to differentiate a diploid from a triploid chromosome set in 99.5% of all cases. The practical implementation of such an approach could for example be achieved using mass spectrometry, a system that uses a competitive PCR approach for absolute copy number measurements. The method can run 20 assays in a single reaction and has been shown to have a standard deviation in repeated measurements of around 3 to 5%. This method was used in combination with known methods for differentiating methylated and non-methylated nucleic acid, for example, using methyl-binding agents to separate nucleic acid or using methylation-sensitive enzymes to digest maternal nucleic acid. FIG. 8 shows the effectiveness of MBD-FC protein (a methyl-binding agent) for capturing and thereby separating methylated DNA in the presence of an excess of unmethylated DNA (see FIG. 8).

A second statistical power analysis was performed to assess the predictive power of an embodiment of the Methylation-Based Fetal Diagnostic Method described herein. The simulation was designed to demonstrate the likelihood of differentiating a group of trisomic chromosome 21 specific markers from a group of reference markers (for example, autosomes excluding chromosome 21). Many parameters influence the ability to discriminate the two populations of markers reliably. For the present simulation, values were chosen for each parameter that have been shown to be the most likely to occur based on experimentation. The following parameters and respective values were used:

Copy Numbers

- Maternal copy numbers=2000
- Fetal copy numbers for chromosomes other than 21, X and Y=200
- Fetal copy numbers for chromosome 21 in case of euploid fetus=200
- Fetal copy numbers for chromosome 21 in case of aneuploid T21 fetus=300

Percent fetal DNA (before methylation-based enrichment)=10% (see above)

Methylation Frequency

- Average methylation percentage in a target region for maternal DNA=10%
- Average methylation percentage in a target region for fetal DNA=80%

Average percentage of non-methylated and non-digested maternal DNA (i.e., a function of restriction efficiency (among other things)=5%

Number of assays targeting chromosome 21=10

Number of assays targeting chromosomes other than 21, X and Y=10

Figure 20:
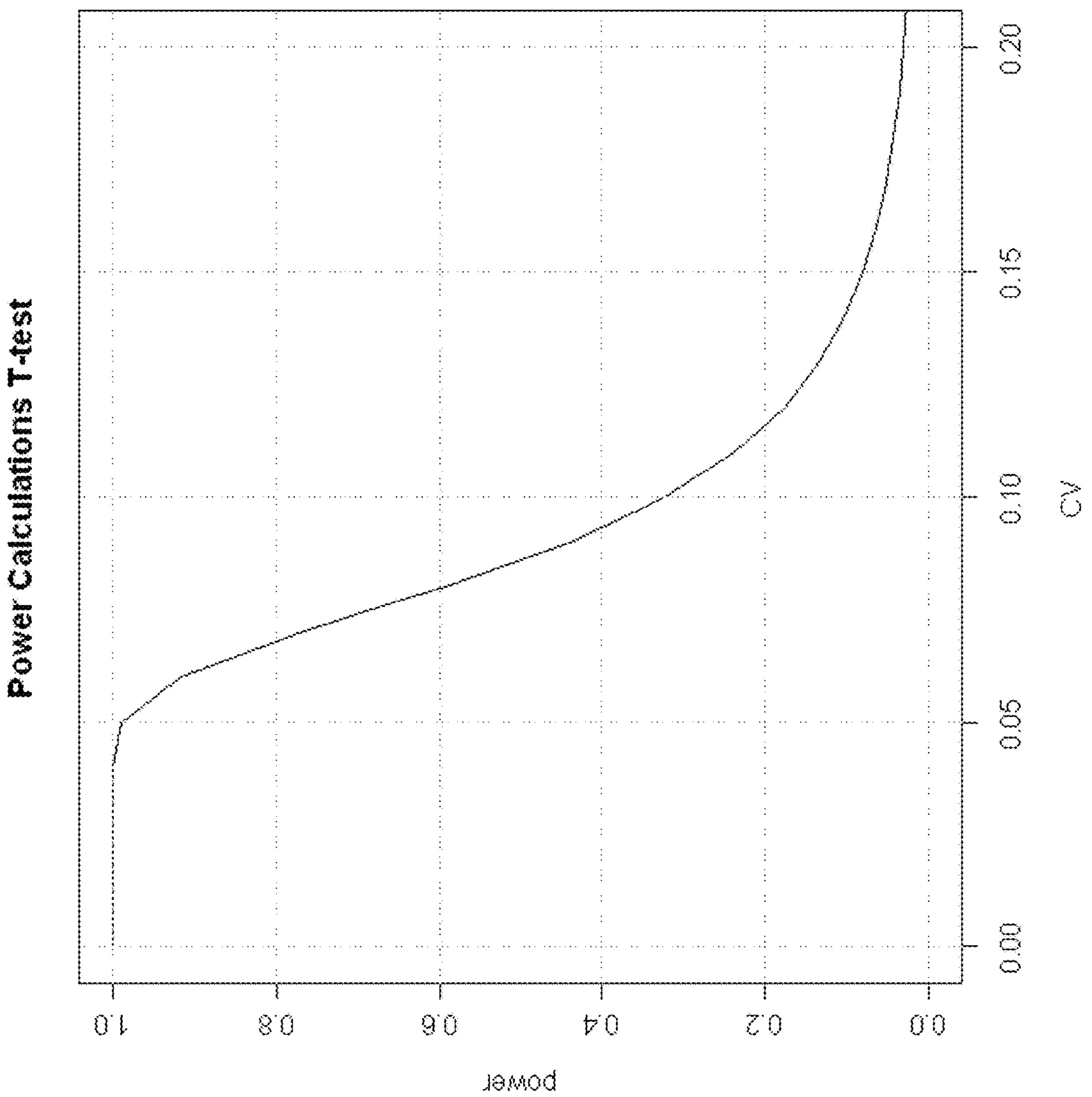
FIG. 20: Shows a power calculation t-test for a simulated trisomy 21 diagnosis using the methods of the invention. The Figure shows the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less.

The results are displayed in FIG. 20. Shown is the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less. Based on this simulation, the method represents a powerful noninvasive diagnostic method for the prenatal detection of fetal aneuploidy that is sex-independent and will work in all ethnicities (i.e., no allelic bias).

Example 3—Additional Differentially-Methylated Targets

Differentially-Methylated Targets not Located on Chromosome 21

Additional differentially-methylated targets were selected for further analysis based upon previous microarray analysis. See Example 1 for a description of the microarray analysis. During the microarray screen, differentially methylated regions (DMRs) were defined between placenta tissue and PBMC. Regions were selected for EpiTYPER confirmation based upon being hypermethylated in placenta relative to PBMC. After directionality of the change was selected for, regions were chosen based upon statistical significance with regions designed beginning with the most significant and working downward in terms of significance. These studies were performed in eight paired samples of PBMC and placenta. Additional non-chromosome 21 targets are provided in Table 1B, along with a representative genomic sequence from each target in Table 4B.

Differentially-Methylated Targets Located on Chromosome 21

The microarray screen uncovered only a subset of DMRs located on chromosome 21. The coverage of chromosome 21 by the microarray, however, was insufficient. Therefore a further analysis was completed to examine all 356 CpG islands on chromosome 21 using the standard settings of the UCSC genome browser. As shown in Table 1C below, some of these targets overlapped with those already examined in Table 1A. More specifically, CpG sites located on chromosome 21 including ~1000 bp upstream and downstream of each CpG was investigated using Sequenom's EpiTYPER® technology. See Example 1, "Validation using Sequenom® EpiTYPER™" for a description of Sequenom's EpiTYPER® technology. These studies were performed in eight paired samples of PBMC and placenta. In addition, since DMRs may also be located outside of defined CpG islands, data mining was performed on publicly available microarray data to identify potential candidate regions with the following characteristics: hypermethylated in placenta relative to maternal blood, not located in a defined CpG island, contained greater than 4 CpG dinucleotides, and contained a recognition sequence for methylation sensitive restriction enzymes. Regions that met these criteria were then examined using Sequenom's EpiTYPER® technology on eight paired PBMC and placenta samples. Additional chromosome 21 targets are provided in Table 1C, along with a representative genomic sequence from each target in Table 4C.

Tables 1B and 1C provide a description of the different targets, including their location and whether they were analyzed during the different phases of analysis, namely microarray analysis, EpiTYPER 8 analysis and EpiTYPER 73 analysis. A "YES" indicates it was analyzed and a "NO" indicates it was not analyzed. The definition of each column in Table 1B and 1C is listed below.

Region Name: Each region is named by the gene(s) residing within the area defined or nearby. Regions where no gene name is listed but rather only contain a locus have no refseq genes in near proximity.

Gene Region: For those regions contained either in close proximity to or within a gene, the gene region further explains the relationship of this region to the nearby gene.

Chrom: The chromosome on which the DMR is located using the hg18 build of the UCSC genome browser.

Start: The starting position of the DMR as designated by the hg18 build of the UCSC genome browser.

End: The ending position of the DMR as designated by the hg18 build of the UCSC genome browser.

Microarray Analysis: Describes whether this region was also/initially determined to be differentially methylated by microarray analysis. The methylated fraction of ten paired placenta and PBMC samples was isolated using the MBD-Fc protein. The two tissue fractions were then labeled with either Alexa Fluor 555-aha-dCTP (PBMC) or Alexa Fluor 647-aha-dCTP (placental) using the BioPrime Total Genomic Labeling System™ and hybridized to Agilent® CpG Island microarrays. Many regions examined in these studies were not contained on the initial microarray.

EpiTYPER 8 Samples: Describes whether this region was analyzed and determined to be differentially methylated in eight paired samples of placenta and peripheral blood mononuclear cells (PBMC) using EpiTYPER technology. Regions that were chosen for examination were based on multiple criteria. First, regions were selected based on data from the Microarray Analysis. Secondly, a comprehensive examination of all CpG islands located on chromosome 21 was undertaken. Finally, selected regions on chromosome 21 which had lower CpG frequency than those located in CpG islands were examined.

EpiTYPER 73 Samples: Describes whether this region was subsequently analyzed using EpiTYPER technology in a sample cohort consisting of 73 paired samples of placenta and PBMC. All regions selected for analysis in this second sample cohort were selected based on the results from the experimentation described in the EpiTYPER 8 column. More specifically, the regions in this additional cohort exhibited a methylation profile similar to that determined in the EpiTYPER 8 Samples analysis. For example, all of the regions listed in Tables 1B-1C exhibit different levels of DNA methylation in a significant portion of the examined CpG dinucleotides within the defined region. Differential DNA methylation of CpG sites was determined using a paired T Test with those sites considered differentially methylated if the p-value (when comparing placental tissue to PBMC) is $p<0.05$.

Previously Validated EpiTYPER: Describes whether this region or a portion of this region was validated using EpiTYPER during previous experimentation. (See Examples 1 and 2).

Relative Methylation Placenta to Maternal: Describes the direction of differential methylation. Regions labeled as "hypermethylation" are more methylated within the designated region in placenta samples relative to PBMC and "hypomethylation" are more methylated within the designated region in PBMC samples.

TABLE 1A

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| chr13 group00016 | chr13 | 19773745 | 19774050 | chr13: 19773518-19774214 | 0.19 | 0.22 | 0.32 | 0.1 | HYPERMETHYLATION |
| chr13 group00005 | chr13 | 19290394 | 19290768 | : — | −0.89 | 0.94 | 0.35 | −0.59 | HYPOMETHYLATION |
| CRYL1 | chr13 | 19887090 | 19887336 | chr13: 19887007-19887836 | −0.63 | 0.74 | 0.21 | −0.53 | HYPOMETHYLATION |
| IL17D | chr13 | 20193675 | 20193897 | chr13: 20193611-20194438 | −1.01 | 0.53 | 0.13 | −0.39 | HYPOMETHYLATION |
| CENPJ | chr13 | 24404023 | 24404359 | : — | 0.57 | 0.17 | 0.49 | 0.32 | HYPERMETHYLATION |
| ATP8A2 | chr13 | 25484475 | 25484614 | chr13: 25484287-25484761 | 0.81 | 0.16 | 0.43 | 0.27 | HYPERMETHYLATION |
| GSH1 | chr13 | 27265542 | 27265834 | chr13: 27264549-27266505 | 0.57 | 0.13 | 0.19 | 0.05 | HYPERMETHYLATION |
| PDX1 | chr13 | 27393789 | 27393979 | chr13: 27392001-27394099 | 0.55 | 0.06 | 0.2 | 0.14 | HYPERMETHYLATION |
| PDX1 | chr13 | 27400459 | 27401165 | chr13: 27400362-27400744; chr13: 27401057-27401374 | 0.73 | 0.12 | 0.26 | 0.14 | HYPERMETHYLATION |
| MAB21L1 | chr13 | 34947737 | 34948062 | chr13: 34947570-34948159 | 0.66 | 0.11 | 0.17 | 0.06 | HYPERMETHYLATION |
| RB1 | chr13 | 47790983 | 47791646 | chr13: 47790636-47791858 | 0.18 | 0.45 | 0.48 | 0.03 | HYPERMETHYLATION |
| PCDH17 | chr13 | 57104856 | 57106841 | chr13: 57104527-57106931 | 0.46 | 0.15 | 0.21 | 0.06 | HYPERMETHYLATION |
| KLHL1 | chr13 | 69579933 | 69580146 | chr13: 69579733-69580220 | 0.79 | 0.09 | 0.28 | 0.2 | HYPERMETHYLATION |
| POU4F1 | chr13 | 78079515 | 78081073 | chr13: 78079328-78079615; chr13: 78080860-78081881 | 0.66 | 0.12 | 0.23 | 0.11 | HYPERMETHYLATION |
| GPC6 | chr13 | 92677402 | 92678666 | chr13: 92677246-92678878 | 0.66 | 0.06 | 0.19 | 0.13 | HYPERMETHYLATION |
| SOX21 | chr13 | 94152286 | 94153047 | chr13: 94152190-94153185 | 0.94 | 0.16 | 0.4 | 0.25 | HYPERMETHYLATION |
| ZIC2 | chr13 | 99439660 | 99440858 | chr13: 99439335-99440189; chr13: 99440775-99441095 | 0.89 | 0.13 | 0.35 | 0.22 | HYPERMETHYLATION |
| IRS2 | chr13 | 109232856 | 109235065 | chr13: 109232467-109238181 | −0.17 | 0.73 | 0.38 | −0.35 | HYPOMETHYLATION |
| chr13 group00350 | chr13 | 109716455 | 109716604 | chr13: 109716325-109716726 | −0.37 | 0.77 | 0.41 | −0.36 | HYPOMETHYLATION |
| chr13 group00385 | chr13 | 111595578 | 111595955 | chr13: 111595459-111596131 | 0.87 | 0.06 | 0.2 | 0.14 | HYPERMETHYLATION |
| chr13 group00390 | chr13 | 111756337 | 111756593 | chr13: 111755805-111756697 | 0.71 | 0.12 | 0.34 | 0.22 | HYPERMETHYLATION |
| chr13 group00391 | chr13 | 111759856 | 111760045 | chr13: 111757885-111760666 | 0.86 | 0.11 | 0.36 | 0.25 | HYPERMETHYLATION |
| chr13 group00395 | chr13 | 111808255 | 111808962 | chr13: 111806599-111808492; chr13: 111808866-111809114 | 0.96 | 0.13 | 0.35 | 0.22 | HYPERMETHYLATION |
| chr13 group00399 | chr13 | 112033503 | 112033685 | chr13: 112032967-112033734 | 0.38 | 0.26 | 0.43 | 0.18 | HYPERMETHYLATION |
| MCF2L | chr13 | 112724910 | 112725742 | chr13: 112724782-112725121; chr13: 112725628-112725837 | −0.47 | 0.91 | 0.33 | −0.58 | HYPOMETHYLATION |
| F7 | chr13 | 112799123 | 112799379 | chr13: 112798487-112799566 | −0.05 | 0.97 | 0.55 | −0.41 | HYPOMETHYLATION |
| PROZ | chr13 | 112855566 | 112855745 | chr13: 112855289-112855866 | 0.29 | 0.15 | 0.3 | 0.16 | HYPERMETHYLATION |
| chr18 group00039 | chr18 | 6919797 | 6919981 | chr18: 6919450-6920088 | −0.38 | 0.88 | 0.39 | −0.49 | HYPOMETHYLATION |
| CIDEA | chr18 | 12244327 | 12244696 | chr18: 12244147-12245089 | 0.23 | 0.14 | 0.23 | 0.1 | HYPERMETHYLATION |
| chr18 group00091 | chr18 | 12901467 | 12901643 | chr18: 12901024-12902704 | 0.16 | 0.15 | 0.43 | 0.29 | HYPERMETHYLATION |
| chr18 group00094 | chr18 | 13126819 | 13126986 | chr18: 13126596-13127564 | 0.41 | 0.07 | 0.34 | 0.27 | HYPERMETHYLATION |
| C18orf1 | chr18 | 13377536 | 13377654 | chr18: 13377385-13377686 | −0.12 | 0.95 | 0.69 | −0.26 | HYPOMETHYLATION |
| KLHL14 | chr18 | 28603978 | 28605183 | chr18: 28603688-28606300 | 0.83 | 0.07 | 0.19 | 0.12 | HYPERMETHYLATION |
| CD33L3 | chr18 | 41671477 | 41673011 | chr18: 41671386-41673101 | −0.34 | 0.49 | 0.44 | −0.05 | HYPOMETHYLATION |
| ST8SIA3 | chr18 | 53171265 | 53171309 | chr18: 53170705-53172603 | 1.02 | 0.09 | 0.25 | 0.16 | HYPERMETHYLATION |
| ONECUT2 | chr18 | 53254808 | 53259810 | chr18: 53254152-53259851 | 0.74 | 0.09 | 0.23 | 0.14 | HYPERMETHYLATION |
| RAX | chr18 | 55086286 | 55086436 | chr18: 55085813-55087807 | 0.88 | 0.11 | 0.26 | 0.16 | HYPERMETHYLATION |
| chr18 group00277 | chr18 | 57151972 | 57152311 | chr18: 57151663-57152672 | 0.58 | 0.08 | 0.21 | 0.13 | HYPERMETHYLATION |
| TNFRSF11A | chr18 | 58203013 | 58203282 | chr18: 58202849-58203367 | −0.33 | 0.88 | 0.28 | −0.6 | HYPOMETHYLATION |
| NETO1 | chr18 | 68685099 | 68687060 | chr18: 68684945-68687851 | 0.65 | 0.09 | 0.22 | 0.13 | HYPERMETHYLATION |
| chr18 group00304 | chr18 | 70133945 | 70134397 | chr18: 70133732-70134724 | 0.12 | 0.93 | 0.92 | −0.01 | NOT CONFIRMED |

TABLE 1A-continued

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| TSHZ1 | chr18 | 71128742 | 71128974 | chr18: 71128638-71129076 | 0.23 | 0.95 | 0.92 | −0.03 | NOT CONFIRMED |
| ZNF236 | chr18 | 72664454 | 72664736 | chr18: 72662797-72664893 | −0.62 | 0.17 | 0.1 | −0.07 | HYPOMETHYLATION |
| MBP | chr18 | 72953150 | 72953464 | chr18: 72953137-72953402 | 0.6 | 0.44 | 0.72 | 0.28 | HYPERMETHYLATION |
| chr18 group00342 | chr18 | 74170347 | 74170489 | chr18: 74170210-74170687 | −0.2 | 0.78 | 0.48 | −0.3 | HYPOMETHYLATION |
| NFATC1 | chr18 | 75385424 | 75386008 | chr18: 75385279-75386532 | 0.23 | 0.14 | 0.84 | 0.7 | HYPERMETHYLATION |
| CTDP1 | chr18 | 75596358 | 75596579 | chr18: 75596009-75596899 | 0.07 | 0.97 | 0.96 | −0.01 | NOT CONFIRMED |
| chr18 group00430 | chr18 | 75653272 | 75653621 | : — | 0.52 | 0.24 | 0.62 | 0.39 | HYPERMETHYLATION |
| KCNG2 | chr18 | 75760343 | 75760820 | chr18: 75759900-75760988 | 0.01 | 0.84 | 0.75 | −0.09 | NOT CONFIRMED |
| OLIG2 | chr21 | 33317673 | 33321183 | chr21: 33316998-33322115 | 0.66 | 0.11 | 0.2 | 0.09 | HYPERMETHYLATION |
| OLIG2 | chr21 | 33327593 | 33328334 | chr21: 33327447-33328408 | −0.75 | 0.77 | 0.28 | −0.49 | HYPOMETHYLATION |
| RUNX1 | chr21 | 35180938 | 35185436 | chr21: 35180822-35181342; chr21: 35182320-35185557 | −0.68 | 0.14 | 0.07 | −0.07 | HYPOMETHYLATION |
| SIM2 | chr21 | 36994965 | 36995298 | chr21: 36990063-36995761 | 0.83 | 0.08 | 0.26 | 0.18 | HYPERMETHYLATION |
| SIM2 | chr21 | 36999025 | 36999410 | chr21: 36998632-36999555 | 0.87 | 0.06 | 0.24 | 0.18 | HYPERMETHYLATION |
| DSCR6 | chr21 | 37300407 | 37300512 | chr21: 37299807-37301307 | 0.22 | 0.04 | 0.14 | 0.11 | HYPERMETHYLATION |
| DSCAM | chr21 | 41135559 | 41135706 | chr21: 41135380-41135816 | 1.03 | 0.06 | 0.29 | 0.23 | HYPERMETHYLATION |
| chr21 group00165 | chr21 | 43643421 | 43643786 | chr21: 43643322-43643874 | 1.14 | 0.16 | 0.81 | 0.65 | HYPERMETHYLATION |
| AIRE | chr21 | 44529935 | 44530388 | chr21: 44529856-44530472 | −0.55 | 0.62 | 0.27 | −0.35 | HYPOMETHYLATION |
| SUMO3 | chr21 | 45061293 | 45061853 | chr21: 45061154-45063386 | −0.41 | 0.55 | 0.46 | −0.09 | HYPOMETHYLATION |
| C21orf70 | chr21 | 45202815 | 45202972 | chr21: 45202706-45203073 | −0.46 | 0.96 | 0.51 | −0.46 | HYPOMETHYLATION |
| C21orf123 | chr21 | 45671984 | 45672098 | chr21: 45671933-45672201 | −0.63 | 0.92 | 0.43 | −0.49 | HYPOMETHYLATION |
| COL18A1 | chr21 | 45754383 | 45754487 | chr21: 45753653-45754639 | −0.18 | 0.97 | 0.72 | −0.25 | HYPOMETHYLATION |
| PRMT2 | chr21 | 46911967 | 46912385 | chr21: 46911628-46912534 | 1.08 | 0.04 | 0.25 | 0.21 | HYPERMETHYLATION |
| SIX2 | chr2 | 45081223 | 45082129 | chr2: 45081148-45082287 | 1.15 | 0.08 | 0.36 | 0.28 | HYPERMETHYLATION |
| SIX2 | chr2 | 45084851 | 45085711 | chr2: 45084715-45084986; chr2: 45085285-45086054 | 1.21 | 0.07 | 0.35 | 0.28 | HYPERMETHYLATION |
| SOX14 | chr3 | 138971870 | 138972322 | chr3: 138971738-138972096; chr3: 138972281-138973691 | 1.35 | 0.08 | 0.33 | 0.25 | HYPERMETHYLATION |
| TLX3 | chr5 | 170674439 | 170676431 | chr5: 170674208-170675356; chr5: 170675783-170676712 | 0.91 | 0.11 | 0.35 | 0.24 | HYPERMETHYLATION |
| FOXP4 | chr6 | 41623666 | 41624114 | chr6: 41621630-41624167 | 1.1 | 0.07 | 0.27 | 0.2 | HYPERMETHYLATION |

TABLE 1A-continued

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| FOXP4 | chr6 | 41636384 | 41636779 | chr6: 41636244-41636878 | 1.32 | 0.04 | 0.33 | 0.29 | HYPERMETHYLATION |
| chr7 group00267 | chr7 | 12576755 | 12577246 | chr7: 12576690-12577359 | 0.94 | 0.08 | 0.26 | 0.17 | HYPERMETHYLATION |
| NPY | chr7 | 24290224 | 24291508 | chr7: 24290083-24291605 | 0.93 | 0.09 | 0.3 | 0.21 | HYPERMETHYLATION |
| SHH | chr7 | 155291537 | 155292091 | chr7: 155288453-155292175 | 0.98 | 0.19 | 0.52 | 0.33 | HYPERMETHYLATION |
| OSR2 | chr8 | 100029764 | 100030536 | chr8: 100029673-100030614 | 1.21 | 0.08 | 0.43 | 0.35 | HYPERMETHYLATION |
| GLIS3 | chr9 | 4288283 | 4289645 | chr9: 4287817-4290182 | 1.24 | 0.06 | 0.24 | 0.18 | HYPERMETHYLATION |
| PRMT8 | chr12 | 3472714 | 3473190 | chr12: 3470227-3473269 | 0.86 | 0.07 | 0.23 | 0.16 | HYPERMETHYLATION |
| TBX3 | chr12 | 113609153 | 113609453 | chr12: 113609112-113609535 | 1.45 | 0.09 | 0.56 | 0.48 | HYPERMETHYLATION |
| chr12 group00801 | chr12 | 118516189 | 118517435 | chr12: 118515877-118517595 | 1.1 | 0.06 | 0.25 | 0.19 | HYPERMETHYLATION |
| PAX9 | chr14 | 36201402 | 36202386 | chr14: 36200932-36202536 | 0.89 | 0.11 | 0.32 | 0.21 | HYPERMETHYLATION |
| SIX1 | chr14 | 60178801 | 60179346 | chr14: 60178707-60179539 | 0.95 | 0.1 | 0.33 | 0.22 | HYPERMETHYLATION |
| ISL2 | chr15 | 74420013 | 74421546 | chr15: 74419317-74422570 | 1.08 | 0.08 | 0.27 | 0.19 | HYPERMETHYLATION |
| DLX4 | chr17 | 45397228 | 45397930 | chr17: 45396281-45398063 | 1.25 | 0.1 | 0.32 | 0.22 | HYPERMETHYLATION |
| CBX4 | chr17 | 75428613 | 75431793 | chr17: 75427586-75433676 | 1 | 0.07 | 0.27 | 0.21 | HYPERMETHYLATION |
| EDG6 | chr19 | 3129836 | 3130874 | chr19: 3129741-3130986 | 1.35 | 0.04 | 0.87 | 0.83 | HYPERMETHYLATION |
| PRRT3 | chr3 | 9963364 | 9964023 | chr3: 9962895-9964619 | −0.85 | 0.9 | 0.09 | −0.81 | HYPOMETHYLATION |
| MGC29506 | chr5 | 138757911 | 138758724 | chr5: 138755609-138758810 | −0.63 | 0.93 | 0.17 | −0.76 | HYPOMETHYLATION |
| TEAD3 | chr6 | 35561812 | 35562252 | chr6: 35561754-35562413 | −1.17 | 0.92 | 0.13 | −0.8 | HYPOMETHYLATION |
| chr12 group00022 | chr12 | 1642456 | 1642708 | chr12: 1642195-1642774 | −1.33 | 0.66 | 0.09 | −0.57 | HYPOMETHYLATION |
| CENTG1 | chr12 | 56406249 | 56407788 | chr12: 56406176-56407818 | −1.07 | 0.95 | 0.19 | −0.77 | HYPOMETHYLATION |
| CENTG1 | chr12 | 56416146 | 56418794 | chr12: 56416095-56416628; chr12: 56418745-56419001 | −0.94 | 0.85 | 0.16 | −0.69 | HYPOMETHYLATION |

Information in Table 1A based on the March 2006 human reference sequence (NCBI Build 36.1), which was produced by the International Human Genome Sequencing Consortium.

TABLE 1B

Non-Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| TFAP2E | Intron | chr1 | 35815000 | 35816200 | YES | YES | NO | NO | Hypermethylation |
| LRRC8D | Intron/Exon | chr1 | 90081350 | 90082250 | YES | YES | NO | NO | Hypermethylation |
| TBX15 | Promoter | chr1 | 119333500 | 119333700 | YES | YES | NO | NO | Hypermethylation |
| C1orf51 | Upstream | chr1 | 148520900 | 148521300 | YES | YES | NO | NO | Hypermethylation |
| chr1: 179553900-179554600 | Intergenic | chr1 | 179553900 | 179554600 | YES | YES | NO | NO | Hypermethylation |
| ZFP36L2 | Exon | chr2 | 43304900 | 43305100 | YES | YES | NO | NO | Hypermethylation |
| SIX2 | Downstream | chr2 | 45081000 | 45086000 | YES | YES | NO | YES | Hypermethylation |
| chr2: 137238500-137240000 | Intergenic | chr2 | 137238500 | 137240000 | YES | YES | NO | NO | Hypermethylation |
| MAP1D | Intron/Exon | chr2 | 172652800 | 172653600 | YES | YES | NO | NO | Hypermethylation |
| WNT6 | Intron | chr2 | 219444250 | 219444290 | YES | YES | NO | NO | Hypermethylation |
| INPP5D | Promoter | chr2 | 233633200 | 233633700 | YES | YES | YES | NO | Hypermethylation |
| chr2: 241211100-241211600 | Intergenic | chr2 | 241211100 | 241211600 | YES | YES | YES | NO | Hypermethylation |
| WNT5A | Intron | chr3 | 55492550 | 55492850 | YES | YES | NO | NO | Hypermethylation |
| chr3: 138971600-138972200 | Intergenic | chr3 | 138971600 | 138972200 | YES | YES | YES | YES | Hypermethylation |
| ZIC4 | Intron | chr3 | 148598200 | 148599000 | YES | YES | NO | NO | Hypermethylation |
| FGF12 | Intron/Exon | chr3 | 193608500 | 193610500 | YES | YES | NO | NO | Hypermethylation |
| GP5 | Exon | chr3 | 195598400 | 195599200 | YES | YES | NO | NO | Hypermethylation |
| MSX1 | Upstream | chr4 | 4910550 | 4911100 | YES | YES | NO | NO | Hypermethylation |
| NKX3-2 | Intron/Exon | chr4 | 13152500 | 13154500 | YES | YES | NO | NO | Hypermethylation |
| chr4: 111752000-111753000 | Intergenic | chr4 | 111752000 | 111753000 | YES | YES | YES | NO | Hypermethylation |
| SFRP2 | Promoter | chr4 | 154928800 | 154930100 | YES | YES | NO | NO | Hypermethylation |
| chr4: 174664300-174664800 | Intergenic | chr4 | 174664300 | 174664800 | YES | YES | NO | NO | Hypermethylation |
| chr4: 174676300-174676800 | Intergenic | chr4 | 174676300 | 174676800 | YES | YES | NO | NO | Hypermethylation |
| SORBS2 | Intron | chr4 | 186796900 | 186797500 | YES | YES | NO | NO | Hypermethylation |
| chr5: 42986900-42988200 | Intergenic | chr5 | 42986900 | 42988200 | YES | YES | NO | NO | Hypermethylation |
| chr5: 72712000-72714100 | Intergenic | chr5 | 72712000 | 72714100 | YES | YES | NO | NO | Hypermethylation |
| chr5: 72767550-72767800 | Intergenic | chr5 | 72767550 | 72767800 | YES | YES | NO | NO | Hypermethylation |
| NR2F1 | Intron/Exon | chr5 | 92955000 | 92955250 | YES | YES | NO | NO | Hypermethylation |
| PCDHGA1 | Intron | chr5 | 140850500 | 140852500 | YES | YES | YES | NO | Hypermethylation |
| chr6: 10489100-10490200 | Intergenic | chr6 | 10489100 | 10490200 | YES | YES | YES | NO | Hypermethylation |
| FOXP4 | Intron | chr6 | 41636200 | 41637000 | YES | YES | NO | YES | Hypermethylation |
| chr7: 19118400-19118700 | Intergenic | chr7 | 19118400 | 19118700 | YES | YES | NO | NO | Hypermethylation |
| chr7: 27258000-27258400 | Intergenic | chr7 | 27258000 | 27258400 | YES | YES | NO | NO | Hypermethylation |
| TBX20 | Upstream | chr7 | 35267500 | 35268300 | YES | YES | NO | NO | Hypermethylation |
| AGBL3 | Promoter | chr7 | 134321300 | 134322300 | YES | YES | NO | NO | Hypermethylation |
| XPO7 | Downstream | chr8 | 21924000 | 21924300 | YES | YES | NO | NO | Hypermethylation |
| chr8: 41543400-41544000 | Intergenic | chr8 | 41543400 | 41544000 | YES | YES | NO | NO | Hypermethylation |
| GDF6 | Exon | chr8 | 97225400 | 97227100 | YES | YES | NO | NO | Hypermethylation |
| OSR2 | Intron/Exon | chr8 | 100029000 | 100031000 | YES | YES | YES | YES | Hypermethylation |
| GLIS3 | Intron/Exon | chr9 | 4288000 | 4290000 | YES | YES | NO | YES | Hypermethylation |
| NOTCH1 | Intron | chr9 | 138547600 | 138548400 | YES | YES | YES | NO | Hypermethylation |
| EGFL7 | Upstream | chr9 | 138672350 | 138672850 | YES | YES | NO | NO | Hypermethylation |
| CELF2 | Intron/Exon | chr10 | 11246700 | 11247900 | YES | YES | NO | NO | Hypermethylation |
| HHEX | Intron | chr10 | 94441000 | 94441800 | YES | YES | NO | NO | Hypermethylation |
| DOCK1/FAM196A | Intron/Exon | chr10 | 128883000 | 128883500 | YES | YES | NO | NO | Hypermethylation |
| PAX6 | Intron | chr11 | 31782400 | 31783500 | YES | YES | NO | NO | Hypermethylation |
| FERMT3 | Intron/Exon | chr11 | 63731200 | 63731700 | YES | YES | YES | NO | Hypermethylation |
| PKNOX2 | Intron | chr11 | 124541200 | 124541800 | YES | YES | NO | NO | Hypermethylation |
| KIRREL3 | Intron | chr11 | 126375150 | 126375300 | YES | YES | NO | NO | Hypermethylation |
| BCAT1 | Intron | chr12 | 24946700 | 24947600 | YES | YES | NO | NO | Hypermethylation |
| HOXC13 | Intron/Exon | chr12 | 52625000 | 52625600 | YES | YES | NO | NO | Hypermethylation |
| TBX5 | Promoter | chr12 | 113330500 | 113332000 | YES | YES | NO | NO | Hypermethylation |
| TBX3 | Upstream | chr12 | 113609000 | 113609500 | YES | YES | NO | YES | Hypermethylation |
| chr12: 113622100-113623000 | Intergenic | chr12 | 113622100 | 113623000 | YES | YES | YES | NO | Hypermethylation |
| chr12: 113657800-113658300 | Intergenic | chr12 | 113657800 | 113658300 | YES | YES | NO | NO | Hypermethylation |
| THEM233 | Promoter | chr12 | 118515500 | 118517500 | YES | YES | NO | YES | Hypermethylation |
| NCOR2 | Intron/Exon | chr12 | 123516200 | 123516800 | YES | YES | YES | NO | Hypermethylation |

TABLE 1B-continued

Non-Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| THEM132C | Intron | chr12 | 127416300 | 127416700 | YES | YES | NO | NO | Hypermethylation |
| PTGDR | Promoter | chr14 | 51804000 | 51805200 | YES | YES | NO | NO | Hypermethylation |
| ISL2 | Intron/Exon | chr15 | 74420000 | 74422000 | YES | YES | NO | YES | Hypermethylation |
| chr15: 87750000-87751000 | Intergenic | chr15 | 87750000 | 87751000 | YES | YES | NO | NO | Hypermethylation |
| chr15: 87753000-87754100 | Intergenic | chr15 | 87753000 | 87754100 | YES | YES | NO | NO | Hypermethylation |
| NR2F2 | Upstream | chr15 | 94666000 | 94667500 | YES | YES | YES | NO | Hypermethylation |
| chr16: 11234300-11234900 | Intergenic | chr16 | 11234300 | 11234900 | YES | YES | NO | NO | Hypermethylation |
| SPN | Exon | chr16 | 29582800 | 29583500 | YES | YES | YES | NO | Hypermethylation |
| chr16: 85469900-85470200 | Intergenic | chr16 | 85469900 | 85470200 | YES | YES | NO | NO | Hypermethylation |
| SLFN11 | Promoter | chr17 | 30725100 | 30725600 | YES | YES | NO | NO | Hypermethylation |
| DLX4 | Upstream | chr17 | 45396800 | 45397800 | YES | YES | NO | YES | Hypermethylation |
| SLC38A10 (MGC15523) | Intron | chr17 | 76873800 | 76874300 | YES | YES | YES | NO | Hypermethylation |
| S1PR4 | Exon | chr19 | 3129900 | 3131100 | YES | YES | YES | YES | Hypermethylation |
| MAP2K2 | Intron | chr19 | 4059700 | 4060300 | YES | YES | YES | NO | Hypermethylation |
| UHRF1 | Intron | chr19 | 4867300 | 4867800 | YES | YES | YES | NO | Hypermethylation |
| DEDD2 | Exon | chr19 | 47395300 | 47395900 | YES | YES | YES | NO | Hypermethylation |
| CDC42EP1 | Exon | chr22 | 36292300 | 36292800 | YES | YES | YES | NO | Hypermethylation |

TABLE 1C

Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| chr21: 9906600-9906800 | Intergenic | chr21 | 9906600 | 9906800 | NO | YES | NO | NO | Hypomethylation |
| chr21: 9907000-9907400 | Intergenic | chr21 | 9907000 | 9907400 | NO | YES | NO | NO | Hypomethylation |
| chr21: 9917800-9918450 | Intergenic | chr21 | 9917800 | 9918450 | NO | YES | NO | NO | Hypomethylation |
| TPTE | Promoter | chr21 | 10010000 | 10015000 | NO | YES | NO | NO | Hypomethylation |
| chr21: 13974500-13976000 | Intergenic | chr21 | 13974500 | 13976000 | NO | YES | NO | NO | Hypomethylation |
| chr21: 13989500-13992000 | Intergenic | chr21 | 13989500 | 13992000 | NO | YES | NO | NO | Hypomethylation |
| chr21: 13998500-14000100 | Intergenic | chr21 | 13998500 | 14000100 | NO | YES | NO | NO | Hypomethylation |
| chr21: 14017000-14018500 | Intergenic | chr21 | 14017000 | 14018500 | NO | YES | NO | NO | Hypomethylation |
| chr21: 14056400-14058100 | Intergenic | chr21 | 14056400 | 14058100 | NO | YES | NO | NO | Hypomethylation |
| chr21: 14070250-14070550 | Intergenic | chr21 | 14070250 | 14070550 | NO | YES | NO | NO | Hypomethylation |
| chr21: 14119800-14120400 | Intergenic | chr21 | 14119800 | 14120400 | NO | YES | NO | NO | Hypomethylation |
| chr21: 14304800-14306100 | Intergenic | chr21 | 14304800 | 14306100 | NO | YES | NO | NO | Hypomethylation |
| chr21: 15649340-15649450 | Intergenic | chr21 | 15649340 | 15649450 | NO | YES | YES | NO | Hypermethylation |
| C21orf34 | Intron | chr21 | 16881500 | 16883000 | NO | YES | NO | NO | Hypomethylation |
| BTG3 | Intron | chr21 | 17905300 | 17905500 | NO | YES | NO | NO | Hypomethylation |
| CHODL | Promoter | chr21 | 18539000 | 18539800 | NO | YES | YES | NO | Hypermethylation |
| NCAM2 | Upstream | chr21 | 21291500 | 21292100 | NO | YES | NO | NO | Hypermethylation |
| chr21: 23574000-23574600 | Intergenic | chr21 | 23574000 | 23574600 | NO | YES | NO | NO | Hypomethylation |
| chr21: 24366920-24367060 | Intergenic | chr21 | 24366920 | 24367060 | NO | YES | NO | NO | Hypomethylation |
| chr21: 25656000-25656900 | Intergenic | chr21 | 25656000 | 25656900 | NO | YES | NO | NO | Hypomethylation |
| MIR155HG | Promoter | chr21 | 25855800 | 25857200 | NO | YES | YES | NO | Hypermethylation |
| CYYR1 | Intron | chr21 | 26830750 | 26830950 | NO | YES | NO | NO | Hypomethylation |
| chr21: 26938800-26939200 | Intergenic | chr21 | 26938800 | 26939200 | NO | YES | NO | NO | Hypomethylation |
| GRIK1 | Intron | chr21 | 30176500 | 30176750 | NO | YES | NO | NO | Hypomethylation |
| chr21: 30741350-30741600 | Intergenic | chr21 | 30741350 | 30741600 | NO | YES | NO | NO | Hypermethylation |
| TIAM1 | Intron | chr21 | 31426800 | 31427300 | NO | YES | YES | NO | Hypermethylation |
| TIAM1 | Intron | chr21 | 31475300 | 31475450 | NO | YES | NO | NO | Hypermethylation |
| TIAM1 | Intron | chr21 | 31621050 | 31621350 | NO | YES | YES | NO | Hypermethylation |
| SOD1 | Intron | chr21 | 31955000 | 31955300 | NO | YES | NO | NO | Hypomethylation |
| HUNK | Intron/Exon | chr21 | 32268700 | 32269100 | NO | YES | YES | NO | Hypermethylation |
| chr21: 33272200-33273300 | Intergenic | chr21 | 33272200 | 33273300 | NO | YES | NO | NO | Hypomethylation |
| OLIG2 | Promoter | chr21 | 33314000 | 33324000 | YES | YES | NO | YES | Hypermethylation |
| OLIG2 | Downstream | chr21 | 33328000 | 33328500 | YES | YES | NO | NO | Hypomethylation |
| RUNX1 | Intron | chr21 | 35185000 | 35186000 | NO | YES | NO | NO | Hypomethylation |
| RUNX1 | Intron | chr21 | 35320300 | 35320400 | NO | YES | NO | NO | Hypermethylation |
| RUNX1 | Intron | chr21 | 35321200 | 35321600 | NO | YES | NO | NO | Hypermethylation |
| RUNX1 | Intron/Exon | chr21 | 35340000 | 35345000 | NO | YES | YES | NO | Hypermethylation |
| chr21: 35499200-35499700 | Intergenic | chr21 | 35499200 | 35499700 | NO | YES | YES | NO | Hypermethylation |

TABLE 1C-continued

Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| chr21: 35822800-35823500 | Intergenic | chr21 | 35822800 | 35823500 | NO | YES | YES | NO | Hypermethylation |
| CBR1 | Promoter | chr21 | 36364000 | 36364500 | NO | YES | NO | NO | Hypermethylation |
| DOPEY2 | Downstream | chr21 | 36589000 | 36590500 | NO | YES | NO | NO | Hypomethylation |
| SIM2 | Promoter | chr21 | 36988000 | 37005000 | YES | YES | YES | YES | Hypermethylation |
| HLCS | Intron | chr21 | 37274000 | 37275500 | YES | YES | YES | NO | Hypermethylation |
| DSCR6 | Upstream | chr21 | 37300200 | 37300400 | YES | YES | NO | YES | Hypermethylation |
| DSCR3 | Intron | chr21 | 37551000 | 37553000 | YES | YES | YES | NO | Hypermethylation |
| chr21: 37841100-37841800 | Intergenic | chr21 | 37841100 | 37841800 | NO | YES | YES | NO | Hypermethylation |
| ERG | Intron | chr21 | 38791400 | 38792000 | NO | YES | YES | NO | Hypermethylation |
| chr21: 39278700-39279800 | Intergenic | chr21 | 39278700 | 39279800 | NO | YES | YES | NO | Hypermethylation |
| C21orf129 | Exon | chr21 | 42006000 | 42006250 | NO | YES | YES | NO | Hypermethylation |
| C2CD2 | Intron | chr21 | 42188900 | 42189500 | NO | YES | YES | NO | Hypermethylation |
| UMODL1 | Upstream | chr21 | 42355500 | 42357500 | NO | YES | YES | NO | Hypermethylation |
| UMODL1/C21orf128 | Intron | chr21 | 42399200 | 42399900 | NO | YES | NO | NO | Hypomethylation |
| ABCG1 | Intron | chr21 | 42528400 | 42528600 | YES | YES | NO | NO | Hypomethylation |
| chr21: 42598300-42599600 | Intergenic | chr21 | 42598300 | 42599600 | YES | YES | NO | NO | Hypomethylation |
| chr21: 42910000-42911000 | Intergenic | chr21 | 42910000 | 42911000 | NO | YES | NO | NO | Hypomethylation |
| PDE9A | Upstream | chr21 | 42945500 | 42946000 | NO | YES | NO | NO | Hypomethylation |
| PDE9A | Intron | chr21 | 42961400 | 42962700 | NO | YES | NO | NO | Hypomethylation |
| PDE9A | Intron | chr21 | 42977400 | 42977600 | NO | YES | NO | NO | Hypermethylation |
| PDE9A | Intron/Exon | chr21 | 42978200 | 42979800 | YES | YES | NO | NO | Hypomethylation |
| PDE9A | Intron | chr21 | 43039800 | 43040200 | NO | YES | YES | NO | Hypermethylation |
| chr21: 43130800-43131500 | Intergenic | chr21 | 43130800 | 43131500 | NO | YES | NO | NO | Hypomethylation |
| U2AF1 | Intron | chr21 | 43395500 | 43395800 | NO | YES | NO | NO | Hypermethylation |
| U2AF1 | Intron | chr21 | 43398000 | 43398450 | NO | YES | YES | NO | Hypermethylation |
| chr21: 43446600-43447600 | Intergenic | chr21 | 43446600 | 43447600 | NO | YES | NO | NO | Hypomethylation |
| CRYAA | Intron/Exon | chr21 | 43463000 | 43466100 | NO | YES | NO | NO | Hypomethylation |
| chr21: 43545000-43546000 | Intergenic | chr21 | 43545000 | 43546000 | YES | YES | NO | NO | Hypomethylation |
| chr21: 43606000-43606500 | Intergenic | chr21 | 43606000 | 43606500 | NO | YES | NO | NO | Hypomethylation |
| chr21: 43643000-43644300 | Intergenic | chr21 | 43643000 | 43644300 | YES | YES | YES | YES | Hypermethylation |
| C21orf125 | Upstream | chr21 | 43689100 | 43689300 | NO | YES | NO | NO | Hypermethylation |
| C21orf125 | Downstream | chr21 | 43700700 | 43701700 | NO | YES | NO | NO | Hypermethylation |
| HSF2BP | Intron/Exon | chr21 | 43902500 | 43903800 | YES | YES | NO | NO | Hypomethylation |
| AGPAT3 | Intron | chr21 | 44161100 | 44161400 | NO | YES | YES | NO | Hypermethylation |
| chr21: 44446500-44447500 | Intergenic | chr21 | 44446500 | 44447500 | NO | YES | NO | NO | Hypomethylation |
| TRPM2 | Intron | chr21 | 44614500 | 44615000 | NO | YES | NO | NO | Hypomethylation |
| C21orf29 | Intron | chr21 | 44750400 | 44751000 | NO | YES | NO | NO | Hypomethylation |
| C21orf29 | Intron | chr21 | 44950000 | 44955000 | NO | YES | YES | NO | Hypermethylation |
| ITGB2 | Intron/Exon | chr21 | 45145500 | 45146100 | NO | YES | NO | NO | Hypomethylation |
| POFUT2 | Downstream | chr21 | 45501000 | 45503000 | NO | YES | NO | NO | Hypomethylation |
| chr21: 45571500-45573700 | Intergenic | chr21 | 45571500 | 45573700 | NO | YES | NO | NO | Hypomethylation |
| chr21: 45609000-45610600 | Intergenic | chr21 | 45609000 | 45610600 | NO | YES | NO | NO | Hypomethylation |
| COL18A1 | Intron | chr21 | 45670000 | 45677000 | YES | YES | NO | YES | Hypomethylation |
| COL18A1 | Intron/Exon | chr21 | 45700500 | 45702000 | NO | YES | NO | NO | Hypomethylation |
| COL18A1 | Intron/Exon | chr21 | 45753000 | 45755000 | YES | YES | NO | YES | Hypomethylation |
| chr21: 45885000-45887000 | Intergenic | chr21 | 45885000 | 45887000 | NO | YES | NO | NO | Hypomethylation |
| PCBP3 | Intron | chr21 | 46111000 | 46114000 | NO | YES | NO | NO | Hypomethylation |
| PCBP3 | Intron/Exon | chr21 | 46142000 | 46144500 | NO | YES | NO | NO | Hypomethylation |
| COL6A1 | Intron/Exon | chr21 | 46227000 | 46233000 | NO | YES | NO | NO | Hypomethylation |
| COL6A1 | Intron/Exon | chr21 | 46245000 | 46252000 | NO | YES | NO | NO | Hypomethylation |
| chr21: 46280500-46283000 | Intergenic | chr21 | 46280500 | 46283000 | NO | YES | NO | NO | Hypomethylation |
| COL6A2 | Intron | chr21 | 46343500 | 46344200 | NO | YES | NO | NO | Hypomethylation |
| COL6A2 | Intron/Exon | chr21 | 46368000 | 46378000 | NO | YES | NO | NO | Hypomethylation |
| C21orf56 | Intron/Exon | chr21 | 46426700 | 46427500 | NO | YES | NO | NO | Hypomethylation |
| C21orf57 | Intron | chr21 | 46541568 | 46541861 | NO | YES | NO | NO | Hypermethylation |
| C21orf57 | Exon | chr21 | 46541872 | 46542346 | NO | YES | NO | NO | Hypermethylation |
| C21orf57 | Downstream | chr21 | 46542319 | 46542665 | NO | YES | NO | NO | Hypermethylation |
| C21orf58 | Intron | chr21 | 46546914 | 46547404 | NO | YES | NO | NO | Hypomethylation |
| PRMT2 | Downstream | chr21 | 46911000 | 46913000 | YES | YES | NO | YES | Hypermethylation |
| ITGB2 | Intron | chr21 | 45170700 | 45171100 | NO | YES | YES | NO | Hypermethylation |

TABLE 2

| GENE NAME | CHROM | START | END | SNPs |
|---|---|---|---|---|
| chr13 group00016 | chr13 | 19773745 | 19774050 | rs7996310; rs12870878 |
| chr13 group00005 | chr13 | 19290394 | 19290768 | rs11304938 |
| CENPJ | chr13 | 24404023 | 24404359 | rs7326661 |
| ATP8A2 | chr13 | 25484475 | 25484614 | rs61947088 |
| PDX1 | chr13 | 27400459 | 27401165 | rs58173592; rs55836809; rs61944011 |
| RB1 | chr13 | 47790983 | 47791646 | rs2804094; rs4151432; rs4151433; rs4151434; rs4151435 |
| PCDH17 | chr13 | 57104856 | 57106841 | rs35287822; rs34642962; rs41292834; rs45500496; rs45571031; rs41292836; rs28374395; rs41292838 |
| KLHL1 | chr13 | 69579933 | 69580146 | rs3751429 |
| POU4F1 | chr13 | 78079515 | 78081073 | rs11620410; rs35794447; rs2765065 |
| GPC6 | chr13 | 92677402 | 92678666 | rs35689696; rs11839555; rs55695812; rs35259892 |
| SOX21 | chr13 | 94152286 | 94153047 | rs41277652; rs41277654; rs35276096; rs5805873; rs35109406 |
| ZIC2 | chr13 | 99439660 | 99440858 | rs9585309; rs35501321; rs9585310; rs7991728; rs1368511 |
| IRS2 | chr13 | 109232856 | 109235065 | rs61747993; rs1805097; rs9583424; rs35927012; rs1056077; rs1056078; rs34889228; rs1056080; rs1056081; rs12853546; rs4773092; rs35223808; rs35894564; rs3742210; rs34412495; rs61962699; rs45545638; rs61743905 |
| chr13 group00395 | chr13 | 111808255 | 111808962 | rs930346 |
| MCF2L | chr13 | 112724910 | 112725742 | rs35661110; rs2993304; rs1320519; rs7320418; rs58416100 |
| F7 | chr13 | 112799123 | 112799379 | rs2480951; rs2476320 |
| CIDEA | chr18 | 12244327 | 12244696 | rs60132277 |
| chr18 group00091 | chr18 | 12901467 | 12901643 | rs34568924; rs8094284; rs8094285 |
| C18orf1 | chr18 | 13377536 | 13377654 | rs9957861 |
| KLHL14 | chr18 | 28603978 | 28605183 | rs61737323; rs61737324; rs12960414 |
| CD33L3 | chr18 | 41671477 | 41673011 | rs62095363; rs2919643 |
| ONECUT2 | chr18 | 53254808 | 53259810 | rs35685953; rs61735644; rs8084084; rs35937482; rs35427632; rs7232930; rs3786486; rs34286480; rs3786485; rs28655657; rs4940717; rs4940719; rs3786484; rs34040569; rs35542747; rs33946478; rs35848049; rs7231349; rs7231354; rs34481218; rs12962172; rs3911641 |
| RAX | chr18 | 55086286 | 55086436 | rs58797899; rs45501496 |
| chr18 group00277 | chr18 | 57151972 | 57152311 | rs17062547 |
| TNFRSF11A | chr18 | 58203013 | 58203282 | rs35114461 |
| NETO1 | chr18 | 68685099 | 68687060 | rs4433898; rs34497518; rs35135773; rs6566677; rs57425572; rs36026929; rs34666288; rs10627137; rs35943684; rs9964226; rs4892054; rs9964397; rs4606820; rs12966677; rs8095606 |
| chr18 group00304 | chr18 | 70133945 | 70134397 | rs8086706; rs8086587; rs8090367; rs999332; rs17806420; rs58811193 |
| TSHZ1 | chr18 | 71128742 | 71128974 | rs61732783; rs3744910; rs1802180 |
| chr18 group00342 | chr18 | 74170347 | 74170489 | rs7226678 |
| NFATC1 | chr18 | 75385424 | 75386008 | rs28446281; rs56384153; rs4531815; rs3894049 |
| chr18 group00430 | chr18 | 75653272 | 75653621 | rs34967079; rs35465647 |
| KCNG2 | chr18 | 75760343 | 75760820 | rs3744887; rs3744886 |
| OLIG2 | chr21 | 33317673 | 33321183 | rs2236618; rs11908971; rs9975039; rs6517135; rs2009130; rs1005573; rs1122807; rs10653491; rs10653077; rs35086972; rs28588289; rs7509766; rs62216114; rs35561747; rs7509885; rs11547332 |
| OLIG2 | chr21 | 33327593 | 33328334 | rs7276788; rs7275842; rs7275962; rs7276232; rs16990069; rs13051692; rs56231743; rs35931056 |
| RUNX1 | chr21 | 35180938 | 35185436 | rs2843956; rs55941652; rs56020428; rs56251824; rs13051109; rs13051111; rs3833348; rs7510136; rs743289; rs5843690; rs33915227; rs11402829; rs2843723; rs8128138; rs8131386; rs2843957; rs57537540; rs13048584; rs7281361; rs2843965; rs2843958 |
| SIM2 | chr21 | 36994965 | 36995298 | rs2252821 |
| SIM2 | chr21 | 36999025 | 36999410 | rs58347144; rs737380 |
| DSCAM | chr21 | 41135559 | 41135706 | rs35298822 |
| AIRE | chr21 | 44529935 | 44530388 | rs35110251; rs751032; rs9978641 |
| SUMO3 | chr21 | 45061293 | 45061853 | rs9979741; rs235337; rs7282882 |
| C21orf70 | chr21 | 45202815 | 45202972 | rs61103857; rs9979028; rs881318; rs881317 |
| COL18A1 | chr21 | 45754383 | 45754487 | rs35102708; rs9980939 |
| PRMT2 | chr21 | 46911967 | 46912385 | rs35481242; rs61743122; rs8131044; rs2839379 |
| SIX2 | chr2 | 45081223 | 45082129 | rs62130902 |
| SIX2 | chr2 | 45084851 | 45085711 | rs35417092; rs57340219 |
| SOX14 | chr3 | 138971870 | 138972322 | rs57343003 |
| TLX3 | chr5 | 170674439 | 170676431 | rs11134682; rs35704956; rs2964533; rs35601828 |
| FOXP4 | chr6 | 41623666 | 41624114 | rs12203107; rs1325690 |
| FOXP4 | chr6 | 41636384 | 41636779 | rs56835416 |
| chr7 group00267 | chr7 | 12576755 | 12577246 | rs56752985; rs17149965; rs6948573; rs2240572 |
| NPY | chr7 | 24290224 | 24291508 | rs2390965; rs2390966; rs2390967; rs2390968; rs3025123; rs16146; rs16145; rs16144; rs13235842; rs13235935; rs13235938; rs13235940; rs13235944; rs36083509; rs3025122; rs16143; rs16478; rs16142; rs16141; rs16140; rs16139; rs2229966; rs1042552; rs5571; rs5572 |

TABLE 2-continued

| GENE NAME | CHROM | START | END | SNPs |
|---|---|---|---|---|
| SHH | chr7 | 155291537 | 155292091 | rs9333622; rs1233554; rs9333620; rs1233555 |
| GLIS3 | chr9 | 4288283 | 4289645 | rs56728573; rs12340657; rs12350099; rs35338539; rs10974444; rs7852293 |
| PRMT8 | chr12 | 3472714 | 3473190 | rs12172776 |
| TBX3 | chr12 | 113609153 | 113609453 | rs60114979 |
| chr12 group00801 | chr12 | 118516189 | 118517435 | rs966246; rs17407022; rs970095; rs2711748 |
| PAX9 | chr14 | 36201402 | 36202386 | rs17104893; rs12883298; rs17104895; rs35510737; rs12882923; rs12883049; rs28933970; rs28933972; rs28933971; rs28933373; rs61734510 |
| SIX1 | chr14 | 60178801 | 60179346 | rs761555 |
| ISL2 | chr15 | 74420013 | 74421546 | rs34173230; rs11854453 |
| DLX4 | chr17 | 45397228 | 45397930 | rs62059964; rs57481357; rs56888011; rs17638215; rs59056690; rs34601685; rs17551082 |
| CBX4 | chr17 | 75428613 | 75431793 | rs1285243; rs35035500; rs12949177; rs3764374; rs62075212; rs62075213; rs3764373; rs3764372; rs55973291 |
| EDG6 | chr19 | 3129836 | 3130874 | rs34728133; rs34573539; rs3826936; rs34914134; rs61731111; rs34205484 |
| MGC29506 | chr5 | 138757911 | 138758724 | rs11748963; rs7447765; rs35262202 |
| CENTG1 | chr12 | 56406249 | 56407788 | rs61935742; rs12318065; rs238519; rs238520; rs238521; rs808930; rs2640595; rs2640596; rs2640597; rs2640598; rs34772922 |
| CENTG1 | chr12 | 56416146 | 56418794 | rs11830475; rs34482618; rs2650057; rs2518686; rs12829991 |

TABLE 3

| GENE NAME | RELATIVE METHYLATION PLACENTA TO MATERNAL | PRC2 TARGET |
|---|---|---|
| PCDH17 | HYPERMETHYLATION | TRUE |
| KLHL1 | HYPERMETHYLATION | TRUE |
| POU4F1 | HYPERMETHYLATION | TRUE |
| SOX21 | HYPERMETHYLATION | TRUE |
| ZIC2 | HYPERMETHYLATION | TRUE |
| CIDEA | HYPERMETHYLATION | TRUE |
| KLHL14 | HYPERMETHYLATION | TRUE |
| ONECUT2 | HYPERMETHYLATION | TRUE |
| RAX | HYPERMETHYLATION | TRUE |
| TNFRSF11A | HYPOMETHYLATION | TRUE |
| OLIG2 | HYPERMETHYLATION | TRUE |
| OLIG2 | HYPOMETHYLATION | TRUE |
| SIM2 | HYPERMETHYLATION | TRUE |
| SIM2 | HYPERMETHYLATION | TRUE |
| CRYL1 | HYPOMETHYLATION | TRUE |
| IL17D | HYPOMETHYLATION | TRUE |

TABLE 3-continued

| GENE NAME | RELATIVE METHYLATION PLACENTA TO MATERNAL | PRC2 TARGET |
|---|---|---|
| GSH1 | HYPERMETHYLATION | TRUE |
| MAB21L1 | HYPERMETHYLATION | TRUE |
| SIX2 | HYPERMETHYLATION | TRUE |
| SIX2 | HYPERMETHYLATION | TRUE |
| SOX14 | HYPERMETHYLATION | TRUE |
| TLX3 | HYPERMETHYLATION | TRUE |
| SHH | HYPERMETHYLATION | TRUE |
| OSR2 | HYPERMETHYLATION | TRUE |
| TBX3 | HYPERMETHYLATION | TRUE |
| PAX9 | HYPERMETHYLATION | TRUE |
| SIX1 | HYPERMETHYLATION | TRUE |
| ISL2 | HYPERMETHYLATION | TRUE |
| DLX4 | HYPERMETHYLATION | TRUE |
| CBX4 | HYPERMETHYLATION | TRUE |
| CENTG1 | HYPOMETHYLATION | TRUE |
| CENTG1 | HYPOMETHYLATION | TRUE |

TABLE 4A

| SEQ ID NO | GENE NAME | SEQUENCE |
|---|---|---|
| 1 | chr13 group-00016 | CAGCAGGCGCGCTCCCGGCGAATCTGCCTGAATCGCCGTGAATGCGGTGGGGTGCAGGGCAGGGGCTGGTTTTCTCAGCCGGT CTTGGCTTTTCTCTTTCTCTCCTGCTCCACCAGCAGCCCCTCCGCGGGTCCCATGGGCTCCGCGCTCAGAACAGCCCGGAACC AGGCGCCGCTCGCCGCTCGCTGGGGGCCACCCGCCTCTCCCCGGAACAGCCTCCCGCGGGCCTCTTGGCCTCGCACTGGCGCC CTCACCCACACATCGTCCCTTTATCCGCTCAGACGCTGCAAAGGGCCTTCTGTCTC |
| 2 | CENPJ | GCTTTGGATTTATCCTCATTGGCTAAATCCCTCCTGAAACATGAAACTGAAACAAAGCCCTGAACCCCCTCAGGCTGAAAAGA CAAACCCCGCCTGAGGCCGGGTCCCGCTCCCCACCTGGAGGGACCCAATTCTGGGCGCCTTCTGGCGACGGTCCCTGCTAGGG ACGCTGCGCTCTCCGAGTGCGAGTTTTCGCCAAACTGATAAAGCACGCAGAACCGCAATCCCCAAACTAACACTGAACCCGGA |

TABLE 4A-continued

| SEQ ID NO | GENE NAME | SEQUENCE |
|---|---|---|
| | | CCCGCGATCCCCAAACTGACAAGGGACCCGGAACAGCGACCCCCAAACCGACACGGGACTCGGGAACCGCTATCTCCAAAGGG<br>CAGC |
| 3 | ATP8A2 | TTTCCACAACAGGGAGCCAGCATTGAGGCGCCCAGATGGCATCTGCTGGAAATCACGGGCCGCTGGTGAAGCACCACGCCTTA<br>CCCGACGTGGGGAGGTGATCCCCCACCTCATCCCACCCCCTTCTGTCTGTCTCCTT |
| 4 | GSH1 | GCTGGACAAGGAGCGCTCACTGTAGCTCTGCTGTGGATTGTGTTGGGGCGAAGAGATGGGTAAGAGGTCAAAGTCGTAGGATT<br>CTGGCGACCGCCTACCAAGGGATTGGGTCCACAGCACAGAGGTCTGATCGCTTCCTTCTCTGCTCTGCCACCTCCAGACAGCA<br>GCTCTAACCAGCTGCCCAGCAGCAAGAGGATGCGCACGGCTTTCACCAGCACGCAGCTGCTAGAGCTGGAGCGCGAGTTCGCT<br>TCTAATATGTACCTGTCCCGCCTACGTCGCATCGAGATCGCGA |
| 5 | PDX1 | TGCCTGACACTGACCCCAGGCGCAGCCAGGAGGGGCTTTGTGCGGGAGAGGGAGGGGGACCCCAGCTTGCCTGGGGTCCACGG<br>GACTCTCTTCTTCCTAGTTCACTTTCTTGCTAAGGCGAAGGTCCTGAGGCAGGACGAGGGCTGAACTGCGCTGCAATCGTCCC<br>CACCTCCAGCGAAACCCAGTTGAC |
| 6 | PDX1 | TCGGCGGAGAGACCTCGAGGAGAGTATGGGGAAAGGAATGAATGCTGCGGAGCGCCCCTCTGGGCTCCACCCAAGCCTCGGAG<br>GCGGGACGGTGGGCTCCGTCCCGACCCCTTAGGCAGCTGGACCGATACCTCCTGGATCAGACCCCACAGGAAGACTCGCGTGG<br>GGCCCGATATGTGTACTTCAAACTCTGAGCGGCCACCCTCAGCCAACTGGCCAGTGGATGCGAATCGTGGGCCCTGAGGGGCG<br>AGGGCGCTCGGAACTGCATGCCTGTGCACGGTGCCGGGCTCTCCAGAGTGAGGGGGCCGTAAGGAGATCTCCAAGGAAGCCGA<br>AAAAAGCAGCCAGTTGGGCTTCGGGAAAGACTTTTCTGCAAAGGAAGTGATCTGGTCCCAGAACTCCAGGGTTGACCCCAGTA<br>CCTGACTTCTCCGGGAGCTGTCAGCTCTCCTCTGTTCTTCGGGCTTGGCGCGCTCCTTTCATAATGGACAGACACCAGTGGCC<br>TTCAAAAGGTCTGGGGTGGGGGAACGGAGGAAGTGGCCTTGGGTGCAGAGGAAGAGCAGAGCTCCTGCCAAAGCTGAACGCAG<br>TTAGCCCTACCCAAGTGCGCGCTGGCTCGGCATATGCGCTCCAGAGCCGGCAGGACAGCCCGGCCCTGCTCACCCCGAGGAGA<br>AATCCAACAGCGCAGCCTCCTGCACCTCCTTGCCCCAGAGAC |
| 7 | MAB21L1 | AGATCCCGGTGCATTTAAAGGCCGGCGTGATCTGCACCACGTACCTATCTCGGATTCTCAGTTTCACTTCGCTGGTGTCTGCC<br>ACCATCTTTACCACATCCCGGTAGCTACATTTGTCTACCGCTTGAGCCACCAGCGTCTGAAACCTGGACCGGATTTTGCGCGC<br>CGAGAGGTAGCCGGAGGCGGTAATGAATTCCACCCAGAGGGACATGCTCCTCTTGCGCCCGTCGCTCAACTTCAGCACCGCGC<br>AGCCGGGCAGTGAGCCATCGTCCACGAAGTTGAACACCCCCATTTGGTTGAGATAAAGCACCACTTCAAATTCGGT |
| 8 | RB1 | ACTATGCCTTGAGGGTCAAAACGTCTGGATTTCCTGATCGATGCTGTCGTCGCTGTCCACGGAGCTACTGTCGCCGTCAGAGC<br>GGGAAGGCACGTTCAGGGAGTAGAAGCGTGGGCTTGCAGAAAGGGACCTGTTGCTGCCTTACATGGGGGCCGGCAGGGTAGTC<br>TTGGAAATGCCCAAGATTGCTTCCGCGCGCGTCAGTTCAGCGGACGTGTCTGCCTGGCACGAGGACCGTTCTACAAACTCGTT<br>CCTGGAAGCCGGGCTCGCTGGAGGCGGAGCTTTGGTTTCCTTCGGGAGCTTGTGGGGAATGGTCAGCGTCTAGGCACCCCGGG<br>CAAGGGTCTGTGGCCTTGGTGGCCACTGGCTTCCTCTAGCTGGGTGTTTTCCTGTGGGTCTCGCGCAAGGCACTTTTTTGTGG<br>CGCTGCTTGTGCTGTGTGCGGGGTCAGGCGTCCTCTCTCCTCCCGGCGCTGGGCCCTCTGGGGCAGGTCCCCGTTGGCCTCCT<br>TGCGTGTTTGCCGCAGCTAGTACACCTGGATGGCCTCCTCAGTGCCGTCGTTGCTGCTGGAGTCTGACGCCTCGGGCGCCTGC<br>GCCGCACTTGTGACTTGCTTTCCCCTTCTCAGGGCGCCAGCGCTCCTCTTGACCCCGCTTTTATTCTGTGGTGCTTCTGAAG |
| 9 | PCDH17 | GCAAGTCGGGTAGCTACCGGGTGCTGGAGAACTCCGCACCGCACCTGCTGGACGTGGACGCAGACAGCGGGCTCCTCTACACC<br>AAGCAGCGCATCGACCGCGAGTCCCTGTGCCGCCACAATGCCAAGTGCCAGCTGTCCCTCGAGGTGTTCGCCAACGACAAGGA<br>GATCTGCATGATCAAGGTAGAGATCCAGGACATCAACGACAACGCGCCCTCCTTCTCCTCGGACCAGATCGAAATGGACATCT<br>CGGAGAACGCTGCTCCGGGCACCCGCTTCCCCCTCACCAGCGCACATGACCCCGACGCCGGCGAGAATGGGCTCCGCACCTAC<br>CTGCTCACGCGCGACGATCACGGCCTCTTTGGACTGGACGTTAAGTCCCGCGGCGACGGCACCAAGTTCCCAGAACTGGTCAT<br>CCAGAAGGCTCTGGACCGCGAGCAACAGAATCACCATACGCTCGTGCTGACTGCCCTGGACGGTGGCGAGCCTCCACGTTCCG<br>CCACCGTACAGATCAACGTGAAGGTGATTGACTCCAACGACAACAGCCCGGTCTTCGAGGCGCCATCCTACTTGGTGGAACTG<br>CCCGAGAACGCTCCGCTGGGTACAGTGGTCATCGATCTGAACGCCACCGACGCCGATGAAGGTCCCAATGGTGAAGTGCTCTA<br>CTCTTTCAGCAGCTACGTGCCTGACCGCGTGCGGGAGCTCTTCTCCATCGACCCCAAGACCGGCCTAATCCGTGTGAAGGGCA<br>ATCTGGACTATGAGGAAAACGGGATGCTGGAGATTGACGTGCAGGCCCGAGACCTGGGGCCTAACCCTATCCCAGCCCACTGC<br>AAAGTCACGGTCAAGCTCATCGACCGCAACGACAATGCGCCGTCCATCGGTTTCGTCTCCGTGCGCCAGGGGGCGCTGAGCGA<br>GGCCGCCCCTCCCGGCACCGTCATCGCCCTGGTGCGGGTCACTGACCGGGACTCTGGCAAGAACGGACAGCTGCAGTGTCGGG<br>TCCTAGGCGGAGGAGGGACGGGCGGCGGCGGGGGCCTGGGCGGGCCCGGGGGTTCCGTCCCCTTCAAGCTTGAGGAGAACTAC<br>GACAACTTCTACACGGTGGTGACTGACCGCCCGCTGGACCGCGAGACACAAGACGAGTACAACGTGACCATCGTGGCGCGGGA<br>CGGGGGCTCTCCTCCCCTCAACTCCACCAAGTCGTTCGCGATCAAGATTCTAGACGAGAACGACAACCCGCCTCGGTTCACCA<br>AAGGGCTCTACGTGCTTCAGGTGCACGAGAACAACATCCCGGGAGAGTACCTGGGCTCTGTGCTCGCCCAGGATCCCGACCTG<br>GGCCAGAACGGCACCGTATCCTACTCTATCCTGCCCTCGCACATCGGCGACGTGTCTATCTACACCTATGTGTCTGTGAATCC<br>CACGAACGGGGCCATCTACGCCCTGCGCTCCTTTAACTTCGAGCAGACCAAGGCTTTTGAGTTCAAGGTGCTTGCTAAGGACT<br>CGGGGGCGCCCGCGCACTTGGAGAGCAACGCCACGGTGAGGGTGACAGTGCTAGACGTGAATGACAACGCGCCAGTGATCGTG<br>CTCCCCACGCTGCAGAACGACACCGCGGAGCTGCAGGTGCCGCGCAACGCTGGCCTGGGCTATCTGGTGAGCACTGTGCGCGC<br>CCTAGACAGCGACTTCGGCGAGAGCGGGCGTCTCACCTACGAGATCGTGGACGGCAACGACGACCACCTGTTTGAGATCGACC<br>CGTCCAGCGGCGAGATCCGCACGCTGCACCCTTTCTGGGAGGACGTGACGCCCGTGGTGGAGCTGGTGGTGAAGGTGACCGAC<br>CACGGCAAGCCTACCCTGTCCGCAGTGGCCAAGCTCATCATCCGCTCGGTGAGCGGATCCCTTCCCGAGGGGGTACCACGGGT<br>GAATGGCGAGCAGCACCACTGGGACATGTCGCTGCCGCTCATCGTGACTCTGAGCACTATCTCCATCATCCTCCTA |
| 10 | KLHL1 | ATGCGCCCTCTGCACCCCTAGAGCCAGAAGACGCTAGGTGGGCTGCGCGCTCTGCCAGGCGAAGGCTGGAGCGCAGACGGCAA<br>AGCCGCGCGTTTCAGCCGTGGTCGGGTCCGCAGGACCTGGGCGTGGGACACCACCAGGCAGGAGCAGAGGCAGGACTGGGAC<br>GCCAAAAGCTGAGAATCCTCGATGCCCGCGCGAGAGCCCCGTGTTAT |
| 11 | POU4F1 | TTCTGGAAACCGGGCCCCACTTGCAGGCCCGGCCACCTTGGGTTCTGGTGGCCGAAGCCGGAGCTGTGTTTCTCGCAGACTCG<br>GGGAGCTACATTGTGCGTAGGCAATTGTTTAGTTTGAAAGGAGGCACATTTCACCACGCAGCCAGCGCCCTGCATGCAGGAGA<br>AGCCCCCAGGGCCCAGGGTCGGCTGGCTTTAGAGGCCACTTAGGTTGTTTTAAGCACATGTGAAAGGGCAGACAGCAGGGGAG<br>CAGGATATGGGTAAGATCTTCGGGTCTCAGAACAGGGGCTGCCCTTGGGCTGTCCCGGCGCCCTGGGCTCTGACACTGAAGGG<br>TGGAATGGAGGAAGGAATGGAGAAAGGACGGTGGAACTTTCGCTTCCCCTCTGGGCCGCCTTCCCAGGGTCATGCCTGAGCTG<br>CTTTGATCCCAGTGTCGCGCATCTTGGTCCGCTACCTCCCAGGCGATAGCTACTGGGCTCCTCGCTGGCCTCACTGGGGGCCA<br>TCCCGGGCAGTGGCCTGCCCTCCGAGGCCCGCGGACCCAGCCCAGAGCTGAGGTTGGAGTTCTCCGGGCCACGTTCCGGGTC<br>GCTTAGGCTCGGAGATTTCCCGGAGACCGTCGTCCTCCCTTTCTGCTTGGCACTGCGGAGCTCCCTCGGCCTCTCTCCTCCTC |

TABLE 4A-continued

| SEQ ID NO | GENE NAME | SEQUENCE |
|---|---|---|
| | | TGGTCCCTAAGGCCCGGAGTGGTTGGCGGTACTGGGGCCCGTCGTCATCTCTGCTTCTAAGGCATTCAGACTGGGCTCCAGCT<br>GGGACCGGCAGAGGAGGTTCTCAAGGAAACTGGTGGGAAATATAGTTTTCTTTCGTCTGGTCGTTTAATTTAAATGCAACTTC<br>CCTTGGGGACATTTTCCTGGACGTTAACCAGACCACCTTGAGATGTCGTTGATGACCTAGAGACCCAGATGATGCGTCCCAGG<br>AAAGTTCACTGCTGACTATTGTCACTCTTGGCGTTATATCTATAGATATAGACCTATGTACATATCTCCACCCTGATCTCTCC<br>GTGGACATGAAACCCACCTACCTTGTGAAAGCCCTACGGGTGACACATGACTACTACGTCTCTGTCCCAACAGGGGCTGGGCC<br>TCCCCTGCCTAATAGTTGCCAGGAGTTTCGCAGCCCAAGTGAATAATGTCTTATGGCTGAACGTGGCCAAGGACTCCTGTGAT<br>TTAGGTCCCAGGAGGAGCAGAGACGTCCCCGCCCCGCCTGGGCCCTGCCGCATTCAAAGCTGGAAGAAGGCGCTGATCAGAGA<br>AGGGGCTTCCAGGTCCTGGGTTAGAACAACAACAAACAAACGAAACTCCACAACAGACACGCCTGCCCATGACCCCACGCAAG<br>GACATAGGAAGTTCTGTCGCCTTCCTGCTCCGCGGATAGCCGCCTGCCGTCTGCTGCCACCAGAACGCACGGACGCTCGGGGT<br>GGAGGTAGTCAATGGGCAGCAGGGGACCCCCAGCCCCCACAAGCGCGGCTCCGAGGACCTGGAAGCGGTGCCTGTCGCTCTC<br>CGCAGGCTCCGCTCTGCCTCCAGGAGCAAGATCCCCAAAAGGGTCTGGAAGCTGTGGAGAAAAC |
| 12 | GPC6 | TTTTTAAACACTTCTTTTCCTTCTCTTCCTCGTTTTGATTGCACCGTTTCCATCTGGGGGCTAGAGGAGCAAGGCAGCAGCC<br>TTCCCAGCCAGCCCTTGTTGGCTTGCCATCGTCCATCTGGCTTATAAAAGTTTGCTGAGCGCAGTCCAGAGGGCTGCGCTGCT<br>CGTCCCCTCGGCTGGCAGAAGGGGGTGACGCTGGGCAGCGGCGAGGAGCGCGCCGCTGCCTCTGGCGGGCTTTCGGCTTGAGG<br>GGCAAGGTGAAGAGCGCACCGGCCGTGGGGTTTACCGAGCTGGATTTGTATGTTGCACCATGCCTTCTTGGATCGGGGCTGTG<br>ATTCTTCCCCTCTTGGGGCTGCTGCTCTCCCTCCCCGCCGGGGCGGATGTGAAGGCTCGGAGCTGCGGAGAGGTCCGCCAGGC<br>GTACGGTGCCAAGGGATTCAGCCTGGCGGACATCCCCTACCAGGAGATCGCAGGTAAGCGCGGGCGCGCTGCAGGGGCAGGCT<br>GCAGCCCTCGGCTGCCGCACGTCCCACTGGCCGCCCGGCGTCCCCTTCCTTCCCCCTGTTGCTGAGTTGGTGCTCACTTTCTG<br>CCACCGCTATGGGACTCCGCGTCTCCGTGTTGGGCGGCGGATGCTCCTGCGGCTTCTTCGGCGGGGGAAGGTGTGCGTCTCCG<br>CCGCCTCATTGTGTGCACACGCGGGAGCACCCTGGCTCCCGCTCCCGCTGCTCTCGCGCCCTTCTACCCCTTAGTTGATGGC<br>TCAGGCCCGGCTGGCCAGGGAGCCCGGGTCACTCCGGGGCGGCTGCAAGGCGCAGACGGAGAGCCGAGCCGGGCGCTCACTCC<br>GCGTTCTGGTTCGGGCAAACTTGGAAGAACTGCGACCGCAGTTTGCCCAGCGCCACAGTCTGAGTGGCGCCTTCTCCACTCCC<br>GCCCTTGCGCCGGCAGGGGCGGTGGAGAGACGCGGAGGGCTCCCCCAGCCCCTCTCTCCCCTATCCGTCCTTCGGGCGACAGA<br>GCGCCCGGCGCTCGGGCCGGGGGCGGGCAAGGCTGGGAGGGACCCTCGCCGGGGACCTGGCCTCTGGACGCCGGCGTTTCAAG<br>GCTGGTTTGGGGACTTCACGGGCTGCCTGTTTCAGATGTGGGGCGGGCTTTCCCGTTAGGGTTCCTCAGTGCTTCCCCAGTTG<br>CTGTTGGCCACTCAGGGCCCGGGGACACCCTGCCACCCGGTCTGGAGCCGGCCTCGTCTGCCAGCGAACAGCCAACTTTAGCG<br>GGTGGCTCAGCTGGGGATT |
| 13 | SOX21 | CACTCAGTGTGTGCATATGAGAGCGGAGAGACAGCGACCTGGAGGCCATGGGTGGGGGCGGGTGGTGAAGCTGCCGAAGCCTA<br>CACATACACTTAGCTTTGACACTTCTCGTAGGTTCCAAAGACGAAGACACGGTGGCTTCAGGGAGACAAGTCGCAAGGGCGAC<br>TTTTCCAAGCGGGAGATGGTGAAGTCTTTGGACGTGTAGTGGGTAGGTGATGATCCCCGCAGCCGCCTGTAGGCCCGCAGACT<br>TCAGAAAACAAGGGCCTTCTGTGAGCGCTGTGTCCTCCCCGGAATCCGCGGCTTAACACATTCTTTCCAGCTGCGGGGCCAGG<br>ATCTCCACCCCGCGCATCCGTGGACACACTTAGGGTCGCCTTTGTTTTGCGCAGTGATTCAAGTTGGGTAACCCTTGCTCAAC<br>ACTTGGGAAATGGGGAGAATCTCCCCCACCCGCAACCTCCCGCACCCCAGGTTCCCAAAATCTGAATCTGTATCCTAGAGTGG<br>AGGCAGCGTCTAGAAAGCAAAGAAACGGTGTCCAAAGACCCCGGAGAGTTGAGTGAGCGCAGATCCGTGACGCCTGCGGTACG<br>CTAGGGCATCCAGGCTAGGGTGTGTGTGTGCGGGTCGGGGGGCGCACAGAGACCGCGCTGGTTTAGGTGGACCCGCAGTCCCG<br>CCCGCATCTGGAACGAGCTGCTTCGCAGTTCCGGCTCCCGGCGCCCCAGAGAAGTTCGGGGAGCGGTGAGCCTAGCCGCCGCG<br>CGCTCATGTTTATT |
| 14 | ZIC2 | AGTCACTCCAGGATCAGAGGCCGCGTCGGTTCTGCTTGGGGCATGGGCAGAGGGAGGCTGCTGGGGCCAAGCCCCGGCTGGAC<br>GCGAGGGAAGAAACTCGTCCCAGGACCCGCACGCCCATACCTGGCTGTCCCAGAGCTCTTCCCTAGGCCGGCACCTTCGCTCT<br>TCCTCTTCCCCACCCCCTAGCCCTTTTGTCTCTTTTTCAGACGGATGTTTTCAGTCTCAAGTGGTTTTATTTTCCGCACAAAA<br>CCCTGAGATCAAGGGCAGATCACAGACTGTACCGGAGGCTCGGGTTTCCCTGGACTCTGTGCTGTTCTGCGTCCCAGGGTTGG<br>CTAGGAAGGAAGGCCTGGGCCGGCGAGGTGACGGGTCTCCCGCCCAGGTCGGCAGGACGGGGGGAGGTGTGTCCCGGTAGGTC<br>CCTGGTGAGCTCACCCGTGGCATCGGGGACCCGCGGGAACCCACCGGGCGCCCACTAGAGACTCGGGTCCTACCCTCCCCCAC<br>ACTACTCCACCGAAATGATCGGAAGGGCGCGCTAGGCCTGCTTCCAAGGGCTCAGTGATAAAGGCCTCAAAATCACACTCCAT<br>CAAGACTTGGTTGAAGCTTTGGGTAGGTTTGTTGTTGTTGTTGTTGTTGTTTGTTTGTTTGTTTTAGCAGACACGTCCTGGAA<br>AGAGGTCCTCAGAACCCAAAGGTTCAATAATGATTTGTGGATGGATTGATTATAGTCTGATATCGCTCTGGTTCCACAGAAAC<br>CCGGAGCTCCTTGGCCCACTGTTACCCCAGCAGACCTAAATGGACGGTTTCTGTTTTTCACTGGCAGCTCAGAACTGGACCGG<br>AAGAAGTTCCCCTCCACTTCCCCCCTCCCGACACCAGATCATTGCTGGGTTTTTATTTTCGGGGGAAAAACAACAACAACAAC<br>AACAAAAAAAACACTAGGTCCTTCCAGACTGGATCAGGTGATCGGGCAAAAACCCTCAGGCTAGTCCGGCTGGGTGCCCGAGC<br>ATGAAAAGGCCTCCGTGGCCGTTTGAACAGGGTGTTGCAAATGAGAACTTTTGTAAGCCATAACCAGGGCATCCTGAGGGTCT<br>GAGTTCACGGTCAAGGCTGTGGGCTACTAGGTCCAGCGAGTCCAGGCCTCGCCCCGCCCCCGAGCTGCCACAGCCAAGATCTT<br>CGGCAGGGAATTCGAGACCAGGGTCCTCCCACTCCT |
| 15 | chr13 group-00385 | TTTCGTGCCGCTGTTTTCAATGCGCTAACGAGGCACGTTATTCTTAGCCGCGTCCGGGAGGGGATCACATTCCTGCGCAGTTG<br>CGCTGCTGGCGGAAGTGACTTGTTTTCTAACGACCCTCGTGACAGCCAGAGAATGTCCGTTTCTCGGAGCGCAGCACAGCCTG<br>TCCCATCGAGAAGCCTCGGGTGAGGGGCCCGGTGGGCGCCCGTAAGCCACAGCGAGTGGTTAGAAGTAGGTTAGGAAGAAGGG<br>GAGGTAAGAAAGCCGAGTAGGGTT |
| 16 | chr13 group-00390 | GTTCGGTGGACAAGGGGGCAGCGCCCACAGCAAGCCGGAAAGAGGGAGGCGCGGGGCCGCGCTTGGGGCCTGCCGCTGCACGC<br>CAGCCTGGGCAAAGAGCTGCCACCTTCTGCGGGCGAAGCGGGTCGGGACGCAGGACGGCAGCGGGGCTGGAGGCAGCTACGTG<br>GGTCCACACCCCCATGCCCTGCAAGGCTCCTTGGCCCTGCTTCTCCTCTGTCTCGGCGGGAGAGGAGCAGCCTCGGTTTTACA<br>GAATTTC |
| 17 | chr13 group-00391 | TGTGCCATTTAGTGAGAGGTGTTTTGGGCAAAGAATCAATTTAACTGTGACTGACCGACGGGCTTGACTGTATTAATTCTGCT<br>ACCGAAAAAAAAAAAAAGCAATGAGCCGCAAGCCTTGGACTCGCAGAGCTGCCGGTGCCCGTCCGAGAGCCCCACCAGCGCG<br>GCTCACGCCTCAGTCTC |
| 18 | chr13 group-00395 | AGAGTCCCAGTTCTGCAGGCCGCTCCAGGGCTAGGGGTAGAGATGGTGGCAGGTGGTGCGTCAACTCTCTAGGGAAGAGGAAC<br>TTGCATTACAAAGACTTGTCTTTCTGAGCTGAAGTCAAAACGGGGGCGTCAAGCGCGCTCCGTTTGGCGGCGGTGGAGGGGCC<br>GCGCGCCCGCGCTGTCCCAGCCGGAGCTGCCCTGGCTGGTGATTGGAGGTTTAACGTCCGGAATTCAGGCGCTTCTGCAGCTC<br>AGATTTGCCGGCCAAGGGGCCTCAGTTGCAACTTTTCAAAATGGTGTTTCTGGAAAATAACAAATTCAGACTCAACTGGTGAC<br>AGCTTTTGGCTATAGAGAATGAAACTGCTTCCCTTTGGCGGTGGAACTCTTAAACTTCGAAGAGTGAAAGAATACAATGAAAT<br>AAAATGCCATAAGATCACTGGATTTTTCAGAAAAAGGAAGACCCCAAATTACTCCCAAAATGAGGCTTTGTAAATTCTTGTTA |

TABLE 4A-continued

| SEQ ID NO | GENE NAME | SEQUENCE |
|---|---|---|
| | | AAAATCTTTAAATCTCGAATTTCCCCCTACAACATCTGATGAGTGCTTTAAGAGCAAACGAGCAAATCCCACCTCGAGAATCA<br>ACAAACCCAAGCTCTGGCCAAGGCTCTCCCCGCGTTTTCTTCTCGTGACCTGGGGAATGTCCCGCCCCATCGCTCACCTGGCT<br>CTTGTCATCTCGCTCATCTTGAAGTGACCCGTGGACAATGCTG |
| 19 | chr13 group-00399 | AGCTGCCCTCTGTGGCCATGAGCGGGTGTCCAGCCCCTTCCAAGGCTGCACCGGGGAGACGCTGGTTTTCTGCTCGCTGTGAC<br>CGAACAAAGCCCCTAAGAGTCAGTGCGCGGAACAGAAGAGCCGGACCCCGACGGGCCGAGTCCCAACGTGAGGCACCCGGCAG<br>AGAAAACACGTTCACG |
| 20 | PROZ | CCTCGGCAGCACCGGCATGGCTGGAGGCCAGTACGGCCAGGTGTGGCGGGAGGGAGCGCCGTCTGGCTTGGGTCGTCCATCCT<br>GACAGGACGCTGCAAGGGCAGGAGCCCCGCGCCCCGTGTCCTGCGCCCCCGCTCGAGGACAAGCCCCAGCCGCCGGTCTCCGC<br>TGGGTTCCGACAG |
| 21 | CIDEA | CTTTAAGAGGCTGTGCAGGCAGACAGACCTCCAGGCCCGCTAGGGGATCCGCGCCATGGAGGCCGCCCGGGACTATGCAGGAG<br>CCCTCATCAGGCGAGTGCCCCGCGTCCCCCTGATTGCCGTGCGCTTCCAATCGCCTTGCGTTCGGTGGCCTCATATTCCCCTG<br>TGCGCCTCTAGTACCGTACCCCGCTCCCTTCAGCCCCCTGCTCCCCGCATTCTCTTGCGCTCCGCGACCCCGCGCACACACCC<br>ATCCGCCCCACTGGTGCCCAAGCCGTCCAGCCGCGCCCGCGGGCAGAGCCCAATCCCGTCCCGCGCCTCCTCACCCTCTTGCA<br>GCTGGGCACAGGTACCAGGTGTGGCTCTTGCGAGGTG |
| 22 | chr18 group-00091 | AGACTTGCAGAACTCGGGCCCCCTGGAGGAGACCTAACCGCCACGGTCTTGGGGAGGTTCCGGAGGGCCTCGGTTGTCTGCAC<br>TCCCAACACCAAGAAACCCCTGAGACGCGAAGCTGCCAGCGTGCTGCCCTCAGAGCAGGGCGACGCAAAGCCAGCGGACCCCG<br>GGGTGGCGGG |
| 23 | chr18 group-00094 | TGCTCGGCTGGGGGGCTCGCTCCGCACTTTCGGTGCCAGAAAATGCCCAGAGGAGCGGGGCGGCCCCAGAGCCTCCTTTCGGG<br>GCGCGAGGCCCGGCGCGTGTGTACGGAGTCCAGTCCCCCCAGGGAGTGGGGTGCCCGCACCTTCCCCTCCGCGCTCGGAGCCA<br>C |
| 24 | KLHL14 | TCTTGCACACCTGCTTGTAGTTCTGCACCGAGATCTGGTCGTTGAGGAACTGCACGCAGAGCTTGGTGACCTGGGGGATGTGC<br>AGGATCTTGCTGACCGACAGCACCTCCTCCACCGTGTCCAGGGACAGGGTCACGTTGGCCGTGTAGAGGTACTCGAGCACCAG<br>GCGCAGCCCGATGGACGAGCAGCCCTGCAGCACCAGGTTGTTGATGGCCCGGGGGCTGGTCAGCAGCTTGTCGTCGGGGGAGG<br>AAGAAGGAGTCCCGGGCTCCTCCTGCGGCGGCGGCTGCTGCTGCTGTGACGGCTGCTGCTGCGGCGGCTGCTGCTGGTCCTTG<br>GGGGCCCCCAGGCCGTCCTGGCCGCCGACCCCTCCCCCGAGAGGGGGGTGGCTGGAGAAGAGCGATCGGAAGTACTGCGAGCA<br>GGAGGCCAGCACGGCCTTGTGGCAATGGAACTGCTGGCCCTGGGCCGTCAGGGTCACGTCGCAAAACAGCTGCTTCCTCCACA<br>GCAGGTTGAGGCCGTGCAGCAGGTTGTCGCTGTGGCTGGGGTCGAAGGTGGAGGTCCTGTCCCCGGATCTGGACATGGCGAGC<br>TGACTCGGTGCACCTGGCTTTAAACCCTCCTCCAACCTGGCAGACAGGGGTGGGGGATGGGAGGGAGGGGAGCAGGGTGGTGG<br>AGCGGGTGGGGTGTGGTCGGGGTGGGGAAGGGTGTGGAGGGGAGGGGAGGGCGAAGAACAAGAATCAAGGCTCAGCTTGACTC<br>CCTCCTGGCGCGCTCCGGACCCCGACCCTAGGAGGAAAGTCCGAAGACGCTGGATCCGTGAGCGCCACCAGAAGGGCCCTGTC<br>TGGGGTCCCGGCGCCGGTTCTGCGCCCTGCGGCTCCTCTCGCCACCTCCCACACACTTCGTCCCTCACTTTCCTAAAACCAAC<br>CACCTCAGCTCGGCTGTTGGCAGCAACAGCAGTGGCAGCAGCGACGGCAAAGTGGCGGCTGAGGCCGAGGCACCTCGTGGGCT<br>CGTGTCCATGCCGGGCCAGATGAAGGGAAAGGCCGGGAAGTGGGGAGCCGGGGGTGCCCTGAAAGCTCAGAGGCGACCGACGG<br>CGAAGGTTCCAGGTCAACTTGTGCCCGAAGCTTTGCTTTTCGCAGTTGGCCCAGTTTGGGGGAGGGGGTAGGAACAGGGGCCC<br>GACCAGCGTGCGGGGTGTGCGAATCTTAGCTCTCCAAAAGCTG |
| 25 | ST8SIA3 | CCTCTGTGTTAGTGCCCTCGGGAATTTGGTTGATGGGGTGTTTG |
| 26 | ONECUT2 | TGATGTCGCACCTGAACGGCCTGCACCACCCGGGCCACACTCAGTCTCACGGGCCGGTGCTGGCACCCAGTCGCGAGCGGCCA<br>CCCTCGTCCTCATCGGGCTCGCAGGTGGCCACGTCGGGCCAGCTGGAAGAAATCAACACCAAAGAGGTGGCCCAGCGCATCAC<br>AGCGGAGCTGAAGCGCTACAGTATCCCCCAGGCGATCTTTGCGCAGAGGGTGCTGTGCCGGTCTCAGGGGACTCTCTCCGACC<br>TGCTCCGGAATCCAAAACCGTGGAGTAAACTCAAATCTGGCAGGGAGACCTTCCGCAGGATGTGGAAGTGGCTTCAGGAGCCC<br>GAGTTCCAGCGCATGTCCGCCTTACGCCTGGCAGGTAAGGCCGGGGCTAGCCAGGGGCCAGGCTGCTGGGAAGAGGGCTCCGG<br>GTCCGGTGCTTGTGGCCCAAGTCTGCGCGCCGAGTCACTTCTCTTGATTCTTTCCTTCTCTTTCCTATACACGTCCTCTTTCT<br>TCTCGTTTTTATTTCTTCTTCCATTTTCTCTTTCTCTTCCGCTCTTCCCCTACTTTCCCTTCTCCCTTTTCTTTTTCTTTCTT<br>ACTCTCTCCTTGTCCCTGAGCTTTCATTGACCGACCCCCCCCCATTTCATTCGCCCTCCCCTCAATGTGCCAACCTTTGCCCT<br>ATTTCCGATCTTCCCAGGTACTGGGAGGCGGGATGGGGGTGTGCGTTTTCCTCTAGGAGCCCTGTCTTTCCAAGACCCACAGA<br>AACCAGGACCTGCCCTTATTCAAAACCCCATGCACTTCAAGTCTCTTTTAGACAACACATTTCAATTTTCCGGGCTGACTAGT<br>CTCCCTGTGCAGAGGCAGTTGAGAGGCTTTGCTCTGCAGAGGGAAAAGAGCTCTCTACTCTCCCACCCACCATATAGGCAAAC<br>TTATTTGGTCATTGGCTGAAGGCACAGCCTTGCCCCCGCGGGGAACCGGCGGCCAGGATACAACAGCGCTCCTGGAGCCCATC<br>TCTGGCCTTGGCGTTGGCGCAGGGACTTTCTGACCGGGCTTGAGGGGCTCGGGCCAGCTCCAATGTCACTACCTACAGCGAGG<br>GCAGGGTGTAAGGTTGAGAAGGTCACATTCACCGCTTTGGGAGGACGTGGAGAAGAGACTGAGGTGGAAAGCGCTTTGCCTT<br>GCTCACCGGCCGTCCTTGCCCCGGTCCCAGCGTTTGCTGGGATTTGCCAGGATTTGCCGGGGCTCCGGGAGACCCTGAGCACT<br>CGCAGGAAGAGGTGCTGAGAAATTAAAAATTCAGGTTAGTTAATGCATCCCTGCCGCCGGCTGCAGGCTCCGCCTTTGCATTA<br>AGCGGGCGCTGATTGTGCGCGCCTGGCGACCGCGGGGAGGACTGGCGGCCCGCGGGAGGGGACGGGTAGAGGCGCGGGTTACA<br>TTGTTCTGGAGCCGGCTCGGCTCTTTGTGCCTCCTCTAGCGGCCAAGCTGCGAGGTACAGCCCTCTATTGTTCTAGGAGCACA<br>GAAACCTCCTGTGTGGGCGGCGGGTGCGCGAGCTAGAGGGAAAGATGCAGTAGTTACTGCGACTGGCACGCAGTTGCGCGCTT<br>TTGTGCGCACGGACCCCGCGCGGTGTGCGTGGCGACTGCGCTGCCCCTAGGAGCAAGCCACGGGCCCAGAGGGGCAAAATGTC<br>CAGGTCCCCCGCTGGGAAGGACACACTATACCCTATGGCAAGCCAGGGTGGGCGACTTCCCATGGATCGGGTGGAGGGGGGTA<br>TCTTTCAGGATCGGCGGGCGGTCTAGGGGAACAATTCGTGGTGGCGATGATTTGCATAGCGCGGGTCTTGGGATGCGCGCGGT<br>TCCGAGCCAGCCTCGCACAGCTCGCTTCCGGAGCTGCGAGCTCAGGTTTCCACCCCCGATCCCCCGGGCTTTCCTCGCACCGC<br>TGAGCCCAGCTTGTGGGGTGCACTCGACCAACGCCCGACAGGGCTGGGGAATGTGACAGGCAGCAGGTTCACCCGGGCTTGGG<br>GAGGGGGAGTTTCCGCTTTGACAGCATTTTCCTTTGCCGTCTGCTGGTGGATTCCTATTCCCAGTCGGTAATCGCCCCGCAGT<br>GTTGATCTAAGAAGGTAAAGAAAACTAGGTTTCCCTGCAAAGAGCCTCCCCCAAATCGGCGGACTCCGGATACTTTGAGTGGA<br>TTTAGAAATTTATGTAATCTTTCTCCTTTAGTTTATTTTTCATCCTCTCCTACAGTTTTCTCTGATTTGCTGTTGGTTCGGGG<br>CAAGATAAAGCAGCCAGTAGAGAGCGATAATAATAGCGGCGGGAAATGAACTGGAGACTGGCTGACAGTTCTTAACATTTTGT<br>CATAGATCCCCCCGAATGTCCCAGGCTGTCTCTGGTGGGTTTTAGTACCCGCCGGCTTCTTGGGCACCGGGGACCAGAAGGAA<br>CTTGGCAGCTGGTCTTAGGGGTACAGTTAAAGGCAGGATGACAGCTATTCTCCTGCTCATCTCAGAGCGCTGCCGCCCCCTCA<br>TGCCGGTCGCGCAAAGAACACAGCTTTAAAAAACACGTGCCTTCTGCCCATATAGGTCTGAAAGTGATGAGGAAAGTAATGC<br>TTCGCCTATTAGCGAGTTTCAGCTTTTAAAATGATCCCAAGCGTTGCTGAGATGAGAAAGCGTGGCATCCCGGGGGTCCTCAG |

TABLE 4A-continued

| SEQ ID NO | GENE NAME | SEQUENCE |
|---|---|---|
| | | CCCCACCCGCGCCCATGGTGCAAGTCTGCAGGGACAGGCCCGGGACAGCACTGCCCACGCTGCTAGATTTTCCGCAGAGGATCGCTGAAGCTGCCTTCGTGGGAGACAGAATGCCTCCTCCAGCGAGTGGAAAAGGCCTGCTGAGGACCCCGCTTTGCTCGAGCATTCAAATGTGTGTCTGTTTTATTACCCTGGGTTGAAAAGGGACAAGAGCTTTAGCCTTTTTATCTGGCCATTTTATCAGCAACTACAAGTGTGTTGAGTGGTTATTATTACATAGGAGGCTTTTCAGTTTGGGGTCAGTAGATCAGTCTCTTCAGACACTGATGCAGAAGCTGGGACTGGTAAGTAGGTATTATGTGCTCGGAGCGCTAGGGGACAGGAGCAAATGGAGAAGAAAAGCGGAGGCTTTCTCCGCCCGGAGTATCGATCGGAATCCCCGCCGGTACGCCGCAGAGGGCCCTCGCCGTTGGGCCCCGGGGGTTTAACAAGCCCAGCCGCTCCGCAGGCGGCTCGGCCGGACTCTCAGACCGGTGCCTGGAAGACACCGTCCCTGCCCCCCTCCCGCCAAACCTGCCTCTTCTCTTTCTCTCATAGGTTATAGGTTCCCTTTCTCTCTCATTTTGGCCCCGCCCCCGGGTCCTGCCAAACAGCCAAGCAGGCCGGGGTTTAGGGGGCTCAGAATGAAGAGGTCTGATTTGGCCAGCGCCGGCAAAGCTCACCCTTAGGCGAGGTCACAACAGAGGCAGGTCCTTCCTGCCCAGCCTGCCGGTGTAGTCACAGCCAAGGGTGGCACTTGAAAGGAAAAGGGAGAAAACTTCGGAGAAATTTAGATTGCCCCAACGTTAGATTTCAGAGAAATTGACTCCAAATGCACGGATTCGTTCGGAAAGGGCGGCTAAGTGGCAGGTGGTTGCAACCCCGCCCGGTCGGGCGGTTCCCAGAGGTTCCCCAAGACCAGCCCTTGCAGGGCGGTTTTCAGCAACCTGACAAGAGGCGGCCAAGACAAATTTCTGCGGGTTCGAGCACACACTCTCGGGCGTTGGGCCCCAGAGACCTCTAAACCAAGCACAAACAAGAAGGGAGTGAGAGAACCCAGGCTAGAACTTGCACGGGCATCCCACTGAGGAAAAGCGAGGCCTCGGTGGCAGGCATGTTTTCTTCCGACGCCCGAAAATCGAGCCGAGCGCCCGACTACATTTACTGCAGAGGTTTCCGCCTCCAGTGAGCCCGGATCCCCCAGCGGCCTGCCCGGAGCTGGTCTCCAGTCCCCGCCGTAGTCCGACGCACGGCCCTCTCCTGGCAGCAAGCTCCCAGCGGCCAGTCTGAAGCCAATTCTGTTCAGGCGGCCGAGGGCCCTTAGCCAACCCACCATGATGTCGCCTGGGCCACCTGATGCCCGCAGCGGCGGGACACGGCCCGGGCAGTGCGCAGTGGCTCCTGCTAGGGGCACCGCGTGCGTGCTTGTCTCCCGCTGCGCCGGGGACGTCCTTGGGTGACACGGGCCGCTGGGCACCTCCCAAGCCGAGGAAACGGACCCCCTTCGCAGAGTCTCGCGCCCACCCCCCAACCTCCCACCTCGTTTCTCGCTGCTAGGGCTCCCGACTCAGCCCACCTCTCCTGGCGGTTTAGTTAGGGATCAGAGCTGGAGAGGCTGAACGCAACCCGTGCCAGTACGGAACAGACGATATGTTTGCCTGCTAGCTGCTTGGATGAATAATTGAAAAGTTCGCTGCAGTCTGTGCTTCGTCAAGTCCCGGGTGCCGGGAGAACACCTTCCCAACACGCATCAGGGTGGGCGGGAGCGGGCAGAGGAGGCGGGACCCGAGGGAGGAGAGTGAACCCGAGCAGGAGAAGCAGCCCAGGCAGCCAGGCGCCCTCGATGCGAGAGGCTGGGCATTTATTTTTATTCCAGGCTTTCCACTGTGTGGTTATGTCACTTTCTCAAACAAATGTGTATATGGAGGGAGATCGATGCTGATAATGTTTAGAAGATTAAAAGAGCATTAATGCTGGCAACAATAACGTAAACGTGTGGACCCAGATTTCATTGATCTGGAACTTGATCCGGCGCGTTTCCAGTAAGCCCGACGGCGCGCTCTTCCCAGCAGAGCGCTCACCAGCGCCACGGCCCCGCGGTTTTCCAGCGGTGCCGCTTCGCCAGCTCTGCGCGGGTTCTCCCGTCTGACCGCAGCTCCTCCCCCGCGAGGCCCCAGCCCGCCTTACTTCCCCGAGGTTTTCTCCTCCTCTCGCGGGGCTCTCTGCCCTCTGCACCCCCTCCCCCGACCTCTGCACCACCCGCCCCTGTGCGCACACACCGCTACTTGCGCTTCCGGCGATCCGCCTG |
| 27 | RAX | AACCGGAGATCTGCTTGGTGAACTGAGAGGAGTCCTTAGGAGAGCGGGGACGCCAGGGGCCGGGGGACACTTCGCTCTCGCCCTAGGGAAGGTGGTCTTGACGCTTTCTATTGAAGTCAAACTTGAAAATATCAGCTGCCGCTGGACTAT |
| 28 | chr18 group-00277 | CGTGAGCAGAACGCCCGCCCTGGAGCAGTTAGGACCGAAGGTCTCCGGAGAGTCGCCGGCGGTGCCAGGTAACGCAGAGGGCTCGGGTCGGGCCCCGCTTCTGGGGCTTGGGACTCCGGGCGCGCGGAGCCAGCCCTCTGGGGCGAAATCCCCGGGCGGCGTGCGCGGTCCCTCTCCGCGCTGTGCTCTCCCAGCAACTCCCTGCCACGGGAAGCTGGGGCGCACCGGGGCAGGT |
| 29 | NETO1 | TAGAAGAGGAAGACTCCTCTGGCCCCACTAGGTATCATCCGCGCTCTCCCGCTTTCCACCTGCGCCCTCGCTTGGGCCAATCTCTGCCGCACGTGTCCATCCCTGAACTGCACGCTATCCTCCACCCCCGGGGGGTTCCTGCGCACTGAAAGACCGTTCTCCGGCAGGTTTTGGGATCCGGCGACGGCTGACCGCGCGCCGCCCCCACGCCCGGTTCCACGATGCTGCAATACAGAAAGTTTACGTCGGCCCCGACCCGCGCGGGACTGCAGGGTCCGCCGGAGCGCGGCGCAGAGGCTTTTCCTGCGCGTTCGGCCCCGGGAAAGGGGCGGGAGGGCTGGCTCCGGGAGCGCACGGGCGCGGCGGGGAGGGTACTCACTGTGAAGCACGCTGCGCCCATGGATCATGTCTGTGCGTTACACCAGAGGCTCCGGGCTCCACTAATTCCATTTAGAGACGGGAAGACTTCCAGTGGCGGGGGGAGGACAGGGTCGAGAGGTGTTAAAGACGCAAAGCAAGAAGGAAATAAAGGGGGGCCGAGAGGGAGACCGAGAGGAAGGGGGAGCTCCGAGCCCACGCTGCAGCCAGATCCGGATGAGTCCGTCCTCCGCCCCGGGCGGGCTCTCGCTCTCGCTGGCCCTCAGCGCCGCGCAGCCAGCAGCATCCCCACCGTGACGCTCGCATCACACCCGGGCGCCGGCCGCCACCATCCGCGCCGCCGCCGTCAGGACCCTCCTCCCGGGCATCGTCGCCGCCGCGGGGTCGGGAGGACGCGGCGCGCGGGAGGCGGCGGTCGCAGGGCGAGCCCCGGGACGCCCCGAGCCGGGGCCGGGGCCGGGGAGAGGGCGCAGCGAGGTGGGGGCCAGTCCAGACCGACGGCAGCGACGGAGCGGGCGGCGGCGGCGGCGCCGGCGGCGGCGGGGTGGCTCAGTCCCCAGTCTCAGACGCGCCGCGCAGCAGGTCGGAGCAGCCTCCCCGGGAGGATGTCCAGCGGCAGCGCTCCTCGCTCCAGCCCTTGGGGATCTTCCGCTGAGGCATTGAAGGCAGGAAGAAGGGGTCCGTCATCGGCTCGCCGGGCTGCGCGCCACCTCTGCTATCTTGCGGAAAGAGGAGCGGGTGGGTGGGCGTCTGGGAGGCGGGCTGGAGGGCGGTGCAGGGGAGCGGGGCGGCCGGGGGGGGGGCCGGGGGGCGGGGAAGGGAGGGAGGAGAAAGGAGCCGGAAGAGGGCAGAGTTACCAAATGGGCTCCTTAGTCATGGCTTGGGGCTCCACGACCCTCCTGGAAGCCCGGAGCCTGGGTGGGATAGCGAGGCTGCGCGCGGCCGGCGCCCCGGGGCTGGTGCGCGGCAGAATGGGGCGCGGCGGCGGCAGCAAGGACATCCCAGCCGCGCGGATCTGGGGGAGGGGCGGGGAGGGGGTGAGGACCCGGCTGGGATCCGCGGCTCGGCCCGCCAGGGCGCAGAGAGAGGATGCAGCCGCAAATCCCGAGCCGGATCCTCGTGCCGGACGGAAGGCGTGGAAGCGGGAGGGGCCTTCGTGTGAAAATCCCTTGTGGGGTTTGGTGTTTCACTTTTTAAAGGTTAGACCTTGCGGGCTCTCTGCCTCCCACCCCTTCTTTTCCATCCGCGTAAAGGAACTGGGCGCCCCCTCTCCCTCCCTCCCTGGGGCGCAGGTTTCGCCGCGGACTCCGCGCTCAGCTTGGGAGACACGGCAGGGGCGCGCCCCAGGGAAAGGCGGCCGTAAAAGTTTCGCGGTTGAGCACTGGGCCTGATGTCCAGTCCCCCCACCAAATTACTCCTGCAAAGACGCGGGCTTCTTGCAATTGAGCCCCCCACCTCGAGGTATTTAAAACCACCCCAAGGCACACACGGACCCCCGTTCCCCCGCGCCACTTCCTCCTACAGGCTCGCGCGGCGCGTTAAAGTCTGGGAGACACGAGTTGCGGGGAAACAGCACCGGAAG |
| 30 | MBP | AAGAAACAGCTCATTTCGGAGCTGAGGACAAGGCGTGGGAAGAAGACGCGTTTGGTTTCACCCAGGCGGGTGGCGGCAAAGCTGTGGGATGCGCGCTGCACACTCCTTCCGTCATCCCGTTCCCACCTTCCACACACACCTGCGGGAGGTCGGACATGTCCTGATTGCGTGTTCATCACGATGGCAAACCGAACATGAGGAGAACGCCACTGACGCTGGGTGCGCCGGCTTTCCCAGCCCTCGTGCATAACGGGGAGGGAGATGCAGAAGTTTTTTCCAACATCGGTGCAAAGGGGAAGCTGAGGTTTTCCTAT |
| 31 | NFATC1 | TCTGTCAGCTGCTGCCATGGGGCAGCGGGAAGGCCCTGGAGGGTGCCTGGGCTGTGTCTGGTCCCGGCCACGCGTCCCTGCAGCGTCTGAGACCTTGTGGAACACACTTGACCCGGCGCTGGGACGGGGTCGGCCCACACGCACCGCCAGCCCGCAGGAGTGAGGTGCAGGCTGCCGCTGGCTCCTTAGGCCTCGACAGCTCTCTTGAGGTCGGCCCTCCTCCCCTCCCGAGAGCTCAGCAGCCGCAGACCCAGGCAGAGAGAGCAAAGGAGGCTGTGGTGGCCCCCGACGGGAACCTGGGTGGCCGGGGGACACACCGAGGAACTTTCCGCCCCCCGACGGGCTCTCCCACCGAGGCTCAGGTGCTCGTGGGCAGCAAGGGGAAGCCCCATGGCCATGCCGCTTCCCTTTCACCCTCAGCGACGCGCCCTCCTGTGCCCGCGGGGAACAAGACGGCTCTCGGCGGCCATGCAGGCGGCCTGTCCCACGAACACGATGGAGACCTCAGACGCCGTCCCCACCCTGTCACTGTCACCATCACCCATCCTGTCCCCTCACGCCTCCCCACATCCCATCATTACTAC |

TABLE 4A-continued

| SEQ ID NO | GENE NAME | SEQUENCE |
|---|---|---|
| 32 | chr18 group-00430 | GAAGTAGAATCACAGTAAATGAGGAGTTAGGGAATTTAGGGTAGAGATTAAAGTAATGAACAGAGGAGGAGGCCTGAGACAGC<br>TGCAGAGAGACCCTGTGTTCCCTGTGAGGTGAAGCGTCTGCTGTCAAAGCCGGTTGGCGCTGAGAAGAGGTACCGGGGGCAGC<br>ACCCGCCTCCTGGGAGAGGGATGGGCCTGCGGGCACCTGGGGCGCCACGCCACAGCCTCTTCCCCTCAGCACGCAGAGA |
| 33 | OLIG2 | TACTCCGGCGACGGGAGGATGTTGAGGGAAGCCTGCCAGGTGAAGAAGGGGCCAGCAGCAGCACAGAGCTTCCGACTTTGCCT<br>TCCAGGCTCTAGACTCGCGCCATGCCAAGACGGGCCCCTCGACTTTCACCCCTGACTCCCAACTCCAGCCACTGGACCGAGCG<br>CGCAAAGAACCTGAGACCGCTTGCTCTCACCGCCGCAAGTCGGTCGCAGGACAGACACCAGTGGGCAGCAACAAAAAAAGAAA<br>CCGGGTTCCGGGACACGTGCCGGCGGCTGGACTAACCTCAGCGGCTGCAACCAAGGAGCGCGCACGTTGCGCCTGCTGGTGTT<br>TATTAGCTACACTGGCAGGCGCACAACTCCGCGCCCCGACTGGTGGCCCCACAGCGCGCACCACACATGGCCTCGCTGCTGTT<br>GGCGGGGTAGGCCCGAAGGAGGCATCTACAAATGCCCGAGCCCTTTCTGATCCCCACCCCCCCGCTCCCTGCGTCGTCCGAGT<br>GACAGATTCTACTAATTGAACGGTTATGGGTCATCCTTGTAACCGTTGGACGACATAACACCACGCTTCAGTTCTTCATGTTT<br>TAAATACATATTTAACGGATGGCTGCAGAGCCAGCTGGGAAACACGCGGATTGAAAAATAATGCTCCAGAAGGCACGAGACTG<br>GGGCGAAGGCGAGAGCGGGCTGGGCTTCTAGCGGAGACCGCAGAGGGAGACATATCTCAGAACTAGGGGCAATAACGTGGGTT<br>TCTCTTTGTATTTGTTTATTTTGTAACTTTGCTACTTGAAGACCAATTATTTACTATGCTAATTTGTTTGCTTGTTTTTAAAA<br>CCGTACTTGCACAGTAAAAGTTCCCCAACAACGGAAGTAACCCGACGTTCCTCACACTCCCTAGGAGACTGTGTGCGTGTGTG<br>CCCGCGCGTGCGCTCACAGTGTCAAGTGCTAGCATCCGAGATCTGCAGAAACAAATGTCTGAATTCGAAATGTATGGGTGTGA<br>GAAATTCAGCTCGGGGAAGAGATTAGGGACTGGGGGAGACAGGTGGCTGCCTGTACTATAAGGAACCGCCAACGCCAGCATCT<br>GTAGTCCAAGCAGGGCTGCTCTGTAAAGGCTTAGCAATTTTTTCTGTAGGCTTGCTGCACACGGTCTCTGGCTTTTCCCATCT<br>GTAAAATGGGTGAATGCATCCGTACCTCAGCTACCTCCGTGAGGTGCTTCTCCAGTTCGGGCTTAATTCCTCATCGTCAAGAG<br>TTTTCAGGTTTCAGAGCCAGCCTGCAATCGGTAAAACATGTCCCAACGCGGTCGCGAGTGGTTCCATCTCGCTGTCTGGCCCA<br>CAGCGTGGAGAAGCCTTGCCCAGGCCTGAAACTTCTCTTTGCAGTTCCAGAAAGCAGGCGACTGGGACGGAAGGCTCTTTGCT<br>AACCTTTTACAGCGGAGCCCTGCTTGGACTACAGATGCCAGCGTTGCCCCTGCCCCAAGGCGTGTGGTGATCACAAAGACGAC<br>ACTGAAAATACTTACTATCATCCGGCTCCCCTGCTAATAAATGGAGGGGTGTTTAACTACAGGCACGACCCTGCCCTTGTGCT<br>AGCGCGGTTACCGTGCGGAAATAACTCGTCCCTGTACCCACACCATCCTCAACCTAAAGGAGAGTTGTGAATTCTTTCAAAAC<br>ACTCTTCTGGAGTCCGTCCCCTCCCTCCTTGCCCGCCCTCTACCCCTCAAGTCCCTGCCCCCAGCTGGGGGCGCTACCGGCTG<br>CCGTCGGAGCTGCAGCCACGGCCATCTCCTAGACGCGCGAGTAGAGCACCAAGATAGTGGGGACTTTGTGCCTGGGCATCGTT<br>TACATTTGGGGCGCCAAATGCCCACGTGTTGATGAAACCAGTGAGATGGGAACAGGCGGCGGGAAACCAGACAGAGGAAGAGC<br>TAGGGAGGAGACCCCAGCCCCGGATCCTGGGTCGCCAGGGTTTTCCGCGCGCATCCCAAAAGGTGCGGCTGCGTGGGGCATCA<br>GGTTAGTTTGTTAGACTCTGCAGAGTCTCCAAACCATCCCATCCCCCAACCTGACTCTGTGGTGGCCGTATTTTTTACAGAAA<br>TTTGACCACGTTCCCTTTCTCCCTTGGTCCCAAGCGCGCTCAGCCCTCCCTCCATCCCCCTTGAGCCGCCCTTCTCCTCCCCC<br>TCGCCTCCTCGGGTCCCTCCTCCAGTCCCTCCCCAAGAATCTCCCGGCCACGGGCGCCCATTGGTTGTGCGCAGGGAGGAGGC<br>GTGTGCCCGGCCTGGCGAGTTTCATTGAGCGGAATTAGCCCGGATGACATCAGCTTCCCAGCCCCCCGGCGGGCCCAGCTCAT<br>TGGCGAGGCAGCCCCTCCAGGACACGCACATTGTTCCCCGCCCCCGCCCCCGCCACCGCTGCCGCCGTCGCCGCTGCCACCGG<br>GCTATAAAAACCGGCCGAGCCCCTAAAGGTGCGGATGCTTATTATAGATCGACGCGACACCAGCGCCCGGTGCCAGGTTCTCC<br>CCTGAGGCTTTTCGGAGCGAGCTCCTCAAATCGCATCCAGAGTAAGTGTCCCCGCCCCACAGCAGCCGCAGCCTAGATCCCAG<br>GGACAGACTCTCCTCAACTCGGCTGTGACCCAGAATGCTCCGATACAGGGGGTCTGGATCCCTACTCTGCGGGCCATTTCTCC<br>AGAGCGACTTTGCTCTTCTGTCCTCCCCACACTCACCGCTGCATCTCCCTCACCAAAAGCGAGAAGTCGGAGCGACAACAGCT<br>CTTTCTGCCCAAGCCCCAGTCAGCTGGTGAGCTCCCCGTGGTCTCCAGATGCAGCACATGGACTCTGGGCCCCGCGCCGGCTC<br>TGGGTGCATGTGCGTGTGCGTGTGTTTGCTGCGTGGTGTCGATGGAGATAAGGTGGATCCGTTTGAGGAACCAAATCATTAGT<br>TCTCTATCTAGATCTCCATTCTCCCCAAAGAAAGGCCCTCACTTCCCACTCGTTTATTCCAGCCCGGGGGCTCAGTTTTCCCA<br>CACCTAACTGAAAGCCCGAAGCCTCTAGAATGCCACCCGCACCCCGAGGGTCACCAACGCTCCCTGAAATAACCTGTTGCATG<br>AGAGCAGAGGGGAGATAGAGAGAGCTTAATTATAGGTACCCGCGTGCAGCTAAAAGGAGGGCCAGAGATAGTAGCGAGGGGGA<br>CGAGGAGCCACGGGCCACCTGTGCCGGGACCCCGCGCTGTGGTACTGCGGTGCAGGCGGGAGCAGCTTTTCTGTCTCTCACTG<br>ACTCACTCTCTCTCTCTCTCCCTCTCTCTCTCTCATTCTCTCTCTTTTCTCCTCCTCTCCTGGAAGTTTTCGGGTCCGAGG<br>GAAGGAGGACCCTGCGAAAGCTGCGACGACTATCTTCCCCTGGGGCCATGGACTCGGACGCCAGCCTGGTGTCCAGCCGCCCG<br>TCGTCGCCAGAGCCCGATGACCTTTTTCTGCCGGCCCGGAGTAAGGGCAGCAGCGGCAGCGCCTTCACTGGGGGCACCGTGTC<br>CTCGTCCACCCCGAGTGACTGCCC |
| 34 | SIM2 | TTAATTCGAAAATGGCAGACAGAGCTGAGCGCTGCCGTTCTTTTCAGGATTGAAAATGTGCCAGTGGGCCAGGGGCGCTGGGA<br>CCCGCGGTGCGGAAGACTCGGAACAGGAAGAAATAGTGGCGCGCTGGGTGGGCTGCCCCGCCGCCCACGCCGGTTGCCGCTGG<br>TGACAGTGGCTGCCCGGCCAGGCACCTCCGAGCAGCAGGTCTGAGCGTTTTTGGCGTCCCAAGCGTTCCGGGCCGCGTCTTCC<br>AGAGCCTCTGCTCCCAGCGGGGTCGCTGCGGCCTGGCCCGAAGGATTTGACTCTTTGCTGGGAGGCGCGCTGCTCAGGGTTCT<br>G |
| 35 | SIM2 | CCGGTCCCCAGTTTGGAAAAAGGCGCAAGAAGCGGGCTTTTCAGGGACCCCGGGGAGAACACGAGGGCTCCGACGCGGGAGAA<br>GGATTGAAGCGTGCAGAGGCGCCCCAAATTGCGACAATTTACTGGGATCCTTTTGTGGGGAAAGGAGGCTTAGAGGCTCAAGC<br>TATAGGCTGTCCTAGAGCAACTAGGCGAGAACCTGGCCCCAAACTCCCTCCTTACGCCCTGGCACAGGTTCCCGGCGACTGGT<br>GTTCCCAAGGGAGCCCCCTGAGCCTACCGCCCTTGCAGGGGGTCGTGCTGCGGCTTCTGGGTCATAAACGCCGAGGTCGGGGG<br>TGGCGGAGCTGTAGAGGCTGCCCGCGCAGAAAGCTCCAGGATCCCAATATGTG |
| 36 | DSCR6 | GCGCAGGTCCCCCCAGTCCCCGAGGGAGTGCGCCCGACGGAAACGCCCCTAGCCCGCGGGCCTCGCTTTCCTCTCCCGGGTTC<br>CTGGGTCACTTCCCGCTGTCTC |
| 37 | DSCAM | TTCCCTCGCGGCTTTGGAAAGGGGGTGCAAATGCACCCTTCTGCGGGCCCGCTACCCGCTGCAACACCTGTGTTTCCTTTCTG<br>GGCACCTTCTAGGTTTCTAGATATTGCTGTGAATACGGTCCTCCGCTGTACAGTTGAAAACAAA |
| 38 | chr21 group-00165 | TGGGAATTTAGGTCGGGCACTGCCGATATGTCGCCTTCCACAAGGCGGGCCCGGGCCTCTGCTGACCGTGCACCGGTCCTGGG<br>GCTGGGTAATTCTGCAGCAGCAGCGCAGCCCATGCCGGGGAATTTGCGGGCAGAGGAGACAGTGAGGCCCGCGTTCTGTGCGG<br>GAACTCCCGAGCTCACAGAGCCCAAGACCACACGGCTGCATCGGATCGGGAGAGGGGCAGTGTCGCCCATCCCCGGAAGGCTG<br>AGCCTGGTGCAG |
| 39 | PRMT2 | CGGTTTTCTCCTGGAGGACTGTGTTCAGACAGATACTGGTTTCCTTATCCGCAGGTGTGCGCGGCGCTCGCAAGTGGTCAGCA<br>TAACGCCGGGCGAATTCGGAAAGCCCGTGCGTCCGTGGACGACCCACTTGGAAGGAGTTGGGAGAAGTCCTTGTTCCCACGCG<br>CGGACGCTTCCCTCCGTGTGTCCTTCGAGCCACAAAAAGCCCAGACCCTAACCCGCTCCTTTCTCCCGCCGCGTCCATGCAGA<br>ACTCCGCCGTTCCTGGGAGGGGAAGCCCGCGAGGCGTCGGGAGAGGCACGTCCTCCGTGAGCAAAGAGCTCCTCCGAGCGCGC |

TABLE 4A-continued

| SEQ ID NO | GENE NAME | SEQUENCE |
|---|---|---|
| | | GGCGGGGACGCTGGGCCGACAGGGGACCGCGGGGGCAGGGCGGAGAGGACCCGCCCTCGAGTCGGCCCAGCCCTAACACTCAG<br>GAC |
| 40 | SIX2 | AGGGAATCGGGCTGACCAGTCCTAAGGTCCCACGCTCCCCTGACCTCAGGGCCCAGAGCCTCGCATTACCCCGAGCAGTGCGT<br>TGGTTACTCTCCCTGGAAAGCCGCCCCCGCCGGGGCAAGTGGGAGTTGCTGCACTGCGGTCTTTGGAGGCCTAGGTCGCCCAG<br>AGTAGGCGGAGCCCTGTATCCCTCCTGGAGCCGGCCTGCGGTGAGGTCGGTACCCAGTACTTAGGGAGGGAGGACGCGCTTGG<br>TGCTCAGGGTAGGCTGGGCCGCTGCTAGCTCTTGATTTAGTCTCATGTCCGCCTTTGTGCCGGCCTCTCCGATTTGTGGGTCC<br>TTCCAAGAAAGAGTCCTCTAGGGCAGCTAGGGTCGTCTCTTGGGTCTGGCGAGGCGGCAGGCCTTCTTCGGACCTATCCCCAG<br>AGGTGTAACGGAGACTTTCTCCACTGCAGGGCGGCCTGGGGCGGGCATCTGCCAGGCGAGGGAGCTGCCCTGCCGCCGAGATT<br>GTGGGGAAACGGCGTGGAAGACACCCCATCGGAGGGCACCCAATCTGCCTCTGCACTCGATTCCATCCTGCAACCCAGGAGAA<br>ACCATTTCCGAGTTCCAGCCGCAGAGGCACCCGCGGAGTTGCCAAAAGAGACTCCCGCGAGGTCGCTCGGAACCTTGACCCTG<br>ACACCTGGACGCGAGGTCTTTCAGGACCAGTCTCGGCTCGGTAGCCTGGTCCCCGACCACCGCGACCAGGAGTTCCTTCTTCC<br>CTTCCTGCTCACCAGCCGGCCGCCGGCAGCGGCTCCAGGAAGGAGCACCAACCCGCGCTGGGGGCGGAGGTTCAGGCGGCAGG<br>AATGGAGAGGCTGATCCTCCTCTAGCCCCGGCGCATTCACTTAGGTGCGGGAGCCCTGAGGTTCAGCCTGACTTTC |
| 41 | SIX2 | CACTACGGATCTGCCTGGACTGGTTCAGATGCGTCGTTTAAAGGGGGGGGCTGGCACTCCAGAGAGGAGGGGGCGCTGCAGGT<br>TAATTGATAGCCACGGAAGCACCTAGGCGCCCCATGCGCGGAGCCGGAGCCGCCAGCTCAGTCTGACCCCTGTCTTTTCTCTC<br>CTCTTCCCTCTCCCACCCCTCACTCCGGGAAAGCGAGGGCCGAGGTAGGGGCAGATAGATCACCAGACAGGCGGAGAAGGACA<br>GGAGTACAGATGGAGGGACCAGGACACAGAATGCAAAAGACTGGCAGGTGAGAAGAAGGGAGAAACAGAGGGAGAGAGAAAGG<br>GAGAAACAGAGCAGAGGCGGCCGCCGGCCCGGCCGCCCTGAGTCCGATTTCCCTCCTTCCCTGACCCTTCAGTTTCACTGCAA<br>ATCCACAGAAGCAGGTTTGCGAGCTCGAATACCTTTGCTCCACTGCCACACGCAGCACCGGGACTGGGCGTCTGGAGCTTAAG<br>TCTGGGGGTCTGAGCCTGGGACCGGCAAATCCGCGCAGCGCATCGCGCCCAGTCTCGGAGACTGCAACCACCGCCAAGGAGTA<br>CGCGCGGCAGGAAACTTCTGCGGCCCAATTTCTTCCCCAGCTTTGGCATCTCCGAAGGCACGTACCCGCCCTCGGCACAAGCT<br>CTCTCGTCTTCCACTTCGACCTCGAGGTGGAGAAAGAGGCTGGCAAGGGCTGTGCGCGTCGCTGGTGTGGGGAGGGCAGCAGG<br>CTGCCCCTCCCCGCTTCTGCAGCGAGTTTTCCCAGCCAGGAAAAGGGAGGGAGCTGTTTCAGGAATTTCAGTGCCTTCACCTA<br>GCGACTGACACAAGTCGTGTGTATAGGAAG |
| 42 | SOX14 | GGAGCCTGAAGTCAGAAAAGATGGGGCCTCGTTACTCACTTTCTAGCCCAGCCCCTGGCCCTGGGTCCCGCAGAGCCGTCATC<br>GCAGGCTCCTGCCCAGCCTCTGGGGTCGGGTGAGCAAGGTGTTCTCTTCGGAAGCGGGAAGGGCTGCGGGTCGGGGACGTCCC<br>TTGGCTGCCACCCCTGATTCTGCATCCTTTTCGCTCGAATCCCTGCGCTAGGCATCCTCCCCGATCCCCCAAAAGCCCAAGCA<br>CTGGGTCTGGGTTGAGGAAGGGAACGGGTGCCCAGGCCGGACAGAGGCTGAAAGGAGGCCTCAAGGTTCCTCTTTGCTACAAA<br>GTGGAGAAGTTGCTCTACTCTGGAGGGCAGTGGCCTTTTCCAAACTTTTCCACTTAGGTCCGTAAGAAAAGCAATTCATACAC<br>GATCAGCGCTTTCGGTGCGAGGATGGAAAGAAACTTC |
| 43 | TLX3 | TTTTCCTGTTACAGAGCTGAGCCCACTCATGTGGTGCCAAGTAGCGACTATCTCTCGGCCACCTCCACCCAGAGCAATGTGGG<br>CGCCCCCAGCGGGTGGGAGCGATTGCCGAGCGGCGCAAGGGCGTTTAACGCCTAACCCCCTCCTCCTGGGTTGCCAAGCCGCT<br>AGGTCGCCGTTTCCAACGTGGCTGCGCGGGACTGAAGTCCGACGACTCCTCGTCCTCAGTAGGAGACACACCTCCCACTGCCC<br>CCAGCCACGCGAGCTATGGGCAGAATCGGGGCAACGGTAATATCTGGATGGGGCAGGCTCCCCTGAGGCTGTGCTTAAGAAAA<br>AAGGAATCTGGAGTAGCCTGAGGGGCCCCACGAGGGGGCCTCCTTTGCGATCGTCTCCCAGCCTTAGGCCAAGGCTACGGAGG<br>CAGGCGGCCGAGTGTTGGCGCCCAGCCCGGCCGAGGACTGGATGGAGGACGAGAAGCAGCCTGCCTCTGGGCGACAGCTGCGG<br>ACGCAGCCTCGCCGCCTCGCCGCCTCAGCCTCGGTCCCAGCGTCTCTAAAGCCGCGCCCATTTTACAGATGCAGGGCAGGGAG<br>ACAAGAGGCATCTCCGGGGGCCGAGTAGAATGATGGCGCGGGTTCTCCCGGCGCCCTGATTTCGAGGCTGCGCCCGGGGCCCT<br>ACATGCAGGCGGGGAGGCCTGGGCCGAAGGCGTCTGCAAGGAGGGGCGAGTCTGCCCGGTCCGGGCAGGGAGTGAGGCCACAG<br>TCAGTTCTCCCTAGGAGGCCGCGCAGCGGGTAGGGTATGGGACTGGGGGACGCAACGGGGACCTGGCCGAATCAGAGCCCTCA<br>GCAGAGAACGCCGAAAACTCTGGGGCCGGCCGCTCGCTTCCCGCTAGTGGGAATGGTTTCCGGTCATCCGTTCCCAGTCCAGC<br>CCCGGGTAGGGAGCTCTGATTTGCAATGCACAGCACTTGCGAGGTTCGAATGCCCCCGCAATTTGCAGATGGAAATACTAAGC<br>CTAGGCCGGGCGTGGTGGCTCAAGCCTATCATCTCAGCCCTTTGGGAGGCCAAGCCGGGAGGATTGTTTGAGCCCAAGAATTC<br>AAAACCAGCCTGAGCAACATAGCGACCCCGTCTCTACAAAATAAAATAAAATAAATTATCCGGGCGTGGTGGCACGCGCCTGT<br>GGTTCCAGCTACTCCGGAGGCTGAGGTGGGAGGATCGCTTGAGTCCGGGAGGTCGAGGCTACAGTGAGCCGTGATCGCACCAC<br>TGCACTCCAGCCTGGGCGACAGAGTGAGACCTTGTCTCAAAAAAGGAAAAAAAGAAAAAGAAAGTAAGCTTCAAAGAAGCTCT<br>GATAATAGTTCTGGGTCGTGCAGCGGTGGCGGCCCCGCGCTCTCGCCCCTAAAGCAAGCGCTCTTTGTACTGGGTGGAGGAGC<br>TTTGAGTAGTGAGGGTGGAGATGCAGCTTCGGGGTGGCGCAGCCACCCTGACACTAGGCCCGGGGTCGCAGTGGGACAGAAGA<br>GTCTGCCGCTCTGACTTGGGCTCTGAGTTCCAAGGGCGCCCGGCACTTCTAGCCTCCCAGGCTTGCGCGCTGGCGCCTTTGCC<br>ATCCGTGCCGAAGTGGGGAGACCTAGCCGCGACCACCACGAGCGCAGCGGTGACACCCAGAGGTCCCACCGGGCCCCTGGGCA<br>GGGTAACCTTAGCCTGTCCGCTTCGGCAGCTTTGCGAAGAGTGGCGCGCAGCTAGGGCTGAGGCTCTTGCGGACCTGCGGTCG<br>AAGCAGGCGGCTGAGCCAGTTCGATCGCCAAGGCCTGGGCTGCCGACAGTGGTGCGCGCTCTGTTCCGCCGCGGCCGGGCCAG<br>GCGCTCTGGAATAGCGATGGGGGGACACGGCCTCCAACTTTCTGCAGAGACCATCGGGCAGCTCCGGGCCTAAGCAGCGACCT<br>CACCGAAGGTTCCTGGGAACCTTTGCCAAAATCCCAGCCTCTGCCTCGGTCCAGCTAAACCGTGTGTAAACAAGTGCACCAAG |
| 44 | FOXP4 | ATAAAGGACCGGGTAATTTCGCGGAATGCGGATTTTGAGACAGGCCCAGACGGCGGCGGATTCCCTGTGTCCCCCAACTGGGG<br>CGATCTCGTGAACACACCTGCGTCCCACCCCGATCCTAGGTTGGGGGGAAAGGGTATGGGAACCCTGAGCCCAGAGCGCGCCC<br>CGCTCTTTCCTTTGCTCCCCGGCTTCCCTGGCCAGCCCCCTCCCGGCTGGTTTCCTCGCTCACTCGGCGCCTGGCGTTTCGGG<br>CGTCTGGAGATCACCGCGTGTCTGGCACCCCAACGTCTAGTCTCCCCGCAGGTTGACCGCGGCGCCTGGAGCCGGGAATAGGG<br>GTGGGGAGTCCGGAGAACCAAACCCGAGCCTGAAGTTGCCATTCGGGTGACTCCCGAGAAAGCCCGGGAGCATTTTGGCCAAT<br>GCGGGTTTTTACCTGAACTTCAGCATCTTCACC |
| 45 | FOXP4 | AATTGGAAAACCCTGGTATTGTGCCTGTTTGGGGGAAGAAAACGTCAATAAAAATTAATTGATGAGTTGGCAGGGCGGGCGGT<br>GCGGGTTCGCGGCGAGGCGCAGGGTGTCATGGCAAATGTTACGGCTCAGATTAAGCGATTGTTAATTAAAAAGCGACGGTAAT<br>TAATACTCGCTACGCCATATGGGCCCGTGAAAAGGCACAAAAGGTTTCTCCGCATGTGGGGTTCCCCTTCTCTTTTCTCCTTC<br>CACAAAAGCACCCCAGCCCGTGGGTCCCCCCTTTGGCCCCAAGGTAGGTGGAACTCGTCACTTCCGGCCAGGGAGGGGATGGG<br>GCGGTCTCCGGCGAGTTCCAAGGGCGTCCCTCGTTGCGCACTCGCCCGCCCAGGTTCTTTGAA |
| 46 | chr7<br>group-<br>00267 | GGGAAGCGATCGTCTCCTCTGTCAACTCGCGCCTGGGCACTTAGCCCCTCCCGTTTCAGGGCGCCGCCTCCCCGGATGGCAAA<br>CACTATAAAGTGGCGGCGAATAAGGTTCCTCCTGCTGCTCTCGGTTTAGTCCAAGATCAGCGATATCACGCGTCCCCCGGAGC<br>ATCGCGTGCAGGAGCCATGGCGCGGGAGCTATACCACGAAGAGTTCGCCCGGGCGGGCAAGCAGGCGGGGCTGCAGGTCTGGA<br>GGATTGAGAAGCTGGAGCTGGTGCCCGTGCCCCAGAGCGCTCACGGCGACTTCTACGTCGGGGATGCCTACCTGGTGCTGCAC |

TABLE 4A-continued

| SEQ ID NO | GENE NAME | SEQUENCE |
|---|---|---|
| | | ACGGCCAAGACGAGCCGAGGCTTCACCTACCACCTGCACTTCTGGCTCGGTAAGGGACGGCGGGCGGCGGGACCCCGACGCAC<br>CAAGGCCGGCGAGGGGAGGGCGTAGGGGTCTGAGATTTGCAGGCGTGGGAGTAAAGGGGACCGCAAACTGAGCTAG |
| 47 | NPY | CTCAGGGGCGGGAAGTGGCGGGTGGGAGTCACCCAAGCGTGACTGCCCGAGGCCCCTCCTGCCGCGGCGAGGAAGCTCCATAA<br>AAGCCCTGTCGCGACCCGCTCTCTGCACCCCATCCGCTGGCTCTCACCCCTCGGAGACGCTCGCCCGACAGCATAGTACTTGC<br>CGCCCAGCCACGCCCGCGCGCCAGCCACCGTGAGTGCTACGACCCGTCTGTCTAGGGGTGGGAGCGAACGGGGCGCCCGCGAA<br>CTTGCTAGAGACGCAGCCTCCCGCTCTGTGGAGCCCTGGGGCCCTGGGATGATCGCGCTCCACTCCCCAGCGGACTATGCCGG<br>CTCCGCGCCCCGACGCGGACCAGCCCTCTTGGCGGCTAAATTCCACTTGTTCCTCTGCTCCCCTCTGATTGTCCACGGCCCTT<br>CTCCCGGGCCCTTCCCGCTGGGCGGTTCTTCTGAGTTACCTTTTAGCAGATATGGAGGGAGAACCCGGGACCGCTATCCCAAG<br>GCAGCTGGCGGTCTCCCTGCGGGTCGCCGCCTTGAGGCCCAGGAAGCGGTGCGCGGTAGGAAGGTTTCCCCGGCAGCGCCATC<br>GAGTGAGGAATCCCTGGAGCTCTAGAGCCCCGCGCCCTGCCACCTCCCTGGATTCTTGGGCTCCAAATCTCTTTGGAGCAATT<br>CTGGCCCAGGGAGCAATTCTCTTTCCCCTTCCCCACCGCAGTCGTCACCCCGAGGTGATCTCTGCTGTCAGCGTTGATCCCCT<br>GAAGCTAGGCAGACCAGAAGTAACAGAGAAGAAACTTTTCTTCCCAGACAAGAGTTTGGGCAAGAAGGGAGAAAAGTGACCCA<br>GCAGGAAGAACTTCCAATTCGGTTTTGAATGCTAAACTGGCGGGGCCCCCACCTTGCACTCTCGCCGCGCGCTTCTTGGTCCC<br>TGAGACTTCGAACGAAGTTGCGCGAAGTTTTCAGGTGGAGCAGAGGGGCAGGTCCCGACCGGACGGCGCCCGGAGCCCGCAAG<br>GTGGTGCTAGCCACTCCTGGGTTCTCTCTGCGGGACTGGGACGAGAGCGGATTGGGGGTCGCGTGTGGTAGCAGGAGGAGGAG<br>CGCGGGGGGCAGAGGAGGGAGGTGCTGCGCGTGGGTGCTCTGAATCCCCAAGCCCGTCCGTTGAGCCTTCTGTGCCTGCAGAT<br>GCTAGGTAACAAGCGACTGGGGCTGTCCGGACTGACCCTCGCCCTGTCCCTGCTCGTGTGCCTGGGTGCGCTGGCCGAGGCGT<br>ACCCCTCCAAGCCGGACAACCCGGGCGAGGACGCACCAG |
| 48 | SHH | TGGAGAACCTTGGGCTCTGTGGCCTCAAAGGTAGGGGTGATTTCGAGGGGCCGGCACCTCACAGGGCAGGTTCCACCGCGGAA<br>ACGCAGTCATCGCCCAGCGACCCTGCTCCTGGCCCTCAGCCTCCCCCCAGGTTTCTTTTTCTCTTGAATCAAGCCGAGGTGCG<br>CCAATGGCCTTCCTTGGGTCGGATCCGGGGGGCCAGGGCCAGCTTACCTGCTTTCACCGAGCAGTGGATATGTGCCTTGGACT<br>CGTAGTACACCCAGTCGAAGCCGGCCTCCACCGCCAGGCGGGCCAGCATGCCGTACTTGCTGCGGTCGCGGTCAGACGTGGTG<br>ATGTCCACTGCGCGGCCCTCGTAGTGCAGAGACTCCTCTGAGTGGTGGCCATCTTCGTCCCAGCCCTCGGTCACCCGCAGTTT<br>CACTCCTGGCCACTGGTTCATCACCGAGATGGCCAAAGCGTTCAACTTGTCCTTACACCTCTGCGAAGACAAGGGGACCCCCA<br>CCGACGGACACGTTAGCCTGGGCAACCGCCACCCCTCCCGGCCCCTCCATCAGCCT |
| 49 | OSR2 | TCTCACGACCCATCCGTTAACCCACCGTTCCCAGGAGCTCCGAGGCGCAGCGGCGACAGAGGTTCGCCCCGGCCTGCTAGCAT<br>TGGCATTGCGGTTGACTGAGCTTCGCCTAACAGGCTTGGGGAGGGTGGGCTGGGCTGGGCTGGGCTGGGCTGGGTGCTGCCCG<br>GCTGTCCGCCTTTCGTTTTCCTGGGACCGAGGAGTCTTCCGCTCCGTATCTGCCTAGAGTCTGAATCCGACTTTCTTTCCTTT<br>GGGCACGCGCTCGCCAGTGGAGCACTTCTTGTTCTGGCCCCGGGCTGATCTGCACGCGGACTTGAGCAGGTGCCAAGGTGCCA<br>CGCAGTCCCCTCACGGCTTTCGGGGGGTCTTGGAGTCGGGTGGGGAGGGAGACTTAGGTGTGGTAACCTGCGCAGGTGCCAAA<br>GGGCAGAAGGAGCAGCCTTGGATTATAGTCACGGTCTCTCCCTCTCTTCCCTGCCATTTTTAGGGCTTTCTCTACGTGCTGTT<br>GTCTCACTGGGTTTTTGTCGGAGCCCCACGCCCTCCGGCCTCTGATTCCTGGAAGAAAGGGTTGGTCCCCTCAGCACCCCCAG<br>CATCCCGGAAAATGGGGAGCAAGGCTCTGCCAGCGCCCATCCCGCTCCACCCGTCGCTGCAGCTCACCAATTACTCCTTCCTG<br>CAGGCCGTGAACACCTTCCCGGCCACGGTGGACCACCTGCAGGGCCTGTACGGTCTCAGCGCGGTACAGACCATGCACATGAA<br>CCACTGGACGCTGGGGTATCCCAAT |
| 50 | GLIS3 | TGGTTTCCTTTCGCTTCTCGCCTCCCAAACACCTCCAGCAAGTCGGAGGGCGCGAACGCGGAGCCAGAAACCCTTCCCCAAAG<br>TTTCTCCCGCCAGGTACCTAATTGAATCATCCATAGGATGACAAATCAGCCAGGGCCAAGATTTCCAGACACTTGAGTGACTT<br>CCCGGTCCCCGAGGTGACTTGTCAGCTCCAGTGAGTAACTTGGAACTGTCGCTCGGGGCAAGGTGTGTGTCTAGGAGAGAGCC<br>GGCGGCTCACTCACGCTTTCCAGAGAGCGACCCGGGCCGACTTCAAAATACACACAGGGTCATTTATAGGGACTGGAGCCGCG<br>CGCAGGACAACGTCTCCGAGACTGAGACATTTTCCAAACAGTGCTGACATTTTGTCGGGCCCCATAAAAAATGTAAACGCGAG<br>GTGACGAACCCGGCGGGGAGGGTTCGTGTCTGGCTGTGTCTGCGTCCTGGCGGCGTGGAGGTTATAGTTCCAGACCTGGCGG<br>CTGCGGATCGCCGGGCCGGTACCCGCGAGGAGTGTAGGTACCCTCAGCCCGACCACCTCCCGCAATCATGGGGACACCGGCTT<br>GGATGAGACACAGGCGTGGAAAACAGCCTTCGTGAAACTCCACAAACACGTGGAACTTGAAAAGACAACTACAGCCCCGCGTG<br>TGCGCGAGAGACCTCACGTCACCCCATCAGTTCCCACTTCGCCAAAGTTTCCCTTCAGTGGGGACTCCAGAGTGGTGCGCCCC<br>ATGCCCGTGCGTCCTGTAACGTGCCCTGATTGTGTACCCCTCTGCCCGCTCTACTTGAAATGAAAACACAAAAACTGTTCCGA<br>ATTAGCGCAACTTTAAAGCCCCGTTATCTGTCTTCTACACTGGGCGCTCTTAGGCCACTGACAGAAACATGGTTTGAACCCTA<br>ATTGTTGCTATCAGTCTCAGTCAGCGCAGGTCTCTCAGTGACCTGTGACGCCGGGAGTTGAGGTGCGCGTATCCTTAAACCCG<br>CGCGAACGCCACCGGCTCAGCGTAGAAAACTATTTGTAATCCCTAGTTTGCGTCTCTGAGCTTTAACTCCCCCACACTCTCAA<br>GCGCCCGGTTTCTCCTCGTCTCTCGCCTGCGAGCAAAGTTCCTATGGCATCCACTTACCAGGTAACCGGGATTTCCACAACAA<br>AGCCCGGCGTGCGGGTCCCTTCCCCCGGCCGGCCAGCGCGAGTGACAGCGGGCGGCCGGCGCTGGCGAGGAGTAACTTGGGGC<br>TCCAGCCCTTCAGAGCGCTCCGCGGGCTGTGCCTCCTTCGGAAATGAAAACCCCCATCCAAACGGGGGGACGGAGCGCGGAAA<br>CCCGGCCCAAGTGCCGTGTGTGCGCGCGCGTCTG |
| 51 | PRMT8 | GAAAGCCATCCTTACCATTCCCCTCACCCTCCGCCCTCTGATCGCCCACCCGCCGAAAGGGTTTCTAAAAATAGCCCAGGGCT<br>TCAAGGCCGCGCTTCTGTGAAGTGTGGAGCGAGCGGGCACGTAGCGGTCTCTGCCAGGTGGCTGGAGCCCTGGAAGCGAGAAG<br>GCGCTTCCTCCCTGCATTTCCACCTCACCCCACCCCCGGCTCATTTTTCTAAGAAAAAGTTTTTGCGGTTCCCTTTGCCTCCT<br>ACCCCCGCTGCCGCGCGGGGTCTGGGTGCAGACCCCTGCCAGGTTCCGCAGTGTGCAGCGGCGGCTGCTGCGCTCTCCCAGCC<br>TCGGCGAGGGTTAAAGGCGTCCGGAGCAGGCAGAGCGCCGCGCGCCAGTCTATTTTTACTTGCTTCCCCCGCCGCTCCGCGCT<br>CCCCCTTCTCAGCAGTTGCACATGCCAGCTCTGCTGAAGGCATCAATGAAAACAGCAGTAG |
| 52 | TBX3 | ATCGAAAATGTCGACATCTTGCTAATGGTCTGCAAACTTCCGCCAATTATGACTGACCTCCCAGACTCGGCCCCAGGAGGCTC<br>GTATTAGGCAGGGAGGCCGCCGTAATTCTGGGATCAAAAGCGGGAAGGTGCGAACTCCTCTTTGTCTCTGCGTGCCCGGCGCG<br>CCCCCCTCCCGGTGGGTGATAAACCCACTCTGGCGCCGGCCATGCGCTGGGTGATTAATTTGCGAACAAACAAAAGCGGCCTG<br>GTGGCCACTGCATTCGGGTTAAACATTGGCCAGCGTGTTCCGAAGGCTTGT |
| 53 | chr12<br>group-<br>00801 | ATCAACATCGTGGCTTTGGTCTTTTCCATCATGGTGAGTGAATCACGGCCAGAGGCAGCCTGGGAGGAGAGACCCGGGCGGCT<br>TTGAGCCCCTGCAGGGGAGTCCGCGCGCTCTCTGCGGCTCCCTTCCTCACGGCCCGGCCCGCGCTAGGTGTTCTTTGTCCTCG<br>CACCTCCTCCTCACCTTTCTCGGGCTCTCAGAGCTCTCCCCGCAATCATCAGCACCTCCTCTGCACTCCTCGTGGTACTCAGA<br>GCCCTGATCAAGCTTCCCCCAGGCTAGCTTTCCTCTTCTTTCCAGCTCCCAGGGTGCGTTTCCTCTCCAACCCGGGGAAGTTC<br>TTCCGTGGACTTTGCTGACTCCTCTGACCTTCCTAGGCACTTGCCCGGGGCTTCTCAACCCTCTTTTCTAGAGCCCCAGTGCG<br>CGCCACCCTAGCGAGCGCAGTAAGCTCATACCCCGAGCATGCAGGCTCTACGTTCCTTTCCCTGCCGCTCCGGGGGCTCCTGC<br>TCTCCAGCGCCCAGGACTGTCTCTATCTCAGCCTGTGCTCCCTTCTCTCTTTGCTGCGCCCAAGGGCACCGCTTCCGCCACTC |

TABLE 4A-continued

| SEQ ID NO | GENE NAME | SEQUENCE |
|---|---|---|
| | | TCCGGGGGGTCCCCAGGCGATTCCTGATGCCCCCTCCTTGATCTTAACGCGCCCGAGGCTGGCTCACACCCACTACCTCTTTA<br>GGCCTTTCTTAGGCTCCCCGTGTGCCCCCCTCACCAGCAAAGTGGGTGCGCCTCTCTTACTCTTTCTACCCAGCGCGTCGTAG<br>TTCCTCCCCGTTTGCTGCGCACTGGCCCTAACCTCTCTTCTCTTGGTGTCCCCCAGAGCTCCCAGGCGCCCCTCCACCGCTCT<br>GTCCTGCGCCCGGGGCTCTCCCGGGAATGAACTAGGGGATTCCACGCAACGTGCGGCTCCGCCCGCCCTCTGCGCTCAGACCT<br>CCCGAGCTGCCCGCCTCTCTAGGAGTGGCCGCTGGGGCCTCTAGTCCGCCCTTCCGGAGCTCAGCTCCCTAGCCCTCTTCAAC<br>CCTGGTAGGAACACCCGAGCGAACCCCACCAGGAGGGCGACGAGCGCCTGCTAGGCCCTCGCCTTATTGACTGCAGCAGCTGG<br>CCCGGGGGTGGCGGCGGGGTGAGGTTCGTACCGGCACTGTCCCGGGACAACCCTTGCAGTTGC |
| 54 | PAX9 | ACAAATAAAACACCCTCTAGCTTCCCCTAGACTTTGTTTAACTGGCCGGGTCTCCAGAAGGAACGCTGGGGATGGGATGGGTG<br>GAGAGAGGGAGCGGCTCAAGGACTTTAGTGAGGAGCAGGCGAGAAGGAGCACGTTCAGGCGTCAAGACCGATTTCTCCCCCTG<br>CTTCGGGAGACTTTTGAACGCTCGGAGAGGCCCGGCATCTCACCACTTTACTTGGCCGTAGGGGCCTCCGGCACGGCAGGAAT<br>GAGGGAGGGGGTCCGATTGGACAGTGACGGTTTGGGGCCGTTCGGCTATGTTCAGGGACCATATGGTTTGGGGACAGCCCCAG<br>TAGTTAGTAGGGGACGGGTGCGTTCGCCCAGTCCCCGGATGCGTAGGGAGGCCCAGTGGCAGGCAGCTGTCCCAAGCAGCGGG<br>TGCGCGTCCCTGCGCGCTGTGTGTTCATTTTGCAGAGCCAGCCTTCGGGGAGGTGAACCAGCTGGGAGGAGTGTTCGTGAACG<br>GGAGGCCGCTGCCCAACGCCATCCGGCTTCGCATCGTGGAACTGGCCCAACTGGGCATCCGACCGTGTGACATCAGCCGCCAG<br>CTACGGGTCTCGCACGGCTGCGTCAGCAAGATCCTGGCGCGATACAACGAGACGGGCTCGATCTTGCCAGGAGCCATCGGGGG<br>CAGCAAGCCCCGGGTCACTACCCCCACCGTGGTGAAACACATCCGGACCTACAAGCAGAGAGACCCCGGCATCTTCGCCTGGG<br>AGATCCGGGACCGCCTGCTGGCGGACGGCGTGTGCGACAAGTACAATGTGCCCTCCGTGAGCTCCATCAGCCGCATTCTGCGC<br>AACAAGATCGGCAACTTGGCCCAGCAGGGTCATTACGACTCATACAAGCAGCACCAGCCGACGCCGCAGCCAGCGCTGCCCTA<br>CAACCACATCTACTCGTACCCCAGCCCTATCACGGCGGCGGCCGCCAAGGTGCCCACGCCACCCGGGGTGC |
| 55 | SIX1 | AGGAGGCGCAACGCGCTGCCAGGGCGGCTTTATCCTGCCGCCACAGGGCGGGGACCAGCCCGGCAGCCGGGTGTCCAGCGCCG<br>CTCACGTGCCTCGCCTGGAGCTTAGCTCTCAGACTCCGAAGAGGGCGACTGAGACTTGGGCCTGGGAGTTGGCTTCGGGGTAC<br>CCAAGGCGACGACAGCTGAGTTGTACCACGAAGCTCAGGCCGAGGCCTCCTCCCTTGTCTGGCCTTCGAATCCATACTGGCAG<br>CCTCTCCTCTCAGGCACTCCGCGGGCCGGGCCACTAGGCCCCCTGCTCCTGGAGCTGCGCTATGATCCGGGTCTTGAGATGCG<br>CGCGATTCTCTCTGAACCGGTGGAGAGGAGGCTCTGCCCCGCGCGGAGCGAGGACAGCGGCGCCCGAGCTTCCCGCGCCTCTC<br>CAGGGCCCAATGGCAAGAACAGCCTCCGAAGTGCGCGGATGACAGGAAAAGATCTTCAGTTCTTCTGCCGCTAGAGAAGTGCG<br>GGATACAAGCCTCTATTGGATCCACAACCTGGAGTCCTGCCTTCGGA |
| 56 | ISL2 | ATCTGCGTGCCCTTTTCTGGGCGAGCCCTGGGAGATCCAGGGAGAACTGGGCGCTCCAGATGGTGTATGTCTGTACCTTCACA<br>GCAAGGCTTCCCTTGGATTTGAGGCTTCCTATTTTGTCTGGGATCGGGGTTTCTCCTTGTCCCAGTGGCAGCCCCGCGTTGCG<br>GGTTCCGGGCGCTGCGCGGAGCCCAAGGCTGCATGGCAGTGTGCAGCGCCCGCCAGTCGGGCTGGTGGGTTGTGCACTCCGTC<br>GGCAGCTGCAGAAAGGTGGGAGTGCAGGTCTTGCCTTTCCTCACCGGGCGGTTGGCTTCCAGCACCGAGGCTGACCTATCGTG<br>GCAAGTTTGCGGCCCCCGCAGATCCCCAGTGGAGAAAGAGGGCTCTTCCGATGCGATCGAGTGTGCGCCTCCCCGCAAAGCAA<br>TGCAGACCCTAAATCACTCAAGGCCTGGAGCTCCAGTCTCAAAGGTGGCAGAAAAGGCCAGACCTAACTCGAGCACCTACTGC<br>CTTCTGCTTGCCCCGCAGAGCCTTCAGGGACTGACTGGGACGCCCCTGGTGGCGGGCAGTCCCATCCGCCATGAGAACGCCGT<br>GCAGGGCAGCGCAGTGGAGGTGCAGACGTACCAGCCGCCGTGGAAGGCGCTCAGCGAGTTTGCCCTCCAGAGCGACCTGGACC<br>AACCCGCCTTCCAACAGCTGGTGAGGCCCTGCCCTACCCGCCCCGACCTCGGGACTCTGCGGGTTGGGGATTTAGCCACTTAG<br>CCTGGCAGAGAGGGGAGGGGGTGGCCTTGGGCTGAGGGGCTGGGTACAGCCCTAGGCGGTGGGGGAGGGGGAACAGTGGCGGG<br>CTCTGAAACCTCACCTCGGCCCATTACGCGCCCTAAACCAGGTCTCCCTGGATTAAAGTGCTCACAAGAGAGGTCGCAGGATT<br>AACCAACCCGCTCCCCCGCCCTAATCCCCCCCTCGTGCGCCTGGGGACCTGGCCTCCTTCTCCGCAGGGCTTGCTCTCAGCTG<br>GCGGCCGGTCCCCAAGGGACACTTTCCGACTCGGAGCACGCGGCCCTGGAGCACCAGCTCGCGTGCCTCTTCACCTGCCTCTT<br>CCCGGTGTTTCCGCCGCCCCAGGTCTCCTTCTCCGAGTCCGGCTCCCTAGGCAACTCCTCCGGCAGCGACGTGACCTCCCTGT<br>CCTCGCAGCTCCCGGACACCCCCAACAGTATGGTGCCGAGTCCCGTGGAGACGTGAGGGGGACCCCTCCCTGCCAGCCCGCGG<br>ACCTCGCATGCTCCCTGCATGAGACTCACCCATGCTCAGGCCATTCCAGTTCCGAAAGCTCTCTCGCCTTCGTAATTATTCTA<br>TTGTTATTTATGAGAGAGTACCGAGAGACACGGTCTGGACAGCCCAAGGCGCCAGGATGCAACCTGCTTTCACCAGACTGCAG<br>ACCCCTGCTCCGAGGACTCTTAGTTTTTCAAAACCAGAATCTGGGACTTACCAGGGTTAGCTCTGCCCTCTCCTCTCCTCTCT<br>ACGTGGCCGCCGCTCTGTCTCTCCACGCCCCACCTGTGT |
| 57 | DLX4 | AGGTCTCTTCAGACTGCCCATTCTCCGGGCCTCGCTGAATGCGGGGGCTCTATCCACAGCGCGCGGGGCCGAGCTCAGGCAGG<br>CTGGGGCGAAGATCTGATTCTTTCCTTCCCGCCGCCAAACCGAATTAATCAGTTTCTTCAACCTGAGTTACTAAGAAAGAAAG<br>GTCCTTCCAAATAAAACTGAAAATCACTGCGAATGACAATACTATACTACAAGTTCGTTTTGGGGCCGGTGGGTGGGATGGAG<br>GAGAAAGGGCACGGATAATCCCGGAGGGCCGCGGAGTGAGGAGGACTATGGTCGCGGTGGAATCTCTGTTCCGCTGGCACATC<br>CGCGCAGGTGCGGCTCTGAGTGCTGGCTCGGGGTTACAGACCTCGGCATCCGGCTGCAGGGGCAGACAGAGACCTCCTCTGCT<br>AGGGCGTGCGGTAGGCATCGTATGGAGCCCAGAGACTGCCGAGAGCACTGCGCACTCACCAAGTGTTAGGGGTGCCCGTGATA<br>GACCGCCAGGGAAGGGGCTGGTTCGGAGGGAATTCCCGCTACCGGGAAGGTCGGAACTCGGGGTGATCAAACAAGGAATGCAT<br>CTCACCTCCGTGGGTGCTTGTGCTGCGCAAGGAATTATTACCGGAGCGGTTGCGATGGCCTTTGCCCGGCGACCCAAGAAGAG<br>TAAGCAAACTACCGTCCACCCAGCGGATCAGGTCCAAT |
| 58 | CBX4 | GATGTCCTGTTTCTAGCAGCCTCCAGAGCCAAGCTAGGCGAGAGGCGTAGGAGGCAGAGAGAGCGGGCGCGGGAGGCCAGGGT<br>CCGCCTGGGGGCCTGAGGGGACTTCGTGGGGTCCCGGGAGTGGCCTAGAAACAGGGAGCTGGGAGGGCCGGGAAGAGCTTGAG<br>GCTGAGCGGGGGACGAACGGGCAGCGCAAAGGGGAGATGAACGGAATGGCCGAGGAGCCACGCATTCGCCTTGTGTCCGCGGA<br>CCCTTGTTCCCGACAGGCGACCAAGCCAAGGCCCTCCGGACTGACGCGGCCTGAGCAGCAGCGAGTGTGAAGTTTGGCACCTC<br>CGGCGGCGAGACGGCGCGTTCTGGCGCGCGGCTCCTGCGTCCGGCTGGTGGAGCTGCTGCGCCCTATGCGGCCTGCCGAGGGC<br>GCCGCCGAGGGCCCGCGAGCTCCGTGGGGTCGGGGTGGGGGGACCCGGGAGCGGACAGCGCGGCCCGAGGGGCAGGGGCAGGG<br>GCGCGCCTGGCCTGGGGTGTGTCTGGGCCCCGGCTCCGGGCTCTTGAAGGACCGCGAGCAGGAGGCTTGCGCAATCCCTTGGC<br>TGAGCGTCCACGGAGAAAGAAAAAGAGCAAAAGCAGAGCGAGAGTGGAGCGAGGGATGGGGGCGGGCAAAGAGCCATCCGGGT<br>CTCCACCACCGCCCTGACACGCGACCCGGCTGTCTGTTGGGGACCGCACGGGGGCTCGGGCGAGCAGGGGAGGGAGGAGCCTG<br>CGCGGGGCTCGTGTTCGCCCAGGAATCCCGGAGAAGCTCGAAGACGGTCTGGTGTTGAACGCACACGTGGACTCCATTTCATT<br>ACCACCTTGCAGCTCTTGCGCCACGGAGGCTGCTGCTGCCCGGCGGCTGCTACCCACCGAGACCCACGTGGCCCCTCCCCAGG<br>GGTGTAGGGGTGACGGTTGTCTTCTGGTGACAGCAGAGGTGTTGGGTTTGCGACTGATCTCTAACGAGCTTGAGGCGCAAACC<br>TAGGATTCCCTGAGTGTTGGGGTGCGGCGGGGGGGCAAGCAAGGTGGGACGACGCCTGCCTGGTTTCCCTGACTAGTTGCGGG<br>GGGTGGGGGCCGGCTCTCAGGGGCCACCAGAAGCTGGGTGGGTGTACAGGAAAATATTTTTCTCCTGCCGTGTTTGGCTTTTT<br>CCTGGCATTTTTGCCCAGGGCGAAGAACTGTCGCGCGGGGCAGCTCCACCGCGGAGGGAGAGGGGTCGCGAGGCTGGCGCGGG<br>AAGCGCTGTAGGTGGCAGTCATCCGTCCACGCCGCACAGGCCGTCTGCGCCGTCGGACCATCGGGAGGTCTGCAGCAACTTTG<br>TCCCGGCCAGTCCCCTTGTCCGGGAAGGGGCTGAGCTTCCCGACACTCTACCCTCCCCCTCTTGAAAATCCCCTGGAAAATCT |

TABLE 4A-continued

| SEQ ID NO | GENE NAME | SEQUENCE |
|---|---|---|
| | | GTTTGCAATGGGTGTTTCCGCGGCGTCCAGGTCTGGGCTGCCGGGGGAGGCCGAGCGGCTGCTGCAGCCTCCCTGCTGCCAGG<br>GGCGTCGGACTCCGCTTCGCTCACTACGCCCAGGCCCCTCAGGGGCCCACGCTCAGGACTTCGGGGCCACACAGCAGGACCCG<br>GTGCCCCGACGACGAGTTTGCGCAGGACCCGGGCTGGGCCAGCCGCGGAGCTGGGGAGGAAGGGGCGGGGTCGGTGCAGCGG<br>ATCTTTTCTGTTGCTGCCTGTGCGGCGGCAGGAAGCGTCTTGAGGCTCCCCAAGACTACCTGAGGGGCCGCCCAAGCACTTCA<br>GAAGCCCAAGGAGCCCCCGGCCACCCCCGCTCCTGGCCTTTTTGCCAACGACTTTGAAAGTGAAATGCACAAGCACCAGCAAT<br>TGACTTCCCTTCCGTGGTTATTTATTTTGTCTTTGTGGATGGTGGGCAGATGGGGAGAGAGGCCCCTACCTAACCTCGGTGGC<br>TGGTCCCTAGACCACCCCTGCCAGCCGGTGTGGGGAGGAGCTCAGGTCCGCGGGAGAGCGAATGGGCGCCAGGAGGTGGGACA<br>GAATCCTGGGAAGGTACAGCGGACGCCCTGGAAGCTCCCCTGATGCCCCAGAGGGCCCTTCCTGGGAAACCTCCCGGGGGGGT<br>GCCCCATACCATCCCACCCGGCTGTCTTGGCCCCTCCCAGGGAGCCGCAGGAGAAACTAGCCCTACACCTGGGATTCCCAGAG<br>CCTTCTGCTGGGGCTCCTGCCCCCGACTTCGGATAACCAGCTCCGCACAGGTCCCCGAGAAGGGCCGCTGGCCTGCTTATTTG<br>ATACTGCCCCCTCCCAGACAGGGGCTGGTCGAGCCCCTGGTTCTGCTGCCAGACTGAAGCCTTCCAGACGCCACCTCGGTTTG<br>GGCCCCCAGGGCCCTCAGGGGCCCCAGGAGAGGAGAGCTGCTATCTAGCTCAGCCACAGGCTCGCTCCTGGTGGGGGCCAGGC<br>TGAAGGAGTGGACCCTGGAGAGGTCGGGAACCTTTTAACAGCCGTGGGCTGGAGGGTGGCTACTAAGTGTTCGGTCTGGGAAG<br>AGGCATGACCCGCACCATCCCGGGGAAATAAACGACTTCTTAAGGGAATCTTCTCGCTGAGCGGGTGCTCTGGGCCAGGAGAT<br>TGCCACCGCCAGCCCACGGAACCCAGATTTGGGCTCTGCCTTGAGCGGGCCGCCTGTGGCTTCCCGGGTCGCTCCCCCGACTC<br>AGAAAGCTCTCAAGTTGGTATCGTTTTCCCGGCCCTCGGAGGTGGATTGCAGATCACCGAGAGGGGATTTACCAGTAACCACT<br>ACAGAATCTACCCGGGCTTTAACAAGCGCTCATTTCTCTCCCTTGTCCTTAGAAAAACTTCGCGCTGGCGTTGATCATATCGT<br>ACTTGTAGCGGCAGCTTAGGGGCAGCGGAACTGGTGGGGTTGTGCGTGCAGGGGGAGGCTGTGAGGGAGCCCTGCACTCCGCC<br>CCTCCACCCTTCTGGAGGAGTGGCTTTGTTTCTAAGGGTGCCCCCCCAACCCCCGGGTCCCCACTTCAATGTTTCTGCTCTTT<br>GTCCCACCGCCCGTGAAAGCTCGGCTTTCATTTGGTCGGCGAAGCCTCCGACGCCCCCGAGTCCCACCCTAGCGGGCCGCGCG<br>GCACTGCAGCCGGGGGTTCCTGCGGACTGGCCCGACAGGGTGCGCGGACGGGGACGCGGGCCCCGAGCACCGCGACGCCAGGG<br>TCCTTTGGCAGGGCCCAAGCACCCCT |
| 59 | EDG6 | TGGCGGCCGGCGGGCACAGCCGGCTCATTGTTCTGCACTACAACCACTCGGGCCGGCTGGCCGGGCGCGGGGGGCCGGAGGAT<br>GGCGGCCTGGGGGCCCTGCGGGGGCTGTCGGTGGCCGCCAGCTGCCTGGTGGTGCTGGAGAACTTGCTGGTGCTGGCGGCCAT<br>CACCAGCCACATGCGGTCGCGACGCTGGGTCTACTATTGCCTGGTGAACATCACGCTGAGTGACCTGCTCACGGGCGCGGCCT<br>ACCTGGCCAACGTGCTGCTGTCGGGGGCCCGCACCTTCCGTCTGGCGCCCGCCCAGTGGTTCCTACGGGAGGGCCTGCTCTTC<br>ACCGCCCTGGCCGCCTCCACCTTCAGCCTGCTCTTCACTGCAGGGGAGCGCTTTGCCACCATGGTGCGGCCGGTGGCCGAGAG<br>CGGGGCCACCAAGACCAGCCGCGTCTACGGCTTCATCGGCCTCTGCTGGCTGCTGGCCGCGCTGCTGGGGATGCTGCCTTTGC<br>TGGGCTGGAACTGCCTGTGCGCCTTTGACCGCTGCTCCAGCCTTCTGCCCCTCTACTCCAAGCGCTACATCCTCTTCTGCCTG<br>GTGATCTTCGCCGGCGTCCTGGCCACCATCATGGGCCTCTATGGGGCCATCTTCCGCCTGGTGCAGGCCAGCGGGCAGAAGGC<br>CCCACGCCCAGCGGCCCGCCGCAAGGCCCGCCGCCTGCTGAAGACGGTGCTGATGATCCTGCTGGCCTTCCTGGTGTGCTGGG<br>GCCCACTCTTCGGGCTGCTGCTGGCCGACGTCTTTGGCTCCAACCTCTGGGCCCAGGAGTACCTGCGGGGCATGGACTGGATC<br>CTGGCCCTGGCCGTCCTCAACTCGGCGGTCAACCCCATCATCTACTCCTTCCGCAGCAGGGAGGTGTGCAGAGCCGTGCTCAG<br>CTTCCTCTGCTGCGGGTGTCTCCGGCTGGGCATGCGAGGGCCCGGGGACTGCCTGGCCCGGGCCGTCGAGGCTCACTCCGGAG<br>CTTCCACCACCGACAGCTCTCTGAGGCCAAGGGACAGCTTTC |
| 60 | chr13 group-00005 | TAGTAAGGCACCGAGGGGTGGCTCCTCTCCCTGCAGCGGCTGTCGCTTACCATCCTGTAGACCGTGACCTCCTCACACAGCGC<br>CAGGACGAGGATCGCGGTGAGCCAGCAGGTGACTGCGATCCTGGAGCTGGTCGCAGCAGGCCATCCTGCACGCGGTGGAGGCG<br>CCCCCTGCAGGCCGCAGCGCATCCCCAGCTTCTGGACGCACTGCACTTGGCCCCATGGATCTCTGTGCCCAGGGCTCAGCCAG<br>GCATCTGGCCGCTAAAGGTTT |
| 61 | CRYL1 | TCTCATCTGAGCGCTGTCTTTCACCAGAGCTCTGTAGGACTGAGGCAGTAGCGCTGGCCCGCCTGCGAGAGCCCGACCGTGGA<br>CGATGCGTCGCGCCCTTCCCATCGCGGCCTGGGCGGGCCCGCCTGCCCTCGGCTGAGCCCGGTTTCCCTACCCCGGGGCACCT<br>CCCCTCGCCCGCACCCGGCCCCAGTCCCTCCCAGGCTTGCGGGTAGAGCCTGTCTTTGCCCAGAAGGCCGTCTCCAAGCT |
| 62 | IL17D | CAGTCCCCGAGGCCCTCCCCGGTGACTCTAACCAGGGATTTCAGCGCGCGGCGCGGGGCTGCCCCCAGGCGTGACCTCACCCG<br>TGCTCTCTCCCTGCAGAATCTCCTACGACCCGGCGAGGTACCCCAGGTACCTGCCTGAAGCCTACTGCCTGTGCCGGGGCTGC<br>CTGACCGGGCTGTTCGGCGAGGAGGACGTGCGCTTCCGCAGCGCCCCTGTCTACAT |
| 63 | IRS2 | AGAGAGACATTTTCCACGGAGGCCGAGTTGTGGCGCTTGGGGTTGTGGGCGAAGGACGGGGACACGGGGGTGACCGTCGTGGT<br>GGAGGAGAAGGTCTCGGAACTGTGGCGGCGGCGGCCCCCCTGCGGGTCTGCGCGGATGACCTTGGCGCCGCGGTGGGGGTCCG<br>GGGGCTGGCTGGCCTGCAGGAAGGCCTCGACTCCCGACACCTGCTCCATGAGGCTCAGCCTCTTCACGCCCGACGTCGGGCTG<br>GCCACGCGGGCAGCTTCTGGCTTCGGGGGGGCCGCGATAGGTTGCGGCGGGGTGGCGGCCACACCAAAAGCCATCTCGGTGTA<br>GTCACCATTGTCCCCGGTGTCCGAGGACAACGATGAGGCGGCGCCCGGGCCCTGGGCGGTGGCAACGGCCGAGGCGGGGGGCA<br>GGCGGTACAGCTCCCCCGGGGCCGGCGGCGGTGGCGGCGGCTGCAGAGACGACGACGGGGACGCGGACGGACGCGGGGGCAAC<br>GGCGGATACGGGGAGGAGGCCTCGGGGGACAGGAGGCCGTCCAAGGAGCCCACGGGGTGGCCGCTCGGGGCGCCCGGCTTAGG<br>AGACTTGGGGGAGCTGAAGTCGAGGTTCATGTAGTCGGAGAGCGGAGACCGCTGCCGGCTGTCGCTGCTGGTGCCCGGGGTGC<br>CTGAGCCCAGCGACGAGGCCGGGCTGCTGGCGGACAAGAGCGAGGAGGACGAGGCCGCCGACGCCAGCAGGGGAGGCGCGGGC<br>GGCGACAGGCGGGCCCCGGGCTCGCCAAAGTCGATGTTGATGTACTCGCCGGGGCTCTTGGGCTCCGGTGGCAGTGGGTACTC<br>GTGCATGCTGGGCAGGCTGGGCAGCCCCTCCAGGGACAGGCGCGTGGGCCTCACCGCCCGGCCGCGCTGGCCCAAGAAGCCCT<br>CCGGGCGGCCGCCGCTAGGCCGCACGGGCGAAGGCACTACAGGGTGAGGGGGCTGCGTGGGGCCGGCCCCGAAGGCGCTGGCC<br>GCCTGGCTGGGCCCTGGCGTGGCCTGAGGCTCCAGACGCTCCTCCTCCAGGATGCGCCCCACGGGGGAGCTCATGAGCACGTA<br>CTGGTCGCTGTCCCCGCCACAGGTGTAGGGGGCCTTGTAGGAGCGGGGCAAGGAGCTGTAGCAGCAGCCGGGAACGCCCCTGA<br>GCGGCTCCCCGCCGGGGTGCAGGGCTGCGGAGAAGAAGTCGGGCGGGGTGCCCGTGGTGACCGCGTCGCTGGGGGACACGTTG<br>AGGTAGTCCCCGTTGGGCAGCAGCTTGCCATCTGCATGCTCCATGGACAGCTTGGAACCGCACCACATGCGCATGTACCCACT<br>GTCCTCGGGGGAGCTCTCGGCGGGCGAGCTGGCCTTGTAGCCGCCCCCGCTCGCCGGGAATGTCCTGCCCGCCGCAGAGGTGG<br>GTGCTGGCCCCGCAGGCCCCGCAGAAGGCACGGCGGCGGCGGCGGCGGCGGCGGCCCTGGGCTGCAAGATCTGCTTGGGGGCG<br>GACACGCTGGCGGGGCTCATGGGCATGTAGTCGTCGCTCCTGCAGCTGCCGCTCCCACTGCCCGCGAGGGCCGCGCCGGGCGT<br>CATGGGCATGTAGCCGTCGTCTGCCCCCAGGTTGCTGCTGGAGCTCCTGTGGGAGCCGATCTCGATGTCTCCGTAGTCCTCTG<br>GGTAGGGGTGGTAGGCCACCTTGGGAGAGGACGCGGGGCAGGACGGGCAGAGGCGGCCCGCGCTGCCCGAGAAGGTGGCCCGC<br>ATCAGGGTGTATTCATCCAGCGAGGCAGAGGAGGGCTGGGGCACCGGCCGCTGCCGGGCTGGCGTGGTCAGGGAGTAGGTCCT<br>CTTGCGCAGCCCTCGGTCCAGGTCCTGGGCCGCGTCCCCCGAGACCCGGCGGTAGGAGCGGCCACAGTGGCTCAGGGGCCTGT<br>CCATGGTCATGTACCCGTAGAACTCACCGCCGCCGCCGCCGTCTCGGGCCGGGGGCGTCTCCGCGATGGACTCGGCGTGTTG<br>CTTCGGTGGCTGCAGAAGGCGCGCAGGTCGCCTGGGCTGGAGCCGTACTCGTCCAGGGACATGAAGCCGGGGTCGCTGGGGGA |

TABLE 4A-continued

| SEQ ID NO | GENE NAME | SEQUENCE |
|---|---|---|
| | | GCCCGAGGCGGAGGCGCTGCCGCTGGAGGGCCGCTGGCCGGGGCCGTGGTGCAGCGGATGCGGCAGAGGCGGGTGCGGGCCGG<br>GCGGCGGCGGGTAGGAGCCCGAGCCGTGGCCGCTGCTGGACGACAGGGAGC |
| 64 | chr13<br>group-<br>00350 | TAACCTAAAGAATGAAGTCATGCCCCGGCCTGCACCCGGGAAACTGCACACAGCGAAAGATCGCCACTGAGATAAAGAGCTGA<br>AAGCTATTCCCCAATTCAGCTGTTTCAGCCGTGCGGTCTCACAATGGGCTCACAGACGGCAGCATC |
| 65 | MCF2L | GTTTCCACAATCCACCTCGTAGCTGGGGCGTGCCGCTTGCCTCGGCTTGTCCCGGCAGAACACTCTTACCTTTAATGGCGACT<br>GAAAAGTTGCCACGAGTTCCTGATCATTGTGGTAGGTGCTGCGTGAAGCTGAGACGTGCGTGAGCCACATCCCAGGGGGCTTT<br>GAGCCCCCACCGCGGCGGCGGCTGAGGGGAGGCTTGTCGTACTCGCACAGGAGGACACAGGGCTGCAGTGTTCACTCCAGGGC<br>CTCTTATCATTGGGATCTGAGGAATTTTCCGAGAGGAAGTGCGAATTAACAATGATGAAAGGTTTGTGAGTGAGTGACAGGCA<br>CGTTCTATTGAGCACTGCATGGGGCATTATGTGCCACCAGAGACGGGGGCAGAGGTCAAGAGCCCTCGAGGGCTGGGAGAGTT<br>CGGAGGATAGAAGTCATCAGAGCACAATGAAGCCAGACCCTGCAGCCGCCTTCCCCTTCGGGGGCTTCCTTAGAATGCAGCAT<br>TGCGGGGACTGAGCTGTCCCAGGTGAAGGGGGGCCGTCACGGTGTGTGGACGCCCCTCGGCTCAGCCCTCTAAGAGACTCGGC<br>AGCCAGGATGGGCTCAAGGCATGAGCCCTCAAAGGAGGTTAGGAAGGAGCGAGGGAGAAAAGATATGCTTGTGTGACGTCCTG<br>GCCGAAGTGAGAACAATTGTATCAGATAATGAGTCATGTCCCATTGAGGGGTGCCGACAAGGACTCGGGAGGAGGCCACGGAG<br>CCCTGTACTGAGGAGACGCCCACAGGGAGCCTCGGGGGCCCAGCGTCCCGGGATCACTGGATGGTAAAGCCGCCCTGCCTGGC<br>GT |
| 66 | F7 | TCCAGCTGCAGCGAGGGCGGCCAGGCCCCCTTCTCCGACCTGCAGGGGTAGCGCGGCCTCGGCGCCGGAGACCCGCGCGCTGT<br>CTGGGGCTGCGGTGGCGTGGGGAGGGCGCGGCCCCCGGACGCCCCGAGGAAGGGGCACCTCACCGCCCCCACCCAGAGCGCCT<br>GGCCGTGCGGGCTGCAGAGGACCCCTCCGGGGCAGAGGCAGGTTCCACGGAAGACCCCGGCCCGCTGGGGCTTCCCCGGAGAC<br>TCCAGAG |
| 67 | chr18<br>group-<br>00039 | ACTTACTGCTTCCAAAAGCGCTGGGCACAGCCTTATATGACTGACCCCGCCCCCGAGTCCCAGGCCGCCCCATGCAACCGCCC<br>AACCGCCCAACCGCCACTCCAAAGGTCACCAACCACTGCTCCAGGCCACGGGCTGCCTCTCCCCACGGCTCTAGGGCCCTTCC<br>CCTCCACCGCAGGCTGAC |
| 68 | C18orf1 | TGCCACACCCAGGTACCGCCCGCCCGCGCGAGAGCCGGGCAGGTGGGCCGCGGATGCTCCCAGAGGCCGGCCCAGCAGAGCGA<br>TGGACTTGGACAGGCTAAGATGGAAGTGACCTGAG |
| 69 | CD33L3 | TCGCCAGCGCAGCGCTGGTCCATGCAGGTGCCACCCGAGGTGAGCGCGGAGGCAGGCGACGCGGCAGTGCTGCCCTGCACCTT<br>CACGCACCCGCACCGCCACTACGACGGGCCGCTGACGGCCATCTGGCGCGCGGGCGAGCCCTATGCGGGCCCGCAGGTGTTCC<br>GCTGCGCTGCGGCGCGGGGCAGCGAGCTCTGCCAGACGGCGCTGAGCCTGCACGGCCGCTTCCGGCTGCTGGGCAACCCGCGC<br>CGCAACGACCTCTCGCTGCGCGTCGAGCGCCTCGCCCTGGCTGACGACCGCCGCTACTTCTGCCGCGTCGAGTTCGCCGGCGA<br>CGTCCATGACCGCTACGAGAGCCGCCACGGCGTCCGGCTGCACGTGACAGGCGAGGCGGCGTGGGAGCGGGTCCCCGGCCTCC<br>CTTCCCGCCCTCCCGCCTGCCCCGCCCCAAGGGCTACGTGGGTGCCAGGCGCTGTGCTGAGCCAGGAAGGGCAACGAGACCCA<br>GCCCTCTCCTCTACCCCAGGGATCTCACACCTGGGGGTAGTTTAGGACCACCTGGGAGCTTGACACAAATGCAGAATCCAGGT<br>CCCAGGAAGGGCTGAGGTGGGCCCGGGAATAGGCATTGCCGTGACTCTCGTAGAGTGACTGTCCCCAGTGGCTCTCAGACGAA<br>GAGGCGAGAAAGACAAGTGAATGGCAATCCTAAATATGCCAAGAGGTGCAATGTGGTGTGTGCTACCAGCCCGGAAAGACACT<br>CGCAGCCCCTCTACCCAGGGGTGCACAGACAGCCCACCAAGTAGTGCCTAGCACTTTGCCAGACCCTGATATACAAAGATGCC<br>TGAACCAGGGTCCCGTCCCTAGAGCAGTGGCTCTCCACTCTAGCCCCCACCCTGCTCTGCGACAATAATGGCCACTTAGCATT<br>TGCTAGGGAGCCGGGACCTAGTCCAAGCACCCACAAGCATGAATTTGCCAAATCTTTTCAGCAACCTCTTAAGGCAACTGCTA<br>TCATGATCCTCACTTTACACATGGAGAAGCAGAAGCAGAGATGATAGAATCTTTCGCCCAAGGCCACATCTGTATTGGGACGG<br>GGGCAGCCTGGCACCCAAGTGCCCATTCCTCCCTTCTGACCAGCCCCCACCCCTCCGGCTCTGGCGTCCAAAGGGCTAAGGGG<br>AGGGGTGCCCTTGTGACAGTCACCCGCCTTCTCCCCTGCAGCCGCGCCGCGGATCGTCAACATCTCGGTGCTGCCCAGTCCGG<br>CTCACGCCTTCCGCGCGCTCTGCACTGCCGAAGGGGAGCCGCCGCCCGCCCTCGCCTGGTCCGGCCCGGCCCTGGGCAACAGC<br>TTGGCAGCCGTGCGGAGCCCGCGTGAGGGTCACGGCCACCTAGTGACCGCCGAACTGCCCGCACTGACCCATGACGGCCGCTA<br>CACGTGTACGGCCGCCAACAGCCTGGGCCGCTCCGAGGCCAGCGTCTACCTGTTCCGCTTCCATGGCGCCAGCGGGGCCTCGA<br>CGGTCGCCCTCCTGCTCGGCGCTCTCGGCTTCAAGGCGCT |
| 70 | TNFRSF<br>11A | ATGAACTTCAAGGGCGACATCATCGTGGTCTACGTCAGCCAGACCTCGCAGGAGGGCGCGGCGGCGGCTGCGGAGCCCATGGG<br>CCGCCCGGTGCAGGAGGAGACCCTGGCGCGCCGAGACTCCTTCGCGGGGAACGGCCCGCGCTTCCCGGACCCGTGCGGCGGCC<br>CCGAGGGGCTGCGGGAGCCGGAGAAGGCCTCGAGGCCGGTGCAGGAGCAAGGCGGGGCCAAGGCTTGAGCGCCCCCCATGGCT<br>GGGAGCCCGAAGCTCGGAGC |
| 71 | ZNF236 | TCAGTGTTATGTGGGGAGCGCTAGATCGTGCACACAGTAGGCGTCAGGAAGTGTTTTCCCCAGTAATTTATTCTCCATGGTAC<br>TTTGCTAAAGTCATGAAATAACTCAGATTTTGTTTTCCAAGGAAGGAGAAAGGCCCAGAATTTAAGAGCAGGCAGACACACAA<br>CCGGGCACCCCCAGACCCTGGCCCTTCCAGCAGTCAGGAATTGACTTGCCTTCCAAAGCCCCAGCCCGGAGCTTGAGGAACGG<br>ACTTTCCTGCGCAGGGGGATCGGGGCGCACTCG |
| 72 | chr18<br>group-<br>00342 | GTGGAAACACAACCTGCCTTCCATTGTCTGCGCCTCCAAAACACACCCCCCGCGCATCCGTGAAGCTGTGTGTTTCTGTGTTA<br>CTACAGGGGCCGGCTGTGGAAATCCCACGCTCCAGACCGCGTGCCGGGCAGGCCCAGCC |
| 73 | OLIG2 | TCCACACCTCGGGCAGTCACTAGGAAAAGGGTCGCCAACTGAAAGGCCTGCAGGAACCAGGATGATACCTGCGTCAGTCCCGC<br>GGCTGCTGCGAGTGCGCGCTCTCCTGCCAGGGGGACCTCAGACCCTCCTTTACAGCACACCGAGGGCCCTGCAGACACGCGAG<br>CGGGCCTTCAGTTTGCAAACCCTGAAAGCGGGCGCGGTCCACCAGGACGATCTGGCAGGGCTCTGGGTGAGGAGGCCGCGTCT<br>TTATTTGGGGTCCTCGGGCAGCCACGTTGCAGCTCTGGGGGAAGACTGCTTAAGGAACCCGCTCTGAACTGCGCGCTGGTGTC<br>CTCTCCGGCCCTCGCTTCCCCGACCCCGCACAGGCTAACGGGAGACGCGCAGGCCCACCCCACCGGCTGGAGACCCCGGCACG<br>GCCCGCATCCGCCAGGATTGAAGCAGCTGGCTTGGACGCGCGCAGTTTTCCTTTGGCGACATTGCAGCGTCGGTGCGGCCACA<br>ATCCGTCCACTGGTTGTGGGAACGGTTGGAGGTCCCCCAAGAAGGAGACACGCAGAGCTCTCCAGAACCGCCTACATGCGCAT<br>GGGGCCCAAACAGCCTCCCAAGGAGCACCCAGGTCCATGCACCCGAGCCCAAAATCACAGACCCGCTACGGGCTTTTGCACAT<br>CAGCTCCAAACACCTGAGTCCACGTGCACAGGCTCTCGCACAGGGGACTCACGCACCTGAGTTCGCGCTCACAGATC |

TABLE 4A-continued

| SEQ ID NO | GENE NAME | SEQUENCE |
|---|---|---|
| 74 | RUNX1 | CTGCCCTCGCGGATCTCCCCCGGCCTCGCCGGCCTCCGCCTGTCCTCCCACCACCCTCTCCGGGCCAGTACCTTGAAAGCGAT<br>GGGCAGGGTCTTGTTGCAGCGCCAGTGCGTAGGCAGCACGGAGCAGAGGAAGTTGGGGCTGTCGGTGCGCACCAGCTCGCCCG<br>GGTGGTCGGCCAGCACCTCCACCATGCTGCGGTCGCCGCTCCTCAGCTTGCCGGCCAGGGCAGCGCCGGCGTCCGGGGCGCCC<br>AGCGGCAACGCCTCGCTCATCTTGCCTGGGCTCAGCGCGGTGGAAGGCGGCGTGAAGCGGCGGCTCGTGCTGGCATCTACGGG<br>GATACGCATCACAACAAGCCGATTGAGTTAGGACCCTGCAAACAGCTCCTACCAGACGGCGACAGGGGCGCGGATCTTCAGCA<br>AGCAGCTCCCGGGAGACCAACATACACGTTCAGGGGCCTTTATTACTGCGGGGGGTGGGGGGGGGCGGGGGTGGTTAGGGGAG<br>GAGGGAGACTAAGTTACTAACAGTCCAGGAGGGGAAAACGTTCTGGTTCTGCGGATCGGCCTCTGACCCAGGATGGGCTCCTA<br>GCAACCGATTGCTTAGTGCATTAAAAAGTGGAGACTATCTTCCACGAATCTTGCTTGCAGAGGTTAAGTTCTGTCTTTGGCTG<br>TTAGAAAAGTTCCTGAAGGCAAAATTCTCATACACTTCCTAAAATATTTATGCGAAGAGTAAAACGATCAGCAAACACATTAT<br>TTGGAAGTTCCAGTAGTTAATGCCTGTCAGTTTTTTGCAGGTGAGTTTTGTCTAAAGTCCCAACAGAACACAATTATCTCCCG<br>TAACAAGGCCACTTTTATCATGCAAAACTGGCTTCAGTCCCGAAAAGCAAGAGCTGAGACTTCCAAAGGTAGTGCTACTAATG<br>TATGTGCACGTATATATAAATATATACATATGCTCTACTTCATAAAATATTTACAATACAATCTGTGGAGAATTTAAACACAA<br>CAGAAATCCATTAATGTACGCTGCAGATTTTTTTAAGTAGCCTTGAAAATCAGCTTCAGTAGTTGGAGCAGTGCTGAGCTAGA<br>AGTACTTGTCATGTTCTCTGTTCTCTCAATGAATTCTGTCAAAACGCTCAGTGCAGAAAATTCAGCGTTTCAGAGATCTTCAG<br>CTAATCTTAAAACAACAATCATAAGAAGGCCCAGTCGATGACACTCAGGGTTCTACAGCTCTCCCACATCTGTGAACTCGGGT<br>TTGGGGATGTTGGTTAAGTTTGTGGCTGGTCCTCTGGTTTGTTGGGAGTTGAGCAGCCGCAGAGTCACACACATGCAAACACG<br>CACTCTTCGGAAGGCAGCCACTGTCTACATCAGCTGGGTGACTCAGCCCTGACTCGGGCAGCAGCGAGACGATACTCCTCCAC<br>CGTCGCCCAGCACCCGCCGGTTAGCTGCTCCGAGGCACGAACACCCACGAGCGCCGCGTAACCGCAGCAGGTGGAGCGGGCCT<br>TGAGGGAGGGCTCCGCGGCGCAGATCGAAACAGATCGGGCGGCTCGGGTTACACACGCACGCACATCCTGCCACGCACACTGC<br>CACGCACACGCAACTTCACGGCTCGCCTCGGACCACAGAGCACTTTCTCCCCCTGTTGTAAAAGGAAAACAATTGGGGAAAAG<br>TTCGCAGCCAGGAAAGAAGTTGAAAACATCCAGCCAAGAAGCCAGTTAATTCAAAAGGAAGAAAGGGGAAAAACAAAAAAAAA<br>CAACAAAAAAAGGAAGGTCCAACGCAGGCCAAGGAGAAGCAGCAGAGGTTGACTTCCTTCTGGCGTCCCTAGGAGCCCCGGAA<br>AGAAGTGCCTGGCGGCGCAGGGCCGGGCAGCGTGGTGCCCTGGCTGGGTCCGGCCGCGGGGCGCCCGTCCCGCCCGCGCCCGC<br>TGGCTCTATGAATGAGAGTGCCTGGAAATGAACGTGCTTTTACTGTAAGCCCGGCCGGAGGAATTCCATTCCCTCAGCTCGTT<br>TGCATAGGGGCGGCCGGCGGCCAATCACAGGCCTTTCCGGTATCAGCCAGGGCGCGGCTCGCCGCCGCCGGCTCCTGGAATTG<br>GCCCGCGCGCCCCCGCCGCCGCGCCGCGCGCTACTGTACGCAGCCCGGGCGGGGAGTCGGAGGCCACCCCCGCGCCCCGCATC<br>CAAGCCTGCATGCTGGCCCGGGGCCCCGCCCGCGTGCGGACCCCTTTCCGCAGCCACACGCAGGCTTGTGCGGCTCCGCGAGT<br>GGCCACGGTCCGGAGACCTGGAAAAAGAAAGCAGGCCCCGCCGGCCCGAGGAGGACCCGGCCGGCGCGCCGCACCCGGAGAGG<br>CCCGGCCCCGCGAGCCGCTGCAGGCAGGCGCAGTGGCCGCCACGAGGCTCCCGAACCGGGCTGCAGCCCGCGGACGGCCCCAG<br>ATCCTGCGCGGCCGCCCAGGGCCAGGCCTCCGCTTCCAGGGCGGGGGTGCGATTTGGCCGCGGGGCCCGGGGGAGCCACTCCG<br>CGCTCCTGCACCGTCCGGCTGGCAGCTGCGGCGAAGCGGCGCTGATTCCTTGCATGAGGCCGGACGGCGTCCGCGCGTGCCGT<br>TTGCTCTCAGCGTCTTCCCTTGGGTCGGTTTCTGTAATGGGTGTTTTTTACCGCTGCGCCCGGGCCGCGGCTCGATCCCTCCG<br>CGCGTCTCACTTGCTGCGTGCGTCAGCGGCCAGCGAAGAGTTTCCTAGTCAGGAAAGACCCCAAGAACGCGCGGCTGGAAGGA<br>AAGTTGAAAGCAGCCACGCGGCTTGCTCCCGGGCCTTGTAGCGCCGGCACCCGCAGCAGCCGGACAGCCTGCCCGGGCCCCGC<br>GTCTCCCCTCCGGCTCCCCGGAAGCGGCCCCCGCTCCTCTCCCCGCCCCCGTGCGCTCGAGCGGCCCCAGGTGCGGAACCCAC<br>CCCGGCTTCGCGTGCGGGCGGCCGCTTCCCCCTGCGCCGGTCCCCGCGGTGCTGCGGGCATTTTCGCGGAGCTCGGAGGGCCC<br>CGCCCCCGGTCCGGCGTGCGCTGCCAACTCCGACCCCGCCCGGCGGGGCTCCCTCCCAGCGGAGGCTGCTCCCGTCACCATGA<br>GTCCCTCCACGCCCTCCCTGCCGGGCCCTGCACCTCCCGGGGCCTCTCATCCACCCCGGGGCTGCAACCCAGTCCCCGGATCC<br>CGGCCCCGTTCCACCGCGGGCTGCTTTGTGGTCCCCGCGGAGCCCCTCAATTAAGCTCCCCGGCGCGGGGGTCCCTCGCCGAC<br>CTCACGGGGCCCCTGACGCCCGCTCCTCCCTCCCCCAGGGCTAGGGTGCTGTGGCCGCTGCCGCGCAGGGACTGTCCCCGGGC<br>GTTGCCGCGGGCCCGGACGCAGGAGGGGGCCGGGGTTGACTGGCGTGGAGGCCTTTCCCGGGCGGGCCCGGACTGCGCGGAGC<br>TGTCGGGACGCGCCGCGGGCTCTGGCGGACGCCAGGGGGCAGCAGCCGCCCTCCCTGGACGCCGCGCGCAGTCCCCGGAGCTC<br>CCGGAACGCCCCCGACGGCGCGGGGCTGTGCGGCCCGCCTCGTGGCCTTCGGGTCGCCCGGGAAGAACTAGCGTTCGAGGATA<br>AAAGACAGGAAGCCGCCCCAGAGCCCACTTGAGCTGGAACGGCCAAGGCGCGTTTCCGAGGTTCCAATATAGAGTCGCAGCCG<br>GCCAGGTGGGGACTCTCGGACCAGGCCTCCCCGCTGTGCGGCCCGGTCGGGGTCTCTTCCCGAAGCCCCTGTTCCTGGGGCTT<br>GACTCGGGCCGCTCTTGGCTATCTGTGCTTCAGGAGCCCGGGCTTCCGGGGGGCTAAGGCGGGCGGCCCGCGGCCTCAACCCT<br>CTCCGCCTCCGCTCCCCCTGGGCACTGCCAGCACCCGAGTTCAGTTTTGTTTTAATGGACCTGGGGTCTCGGAAAGAAAACTT<br>ACTACATTTTTCTTTTAAAATGATTTTTTTAAGCCTAATTCCAGTTGTAAATCCCCCCCTCCCCCCGCCCAAACGTCCACTTT<br>CTAACTCTGTCCCTGAGAAGAGTGCATCGCGCGCGCCCGCCCGCCCGCAGGGGCCGCAGCGCCTTTGCCTGCGGGTTCGGACG<br>CGGCCCGCTCTAGAGGCAAGTTCTGGGCAAGGGAAACCTTTTCGCCTGGTCTCCAATGCATTTCCCCGAGATCCCACCCAGGG<br>CTCCTGGGGCCACCCCCACGTGCATCCCCCGGAACCCCCGAGATGCGGGAGGGAGCACGAGGGTGTGGCGGCTCCAAAAGTAG<br>GCTTTTGACTCCAGGGGAAATAGCAGACTCGGGTGATTTGCCCCTCGGAAAGGTCCAGGGAGGCTCCTCTGGGTCTCGGGCCG<br>CTTGCCTAAAACCCTAAACCCCGCGACGGGGGCTGCGAGTCGGACTCGGGCTGCGGTCTCCCAGGAGGGAGTCAAGTTCCTTT<br>ATCGAGTAAGGAAAGTTGGTCCCAGCCTTGCATGCACCGAGTTTAGCCGTCAGAGGCAGCGTCGTGGGAGCTGCTCAGCTAGG<br>AGTTTCAACCGATAAA |
| 75 | AIRE | TTCGGAAGTGAGAGTTCTCTGAGTCCCGCACAGAGCGAGTCTCTGTCCCCAGCCCCCAAGGCAGCTGCCCTGGTGGGTGAGTC<br>AGGCCAGGCCCGGAGACTTCCCGAGAGCGAGGGAGGGACAGCAGCGCCTCCATCACAGGGAAGTGTCCCTGCGGGAGGCCCTG<br>GCCCTGATTGGGCGCCGGGGCGGAGCGGCCTTTGCTCTTTGCGTGGTCGCGGGGGTATAACAGCGGCGCGCGTGGCTCGCAGA<br>CCGGGGAGACGGGCGGGCGCACAGCCGGCGCGGAGGCCCCACAGCCCCGCCGGGACCCGAGGCCAAGCGAGGGGCTGCCAGTG<br>TCCCGGGACCCACCGCGTCCGCCCCAGCCCCGGGTCCCCGCGCCCACCCCATGGCGACGGACGCGGCGCTACGCCGGCTTCTG<br>AGGCTGCACCGCACGGAGATCGCGGTGGCCGTGGACAG |
| 76 | SUMO3 | ACGCACACTGGGGGTGTGATGGAAAGGGGGACGCGATGGATAGGGGTGGGCGCACACTGGGGGACGCGACGGGGAGGGGTGAG<br>CACACACTGGGGGTGTGATGGAGAGGGCGACGCAATAGGGAGGGGTGGGCGCACACCAGGGACGCGATGATGGGGACGGGTGG<br>GCGCACACCAGGTGGCATGATGGGGAGGAGTGGGTACACACCATGGGGGGCGTGATGGGGAGGCGTGGGCGTACACCGGGGGG<br>CGCGATGGGGAGGGGTGGGCGCACACCGGGGGACGCGATGGAGGCGGTGGGTGCACACGGGGCGCGATGGGTGGGAGTAGGTG<br>CACACTGAGGGCACGATTGGGGAGACACGAAGGAGAGGGGTGGGCGCACACTGGGGGACGCGATGGCCGGGACACGATGCGGA<br>GAAGTGGGTGAATACCGGGGTCGCGATGGGCGCCCTGGAAGGACGGCAGTGCTGCTCACAGGGGCCAGGCCCCTCAGAGCGCG<br>CCCCTTGGGGGTAACCCCAGACGCTTGTTCCCGAGCCGACTCCGTGCACTCGACACAGGATC |
| 77 | C21orf70 | CCACAGGGTGGGGTGCGCCCACCTGCCCTGTCCATGTGGCCTTGGGCCTGCGGGGGAGAGGGAATCAGGACCCACAGGGCGAG<br>CCCCCTCCGTAGCCCGCGGCACCGACTGGATCTCAGTGAACACCCGTCAGCCCATCCAGAGGCTAGAAGGGGGA |
| 78 | C21orf123 | TTGAGGTCTCTGTGCATGCTTGTGCGTACCCTGGACTTTGCCGTGAGGGGTGGCCAGTGCTCTGGGTGCCTTTGCCAGACAAC<br>TGGTCTGCCGGGCCGAGCATTCATGCTGGTC |

TABLE 4A-continued

| SEQ ID NO | GENE NAME | SEQUENCE |
|---|---|---|
| 79 | COL18A1 | TGACGCGCCCCTCTCCCCGCAGCTCCACCTGGTTGCGCTCAACAGCCCCCTGTCAGGCGGCATGCGGGGCATCCGCGGGGCCG<br>ACTTCCAGTGCTTCCAGCAGG |
| 80 | PRRT3 | AACACACTGTCTCGCACTAGGTGCTCGCGGAAGAGCGCGGCGTCGATGCTGCGGCTCAGGTTGATGGGCGATGGCGGCCGCAG<br>ATCCAGCTCGCTCAGCGATGGCGCCGGTCCCACACCGTTGCGGGACAGTCCCGGGCCACCCTGGGGTCCGCGACCCAACGACG<br>CAGCCGAGCCCCAGGCGCCTGAACTGGGCGTGGCCAGCTGCCCACTCTCCGCCGGGTTGCGGATGAGGCTCTTGCTGATGTCC<br>AAGCTGCCTGCACCAACGTTGCTGGGCCCTGCATAGCAGTTATTGGGTCGCTCCGGCACCTCGCTCTTTCCTGACGGCGCCGG<br>GCACGCCAGACGCATCAGCTTAGCCCAGCAAGCGTGCTCCGTGGGCGGCCTGGGTCTCGCGGCAGCCACCGCGGCCAACGCCA<br>GGGCGAGCGCCCATGTCAGCTCCAGGAGGCGCAGCCAGAAGTGGACACCCCACCAGGCCCACGAGAAGCGGCCCACGCGGCCT<br>GGGCCCGGGTACAGCCAGAGCGCAGCCGCCAGCTGCAAGCCGCTAGCCAGCAGCCCCAGCGCGCCCGCCACAGCCAACAGCCG<br>AGGGCCCGGGCTGGCATCCCAGCCCCGTGGGCCGTCCAGCAGGCGGCGACGGCACAGGCAGAGCGTGCCCAGAGCCAC |
| 81 | MGC29 506 | GTCTGCACGAAGCCCGCGGCGGCCTGCAGGGGGCCCAGCGACTCGTCCAGGGAACCGGTGCGCAGGAGCAGCCGGGGGCGCGG<br>CGCGCCGGCCGCCCTTGGGGGACTCTGGGGCCGGGGGCGCAGCTCGATCTGACGCTTGGGCACTGTCCGGGGCCTGGCGGGCG<br>CGGCGCCCTCCTCCAGAGCCACCTCCACACACTCGAACTGCGCTGGGGCGGCAGGACTTGGCCCACGGGGCCGCAGCTCTAGG<br>TAGGTGGCCCAGCGGGAGCCACCATCGGGGACCTGGGACTGGCGTGGGACCGCGGCGGGAGACGCTGGCCCCGGCGGCAAGGG<br>GCTGATGAAGGCCGGCTCCGTGAACTGTTGTTGCGCCTCGCGATCGTCTGCGCCGGAGCAGCCGAACAGGGGTCCGACGCCGA<br>AGATGACTTCCATCTCCCCCGACGGCAGCGTGCGCAGCTGGGGCTGGGGTGGCCGTGGGCCGGAACCTGGCCTCGCGGGAAA<br>CCCGAGCCGGGCCCGTGCCGCTGGCGGCTATTCTGGGCGCTGACGGACAGGCGAGGCTGCGCGCCCGCCCCCCGCCCAGGAGC<br>CACCCAGGGCCAATTCGCTGGGCCTTTCGCGTCCGGCCCAACGTCCGGGGGCTCCGGAGAACCTGGAGCCGTGTAGTAGGAGC<br>CTGACGAACCGGAGGAGTCCTGGCGCCGCGCGGGGGCCGTGGGCAGCTGCCTCGGGATCCCAGGCAGGGCTGGCGGGGCGAGC<br>GCGGTCAGCATGGTGGGGCCGGACGCCGTGCACTATCTCCCTCGCATTCGCCTCCGCTGGTGGCGC |
| 82 | TEAD3 | CTGGAGAGAACTATACGGGCTGTGGGAGTCACCGGGCGACTATCACCGGGCCTCCTTTCCACATCCTCCTCCGGGAAGGGACC<br>CCGTTCCGGGCCTCGACCGGCGCAGACTGGGCTGACCCACTTTCTTGGGCCCACTGAGTCACCTCGAAACCTCCAGGCCGGTA<br>GCGGGGAGGAGAGGAGGAGCAGGCGGGGGTGCCAAGGTGTGGGCTGCGCCCTGGTTAGGGGGCGAGCCCGGCTTGTTTATGAG<br>GAGGAGCGCGGAGGAGGATCCAGACACACAGGCTTGCGCGCCCAGACTCGCCCGGCCAGCGGCTGGCGGCCTCCGACGTCACC<br>AAACCGGTTGGGTGAGAGGGCAGAGAGCAGGGGGAAGGGCCGCAGTCCCGCCCGCGCCCCCCGGCACGCACCGTACATCTTGC<br>CCTCGTCTGACAGGATGATCTTCCG |
| 83 | chr12 group- 00022 | GAGTGCGGAGTGAAGGGGTGCACTGGGCACTCAGCGCGGCCCTTGGGAGGCAGGGCCGCCCCAGCCTGCCCTCCTGTCTGGGA<br>AGGCCGTCCAGAAGCAGGAGCCCCGGGGAAAACAACTGGCTGGACGGGGCGGCCTTCAGTGTCTCTCCCAGCCTGAGAGTCGC<br>TTCCCACCACCTGGGCACGAACCTGCTCTGCGATCTCCGGCAAGTTCCTGCGCCTCCTGTCGGTAAAATGCAGATCGTGGCGT<br>CTT |
| 84 | CENTG1 | TCTTCTTTCCGCCCCTAGGGGGCACAAGCGGGCATGTCCAAGCGCCTAGGAGCCCGTACCGCTGGGGACCTCCCCTTCCGCGA<br>ACCCCGAGCGGGTAGACCCAGAGCAATCCGAGTGTGGAAACAATGGAGAGGGGGCGTGTTGAGCTGGGGTCTCCATGCCTCGT<br>TGGGGAGAGGGAGGTGAGTTTGTGTCTTCTGGAAGGCGTGGGGGCTGTGCCCTCGTGGGGGTAGGAAGTGCTCCCGTGGGGCG<br>GGGTGCGGATCGGAGAGGTGAGTGGGTGCGTCTGTCCAGCGGTGGCGCCCGGTGTGGTCGTGCCCGGCCCGCGTGGGGATGGGG<br>GTGTCTCTCCCGCTGGGCAACTATACCAGCGCAACCGGGGCGTCGGCGCGGCCCACGCTAGCGGCGCTGCTCCGGCGGCGGGG<br>GCTGGGCGTGGCGGTGATGCTGGGCGTGGTGGCCGCGCTGGGCGTGGTGGCCGCGCTGCCGCCCTCACCCGGGCAGCCGTGCT<br>GGAGAAGGATGTCGGCGCACAGCTGGCTTCCAGCCTGGCGGGCGTAGAACAGCGCCGTGCGGCCCTGGGCGTCACGGGCCGCC<br>ACGTCCGCGCCGTACTAGAGGGCGGAAACGGCCGCGTGACCGCGCGTCCCCAGGGCGCCCACACCCGGCGCCGCCTCCCCCAC<br>ATGGCCAAGCCTACTTCCGGGGTCCCTCTGGGAATTTCGGGCTTTCCCGCGCCAGGCGTTTTCCGAGATGAAGCCTCAAAGAC<br>CCCCTTTCCTCCCCCCAGCTCACGTACCCACAGCAGCAGTTGCGTGATGACGACGTGGGCGAGCTCGGCCGCCAGGTGGAGTG<br>GGGAGCGCAGCTGTGGGTCCTCTACGCTGGTGTCGAGCGGCCCGTGTCGCGCATGGGCCAAAAGCAGGAGAACGGTAGCCACG<br>TCCTGGGCCTGCACGGCGGCCCACAGCTGGCGGCCCAGCGGCTCCTCCGAGGTGCTCAGCGGCGCCAGGAACAGTAGCTGCTC<br>GTACTTGGCGCGAATCCACGACTCGCGCTCCTCCCTGCAAGACCAGGGATCAACGGAAAAGGCTCTAGGGACCCCCAGCCAGG<br>ACTTCTGCCCCTACCCACGGGACCGTCTCAGGTTCGCACACCCTCAGCAACCCTCCCCCCGCTCTGTTCCCTCACGCTTACCG<br>CGAAGAGTCCCGCGAGGGCTTGGCACGGCCTCGCGTGTCGCTTTCCCACACGCGGTTGGCCGTGTCGTTGCCAATAGCCGTCA<br>GCACCAGGGTCAGCTCCCGTGGCCAGTCGTCCAAGTCCAGCGAGCGAACGCGGGACAGGTGTGTGCCCAGGTTGCGGTGGATG<br>CCAGAACACTCGATGCAGATGAGGGCGCCCAGGTTCAAGCTGGCCCACGTGGGGTCTGCGGAAGGAGCGTAGAGGTCGGCTCC<br>CAGCCGGGCAGCACAGGCACCCCGGCATTCACTACACTCCCTAGCCCCTCCGCTGCCTCCTGGCACTCACTGGGGGCCCCGCA<br>GTCCACGCAGATTGAATTCCCCTTGGCGTTCCGGATCGCCTGGAT |
| 85 | CENTG1 | AGCCAGGTCCAGCCCCCGCGCCTGACACCGGCCGGACGTTCCCGGGGCGCCGCAGCTGCGGCGGGAACTCTGGGATCCGGAGC<br>CATCTGCTCCCACCCGCTCCGGAGCCAAACCCCGGGGGCCGCCTCCGCTCCGGACCCGCCTCCTCTCCCGGGAGTGTGAGCC<br>GAACCAAGAGTCTCCTGCCTATCTCCTCCAGTAGGAAAATAGTAATAATAATAGACACCCTGCCCCCGTAAAAAACACTACCT<br>TCCCCGTACCGCCTCCCAAGTCTCCCGGGGTACGGATTGCCTTTGCAGCAGTTCCGCCCCACCTGACTCACTCCAGGGTCAGC<br>CCCGGGTGGGTTTCAATGCGGCTCTGGGGAGGGGGTGGGCAGTGGGGGAAGTGAGGCTTCCTATCCGCCCCCTCTCACTTCAC<br>ATTTAAATATTCTGCACGTTCCAGCCCCCGCGGACTCGCGTACCGCCCAATCCGCCTTCACCGCACGAAAAACATCACTAGCC<br>TGCTCTCAGCCCAGGGGACGACTAGTCCCTGGCGAGAAGCTGCCTGCAAGGTCACTGTCATGCCACCTGCCCCAAGTGCTCAG<br>GGGAAACTGAGGCTTCCTCATCCCCTTCACCTTCAACGTCGCTCTAAACACGGCAAAGCCCCGTTTCCATGCTCCCAGAGTTC<br>AGCTGAGGCTGGAAGTGGGGTCCTGGGCTTCTCTGGGAGCAATTTTCTAGTCACTCTGATCAAGGACGTTACTTTCCCAGAAA<br>GCTCTGAGGCTGAGTCCCTCTGAAATCAAGTCCTTTCTCCTGTCGCACAATGTAGCTACTCGCCCCGCTTCAGGACTCCTATT<br>CTTTGCCCCAATCCTTGACAGAGGGGTGAGCTTGGTTCATCCGCCCACCCCAGAGAAAAGCTTCCCTAGTTTCCTGGACCTCG<br>CTCCTCCACCCCAAGCTGAGCATTCCAGGTACCCTTCCCTCCCTGTTCTCAAGCCCTGACTCAACTCACTAGGGGAAGCGCGG<br>AGCTCGGCGCCCAGCAGCTCCCTGGACCCGCTGCCAGAAGACAGGCTGGGGGGTCCGGGAAGGGGCCCGGAGCCAGGAGGCCC<br>TCCTGTGCTCTTGGTGAAGATGCCGCTGATAAACTTGAGCATCTTGCGGTCACGAGTGGATGCTCGGCCCCCCTCCCGGCCCC<br>GTTTCAGCCCCGGAGCTGGAGGCTCCAGAGTGATTGGAGGTGCAGGCCCGGGGGGCTGCGCGGAAGCAGCGGTGACAGCAGTG<br>GCTGGACTCGGAGTTGGTGGGAGGGTTAGCGGAGGAGGAGAGCCGGCAGGCGGTCCCGGATGCAAGTCACTGTTGTCCAAGGT<br>CTTACTCTTGCCTTTCCGAGGGGACAACTTCCCTCGGGCTCCAGCCCCAGCCCCGACCCCACCAGAGGTCGAAGCTGTAGAGC<br>CCCCTCCCCCGGCGGCGGCGGCGGTGGCGGCGGCAGAGACCGAAGCTCCAGTCCCGGCGCTGCTCTTTGACCCCTTGACCCTG<br>GGCTTGCCCTCGCTTTCGGGCCATGACAGGCGGCTACCCGCGCCCTTGCCCCCGCCGGCTTTGGCTCCACTCGTGGTCACGGT<br>CTTGCAAGGCTTGGGAGCCGGCGGAGGAGGCGCCACCTTGAGCCTCCGGCTGCCGGTGCCAGGTGCGGAGAGGATGAGCCAG |

TABLE 4A-continued

| SEQ ID NO | GENE NAME | SEQUENCE |
|---|---|---|
| | | GGATGCCGCCGCCCGCCCGGCCTTCGGGCTCCGGGCCGCCCCAGCTCGGGCTGCTGAGCAGGGGGCGCCGGGAGGAGGTGGGG<br>GCGCCCCCAGGCTTGGGGTCGGGGCTCAGTCCCCCGGAGAGCGGGGGTCCCGGAGGGACGGCCCAGAGGGAGAGGCGGCGGCC<br>GGGAGCGGGGGAGACTGGGCGGGCCGGACTGGCCGGAGCCGGGGACAGGGCTGGGGGCTCCGCGCCCCCGGTGCCCGCGCTGC<br>TCGTGCTGATCCACAGCGCATCCTGCCGGTGGAAGAGACGTTCGTGCCGCTTCTTGCCCGGCTCCTCCGCGCCTCGGGGGCTG<br>CCAGGATCCCCAGTCTCGGAGCCTCTGGCACCGGCGGCGCCGGCCGCGGCCGCAGACGGAGAAGGCGGCGGCGGAGGCACCGA<br>CTCGAGCTTAACCAGGGTCAGCGAGATGAGGTAGGTCGTTGTCCGGCGCTGAAGCGCGCCCGCGCCCCGGCTCATGGGGCCCG<br>GAGACCCCCGAGCTGGGGAGGGGAGGGGACTCCCCCGGACTGCCTCAGGGGGGCCCGGCCATGGGGCCGCCCTGCTCGCTGCC<br>CCCAGCCCCCGGACCCCGCTGAGCCCCCGGCCCGGCTCCGCTGTCGCCGCCGCCTCCGCCGCCTCCGCTTGCGCCCCCCTCCC<br>ATCACATGGGGCGCCCCCTCCCCATGCTCCCCGCCCTGCGCCCCCACCCTCTTGGAGCCCCGGGACCTTGGTGCTGCTCCAGG<br>GAGGCGCGCCGGACCGTCCACCCCGGCCTGGGTGGGGGCGCTGAGATGGGTGGGGGAGGGCGGGGAGGACAGTAGTGGGGGCA<br>AATGGGGGAGAGAGAGGAAAAGGGAGCAGAAAAGGGGACCGGAGGCTAGGGGAAACGAACCTGTGCGGGGGAGGCAGGGGCGG<br>GGAATTGGGACTCAAGGGACAGGGGCCGCGGATGCGGTCGGAAAGAGGGTCTAGAGGAGGGTGGGAAGCTAGTGG |
| 86 | chr18 group-00304 | AGGAGCGCAAGGCTTGCAGGGCATGCTGGGAGAGCGCAGGGAACGCTGGGAGAGCGCGGGAAATACTGGGATTGGCTCCCGAG<br>GGCTGTGAGGAGGGCACGAGGGGACACTCCGATGAAGGCAGGGCACGCGGGGCGAGCCGGGAGCGTCTCCTGAGGGCAGCGAG<br>GAGGGAGCTGAGGCACGCGGGCTCTCAATCGACGCCCCACAGAGACCAAGAGGCCTGGCCTTGGGGGGCAGCTGCTTGAAGGA<br>GGCAGAGCGGAAGCGAGGGAGACTGCTGGAGGCCCTGCCGCCCACCCGCCCTTTCCTCCCCCTGAGGAGACGCCTGACGCATC<br>TGCAGTGCAGGAGGCCGTGGGCGTTAGAAGTGTTGCTTTTCCAGTTTGTAAGACCATTTTCCTGATTCTCTTCCCCACGGTTG<br>CGGAGGAGCAGGTCAGGGCCGCCATGAGGGCAGGATC |
| 87 | TSHZ1 | TCGACCGCTACTATTATGAAAACAGCGACCAGCCCATTGACTTAACCAAGTCCAAGAACAAGCCGCTGGTGTCCAGCGTGGCT<br>GATTCGGTGGCATCACCTCTGCGGGAGAGCGCACTCATGGACATCTCCGACATGGTGAAAAACCTCACAGGCCGCCTGACGCC<br>CAAGTCCTCCACGCCCTCCACAGTTTCAGAGAAGTCCGATGCTGATGGCAGCAGCTTTGAGGAGGC |
| 88 | CTDP1 | TGTGCCGTCGCACACAGACGCCCTCAACGTCGGAGAGCTGTGAGCGGGGCCGTGCTCTTGGGATGGAGCCCCCGGGAGAGCT<br>GCCCGCCAACACCACTCCGACGTGATCCATGCTGGACATAAAGTGCTCTTCCCTCCGCTAGTCATCGGCCGAGCGGGCCCCTC<br>GCTCCTGGGTGTAAGTTCTTTCTGTGCGTCCTTCTCCCATCTCCGTGCAGTTCAG |
| 89 | KCNG2 | CCATGCGCCGCTGCGCGCGCGAGTTCGGGCTGCTGCTGCTGTTCCTCTGCGTGGCCATGGCGCTCTTCGCGCCACTGGTGCAC<br>CTGGCCGAGCGCGAGCTGGGCGCGCGCCGCGACTTCTCCAGCGTGCCCGCCAGCTATTGGTGGGCCGTCATCTCCATGACCAC<br>CGTGGGCTACGGCGACATGGTCCCGCGCAGCCTGCCCGGGCAGGTGGTGGCGCTCAGCAGCATCCTCAGCGGCATCCTGCTCA<br>TGGCCTTCCCGGTCACCTCCATCTTCCACACCTTTTCGCGCTCCTACTCCGAGCTCAAGGAGCAGCAGCAGCGCGCGGCCAGC<br>CCCGAGCCGGCCCTGCAGGAGGACAGCACGCACTCGGCCACAGCCACCGAGGACAGCTCGCAGGGCCCCGACAGCGCGGGCCT<br>GGCCGACGACTCCGCGGATGCGCTGTGGGTGCGGGCAGGGCGCTGACGCCTGCGCCGCCCAC |

TABLE 4B

| SEQ ID NO | GENE NAME | SEQUENCE |
|---|---|---|
| 90 | TFAP2E | GTCCTAACATCCCAGGTGGCGGCGCGCTGGCTCCCTGGAGCGGGGCGGGACGCGGCCGCGCGGACTCACGTGCACAACCGCGCGG<br>GACGGGGCCACGCGGACTCACGTGCACAACCGCGGGACCCCAGCGCCAGCGGGACCCCAGCGCCAGCGGGACCCCAGCGCCAGCG<br>GGACCCCAGCGCCAGCGGGACCCCAGCGCCAGCGGGACCCCAGCGCCAGCGGGACCCCAGCGCCAGCGGGTCTGTGGCCCAGTGG<br>AGCGAGTGGAGCGCTGGCGACCTGAGCGGAGACTGCGCCCTGGACGCCCCAGCCTAGACGTCAAGTTACAGCCCGCGCAGCAGCA<br>GCAAAGGGGAAGGGGCAGGAGCCGGGCACAGTTGGATCCGGAGGTCGTGACCCAGGGGAAAGCGTGGGCGGTCGACCCAGGGCAG<br>CTGCGGCGGCGAGGCAGGTGGGCTCCTTGCTCCCTGGAGCCGCCCCTCCCCACACCTGCCCTCGGCGCCCCCAGCAGTTTTCACC<br>TTGGCCCTCCGCGGTCACTGCGGGATTCGGCGTTGCCGCCAGCCCAGTGGGGAGTGAATTAGCGCCCTCCTTCGTCCTCGGCCCT<br>TCCGACGGCACGAGGAACTCCTGTCCTGCCCCACAGACCTTCGGCCTCCGCCGAGTGCGGTACTGGAGCCTGCCCCGCCAGGGCC<br>CTGGAATCAGAGAAAGTCGCTCTTTGGCCACCTGAAGCGTCGGATCCCTACAGTGCCTCCCAGCCTGGGCGGGAGCGGCGGCTGC<br>GTCGCTGAAGGTTGGGGTCCTTGGTGCGAAAGGGAGGCAGCTGCAGCCTCAGCCCCACCCCAGAAGCGGCCTTCGCATCGCTGCG<br>GTGGGCGTTCTCGGGCTTCGACTTCGCCAGCGCCGCGGGGCAGAGGCACCTGGAGCTCGCAGGGCCCAGACCTGGGTTGGAAAAG<br>CTTCGCTGACTGCAGGCAAGCGTCCGGGAGGGGCGGCCAGGCGAAGCCCCGGCGCTTTACCACACACTTCCGGGTCCCATGCCAG<br>TTGCATCCGCGGTATTGGGCAGGAAATGGCAGGGCTGAGGCCGACCCTAGGAGTATAAGGGAGCCCTCCATTTCCTGCCCACATT<br>TGTCACCTCCAGTTTTGCAACCTATCCCAGACACACAGAAAGCAAGCAGGACTGGTGGGGAGACGGAGCTTAACAGGAATATTTT<br>CCAGCAGTGA |
| 91 | LRRC8D | CACCTTCCCCGAGGTAATTATTTTCTGGGGGGTAGGGGTGGGGGTTGGGAGGGTGAAGAAAGGAAGAAAAAGAAGGCCGATCACA<br>CTGGGCACCGGCGGAGGAAGCGTGGAGTCCATTGATCTAGGTACTTGTGGGGAGGGGAGAACCCGAGCAGCAGCTGCAAACGGAA<br>GGGCTGTGAGCGAGCGGGCGGGCGGGTGGCTGGCAGCGAGGCCACCAGCAGGGGGGGCCCGGGCCGAGGCCGCGCCACCTCGGCA<br>CCACGCGGGCAGCCGGTGCGGCGGGGTCGCCACGGCCAGGGGAGCGCTGGGTGCCCACCATGGCAGTTATGCAAGCGGTGACCCC<br>CTGGTCTTGCCTCCCCGCCGCCCTGCACTCCTTCCTCCCCGCTGCCGACACTTGGATCTCTCTAGCTCTTTCTCTCCCCTGTGTT<br>TTCAAACAGGAAGTGCACGGCTGTCTATAACGTGCTGCCGGGTCTCAGGATGGAGGAGTGAAGTCTCCTGTCGCCGTGGTTCCAG<br>CCTCCGGAGCTCGCCCAAGCCGCGTCCCCAGAGAGCGCCCTGAGAGAACAGGGTGGCCGCTTGGTCCAGGTGCGCGGGGTCGGGT<br>CTGGGTCCAGGGAGCGGGTCGGGAAGTCTGCGGCACGGAGCACTGCTAGTGTCGGATCTGCATCTCCAGCTCTGTGCTGCAGCTT<br>CACTTGCCCGCCCCCCACCACTGGCTTCTCACCCGGGGTCTCTGCCAAACTCTGGCTGCTGCCGCCCTGGGTTCGGGCCGGCGGA<br>AGGCCCTGGGCGTGCGCTGCGGAGCCGCCTGCGAGGACTCCACTAGGGCGCTTTCCAGGCTGGACTGCCCCGGGCTGCGCTGGAG<br>CTGCCAGTGCTCGGGGAGTCTTCCTGGAGTCCCCAGCTGCCCTCTCCACC |
| 92 | TBX15 | CTCTTCCCAAGTTACGCCACCGGTCGAGGACGGCAGGAGACCCCCGAGTGCAGAGAAAGCTCAAACCGGCAGCGAAGTCGGTCCT<br>AGCCAAGCTGAAAAAACGTCTCGGATTTCGCGGACAGCGGCCTAGACACAGCCCGATCTTCCAGTCCTAGTGCCCTGGTCGAGAC<br>GGTTCTATCCTTTTGCAAAGAAGCCGGAAA |

TABLE 4B-continued

| SEQ ID NO | GENE NAME | SEQUENCE |
|---|---|---|
| 93 | C1orf51 | TCTCGGTTGCAATCCCCACCCTCCTCACCCAGCAGGGCAGGAGGCACCCAACTTGGAGGAGAAAGGGGTGGGGGAGGTGAAACAG AGACCGGAGAGTCACGAGGGCTGGGCCGCCGAGAGCAGGAGAATATACCGTGTCACACACCTCCATTCTCTCACACACGTTGCAG ACACAAATCACTGACGGTTTCCACGTGCTGCGCTCGTGAGCGGAGGTGTTCAAAGAGGGGGCAGATGAGTTACTTCCCGAGACGG AACCGGGGGTCCCACGTCCGCCGCCTTCAGTAGCACAACCAATCTCTGAACACTCAAACCGCGCATCTCTGGCGCATCACCATCC TATTTAAGGCCACGGGCTCCGCCCTTTTCCTCCCCTCCCTTCTTTTCCACTCTTTTTCCA |
| 94 | chr1: 179553900- 179554600 | CTGCCAGAGATGTGTCTGTCTTGCGCCCCGCATGCACTGCCTGCGGGGCTGCGCTGCACTCCCCGGCGGCGCCACGGGTCTGGCC CCCGCGCTTCTACGTGTTGGGGGGATGCATGGACCTTGGAGATCCGTAGTTGGCCCTAACCTTCTCGGAATCTCCTCTGCACGCG CTGCCTGTTCCTCCTCTGCACGCTCTGTCCGTTCCTTTGCAACTTCTGTGGGAATTGTCCTGGCGTGGGAAACGCCCCCGCGCTC TTTGGCACTTAGGGTGTGAGTGTTGCGCCCCTTGCCGCAGCGCTCAGGGCAGCATCCCGCTCGAGGATGCAGGGTTCTCACCAAG CAGTGAGGGGGACTCACGCGCCGCCGGGGAGCGGAGCCAGGCTCCGAGAAGGGAGCAGGCTCGAGCCGCTGGGTTTTCGCAAGCC TTGGGGCCTCTGGCCGCCCTTCCATGCCTCCGGGCGCGGGCGGCTCAGCAGGTCCCCGGCTTCGGGAAGTTTTGTGCGCGGATCG CTGGTGGGGAGGGCGCGCGGGCCAGTGGCTGAGCTTGCAGCGAAGTTTCCGTGAAGGAAACTGCATGTGCCTTTGGAGGCGACTC GGGACTGCTGTAGGGTGGACTGGGTGTCTATGGAGTTGCGGGTCAGAGCGAGTAGGGTGGGTCCTTTCCTGGGACAGGACTGGGA ATTGGGGCTCGAAGTAGGGG |
| 95 | ZFP36L2 | AGGGGTGTCCTCCAACATCTCTGAACCGCCTTCCCTTCCTCCTCACTGGCGCCCTCTTGCCTCAGTCGTCGGAGATGGAGAGGCG GCTGAAGATTGGCAGGCGGCGGCCAGGGTCGAGGCTGGGAGACTCAGAGCCGCTGAGGCTGCCGGAGCTCAGGGAGCCGCTTAGG TAGCTGTCGCGGTCCGACAGCGAGTCCGGG |
| 96 | SIX2 | TCTGACTCTCGGGCTGGAGCAGCCGAGACAGCGCTCCCCAGCGGGACTACAGAATCCCGGGTGTCGGCCTGGGGGCCCTGGATTG GCAGTGGTGGAGTCTTCTGAGCCTAACAGCTACTAGGAATGACAGAGTTGCAGATGGCTTTGTCGCCCGCGGGGCGGCTCAAGCG TCCTGGGTCCCAGGCCTCTGTCCTACGGCCAGGCCGCCGGCTCAACGGGCCGAAGGGAATCGGGCTGACCAGTCCTAAGGTCCCA CGCTCCCCTGACCTCAGGGCCCAGAGCCTCGCATTACCCCGAGCAGTGCGTTGGTTACTCTCCCTGGAAAGCCGCCCCCGCCGGG GCAAGTGGGAGTTGCTGCACTGCGGTCTTTGGAGGCCTAGGTCGCCCAGAGTAGGCGGAGCCCTGTATCCCTCCTGGAGCCGGCC TGCGGTGAGGTCGGTACCCAGTACTTAGGGAGGGAGGACGCGCTTGGTGCTCAGGGTAGGCTGGGCCGCTGCTAGCTCTTGATTT AGTCTCATGTCCGCCTTTGTGCCGGCCTCTCCGATTTGTGGGTCCTTCCAAGAAAGAGTCCTCTAGGGCAGCTAGGGTCGTCTCT TGGGTCTGGCGAGGCGGCAGGCCTTCTTCGGACCTATCCCCAGAGGTGTAACGGAGACTTTCTCCACTGCAGGGCGGCCTGGGGC GGGCATCTGCCAGGCGAGGGAGCTGCCCTGCCGCCGAGATTGTGGGGAAACGGCGTGGAAGACACCCCATCGGAGGGCACCCAAT CTGCCTCTGCACTCGATTCCATCCTGCAACCCAGGAGAAACCATTTCCGAGTTCCAGCCGCAGAGGCACCCGCGGAGTTGCCAAA AGAGACTCCCGCGAGGTCGCTCGGAACCTTGACCCTGACACCTGGACGCGAGGTCTTTCAGGACCAGTCTCGGCTCGGTAGCCTG GTCCCCGACCACCGCGACCAGGAGTTCCTTCTTCCCTTCCTGCTCACCAGCCGGCCGCCGGCAGCGGCTCCAGGAAGGAGCACCA ACCCGCGCTGGGGGCGGAGGTTCAGGCGGCAGGAATGGAGAGGCTGATCCTCCTCTAGCCCCGGCGCATTCACTTAGGTGCGGGA GCCCTGAGGTTCAGCCTGACTTTCCCGACTCCGCCGGGCGCTTGGTGGGCTCCTGGGCTTCTGGGCTCACCCTTACACCTGTGTA CTAAAGGGCTGCTACCCTCCCGAGGTGTACGTCCGCCGCTCGGCGCTCATCGGGGTGTTTTTCACCCTCTCGCGGTGCACGCT TTTTCTCTCACGTCAGCTCACATCTTTCAGTACACAGCCACTGGGTCTCCCTGCCCCTCCAGCCTTTCCTAGGCAGCTTTGAGGG CCCAGACGACTGAAGTCTTACTGCTAGGATGGGAACACGATGAAAAAGGAAGGGGCCCAGTCAAAAGTCCTCTCCTCTTCGGTTT TTCTTCAACTGTCCTTCACAAAAACATTTATTTCTGTCCCAGCGCCCTGGCGGATTTCGGCAGATGGGCCCTAGGGGGTTGTGGA GGCCAAATTCCCAGGATGCTGGTCCTGCCTTTTTCATTGGCCAAAACTGTATTTCCTACAACGACTAAAGATAACCAAGAACTGA GTAGACCCTGTTCTCTCACCAGATCTCCCTGGCTCTGTTTAACTTTTCCTGGTGCAATGCGATGGCACCACCAGCTCCCCAGGCA GGCACCACTCCCTCAAGATACCATTTGGGGTAGGGATTTGAGTCCTGGAGAGGGTCAGCGGGGCGCCGGGGTGGGGGTGGGAAGG AGACTGACAGGGACACACCGCGAGCTCCGCATACTCTCCTCTGCCCCCTGTAGCCCGGGGCTTTAATGACCCCAAGCAGATTTCC TGTCTCTGGTCTAGCCAGCTGCCCCTAGGGCTGGATTTTATTTCTTCATGGGGTTTCACCCTAAAGGGCCCCCTGGTCATGGGAC CTGGTTGGGAACAAATGAAAGATGTCTTGTAGCAAATGCTTTCAGGGGAGCAGAAAAGAAGATTGGGCACTTCCAGTCACTTGGT CACTTTAGGTGGCTGGAACAAAACTGGTGACTTTCACGACTGCTACAGGGTGAGGGGGTGAAGGGTGGCAGAGAGGTGACAAGCC ACTGGGAATCCTATTCAGTGGGGATGCCGACAGGGAGTGGCTGTAATCAACTGAGCAACATCTGTGTGAATGTTATTCACAGGTC AGGACAGCAGCTTGGTCTTCCCAGGTGAGGAACTGAGGACTGGCCTGCATAGATTTGTGCAGTAGGTGAGTAGCTTCCAAATTTA TTTTCAGAACTTCCATGTAGTACCTGCCTCTCCATTTAAATATTTTTTAAAATTTTATTTATTTAAATATTTTCTTGGTTAGCTT TCCAAGAGGGAGGAAAAGAGGGGAGTTGCAACAAGTAGTGCCCCTATGCTGGGATTCATTTTCCAGAGTAAAGCCTGGGACTGGC ACCCTGACCCCTACCGGCAGGTGAAAACTCCAGGCAAACTGCTGAGATCCCACCTGGGCTGGCTGAGATAGTGCCTGGGGTGCAT CCCTCAGCAGCTGCCACCTGGCCCTGGGGCCATCTCTTTCTCTGGCATCAAGCAGCCAGGTGTCAAGGCCTTCCCAGCAATCCA TGCTGCATGGCTGGGTCTTGTTCTAGCAGGTCGATGGGCAGGGACTGGTAGCTTAGCCAGGGCACCAGTGCGTGGCTGTGGGTTT GTGTGCTTCTGTGGAGAAGCATGATGTGTATGTGTGTGTGTGGGCACAGGCATGAGGAAGGGTTCATTTGTGCAGGTATCTCCCA TGTATATCAGTGTGGGAGAGTGCCTGAGGATGTGTTTGTGTGTCTGAAAATGGGCGGAGGGTCTGTTGTGCTAATGTGTGCAGGG GTGAACATGTGTGTGACAGTCTGTGTGTTTCCCTGAGTGGTGGCTGCGTGAGAGGGTGAGGGGATTGGTGTTGTCTACCATGCC CGGCACATAGCAGGCTCTTAATAATCTTGAATTTAATTAATGTTAAATGTGTATGTTCCCATCCTTGTGGAAGTTGGTATAGAGC CTGTTTTCCTGTGATTGTGAGACTGGAAAATGGGGGACGGGCAGGGGCGAGACAGGATACAGAGGCTACTGTTTTCTTCCTCCCT AGAAGTAAGTACATAGAAGAGTGGGCTCTGGCACCTCACGGGACATCACCAAGTCCTGTGTGGCTGGCTAGGCTGTCCCAAGGTG GCTTCAGGCATCACTTGAATCTTTTGAGACCTTCAGGCAGTAGCCTGCCATTCACCCTGTCAGTCAGCAGAAGTTGGGCCCACAC AGGCCATAGAAACACAGAGCAGTTCCCGGGAGGACCTGAGCTGTCCCTGAGAGCAGAGCTTCCAGGAGAGGCCGCAGGAACTGCC TTGACCGGAATTCCTCTTGGGGTGCAAAGGTGGAGGGACACATGGTGCGACCCCAGGCAGAGGACTGCAGCCACTCCGTGCAGTC CCAGCCTCTGGGGTAGCCCCTTGACCTCCAGGCCTGCACAGATCCAAGGCCGAGGTCCAGGCTCCAGCGCCAAATTAGCTGGCCT AGCAGCCTGCAGCCGCTCTAATCTCAACTAGGAAGGAATCCTTGCGCTTAGAAAGTCCAAGCGAAAGGGTATTCTGATTTTATCC CGGTTTTACCAGAAAATGCTGAAAGGAAAAGCCCCGAGAGGACACAGTGCTCTAGGAACTCGGGGCGCCACGAGCGCCTCATCCC CTCCCTTCCGCCCGGCCGCGGTGCCCTGGTCGCTGAGGGACGCGGTCAGTACCTACCGCCACTGCGACCCGAGAAGGGAAAGCCT CAACTTCTTCCTCTCGGAGTCCTGCCCACTACGGATCTGCCTGGACTGGTTCAGATGCGTCGTTTAAAGGGGGGGGCTGGCACTC CAGAGAGGAGGGGGCGCTGCAGGTTAATTGATAGCCACGGAAGCACCTAGGCGCCCCATGCGCGGAGCCGGAGCCGCCAGCTCAG TCTGACCCCTGTCTTTTCTCTCCTCTTCCCTCTCCCACCCCTCACTCCGGGAAAGCGAGGGCCGAGGTAGGGGCAGATAGATCAC CAGACAGGCGGAGAAGGACAGGAGTACAGATGGAGGGACCAGGACACAGAATGCAAAAGACTGGCAGGTGAGAAGAAGGGAGAAA CAGAGGGAGAGAGAAAGGGAGAAACAGAGCAGAGGCGGCCGCCGGCCCGGCCGCCCCTGAGTCCGATTTCCCTCCTTCCCTGACCC TTCAGTTTCACTGCAAATCCACAGAAGCAGGTTTGCGAGCTCGAATACCTTTGCTCCACTGCCACACGCAGCACCGGGACTGGGC GTCTGGAGCTTAAGTCTGGGGGTCTGAGCCTGGGACCGGCAAATCCGCGCAGCGCATCGCGCCCAGTCTCGGAGACTGCAACCAC CGCCAAGGAGTACGCGCGGCAGGAAACTTCTGCGGCCCAATTTCTTCCCCAGCTTTGGCATCTCCGAAGGCACGTACCCGCCCTC GGCACAAGCTCTCTCGTCTTCCACTTCGACCTCGAGGTGGAGAAAGAGGCTGGCAAGGGCTGTGCGCGTCGCTGGTGTGGGGAGG GCAGCAGGCTGCCCCTCCCCGCTTCTGCAGCGAGTTTTCCCAGCCAGGAAAAGGGAGGGAGCTGTTTCAGGAATTTCAGTGCCTT CACCTAGCGACTGACACAAGTCGTGTGTATAGGAAGGCGTCTGGCTGTTTCGGGACTCACCAGAGAGCATCGCCAACCAGAACGG |

TABLE 4B-continued

| SEQ ID NO | GENE NAME | SEQUENCE |
|---|---|---|
| | | CCCACCCGGGGTGTCGAGTCTTGGTAGGGAAATCAGACACAGCTGCACTCCCGGCCCGCGGGCCTTGTGGCATATAACCATTTAT<br>ATATTTATGATTTCTAATTTTATTATAAAATAAAAGCAGAAATATTTCCCGAAGAACATTCACATGAGGGCATTACGGGGAGACG<br>GCAAGTCGGCGGCTCGGGGGGCGCGCTCAGCCGGGAGCGCTGTAGTCACAGTCCCGGGAGGAAGAGCGCG |
| 97 | chr2:<br>137238500-<br>137240000 | TGGAACAAGTGTCAGAGAGTAAGCAAACGACTTTCTGAGCTGTGACTCTGCTCCTCGACTGCCCACGTGCTCTCCGCTGTCTGCA<br>CTCCTGCCTCACCTGGGCTGACTCGGACTCTCCACCTCCTTTGCTGCTTCCGGCATGAGCTACCCAGGAGCCTAAGGCGCTCCTT<br>CCCGCAACTCCGGTCCCCGCGCCCCGGGACTGCAAATCCTTTAAACAGAGGCCCCAGAGCTAGGGGTTTTCCCAGGCTCTGGTGG<br>GCGTGGGCTGACAGTCGCTGGGAGCCCCGCAACAGGGGGGATGTCCAGGCAGGTATGCACCCAGCTCCCGGCGTTTCCCGGAGTC<br>ACCACAATGTTTCCCTTTCTCTCTCCCCCACGTATGCTGCTAGGGGTACTCCCCAGATAGGATTTTCTTTGTCTTTTCTCCTAGT<br>AACACCGAAGCCCTCTCGTGCCCGGGGACTGCAGAGGAACGCCAGACCATCCGGACCTTGCGGGATGGCTCGGTGTGTGTGTTTT<br>ACTGTGTGTCGGAGTGTCGCGCATGTGTGCGTGTTGGGGCGCGTTATCAACAGGGGCCTAGGGCACCCCCACTCTTTCTTGCTCT<br>CTTCCCCCATCACTTCATGGACCTCCGAGGCGCAAAGCGCTCGACCCTCTCCTGGGCTCAGTGGCTTGGGTACTCCGGGCTGAGC<br>TCAGCTGGGGAGTCCCCTTACCCAGCCCGCACCGGCACCCCGAAGCTTCAAAGTTGCGGCAAACAGTTGCGGGGAGCAGAGGAAC<br>TGAGGTCCAGGCCAGCGCGCCCGCGGTCGCTCGCCTTGGGGAGCAGGCTGAGCCGAGGGTCGTGCGGGTGCGCGGCAGAGGCGGT<br>AGGAGGCGGAGGAGAGGGGGGAGAAAGAGGGGGCGGTGGGGAACAGCTGCCGGGGTAGGCGAGGCGCAAGGTGGCTCCCCGCGGC<br>CCCGCGCCCCGCGGCTCTCGGACGCACCAGGCAGCCAATGGCTGCGCAGAGGTGTACAGCAGATGGCGTCTGACTGCGCCGTTCC<br>TTCCTCCTCCTCCTCCTCCTTCTCTTCCTCCTCCTTCTCTTCCTCCTCCTCCTTCAGTGCTGAGGAGCCAGAGTCG<br>CCGCCGGGTTGCCAGACGCTGGAATGGGTGGTCTTCCGACACACACCACCATCTTTCTTGCGCTCGGGAAGCTCGGGGCTCAGCG<br>GCTCCCAGAGGTTACGGCGGCGGCTCTGGCGAGACGGGTGAGTGCAAGCACGCGGAGCCCCGAGTCGGGGATGCCGGGCCCCCTG<br>GCCGGCCGACTGGGGCGCGGGGTGGCAGCGCCGGGGAAGGGGGCGCGCTGCCGGCGCAGACTTTGCTCTTTCCTCGCCGGACAGC<br>CATCGTCGCCCCTTCTCCCAGCCAGACGCGGGAACTTGGAAGCGGATCTTCTCGGACGCCTCTGGCTTGGGGCTGCGGGAAGCGT<br>GGGCTGCCCGGGGCGCAGTGTGCGGAGACCCTCTAGGCGGGCGGGGACGCCCCAC |
| 98 | MAP1D | GTTATTATCCACGGGGTCCTAATTAAAGCTTGATTAAAATGCCCTTCTTTCTCTAAAAAATTACGAACTAGGCAACTTCATACAT<br>TTTGAATGGCGCAGTGTTTCCTCTTCCAACTGTTTAGTTTGTAGTATACTATGTAAGCAACATCAATTATCAACCCTTGCAAGAT<br>GACAACATGAGCCTGTGGGGGAAGCACTTGAGGGGAGGGAGGAGAAACTTCTCTTTTTTAATAATCAGCCGGAAACAATGTTTAA<br>CAAGAATCTGATGAGGTCACTGCAGTAAATATTTTTCCTCTTACAGAGCCAATCATCACGGAGGGATCCCCTGAATTTAAAGTCC<br>TGGAGGATGCATGGACTGTGGTCTCCCTAGACAATCAAAGGTGTTTGCTTTCTGCTCTGTTGCTTTTAAATTGTATGGGAAAGGA<br>AGATTGGTCCGACGGCGCGCTTGTGGCCCGGCCGGAGCTTGCGTGCGCGTTCTGACGGCTGGGTGCTGTGTTACAGGTCGGCGCA<br>GTTCGAGCACACGGTTCTGATCACGTCGAGGGGCGCGCAGATCCTGACCAAACTACCCCATGAGGCCTGAGGAGCCGCCCGAAGG<br>TCGCGGTGACCTGGTGCCTTTTTAAATAAATTGCTGAAATTTGGCTGGAGAACTTTTAGAAGAAACAGGGAAATGACCGGTGGTG<br>CGGTAACCTGCGTGGCTCCTGATAGCGTTTGGAAGAACGCGGGGGAGACTGAAGAGCAACTGGGAACTCGGATCTGAAGCCCTGC<br>TGGGGTCGCGCGGCTTTGGAAAAACAAATCCTGGC |
| 99 | WNT6 | TCCCTGCTGTGGGACCCGAGGAGAGGAGAACTGGTTCGCT |
| 100 | INPP5D | TCTCTCTCTCTCTCTTGCTTGGTTTCTGTAATGAGGAAGTTCTCCGCAGCTCAGTTTCCTTTCCCTCACTGAGCGCCTGAAACAG<br>GAAGTCAGTCAGTTAAGCTGGTGGCAGCAGCCGAGGCCACCAAGAGGCAACGGGCGGCAGGTTGCAGTGGAGGGGCCTCCGCTCC<br>CCTCGGTGGTGTGTGGGTCCTGGGGGTGCCTGCCGGCCCGGCCGAGGAGGCCCACGCCCACCATGGTCCCCTGCTGGAACCATGG<br>CAACATCACCCGCTCCAAGGCGGAGGAGCTGCTTTCCAGGACAGGCAAGGACGGGAGCTTCCTCGTGCGTGCCAGCGAGTCCATC<br>TCCCGGGCATACGCGCTCTGCGTGCTGTGAGTACAACCTGCTCCCTCCCCGGGCACAGATATGACAGAGGGGCTTAGAGGGGGCC<br>CAGCTTTGAGATGGGTTGTTCTTATGTCACAGGACAGAGTGATCTGACATGCACACTTCCCCGCCACCCTGTCAT |
| 101 | chr2:<br>241211100-<br>241211600 | TGTCCTCGAAGAAGGGCCTGAGCAGCAGCAGAGGACCCCAGGCGACCGTGCCTGAGCCGGGCGCCGACGACGACTGAGCACCTGA<br>TATGTCCCCGGCACTCGCAGCCCCGCGGCCGGAGTCGCTGTGGGTGAGCGGTCGTCGAGCTTCACAGAGGCCGGGCTCTGTGCCA<br>GGGCCCCGACAGGGCAGGAAGCAGATAGAGTCCCACAAGCACAAGCCCAGTGCGCAGAAAGGGTTACTTAAAAAATAAGTTCTGT<br>GATAAAATCAAACAGGGTGAAGGGCTGGAAACAGGTCATGAGGGCGCAAACAGGTCGTGAGGGCGCAAACAGGTCGTGAGGGCGC<br>AAACAGGTCGTGAGGGCGCAAACAGGTCGTGAGGGCGCAAACAGGTCGTGAGGGCGCAAACAGATCGTGAGGGCGCAAACAGGTC<br>GTGAGGGCGCAAACAGGTCGTGAGGGTGCAAACAGGTCGTGAGGGCGCAAACAGGTCGTGAGGGTGCAAACAGGT |
| 102 | WNT5A | AAATGAGACCTCTGGGGAGACTGTCAACCCCAGGGGTAAAACAAAAATTCTGATCAGAAACTGAGTTTCCCAAAGAAGGGGCTAA<br>ATGTTTTCCAACACTTTCGGGGCTCAGGGAAGATGACTCTGTAAGGACACTGAGAATCTTCCTCGCGTGCCACGGGGAGGAGGAC<br>TGGGGGCGTTTGAGGGGCTCAGCGCACCAGAGGAGTGAGGTGGAGGAGGGCGTTCCCGCGTCCTCCTCTTCAATCCAGAGCAGCT<br>CAACGACGTGGCTCCCTTTCTATGTATCCCTCAAAGCCTTCGCGT |
| 103 | chr3:<br>138971600-<br>138972200 | TAGGCTCTAGTGGACCTAGCAGTGGGAGAGCTACTTGGGCTGGTTTCTTTCCTGACGCTGCAGGGATGGGCATCGGCCTGGAACC<br>AGAAGCGCAGGAGCTGGGCCACGGCAGAGTAATTAAGAAAATAATGAAATTGATGGCGGATGGGGGCGCTAGAAATCCTGGGGCG<br>TCTACTTAAAACCAGAGATTCGCGGTCGGCCCCACGGAATCCCGGCTCTGTGTGCGCCCAGGTTCCGGGGCTTGGGCGTTGCCGG<br>TTCTCACACTAGGAAGGAGCCTGAAGTCAGAAAAGATGGGGCCTCGTTACTCACTTTCTGCGGGTCGGGGACGTCCCTTGGCTGC<br>CACCCCTGATTCTGCATCCTTTTCGCTCGAATCCCTGCGCTAGGCATCCTCCCCGATCCCCCAAAAGCCCAAGCACTGGGTCTGG<br>GTTGAGGAAGGGAACGGGTGCCCAGGCCGGACAGAGGCTGAAAGGAGGCCTCAAGGTTCCTCTTTGCTACA |
| 104 | ZIC4 | GAGGTTGCTGACTCAGGAGCCAGGAGCTGAGAAACTCCTAGGCTAGCAGCCGTTGAGCCTAATTTTATTTTCTGGCTTTCTCCGA<br>AATGTCTCGTTTCCCTCATCTTTCTGGTCCTTTTCGTCTCTCTTATTTTCCCCAAAACGTCTACCTCACTTCGTCTTCCTTTCTC<br>CTCCCCTCCCCCTCTCTTTCCTCTATACTCTCTTCCCATTTAGCCTTGCAGGCCCCTCCTCCCCGGTGTTGGAGAGCTCAAAGAC<br>GCGCGAAACTCAAGGATCTGGCCCTGACCAGGGACGGGATTAGGCGGGAAGTGGTGACGGCCTGAAAAGGCTGGGCTCGAACCCG<br>TGCCTTCCTGAAAGGACTCTCCCCGCCACAAGTCACACCCACCCGCAGGCCTGCTGGCCAAAGAAACAAAGGAGTCGGGCGTGGA<br>TCCAGGAGAAACAGGTTTTCGCTCTCGGATCTCCCTGGGCAAATCAGGGATCCTGAGCGCTATACCCCGCAGTCGTACGGAGCCT<br>CTGGGAAAGGGGATTTAAGGGTGACTTCCACTTTCAGCTTCGGCTACTTGTTGCCTGCGGTCCAAGCCTTCTCTGCTTCCTCCTA<br>CCTCGTCTTAGGCCTCTGTAGAAAGTGCACGCCGCGTTTCCCCTTCCAGGCTCTGAGAGGGCCTGCAGGCCCGTGGCCGCCTCCG<br>ACAAGATGCCTTCCAGTGCTAGGGGGGCCACTTTGGCGGGATGGGGGTCGGTTGGTTAAAAAAAACTTAAGTTCTGGCTCAGTCG<br>AGTGTGGCAAAAGCCGAGGGTCGGGGGTTGGGGGG |
| 105 | FGF12 | TACTGACCTGGTCTCCGCCTCACCGGCCTCTTGCGGCCGCTGCAGAAGCGCACTTTGCTGAACACCCCGAGGACGTGCCTCTCGC<br>ACAGGGAGCGCCCGTCTTTGCTGGGGCTGGAGCGGCGCTTGGAGGCCGACACTCGGTCGCTGTTGGACTCCCTCGCCTGCCGCTT<br>CTGCCGGATCAAGGAGCTGGCTATCGCCGCAGCCATAGCTGCTCAGCGAGGGCCTCAGGCCCCAGCCTCTACTGCGCCCTCCGGC |

TABLE 4B-continued

| SEQ ID NO | GENE NAME | SEQUENCE |
|---|---|---|
| | | TTGCGCTCCGCCGGGGCGAGGGCAGGACCTGGGCGGCCAGGGAAAGGGCAGTCGCGGGGAGGCAGTGCTAAAATTTGAGGAGGCT<br>GCAGTATCGAAAACCCGGCGCTCACAAGGTTAGTCAAAGTCTGGGCAGTGGCGACAAAATGTGTGAAAATCCAGATGTAAACTTC<br>CCCAACCTCTGGCGGCCGGGGGGCGGGGCGGGGCGGTCCCAGGCCCTCTTGCGAAGTAGACGTTTGCACCCCAAACTTGCACCCC<br>AAGGCGATCGGCGTCCAAGGGGCAGTGGGGAGTTTAGTCACACTGCGTTCGGGGTACCAAGTGGAAGGGGAAGAACGATGCCCAA<br>AATAACAAGACGTGCCTCTGTTGGAGAGGCGCAAGCGTTGTAAGGTGTCCAAAGTATACCTACACATACATACATAGAAAACCCG<br>TTTACAAAGCAGAGTCTGGACCCAGGCGGGTAGCGCGCCCCCGGTAGAAAATACTAAAAAGTGAATAAAACGTTCCTTTAGAAAA<br>CAAGCCACCAACCGCACGAGAGAAGGAGAGGAAGGCAGCAATTTAACTCCCTGCGGCCCGCGGTTCTGAAGATTAGGAGGTCCGT<br>CCCAGCAGGGTGAGGTCTACAGAATGCATCGCGCCGGCTGCGGCTTTCCAGGGGCCGGCCACCCGAGTTCTGGAATTCCGAGAGG<br>CGCGAAGTGGGAGCGGTTACCCGGAGTCTGGGTAGGGGCGCGGGGCGGGGGCAGCTGTTTCCAGCTGCGGTGAGAGCAACTCCCG<br>GCCAGCAGCACTGCAAAGAGAGCGGGAGGCGAGGGAGGGGGGAGGGCGCGAGGGAGGGAGGGAGATCCTCGAGGGCCAAGCACCC<br>CTCGGGGAGAAACCAGCGAGAGGCGATCTGCGGGGTCCCAAGAGTGGGCGCTCTTTCTCTTTCCGCTTGCTTTCCGGCACGAGAC<br>GGGCACAGTTGGTGATTATTTAGGGAATCCTAAATCTGGAATGACTCAGTAGTTTAAATAAGCCCCCTCAAAAGGCAGCGATGCC<br>GAAGGTGTCCTCTCCAGCTCGGCGCCCACACGCCTTTAACTGGAGCTCCCCGCCATGGTCCACCCGGGGCCGCCGCACCGAGCTG<br>GTCTCCGCACAGGCTCAGAGGGAGCGAGGGAAGGAGGGAAGGAAGGGGCGCCCTGGCGGGCTCGGGATCAGGTCATCGCCGCGC<br>TGCTGCCCGTGCCCCCTAGGCTCGCGCGCCCCGGCAGTCAGCAGCTCACAGGCAGCAGATCAGATGGGGATTACCCGCCGGACGC<br>AAGGCCGATCACTCAGTCCCGCGCCGCCCATCCCGGCCGAGGAAGGAAGTGACCCGCGCGCTGCGAATACCCGCGCGTCCGCTCG<br>GGTGGGGCGGGGGCTGGCTGCAGGCGATGTTGGCTCGCGGCGGCTGAGGCTCCTGGCCGGAGCTGCCCACCATGGTCTGGCGCCA<br>GGGGCGCAGGCGGGGCCCCTAGGCCTCCTGGGGCTACCTCGCGAGGCAGCCGAGGGCGCAACCCGGGCGCTTGGGGCCGGAGGCG<br>GAATCAGGGGCCGGGGCCAGGAGGCAGGTGCAGGCGGCTGCCAACTCGCCCAACTTGCTGCGCGGGTGGCCGCTCAGAGCCGCGG<br>GCTTGCGGGGCGCCCCCCGCCGCCGCGCCGCCGCCTCCCCAGGCCCGGGAGGGGGCGCTCAGGGTGGAGTCCCATTCATGGGCTG<br>AGGCTCTGGGCGCGCGGAGCCGCCGCCGCCCCTCCGGCTGGCTCA |
| 106 | GP5 | GGGGGACACAGAGAGGAGGGGTTGCGGGCCTGTGAGAATGAAGAGCACAGAGCGGAGAGGGGGGAGGAGGAGGGAAAGGAAGGCGT<br>GGCAGTGAGAGAGAAGAGGAAGAAGAGAGGAGGAGTGGGGAGGGGAGGGAGAGCAAGACAGCAGCGGGTCTGGATTCCCCTCCGA<br>GCCACATCTGGTCAGGTTCTAAGTAATTAGAAGATTTTCCCATTGGTTTACCCAAGGGCTCTCTCTCTGATTAATTTTCGAAAGA<br>GTTGGCCAATTTTAATCATAGCAAACACGATGATCACGGTGATCATGGCCTGAACAGCTAAAAGCAGAAAATAAAACCCCCAGAA<br>CGGACTATGATCTTGACCTTTGCCCGTGGTCACCGGCTGGGCCCACACCCAGGGTTCTGAGCTGTTGGGAGCCAAGGCTGGGTGG<br>ACAGGGGCTTCCGAGGAGCTGTCCGCAGCGGGGCGGGGAGGCGGGCCCCGGGGGCCCGGGCACTCCGCGTCACCCCCCGGCAGGG<br>CCCAGAGCGGCAGGCCGGCGTGCGCCCCAGGGCCTGCGCACCGTGGGGGCTCTTCCCCGCCCACGAGGCCTAGGTGCTGCCGCAG<br>CCACCCCAGGAAGGGCCCCAGGCCACAGTCGCAGCGCCAGGAGTTGTGCCCCAACAGGACCTCCGTCAGCCGGGGCAGAGCCCCA<br>AACACGTCGCCAGGCAGGGTCTCCAGCTGGTTGTGGTCGAGCTGGACGCTCTCCAGGCTGCTGAGATTGCGGAAGAGGGCACGGG<br>GCAGGGCGCGCAGCCTGTTGCGGCGCAGGGACACC |
| 107 | MSX1 | GCCCCGGTGCACCGCGCGTCCAGCCGGCCCAACTCGAGCTAGAAGCCCCAACCACTGCCCAGTGCCTGAGTTGCAGTCTTGGGTC<br>CTTTAGAAACCTGGAGATGTGCGTAAAATTCAGATGCCGGTATTCCCGAACTTCCCCAGGCCTCAGCATATCTCGGCGGCCTGTG<br>GACAGATGGGAGGCTACCAATCGCTCCGGCGTCCGCAGCCCGACCCCTGCCGCCAGACCCCGGACGTCTTCCGGATAATAAAGTT<br>CCCGCTCTAATTCATTTTCCCTAATCTGGACGCCCCTAATCTACAGCTTTTATTGCGCCCAGTTAAAAGTCGAGGGAATTCGCTG<br>TCCCTCCGCGCTCGGATAATTACCCCTAAATGGCCACGGCAGCCCCTTGTGTTTCCTGGAGATTAGAACCCCGCAGTCATCAATG<br>GCAGGGCCGAGTGAGCCGCCAATCACCTCCGCTCACTCCCTGAGAGCCGCTGGCCTGGGCCGCAGGAGGAGAGGCCATAAAGCGA<br>CAGGCGCAGAAAATGGCCAAGCCCCGACCCCGCTTCAGGC |
| 108 | NKX3-2 | AGGGTGCCTCTGTTCAAATTAGAAAAAGGCGCCCCCTCAGGGCAGACTCAGCCCAGCTGCCAGGGGACAAGTCCTGGCTAACGGG<br>AGCTGGAGCTGGGTTTCACCTCCAGGTGCCTCCTTGGCGGGGCGCCCCGTGCAGGCTACAGCCTACAGCTGTCAGCGCCGGTCCG<br>GAGCCGGAGCGCGGGAATCACTCGCTGCCTCAGCCCAAGCGGGTTCACTGGGTGCCTGCGGCAGCTGCGCAGGTGGAGAGCGCCC<br>AGCCTGGGAGGCAGTAGTACGGGTAATAGTAGGAGGGCTGCAGTGGCAGAAGCGAGGGTGGCCGCAGCACTTCGCCGGGCAGGTA<br>TTGTCTCTGGTCGTCGCGCACCAGCACCTTTACGGCCACCTTCTTGGCGGCGGGCGCCGAGGCCAGCAGGTCGGCTGCCATCTGC<br>CGGCGCTTTGTCTTGTAGCGACGGTTCTGGAACCAGATTTTCACCTGCGTCTCGGTGAGCTTCAGCGACGCGGCCAGGTCTGCGC<br>GCTCGGGCCCGGACAGGTAGCGCTGGTGGTTAAAGCGGCGCTCCAGCTCGAAGACCTGCGCGTGGGAGAAAGCGGCCCGCGAGCG<br>CTTCTTGCGTGGCTTGGGCGCCGCCGGCTCCTCCTCCTCCTCCGCGACGCCTGCCGGCCCGCTGCCGCCCCCGCCGCCGGCCCCG<br>CTGCACAGCGCGGACACGTGTGCACCTCTGGGGCCAACACCGTCGTCCTCGGTCCTTGGGCTGCGGTCGCCTGCGGACCCCGGTG<br>GGAACAGAAACAAGAGACTGTCAGCGCCACAGACGAGGTGAGGCCGGGCCTCAACTGCAGGGGTCACGGGAGTGGGGCGGAAATA<br>CACTTTGATCCCACTCAAGCGGAGCGGAGGTCTGGGAGGCCCTGGGCCCGGGAGACCAGTCTTAGACTCTTGCCCCACTGGGTAT<br>CCCATCTAGGCCTCTTCTGGGGAGGGCGGCAGACTCAGCCGCTGTGTCAACGCTGTGTTGTCGAGACCAGCTCCCCACCCTCTCT<br>GGGCCCCAGGCTCCCCTCAGTAACTTGGGGCACTCGACCCGAGCATCCGCGAAAGCCCTCCCGGCTCTCAGCGTTGAGCATTGGG<br>ATTCTAGACTGCATTTCCGTCTCTCTGCTTGGGTTCACGCGCCTCTCCACACTTAGTTCACACGCACACACGCGCGCGTCCTCGC<br>AGCACACACTTGTCTGGTGCAGGTAAGGGAAGGTGGAGGCGGATCCTGGGGCCAAAGGTATTTAGAATCTTTCACCCTCAGCCGC<br>CTGGGATTGCTGTGAGAGACATGGAAACAGGCTGAGCCGAGGCCTTAGATGAGAGGATGGACTGGAGAGTAAAGAGGGAGGGTTG<br>CCCCTGCATCGAGTTTTTGGACCCTGATCCCACACCAGCTTCTCGGTCTCGTACCCGCCCTTCCGAAGAACTCCAGCAGAAAGGT<br>CCAGCGGTCCCCTGTGCTTGAGGCCTACAGAAGCTTGTACCCAACTAGGGCAGGCACCCGGGTCTTCCAGACCACAGGACAGGAC<br>AGGCCACGGCTGAGGAGGCCTCTCTCCTGCCTCCAGGATGAACTAAAGACCCAATCCGGGATCTTCGGCCTAGGGCTGCTCTCCC<br>AGACCTGGGGTCTGAGAAAGCCAAACCAGCCCTTTCCCCAAAGCTCTAGTTCTGCAGATTCTCAGCTCTGGCCCACTCGGAGGTG<br>TTCTTCACCACCTATCCACCTACTGTGGGGCCCGGCCCTGGGACCTTGAACTGGCAGGTCTCTGGTCCAGAGCTAGGTCACTGGC<br>TACCTGAGGTCTCTGAACCCCTCACTTTTCCGCTTCCCTGATTTTGGGGATTTGGGGACAGACACGGCAGAAAGCACTGGCGACG<br>AACTCAAAAACTCCCGAACGCAAGGGGCAGCGGTTCTCCCAACCCAGTCTAATGCACATTGGCCCAGGATGTCTCAGGCCTCACC<br>CCAGGACGTAGGGCTCTGAGGAGCTACTCCGGTCTCTCGCGGGCT |
| 109 | chr4:<br>111752000-<br>111753000 | GAGAAGGGATGTGGCGGGGGGCTCCTCCGGCCCTGGACTCCCTGGGTGGACTAGAAAAGGGCAAAGAAGTGGTCACATCTGTGGG<br>CCAGACTGGTGCGCGATCTTTGGAGGCGCAGCAGCAAGGCCGCGCCAGGGCTGAGCCCAGACCGCCCACGAGGAGGCCCGCCAGG<br>CCCGGAGCAGCGGCGCGTGCGGGGGCGTGCCGAGCGCAGGCTCTAGGGCCCCTGCTTCGCCCCAGCTGGACCCCGCGGGCGGTCG<br>GTGCAGCTCGAGCGTGTGGGCTGCGATGCCCTGCCTGAGACTTCGGGCTAGGGATGCGGGCGGGAAGTGGGGGTGCGGCGGCAGC<br>TGCAGATTAGATTCCTTTTTTTTTTGGCCGGAGGGACGTGCAAACTTCTAGTGCCCGGGCCAAGAGGGCGACCCCGGAGGTGCGT<br>AGGTGGCCCTCCGGGTTCCCGCTTCTCCTAGTGCCTCTGAAAATACCGTCAGGGTAAAGGGAGACAGGCAGTAAGTCTTACCACC<br>ACCGCCCTTTCCCCATGTCATTGGCCAAAAACTGAACATTAAGATAAAGCAGCTGTTTCAGTCAATGGAAAGCGGTAGGGCGAGG<br>TTGTACCCAAAACCCGGTTTAGACGGCCAATGAAGTCCTAGGAAAAGCCGCCCCGGGGGCACGTTCAGGTGGAGCGGCTGCACCT<br>CGGGTCGTTCTAAGGGATGGGCTGCGTGGTACCCACGGAATTCATGGGTCCAAAAGGTCCTGGTCACCTGTCCAAACATCCATCC<br>CCTGGCGCATGGCGGTTGACAAGATGGCCCGGCCACCCAGAGGAAGGAGGATCCGGGACGGGGAACTTCGCGCCGGGAAGCTGTA |

TABLE 4B-continued

| SEQ ID NO | GENE NAME | SEQUENCE |
|---|---|---|
| | | GCCCAGAGCTGCAGCTCAGCATTCGCAAGAGATTCATCTTTTTTTTCTCTCGTGTTCGGAGAAACAGATAAACAAGACACCGCCT<br>CATCAGATAAGAACGTCTCCTTCGATGTCACGGATTTCAAGAGGTAGCTGGAGAAACTGACGTCA |
| 110 | SFRP2 | CAGGTCAGGCAGAACTTCTGCCCTTCCCGCTACTGGCACCCCAAGCAGGGATGCACTGGGATGCGTGGCAGGGGCGGGATCTCCT<br>GGGAGCGTCTCAGCCCAGCAGGGAGTGGGGAAGCAAGAGGGAAGGCTTACCTTCCTCGGTGGCTGGCAGGAGGTGGTCGCTGCTA<br>GCGAGGGGGATGCAAAGGTCGTTGTCCTGGGGGAAACGGTCGCACTCAAGCATGTCGGGCCAGGGGAAGCCGAAGGCGGACATGA<br>CCGGGGCGCAGCGGTCCTTCACCTGCACGCAGAGCGAGTGGCATGGCTGGATGGTCTCGTCTAGGTCATCGAGGCAGACGGGGGC<br>GAAGAGCGAGCACAGGAACTTCTTGGTGTCCGGGTGGCACTGCTTCATGACCAGCGGGATCCAAGCGCCGGCCTGCTCCAGCACC<br>TCCTTCATGGTCTCGTGGCCCAGCAGGTTGGGCAGCCGCATGTTCTGGTATTCGATGCCGTGGCACAGCTGCAGGTTGGCAGGGA<br>TGGGCTTGCAATTGCTGCGCTTGTAGGAGAAGTCGGGCTGGCCAAAGAGGAAGAGCCCGCGCGCCGAGCCCAGGCAGCAGTGCGA<br>GGCGAGGAAGAGCAGCAGCAGCGAGCCAGGGCCCTGCAGCATCGTGGGCGCGCGACCCCGAGGGGGCAGAGGGAGCGGAGCCGGG<br>GAAGGGCGAGGCGGCCGGAGTTCGAGCTTGTCCCGGGCCCGCTCTCTTCGCTGGGTGCGACTCGGGGCCCCGAAAAGCTGGCAGC<br>CGGCGGCTGGGGCGCGGAGAAGCGGGACACCGGGAGGACAGCGCGGGCGAGGCGCTGCAAGCCCGCGCGCAGCTCCGGGGGGCTC<br>CGACCCGGGGGAGCAGAATGAGCCGTTGCTGGGGCACAGCCAGAGTTTTCTTGGCCTTTTTTATGCAAATCTGGAGGGTGGGGG<br>AGCAAGGGAGGAGCCAATGAAGGGTAATCCGAGGAGGGCTGGTCACTACTTTCTGGGTCTGGTTTTGCGTTGAGAATGCCCCTCA<br>CGCGCTTGCTGGAAGGGAATTCTGGCTGCGCCCCCTCCCCTAGATGCCGCCGCTCGCCCGCCCTAGGATTTCTTTAAACAACAAA<br>CAGAGAAGCCTGGCCGCTGCGCCCCCACAGTGAGCGAGCAGGGCGCGGGCTGCGGAGTGGGGGGCACGCAGGGCACCCCGCGAG<br>CGGCCTCGCGACCAGGTACTGGCGGGAACGCGCCTAGCCCCGCGTGCCGCCGGGGCCCGGGCTTGTTTTGCCCCAGTCCGAAGTT<br>TCTGCTGGGTTGCCAGGCATGAGTG |
| 111 | chr4: 174664300-174664800 | TGCGATCATTAAAATCAGTTCCTTCCCTCCTGTCCTGAGGGTAGGGGCGGGCAGATTTTATTACTTCTCTTTTCCTGATAGCAGA<br>ACTGAGGCGGGGTTGTGGAGGAGCGACGGAGGACCACCTCTAACTTCCCTTCACTTCCTGGATTTGAAGCCTCAGGGCCACCGGC<br>CTCAGTCCTGTTACGGTGGCGGACTCGCGAGGTTTTCCAGCAGCTCATTCCGGGACGGCGGTGTCTAGTCCAGTCCAGGGTAACT<br>GGGCTCTCTGAGAGTCCGACCTCCATCGGTCTGGGAGCGAGTGGTTCGAGTTCAGATGCTGGGAACCGTCGCTTCTCCCCGGCCG<br>GGCTCGCTGTTTTCTCCTCCGCTCGCCGTCATCAAGCCCGGCTATGAGCAGGGCTTTAAATCCTCCCTCCCTCACCCGCAGGTTT<br>ACCGAGCAGCCCCGGAGCTCTCAGACATGCTGCGCTGCGGCGGCCAGAGGAGGGGTGGGGGCATTGCCCTCTGCA |
| 112 | chr4: 174676300-174676800 | GGGCTTGGGCCGCAGGCTTCCCTGGACTTCCGCAGTCCCCCTTCTCCCCATTCCAGAACCTGCCGAGCCCCTGCTGCATCTGGGA<br>CCCGCCTTCACCGTTTCCCAATCCCAGCGGTTAGCCCCTGCGCCCCCTTTTTGGTCTCCACTTTGCCGTTCGAAAATGCCTAGGT<br>TGGTGGATCGACCCTCCGCGGAGCAAAGACGGATGGCTGGCAGGAGCAGGTTCAGGAGCTGGGCCAAGGTATTCTCTGCTTCCGC<br>CTTTGTGTCCGCCCCCCCGCCCCCTGCTCCCCGCTTCCCGCCAGCATCTCTCCTTTTCTGCTCAGGAGTGTTTGGCCCGGCGGTC<br>CACCCCGGCTTCCCGAGATACGCTAGAGTTGCCCCCACGTCCTGTCCGCCGCGCCCCTACCCACCGGGTTGCCTTCGGGGCCCTT<br>CGGTGCTGTGTAGTCGGCGTGGCGCTGTGAGCTAGGCGAACAGGAACCCCCAGGCCCGCCACGTCTACGCTATTA |
| 113 | SORBS2 | TTCTGGGGCCTGGATGGGTGCGAGCGGGACCCGGGGGAGTGGGAGTCGCCAGGCTCTGAGCAAGCAAGGGCTGCACCTGCACCTC<br>TGCCGGGCATGAAGAAAGGTAAGGAAGGAAGGAGCTCACCCGGGTGGGAGACAGAGCCGGGGCGCGCGAGCTTGGTGTGGGGGCG<br>CCACTCCGGGGCGGAGGGGAGGGGCTACCAGTGACTTCTCCGAGTCGGGAGCTAGAAAGAGGCTTCCGGCCAGGTTCCCTTGGAA<br>CAGGTGTCGGAGTTGTTGGGAGAGGGGGCTGCAAGAAAGAGGGGTGCAGAAACTGGTTCATTAGATGGAGGCTCTGGGCGGAACC<br>GCGAGGACACCCTGGCAGCGCGCTGTGCCTGCGTTAGGCCGGGAGGGGAGAGGCCTCCGGACGGCGAAGTGTCCCTAGGGACCCA<br>GACGCCTCGGGAGCGATCCGGGCCGCTGCGAAGCCCTGCCCACCAGGAGTGGATCCCCAGGATTCACCTCCCGGCTGCCTGCTCT<br>GAGCTGAGAAGGGGATCTGGTTCTTCACAATACCGTGGATGGCGGGGAAGGGGAGGGAGCCTGGGGTAAAATCCCATCTTGGTTT<br>CCTCG |
| 114 | chr5: 42986900-42988200 | TGTCACAGAAACCCCAGCAGCGCAGCCACCGGACTGGGTTCTGGAGGCCGAGCCGCAGTCCGTGCGGCGGCGCTGGGAAGAGAAG<br>GCGCCCCGGCAGCTCCCCTGCCACCGGCCCCGAGGAGCGGCTGGCTCCCCCAGCCCAGCGCCGCCGCCGCCCGGTAACTCCAGGC<br>GCAACTGGGCGCAACTGGGGCAGCTGCGACACCGAATCCCTCACATCTGCAACCTGGGTGCTGCGGCCACTGAGAAAATGGAGGC<br>GCAGACCAACGAGCGGTGCCGCGACCGAGAGACCTCGGCTGGCGAAATGGTGGTGCCGGGAGCCTGCGAGTGACGCCAGCCGGCG<br>GGGTTGTCAAGGACAACATTCGTTTTGACGCAGCCAATGGCGCCGTCACCAAGAAACCATCGACTCTGAGAAAAAAGAGAGGTTC<br>GGCCACCGAGAAACTCCGTACGACAAGTGCTGTGGCAGAAAAACCGCCTACTCCGCGCCACAGGCAAAACAGCCAATGGAAACCC<br>CAGGTGCTGCGACCGTGACACCGGCACTAGAGGGTCTCGGATGGAGAAAGCGGCGCACGGAGACCAGGAAACTATGTGTAGCACA<br>ACTAGCAGAAAACCGTCTGGTCGGCCATCCGGGAGAAAGCGCGGATCAGAAACAAGCGACTTCGATGCAGGGAACCGCGCAGCCA<br>CTGAAGAAAGTGACCCACGTGGCAGTGGTGCCAGCGAAACACTGCAGTTTGGACGGCAGCTGTGGGGATGCCACAGAGAAACATG<br>CACTGCCACTGAAGTACATCCAGCTCCGCGGAGCTAGTGTTCATATGATCAAGAAACCGCCAGTTGGGCTCTGCTAGAAACTTTT<br>AGTCCTCCCTTAACGGCTATCCTACCCACAACAGACAATGCCTTTACCCAGCACCTAGCGGTGCTGAGACCCGCCTGGGCCAGCA<br>CAGAGCGCAGAGCAGTACGGGTACGGAGAAACGCCGGACTCAGTGAAACCAGCCTTGCCTCCAGCGGATTCCCCGGCTTCGCCGG<br>ACGCCACAGGCAGAGTGCCGCGGGGAAACCTCTGGCTCCCTAAACCGATTAGATTGTGGAGTGGGGGGGACACTCACAAGTTGT<br>GTGGAAGGGAACCAGCGGCAATGGGACCCGGCGAGCACTTGCCCGCAGCAAATGCCTGCGCTGCTGCAAAAAAAACAACTTTTGG<br>CGCAAAGAATGTTGCGGCCAGAGAGCATCCGCTGTCGCTGACAAAGGAGTAGCAATGGCAATGAGAAACCGCCGGCGCCACGGCC<br>GACCGCGGCGGCTCACGCCTATGAT |
| 115 | chr5: 72712000-72714100 | CAAACGCTGAGAGACAAAAAGACACCAACACCCACCAGGACTGCGTCCTGCCAGCTCTTCACTCCGCTGACCTGACCTTCCACGC<br>CCCTAGTCCTCGAGCGGACTTGACCTGTGGGGGAGTACCGAACCGTCCCCATGAGGCCCTCCAAGCGGCCAGGTGGCCTCCGCCA<br>CTCTCTCCACCCCCACCTCCTCCACCCCCAGCCCATCGGTCCATCTTCGATCTGCAAAACACGCCGGGTCAGCGACGCATCGGT<br>CCCAGGCTTGTGACCACCTCTTTCTCTGTTACTTGGGGAGCCAGGCCCACCGCTCAGGATCACAGTGAGGAGAAAAAAGACACAA<br>ACGCCAGGACAGGGCGGCTGGGGAAGGAAACTGCTAGGGACCGCTCATTGTCAGCCTGGCGTGTCCCACGGATCGCAGGACCCGT<br>CGAGGCTTTGCTCTCTGCGACCCGAATACTCCTGGGCCTCTCGACCTCCTCCTCGGACTCAGGCGTCCGCGTCTCCGGTCATCAC<br>GGGAGACCAATTGGTTTACAAATAGTGATGATAAACCTGGGACCGACCTTGGGGCTGTGTAAAAGTCTACTGACAGATGTAATGG<br>AGGGTTGTTAGCAGTCACAAAGCCTGTCGGACCCGTAGCATTAGTTCAAGAGACTATTTTCGTGTCGCACCAAAATTACTGCGCG<br>TGTAAACCAATTTCCCCGACGGAAGAATAAACAGAGATTCGTTTGAAGCGCGAGATGAAAACAGATGGGGTATCGCAAACAGTTC<br>CCCAAAATACAACAGACTTCTGGGCCAATTACACGTGGTTAGCTCTGAATGGCAGAGGAAATAGTTTTCTTTGCTGCTAAATGTC<br>ACAAAAGTCACCTAAAGGCACAGAGGAGGCCGCTCTGTTTTTGCGAAACTTGCTAAAATTAATCTGCGCTGGGCCACTTGCAGAA<br>AGCAGAACCACCTCCCGCCCCCACCTCGCCTCCAGCCGCCGGGGTTCAGGCGTTTGTGAAAGACAGAACCTTTGGGCTAGGGACC<br>CGGGCACTGGTGCTTCGAAGTCCGAATCCGCCGGCCGAGAAAACGACGAGAGAAAGAAAATCCAGCGGGCGCTCTCTCCAGCGCC<br>AGGCCGGTGTAGGAGGGCGCTGGGGCTCGGCCTGCCACCCCTACCCGACATTGGGAAGCAGCCCCTGCGCTCCCGCGGCGCCTCA<br>GCCTCCGGTCCCCGCCCCGAGGTGCGCGTTCCTCCTCCCGCATGCCCGTCTCGGGCCCCACGGAGCAAGAAGATAGACGATGACG<br>AGGCGCGCCCATCCATCCGGGCCGACGAGGTCAGGCCCGCGCCACAGGCAAAAATTGCGCAAGCCCGGCCGCAGGGATTTCGCGG |

TABLE 4B-continued

| SEQ ID NO | GENE NAME | SEQUENCE |
|---|---|---|
| | | GCGCCTGGGTCCCAGGTGCGCGGCCGAAATCCTCAGGGAAAATCCCGAGGGGCCAACGGTCTAGGCCACAGGGCTGCTGGGCCCG<br>GGCCTGGCTCAGAGCGCATTCGGGCGGGGAGGCGCACGCCGCACCCGGGCCTCTCCTCCGAGCCCGAGGCAGGCACTGAGCTCC<br>GGGCCAGCCAGGTGCCTCCCGGCTGGTGCGAGACCCCGGGCCTGCTGGGAGGCGTGGGCAGGGCAGGGCAGGGCTGAACCCCAGC<br>GACTGAATCTCGAAGGCAGGAGGCCTCGGAGGTCATCGGCCCAGCTCGCCTGAAACTGTCCCTGCTCGTGCCAGGGCGCGGGCAG<br>AGGAGAAAGGACAGGGCGGAGCAAGCCCACTGCAGAACTGCGGTCGGTGGCTGCGAAGGGTCCGGGTCACCGCGCTCCCGGACGC<br>CGGAAGCCGCGCTGGCGGGGCCGCGGGGAGGGAGGCTGGGTACCGGGGCCGTCCGGCCGGAGGAAGCGGCTCCGGCCGCGCTGTC<br>CGCGCTTGGGAGCCGCGTGCAGGGTTCAGCCGTGTTTCAGTTGCCCTCTGACCTGACCCCGGGCGCACAAAGGCCTCCCGGGTGC<br>GCCGCCATGGCCCAGTCTTCCAGTCGCTGCCAAATTAATGAGCCCACGTCAGGTTGGGTTTACAGCTCGGCCGGGAAGCAGCCGA<br>GTGGAAAATGAGCTCGGGGCCGCTCCAGAGGCTCCCGCACAACTGCAGAGGCTGCCCGCG |
| 116 | chr5:<br>72767550-<br>72767800 | TTTCCAAGACAGAAGGAGGGAACTAGGCGCCTTTTTTCCACTCCGCTGACCCCAACGTCTGGGCTGTGCGTTGTAACGCAGTTGG<br>CGGGGCCTTCAGCTTGGGATGAGGGCGAAGGGGCTCGGGATGGGTGGGAAAGCAAGGACCGGGCAACAGGTGGGGAGGTGGCGGA<br>CTTTTGTCTCGGGGAAGGAAATCGGCTGTGCTGAAAGGGCGGAAAGCAGTAGCGCACAGAACTAGTGTCTGCGGGGTCCC |
| 117 | NR2F1 | CCCTCCTGTGGCTGCTTGGGCAGACGCCTGTGGCCTGTCGGATGCGGCCCACATCGAGAGCCTGCAGGAGAAGTCGCAGTGCGCA<br>CTGGAGGAGTACGTGAGGAGCCAGTACCCCAACCAGCCCAGCCGTTTTGGCAAACTGCTGCTGCGACTGCCCTCGCTGCGCACCG<br>TGTCCTCCTCCGTCATCGAGCAGCTCTTCTTCGTCCGTTTGGTAGGTAAAACCCCCATCGAAACTCTCATCCGCGATATG |
| 118 | PCDHG<br>A1 | TCCTCCTTTGTGTATGTCAACCCAGAGGATGGACGGATCTTTGCCCAGCGTACCTTTGACTATGAATTGCTGCAGATGCTGCAGA<br>TTGTGGTGGGGGTTCGAGACTCCGGCTCTCCCCCATTGCATGCCAACACATCTCTGCATGTGTTTGTCCTAGACGAGAATGATAA<br>TGCCCCAGCTGTGCTGCACCCACGGCCAGACTGGGAACACTCAGCCCCCCAGCGTCTCCCTCGCTCTGCTCCTCCTGGCTCCTTG<br>GTCACCAAGGTGACAGCCGTGGATGCTGATGCAGGCCACAATGCGTGGCTCTCCTACTCACTGTTGCCACAGTCCACAGCCCCAG<br>GACTGTTCCTCGTGTCTACACACACTGGTGAGGTGCGCACAGCCCGGGCCTTACTGGAGGATGACTCTGACACCCAGCAGGTGGT<br>GGTCCTGGTGAGGGACAATGGTGACCCTTCACTCTCCTCCACAGCCACAGTGCTGCTGGTTCTGGAGGATGAGGACCCTGAGGAA<br>ATGCCCAAATCCAGTGACTTCCTCATACACCCTCCTGAGCGTTCAGACCTTACCCTTTACCTCATTGTGGCTCTAGCGACCGTCA<br>GTCTCTTATCCCTAGTCACCTTCACCTTTCTGTCAGCGAAGTGCCTTCAGGGAAACGCAGACGGGGACGGGGGTGGAGGGCAGTG<br>CTGCAGGCGCCAGGACTCACCCTCCCCGGACTTCTATAAGCAGTCCAGCCCCAACCTGCAGGTGAGCTCGGACGGCACGCTCAAG<br>TACATGGAGGTGACGCTGCGGCCCACAGACTCGCAGAGCCACTGCTACAGGACGTGCTTTTCACCGGCCTCGGACGGCAGTGACT<br>TCACTTTTCTAAGACCCCTCAGCGTTCAGCAGCCCACAGCTCTGGCGCTGGAGCCTGACGCCATCCGGTCCCGCTCTAATACGCT<br>GCGGGAGCGGAGCCAGGTGAGGGGCTCGGCGCCGCCCCGGGCGACCCCTGGGGGCGGCACTGGAGAAGCCGCCCGTCCTCATAAG<br>GGATTGAACTTGCATCCACTCCTCTCCGGCCGGCTTGGTCGCTGGCTGCGCTCCACCCGATTCTCGGGATCATTGGACCGTTTGC<br>GCGAAACCAGAGTGGCCGATTAAGGGATGGGGCTCCGAGCACCGGGGGTGGTGGCGACTGTGGGCGAGGGGAGGTGGGACCGACC<br>CCCACCCCTACACTCAAAAAAGGCCGGGGCCTCCTTCGAGCTTCCGGTGAATTTCGGGCGATTTCCGCGGGTGTCGGGGGTCCCG<br>GGAGGAGGCAGTCACAGATCCACCCCTGCAGCCAGCCTCCTAGGCGCCGGCTCCGGCACGCTTCGCCGGTCTGTAGATTTCCTCT<br>TCGATTTCTCCCCAGCTCCCAGCATCTGTGACTTCACTGTTACCCTCCCTATCCCCGCATCACCCAACCGCACCTGTCTGCGGGA<br>CTTAGGTGTGCGCGCGGGGCTCATGCGTGTCCTCCCTGCTGGCCACCCCCACGGCCCACACAAGTTGCACGGGCTCGCCACGCCC<br>CGCCAACACGTGCGCGGACGCACGCACGCACTCCTCGCACGTGGGCTTACGCGAATACCAGCTTTCACTGCCACTCGCTCGCGGC<br>CAGATTCACAGGCCTGTTCCGGTCCACTCGCAGCTCCCCTCTGCCGCTCCCTCCGCCGGGCTCAGGAGTACTCGTAGCTGATTGT<br>GCGCGCCTGAGGGTCCCAGATCGCGGCCGCCCAGGACCAGGCGAGGACTCCGGAGCCTCCTCTCACCTCTCCCACCTGCGCCCCG<br>GGCTGGGCCGGGTCGCCTGGGGGGCGGCCTGAGCGAGGCGCGGGGCCAGGAGCGCTGGAGCGACTGCCGCTCTAAGTGCCGGGCG<br>GGCAGGACTCTACGATCCTTGGGCCAGAGGTCCGGATGGTCCCGGGACTCCCGTCTCAAGGGTCGGCGACCCCTCAACCCAGAAGC<br>CTCGAGCAGGCGGACAGGCAGAGCTGCCCAGTGGCCGAGGCGCGG |
| 119 | chr6:<br>10489100-<br>10490200 | ATTTGTCGTTGTGCCATTGCTGCCACTGTTGTTCTTGTCCAGGGAAACACCGGTGGCCAACCCAGATCGGATACAATGGTGCGGC<br>TCTGGACTGAGCCTCCAACCACATTAGCCATGGGCAGCATTGTTGCTGCCGCTGCTGTTATTTTAATTATGATTGTACGTTAACC<br>ACCACCTTCCTTCCTCTGCCTCCCTTCAGCTGCAATGATGTATGTTACTTTTTGGTAACTGGATTTCATTAACATTTATGAACTC<br>TCATAAAGTAGTAGAAAAAGCAATTTGTGTGGAAGAATTTTCCACCTCATTAAACAGTGTTCTTTTGGGGGTCAAGCTGATATTT<br>TTTTTGTTGTTAGATTTTTTTTATAGGTCCTTTGTCCTTCCCTAAGCCCTGGGGGATGAAAGGAGAGCCGTCCACCCAGCGAGGG<br>GCTTGTGTGCCCTAGAGGGCGCTGGGCCCCGCGCGCTTTCCTGGCTGTCCCCGCCGGCTTTCCACCCTCCCCAAAGCCCAGGTGC<br>CCACCGTGGGTCGCTGCGGCCTTTCCCCTTCTTGGCCAAATCCGATTACTTCGCAGCCTGCAGATGGCATCGCCGGCTAAGGGCA<br>GCCTGCGGCAGGTCCCCGAGCCTGAGCACTCCTCCTATCTGGGGCCTGAGAGGACGCTCTGGGCTTTTTCCCAGGCCCAGGGTGC<br>GCGGCCTGCTAGCGCCTTTCGAGGCACAGTCCCAAGATAGGCTCTTGTCCTTCGACGCCCCCTTGGCACAAGCGCACTGGCGCCC<br>TCCGCTCAACCCACCTTGCCTTTGGGGCGGGCTTCAACCCTGGGAAGACAGGCCTGGGGGAAGCGAGAGGAGAGGCCCGAATAGA<br>GGTTCCGGCTCAATCTTTCCCAGACGGAGGCCTGGTGTTTCCAGCTCAGTTGCATCTTCCAGCCGCGGGCTCCTGGCCCAAACAG<br>AATGTGTTTGCTTTCACACCGGGACGGCAAGCGGAGTCCGCCTCAGTGAGCAGCGAGCTGCGCAGTCCGGACGGGTGTCGCCCCC<br>AGAGACTCGCCAGCCGCCCCCAGACACTCGCCAGCCGTCCCCATCTCTAATCCACCGTCCAGGCCCGGGCCCTGGGAAGA |
| 120 | FOXP4 | CCGTGTCTCCCTTAAGAACTGGGGCCTCATCTCCACTCCAGCTGCGCGTGCACGTGTGCTCCCGGCAGGACGCGCGCCCAGGAGC<br>GCGCTGGGGGCTGCCCCGCCCCTCTCTCCCTCCCCCGCGGGTAAACTCCGGGCATCCATCAGTCTGTTAATTGCACTAATTAGAG<br>ATCGCAGAGGTGTTAATTGGAAAACCCTGGTATTGTGCCTGTTTGGGGGAAGAAAACGTCAATAAAAATTAATTGATGAGTTGGC<br>AGGGCGGGCGGTGCGGGTTCGCGGCGAGGCGCAGGGTGTCATGGCAAATGTTACGGCTCAGATTAAGCGATTGTTAATTAAAAG<br>CGACGGTAATTAATACTCGCTACGCCATATGGGCCCGTGAAAAGGCACAAAAGGTTTCTCCGCATGTGGGGTTCCCCTTCTCTTT<br>TCTCCTTCCACAAAAGCACCCCAGCCCGGTGGGTCCCCCTTTGGCCCCAAGGTAGGTGGAACTCGTCACTTCCGGCCAGGGAGGG<br>GATGGGGCGGTCTCCGGCGAGTTCCAAGGGCGTCCCTCGTTGCGCACTCGCCCGCCCAGGTTCTTTGAAGAGCCAGGAGCCTCCG<br>GGGAAGTGGGAGCCCCCAGCGGCCCGCAGACTGCCTCAGAGCGGAAGAGGCAGCCGCGGCTTTGACCCAGCTTCCTTCCGACGGC<br>ATCTGCAGGAGCCTCTAGGCCTGACATAGGCTCCGAGGTGCCCTGGCTCCCCCACGGGGAATGCTGAGGGTTGGGCCACTAGGTC<br>CTGCCTAAGTGCAGGACCTGAGCCTCAGACAAATC |
| 121 | chr7:<br>19118400-<br>19118700 | GGGATTGCCGGCTTTGAGAAAATATGAAGAAACCGATTTCTCCTTCCACTTTGCCAGTGCACTTTCCTTCCACTTTCACTGGTGC<br>TGGGGGCGGCGCACTCTTTACGACATATAAGCGGAAAATTCTGCAAAAGTGGCCCCCGGGGATCCCCGCCCGACCCCTGTCTGTC<br>GCTAATGTGGGCCTGTCTCCGGAAATTCGAGGTTGGGCCTTTGCCTGAATCTGTTGCTATTGCTCCCCTTGCTACCGCTGACACT<br>TGGCACCGCCGCCTCCTAGCAGCGGCCAGACGCGGGGCTGGGGGC |
| 122 | chr7:<br>27258000-<br>27258400 | GTTGCGAGCGCGGCACAGGTTGCTGGTAGCTTCTGGACTCTGGAGGCTTGGCCTTCCTTCTAAGCCGATGGCGGGGAAAGAACCT<br>CGTTTCCACAGCTTCCCCGACCCCCGCCGCTTGCCATTTGGGGACGGGAAGCGCGCCCGGGTCGCTTCACGTCCCTCTGGGCCGG<br>AGCCCTTTCCATGGCTGGCTCCTCTGGGGGCCCTTGGGCCTGTGAGCAGCGTCTACTTCCCTCAGAGAAGAATCCTTTCCTTCCC |

TABLE 4B-continued

| SEQ ID NO | GENE NAME | SEQUENCE |
|---|---|---|
| | | CCATCGAAGTGTCCCTTTCTGTATCCTGAAATAACCCCTCCTGGGTGAGGCCAGTTCCCCTCTGTCGCCCTCCTCCCGCAGGCGT<br>CCGGGAGCCTCGTGAGGACCCCGTGCAGTTGAGTCCAGGCGACAGGTGCCTCCCCAGGTG |
| 123 | TBX20 | CAGTGCGCCCCTTACCGGAGCACCCATGGCCTCCCGCGTTACCCCAAATTTTGTAGGCAGACTGTCAGAGTTCGAAGCCAGCTGT<br>GTCCTCTGCGGGCCGTGTGACCCTAGGCTATCTGGGCTGCTCGGAGCCTTAGTTTCCCTAGTTGTGAAGAGGGAGGGTGTGACCA<br>TGGCCCGGAGCTCTCCGAAAGGCTGTGCGGATTGCTCGGTGGCGGGATGTGGAGCGCGTCTTCTATGATGCCAGGTGCTGGCCAA<br>GCGCTCGATGCAGGCTGCTCCAGTTAGGTCGATGCGATGGCGGGAAGCACTTTCCTCTGCAATGGAGAGACGCCGACACCCCGAG<br>CCCGAAGGCTTGCAAGGCGCGCTCTCGCCACTGGGGTCGGGGATCCGTGGGTTCTCTATCCCGCTTACCCACTCCATCCTTAGCA<br>GCTGTCGTCGGTCCCAGACCTCTACCTTGGAGAGACCAAGGCGGCCCAGAGCCCAGGAGACTACTGCGCGGTACGCCAGGATCCA<br>GAAGTGGATTCTGACTTCTAAAGACCCCTCCCAAGCCAACGCTATCAGGGTCCCTGCAAGCGGTTGACTGTGGCGGAGGCAGAAC<br>CAAAACCTTTGCTCTGCCCGCGGCGCTCCAGCCTCTCACCCAGGACAGTGCTCTGGGCTCCAGCCGCTGCAGTGGGGTCGGGACA<br>CAGACGCCGAGTTAGAAGCCCCGCCGCTGCAGGTCCCTGCTTGGTCGGCGCGGTGACGGTGTCGCTGGCGGCGGCGGGGGCCTTC<br>CTTTGGCTGCCCGGCCATTTAATCAGAGCTATTAT |
| 124 | AGBL3 | TTTAGTATTTAAGGAGAAAAGCCTCATTTTCCAGAATCGAATAAGCGAATTAATCGCACAATTGTGTAGAATGGAACTCAGTCTG<br>TAAAAAATCAAGACCAACGTACTTTTTAATATTCTAACATCTCCAAGTAGTAGTTACAAGTATTGTACCCATGAAGTCCAGGTAA<br>TTAATTTGTTCAATGTCACACTGTTAAAAGTCAGGTGGGCTCCAAAGCACAGTCCTAACCAGCATGCTCTACTGCCTCCTCTGAG<br>GCAACAGCCGAAGTGCAGACCACTGGGAATAAATAGCTGCCCGGTCTTCCCCACTCCTAAATTCTCCCGACAGACCCCAAAGCCT<br>CTCTGAGAGCCTCTCTGACCGCCCTGCGGCCCACCCCGAGTTCCCGGCATCCTCTGGGATCCCTCTTCCTGGAGCCAAAACCTAC<br>GCAGGCTCCTTTCCTCCGAGCTGGTTGCTAGGTGATCTCCGAAGGCTGTCCGAAGTCTCGCGAGGGCGGACCCGTTGCCTGATGA<br>CGAGAGTTGGGAGTGTGGCTGGGGCTGCGGATCTCCAGCAGTGGCGTTACTTCTAGCGGCTGGATACCGGGTTCTCCGCGAGATC<br>GCGAGATCCCGAGATATTCTCCCCGCACGGAAGCGACGACTGGCCTGGCCAGAGGACTCGCGTGGGAGCGAGGTGCCGGCCCCGA<br>CAGGACGGTGAGGTATGCAGAAGTAAGGCGGGGCGCCCCCTGCGGGAAGCGAGCGCGCCCCGGAAAATGAGCGCCTCCCCACACC<br>AAGGTGTCCAGGAGTGAGTGCGGGAAGGAACTCGGCCGCCCGGAGTTGTGGCCTCATCGTGCTTCCCGCCAAAAACGCCTTGGTA<br>CTGTCGGGACGCGGCTAAGCGTGGACGCGCCCGCATCTGCCCCTCCTCCGCAGTGGTGGAAGACACCCGCGGAGCGCCGGTGGAT<br>AAGGGCCGTTTCCTGAGACCAGAGCTGTATCCGCAGCAGGTCAGCACTTCGTGCGCCCTGTGTGC |
| 125 | XPO7 | AGCGGCGCTGTTCCCGGGCTGGGTGCAGCTGCTAAGGACAAGGCCCCTGCTCCGAAGAACGCGGTGGCTCGGGGATACCCTGAAA<br>GGGACGGCCATGGCGCACATGGGATGCCCTAGGGTTCGTGGGAGGGCATGCAGGCGCAGCCCCCGCAGGGGTTGGCCTGCCAGAG<br>AAGGCAGGGGAGAGCACTCGGGGCTGCACAAATGGTGTGGCCGGAGGGAAGGTGCAGCCTTGTGTGTGTCTGGATGAGGGCTGGG<br>CATAGGAGCTTGGTATTTGATCCTGAAAGCTCTGCGTTTCCAAAG |
| 126 | chr8:<br>41543400-<br>41544000 | GAGTCATACTTGTAGTCACATCCTTTTCCTTTCTCCAACCCACTGGTTAATCATGAAAGGCTCTTCTGATTGGCTGCCTCCTGGC<br>AGTAGTGCCTCAGCGCGACGGTTCGGGAGCAAATAAATAATTCCCGCTGGGAAGCTGTTTCTCAGACAGGAGCAGCGACACCCCT<br>GCCACGCCTGCCGCCTGGAGTTGAGTGGGGTAAGCACGCCGGCCTCCAGGAATCGACGGTGCCACGTGGTTCTTCTTGCACTTCT<br>CTTCTTCTCCAGTTTCAGGGGACACCGTGGGGTGTGCGAGCCCGGGGGAGCGCAGGGAAGGGCGGGTTGGGCTGCAGGTGGGAAT<br>GTGCGGTCCTTCTGCGCCCTCAACAGAGCTTCCTTCCTTTTTGCCAAGGTCCCCGTGCCGCCTTCAGCGCGCCTCCTTATGCACC<br>TCTACCTCTGCTGCAGCGTACCTCTTCCGCAGCCCTAGCGGCCTCCCCGAGGGGCGCCGCGGCCTCGGCTGTCCCTCCCCTGCCT<br>GGCACGACCACCTGACCCCCAGCGACCCAAGAAGCAAGTTGTGTTTGCAGACGCAAAGGGGCTGTCGTTGGTATCGGTGCACTGG<br>TTTGA |
| 127 | GDF6 | ACACTTTCTGTGTGGGAGGGCACAAGACATGGGCTATGACATGGCCAGAGACCCCACCTTCTTTACACATGTAAAAACCAACCAA<br>ATCAAGATGCGTCAACGGTGATTCTTCCTCCCACATTGTTTCCCTTTTTAAACTGTTATTTTTTCAATCCATGGAGCAGTTGAGA<br>AACGGGTATGCATCTCTCCTCCCCTCCCCTTCTATCAAAGCCTGTAAGACACATAAGGAAATCCAAAGCCACAGTAATAGAGAGA<br>GAGAGAGAGAGAGAGAGAGAGAGAGAGAGAGAGAGAGAGAGAAAACAGAACAAAAGAAATCCTCCTTGGCTTGTTTTTCCAGGGTGG<br>CCAGGCAAGGTGTGAAAATCCATATTTCCCTCTGGGCTGGCAGGTAGAAGTTACTGGGAAGGCTGCGCTCCCTTCTCTCCCACCG<br>GCTCTCACATCCAGGCTGTTCCCTCACCCTCAGCCTCCCCCAGCGCCAGCTTCCTCCTCCGCCTCTCTGCAGCCAGGCCTCCCCT<br>GCAAGGCGGACCTTGGCCCACCTTGGTTCCGGGCCAAGGCGGCGGGAAAGGCACCGCTACCTGCAGCCGCACGACTCCACCACCA<br>TGTCCTCGTACTGCTTGTAGACCACATTATTGCCCGCGTCGATGTATAGAATGCTGATGGGAGTCAATTTGGTGGGCACGCAGCA<br>GCTGGGCGGGGTGGAGCCGGGGTCCATGGAGTTCATCAGCGTCTGGATGATGGCGTGGTTGGTGGGCTCCAGGTGCGAGCGCAGC<br>GGGAAGTCGCATACACCCTCGCAGTGATAGGCCTCGTACTCCAGGGGCGCGATAATCCAGTCGTCCCAGCCCAGCTCCTTGAAGT<br>TCACGTGCAGGGGCTTCTTGCTGCAGCGTAGCCTGGACTTCTTGCCGTGCCGCTTGCCATGGCGACTGGCGAAGGCCGTGCGCCG<br>CCGCCGGCGGCCGGGCGAGGGCAGCCAAGGCCTGGCATCCGGGGCGCCCGACGGCGGCGGCCACGACCCCTCGGCGCCCGCGCCC<br>GGGCCCGCAGCCTCGGCCGAGCCCAGCTGCTCGCGCATCTCTGCGAACAGGTTCTTGCGCTGGGATCTGGTGAATACCACCAGCA<br>GGGCCCGCTCCTGGGGAGGCCGCACCCTCCGGCCGAAGCCCAGACTCCGCAGGTCCGGGGGCGGCGGTTGCTGGGGTCCCCGCGC<br>GCGCGCCTCGGCCTCCCCGGCGTCCAGCTCGCCCCATGCGGCCCGCAGCTCCAAGCACAGCTGCTTCCAGGGCTGGTGGCGCAGG<br>CCCTGCCACACGTCGAAGACTTCCCAGCCGGCCGGCGGCGCCCCCTGCGGGTCCAGGGTCCGCGCGTCCAGCAGTAGGGGCGAAA<br>GGCAAGGGAAGAGCTGCACGTGGAGCGGCCCGGCTGGTGGCCCCCAGGGCGCTGAGGGCGCCTGGCGAAAGAGCCGCAGCTCCGC<br>GCCCACCAGCTCTTCTTTGTCTGAGAGCATGGACACATCAAACAAATACTTCTGTCTCCGGAGAGGAGTGTGCGAGAGATCGTCT<br>GCGAGATAAAAAATAATTACAGTCAGTTTCACTTAAGGGGGAGATCAGCCCGGTGCTCTTCGGCCGCCCCGGGAGGAAAAGGGCG<br>GGGAGTGGGGGCAGGTCGGCCGGGCAGTCCAGCTTGCCCGGCCCAGGGCCTGACCACCCCGGCTCCCCATCTGGCTGGTGCATGG |
| 128 | OSR2 | GCCCGCTGTGAATGTAGGTGAGGTGATCCCGGGAACCTGGGTCTGAAATCAGACCTGTGTTGCCATTGGGAGCACGGAGAGAGGG<br>GAAGCGCCCTGCTTAGGCCCAGGCCGGGCGTCCTGGTGGTGGGACCGCAGCCGCACTCACCTCCAGGCCAACGGACAAGGTTCCT<br>GCAAGCCAGCAGGGCCACTCTGTGCTTGGCCTACTGCAGCTCCCCTGCAGCTCCTTTCCTCTCCCTCCCCGGAGCGCTCTCCTCT<br>CTCCTCTCCCCTCTCTTCTCTCTCCTCTCTCGTCTCCTGGGGCATCCCGGGTGGAGGGATGTAGGGGTCGCTCCTCGGTGCCAGG<br>CCGGGAAGCAGCTCAGGCCTCCCAAGAGCTTGGCGCTCAGTCTGGGAAAAGGGGTTCCTCTGGCCTCAGGGACGTTCTCCGCCCC<br>CACCCCACCCCCTGGGAGCCTGAACCATCTGGAAGGGATCTTAGTCGGGGGTTGGGAGGAGAGCCCGTGGATAGGAGGAGGGGGC<br>GATTCTAGGCCGAATCCAGCCCCTGAGGTGTCACTTTTCTTTCCTGCGGCCCGTCACCGCTGATAGATGGGGCTGAGGGCAGAGG<br>AAGGAAAAAGAAAACCTCCGAGGTCAGTGCGGGGCGAGGTGAGCCCCTCCCAGGGCCCTCTGGCCCAGGAGGATGAAGCGCGCCG<br>GCTTCGCTCTTGCACGCCGGCTTGCCATCCGGGTAAGCGCGGGAAAGGCGGCCACAGGGCGCGGCGGCAGCGCAGCGCGTGGGAT<br>CTCACGACCCATCCGTTAACCCACCGTTCCCAGGAGCTCCGAGGCGCAGCGGCGACAGAGGTTCGCCCCGGCCTGCTAGCATTGG<br>CATTGCGGTTGACTGAGCTTCGCCTAACAGGCTTGGGGAGGGTGGGCTGGGCTGGGCTGGGCTGGGCTGGGTGCTGCCCGGCTGT<br>CCGCCTTTCGTTTTCCTGGGACCGAGGAGTCTTCCGCTCCGTATCTGCCTAGAGTCTGAATCCGACTTTCTTTCCTTTGGGCACG<br>CGCTCGCCAGTGGAGCACTTCTTGTTCTGGCCCCGGGCTGATCTGCACGCGGACTTGAGCAGGTGCCAAGGTGCCACGCAGTCCC<br>CTCACGGCTTTCGGGGGGTCTTGGAGTCGGGTGGGGAGGGAGACTTAGGTGTGGTAACCTGCGCAGGTGCCAAAGGGCAGAAGGA |

TABLE 4B-continued

| SEQ ID NO | GENE NAME | SEQUENCE |
|---|---|---|
| | | GCAGCCTTGGATTATAGTCACGGTCTCTCCCTCTCTTCCCTGCCATTTTTAGGGCTTTCTCTACGTGCTGTTGTCTCACTGGGTT<br>TTTGTCGGAGCCCCACGCCCTCCGGCCTCTGATTCCTGGAAGAAAGGGTTGGTCCCCTCAGCACCCCCAGCATCCCGGAAAATGG<br>GGAGCAAGGCTCTGCCAGCGCCCATCCCGCTCCACCCGTCGCTGCAGCTCACCAATTACTCCTTCCTGCAGGCCGTGAACACCTT<br>CCCGGCCACGGTGGACCACCTGCAGGGCCTGTACGGTCTCAGCGCGGTACAGACCATGCACATGAACCACTGGACGCTGGGGTAT<br>CCCAATGTGCACGAGATCACCCGCTCCACCATCACGGAGATGGCGGCGGCGCAGGGCCTCGTGGACGCGCGCTTCCCCTTCCCGG<br>CCCTGCCTTTTACCACCCACCTATTCCACCCCAAGCAGGGGGCCATTGCCCACGTCCTCCCAGCCCTGCACAAGGACCGGCCCCG<br>TTTTGACTTTGCCAATTTGGCGGTGGCTGCCACGCAAGAGGATCCGCCTAAGATGGGAGACCTGAGCAAGCTGAGCCCAGGACTG<br>GGTAGCCCCATCTCGGGCCTCAGTAAATTGACTCCGGACAGAAAGCCCTCTCGAGGAAGGTTGCCCTCCAAAACGAAAAAAGAGT<br>TTATCTGCAAGTTTTGCGGCAGACACTTTACCAAATCCTACAATTTGCTCATCCATGAGAGGACCCACACGGACGAGAGGCCGTA<br>CACGTGTGACATCTGCCACAAGGCCTTCCGGAGGCAAGATCACCT |
| 129 | GLIS3 | CACTCCCCCGCCGCCTCCGCCCCTAACCCTCGGCCCCGTGCGCGAGCGAGCGAGGGAGCGAACGCAGCGCAACAAAACAAACTAG<br>TGCCGGCTTCCTGTTGTGCAACTCGCTCCTGAGTGAGTCGGGGGCCGAAAGGGTGCTGCGGCTGGGAAGCCCGGGCGCCGGGGAC<br>CTGCGCGCGCTGCCCGGCCTGGCCGGAGCCTGTAGCCCGGGGGCGCCACGGCCGGGCTCGCAGTCCCCCCACGCCGGCCCCCCGG<br>TCCCCGCCGAGCCAGTGTCCTCACCCTGTGGTTTCCTTTCGCTTCTCGCCTCCCAAACACCTCCAGCAAGTCGGAGGGCGCGAAC<br>GCGGAGCCAGAAACCCTTCCCCAAAGTTTCTCCCGCCAGGTACCTAATTGAATCATCCATAGGATGACAAATCAGCCAGGGCCAA<br>GATTTCCAGACACTTGAGTGACTTCCCGGTCCCCGAGGTGACTTGTCAGCTCCAGTGAGTAACTTGGAACTGTCGCTCGGGGCAA<br>GGTGTGTGTCTAGGAGAGAGCCGGCGGCTCACTCACGCTTTCCAGAGAGCGACCCGGGCCGACTTCAAAATACACACAGGGTCAT<br>TTATAGGGACTGGAGCCGCGCGCAGGACAACGTCTCCGAGACTGAGACATTTTCCAAACAGTGCTGACATTTTGTCGGGCCCCAT<br>AAAAAATGTAAACGCGAGGTGACGAACCCGGCGGGGAGGGTTCGTGTCTGGCTGTGTCTGCGTCCTGGCGGCGTGGGAGGTTATA<br>GTTCCAGACCTGGCGGCTGCGGATCGCCGGGCCGGTACCCGCGAGGAGTGTAGGTACCCTCAGCCCGACCACCTCCCGCAATCAT<br>GGGGACACCGGCTTGGATGAGACACAGGCGTGGAAAACAGCCTTCGTGAAACTCCACAAACACGTGGAACTTGAAAAGACAACTA<br>CAGCCCCGCGTGTGCGCGAGAGACCTCACGTCACCCCATCAGTTCCCACTTCGCCAAAGTTTCCCTTCAGTGGGGACTCCAGAGT<br>GGTGCGCCCCATGCCCGTGCGTCCTGTAACGTGCCCTGATTGTGTACCCCTCTGCCCGCTCTACTTGAAATGAAAACACAAAAAC<br>TGTTCCGAATTAGCGCAACTTTAAAGCCCCGTTATCTGTCTTCTACACTGGGCGCTCTTAGGCCACTGACAGAAACATGGTTTGA<br>ACCCTAATTGTTGCTATCAGTCTCAGTCAGCGCAGGTCTCTCAGTGACCTGTGACGCCGGGAGTTGAGGTGCGCGTATCCTTAAA<br>CCCGCGCGAACGCCACCGGCTCAGCGTAGAAAACTATTTGTAATCCCTAGTTTGCGTCTCTGAGCTTTAACTCCCCCACACTCTC<br>AAGCGCCCGGTTTCTCCTCGTCTCTCGCCTGCGAGCAAAGTTCCTATGGCATCCACTTACCAGGTAACCGGGATTTCCACAACAA<br>AGCCCGGCGTGCGGGTCCCTTCCCCCGGCCGGCCAGCGCGAGTGACAGCGGGCGGCCGGCGCTGGCGAGGAGTAACTTGGGGCTC<br>CAGCCCTTCAGAGCGCTCCGCGGGCTGTGCCTCCTTCGGAAATGAAAACCCCCATCCAAACGGGGGGACGGAGCGCGGAAACCCG<br>GCCCAAGTGCCGTGTGTGCGCGCGCGTCTGCGAGGGCAGCGGCGGCAGGGGGAGGAGGAGGCAGAGGCGGGGTGGCTGGACCCTC<br>GGCATCAGCTCATTCTCCCCTGCTACACACATACACACACAAATAATGTTTCTAAAAAGTTCAGTTGCGACTTTGTGCCTCGCCT<br>GTCCTGTTCATCCTCGTCCTGGGCCGGGGAATGCTTCTGGGGGCCGACCCCGGGATGCTGGCTAATTGCTGCCGGCGGGTTCCGT<br>CGCCGGTGTGACCCTGGACGGCGCGGACGGCGTACAGGGGGTCCCGGGAGGGGCAGTGGCCGCGGCACTCGCCGCCGGTGCCCGT<br>GCGCGCCGCGCTCTGGGCTGCCCGGGCGGCGCAGTGTGGACGCGG |
| 130 | NOTCH 1 | CTGAAAAGCCGTCAGGGAAACCACACATGTTCAACCCCTGGCGGCTCCCCCAAACCTCTCATTTCCAGTAACTGTGTGTTTCCGC<br>TCGTCAACAGCTGAAACCGAGCGGAACTTGGGGGGCCCCACCACGCGGCCCTGCTGTGCGGCACGGGGCTCATCTGTCCCCCGGC<br>TGCGGGGAGTCAGCTCTCACCGCCCACCTCCTTCCCAGATAGTCTCTGTGCCCACTCGACGGCCCGGCAAGCCCAGCCCCTGCCT<br>GCCACGGCCACAGCAGCCTCAGAGAGCTGCCCTCTCTGGCCAGGGTCAGGGCCTGAGCTGCTGCCTCCCGCAGGGTCGAGGGCAG<br>GACACTTGTCTGAGGCTTGGGTGGGGCAATGGCACCTCCTCAGGGCCTCAGCCCCCGGGCAGGCTCGGTGACCATGGGCCTACAG<br>CAGGGAAAATTCTGGGCCAAAAGCTCCAGCCTCCTACTAGGGCATCTGTCTGCAAATGCACCTTAACCTGACCGCTTGGGCTGTG<br>GGGGAGCCTGTTTCAGGGAAAGTGAGGGACGCGCCAGTTTCCTCCTTTGGACTTGATGAGGCACGAACGCATCTCTAATAAAGCC<br>AGGTCTCCCCGCCGTGGCTCCCTGGGCGGGTGCCTGTGGCTCGGGCCATGAGTCACGCTGGGTAACCCCACTACGGGGAAGAGGG<br>CAGGAAGCTGGGAGCCACCGCCTCTGTGCCCGGTTGTCATCTCGGCACGAGGGCGACCGTCGGCTTCGTCCTGCCCTCATGGCTG<br>AGGGCTTTTGGGATGTGGCGGGAGACGGGGGAGTC |
| 131 | EGFL7 | AAATCATCAGAATGGCTAAAATGAAAAAGACAGACAACAGCAAGTGCTGACAAGGGTGTGGGGCGGCCAAATGCTCCTGCACTGC<br>TGGCAGGGGACCTGAGAACTGCAGGGCATTCCCTGGCTTCCTGCCCCTCCTGGGACTGGGGACCCCCCAGGGACAGCCTAAGGGA<br>ACTGCATTTATCTTCACGTCTGCCAAAAGATAACACGAAGATGTTCAAAGCTAAGCCCCCAGGCTGGTAAGAGCTCCAAGGCACC<br>AGCAGTGTGTGCAGAACTGGGGGGAGTCTGTTCTCCCAGGGATGCTCCCATCACCTGCTGCCAGCAGTGGGGCATGCCGGTCCCC<br>TGGGGTGTGGCCAAGGGGCTGTGTCTCCTGCCCGGGCTGCCGGCCCCTCTCAGGTTCACTTTCCCATCTCTAAGCCCACGTCTCG<br>CTGCAGTTCAAGTTTGCCAGGCCACCAACGGGTGACACGCCCGGCGCAGTGGGGGACTCCGCACTTTCTGCGCAC |
| 132 | CELF2 | ACCCTTTGTGCCTGGGTCCCATAAACAATGTGCTTTTTAAAGGGGAGCCCCCTCCCAGCTCCGGCCTTTTTCTCCAGCGTGGGCA<br>GCCAATCAGCTGCGCAGAGCTGCATAGCTGGACCGCTTTCCATTCTGAGTAGCAACAACGTACTAATTTGATGCACACATGGATG<br>CCTCGCGCACTCTGCAAATTCATCACCCGCATCTTGCATTAGTCATCTGACGGACTGCCAAGTGTTTCATTTTCTTTCCATGTGA<br>CTTTATTATTACCACCTCTCTCCTCTCTTCCAAAAACCTCCCAAAAAGGGCGGTGGGGCGGGGGGCGGGGCAGGGAGAGGGAGAG<br>AAATCCAGCAGACATCTAGCTCTGCCTTTCTTTCCCAGCCACAGCCAGGGTAGGGCTGATAAGGCGCTGATGCGTTGATGGCAGC<br>CTTGCAGAGCTAGACCTGCACTTAACTTGCAGCTGCCTCCCGAGCCTCCAAGATGTCCACGCCCTGGGTGACAGGCGGCAGGGCG<br>CTGCCCCGTGCTCCCCCGGCTCTGCTCGACAGCAGCACGCAGTGAGAGCCTCGCCGCCGCCGAGGAGCAACTCATGGTGCCTCCG<br>CTTTGTTTTAGTTCATCAAATTTCTACGACTCATTAGGCACTTTGCCACTGCTCTTCTTCCTCCTCCTTCCGCCTCCCCGCTCCC<br>CCACCCCCACTATTTTTTCTTCCTGTCCCTCATCGTGCCGCCCTAACTCTGGCTCCCGGTTCCGTTTTTGACAGTAACGGCACAG<br>CCAACAAGATGAACGGAGCTTTGGATCACTCAGACCAACCAGACCCAGATGCCATTAAGATGTTTGTCGGACAGATCCCCCGGTC<br>ATGGTCGGAAAAGGAGCTGAAAGAACTTTTTGAGCCTTACGGAGCCGTCTACCAGATCAACGTCCTCCGGGACCGGAGTCAGAAC<br>CCTCCGCAGAGTAAAGGTACAGAGCGCGGGGCGGGGGTCGCCAGGCGTCCAGGTGGGCGTCGCGGGGCACTGGGGCTGTCCGAGC<br>CCCCAGCCTGCAGGAGGAAGGGCGGGTAGGCAGGAGGGCTGGAAGCAGCCGGTGCTGGCGGCCCCTGTGCTCCAGGGGCTGCTCC<br>CGACTCCTCCCCGCACCCCCGCCCGCCTGCCCGCCGGGACAGGTTGGAGGCGGGAGAGAGGGACCGAGGCAGGGCGGGAGCGCAG<br>AGGCTCGGTC |
| 133 | HHEX | TAACAAATAAGCCGCCCGTGGTCCGCGCTGTGGGTGACCCTTGGCGCCTTCGAGGTCTGGAGCCCTAGGGTAAATAAGGAAACGG<br>GGCGCCTCTAGAGTTTTAAATGAACTCTGTTATTGGAAGCTTCAGTAGGGACCCTGAAAACAATTAACGTCTTAATTAGCATTTT<br>AATGTCTCCATTATTACGGCGCGGGCTCTAGCTCAGCCCTTTACCTTACCTTCTCACCGTTAACAGGGGAGGGGGATTGTATTTT<br>TAGTTCATCTTTTTATGTTTTTGAGTTGTTATCCTGTCTGTCTGATTCCAGCCTCGAGGGTTTGATGATGCGGCCCGAGCCTGGC<br>TGTGGTCGCCTGTCGGGGCTGGAGCGGGACCCTCAGCCGGGCCGGGCCTGGGGGCTAACGTTTTCACAGTGCGCCCTGAGTTTCC<br>TTGGGTTACTGCTGGGACCGCGCAGGAGGAAGCAAAGAGTTTTTCGAGCTAGACCAACAGGAAACACATTGACGGAAATGTTGCC |

TABLE 4B-continued

| SEQ ID NO | GENE NAME | SEQUENCE |
|---|---|---|
| | | ATAGCCCATGGGGTGGCTTTAACTGGCCGCCCCCGCGGGCTGGGTGTGAAATCAGAGGAGGCCGCGGCTCCCCCGGCCAGGATTGGAGGCTCCTCGCGCAACCTAATGCGGGTGTCCGGGCCCGAGCGCTTCCCGCGCAGCCAGGCCTTGTCGGTGCAGCAGCCCCGCTCCTCCCCAACACGCACACACCCGGTGTTCGCAAGTGCGGCTCACCAAGGGAGATCCAAGGGGGCAAAAAGTTATGTATAAATCCGAGAGCCACTGGGGAAAGAGGGTCGTGGTATTGTAAG |
| 134 | DOCK1/ FAM19 6A | CTACCCTGTGCTATCCTGAGCTGTAGTCTTCTGAAATGATCGTTTGGCTTCCCAGCCAAGGCAGGGCTCCCCCAAAGTTCATTCCCACTCTTGCAGTTTCACCTCGGGATGCTTCCGCAGAATTTCAGCGCCTAAGCAGACAAGGTCAAAGTAAACCGCTTCACCGCTGCTTCTGGCGCAGGGGCCCAGAGCGCGTGCAGCTCCCCAGCACAGACCAACAGCAGGAGAGGGGTCCGGGCGGGAGCCCTGGGCTGTAGATAAGCAAAACGCACCCATTTTCTCTCCTATTTACTCCAGAGGCACCTCTCCTCCCCCACTCCTGGCATCTCTTTATCACTGGCTCCCTCTCCCTGTGGCATATTTTTGGGTAGTAGAATGCTGAGGTCACAGGGAGCGGCTCTTTATCCAAGCAGTGGGGACATCAGCCTGGAGCCCTGAGCATGAACCAGCAAGATGCAGACTCTCGCTCTTGACTTTGGGCTCCAGGAGCTGCCCCGACC |
| 135 | PAX6 | CAGTGCTCCGCTCCGGGAAATTGCATCGTCACGACAAACGGGACCGTGATAAAACGACCCTTTCCGTCCTTATTTGTAGATCACTCAGACGAGATTGAACTGCACTTGTTTCCCCTTCGAGGGGAGCCGCGTTTTCAGGGTAGCCGAAGGCTTGGGGCTGAGGGGGGGCCCTCACCAAGGCGCGGGTGGGGGCCGGAGCCTCAACTCGATGAGAAGTGACAGGCGTTTGGGGGATCTGGGCTCCGGCCGGGACCAGCGCAAGCAGGGACTTTGCGGGGACACCGCTTCTCCAACAGAGCAAGGCCTGGCCCACGTTTCCGGTTTCTCCTAACTTCCTTTTATTGCCTTCCTTTGCTTCGCAAGTTCCATCTACCCCTCCAGCTACAGAGCCCCACCTCTAGGCACAGGAAGCTTCCCGGAAAAAGAAAGGCTGTCCCAGAAAGAGACCGAGAGAGACTTTCCAAACTTCGGGCATAGCCACGGCAATTCCCAGTCTGCTAATGCCAAGGCGGGCGCGTAAGGCCGCCTAAATCTAGACCTCCCTCCTCACTCATTTCAAAAAATAACAACGTGCCAGCCACCTCCCGCAGATACCGCCGGCTGGTGCTTGCCCAGGAGACGCCAGGGCCAGAGCGCCACTCCCAGCATCGAAATGGCAGAGAGAAAGCGCAGCTCCAAATTCCCCTTCAGAGGTTAAGCCTCAATCATTGTGTCCCTTCCCTAGGGACTGCTGGCGCTCTCGCCCACTGGCGATGATTATGCGCCTAGAACTCGACCGCGAAGCAACTAATAGGAAAACATATGGTGTCAATTTGGATGCTCCGCGCCTCGCGCACACCCGGGAACGAGCGGCACAAAGCCCTGCCGGCCGGCCCGCGACCCCGCGCCCCTCGGGGCCTGCCAGCCGGGCCGCAGCGACAAACGCTCAGGGCTGCGCGCCCTGGCTGGGGCCCGCCCGAGAGACAGCCTGCGGCTGGGGAGTCTGAGCTCCAAGGGGAGAGCCCAGCCGCCGAAGGCGAGCCTACCGGCCAAGCCCTGGGGTCCGGCAGGTTCTGCACAACTACTCCCGCAAAGCTCGCCACCTTTGTGCCCTTTCCTCAG |
| 136 | FERMT3 | GGGCCCTCGCGGCTCAAGCGCCAGCGCTGGAGAGAGAGTCTGAGGGTACCACGGGCGTGCTGGCCTGGGTGCTCACTCCCGCCCTCCTTCATGAGCGGCTTTCCTCTGGGTGTGTCCAGGGCATCACAGAGCTCTTCTGCCCAAACCCGGAGGCCTACCAGGGCCTGCCCACCTTGCCTCCTTCCACACTCTCTGTAGCAGCAGCCGCAGCCATGGCGGGGATGAAGACAGCCTCCGGGGACTACATCGACTCGTCATGGGAGCTGCGGGTGTTTGTGGGAGAGGAGGACCCAGAGGCCGAGTCGGTCACCCTGCGGGTCACTGGGGAGTCGCACATCGGCGGGGTGCTCCTGAAGATTGTGGAGCAGATCAGTGAGTGTCCGCTGCCCGCTTGCTGAACTCGGCACCATGGGCGGCCGCCACGGGTGTCTCTGGGCACTTCCGGGCCATCCCTGCTGCTCAGCTCCCGATAATGGTGTCACGGTGACTCAGGCATTAGC |
| 137 | PKNOX2 | TGTTTACGGAATCGGGATCGAGGGGCCGATAAGTAGTTTACACGCCGGCCAGAGCAGAGGGCTGGAGGTCGGAGTTGGGGGCTGGAGGAACGGGTGGCGTTTTTAGGATTCAGTAACAGGATCACAGCTTTTTCTTGTGGTGGAAGCTATTGGAATTTGGGGAGGGTAGCACGAGGGGTCCTGCAGCTCCGCGTGTGAAAAAGCGTTTAGGTAGGCGATGAAAGTAGTTGATCTGAGCCATGGCAGGCGAGCCCCGAATTTTTGCTGCTTCCCCCTGAAAGTGTTTCTTTAGGAGGAGAGGACTTGGGCCACACAGGACCCGGTCCTAAGAGAGCGATTCCGGGAAGCGGACAGATCGAAGAGACCTTCTGGGCGAAGCGGCAGGGCAGCCTCGCGGGGCTGGGAGTGGATCTGAGGTCCCGACCCAGGCGGCTCGGAGTGCTCCAGGAGCCACCTGGGTCTGCGGGCGCAGCGCGGCGGGGCGGGAGCGGTGGCCCGCAGGGGCCGCGGCCTGCGATGAAGGCCGGGGGGCAGCGCTAGCAGCGAGGTGCCACAGTGGGCCGAGGAGTCTGGGCTGTGGCCCAGGGTAGGACCGGCTCA |
| 138 | KIRREL3 | ACCTAAACCAAGCTCTCCCTCCCTGCCGTCTCCTTCCCTGGCCTGGGTCTGAAGGAGAGGAGGTGCCCAGAAGTTCAGAGCGGCATAACCACAGAGATACTACCTAATTAACATACCAGAAGCATAAAGAACTCATTTGCATTGGAGAGT |
| 139 | BCAT1 | ATAACTACGGGGGTGGGGGTGGGGAAGGAAGAGATCCAAGGAGGCAGAAGGCTGCGGTCAAAATATTTTGGGGTGGCAGAGTCACGTAGGATGTGGCTGTGGGTTCTGGCAGCCCAGAGATTCAGCTCCCGCCTCCTCCCTCAGAGCGAGTCCATAGCTACCCTCACGTCCCCCGTGGCGGTCCTCGCCACGCTCCGGAGCGGGTTACCCATGAGGGTGCTAGACCTGGGCAGCGGGAACCTCGAAGAGGTGGAGATTGCAGGCTGGGACTCCAGATTTCGGGCAGGGATGCGGGGAAGGGAAGACGCCTCGCTGGAGGCGGAATGGAGGGCAAGGCGAAGGAGGATGGTGCAGGAAACGGCGACAAGGCGCCCGGCCAGGCCCGCGAGCTACCGAGACCCGGGTTCCAATCCTCCCCCCTTCCGCAAACGCCCGGGTTCGAGGTACCTGGCGGGCAAGGGCCGCAGCGGAGCGAAGCGGGCTGGCCATGGGGAGGCTGCGGGGACGCGGGGCTGCAGAGAGCGGCAGTGGCACGGAGCGCGCGGCTGGAAGCGAAAGCAGGCGGTGTGGCCAAGCCCCGGCGCACGGCCCATAGGGCGCTGGGTACCACGACCTGGGGCCGCGCGCCAGGGCCAGGCGCAGGGTACGACGCAACCCCTCCAGCATCCCTTGGGGAGGAGCCTCCAACCGTCTCGTCCCAGTCTGTCTGCAGTCGCTAAAACCGAAGCGGTTGTCCCTGTCACCGGGGTCGCTTGCGGAGGCCCGAGAATGCGCGCCACGAACGAGCGCCTTTCCAAGCGCAGATATTTCGCGAGCATCCTTGTTTATTAAACAACCTCTAGGTGAATGGCCGGGAAGCGCCCCTCGGTCAAGGCTAAGGAAACCTCGGAGAAACTACAT |
| 140 | HOXC13 | CAGTCCAGCCGCTTGCCTCACTTCTTCCCGCTTGCCTTATCTCCCCGCAGACGTGGTTCCCCTGCAGCCCGAGGTGAGCAGCTACCGGCGCGGGCGCAAGAAACGCGTGCCCTACACTAAGGTGCAGCTGAAGGAGCTAGAGAAGGAATACGCGGCTAGCAAGTTCATCACCAAAGAGAAGCGCCGGCGCATCTCCGCCACCACGAACCTCTCTGAGCGCCAGGTAACCATCTGGTTCCAGAACCGGCGGGTCAAAGAGAAGAAGGTGGTCAGCAAATCGAAAGCGCCTCATCTCCACTCCACCTGACCACCCACCCGCTGCTTGCCCCATCTATTTATGTCTCCGCTTTGTACCATAACCGAACCCACGGAAAGACGCTGCGCGGGTGCAGAAGAGTATTTAATGTTAAGGAAAGAGAAGAACCGCGCCGCCCGGAGGCAGAGAGGCTCCATGGCCGTGCTGCTGGGCCATCCCCAACTCCCTATCCCATCCCCAGCCTCCACCCCCATCCAGATGGGACTCACGTGGCTTCAACAGCTTTGGAAATGGGTCCCGAGTGGGCCGTGCGAGGAAGGCTGTCGACCTCTACTCCTCCTTGC |
| 141 | TBX5 | CAAGATCGACTTTCTTAGGAAGGGGGAGAGGAGGGAACTCTTCACGAAGGGAGGTGGGAGTCCACCTCAGACCTCTATTGGAAGGAAATCGAGTTGTTCCGGGGGACTGAGGTCTCTTGCATAAGGCATGGGATCCTTATTATTATTATTATTATTATTTTTAAATCCCCCGCGGAGGAGCTCTGGGCAAATGAATACCGAGGCGCCGCTCTAGCTGGTTAGGCTTGGGATGCGATAACTCAGTGCCCTCTTGCAGACTTGCATAGAAATAATTACTGGGTTGTCGTGGAGGGGACACGAGACAGAGGGAGTTCTCCGTAATGTGCCTTGCGGAGAGAAAGGTCCAAGAATGCAATTCGTCCCAGAGTGGCCCGGCAGGGGCGGGGTGCGAGTGGGTGGTGGAGTAGGGGTGGGAGTGGAGAGAGGTGGTTTCTGTAGAGAATAATTATTGTACCAGGGCCCGCCGAGGCACGAGGCACTCTATTTTGTTTTGTAATCACGACGACTATTATTTTTAGTCTGATCAATGGGCACAATTTCTAAGCAGCGCAGTGGTGGATGCTCGCAAACTTTTGCGCACCGCTGGAAACCCACTAGGTTGAGTTGCAAAACGTACCGCGTAGACGCCCCTGGTGGCGCCGAGAGAAGAGCTAGGCCTGCCCAGCACAGAGCCGGAGAGCGTCGGGCCTTCCGGAAGGGTAAGTTCTCCGCCAAGGGGTCCCGAGGGAGCTGGACGTCTGAATCTGGACTTGCCCCCAGCTTCGGGGTTCGATTCTGGGTTTTGCGCGTCCCCAACCCCCAGGGCTTTCCGAAGCATGGCCTGGCTCCAGGCCCGGTCCTGTAAGGACTGGAA |

TABLE 4B-continued

| SEQ ID NO | GENE NAME | SEQUENCE |
|---|---|---|
| | | CGGCAGCAAAATGTGCAGGGAGGCAGTCGGCCGGCAGAGCTGCGGCGGGAGCCAAGGTCAGGCCCGCGGGGAGAGCGGGCAGCTT<br>CCAGCGCCGGCCACAAGCTCCCAGGCCAGCTGGGCCGCAGACCCCTTTGCTTCCAGAGAGCACAACCCGCGTCCTTTCTCTCAGC<br>CAGGCTGCAGTGGCTGCCCCGAGCTTCGCTTTCGTTTCCCAAGCTGTTAATAACGATATGTCCCCAAATCCGAGGCTCGTGTTTG<br>CTCCCAGATGCCAAGAACGCAACCCGAAATCCTTCTCCCAAACCCTAGGTCGACGAGATGAGTTCCTACTTGACCTCTGAGCCGA<br>GGTGGGCCGGAAACCGAGGCCTAGGCCCCGCCGGGGCTGCAAGGAAAAGGGGAAACTCCGAGCGTAGCGTCTTTTCCTTGTGGTT<br>CCTTTCTCCGGCATCCCGGACTGCGGGCCCTGCAGCCACCTGGACCGGCATTCAAAGGATTCTGCAAGTCCAGCTTCACAGACTG<br>GCTTTCCCAGACGCTCCGAAGCCCGCACCACGAACAGAATAAAGGAGAGACGAGAGATCGCAACTAGATTTGAGAATCCTCGTTC<br>TTTTCCCCAATCGTTCGGGCAGTAAACTCCGGAGCCGGCTACAGCGCGCATCCTC |
| 142 | TBX3 | ACTGTCCTCCTCCCTCAATTGCCTATTTTTTGCCCATAGCTCTAACTTAACCCTGTGATCACCCCAGATCGCTACTTCTGACCCC<br>CATCTCCTCTCCCACACCAACCTCCAGCGCGCGAAGCAGAGAACGAGAGGAAAGTTTGCGGGGTTCGAATCGAAAATGTCGACAT<br>CTTGCTAATGGTCTGCAAACTTCCGCCAATTATGACTGACCTCCCAGACTCGGCCCCAGGAGGCTCGTATTAGGCAGGGAGGCCG<br>CCGTAATTCTGGGATCAAAAGCGGGAAGGTGCGAACTCCTCTTTGTCTCTGCGTGCCCGGCGCGCCCCCCTCCCGGTGGGTGATA<br>AACCCACTCTGGCGCCGGCCATGCGCTGGGTGATTAATTTGCGAACAAACAAAAGCGGCCTGGTGGCCACTGCATTCGGGTTAAA<br>CATTGGCCAGCGTGTTCCGAAGGCTTGTGCTGGGCCTGGCCTCCAGGAGAACCCACGAGGCCAGCGCTCCCCGGA |
| 143 | chr12:<br>113622100-<br>113623000 | CTCAGGGAATCACATGTCCGCCTGGCCTGGCCTGGTACCAAATGTTTATAGACAGGACGAGGGTCGCTGGAATCGCCTCGCTCCT<br>TTCAGCTTGGCGCTAAGGCGCGAATCTCGATCCTCCTAGTATTTCTCTGGCGTCTGTCTCTATCTCAGTCTCTGCTTTTGTCTCT<br>TTCTCCCTCCCTCCGCCCCAGTCTTTCCGTCTCTTTTTCCTCGAATGCACGTGGAATTCGGAATTGAAAATTGAGGTCAGAATCT<br>CCCTTTTTCTTCCAGTTATCCGCGCCGCTGCCCCACGCCTAGCGGCTTGGATCTGCATAGACATCTATCTACCCGCAACAAGATC<br>CGAGCTGCAGAAGCAAACCTAATCTGTCTCCGCACCATCCCCTGCTCTGTAGACCCACTGCCCCATCCCACGCCACATCCTTGAG<br>GTTCAAGTAGCGACTCCAGCGGATGATTCGGAGAATGCCCTGCTTTCCAAAGGCCCCAACCCGTGTTTTTATTTTCTTTTTCCTT<br>TGCCCGCTTGACCAACTTTGGTTTCTTTCAGGGCCCGGAGGTGCCTGCGCCGCGCTTGGCTTTGCTTTCCGCCGCCCCAGGAGAC<br>CCGGGACTGTGGTTTCCGCTCGCCACATCCCAGCCTGGTGCGCACACAAGAGCCTGGCGAGCTTCCCTCGCGCGCTTACAGTCAA<br>CTACTTTGGGCCTCGGTTTCCCTGCTCCTTGTAGATCAGAGAAGGGACGGGCGAAATGCCTGCGAGGGAGGGTTGGCGAATGGGT<br>TGGTTGGTGGCAAGACTGCAGTTCTTGTACATGGACGGGGGTTGGGGGGTCAACACTGGAAGAACTCCTGCCTGACGCCAAGAGC<br>CACCCGCTTTCCAGCTCGTCCCACTCCGCGGATGTTTACCCACCTTCATG |
| 144 | chr12:<br>113657800-<br>113658300 | TTTGGGGCACCCAACCCTTCCCAAGCCTCGGTTTTCCCGATCTTGTGGGATCCTTGCGGCGCGAATGGGGTTGGAAGCACCTTGG<br>AAGCTACAGAGTACCGGGTCGGGACAATTTCCGGCACTGCCCCAGTTCAGTGGTTTATAGAAAATTTCTTTCTCTCTCTCAGGTC<br>CACTAAGACCGAGAGAGAGAGAGAAGTCGACTCTGGCACACCCGGGCGAGGGGCTGCCGGGATTCGGGAGCTGGCGCGGTTGATT<br>TTTTCCGAGAATCCTCCACTTGGGGTGACGTCGGGCAGCGCGCGCGGGCCGTGAGGTTAATGCCCAGGCTTTTCTCTAAAGCGTC<br>CGGGAATGATCCGGCGAATAAAACGGGTGTCTGCAAAGTTAATGAATTGTACAAGGAGGCTGAGGGTGGGGACTTCGACCCGGGG<br>AGCCAGAGGCGGTTCTGGTGGACGCTTCCCCGTGCGCCTAGGGGTGCGCTGGGCTTTCCCAGCCGAGGTCTGCAG |
| 145 | THEM233 | CCAGACAGTTAAGGTAAAACGTTGAAGTCAAGAGGAAGTAGTGAGTCTGTTGCCAACTGGATAGGGTTGGTCCTGTCCCATCTAA<br>ATGTATTAGAATTAAGTGGCTTTTAAAAATGAGCTGGTCATCTTCAGCCCACGGGCTGGCCAATTTGGAACTTAATGGGCCTTTG<br>CGTCCTCCTTCCCTGAGCCTCCTTTTATTCCAGACTTCTCAGTGTGAGTCTGTGCGTCCCTCCGACGATCTCAGGGAGTGGGGTG<br>CCTTCATCTGCCTGTTCCCTGTTCCTCAGGCTGACGCTCCCGCTGTCCTCCCCGCCTCCCCTCACTCCTTTTCTCCCTCCCTTCC<br>TCCTTGTGGGGAGGCTCTTGGCCAGGGTCCCTGAGCCCGGGCGGGTGCTGGCAGAGGACGCAGAAGGGGTGAGGTCACGTCTCCC<br>TTGAGCCCCGAGCCGCTGGCTTTTCAGAGCCTCGCCACAAGCCGGCGGCCAGAGCCCCAGACCACACAGACCGTGCGCTCCTCCG<br>CCCTCCCGGCGCCGCCGGCCTCGCCCATGTCTCAGTACGCCCCTAGCCCGGACTTCAAGAGGGCTTTGGACAGCAGTCCCGAGGC<br>CAACACTGAAGATGACAAGACCGAGGAGGACGTGCCCATGCCCAAGAACTACCTGTGGCTCACCATCGTCTCGTGTTTTTGCCCT<br>GCGTACCCCATCAACATCGTGGCTTTGGTCTTTTCCATCATGGTGAGTGAATCACGGCCAGAGGCAGCCTGGGAGGAGAGACCCG<br>GGCGGCTTTGAGCCCCTGCAGGGGAGTCCGCGCGCTCTCTGCGGCTCCCTTCCTCACGGCCCGGCCCGCGCTAGGTGTTCTTTGT<br>CCTCGCACCTCCTCCTCACCTTTCTCGGGCTCTCAGAGCTCTCCCCGCAATCATCAGCACCTCCTCTGCACTCCTCGTGGTACTC<br>AGAGCCCTGATCAAGCTTCCCCCAGGCTAGCTTTCCTCTTCTTTCCAGCTCCCAGGGTGCGTTTCCTCTCCAACCCGGGGAAGTT<br>CTTCCGTGGACTTTGCTGACTCCTCTGACCTTCCTAGGCACTTGCCCGGGGCTTCTCAACCCTCTTTTCTAGAGCCCCAGTGCGC<br>GCCACCCTAGCGAGCGCAGTAAGCTCATACCCCGAGCATGCAGGCTCTACGTTCCTTTCCCTGCCGCTCCGGGGGCTCCTGCTCT<br>CCAGCGCCCAGGACTGTCTCTATCTCAGCCTGTGCTCCCTTCTCTCTTTGCTGCGCCCAAGGGCACCGCTTCCGCCACTCTCCGG<br>GGGGTCCCCAGGCGATTCCTGATGCCCCCTCCTTGATCCCGTTTCCGCGCTTTGGCACGGCACGCTCTGTCCAGGCAACAGTTTC<br>CTCTCGCTTCTTCCTACACCCAACTTCCTCTCCTTGCCTCCCTCCGGCGCCCCCTTTTTAACGCGCCCGAGGCTGGCTCACACCC<br>ACTACCTCTTTAGGCCTTTCTTAGGCTCCCCGTGTGCCCCCCTCACCAGCAAAGTGGGTGCGCCTCTCTTACTCTTTCTACCCAG<br>CGCGTCGTAGTTCCTCCCCGTTTGCTGCGCACTGGCCCTAACCTCTCTTCTCTTGGTGTCCCCCAGAGCTCCCAGGCGCCCCTCC<br>ACCGCTCTGTCCTGCGCCCGGGGCTCTCCCGGGAATGAACTAGGGGATTCCACGCAACGTGCGGCTCCGCCCGCCCTCTGCGCTC<br>AGACCTCCCGAGCTGCCCGCCTCTCTAGGAGTGGCCGCTGGGGCCTCTAGTCCGCCCTTCCGGAGCTCAGCTCCCTAGCCCTCTT<br>CAACCCTGGTAGGAACACCCGAGCGAACCCCACCAGGAGGGCGACGAGCGCCTGCTAGGCCCTCGCCTTATTGACTGCAGCAGCT<br>GGCCCGGGGGTGGCGGCGGGGTGAGGTTCGTACCGGCACTGTCCCGGGACAACCCTTGCAGTTGCGCTCCCTCCCCCACCGGCTC<br>ACCTCGCCTGCAGCTGGGCCACGGAACTCCCCGGCCACAGACGCA |
| 146 | NCOR2 | CTCTCTGGGCCTTAGGAAAATGGAAATGACACCTGTACCTGCCCTTCCAGGACTGACAGGAGGGGCTGCTCCATGAAACCTCACT<br>GCTGCGGTCATAATGTCATTATCTTTTGCCTTAAAGGGATTTCTTCTGCACCAGCACCTAAAGTGGCAGCCCCTTACCCTTGGCC<br>ATCAGCTGGACCCTGGTGCTCTCCTGGAGCCCAAAACCTCTGTTTTGTGTTGCATCCTGCTGACCAGCCACAGTCCACACCCATC<br>TGAGTGTCTGAGCAGAACAGCCCAGAGGCCACACCAGGATGGCTTTCCACCGGTCACCTTCCCCCACCCACTCATAAACCCTGCG<br>TCTCTGGGGGAGAGGGTGGCGAGGTCCCCTCCCCACATAGATGGAAACACTGAGGCCTGATTCATGGTGCCCCCTGTGAAGCGCC<br>TCATGGCCAGCACCGGGGGGCAGCAGGCCAGGGCGGGGACACATACCCGGTTCTCGTCGTAGATGATCTGCACCAGGCTGCGGTG<br>CTTCGACTCGATGGGCGGCGGTGACACGGGCTTCTCAGGCTCGGGCGGCTTGGCAGCCTCCTCCTCCAGCTGTTGCTGTGGGGAG<br>AGGCA |
| 147 | THEM1<br>32C | CTTGAAAACTCCCAGCCCCCTTTGTCCAGATGGGGATGGAGGTGGCCAGGCTGCCCCGTTGATTGTGTGCCGAGGAGCCCTCCCC<br>GGGAAGGCTGTGATTTATACGCGCAGGCTTGTCACGGGGTGAAAGGAAGGGCCACTTTTTCATTTTGATCCAATGTTAGGTTTGA<br>AAGCCACCCACTGCTGTAAACTCAGCTGGATCCGCGGGCCGTGATTAAACACATTGCCCGCTTTGTTGCCGAGATGGTGTTTCGG<br>AAGGCGCTGTGAATGCACTTCCCTTTGCGGGGCTCACACAGACAAGATGTGTGTTGCAAGGATGAGGCGCCTGCTCGGCCTCCAG<br>CCCAGGGCCGGGAAGGGAGAAGGTGCTGTGCGTCGCTGCCTGTGTCGCCCGCGGCTCTCC |

TABLE 4B-continued

| SEQ ID NO | GENE NAME | SEQUENCE |
|---|---|---|
| 148 | PTGDR | CGCGTCAGGGCCGAGCTCTTCACTGGCCTGCTCCGCGCTCTTCAATGCCAGCGCCAGGCGCTCACCCTGCAGAGCGTCCCGCCTC<br>TCAAAGAGGGGTGTGACCCGCGAGTTTAGATAGGAGGTTCCTGCCGTGGGGAACACCCCGCCGCCCTCGGAGCTTTTTCTGTGGC<br>GCAGCTTCTCCGCCCGAGCCGCGCGCGGAGCTGCCGGGGGCTCCTTAGCACCCGGGCGCCGGGGCCCTCGCCCTTCCGCAGCCTT<br>CACTCCAGCCCTCTGCTCCCGCACGCCATGAAGTCGCCGTTCTACCGCTGCCAGAACACCACCTCTGTGGAAAAAGGCAACTCGG<br>CGGTGATGGGCGGGGTGCTCTTCAGCACCGGCCTCCTGGGCAACCTGCTGGCCCTGGGGCTGCTGGCGCGCTCGGGGCTGGGGTG<br>GTGCTCGCGGCGTCCACTGCGCCCGCTGCCCTCGGTCTTCTACATGCTGGTGTGTGGCCTGACGGTCACCGACTTGCTGGGCAAG<br>TGCCTCCTAAGCCCGGTGGTGCTGGCTGCCTACGCTCAGAACCGGAGTCTGCGGGTGCTTGCGCCCGCATTGGACAACTCGTTGT<br>GCCAAGCCTTCGCCTTCTTCATGTCCTTCTTTGGGCTCTCCTCGACACTGCAACTCCTGGCCATGGCACTGGAGTGCTGGCTCTC<br>CCTAGGGCACCCTTTCTTCTACCGACGGCACATCACCCTGCGCCTGGGCGCACTGGTGGCCCCGGTGGTGAGCGCCTTCTCCCTG<br>GCTTTCTGCGCGCTACCTTTCATGGGCTTCGGGAAGTTCGTGCAGTACTGCCCCGGCACCTGGTGCTTTATCCAGATGGTCCACG<br>AGGAGGGCTCGCTGTCGGTGCTGGGGTACTCTGTGCTCTACTCCAGCCTCATGGCGCTGCTGGTCCTCGCCACCGTGCTGTGCAA<br>CCTCGGCGCCATGCGCAACCTCTATGCGATGCACCGGCGGCTGCAGCGGCACCCGCGCTCCTGCACCAGGGACTGTGCCGAGCCG<br>CGCGCGGACGGGAGGGAAGCGTCCCCTCAGCCCCTGGAGGAGCTGGATCACCTCCTGCTGCTGGCGCTGATGACCGTGCTCTTCA<br>CTATGTGTTCTCTGCCCGTAATTGTGAGTCCCCGGGCCCCGAGGCAGCAGGGCACTGAGACTGTCCGGCCGCGGATGCGGGGCGG<br>GAAGGGTGGA |
| 149 | ISL2 | CTTCCGCCGCGGTATCTGCGTGCCCTTTTCTGGGCGAGCCCTGGGAGATCCAGGGAGAACTGGGCGCTCCAGATGGTGTATGTCT<br>GTACCTTCACAGCAAGGCTTCCCTTGGATTTGAGGCTTCCTATTTTGTCTGGGATCGGGGTTTCTCCTTGTCCCAGTGGCAGCCC<br>CGCGTTGCGGGTTCCGGGCGCTGCGCGGAGCCCAAGGCTGCATGGCAGTGTGCAGCGCCCGCCAGTCGGGCTGGTGGGTTGTGCA<br>CTCCGTCGGCAGCTGCAGAAAGGTGGGAGTGCAGGTCTTGCCTTTCCTCACCGGGCGGTTGGCTTCCAGCACCGAGGCTGACCTA<br>TCGTGGCAAGTTTGCGGCCCCCGCAGATCCCCAGTGGAGAAAGAGGGCTCTTCCGATGCGATCGAGTGTGCGCCTCCCCGCAAAG<br>CAATGCAGACCCTAAATCACTCAAGGCCTGGAGCTCCAGTCTCAAAGGTGGCAGAAAAGGCCAGACCTAACTCGAGCACCTACTG<br>CCTTCTGCTTGCCCCGCAGAGCCTTCAGGGACTGACTGGGACGCCCCTGGTGGCGGGCAGTCCCATCCGCCATGAGAACGCCGTG<br>CAGGGCAGCGCAGTGGAGGTGCAGACGTACCAGCCGCCGTGGAAGGCGCTCAGCGAGTTTGCCCTCCAGAGCGACCTGGACCAAC<br>CCGCCTTCCAACAGCTGGTGAGGCCCTGCCCTACCCGCCCCGACCTCGGGACTCTGCGGGTTGGGGATTTAGCCACTTAGCCTGG<br>CAGAGAGGGGAGGGGGTGGCCTTGGGCTGAGGGGCTGGGTACAGCCCTAGGCGGTGGGGGAGGGGGAACAGTGGCGGGCTCTGAA<br>ACCTCACCTCGGCCCATTACGCGCCCTAAACCAGGTCTCCCTGGATTAAAGTGCTCACAAGAGAGGTCGCAGGATTAACCAACCC<br>GCTCCCCCGCCCTAATCCCCCCCTCGTGCGCCTGGGGACCTGGCCTCCTTCTCCGCAGGGCTTGCTCTCAGCTGGCGGCCGGTCC<br>CCAAGGGACACTTTCCGACTCGGAGCACGCGGCCCTGGAGCACCAGCTCGCGTGCCTCTTCACCTGCCTCTTCCCGGTGTTTCCG<br>CCGCCCCAGGTCTCCTTCTCCGAGTCCGGCTCCCTAGGCAACTCCTCCGGCAGCGACGTGACCTCCCTGTCCTCGCAGCTCCCGG<br>ACACCCCCAACAGTATGGTGCCGAGTCCCGTGGAGACGTGAGGGGGACCCCTCCCTGCCAGCCCGCGGACCTCGCATGCTCCCTG<br>CATGAGACTCACCCATGCTCAGGCCATTCCAGTTCCGAAAGCTCTCTCGCCTTCGTAATTATTCTATTGTTATTTATGAGAGAGT<br>ACCGAGAGACACGGTCTGGACAGCCCAAGGCGCCAGGATGCAACCTGCTTTCACCAGACTGCAGACCCCTGCTCCGAGGACTCTT<br>AGTTTTTCAAAACCAGAATCTGGGACTTACCAGGGTTAGCTCTGCCCTCTCCTCTCCTCTCTACGTGGCCGCCGCTCTGTCTCTC<br>CACGCCCCACCTGTGTCCCCATCTCGGCCGGCCCGGAGCTCGCCCACGCGGACCCCCGCCCTGCCCCAGCTCAGCGCTCCCTGGC<br>GGCTTCGCCCGGGCTCCTAGCGGGGAAAAGGAAGGGGATAACTCAGAGGAACAGACACTCAAACTCCCAAAGCGCATGATTGCTG<br>GGAAACAGTAGAAACCAGACTTGCCTTGAAAGTGTTTAAGTTATTCGACGGAGGACAGAGTATGTGAGCCTTTGCCGAACAAACA<br>AACGTAAGTTATTGTTATTTATTGTGAGAACAGCCAGTTCATAGTGGGACTTGTATTTTGATCTTAATAAAAAATAATAACCCGG<br>GGCGACGCCACTCCTCTGTGCTGTTGGCGCGGCGGGAGGGCCGGCGGAGGCCAGTTCAGGGGTCAGGCTGGCGTCGGCTGCCGGG<br>GCTCCGCGTGCTGCGGGCGGGGCGGGCCCGGTGGGGATTGGGCGC |
| 150 | chr15:<br>87750000-<br>87751000 | AGTTTGGGGAGCCTTTTCTCCATTTGAGAAAAAACAAACTTACAGCGAGGGGTGAGGGGTTAGGGTTTGGGATTGGGGAAAATGT<br>GGGTGGGGAGCCCCCCCAAGGAAGTGAGGAGGGGGCTGCAAGGATTACACCTGGGCATACGTTTCCCTAGAAATCACATTCATTG<br>TATTTTTATAATTTATTCTAAATCTTTCATGCGAAGAAAGTCAGTAGTGAGTGTTAGTACTGGTGGCCCTCCTGATCACACTTGC<br>ATCTCTTGAGTGTGCCTTAAAGGTCTTGGGAATGGAAAATATAAAAACTGCTTCGTGATGCGTCATCTTTATCCCCCACTCCCCC<br>ACCCATTCCAATATATTTTCTACTTCCAGCCTAAATTCGGGGCCCCCTACCGAGGCCGGCCATGATCTTGAGGGCGGCATAGGGG<br>AGGCCGCGCTCTGTCCACCCCAGCCTGGTGATGCCGTTCGCTTCTTGTGCCCGGTATTGTGGGCTACATGCCTTTCCGGCGTACG<br>GAGCTGAGCGTCCAGGCCAGTGCCCCTCAACCTCTCAGTAATGTTTACCCGAGGCCGTCGTGCAATGAGACTATTCGCATGGCAT<br>TGTCAACGCGGCGGCGCGCGTCTCGGCCCTCCGCGGCTTGCCAGACTGTCCTGCAAACCACCTCACCCGTCTCTTTGGCGCAG<br>GAGACTCAGGCTGTAACCGGAGAAAACACTTCACCCTGGAACCCTAACTCAGGTCCTGGCAAAAGATGCGAGAGGAAGACTTGCT<br>CTCTTAATAAATCTCGGCCGCCCGCACATCTGGCCCCTAGACCTGCTCGGTAGAGGACTGGCTGGTGGATGCGCGGTCCAGGCCG<br>TGGGCACTCGACCCACCTCTATTTTCCTTCCCGAGGCGCCCCTGGATTACCACTTTCGGTTTGCGCTTACATCCGGGATGTCGAA<br>TTTCCCAGGGAATCATAATTATTTTATCTATAATTTATTCTAACCCCAAGGTTCCAAGAAAATCT |
| 151 | chr15:<br>87753000-<br>87754100 | ACATTCCTTCTAAAATGTGGGCTTTCTGTGTACATGGGCGCGCATTCCCAGGACTCGGTTCCCTGGGTGGAATTCACCCAGGAAT<br>ACAATCGATTTTCTGAACCTGCGTAAGGCCACAGGCAGCTCTGAAAATGAAAGCGTTTGCTAAGTGGGGAGATCTCACCGATCG<br>AACGTTTAAAAATGGCTTTGTCTTCATTCAGCTCTCCCGATTTATTCTGTGTTTTACAAATAGAAGCTCAGAGCTTCTGTCGCCC<br>AGTCCTTGCATGACTCATGGCGGTGGCCACACGGGTTTCAGGGATAACGGGATGTTTAGAAAATCGCTGCATATCGGAGTTTCCT<br>AGCACGTTCCATTTATACTGAACGCAGGCGGCCGCTGAAAATCCAGCCTCGACTCTTGCTAATGACTGGGTAGGACCCTCGGGGT<br>CCTGCGACGGTGCTGGAGGGTGTTCCCGGCTCCGATGTGGGGAGGCCTGCGCGGGGACTAGGTTCTCGAGAGGCGAGCGGGCGCG<br>CCAGAGAACCCGAGACTGCTGCGGGGCCGGATGCGGGATCCCTGGGCTGCGGTTCTACGCAGAAACGCCAATGGCCATGCCTCCC<br>CAGCTCCTCCCAGCCCCAGTCACTAGGCCGGCGCCTGGCCCGGAGATCCTCCCAGAGCCCTGGCGGTGCCATCATGCCGGAGAAG<br>ACAAGCTCGGCCCCGCTGGAATTCGCTCCAAACACAGATGCTCATTTTTGGAATATTCTAGAAAAATAACAAGATCTTGTTTGTC<br>GTTATGATTCACGGGAGGTAACTGATGGGAGGGCCATTTACATGAGGGCAGACACTGTGGGGCGAAGGTGACTTCTGGACGTAGG<br>CTTTAAAGTAGGAACGGCTCCAAATTCCCAATATCTCCGGCCTTACCGGTTGCAAATCGGACCCCTGCGGGAAAACCAGACACTT<br>CTGTTTCGTGGCTTTCGGGCTGCCTCCAGCCCACGCAGGCTCGTTTAGTCCCCGTGGAGTCAGCCCCGAGCCTTCCTAGTCCTGG<br>AACAAGGGCTCCAGGTCGCGGCCGCGGGAAGCCGCCAAGAGGGCGGGGAGTAGGGATTCCCTCCAGCTCCGCAGGGCATC |
| 152 | NR2F2 | TCCTCCTCGGCCTCAGATGTCGTCCCACCTGCCCACGAGCAGGGAACCTGGAACCCACTCTCCCGGCAGTCCCCAGCGGGTTCCG<br>CCACCCGGCGGCCGCCCCTGACACCGAGTGGGTGGGAGGAAGAGGCAGCTGGCGGGGATGGGCCATTGAGACCTCTTGAAAAATA<br>TTAAAAGACAGGATGGGTAGAGATTTCTCCGGGAGAAAGTTCGAGGGTGCATCGGGTCGCGGCTGGGAGGAGTACCCGAAATGCC<br>AGCAGGAGAAATGCAACCTGTTTAGGCCACACCTTCAATCCCCGAGGCTGTCTGGAGAGACTGCGTGCGGGGGACTTGCCGGCGT<br>TCCCACACCGCGCCTGCAATCCACTCCCGCGGCTGCCTGGCCTCTGCCACTCGCGGCTTGAAGCCAGTGGCTCTCAAGCCCTCGG<br>CCCCGCGGCGGCCCGCGCAGCCTTCACCCGGCGCCGGCACCACGAAGCCTGGCCGCAGTGGACTCCCCGCAGCTCGCTGCGCCCT<br>GGCGTCTCCCGTCGAGGAGGGAGGGACGGAGGCCTGAGCCGGGAGCTCCCTGGCGGTGGTCGGGCCGCCCCCCTTGAGGCCTGCT<br>CCCCCCTCTCGGCCTCGCCAAATCCCTGAAAGCCCAGTCCCCCTTCGTCACCCCGGGGGCTTCTAATCACTCGGTATCGATTTCC |

TABLE 4B-continued

| SEQ ID NO | GENE NAME | SEQUENCE |
|---|---|---|
| | | CTAACTCTTTTCATCCTGTTGAAGACACATCTTAAAACACTCCAGCCCGGAGTGTGCTCTGGGCTTTATCCACACTAATAAAATG<br>ATTTACCCTTCTCTCCGCGCTCTCCTCACAGAGGAAAATCGTTCGAGCCCCGGCTATTTGTGTGTGATCAGTAAATATTTAGTGC<br>GCTGACATCCTTAGCTGGGCTTCGGATCGATTCGGGGCCCACCGGGAGGTGCGCACGGTCCGGGCGGGGCCGCGCCGAGCTCGCC<br>GAGGGGGCTCCTCCCGCCCTCGCCGCCGGCCGCTGATTTACGGCCCCTGCAACCAGCTAAGGGGGGCGAAAGCGCGCCTGGAAAA<br>TTGGCTTTTCAACCTTTTACTTTTGACATTCAGCCACTTCCCCAGGCTCTAATTCTCGCCCGCACTCCTCCCTCCCGCCCTACTA<br>AGGGTTGCCCTGTGCGCCCTGCGAGCCCTTCCAGCAGCAACGCGCGGCGCTCGCGCCCCCTCGGCCCGGGGACCACCTATCACAG<br>CCCTGAGCCGCGACGCGGGGAGGCCCCGGCCCCTGCTATGGGGGTCGCCTCCTTCGAGGAGAGATGCTCTCCGCCCGCCCACACC<br>TCTGAGGGAGGAGAGGGGGTGGAGAAGCCCAGAGCTGCATCTGCTGGATGACGAGCCGCTCTCCCTGCTACCCTTTCTCCGACCC<br>GTCGGCCTTTCTCCTACTCTGGAGACTGATCCTCGACGTCCATCGGGCCGGATGGCGTCGGGTGGAAGCGTTACTTTCCTCGCAG<br>AAAAACTCCTCCTCTTTCCTAAGATCAGAAAAAGCGCTTAGCTTGGAATTGTTAG |
| 153 | chr16:<br>11234300-<br>11234900 | CCTAGGCATTCTCAGCCCGTTTTGCTGGAGGGGGCATTTGAGGCCTGGCCAGCTTAGCCAGCCTACAAGGAGTGTTACTGGGGTG<br>AAAACAGCCAGCGGGGACCAGTCTGCTTGTGGCCCGCCAGGTGCCTGGGATGGGGAAGCAGCAAATGCCCACCTTCCTGCCCAAC<br>CCCCTCCTCCCTCTTCATGGGGGGAACTGGGGGTGGCAGCGGCTGCCGGGTGCGAGCGGGCTCAGGCCTGTGGCCCTGCCTGACG<br>TTGGTCCCCATCAAGCCATGTGACGAGACCAGGCCACAAGAAAGAGGTTTCAACAAGCGCTGCCTCCGCGGCCGCGTCTATCTCA<br>GTCTGACTACCTGGAAGCAGCACTCCACCCTCCAGCCCAGCGGCCCTCGGCTCAGCTGCCAGGTCACCGGCAACCCCGGGAGCGG<br>TGGGGCAGGGGCTGCTCCGCCAGCCTCTGTGATGTTCAGGCCGGGCTGCACCAGCCCGGGACCCCTAGGTG |
| 154 | SPN | GCACTGGTTCCCCTTTACCTGAGCCAACAACCTACCAGGAAGTTTCCATCAAGATGTCATCAGTGCCCCAGGAAACCCCTCATGC<br>AACCAGTCATCCTGCTGTTCCCATAACAGCAAACTCTCTAGGATCCCACACCGTGACAGGTGGAACCATAACAACGAACTCTCCA<br>GAAACCTCCAGTAGGACCAGTGGAGCCCCTGTTACCACGGCAGCTAGCTCTCTGGAGACCTCCAGAGGCACCTCTGGACCCCCTC<br>TTACCATGGCAACTGTCTCTCTGGAGACTTCCAAAGGCACCTCTGGACCCCCTGTTACCATGGCAACTGACTCTCTGGAGACCTC<br>CACTGGGACCACTGGACCCCCTGTTACCATGACAACTGGCTCTCTGGAGCCCTCCAGCGGGGCCAGTGGACCCCAGGTCTCTAGC<br>GTAAAACTATCTACAATGATGTCTCCAACGACCTCCACCAACGCAAGCACTGTGCCCTTCCGGAACCCAGATGAGAACTCACGAG<br>GCATGCTGCCAGTGGCTGTGCTTGTGGCCCTGCTGGCGGTCATAGTCCTCGTGGCTCTGCTCCTGCTGTGGCGCCGGCGGCAGAA<br>GCGGCGGACTGGGGCCCTCGTGCTGAGCAGAGGCGGCAAGCGTAACGGGGTGGTGGACGCCTGGGCTGGGCCAGCCCAGGTCCCT<br>GAGGAGGGGGCCGTGACAGT |
| 155 | chr16:<br>85469900-<br>85470200 | TGTCCGACAGGCACACAGAGCGCCGCCAGGCACGGCCCTCATTCTTCACCCCGAGCTCCCGCAAGGTCGGCGAGGAGGCTGGAGC<br>AGCGGGTAGGAAGCGGGCCGAGGCTCCCCCGACGCTGGGCCGCAACTGTCATCGCAGATCCCTGAAAAACGAGCTCTGTAATCGT<br>TGCCGTCAGCGGGTGTACAATTGCAGCCTTATGTTTCCTGCCGCTGTTTACCTTCCTGAGCGGCGCCCAGAGATGCACACACGCT<br>GCCCTGAAGCGGGACGTGACCTCTGGGCACCTGTGAGGTCCTGGG |
| 156 | SLFN11 | GTCGGCTCCTGCGCTCCCAACGGGGTGGCCGTTTCCTTCCTCGCACCCTCTTCTCTCCCGGTGCCTGCGGTCCCACCTTCCAGAT<br>ACCCCTCGGAGAGTCCAGCTGAGCTCTCGCCAGAGCTTTCCCCTTCCAACCCGCTCGACTTGCCCAGATCCCAAGCTGGGCTTCT<br>CTCTCCATCGCCCCAGAAAGTGGGTCTTGGAGACCGAGGCAAGAATTTGGGCCTCCGCTTCTGTTCCAGACCCCGGACCCCTTGC<br>CAAAATGCGGCAGATGTGCAGATTGGGCCGCGCTTGGTTCCTGGCTGGGTTTATGGAGCCTGCGGCTGAGGCAGGCTCCGCAGAC<br>CCCGAGCCAGAGTGGGATTTAACGGCGGCCGGTGCGCTGTGCTTGGTCAACCCCGGTAACCGTCACGCTGCTAGTGATATGAAAA<br>AAACCTGCCAGCGTTCTGCTTTTCTGCCCCGCTGCAGTCTTTAGCACCCGCCAGGATTCTGTCCGAGTGTTTGGA |
| 157 | DLX4 | TTTAGTGTGTGCATAAAACATCCCAGCTAATCTCAAATAGACTTTTCCTGAGCAGAGGCTGAAATTTGCAAGTAATGCAAAGAAG<br>ACTCCGGGAGAGCGTCGCCGATGGTGGAGCGGGAGACGGGCGTGGGGAGCCCCACTGCAGTGCTGGGATCGAAGTGGTGCTGACC<br>CCAAGACCTCTCCCCTCCTCCTCCCCCGGGAGCTTCTCCAGGGTTATTTGGGAAATGAGGGGGAACTCCAATCCCTGAGAAAGCG<br>CTCAGGGGCTTGCTGAGGTGAGCGCAAATGGAAGCACAAGGCCGGGCTGGCCGTGGGCTCAGTAACCAGTCGGCTGCCCGGCTTG<br>CGCCAGCACTAAATGCTCGATCAGAAAGAGAAAAGAGGCGCAATAATTCCAAATTTCAGGAAAAGTCAAATCGGAGAGGGGGGA<br>CGCAGGTCTCTTCAGACTGCCCATTCTCCGGGCCTCGCTGAATGCGGGGGCTCTATCCACAGCGCGCGGGGCCGAGCTCAGGCAG<br>GCTGGGGCGAAGATCTGATTCTTTCCTTCCCGCCGCCAAACCGAATTAATCAGTTTCTTCAACCTGAGTTACTAAGAAAGAAAGG<br>TCCTTCCAAATAAAACTGAAAATCACTGCGAATGACAATACTATACTACAAGTTCGTTTTGGGGCCGGTGGGTGGGATGGAGGAG<br>AAAGGGCACGGATAATCCCGGAGGGCCGCGGAGTGAGGAGGACTATGGTCGCGGTGGAATCTCTGTTCCGCTGGCACATCCGCGC<br>AGGTGCGGCTCTGAGTGCTGGCTCGGGGTTACAGACCTCGGCATCCGGCTGCAGGGGCAGACAGAGACCTCCTCTGCTAGGGCGT<br>GCGGTAGGCATCGTATGGAGCCCAGAGACTGCCGAGAGCACTGCGCACTCACCAAGTGTTAGGGGTGCCCGTGATAGACCGCCAG<br>GGAAGGGGCTGGTTCGGAGGGAATTCCCGCTACCGGGAAGGTCGGAACTCGGGGTGATCAAACAA |
| 158 | SLC38A<br>10 | CATGGTGCTTCAGGAAGGGAGGGGACGAGAGCCCTGGGCTTGTGGTGTCCACGTGGACAGCTAATGAGGAGCCTTGCCGATGAGG<br>AGCATGCGTTCCCGACGGGGCGGCCGAATGCGGAAGGAGCCGCCATTCTCTCCGCCCTGACCGCGGGATTCTCTGCAGCAGATGA<br>GAAACGGCGCTGACTCAGCAGGGTCCCTCCCAGGCCCCGAGCGGTCATCTGGTGACCCCCGCGCTTCCCCCACGGCCCAGCCGGA<br>GAAGGGCAAAGGGAAGTCCCGGCTCCAAGGCGCACCCAGAGATGCGGTGCATGTGGCAGGATGGCCCAGCCCCGTCGGCAGCCCC<br>AGCTTCCTGCCCCTGGTTTCCTTCCTCCCACGGGCTACAGGCCTCTGATGAGCTTTGGAAAGCAGGAAACACACAGGCTAGTAAC<br>TATGAATGGGTCCAAAAAACACTCCTTATTACTTTAAACTACTTAGGAAGAAGCACAGCGTTGCCAAACGCCAGA |
| 159 | S1PR4 | GCGCGGGGGGCCGGAGGATGGCGGCCTGGGGGCCCTGCGGGGGCTGTCGGTGGCCGCCAGCTGCCTGGTGGTGCTGGAGAACTTG<br>CTGGTGCTGGCGGCCATCACCAGCCACATGCGGTCGCGACGCTGGGTCTACTATTGCCTGGTGAACATCACGCTGAGTGACCTGC<br>TCACGGGCGCGGCCTACCTGGCCAACGTGCTGTCGGGGGCCCGCACCTTCCGTCTGGCGCCCGCCCAGTGGTTCCTACGGGA<br>GGGCCTGCTCTTCACCGCCCTGGCCGCCTCCACCTTCAGCCTGCTCTTCACTGCAGGGGAGCGCTTTGCCACCATGGTGCGGCCG<br>GTGGCCGAGAGCGGGGCCACCAAGACCAGCCGCGTCTACGGCTTCATCGGCCTCTGCTGGCTGCTGGCCGCGCTGCTGGGGATGC<br>TGCCTTTGCTGGGCTGGAACTGCCTGTGCGCCTTTGACCGCTGCTCCAGCCTTCTGCCCCTCTACTCCAAGCGCTACATCCTCTT<br>CTGCCTGGTGATCTTCGCCGGCGTCCTGGCCACCATCATGGGCCTCTATGGGGCCATCTTCCGCCTGGTGCAGGCCAGCGGGCAG<br>AAGGCCCCACGCCCAGCGGCCCGCCGCAAGGCCCGCCGCCTGCTGAAGACGGTGCTGATGATCCTGCTGGCCTTCCTGGTGTGCT<br>GGGGCCCACTCTTCGGGCTGCTGCTGGCCGACGTCTTTGGCTCCAACCTCTGGGCCCAGGAGTACCTGCGGGGCATGGACTGGAT<br>CCTGGCCCTGGCCGTCCTCAACTCGGCGGTCAACCCCATCATCTACTCCTTCCGCAGCAGGGAGGTGTGCAGAGCCGTGCTCAGC<br>TTCCTCTGCTGCGGGTGTCTCCGGCTGGGCATGCGAGGGCCCGGGGACTGCCTGGCCCGGGCCGTCGAGGCTCACTCCGGAGCTT<br>CCACCACCGACAGCTCTCTGAGGCCAAGGGACAGCTTTCGCGGCTCCCGCTCGCTCAGCTTTCGGATGCGGGAGCCCCTGTCCAG<br>CATCTCCAGCGTGCGGAGCATCTGAAGTTGCAGTCTTGCGTGTGGATGGTGCAGCCACCGGGTGCGTGCCAGGCAGGCCCTCCTG<br>GGGTACAGGAAGCTGTGTGCACGCAGCCTCGCCTGTATGGGGAGCAGGGAACGGGACAGGCCCCCATGGTCTTCCCGGTGGCCTC<br>TCGGGGCTTC |

TABLE 4B-continued

| SEQ ID NO | GENE NAME | SEQUENCE |
|---|---|---|
| 160 | MAP2K 2 | GGGCGGGTTGCCACACTGTCCCCTTTCTGCATGGGAGGAAGGGGGCTCGAGAACTGAGTCAGCCACACAAAACGAGGATGGACAG AACTCCTGAGTAGCGAGGGTGCCTGCCGGGCGCGAGGAGGAGGGGGAAGACGAGGAAGACGAGGAGGAGGAATAGGGAGCACCAC ATGACAGAGGGGCTGCCTCAGACCACAAAGCGCTTCCTCATCCTTTCCTCGCCCTTTGATGCCGCCGGCAACGTGACTCTGCGAG CAGCGGGGCAGACGCCAGGTCTCCCTCGCAGGCGGGAAAGGGGCTCCAAGGCGGGTGCTGCCTTGCTCGGGTCACATGGCTACGT GGGGGCCTTGCTCAAATTCACTTCCTGCCTTCATTACAAAACTGTCAAAGGGGATCGCACGTTTGCAGGGTGTCACCCAAGCATT CTGGTTTTGCAAACGACGCTGTGCGGCAGGCGGTCTGATACCTGATGAGCTCGGTGTGGCGGGGTCGGCAGCATTTCCTCCGGGG TTTTGAGCTCTGGCCACTTCTCCTTTTGTTCCACCCAATCTCACCCACTTCTGGGCTTCGAGGCCAGAGTGTCTTAACAAGGGGG CACGT |
| 161 | UHRF1 | GAGCGAGACTTTGTCTCAAAAAAAAAAAAAAACCAAATAAATTGAAAGCTGAGAAATTCAGAGCACAAGAAGACAAGCGCGCCCCC TCTTTTAGCTGTCAACATGGCGGAGCCGTCCCTGGTGACGCAGCCTCCAAAGGCCTCCCTGTGCCCTCCTGAGACCGCAAGAGGG AAAGTGGCAGCGACAGTGATCGTGGTGTCTTTGTGGCGGTTGTGTTGACCTCACTGACCCCCGAAGTGCCGCTCTAGGGTCTGTC CTCAGCGGTGACCCGGCCGGGTCGAAGGGCAGAGTTCCGCTGTCACTAGCCCTCCACCCGTCCTGTGTGCTGGGATGCCCTCGCG GCGCCGTCCACGCCACCGCCGCCCCCTCTTGTGGGTTCTGTCTCCTCCGTGTCTAGGATCCTCCTGCATCCGTTTTTCCTTCCTC CCTTCTCTCCCTCCGTCTGTCTTGCCCGCACCTGAGGTTGTCGCAGAGGCGCTGAGACGGGCCAGCAGGAGCTGT |
| 162 | DEDD2 | TGCTGTCCCGGTCCTGTCGCAGTCCTCAAAGATGCTAGAGTGACAGTCCTCTAGGGGTAGAGATGGTCGTCCTCCCAGGAGAAGG TGGCCCGGAGACTTGGAGGTGGGATCAATCCTGCCAGTCCTGGATCAGGAGGCCTCTGTCGGGCGCCGCCCCCCTTCCTCCTCCA TCAGCAACAGGCGGCGCCGGCCAGCCTCATAGTCAGCCTCATCCACACTGACCAGCAGGCGAACAGCCTCCCGGCCCACAGCCTC TCGCAGGGCCTCAGTCAGGAACACGCCCCGCAGGGCCTGCAGCAGGGCGCCACTCAGGTAGTCGCCCCAGAAGGCGTCCAGATAG GAGAGCTCTGAGAACTTGATGTCACAAACCACAGAGCCCAGGTCCCTTGAGCGCAGCACTGCGGTGGCCTGCCCAAACACGTCCA GCTGCCGCGCCAGCGCCTGGGGCCGCCGGGATGCCACGCCCTGCTCCAAGGCTGGCCCATGCTCGCAGTACTCTGCTCGAACCCG GAGCCGGATGTCTGCAGGGGAAGGAGGGATTTGTCAGGGAGGGGGCCAACACTAGACACACTTATGGGGAACGCCACCCTTCCTC CCTCC |
| 163 | CDC42E P1 | TGATGCCCGGCCCCCAGGGGGGCAGAGGCGCCGCCACCATGAGCCTGGGCAAGCTCTCGCCTGTGGGCTGGGTGTCCAGTTCACA GGGAAAGAGGCGGCTGACTGCAGACATGATCAGCCACCCACTCGGGGACTTCCGCCACACCATGCATGTGGGCCGTGGCGGGGAT GTCTTCGGGGACACGTCCTTCCTCAGCAACCACGGTGGCAGCTCCGGGAGCACCCATCGCTCACCCCGCAGCTTCCTGGCCAAGA AGCTGCAGCTGGTGCGGAGGGTGGGGGCGCCCCCCGGAGGATGGCATCTCCCCCTGCACCCTCCCCGGCTCCACCGGCCATCTC CCCCATCATCAAGAACGCCATCTCCCTGCCCCAGCTCAACCAGGCCGCCTACGACAGCCTCGTGGTTGGCAAGCTCAGCTTCGAC AGCAGCCCCACCAGCTCCACGGACGGCCACTCCAGCTACGGTGAGGGCCTGGGCCATCTTGGCCCACTTTTCAGA |

TABLE 4C

| SEQ ID NO | GENE NAME | SEQUENCE |
|---|---|---|
| 164 | chr21: 9906600-9906800 | GGCCGGGCAAAAAGCCGCCGCAACAAAAAGCTGCGCTGACGGGCGGAAAAAGCCGCGGCGGCGGAGCCAAAAAGCCGGGGCGGCA AAAAGCCACGGTGGCGGGCGCAAACAGCCGCAAAAAGCCGCGGTGGTGGGGGCAAAATCAGTGGGAGCAGGGGCAAAAAAACACA AAAAGCCGCGGCGGCGGGGGCAAAAAGCCA |
| 165 | chr21: 9907000-9907400 | TGGCTTTGCTGGAGTGTGATGTGATAGGAAATGTGCAGCCAAAGACAAAAGAAGATGTAAGTAGGCTTGACTCATTGCAGCTAAG AACCCAGATGTTACCTTGAGGGTATTAACTAATAAGCAGTTTAAATCAGAATGGCACATTCTGATTTGTTTTTTGTATGTTCACA TTTGGCAGGCATAGATACTGTTTGAAAAGAGAAAAGTCAGTACATAGAGGTAACAAGCTTAAATATGTGCCAAGTCTAGAAACAA GAGACTAGGGGGATAAGGACCTTTCGAAATTAAATGCAAGATTTGAAAACTGATTGGCTGGGGGATGAGGCAAAGGCAGGTCTTT AAGGTCAATCCCTGTTTTGCTTTAAGTTGTTAGCGGGTGGTTTTATCATATATTGTAGAA |
| 166 | chr21: 9917800-9918450 | TTCCTGGGAATGTCAGCTAACCTGAGCCTAGGGGCCTGAGCCCAAGGGCAGACTGAGGCTCCCCCAGCACAGGGAGGTGCTGCCT GTGACAAGGGGTAGTGCTGGCACAGTGCAGGCTACTCCCTAGAAAGATCAGCTTGAATATGCAGGAAGAGCAGGACCCTCGGGCT GAGGCAGAGGTGGAATGGGAAGTGCATGGTGGTAATTTAGTTCTCCAGAGGCCAGAAGTAGGAGGAGCGGTTGGAATGCTGATGG CCCAAAGGGAAACCCTGGACTACCCTGGCCTCCCACAGGACTCTCATAGTAATTGCGGCTCCCTGCAGTGGTGAGGCCAGAAGGA GTGTTGCCCAATGCTGTCATCATCCAGTCCACCCCCCACCCACCATCAACAGATGAGTATGGTCATGAGTGTGGTCACCTCATCA GTCATTTGCTCAGTTGTGAAAAAGAAATTGTTCAGAGAAGAGCAAAGTGTTTTTCCATGAGCCAAAGGTCAGCCAAGTTATGCTA ATGAGGAGGACTGGAGACAGCGTGTCACAGACACCGAGAAGGAGCACTGGGCAAGGGCACTTCTCCCAGGGCAGAGCCCACAAGA AGCGTCCTGGCACCAGACACTCAGGGAACTGAAGGCTGGCAGGGGCCCGCCCAGT |
| 167 | TPTE | TCCCCCCAGCTGGGTATAAGCAAACTTTCCTGTCTATGGGCCGCAGAGACCACCATCTAGTTCCCCCGCCAAAACTTTACATGAT TTTAATTCTCCTGATGAAGATGAGAGGATAACAGCCAACAGAGAGGGCAGAGGATGGGATGGGACTCCCTTGCTCAGAGACCTCA CCTCTAGGTCTTTACCTCCTATTGAGAATAAGTCAGTTCTGTAGTAAGAACTCTGTGTCCACGGCAACCCCAAACAGAATCCTAG CGCTCTTGTGATTCTTGTAGAATGGGGAATAGAACGAGCTTGGCCCAAGACTGCACAGACTTAAAAACATACTATTCTTTGAAAA TGGCAATCATTAAAAAGTCAGGAAACAACAGGTGCTGGAGAGGATGTGGAGAAATAGGAACACTTTTACACTGTTGGTGGGACTG TAAACTAGTTCAACCATGGTGGAAGTCAGTGTGGCGATTCCTCAGGGATCTAGAACTAGAAATACCATTTGACCCAGCCATCCCA TTACTGGGTATATACCCAAAGGACTATAAATCATGCTGCTATACAGACACATGCACACGTATGTTTACTGCAGCACTATTCACAA TAGCAAAGACTTGGAACCAACCCAAATGTCCAACAATGATAGACTGGATTAAGAAAATGTGGCACATATACACCATGGAATACTA TGCAGCCATAAAAAATGATGAGTTCATGTCCTTTGTAGGGACATGGATGAAATTGGAAATCATTCTCAGTAAACTATCGCAAGAA CAAAAAACCAAACACTGCATATTCTCACTCATAGGTGGGAACTGAACAATGAGAACACGTGGACCCAGGAAGGGGAACATCACAC TCTGGGGACTGTTGTGGGGTGGGGGGAGGGGGGAGGGATAGCATTGGGAGATATACCAAATGCTAGATGAGGAGTTTGTGGGTGC AGCGCACCAGCATGTCACACGTTTACATATGTAACTAACCTGCACATTGTGCACATGTACCCTAAAACTTAAAGTATAATAAAAA AAATACTGTTCTGCCATACATACAGATACTCATTAAAGATGAGGGAGAAGGGCATGGGGTGGGGGAGAATGTACCAAAACCAAAG ACCACAGGATAATAACCTCAGAGCAGAGACTATCTCTCTAGTTATTTTTTCTTTTGTATGTAATGGAGAGGATTATTATTTACTC TGATGAAGAAGTTTACATCAAGTGTTCAGCTTCCTTTGTGGGTTACAGAGAATAACCAGAGGGCTCAGTTATGCTCTCTGAATAA CTATGTTTGCTTAGTGTTTTCTAAACAATATTAAATTTCACTAAAATAGACAAGGTTGATAGGACTTGGGGGCATAACTCATTGA |

TABLE 4C-continued

| SEQ ID NO | GENE NAME | SEQUENCE |
|---|---|---|
| | | CTCAAGCTATCATTTTATAGGATTGTGAGAAAACAAATAGATGAACATTTAAAATACACTCATATTCTCGCTAGAAAAGAGGATT<br>TTGAATATTCTTACATCAAAGACATGGTAAATGTTTAAGGCAATGAATATGCTAATTACCATGATTTGATCATTATGCAATGTAA<br>AATGTACTGAAACATCACATTGTACCTCATAAATATGTACAATTTATTATGTGCGAATTAAAATTTTGAGTATAAGAAAAAATAA<br>ACTTCAATTGTAAGAAAACAACCCAACTTTTAAAAAACGGGCAAAATACGTGAACAGATACTTCACTAATAGAGATTTGCAACTG<br>GCAAATAAGCAAATGAAAAACTGGTCATCATCACTATCTATTAGAGAAATGCAGATTAAAACTACAATAAGAAACAATGCTGCCC<br>GTCCAGACGCATTGTTTTGACCGTTTCCAACTTGTCCCAGCCCTTCCCGGGGCATCGCTGGGGACCCTACGCCGACGTCCCCCCT<br>CCGCCCGCGCCCCAAGGGCCGACTGGGCAAATTGGGAGACCCGCCCCGCGGGGCGACCCAACTTTTCGGAACAGCACCCCACCGC<br>CCACCCCCGCAGACCCCCGGACCCCCGCTCCCGGCGGAGACTCAGGGAACCCCGCACCCCAAGCCCTTCTAAATCGTGCAGCGTG<br>AGTGTGACGGCCAAGAGCGGATGCAGCCCGGGATCGCCCGCACCTTCCCGTGGGCGGAAGCGCAGGAGCCAGCTGGGGAGGGGGC<br>GCCCTAGAGGAGCGGCTAGAAAGCAGACACGGGGAACTCAGGTCATCCTGGGGGGGGACAAGACAACGAGAGCCGGGCGCCTCGG<br>GGGCGGCGCGGGAGCCTCCGCAGGACCGGGCGGGCGCCCCGGCTGGCGCGGGCGGGGGGCGCGCCCCCTTTACCTGCGGCTCCGG<br>CTCCTAGGCCATTTCCTCACGCGGCGGCGGCCGGGACTGAGCTAACACCACTCAGGCCGGCCGGGTTTGAATGAGGAGGAGCGGG<br>CGCGGAGAGGAGGGGACGGGGAGGGCGGAGGGAGGGAGGGAGGCGTCGCGGAGTTTTTCTCGGCCTTTTGTGCGGACACCTCCCG<br>GATTCCGCGCCCGCACCCGGCCCCCCAAAAGACACGGGGAGCCGCGGGCGAGGGGTTCAGCCATCCGCCGAGGCGCCTAGTGCCT<br>TCGCGCCTCCAAGACCCCCCCCCAACAAAAAGGAGCGTCCCCCACCCCTACCCCCGCCCGGAGGACTTAGGGCCTGGGCTCACCT<br>CGGGCGCGGAGCTAAGTGTAGGCGCCGGGGGTCCCTAGAGCCGCCGGGGCGCAGCGAGTCCGGCGCTGGGTAACTGTTGGGTCAG<br>AAACTGTTCAGGTAGCAGCTGTTGTGCCCTCCCTTGGCCCCGCCGCTCGGAGACGCCCCGCCCCCTGCCTTGAACGGCCGCCCGG<br>CCCCGCCCCAGCGCCCACGTGACTAGCATAGGCGCGCCCCCGTTCCGCCCGCCGCCGCAGACTCCGCCTCCGGGACGCGAGCGAG<br>CGGCGAGCGCGCGCACTACCAGTTCTTGCTCGGCGACTCCCGCGCACGCGCGCGCCGTGCCACCCTCCCCGCACCCCTCCTCCCG<br>CCATCCGGCTTAACGTGGCGGGCGCGCGCCGCGGCAGTAGCCGTGACAGGTACCCGGCGGGGCGGGGGGGGAGGGGGTTGGCCCG<br>CGAGGGTGTGCGCAGGCACAGACCCGGGTCCTGTCCCCGCCGCCCCCTCCTCTGCAAGGTGTGCCTGGGCGAGGGGAGGGGCCCG<br>CGGCCCGAACCCCTGGGTCACCCCCGAATTACAAACAAAAACCTTAACGCCATTGCTCGCGGGTTAGAAGGCAGCTGTGCGTGCT<br>CAGGAAAAGAAGCCACGCACAAGAGACCGCACGCGGCGTGGATACAGTGACACGAAACACCCAAAATCTCTTTTGAAAGGGAAAC<br>CAGGCACAGTGGCTCATGCCTATAATCCCAGCACTTTCGGGGGCCAAGGCGCTCACCTAAACCCGAGAGTTCAAGACCAGCCTGG<br>GCAATACAGCGAAACCCTGTCTCTACGAAAAATATAAAAATTAGCTGGGCATAGGGCTGGGCACGGTGGCTCACGCCTGTAATCC<br>CAGCATTTTGGAGGCCGAGGCGGGCGGATCACGAGGTCAGGAGTTCCAGACCATCCTGGCTAACACAGTGAAACCTTCTCTCTAC<br>TAAAAATACAAAAAAAATTAGCCGGGCGTGGTGGCAGGTGCCTGTAGTCCTAGCTACTTGGGAGGTTGAGGCAGGAGAATGGCAT<br>GAATCAGGGAGCGGAGGCTGCAGTGAGCTGAGATTGCGCCACTGCACTCCAGCCTGGGGGACAGAGTGAGACTCCGTCTCAAAAA<br>AAAAAATAATAATTAGCTGGGCATGGTGGCTGGCACACATGGTCCCAGCTACTCAGGAGGCTGAGGTGGAAGGATCTCTTGATCC<br>CGGGGAGGTCAAGGCTGCAGTGAGCCAAGATGGCATCACCGCACTCCAGCCTGGGCCACAGACCCTGTCTCAAAAAAAAAAGAGA<br>AAGTGGGGAAGAAAATGTAATACAAATTAATATACCAACAGCAATTAGTGAGTACTTTTTCCATGGAGCTGGGAGAGGGAATAAA<br>TGTTTGTAAAATTAAAATGTTCTACGCTAGAAATCAACTTTCCTTCTATGCTTTCTTTACTTCACCCCTTATAGCTACTTAGTAA<br>ATCTCACAAATCCTATCCTTCTGATCTCTCTGAAATGTATGTACCCTTTCCCTTCTATTCTCACCACCCATGTTTCTTTGTTTCC<br>TTCTAGCCTGTGTAATAATCTCATAATCGCACCTCCTGTACCTGCCTTCTTTCTAGTCCAGAATACGTTTTCCTAAATTCCACCA<br>ATAACCATCCTGCTACTGCTTTGTGTGAAATTCTCCAAAAAAAATTTTACTTTTCCAAAATAAGTCAGGCTCCCTCTCTTAGGAT<br>ACAAAACCACACCATGGTCCCAGCCAATCTTTCAGCCTGATTCACTCAGTATATATTTATTGACCTCTCCTTTCTCCCAAGCACT<br>TGGCTAGATAATAATTAAAGAGTGCGGCACAAAACAAATTGGATTCCTCCCCTCATGGAGCTTGTATTTTCACAGGAAGCACAGA<br>CATTAAATAAATTAAAACACAAAAAAATAGACAAGCATATAATTACAGTATGTATCCTAGAGAAATATCACTCATGCAGAAAGCA<br>TACACAAGGATGCAGCACTGTTTCCAATAGCGAAAAGCTAGAAACAACCTACATGTTCACCAAAAGAAAATGGCCACATAAACTA<br>TACCATATCCAAATTATCCAAATTTTAGAATATAGACAACAGGTTGGGCGCGGTGGCTCACACCTGTAATCCCAGCACTTTGGGA<br>AGCCGAGGCGGGTGGATCACAAGGTCAGGAGTTCAAGACCAGCCTGGCCAACATGGTGAAACCCCGTCTCCTCTAAAAAAACAAA<br>AAAATCAGCTGGGCACTGTGGCAGGAGCCTGTAATCCCAGCTACTGAGGAGACTGAGGCAGGAGAATCGCTTGAACCCTGGAGGC<br>AGAGGTTGCAGTGAGCCAAGATCGCGCCACTGCACTCTAGCCTGGGTGACAGAGCAAGACTCCATCTCAG |
| 168 | chr21:<br>13974500-<br>13976000 | TGTAGGAGTCCTCCGGTGCTGGAGTCCAGAGCACAGTGAGGCTGGGTCCTCCCGTGCCATAGTGTAGGGCATGGCGGGACAGGGA<br>TCCTGCCCTGCGATAGTCCAGTGCTTGAGTCCGCAGTAAGGCAATGGTCCTCCAATGCTGGAGTTCACGGCGTTGTGGGGTCGGG<br>GTCCTTTGGTGACTTAGTCCAGGGCGTACCAGGGCGGGGGTCCACAGTTGCCATAGTGAGGATCTTGGAGGAAGGTGGTTCCTGC<br>CTTGCTGTAGTCCGGGGAGCAGGGGGCAGGGGTCCTCTCTTGTCAGAGTCTCTGGCGCGGGGTGGGGGTGGAGGTGGGGGTTTTC<br>CTATGCGATAGCCCACGGGTCGGTGAAGCCGGGTCCTCCCGTGCCTTTGTCCAGGGCGCAGGGGGGCGAGGGTCTTCGGTGGTGG<br>AGTCCGCGGAGCGGCAGGACGGGGGTCCTCCAGTGCCATATTCCAGGGCGCGGCGGAGTGGGGGACCTGTCCTGCAGTGGTCCAG<br>GGCATGTGGGAGTGGTGGTCCTGCTGTGCCTCAGTCCAGTGCGCGGTGGGACGGCGGTCCTGCTGTGCTGTAGTGCAGGACGCGG<br>TGGCGCAGGGGTAGTCCAGAGAGCGCCGTGGCAGGGGGTCCTCCAGTGCTGGAATCCAGTGCAAGGCGGGTCAGGGGTCTTACCG<br>TGCCGAAGTCGGTGGCAAGGGTCCTCCCGTGCCATAGTCTAGGGGGCGACGGGGCAGGGTTCTCTAGTGCAGGTGTCCAGGGTGT<br>GGCAGGGCAGGAGTCCTCTTGTGCAGGAGTCCAGGACGTAGCCGAGGAGTCCTCCAATGTCAGAGTCCAGGGCTCTGCGGGGCCG<br>GGTTCCCCCATGCCAGAGTGTAGGGCGCGTTCAGGTGAGGGTCTTGGCGTGCAGTAATCCAGGGTGCGGTGGGGCAGGGGTAGTC<br>CAGACCTCCATGGCGGGCGTCCCTCTGTGCAGGAGCCCAGTGCCTGGCGGATCGGGGGTCCTTCTGTGCTGTAGTCCAGGGCACC<br>GCAAGGTGTGGGTCCTCTGGTGCCCTAGTCCAGGGGGCGGCGAGTCAGAGGTTCTCCCGTGTCTCAGTCTAGGGCCTGGTAGGAC<br>TGGGGTCCTGGAGTCCACGTGGTAGCCCAAGTTGCCGCAGGACCAGGTACTCTGGAACCACAGTCCAGGGCGCTGAGGGGCAGGA<br>GTAGTTCAGGGCGAGCCGGGGCCCAGGTCCTCGGGAGCCAGAGTCCAGGGTGTGGAGGGGTGGGGGTTCTGCAGTGGCACAGTCC<br>AGGACACCGCGGGGCGGGACAGGGCGGGGATCCTCCCGTGCCTTAGTCCAGGGCTGAGCCGCGGGAGAGGTCCTTCAGTAGCACA<br>GTCTAGCGCACGGCGTTGCAGGTGTCCTCCAGTGCCTGAGGCCACGGCAGGTCGCGGGTCCCACTGTGCTCTAGTTCAGGGCGGA<br>GTGGGTCTGAGGTCTTCTCCTGCCTCAGTCTAGGGCGCTGGAGAGCGGGGATCCT |
| 169 | chr21:<br>13989500-<br>13992000 | GGGTTGGTCCTAGAAAGCGTGAGGATCGCCGAGTGCACTGCCCTCCCAGCCTAGGGTCCACTCTTCCTTGGCCCGAGCCCAGAGC<br>TCGGGGTTTCAGGCGCTGGGCCCTGTGCAGCTGCCCAGAATAGGCTGAGCGGCAGGTTCCCGCCCTGGCAAGGGATCCAGCAGTG<br>GAATCCTCACTGCTGTTGGCTGCGGGCAAGGTCAGCGGGGTTTCCATCGCTGCTGGTGGGAGCCACCTGGCGGTGGTAGCTGCAA<br>GTGAGCGCGTGGCAGAGACTGGCAGGGCTGGTCCCAGACACCCTGAGGGTCTCTGGGTGCATCGCCCTACCACCCTAGGGTCTGC<br>TCTTCCTTAGCCTGCTCCCAGGACGCGGTGTACGAGGGCTAGACTCTGAGCAGCCTCCAGGATGGGGCTGAGCAGCGGATTCCTG<br>CCCTGCTGCAGCTACAGTCTGAATTAGGCGCCACCGCAGTATCTGGCCCTGGGGTACGTGCTACTGGGTGGCATGGACAGAGATG<br>GGGGCTGCCACAGCTGCTATGGGGCTGAGCAGCCGATTCTCGCCCTGCTGCAGCGGGCGACCGCTGCAATCCCCAGCGCTATGGG<br>ACCGACCACCTGACTTAGATGCCTTGGAGGCATCCGGTCCTGGGGTCTTGCTGCTGGTGTCTGCGGGCAGGGTCACGGCTGCCAC<br>TACTACTGCTGTGCGCCATGGGCAGGTGCCAGCTGCAGCTGAGTCCGAGGCAGATGCTGTCAGGGCTGGTCTGAGGTTGCCTAAG<br>GGTGGCTGAGTGCACCACGCTTCCACCCCAGGGTCCGTTATTCCTAGGCCGGCTCCCAGATTGCAGGGTTGTGGGCGTTGGACAC<br>TGTGCAGCCATGAGGATCTGGTTGGGTGCAGATTCCCGCCCTCCTGCAGCTGAGAAGCCAATCTCATAACAGGCGCTGCAGTGAC<br>CTCTGGCTCTGCGGTCCGCGCTGCTGCTGGAGCTGGCAGAGAACAGAGCTGCCACCGCTGCTGCTTCCAGGAGTGTGCAGCTGGC<br>AGCTGCAGCTGAGCCCGTGGCGGAGGCTGGAAGGCCTTATTCCAGAAGCCTTGAGGGTCCCCGAATGCACCGCCCTCCCACCCTA |

TABLE 4C-continued

| SEQ ID NO | GENE NAME | SEQUENCE |
|---|---|---|
| | | AGGTCCAGTCTTCCTTGCCCGCGCCCAGAGAGTTGGATTGCAGGCGCTGAGCACAGTGCAGGTGCTGGGATGGGGCTAAGCTGAA<br>AGTTTCCGCCCTCTGGCTGCTGCGGGGCCGACAGCCTGAGTTATGCGCCGCGGCGGCTTTTGGTCATGGGATCCGCACTGCCGGT<br>GGCTTGCACAGGGTCGGGGGCTGCCACAGCTGCTATAGTTCACCGTGTGCACGTGGCAGCCGCCCCTGAGCCCACCGCTGAGGCT<br>GCAGGGCTGGTCCGGTCCCAGACGGCCTGAGGGCCATTTGCCCGCGCCCAGATCCGGGTGGCTGCGCTGGGCACTGTGCAGCCTC<br>CCGGAATCCGCTGAAGGGCACGTTCCCGCTCTCCTACAGCTGTGGGCCGACTGCCTGATTTTGGCCACTAGGTGGAGTCTGGCTC<br>TAGGGTTTCGAGGCCGCTGGTGTTGGTGGGCGGAGTCCGGGTTTGCCACCGCTGCGCTCCATGAGCAGGTAGCAGCTGCAGCGGA<br>GCTTTAGACCGAGGCTGGCAGGGCTGGCCCCAGACGGCCTGAGGGTCAGGGAGTGCAGGGTCCTCCCACCCTAGGTCCGCTCTTC<br>CTTTCCCCTTACCCAGAGCGGGTTGTGCGGGCTCTGGGCTCTGTGCCGGCGCTGGGCTCTGTGCAGCCGCCGAGATGGGGCTGAG<br>CAGCGGATTTCCTCCCTGCTGCAGCTGGAGGACGATTACCTGCACTAGCCGCTGAGGCGGCATCTGGCCCTGGGTTACTGCAGCT<br>GGTGACGCGGGCAGGGTCAGGGTTGGTTGCAGGTGGCAGCTGCTGCTAAACCCATTGCGAGCCTCAGGGTCACCAAGTTCACCGT<br>CCTTTCATCATAGTATCTGATCTTTGGCCCGCGCCCAGAGTGCGGACTGGCCTGCGCTGGGGACTGCATAGCTTCTGGGGGCCGG<br>TCAGCGCCAGTTTCACGTCCTCCTGCAGCTGCGTGGCCTAAGGTCTTAGGCGCCGCGGCGCTATCTGGCCCTGCTGTCGACGCTG<br>CTGGTGGTGGGGACAGGGTCAAGGGTTGCCACTGCTGCTCCCGTGCGCCATCGGCAGGTGGCAGTTGCAGATGAGCCCACAATTG<br>AGGCTGTTGGGGCTGCTCCCAGGTTGTTAGAGGGTCGCCGAGTTCACCGACATGCCACCCTAGGTTACGCTCTTGGCCCGCACCC<br>AGAGCGCCGGGTTACGGGTCCTGGGCCCTGTGCAGCCACGGGGATGGTGCTGAGTGCAGGTTCCCGTCTTCCTGAGATGCGGGGC<br>GACCACTGGAATTAGCCTCTGTGGTGGTATCTGACCCTAGGGTCCGAGCTGCTGGTGGCGTGGGCGGGGTCGAAGTCGCCTCTGT<br>TGCTGCGGCGTGCCATTTGCACCGTCCTCTGGTAC |
| 170 | chr21:<br>13998500-<br>14000100 | AAATACTCTACTGAAAAAACAGAAATAGTAAATGAATACAGTAAAGTTTTAGAATACAAAATCAGCATAGAAAAATCAGTCGCAT<br>TTCTATACCCAACAGCATACCATCTGAAAAAGGAATCAAGAAACCAATCCCATTTAAAATAGCTATAAAAAAATGCCTGGGAATA<br>AACTAAGCCAAATAAATATGTCTAAAATGAAAACTATAAAACATTGATAAAAATCAATTGAAAAAGATACAAATAAAGGGAAAGT<br>TATCCCATTTTTATGAATTAGAAGTATTAATACTGTTAAAATGACCATCATACTCAAATCAGTCTATAGGTCCAATACAATCTCT<br>AACAAATTTCCAATGTAATTCTTCAGAGATGTTAAAAAAGGTTTTAAAAATCGTTCTGCGGATGTTAAAAGGATTTTTAAAACGC<br>TTTTTTCGTTCTGCAGGCGAAGGCTGTGGCCGTGCTCCCGCCGGCCAGTTCCCAGCAGCAGCGCATTGCCCCTGCTCCACGCCTT<br>CGCTCCAGGCCCGCAGGGGCGCAGCCCCGCGGGAATCAGCACTGAGCCGGTCCCGCCGCCGCCCCAGTGTCCGGGCTGCGACTGC<br>GGGGAGCCGATCGCCCAGCGATTGGAGGAGGGCGACGAGGCCTTCCGCCAGAGCGAGTACCAGAAAGCAGCCGGGCTCTTCCGCT<br>CCACGCTGGCCCGGCTGGCGCAGCCCGACCGCGGTCAGTGCCTGAGGCTGGGGAACGCGCTGGCCCGCGCCGACCGCCTCCCGGT<br>GGCCCTGGGCGCGTTCTGTGTCGCCCTGCGGCTCGAGGCGCTGCGGCCGGAGGAGCTGGGAGAGCTGGCAGAGCTGGCGGGCGGC<br>CTGGTGTGCCCCGGCCTGCGCGAACGGCCACTGTTCACGGGGAAGCCGGGCGGCGAGCTTGAGGCGCCAGGCTAGGGAGGGCCGG<br>CCCTGGAGCCCGGCGCGCCCCGCGACCTGCTCGGCTGCCCGCGGCTGCTGCACAAGCCGGTGACACTGCCCTGCGGGCTCACGGT<br>CTGCAAGCGCTGCGTGGAGCCGGGGCCGAGCGGCCACAGGCGCTGCGCGTGAACGTGGTGCTGAGCCGCAAGCTGGAGAGGTGCT<br>TCCCGGCCAAGTGCCCGCTGCTCAGGCTGGAGGGTCAGGCGCGGAGCCTGCAGCGCCAGCAGCAGCCCGAGGCCGCGCTGCTCAG<br>GTGCGACCAGGCCCTGTAGCTGTGACTTGGCTGTGGGGCTGGCCCGCCTCCCTGACCCCTGTCAGGCGGAGCAGCTGGAGCTGAC<br>CCACGGGCCTGGGCTTTCGAGCGCTTTGTCCAGGCGCTAATGATGGGAAGGTGAAAGGTGGGGGTGGCCACACCCTGCAGTCAGG<br>GTGGCAGGTGTCAGAGGCCACATGCAACCCACTGGTTTTGTCTTTTCCAGGATGCTGATAAGTTTCCCGCGGCCCCCGGAGCAGC<br>TCTGTAAGGCCCTGTAATTGCCTTTCGTTCCCTTCTGCTCTATTGAGGAGTGGGAAGATGACAAAGTGTTTTTGCTCAACCCGAA<br>GGAAAATGCACATGGGAGGACACACCGGGTTACTATTTGAGTAGCCCAGACAGGAGAGCAGCGGTCTGCT |
| 171 | chr21:<br>14017000-<br>14018500 | TGGGTGGATTGCTTGAGCCCAGGAGTTCGAGACCAGCCTGGACAAAATGGCAGAAACTCCATGTCTACAAAAAATACAAAAATTA<br>GCCGGGCATGATGTTCTGCGCCTGTAGTCCCAGCTACTCAGGAGGCTGAGGTGGGAGGATCGCTTGAGCCCAGGAGGCGGAGTTT<br>GCAGTGAGCTGAGATGTCACTGCATTCCAGCCTGGGAGACAGAGCCAGACTCTGTCTCAAAAGAAAAAAAAAAAAGAAAAAAAGA<br>AAAGAAAAAACGAAATTGTATTCTGAATACATCTTCTAAAACACTACATTTACTTGCACTATATTAAACTGGTTTTATCCTGACC<br>ACAATTGCAGGTGAAAGATACCACTGTTGTTCTATTTTTCTGGTAAGTAGAGTGAGCCATGTCTTCCCCAGGGAAAGACGCCTCC<br>TAAAAATTTGTAGGACCACCTTTGGTTTTCTTCCAGATATTTTTTTTGTCATCGCTTTTCCTGCGCCCAATTCCCATCTGTCTAG<br>CCCTTCTGCCTCCGCTGGTCTTTTTCGCGAGCCTCTCCCCAGCCGCAGGTATTCGTCTGGGCTGCAGCCCCTCCCATCTCCTGGG<br>GCGTGACCACCTGTCCAGGCCCCGCGCGCTCTGTGTGGTCGCTGCTGCAGTGTTGTTGTGGCTGTGAGAAGGCGGCGGCGGCGGC<br>GGAGCAGCAGCCGGACCAGACTCCCTAGTAGCTCAGGCGCTGCCCTGCGCCGGCCCTGGCAGGGAGCCTGGTGAGATGGTGGAGG<br>AGGAGGCTGTGCCGTGGCTGGCCTTGCTGTGTCCTGCTGCCTGGTTAGAACCCCATCCCCGTCCCCCGTCTCCTCCGGGGGGTGA<br>GGAGGAGCTGGAAGAGGGGCCGGCCTCTGTCCGGCCCGGCCAGGCGGCAGTCACCCTCTGAGGAGGCAGCGCCCGGGGAGGGGCC<br>TCCCAGGCGGCCGCCGCCGCCAGGGGGAGGCGCTGGGAGTGGGAGTGGGAGCGGGACCTCAGCTGCCAAGCTCGGCCCGGACCCT<br>AGGTGCGGGGGAGGCGGGGTCCCGGGCTCGGGCTGCCTGCCCGGACCTGGCGGGGATGGGCCCGTGCGGCTCCGGGTGTGGGACG<br>TACCCTCAGAGCGCCCGGGGTTATTCCCACTGACTCCAGGGAGGTGAGTGTGCGCCCTTCGCTCCCTGCCGTGTCTGTGAGGGTC<br>CATCGTTGCCGGAGACTGGAGGTCGGGGGCCATGGGAGCCCCGGGGCGAACGGTGCGGACATGGGCCTTGTGGAAAGGAGGAGTG<br>ACCGCCTGAGCGTGCAGCAGGACATCTTCCTGACCTGGTAATAATTAGGTGAGAAGGATGGTTGGGGGCGGTCGGCGTAACTCAG<br>GGAACACTGGTCAGGCTGCTCCCCAAACGATTACGGT |
| 172 | chr21:<br>14056400-<br>14058100 | GTCTCTAGGACACCCTAAGATGGCGGCGAGGGAGACGGTGAAGGTTGGCTCCCGCCTGTCTGGGCTCTGATCCTCTGTCTCCCCC<br>TCCCCCTGCGGCCGGCTCATGGCCTGGCGGAGGCCCGAACCAAAGACCTCCGCACCGCCGTGTACAACGCCGCCCGTGACGGCAA<br>GGGGGCAGCTGCTCCAGAAGCTGCTCAGCAGCCGGAGCCGGGAGGAACTGGACGAGCTGACTGGCTAGGTGGCCGGCGGGGGGAC<br>GCCGCTGCTCATCGCCGCCTGCTACGGCCACCTGGACGTGGTGGAGTACCTGGTGGACCCGTGCGGCGCGAGCGTGGAGGCCGGT<br>GGCTCGGTGCACTTCGATGGCGAGACCATGGAGGGTGCGCCGCCGCTGTGGGCGCGGACCACCTGGACGTGGTGCGGAGCCTGCT<br>GCGCCGCGGGGCCTCGGTGAACTGCACCACGCGCACCAACTCCACGCCCCTCCGCGCCGCCTGCTTCGAGGGCCTCCTGGAGGTG<br>GTGCGCTACCTGGTCGGCGAGCACCAGGCCAACCTGGAGGTGGCCAACCGGCACGGCCACATGTGCCTCATGATCTCGTGCTACA<br>AGGGCCACCGTGAGATCGCCCGCTACCTGCTGGAGCAGGGCGCCCAGGTGAACTGGCGCAGCGCCAAGGGCAACACGGCCCTGCA<br>CAACTGTGCCGAGACCAGCAGCCTGGAGATCCTGCAGCTGCTGCTGGGGTGCAAGGCCAGCATGGAACGTGATAGCTACGGCATG<br>ACCCCGTTGCTCCCGGCCAGCGTGACGGGCCACACCAACATCGTGGAGTACCTCATCCAGGAGCAGCCCGGCCAGGAGCAGCTCA<br>TAGGGGTAGAGGCTCAGCTTAGGCTGCCCCAAGAAGGCTCCTCCACCAGCCAGGGGTGTGCGCAGCCTCAGGGGGCTCCGTGCTG<br>CATCTTCTCCCCTGAGGTACTGAACGGGGAATCTTACCAAAGCTGCTGTCCCACCAGCCGGGAAGCTGCCATGGAAGCCTTGGAA<br>TTGCTGGGATCTACCTATGTGGATAAGAAACGAGATCTGCTTGGGGCCCTTAAACACTGGAGGCGGGCCATGGAGCTGCGTCACC<br>AGGGGGGTGAGTACCTGCCCAAACTGGAGCCCCCACAGCTGGTCCTGGCCTATGACTATTCCAGGGAGGTCAACACCACCGAGGA<br>GCTGGAGGCGCTGATCACCGACGCCGATGAGATGCGTATGCAGGCCTTGTTGATCCGGGAGCGCATCCTCAGTCCCTCGCACCCC<br>GACACTTCCTATTGTATCCGTTACAGGGGCGCAGTGTACGCCGACTCGGGGAATATCGAGTGCTACATCCGCTTGTGGAAGTACG<br>CCCTGGACATGCAACAGAGCAACCTGGAGCCTCTGAGCCCCATGAGCGCCAGCAGCTTCCTCTCCTTCGCCGAACTCTTCTCCTA<br>CGTGCTGCAGGACCCGGCTGCCAAAGGCAGCCTGGGCACCCAGATCGGCTTTGCAGACCTCATGGGGGTCCTCACCAAAGGGGTC<br>CGGGAAGTGGAATGGGCCCTGCAGCTGCTCAGGGAGCCTAGAGACTCGGCCCAGTTCAACAAGGCGCTGGCCATCATCCTCCACC<br>TGCTCTACCTGCTGGAGAAAGTGGAGTGCACCCCCAGCCAGGAGCACCTGAAGCACCAGACCATCTATCGCCTGCTCAAGTGCGC |

TABLE 4C-continued

| SEQ ID NO | GENE NAME | SEQUENCE |
|---|---|---|
| 173 | chr21: 14070250-14070550 | TAAAAATAAATTGTAATAAATATGCCGGCGGATGGTAGAGATGCCGACCCTACCGAGGAGCAGATGGCAGAAACAGAGAGAAACGACGAGGAGCAGTTCGAATGCCAGGAACGGCTCAAGTGCCAGGTGCAGGTGGGGGCCCCCGAGGAGGAGGAGGAGGACGCGGGCCTGGTGGCCAAGGCCGAGGCCGTGGCTGCAGGCTGGATGCTCGATTTCCTCCGCTTCTCTCTTTGCCGAGCTTTCCGCGACGGCCGCTCGGAGGACTTCTGCAGGATCCGCAACAGGGCAGAGGCTATTATT |
| 174 | chr21: 14119800-14120400 | CGCCACCACGTGCGGGTAGCGCCGCATCGCCCCAGCCGTGTTCCTTGGTCTCCGTCTCCGCCGCGCCCGCCTGGTGAACTGGAGCACAGGGACCATAGTTCTGGAAATTTATCCTTTTTCTCTCCATGGATTCAGCAGCAGTGTCTAAAAGAAAAAAATTCATCAATCATTTATGTATATTTTAATATAAAGGTAAAACACTGCGAACCAGTGGAACCGGATAGAAAGTAATTCAGTTTTACAGAACACAACTGTTTTTCAGGCTCTTTTATTAAATATAAAAGAGCCATATATATTTCTGTGGAATTCAAAATTCAACATTTTATTTTATTTTTGAGATGGAGTCTCGCTCTGTCGCCCAGGCTGTAGTGCAGTGGCGCGATCTCGGCTCACTGCAACCTCAGCCTCCCGGGTTTAAGGAATTCTCTGCTTCAGCCTCCTGAATAGCTGGGATTACAGGCGCATGCCACCAAGCCCAGCTAATTTTTTTTGTATTT |
| 175 | chr21: 14304800-14306100 | CCCTGAACAGTCAGAGTTTACTGCCCACTTTTGCTGGAGGAGAAGCTCCTGAACAACTAGAGAGACTGTGGTTCCCAAAGAGCAGCCTGTAGGCCTGAGGACTGCTCTATGACCGGCGTCAGTCCCTGCCTCCCTCCCTCCGTCCCTCCTTCCCTCCTTCCTTCCCAGGCCTTCTCTGACTACCAGATCCAGCAGATGACGGCCAACTTTGTGGATCAGTTTGGCTTCAATGATGAGGAGTTTGCAGACCATGACAACAACATCAAGTGAGTCCACTTGGATGCCCCCTGCACGAGGCACGACTCCCCCTCCTCGCTGCTGAAGTCCCATGGGGGCAGCTCCCTTAGTCCTTGCCGGGAGATAACAGGTGTTTCCAGTTGCATGAGGGTGCTGAGGCCCCCAGTGAGAACCAGGGGAGGAGCACTGAGGCCTCAGATGAGCACCGGGGGAGGAGCCCTGAGGCCCCAGATGAGCACCAGGGGAGGAGCACTGAGGCCCCAGATGAGCACCGGGGGAGGAGCGTTGAAGCCCCAGATGAGCACCAGAGGAGGAGAGCTGAGGCCCCAGATGAGCCCCGGGGGAGGAGCTCTGAGGCCCCAGACGAGCACCGGGGGAGGAGCGCCGAGGCCCCAGATGAGCACCGGGGGAGGAGCGCCGAGGCCCCAGATGAGCAGTGGGGGAGGAGCCCCGAGGCCCCCAGATGAGCAGTGGGCGGGGCAGGGAGCGCCGAGGCCATCCCCCTTGCTCTTGCAGCGCCCCATTTGACAGGATCGCGGAGATCAACTTCAACATCGACACTGACGAGGACAGTGTGAGCGAGCGGGGCTGTGCGGGGTCATGCAGGCACCCTGTTCCCAGGCAGCTCAGGCCGCGCCCATGGCTCGGTCTGTGGTGGGCCTGTGCGGTGGGGCTGGGAGAGGCCCCTCTGTGGAGCTAGGAACAGTCGCTTTTCTTGACCCTCCCCATCATGCCCTCCAGCCCATGGCGCCCACATCCTGAACTAAGCCCCTCTGGGAGCCCTGTGGGGAGAGCGCCTCCTGTCTCCCCCAGACCCTCTGGAAACTGACCTTGGCGTTTTACTCTGCAGCCCAGCGCGGCTCTGAGGCCTGCTGCAGCGACCGCATCCAGCACTTTGATGAGAACGAGGACATCTCGGAGGACAGCGACACTTGCTGTGCTGCCCAGGTGAAGGCCAGAGCCAGGTGCGGGGCCTGCCCATCCCCCCAAAGCCTCTGCCGAGGAGGTGCAGCCCCCAGAACACCCGTCAGATGCCCAGACGCCCTGCTGTTTGTTATGCCGG |
| 176 | chr21: 15649340-15649450 | TTTGGGCCACGAGGCAAGTTCAAAGCGGGAGACTTTTGTTTTATAAAATGATGGTGAGCAGCTCCGGTTTTATGTCAAACATCAGGGTTTCGTGCAGGATATAAACATTT |
| 177 | C21orf34 | ATTGCCGTACTTTGCTTCCCTTTGTATGTATTTCTTGTATGCTGCCGAGTCACTGATGGCTAGCTCTGTCTGGCAAGTAATTCAAAAATGCTGTTTATGTAGAAAGGAAAGGTAGGGACTTTACCACACTCTGTCATTAAAGGGAGCAATTGAAGAACAAAGGAACTGAGTAAATACCTATATATTGCCTTTTGTGTTGCGAAACACTGTAGCACAAACACATTTGTGTTCAGCCAAATGTTTTACTTCCTTTTGTAATAACGCATATAGTAGGTTGTCTCCACATATGTACAAGAATCCATATTTTATTTAAACGTATATAGTCAATTGTTCATATTTATAGGCTGCAAACATTTCTCAATCTCAAAGACTTTTACATATCCACTCCCACACAGCTATTTGTTATTATTTTAAAGTTCTTAAATTAAAAAAAAAAAATAAAATATACTAATATCTCTGTTGGTTGATTTTATTAAGCAACTTAGGATTTCAACACAGTTTAAATCATATTGATGACTCAGATCCTGGCAGGTCTTACAATTCCTGTGAAATGAGAGCACAGCTAATAAAAATATTAAGCAATTACTTTTATTAAAATCATAGGGTTTTTTTCATTATCACATAGAAATGATTGATCTATACAGATTGGTCTCACTCATGTGTCTTTTGGGCTGCTTGGGAGCTTCATGTAGAAGTGGAAAGTCCCCTTTGCTCTTCCTTCGACCAAGGTGGGGAAAATGAAGGCATAGAATACAATCTAGGGCTATTAAAGAATTGCTGGCATTACTTCTCTCTATCACGTGTGAGCCTGGCTGCCTGCTTCCTGAGGTAGGGGATCCAGGATGAGACTGTGCCGGAGCCTGTTTCCACAACTGCATTTGGAGATCCGTCTTATTGATTAGCGGGGGAAAGGGGTGGGGATCAGGAGTGTGAGGTGAGGGGAGGACCAACTGACGACTGGCTCAATGAAGCACAAGACATTTTCTTCCGGAAAGATGTCAAACAACTGAGAAACAGCCAGAGAGGAAGTAGAAAGGTGGAAAAATGAGGAGACCCTGGAAGAAATGAAGGCATTTCCTATGAGACAGCCTTGGGGCTTTTTTCTTTTCTTTCTTTTTTTTTGCTTCCATCATCTGACCTGCAAAGGCTAGAGTGACAGCGTCATGCAAATGCTGCAGTCCAGCAGGTCTGGGAGAGGGTGGATGCTAGACTGTGAGTTAATGTTAATGATGAGCGCAGTGAAAATACCAGCCGCTGCCACCCCCTGCTCACAGAAGCGCTCTGAGTCAGCATCAGATGCTTTGCCTCGCCTCTCGCTGTGTATCTGTATGCCTGTGTGCGCGCGCGTGCTCGCTCGGGCATCCGTGTCTAGCCGAGGGGAGGGGGTGGCGTGTGAGTGCGTGGAGGGTAAAAGCCAGTCAGTCAGTGAGAAGCAAAGGTACGTTGGAGAGCAACTAAAATCTGACTGATTTCCATCTTTGGAGCATCAGATGTATTCCC |
| 178 | BTG3 | GCAGCCTCCTCCTGAAAAATGTAAGCCATTTCCACTTTGTAAAGCTACGTTTATATTCCACCACGATACGATGGAAAAGAAAACCCAAGGCAATTTAATATACGGGTTGGGAAGAAAGTTTTGCTGATGGAACTACATTAGCCTCCACTCCAGCAAAGCAAACAAGGAACCACACTAAAGAAATGTACTGAATCTTTTAA |
| 179 | CHODL | TGCCTGAGCGCAGAGCGGCTGCTGCTGCTGTGATCCAGGACCAGGGCGCACCGGCTCAGCCTCTCACTTGTCAGAGGCCGGGGAAGAGAAGCAAAGCGCAACGGTGTGGTCCAAGCCGGGGCTTCTGCTTCGCCTCTAGGACATACACGGGACCCCCTAACTTCAGTCCCCCAAACGCGCACCCTCGAAGTCTTGAACTCCAGCCCCGCACATCCACGCGCGGCACAGGCGCGGCAGGCGGCAGGTCCCGGCCGAAGGCGATGCGCGCAGGGGGTCGGGCAGCTGGGCTCGGGCGGCGGGAGTAGGGCCCGGCAGGGAGGCAGGGAGGCTGCAGAGTCAGAGTCGCGGGCTGCGCCCTGGGCAGAGGCCGCCCTCGCTCCACGCAACACCTGCTGCTGCCACCGCGCCGCGATGAGCCGCGTGGTCTCGCTGCTGCTGGGCGCCGCGCTGCTCTGCGGCCACGGAGCCTTCTGCCGCCGCGTGGTCAGCGGTGAGTCAGGGGCCGTCTCCCCGAAGAACGAGCGGGGAGAGGGGACCACGGGGCGCGGCGGGCAGCCTGTTCTCGGGCGGAGGCTCTCCGGGGCGTTGGAAACCTGCATGGTGTAAGGACCCGGGAGGAGGCGGGGAGAAATTGATTGTGCTGTTCTCCTCCCTCTCTTCTCTAACACACACGCAGAAAAGTTTAAATTTTTGTGAAGCGCTTGCTTACGTAGCTGCGGAGCGAGCCTCTGCTTCATTACGAGCGGCATAGCCTTTTTCAGGAGTGATTTCCACTTTCTTTGTGAGAGAGTTGACCACAC |
| 180 | NCAM2 | TTCAATTTACACTCGCACACGCGGGTACGTGGGTGTTCGGGGTAGGGCACTGATCTGGGGAAGGTCTCCCCCCCGCGACCCAACTCATCTTTGCACATTTGCAGTCCTCCCTCGGTGCACTCCTGGCGGGGATCTGGCCAGTGCAGCGCACTGGGACCGAGGGCAGAGCCCGCGGAGTGAGGCCAGGAGAGACTTCAGGCCTCTAAGGACACAGCTGAGGCTAAGGCTGAGTTGAACGCAGCCCCTCCCGCGGCTCGTCCCCTCTCCAGTGTCTCTCCCGTAAGGTGCCGCTCCCAACAGCAATGGGTCGAGATGTAGAGGAAACACTCTGTACGTTATTTTTCCGCCCACCCTTTAGCGCCTGAGGAGACAGACAGTGTAGACTTTAGGGTACAATTGCTTCCCCTCTGTCGCGGCGGGGTGGGGAGCGTGGGAAGGGGACAGCCGCGCAAGGGGCCAGCCTGCTCCAGGTTTGAGCGAGAGAGGGAGAAGGAGGTCCACGGAGAGACAAGAATCTCCCTCCTCCCACGCCCAAAAGGAATAAGCTGCGGGGCACACCGCCCGCCTCCAGATCCCCCATTCACGTTGAGCCGGGGCGCG |

TABLE 4C-continued

| SEQ ID NO | GENE NAME | SEQUENCE |
| --- | --- | --- |
| 181 | chr21: 23574000-23574600 | TCATTATCCGATTGATTTTCCTGGTATCACATCACTTAAGTTTAAGTAGCTCTTATGTTACTTAGTAATGACTGCAAAACACGAGTTGTGATGCGGGCAATTTGGATACAACAAAAAGAAGCCATTAAGTTTGTTCGTTAGTTAACAGGTGAAAGCTCTCAAGTTATTAAGGATAAAAATGCTAGTATATATATATATGGTTTGGAACTATACTGCGGATTTTGGATCATATCCGCCATGGATAAGGGAGGAATACTATAATCAGGTTTGTTTTAAATTCCATGTCTAATGACTTCGTTATCTAGATCACCTGTAGAGCTGTTTTTATTGTAGGAGTTTTCCTTGGTTTTAATCTTTTGATTTGTTTTTCATGTTAATACTGAAATTTTTAAAAATTGCATATTGTACTTCCTATATGAAAATTTTACTATGTATTTTTATTTTTATTTTCCTTTTCCTTTAGGAAGAATTAGTTTGTTCCCTGACAGAGTTAGAGTAAGGGCAAATTACTTGTCTCTATAAACAACTCAGATGTTTTGAGCCGGTGTTGTAGGGGTTATCTTTTTCTGGTTTTGCATTTTATTATAGGACATAGTGCTT |
| 182 | chr21: 24366920-24367060 | AGAAAGAAGAAATCCGGTAAAAGGATGTGTTATTGAGTTTGCAGTTGGTGTTTGATCTTGCACAGATTTTCTCAGGGGCCTTAAGACCGGTGCCTTGGAACTGCCATCTGGGCATAGACAGAAGGGAGCATTTATACGCC |
| 183 | chr21: 25656000-25656900 | CGAAGATGGCGGAGGTGCAGGTCCTGGTGCTCGATGGTCGAGGCCATCTCCTGGTCCGCCTGGCGGCCATCGTGGCTAAACAGGTACTGCTGGGCCGGAAAGTGGTGGTCGTACGCTGCGAAGGCATCAACATTTCTGGCAATTTCTACAGAAACAAGTTGAAGTACCTGGGTTTCCTCCGCAAGCGGATGAACACCCACCTTTCCCGAGGTCCCTACCACTTCCGGGCCCCCCAGCCGCATCTTCTGGCGGACCGTGCGAGGTATGCCGCCCCACAAGACCAAGCGAGGCCAGGCTTCTCTGGACCGCCTCAAGGTGTTTGACCGCATCCCACCGCCCTACGACAAGAAAAAGCGGATGGTGTTCCTGCTCCCTCAAGGTTGTGCGTCTGAAGCCTACAAGAAAGTTTGCCTATCTGGGGCGCCTGGCTCACGAGGTTGGCTGGAAGTACCAGGCAGTGACAGCCACCCTGGAGGAGAAGAGGAAAGAGAAAGCCAAGATCCACTACCGGAAGAAGAAACAGCTCATGAGGCTACGGAAACAGGCCGAGAAGAACATGGAGAAGAAAATTGACAAATACACAGAGGTCCTCAAGACCCACAGACTCCTGGTCTGAGCCCAATAAAGACTGTTAATTCCTCATGCGTGGCTGCCCTTCCTCCATCGTCGCCCTGGAATGTACGGGACCCAGGGGCAGCAGCAGTCCAGGCGCCACAGGCAGCCTCGGACACAGGAAGCTGGGAGCAAGGAAAGGGTCTTAGTCACTGCCTCCCGAAGTTGCTTGAAAGCACTCGGAGAACTGTGCAGGTGTCATTTATCTATGACCAATAGGAAGAGCAACCAGTTACTATTAGTGAAAGGGAGCCAGAAGACTGATTGGAGGGCCCTATCTTGTGAGC |
| 184 | MIR155HG | GCCTGAAGACCATTTCTTCCTCTCTTAGGGACCTGCTGGTCTCCAGCTGATTCGGTCCAGGAGGAAAAACCTCCCACTTGCTCCTCTCGGGCTCCCTGCAAGGAGAGAGTAGAGACACTCCTGCCACCCAGTTGCAAGAAGTCGCCACTTCCCCCTCCAGCCGACTGAAAGTTCGGGCGACGTCTGGGCCGTCATTTGAAGGCGTTTCCTTTTCTTTAAGAACAAAGGTTGGAGCCCAAGCCTTGCGGCGCGGTGCAGGAAAGTACACGGCGTGTGTTGAGAGAAAAAAAATACACACACGCAATGACCCACGAGAAAGGGAAAGGGGAAAACACCAACTACCCGGGCGCTGGGCTTTTTCGACTTTTCCTTTAAAAAGAAAAAAGTTTTTCAAGCTGTAGGTTCCAAGAACAGGCAGGAGGGGGGAGAAGGGGGGGGGGGTTGCAGAAAAGGCGCCTGGTCGGTTATGAGTCACAAGTGAGTTATAAAAGGGTCGCACGTTCGCAGGCGCGGGCTTCCTGTGCGCGGCCGAGCCCGGGCCCAGCGCCGCCTGCAGCCTCGGGAAGGGAGCGGATAGCGGAGCCCCGAGCCGCCCGCAGAGCAAGCGCGGGGAACCAAGGAGACGCTCCTGGCACTGCAGGTACGCCGACTTCAGTCTCGCGCTCCCGCCCGCCTTTCCTCTCTTGAACGTGGCAGGGACGCCGGGGACTTCGGTGCGAGGGTCACCGCCGGGTTAACTGGCGAGGCAAGGCGGGGGCAGCGCGCACGTGGCCGTGGAGCCCGGCCTGGTCCCGCGCGCGCCTGCGGGTGCCCCCTGGGGACTCAGTGGTGTCGCCTCGCCCGGGACCAGAGATTGCGCTGGATGGATTCCCGCGGGCAGAGGCAGGGGGAAGGAGGGGTGTTCGAAACCTAATACTTGAGCTTCTTTGCAAAGTTTCCTTGGATGGTTGGGGACGTACCTGTATAATGGCCCTGGACCAGCTTCCCTGTTGGAGTGGCCAGAGAAGTGTGTAAAACACACTAGAGGGGCAGGGTGGAAAAAGAGACTGCCTTCAAAACTTGTATCTTTTCGATTTCATTTTGAAAAATAACTACAAATCTATTTTAATTTTACAAAGTTAGACTCATAGCATTTTAGATATCAATGTCTTCATTTAACAGAAGTGAAGATGGAGCAAACGCTCAATCAGCGTCTGTATTTATTCGCTCCTGTTGTGCCAGGGTGCGTTTTTGCCGAGCGGTTGCCTTTCTTTACTCACAAAACCCCCTTGATGTCTGTCCTCCACGTTTTACGAGGGAGAGCCGGATCTTTTGAAGTTTGTATCATCTAAAGCAGGTATATTGGGATGACTATGGATAGAATTTAACCTGAAAACACTGAAGTTGACAGCTGACAAAG |
| 185 | CYYR1 | CATAACAAGAGTCATTCTAATGTGATTATATAAAGGACCCGAAGCTTTGCTTTTAAAATTCAATACTTAGGTAGAAAGAAAATGATAACTTTTTCCCTTTGATTTTTATTCACTATTTTTATAACACTAGCAGCCCTGAGACACCGGATTGGAAATATCTATGCCTCTTGATGTTACCTGGGCACCACTGCATCACAGTCCT |
| 186 | chr21: 26938800-26939200 | AATAGTAATTGCCAACAGTCAAGATATGTACTACCACCAAATTCCGTGTTATTTGTGATCAAAAGATATACACAGATACTTGAAAACTGATTTCTACGTTGCATATGGGAAAAATACCTCATTTTTCTCAGCTGTCCATTATTTTTGAGATATTATGTGCAGTGATAGTAAGAACAAGCAGATTTGGAACACATCAGCAATAATTTTTTCAATCAGAGTCCTGCCAAAATGAAAGAATTTGACAGTATCCGGCACCCTGTACTCATGCTTGGCTTCTGTAGAAACTGTGGCTTGCAAAAGGGCAGCTGGGTACTGTGTTTTGGTACCTCATTCTTTAAACGTATAATGGGAATCTGGTTGGTTCAGGAAAACCCTTGCCTACTTATTATTACTCTGTTTT |
| 187 | GRIK1 | GGCCCATACTTAATGTATTTTTAAACGTTTTAACATTTACTAATATAGAACCTTCTATTGCCTATTTCCTTCTGGTTTATTCCCTTTCCTTCTGTCATTGAAGAAATGGTTCTAGTGGTAGAAATACTCCACGATTGAGAAGAATGTGGGAAGAAAGGAGGGCTGGTGGGTAAGAATTGCTCATGATGTCTCCCTCTGAATTCTGTGCTCTCACAATGACACTCCAATGTGTGGTTTGACGCCTGGAAGA |
| 188 | chr21: 30741350-30741600 | TGCTTCAACCGGAAATGTGGTTGAATTACCCTTACAGTGAACCTGATCAGTGGTAACAGGAGATGCTAGAACAGGAAAAGACAAGTTTCCCCTTTCCTCCCTATCCCATCAATTACTTTGAGGTGTATTTTTTCTTTGCAACCCCTCCAGAGAAGTCGGCAATGTTTAACGAGCATGCCTGCCAAGTGGCTTGCCTTATACCTCATTATGAAGTGATACTCAGGGCCACTAACACATCGCACAGCATTGC |
| 189 | TIAM1 | TATGATTCCCTCGATTTCCCTCAATCTTAACCATTGTGGATCACAGCAGGAGGGCCAGAAAGTGAGCTTCAGCCTGGCACCGGGACCTCAGCCTCTCCCTTAAACTTTCCCTAATCCTCGGAGCTAGTGTTACTCAAGTGACTCCACAGTGTTGCCCGATCCCTTCAGACATGGCCTTGATGATCTCCAAAACTCATGCTACCTTTGCCAGCCTAAAGCATCCACTCTGTGCCCCAAAACGTGAATGTCAAATACCCTTCAAGGCAGAAGGCTATTTCTATTTTTGTTTGTTTCTGTTTAAGGCAACAATCACCAACATTTGGTACACATGAGCCATCCTGTGAAACATCAAGGCGCTTCGTTGGCAGCAAGTCAACTTCGGTTTCAGAAGAAAGCTGCACTATTTCCTGAGGTTAGAGGTTTAAACCAAAACAAGACAACCACATTTTAACCCCAAATCTGCCGACTGAGGGTAACCATGATCCTTCCTTCACAGCACC |
| 190 | TIAM1 | TACTAAATCAACCCAAACCCGAGAACCCGGTCATGGAGAAATAAATGATAGTAATCTATGCTGTTCATCTGTTCCATCACTCACTCACTCTCTTGCTGAACAAGAAAGGGCCACCCATGTAGCAAACCACATGTAAAGAGCCGGGAAGAC |
| 191 | TIAM1 | TATTATTTTGTTCAAAGTAGACGGGTATACTAACATCTGTGGGCAAGTTTACCACACGCCACTTAAAACAGGCTAACAGGGTCATATGCCAAAACGTTCAGGTTTGCATTTTTGAAAAGCTCAGAGATCTGACAGATGTGTTCCGGCCGCGATTTAACATGCGGCTCCAGTGAGAAGGAAGCAGATATGACAAATGGTTCACTTATTTCAGAACTAAAACCCCAGAGGAGCAGCCTGAGCCAAAAAGGGAAGTGATCAATGGAAAAGACGGTCGAATCTGCTCACAGGCAAGGCAAGGGG |

TABLE 4C-continued

| SEQ ID NO | GENE NAME | SEQUENCE |
|---|---|---|
| 192 | SOD1 | AAGACCTGGAGTTTCCATTACACCGAATTGGCACTTAATAACTGTTGTCGGAGCATTTCTTAAGCCACATTTTCGTAAAGTGGCT<br>TTAAAATTGCTCTGCCAGTAGGCAGGTTGCTAAGATGGTCAGAGACAAACTTCTGAACGACTCTTGTAAAATATACAGAAATATT<br>TTCAGAACTTTTATCAGTAAAATTACAAAACGTGTTGCAAGGAAGGTGCTTGTGATAACACTGTCCCCAGAACCTTAGTGAAGTT<br>ACCAACTGGTGGAAAATTTTCTCTTGCACTCGGCTTAAAAATCAT |
| 193 | HUNK | GCAGGGGTGACTGGTCCTCTCTCTCTGCACCTCGCAGGATTTCTCTGGAAGATCTGAGCCCGAGCGTCGTGCTGCACATGACCGA<br>GAAGCTGGGTTACAAGAACAGCGACGTGATCAACACTGTGCTCTCCAACCGCGCCTGCCACATCCTGGCCATCTACTTCCTCTTA<br>AACAAGAAACTGGAGCGCTATTTGTCAGGGGTAAGTGCGACCCTAGAGGCGATCGTCTCTGCTGTCTGTGGAAAAAAGAGCTCCT<br>ACACCCAAAGTGCTTCTCAGTTGCTGACACTTGATCCAAGCTGCTAATTTAATCTAATGTGAGGCTGAGTTTTCTGAATGTGGGA<br>TAAAGTCGTAGCTAAACCTGCTTCTCAGGGAGTGCCTTTTATCTGCAATGTTTTTCAAAT |
| 194 | chr21:<br>33272200-<br>33273300 | AAGTAACGGGATCAAATTAATTATTATTTTGGTGGCCGCCTCTCTTCTCCACCCCAAGCCAGGCAAGACTCACCCTCGGCCCTGC<br>CCGCCCCAGCATTTCAAATGGAATACCTAGGTGGCCCAGGGGGACCCCTGACCCCTATATCCTGTTTCTTTCTGCCTGCTTTGCT<br>ACTTTTCTCCTTGATAAAAGGAGAGAGTGAGAGATAATTAACAAAAAACATGGCCCCAGGACAATGAAACAACTGGCCTTGGCCG<br>GCCAGAAATGTATCCTGGTTTTCTAGGTGAACTTTCTCCCATCAATCTTTCCTTTAACCTCTCTGTTAGTGGAAGCAATAGGAAC<br>ACCCCTCCCCTCCCCTGAGCAAATGCTTTCTTTTGACTGGAAACAAAACAGGGGCTCGGCGAAGGCTGAGGTGAAATCTGGGTGG<br>CATGGGCGCCGCACAATGGGGCCGCTGTTCCCCGGCCCGGGCTTGTGTTTTACAACAGGGGAGGGGCGGGCGTGAATGGTCTGAT<br>GATTGGAACAATCCCCCCGATTCAGGCCTACAAACGCATCTTCTGTTCCACACCGAGGGGACAGAAAGGAGAAAAGTGACAAAGA<br>ACGCGGGGCGGGGGGAATTAAAACAAAATGCGCTCGACTAAAAAATCTCTCATATCCTGCATATTCCAGAAAGCGGCTCTATGGA<br>GAGAGCCTTCAGGAGGCCTCAGCCATATCTGAATGGCTTTCTCTGGCCTCTGATTTATTGATGAAGCTGAAGCGACTTGCTGGAG<br>AAAGGCCTGGAGCCTTCTTTGTCTCCGAGATGAAGTACAATAGGCCACAGGGCGGAGATCTCTTGTGATGCTCTCGGGTCCTGCC<br>TTTCTCTTGCCCTCTCCTCCCTGCAAATACCAGCAGCGGTGACAAACGATTGGTGGTGTGCCTGGGAGAGCCGGTGACAAGACTG<br>GGCCACTTGAGGTCTCCTTAAGAGGGTATTATGGCCAGGGCGACGTTTGTGCTGTGAAGATGGCACACTCCATTTTGTCAATGGC<br>TCTCATCGGCCCAGATAATCGCCCCCTGCCTGCCTGTCAGGGGCGCAGCCGGCCGATTCATGGCGCCCTCGGAGAAAGTA |
| 195 | OLIG2 | GTCTTTCCCGCCCCCTTGTCTAAACTCAAAACCGAGTCCGGGCGCGCCTTGCAGGGCGCCCGAGCTCTGCAGCGGCGTTGCGGGC<br>TGAACCCATCCGGCACAAACTGCGGGCCACTGGCCCCTCACACCTGGGAGTTTGCGGCGCTGGCCTGCAGCCCGGGGCCCACGTG<br>GCGGAAGCTTTCCCGGGCGCGCGCTGCGCAGCCCCGCGGGGCCGGGGAGACACCGCTCGGGAGTCCTCCGCTCGGCTGCAGAATC<br>TTTATCAGCTGCACTTTACCGCAGCCCTGGCTAGGACGCTAGGCGGTGGAGCGCCCTATCCAGGTGCGCCGCCGCACCATGGATC<br>ACCGCGCCCGGTCCCGCAGTCCCGCCATGGCCTGGGGAGGCCCGAAGCCCGGGGACAGTGGCCGGCCCATCTCCGGCTCCGCGGA<br>CCCCCGGCTCAGGCGGGAGGGCAGGCGGGTCCCTGCAGGCCCCCAGGGAGCCCGGGAGCCTCTCTCTGGCGTCATTCAGTCCCGG<br>GGCAACCTGAAGCGCGGTAGATATTGGAGAGGGGGCGTCTGTTGGGGGGACCTGGCGTCATTACTGATGGCTAGCAGGGAGGAGG<br>GAACGGGTTGTCACCTCGGCCTCATAAGGCCGTGAGTGAGTAGTCCAGGGCCTCTTCAGGCATTTTTGAAACTGGATTAACTAGG<br>GGGGAAATTGTAGCACTGAAGCCACCGTGACTGTCTTTTGCGCTGTGTGGAAACTCCGGTAAAACTCTTTGGGCAACAGTCTTAT<br>CACCAGCTCTTCAACGTGTGCAGCCCTTCTGGTCCTGTCCCTGTTCTGGGCCCCAGGAATGCAAAGCAGGTCCAGGCACTGTGAA<br>GACCCTGGCGGTGGAGGAAGAGGCTTCCCGGCTGTGGAGGAAGCCAGACCCTTACAACACAAGACGAGAACCAGACCTGCGTGGG<br>GGAGCTCTGGATGCTACAGGGGCTCAAGGAGGGGTGGAGGGGCCTTCCCAGGCCAACCCCTGAACGGCTTGGACAAGATGCTCAG<br>ATGGACGGGAGGAACGGCGTGTGGGATGGGGGAGCTGGAGGCGGGTGGGTGGGGGGGGGAGGATGGGGAAAGCGCTGGCCCACCC<br>AGTGTGGGAGGGGTAGAGGAAAAGCCCGCAGGGGCCAGGTTGGGACCCCGTAGGCCGGGTTAGAGGGCTTGGACTTGATCCTGAC<br>AGGCGACAGGGAGACATATTGCTACTTATTATGTGCACAGTGGCCAGATCTCTAAAGAAAACACCATCCCCCACCCCCACCCCCC<br>ATATAGTAAACCAGGTGGTCCGCCCAGTGCTCCCAGGGAGGTGATGGAAATCCCACTCCATACCCTGCGGTGAGGGGTTCCATG<br>CCCTCCACGTGTGCAACTACTCCGGGCCCAGGGAAACACTGGGCCCCATCCGGTAACCCCCGGCCCAGTCGGGTTTCCCAGTTCA<br>CATTATAACCAAACGGTCTTGCCAGCTAGACAGACAGACACCCCTGACCTGTTTACCCTGATCCTCTGCTCTCAGGATTAATCAC<br>AACTTGTCGAAGGGGGTGGCTTCCAGTGGGGTGGACCGCTCTGTCAATGCCAGCGTGTGTCTAGCATCTCCTGGGGTGGGGGTGT<br>GGGGAAGGGAGGTGTAGGATGAAGCCCTAGAAGCCTCAGGCAATTGTGATCCGGTGGGCTGGATACTGAAGCCCACCCCTGCCTT<br>GACCTCAATTTTCAGTATCTTCATCTGTAAAATGGGAACAACCTGCCTTCCTCCTAGCCCTAAAGGGGCTGCTGTCAAGATTGGC<br>TGAGATAGCTGTTTGCAAGCTGAGCTCAATGAAAGTTCATTGTGTCCCCCTCAGTCCTATCCCAATATCGTCTCACTGCAAAGGT<br>GGGGGGCAGCTTAACTTCAAGGGCACTTCAAGGATAGCCAGGTGGCTGTCAGCCCAGCTTTCCAGGATGGGAGCAGGATCTTGAC<br>AGAAGGGTTGACTGGGAGGGGCAGTTGCTGGTTTGGGCTTCGTTAGGTTGCATTTTTGTTTGTTGTCCTTTCATTTCCCTGGGGC<br>AGCACCCCTTCCTGCAAGCTCCAGGCCTTCCTCTGGAATGCTCCTAGAGCCCAACCTCTGCTGGTGCCTGAGCTTAAGCCAGGCC<br>AGCTAAGGGGATCCTGGATTCACACGGCCTCACAGTCACTCAGATTGTTAGCAGAAGACAAAAATTACAAGGGGAGGGCGTCATG<br>TGATTCTTACACACCCTCCAAATCCAGCAGACACCTTGGAAGCCACAGGTAGCTTCAAGAAACCCATTTTACGGATGAGAACCTG<br>AGATGGAGAAAGGACAACTGGAGATCTCTGAGTCTCTGAGCCCACACTCCCTACCTCCCTGCACCTCCAGGCACTCTGCTGGCAG<br>GATCTTGGGCAAATGCCCACAGCTCTCTGAGAGTCAGTTTTCCTGTCTGTAAAATGGGAGTCATACCTTCCTCCTATGGCCGGTG<br>AGAGACTAAATTAAACTATGTCTGTCAAGACACCTGAAACTCCTGGCACAATTTAGGTTGCCTTCAAGTGGTCACAGTTGTCATT<br>AGGTGGAAGTCAACACCCCAATCATTGTAAAGGTGCCCATATACCCCAAGATCCAGATTACAGCTCTCACAGTTTATTATATACA<br>GCGAAAAAACACATAACACACCTTTGCCCACATTTACATGTATTTTACGGACCATGTTTCACATCAGTCCGCATGCACATCTGCA<br>CGTGTGTGCATTCGGCAGTATTTACCAAGCACCTGCCAAGTGCCAGGGCCTGTCCTCCGCACCCGGCGTGAACTGTCCTGGACCA<br>GTCCCGGGAGCCGCGGTTCTGACCAGCCGTGCTGACCCTGGACGACTCCATGAGCTGTTTTGTGAGAAAGACACGCCATTTGTTT<br>GCAGAGTTCTGACTTCTGAGGGGTCATGTAGCACATGTTTGGTAGCCAAACGCTGTCATTCACGACCAGGAGCGATGGCTGCAAT<br>GCCTTTTTCTTTGCTTTGCTTTCCGGTGCCGGGAGCCTTGCCTCCCGCCGCCACCCCTGGTCAGCTCTGCGCAAGAACGTCGTTC<br>TGTTTGGCAGCCAGGCCGAGACGCAGCCTGAATGTGAGCAGGAACTCGGAGAAGGGAAGGGAGAGAATCAGAAAGAAGGCCCGGG<br>AGGGACCCGGGAAGCAGTGGGAGGTCTGCGCCCTGGAGCCCCGCGAGAGCCCGCCGGTTTGGCACGGGCTCCTCCCGGGCCGCCC<br>GGCGGTCCAACAAAGGCCGGCCCCGACACGCACCCGGTCTTTTGTGGGAGAGAAACACAAAGAAGAGGGAAAAACACGGAGGAGG<br>CCAACAGCACCAGGACGCGGGGGCCAACCAGGAACTCCCGGAGCCGGGGCCCATTAGCCTCTGCAAATGAGCACTCCATTCCCCA<br>GGAAGGGGCCCCAGCTGCGCGCGCTGGTGGGAACCGCAGTGCCTGGGACCCGCCCAGGTCGCCCACCCCGGGCGCCGGGCGCAGG<br>ACCCGGACAAGTCCTGGGGACGCCTCCAGGACGCACCAGGGCAAGCTTGGGCACCGGGATCTAATTTCTAGTTATTCCTGGGACG<br>GGGTGGGGAGGCATAGGAGACACACCGAGAGGTACTCAGCATCCGATTGGCACCAGGGCCAAGGGAGCCCAGGGGCGACACAGAC<br>CTCCCCGACCTCCCAAGCTACTCCGGCGACGGGAGGATGTTGAGGGAAGCCTGCCAGGTGAAGAAGGGGCCAGCAGCAGCACAGA<br>GCTTCCGACTTTGCCTTCCAGGCTCTAGACTCGCGCCATGCCAAGACGGGCCCCTCGACTTTCACCCCTGACTCCCAACTCCAGC<br>CACTGGACCGAGCGCGCAAAGAACCTGAGACCGCTTGCTCTCACCGCCGCAAGTCGGTCGCAGGACAGACACCAGTGGGCAGCAA<br>CAAAAAAAGAAACCGGGTTCCGGGACACGTGCCGGCGGCTGGACTAACCTCAGCGGCTGCAACCAAGGAGCGCGCACGTTGCGCC<br>TGCTGGTGTTTATTAGCTACACTGGCAGGCGCACAACTCCGCGCCCCGACTGGTGGCCCCACAGCGCGCACCACACATGGCCTCG<br>CTGCTGTTGGCGGGGTAGGCCCGAAGGAGGCATCTACAAATGCCCGAGCCCTTTCTGATCCCCACCCCCCCGCTCCCTGCGTCGT<br>CCGAGTGACAGATTCTACTAATTGAACGGTTATGGGTCATCCTTGTAACCGTTGGACGACATAACACCACGCTTCAGTTCTTCAT |

TABLE 4C-continued

| SEQ ID NO | GENE NAME | SEQUENCE |
|---|---|---|
| | | GTTTTAAATACATATTTAACGGATGGCTGCAGAGCCAGCTGGGAAACACGCGGATTGAAAAATAATGCTCCAGAAGGCACGAGAC<br>TGGGGCGAAGGCGAGAGCGGGCTGGGCTTCTAGCGGAGACCGCAGAGGGAGACATATCTCAGAACTAGGGGCAATAACGTGGGTT<br>TCTCTTTGTATTTGTTTATTTTGTAACTTTGCTACTTGAAGACCAATTATTTACTATGCTAATTTGTTTGCTTGTTTTTAAAACC<br>GTACTTGCACAGTAAAAGTTCCCCAACAACGGAAGTAACCCGACGTTCCTCACACTCCCTAGGAGACTGTGTGCGTGTGTGCCCG<br>CGCGTGCGCTCACAGTGTCAAGTGCTAGCATCCGAGATCTGCAGAAACAAATGTCTGAATTCGAAATGTATGGGTGTGAGAAATT<br>CAGCTCGGGGAAGAGATTAGGGACTGGGGGAGACAGGTGGCTGCCTGTACTATAAGGAACCGCCAACGCCAGCATCTGTAGTCCA<br>AGCAGGGCTGCTCTGTAAAGGCTTAGCAATTTTTTCTGTAGGCTTGCTGCACACGGTCTCTGGCTTTTCCCATCTGTAAAATGGG<br>TGAATGCATCCGTACCTCAGCTACCTCCGTGAGGTGCTTCTCCAGTTCGGGCTTAATTCCTCATCGTCAAGAGTTTTCAGGTTTC<br>AGAGCCAGCCTGCAATCGGTAAAACATGTCCCAACGCGGTCGCGAGTGGTTCCATCTCGCTGTCTGGCCCACAGCGTGGAGAAGC<br>CTTGCCCAGGCCTGAAACTTCTCTTTGCAGTTCCAGAAAGCAGGCGACTGGGACGGAAGGCTCTTTGCTAACCTTTTACAGCGGA<br>GCCCTGCTTGGACTACAGATGCCAGCGTTGCCCCTGCCCCAAGGCGTGTGGTGATCACAAAGACGACACTGAAAATACTTACTAT<br>CATCCGGCTCCCCTGCTAATAAATGGAGGGGTGTTTAACTACAGGCACGACCCTGCCCTTGTGCTAGCGCGGTTACCGTGCGGAA<br>ATAACTCGTCCCTGTACCCACACCATCCTCAACCTAAAGGAGAGTTGTGAATTCTTTCAAAACACTCTTCTGGAGTCCGTCCCCT<br>CCCTCCTTGCCCGCCCTCTACCCCTCAAGTCCCTGCCCCCAGCTGGGGGCGCTACCGGCTGCCGTCGGAGCTGCAGCCACGGCCA<br>TCTCCTAGACGCGCGAGTAGAGCACCAAGATAGTGGGGACTTTGTGCCTGGGCATCGTTTACATTTGGGGCGCCAAATGCCCACG<br>TGTTGATGAAACCAGTGAGATGGGAACAGGCGGCGGGAAACCAGACAGAGGAAGAGCTAGGGAGGAGACCCCAGCCCCGGATCCT<br>GGGTCGCCAGGGTTTTCCGCGCGCATCCCAAAAGGTGCGGCTGCGTGGGGCATCAGGTTAGTTTGTTAGACTCTGCAGAGTCTCC<br>AAACCATCCCATCCCCCAACCTGACTCTGTGGTGGCCGTATTTTTTACAGAAATTTGACCACGTTCCCTTTCTCCCTTGGTCCCA<br>AGCGCGCTCAGCCCTCCCTCCATCCCCCTTGAGCCGCCCTTCTCCTCCCCCTCGCCTCCTCGGGTCCCTCCTCCAGTCCCTCCCC<br>AAGAATCTCCCGGCCACGGGCGCCCATTGGTTGTGCGCAGGGAGGAGGCGTGTGCCCGGCCTGGCGAGTTTCATTGAGCGGAATT<br>AGCCCGGATGACATCAGCTTCCCAGCCCCCCGGCGGGCCCAGCTCATTGGCGAGGCAGCCCCTCCAGGACACGCACATTGTTCCC<br>CGCCCCCGCCCCCGCCACCGCTGCCGCCGTCGCCGCTGCCACCGGGCTATAAAAACCGGCCGAGCCCCTAAAGGTGCGGATGCTT<br>ATTATAGATCGACGCGACACCAGCGCCCGGTGCCAGGTTCTCCCCTGAGGCTTTTCGGAGCGAGCTCCTCAAATCGCATCCAGAG<br>TAAGTGTCCCCGCCCCACAGCAGCCGCAGCCTAGATCCCAGGGACAGACTCTCCTCAACTCGGCTGTGACCCAGAATGCTCCGAT<br>ACAGGGGGTCTGGATCCCTACTCTGCGGGCCATTTCTCCAGAGCGACTTTGCTCTTCTGTCCTCCCCACACTCACCGCTGCATCT<br>CCCTCACCAAAAGCGAGAAGTCGGAGCGACAACAGCTCTTTCTGCCCAAGCCCCAGTCAGCTGGTGAGCTCCCCGTGGTCTCCAG<br>ATGCAGCACATGGACTCTGGGCCCCGCGCCGGCTCTGGGTGCATGTGCGTGTGCGTGTGTTTGCTGCGTGGTGTCGATGGAGATA<br>AGGTGGATCCGTTTGAGGAACCAAATCATTAGTTCTCTATCTAGATCTCCATTCTCCCCAAAGAAAGGCCCTCACTTCCCACTCG<br>TTTATTCCAGCCCGGGGGCTCAGTTTTCCCACACCTAACTGAAAGCCCGAAGCCTCTAGAATGCCACCCGCACCCCGAGGGTCAC<br>CAACGCTCCCTGAAATAACCTGTTGCATGAGAGCAGAGGGGAGATAGAGAGAGCTTAATTATAGGTACCCGCGTGCAGCTAAAAG<br>GAGGGCCAGAGATAGTAGCGAGGGGGACGAGGAGCCACGGGCCACCTGTGCCGGGACCCCGCGCTGTGGTACTGCGGTGCAGGCG<br>GGAGCAGCTTTTCTGTCTCTCACTGACTCACTCTCTCTCTCTCTCCCTCTCTCTCTCTCTCATTCTCTCTCTTTTCTCCTCCTCT<br>CCTGGAAGTTTTCGGGTCCGAGGGAAGGAGGACCCTGCGAAAGCTGCGACGACTATCTTCCCCTGGGGCCATGGACTCGGACGCC<br>AGCCTGGTGTCCAGCCGCCCGTCGTCGCCAGAGCCCGATGACCTTTTTCTGCCGGCCCGGAGTAAGGGCAGCAGCGGCAGCGCCT<br>TCACTGGGGGCACCGTGTCCTCGTCCACCCCGAGTGACTGCCCGCCGGAGCTGAGCGCCGAGCTGCGCGGCGCTATGGGCTCTGC<br>GGGCGCGCATCCTGGGGACAAGCTAGGAGGCAGTGGCTTCAAGTCATCCTCGTCCAGCACCTCGTCGTCTACGTCGTCGGCGGCT<br>GCGTCGTCCACCAAGAAGGACAAGAAGCAAATGACAGAGCCGGAGCTGCAGCAGCTGCGTCTCAAGATCAACAGCCGCGAGCGCA<br>AGCGCATGCACGACCTCAACATCGCCATGGATGGCCTCCGCGAGGTCATGCCGTACGCACACGGCCCTTCGGTGCGCAAGCTTTC<br>CAAGATCGCCACGCTGCTGCTGGCGCGCAACTACATCCTCATGCTCACCAACTCGCTGGAGGAGATGAAGCGACTGGTGAGCGAG<br>ATCTACGGGGGCCACCACGCTGGCTTCCACCCGTCGGCCTGCGGCGGCCTGGCGCACTCCGCGCCCCTGCCCGCCGCCACCGCGC<br>ACCCGGCAGCAGCAGCGCACGCCGCACATCACCCCGCGGTGCACCACCCCATCCTGCCGCCCGCCGCCGCAGCGGCTGCTGCCGC<br>CGCTGCAGCCGCGGCTGTGTCCAGCGCCTCTCTGCCCGGATCCGGGCTGCCGTCGGTCGGCTCCATCCGTCCACCGCACGGCCTA<br>CTCAAGTCTCCGTCTGCTGCCGCGGCCGCCCCGCTGGGGGGCGGGGGCGGCGGCAGTGGGGCGAGCGGGGGCTTCCAGCACTGGG<br>GCGGCATGCCCTGCCCCTGCAGCATGTGCCAGGTGCCGCCGCCGCACCACCACGTGTCGGCTATGGGCGCCGGCAGCCTGCCGCG<br>CCTCACCTCCGACGCCAAGTGAGCCGACTGGCGCCGGCGCGTTCTGGCGACAGGGGAGCCAGGGGCCGCGGGGAAGCGAGGACTG<br>GCCTGCGCTGGGCTCGGGAGCTCTGTCGCGAGGAGGGGCGCAGGACCATGGACTGGGGGTGGGGCATGGTGGGGATTCCAGCATC<br>TGCGAACCCAAGCAATGGGGGCGCCCACAGAGCAGTGGGGAGTGAGGGGATGTTCTCTCCGGGACCTGATCGAGCGCTGTCTGGC<br>TTTAACCTGAGCTGGTCCAGTAGACATCGTTTTATGAAAAGGTACCGCTGTGTGCATTCCTCACTAGAACTCATCCGACCCCCGA<br>CCCCCACCTCCGGGAAAAGATTCTAAAAACTTCTTTCCCTGAGAGCGTGGCCTGACTTGCAGACTCGGCTTGGGCAGCACTTCGG<br>GGGGGGAGGGGGTGTTATGGGAGGGGGACACATTGGGGCCTTGCTCCTCTTCCTCCTTTCTTGGCGGGTGGGAGACTCCGGGTAG<br>CCGCACTGCAGAAGCAACAGCCCGACCGCGCCCTCCAGGGTCGTCCCTGGCCCAAGGCCAGGGGCCACAAGTTAGTTGGAAGCCG<br>GCGTTCGGTATCAGAAGCGCTGATGGTCATATCCAATCTCAATATCTGGGTCAATCCACACCCTCTTAGAACTGTGGCCGTTCCT<br>CCCTGTCTCTCGTTGATTTGGGAGAATATGGTTTTCTAATAAATCTGTGGATGTTCCTTCTTCAACAGTATGAGCAAGTTTATAG<br>ACATTCAGAGTAGAACCACTTGTGGATTGGAATAACCCAAAACTGCCGATTTCAGGGGCGGGTGCATTGTAGTTATTATTTTAAA<br>ATAGAAACTACCCCACCGACTCATCTTTCCTTCTCTAAGCACAAAGTGATTTGGTTATTTTGGTACCTGAGAACGTAACAGAATT<br>AAAAGGCAGTTGCTGTGGAAACAGTTTGGGTTATTTGGGGGTTCTGTTGGCTTTTTAAAATTTTCTTTTTTGGATGTGTAAATTT<br>ATCAATGATGAGGTAAGTGCGCAATGCTAAGCTGTTTGCTCACGTGACTGCCAGCCCCATCGGAGTCTAAGCCGGCTTTCCTCTA<br>TTTTGGTTTATTTTTGCCACGTTTAACACAAATGGTAAACTCCTCCACGTGCTTCCTGCGTTCCGTGCAAGCCGCCTCGGCGCTG<br>CCTGCGTTGCAAACTGGGCTTTGTAGCGTCTGCCGTGTAACACCCTTCCTCTGATCGCACCGCCCCTCGCAGAGAGTGTATCATC<br>TGTTTTATTTTTGTAAAAACAAAGTGCTAAATAATATTTATTACTTGTTTGGTTGCAAAAACGGAATAAATGACTGAGTGTTGAG<br>ATTTTAAATAAAATTTAAAGTAAAGTCGGGGGATTTCCATCCGTGTGCCACCCCGAAAAGGGGTTCAGGACGCGATACCTTGGGA<br>CCGGATTTGGGGATCGTTCCCCCAGTTTGGCACTAGAGACACACATGCATTATCTTTCAAACATGTTCCGGGCAAATCCTCCGGG<br>TCTTTTTCACAACTTGCTTGTCCTTATTTTTATTTTCTGACGCCTAACCCGGAACTGCCTTTCTCTTCAGTTGAGTATTGAGCTC<br>CTTTATAAGCAGACATTTCCTTCCCGGAGCATCGGACTTTGGGACTTGCAGGGTGAGGGCTGCGCCTTTGGCTGGGGGTCTGGGC<br>TCTCAGGAGTCCTCTACTGCTCGATTTTTAGATTTTTATTTCCTTTCTGCTCAGAGGCGGTCTCCCGTCACCACCTTCCCCCTGC<br>GGGTTTCCTTGGCTTCAGCTGCGGACCTGGATTCTGCGGAGCCGTAGCGTTCCCAGCAAAGCGCTTGGGGAGTGCTTGGTGCAGA<br>ATCTACTAACCCTTCCATTCCTTTTCAGCCATCTCCACTACCCTCCCCCAGCGGCCACCCCCGCCTTGAGCTGCAAAGGATCAGG<br>TGCTCCGCACCTCTGGAGGAGCACTGGCAGCGCTTTGGCCTCTGTGCTCTTTCCT |
| 196 | OLIG2 | CCGGCACGGCCCGCATCCGCCAGGATTGAAGCAGCTGGCTTGGACGCGCGCAGTTTTCCTTTGGCGACATTGCAGCGTCGGTGCG<br>GCCACAATCCGTCCACTGGTTGTGGGAACGGTTGGAGGTCCCCCAAGAAGGAGACACGCAGAGCTCTCCAGAACCGCCTACATGC<br>GCATGGGGCCCAAACAGCCTCCCAAGGAGCACCCAGGTCCATGCACCCGAGCCCAAAATCACAGACCCGCTACGGGCTTTTGCAC<br>ATCAGCTCCAAACACCTGAGTCCACGTGCACAGGCTCTCGCACAGGGGACTCACGCACCTGAGTTCGCGCTCACAGATCCACGCA<br>CACCGGTGCTTGCACACGCAAGGGCCTAGAACTGCAAAGCAGCGGCCTCTCTGGACCGCCTCCCTCCGGCCCTCCTGAGCCCTAC<br>TGAGCCCTGCTGAGTCCTGGAGGCCCTGTGACCCGGTGTCCTTGGACCGCAAGCATCCTGGTTTACCATCCCTAC |

TABLE 4C-continued

| SEQ ID NO | GENE NAME | SEQUENCE |
| --- | --- | --- |
| 197 | RUNX1 | GGACGCGGCCCGCTCTAGAGGCAAGTTCTGGGCAAGGGAAACCTTTTCGCCTGGTCTCCAATGCATTTCCCCGAGATCCCACCCA<br>GGGCTCCTGGGGCCACCCCCACGTGCATCCCCCGGAACCCCCGAGATGCGGGAGGGAGCACGAGGGTGTGGCGGCTCCAAAAGTA<br>GGCTTTTGACTCCAGGGGAAATAGCAGACTCGGGTGATTTGCCCCTCGGAAAGGTCCAGGGAGGCTCCTCTGGGTCTCGGGCCGC<br>TTGCCTAAAACCCTAAACCCCGCGACGGGGGCTGCGAGTCGGACTCGGGCTGCGGTCTCCCAGGAGGGAGTCAAGTTCCTTTATC<br>GAGTAAGGAAAGTTGGTCCCAGCCTTGCATGCACCGAGTTTAGCCGTCAGAGGCAGCGTCGTGGGAGCTGCTCAGCTAGGAGTTT<br>CAACCGATAAACCCCGAGTTTGAAGCCCGACAAAAAGCTGATAGCAATCACAGCTTTTGCTCCTTGACTCGATGGGATCGCGGGA<br>CATTTGGGTTTCCCCGGAGCGGCGCAGGCTGTTAACTGCGCAGCGCGGTGCCCTCTTGAAAAGAAGAAACAGACCAACCTCTGCC<br>CTTCCTTACTGAGGATCTAAAATGAATGGAAAGAGGCAGGGGCTCCGGGGAAAGGGAACCCCTTAGTCGGCCGGGCATTTTACGG<br>AGCCTGCACTTTCAAGGACAGCCACAGCGTGTACGAAGTGAGGAATTCCTTTCCACCAAGAGCGCTCATTTTAGCGACAATACAG<br>AATTCCCCTTCCTTTGCCTAAGGGAGAAAGGAAAGGAAACATTACCAGGTTCATTCCCAGTGTTTCCCTGGAGTAATGCTAGAAT<br>TTACTTTTGTCATAATGCAAAATTAAAAAAAAAAAAAATACAACGAAGCGATACGTTGGGCGGATGCTACGTGACAGATTTTTCC<br>AAATTTTGTTGCGGGGAGAGGGAGGGAGGAGAATTGAAAACGGCTCACAACAGGAATGAAATGTA |
| 198 | RUNX1 | TTTTTAATGCTCAGAGAAGTTCGTATTACTGATTCGGGAACACTGAGTTTTTCAGCTCCTGTAAAACTATTTTCAGGTTTATTTT<br>CAAGTACATTCTTTA |
| 199 | RUNX1 | CACCCTAGAGGCAAGGACGGGGTCTGTGTCAAGAGGCTTCCCAGAGAAGTGAAAACTCTGCAGGTGCAGCCGCTGGGAGAGCATC<br>AAGAAGGGCAGGGTGGAGGGGCAGGGGGCGAAGGGAGGGGGTGAAGCCCGCACCCTACCCCCACATGAAACTGATTCCACTACCC<br>CATCTCTGCAAGCGTCCAGAGGCAGAGAGGCCAACATTTCGGGGACAGCTTGGAGGCGGGAGATTTAGGCAGGGCTCCTTAAACT<br>TTTATGTGCATGAAAATCAGGCCAATCACGGGGCTCTTGAGCAAATGGGGACGATGATTCAGCAGGTCTGGGCTGAGGCCTCAGA<br>TTCTGCACTTCTAACAAGTTCCCAGGTGGTAGTGATGCTGCCAGTCCAAAGACCACACTG |
| 200 | RUNX1 | TGCTTCAGTGGGGTAAACTTGAACCGCTGAGAAGACAAGCAGGGAGTCGGTCTCGCTGAGATTTTTACCTGTGGTTCTAGGAACG<br>CAGAGGCATGTGAGTGTTCAGGCTTTGCATAGACCACTAAGCCACTTCTAAGAACAAGGCTACCTGAGCCATTTTGCAAAAATAT<br>GTACGTGCCGAGGCTTTTCCTCCCCACACCTACCTCAACTCTTTCTGCCGACACACTGCACTTTTCAAGGGAACCCAAGTTTGGG<br>TTCGGCAAGAATTGTACGTTGCACACCGTGTGTGATAATTCCAGGGAATTTCAATCGCATCTTGTCTTCCTTCCTAAGCAAATTC<br>GGTGGGAACCTGGTGTGGTGTGATAGAAAAAGCCCCGAGTTCTCTGTGGTAGACCACATCAATTTCATGTGCCAGTCTCTCAGAC<br>TCCGGCTTGCCTCTCTCAAGGAAGGGAACAATGGTTTGCTTGGCTTCACTCCTCTCTTTCCCCCCAATTTCCACATGGGTATCTG<br>GCTAAAAATGAGTTACAGGTTTCCTTCTGTGAGAATTGCATGGACTGATAAAGTACCATCCCAGGAAGAAAACAAAGATGCTGTC<br>TTCCCTTTCGGCTCACAGTTGCCGTTGGGGAGGGAACACACGCTGTAAATTATAGGCAGCCAGAAGTGACCGCATTGACCACTGC<br>GAGTGGCCCAGCTATGGCAACAGGCTGAGAACTCTGGGGGAGAGCCATTTGTTGGCAGGGATGGTGATTCTTCTAGCATCAAGCT<br>CTAAGATGATGACCAAACGGTATCAAAAGAAATGATATTTTGCTACCTCTCCGGCTTGGGTGAATGATGTGGACAGTTAACCTGG<br>ACAATTTAAACCTTTATGTTGATGGATCACTTGGATGAAATTAACCAGGAAATTGCCAAGATTTCACTTGGCCCTCTGACATCAA<br>ATCTCAATATTATATTACCAAATTAGAGATTCTAAAGAACCCTGAGTTCCTTTCACTGAAAGGAAGGAGTGGAAAAACCTTTCCA<br>GATGATCCCTTTTGAGTCTTGGTGCGAGCTCAGGCCCTCCCTACACTGCCTCCGTGAAAGCTAACCGACCCTTGTTCCTAACCTA<br>GCGCAGGTCAGCTGAGTGTCCATCGGGCACAGGAGCCCTGGGCTTGTCCGGGAGATAGCCAGACTCCTGCTATTTCCTGATGTCT<br>GCATAGCTCAGCGTGTCCCTCACCATCTTTGCCGTTGGCCAGTAAGGAGAGCCCCAGGGGCCAGCACTGCACACTGAAACCCAAC<br>CTATTGCTCAATGGAATGCTTAAAAATTTCCTGAATCTGCCTTCCTGAGTTGATAAAATAGGAAACAATACACGTTCTGAGGGGG<br>TACTGAAAGCAGAGTAAAGCCAGGAAGATCTTTTTTTTCTGTTATTCTATACAAATATTGCTTCCTCTGCTTGTTAGCAGCCCAG<br>AGGAAATGCAGCCAGGGAGCCGTTTGCAGCTTTTCACCAGTGGCCGGTGTCTCTGTGTTACCAACCAAACGACGCTGCAAGACTA<br>GTGACTAACGCACGTCTGCATGATTCAACTTCACTAAAATTCCCTCTGCTGCCAGTAAAGAAGCACTTGAAAACTCTTTAATTTG<br>AAACTTGAGCTTGGTTAATGACTTGTTTTCTTCTCTTTCTCTTTAACTTCTCTCTTGCCATCTCCAACACACACACACACACACA<br>CACACACACACACACACACACACACACACTCTCTCTCTCTCTCTCTCTCTCTCTCTCTCTCTCTCATCAAGTTTTTTAATTTCAG<br>GGACCCGGAAACATACAGCCCCGTGCATTCACAATAGCATTTGCTGTGATAAAGTGGCCGGCAAGCCCTCTGCATTCCCCTGCTC<br>ACTTAGCTGTATGAATAAATAATGAGTCACAGATACAATTTGGGTGCTCAAGAGAGTTTGTAGCCAGAAAATTAATTATTCTCCC<br>ATCCCAGCCCACTCCATCTCAGCTTTGCCAAACCATCAAGATACACTTTGCAGGCACTGGTCAGAGTGCGTGCCCCGACGCACAC<br>GGCAATGCCTTTGAGACATTTTATGTTATTATTTTTGTTTGTTTAAGCACAGCCCTCTTTTACCACGAAAGATACACAAGACGCA<br>CATGCACACACATACTCACACACTCACAGCTCAACCACAGCTTTGTCCATTTCAAGAGGCTGGTTTCAAAAATGGAGACAGGTTT<br>TCCACCCTGGCTGTTCCTATTCATAAGCCTGTAATCTAACGACTTAAGCTGCGAGAATGCTTAACTCGGGAAACTTCTCTATTGC<br>CCTTTTCCAGAGAGACCTCGGTATGCCACAATTTGCTTCCTTTCTCTCTTGAAAGATGCTGGTTGTCTCTTTGCATTGAGGCTAC<br>AAGGAAAAACACAGCACAGCCCCATGCTGATGATTTTAACCTAACCAAGTCTGTCAGTCTCCTGTACTCTCTGCCTTATAGAGAC<br>AGCTGCCTTGCCACTTTGGCCCTGAAGTCCCCAGGCTGGTGCAAGGCTATCTGAGAGCCTCCGCCTCCTGCCCCACACTGGCACC<br>AGCCCTCCTGGCTGGCTCTGTGCATGTGCCTGCTAAGCCCCAGGGCAGGCTGCATTCTGGGCCACACAGCATGCCGAGTTAAGGA<br>TAACTCAGACACAGGCATTCCGGGCAAGGGACAGCAAAATAAAACCCAGGGAGCTTCGTGCAAGCTTCATAATCTCTAAGCCTTT<br>AAACAAGACCAGCACAACTTACTCGCACTTGACAAAGTTCTCACGCACCGACTGAACACTCCAACAGCATAACTAAGTATTTATT<br>AAAACATTTCTGAAGAGCTTCCATCTGATTAGTAAGTAATCCAATAGACTTGTAATCATATGCCTCAGTTTGAATTCCTCTCACA<br>AACAAGACAGGGAACTGGCAGGCACCGAGGCATCTCTGCACCGAGGTGAAACAAGCTGCCATTTCATTACAGGCAAAGCTGAGCA<br>AAAGTAGATATTACAAGACCAGCATGTACTCACCTCTCATGAAGCACTGTGGGTACGAAGGAAATGACTCAAATATGCTGTCTGA<br>AGCCATCGCTTCCTCCTGAAAATGCACCCTCTTCTGAAGGCGGGGGACTCAATGATTTCTTTTACCTTCGGAGCGAAAACCAAGA<br>CAGGTCACTGTTTCAGCCTCACCCCTCTAGCCCTACATCTCTCTTTCTTCTCCCCTCTGCTGGATACCTCTGGGACTCCCCAAGC<br>CCTATTAAAAAATGCACCTTTGTAAAAACAAATATTCAAATTGTTAAAGATTAAAAAAAAAAAAAAAAGCCAGCGCCGCCTTGGCT<br>GTGGGTTGGTGATGCTCACCACGCTGCGAAACCCTGTGGTTTGCATTCAGTGTGATTCGTCCTGCCTGCTGACCACTATGCTGGG<br>TTCAGACTTCTGACACTGCCAGGCTACCCAACTTGTGGTTCTGTGGTTGTTTATGAGGCCCAAAGAAGTTTTCACACAACCCAAA<br>TTACAAATTTAACTGTTCCCCTTTCCACAGCCCATCTCAATTGGTTCTTGCCAATCATGTGACTTAAGTGATGTCAATTTTTTTT<br>TTTCTTTTCTGAGCAATGCCCTTCCTTCCCTCCACCTGCCCTCCCCCAGGCTGTGCAAGAAAATAGCCGAGTAGACTTTGCAAGA<br>GGGGGGGATGTAGAAAAAAGTGACTCAGTCACTTATTATATCTCAATGGTCTTTGCTGATTTAGTACAACTCGGCTCCTGTTGTT<br>ATTTGTGGTTTTTGGAACTACTGATTATTTTGATAAAGATTTCATTGCTGCTTATTCAATAGTAATTCAACGCTGGCATCAAGCC<br>GCTGCTCCGACAGGATGTGGATCCCATCATTTAAAATGCTAGGCATCAGCTCCGGGAGAGTTAAGTCCTTGGTAACGTCTATCAT<br>GGCATAAGTGAAACTATAAAAGGGAAAAATAAATAAAAAGAAATGTTTTGGTGAGAGTCTGACCCCTACAACGGGCTGGCAACTC<br>ACAGGTATTTTAAAGCCTGGGAAAGGGAAAGAATTTTACTTTTGAAATAAAAGGACTGTTTTAATGAAACCAAAATTATGTGGTT<br>TTATTCCCCCTAAATGGACAACTTTAGTATGTATCTCTTTCAGTAAAGAGATAAAATCATAGTACAGTCTTAACACACACACACA<br>CACACACACACACACACACACACACACACAAATTAGGAAGCTAAAGGAAAACAAAGCAGAGAGAATTTCTGTATTTGGGACAAAGCA<br>GTGGTTACTCTGCAGATGTTTATTTGTATTGTCACTTGGGAAAGCTCCCTGTATTGCCTTTCTCTAGTTCAATTCAAATCAATAG<br>GCTAATTTACACCTGTAGGTAAAACTACACTTTGAGCACATGAGGATGCCACAATAGAAGGGGAACCAGGAGGAGACACTTCTCC<br>TGGGGCTGACTAATGAATATTATATAGCGCGTCCTCTACCTTAGAAAGACATGCCTGTTTGAAGATGCTAAAAACAGGATAATTT<br>TGTAAGTGGGCAAACCACTGTGGTCACACGTATTTCATTTTCCGGCCCCACTGGCTTTACCTGCTGACAACTAAAACGTCATTTT |

TABLE 4C-continued

| SEQ ID NO | GENE NAME | SEQUENCE |
|---|---|---|
| | | GTTTTGTAGTTCCAAGATGAAGAAAGGCTTATTTTCCTGATTTACTACCTTATTCATTTGGCTCTGCTCTGCCTACATCCGCCAT AGCACTCTGCGCACGTGAAATTTCGACACATAGGGTCAAGAGAACCTGTGTGATGATGGGTTGTAAATGCCAGTCCTGGATTCTA AGCTGCAGTAGCCAGCACAGGCACTTCAGAAAGGCTGAACTCCCACAACACTCCCTCGGTTTTCCCTCATCCACTTAATTTCACA CACACAAAGACCCACAACGATAGTAGCTTCCATGGCACAAGTCTTTCAAAAGGAACAGACACAATTTTTACTTACTCCTGTTTTG ACTAAAGCAGGAATTGAAACTCAACAGACCGCTTTCTCTTACACTTGTGAGAAGTTAGCTGGCCACATGT |
| 201 | chr21: 35499200-35499700 | AGGGAAAAGAGATAACGAAAGAAAGAAAGAAAAAAAAAAAGGGCCGGCAATTTCATGTACATTTGTTTTGGCATTCGCTGAATTCT AGAGATGAAAACAATCTCCTGCTTTTAATTCAGTCCACGTGCAACAAAGTTGTACGTTGGGAGATCTGGCTTTTAATAAGAACGA TTAACAAGCGTTTTTGATCACAGGAAGTTGAGAAGAGTCGCTGCTTCTAAGAATACAATAAACATTGACTAGCAGTTAGACGGTC CATCTTTCTCTATCAGCCGTTTAGCAGCCTCTACTTTGATTTGGGGCAAATGCGAGATGGGACCAGGAGAGAGCTCCCCACACCC CCACCACCACGTGGGCAGTGGTTCTGTTCCAGAGCGCCTTCCTTCCTGTCCAGGGAGGCAGGCTGCTGAGGCCGTTTCTGGGCAA GAGGCCATTGTCGGGATATTTGCTTTAGATAGCTTGCAGCTGGGCTGAGTGGGTGTTTCATTCAGACTCAACACA |
| 202 | chr21: 35822800-35823500 | AGCCTGGCGCACCCGCCCTAATTTGAGTCAGGGACCCTAGGCGCCTGCAGCTCCGGTTCGGGTTGAGTGCCTCCTGTCAGGATGT GAAGCTGCTGTCCCCCCCGGGGGCCTCCAGCACTGCTGAGGACTCAGCAGTCAGCCTCTCCTCCCACTTGGGCTCATTTACAGAG AGCATCTCCAGGAATCAGTCATGGGGAAAGGGGAAACGCGGAGTGACAACACAACACGTAGAAAGTTCTCTGCCGCCTTGGTCAG GCTTGTCAGCCTCACAGCCCATCCTGCTCCTGCGGGAGGAAAAGTGAGCAGAACTCAGCCCGGAGATGAGCCGCAGGCCGGCAGC CCCTGCCTCTGCCCTGCTTGTTGTGACTGCAATGCAAGGCTCTCTGTAGGTGCGGGGGATTCGGGTTAAATGGGTCTCCAGTGGT CCAGCGCTCCCAGCAAAGGCCGACCACAAGAATTAGCGGGCTAGTTATTTACCATAACCATATACAAAACCACAAGCATCAGCGT TCCCTCAAATACATCCGAGACGCTGTATATCTCTTTATTAAAGCCTGTCAGGGTTTGTTATTGCACAGCTTGGCCTTGAACCCCA ACTAAACCAGGCTGCTTGAGCAAAGAACCAAGCAATGCAAGCATTCAGGCAGGACCATTATAACCCTGAGGCCAAAGGCAGAAGC AGGGAGAGGAGACGTCTTCC |
| 203 | CBR1 | AGACCAGCCTCGGTCTTCGGCCTGCGGGTTCTGCAAAGTCAGGCTAGCTGGCTCTCCGCCTGCTCCGCACCCCGGCGAGGTTCCG GTGGGGAGGGGTAGGGATGGTTCAGCCCCGCCCCGCTAGGGCGGGGCCTGCGCCTGCGCGCTCAGCGGCCGGGCGTGTAACCCAC GGGTGCGCGCCCACGACCGCCAGACTCGAGCAGTCTCTGGAACACGCTGCGGGGCTCCCGGGCCTGAGCCAGGTCTGTTCTCCAC GCAGGTGTTCCGCGCGCCCCGTTCAGCCATGTCGTCCGGCATCCATGTAGCGCTGGTGACTGGAGGCAACAAGGGCATCGGCTTG GCCATCGTGCGCGACCTGTGCCGGCTGTTCTCGGGGGACGTGGTGCTCACGGCGCGGGACGTGACGCGGGGCCAGGCGGCCGTAC AGCAGCTGCAGGCGGAGGGCCTGAGCCCGCGCTTCCACCAGCTGGACATCGACGATCTGCAGAGCATCCGCGCCC |
| 204 | DOPEY2 | AAACGTTTAAAATATATTTCTAAACAGAATGGGCCAATTCAGTCACAGTAACTGTTGATCTCCATAGCAGAGCAACCCACAAAGA CAGAACTGATTTTTTTCCCATAATCAGGGGTGAAAAATATACAACTTGTTTCTGAACCAAAACCACAATTTCTGCAGTTTAAAAT GTTTCACTGCTAATATGGCCCTGGTAGAAATTATGTAGTTTCTTTTCTTCTTTAAAAAAAAAAAAAATTAAAAAAATTTCCTAAG ACACTAAATGCTCCATCTGGAATGTAGATTCTGATCACAAAGCAGCTCAGTTAACCTAAAAAATAAAAAATTCCCATCACCTGTC TCAGTAGGGCCTGAGAGTAGTGTGGGGAACCCCAGCTTTGGTATGGAGAGTCATGGCCCCTTGAACCAGATAGAGACCTTGAATA GCCATAGCTGGTGCTTCTCTCAGGATAAACTCTGATGTAGGAAGTATCACCCTCATGAGAGTGGAATTTGGTCATCCAGTTGACG CAGGGCATATTCCATGTCTTCTTTTCTGAGACACCCAACCATCCCCACTCCATCCTTCTGCACATCCGTGTAACAGGCATCCCCA GCTTCTCGCGTGTGATCCTTCAGGTCCTGCCAGCTGCCTGATGGAAGAAGTCCATTTCTTCCATAAATAGCATCCTCTGCATCTC GAGGGTCCTCGAAGCGCACGGAGGCGAAGGGCACAAGGCCGTACCGGCTCTTGAGCTCGATCTCGCGGATGCGGCTGTACTTGTA GAACAGGTCCTGCGGCTCCTTCTCGCGCACGTGGGTCGGAAGGTTTCCCCACGTAGATGCACCCGTCGCCCTCCCAGCCGCGCTC GTGTCCGCCCAGCCGGACAACCGCACCGCCCGACGCTGCTGGCCAGCCGCAGCCCGCATCCGCCCGTATCGCCGCCGCTGCCGCC TCAGCACGGCTGCCCCCGCAGCGTCTGTTTTGTTTTATTCTAACAGGGTCTCTCTCTGTCGCCCAGGCTGGAGTGCAGTGGCGTG ATCTTGGCTCCCTGCAACCTCTGCCTCCCGGGTTCAAGCGATTCACCTGCCTCAGCCTCCCAAGTAGTGGGCATTATAGGTGCCA GCTAACCATGGCCGGCTAATTTTTTTTTTTTTTTTTTTTTTTTTTTGAGACAGAGTCTTGCTCTGTCACCCAGGCTGGAGTGCAG TGGCGCGATCTCGGCTCCCTGCAACCTCCGCCTCCTGGGTTCAAGCGATTCTCCTGCCTCAGCCTCCTGAGTAGCTGGGATTACA GCTATGTACAGCGATGTCTGCAAAGATAGGGATTTAACAGCACTCATATCTTCATGTTCATAAAAAAGTCCTACACGCGTGATGT ACGTCTAGATCTTTCCTTTTGTCACAGGATATAGCACGGTAGTTACGGATATAGTCTCCGCAGTGCCTGGGTTTGACTCAGCTTC CCCACGTACTGTCCTGCGCATATTTTGTGTCTCAGTTTCCTCATCTTTAAGGTAG |
| 205 | SIM2 | CACGCGCCCCGGCCTGGCTGGAGGGGCCAACCCAGCGGGGCCCGCCTGCCCGCCGGCCTTTCTGTAACTTTCTCTCTTTAAACTT CCAATGAATGAACGTGCCTCTTCTTACGGATTTGTTTAGATTAGGGAATAGATTCCTCGCTGATAGCGTTGCTTTGCAAATAAGA CCTCCTATATTATTCAAACCAAACGAGTTTGTGTCTTTAAAGGACTATAGCAGCCCCATTCTATGTTAAGGGTTGGCTATTACAA TTATTATATGCTTAGGGAAAAAATGTAAGCCCCGTAGTTTGTGCTTTTCTTGATGTACAGAAAGGTTTATCTTAGGTGGATAGGT TTTGTTTTGTTTCTTAAATGGGATTTTTTGGTTCGTGTCTTTGAAGGGCTGTTTCGCGACGTCATTAATGAACTAATCGGTTTT CAGATTTCAAGACGGTGTGTAATTGATGTAACCACTGAGGAATTTCAGTGCACACCAGACTAAGACTCTTCCAGCGCAGGGGATT CCAGATGCTTCTTGGGCCCTCTGGAAGCCATGGGGATGTTTCCAGACCGAAAGGAGGGCTTTGCTGGGGAGCAGATGTGCTGCCT CTCCCCGACCCAGGATTTTGAGGCCATGTTTCCGTTAATCTGGACCGAGAGCCCTCTGGGAGAGGGAGGCAGGTCGTAGGGGGCG GGGGTGAGGGGGAGCGAGATGAGGTCGTCGCTGGACGCTGGGCTCCCTTGTCGTTGTCCTTTTCCCCAGAATCCATGGTCAGGCC TAGGGAGCCACCCCTGGGTGCTCGAGATGAGTCCCCACCCTCACTGAAGGTCGGTCACTGGATGTTTGTGTGCATCGTAAGGGGC CCACCGAAGTCCCGAAGCCTTCTCAGGGACCAGCGAGAAAGAGGAGCAGGCTTGGGAGACAGGGAAGGAAAATGCAGGGGAAAGG GCTCACCCCTCGACCCCAGGTAAAATTAGAAGGAACGTGTGGCAACCCAGGTGCAGCTTTGGTCGCTCGCTCAAGGACTTTGCTA GTCACTACCATTAATTAATTAATCACTATCATTAACTACCAAGGACACCGTTTTTATTCCCCTAAAAGCGTCACCTTGAGGGGAA TGGAGAATTGGGCAGCAGCTATGCAAATCCTGGGACAGGAGACACTGCCTGAGGACCCTCTCTCACTCCCAATCCCAGAACCCGA AGTTATCCCCGACAACCAAGTCCAAGCACATGAACCAAGACGATCAGCTTCAGGCAGCTCCTTACCCCCACAAGCGGCCCAGGAG GTGGGCATTATCCCCCACCCCTGGGATTTCTCCATCCCTCCCTCTTCTCTCCTGCGGGAGAGAGAGCTGTGGTCACCCAGTTGGG CGCGATGGCTCTGGACTAATGGGGTCTCTAGACCCAGGGCACAAAGGCCAATCTGCCAGGGGTTACTGCATGTAATGAGATAATC AGACATGTTGACCAACCTAAAAGAAAAGACTCTCCCAGGGAGTAACTCCCAGTGAAATAATTTATTAAAAAAAGCAAAAAAGAGA CATAAATTTCTCTCTACTACTTGAGGAAACAGCAAACAGAACGAATTAGGGTCTTGGCCTCTGCAGGAATAAATTATTTCCGACT TGGTCTGGATACCTGTAATTATTTGTAAGCTGTGGGTAGTAATACTGTAATTGTCCCCCGGTCCTTTCTGGAAGTAGCAATGACC CCAAGGACAATTGGTGACGTCTCCACAGGGTTTACACATGGAAAGGAGTGAAAAATCGAGGAATTCTTTCAGATAGCCCAGACCA AAAATCCTCTCAGCCATGAAAAGGTCATATATGTGATGCTGGGCCAAGCGGACTTTTCTGGAGTAACCATATCATAACTGATTGC GGATGTAGACAAGAGCGTATAAACCAAATAGGCTTGAATCAACGCAGTCCTGGATTTTCTGTTGCCTCTGCTTGCTGGGGCAGTG GAAGTTCTTAAACTCCACTTCAGAGGTTGGAAATTCTTCCCCCTCCCCCACCTCCTTAGTGACAAGGTCTCTGATCTCCTGCTGC CACTGCAATAGCCTCTCCCATCCCGCGGGGAACGGCCGGAGTTCTTCCCTTGATCTCTCCCGAGTCGGCTTCCGCTGGGGATGGA TCGCAGGTAGGCGCCGGCGCGGCCTGGGGAAGAACAGTTGCGGAGCATCTGAAGCGGAAAATCCAAGCAGATGTGAGGCGATCCG GGCCCGCCTCGTTCCTCTTGGGGCCTGAATTTCTTCCAGATAAGTTTCCTAATGGAACATTTCTAAGAGGTGGGGTACGAGGCGG |

TABLE 4C-continued

| SEQ ID NO | GENE NAME | SEQUENCE |
|---|---|---|
| | | CTTGCTCGCACGCGCAGTGGGACAGACTGCGGGTGGGGACGTACTGAGAGGTCCGGACCTCAATGCGTCCGACCCGTCTCCACAC |
| | | CGCCCTTTTCCAGCCCCCAGTCTCCTTTCATTCCCTACTCTTCAGGCTCCTTTGGGGCCAGTGGGTGAACCGCCATTTAGAACGG |
| | | TGCCTCGGACTCGGGGGTCGTGCGCTCCATCTCTGCCTCCCCCCTGGGGCCCGCGAGGCTGGTCCGGGCTTTCTGAGCTGGGCGT |
| | | TCGGCTTTAGGCCCAATACCTGGACCAGGAATTTCTTCTCCCCGCGCCAGAAGGGAAAGACATAGGAGGTGTCCCAATCTGCGGT |
| | | CACCGCCGATGCTCCTGACCACTCTAGTGAGCACCTGCCCGGTACTTTTCCATTCCAACAGAGCTTCCAGCTTCATACTAACTAT |
| | | CCCACATACGGCCTGTGGGTATTAGCTCTAAGTGTCCTTTTCCGAGGGCCCGAGGCTCCCCCTCCAGCAGGGAGAGCTCCGGGAC |
| | | GGCCCCCACCAAGGGTTGGGTTTCTTCCTTCACAATTCCACAGAGGCATCCCTGTCCTTCCTACCTGGGAAACCTCGAGGTGCGG |
| | | TGCCCGTGTACTTCTGGTACTTTGCGTGGTGCCATCAGGGACCCCAGAGCCACAGCTGCGTGTGTGTGTGGATGTGTGTGTGTGT |
| | | GTGCGCGCGCGCGCGTGTACGGCGAAAGGATGTGCTTGGGGGAGCCGAGTACACAACGTCTGCTTGGGCAGCTGCTGGGCAGGCG |
| | | TTGGGCCTGGAGGTATCTCACACCCACGTATCTTCCAGTCTTCAAACACGGCATTGCTCTGCCTCCCGTAGCGCGCTTCGAACCT |
| | | GCCTCGCGGACACGTGAACAGAGGCTGTCCCTGGGAAGATAAGTGCGCTTTCCCGTAAAATCCGGGAAATTTGCCTTGAGGAAAG |
| | | TTTCCGTTCTTGTTACTTGTCGGGTTTCTCCCACTTCCACTTAGCCATGTTTCTGCGATCTGGGTAATCCCTTTCAAGCCCAGGA |
| | | GGAATTCTCCCGGGTCCATAATTGAGGGTCGGAAGCCGTGGGGGTGAGAAACGCATTAAATCCTCCCGAAGCCCAGGAGGTGCCA |
| | | GAGCGGGCTCAGGGGGCCGCCTGCGGAAGCTGCGGCAGGGGCTGGGTCCGTAGCCTCTAACCCCTTGGAGCTCCTTCTCCCAGAG |
| | | GCCCGGAGCCGGCAGCTGTCAGCGCAGCCAGGAGCGGGATCCTGGGCGCGGAGGTGGGTCCGACTCGCCAGGCTTGGGCATTGGA |
| | | GACCCGCGCCGCTAGCCCATGGCCCTCTGCTCAAGCCGCTGCAACAGGAAAGCGCTCCTGGATCCGAAACCCCAAAGGAAAGCGC |
| | | TGTTACTCTGTGCGTCCGGCTCGCGTGGCGTCGCGGTTTCGGAGCACCAAGCCTGCGAGCCCTGGCCACGATGTGGACTCCGCAA |
| | | GGGGCTAGGGACAGGCAGGGGGAGAGCCCGGGTTTGCGCACACCTTCCAGCCCCTGGAGGGAGCCTGCTCGGCTTCGAACGCCTT |
| | | CGAACTTTTGACCTTCAAAGGAGTCCCTGGAAAAGGTCAGGAGCGCCTGCTGCAGGCACGGTTGCCGAAGGCCAGGCCTTCCTGG |
| | | CGCAGGGGAGGGCCAGGGGAGGGAAGCGGATACTCAGTCGCTGTCCGACGGCGAGTTTTCGGAGCAGCAGGCTCATGATCCCGGG |
| | | CCAGTGGCGAGAGCAGTGACACCGAGAACCCAAATCTCCGCGCCCCCATCCGCGGCCCGGTGTCCTCCCGGCCCCTGCTGACCTC |
| | | CAGGTCACGCACCCCACTGCTCCACGGCTCTGCAGCCTGTGGCACACGGCCGAGAGTCCCCACATGATCTCGACGCCAAGGTAAG |
| | | GAATTGCCCTGCGTCCTCTGAGCCTGTCTCTGGCCTGGGGGGCCGGGAAAGCTGCACTCCTGGAAGAGGTGGGGTTATGTGACCG |
| | | CCGCTGCAGGGGTGCGCGGAGGACTCCTGGGCCGCACACCCATTTCCAGGCTGCGGGAGCCGGACAGGGGAGGGCAGAGGGGGGA |
| | | CAAAAGGACTCTTTAGGTCCAAAATGACCCTGAAGGAGAGTCCAGAATGCCCAGTGGCCGCGTCTGCAACGGAGTCTTCTTTCTC |
| | | CAATTGCCTTCTGCCCCATCACCATGGGCCCCACCTGCGCCACCTGCGCCCACCCTGTGACCCTGGCTCAGCGACCTTGGCCCTT |
| | | AATCGCCCAACGCCGATTCCTCAAAATTCCGGCTGCGCTGAATCGGGCTGCTTTTGCCGCCGCCCCGGCAGTTGGGCCCTGTTTC |
| | | CGCCGGCGCCCTGGGAGAGGCCTCACCACTCGGCTGGGCTCCCTGGCCCCTCCCTTCCCCTGGCCTGAGCGCCCCTGCGGCCTCC |
| | | CGCTCCTCCTGAGAAGGCGACAATCTCTTTGCACCTTAGTGTTTCGAGGACAGAAAGGGCAGAAGGGTCACTTCGGAGCCACTCG |
| | | CGCCGTTTTCACGTGTGTGTGTAATGGGGGGAGGGGGGCTCCCGGCTTTCCCCTTTTCAGCTCTTGGACCTGCAACACCGGGAGG |
| | | GCGAGGACGCGGGACCAGCGCACCCTCGGAAGGCTCGATCCTCCCCGGCAGGGCGCCTGGCCAACGAGTCGCGCCGCCTCCTCTC |
| | | GGCCGCGCCTGCTGGTGACCTTCCCGAGAGCCACAGGGGCGGCCTCGGCACCCCTCCTTCCCTCGCCCTCCCTGCCGCCCATCCT |
| | | AGCTCCGGGGTCCGGCGACCGGCGCTCAGGAGCGGGTCCCCGCGGCGCGCCGTGTGCACTCACCGCGACTTCCCCGAACCCGGGA |
| | | GCGCGCGGGTCTCTCCCGGGAGAGTCCCTGGAGGCAGCGACGCGGAGGCGCGCCTGTGACTCCAGGGCCGCGGCGGGGTCGGAGG |
| | | CAAGATTCGCCGCCCCCGCCCCCGCCGCGGTCCCTCCCCCCTCCCGCTCCCCCCTCCGGGACCCAGGCGGCCAGTGCTCCGCCCG |
| | | AAGGCGGGTCTGCCATAAACAAACGCGGCTCGGCCGCACGTGGACAGCGGAGGTGCTGCGCCTAGCCACACATCGCGGGCTCCGG |
| | | CGCTGCGTCTCCAGGCACAGGGAGCCGCCAGGAAGGGCAGGAGAGCGCGCCCGGGCCAGGGCCCGGCCCCAGCCGCCTGCGACTC |
| | | GCTCCCCTCCGCTGGGCTCCCGCTCCATGGCTCCGCGGCCACCGCCGCCCCTGTCGCCCTCCGGTCCGGAGGGGCCTTGCCGCAG |
| | | CCGGTTCGAGCACTCGACGAAGGAGTAAGCAGCGCCTCCGCCTCCGCGCCGGCCGCCCCCACCCCCCAGGAAGGCCGAGGCAGGA |
| | | GAGGCAGGAGGGAGGAAACAGGAGCGAGCAGGAACGGGGCTCCGGTTGCTGCAGGACGGTCCAGCCCGGAGGAGGCTGCGCTCCG |
| | | GGCAGCGGCGGGCGGCGCCGCCGGGTTGCTCGGAGCTCAGGCCCGGCGGCTGCGGGGAGGCGTCTCGGAACCCCGGGAGGCCCCC |
| | | CGCACCTGCCCGCGGCCCACTCCGCGGACTCACCTGGCTCCCGGCTCCCCCTTCCCCATCCCCGCCGCCGCAGCCCGAGCGGGGC |
| | | TCCGCGGGCCTGGAGCACGGCCGGGTCTAATATGCCCGGAGCCGAGGCGCGATGAAGGAGAAGTCCAAGAATGCGGCCAAGACCA |
| | | GGAGGGAGAAGGAAAATGGCGAGTTTTACGAGCTTGCCAAGCTGCTCCCGCTGCCGTCGGCCATCACTTCGCAGCTGGACAAAGC |
| | | GTCCATCATCCGCCTCACCACGAGCTACCTGAAGATGCGCGCCGTCTTCCCCGAAGGTGAGGCCTCAGGTGGGCGGCCGGGGACG |
| | | CTGGGGAGCCCGGCGGCCCCGGCCCAGGCGGGAAGCGCAAGCCAGCCCGCCCAGAGGGGTTGCCGCGGCCTGGCGTCCAGAGCTG |
| | | GGGCGTCTGAGGGAGGTTGCGTGAGGGTCTTCGGCTTCGGCGCTGGCTTGGGGCGAGGGGCCAGGGCCTTGGCGGCCCAGGCGAC |
| | | CAAACCCTCTCCTGGTCCAGGGCTGGGTGAGGGCGAATTACGAATTGTTCCAGGGGCAGGCAGTCCCCCAGCCCGCACGGCCAGC |
| | | GAGTTCTTTCTGGTTTTGTTCTTTCTCCCTTTCCTCCTTCCTTCCTTCGCCAGTGCATTCTGGTTTGGTTTGGATTTTTTTCTCT |
| | | CTTTCTTTCCTTTCTTTCTTTCTTTCTCTTTCTTTTTCTTTCTTTCTTCCTCTTTCTTTCATTCTCCCCTTCCTTCCTTCCTTGG |
| | | CCCCCTCTCTCCCTCCCTCCTTCCTTCCTTCCTTTGCCAATGCATTGGTTTGTTTTCTTTCCTTTTCTGCTTTCCTTCCTTTCTT |
| | | TGGAAGTTCACTCTGGTTTTGCTTTCTTTCTTTCCCCATCCCTTCCTTTCTTTATCCCTCCTTCCCTTCCTCCTTTTCTTTCTAC |
| | | GATTCCCTTTATTTTTCCTTCATTCCTCCCTCTTTTTGTCTCTTCTGGAGGAGGTGAAGGAGGGTCAGCTTCAGGCGCTGCGAGT |
| | | CAGCGGGGATCACGGTGAGGCCCAAGCACTGCAGGCTGAGGCCACAGAGCGAACACTTGTGCTGAGCCGGGCCCTCTCGTGAGGC |
| | | TGGGGTGCGGGAAGTCCGGGCAGGAGAGACCCGCCCCCGCCGTTGCTGAGCTGAGACCCGGCTGAAAGAGAGGGGTCCGATTAAT |
| | | TCGAAAATGGCAGACAGAGCTGAGCGCTGCCGTTCTTTTCAGGATTGAAAATGTGCCAGTGGGCCAGGGGCGCTGGGACCCGCGG |
| | | TGCGGAAGACTCGGAACAGGAAGAAATAGTGGCGCGCTGGGTGGGCTGCCCCGCCGCCCACGCCGGTTGCCGCTGGTGACAGTGG |
| | | CTGCCCGGCCAGGCACCTCCGAGCAGCAGGTCTGAGCGTTTTTGGCGTCCCAAGCGTTCCGGGCCGCGTCTTCCAGAGCCTCTGC |
| | | TCCCAGCGGGGTCGCTGCGGCCTGGCCCGAAGGATTTGACTCTTTGCTGGGAGGCGCGCTGCTCAGGGTTCTGGTGGGTCCTCTG |
| | | GGCCCAGGAGCTGGGAGGGCTGCGCCGGCCTCTGGAGCCCCGGGAGCCAGTGCCGAGGTAGGGAGACAACTTCCGCCGCAGGGCG |
| | | CCGGACGGTCGGGGCAGAGCAGGCGACAGGTGTCCCTAGGCCGCAGGGCGCTTCCATAGCGCCATCCCCACCAGGCACTCTACTC |
| | | GAAATCGGAAAGCTCGACCTTTTGCGTTCGCCTCTGCCAAGCCTGTTATTTGTGCTGGCCGCTGGGTCTGGAGCTGCGCTTCTCG |
| | | GCCCCTCCCCGGTGGAGCGCAGAGGGCTGGTCTGCAAGCGCGGCCTCCAGCCCCGCGGCTCCCCGGCCCAGGAGCCAGGCGCGGG |
| | | CTGACCCGGGAGCACCCGGCAGCGGAGGGGGCTGGAAGCGGACCCTAGGCCTCTCCTGTGCCACCCGGCCCTACCGCGCGGCCGC |
| | | GGGGCGCTCTCCTCTCGGGCGCAGCGGTCCTTCAGCCCAGGGCAGGTTCCTCCCTTTCCTACTCGGAACGTGGCAAAGATACCCC |
| | | AGTCCCAGCCCCTCCAGCTGAGAGCTGTTGCCCAAGGTCGTCGCTACTTGTCCGCTCAATGGTGACCCCTTGGCAGAGAACTAGG |
| | | GATGATTCCACTCCGGTTGATGTTTTAGGGGAAATTAAAAGAACATTCGGTTTTCTGAGTCTCCTTCCGGGGAGGCGTGGTGGTA |
| | | ACTGGTTTGCTGGGAAGAGCCGTTCCTTAACCGCATGCAACAAAGCAGGTGTGGAATCCGGACGAGAGGGCACTCACTGCCTTCT |
| | | GCCCCCTTTGGAAATAGAAAAAGCCTTCGAAGCAGCAATCCAAAGATCAAATGATTTGCGGTCAATGATTTCAATTAAACCAGAA |
| | | ATTAGTAAGGGAGGGCCGAGAAGACACGGCTGCTCAGAAGCTGTTCGCTGTTTGAGGGATTTCCCGGAGAGCCTGTTAAAAGATG |
| | | CGAAGTGGTGGGTGTACCGCTCAGCCACCTTTAAACCGGCTCTGTGCGTTCTGGCTCTGGAAAGCAAGTCTCCAGGCATTTGGGC |
| | | TCAGAATTGCTGGGCCCCGAGTTTGGGCGGGGGTGGTCCTTCTGGGGGTCAGGCCTTGAGCAGCTTGCACTGGTGGCAGGTTTGG |
| | | GAGCAGTTGAGGGGCTTCCTGTGTGTCTTTTGGAGGGGGTGACCCTGGAAGTTGGCACTCTGGAAGGGAGCTGTTTGGCCCTAGA |
| | | GTTTTGGAAAGGGCCCTGAACCTGTTCGGTCCCCCTCGGAAAGGGAAGGGAGCAGTGGCTTAGTCCCTCCCTCCTCCATTCGTGC |
| | | AATGCCTGGGGTAGGGGTAGACCTGGAGCCGGTGGACTCATATCCTTGGAATTCGTCAGGACAGCTGCTCCGGGGCCTTGGCCCT |
| | | CAGTCAGTCTGGGGCTGAGGAGTAGGGAAGCTGGGAACTTGGGGCAGAGGAAGAAGATGCGTTTAGAAAGACCTCCATTATGCAA |

TABLE 4C-continued

| SEQ ID NO | GENE NAME | SEQUENCE |
|---|---|---|
| | | ACTGGAGTCCATTTATGCAAACTGGTCACCCTTCCAGTAGCTCCAAAGAGTGGCAGTGGAGTGGCATCTTGATTGATTTAACCTC |
| | | TTCTCAGGGGACCTGGGTCTGCGAGGGAGGATATGGCTGCGGGGTTGGAATAGGATCTGTCTGAGCTGCCAGGGTCAGGGTGGTG |
| | | GCCCTAGGGAGGTTTTAGGGCCAGGGTGGTCCCGGGCTGTGGCAGGGGCTCTCAGATCGCCTCGGGCTCTCAGCTGCAAGGTGAA |
| | | AAATACCATGAGGAATTGATCTGCCAAGGGCGGTCTTGTCTCAAAGCAAGTGGATTGCTGGGGTAAAGAATCTAGAGACCAGCTT |
| | | AGGACTCTGGGAGGAAGAAAAAAAAAAAAAGAATAGCATAGTCCTAAGGAACTGCAAGGATCACCAGATTAACCCTTCATACCTG |
| | | GGGAAATTAAGGCCAGACATGACACAGGCCTTTCCCAAGGCTCTGTAGCAAGGGCAATAGCAGGCCAGTTGCTGCCACTGCGGTC |
| | | CTGTGGGGCATGTTCTCACTCCACTGCACCCAGGAGGCTGCCAGCCTCTGTTCCTTTTAACATAGATCTCCTCAGTTGTTAAGAC |
| | | AGAAAGAGGAACTCAGAGGGGTCCCTGTGTGCAAGGCAGAGGGAGACCACCAGAACCAGGGTAAGCACCCCACTTGGTAGCCAGT |
| | | TCAAGGACTTGGGGATGTTTTCAACATTTACAGCGAGGTTTGAGGCCCCATTGTCATGCAGCGCTACTCGGCCTTGGTCTCCTTA |
| | | TCTGTAAAATGGGCCCATTAGCAATGCACAGGGTTGCTGTGATGAAGGGTGAGGTCCCACAAGCAAAAGCTGTGCAGTGAGGGGG |
| | | GAATCCTAAGCATTGTTCCTATGCCATTCACCCCTTCCTGTGAGCTCCCCATATTCCCTGGCTCAAAGGAGTCTTGAATGGCAGG |
| | | GATGGAGGACTCACTGCCTGGACTTTGAAGACCCCTGCTTTCTGGGTGACCACCTTTTCTTCCCTTTGACAGTGAACTAATACAT |
| | | TGGAGGTAGATAGTGCTGGGAAGAGGACAGGAGACCACGGCTGACTTTGGACATGGGCTCGAAATTGATAACTTGATGAGTCTTG |
| | | GAGGGTGGTTAAGATAAGCTCGGGGCTGGGGCAGCGCTGAGGTCTGATGGTCAGCCAGCCCTCCCCAAAGTGTGGCCCTCCGTTC |
| | | TGGAGATAGGGGCTTTGGAAACTGCAAAAGCGTCCTGGCAGGCCAGCTCTGGTTGCTCCCTGGCCATAGCTGCTCTGACTACAGG |
| | | CAGCAGGACGCAGGTCGGCCTCTGCCCATCGGAGGTCAGAGGCAGGGCCTCCAGCACCAGACTCAGCAGTGCCACTGCAAACCTG |
| | | GCACAACAGGCTGGTCCCAGGACTCAGCTCAGCAGTGAAGTTGGAAACCAAGGTTGAGTCTCCCCATCTCCCTTTCCCCAACCCG |
| | | AAAGACCCAAGATGGGTGTGGGTGAAAGAGGGAGAAAGAATTGCTACTCCAGAAACTGTCATTTGCCCACACGAAACGAGGTGGG |
| | | GTTCAAGGTCTGAACTCTTCCAGTGCCTGGGTGCCTTTGGGTTTAAATTCAGCTGCAGGTGCCCCCATCACCACTTCCACCTGAG |
| | | CACACCACGAGAAGCCAGGTTATCTTAGAAACTGTTTCCCGGAATCAAAGCGACTTGATTTGGAGAGTTGGGTGAGGAGAAACTC |
| | | ACCCCTATACCCCTCAGGGCGTCAGAGATGTGAGGCAATTCTCTACCTCCGCTGGAAAAAATGCAGATTTATTAAAGGTCGACTG |
| | | TTTAGCAGAACAACGTAGATTTTTTACAACGCTTTCCCCGTCTCTGCTTTGAAGCCTGCCAGGCTGCAGCTGGGGATCCAGGAGG |
| | | GAAAGCCCGCAGGCGCAGAGGGGACAATCCGGGAAGTGGTAAAGGGGACACCCGGGCACAGGGCCTGTGCTTTCGTTGCAGGCGA |
| | | GGAAGTGGAGCGCGCGCTGCAGATTCAGCGCGGGGCTAGAGGAGGGGACCTGGATCCCTGAACCCCGGGGCGGAAAGGGAGCCTC |
| | | CGGGCGGCTGTGGGTGCCGCGCTCCTCGGAGCCAGCAGCTGCTGGGGCGGCGTCCGAACTCCCCAGGTCTGCGCACGGCAATGGG |
| | | GGCACCGGGCCTTCTGTCTGTCCTCAGAATACGTAGGATACCCGCGGGCGACAAGCCGGGCCAGGCTAGGAGCCTCCTTCCCTGC |
| | | CCCTCCCCATCGGCCGCGGGAGGCTTTCTTGGGGCGTCCCCACGACCACCCCCTTCTCACCCGGTCCCCAGTTTGGAAAAAGGCG |
| | | CAAGAAGCGGGCTTTTCAGGGACCCCGGGGAGAACACGAGGGCTCCGACGCGGGAGAAGGATTGAAGCGTGCAGAGGCGCCCCAA |
| | | ATTGCGACAATTTACTGGGATCCTTTTGTGGGGAAAGGAGGCTTAGAGGCTCAAGCTATAGGCTGTCCTAGAGCAACTAGGCGAG |
| | | AACCTGGCCCCAAACTCCCTCCTTACGCCCTGGCACAGGTTCCCGGCGACTGGTGTTCCCAAGGGAGCCCCCTGAGCCTACCGCC |
| | | CTTGCAGGGGGTCGTGCTGCGGCTTCTGGGTCATAAACGCCGAGGTCGGGGGTGGCGGAGCTGTAGAGGCTGCCCGCGCAGAAAG |
| | | CTCCAGGATCCCAATATGTGCTTGCGTGGAGCAGGGAGCGGAAGAGGCAGCCGGTCCTCACCCTCCTCTCCCGCCACGCACATAT |
| | | CCTTCTTGACTTCGAAGTGGTTTGCAATCCGAAAGTGAGACCTTGAGTCCTCAGATGGCCGGCAACGCGCCGAGGTCACGCTCCC |
| | | CAGAAACACCCCTCTCCCCTCCCCTACCCCAGCTCCCCCTGGGGCGGGTGGTAATTGGGGGAGGAGAGGCCGCAGGCAGGGAAGG |
| | | GGTGGGAAAGCCAGAGAGGGAGGCACAAAGTGATGGCAGCCCGGCAAACACTGGGGCTTCGGGCTGGGCCGCGCTCGTTTAATCC |
| | | CACAAAAATCCCATTTTGGAGGTGAGAAATAGAGGTTAGAGGTCGGGCCCTTCTGGAGATCAGACCGAGGAGACGGGCCCAGCTG |
| | | GCGTCTTAAAGCAAGGAGGGGGAGTCGGGAGGAGGTGAGACCCCTGCACCCAGGTGGGGCTCCCAAACCGTTCTGGATTTACCAC |
| | | ACTCCCAGGTCCGATTTTCCATGGAGGGCTGGGGTTAGGGACTGGCACCTTCTTGTTGTTAACCGCATTTGATATTCACAAGAAC |
| | | CCTGTGAGGAGACTTTGTCACCGTTTTTAGATGCCTGAGGTTGCCGGAGGGGCAGTGAGAGAATCGTCTAACCTGGTGTTCCTAC |
| | | CACAGTCCAGGCCCTGTGTCCTGGGCTGGACCCACAGCCCCTGCCACCACCCAGAGGAAGGCGCGAAGCTGGCTGCCTCCTTTAC |
| | | GGGTCTCCCTTAGGTGCCCTCATGAAGGGGGACGGCCACCTCACAGTGCAGGAACTATCTCCCCGTTTGCTCCCAAATAGTCTTC |
| | | TTGGTGTGGTGCTGTCTATGGTCTGTGACCTGCATCTGGAGTTACCCCCAGGACCAGCTTCGGAAGAGGAGGGATCGCTTGGAGG |
| | | CCGTGCAGTGTGAGGAACGGCAGGCAGGGTGTGGGACCAACATGCACACACTCGCAGGTGCTGGGGCCAGGGAGGAATGAGGCGC |
| | | TGGCTCCCTTTCCCTCCATTTCTCCCTGGGGGTCCCAGCAACCTGGCCATCCCTGACTTCCAACAGCACAGCGTCCCCACAGGTC |
| | | CTGCAGTGCTCTGCAGGGGTGCAGGGAGCTCCCCTCCCCCCAGCCGCAACCTCACCTTCCTCACCCCCACCCCTCCGGCAGGAAA |
| | | CCACAGGCTGGGTTGGGGACCCCTGGTGCTCCAAGAGAGCAGTGAGTGCTGGGAGCCGCTAACCCCGAGGCGCCTAGCACAGACT |
| | | CTTCTCACCCCTTATTTCTGAAATAAAGCCCTTCCTTAGGTCCAGATGAGGACCACGTGCTCAGTGCCTCACTTTCGTGGGAGTG |
| | | TATATCACTTTACAGTATCAAGACAATTTTCTTTCGTTACAAATCTTTATTTAGTCTCTGCGTTTAGACCAAAGTAGATTTTTAT |
| | | GGGCTGAGTGAAAAAACCTCGCCCGCATTGGTTTCTGATGGAACAGCTGGCAGCGCCACGGCCCCGGGTGGGGTGGCCTAGAGGC |
| | | AGGGGTGCTTGGGAGGAACATCTAGCACCCGACCACCTCCACCAGGTGGGAAAGGGACGTTTGCACCAAATCTCCGCCGGCAAAG |
| | | CAGAGGCTTTGGGGAATTACAGAAAAACTATAATGATCTAAAAGAGAACAAGTTATCTTGAACTGTGCGGGTATTTGAATCATAC |
| | | AGAAAATTGTCCTGTGTGCCCAATGCACTTTTGCATGTAGAGCCAGGGCCTTCGAGGAAGCTTTCAGGAGATCCCGGGCAGCGGA |
| | | GTCTGGTCTGGAGTTTCATTTCCGTAGGTGCAGATTTCTCCCCAAGTCTTCCCGCCATGGGCTTTGCAAGAAGCCAGGGCCCAGA |
| | | GGCCACGCTCACCGTTAACACTGCACAGGGCAAAGGTGGCTCCAGGACAACTGCCCAACCCCAGGAACGACCCAGCAGCAGAGAA |
| | | AAGGACAGCTGCCAGGGTGCCTTTGTCGCTTTTTGGAAATCAGAATTCCTGGGTCCTTAGTTAAGTCTTACTTCACCAAATCCCA |
| | | GGACCTTCACATTTTGGTTCTTGCCATTGCTAACAGTTGTAAATGCTGCCGCCACGAGGCCTGGGAGGAAGGACCCGCTGGTGAG |
| | | AGCACAGGGAGTGCTGCTGTGATCACGGTGGTGATGCGGGGTGAGCGCGATTTCCCGGGATTAAAAAGCCACCGCTGCCCCCGTG |
| | | GTGGAGGCTGGGGGCCCCCGAATAATGAGCTGTGATTGTATTCCCGGGATCGTGTATGTGGAAATTAGCCACCTCCTCAGCCAGG |
| | | ATAAGCCCCTAATTCCTTGAGCCCAGGAGGAGAAATTAAAGGTCATCCCTTTTTAAATTGAGGAATAGTGGTTTTTTTTAACTTT |
| | | TTTTTTTTTAGGTTTTTAGTTGCCGAATAGGGAAGGGTTTGCGAAGCCGCTGCCCTGGGCCGAGGTGCATTTTACGCTTCCAGAG |
| | | GTCGAGGCCTCCAGAGACCGCGATGCCCAGGGCGTTCCCGGGGAGGCTGAGAGACCCAGGGTGCTCTGGGTGACTGCACGGCGAC |
| | | TCCTCGGGAACCCACTCGTGGCTGCCCGCTTGGAAGGGCTTTGCGGCCCCGGGAACGATCTCCAGGATCTCCACGGCTGGTCAGG |
| | | TTCCCCGTCCCTCGTATCCCGCGCTGCCCGGGGGCTCCTGCCTTTGGTTCAGTGCTCGCGGCACCACCGCACTCAGGACGGCAGT |
| | | GGGGGGCTGGGGCTGGGGCTGGGCCTGGCCCAGCGTGGGTTGGGGCGGGGGACGCGCCAGCAGCGCCCGCAGCTCGCTCCGCAGG |
| | | GGTCGCAGCCAGGGGTCGGGAGCTAGGCTCGTGGGCCGGGAGACGCCGGGCGCGTTGTCCTCCGGGGAGGTTGGGGTGCAGGCGG |
| | | TGCACCGACCCTCGCCATCTGGCGCTGCAGCCACCAGCCACGGCGCTTAGTGGAGGGTCTGCGGCCAGGCTCCCGGCGGAAAGAT |
| | | TCCGGGGAGGGCTCGGGGGTTGTCCCAGCCCGCGCTAAGCGCCGCAGCCTCGCCCGGCTTTCCTGCTTCCTCGGACTGTGCAGGG |
| | | GAAGCCTGGGGTCTCGCGGGGCGCAGCAGTCAGGTCGAGGGTGCAGCAGGAGGGGAGTCCTGACGGGCAGGTCCCTCTTTCCCCT |
| | | GGTGCGCAACACTGGTTGGTAGCTTTTGCGGAGGTGGTGAAGAAGGGCAGGAGGCCTGTTGAGCGGAGGAGTCCGGGGATCCCTA |
| | | ATTATGTGACAGGAGACCCTTTCCAGTTCGGCCTGTGGCCCATCCCTCTCTCACCGCCGGCAGATTGGAGTCTGCTCTCGGGGAG |
| | | CCCCCAGGTAAACCCCTCACAGGGAGAAGGTTTCGGATTGGAAGGAGGACCGCGCTCGTGGGGCGCCTGTGAGAGCTGGGAAGCC |
| | | CAAGGGGTAGCGTGTAGGGGGTTTTTTATGCGGGAGGAGCTGCCTCCTGGGCGGCGGGGACTTTCTGTCTCAGCCTGTCTGCCTT |
| | | TGGGAAAACAAGGAGTTGCCGGAGAAGCAGGGAAAGAAAGGAGGGAGGGAAGGAGGGTCCTTGGGGGAATATTTGCGGGTCAAAT |
| | | CGATATCCCCGTTTGGCCACGAGAATGGCGATTTCAAAGCAGATTAGATTACTTTGTGGCATTTCAAATAAAACGGCAATTTCAG |
| | | GGCCATGAGCACGTGGGCGACCCGCGGGAGCTGTGGGCCTGGCAGGCTCGCACAGGCGCCCGGGCTGCCGGCCGCTGCGGGGATT |
| | | TCTCCCCCAGCCTTTTCTTTTTAACAGAGGGCAAAGGGGCGACGGCGAGAGCACAGATGGCGGCTGCGGAGCCGGGGAGGCGGCG |

TABLE 4C-continued

| SEQ ID NO | GENE NAME | SEQUENCE |
|---|---|---|
| | | GGGAGACGCGCGGGACTCGTGGGGAGGGCTGGCAGGGTGCAGGGGTTCCGCGTGACCTGCCCGGCTCCCAGGCATCGGGCTGGGC |
| | | GCTGCAGTTTACCGATTTGCTTTCGTCCCTCGTCCAGGTTTAGGAGACGCGTGGGGACAGCCGAGCCGCGCCGGGCCCCTGGACG |
| | | GCGTCGCCAAGGAGCTGGGATCGCACTTGCTGCAGGTAGAGCGGCCTCGCCGGGGGAGGAGCGCAGCCGCCGCAGGCTCCCTTCC |
| | | CACCCCGCCACCCCAGCCTCCAGGCGTCCCTTCCCCAGGAGCGCCAGGCAGATCCAGAGGCTGCCGGGGGCTGGGGATGGGGTGG |
| | | TCCCCACTGCGGAGGGATGGACGCTTAGCATGTCGGATGCGGCCTGCGGCCAACCCTACCCTAACCCTACGTCTGCCCCCACACC |
| | | CCGCCGAAGGCCCCAGGACTCCCCAGGCCACCTGAGACCTACGCCAGGGGCGCCTCCCGAGCGTGGTCAAGTGCTTTCCAATCTC |
| | | ACTTCCCTCAGCAGGTTCCACCCAGCGCTTGCTCTGTGCCAGGCGCCAGGGCTGGAGCAGCAGAAATGATTGGGCTGCTCTGAGC |
| | | TCTGAAGCATTCGGCCGCTGTGTGTGTGCAAGGGGCGCAAGGACGGAGAGACAGCATCAATAATACAATATTAACAGGAGCACTT |
| | | GTCCAGAGCTTACTGCAAGCCACATTCAGTTCCGGACCTTATTGACTTCCCCCTCCCATCTAGAGTGGATTCTGGTTTTTCAATT |
| | | TGTTTTGTTTTGTTTTTTGTTTGTTTGTTTGTTTTTGAGACGGAGTCTCACTCTGTGGCCCAGGCTAGAGTGCAATGGCGCGATC |
| | | TCGGCTCACTCCAACCTCCGCCTCCCGGGTTCAAGCGATTCTCCCGCTTCAGCCTCCCGAGTAGCCAGGATTGCAGGCACCCGCC |
| | | ATCATGCCTGGCTAATTTTTGTAGAGACAGGGTTTCACCCAGGCTGGTCTCGATCTCCTGACCTCCGATGATCCGCCCACCTCAG |
| | | CCTTCCAAAGTGTTGGGATTACAGGCGTGAGCCAACGCGTCCTGCCTTGATTCTGTTTTTAACTCCATTTTTTAGAGGAGGAAAT |
| | | TGAGGCACAGAGAGGTTAAATAACATGTCTAAGGTCACACAGCAAGGGGTGGAGCGGAGTTAGCCCACTGGCCTAGCTCTAGAGC |
| | | CCACCCGGATAACCAGAACTTGGTGAGGCCTCCGGGCTCTTGCTTGGTTTGGAGCCAGGTGCTTAGCGCCCCGAGCCCGGGGCCA |
| | | TTCACCCTGCAGGAGCTGCACGCGCCCCTGACCTCGGCTTTTCCCTGGCAGCAGAGGGGCTTTGCGGGTCGGCCGGGTAGCCCTG |
| | | AGCACAGCTCGCCACTTCCAGGTGGGCTGTTGGCGCTGGCTGGGGACACATCCCGATCTTTCAAATGCCCTTTACAGAGCCTCAT |
| | | CAACGACCCGATTCATTCCCCCCTCCTGTCATTTGTCTCTGCCATCGAAAAATGCCTACCGAGAGCTGCTCTGCATTTCCGCCCT |
| | | CTATTTTGTGTTTTACTTTAAAATAATAATAAAAAAAATGTTGGCTGCAGGACGCCATGACTTAGGTCAGCGAGTCAGCCGCTAG |
| | | CTCTGCATTTCCAAAAAGCAGATCTTTTCACAACTCTCTTGCCCCAAGTGCCCTGGTGTGGTTTATTTTTTAAAATGCATGCCTG |
| | | CGGAAGAGAAGACCCGGGGAATATTCGAAACCCCGAGCTTTTACAACATAAAGCGCATGGTGTGGCCGCGGCGAGTAATGGCGCT |
| 206 | HLCS | CAAATCACTTGAACTCAAGTTCAAGACCAGCCTGGGCAACATGGTGAAACCACATCTCTACAAAAGTAAAGAAAATTAGCCAGGC |
| | | ATGGTGCTGTGTGCCTGTAGTTCCAGCTACTCCTGGGGAGGTCGAGGCTGCAGTGAGCCGCAATCACGCCACTTGTACTCCAGCC |
| | | TGGGCGACAGAGCAAGTCCCCATCTCAAAAAAAAAAAAAAAAAAAAAAAAAAAAAAGGCTGGGTGTGGTGGTCCCAGATACTCAGAG |
| | | GCTGAAAAGGGAGGATTGCTTGAGCCCAGGAGTTCAAGGCTGCAGTGAGCTGCGATCACATCAATGCACTCCATCCAGCCTGAGC |
| | | AATGGAGTGAGACCCTGACTATATTTAAAAAAAAAAAAAAATAGGAAGAAACAACTCAACCACAGGGCTAGTATGTTACTCGGTTA |
| | | TAAAATGATAAAGCCCTAAACAGAGAATTAGCCCGTTTCCAGAAGAGGCCAAGAACAGATGATACAGCTGAACTGAACTCCTGCC |
| | | TGTACAGCTCGTTTTCTACAAGATTCCAGACCTGGAAGATGATGGCATCCAGCCCCCATTGAAGCACCTCGAACAAGAAAAACGC |
| | | CGAGTCCGAAGAGCCAGGCCTTGAACACACGATTCCTGTCTATAAATAACTCCCCCTGGGGAATAAAAAGCAGGATCCAAGGCAG |
| | | GAAACCCGAGCCGTGGAATCTGGTAAGTTCTTAGGAAACCCACTCACGGGCCTGAGTCCCCCGTGGAAGCGGCGACTTCGGCACC |
| | | TGGACACCCGAGTCCCCAGAGCCCCGGGCGGCCGCGCGTCCCTACCTGCAGGCCTGATACCGGCCGCGGAGCGCTCCTGGCCCCG |
| | | CTCCCGCCAGGCTCCGGGACCGCTGAAACGCACCCAGGGGGGTGAAGGCGTAGTCGCCAAGGACAGCGCAGATGGCAGCGGAGGC |
| | | ATGGGAGCCGGAACCTACCGTGGCAAAGGGCCAGGTCGGGACGCCCCTCGGCGCAGCCCCAAATCCTGCCCGCGCCCCAGCCCCG |
| | | CTCAGGCCGCGCCCCTGCCACCTCTGGCCACACGGGCTGAGACGTCTGGCTCCTGCACAGCGCACTTCCCGCTGCCCTTCTCCAC |
| | | TGGCTGCTCAGGCCCTGCCTCGCCAGCACGGCATCCGCGGGGGATCCCTACCTGTCCTTTAGGGCTTGCCTCATAGGTCAAACGT |
| | | CACCTCCCAGGGAGGTATGGCCTGCCCCCTGGCCAGGTGGGCCCCTTCCACGCTCGCCTGCAACACCACCCACCCACCTTGATAA |
| | | CTGCTTGTAAAGGTTGTACTGCTTTCCCCCTTGAGACTGCAAACCTTCAAGGGCAGGAAATGGGTCTGTTTTCCTGGCAAAATAA |
| | | TGAAGTTGGCTTAAGGTTTTGCTGAATAAAATGAGTGACAGACAAAAGTAGCCAAATTTGGCACTCCTGATGGGTTATTTGATGA |
| | | AGGAGGTGCAATGTATGGGCTTAACTAGTTATTCTGGATTTCTTTCCCCATGTTA |
| 207 | DSCR6 | CAAGGCCGGTGCACGCGGACCCGAGGATTCGGTAGATGTCCCCGAAGACCCGCTGCCGCTCTAAGGCGGTGGAAGCGAGATTCTC |
| | | CGGAAACCCAGGGAATCCGATGCTCGCACAGGACCAAAGCCCGAGGCCGCGGGGACCACAGAGGGACGGAGAAGCCGGGACTCCT |
| | | CACATCCCACATCCGGCAGGGGAAGCCCAG |
| 208 | DSCR3 | CTGATAATAAAGTTTTACCATTTTATAATTTAAAAATGTAAATATGGAGTTGGGCATGGTGGTTGGGAGGCTGAGACCAGAAGAT |
| | | CGCTTGAGCCCAGGGGTTTGAGACCAGCCTGGGCAACATGCAGAAACCCTGTCTCTACAAATAAAAAATTAGCCAAGCGTGGTAG |
| | | CACGCACCTGTAATCCCAGCTACTCGGGAGGCTGAGGCAGGAGAATCGCTTGAGCCTGGGAGGTGGAGGCTGCAGTGAGCTGAGA |
| | | CTGTACCACTGCACTCCAGCCTGGGTGACAGAGTGAGGCTCTGTCTCAAAAAAACAAAACACAAAAAAACAAACAAAAAAAAGCA |
| | | AATATATGTAAAAATAGGAAGTGCGGTTTCCCAAAATGAGGTCTGTAAACAACTGATCTAGAAAATGTTCTGGAAAAAGTAAAAA |
| | | AGGATCAGGATCTGAGGTCAACTGACCTCTCCCTGCGCTCTGGACAGGCAAACAGGCAAGGTTCCCTCTGAGGCCGTAGCGGCTT |
| | | CTCGTGGGCGAGTCCCTGTTCGCAGGTGACGTGTGGACCACGCTCTTCCGAAGCGTCTGGCCTGTGTGCTCTCGGGGAGGGGACG |
| | | CAGGTCAGCCCACCTAGCCGATGGCTAACAAGTCAGTTTGTTTTCTGAACGGAAGCTTAAACCTAGAAAAGTAACTGGGTTGGGG |
| | | TGGGGGTGTAGCCACATGCAGTAAAAGCACTGCCTGTCTGTATAACAACGACCTGATGAAAAAAGGAACGCGTGAAATGGGGAGT |
| | | GTTAGGGCGTCACAAACTCCAGTGTGGTTGAAATGAAAGCAGAAAGCAAATGGCAAGCTGGCTTCCCCTTCCAGCTTTTCACAAC |
| | | CCTGCCTTGCTCATGGTCAGCCCCAAGCACGGGCGGAAGAAAGGACTGGAGGGGAGGGAAAGGGGTGGGGAGCGAGGGTACCAGA |
| | | GGCGTGGGAGGACGGGGACAAAGGGGCAGCAAGGGACCGGCGGAAAGGAAAGTCGGCGTTAGCTGGATTGGAAACAGTCCAGACA |
| | | GAACGATGGGCTCTGCTGCCTCCGGGTGGGGCACCAAGCGGGGAGCGGGGCCACGAGGCAGGGGACAGTGAAGCACCATGCAGCG |
| | | CCCACCAGCCGGCAGCGCCCACCAGCCTGCGCTGCGCTGCACATGGTACCCGCGGCCCCAGCTGGCCAGTGTGTGGCGGAGATGA |
| | | GACCCTCGTGAAGAGACTAAGCGGCCACAGCAGGGGGAAGGGTTGCTCACATAACCCCATACTGCTCACACTACGAGGTTAACTG |
| | | CCGTGAGATCTGCCTGCAGCCAGCAGAAACCCGTTCTAGGAAAACGTTGCCCAGTGACTTCAGTGAGTGCCACTGACCCGGGCGC |
| | | CTCCGCCCCGGCGTCCGGCAGCAGCACCGATTGCGCAGGAGGCACCTTGCAAACAACCTTTCCTGATCCGCGCTGCAGTTCCCAG |
| | | GCCGGTTGCAGCCGTTTCACAGAGACTGCGCACACAAAGCGTCTCCGTGCCCTGCCATTCACCTTTCGACACAGCCGCAACCCCT |
| | | CTTTTCAGTGTTAAAACCTGGCGCCAAAAGGAACATGCGATGTGACGTGTTACCTCTGCGCATGCGCCGGGCATTCCCAGCGCCC |
| | | CGAACCTGATGAACGCGCGGTGGGGACCCCAGGCTTCCGTGCTTTCGTTTTCCTGGAAGCTACGTGTCCTCAGTCTACATATTGT |
| | | TACCTGGAAAATAAAGTTTTCTCCTTTTTTCTTCCTTTGTTAACAGGCAGAAGGTGTAGGCTGCAGGTTTCGGGCCTAAGAGAGG |
| | | GCATGGCTGGCGACACGGAGTAGACTCCTAGATGACATAACGGAGGCGAGTCTGCACCGGGGACTCGGCATTAGGAGGAGGCAGA |
| | | GGAAAAGCCCACCACCGTGGCCGAGGGAGATCTAGCAAGCAGCTTGCAGGGGGTGAAGTGTGTGCAAAGCAGGCTGAGACCTGTC |
| | | CAGTATCGAAACACGCCGCGGTGGTCAAGCAGGCTTTACCATGCT |
| 209 | chr21: 37841100-37841800 | TGAGGCTCAAAACAGGTGTCTGTGAGCTTCACAGGCGGTAAGGCCGTGTCTACATGGCCGGGACATGCATCCCGGGGCTGCCCCT |
| | | GCCGTGCTGCCCGAGTGCACGGGGGATGAGGACCTGACAAGGCCATTGATCTTGCGGGAGCTTCCTGAACTACTCCAGCGTGAAA |
| | | ATCTTCCAGAAGGATTCTCCACAGGGCAATGAGGCAAGAAATTTACAGCTTAGCCTGATTAATGGGCCAGGCAGTTAAGAGTTCT |
| | | TTGCCAAGCTATGAGCATAATTTATAGTCATCACGGCAGGAGGAAAGGCCACATAACTCACATCCTTAAAGGGCCCTTAGAACAA |
| | | GAGACACGCCGGATCATTGAAAACGTCTCCACTCCTGGCGCCAAAAGAGATCGGCACGTTTCTGGGTATTCTGGTCAAAGAACAG |
| | | GGAGTCTGGATTAATATACACGGCAGAAAAAAGCGAAGAAAAGACACACAGGTCATATATTTCTGACTGATATTCCGTTTGTTGT |

TABLE 4C-continued

| SEQ ID NO | GENE NAME | SEQUENCE |
|---|---|---|
| | | TTTCGGAGGGACTTGGTATTTATTTAACCACATTCTCACTTGACACGCCCCCTCCCCACACCTTGTAAATGCCTTCCTCTTTAGC<br>CGAGTCATTTTTCATCACATAGAATTGAAATGTTGCCAGGAAGGCGGTTTATGAGATTGTAGAAATGGCACTAGAGAAAGCAGTG<br>TGAAAAGAGGCCTAGAACGT |
| 210 | ERG | TCTCTACATGCTATCTACTAAAAACTTAGGCAAGGAAATGCATCAGACCAAACACCCCACAGCACAGAGAACCGACCGGCCATTG<br>CTTTCCAATCTCCGCAAACCTAACCATTGCTGGAAGAAATCTTACTCACAGTGCACAGACAGTAGGTATTTTATTGAAGATAAAC<br>ATATAGTGGAACAAACCAAATTACCCCCATTTGAGTTACGTGAGCACTCAGTTCTCAGCGTGGATGTCCCACAAATCAAGTCAAC<br>ATTTGCGTCCCATTACCAGCAGCCACTTGCCGAGTATCTCTTCGCTTCCACTGGGACTGCCTGGCATCCCTGATGCTAAGGAGCC<br>ACTGAAGAGCCTCCAAATGTCTGACATTCACAAACGCATCTTTTGCTTTGACCCGACCCTTCAACCTCTCCGAGTCTGCTGCCTT<br>TTCTCAGACACACATCCAGGCACCGTTAGGGATAGTTAGAGAATCTGAAAATTCAGAAGCGCTCCGAAAAGCCTTTCCAAAAGTA<br>ATCCACAGCACTCAACAGTGAATTTAGAAACCCCAATTTTTTTCTGAGTTTGAAGTTTTTAAGCCTTGCGGATGGTTGGAGTAGG<br>AAAAA |
| 211 | chr21:<br>39278700-<br>39279800 | TCAGACAAGCTCTGTGCAGTCGGAATTTTTTAAAGATGCACTGTCACTTGAGGAAGACAGGTGATCTTCCTGCGGCACAAATAGA<br>AGCAAAGAGATTTCTCTTCTTCTCTGTAGAGCAACACAATTGATAAATGGCCGATAATCTCCACCAAATTGGCAGCAGTAGGCTG<br>CCCGAAGGCAGCAGGCATATTCGTCTTTGTGAATTGTTTTACTATGATGCTGTCACATTTCCAGGAATAAGACGGTTAAAATGAT<br>ATATTGTTGTGGTTTGGCATTTGCAGCTTTGCTCTGACTTCCCTGGTAACTGCCAACATCTGCAAATTATTATGTGCTTAAAAAA<br>AAAATCAACCGCCACCGCAGGCTGCCCCCACGGTCCCTGGCTGGGCCAGGCCTCCTGCCAGGCCACAGGGCAGAGTTCTTGGACC<br>AGGAGGCAGCAGGGTCAAAACCCAGGTTGCCTAGGAAGCCCCCAAAGACAGTTATGGATAGAGCTGGGAGCCCGAAACACATGCG<br>GCAGTCTCTCAGTTTCCAGGTACCGGTTCTCACATCATCCATGCATGTGTTTGAGGAAAAACAAAAAAAAATTGATGGTTGCCAA<br>AAACAAAAATGCTTCCATATCAAAGTTTATCAGTGTCAATGTCAAGAGACTTCTGGTTCGTAGACTCATTTTGGCTTGAGGCCAC<br>CAGAAGTGAACTCTGGTTTCTAAATGCAGAAGCAGAGGCACTGGCCGATCATGGAAGATGCAGGGAACTGTTCAAGAGGCCCAAG<br>CCTGGTGCTCAGAAACTTGGCAGGATCAAGCATCTCGCCCAGGAATTCATCCCCTGCTTGTCTAAGCCGGCTGGCTCTCGTGACT<br>GACTCGGAACAACAGAGCAGATGTTTGCGTGGGAGGCAAGCCTCACCCAACATCTGTCCTGCGGCGGGAAGGCCTGGGTGTTCAC<br>AGATAGAGCTGGAGTTCCCCGGTGGGTGGCACAGACAATTAGCTGGGGCTGCCTCACATGTAATCTAATTACAGGGGAAACAGGC<br>TCAAACACCGGGTGATAAGCAGCGCAACTGTTTCGGGTGACTCTGTAATTTTTCCTCCATTAATTTTCTCCATAACGCAC |
| 212 | C21orf129 | GTTGCCTGGGATATGCTTATATCAAAAACTTACGTGTCACTTACCTAGCATTTGCATTTCACTGGGCCTCCTAAATTCTGTGTGG<br>TAACCGACTGCCACCGGACATGCTGTTTACTTCTCTATCCTCACGCAGCCAGTTGCCACATTCAACATAACACTGCAAATATTGC<br>CGGTGGATCCTGACTTCCTCGTGGACCCTACTGTGTCGGGAAAAACAAACAAACGAACCCTGGAAGGAAACACCATGAGT |
| 213 | C2CD2 | TCATAAATATTTCCAAATGTATTCCTATTTGTCTCTACAGAGTCTAACAGACATAAATAGCGAATTGAAGGTTCTGTCTTAAAAC<br>CCAGCAGAAAGAAAAACAATGACCAGAAAAAAAAAACAATTGTCTTTGGCTTCCCAAGAACAGCATCGGATTTCAACTGGAACCA<br>CAGATGGTCCGTTGATAGAAGCGACTACTTTTTAGCTCTGGAGGACGACAAAAGGAACCAGCTTCTTCCTGTGGGTGTCACAGCG<br>AGGTCGCCTGGCCACATCAGGTACCAGAGCGAGCGCCCTCACCTGATAGGCCCTGTACAACCTCAGCCACAGCACTGTCAGGAGG<br>AACACGCGGAACTAGCAACCTAGGAGGGTAAAGGCGGAGTTGGGAGGGAACACGAGGCAGGCAGGTCGGCTGGCTGCTGAGCTAC<br>AGGCTGCACTCCTAGGACGTCTACGTGTAATTGAGAAAAATAAGACAAAAATAACTTACTGTGCAGGCAATTAATTCTGGTTGGC<br>ATAGCGATCCTCTTAAGTTAAAGGGAATGAGCATGAGATGAAGAGAAGTAAGAGGCAGAAAGAATTATGCAAGAGCAACATCAGA<br>GTGGA |
| 214 | UMODL1 | ACGCCGAGCCGCCTCTGCAGGGGAAACCGAAGCAGATGTGGTGAGATAATACATCCAACCCTGAGTGCTACTCTAACCTGCCAGA<br>GGCGGAGGGTTCTCAGTGAGATGAAAGCATTACAGATGCGTTAGATCTAAGGGAGGGGCCTGCAGATGCGCAGCTGGCAGAGAAA<br>CCAGGGAGGGGCTGAACTGTCAGTCGCGACCACCAGGGATCTGAATCAGTTCACCGACAGCCTTGGGGACATTCACCTTGGGCTC<br>CACAACCTGTCAGAAATGCCCCCAAGCCCAAAGGCGTCGAGAGAATGGCCAGGTTGTTTCAGATTGACACATATCCTAATGTACA<br>AGTCAGCCCACACACCCCACGTGCACTGAGCGTCTCTTGTTGTTCACCCCAAATAAACTCTGCCGGAACTGGGGCGGGACTCGCA<br>GGGGCGGAGAAGGGGGGAGACGGGCAGAGGGCAGAAGTGGATGGTGAGAAGAGCCAATGGAGGGGCCCCGTGAGAGTGAGCAAGG<br>CTGCACCCCTAACCGACGTCCTGGGGCTACTGTACAAACAAAGAACCACAGGCTGGGAGGCTGAACAACAGACCTGCACTCTCTC<br>GCAGCTCGGAGGCTGCAGGTCTGAAATCGAGGGGCTGACAGCGCTGGTTTCCTCTGGAGGCTGCGAGGGAGAAACCGTCCCCTGC<br>CTCTCCCAGGCTCTGGGGTGAGCCCTTCCTGGCATCCCGGGCTCATTGTAGATGGATCACTCCAATCTCCATGGCTTCTCAGGGC<br>TTCCCTCCATGCACCTCAAATCTCTCTCTCCTTCCTTTTGTAAGGATGCCAGTCATTGGATTTAGGTTCACCTTAAATCCAGGAT<br>GATCTCATCTAAATTACATCTGCAAAAAGACCCTTTTTCCAAGTAAGTTGACATTCACAGGTACCTGGGGTTAGGATTGGACATA<br>TCTTTTGCAGGGGTGCAGGGGGCTGCCACTGAGCCCGCTGCACAGGGTGACCTGGGCCAAGGGCCCTTCACTTTCACTTCCTCAT<br>TGGCAAGCTGCCCTGTGTTTGGACTGGGTCGAGGCTGTCAACCTTGCTGCCCCTCGGAGTCCCCCCTGGTGTCCCCCAAACAGAT<br>TCTAAGCTGCTTTCCTGGGGCTGGAGGCCAGGCATTGGGATTTTTTAAAGAGCTTCCCAGCAGGTGAGCAGCCTTTCATGGGTAT<br>CAGGAGACCTTCCTGGCAAATGTGGTGAAGGTCCTTCCTCCTGAGCGATGCCTTAGACCCAGGAGCCCAGGGAGGCTGCTCACCT<br>GATCGTTAGGACAGGAGCAGTGGAAACCTCTGGCCTCAGACCCCCTGGAGGAATCCCTCCCTCTAAGACTCTGGGACTGGTGCAC<br>GCAAGGAGCTATCGTGAACATTGCTCCCAACTGGCCGCTTGCTTGTCCCCCGGCTCCCCTTGGCCCCAGTGGCGGCTTTGCCTGA<br>ATTAGAGGGCGTGAGAGCCACCTGTGTCTCAGCACTGCAATTAAAGCAGGAAGCCCTTTCGGAAGCAGCCGTGTGCACCAGCCTC<br>CCATGGGTGGAGCAGAGCAAACCACCCACTTCTGCCCTCTGCCCTTCTTCCCTTTTCTCGACACCCTGCGGCCCCCCAGTTTCAG<br>CAGAGTTTATTTGGGGTGAAAAACAAGAGATGCTCAGCGCCTGTGGGATGTGTGGGCTGACTCGTACATTAGGATGTGTGTCAAT<br>CTGAAATAACCTGGCCGTTATATGGATGCCTTGGGGCTTGGGGGGTTTCTGGCAGTCTGTCGAGCCCGAGGTGAATGTCCCCAAG<br>GCTGCTGGTGAATCAGATCCCTGGCGTTCTCCGTTGGCAGTTCAGCCCAACAGTTTCTCTGCCGGCCGTGCCTCTGCAGGTCCCT<br>CCTCTGATCTGATTGGATTAATATTTGAATCAATAGACTGAGTCAAGCAGAATGTGGGTGGGCCTCATGCAATCAGCTGAAGCCC<br>TGAAAAGAGCAAAAGGGCTGCCCCTTCCCCCGAGGAGGAGAGAAC |
| 215 | UMODL1/<br>C21orf128 | CACATTTCAGAGCTGAGGTGCTGGTGCGGGCAGGTCTCCTGAGCTGGGGGGTCAGCTGTGTGGCCAGTGATGGTGACGCCTCAGG<br>CCGTGCATGGCCGGGGAGGCGGCCCTGCCTCTGCACTCTTTTGACTCCATGACTACTGGTGTCTTCGGACGCCAGAGTCGGGGGA<br>GCAACCATGGGGCACCGCCCCTGCCTGGGGAGGCAGCACGAGGCCTGAGCCCAGCTTACAGGGGGACATCCACCCCCGCTGAGAG<br>CCCCACCTTCACGGCGAGGATCTGTAGAAGAAGACATTTGATATTACTCGGCAAAAAAAACAAGAAACGAAAACACAAAAAGAGC<br>TCCTCTGAAGAAGAAAAGGTATTTGCGCTGTGGTCCACCTAGAAATAATGTTGTTGGCACAACTAGAGCATTCCTCAGTCATTCA<br>GGAGCACTCCCTGCCGGTGCGTCCACATGTCCCAACCCCGATAGATGAGGCGCTGTTCGCCCGTGGAGGGGTCAGGTTGTCGTGA<br>CCTTATCTTTACCCTTAGGCCGTCCATCCCGGGGCCTGGGGTTTCCTGCGCCAGTCACGGTGGGCTGTGTAGGTGGCCATGTGTT<br>CGGTCTTTCCCCAGGAGGTACGTACCATGTGCTGGGAGGCCTGGAGGCTGAGCCGCCCCCCGCGCCTATGAGTTGCACCCTCACA<br>GCGGCGGCCAAACCTCCTGC |

TABLE 4C-continued

| SEQ ID NO | GENE NAME | SEQUENCE |
|---|---|---|
| 216 | ABCG1 | CAGGCTTGAGCGGTGACTGGGAGACCCCGGGAATGGAAATGGCGCTCAAATGCTGGTGTGGTGTCCGCAGGGGAACGGCCCGCGG<br>GTGTGTGGAGTCTGCGCCCCTGTGGCTTCAGCTGCGTCGGGGGACTGCGGGAATCTTCCAGACTCCAGTTTAAATCAGAGAGGTG<br>TGTCCACGAAAAGAGTCAAACTAAAACATT |
| 217 | chr21:<br>42598300-<br>42599600 | AACGAGACAGTGCAAAAAGCCGCTGCCTGGTGACCTGGCATGCAGACTCGGCCCTCCCACTTGCACGGTGATCCACTGAAGACAA<br>CAGCTGCCTCTGTACTCACGCTCCCCCACACTCCCCTCCTTCCTGCCCTGGTTTCTCCATCCCTAGATGCCATCCCATGCCCCAA<br>ACCATCCGCCAAGCACAATAACCTCGCCCCCACCCACCCCATGAGGTCACTCGAGTTGACAACCAGATAACAGTTTTTGTTTTGT<br>TTTGTTTTGTTTTGTTTTGTTTGTTTTTGAGACGGGGTCTCGCTCTGTTGCCCAGGCTGGAGTGCAATGACGTTATCTCGGCTCA<br>CCACAACCTCCGCCTCCCGGGTTCAAGAGATTCTTCTGCCTCAGCTGCCTGAGTAGCTGGGACTACAGGCGCGTGCCACCATTCT<br>CAGCTAACTTTTGTATTTTTAGTAGAGACAGGGTTTCATTATATTGGCCAGGCTGGTCTCGAACTCCTGACCTCTTGATCCGCCC<br>ACCTCAGCCTCTCAAAGTGCAGGGATTACAGGCGTGAGCCACCGCGCCCAATAGCAATTTGATGACCCATCCCCTCCACTGCTGG<br>GAAAAGGCTGGGCACCGCCCACACTCCATGCAGCTCTCTTTCCCTGGCTCGGAATCGCTGCAGGCGCCACAGACCAGACGCGCAC<br>TGTTCCCCACTCCTGCTTATCGGCCGCGCGGCATCCCCTTGTCGCAGCACTCCAGCATCCATGCAGCCGCGCGGCACCCCGTCTT<br>CGGAGCACTCCAGAATCCATGCAGAGCGCAGCACCCCACATCCAGAGCGCTCCAGAATCCATGAAGCACGCGGCACCCCCTCGTC<br>AGAGTGCTCCAGAATCCATGAAGTGCGCAGCACCCCTTAATCGGAGCGCTCTAGAACCCGTGCAGCGAGCAGCACCCCACACCCG<br>GAGCGCTCCAGAATCCATGAAGCCAGCAGCACCCCACACCCGGAGTGCTCCAGAATCCACGCAGCACGTGGCATCTCCTCGTCAT<br>AGCGTTCTAGAATCCATGCAGCGAGCAGTACCCCACACCGGGAGCGCTCCAGAATCCACGCAGCGTCTGGCACATCTTTATCAGA<br>GCGCTCCAGAGTCCATGCAGCCACAGTCCTCCAACGGACCCTGAGATTGTTTCTGCAAAAGGCCATGCCTTCATAAATCTGAAAA<br>TTTGGAAAACATCCTTCTACTTATATCCTTACAACCCACCATTCAAGCTGTAGAAGCCTTTCTGGAACCCCAAGCAGAAGGATAT<br>CCAAAATGTAAAAACGGTGGGGCCT |
| 218 | chr21:<br>42910000-<br>42911000 | ATAGTGCGACTGTTCCGAAGTCTTTATCACAGTTACTGGTGATGCTTTTTTCCAGATGTCCTCGACGTGCACCCATGAAGGGCTC<br>CACCTGAGAGTGCCAGGGTCCTCCGTGGGATGGGGCTGGAGGGGGTGCTCTTGCCGTCCTGGGCTCCCAAGCAGCCATAGGAACA<br>ATAGGGTGATGGGGTCCCAGAGATAGAGGCCAGTGACAGCAGCGCTTTGAACCCCTCACACGGGCACGGGCCCTCTGGCAGGGAT<br>GGGCGTCCCGGTCACACGGAGATGGGGGCTGCTGCTGCCTGCAGGTAGAGGAAGGGACGTGTTTGGCAGTCCTGTGACCCCTGGG<br>CACCTCGCCTCCCCCACGGCCGGCTCTGCTTGTAAACAGACAAGTGCACAAGCGCAGCCCGGTGAAGGCACAGCGGTCCCAGGAG<br>GCATCTGGGCTGCACCCCAGCGAGCCGCCCATACACGTGGAGATGCCGGCCAAGGCCCTGCAGCACACGGCAGAGGAAGGCGCGA<br>TGGGAGCCATGCTGGGCCCGGAAGGTGCCGCCGCCCGGAGCTGTAGCCATCACTCCAGCTCTTCTTTTAAGTGTTCCCAGAAATT<br>GTGACCCACCAAAATCTGAGAGCACCCGACAGTAAGCCAGAGGACCTTGATGTGAGATCCCAGCACGGTGTGGGGGCGGACTGTG<br>GTGGGTGCTGTCTCGGCCCCCACCCCTTCCACAGGTCGGTGTGCACATCCCACGGCGCCTGCTAAGCTGCAGTCTTCTCCAAAGG<br>GGTCACTCTCCGTGGGAAGGGAGCCACCCGCCCCCGGGTGATGTCCCCAGTCAGTGACTGACGACAGTCCCCAGCCGAGGTGAGG<br>GACCAGCTCCTGCATCCCTCACTCCGGGGCTTGCCTGTGGGCCAGGGTGGGGGCGAGCCTCAGCAGAGACCGCGTCCCCCTTGCC<br>TGTCCTGCCCTGCCTCCCCTGCCTCCCCCGCGCCTCTGCTGAGCACGCCCAGAGGGAGCTGCTTG |
| 219 | PDE9A | CACTTGAAAAGCACAACTCATGGTGCCAAAGCTCTGACACGGACTCCACTGGAGCTGTGGGCAGGGGGTGCCAAGGTACCGAGTT<br>CCAAGCCGTTGTTATTTGAGAGCGTGCCCCCCGCCATGAGAGCAGGTGGGGGGACATAAAGTGACACAGGATGGACTGGCCAAAG<br>GCTGAGGACGATCACTTACCTCACAGGATGATGCCACCCCCACGGACAGGCAAGGAGCTCTCACCTTCCCCAGGACCCCAGCTGC<br>CACCAGAGCTCCAGATGGCCCTGGGGGTGTCTGTAAAGCCTGTGACCGTCCACCAGGTGGAGACCAGGCTGGCCAGGGGAGGGAG<br>AGGAAGTGACCACTGGCCCTGGCACTGGCTGGCCGGCTCCAGCAGGCCCGAAGGGGAGGGAGGAGCCTGGGTGCACCAGACTCTC<br>TCAATAAGCAGCACCCAGACACTTAACAGATGGAAAGCGGTGGCTTGGAACTCACTTCCAACGAAACAATAGCAC |
| 220 | PDE9A | AGCACCTCCTACCCACCCTCCCCATTCCTGCCATCCCCAGGGTCCAGGGAGCCCAGATTCCAGGGAAGGGTTGCATTAGCTCCC<br>ACTCGGAGTCCTGATGCAGCAGAGACAGACAGAGGCCCTGGGAGAAGTGAGCATGAATTATTAAGACAAGACAAGGGTGAGGCCC<br>CAGAGAGGGGGTGGCGGAAGGGTCATGTTCATGCAGCGAGAGTGCTTCGAGCTTGAACCGCGTATCCAGGAGTCAAGCAGATTG<br>CAACTGGCGAGAGGCCTTCAGAAATGCCCCGTGAGAGTCCTGTGTGCAGAGCTCCATCTCAGCACACTTCCTGTTCTTTTGGTTC<br>GTCGATTTTTGCATTTTCAGTCCCCTGTGATCCATTATTTATAACAGTGGAGATTGGCCTCAGACACTAGCAGTGAGGAAAACAA<br>AAGCGAAGCTACGCAGAAAAATGACAAGAGTGATGAGCACAGCAGTCATGACAAATGAGCCCTGTGCGGAGGCCCGGGATCCGCG<br>CAGATGCCGGCGCGGGGGAAATGGGCCCTGAAATCCCACCGTCAGGCCAGGCAGCTCTGAGCGTGACCTGGAGGGCTGTTCAGAC<br>GGTCTGGGTAGCCGTGTCCTGCGCATGAACATCCTCCGTCGGGAGAGGAATTCCCCACGGATTATCAGAGCTGCTCCCTCCACCC<br>CCCGCCACGTCCCACGCGGGCCACATCAACTCCCTCTGCAGCCTCTGGCCAGCGGCTGAGCCCTCCGTGTCTCCCCTCGTTAATG<br>CCTCCTTCACCATCCCCTCCTGAAGTTTCCCCCATTGCATACACGCGCTGAGGCCCACCCGGTATCAAGGACTCCCATTGCTTGC<br>GAAAAAGATTCCACCCCTCTTAGAACAGAGACCAGGGCCGCTGTAGCAAATGGCCATAAATGCCACAGCTTAAAACAACAGAAAC<br>GGATTATCTCGCAGCTCTGGAGGATGGAGTCCAAAATCTGAATCGCTGGGCTGAAATCCAGGTGTGGGCAGGGCCGCGCTCCCTC<br>TAGAGGCTCCCCCGGAGATTCCCTTCCTTGCCTCTTCCAGCTGCTGGTGGCTGCCAGCAGTTTGGGAATTGCGGCCGCATCACAC<br>CACCTTTCTGTTTGTTGTTGACATCCCCGCCTCCCCTGCCTGCGGGGTCTTAGATGTCTCTCTCCTTCCCACTGAGTTTCACTCC<br>ACATTTGAATTGGATTAACTCATGCCATGTTAGGCAAACGTGCCCCTCAAATCCTTCCACTTAACAGACATTTATTGAAGGTTCC<br>TGTGTGCGGGGCCCAAGAGAAGGGA |
| 221 | PDE9A | GAATGTTCAAAGAAAGAGCCCTCCTTGCCTTCCTCTTCTTCCACCCCTGCCCTCTGCAGACTGGGGTTCTGTAGACCCCCAAAGT<br>AAGTCCGCCACACCGGAAGGAAGTGAGTTACACAGGGGCCCACATGGGAACCGCTTTTTGTCCTGTCTTGGTGGGAAAATGGCCA<br>CGACCCCAGCCCAGGCTCTGCCACGCCACA |
| 222 | PDE9A | CCATCTTCCTAGGCCTGCGTTTCCCCCACACCGGGGACTTGTGCTGGAAAGAAAAGCTGCGTTGGCAGCCAGGAGCCGGGGAAAC<br>TGTCCAGGGAGGCATCCTCTGCGATGAAGGCGGGGCCTCGGCGTGGCCCGTTCCGCGCTCTGTCCAGCCCTGGAGAAGCCCCACC<br>CTCACCGAGCTCGAAATACCCCCTCCCTGAGAGCCGAGACTCATGGCCGGGACCCCTTGGACAGAAGATGCGGATGCTAACCCGG<br>CGCTTCCACCACAGCCCCGGCGGCACTGGGGAGCGAGCGCGGCCATCCCGCGCGTAGGTGGTGTTTCTCTGCAGGCGCCAGTTTC<br>ACCGCGGGCGCCCAGGATCCTCAACGGTTCTGTTGTGATGTGATTCCCCTCTTCGACTTCGTCATTCAGCCTCAGTCCCTCAGTC<br>CCCAAATACCGAAAGGCAGTCTTTTTTTTTTTTTTTTTGAGACGGAGTTTCACTCTTGTTGCCCAGGCTGGAGTGCAATGGTGCGA<br>TCTCGGTTCACTGCAACCTCCGTCTCCCTGGCTCAAGCGATTCTCCCGGCTCAGCCTCCCGAGTAGCTGGGATTACAGGCACCTG<br>CCACCACGCCCGGCTAATTTTTTGTATTTTTAGTAGAGACGGGGTTTCACCATGTTGGCCAGGATGGTCTGGAACTCCTGATCTC<br>AGGTGATCCACCCGCCTCTGCCTCCCAAAGTGCTGGGATTACAGGCGTGAGCCACCGCGCCCGGCCTTTTTTTCTTTTTTCTTTT<br>GAAGTTAATGAACTTGAATTTTATTTTATTTACAGAATAGCCCCCATGAGATACTTGAAGACCCGGTGCCAAGCGACAGTGTTGA<br>CCCCAGGTGGTCAGTCCTGCCTGGCCCCTTCCGAGGGATGCGCCTTCACCATAACCATGTCACGGACAGGCGTGTGGGCAAGGGG<br>GCATCGCTGTATTTTTCACAACTCTTTCCACTGAACACGACAATGACATTTTTCACCACCCGTATGCATCAACCAAATGAAAAGA<br>TGAGCCTGTGACATTCCCGTGCGTAGAGTTACAGCTTTTCTTTTCAAAACGAACCTTCAGTTTGGAGCCGAAGCGGAAGCACGTG<br>GCGTCTGACGTCTCCAGGGAGACCCGCCGCCCTCGCTGCCGCCTCACCGCGCTTCTGTTTTGCAGGTAATCTTCAGCAAGTACTG |

TABLE 4C-continued

| SEQ ID NO | GENE NAME | SEQUENCE |
|---|---|---|
| | | CAACTCCAGCGACATCATGGACCTGTTCTGCATCGCCACCGGCCTGCCTCGGTGAGTGCGCGCTGCGGGCTCTGCCCGGTGACGC<br>CACGCGGCCTCCTCGCCTTTTCGGGATGGCTGGGAGGGGCGGGAAGAGGCGCTGAAGGGCCCGAGGCACCGGCCTTCTACAAGGG<br>GCTCTTCGAAATCAATCAATGCGCAGAATCCCGAGGGAGGCTCAGCCGCCCTCCGGGCCTCTCTGCCTCCACAGGTGATGGCTGT<br>GTCCACAAGGAGGAAACCGTCGGGCTGAATTAAACAGAACCGCCCTCCTAAGAGTGTGGGTTTTTCTGCCGGGCGTGGTGTCTCA<br>CACCTGTAATCCCAACACTTTGAGAGGCCGAGGTGGGCAGATCACCTGAGGTCAGGAGTTCGAGACCAGC |
| 223 | PDE9A | AGGCAGCAGGGTTAGGACTTCAACATACAACTTTTGGGGGGAGATGTACTTCAGCCCATAACACACCACGTGGGAGGATAACACC<br>GATTTCAGAGCTTGCAGAGGAAGCCGCCAGGAACTCCAGTGAGACATCAGCCCCCAGGTGCCTGTCAGGCACGCCGGGCTGTGGG<br>GGGCACCTGGGCCCATCTGAGTAACGGAGGCGCATCCGCACTTCCCCCAGGAGTACATTTTTAGAACCCACAGCGCCATAAACCA<br>AAGACAAGGAGACTTCCTGGTGCCCCGTCAGCTTCTGGAGGCGACGTTCTCGGCTGACAGCTCTGGCAGCCTCCCCTGTAGGTGA<br>GAGACAGGTAAATGGGACTCTTGCTTCCAAAACGGAACAGGGTAAAAATTCTCAAGCGTT |
| 224 | chr21: 43130800- 43131500 | TGCTGCACCCCCGCTGCCCTCCCTCCCGCTGGCCGGCAGCACCTTCTCCACCCGGGCCCCTCTGCTCACAGCGCTCCCCGCCCCC<br>GTCTCCCCGAGGGGCGGGGAGCCAGGACATGGCCCTGAAAGCCTAGCCCTGGCCTTGACCTCCCCAGAGCGCCCTCCCCACCCTC<br>CGCCCTCTGCCAACCCTGGCCCCTGCCCTGGCCCCGTCCTTGTCCTCTGCTGCTGGCCTTGGGGTCGCGCCCCGCAGACTGGGCT<br>GTGCGTGGGGGTCCTGGCGGCCTGTGCCGTCCCACGCCTACGGGGATGGGCGAGGTCCTTCTTGGGGCTTCTCTTACCCACTCTC<br>CAGTCACCTGAGGGCGCTGCTTCCCTGCGGCCACCCCAGGTTTCTGTGCAGCCGAAGCCTCTGCCTCTGCGGCCGGGTGATCCCA<br>AGACCCCGGGGTCCAGGGAGGCACGGGATCTGCTCCCCCGGTCCCAAATGCACCGGCTGCGCCTTAGGAGGGACGGCCTCCACCC<br>ATGGCGCTGGCGCCCAGGGGCCGCTCCTCGGACTACAGCACTTGCTCGTCGCCCTGCGCCCTGTTTAGTTCTCATCACCAGCAGC<br>CTGGACTAGGGCCCTGGTCCTTCTGGCCTCCTTCCACAGCCCGCTGCACATCTCACCCACTTCCCCGAGGTGCTGTCATTGTTTA<br>GCTGGGCCCCTCAGCCTCCG |
| 225 | U2AF1 | TTAAAGGGGAGTGGTTGTATGAAGAGTTCCTCAGTCAAAGGTGTGCAGCTGGGAAGCCCACCCCACCTAAGAGGGAGGTCTGACA<br>AACTGTCCACACTGAACCACTCAGACCTGCATCAGGGCCCCGTTTCTTCCATAAGCCGCCAAGTACAGCCCTGAGTCAACTGAAC<br>TCAGGCCTGGGAGGCTTCCCAAAGCTGACTTGACTCAGCTTTGAACTGAAATGACCGTACCATGACAACCCTGATGAAAAGCTAA<br>ACTGAGCCCAATTATTCAACAGTAAAATTCAGTTGGTCTCACTCA |
| 226 | U2AF1 | TGCTACCAGCTGCTTGGGCTTGGGCAAGTCACCCTAGCTCTCAGATGTCATCTGTAAATGATGACAATGCCAATGTGGCACTGTT<br>CTGAGAGTCAGACAGAACGTATGTGTGCTTCACATATGGTGCTCATGAAGTGCTATCATTATCTAAGGAAAACAGAAAACGAAGT<br>TCAGAGTCTCTCTAAACGCATGACACCAGACCAACAGGGAGTTTCAAAAAATAGGTCTGAAGTAAATCAATTCTCCTGGTCTCAA<br>TACACTGAAAACAAACTATTAGGGGACTGACCGAACCCACCTTAGGAACCACCTTACGTCACCTTCTGTCTCTACTGCAAAACCC<br>TCCCTTAATACTGTTCAAATACGCTGACAATCCAGATCCATATCCAATGGAACCAGCAATCATGCCTGTGTGCCAGCAATGTCAG<br>GGAGGGAAGCCGATCTCTGATGAAT |
| 227 | chr21: 43446600- 43447600 | CAGGTGCCGGCCACCACACCCGGCTAATTTTTGTGTTTTTAGTGGAGACAGGGTTTCGCCATGTTGGCCGGGCTGGTCTCAAACT<br>CCTGACCTCATGTGATCCACCCGCCTCGGCCTTCCAAAGTGCTGGGATTACAAGTGTAAGCCACTGCGCCCGGCCAAGAGTGAAG<br>TTCTGATAGCTGGGGTAAGAAAGGCCGTGGGAACAGCCGGTTTCAGACACGCTGGGTCTAAGACGCTGCGTCTGGCGCTGCTCGG<br>CATCCAATGGGAGCCGTGGAGAAGCCAGGCGAGTGCGTAGGGCGGAGCCAGCGCACAGGAAATAGGACGTGATGAGGTCAACCGG<br>CTGGTCCAAGTGTGGACGGAAGTAGAGGATGCAAGCACCGAGCCCCGGGGCCCCCAGCATTGGCGGGGAGGAGCTCGCGGTGCGG<br>GAGAAGCAGGGGACCGCGCATCCTGGAGACCAGGTGGAGCCAGTGCGCCCGGAAGGGGCGTGGCCCGCTGACAGCCGCCCAGGAG<br>GCCGGGGGAGGCCTGGAGCCGAGGGCCGCGCGTGGCAATGTGGAGAGACATTTTGGTGGAGTCATGGGGCCACAGCCTGATTGGT<br>GAGAACAGGAAGGGAAATTGCAGATGGGCCTGGGCCCCCTGGCTCCCGCATACTCCAGGACCAGGGCTGAGTCATCGTTCACCGT<br>GTGTGACCAGGGCCCCGTGTGGCCGGCTGTCACTCGGTATCCAGTTACCCTGGGCAGACCACTGGCGGCACCCCCCAGCCAGAGG<br>CCGCAGCAACACACACGCCTGCAGGCGACCAGGCCGGACTGCATGCCCCGTGGGGGAACTGAGGGCGTTTCAGTAACAGAGTGTT<br>AGGGGACACGGGTTGGGTGGCTTGGAAAGGGCCTAAGGTGGGGTTTGTTTTAGATTGGGGTGGTGAGGGCGCAGGGGCCCGGTAG<br>GATTCTCTAACAGGGCAGCAGCCACTCATTTAGCAACAGGAGAGGCGTCCAGCGTTTCGTGGGCT |
| 228 | CRYAA | ACCCAACCACAGGCCTCCTCTCTGAGCCACGGGTGAGCGGTGCAGGTTCTGCTGTTCTGGAGGGCCTGAGTCCCACCCAGCACCT<br>CATAAACAGGGTCCTCCCCAGGGCTGCTGCAGTAGGCATCAACGCCAGGGTGCAAAATGCCTCAGGGAGCCAAGGCTGAGCCAGG<br>GGAGTGAGAAGGAGCATGTGGAAGTGCGTTTTGGAGAGGCAGCTGCGCAGGCTGTCAGCAGGCTCCGGCCGCTTCTATAGACAGC<br>ATGACACCAAGGGCAGTGACCTCATTCCACAGGCTGAGTCCAGCCAGCCAGCCAAGCATCACCAGCCAGACGATTGACCCTAACG<br>GACCAACCAACCCGTAACGACCCCTCCTACCATAACCAGTAGCCAGCCAGCCCATAACCAGCCAACTTATCTATAACCAGCCACC<br>TGACCATAGCCAAACAACCAGCCGGCCCACCAGTAGCATTCAGCCCCTCAGCTGGCCCTGAGGGTTTGGAGACAGGTCGAGGGTC<br>ATGCCTGTCTGTCCAGGAGACAGTCACAGGCCCCCGAAAGCTCTGCCCCACTTGGTGTGTGGGAGAAGAGGCCGGCAGGTGACCG<br>AAGCATCTCTGTTCTGATAACCGGGACCCGCCCTGTCTCTGCCAACCCCAGCAGGGACGGCACCCTCTGGGCAGCTCCACATGGC<br>ACGTTTGGATTTCAGGTTCGATCCGACCGGGACAAGTTCGTCATCTTCCTCGATGTGAAGCACTTCTCCCCGGAGGACCTCACCG<br>TGAAGGTGCAGGACGACTTTGTGGAGATCCACGGAAAGCACAACGAGCGCCAGGTGAGCCCAGGCACTGAGAGGTGGGAGAGGGG<br>GGCGAGTTGGGCGCGAGGACAAGGGGGTCACGGCGGGCACGACCGGGCCTGCACACCTGCACCATGCCTTCAACCCTGGGAGAGG<br>GACGCTCTCCAGGGGACCCCGAATCAGGCCTGGCTTTTCCCCAAGGGAGGGGCCGTGCCCACCTGAGCACAGCCAGCCCCTCCCG<br>GTGACAGAGGTCACCATTCCCGAGCTAATGTGGCTCAGGGATCCAGGTTAGGGTCCCTTCCCGGGCTGCACCCAGCCGTCGCCAG<br>CTCCATCCCTGTCACCTGGATGCCAGGGTGGTCTTAGAAAGAACCCCAGGAAGTGGAGTGCCCCGGGTGGCCGCCTCCTAGCCA<br>GTGTACATCTTCACATGAACCCTACCTGAGGAAGCCAGTCCCCGACGGCATAGCTGCATCCGCTTGGAATGCTTTACAGGCATTG<br>ACACCTTCGCCTCACAGCAGCACTTTGGAACCAGTGTCCTCATTATTCCAGGGCACGGCTGGGGAACAAGGGGGTCCTCAGCCTG<br>CTGGGTCCCACAGCTAGTACCGGGCAGGTGGACGGGAGCTTCTCCCCACAGTCACCCTGATGCCCCGCTCTTGCTCGGCTGGAGG<br>CCTCGGATCTCCGTGGTGTTGAGGGAGCCGGGGCACTGGAGCCCTGGTGACCTGCATCTCCTGGCGGAGCCGGGAAGAGCTCATG<br>GACTGTCACAGATGGACAGTGCCCCGCGGGGGCTGGAGAGCAGAGTGGGGCTGGAAGGTGGAACTCTTAGCCAAAGTCTTGGTTT<br>CTTTTGGCCAGGGTCCTCTTTCAATGGCTGGAGAAGGTGGTGCTGGGGGGTGAACGCTGACCTCCTCATGTGCTGCCCCTCCCTC<br>GCCTGGGCCCGGTAAAGCCCCCACGTAGCCCCAGCCAGCCTGGAACATGCTTCCTGAGCTCCCAGCTCTTGGTCTTTGCACCCAG<br>TGGAGGAGGAGGTCAGCCCAGGGAGCTGAGTCTGCGGTTTAGGGCGTCCAGGGGACGTGGAAGCATGTGGGTCGTCTGGCCACAT<br>TAGGTAGGGCTGCAGAGACCTGGGCTAGAGCAGTCCTGCGGGGTCTGGAAGGGGAAGACTGGCTGAGGTGCGGGGCCTGGTCTGG<br>AATGATCCTGCGATTTTGGAGTGAAGCCATGGAGCGGGAAGAGACAACCCCCCGCGGGGAATAGCCCGGCAAGTGGCCACGAGGC<br>CAGGCTGAGGTCCAGAGAAGCAGGGGCATGAATCCATAAATCCCAGGGGGCCTGGCCATGGGATGTGCTGGCTGCACCCGGCCCC<br>TGTGAGAGCCCCCGCAGGCTGGCCCCCTTCTGCAGTCAGTGGGGCTGGGGCAGCTTCTCTGGCATGGGGCGAGGCAGCCGCCTGC<br>ACAGTGGCCCCCCTGACTGTGCGCCCCCACCCTCTCCAGGACGACCACGGCTACATTTCCCGTGAGTTCCACCGCCGCTACCGCC<br>TGCCGTCCAACGTGGACCAGTCGGCCCTCTCTTGCTCCCTGTCTGCCGATGGCATGCTGACCTTCTGTGGCCCCAAGATCCAGAC<br>TGGCCTGGATGCCACCCACGCCGAGCGAGCCATCCCCGTGTCGCGGGAGGAGAAGCCCACCTCGGCTCCCTCGTCCTAAGCAGGC |

TABLE 4C-continued

| SEQ ID NO | GENE NAME | SEQUENCE |
|---|---|---|
| | | ATTGCCTCGGCTGGCTCCCCTGCAGCCCTGGCCCATCATGGGGGGAGCACCCTGAGGGCGGGGTGTCTGTCTTCCTTTGCTTCCC<br>TTTTTTCCTTTCCACCTTCTCACATGGAATGAGGGTTTGAGAGAGCAGCCAGGAGAGCTTAGGGTCTCAGGGTGTCCCAGACCCC<br>GACACCGGCCAGTGGCGGAAGTGACCGCACCTCACACTCCTTTAGATAGCAGCCTGGCTCCCCTGGGGTGCAGGCGCCTCAACTC<br>TGCTGAGGGTCCAGAAGGAGGGGGTGACCTCCGGCCAGGTGCCTCCTGACACACCTGCAGCCTCCCTCCGCGGCGGGCCCTGCCC<br>ACACCTCCTGGGGCGCGTGAGGCCCGTGGGGCCGGGGCTTCTGTGCACCTGGGCTCTCGCGGCCTCTTCTCTCAGACCGTCTTCC<br>TCCAACCCCTCTATGTAGTGCCGCTCTTGGGGACATGGGTCGCCCATGAGAGCGCAGCCCGCGGCAATCAATAAACAGCAGGTGA<br>TACAAGCAACCCGCCGTCTGCTGGTGCTGTCTCCATCAGGGGCGCGAGGGGCAGGAGGGCGGCGCCGGGAGGGAGGACAGCGGGG<br>TCTCCTGCTCGCGTTGGACCCGGTGGCCTCGGAACGATGG |
| 229 | chr21:<br>43545000-<br>43546000 | TTTTTGTGTTTTTAGTAGAGATGGGATTTCACCATGTTGGCCAGGCTGGTCTCAAACTCCTGGCCTCATGCAATCCTCCTGCCTC<br>AGTAGTAGTAGTTGGGATTACAGGTGTGAGCTGCCATGCCCAGCTGCAGGTGCGGAAGCTGGGGGCCTCAGAGACTGTGGACTCC<br>TGGCCGGTGAGGAGCGGCATGGGCCGGGAGAGCTGACTCTTCAGCGGGACTGAGGTGGCTGGAGCGTGACCCTTTCCTGAGGGCA<br>AACAGGGAGGGCCTTGGAGCCCGGCGCTCAGGACAGGCCCCTGCTGGCCCGGCAGCCTGAGCTTCCACACTTTTCCAGGGCGTCT<br>CGAGTTCGCCCACAGAGCTGTTGTTTCAGGATAAAAAATGCCCTTGTATTCCACGTTCCAGTTCAGAGGCCCGTCTGTTCCCAAG<br>AGCGGAGGCGTCAGCCGCATGAGTCCCACCGGAAGCCGGGTTGCCGGGTCCCCGTCCCTGCCCTGCAGACGACGCATTCCGGAGC<br>CCCCTGTGGGCGTGTGCCTGGGGCCCGAGCTCAGGAGCAAGGCCTGCGTGGACCTGTTGTCTGAAACAAGCCAGTAGACAGCTGC<br>GTCAATGCAGGCAAGCTGAACAGGGCTGCTTTTTCAGCCTGACAACCCCAGGGGCTGAACAGGAGCTGGGGGAGGAGCAAGGGGC<br>CGTTCCCCTGCCCCACAGCACAGCACACGACCCCGCCTTGGAACCTGGGGCCCGGGGTGAATCGAGGGTCCTGGAGCAAGAGGGG<br>CTGCTCCACAGGAGAGCCTGTCCCGCCACCCCTCAGCCACCAGATTCGGGGCTGCTGGACTTGTTCTCAAACCTGCACAGTGAGT<br>GACAGCTGCTGAGACGGAGGTCTCAGGCAGTGCAGGTGAATCAGCAT |
| 230 | chr21:<br>43606000-<br>43606500 | TCCTTATTTTTTAGTTCTCAAGCCCTGTAGGGTGTTTTCGGTCGCAGTTGTTTGGGCTGTGGTCCTGACCCTCCTGAGTTCCAGT<br>GGCTCTGTTCAGGAGAGCTGCCTGGGGCCGGGACTTCTGAAACACACACTGAGCCACAGGCCGGCCCGGCGGCTTGGGTTCACCG<br>CCGCCTCTTTGTGTGTGATGTCCTGGGATAGGCCCGTGCACGTTCAGATGACACTGTACATATAAATAACTTGTAGCCGAGAACA<br>GGATGGGGCGGGGAGGAGGGGAGGGCAGAACGTACCACAGCAGCAGAAGTCACTGTGGATGCCTTCGTAAGTTGCATGGAAGGTT<br>TTTAAACCTAGCCCTGCCGAGCAGCCCTCTCCTGGTCCGGGAGAACGATGGGGAGAGAGCTGGCGTTCAGCTTTCATCACTGGAG<br>CCGTTCCTTCTTCCGGCCCCCCGAGGGCCTGTCCATGATCACACTTTGTCTTGTTTCGGGGGTGGCCCCTGTGAC |
| 231 | chr21:<br>43643000-<br>43644300 | CAAGCCTGTGGTAGGGACCAGGTCAGAGTAAACAGGAAGACAGCTTTCGGCCAGGCGGTGCACCTCGGTGCCGGTGAGTGTGAGC<br>GTGTGTGCGTGTGCACGTGTGCAGATGTGTGTGGACGCTCCCTTCTCCGCAGCAGCTCCTGACCCCCTGCAGGTGACCCTCAGCC<br>AGCCCCAGGGCTGCCCCCACTCTCCCCTGTGGACACCTACCTCATTTGGGGTGAAGTGGGGGGACTGGGGTGTGAGGGGTGCTTT<br>GGGGGGCACACTTCGACCCCTCTCTCTGCAGGCCAAGTCCTGAGGCTCAGTTTCCTCCTCTGTGCCCCGGCGACGTGGTGCAGGC<br>CTCGCGAGTGACGTGAGGGTTCATGACCCAGGTGTGGGCAGCCAGCCCTTCACGGGAGGCCACCCACCTGGCCACAGTGCCTGGG<br>AATTTAGGTCGGGCACTGCCGATATGTCGCCTTCCACAAGGCGGGCCCGGGCCTCTGCTGACCGTGCACCGGTCCTGGGGCTGGG<br>TAATTCTGCAGCAGCAGCGCAGCCCATGCCGGGGAATTTGCGGGCAGAGGAGACAGTGAGGCCCGCGTTCTGTGCGGGAACTCCC<br>GAGCTCACAGAGCCCAAGACCACACGGCTGCATCTGCTTGGCTGACTGGGCCAGGCCCACGCGTAGTAACCCGGACGTCTCTCTC<br>TCACAGTCCCCTTGCGTCTGGCCAGGGAGCTGCCAGGCTGCACCCCGCGGTGGGGATCGGGAGAGGGGCAGTGTCGCCCATCCCC<br>GGAAGGCTGAGCCTGGTGCAGCCAGGGAGTGAGGGGGCGGGAAGCCGGGGTGCTGCCCTGAGGGTGCCCCGACACGCTCTCCTGG<br>GGCCCTGAGCGGCTGCCACGTGCGTCCAGGGTTCTGGCCACAGGGTGGGCAGGGGCCCTGTGCTCCTCACTGGAGGCCCCTGAGG<br>CTCTGGAACTGAGACCATCCACCCGCCGGCCCCCTCTCGCCGGCTCCGGCACCCCTGCCTACTGTGACTTCCTGCCCCGGACTCG<br>CTCTGCCAGCTTGGGGCAAACCACTTCCCTCTGGGGTTTTCACTTCCCTCTTTCCCAAGTGGGGAAAGACCACCTGTCCCCGACC<br>CAGAAAGGGCCCCTGCCCGAGGGCAGCAGCAGTGCCAGGCTGGCATGTGAGGCTTGGGGCAGGCCCGGCCCCCAGAGGCACAGGG<br>CGATGCTCTGTGGGACGCTGTGTCGTTTCTAAGTACAAGGTCAGGAGAGGAGCCCCCTGACCCCGGAGGGGAGGAGAGGCAGGGC<br>AGGAAACCGCCACCATCTCAGCCCA |
| 232 | C21orf125 | GCCCACTGTGGGTGTGCCCGTGTGTGTGGCTGTGAGGCGTGAGTGCAGGCGTGAAGTGTCTGGGAGTGGGAGCGGGCATGAGTGT<br>GTGCCACGGGCCTGCTGTTGGGTCCTTGGAGGCCACGGTTGCCCCTGAAGGGACTGCAAGCTCTTTTTTGATTTGTAGTTATTTG<br>AGAAGTCTATACAGGAAGAAAATTAAACCG |
| 233 | C21orf125 | AGCGCCCAGCGCAGGGCCGGGACCCAGAGTGGACTCTACCGTGGGGCTGCCTCAAAGAAATCTCAGCAAACACAGGAAGCCAGCC<br>CACCCGTGCAGCCATGGGGCCAGGAAGCCCGCCCTTTACCAAGTCATTTGGGCATTTTTTCTCTGTGCTAACAGCCCAGATGGAG<br>CCATAGCCTCAACCTCTGTGTTCTGATAACACCAAGCTGGGACGCCGGAGCCATGCAGGGGACAGTGCCCGGCCTGAGGCTGCAG<br>CCTGGGTCTGGATGCCTTTCTAATTCAGGGCCTCCTCATGGCCTGGTTCCATAAATGGTCAAATGCAGCCTGACAGCGCAGCCTC<br>CTATCAGCGCTGGGCTCCGTACCGCCACACAGCCCACATACCCCGTTCCCCAGGAGACGCCCGCAGGTGGGCAGCGTCACTCCCA<br>CCCGCCGAGCACACGCTGTCCCCGTCTCGTGTCCCGAGGAGCCGGAAGCAGCTGCTTCCTCCCAGCCTGAAAGCTGCACCTCGGG<br>CTGCACTCGGCTCCCCGAACCCGCCCTCCGCTGCCCTGCAATTCGCCAAGGGAGCTACCCTTCCCATATAAAAATTTCACCTCCA<br>TTTCCTTGTAGAGAAGAAACATTTCTGACAGCAAGGAAGATTCTAATTTGAAAAGCAAGTGATTCATCTCCCGGTGCCAAACAGC<br>AGACGCAGGCGTTACCAGTCTGGGTGGGGCGCCCGAGCTGGGGACCTGGGGTCCTCTGGGAGGGGCAAGAAGGCAGCGATGCTGG<br>CCCCCGCCTCCATCTGCCCATCCCATCTGCTTCCACACACCGCCCTGCCGTAGCTGCTTGCAGCCCTTCTCTGTCAGTTTCTCCA<br>TCTTTTGGTTTGGTGATAAATGAGAGTTCCCATCGGGTGTGCCACCCTCTGTGTGACGGGGAGCAGAGAAGACCCTGCGTCCAAG<br>TCCTCCTGGGGGAAGAGCGAAGATGCTGGGACCAGCCCCAGCTGTCAGGGGGTCTCCAATCCCAG |
| 234 | HSF2BP | GGAACGGAGAGCCGCCAGGCCCAAACCTCCCAGAATTTGCGCAGTATTCTCGGCCTAGAGAGCGAGGAGTGGCCTTGGCGAGGTC<br>CCTCTTTGGCTCTTCTGGCTTAGCCGGGGTTTTAAACTTGTTATCTGCAAAGCAGAAGGAAAGTCAGCCCCTGATGTAAGTGTCA<br>AGTAAAATAAATCGGATGGGTCCTTTCCTGTTTGGCGAGGAATGCTACACTAAGGGGGACTGCGTTCAAATGGGCAGTCTTTGCT<br>GGAAACCTCGCCTCCGCGCGCCTTCCCTCGCTCGGATTCAGGCGCTTTTACGTTAAGGGTTGAATTTTTGTGTCAACAGGCACCT<br>CGGGAGGTCGCCTAGACAACTGAGCGGAGCAACTGAGATAACCCCCGCTACGTGTGGAGTGACCTAGTCCATTAACTTGCCCCAG<br>CACGCCCGCTGAGTCCGCAAAATATAGGATGGCCTCGGGTTTTAGATGAACCCAAAGCTAAGATTTCTTCCCTCTCTGGAATTAG<br>CAAGCAGCCCGCCCTGCCCAACTCCCCTGGAAGCGCGCGTGCTCGCCAGGCCTCGGGACGCCTGCGCGGGCGCCCTTGCACTGGC<br>ACCAGGGCTCCGGGGTAGGGGCGCACCGATCTGCCCAAGCCTCTGCAGGCACTGGAGGAAGGCGAGCCCTCCACCCGCTCAACAG<br>GCCCCAGTGCCGGCCTTTCCTTCCAGTCTCAACTCCACCCGGGGGCCCGGGGGCTCCACAGTTAAAAACTCCACGCCACGGAGAT<br>CGCAGGTAAGCTGCTGGCTCAACGAGGTGTGCTAAATGGGATTAAAGATCCTGGACCGTGGCCAGGCGCGGCGGCTCAAGCCTGT<br>AATCCCAGCGATCAGGGAGGCCGCCGCGGGAGGATTGCTTGAGCCCAGGAGTTTGAGACCAGCTTGGGCAACATAGCGAGACACC<br>GTCTCTACAAAAAAATAACAAATAGTGGGGCGTGATGGCGCGCGCCTGTAGTCTCAGCTACTTGGGCGGTCGAGATGGGAGGATC<br>GATCGAGTCTGGGAGGTCGAGGCTGCAGTGAGCCAGGATCACCGCCAAGATCGCGCCACTGCATTCCAGCCTGGGCGACAGAGGG<br>AGACCCTGTCTCAAAAACAAACAAAAAATCCTAGACCGTTTACAAACAGCCTTCCGTCTCTTCCTGGTCAAGTCCTAACCCTGGC |

TABLE 4C-continued

| SEQ ID NO | GENE NAME | SEQUENCE |
|---|---|---|
| | | TAACCTCGCCGTCTACAGCCTGAATTTTGGCAACCGAAAGGCAGCGCCGGCGCCACGTGCACACGGGCTGGGCCGCTCCGCCAGC<br>TGCCAGGGCCACTGCCGCGCTCACT |
| 235 | AGPAT3 | CGCACACACAGCACAGACGCCTGCATCTTCCCATGCGTGGTTTCTGCTCTTGCCTCTCTGGGTTTTTGTTTCACTTCGGTCGAGT<br>TTTTGGTGGTGTTGAGCGGATAGCCGGGGAAGTTGGAGTCTTGTTTGTGGCCGCCTCGTGCTCGTGTCTGTATCTAAGATCCTCA<br>GGCTGCTCCTTTTTGGGTAAGGTCTGTTGCTTCTCTAGGAACAGTGACGGTGGCAGAGCCCGTGGCCCCTCTCTCCTGTCCCAGA<br>GCCAAGCTGTTTCCTCTCCCCACTCCCGGGCACCCTGCGGGCAAG |
| 236 | chr21:<br>44446500-<br>44447500 | CACAGCCCAGCTTCAAGCCTGGCCGACCAGGGGTTTGGCATGAAGACCCCGGCAGGGCTGGGGCTGTGCTGGAATCCACCCGGAA<br>GTTTCCTGCCCCTTGGGCTGCCCACCAGGTCCCCTTTCTGCTCTGATCAAGCTGGACAAAACGTCGTGGGGCCACAGCACAGGGG<br>GCCAACGCAAGCTGGGATCGTCAGACGTTAGGAAATCCCAAGGAAGAAGAGAAAGGGGACACATTCGGGAGACGTCGGCACACGC<br>TCGAAGCAGCGGACAGGCACCTCTCTGTGGACAAGGCAGACTGGGCGGCCGAGATTCCGCATAGATGCCTGCTTCCTCCACGACC<br>TCCACGTGTGGCTGGCCCAGTCCGGGTCCCCCTCACCTCCTCTGTCTGTCTTGGTGGCCTCACGCCGTGGGCTGTGATGCCGGCT<br>ACGCTGCTTGGGTGGCCAAGGGTCTGAGCTGCAAGACGCCCAGCCTGGGTCTCTCCCGAGCTCTCCCACGTCCTGTCTGCTCCTC<br>CTCCGAGCTCCCGGTTGACTCTCACGACTGCACCAGCCTCTCCCCCAGGAAGGCGTGGAAACAACCTCCTTCTCCCAGGCCCGCT<br>CTGCCTCCTGCGTTTCAAGGCAAATCCGTTCCTCCAGGAGATGATGCAACCACATCCTGTTGGAGCCCAGAGAAGTGCGGATGCA<br>GCCCGGGGCTCTTTCTTTCCTAGAACCCTGCCTGGGAGTGGCTTCCCTGAACTAAGGACAGAGACTTTGTCTTCGTTGCCTCTCG<br>GCCTGTGGGCACTGAGCATACAGTAGGTGCTCAGTAAATGCTTGCAGGCCGATGCCCAGAGCCATTAGCCCTCATCATGGTGAGC<br>TCGGCAGCCGGTGTTGGGGCTGGGCTGGGCCTAGGTGTGCGTGGGGGCGGTGCTGGTCTGCTTTGCTGGGAGCCATGGACACCGG<br>AGGAACAGGGCCCCATCAGTGCGGTCAGAGTGCAAACTCGGAGCGTCCTTCTCTGGAAAACGAAT |
| 237 | TRPM2 | GGGAGGGGGCGTGGCCAGCAGGCAGCTGGGTGGGGCTGAGCCAGGGCGATCCGACCCCGAACCGGAGCTTTTAGCACTTTGAGTC<br>CCTGTACTCAGAGGTCTCCTGCAGCCGGGAATCCCACTGTGCTGTGGTCCCTGGCAGCCAGCACCCACCCCCAGCTTCTCCGTCA<br>AGGTTGAGGACGGAGCACTCCTGCCTCTGATTAACTGGACGCAGGAGAAGCAGTTGCTTTAATCCGGAGCCTTGAGTTGGGACAG<br>ATAATGAGTCATTCAACCAGATTTTCCAAGGACACACTAACTTTGGTATGATGCGTGTGTGCCCCTGAATCCACGTGGTCAGGAA<br>AGCCCAGGGAACACTGGCCTGTGACTCACTGAGCAGGTTCCCTTGTTACCCCGAGGGGTGATTTACTCCTCTGACAGTGACACGG<br>ACACTGTGCGTCCATTCCCCGGGCGGGCAGAGGACACTCCCAGATGCCCACGAGGGGCCCAGCAAGCACTGGCCA |
| 238 | C21orf29 | CTGCAGGACCTGCTCGTTCACAGATGTTCTCCTAGAAGCAGAAGCTGTTTCTTGTTGCAAACAAATTTGCTGTGTCCTGTCTTAG<br>GAGTCTCACCTGAATTTACCAAGGATGCATCTGTGCTTGGGGATGGCTCGGTTTGAGGGGTCTGAGGAGCGGCTCCCCTGGATCC<br>TTTCCTCCCCAGGAGCCCACCTGCCGAGCTGTCAGCGTCAGCCCCACATCTCAAGATGAGGAAATGGAGGTCGAAGCCATGCACA<br>CGCAGGCGTCCTGCTGACATGCAGGCCAGGCGGGTGCCTCTGTATTCAGCAGCCTCAGGGCTGTGGCCAGTTCAGGCAGCAGAGG<br>GGCCTCATCCCGGTGCTTCCCTGCAGGCAGTTGTGGGGCCGGCCTGCAGCAGGGGCTCAGACAGGGCCTTGGGAGAGGGAGGGAT<br>CACAGAGGTGTCCAGTGACAGGCAGGGCGGGCAGAGCCCATGGGGCCTTGGGCTCCTCACTCCTTCGGTCAGTCAGGGTGACATC<br>TGGAGCCACCTCCATTAATGGTGGGTTATGATTTGGTTCCCATGCAGCCCGTGCCAGCTCGCTGGGAGGAGGACGAGGACGCCTG<br>TGATC |
| 239 | C21orf29 | AAGAGGAAATTCCCACCTAATAAATTTTGGTCAGACCGGTTGATCTCAAAACCCTGTCTCCTGATAAGATGTTATCAATGACAAT<br>GGTGCCCGAAACTTCATTAGCAATTTTAATTTCGCCTTGGAGCTGTGGTCCTGTGATCTCGCCCTGCCTCCACTGGCCTTGTGAT<br>ATTCTATTACCCTGTTAAGTACTTGCTGTCTGTCACCCACACCTATTCGCACACTCCTTCCCCTTTTGAAACTCCCTAATAAAAA<br>CTTGCTGGTTTTTGCGGCTTGTGGGGCATCACAGATCCTACCAACGTGTGATGTCTCCCCCGGACGCCCAGCTTTAAAATTTCTC<br>TCTTTTGTACTCTGTCCCTTTATTTCTCAAGCCAGTCGATGCTTAGGAAAATAGAAAAGAACCTACGTGATTATCGGGGCAGGTC<br>CCCCGATAACCCCCAGCTGCAGATCGAGGCCTAGTGCGAGCACAGGTCCCCCCAGACCCTTCCCAGTGCCCACCAACCGGCGGCC<br>TAGGCCAGGTAGAACTGGCAGCGCCTCCCCTGCTGCAACACCAGGCTCTGGTAGAAACTTCAGAAAACATGCACCGGCAAAACCA<br>AGGAAGGGTGGCTGCGTCCCGGGTTCTTCCGCGCAGCTGTGTGTACACGCATGCACACACCCACACGCACACACCCACGTGCACA<br>CCCCCATGCACACGCACCCACTTGCACGCCCATGCACGCACACACGCGCGTGCACCCATGCGCACGCACCCATGCACACACACGC<br>GCGCACACACCCACGTGCGCACCCACATGTACACACCCACGTGCACACACCCACGCGTACACACCCACGCGCACACACCGCTGTC<br>CCCAGCCGTGCAGAACGATCCTCCCTGAGTCCCCGGCTCCGACCCACACGCAGCACTCGCTAAACGCTTCCCACGCAGTCGTTTT<br>GCTGGGTTGCGCTTCACCCACTTCTCAGAGGGGGCGGCCGAGGCAGAGGTGTCGGGGATCGAGCAGCTCCGGGCCTCAGGGGTCG<br>CCCCGCCACCGTTTTCCTTTCCCAGATGCTGGGACGGGGGCAGGGAGGGGCTCCCCAGGCTGAACCCGACTAGGTCACCCTAGAA<br>GCGAGGCGAGCTTCTCTTCTGTTTTTCTTCGGCGCCCCTGAGCCCCTGACAGTGCCCAAGCTGCCCATGGGATTGGATTCGCCAG<br>AGCCTCCTACGCAGACCCCACCCAGGGCCAAAGCCAACCCCAAGCCCCACCACCTTGGTGGTGTGGGATGAAAAGTGAGCCATCG<br>AGAGATGGGGTCCCCCCACCCCCAACCCCTCCAAGGACAAAGGCGGGCTGGGAAGCACCCGCTTTCACGTCCGCCCCTGCCCGGC<br>TTTCCTAGCGGAATTGGCGCCGGCATCAGTTGGGGGTTGTGGGATCAGTGAGGAATCCCGTGGGGTCGCCTCCATTTATCAGTTG<br>TGTGGGGTTGGGCGAGCACCCCTAGCCCCAGCCCAGGCGATCAGGGCGCGAAGCCCACTGGACGCGGATTTGGGATTAGGACGGG<br>GGTGACAGCCAGGAGGACCGCACCTGCCCTCCCCACTCCTGCCGCTCCACCCCTGCCCCCACCGCAACACCAAGGTCTCCACCAG<br>GAAGATGGGGGTGGGGAAAGGACGCGGGGTGGGGGGGGGTGCGGGGAGAGAGGACACAGGGTCGGAAGGGTGAGGGGTAGTGGCA<br>GAGGCGGAGGCCGAGGCCACGCAGCTGCGGGGCGCAGGGAGGGGCAGAGGAGGGGGCGTTCAGATGGGAACCTAGTCCAGACCCGT<br>CGGGGCCCTCGTGTGCGGCTCGTTATCCTGGAACCAGAGAGGCTGGAGACCCTTGGCTTGTCTGGAGCGGAACCGTAGTGTCCAA<br>TAGAGTGTGTGGGGCTCAGCCCTAAAGCTAAACATTCTTTATTTCCTGATGACCATGGGGGCGGAGCGGGGGAAAAGCCCTGGCC<br>TTATAGTTTAGAATTTTATAAAAGGAAAGGCGTGGCCACTGACAATTTGCGCTTCAGGAGTCCCAGAGTGACCGCCTGGCTCGGA<br>GCAGGGAATGAGGGGGTCCTTAACTCTGAGATTTGTTTTCTGAGAGACAAAGGTGATGGGTGAGGCGGCTAAGCCTCTGATTCTC<br>TATAGGTGGCGGTCATTCATTTCAGAACATGAATGGATTCAGTAAATAAACATGATAGAAAAATGCCACAAGCCCTAGGCCCATT<br>GGAGTGGACTGGACAGTCTGTTCCCAGTGTGTCCCTCAGCCTCGGTCCCCCACCCTTCCCGGAGCCCTGGGGGTCACACACATCC<br>CTCCTGGCTGCCTAGCCTGTGCCCCCCGATTCCCCCCCTCCCCGCCCCGCGCGTGCACACACACACACACACACACACACACACA<br>CACACACACCACACAGCACGAGGCGACAGAGATATGAGAGAGAGCGAGCGAGAGAGGACGGGAGAGAGAGGGAGTGCAAGTGTGC<br>GCTGGGGGTAACCCGTGCATGCATGCATTGGGGGTAACAGGCTGGAGCTCAGATCCCTCCCCCAGCCCCCAGCAGGGGGGACTGC<br>AGGCTCCTGGTCTGAGTGGGGAGCTGGGCCCCCTGGACAGAGGACTGGGCTGCGGGGTCAGGAATGGGCACACTTCCTAACTGCA<br>GGACACTCTAAGGGCTTTGGTCATGCACACGCAGCCAAGAGAAGGTGTCGCTGGCACACAGCCTTCCAGGAGCGGACTTGGAGAC<br>CTCGCCAAGGACCAGGACTCCCCAGCACTCACACTCCCTTAGGCGCTGAAGTCCAGAGGACAGAGGTTGAGGGCAGAGCTCCTGG<br>GAGCACCAGTGGAAGTAGGAGGGCTGGGCTGGAAAACCTCCCCCAACCTCCTATTGCAAAGAGGCTCCAGCCAGCAGCCTCCACA<br>CCCCAGTGATCTTTTAAGATGCAAATCTGCGCCATCATTTATTTCCTCAGTGCCTTCTCCAGCTCCTGGGATGCACACTGCCCGT<br>CCCCAGGCCCAGAGACCTGACCACCCTCATTCCTCCCTCAGCCCACCCTGGGGTCTCTCCACCAGCTGACAGCCTTCCTGCAGTC<br>CCCTCCCCGAATGCTGCTCCCTGAGGCCCTCCTGGACACCTGCAGGGCAGGCACAGCCCGCGGGACCTCACAGCACTTGCTCCGG<br>GCAGAGCTGCAGTTTGGCCAAGTTGCCAGCTCCGTGTGGGCAGGGGCCCTGGCCTGTGGCTGCCACATCCCGGGTGGGGGCACGG<br>CCTTTCCTGGCGTGGATGCTGAGCAAACGTAGGGGGAAGGGGAGTGAATGAGGAGAGCCAGGTAGCTCAGGGGCTGAGGCCTCAC |

TABLE 4C-continued

| SEQ ID NO | GENE NAME | SEQUENCE |
|---|---|---|
| | | TGAGCAGGGTCCCGCGTGACCGGTCCCCACCGCTGACGGTTCCTGGGGTAACACTCAGGACAGGGAGAGGCAATGGAAAGAGACG<br>TGGCCGCCCTCGCATCCTGCAGCTCCCGCACTCCCAGCCTCCCAGCCTCCCACCCAGCCCCCCAGAGCCCACCAGTGACCCCGCC<br>CACTGGGTCCTCAGATGGCTCCCACGGGATCTCCTGCCTTGATCTCCTGTCCACATGGAGGTGAAGTGGGTTGCTCTGAATGAGG<br>GGTGCCGAGCCTAGGGCGCAGCCCACTCTCCTGGGTCCGCAGCATCACGCAGCCCGGACCACAGGCTCCTTACAAGAATCGGAAG<br>GGTCCCTGCAATCGCCCTTCGCACTGAGGCTTCCTACTGTGTGGTGTAAAAACACAGGCTTGTCCTCCCTTGCTGCCCACGGGGC<br>TGGAGCCGCCTGAAAATCCCAGCCCACAACTTCCCCAAAGCCTGGCAGTCACTTGAATAGCCAAATGAGTCCTAGAAAGCGAGAG<br>ACGAGAGGGGAATGAGCGCCGAAAATCAAAGCAGGTTCCCCTCCTGACAACTCCAGAGAAGGCGCATGGGCCCCGTGGCAGACCC<br>GAACCCCCAGCCTCGCGACCGCCTGTGACCTGCGGGTCAACCACCCGCCGCGGCTCCACGCCGTGGGCACAGACTCAGGGAGCAG<br>GATGAGAAAGCTGAGACGGCGCAGCCACGGCCCGGTGCCTTCACGCGCACAGCGACACAGCCCCAGCCAGCGGGGCCCACGCTAA<br>GGCGGAATCCCACAGAAGCCTACAGAGCGAGCGCGCGCCTGTGCTTCCCAAAACGGAATGGAACCAAGGTGACTTCTACAGAACG<br>ATCTGAAGCCCTGGCTGGCCCTTATGCTAGTCTCTTGGGAGCGTTCCAAATGCAGCTCAATATTACTTACTTGACTTTTATCTTT<br>CCTCCCTGGTTCGTGGTATTTATAACTGGGTCATCTTTTAACTATTTGCAACGTAGCTTCAGGGGAGAGGGGGAGGGCTTTATAA<br>ATAACCTGTATTATTATTATGCAGGTTGATTCTGTTCCCTGAGCTAAAGGGAACATGAAAATACATGTCTGTGACTCATGCCCCC<br>CCACCCCCACTCCAGGGTGTGCTGAGGAGTCTCTCAGCTGCCCCGGGGTCCTCGAGCAGGGGAGGGAGAAAGGCTGGCGCTGCGC<br>CCTCCATCGCGTGAAGCCAGGGGATTTTGCTCTGCGACAAGCTGACTTGGCTCTCGTATTGTTTGCAGAATCACCCAGTTCCAAG<br>GCAGTCCCTGCGGGCAGGTGCAGCTGTGCGGGAGCTTCAGTCCTGTCCCCAACACCCAGGCAGTAATGGTTCCAGCACGGAAGGT<br>CTACCTACCTCCCACTGCACAGCCCGAGGGCTGTCCTGGAGGCACAGCCATCCGTCCCTGGGTGGGCAGGCACGTTTATGACCCC<br>CACCCCCACCCCCACCCCCCACGCGAGTCAGCACGTTCCATACTCGGGTGATCGTGCTCATCCCCTGGTCATGTCATCGGGATCT<br>GAGTGCCATCCGAGCAGAGAGCTGTGGCCCGGTGCCGGGGGTGGACTTCATCTATTCCAGGGAACCAAGGATGCATGATTTGCAA<br>ACAAAACCAGAAGCGCAAGCCATCTCCTCGCCTCCCCTGATAGCCGTGCTGCGGAGCCTGAGTGCTGGAG |
| 240 | ITGB2 | CAGGAACCACGGGACCTGCTGCCTAGCGGCCCTGTTCCACCCTTGGCCGCTCGCAAAATGTTTAGGCTTCATAAGGTTTGCCCAG<br>GGTCACAAATTTAACTCACAGCAAACAATGAAATCAGCGCATGATTTTCGAGCCCTCGTGGTCACCCTCCCTTCCTCCTGCCCTT<br>TCCTGCATGGGCAGCAGCAGGGTGAGGAGCTGCTCTCCCCAGGCCCAGGCTGGAGTCCCTCAGACGACCTGCCGGCCAGGGTACC<br>CCCCTGCCCCCACACAGCGCCTGACAGAGCCCCCCACACTGGGGGAACGTGGGGACCCAAGCAGGGGCAGCGGCCTCACCGGGCA<br>GGCGGCGACCTGCATCATGGCGTCCAGCCCACCCTCGGGTGCATCCAGGTTTCCGGAAATCAGCTGCTTCCCGACCTCGGTCTGA<br>AACTGGTTGGAGTTGTTGGTCAGCTTCAGCACGTGCCTGAAGGCAAACGGGGGCTGGCACTCTTTCTCCTTGTTGGGGCATGGGT<br>TTCGCAGCTTATCAGGGTGCGTGTTCACGAACGGCAGCACGGTCTTGTCCACGAAGGACCCGAAGCCTGCAGGGCACATGGAGGG<br>GCTGG |
| 241 | ITGB2 | TGCGTTTAGTGTAAAAATATCAGGTGTGGCTGCACGGAGTGAAAAATCACAGGCTCCACGGAGCCGGGAGGCCTGCTGCCCTGCC<br>CTCTTGCTTTGATGAGGAAATGGCGACCGCAGAAGGAAATGTAGCAGCACCGGCAACCGGCATCCGTGGGGCCACGCCGGGCTGC<br>TTCCCAGGGCCCTCCAGCCAAGCAGCCACAGGAAAGAGTAGATGTTGATCCCAAGCTAGGACTGAGGAGTCCGTCCCTAAGAGCC<br>GAGGGAGTCAGGTGGGCGAAACTGGCCGCATGTCTGGGTACAACTGCTCAGGGTTTCTCATCTGCTGAATCACCAAGCTAGGTTC<br>TGAAGCCAGGCGTGAGTGAGCAGGACTGGAGCAGGATTCTGGGAACAATCTTTTCCCTCC |
| 242 | POFUT2 | GCTGGGGAACTGAAGGAAGGGCTGTGGAGCCTGAAGCCTGGGCCTGGCCTGTGCTGCGGCCGCACCGCTGGGTGATGCAGGAGCC<br>ACTCCACCTCCCTGGCACCCCAGCCTCATCCGGCAACCTGGGAGCGTGGGCCTCCTGCCCCTCCAGGGAGGCCCTGGCCGTGTCC<br>TCATGGGGCCCCTCCAGGTCCTTGTGGCTCCAGGTCGGGACAGTGGCTGTGAGATCTGACCCTCCCGTTCCCCCTCCACCAAGTA<br>GGAGAAACCCCGGAGCATGAGCCCTCGTCCTTCACCGTCCCGGGGACAGGGGGACCCCCAGATGCTGCACGGCTGACAGGCCAAC<br>GTGGCAGAAGCTCCAGCTTCACAGGAAGCCAGTGACCATGAGAGTCTGTAGCTGTAACGAAGCCACAGAGCTGTGGCTTTCTTTC<br>CCCTTCAGCTCTAGGAAAGGTTATCTGCCCTGCACAGATCTCCGGAGGCCTGGCTGGGCTCTGAGAGCATCAGACTGATTATCGT<br>AAGAAAATAATCTCTGCAGACACATTCCTTGCTAGAAGCAGGGGACAAAGCCCAGCTTCAAAGACAATTCCACACACGCCCTCCC<br>TGCCCTGCACAGCTGCCTGCCGGGTGGGAGCAGAGCCCTTGCAGCCGGGCTCAGGGGCCTGGGCAGGGACAGCGTGTGGCAGGGG<br>CACAGCTGAGACAGGAGCCTCAAAGCGACACCAACCCGACGTGAAGCTACAGTTGAGGAGACACAGCTGCCCCCATTCCCGGGCC<br>TCATCTCCACAGTGAGACGCTGGACTCTCTCCCTGACCCACCGTCTCTTAGAACCTCCCCTCCATCCGGAGCAGTTCGGCAGCCC<br>CAGGGCAGCCAGGGGAACCCTGCCGAGTGCCTCTGGGCCGCCACAGACCGCAGAGCCCGCGGGAGCCTTGCTCACACAGCCTCAG<br>GTCCACTGTGGTCTTGGGGGAAAGCCCTGTCCTGGGACAGGGGAGCCGGGGGTCCTGGCCCTGGACCACCATCTGGGGACCACGT<br>TGTCACGCCTGCAAAGCTCCCTGCCCCACCCCCATGTGCCGGCTGGTGTTGACACCTTTGTAGAGTGGGAACCTGCCTCCGACCC<br>CAGCCTGCAGCCACAGGGCAGGTTATAGACCAGGTGAGAGGGCGCCGCGCCCAGAACCAAGGAGCACAAGTCCGCAGTGCCCATG<br>AGATCCTCATGCTGGCCGGCGCAGGAGCCATCCTCGGCCTCTGCAGGTCCTCGTGGGAAACCGCGGGGGCACGTGGGGCGGCTGC<br>AGGGTCCGCAAAGCCGGCTGTTTGCGAAGGGCGCAGCTCCACCTGGAACAGCCGAGGCCGCCCACGCGCTTCCCGCGGGATCAGA<br>GCAGCCTCCACGGCTGTTGTCTCAGGCACCACGGGATGCCTTTCTTCGTTTCAATAGCTGTGGGAAAGCCTCAATCGGTCCTGAA<br>AGAACCCAGATGTGCAGCAATGACAAGGCCTTCTCTGAGACTCTAGAACCTTCTGCCATCTCAGACAGGAGGGAGCCGTGAGGCA<br>GGCGGGAGATTTGCAGTCAGCAAAGGACGGGCAGGTGGGGCAGCTGCACACCCAGGGCCCTCTCCACGGTCTTCCCGGGCCCACC<br>CCTCCCGCGGTCCTGGGTCATCCACCTGCTGGCCTCACTCTGCCCACGCGGCCAGGTCCCACCGGCCCCTGAGCTCAACAGACCA<br>AAGCTGGCCCGACCCCACCCCCAAGAAGAATGAAACAATTTTTTTTACCTCTTGCAGAAAAGTAAAAGATCATTTATTCATTCT<br>GTTTCTAGATAGCAAAACTAAGTGTCAAAAGCACCTTCTGCACACAGTCTGCACACACTGGCCGGTGGTCCTGTTCCCGCAAGGT<br>TGAGCTGTGTTCCAGAGACATGGGTCCTCCGGGTGATGAGGAGCCGCTGGAGGGCCCTGAGCTGCACGTGCTAATGATTAACGCC<br>CCGTCCGTGCTGGCCGGTTTCTCAAATGCCTCCTGACGATTGCGC |
| 243 | chr21: 45571500-45573700 | GGCCTGAGGAGTCAAACGGTGCAAACCCTGCCCCACTCTGTTTGGGAAGCACCTGCTGTGTGGCAGGCGCTGCGCTTGGTGCTGG<br>GGATAGACCATGGGGAAGAAACACACAGAACCTGCCCTGCTCTCAAGGAACAGGCCCTGGGGGCGGCCAGGGGCAGAGACCCAAG<br>GCAGACACCCACACAGTGGCGTAATGACAGTGCTTATGGTGGGGACCTGGCTGCACAGCAGGTCAGCAAGGGGATGTTCAGGTGA<br>CACTGGGGGCACGGAGACCCAGGGGAGAGTGGATTGACAGAGGGGACGCTGGGCAAATGTCCCGAGGCTGAGGTGGAGTTGCGGG<br>AAGGAGGAGGCTGCCGGGCAGAGGCGCAGAGAGCTTTGCAGGTGTTGGCAGAGACCAGCAGGCCCTGCGAGGCCTGGGGTGTGTC<br>CTCAGCTGGGAGGGCCATAGAAGGATCTGGGCTTGCAGATGCTGGTGCAGACTGGAGGCCTGGGGTGTGAGAGTCCAGGCGGGGC<br>TCCTGCCAACACCCAGGGGAGTGGGCCTGGGCCAGGTGGACCGGGAGCTGGCACGGTGGTCAGGTGCTTGGAGGCTGCGTGCCAC<br>GCTGGGGACCTGGAGGTGTGTGAGGAGGTGTCTGTTGCTCCTGGGGCTGCCGCCTGCAGGGCTGGGTGTGCAGCAGTGCGGGGCA<br>ATGAAGTGGGCGGGTTCTGGGATGGTGGACGTTCCCTTTGTTGGGAACGTGTTGGTGCCAAGCTGCCATTTGAGTTTGGCTCTGA<br>GGGGTCTGGGCAGGGGACACACAGGGAATCACACAGGATGGAGTGAGTTCCCAGGGACCCAGGGTGGCTTGGCCTGAGAACAGCT<br>CCCACTCCCAGATGTGTGGGAAGCCCTCGGCACCAAGCCTCAGCCTCTCCATCTGTGAAATGGAGACAACGTCACTGGACTTGCA<br>GGCTGTCCATGAGGGTGATGCGATCAGAAAGGGTGGAGTTCCTGAACGCCCCGGGGTCGGGGTCTCACAGCAGGAGCTTAGCTGG<br>TGTCGGCATCTCCTGGACCCGTCCTCAGCTCCGAGCGCCCAGTCCTGCCACCTGTGTCCAAGTCTGCACTGTGCCCACGAGGCCC<br>TCAAGGCCGCAGACAGCCCCACACTTCTCGGACGCCGCCCAGCACGGTCCTTGTGTGAGGTGGACACTCCTTCTGGACGCCGCC<br>CCAGCACGGTCCTTGTGTGAGGTGGACACTCCTTCTGGACGCCGCCCCAGTACGGTCCTTGTGTGAGGTGGACACTCCTTCTAGG |

TABLE 4C-continued

| SEQ ID NO | GENE NAME | SEQUENCE |
|---|---|---|
| | | GAAGGAGTAGTAACTCTTGGGTGGTCGGGTAGTTGCCATGGAAAGGGGCAGTAATGCCCAGGTATTGCCGTGGCAACCGTAAACT |
| | | GACATGGCGCACTGGAGGGCGTGCCTCATGGAAAGCTACCTGTGCCCCTGCCCTGTGTTAGCTAGGCCTCAATGTGGTCCAGTAT |
| | | CTGAGCACCGCCTCCTGCCTCAGATGTTCCCGTCTGTCACCCCATTACCAGGGCGGCACTTCGGGTCCTTTCCAGCCATCATTGT |
| | | CCTGGCATTGCCACAGTGGACACTGCCACACAGGCTTGTGTGCTTGCGCGTACCCAGGTCCTCACCTCTCTGGGATAAACCAGGC |
| | | ACGTGGCGGCCGCCCCATTTTCCACCCGCCAGCGGTGGAGGAGTTGCCCAGCCTTGCAGGAAAACAGCTCTCATGCCAGCAGCGG |
| | | AGCATCCTATTCAAGTTTTCTCAGGGCTGCCAGCACAAATGCTGCATGCCGGGCGGCTTCCTCAGCAGACCGTTGTTTCTCTGCG |
| | | TCCTGGAGGCTGGACGTCCCAGGTCCCCGTGTGGCAGGCCCGGTTCCTCCCGCAGCCTCTCCTTGGCTTGTGGGCGGCGTCTCCT |
| | | CCCTGGGTCCTCGCAGGGCCACCCCTCCGTGTGTCTGTGTCCTCCCTCCCCTTATAAGGACCCCAGGCAGACTGGATCAGGGCCT |
| | | GCCCTAAGGACTGAATTTTACCTTAATCACCTCTTTAAAAGCTGTCTCCAAATACAGTCACCTTCTGGGGTCCTGGCTGTTAGGG |
| | | CTTTGATGCATGGATTTGGGGGACACCGCTCAGCCCCTAACAGCCCCCATCCTCTGCCTGCCTTTACCATGGGGCTGAGCCCAGC |
| | | CCTGCAGGAGTCCCCTGGTTTGATGTCTGCTGTGGCCACGGCGACCCTCAGGCTGCTCCAGCCGCACTTGTGCTT |
| 244 | chr21: 45609000- 45610600 | GGGGAGTCTCCAGGGGCTGGGGCTGGAGCCGCATCAGAGAGGAAAGGGGTGTTTGAAAAAGGGGCAGGGCCTGGGACCCAGGAAA |
| | | CTGTTCTTCCAGAGACACCCGTGAAGCTGAGCTTTGCCTCTCAGGGAAGCTGTGACCCCACGGGTGCTGCCCAGAGAGATCGGGC |
| | | CAGGTGGAGCCAAGATGGACTGGAATTCCCCGACGGGGACAAGGGGCCGGACGAGGCTGACTTGCCCTGTCTGATGAATGGTCAG |
| | | GTTTGCTTTTTCTCCTGAAAACACGAGGCAGTGATCCCGGCCAGCTAATTCCAGCAGACTGGAGACGGGATGGTGGAGAATGAGG |
| | | CTGTGGGCGGGAAGAGCAGATGGGACTCGCCAGCATCCTCACGGCAGGGCCGCGCTATTGCCCTCCCTCCCCTCCTACTCTCTGG |
| | | GGTCCCAGGAGCCCCAGATACGCAATGCTGCCAGGCGATTTCTGGCGCCCCGCAGACCCCTGCCCCTGGAGTTGGGCCAGGTCCC |
| | | GGCTGGAGCAAAGGGGGCTCCTTCAAGCCCGCTCCTCCCTGTCAAACCCGAGGAGCCTGACAGGCGCAGCGTCACCAGCGTCACC |
| | | GGGCCATAGTGAGCGGCCAAGCCAGCGTCACCGGGCCATAGTGAGCGGCCAAGCCAGCGTCACCGGGCCATAGTGAGCCGCCAAG |
| | | CCAGCGTCACCGGGCCATAGTGAGCCGCCAAGCCAGTGTCACCGGGCCATAGTGAGCGGCCAAGCCTTGGTCTGCCAGAGCCGGC |
| | | CGCACCAGAAGGATTTCTGGGTCCCCAGTCCTGGAGGAGCACACGGTTTACACCAGGCCTTGGGAGGGGAAGAGGCAAGGCGTGG |
| | | GCCCAGCCCTCACTCCCCAGGAGAAACCCTGTTTGAGCGGCAGAGGAGACTGGAGAGACCCCAGGGCGGGGATCCCTGAGAGGAG |
| | | AGAAACCCGGAATTCATCCACGGAGGCGTTCACCCAGAGGAGACCCGGAGCTTCTCCAGGAGAGGCTGGATTGCTCCAACAGGGG |
| | | CCCTGAGGAGCTGATGGCAAGAGCGGAAGGCAGCTCTGACTCGTGCGTCTGACTCCAGGTGTGGCCGTTGGGGCTACAGTGGGAC |
| | | CAGCCTGTTGTCACTGAACCCACAAAGTGCCTCCGAGCGCGGGTGGAGAGAGGGGGACCTCCCACCGTCTGCTGGCCTTGAATCT |
| | | TGAATCTAATTCCCGTCTGTGCTTTGATGGGAGAGGCACTGGGAGCGGGCGGCTTTTTCAGTTCCTTTTATCTTGAATGGCCTTT |
| | | GGGGGATTTTCACAGATTCTGAGTTCAAAGCCCAGGGAGGTGTGGGAACGTGACATTCCTCACCGCATTCCTCACCGCATTCCTC |
| | | TGTAAACCAGGCGGTGTTGGCACCCATGAGCCTGTGTCTTCTATGACATCAGGAGTTTTATCCCTCACGTCAGAAATCAGGGTTC |
| | | CAGGCGCCTTGGTTTTTCTTGGCGCCAGCGGCTTGGCTATAGAAGAAAAACTGAAGGGGCCAGGTGCGGTGGCTCACACCTGTAA |
| | | TCCCAGCACTTTGGAAGGCCAAGGCGGGTGGATCACGAGGTCAGGGGTTCGAGACCAGCCAACATGGCAA |
| 245 | COL18A1 | GCTCCTCAGGGGGAGGTTCGGGGCCTTTGGTCTCTGGACTTGGGCAGCAGAAAGGAAACATCCCTGGGGGCCTGTGGTGACCCCC |
| | | ATCCTCCCCAGGGTGGTCTGGCAGGGGACACTGTTTTCCAAAGCAAAGCCAGAGCGCCAAGGGCTCTCGGGATTCACGAGATCCA |
| | | CATTTATCCCAAGTTAGAACAGCACATCTGTGCGTGCAAACTTCATTCTGACTTCGGCCGGCTGTCCTTCTTGCCCAAAGCACCG |
| | | TGAGGCCTCATCCCTGCATCCCTGTTGCTTCTTTCATGTGGGATGAGAACCCAGGAAGGGGCTGAGTGTGACTCCTCTGGTTTTT |
| | | AGAGAGCACTGCCCCCGCCCCGCCCCCTCCTGCTTCCCCACCTTTTCACAGTTGCCTGGCTGGGGCGTAAGTGAATTGACAGCAT |
| | | TTAGTTTGAGTGACTTTCGAGTTACTTTTTTTCTTTTTTTGAGACAGAGTCTCGCTCTGTCGCCCAGGGTGGACTGCAGTGGTGT |
| | | AATCTTGGCTCACTGCAACCTCTACCTCCCGGGTTCAAGCGATTCTCACATCTCAGCCTCTGGAGTAGCTGGAATTACAGGCGCC |
| | | CGCCACCACACCTGGCTAATTTTTGTGTTTTTAGTAGAGATGGGGTTTCACCATGTTGGCCAGGCTGGTCTCGAACTCCTGACCT |
| | | CAGGTGATCCGCCTGCCTTGGCCTCCCAAAGTGCTGGGATTACAGGTGTGAGCCACCGAGCCTGGCCTGGAGTTATTTTGGGAGA |
| | | GGGCAGCCCCTGGTTCAGCGTGGCGAGGCTGCGCTTGCTCTCCCGGGCGGCGTCCACACCCTCCTCGCCGAGATGGAGAAGCCC |
| | | AAACCCCTGCAGCGCTCCCCCATCACGTCCGGCCCTGGAAGCCCCCGGAAACCCTGCCACGCCCTGAGTGGGAGAGCGCAGGTCC |
| | | CTTTCCGGCCCTGGAAGCCCCAGAAACCCTTGGGTGCCAGGCCTGGCCGGGACAGCAGCGACACTGCATGCTCAGCCCTTGCGT |
| | | GAGACCACGGGAGTGTCCGCCCTCTGCACGTGCTGCTGATTGCCCACTTCGTCCAGCAGGTTTGGGAGCTTGTGGCTGCATCCTC |
| | | CTGCAGACACTTGCCCATTCTGGGGCCTCCTCTCTGTCTTTTCTCCTCTGTTGAGGGGTCTGGGAGGGAGGCCTTGGAGGGTACC |
| | | CATGCTGCTGGGACTGATGCTCCCCGCGGTGGAAGGAGCTGCCTCTTGAACAGCAGGGGGCTGAGCAGAGGGGAGGGGATGCGGG |
| | | GGTGCCGTGCACACAGGTGCTCTCAGGACGCAGGGGCTTCTCAGCCCTGCTGTCCCAGGGCTGCACTCCAGCAGGGCAGACTCCT |
| | | GAGGTGCAGACACCCCAGCTTCACGCTCACACTTCTGGAAGGCGATGTCTGTGCGTTTGCTTTCTGCTGCAGTTTAAAAAGCCGG |
| | | GCTCTCTCCGGAGCGTGTGTAGGGCCTGGTCACTGGAATATCTGGACTCAGTGTTAATGGCAGCCACGCTGGGGGCTGGGCCCAG |
| | | CTTTCTGTTCTCCGTGTGGGTGCCATATCCACCTCCATCGCAGCCCTTTCTCTCTCGACCTTTTAAATCACAGTGTCACCTCCCC |
| | | CTGCTGTCCTGCCAGTGGCCCCTGGAGGCTTCTCCCCACCCCTTTCTTCTGGGGCAATTCTTAAGGCTGGCATTGAATCAGGAGG |
| | | CCAGATGTGGCCCCTAGTAACTCACCAGCAGTCCCTGAGGCTTCTGGCTCCCCTGGCCCACCAGCCTCCCATGTCTGCCTCAGGC |
| | | CTCTTGACCCGCCTGGCACTGACCAGACTGTGTGCCCGGGTGCCGTGCCCATGGGCTCCGCCTCCCCCAGGCAGGCCCCCTCTTG |
| | | CTCCGCGGCCACCCCTGCTCTTGACCTCACACCTCTGCGGTGTGTCTGGACACACCAGCACCACGGCGGGCGGGGAGCGGAATTC |
| | | TCCAGGTGGGGTGGGCAGGCCGGCGGGTGTTGAGGTCTCTGTGCATGCTTGTGCGTACCCTGGACTTTGCCGTGAGGGGTGGCCA |
| | | GTGCTCTGGGTGCCTTTGCCAGACAACTGGTCTGCCGGGCCGAGCATTCATGCTGGTCGCCATCACGTGACTCCCATGCGCCCTG |
| | | GCCCTGGGGTTGGGTCTGCAGGACTGAGAACCAGCGGAAGGGGGGCGAGGCCTCGGGAATGCGCCGGCAACTGGCGATGAGCTCA |
| | | GGCCTGACTAATGAGCCCAGGTGACTCATACACCCGGGGCCTGGATGAGTCTGACTGGGTCAGGACTTCCCTGCTTGTTCTGTCC |
| | | TGGGAGATGTTGTCCCTGGCCCTGCAGAGCCGGGAGGACACGAGGCCTCCTGGGTCACAGCCAACGCAGCCTACTCCTGCCCACT |
| | | GCTCGCGCCGGCCAAGGCCCGTCGGCACCACCTCCTCCATGAAGCCTTCCTGACTGCCCCCATCCCTCTGTGGGCAGCTCGAGTG |
| | | TGCATCTTGAGTGCTGTGCAGGTTGGGGTCCGGCGCTCCTGCAGGCAGGCGGCGTCTGGGCCTGGGGGCTCTCAGAGTTTGAGGA |
| | | GCGTGTGGTGAGGGTGGCCTCGGGCCTCAAAGACGCAGCGCTGTGGGAACCGGGAGACTGGCTGAGCCCGCTCTGAGGAAGGTGG |
| | | GGCCAGGGGCACCCTCAGCTGACCCGGCGTGCAGGGGTGACCAGCCAGGCGTGGCCAAGGATGGGGTCTCTGGGATCAGGAGACT |
| | | TCAGTAGCAGCCAGGACCGAGGCCACCAGTTTCCACCCTGGCATTTTCCATCTTTTGAAGGACTGGAAACGATTGGATTCTTTAA |
| | | CTTTTTTAAGTTGAGGTGAAATTCACAACGCATAAAATTAACCATCTTAAAGCGAACAATTCGGTGACATTTAGTACAGCCAGAA |
| | | GGCTGTGCAGCCATCACCACTGCCCAACTCTAGAACATTCACACGCCGGAGAGAGGGAGCCCTGGGCCATCACGCAGCCACCGCC |
| | | CGGCCCCAAGAACCTGCGAGTCCACTTTCCACCTCTGGATCGGCGGTTCTGGACGTTCATGCAGGTGGTTCCCGCAGTGCGAGGC |
| | | CTTTTGTTTCGGGCTCCTCTCACAAGCCTCACGTTTCCAGGTACGTCGTGGTGTTGTGCAGACCCACAATTCATCCCTTTTCATG |
| | | GGTGTGTAATAGTCCACCATAGATTCTCTACGTTTTAAAGCATGTTTTATGTGCCTGAAATGTCTCTGCACTCGAGACTATAGCT |
| | | TGCTTTCTTTCTTTTCTTTTTTTTTTTTTAATTTGAGACGGAGTCTTGCTCTGTTTTCAGGCTGGAGTGCAGTGGTGCGATCTCG |
| | | GCTCACTATAACCTCTGCCTCCCAGGTTCAACTGATTCTTTTGCCTCAGCCTCCCGAGTAGCTGGGACTATAGGCGCGCCACCCC |
| | | ACCCGGCCAATTTTTTTGTATTTTTAGTAGAGATGGGGTTTCATCATGTTGGCCAGGATGGTCTCGATCTTCCGACCTTGTGATC |
| | | TGCCCGCCTCGGCCTCCCAAATTGTTGGGATTACAGGCGTGAGCCACCGCGCCCAGCCGAGACTACAGCTTTCTTTAACTGCATC |
| | | CCTGGAGGGATCTGAGAGTCTCTTTCCCTGTCTCCTTTCCTTGGAAAACATTTCAGCCAGGGCTCCCCAAGATGAAAGGCCAGA |
| | | GTCCCAGGCATGGGCGTTGCAGGTGCACAGTTGCCACGGGGAGCTGTGGGTGATGGTCGCTGTCAGCGATGGCTGCTGCAGGTCC |

TABLE 4C-continued

| SEQ ID NO | GENE NAME | SEQUENCE |
|---|---|---|
| | | CTGTGAGGAAGGGGCAGTGCCACAGCAGGAGGAGAGGGAGTCAGCGGACGTTGATTGGCAGTGCCCGCCCATTCCATCATTCAGT |
| | | CACCCACTGTGCACCCAGCACCCAGGCTCGGCTGCATAGAACATGGCCCAGGAAGGCTCCACTTCCTGTCTCCTCTTCTCCCCTC |
| | | TCCAGTCTCATGATGGGGCTGGAGGCATCTTCTAGTTTTGAGTTCTGAGCTAATGAACATGCTCATGAGCAGGCGGCAGGATCCC |
| | | AGGACGGTGGAGCTGGGAGCCTGACTGCGGGTGACGGACAGGCTCTGGCAGCCCCTGTCAGCATCCTCTCCAGGGCATGTGAAAG |
| | | CCAGTGTGTCCTCAGCTGCCAGTGCCCCCTCCCCACCTCCTCTGGGCCCATGTGCACGGGACCTGGGCTCCCCCAACCAAGCCTG |
| | | CCCGCCTTGGTTCAGCAGAACGGCTCCTGTCTCTACAGCGGTGCCAGGCCAGGAGTGCTGTGTCTGTGAAGCGGGGTCATGGTTT |
| | | TGGGGCCCTCATCTCCCTCGCGCCCTCTCATTGGGGACCCCCCGTCTCCCTAGCGCCCTCTCGTCCTCTCCTGCATGTGCTGTGT |
| | | CTGTGAAGCGGGGTCATGGTTTTGGGGCCCCCCGTCTCCCTAGCGTTCTCTCGCCCTCTCCAGCATGTGAAGTGGGGTCATGGTT |
| | | TGGGGGCCCCCATCTCCCTAGCGCCCTCTCGTTGGGGACCCCCCGTCTCCCTAGCGCCCTCTCGCCCTCGCCTGCATGTGCTGTG |
| | | TCCATGAAGTGGGGTCATGGTTTGGGGGCCCCCTATCTTTCTAGCACCCTCTCGCCCTCTCCTGTATGTGAAGTGGGGTCATGGT |
| | | TTGGGGGCCGCCATCTTTCTAGCGCCCTCTCGCCTTCTCCTGAGCGTGTGGAACTCTGTGGTGGTCAGAGCTAAGGTTCTGAATA |
| | | GGTCGAAGCACCTCCCCGGTGCCTCTCACCCTGAATGCTCTGGGAGGACACAGCCTTTTCATAGGCTACGACTGACATGGCAGGA |
| | | GGGGCCTGCCTGCCACCCGGGTCCTCTGCTGCCTGCTGCTTGCTGGGGAGGGGGCTCGAGACTGGGATCCTGGGCTTCTGCTCCA |
| | | GCTGTGCCCAAGGGAGCTGCTGAGGAGGGACCGGGTGGGGCATCCACTCTGGGCAGGTTCAGGGTCATTCTTGGTGACCCCGGGT |
| | | CCGGTTACAAAGGCTGATGGAGCGCGTGGGTGGCTGCCTAAGTCTCTGGAAGCCCAAGAATGTGGAGATGGCGCGTCTCGGCCCG |
| | | GGGTCTCGTGGCTGGTCTGGGAGAACTTGCCTTTATTTCTAGGCAGGAGGCTGCACTGCAAGGGAGCGTCAGTGGCCCGGCTGGC |
| | | TTTCCCCGGCCCTCAGCCCGCACTCGTCCACCAAAGCAAGCTCCTTTGTGGGGCTGCCCTGGGAAGCCGGGATCACGAGGCTCTG |
| | | CCGGCCGTGGTCACCCCATGAGGCAGGGTCAGCTCGGGAGCAAGGCGGATCAGATGGAACAGAACACGTAGACCACCTCGCCCGC |
| | | CCTTAGTCAGCTGGGCCATTGAAAATCAAGTCCGTAGAAAGACCTAGAAATAAGTCCCGGGGTGCCCTTGCCTGTTGACGGGCGG |
| | | GCCGAGCAGGACTGTTCTCAGGCAGGCACTGGTCTCTTGGCTTCCAGGTGGTTTGTTTGCTGGTTTGAGGCTGGGGGTGACGCTC |
| | | CTGTGCGGGAGGAGGTCGCATTCCATTCATAGCGGCTTATCTGGGCTGTCAGGCAGGCCTGGGAGGGAGCCTGCCTCTGTGCTCT |
| | | CCAAGGGTGGGCGACGGACAGACAGGGTGTCCCACCCCTTCTGGGCCAAGGACAGAGGGTCAGTGTTTGCAGAGACCTGGGGAGG |
| | | CCCAGGTGACCTCCACCGAGCACCTGCTGTGTGCAGGGCCAGTGCTGGCTGCAGAGACAGCGGAGCGTGTGTGGACCCGGCGGCC |
| | | CAGGGGAGGGGGGCAGGCAGGACCCGGCGGCCCAGGGGAGGGGGGCAGGCAGGACCCGGCGGCCCAGGGGAGGTGGGCAGGCAGG |
| | | ACCCGGCGGCCCAGGGGAGGGGGGCAGGCAGGACCCGGCGGCCCAGGGGAGGGGGCAGGCAGGACCCGGCGGCCCAGGGGAGGGG |
| | | GGCAGGCAGGACTCGGCGGCCCAGGGGAGGGGGGCAGGCAGGACCAGGCGGCCCTGGGGGTCAGGGGTGGAGGCCAGGCCTAGAC |
| | | GGCCCACAGGAGGGTGGACTCATTCTGACCGATTCCTGGAAGCCCCCGGAAAGTGGTGATGTTCTGGAGGGCCCAGCAGACCCCA |
| | | AGGCCCCCAAGACAATCCCAGCTGGCTCTCTGCGGCTCTCGGTGTCTGCCATTTGAGACAATTTGGGCACAGGCAGGGCAGGCCG |
| | | TCGCGGACGGTCTAAGCCGCGCGCATTGGTGGGGGCAGCAGAGCCCCTGCTCTCAGCTCCTCGGGGTACAGCGGGGGTACCAGGC |
| | | GGGTGAGTGGGTGGGTGGTCACTGCTCCTGCCAAGGGCAGCCCTGGTTTGGTTTGCACTTGCTGCCCTGGTGACGGCTGCTCTCA |
| | | TTCCTGCCCCATTGCTAACAAGGGTGTCATAAGCTACTTTCCCGGCCCACATCCTATTAAGCCCATGGAGACCCTCCCACAGCTG |
| | | AGCCTGCTGTGGGCTGCAGGCCCTGGGCGGTGCCCACCTCGGTCCCCACTGGCCTCCTTCCAGCACTTTAGAGCAGACACAGGTT |
| | | GGAGATAAGGAAAGTTCCAGAGCACAGACTGGAACAAGCCCCAGGCCTCTCCCTGCCCCAGCAGGGCCTCCCTGGATTTGGGGGA |
| | | CAGGTGCCCTCATGGGGGGTCCTGAAGGTCAGAGCTGGGGCTGGGGCTGGGCTGGCGGAGGTGGCCTTGGCGGAGGCCACATTCC |
| | | AGGGTCTCAGTGAGAGTCTGTGGCAGGCAGCCTTGCAGATGCCGCTGAGGGACCCCCCACTTCATGTTGTGGGTGATGTGGTCCA |
| | | TTGATTGCCTCCAGGTTTAAATCAGGTGGATATTTACCTAGCGGCCTCCTCTCCCTCTGCACAGGGCCTGGAGTGGGATGGACTG |
| | | GGGTGCTCAGCTGGAGGCTCTGCAGACACAGCCCCCTGGGCTATGCAGGCCCTGCTGGGAGCCACATTGCCATTTTTCATCACCC |
| | | ACTTTTTGGGTGAGAACCCCCTCGAGTCCTAACATCTGCCGCATCTCAGAGCCTGTGGCTCCAGTCAGAGCATCTGGACCATACT |
| | | GCTGGGGTCAGAGCGCGGCAGGACAATGGC |
| 246 | COL18A1 | TGCCACCACCATCTTCAGGTAGAGCTTCTCTCTCCTCCTTGCTGGGCGGGGCCCCTCCCTGGGGAAGCCTGCAGGACCCAGACAG |
| | | CCAAGGACTCTCGCCCGCCGCAGCCGCTCCCAGCCAGCAGCTCCAACGCCCTGACGTCCGCCTGCGCACGCCACTTCTGCACCCC |
| | | CTGGTGATGGGCTCCCTGGGCAAGCACGCGGCCCCCTCCGCCTTCTCCTCTGGGCTCCCGGGCGCACTGTCTCAGGTCGCAGTCA |
| | | CCACTTTAACCAGGGACAGCGGTGCTTGGGTCTCCCACGTGGCTAACTCTGTGGGGCCGGGTCTTGCTAATAACTCTGCCCTGCT |
| | | CGGGGCTGACCCCGAGGCCCCCGCCGGTCGCTGCCTGCCCCTGCCACCCTCCCTGCCAGTCTGCGGCCACCTGGGCATCTCACGC |
| | | TTCTGGCTGCCCAACCACCTCCACCACGAGAGCGGCGAGCAGGTGCGGGCCGGGGCACGGGCGTGGGGGGGCCTGCTGCAGACGC |
| | | ACTGCCACCCCTTCCTCGCCTGGTTCTTCTGCCTGCTGCTGGTCCCCCCATGCGGCAGCGTCCCGCCGCCCGCCCCGCCACCCTG |
| | | CTGCCAGTTCTGCGAGGCCCTGCAGGATGCGTGTTGGAGCCGCCTGGGCGGGGGCCGGCTGCCCGTCGCCTGTGCCTCGCTCCCG |
| | | ACCCAGGAGGATGGGTACTGTGTGCTCATTGGGCCGGCTGCAGGTAACTGGCCGGCCCCGATCTCCCCACCCTTTCCTTTTTGCC |
| | | TTGCCAGGTAAGTGTGGGCGGGGCTGACGTGAGCCTGGTACAGGTTCCCCCCACATCGAATCTCTACGTTCAGGGGCCCGTGGCC |
| | | CTCGGGAGGTGGGAGAGCTGGGAGTGAGGCCTCCTGTGTGGGGAGGAGGCCGGCGTCTGGACAGGAAGAGGGCTGGATGAACCGC |
| | | AGCCGATGTGTCCAGGTGCCACCTGGGCCTGGAGCTCCCTGAGCATTTTAGCGCATTTAGTCCTCAGCACGGTCCCGAGATACCC |
| | | TGCCATGCCCCGAGTCACAGAGGGGAAACTGAGGCGTGGGGCAGTGGCGTGACTCACCCCAGGGAGCCGAGATTCCCGCTCAGGT |
| | | GTGGCTGCATCGACCTTGCTCCGGTCACTAAGCTGCACGGTTCGATGCGCTTCCTGGGAGCCCCAGCGTGCTCGGGCCAAGGGTG |
| | | CTGCCGCGTGGGCAGTGCAGAGACCCTACCAGCGTGGGGACCAGGGAGGTCTGCAGGGCCCGTCCTGAGAGGGAGCCTTTCATGT |
| | | CCCCCTCCCCATCCTGAAGCACACAGCCTCCCTGCCACAGTGGGGGCCGCTTCTGGGCCCAGGGGACGTTGCCCCATCACCGTGT |
| | | GGCCTGGCCTTGTTGCTGGCTGGACAGTTGGGGGCAGGAAGAGGAGGGAAAGGGGGACTCTTTAACCTCCTGGGGGCAGGGGCAG |
| | | CCCAGAAAGGACCCCAGCAGATCCCTCCTCTGTGTCCGGGAGTAGACGGGGCCCC |
| 247 | COL18A1 | GGGCTCCACAGCGGCCTGTCTCCTCACAGGGTTCAGCCCAGTCTGCTCTCACTCATTTGCTGATTCATTCTTTCATTCAGCCAGT |
| | | CAATAGTCATGGCCCCTCCTGTGTGCCGGGTGGCCATGGATATTGCCCTGGGTAACACACAGCCTGGCCCTGTGGAGCAGACAGT |
| | | GGGGACAGCCATGTGGACAGGGTGCAGGTGGATGGCAATGGCAGCTGGGTCAGGAGGGGCTGAGGGCCGTGGGGAAAGGTGCAGA |
| | | ATCAATAGGGGCATCCGGACTGGGGTGCAGGCCTGGGGGCTGGGATTTCTAGGGTGGAGGTCACCTCTGAGGGAGACAGAGCAAG |
| | | GCCCTGGGAGATTAGAAGGTCGAAGGTCGCCGTGTTGAGGTCAGGGGCCCTGAATTGGAGCCGCGGCAAAGGAGAGGGCAGGTCA |
| | | GGGCACGTGGTGAGTGATTGCTGCGGCTTCTGAGCACGGCTGGGTCTGTGGGGCCTGAGCAGAGGTGACCCGCGATCCGGCGCCA |
| | | CGGCAGGCAGGACTCCCCACCCTTGCTGCTGCCTACACCCCCAGGGCAGCCCCAGAGTCGGGGGCGCAGCTCCCTGCTTGCCAGT |
| | | TCAGAGCCCAGCCCCTCTCACCCAGCCCAGAGGAGGACACAGATGGAGGAGGGGCACCCGGAGGGTCCCCCCGCCGACAGGCCCC |
| | | ACGTCTCCCACCTGCAGGACAATGAAGTGGCCGCCTTGCAGCCCCCCGTGGTGCAGCTGCACGACAGCAACCCCTACCCGCGGCG |
| | | GGAGCACCCCCACCCCACCGCGCGGCCCTGGCGGGCAGATGACATCCTGGCCAGCCCCCCTCGCCTGCCCGAGCCCCAGCCCTAC |
| | | CCCGGAGCCCCGCACCACAGCTCCTACGTGCACCTGCGGCCGGCGCGACCCACAAGCCCACCCGCCCACAGCCACCGCGACTTCC |
| | | AGCCGGTGGTGAGTGCCCCCCCAAAGTGGGCTTGGCTCCATCTAGCCCCTCGGCTCTCGGCAGCAGAAGAGGGCCCAGCCCCTGC |
| | | AGAGCTGCTGGGGGTCCCAGGCTTCGGCCATGGGTGGGGGTCTGGCGGCTCAGGGCCACTCAGGGCGGCTTGGCTGGCCCTGGGA |
| | | CTTGCCCTCTGGTGGCCAAGCAGTGGTCATGAAAGTCCAGCCGCTGTCACATCCTTGAGGAACCGGCGTACCTCCGCCTACAGCG |
| | | GCAGCTGGGGGCACCCACGTGGCCCGGGGCTGCTCTGACCTGGCAGCGTATGGGGGCTGCTGCCTGGGCCCCTCAGTGTGTCACT |
| | | TGCGCGCCTCCCGCTCAGCGCCCCTCGGCCGTGCCTGTCCACACAGGTGCGGGGCCGGGGTGGTGCGCCCGGGGCCTGGGTGCAG |
| | | GGGGCAGCGTGGGACACAGCCCGTGACGCGCCCCTCTCCCCGCAGCTCCACCTGGTTGCGCTCAACAGCCCCCTGTCAGGCGGCA |

TABLE 4C-continued

| SEQ ID NO | GENE NAME | SEQUENCE |
|---|---|---|
| | | TGCGGGGCATCCGCGGGGCCGACTTCCAGTGCTTCCAGCAGGCGCGGGCCGTGGGGCTGGCGGGCACCTTCCGCGCCTTCCTGTC<br>CTCGCGCCTGCAGGACCTGTACAGCATCGTGCGCCGTGCCGACCGCGCAGCCGTGCCCATCGTCAACCTCAAGGTGGGTCAGTCC<br>AGTCCTGAGGGCGCGGGCTCCTCGGCCCCCACTTGACCTCTGGGGTGAACTCCCAGCGGGGAGCTCCCCTCTAGGGCCTCTGGAG<br>GCCACCATGTTACAGACACTGGCGCCTAGGCTGGCGACTTCAGGGCAGGCTCCGGGTGGGTCACACCCCTCCAGGCTCAGGCCAG<br>GCCTCTGCATCCCTGGGCACTGCCACGTCCCCCAGGGCATCCCATGAGGCCCCCCGTGGCCCCCTGACCCCCCGCTCCCCCGGC<br>AGTGCCCCTCAGAGGGTCCCATGCTGCTGGACCAAGTGTCCACACAGGTGATAGGGCTCACATACAAGCCTGGAATCAGGAACCG<br>TCCTTTGGGCCTCTAGTGCCATGCGGGCTGGTGGCCCCTCTGCCA |
| 248 | chr21:<br>45885000-<br>45887000 | GCCTGGAGTGTAGTCCTGCTGAAGGCCAGAGACCACACACTCCACCCAGACTCCGGATCTCCCTCCCCAGCAGGGGGATGGAGGC<br>CCTGCCGCTGGGAGTGCTGGTGTTATGTGGAAGGGCTGGGCTTCTCCAGGGCTCCTGGGAGGCCTAAACATCTTGCAAGGTTTTG<br>ACGTTAATTACTATTATGATTGCTTTCTGTGTGTTACTGTTTTCCCCACACTTTAGCCAGCTAATGTGGAGCTACAGAAGGCCCT<br>CGCCCCTACCCCTCCAGATGTCCCAGCCCATGACAAGCAGGAAGGCCGGGTGCTGGGAGACTTCCTGGGGCTGGATCTGACATCA<br>TTCCAAGCAGATGATAACCTGCCTTCCCGATTTCCAAACCCACAGCAAGACACCCTGGAGTTATTTATAAATGCGAGCCCCTGGG<br>TGCACTTCTGACGGGACCAGCACCCTGACGGCCATGAGAGGGTGGAGACAGCGCACCCCGAGCTCAGGGAGGCAGGAAACTCTGG<br>ACCTGGAGGCCGGGCACCATGAGGGACACGCTGCAGGCCCAGCTGCTGCCGCCTGGGGCGGGGCTGCCCTGCAGGCTCCGGGAAA<br>ACCCAGAACCAGGCCGGATCAGCGTGTGTCAAGAGGCGGGGCGTGAGAGATGAGCTGCTTTTTTTCTTCACAGGGTTGGCAGGAA<br>CTGCAAATAATAGAAAGTCTTTAGGGTCTAACACGCTGCCCTGAAAACACTATCATTACTTTCCTAATGACTAACTGTGTCTTTC<br>AGCCGGCGGGGCAGGCAGCTGAGGCCGCAGGCTCCCGCAGAGGACCGGGGGAGGCTGGCAGCCTGTAATCTGGGGGCGCTGACAG<br>TGCTCTGCCCAGACCCTCGCGCCAGCTCCAGCTCCAGCACAGCAGCCCTGGGTCCCTCTGGCCCCCTGCCCGCAGAGTCCAGGTG<br>TGGCAGAGGCCGCCCAGTATCCCTTCTCCTCCTCCTTTTCTAAAAACAGAGTCTCACGATGTTTCCCATGCGGGTCTCCAACGCC<br>TGGGCTCAAGCGATCCTTCTGCCTCGGCCTCCCAAAGCGTTGGGATTAAGGGGCGAGCCACCGCGCCCGGCCCACCTTCCCTTCT<br>GGTTCATTTCCAGTAAGGTCCTGTCCACAGCGTCCTTCCCAGCATTCCCACCAGGCTGCAGGCCTTGGCCTCCCTCCCCTCCATT<br>CTCATTCTCCCCGAAACCGCCAAGCGCGTCCAAAGCACGGGTTCGCCAAGCGCCCCCCCCGCCCCACTCCACATTCCCTTCCCCG<br>CCGACTCAGCCTCCGTAGCTCGCGGACGGCCCCTCCTCACGCCAGCCCAGGCTTTTTTTTTTTTTTTTTCTTCTATTTTAAGGTT<br>GTCTTTTAATGACACAAGCGACATTTGGAGACAAAAGGACACATCTCTTCCTGACCCACCTCCAACCCCAGCTGACGGCCGCCCT<br>GAGCCTGGCGTAGACGGCCCGGAACGTTCCCTGCGTGGGTTCCGTCCATCCCGAACCCCTGTCCCCGCGCCGGCTCCGGGGGTGC<br>TCGGGGGGCCGCGTGGGGTCTGTGACGTCGCCTCGAGGCTGCATCCCGGTGACCCGGCAGCCCCTGGCGCTCGCGGGAGGCGGGC<br>GGGCGCGGACCCCAGGCTTTAGGGCGCGATTCCTGCAGCTGGCTGCCGGCCCGAGGTTCTGGGGTGTCTGAGGTCTCGGGCGGGG<br>CGAGGACGTTTCTCCGGCTCAGCCCCCCCACCTCCTGCCCTGCCGCCCCCCACACCCAGCTCCCCACGGACGCCAAGAGGCGCCT<br>CCCACCCCGGCGAGGACCCGCGGGAAACGGGGCCCAGGCGCGGCGACTGCGGAGGACGCGCCTCGGCCCCAGCGCCCTGGTCCT<br>CGGGGCGTCCGGCTGCCCTTGCCCGAGGCCGGGGCGGGCGCTCAGCGCCGCGGAAGAAACGCCCGGGCGGGGACGCACAGCGAGG<br>CGGGCTCCGCGGGAAGTACCGGGAAAACGGCGCGGAGCGGAACAG |
| 249 | PCBP3 | TGGAGCAATCCCAGAGAGGCTGAGGTGTTCAGGCTGGCCCCAGATGCACACGAGCGTGAAGCCTGTTCAGAAGCCAGCTCCTCAC<br>ACCCTCTCCCCTGCCAGAGGCTCCAGCACCCCCTCCCCTCTCCTCTCCCCTCCCTTCCCTGTGGTCCTCCTGCCCACCCCACCCC<br>CGTCTGCATGTGCACCGTCACGGAGATGCGTGTACTAGGGCGGAGGTCGGGGACAGTCGTCAGAAGGACACAGGAAAGAAGGGAA<br>CAGGAATCCCATAACAGAACATTATCCGGCAGGAGTAATTAACACAGGCAGGACTGGAGGCTTTGTTTTGTTTTGCTTAAAAAAC<br>AGTGGTATTTAAATTAATGGGCATGGGAAGACTATTCAGTGAAAGACATCGGTCATTGAGGTATCTATTCAAAAACACGGTTTAG<br>TACTCTGCCACACACCGAACGCAACGCCACAGCAGCCATAGAAGCGTGTGTGGCTGTTTAACGTGGTCTTTTTGGGGAGGGCATC<br>CTAGGCAGAGCAGGCGTGGAAGGGAAGGCGGCGGACGGAACAAAACGCGGGCACGCAACGGCTGCTGCGCCGGATCTGAGGCAGG<br>GCCAGCCTGTGGGAGCAGCAACATCGCTCGCAGGACAGCGATGGAGCCCCCACGAATCCGCGTGAAAGCAGCAACCACCTAGAAA<br>TGAACGTACAGCTGCTTAGAAACAGAATACGGATGACCCGAAAGACTTCCCGATGGTAGTCACCAGCATACAGGACCTGACACGG<br>GCGTGCGGGCAGGGTGTGCCGCTACGGGGTCCCTGGCGCACCTGCTACCCCTGCTACCCGCATTCACCGCACGCGGAGGGTGCGG<br>GCCGTGAAGGTTATACATGCAAATATCCTTCCACCAGCCAGTTCTCCTTCCAGGAATCTGCCACCCGACCCTTGTGTTGTGCACA<br>GACATGGTCCAGGTGTTTGCGACGTGATTGTTTATCAGAGAGAGAGAAGGGAAATCTCCAGGCTCGCTGTAGCTGCAGGAGCTCT<br>GGGGGCTGCGCCCATCGTGGAGACGGATAGCTGTCTCTCATGAACACAGGACAGCAAGTCCGGCTGCGGCCACAGAAGACTCGCC<br>CTCCTGGACGCAGCGTCTTCCTTCCTCAGCCCCACACTGGAGGTGGCCAGTGCCATCCACAGCAGAAGGGGCCAGCCGGGACCAG<br>GCTCACGCCGTGGAATTCTGCTCTGTGGTAAGAGGAAGAGCGATAGCTGGAACCCAGCGCCGTCGCACACACAGCGGGGAAGAGT<br>CTCAGAAATGTTACTTTGAGTCAAAAAGCTGGACAAAAAAAGGCGCAAGCCAGATGGTGCTGAAGAGGCCACAGGAGGCTGGCAG<br>CCAGGGGGTCTGGCACCTCACTCGGAGGCGCAGTGGGCCCGTCCGGAATTAGTGGCCATACGGCAAGTGCCGAGTGGACATCAAA<br>CCGTCACTTCAGACTCCTGCGCTTCACTGCCTGTCGGTTATGCCTGGGTTTTGAAATCAAGTCACAGAACACCTGGAATGTGGTG<br>TTTACGCAGAACAAAGCGGGTGCCTCGGAGGAGAGAGCCTAGGGACAGGGGCACCTCCCGGTGTGGGTGCCCAGGGTTGCAGGGT<br>GGCTTCCTCTGTCTGCGCGGTTTTCAGAGCCCCAGGGTCCTGCCTGCCCGGCTGCCTGGAGGCGGCCCACATCCTGCTCTGCGCC<br>GCCGAATCTCAGCCTGAACAGCTTCGCTGGTGTTTGTGTTGACTTATTTGTTCTTTTTTTTTTTTTTTTTTTTAAATAAAGGAT<br>TCCGATGCTGTTACAGTCAATAAAAGCCACAGGTCTGGGTGACCTACAAATGTGTGTGTCTGACTTTCTGCAGTTTAAATCGCCA<br>CTGAGCCTTAAGGCGTCTGGCCCGCGCATTGAGGAATCCACGTGGGTCTCGGGGTCCCCATGCCTGCCCAGCTCCCTGCTTCAGC<br>CTGGGCGGGTCTGGCGGGCATTTCTGCGAGCCTGTCCCTGGGCCCGCCTCCTGGCCAGACTTCCAGAAACATTGTCCACATCCCC<br>GTTGCACGTCCCCCCGTCACCGGAAACTGCAGCCCACAGCACTGGGAAGAACCCGGGAGGCAGGCGTTAGGACGGGGTGGCCGAG<br>ACAGGGAAGGGAGCCATGGCGGACGTCCTCACCCAAGCCAGGGCTTCCTGCCCCTGTGGTACTGACAGGAGCCCCGCAGGACGTG<br>GGGTTGGCTTTGGGCAGCTCGGTGGACACTTCTCTTTCAGATCCTGCCACAGCAAAGCTCACGAGACTCACTTCTTCCCATTGGA<br>ATTCACTAAGAACAAATTCAACAATTCAGACGCCCCAGCTGGAGGTTTATTTTATGGATTTTACCTGTGCGGTATTTAGGGTTGT<br>GTTTATGAATAAAGGTGTGCGTTCTGGCAAGTAGAAATACAGAGCTTGTCTTTCACCCAAGTATCTGTAACTTTCTCCAATGCAG<br>ACACTAAAATGCAATAAAAACAAACCAAACCCATTAAACATGAATTAGATGAGGCAGGCTGATGGGAGGTTGTGGGATTAACAGG<br>CCGTCAGCGGATTGAAGCTGCGCACATCGCTGGGATGCTGCTGCGGGAGGATTCGGTCTAATCCGGGAGCATCTGGCTGGGCAGT<br>GGGCAGCGTCTGCAGTCGTGGCTGCTTGAAGGTATGAAGGTTGTGGCCTTTGCTTCCCCCCATCAGGCTGCCCCACCCTGGACCC<br>CACCCAGACCCCTCGGGCACCCTGGGGTCATCTTCAGCTCCCCCTTCTCTTCCTTCCTTCTCTTCCGCCTGGGCCCCTACTGTGA<br>CCCGAGGTCAGCAGAGGACCCTGGCAGGTGGCTGCTCCCTGGGACTCGACTGTGCAGGTGAGGCTTGGGGTGACCGCTGCTCCTG<br>CTCCTGCTCCTCTCGCCGTCCCCACCCTCCTCCATCATGCTGTCAACATGCATGTGGGCTGCAGCCCTCAGCCTGCAGGACGCTG<br>TCAGTGCAGCTCCTCAGTGGCCAGG |
| 250 | PCBP3 | ATCTTGTCTTCCTTGTCCCAGTCCTGGAACCAGCCACTGCCCCAGCAGCTCCTGTGTGTGGTGGCATGTTCTGGAAGCCAGGATG<br>CATGGTGCTCCTGGGCTGCTGTGGGTCCTGGGCTGCTGTGGGTCCCGAGCTGCTGTGGGTCCTGGGCTGCACCCCTGCAGAACAC<br>TTCCTTCCATGTTCAGCTCCCTATATGGAACCCCAGTTCCAGCCCCACAGCACAGGGTCCCCCAGTTCTTCCTGCCTCAGGTGTG<br>CACCACGAGGAATCCAACTGCCAGTATCTGTGCGTGGCCTCCCGCCGGGAGGAGGCTGCCGGAGGCTCTGAGCTCTAGCCCCACA<br>GCACTGGCACATCCTAGATTTCCGGGAAGACACGGCCTCCTCCCCAGGGGAAGGTGGTGGTGCCCACACCCAGAGCATTCATTCC<br>TGCAGTGGAGACAGAGGGACCTGCCTCTCCAACTGTGGGTGTCAGGAGCCAAGGCGCATGGTAAATGGGGCTCTCTGTGAGGCCA |

TABLE 4C-continued

| SEQ ID NO | GENE NAME | SEQUENCE |
|---|---|---|
| | | GGTGCACGGCCCCATCTCCAGCAGCAGCGGCCATGCCACCCAGCTGCACTCTGTGGGGGAGGTGCCATGATTGACGGGGGCCCCT<br>CCCTGTGTCCAGTGTCCTCCTCCCTCCACGGGCCCCTCTGCACACCGTCCTCACAGTCTCCCTCTGCACACCGTCCTCACAGCCT<br>CCCTCTGCACACCATCCTCATGGTCTCCCTCTGCACACCGTCCTCACAGCCTCCCTCTGCACACCGTCCTCACAGCCTCCCTCTG<br>CACACCGTCCTCACAGCCTCCCTCTGCACACCATCCTCATGGTCTCCCTCTCCTTCCACAGACCCCTCTGCTCGCCATCCTGACG<br>GCCTCCCTCTCCCTCCACGGACCCCTCTACACACTGTCCTCCCAGCCTCCCTCTACACGCCATCCTCACAGCCTCCCTCTCCCTC<br>CACGGGCCCCTCTACACACCGTCCTCACGGCCTCCCTCTCCCTCCACGGGCCCCTCTGCACACCGTCCTCACAGCCTCCCTCTCC<br>CTCCACGGGCCCCTCTGCACGCCGTCCTCACGGCCTCCCTCTGCCTCCACGGGCCCCTCTGCACGCCGTCCTCACGGCCTCCCTC<br>TGCCTCCACGGGCCCCTCTGCATGCCGTCCTCACGGCCTCCCTCTCTCTCCACGGGCCCCTCTGCACGCCGTCCTCACGGCCTCC<br>CTCTCTCTCCACGGGCCCCTCTGCACGCCGTCCTCACAGCCTTCCTCTTTTTCCACAGACCCCTCTGCACGCCGTCCTCACGGCC<br>TCCCTCTCCCTCCACGGGCCCCTCTGCATGCCGTCCTCACAGCCTCACCGACGTCACCATTGCTGGCCCCGCTTCAGGTGACAGG<br>CCACAGTAGCACCTGTCAGCTCTGTCCCGCTGCTGGACAGGGAGATACTGGGCCACTCAGCCCAGCGGGGAACGTGTGTCCCGAA<br>ACTGCCTTGGGCTCGCCATCAGAACTGTGGCAGCATCTTCCAGCGTTCCTTTTAACAGGCTGCCGTTGGAATAGGAGTCACGGAG<br>CAATTGCAGTGCTAAGTTTTCTTTAAGTCACACAATTGAAGGAGGCTTTATTTTTCACACATTTCTTCCAGAGTTTCCTGGTAGC<br>CTGAGTGCATGGGTGATGCCCCCTGAGTTATTTATCAGGGGCAGCCAGCTGCCCTCCCCCGGGGCACTTACAGTCAGCCCATCTC<br>TGTCCTGGTCAGGTGGGCGCCAAGGAAGACCCGGCTCAGGGCCTCTGTATGGGCAGCCTGGCTTGTACACACACCCCTCCCCACC<br>AGCAGATTCTGAATTCTCCCTTCTTCATGCACACCGGGAAGGTCCCTTCTGCACTCATACCGGGAAGGTAGGCAGGTTTCGGTAG<br>TGTCTGCCTCCAGTGTTTTCCTCCTCCTGCTCTATGACATCATCTTTCTGTGATTTTTTTTTTCTTGCAGGAAGTTGGAAGCATC<br>ATCGGGAAGGTAATTATTGATTGAATCTCTGCCTCTCCTGGGGTCTCTGTAAGGGGATGGTGAGGATGGCAGCCTCCCTGGGTAC<br>TAGGTGGCACCCAGTAGGTGCGCCTTTCCCAGTTGGTGGGTGGTCTGTGTTCCATGAAGACAGGACCCCAGAGGTGTCGCCTTTA<br>TGCTGTATGACATTGAAGCTGGTCCCTGGCTCTGCGTGGCCTGAGGGGAAGGGGTTCACTCCAGCTGGTCACCTCGCTGCCCCCT<br>GCCCGTGGCCTTGGTGGCCAGTCCTTCTTTCCCGGTTGAAGACCCCACGAAGAATGATTTCTCACGCCTTCTTCAGCCGGCTGTG<br>TAGTCTGGGTGGTCTCCAGGAGTGCCAGTGGAGGCAGCAGCCCCCAGACAATTCCTTTCCAAATCAGGGCTGGCCCGGGGGAAGT<br>AAGGCCCAGTTTGGAAGCCTGCTGCCCCGGGAGGCCGAGCAGTGAGGGCCACCTCCCTGTCTTCATCACATTTTCACCGCTTCCG<br>GGGGTCCTTCCCCTCAGTCCCACCATGGGGGCGCC |
| 251 | COL6A1 | GCTGGACACCTCTGAGAGCGTGGCCCTGAGGCTGAAGCCCTACGGGGCCCTCGTGGACAAAGTCAAGTCCTTCACCAAGCGCTTC<br>ATCGACAACCTGAGGGACAGGTAGGAGGGACGCCCCGTGACCTTCCTCCTGTGCTTCTGGGCCTCTTGGAGGGAGGGGTGGGGGC<br>CCAGGGGAACACGGGTGCGACGGCCTCAACCTCCTAAGGTTGGGCGAGCGTTGCCCTGACCGGGGCCCCTCCCGGCGCCCTCCAG<br>AGTGAGGCCGGGGCCCTTTCCGGCGCCCTCCAGAGTGAGCTGGTCTGAGCCTCTCCCAGCGCCTTCCAGAGTGAGCTGGTTTGAG<br>ACCCTGCTCGCGGGGGTGGCACCTGTTCAGCAGGGCCGAGGTGACAGTGAGGCTGAGATGTAGGGAAGAGAGGCTCCCGCAGGCT<br>GACCGAGAGGGCTCAGCGCACTGGCCCAGACACGCAGTCCTGCCTGGTGCGCGGGAGCCCCTCACTAACCACCTGGACCCTGGTT<br>TGTTCCGTGGGCAGTGAGAGCCTCTACCTGGGTCCTGGATCCCACGTTCTGAAGGTCCCCGACTCGGGAGCCAGGAGGGGTGTCG<br>CTCTGCAGCCCCAGGGCCCCCAGGCTTGGTTCTGGGCTTGGGACACGGCACCCTCTGCTCCACGTTCCTCCATCTGTGCGTGTGG<br>CTGAGGACAGACCGGGGGGAGAGGGGAGTCGGTCCTGTGGGTGCACAGGGCCGCTGAGGGGGGGGCATGTAGAACGGGGCTCCCC<br>CACTGAGACGGGTCCTGGCAGTGGGGACACAGCTTAGCCGGCGTAGGAACCCCCGTCCTCCTTGACCCTGCTGACTGGCCGCTGG<br>GCCGGAGCCTCCCGCCACCAGAAGGGGCACAGTCAGAGGCTGCCGGTAACAGCAGGGTGGACCTTCCAGCCCACACCGTGCCCAG<br>CAGGAGCCATTGGTACCAGGAACCCTGAGCTTAGTGGACATGGCCAGGCCCGTGCGGCAGTGTTTGGGGGGGGTCTGGCTGTGG<br>ATGGCACCGGGGAGGGGCGGCCGCGTGGCCCAGCGTCCCCCGAGTCGCCCTTGTTGCCTTTACTCAGTCTCCCCATGACTCAGTT<br>TCCCACCTGTGAAATGGGGCGGAGTCATCCCCATGTCGCTGCCACTGGATTCCTGCAGGCGCCGTGGTCACTCTGCTGAATGGAT<br>GGGAGGGTGGGTGGGGCAGAGGTGGGCCCACCCCAGGCTGGGGCAGAGCAGACCCCTGAGAGCCTCAGGCTCAGGTGCTCAGAGG<br>GCAGCGAGGGGGCTGCTCAGATCCCCGGGGTGCCTCCTTCCCCCACTGTCATGCTGCCCCACTGCAGGCCCAAGGACCCCACCCC<br>AGCAGGGCCACACACTCAGGGCTCCTGGTCTGAGGGCCTGAGGGATCGGGGCGCAGGTCGCTTGCTGGCCACACCCGCCTGCACA<br>GCCTTCCAGGAGGGCCGGCCTCAGGGCCACAGGGCAAGTCCAGCTGTGTGTCAGCCACGGCCAGGGTGGGGCAGCCTGTCCATCT<br>GGGTGACGTCGCGCCCTGGGACGGGTAGCGATGGCGCCAGGGGCCGCCCGCCTCACGCCCGCCGTGCCTGTTCCTGGCAGGTACT<br>ACCGCTGTGACCGAAACCTGGTGTGGAACGCAGGCGCGCTGCACTACAGTGACGAGGTGGAGATCATCCAAGGCCTCACGCGCAT<br>GCCTGGCGGCCGCGACGCACTCAAAAGCAGCGTGGACGCGGTCAAGTACTTTGGGAAGGGCACCTACACCGACTGCGCTATCAAG<br>AAGGGGCTGGAGCAGCTCCTCGTGGGGTGAGTGGCCCCCAGCCTCCTGCCCACGCCAGTTCTCACGCGTGGTACCCAGCCTGGGC<br>TGGGGTTGGCCTGGGGTCCCTGTGCGGCTTCAGCTGCAGCCTCCCTGTTCTCTTGGAGGCTGCACGGCCTCCCTGACCCACTTTG<br>TGGGCAGGAAAGAGACGGAGACAGACAGAGACAGAGAGAAACAGAAACAGGGAGAAACAGACACAGAGAGAGACAGAGACAGAGA<br>GAGATAGAGACAGAGACAGAGAGAGACAGAGACAAAGAGTGACAGAGGGACCAAGACAGGCAGACAGAGACAAACAGAGACAGAG<br>ACAGAGACACAGAGAGAGACACAGAGAGACAGAGACGGGAACAGAGACAGGCAGACAGAGACAGAGAGAGACAGAGACAGAAACA<br>GAGACAGAGGGACAGAGACAGGCAGAGAGAGACAGAGAGACAGAGACAGAGACAGACAAACAGAGACAGAGAGACAGAAACAGGG<br>ACAGAGACAGAAAGAGAGAGAGACAGAGGGAAACAGAGAGAGACAGAGACAGATAGAAAAAGACAGAGGCAGAGAGAAGCAGAGA<br>CAGAGAAACAAAGACAGTCAGAGACAGACAGAGACAGAGACAGAAACAGAGACAGAGAGACAGAGACAGAGGGGCAGAGACAGGC<br>AGACAGAGAGACAGAGACAGAGACAGCGAAACAGAGACAGAAACATACAGAGACAGAGAGACAGAGAGAAGCAGAGACAGACAGA<br>GGCAGAGAGACAGAGAGAAGCAGAGACAGGGACAGAGACAGAGACAGAAATAGAGAGATAGAGACAGAGGGACAGAGACAGAGAG<br>ATAGAGACAGAGAGGGAGACAGAGAGATAGAAGCAGAGAGAGAGAGACAAAGACAGAGGCAGAGAGACAGAGAGAGAAGCACAGA<br>CAGAGACAGACAGAGAGACAGGGACAGACAGAGACAGAGAGACCGGAAACAGAGGCAGAGAGACTGAGAGACTGAGAGAGACGGG<br>GTGGTTTTCCCCACAGCATCAACACCAAGCAGGGCTAGGATCACTGAAACAGACTCATCAGACCCGAAGCATGCGCTTTCTCGGG<br>GTTTTTCTGGACTGAGGGGTTTCCTCTCATCCCAGTGTCCAGCTGTGGGGACGCAGGGGCCGCAAGCCCCGGAGTGTCCAGAGGG<br>GAACGTGGCCTCCCCACACCCAGCCCTTCACGAGGCCTCAGGATCCCAGTGGGGGTACCCGAGGCTGCCCTGTCCAGCCAGGCGG<br>TGCGGGGGGTTTGGGGAGAGCCTCTCCCCGAGGTCGGTCTCAGAGGGCCACATGGCCGGTGTGGGCCGGACATTCCCTTTCCAAT<br>GGTTGTGCCCACTTCCCTCCAGAGTTGGTGCCAAGCTGGGACCTGGGGGACTTGGAGTCTCAGGAAGTCGTCCGCTGTCTGCAGG<br>GGGTGCATGGGGGATGTGGCCACACACGTCAGAGTGCGGCCCCCTGTGGAAGCCACAGACAGACACGACTCCCCTAAATGAGCTC<br>GCCCTTCTGGCCGAGATGCTCAGCGTCCCCAGCAGGCTGCCCGACTGCCCTGCGATACTGCCCTCCTTCCTGCTGCTCCCACTTT<br>CCCTTTCGGGGGGTTGGATTTGGGGCATTCAGGGATCGCCCTGTTGTTTGCTCATCACACCCATTTCCTGCAAGAGCCACGGTGA<br>CCGAGCAGCCTTGAGTTGAGGCAGCTTGTGGGTAGACGCGGCGGGCATCTCGGAGGGGCACGCTCCCTGCCACCCTCAGCCTCCA<br>CTCACTGGTCAGGGGCTTTGCGCCCCAGGGCACCCCAGGAACCGAGCCTCCTTTGGGGTCATGGGTGCCTCTCCTGGGAGGGCGT<br>GGATTTTCCAAAGCAGTTTAGAGAAATGAGACCCACAGGCGTTATTTCCCATGGTGAGGTTCTTTTCAGTAACCCCCACCGTATA<br>GCCAGGATCAGCAAAGAGAGGCGGCTCCTCCCGGTGAGACAGGGACCAGCACCTCCCGGACAGGCTTGGGTCTCCCTCCAGTTCC<br>CCCACCTAGTCTCGAGGTCTCACGCTGCCCTCTCCTGTCCAGGGGCTCCCACCTGAAGGAGAATAAGTACCTGATTGTGGTGACC<br>GACGGGCACCCCCTGGAGGGCTACAAGGAACCCTGTGGGGGGCTGGAGGATGCTGTGAACGAGGCCAAGCACCTGGGCGTCAAAG<br>TCTTCTCGGTGGCCATCACACCCGACCACCTGGTAGGCACCGGCCCCCCCCGGCAGATGCCCCCAACCACAGGGAGTGGCGGCTG<br>CAAGGCCCCCGGCAGCTGGGACCGTCTTTTGGTCCTCGGGAGGGTGTGGGTTCTCCAGCCGGCCACCCTTGCCCCTGAGAGGCCA<br>GCCCCTCCTGCTGAGGAGCCTGGAGCGCCCCAGCCCAGCCTCCCCTCTGGCCCTGTGGGAAGCGGCCCCGGCCGTCAGGGGTCCC<br>AGCCCTGCTCAGCCCACCCTGAACACTGCCCCCAGGAGCCGCGTCTGAGCATCATCGCCACGGACCACACGTACCGGCGCAACTT |

TABLE 4C-continued

| SEQ ID NO | GENE NAME | SEQUENCE |
|---|---|---|
| | | CACGGCGGCTGACTGGGGCCAGAGCCGCGACGCAGAGGAGGCCATCAGCCAGACCATCGACACCATCGTGGACATGATCGTGAGG<br>CCCCTGCCCAGGAGACGGGGAGGCCCGCGGCGGCCGCAGGTGGAAAGTAATTCTGCGTTTCCATTTCTCTTTCCAGAAAAATAAC<br>GTGGAGCAAGTGGTAAGAGCCCTCCCCACCACCCCCAGCCGTGAGTCTGCACACGTCCACCCACACGTCCACCTGTGTGTTCAGG<br>ACGCATGTCCCTATGCATATCCGCCCATGTGCCCGGGACACATGTCCCCTGCGTGTCTGCCCGTGTGCCCGGGATGTGTGTCCCC<br>CTGCGTGTCCACCTGTGTGTCTGCCCATGTGCCTGGGACATGTGTCCGCCTGTGCGTCCATCCGTGTGTCCGTCTGCCCATGTGC<br>CTGGGTCGCATGTCACCCTGTGTCCCAGCCGTATGTCCGTGGCTTTCCCACTGACTCGTCTCCATGCTTTCCCCCCACAGTGCTG<br>CTCCTTCGAATGCCAGGTGAGTGTGCCCCCCGACCCCTGACCCCGCGCCCTGCACCCTGGGAACCTGAGTCTGGGGTCCTGGCTG<br>ACCGTCCCCTCTGCCTTGCAGCCTGCAAGAGGACCTCCGGGGCTCCGGGGCGACCCCGGCTTTGAGGTGAGTGGTGACTCCTGCT<br>CCTCCCATGTGTTGTGGGGCCTGGGAGTGGGGGTGGCAGGACCAAAGCCTCCTGGGCACCCAAGTCCACCATGAGGATCCAGAGG<br>GGACGGCGGGGGTCCAGATGGAGGGGACGGCGGGGGTCCAGATGGAGGGGACGGCGGGAGTCCAGATGGAGGGGATGGCGGGGTC<br>CAGATGGAGGGGACGGCGGGGTCCAGATGGAGGGGACGGCGGGGTCCAGATGGAGGGGATGGCGGGGTCCAGATGGAGGGGACGG<br>CGGGGTCCAGATGGAGGGGACGGCGGGGTCCAGATGGAGGGGACGTCGGGGCTCCAGATGGAGGGGACGGCGGGAGTCCAGATGG<br>AGGGGACGGCGGGGTCCAGATGGAGGGGACGGCGGGGTCCAGATGGAGGGGACGGCGGGGTCCAGATGGAGGGGACGTCGGGGCT<br>CCAGATGGAGGGGACGGCGGGAGTCCAGATGGAGGGGACGGCGTGGTCCAGATGGAGGGGACGGCGGGGTCCAGATGGAGGGGAC<br>GTCGGGGCTCCAGATGGAGGGGACGGCGGGGGTCCAGATGGAGGGGACGGCGGGGTCCAGATGGAGGGGACGGCGGGGTCCAGAT<br>GGAGGGGACGGCGGGGTCCAGATGGAGGGGACGGCGGGGTCCAGATGGAGGGGACGGCGGGGTCCAGATGGAGGGGACGGCGGGA<br>GTCCAGATGGAGGGGACGGCGTGGTCCAGATGGAGGGGACGGCGGGGTCCAGATGGAGGGGACGTCGGGGCTCCAGATGGAGGGG<br>ACGGCGGGGTCCAGATGGAGGGGATGTCGGGGTCCAGATGGAAGGGACGGCGGGGTCCAGCAGGCAGGCTCCGGCCGTGCAGGGT<br>GTGGACTGTCCCGGGGGCGCTGGGGGCTTCTGAGGGTGTCTCTGTCCGCCCTGCCCTCAGCCGCACTCTGTTCAGAAGGACCTTT<br>CTGGAGGTAGGAGGGTGAGAATGTGGGTCCCCTGCTTCTGTGTGGCTCAC |
| 252 | COL6A1 | GGCCGGGGAGGCGGGGAGGCTGCCCCAAGAGTAAAAGCCTTTCTGACGTGCGCAGGACGCGGCCCTGACTGGTCTAACTGACTCT<br>TTCTCTTCTCCTCAGCTTGCTGTGGTGAGACCCAGGCTCTAGCTCCTGAGAGAATGGATCCCGGGGGTCGGGGAGCGAGGCCTGG<br>GTCCCACACATGTCACAGGACAGCACATGGCACTCTGGTCCCCGCCCGCAGCTCCCTGCACCTGCCCGCCCCCTCTGGGGCCTGC<br>TCCAAGCCAGCAGGGTTCCCGGGTGTTGGGCTGGGCCCCGCCCTCTTTCACCCATAACTGAAATAACCAGGAGCAGGCTTGGGGG<br>GGTCCCTGCTCCATCATTCTGGCCCACAGGCCCCACCCTAGCCTGGCTGAGCAACGCCAGCCCTGACCAGCCGCCGGACAGAGCA<br>GCCTTTACGGGGCCATGGGAGGGGGTGGGCTTTTCTGGGGCTGAGACGGGGGGACCCCAACGTGTCAGGTGAGGATGTGGCAGCC<br>AAGGAGGGGCCAGGGCGGTGGAGGGGAGGGGCCAGGGCACTGGAGGGGAGGGGCGTGCTCTGCTGACACCGCCCCCGCCTGCAGA<br>ATGCAAGTGCGGCCCCATCGACCTCCTGTTCGTGCTGGACAGCTCAGAGAGCATTGGCCTGCAGAACTTCGAGATTGCCAAGGAC<br>TTCGTCGTCAAGGTCATCGACCGGCTGAGCCGGGACGAGCTGGTCAAGGTGAGGCCTCGCCCCGCCCGGCTTTCTCAAGCCCAGG<br>TGCACCCCGACCCTGCCGGCCGCCCCTGCCCGCGCCAGACCTCAGCCTCCCGAGGCCACCGCTGCATCCCTGTGACTTCCCTACT<br>CATGACAAGGATGCCAGGCACGCGCCAGCCCGTCCAGGCCTCCAGCTCCACCTGGCGAGGCTGGCCCATTGTACACAGGCGCCCC<br>AGATGAGGGAGGGTCTCCCCCTCTCCTTGAAGGGCGGTAGTCTGGGGTCCTGAGTGCTGGGTGTGGGCTTGTCCCTCGTGGACAG<br>AACCCAGGAGGGCTTCATCCACCAAGGAAGATTGCTTTGCAGGGTACCCAGGTCCCGGGGGCTGTGCCACCCTCTGGGCACCCGG<br>AGCCAATCGCAGGGTACCCAGGTCCCGGGGGCTGTGCCACCCTCTGTGCACCCAGAGCCAATCGCAGGGGACCCAGGTCCTGAGG<br>TCCTGGGGGCCATGCCACCCTCTGGGCACCCGCAGCCAATAGAGTCACCCTTGGGAAGCTTATGCGGACCTGGGGCAGCACTCGC<br>GTCCTGACCCCGGTGCCGGTCCCACAGTTCGAGCCAGGGCAGTCGTACGCGGGTGTGGTGCAGTACAGCCACAGCCAGATGCAGG<br>AGCACGTGAGCCTGCGCAGCCCCAGCATCCGGAACGTGCAGGAGCTCAAGGAGTGAGTGCCCCACGCGGCCAGGACCCTCCCACC<br>CCTCGCCCCGACCGCTGTTCCCACGGCAGGTCGGCCCTGACCCCTGATCCCAGGTGGGCTCGGCCCCGCGGCAGGCCTGGCCCCA<br>ACCGGCCCTTCCTGCCCTTTGCTATGCAGAGCCATCAAGAGCCTGCAGTGGATGGCGGGCGGCACCTTCACGGGGGAGGCCCTGC<br>AGTACACGCGGGACCAGCTGCTGCCGCCCAGCCCGAACAACCGCATCGCCCTGGTCATCACTGACGGGCGCTCAGACACTCAGAG<br>GGACACCACACCGCTCAACGTGCTCTGCAGCCCCGGCATCCAGGTGGGGTGGCCACCCCCAGGCTGCACCTGCCCCGCCTAGGGC<br>GCCCCGCCAGCCAGGGTGGCCTTGTCCCCAGAAAGACGAGGGCAGAGCAGGCTGCGCCACACCGATACTGTCTGTCCCCACAGGT<br>GGTCTCCGTGGGCATCAAAGACGTGTTTGACTTCATCCCAGGCTCAGACCAGCTCAATGTCATTTCTTGCCAAGGCCTGGCACCA<br>TCCCAGGGCCGGCCCGGCCTCTCGCTGGTCAAGGAGAACTATGCAGAGCTGCTGGAGGATGCCTTCCTGAAGAATGTCACCGCCC<br>AGATCTGCATAGGTGCGCATGGGGCCACCCGGGCAGTCCCAGATCTGCGTAGGTGCGCGCGGGGCCGCCCGGGCAGTCCCAGATC<br>TGCGTAGGTGCACGCGGGGCCGCCCGGGCAGTCCCAGATCTGCGTAGGTGCACGCGGGGCCGCCCAGGGCCGTCCCAGATCTGTG<br>TAGGTGCGCGCAGGCGCCCAGGGCTGTCCCAGAGGCCTCCTCCCAGCTCACTGTTACCTCCAGGGGCACGGCCACCCTGTAGGTG<br>CGCACGGGGCCGCCTGGGGCTGTCCCACAGGCATCCTCCTCCCGGCTCGCTGTGACTTCCGGGGGCACGGCCACCCCTGTGCTCG<br>GCCGGGAGGTCCTGTGACATCTCCTTGCGGGGTTATAGGTGGAGCAGTGGGCTCACACTGCACGGCTTTTCTCTTTTACAGACAA<br>GAAGTGTCCAGATTACACCTGCCCCAGTGAGTACCTCGGCGGCCGGGACACGTGGGGAGGAGGGCACCGTGGTTGGGGCGAGGGC<br>TCTGAGAGGACGGGGCTCTGGGAGGAGGGCCTGGCGGTCACGAGAGTAGGTGCATGGCTCACTCCGGTGGCTGAGCACCACCGTG<br>CCGTGCCCTCTCTGGGGAGCTTAGACGCTCTCTGGCCGGCCCACTGCGGCTGCATCACCAGGGCCTCATGCTAACGGCTGCCCAC<br>CCCGCCCCGCAGTCACGTTCTCCTCCCCGGCTGACATCACCATCCTGCTGGACGGCTCCGCCAGCGTGGGCAGCCACAACTTTGA<br>CACCACCAAGCGCTTCGCCAAGCGCCTGGCCGAGCGCTTCCTCACAGCGGGCAGGACGGACCCCGCCCACGACGTGCGGGTGGCG<br>GTGGTGCAGTACAGCGGCACGGGCCAGCAGCGCCCAGAGCGGGCGTCGCTGCAGTTCCTGCAGAACTACACGGCCCTGGCCAGTG<br>CCGTCGATGCCATGGACTTTATCAACGACGCCACCGACGTCAACGATGCCCTGGGCTATGTGACCCGCTTCTACCGCGAGGCCTC<br>GTCCGGCGCTGCCAAGAAGAGGCTGCTGCTCTTCTCAGATGGCAACTCGCAGGGCGCCACGCCCGCTGCCATCGAGAAGGCCGTG<br>CAGGAAGCCCAGCGGGCAGGCATCGAGATCTTCGTGGTGGTCGTGGGCCGCCAGGTGAATGAGCCCCACATCCGCGTCCTGGTCA<br>CCGGCAAGACGGCCGAGTACGACGTGGCCTACGGCGAGAGCCACCTGTTCCGTGTCCCCAGCTACCAGGCCCTGCTCCGCGGTGT<br>CTTCCACCAGACAGTCTCCAGGAAGGTGGCGCTGGGCTAGCCCACCCTGCACGCCGGCACCAAACCCTGTCCTCCCACCCCTCCC<br>CACTCATCACTAAACAGAGTAAAATGTGATGCGAATTTTCCCGACCAACCTGATTCGCTAGATTTTTTTAAGGAAAAGCTTGGA<br>AAGCCAGGACACAACGCTGCTGCCTGCTTTGTGCAGGGTCCTCCGGGGCTCAGCCCTGAGTTGGCATCACCTGCGCAGGGCCCTC<br>TGGGGCTCAGCCCTGAGCTAGTGTCACCTGCACAGGGCCCTCTGAGGCTCAGCCCTGAGCTGGCGTCACCTGTGCAGGGCCCTCT<br>GGGGCTCAGCCCTGAGCTGGCCTCACCTGGGTTCCCCACCCCGGGCTCTCCTGCCCTGCCCTCCTGCCCGCCCTCCCTCCTGCCT<br>GCGCAGCTCCTTCCCTAGGCACCTCTGTGCTGCATCCCACCAGCCTGAGCAAGACGCCCTCTCGGGGCCTGTGCCGCACTAGCCT<br>CCCTCTCCTCTGTCCCCATAGCTGGTTTTTCCCACCAATCCTCACCTAACAGTTACTTTACAATTAAACTCAAAGCAAGCTCTTC<br>TCCTCAGCTTGGGGCAGCCATTGGCCTCTGTCTCGTTTTGGGAAACCAAGGTCAGGAGGCCGTTGCAGACATAAATCTCGGCGAC<br>TCGGCCCCGTCTCCTGAGGGTCCTGCTGGTGACCGGCCTGGACCTTGGCCCTACAGCCCTGGAGGCCGCTGCTGACCAGCACTGA<br>CCCCGACCTCAGAGAGTACTCGCAGGGGCGCTGGCTGCACTCAAGACCCTCGAGATTAACGGTGCTAACCCCGTCTGCTCCTCCC<br>TCCCGCAGAGACTGGGGCCTGGACTGGACATGAGAGCCCCTTGGTGCCACAGAGGGCTGTGTCTTACTAGAAACAACGCAAACCT<br>CTCCTTCCTCAGAATAGTGATGTGTTCGACGTTTTATCAAAGGCCCCCTTTCTATGTTCATGTTAGTTTTGCTCCTTCTGTGTTT<br>TTTTCTGAACCATATCCATGTTGCTGACTTTTCCAAATAAAGGTTTTCACTCCTCTCCCTGTGGTTATCTTCCCCACAAAGTAAA<br>ATCCTGCCGTGTGCCCCAAAGGAGCAGTCACAGGAGGTTGGGGGGCGTGTGCGTGCGTGCTCACTCCCAACCCCCATCACCACCA<br>GTCCCAGGCCAGAACCAGGGCTGCCCTTGGCTACAGCTGTCCATCCATGCCCCTTATCTGCGTCTGCGTCGGTGACATGGAGACC<br>ATGCTGCACCTGTGGACAGAGAGGAGCTGAGAAGGCAACACCCTGGGCTTTGGGGTCGGGAGCAGATCAGGCCTCAGTGGGCTGG |

TABLE 4C-continued

| SEQ ID NO | GENE NAME | SEQUENCE |
|---|---|---|
| | | GGCCGGCCACATCCACCGAGGTCAACCACAGAGGCCGGCCACAGGTTCTAGGCTTGGTACTGAAATACCCCTGGGAGCTCGGAAG<br>GGGAGTTGAGATACTGCAGGGCCCATAGGAAGAAGTCTTGGGAGGCTCCACCTTTGGGGCAGAGGAAGAAGTCTTGGGAGGCTCC<br>ACCTTTGGGGCAGAGCAAGAAGAGGGCGGAGGGCAGAGGCAGCGAGGGCTCATCCTCAAAAGAAAGAAGTTAGTGGCCCCTGAAT<br>CCCAGAATCCGGGGTGCACGGCTGTTCTGGGGGCCGCTAGGGGACTAAGAGGATCGGCCGAGGGCTGGGCTGGAGGAGGGCAGCA<br>GGGATGGGCGGCGAGGGTGAGGGTGGGGCTTCCTGAAGGCCTTCACCTGCGGGGACCCCGGCGAGCCCCTCAGGTGCCACAGGCA<br>GGGACACGCCTCGCTCGATGCGTCACACCATGTGGCCACCAGAGCTGCGGGAAAATGCTGGGGACCCTGCATTTCCGTTTCAGGT<br>GGCGAACAAGCGCCCCTCACAGAACTGCAGGTAGAGACGGGCCCGGGGCAGACGCAGTGAGGCGGTGGGCGGGGCCCGGGGCAGA<br>TGCAGTGAGGCGGTGGGCGGGGCCCGGGGCAGAGGCAGCGAGCGGTGGGCGGGGCCCGGGGCAGACGCAGTGAGGCGGTGGGCGG<br>GGCCCGGGGCAGAGGCAGCGGGTGGTGGCCGGGGCCCGGGGCAGACGCAGTGAGGCGGTGGGCGGGGCCCGGGGTAGTCGCAGTA<br>GGTGGTGGGCGGGGCCCGGGGCAGACGCAGTGAGGTGGTGGGCGGGGCCCGGGGCAGACGCAGTGAGGCGGTGGGAGGGGCCCGG<br>GGCAGACGCAGTGAGGCGGTGGGCGGGGCCCGGGTCAGAGGCAACGGGTGGTGGGCGGGGCCCGGGGCAGACGCAGTGAGGCGGT<br>GGGCGGGGCCCGGGGCAGATGCAGTGAGGCGGTGGGCGGGGCCCGGGGCAGATGCAGTGAGGCGGTGGGAGGGGCCCGGGGCAGA<br>CGCAGTGAGGCGGTGGGCGGGGCCCGGGGCAGACGCAGTGAGGCGGTGGGCGGGGCCCGGGGCAGACGCAGTGAGGCAGTTGCCA<br>GCCTCTCTCAGCTGCCTCATGGGATTCGCACTGCAGCTGCGGCCCTGGCGCGACAAGGGCTGGACTTGGCCAGCGGGACGGTCCC<br>TCACGGCGCTGAGGCCCACACTCTGCGTGGAGCCTCCCCGTGCCCAGGCTACCCTGCAAGGTCCTCGGAGAGGCTTCCTCCAGCC<br>CCAGCCCCCACACAGCTCCGGCCCAGGCCCGCTCTTCCCCATCCCAGTTGCTTTGCGCTGTATACGGCCAGGTGACCCCGAGCCG<br>GCCCTGAGCCCTCGTCCCGGCTTCCTCCCCTGTAAGCTGGGTGAAGGACTCCATGGCACCCACCTGAGAGGGTTGTGGCGAGGCC<br>CAGGCCCCTCGTGCCCACACGGCCGGCGGCCCATGCCTGGCAGGGGCTGGGAGGAGGCTGGGGCGACCAGAGGGGAGCGGCCTGT<br>CCTGGAGGAGGCCCAGGGACCCTGGTGAGAGGGTCTCTCCCAAGTGCTCTCTATGGGACCCCCTTCCTCTGCGCCCGTCCTTCAC<br>GGACCTCTCCGGGTCACCCCTGGGCTGCACACTGGGTTCAGGGGGGCCTTGAGGTGGGGCCCCTGTTCCCAAGTCCCGGCGGGGT<br>TTCTCCTGAACCTCAACCCATCCTCACCTGCGGGCATTCCCATCCCCCAACGCCTGGGTCACCAGGATTCCAGGCAGGAGGGGCG<br>GTGGGGGTTACCAAGGCCCGGGTTGCCATGCAGAACCCCCAGCCACCACGCAGACCCCCACGGGGCCCAGGGAAGCTCCTGGTCT<br>CACACTGCACCTCACACTTCCTGTGGGGGCAGACTCCAAGGTCCCGGCCTCTCATCTTGTAGAAACTGAGGCACAGGAGGGACAC<br>ACACTCCCACGGCCGGTCACCGTGGCCCCCACACCTCCCACTGGACTGACACCTGGCCAGGCTCCGGACACCCGTGGCACAGCCT<br>CAGCCCCTGCGGCCCCTGCTCCGTGGCCCCCAGGCCCCAGCTCCCATGTGCACGTCCTGCCTCAGGCCTGGAGGCCCCTCGGCCC<br>CAAATAATCAGACAATTCAACAGCAAAACTACTTTTTTCAGGCTGGCAGGACTCTGGGCAACCCCCTGCAACAGCCCCCTGCCCT<br>ATCACAGCCACCCTTGCCTCCCAGGCACGGAGACCCCACCATCAGGTCCCAGCCTTGGTTCATCCCCAAGCACCCTGTGTGTTGG<br>GATGGCGATGCTGGCTGAGCCCCTGCATCC |
| 253 | chr21:<br>46280500-<br>46283000 | AGGGCGTTTGGGAACACCCCTCCCGGAGGGGTGAGGCGGCCCAGCCTGCGGCTGCCAGAGGACACAGGTTCTGCTGCGGAACCTG<br>CAGACATGGCCATAACAGGCCACAGTGCTCGGGCCCACACAGCCTGGACCCACATGGCCCTGTGTCACCTCCTCAGGGGCAGGCT<br>TCAGGGCCTCGACCCTAGAGGCTGCCCCTCGGTTCTGCTCCATGGACGGCGCAGGCAGGCCCAGGCCTGTGACGAGTTCACGGAA<br>GCTCCAGGATGACCCCCGCTCTGCGCCCTCCTCCAGCATTCCAGACCACAAACCACTCTGGGCTAAAACGAGGCATCGCCAGAGC<br>ATCCCACTTCCTCGGAAAGCTGCGGTCTGGGGACGCGTCTTGGCCCTGAAGAGGCTCCAGATGGCTCCCATCAGGCCTCTCCGCC<br>TACGTGCGGCCGACATGGAGTGACAGAGCGTCGGGGACACAGAATTCAGAGCTGGGCCTGGGGCTGCTTTGAGATACTGATGGCT<br>GCCAGGGGGCACAGAGACCCGTCCTGCAGACAGGGCTGTGAGGGCCACAGGGGGCCTCGGGGAGAGGCAGTGGGAGGGAGGACAG<br>TGGGGGCCTCCAGCTGGGTGAGCAGCTGGAGCGAGGGGGGCCCGGGGCTTGTGATGGTGCTGCCGACCCTAGAGGTGCCGGCCCC<br>ACGATGGAGAGCACGTAGTGCCCCCCGGGAGTCAGGAGGCCGGGCCTGACCTCGGGGGCTGCAGCCAGGGGAGGCCGGCACCCCA<br>GATAACCCCCAAAGAACTGCAGGCCCTGAGGCGAGGCCAGAGTGGGGGCGGGGGCAGGTCCCAGCCGAGGAGGTGCTCCGTGCTG<br>CCTCAGCAGAACCCATGATGGGCTGGCCCAAGGCTCTGAAGGTGGAAAGGCCTCACACATTCTGCCCCGGCTGACGCCTTCCTTG<br>GGCCAGTGCTCGGGGGTGTGTAACAAACGCCAAGACGCATTGTAAAGAAGGAAGCCTGCGTTTCCATCACCGGCTTAATATCAAA<br>CAAAAGTGCAATTTTGAAAATGTAGTCCAAGGTTTTCTGTGGTGCGGAAATGGCCAGGCCAGACCTCCGTGGGTGGTCCTTCGTG<br>TCCACGTCAGCGCCCTACATCCACACTGTGGGCACCATGACCTCACATGCGGAGCGGAGCAGGGCCGGCGCCCGGAGAGCCAGGC<br>TGGTCACGAACGAGGCCTAGAGGGCGTCAGGCCCCAAAGCACTCACAGGCTTCTCCTCTGTCCTCGGGGCCTTCAGACACCTGCA<br>TGCGCCGATTCAGCCACCCGCGCGCGCCGATTCCCCTGGCCATGGGGTTTCCAAAGTGTGTGCTCAGAGGACAGTTTCCTCCAGG<br>ATGACCTGTCAGTGGCTCTCTGTGCCGGGGACGTCGCGTGCTGGGTCCCGGTCTGAATGCTTCCTAACGATTTACCCAGTTCCTT<br>TTCTCCACTCAGGAGGCGTTTGCTGAGAGGCACAGGCTGAGCCCCCGTGCTGATGCCACGACCGAGGGAACGGGTCTCCCTGTCG<br>GCGTGAACTGACCCGGCCAGGCGTCCACTGCCACTCGGACTGTCTCCCAGGCACGTGGCGCCCACACGGGCAGAACACGCCCTCC<br>ACACACGCGGCTTCGGGCAGAACACGAGGCGCCCTCCACACACGCGGCTTCGGGGCTTGTCATGAAAAAAGCTGAATGCTGGGGG<br>TGCAGCTTTCACCAACAGAATCCCGTTTGGAAGGGACGCGGTGAGACATGATCCACCCTAAGTTGTGATCCTGGGTGAGCCGCCG<br>TCCACACCCTGCTGAGGGTCCCTTCACCCACTTTATTCTCCAGAAAACCCTGCCCATCAGGGCTGAGTCCCACGCCTTCCCTCTC<br>CGTCCAGGCCTGGCTTTGACCTCTGGGGTCGTGTGGGGCACAGGGGACACCCTATCCAGGCAGAGGCCCTACGGCTATCTGGAGG<br>AAGTGGTGGGAGCTGGGCTTCTGCCTGGAGGATGCACCCAGAGGGGTCACAGTCCACACAGAGACACACGGGTGCCTTCCAGATG<br>GCTGAGCCAGTCCAGCCCAGAAGGGCCTGGGGGTTGGGGGCTGCACCTGGCCTGTCCCCACCAGCAGGGCTCAGGGCTTCCCAAG<br>GTGTGTGGGGGACGGGGCAGCACCTCTCAACCAGGTCACCTGAAACCCGAACTGAAAGGCATCCTAAGTTAAGACATTAACTCCC<br>ATTGTCAAGGTGCCATCGTCAATTCTGTCTCCAAATCCTTCTTTGTTATTTCATGTATTCACAGAGTGACGCTCCGTGTTTCGTT<br>CAGCCTGCAGGCCTGCAGAAGCTGCATCTCGGGATGGCCAAGAGCCCGGCCAGGCCCCACGGCTGCACCCAGGACGGGATTCATG<br>CCCCATGCCTGGCTTCTCACGACCACAGAGTGCCTTTCCCGGGACTGGATGGAGGCAGAGTGAGAGAAGAGCCTGGAGCAAGTGT<br>TTTGGACCACAGTGATCAAACACGGAGCCCGTGGG |
| 254 | COL6A2 | AAGAAAGGCCAGACCGGGCACGGTGGCTCACGCCTGTAATCCCAACACTTGGGGAGGCCGAGGCGGGCAGATCACCTGAGGTCAG<br>GAGTTCGAGACCAGCCTGGCCAACAGGGTGAAACCCCGTCTCTACTAAAAATACAAAAAAAAATTAGCCGGGCGTGGTGGCAGGC<br>ACCTGTAATCCCAGCTAATCGGGAGGCTGAGGCAGGAGAAAATCACTTGAACCTGGGAGGCGGAGGCTGCAGTGAGCTGAGATCG<br>CGCCACTGCACTCCAGCCTGGGTGAGGGAGCGAGACTGTCTCAAAAAAAAAAAAAAAAAAAAAAAAAAAGGAAAGAAAGGCCCGG<br>TGAGATGCTTTCTCTTAAACACGGCCCTGCACGTTGAGTTGCTGCCTCCTGTGGCCTATTTCACGTTTATGCAAAGTCGGGCGCC<br>TGATGCGGGGCTCACCCGCCACAAGCAGGGGTCCTGGTGCTGCTCATGGAAGGGGCCCTACCCAGCCCGCGGGGCACTGGCTGGG<br>ACGGGGCTGCCCAGGTCCGCCCAGGATCCAAACACCCAGCCCCGCCCAGCGGCCCTTCCTGGCCTGCAGTGGAGGCTGTAATGGG<br>CAGGGGTGGTGGGAATCCCAGCTCACAGGGCGCCTGCTCTTAGAAGGGCGGCATCTGGGTCCAGAGGTCAGAAACGTCAGATGCC<br>CATCCCAGAAGTGGCGGGGA |
| 255 | COL6A2 | GGGTGAATGAGTAGATGTATGGGTGAGTAGGTGGGTAGGTGGGTAGATGGATGGGTGGGTGGGCGAGTGTGTGGTTAGATGATGG<br>ATGGCTGAATGGATGAGTGGGGGATGGATGGGTGAGTGGGTGTATGTATGGATGGGTTAGTGGGTGGGTGGATGAATGGATGGG<br>TGCATAAAGGATGGATGGATGAATGAGTTAGTGGGTTGGCAGATGGATGGATGGGTGAGTCAGTGGATAGATGGATGGGTGGGTG<br>GATAGAGGATGGATGGTTGGGTAGGTGATGGGTGGATGAGTGGATAGATGGGTATGTGAGTGAGTGGGGGATGGGTAGGTGGGT<br>GGATGGATGGTTAGGTGAATGAGTGGATGGACAGACGGACAGTGGGTGGATGGATGAGTGAACGGATGGACCGATGGATGAATGG<br>GTGGGTGGGTAGAGGATGGACGGACAGGTGAGTGGGTGGGTGGATGGATAGATGGGTAAGTGAGTGGATAGATAGATGGGTGGGT |

TABLE 4C-continued

| SEQ ID NO | GENE NAME | SEQUENCE |
|---|---|---|
| | | GGACAGAGGATGGGTGGATGAATGGATGGGTTAGTGGGTGGCTGGGTGGATGGATGATGGATGGGTGACTGGGTGGATGGATGGA<br>TGGGTTAGTGGGTGGCTGGGTGGATAGATGGATGGGTGATTGGGCGAATGGGCGAATGGGTGGATGGGTGGGCGTGGAGTTGGTG<br>GGTACATGATAATGGGGTGGAATACCCATGGATTGGAATGAGCTGTTTTGGCTGCTATTTCTGGGACACCCAGCTCTGCCAGGCC<br>CCTACCCCTCTGGTGGGCCAGGCTCTGACGGTGGCCACTCATGGCCTTTCTAGCTCTGGTGCCAGCATAGGGAAGGAGGAGGCAC<br>AGCCTTGTCTTACTCCTTGCACCTGTTAGCCCCCCCCCCGCCAAGGGAGGACCCGTGGTTGGGGACAGCACAGGGGGCCCTGCT<br>GTGTGCAGGGACTGTCCCTGGGGCCACTGAAGCCCACCTGTTCTTGTTCCTTCTCAGGCGGATCCTGGTCCCCCTGGTGAGCCAG<br>GCCCTCGGGGGCCAAGAGGAGTCCCAGGACCCGAGGTAGGTTGGTGGCCAGTCCCCATGCCCTCCCCCCAACCTGCCAGGCCAAC<br>ACACACCCAAGCCTCGTGGTTCTGCCCACGGTGGACCCACGTATCAGTGGGCAGTGGCCTGGGAGAGACTCAGCCACCCAGCCTT<br>GGCCCCAGAGTCTCAGCCTCATCCTTCCTTCCCCAGGGTGAGCCCGGCCCCCCTGGAGACCCCGGTCTCACGGTAGGTGTCACAT<br>GGGGCAGAACCAGTGTCCTTCTCCTGCCAAAACTAGACACCAAGAGCAGCAGGGGTGGGGGAAGGTCAGCTGGCACGGTCAGAGA<br>GCAAGATCAGTGGAGGAGGTCAGAGGGCAAGGTCAGAGAGCAAGCTTGGTTGGGGAAGGTCACAGGGCAAGGTTGGTGGGGGGAG<br>GAGGGTGGCAGCGAGGTTGGTAGGGACAGGACCCGCCAGCCTCCCCGCATGGCTGCCTCCACACGTGGGCTGGAATGTCCCGGGA<br>CCCCCAGGCCAGGACCTTGCTGTGGAAACTCTTCTGGGGCCCCGGGGGGACTACCCTGCCTGCCGTGTGCATTGCAGGAGTGTGA<br>CGTCATGACCTACGTGAGGGAGACCTGCGGGTGCTGCGGTGAGGCACTGCCCACGGCAGGGTCGGGGCCCATGCACCGGGTGGAG<br>GGCGGGAGTGCAGCAGGGCTGGGTCATCGCTGGGTCCTGCATGTGCACGTGACCCTAGGGTCTGAGGTCTCCCCGGTACCCCCCG<br>ATGACCCTGCCACCCCCCCAGACTGTGAGAAGCGCTGTGGCGCCCTGGACGTGGTCTTCGTCATCGACAGCTCCGAGAGCATTGG<br>GTACACCAACTTCACACTGGAGAAGAACTTCGTCATCAACGTGGTCAACAGGCTGGGTGCCATCGCTAAGGACCCCAAGTCCGAG<br>ACAGGTCAGCGGGGCAGGGGCGGGTGCAGCATTGCGGGGGGCCGGGCGGGGCGTGGGAGGCGATGAGATGGGAGAAGTCCAGACG<br>CGTCCCTCCAACGAGGGCCTCTGCATGGCTGGGGATGCCCCAGACCCCGAGGCCTCTGGCAACGACCTCACGCGTGCGGCTTGCA<br>GGGACGCGTGTGGGCGTGGTGCAGTACAGCCACGAGGGCACCTTTGAGGCCATCCAGCTGGACGACGAACGTATCGACTCCCTGT<br>CGAGCTTCAAGGAGGCTGTCAAGAACCTCGAGTGGATTGCGGGCGGCACCTGGACACCCTCAGCCCTCAAGTTTGCCTACGACCG<br>CCTCATCAAGGAGAGCCGGCGCCAGAAGACACGTGTGTTTGCGGTGGTCATCACGGACGGGCGCCACGACCCTCGGGACGATGAC<br>CTCAACTTGCGGGCGCTGTGCGACCGCGACGTCACAGTGACGGCCATCGGCATCGGGGACATGTTCCACGAGAAGCACGAGAGTG<br>AAAACCTCTACTCCATCGCCTGCGACAAGCCACAGCAGGTGCGCAACATGACGCTGTTCTCCGACCTGGTCGCTGAGAAGTTCAT<br>CGATGACATGGAGGACGTCCTCTGCCCGGGTGAGCGTGTGGGCGCGGGGCAGTCGGCCGAGGAGCAGCAGGCCCCAGCCGCTGTC<br>TAGCGTGAGCCCCAGGGACACCCCTCACCTGAGGGATGAATGTGCAGCCCAGGATCTTGGGCTGTGGGTGGGAAGGGGTCGGGCC<br>CTCTCGGGGCTGCAGGGCAGAGGCCAGCTGCACCCTGAGCCTGTCTAGGCAGATCAGTGAACGGCCGCTGAGGGTTCGCTAGGGA<br>CTGACCCTGGCCTGGCCCGGCCTCTCTCCTCTCTTCCAGACCCTCAGATCGTGTGCCCAGACCTTCCCTGCCAAACAGGTAATGC<br>AGGGCACCCTGAGCCACCACCCCAGACTAGCAAAGCAGCCCTGGTGTCCTTCCTCCTCGAGGGCCGGGCTGGGGGAGGGGCCGTG<br>CAGGGACCCGGGGGGCGGCGGAGCCACTGCGGAGGCTGCTCCTTAGGGAGATGGCCCCAGGATGGCAGCACAGGGGAGGAGGGGC<br>TTGGGGAAGGCAGGCTCCCAGGAACGCAGGAACAGCATCACGAGGCCATGAGGTGGGTGCTGCTAGCCTGGCGCTGTGCTCGGCA<br>TGTGGCCACTGGTCTTGAAGGCCCACCATGGGCCTTGCAGTCTCCCTCAGCTGCCGCCCAGCTCCCATGGGCTGGCCGTGCATGT<br>GCCACTCGGAGGAAGCCCTGGATTCAGTGAGTGAAACCATCCCGGGGTGGAAGCACTGACACCCCCCAGCACCAGCAGGTCTTGC<br>TCCAACCCTGGCCTGCCTCGGAGCTGCAGCTGCGGCTCTCACATCTCTGGGAGTGGGGGAGCCCATGTCCCGGATGTGGCCCACG<br>TGGGTGTGAAGCTGGAGCTGGGGGTGCCGTCCAGGCTCTGCTGGACGTGGTGCTGCCCCCATGGTGCACTGCTGCACCGTACCTG<br>GGCCCACAGGAGGTCCCCGGGGGCGTTAGGAGCTGAGTCCCCCTCAGTGAGCCGTCCCCTCCAGGAGTGTGAGGGTAGGGATGCC<br>ATGGAGACAGGGTGGGAGGGTCCGACCTGGAGGACCACAGGGAGGAAACCTCAGGGTCTGCGGTACGAAGTCAGCGCTTCCTCAG<br>CACGCGGGTCGCGGTGTGCGTTCGGGCGTTCCATGGGGAGCTCCCGGTGGGTGAGCTGGGCCACTGAGCACATTCACAGGCCCTG<br>AGGCTGCCCCAGGGGAGGAGCCGTGGACTCAGAGCCGAGGTTCCCCATACGTGCTGCGACAGAGAACCTAGGGCTTGCACCTGGG<br>TCTGGCTGCCCTTCAGCAGGCGGGCAGCCTCTGGCCCCACAACAGTGGGCTGTGCTTCTGCCGCCAAGGTGCAGGCGTCCTCCCC<br>CAGGGTCCACATCAGCAGCAGGGGCACCTGGACCCTGAGGGCAGGAACCAGACCTTGGCTCCTCCACCCACCCCCTCGTTCCTGA<br>TGGGGCAGGGAAGTCTCGGGACCCCATGATGGGCGACATGGCGATGGTCACTGTGGGTGCTTTGCTATCAGGTGGGGGGCCTTCC<br>TCTCCACTCTGGGTCCAGTGTGAGTGGCCGCTATGGCTTCCCCTCCACTCCAGGTTCTATCGTGAGTGGGTGGGTGCTGCGTCTG<br>TGGATGTCACGTGACCTTTCCTCTTTAGCCTATCATTGTAGTTGGGAGTTAGTTAGCCCGTTGAGCGTCATTGAATTTCCAGTGT<br>TGAGCCAGCCCTGCGTGCCCGGGATAAACCCACCTGGCCGTGGTGTGTGGCCCTGTTTATGCACGTGGGCCCTGATTCGCTGATG<br>CCTGCCTGAGGGTTTGCGCTTATCGGCGACATCAGCCTGCACTTTTCTTTTCTCGTGATCTCTCTGGTTCTGGCCTCAGGGTGAC<br>GTGGGCCTCGTAGGGTCCTGTGGTGGCTCCTCCCCAGACGGTGACATGGAGTGAGCCCATTCTCCCTCCTGGGAGTGGGTCACTC<br>AGGCCACCAGAGCACCACAGGGAAAGCAGCCAGGGAGGACACGGAGGCCCTTGAAGCTCTGGCCTCTTCTGAGGCCTCCAGGACC<br>TGACAGTGAGTGGGAGCAGCCCTGGCAGAACCCCTCCCCTCCTCTCGGCCGCCCTGACACCTCATCCCCGACACTCAGAGCTCAT<br>CCTCCTTCCCAGCTGTTTCCAATTTCAAAGTGAACTCGACCTTGTGGCTCCAGGAGATGCAGCAGGGACAGTGTTAAATCGGCTT<br>TCACCAGCCCACACGGCCAGGCATCCTCCTCGGCCCTCCTGGGCACTGGGTGGACACCACTGGCTGTGGCCTGGCCCTGGCCTTC<br>TCCAGACAGCCCTGTCCACCCCAAAGCCCAGCCACCCTGGGCCTGCAGCAGGCCTGTGGAGTTCTCAGTTGCGTGGGGACCAGAG<br>GGTGCTGGAGAAACAAACCAGACGCAGCTGAAGGCAGTCAGGGCAGGGCGCAATCAGCGATAAGAGCTGCATAGGGGCCACAGCG<br>TAACCTGAGCTCCAGTCGGTGGAAAGAAAAGGCAGAGACGTTGCAGAGGCCAGGTCTGCTCAGGGGAAGACAGTTCTGGGTGTAG<br>AGGACTCACATCCCAGAGAGGCTGAGGAAGGGTTTACCACCGCAAGCTTTCTCAGGCGGGCTCTTGAGGGGTGGCTGGGGTCTTC<br>CTGGCGACGGGCCTGCGGCACTGGAAGCCCTACTGGAGTTTGGCCTGTCTCCGGCACAGGTTTGGACGGAGCTGTTTTGTGCTGA<br>AAGGTTTTCTCGGGGTCCGTGGTGTCCCCCAAAGGTGCCACCGTGCGGGTCTCCTAGCTCCCTGCCAGCTTCCTGTCCCTGTGCT<br>CACTGCCCCCACGCCTCCTGCCAAGGCCGAGCCACACACCCGCTCCACCTGCATTTCCTCTACCGACTCGCCAGCCCAAATGCCG<br>CTCTTCACTCTGGCCTCGCTGAGCGGCTGCCCGAGGAGGAGCTCTAGGCCGACGCCCACCGCAGGCCTTACAGTCTTCTCTGGAC<br>GCTCCCTTGCAGATGCACCGTGGCCTGGCGGCGAGCCCCCGGTCACCTTCCTCCGCACGGAAGAGGGGCCGGACGCCACCTTCCC<br>CAGGACCATTCCCCTGATCCAACAGTTGCTAAACGCCACGGAGCTCACGCAGGACCCGGCCGCCTACTCCCAGCTGGTGGCCGTG<br>CTGGTCTACACCGCCGAGCGGGCCAAGTTCGCCACCGGGGTAGAGCGGCAGGACTGGATGGAGCTGTTCATTGACACCTTTAAGC<br>TGGTGCACAGGGACATCGTGGGGGACCCCGAGACCGCGCTGGCCCTCTGCTAAAGCCCGGGCACCCGCCCAGCCGGGCTGGGCCC<br>TCCCTGCCACACTAGCTTCCCAGGGCTGCCCCCGACAGGCTGGCTCTCAGTGGAGGCCAGAGATCTGGAATCGGGGTCAGCGGGG<br>CTACAGTCCTTCCAGGGGCTCTGGGGCAGCTCCCAGCCTCTTCCCATGCTGGTGGCCACCGTGTCCCTTGCTGCGGCTGCATCTT<br>CCAGTCTCTCCTCCGTCTTCCTGTGGCCGCTCTCTTTATAAGAACCCTGGTCATTGAATTTAAGGCCCACCCCAAGTCCAGAATG<br>ACCTCGCAAGACCCTTAACTCACTCCCGTCTGCAGAGTCCTTCTTTGCTGCATCAGGTCACCCTCACAGGCTCCAGGGTTTGGGT<br>GTGGAAGTCTTTGGAGGCCCTTACTTAGCGGCCCAGCTGGGCTGCCGTGCGTCTGGGATGGGGCTGAGGGAGGGTGCTGCCCAGG<br>TGCTGGAGGATGTTCCAGCACCAGGTTCCAGCGGAGCCTCGGAAACAGGCCCCAGAGGCTGGTGAGCCTCGCTGGGTGTGGGCAC<br>TAATCCCGTGCATGGTGACTCGTGGGCGCTCACGGCCCACCTGGTGGCAGGTGAAGGCTTCCGGTTGGGCAGCAGATAGTCCTGG<br>GGGAAGCTGGCAGTCCTGGCACCATGACGTATCTGGGCTGGTGTCATGCACAGTAGGGCGAATGGCCACAGCTGCCTGCCAGCAG<br>CCCTGATCCCGGGGTGTCTGCACCCTTCCAGCCCAACCTCTGGGTCTCCAAAAGCACAGTCGGGGGAGCATCCACCAGGCACAAC<br>CTCTGCGGTCCTCAGAGGACTGAGCAGAGAATCCCAGGGTCCACAATGTTGGGGAGCGGCAGGGATCACCATCCAAAGGGAGCGG<br>CCCCCACGGCGAGCTGACCCCGACGTTCTGACTGCAGGAGCCCTCATCCAGGCTGGGCTCCTGCCGGGCACGGCTGTGACCATTT<br>CTCAGGGCCAGGTTCTCGTCCCCACACCCACTGCACAGGGCAGGCCAGGCTGGTCTTCCCACTGTGGGGATGAAGGATCCTCCAC<br>AGGAGGAGGAGAGCAGAGTCCACAGACATCCCAACAGCCTCAGCCTCCCTGTGCCTGGCCGGCCCCCACAGCTTCCCCGTCTCCT |

TABLE 4C-continued

| SEQ ID NO | GENE NAME | SEQUENCE |
|---|---|---|
| | | CCAGGCCCCACAGACACTGATGAATGGACAGAGACCCCCAAAACCAGCTGCCCCTTGCATGTCTGTCTCCATATGTTTGGTGACA<br>GCAGTGAAAATGTTATTAGTTTTGAGGGGGTTTGGGAAGCCCAGCGGTACCTGAGGAGTTTCTGGACATTTAAGCCGGTTCCTAG<br>GTGTGGCCTTAACAGGGAGGCTGCCCTTCCTTTCACTGAATGAGCTGCGTCACTCATAAGCTCACTGAGGGAACCCCATCTGCCA<br>GCTCGTGCGTGCTCAGACGGCGTCCATGTCTCAAGCGTTCTGTGAAGGCTGCGGTGCAGCGTGAGGTCACCCTGCTGTGTTCAGA<br>GCTTTGCTCACTGCCTGCGGGGCTGGACCGTTGCACCTCCAGGGCCCCCAGAAACCGAGTTTCGGGTCAGGGTCCTCTGTGTGCA<br>TTCCTGGGGGTCCATGTACCAGCTGTGACGACGTCCAGGGGTTGGGCTGAGAAGCAGACACCCTTGGGGAAACTGGCTCTGTCCC<br>TCCCCTCCCCCATCCCAGGAGCTGAGGTCTTGGTGAGGCCACAGGGCCAGGTCCACGCAAGGACTGTCCGTGTCCTGTCCTGTGG<br>TCTCTGGCCCCACGTGACACCCACACGTGTGGTAGGCAGCCTGGCCTGGGTTGTGGCTATGGCCAGGCCCCCAAGCTGTCCCCGA<br>TGCCCAGGGCTGGTGACCACCCAGGCAGGTGGGGGCCCCACTTGGTAACAGAGTCATAGGGCAGAACCCACCTGGGCTGCCACAG<br>AAGGTCTGGCTGCCCCTGTGCCCACTGCTCCCCACCATGGCCAATCAGAAGAGTCAGGGGCTCCTGGTCTTTCCGGGAGGGACGT<br>GGCCCAGCCAGCTCTAGGTGTTCTGAGCAGCTCTGGGACCCAGCGATTGAGGGGTCAGGCTGGGGGTGTCAGAGCCAGGGTCCTC<br>CTTAAGTACCTCCCACACTACACAGACAGTGGCCCTTTTGTGGGCAGCAAATTCTTGAGCCATGAAAGGATGCTTTGGGCCCCTT<br>CCCTCCCAGGAGGGCAGCCTGTGCAGGGATGGTGCTCAGCAGGTGGACAGGGCCTGGGGCCTGTGTCAGGGTCTCAGGCCTGGGA<br>GCACCAGCAGAGGAGATGGCGGCTCCCAGCAGTGCCGCCTGAAAGTGTCTTGGGCTAAGGACCCACACCCAGGGCTGCCCTGCAG<br>AAACGCCCCCGCAGAGCCCAGTGGTCTGTGAGGTTGCAGGCAGGGTGCGAATGGAAGGGCACAGGTGCGGGGCTGGCACCTGCCC<br>GGTCCTGCCCACCTCCCCTCCGCCCAGCCCGCACCTGCGTCTCCCCACAGAGCTGTCCGTGGCACAGTGCACGCAGCGGCCCGTG<br>GACATCGTCTTCCTGCTGGACGGCTCCGAGCGGCTGGGTGAGCAGAACTTCCACAAGGCCCGGCGCTTCGTGGAGCAGGTGGCGC<br>GGCGGCTGACGCTGGCCCGGAGGGACGACGACCCTCTCAACGCACGCGTGGCGCTGCTGCAGTTTGGTGGCCCCGGCGAGCAGCA<br>GGTGGCCTTCCCGCTGAGCCACAACCTCACGGCCATCCACGAGGCGCTGGAGACCACACAATACCTGAACTCCTTCTCGCACGTG<br>GGCGCAGGCGTGGTGCACGCCATCAATGCCATCGTGCGCAGCCCGCGTGGCGGGGCCCGGAGGCACGCAGAGCTGTCCTTCGTGT<br>TCCTCACGGACGGCGTCACGGGCAACGACAGTCTGCACGAGTCGGCGCACTCCATGCGCAAGCAGAACGTGGTACCCACCGTGCT<br>GGCCTTGGGCAGCGACGTGGACATGGACGTGCTCACCACGCTCAGCCTGGGTGACCGCGCCGCCGTGTTCCACGAGAAGGACTAT<br>GACAGCCTGGCGCAACCCGGCTTCTTCGACCGCTTCATCCGCTGGATCTGCTAGCGCCGCCGCCCGGGCCCCGCAGTCGAGGGTC<br>GTGAGCCCACCCCGTCCATGGTGCTAAGCGGGCCCGGGTCCCACACGGCCAGCACCGCTGCTCACTCGGACGACGCCCTGGGCCT<br>GCACCTCTCCAGCTCCTCCCACGGGGTCCCCGTAGCCCCGGCCCCCGCCCAGCCCCAGGTCTCCCCAGGCCCTCCGCAGGCTGCC<br>CGGCCTCCCTCCCCCTGCAGCCATCCCAAGGCTCCTGACCTACCTGGCCCCTGAGCTCTGGAGCAAGCCCTGACCCAATAAAGGC<br>TTTGAACCCATTGCGTGCCTGCTTGCGAGCTTCTGTGCGCAGGAGAGACCTCAAAGGTGTCTTGTGGCCAGGAGGGAAACACTGC<br>AGCTGTCGCTCGCCCACCAGGGTCAATGGCTCCCCCGGGCCCAGCCCTGACCTCCTAGGACATCAACTGCAGGTGCTGGCTGACC<br>CCGCCTGTGCAGACCCCACAGCCTTGATCAGCAAACTCTCCCTCCAGCCCCAGCCAGGCCCAAAGTGCTCTAAGAAGTGTCACCA<br>TGGCTGAGGGTCTTCTGTGGGTGGACGCATGATTAACACTAGACGGGGAGACAGCAGGTGCTGAGCCTGTTGTGTTCTGTGTGGA<br>GATCTCAGTGAGTTTTTGCTGTTCAGACCCCAGGGTCCTTCAGGCTCAGCTCAGGAGCCCCACAGTGAACCAGAGGCTCCACAGG<br>CAGGTGCTGACCTGACAGGAGTGGGCTTGGTGGCCATCACAGGGCACCACAGACACAGCTTGAACAACTACCAGTATCGGCCACA<br>GGCCTGGAGGCATCAGCCGGGCCATGCTTCCTCTGGAGGGCTAGAGGAGGACTAGAGAAGGGCCTGCCCCGGCCTCTCCCCAGCA<br>TCCCAGGGTTCCTGATCTCCTGGATAAGGATACAAGTCACCACACTGGACTGGGGCTCAGCCTGCTCTAGAATACCTCACCTAAG<br>TCACAGTGGACCAGGCTCAGCCTGCTCTAAGGTGAGCTTACCCGAGACACTGGACCAGAGATCAGCCTATCCTGGGATAAGCTCA<br>CCCGAGTCACACTGGACCAGGGCTCAGCCTATTCCGGGATGAGCTCACCCGAGTC |
| 256 | C21orf56 | GACACTTCCATGACTGCAGCTGACCAGTCCACCTGCCAGCGGTTGACCACTCCCACTTCGCCAGCGACCGAAGGGGAGGGGAGGG<br>GCCTCACCTGAGGGCAACAGCAGAACCCACCACCTGGTCTTGCTTTACTCAGACCTGAGGGTGTGAAAGGTGCCCGTGACCTCCC<br>GCATCAGGGAGCTGGCCGCCACCCTCGACTCCCGGGGAGCAGGCGTCCCGCGACCCCCTCATCTACCAGGCCATCTGAGCTGGGC<br>GGCGCCTCACCTCCGCTCCCGGGGGAGCCGGCCTCAGGGTAGGCATGCGCCCTGGGTGGGAGCAGGTCGTGGCCGCCGCCCTCCT<br>GGCAGCTCTGGCTGAGCAGCCGCCGCAGCATCTGATTCTCCTTCAGGAGGCGCACCTGCTTCTTCAGGTCCGCGTTCTCGCTCAG<br>GAGCCGGCTCATCAGCTCGCCGCCTTCAGCCATGGCGGGTGCGTCCCTCCTTGTCCCTCACGGCTCCTGCAGCCCCATGGAGGTG<br>GGAGCCCAGAGCCCGCAGGCACCACAGAAACAGCCCAGGCACGGAGTTCCGTAGCCACCACCGCCTTCCACGCCTTGTGATGTCA<br>CTGCCCTAGTGATGAGGTGCCCAGCACCCTGCCTGCCCCCGCGATGGCTCATGGCCCCGTTGAGGCAGTGAAGCTGGAGGCCCGT<br>GGCGTGCACAGGCAGCCACTCCCACATTATGACCAGGGCCCGAGAATGCCAAGGACATTAGGCAGCTACGGGATGTAGCGACTGT<br>ACTCCAAGAGGGGCGTCCAAGCCACTCCCCATTGA |
| 257 | C21orf57 | AGGTGGAGGTTGCAGTGAGCCCTCCTCCCCTCCTCCCCCTTCCCTTCCCACCTCCCATGCCCCCCTTTCTTCCTCCCACTCCCCT<br>CCCGAGGCCCCGCTTATTCTCCCGGCCTGTGGCGGTTCGTGCACTCGCTGAGCTCAGGTTCTGGTGAAGGTGCCCGGAGCCGGGT<br>CCCGCCTTCGGCCTGAGCTAGAGCCGCGCGGGCGGCCGGCTTCCCCCAAACCCTGTGGGAGGGGCATCCCGAGGAGGCGACCCCA<br>GAGAGTGGGGCGCGGACACCTTCCCTGGGGAGGGCCAG |
| 258 | C21orf57 | CCTTCCAGATGTTCCAGAAGGAGAAGGCGGTGCTGGACGAGCTGGGCCGACGCACGGGGACCCGGCTGCAGCCCCTGACCCGGGG<br>CCTCTTCGGAGGGAGCTGAGGGCCGCGTTCCTTCTGAAAGCGGGACGCGGGAGGGGTGGAGGCTGCGGGGAGCCGGGGTCGCACA<br>CGAATAAATAACGAATGAACGTACGAGGGGAACCTCCTCTTATTTCCTTCACGTTGCATCGGGTATTTTTCGTTATTGTAAATAA<br>AACGGTTCCGAGCCGTGGCATCGAGAGGGCGTCTGGAGTTCAGGGAACGCGTGGCCCCCGCCCGGGAGCACCGCGCAGCGCTCGC<br>CTCTCGCCCTTCAAGGGGGTCCCTGCCCGGAGCCTGCGCCCCCGGAGAGGAAGGGGCTCGAGGGGCTTGGGTGCCGCAGCGCGTC<br>CTTCCGTAGAAAAGGCTTGCGTCAGTATTTCCTGCTTTTACCTCCTGAG |
| 259 | C21orf57 | CAGTATTTCCTGCTTTTACCTCCTGAGTATTGGAATATTCGAGTAAACCCTGGAGTTTCAGCGCCAGCGCACGCCTCTTCATCAG<br>GGCAGCGCGTCGCGAGCGCGCTGGTTCCCCGGGGCCTCCCGGCCACGGACACCGCTCTAGCCAGGGCCACGGCGAGGCCGCCGAG<br>CAGCACCTCAGAGACCTGCGTGAGTTCTAAAGCCTGGGGCTACTACAATTCTGCTCATCTGTTTGTCCTGTGAAATGATTCAGGG<br>ACATGAAAATGCCTTCCCACTGACTTGCGTCCTGTCTTAGCCTGGACTTGTCCCCTTGGGAACACGGGCCAGGCCCCTCTGTTCC<br>TGAAGT |
| 260 | C21orf58 | ATGTCTGCAGGGAAGAAGCAGGGGGACCCTGAATAAAGTTTCCGTTTTTCCTATTTGTTAAAGTGATAGAGCATTATAGGACCAG<br>AGAACAGGTGTGTCTGTACACTGTGCAGGTCCCCGGGGCAGGCTCTGAGTCCGTCTGCACACGGTGCGGGTCCCCGGGGCGCGCC<br>CTGAGCCCGTCTGCACACGGTGCGGGTCCCCGGGGCGCGCCCTGAGCCCGTCTGCACACGGTGCGGGTCCCCGGGGCGCGCCCTG<br>AGCCCGTCTGCACACGGTGCGGGTCCCCGGGGCGCGCCCTGAGCCCGTCTGCACACGGTGCGGGTCCCCGGGGCGCGCCCTGAGC<br>CCGTCTGCACACGGTGCGGGTCCCCGGGGCGCGCCCTGAGCCCGTCTGTACACGGTGCGGGTCCCCGGGGCGCGCCCTGAGTCTC<br>TACTAAAAATACAAAAATTAGCCAGGCGTGGTGGTTCAAGCCTGTAATCCCAGCTCCTTGGGAGG |
| 261 | PRMT2 | CATACATGGTTATTAGAAAAGGCATCTCATCCAAATGTGGTGGCTCGTGCTTGTAATCCCAGTGCTTCAGGAGGCCAAGGGAGGA<br>GGATTACTTGAGCCTAAGAGTTTGAGACCAGCCTGGGCAACACAACAAGACCTTGCCTCTACAAAAAACTTAAAAACTAGCTGGG<br>TATGATGGTGCACACCTGTAGTCCCAGCTACTTGGGAGGCGGAGGCGGGCAGATCGCCTGAGGTCAGGAGTTCGAGACCAGCCTG |

TABLE 4C-continued

| SEQ ID NO | GENE NAME | SEQUENCE |
|---|---|---|
| | | GCCAACATGATGAAACCCCGTCTCTACTAAAAATACAAAAATTAGCCGAGTGTGGTGGTGCATGCCTGTAATCCCAGCTACTCAG<br>GAGGCTGAGGCAGGAGAATCACTTGAACCCGGGAGGCGGAGGTTGCCATGAGCCGAGATCACGTCACTGCACTCCAGCCTGGGTG<br>ACAGAGCACAAAAGACAGGCATGACTTTGTACTTAACTGCTCAGCTTTGTAATCACTGGGGGCCCAGATGCTCACTTGGATTCTA<br>ACTTTGTTGGCATCTGGGCCTAAAAGCCGTGATGCAGGTGAGCAATGATGCAGAGGGCTCTGTGCGCCTGGCGGGCTCTGTTTGC<br>CTGCTGGGCTCTGTGCGCCTGCTGGGCTCTGTGCGCCCGGGAAGGTGCGGCCACCCTCACGCGGAAGGCGGCCAGCGGATCCCGG<br>TGCGCGCAGCTCCCAGCGCTGGGGTTCCAGCGCCCCGCCTCTTCCTATAGCAACCAGCGGGACCTGCCGTCCCCCGGGGCACCCC<br>GAGGGGTCTGCGCCCGCTTCTTTCCGAAACGGGAAGGCGCTGGGGGCTCGGCAGCCAGAGGGACGGGTTCAGGGAGCGTCCGGTG<br>AGCCTAAGACGCGCCTTTGCCGGGGTTGCCGGGTGTCTGCCTCTCACTTAGGTATTAGGAACCGTGGCACAAATCTGTAGGTTTT<br>CCTCTGGGGGTGGGCGGAGGCTCCAAACCGGACGGTTTTCTCCTGGAGGACTGTGTTCAGACAGATACTGGTTTCCTTATCCGCA<br>GGTGTGCGCGGCGCTCGCAAGTGGTCAGCATAACGCCGGGCGAATTCGGAAAGCCCGTGCGTCCGTGGACGACCCACTTGGAAGG<br>AGTTGGGAGAAGTCCTTGTTCCCACGCGCGGACGCTTCCCTCCGTGTGTCCTTCGAGCCACAAAAAGCCCAGACCCTAACCCGCT<br>CCTTTCTCCCGCCGCGTCCATGCAGAACTCCGCCGTTCCTGGGAGGGGAAGCCCGCGAGGCGTCGGGAGAGGCACGTCCTCCGTG<br>AGCAAAGAGCTCCTCCGAGCGCGCGGCGGGGACGCTGGGCCGACAGGGGACCGCGGGGGCAGGGCGGAGAGGACCCGCCCTCGAG<br>TCGGCCCAGCCCTAACACTCAGGACCGCCTCCAGCCGGAGGTCTGCGCCCTTCTGAGGACCCTGCCTGGGGGAGCTTATTGCGGT<br>TCTTTTGCAAATACCCGCTGCGCTTGGACGGAGGAAGCGCCCACGCGTCGACCCCGGAAACGAAGGCCTCCCTGATGGGAACGCA<br>TGCGTCCAGGAGCCTTTATTTACTCTTAATTCTGCCCGATGCTTGTACGTGTGTGAAATGCTTCAGATGCTTTTGGGAGCGAGGT<br>GTTACATAAATCATGGAAATGCCTCCTGGTCTCACCACACCCAGGGTGACAGCTGAGATGCGGCTTCTCCAGGGTGGAGCCTCCT<br>CGTTTTCCAGAGCTGCTTGTTGAAGTCTTCCCAGGGCCCCTGACTTGCACTGGAAACTGCTCACCTTGGCATCGGGATGTGGAGC<br>AAGAAATGCTTTTGTTTTCATTCATCCTAGTGTTCATAAAATGGAAAACAAATAAGGACATACAAAAACATTAATAAAATAAATT<br>AATGGAACTAGATTTTTCAGAAAGCACAACAAACACAAAATCCAAGTATTGCCATGTCAGCAACACATTCCTACTTTAAGTTTTA<br>TGAAGTTAATTGGAGTAGTGGAGAACAAAAGTGGATGTGGGGCAG |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow.

The invention claimed is:

1. A method for determining the amount of fetal nucleic acid in a sample comprising:

a) contacting nucleic acid from a pregnant female, which nucleic acid comprises fetal nucleic acid and maternal nucleic acid, the combination of the fetal nucleic acid and the maternal nucleic acid comprising total nucleic acid in the sample, with a methylation-sensitive restriction enzyme that digests nucleic acid at non-methylated sites, thereby enriching methylated nucleic acid;

b) amplifying in a single reaction vessel nucleic acid not digested in (a) at loci consisting of a locus comprising a polynucleotide of SEQ ID NO: 42 or a portion thereof and a locus comprising a polynucleotide of SEQ ID NO: 52 or a portion thereof, thereby generating amplification products; and c) determining the amount of the fetal nucleic acid in the sample based on the amplification products of SEQ ID NO: 42 or a portion thereof and SEQ ID NO: 52 or a portion thereof in (b).

2. The method of claim 1, wherein determining the amount of fetal nucleic acid comprises use of a PCR-based method.

3. The method of claim 2, wherein the PCR based method is real time PCR.

4. The method of claim 1, wherein determining the amount of fetal nucleic acid comprises use of one or more processes selected from mass spectrometry methods, RT-PCR, digital PCR, array-based methods, sequencing methods, nanopore-based methods, nucleic acid-bound head-based counting methods, competitor-based methods and methods for separating nucleic acid using agents that bind nucleic acid based on methylation status.

5. The method of claim 1, wherein determining the amount of fetal nucleic acid comprises introducing one or more competitors at known concentrations in (b).

6. The method of claim 5, comprising determining the absolute amount of fetal nucleic add in the sample.

7. The method of claim 1, further comprising determining the amount of total nucleic acid present in the sample.

8. The method of claim 7, comprising determining the concentration of fetal nucleic acid in the sample by comparing the amount of fetal nucleic acid to the total amount of nucleic acid.

9. The method of claim 8, wherein the concentration of fetal nucleic acid is used in conjunction with a diagnostic method to determine a fetal trait, wherein the diagnostic method requires a concentration of fetal nucleic acid to meet certain clinical sensitivity or specificity requirements.

10. The method of claim 1 further comprising:

i) determining the digestion efficiency of the methylation sensitive restriction enzyme; and ii) determining the presence or absence of Y-chromosome nucleic acid and if present, determining the amount of Y-chromosome nucleic acid for a male fetus.

11. A method for determining the amount of fetal nucleic acid in a sample comprising:

a) contacting nucleic acid from a pregnant female, which nucleic acid comprises fetal nucleic acid and maternal nucleic acid, the combination of the fetal nucleic acid and the maternal nucleic acid comprising total nucleic acid in the sample, with a methylation-sensitive restriction enzyme that digests nucleic acid at non-methylated sites, thereby enriching methylated nucleic acid;

b) amplifying in a single reaction vessel nucleic acid not digested in (a) at loci consisting of a locus comprising a polynucleotide of SEQ ID NO: 42 or a portion thereof; a locus comprising a polynucleotide of SEQ ID NO: 52 or a portion thereof and a locus comprising a polynucleotide of SEQ ID NO: 163 or a portion thereof, thereby generating amplification products; and c) determining the amount of the fetal nucleic acid in the sample based on the amplification products of SEQ ID NO: 42 or a portion thereof, SEQ ID NO: 52 or a portion thereof, and SEQ ID NO: 163 or a portion thereof in (b).

12. The method of claim 11, wherein determining the amount of fetal nucleic acid comprises use of a PCR-based method.

13. The method of claim 12, wherein the PCR-based method is real time PCR.

14. The method of claim 11, wherein determining the amount of fetal nucleic acid comprises use of one or more processes selected from mass spectrometry methods, RT-PCR, digital PCR, array-based methods, sequencing methods, nanopore-based methods, nucleic acid-bound bead-based counting methods, competitor-based methods and methods for separating nucleic acid using agents that bind nucleic acid based on methylation status.

15. The method of claim 11, wherein determining the amount of fetal nucleic acid comprises introducing one or more competitors at known concentrations in (b).

16. The method of claim 15, comprising determining the absolute amount of fetal nucleic acid in the sample.

17. The method of claim 11, further comprising determining the amount of total nucleic acid present in the sample.

18. The method of claim 17, comprising determining the concentration of fetal nucleic acid in the sample by comparing the amount of fetal nucleic acid to the total amount of nucleic acid.

19. The method of claim 18, wherein the concentration of fetal nucleic acid is used in conjunction with a diagnostic method to determine a fetal trait, wherein the diagnostic method requires a concentration of fetal nucleic acid to meet certain clinical sensitivity or specificity requirements.

20. The method of claim 11, further comprising:

i) determining the digestion efficiency of the methylation sensitive restriction enzyme; and ii) determining the presence or absence of Y-chromosome nucleic acid; and if present, determining the amount of Y-chromosome nucleic acid for a male fetus.

* * * * *

SEQUENCE LISTING

<160> NUMBER OF SEQ ID NOS: 351

<210> SEQ ID NO 1
<211> LENGTH: 305
<212> TYPE: DNA
<213> ORGANISM: Homo sapiens

<400> SEQUENCE: 1
cagcaggcgc gctcccggcg aatctgcctg aatcgccgtg aatgcggtgg ggtgcagggc 60
aggggctggt tttctcagcc ggtcttggct tttctctttc tctcctgctc caccagcagc 120
ccctccgcgg gtcccatggg ctccgcgctc agaacagccc ggaaccaggc gccgctcgcc 180
gctcgctggg ggccacccgc ctctccccgg aacagcctcc cgcgggcctc ttggcctcgc 240
actggcgccc tcacccacac atcgtccctt tatccgctca gacgctgcaa agggccttct 300
gtctc 305

<210> SEQ ID NO 2
<211> LENGTH: 336
<212> TYPE: DNA
<213> ORGANISM: Homo sapiens

<400> SEQUENCE: 2
gctttggatt tatcctcatt ggctaaatcc ctcctgaaac atgaaactga aacaaagccc 60 tgaacccccct caggctgaaa agacaaaccc cgcctgaggc cgggtcccgc tccccacctg 120
gagggaccca attctgggcg ccttctggcg acggtccctg ctagggacgc tgcgctctcc 180
gagtgcgagt tttcgccaaa ctgataaagc acgcagaacc gcaatcccca aactaacact 240
gaacccggac ccgcgatccc caaactgaca agggacccgg aacagcgacc cccaaaccga 300
cacgggactc gggaaccgct atctccaaag ggcagc 336

<210> SEQ ID NO 3
<211> LENGTH: 139
<212> TYPE: DNA
<213> ORGANISM: Homo sapiens

<400> SEQUENCE: 3
tttccacaac agggagccag cattgaggcg cccagatggc atctgctgga aatcacgggc 60
cgctggtgaa gcaccacgcc ttacccgacg tggggaggtg atccccccacc tcatcccacc 120 cccttctgtc tgtctcctt 139

<210> SEQ ID NO 4
<211> LENGTH: 292
<212> TYPE: DNA
<213> ORGANISM: Homo sapiens

<400> SEQUENCE: 4
gctggacaag gagcgctcac tgtagctctg ctgtggattg tgttggggcg aagagatggg 60
taagaggtca aagtcgtagg attctggcga ccgcctacca agggattggg tccacagcac 120
agaggtctga tcgcttcctt ctctgctctg ccacctccag acagcagctc taaccagctg 180
cccagcagca agaggatgcg cacggctttc accagcacgc agctgctaga gctggagcgc 240
gagttcgctt ctaatatgta cctgtcccgc ctacgtcgca tcgagatcgc ga 292

<210> SEQ ID NO 5
<211> LENGTH: 190
<212> TYPE: DNA
<213> ORGANISM: Homo sapiens

<400> SEQUENCE: 5
tgcctgacac tgaccccagg cgcagccagg aggggctttg tgcgggagag ggagggggac 60
cccagcttgc ctggggtcca cgggactctc ttcttcctag ttcactttct tgctaaggcg 120
aaggtcctga ggcaggacga gggctgaact gcgctgcaat cgtccccacc tccagcgaaa 180
cccagttgac 190

<210> SEQ ID NO 6
<211> LENGTH: 706
<212> TYPE: DNA
<213> ORGANISM: Homo sapiens

<400> SEQUENCE: 6
tcggcggaga gacctcgagg agagtatggg gaaaggaatg aatgctgcgg agcgcccctc 60
tgggctccac ccaagcctcg gaggcgggac ggtgggctcc gtcccgaccc cttaggcagc 120
tggaccgata cctcctggat cagaccccac aggaagactc gcgtggggcc cgatatgtgt 180
acttcaaact ctgagcggcc accctcagcc aactggccag tggatgcgaa tcgtgggccc 240
tgaggggcga gggcgctcgg aactgcatgc ctgtgcacgg tgccgggctc tccagagtga 300
gggggccgta aggagatctc caaggaagcc gaaaaaagca gccagttggg cttcgggaaa 360
gacttttctg caaaggaagt gatctggtcc cagaactcca gggttgaccc cagtacctga 420
cttctccggg agctgtcagc tctcctctgt tcttcgggct tggcgcgctc ctttcataat 480
ggacagacac cagtggcctt caaaaggtct ggggtggggg aacggaggaa gtggccttgg 540
gtgcagagga agagcagagc tcctgccaaa gctgaacgca gttagcccta cccaagtgcg 600
cgctggctcg gcatatgcgc tccagagccg gcaggacagc ccggccctgc tcaccccgag 660
gagaaatcca acagcgcagc ctcctgcacc tccttgcccc agagac 706

<210> SEQ ID NO 7
<211> LENGTH: 325
<212> TYPE: DNA
<213> ORGANISM: Homo sapiens

<400> SEQUENCE: 7
agatcccggt gcatttaaag gccggcgtga tctgcaccac gtacctatct cggattctca 60
gtttcacttc gctggtgtct gccaccatct ttaccacatc ccggtagcta catttgtcta 120
ccgcttgagc caccagcgtc tgaaacctgg accggatttt gcgcgccgag aggtagccgg 180
aggcggtaat gaattccacc cagagggaca tgctcctctt gcgcccgtcg ctcaacttca 240
gcaccgcgca gccgggcagt gagccatcgt ccacgaagtt gaacaccccc atttggttga 300
gataaagcac cacttcaaat tcggt 325

<210> SEQ ID NO 8
<211> LENGTH: 663
<212> TYPE: DNA
<213> ORGANISM: Homo sapiens

<400> SEQUENCE: 8
actatgcctt gagggtcaaa acgtctggat ttcctgatcg atgctgtcgt cgctgtccac 60
ggagctactg tcgccgtcag agcgggaagg cacgttcagg gagtagaagc gtgggcttgc 120
agaaagggac ctgttgctgc cttacatggg ggccggcagg gtagtcttgg aaatgcccaa 180
gattgcttcc gcgcgcgtca gttcagcgga cgtgtctgcc tggcacgagg accgttctac 240
aaactcgttc ctggaagccg ggctcgctgg aggcggagct ttggtttcct tcgggagctt 300
gtggggaatg gtcagcgtct aggcaccccg ggcaagggtc tgtggccttg gtggccactg 360
gcttcctcta gctgggtgtt ttcctgtggg tctcgcgcaa ggcacttttt tgtggcgctg 420
cttgtgctgt gtgcggggtc aggcgtcctc tctcctcccg gcgctgggcc ctctggggca 480
ggtccccgtt ggcctccttg cgtgtttgcc gcagctagta cacctggatg gcctcctcag 540
tgccgtcgtt gctgctggag tctgacgcct cgggcgcctg cgccgcactt gtgacttgct 600
ttccccttct cagggcgcca gcgctcctct tgaccccgct tttattctgt ggtgcttctg 660
aag 663

<210> SEQ ID NO 9

<211> LENGTH: 1985
<212> TYPE: DNA
<213> ORGANISM: Homo sapiens

<400> SEQUENCE: 9
gcaagtcggg tagctaccgg gtgctggaga actccgcacc gcacctgctg gacgtggacg 60
cagacagcgg gctcctctac accaagcagc gcatcgaccg cgagtccctg tgccgccaca 120
atgccaagtg ccagctgtcc ctcgaggtgt tcgccaacga caaggagatc tgcatgatca 180
aggtagagat ccaggacatc aacgacaacg cgccctcctt ctcctcggac cagatcgaaa 240
tggacatctc ggagaacgct gctccgggca cccgcttccc cctcaccagc gcacatgacc 300
ccgacgccgg cgagaatggg ctccgcacct acctgctcac gcgcgacgat cacggcctct 360
ttggactgga cgttaagtcc cgcggcgacg gcaccaagtt cccagaactg gtcatccaga 420
aggctctgga ccgcgagcaa cagaatcacc atacgctcgt gctgactgcc ctggacggtg 480
gcgagcctcc acgttccgcc accgtacaga tcaacgtgaa ggtgattgac tccaacgaca 540
acagcccggt cttcgaggcg ccatcctact tggtggaact gcccgagaac gctccgctgg 600
gtacagtggt catcgatctg aacgccaccg acgccgatga aggtcccaat ggtgaagtgc 660
tctactcttt cagcagctac gtgcctgacc gcgtgcggga gctcttctcc atcgacccca 720
agaccggcct aatccgtgtg aagggcaatc tggactatga ggaaaacggg atgctggaga 780
ttgacgtgca ggcccgagac ctggggccta accctatccc agcccactgc aaagtcacgg 840
tcaagctcat cgaccgcaac gacaatgcgc cgtccatcgg tttcgtctcc gtgcgccagg 900
gggcgctgag cgaggccgcc cctcccggca ccgtcatcgc cctggtgcgg gtcactgacc 960
gggactctgg caagaacgga cagctgcagt gtcgggtcct aggcggagga gggacgggcg 1020
gcggcggggg cctgggcggg cccgggggtt ccgtcccctt caagcttgag gagaactacg 1080
acaacttcta cacggtggtg actgaccgcc cgctggaccg cgagacacaa gacgagtaca 1140
acgtgaccat cgtggcgcgg gacgggggct ctcctcccct caactccacc aagtcgttcg 1200
cgatcaagat tctagacgag aacgacaacc cgcctcggtt caccaaaggg ctctacgtgc 1260
ttcaggtgca cgagaacaac atcccgggag agtacctggg ctctgtgctc gcccaggatc 1320
ccgacctggg ccagaacggc accgtatcct actctatcct gccctcgcac atcggcgacg 1380
tgtctatcta cacctatgtg tctgtgaatc ccacgaacgg ggccatctac gccctgcgct 1440
cctttaactt cgagcagacc aaggcttttg agttcaaggt gcttgctaag gactcggggg 1500
cgcccgcgca cttggagagc aacgccacgg tgagggtgac agtgctagac gtgaatgaca 1560
acgcgccagt gatcgtgctc cccacgctgc agaacgacac cgcggagctg caggtgccgc 1620
gcaacgctgg cctgggctat ctggtgagca ctgtgcgcgc cctagacagc gacttcggcg 1680
agagcgggcg tctcacctac gagatcgtgg acggcaacga cgaccacctg tttgagatcg 1740
acccgtccag cggcgagatc cgcacgctgc accctttctg ggaggacgtg acgcccgtgg 1800
tggagctggt ggtgaaggtg accgaccacg gcaagcctac cctgtccgca gtggccaagc 1860
tcatcatccg ctcggtgagc ggatcccttc ccgagggggt accacgggtg aatggcgagc 1920
agcaccactg ggacatgtcg ctgccgctca tcgtgactct gagcactatc tccatcatcc 1980
tccta 1985

<210> SEQ ID NO 10
<211> LENGTH: 213
<212> TYPE: DNA
<213> ORGANISM: Homo sapiens

<400> SEQUENCE: 10
atgcgccctc tgcaccccta gagccagaag acgctaggtg ggctgcgcgc tctgccaggc 60
gaaggctgga gcgcagacgg caaagccgcg cgtttcagcc gtggtcgggt ccgcaggacc 120
tgggcgtggg gacaccacca ggcaggagca gaggcaggac tgggacgcca aaagctgaga 180
atcctcgatg cccgcgcgag agccccgtgt tat 213

<210> SEQ ID NO 11
<211> LENGTH: 1558
<212> TYPE: DNA
<213> ORGANISM: Homo sapiens

<400> SEQUENCE: 11
ttctggaaac cgggccccac ttgcaggccc ggccaccttg ggttctggtg gccgaagccg 60
gagctgtgtt tctcgcagac tcggggagct acattgtgcg taggcaattg tttagtttga 120
aaggaggcac atttcaccac gcagccagcg ccctgcatgc aggagaagcc cccagggccc 180
agggtcggct ggctttagag gccacttagg ttgttttaag cacatgtgaa agggcagaca 240
gcaggggagc aggatatggg taagatcttc gggtctcaga acaggggctg cccttgggct 300
gtcccggcgc cctgggctct gacactgaag ggtggaatgg aggaaggaat ggagaaagga 360
cggtggaact ttcgcttccc ctctgggccg ccttcccagg gtcatgcctg agctgctttg 420
atcccagtgt cgcgcatctt ggtccgctac ctcccaggcg atagctactg ggctcctcgc 480
tggcctcact gggggccatc ccgggcagtg gcctgccctc cgaggcccgc gggacccagc 540
ccagagctga ggttggagtt ctccgggcca cgttccgggt cgcttaggct cggagatttc 600
ccggagaccg tcgtcctccc tttctgcttg gcactgcgga gctccctcgg cctctctcct 660
cctctggtcc ctaaggcccg gagtggttgg cggtactggg gcccgtcgtc atctctgctt 720
ctaaggcatt cagactgggc tccagctggg accggcagag gaggttctca aggaaactgg 780
tgggaaatat agttttcttt cgtctggtcg tttaatttaa atgcaacttc ccttggggac 840
attttcctgg acgttaacca gaccaccttg agatgtcgtt gatgacctag agacccagat 900
gatgcgtccc aggaaagttc actgctgact attgtcactc ttggcgttat atctatagat 960
atagacctat gtacatatct ccaccctgat ctctccgtgg acatgaaacc cacctacctt 1020
gtgaaagccc tacgggtgac acatgactac tacgtctctg tcccaacagg ggctgggcct 1080
cccctgccta atagttgcca ggagtttcgc agcccaagtg aataatgtct tatggctgaa 1140
cgtggccaag gactcctgtg atttaggtcc caggaggagc agagacgtcc ccgccccgcc 1200
tgggccctgc cgcattcaaa gctggaagaa ggcgctgatc agagaagggg cttccaggtc 1260
ctgggttaga acaacaacaa acaaacgaaa ctccacaaca gacacgcctg cccatgaccc 1320
cacgcaagga cataggaagt tctgtcgcct tcctgctccg cggatagccg cctgccgtct 1380
gctgccacca gaacgcacgg acgctcgggg tggaggtagt caatgggcag caggggaccc 1440
ccagccccca caagcgcggc tccgaggacc tggaagcggg tgcctgtcgc tctccgcagg 1500
ctccgctctg cctccaggag caagatcccc aaaagggtct ggaagctgtg gagaaaac 1558

<210> SEQ ID NO 12
<211> LENGTH: 1264
<212> TYPE: DNA
<213> ORGANISM: Homo sapiens

<400> SEQUENCE: 12

```
tttttaaac acttcttttc cttctcttcc tcgttttgat tgcaccgttt ccatctgggg     60

gctagaggag caaggcagca gccttcccag ccagcccttg ttggcttgcc atcgtccatc    120

tggcttataa aagtttgctg agcgcagtcc agagggctgc gctgctcgtc ccctcggctg    180

gcagaagggg gtgacgctgg gcagcggcga ggagcgcgcc gctgcctctg gcgggctttc    240

ggcttgaggg gcaaggtgaa gagcgcaccg gccgtggggt ttaccgagct ggatttgtat    300

gttgcaccat gccttcttgg atcggggctg tgattcttcc cctcttgggg ctgctgctct    360

ccctccccgc cggggcggat gtgaaggctc ggagctgcgg agaggtccgc caggcgtacg    420

gtgccaaggg attcagcctg gcggacatcc cctaccagga gatcgcaggt aagcgcgggc    480

gcgctgcagg ggcaggctgc agccctcggc tgccgcacgt cccactggcc gcccggcgtc    540

cccttccttc cccctgttgc tgagttggtg ctcactttct gccaccgcta tgggactccg    600

cgtctccgtg ttgggcggcg gatgctcctg cggcttcttc ggcgggggaa ggtgtgcgtc    660

tccgccgcct cattgtgtgc acacgcggga gcaccctggc tcccgcctcc cgctgctctc    720

gcgcccttct accccttagt tgatggctca ggcccggctg gccagggagc ccgggtcact    780

ccggggcggc tgcaaggcgc agacggagag ccgagccggg cgctcactcc gcgttctggt    840

tcgggcaaac ttggaagaac tgcgaccgca gtttgcccag cgccacagtc tgagtggcgc    900

cttctccact cccgcccttg cgccggcagg ggcggtggag agacgcggag ggctccccca    960

gcccctctct cccctatccg tccttcgggc gacagagcgc ccggcgctcg ggccgggggc   1020

gggcaaggct gggagggacc ctcgccgggg acctggcctc tggacgccgg cgtttcaagg   1080

ctggtttggg gacttcacgg gctgcctgtt tcagatgtgg ggcgggcttt cccgttaggg   1140

ttcctcagtg cttccccagt tgctgttggc cactcagggc ccggggacac cctgccaccc   1200

ggtctggagc cggcctcgtc tgccagcgaa cagccaactt tagcgggtgg ctcagctggg   1260

gatt                                                                1264


<210> SEQ ID NO 13
<211> LENGTH: 761
<212> TYPE: DNA
<213> ORGANISM: Homo sapiens

<400> SEQUENCE: 13

cactcagtgt gtgcatatga gagcggagag acagcgacct ggaggccatg ggtgggggcg     60

ggtggtgaag ctgccgaagc ctacacatac acttagcttt gacacttctc gtaggttcca    120

aagacgaaga cacggtggct tcagggagac aagtcgcaag ggcgactttt ccaagcggga    180

gatggtgaag tctttggacg tgtagtgggt aggtgatgat ccccgcagcc gcctgtaggc    240

ccgcagactt cagaaaacaa gggccttctg tgagcgctgt gtcctccccg gaatccgcgg    300

cttaacacat tctttccagc tgcggggcca ggatctccac cccgcgcatc cgtggacaca    360

cttagggtcg cctttgtttt gcgcagtgat tcaagttggg taacccttgc tcaacacttg    420

ggaaatgggg agaatctccc ccacccgcaa cctcccgcac cccaggttcc caaaatctga    480

atctgtatcc tagagtggag gcagcgtcta gaaagcaaag aaacggtgtc caaagacccc    540

ggagagttga gtgagcgcag atccgtgacg cctgcggtac gctagggcat ccaggctagg    600

gtgtgtgtgt gcgggtcggg gggcgcacag agaccgcgct ggtttaggtg gacccgcagt    660

cccgcccgca tctggaacga gctgcttcgc agttccggct cccggcgccc cagagaagtt    720

cggggagcgg tgagcctagc cgccgcgcgc tcatgtttat t                        761
```

<210> SEQ ID NO 14
<211> LENGTH: 1198
<212> TYPE: DNA
<213> ORGANISM: Homo sapiens

<400> SEQUENCE: 14
agtcactcca ggatcagagg ccgcgtcggt tctgcttggg gcatgggcag agggaggctg 60
ctggggccaa gccccggctg gacgcgaggg aagaaactcg tcccaggacc cgcacgccca 120
tacctggctg tcccagagct cttccctagg ccggcacctt cgctcttcct cttccccacc 180
ccctagccct tttgtctctt tttcagacgg atgttttcag tctcaagtgg ttttattttc 240
cgcacaaaac cctgagatca agggcagatc acagactgta ccggaggctc gggtttccct 300
ggactctgtg ctgttctgcg tcccagggtt ggctaggaag gaaggcctgg gccggcgagg 360
tgacgggtct cccgcccagg tcggcaggac ggggggaggt gtgtcccggt aggtccctgg 420
tgagctcacc cgtggcatcg gggacccgcg ggaacccacc gggcgcccac tagagactcg 480
ggtcctaccc tcccccacac tactccaccg aaatgatcgg aagggcgcgc taggcctgct 540
tccaagggct cagtgataaa ggcctcaaaa tcacactcca tcaagacttg gttgaagctt 600
tgggtaggtt tgttgttgtt gttgttgttg tttgtttgtt tgttttagca gacacgtcct 660
ggaaagaggt cctcagaacc caaaggttca ataatgattt gtggatggat tgattatagt 720
ctgatatcgc tctggttcca cagaaacccg gagctccttg gcccactgtt accccagcag 780
acctaaatgg acggtttctg tttttcactg gcagctcaga actggaccgg aagaagttcc 840
cctccacttc ccccctcccg acaccagatc attgctgggt ttttattttc gggggaaaaa 900
caacaacaac aacaacaaaa aaaacactag gtccttccag actggatcag gtgatcgggc 960
aaaaaccctc aggctagtcc ggctgggtgc ccgagcatga aaaggcctcc gtggccgttt 1020
gaacagggtg ttgcaaatga gaacttttgt aagccataac cagggcatcc tgagggtctg 1080
agttcacggt caaggctgtg ggctactagg tccagcgagt ccaggcctcg ccccgccccc 1140
gagctgccac agccaagatc ttcggcaggg aattcgagac cagggtcctc ccactcct 1198

<210> SEQ ID NO 15
<211> LENGTH: 377
<212> TYPE: DNA
<213> ORGANISM: Homo sapiens

<400> SEQUENCE: 15
tttcgtgccg ctgttttcaa tgcgctaacg aggcacgtta ttcttagccg cgtccgggag 60
gggatcacat tcctgcgcag ttgcgctgct ggcggaagtg acttgttttc taacgaccct 120
cgtgacagcc agagaatgtc cgtttctcgg agcgcagcac agcctgtccc atcgagaagc 180
ctcgggtgag gggcccggtg ggcgcccgga ggccgctgga gggctgtggg agggacggtg 240
gctccccact cccgtggcga agggcaggca aaccagaagc ctcttttgag agccgtttgg 300
gattgagacg agtaagccac agcgagtggt tagaagtagg ttaggaagaa ggggaggtaa 360
gaaagccgag tagggtt 377

<210> SEQ ID NO 16
<211> LENGTH: 256
<212> TYPE: DNA
<213> ORGANISM: Homo sapiens

<400> SEQUENCE: 16
gttcggtgga caagggggca gcgcccacag caagccggaa agagggaggc gcggggccgc 60
gcttggggcc tgccgctgca cgccagcctg ggcaaagagc tgccaccttc tgcgggcgaa 120
gcgggtcggg acgcaggacg gcagcggggc tggaggcagc tacgtgggtc cacaccccca 180
tgccctgcaa ggctccttgg ccctgcttct cctctgtctc ggcgggagag gagcagcctc 240
ggttttacag aatttc 256

<210> SEQ ID NO 17
<211> LENGTH: 189
<212> TYPE: DNA
<213> ORGANISM: Homo sapiens

<400> SEQUENCE: 17
tgtgccattt agtgagaggt gttttgggca aagaatcaat ttaactgtga ctgaccgacg 60
ggcttgactg tattaattct gctaccgaaa aaaaaaaaaa aaaaaaagca atgagccgca 120
agccttggac tcgcagagct gccggtgccc gtccgagagc ccccaccagcg cggctcacgc 180 ctcagtctc 189

<210> SEQ ID NO 18
<211> LENGTH: 707
<212> TYPE: DNA
<213> ORGANISM: Homo sapiens

<400> SEQUENCE: 18
agagtcccag ttctgcaggc cgctccaggg ctaggggtag agatggtggc aggtggtgcg 60
tcaactctct agggaagagg aacttgcatt acaaagactt gtctttctga gctgaagtca 120
aaacgggggc gtcaagcgcg ctccgtttgg cggcggtgga ggggccgcgc gcccgcgctg 180
tcccagccgg agctgccctg gctggtgatt ggaggtttaa cgtccggaat tcaggcgctt 240
ctgcagctca gatttgccgg ccaaggggcc tcagttgcaa cttttcaaaa tggtgtttct 300
ggaaaataac aaattcagac tcaactggtg acagcttttg gctatagaga atgaaactgc 360
ttccctttgg cggtggaact cttaaacttc gaagagtgaa agaatacaat gaaataaaat 420
gccataagat cactggattt ttcagaaaaa ggaagacccc aaattactcc caaaatgagg 480
ctttgtaaat tcttgttaaa aatctttaaa tctcgaattt ccccctacaa catctgatga 540
gtgctttaag agcaaacgag caaatcccac ctcgagaatc aacaaaccca agctctggcc 600
aaggctctcc ccgcgttttc ttctcgtgac ctggggaatg tcccgcccca tcgctcacct 660
ggctcttgtc atctcgctca tcttgaagtg acccgtggac aatgctg 707

<210> SEQ ID NO 19
<211> LENGTH: 182
<212> TYPE: DNA
<213> ORGANISM: Homo sapiens

<400> SEQUENCE: 19
agctgccctc tgtggccatg agcgggtgtc cagccccttc caaggctgca ccggggagac 60
gctggttttc tgctcgctgt gaccgaacaa agcccctaag agtcagtgcg cggaacagaa 120
gagccggacc ccgacgggcc gagtcccaac gtgaggcacc cggcagagaa aacacgttca 180
cg 182

<210> SEQ ID NO 20
<211> LENGTH: 179
<212> TYPE: DNA
<213> ORGANISM: Homo sapiens

<400> SEQUENCE: 20

```
cctcggcagc accggcatgg ctggaggcca gtacggccag gtgtggcggg agggagcgcc     60

gtctggcttg ggtcgtccat cctgacagga cgctgcaagg gcaggagccc cgcgccccgt    120

gtcctgcgcc cccgctcgag gacaagcccc agccgccggt ctccgctggg ttccgacag     179


<210> SEQ ID NO 21
<211> LENGTH: 369
<212> TYPE: DNA
<213> ORGANISM: Homo sapiens

<400> SEQUENCE: 21

ctttaagagg ctgtgcaggc agacagacct ccaggcccgc taggggatcc gcgccatgga     60

ggccgcccgg gactatgcag gagccctcat caggcgagtg ccccgcgtcc ccctgattgc    120

cgtgcgcttc caatcgcctt gcgttcggtg gcctcatatt cccctgtgcg cctctagtac    180

cgtaccccgc tcccttcagc cccctgctcc ccgcattctc ttgcgctccg cgaccccgcg    240

cacacaccca tccgccccac tggtgcccaa gccgtccagc cgcgcccgcg ggcagagccc    300

aatcccgtcc cgcgcctcct caccctcttg cagctgggca caggtaccag gtgtggctct    360

tgcgaggtg                                                            369


<210> SEQ ID NO 22
<211> LENGTH: 176
<212> TYPE: DNA
<213> ORGANISM: Homo sapiens

<400> SEQUENCE: 22

agacttgcag aactcgggcc ccctggagga gacctaaccg ccacggtctt ggggaggttc     60

cggagggcct cggttgtctg cactcccaac accaagaaac ccctgagacg cgaagctgcc    120

agcgtgctgc cctcagagca gggcgacgca aagccagcgg accccggggt ggcggg        176


<210> SEQ ID NO 23
<211> LENGTH: 167
<212> TYPE: DNA
<213> ORGANISM: Homo sapiens

<400> SEQUENCE: 23

tgctcggctg gggggctcgc tccgcacttt cggtgccaga aaatgcccag aggagcgggg     60

cggccccaga gcctcctttc ggggcgcgag gcccggcgcg tgtgtacgga gtccagtccc    120

cccagggagt ggggtgcccg caccttcccc tccgcgctcg gagccac                  167


<210> SEQ ID NO 24
<211> LENGTH: 1205
<212> TYPE: DNA
<213> ORGANISM: Homo sapiens

<400> SEQUENCE: 24

tcttgcacac ctgcttgtag ttctgcaccg agatctggtc gttgaggaac tgcacgcaga     60

gcttggtgac ctgggggatg tgcaggatct tgctgaccga cagcacctcc tccaccgtgt    120

ccagggacag ggtcacgttg gccgtgtaga ggtactcgag caccaggcgc agcccgatgg    180

acgagcagcc ctgcagcacc aggttgttga tggcccgggg gctggtcagc agcttgtcgt    240

cgggggagga agaaggagtc ccgggctcct cctgcggcgg cggctgctgc tgctgtgacg    300

gctgctgctg cggcggctgc tgctggtcct tgggggcccc caggccgtcc tggccgccga    360

cccctccccc gagagggggg tggctggaga agagcgatcg gaagtactgc gagcaggagg    420
```

-continued ccagcacggc cttgtggcaa tggaactgct ggccctgggc cgtcagggtc acgtcgcaaa 480
acagctgctt cctccacagc aggttgaggc cgtgcagcag gttgtcgctg tggctggggt 540
cgaaggtgga ggtcctgtcc ccggatctgg acatggcgag ctgactcggt gcacctggct 600
ttaaaccctc ctccaacctg gcagacaggg gtgggggatg ggagggaggg gagcagggtg 660
gtggagcggg tggggtgtgg tcggggtggg gaagggtgtg gaggggaggg gagggcgaag 720
aacaagaatc aaggctcagc ttgactccct cctggcgcgc tccggacccc gaccctagga 780
ggaaagtccg aagacgctgg atccgtgagc gccaccagaa gggccctgtc tggggtcccg 840
gcgccggttc tgcgccctgc ggctcctctc gccacctccc acacacttcg tccctcactt 900
tcctaaaacc aaccacctca gctcggctgt tggcagcaac agcagtggca gcagcgacgg 960
caaagtggcg gctgaggccg aggcacctcg tgggctcgtg tccatgccgg gccagatgaa 1020
gggaaaggcc gggaagtggg gagccggggg tgccctgaaa gctcagaggc gaccgacggc 1080
gaaggttcca ggtcaacttg tgcccgaagc tttgcttttc gcagttggcc cagtttgggg 1140
gagggggtag gaacaggggc ccgaccagcg tgcggggtgt gcgaatctta gctctccaaa 1200
agctg 1205

<210> SEQ ID NO 25
<211> LENGTH: 44
<212> TYPE: DNA
<213> ORGANISM: Homo sapiens

<400> SEQUENCE: 25
cctctgtgtt agtgccctcg ggaatttggt tgatggggtg tttg 44

<210> SEQ ID NO 26
<211> LENGTH: 5002
<212> TYPE: DNA
<213> ORGANISM: Homo sapiens

<400> SEQUENCE: 26
tgatgtcgca cctgaacggc ctgcaccacc cgggccacac tcagtctcac gggccggtgc 60
tggcacccag tcgcgagcgg ccaccctcgt cctcatcggg ctcgcaggtg gccacgtcgg 120
gccagctgga agaaatcaac accaaagagg tggcccagcg catcacagcg gagctgaagc 180
gctacagtat cccccaggcg atctttgcgc agagggtgct gtgccggtct caggggactc 240
tctccgacct gctccggaat ccaaaaccgt ggagtaaact caaatctggc agggagacct 300
tccgcaggat gtggaagtgg cttcaggagc ccgagttcca gcgcatgtcc gccttacgcc 360
tggcaggtaa ggccggggct agccaggggc caggctgctg ggaagagggc tccgggtccg 420
gtgcttgtgg cccaagtctg cgcgccgagt cacttctctt gattctttcc ttctctttcc 480
tatacacgtc ctctttcttc tcgtttttat ttcttcttcc attttctctt tctcttccgc 540
tcttccccta ctttcccttc tccctttttct ttttctttct tactctctcc ttgtccctga 600
gctttcattg accgaccccc ccccatttca ttcgccctcc cctcaatgtg ccaacctttg 660
ccctatttcc gatcttccca ggtactggga ggcgggatgg gggtgtgcgt tttcctctag 720
gagccctgtc tttccaagac ccacagaaac caggacctgc ccttattcaa aaccccatgc 780
acttcaagtc tcttttagac aacacatttc aattttccgg gctgactagt ctccctgtgc 840
agaggcagtt gagaggcttt gctctgcaga gggaaaagag ctctctactc tcccacccac 900
catataggca aacttatttg gtcattggct gaaggcacag ccttgccccc gcggggaacc 960
ggcggccagg atacaacagc gctcctggag cccatctctg gccttggcgt tggcgcaggg 1020
actttctgac cgggcttgag gggctcgggc cagctccaat gtcactacct acagcgaggg 1080
cagggtgtaa ggttgagaag gtcacattca ccgctttggg aggacgtggg agaagagact 1140
gaggtggaaa gcgctttgcc ttgctcaccg gccgtccttg ccccggtccc agcgtttgct 1200
gggatttgcc aggatttgcc ggggctccgg gagaccctga gcactcgcag gaagaggtgc 1260
tgagaaatta aaaattcagg ttagttaatg catccctgcc gccggctgca ggctccgcct 1320
ttgcattaag cgggcgctga ttgtgcgcgc ctggcgaccg cggggaggac tggcggcccg 1380
cgggagggga cgggtagagg cgcgggttac attgttctgg agccggctcg gctctttgtg 1440
cctcctctag cggccaagct gcgaggtaca gccctctatt gttctaggag cacagaaacc 1500
tcctgtgtgg gcggcgggtg cgcgagctag agggaaagat gcagtagtta ctgcgactgg 1560
cacgcagttg cgcgcttttg tgcgcacgga ccccgcgcgg tgtgcgtggc gactgcgctg 1620
cccctaggag caagccacgg gcccagaggg gcaaaatgtc caggtccccc gctgggaagg 1680
acacactata ccctatggca agccagggtg ggcgacttcc catggatcgg gtggaggggg 1740
gtatctttca ggatcggcgg gcggtctagg ggaacaattc gtggtggcga tgatttgcat 1800
agcgcgggtc ttgggatgcg cgcggttccg agccagcctc gcacagctcg cttccggagc 1860
tgcgagctca ggtttccacc cccgatcccc cgggctttcc tcgcaccgct gagcccagct 1920
tgtggggtgc actcgaccaa cgcccgacag ggctggggaa tgtgacaggc agcaggttca 1980
cccgggcttg gggaggggga gtttccgctt tgacagcatt ttcctttgcc gtctgctggt 2040
ggattcctat tcccagtcgg taatcgcccc gcagtgttga tctaagaagg taaagaaaac 2100
taggtttccc tgcaaagagc ctcccccaaa tcggcggact ccggatactt tgagtggatt 2160
tagaaattta tgtaatcttt ctcctttagt ttatttttca tcctctccta cagttttctc 2220
tgatttgctg ttggttcggg gcaagataaa gcagccagta gagagcgata ataatagcgg 2280
cgggaaatga actggagact ggctgacagt tcttaacatt ttgtcataga tccccccgaa 2340
tgtcccaggc tgtctctggt gggttttagt acccgccggc ttcttgggca ccggggacca 2400
gaaggaactt ggcagctggt cttaggggta cagttaaagg caggatgaca gctattctcc 2460
tgctcatctc agagcgctgc cgccccctca tgccggtcgc gcaaagaaca cagcttttaa 2520
aaaacacgtg ccttctgccc atataggtct gaaagtgatg aggaaagtaa tgcttcgcct 2580
attagcgagt ttcagctttt aaaatgatcc caagcgttgc tgagatgaga aagcgtggca 2640
tcccgggggt cctcagcccc acccgcgccc atggtgcaag tctgcaggga caggcccggg 2700
acagcactgc ccacgctgct agattttccg cagaggatcg ctgaagctgc cttcgtggga 2760
gacagaatgc ctcctccagc gagtggaaaa ggcctgctga ggaccccgct ttgctcgagc 2820
attcaaatgt gtgtctgttt tattaccctg ggttgaaaag ggacaagagc tttagccttt 2880
ttatctggcc attttatcag caactacaag tgtgttgagt ggttattatt acataggagg 2940
cttttcagtt tggggtcagt agatcagtct cttcagacac tgatgcagaa gctgggactg 3000
gtaagtaggt attatgtgct cggagcgcta ggggacagga gcaaatggag aagaaaagcg 3060
gaggctttct ccgcccggag tatcgatcgg aatccccgcc ggtacgccgc agagggccct 3120
cgccgttggg ccccgggggt ttaacaagcc cagccgctcc gcaggcggct cggccggact 3180
ctcagaccgg tgcctggaag acaccgtccc tgccccccctc ccgccaaacc tgcctcttct 3240
ctttctctca taggttatag gttccctttc tctctcattt tggccccgcc cccgggtcct 3300
gccaaacagc caagcaggcc ggggtttagg gggctcagaa tgaagaggtc tgatttggcc 3360

-continued agcgccggca aagctcaccc ttaggcgagg tcacaacaga ggcaggtcct tcctgcccag 3420
cctgccggtg tagtcacagc caagggtggc acttgaaagg aaaagggaga aaacttcgga 3480
gaaatttaga ttgccccaac gttagatttc agagaaattg actccaaatg cacggattcg 3540
ttcggaaagg gcggctaagt ggcaggtggt tgcaaccccg cccggtcggg ccttcgcaga 3600
ggttccccaa gaccagccct tgcagggcgg ttttcagcaa cctgacaaga ggcggccaag 3660
acaaatttct gcgggttcga gcacacactc tcgggcgttg ggccccagag acctctaaac 3720
caagcacaaa caagaaggga gtgagagaac ccaggctaga acttgcacgg gcatccccact 3780 gaggaaaagc gaggcctcgg tggcaggcat gttttcttcc gacgcccgaa aatcgagccg 3840
agcgcccgac tacatttact gcagaggttt ccgcctccag tgagcccgga tcccccagcg 3900
gcctgcccgg agctggtctc cagtccccgc cgtagtccga cgcacggccc tctcctggca 3960
gcaagctccc agcggccagt ctgaagccaa ttctgttcag gcggccgagg gcccttagcc 4020
aacccaccat gatgtcgcct gggccacctg atgcccgcag cggcgggaca cggcccgggc 4080
agtgcgcagt ggctcctgct aggggcaccg cgtgcgtgct tgtctcccgc tgcgccgggg 4140
acgtccttgg gtgacacggg ccgctgggca cctcccaagc cgaggaaacg gaccccccttc 4200 gcagagtctc gcgcccaccc cccaacctcc cacctcgttt ctcgctgcta gggctcccga 4260
ctcagcccac ctctcctggc ggtttagtta gggatcagag ctggagaggc tgaacgcaac 4320
ccgtgccagt acggaacaga cgatatgttt gcctgctagc tgcttggatg aataattgaa 4380
aagttcgctg cagtctgtgc ttcgtcaagt cccgggtgcc gggagaacac cttcccaaca 4440
cgcatcaggg tgggcgggag cgggcagagg aggcgggacc cgagggagga gagtgaaccc 4500
gagcaggaga agcagcccag gcagccaggc gccctcgatg cgagaggctg ggcatttatt 4560
tttattccag gctttccact gtgtggttat gtcactttct caaacaaatg tgtatatgga 4620
gggagatcga tgctgataat gtttagaaga ttaaaagagc attaatgctg gcaacaataa 4680
cgtaaacgtg tggacccaga tttcattgat ctggaacttg atccggcgcg tttccagtaa 4740
gcccgacggc gcgctcttcc cagcagagcg ctcaccagcg ccacggcccc gcggttttcc 4800
agcggtgccg cttcgccagc tctgcgcggg ttctcccgtc tgaccgcagc tcctcccccg 4860
cgaggcccca gcccgcctta cttccccgag gttttctcct cctctcgcgg ggctctctgc 4920
cctctgcacc ccctcccccg acctctgcac cacccgcccc tgtgcgcaca caccgctact 4980
tgcgcttccg gcgatccgcc tg 5002

<210> SEQ ID NO 27
<211> LENGTH: 150
<212> TYPE: DNA
<213> ORGANISM: Homo sapiens

<400> SEQUENCE: 27
aaccggagat ctgcttggtg aactgagagg agtccttagg agagcgggga cgccaggggc 60
cgggggacac ttcgctctcg ccctagggaa ggtggtcttg acgctttcta ttgaagtcaa 120
acttgaaaat atcagctgcc gctggactat 150

<210> SEQ ID NO 28
<211> LENGTH: 339
<212> TYPE: DNA
<213> ORGANISM: Homo sapiens

<400> SEQUENCE: 28
cgtgagcaga acgcccgccc tggagcagtt aggaccgaag gtctccggag agtcgccggc 60
ggtgccaggt aacgcagagg gctcgggtcg ggccccgctt ctggggcttg ggactccggg 120
cgcgcggagc cagccctctg gggcgaaatc cccgggcggc gtgcgcggtc cctctccgcg 180
ctgtgctctc ccagcaactc cctgccacct cgacgagcct accggccgct ccgagttcga 240
cttcctcgga cttagtggga gaaggggttg gaaatgggct gccgggactg ggggagctgc 300
tctctggaag cagggaagct ggggcgcacc ggggcaggt 339

<210> SEQ ID NO 29
<211> LENGTH: 1961
<212> TYPE: DNA
<213> ORGANISM: Homo sapiens

<400> SEQUENCE: 29
tagaagagga agactcctct ggccccacta ggtatcatcc gcgctctccc gctttccacc 60
tgcgccctcg cttgggccaa tctctgccgc acgtgtccat ccctgaactg cacgctatcc 120
tccacccccg gggggttcct gcgcactgaa agaccgttct ccggcaggtt ttgggatccg 180
gcgacggctg accgcgcgcc gcccccacgc ccggttccac gatgctgcaa tacagaaagt 240
ttacgtcggc cccgacccgc gcgggactgc agggtccgcc ggagcgcggc gcagaggctt 300
ttcctgcgcg ttcggccccg ggaaaggggc gggagggctg gctccgggag cgcacgggcg 360
cggcggggag ggtactcact gtgaagcacg ctgcgcccat ggatcatgtc tgtgcgttac 420
accagaggct ccgggctcca ctaattccat ttagagacgg gaagacttcc agtggcgggg 480
ggaggacagg gtcgagaggt gttaaagacg caaagcaaga aggaaataaa ggggggccga 540
gagggagacc gagaggaagg gggagctccg agcccacgct gcagccagat ccggatgagt 600
ccgtcctccg ccccgggcgg gctctcgctc tcgctggccc tcagcgccgc gcagccagca 660
gcatccccac cgtgacgctc gcatcacacc cgggcgccgg ccgccaccat ccgcgccgcc 720
gccgtcagga ccctcctccc gggcatcgtc gccgccgcgg ggtcgggagg acgcggcgcg 780
cgggaggcgg cggtcgcagg gcgagccccg ggacgccccg agccggggcc ggggccgggg 840
agagggcgca gcgaggtggg ggccagtcca gaccgacggc agcgacggag cgggcggcgg 900
cggcggcgcc ggcggcggcg gggtggctca gtccccagtc tcagacgcgc cgcgcagcag 960
gtcggagcag cctccccggg aggatgtcca gcggcagcgc tcctcgctcc agcccttggg 1020
gatcttccgc tgaggcattg aaggcaggaa gaaggggtcc gtcatcggct cgccgggctg 1080
cgcgccacct ctgctatctt gcggaaagag gagcgggtgg gtgggcgtct gggaggcggg 1140
ctggagggcg gtgcagggga gcggggcggc cggggggggg gccgggggc ggggaaggga 1200 gggaggagaa aggagccgga agagggcaga gttaccaaat gggctcctta gtcatggctt 1260
ggggctccac gaccctcctg gaagcccgga gcctgggtgg gatagcgagg ctgcgcgcgg 1320
ccggcgcccc ggggctggtg cgcggcagaa tggggccgcg gcggcggcag caaggacatc 1380
ccagccgcgc ggatctgggg gaggggcggg gagggggtga ggacccggct gggatccgcg 1440
gctcggcccg ccagggcgca gagagaggat gcagccgcaa atcccgagcc ggatcctcgt 1500
gccggacgga aggcgtggaa gcgggagggg ccttcgtgtg aaaatccctt gtggggtttg 1560
gtgtttcact ttttaaaggt tagaccttgc gggctctctg cctcccaccc cttcttttcc 1620
atccgcgtaa aggaactggg cgccccctct ccctccctcc ctggggcgca ggtttcgccg 1680
cggactccgc gctcagcttg ggagacacgg caggggcgcg ccccagggaa aggcggccgt 1740
aaaagtttcg cggttgagca ctgggcctga tgtccagtcc ccccaccaaa ttactcctgc 1800

```
aaagacgcgg gcttcttgca attgagcccc ccacctcgag gtatttaaaa ccaccccaag   1860

gcacacacgg acccccgttc ccccgcgcca cttcctccta caggctcgcg cggcgcgtta   1920

aagtctggga gacacgagtt gcggggaaac agcaccggaa g                       1961
```

<210> SEQ ID NO 30
<211> LENGTH: 314
<212> TYPE: DNA
<213> ORGANISM: Homo sapiens

<400> SEQUENCE: 30

```
aagaaacagc tcatttcgga gctgaggaca aggcgtggga agaagacgcg tttggtttca     60

cccaggcggg tggcggcaaa gctgtgggat gcgcgctgca cactccttcc gtcatcccgt    120

tcccaccttc cacacacacc tgcgggaggt cggacatgtc ctgattgcgt gttcatcacg    180

atggcaaacc gaacatgagg agaacgccac tgacgctggg tgcgccggct ttcccagccc    240

tcgtgcataa cggggaggga gatgcagaag ttttttccaa catcggtgca aaggggaagc    300

tgaggttttc ctat                                                      314
```

<210> SEQ ID NO 31
<211> LENGTH: 584
<212> TYPE: DNA
<213> ORGANISM: Homo sapiens

<400> SEQUENCE: 31

```
tctgtcagct gctgccatgg ggcagcggga aggccctgga gggtgcctgg gctgtgtctg     60

gtcccggcca cgcgtccctg cagcgtctga gaccttgtgg aacacacttg acccggcgct    120

gggacggggt cggcccacac gcaccgccag cccgcaggag tgaggtgcag gctgccgctg    180

gctccttagg cctcgacagc tctcttgagg tcggccctcc tcccctcccg agagctcagc    240

agccgcagac ccaggcagag agagcaaagg aggctgtggt ggccccccgac gggaacctgg    300

gtggccgggg gacacaccga ggaactttcc gccccccgac gggctctccc accgaggctc    360

aggtgctcgt gggcagcaag gggaagcccc atggccatgc cgcttccctt tcaccctcag    420

cgacgcgccc tcctgtgccc gcggggaaca agacggctct cggcggccat gcaggcggcc    480

tgtcccacga acacgatgga gacctcagac gccgtcccca ccctgtcact gtcaccatca    540

cccatcctgt cccctcacgc ctccccacat cccatcatta ctac                     584
```

<210> SEQ ID NO 32
<211> LENGTH: 349
<212> TYPE: DNA
<213> ORGANISM: Homo sapiens

<400> SEQUENCE: 32

```
gaagtagaat cacagtaaat gaggagttag ggaatttagg gtagagatta aagtaatgaa     60

cagaggagga ggcctgagac agctgcagag agaccctgtg ttccctgtga ggtgaagcgt    120

ctgctgtcaa agccggttgg cgctgagaag aggtaccggg ggcagcaccc gcctcctggg    180

agagggatgg gcctgcgggc acctggggga accgcacgga cacagacgac actataaacg    240

cgggcgagac atcagggacc gggaaacaga aggacgcgcg tttcgagcag ctgcccagtg    300

ggccacaagc cccgccacgc cacagcctct tcccctcagc acgcagaga                349
```

<210> SEQ ID NO 33
<211> LENGTH: 3510
<212> TYPE: DNA
<213> ORGANISM: Homo sapiens

<400> SEQUENCE: 33

```
tactccggcg acgggaggat gttgagggaa gcctgccagg tgaagaaggg gccagcagca      60
gcacagagct tccgactttg ccttccaggc tctagactcg cgccatgcca agacgggccc     120
ctcgactttc acccctgact cccaactcca gccactggac cgagcgcgca aagaacctga     180
gaccgcttgc tctcaccgcc gcaagtcggt cgcaggacag acaccagtgg gcagcaacaa     240
aaaaagaaac cgggttccgg gacacgtgcc ggcggctgga ctaacctcag cggctgcaac     300
caaggagcgc gcacgttgcg cctgctggtg tttattagct acactggcag gcgcacaact     360
ccgcgccccg actggtggcc ccacagcgcg caccacacat ggcctcgctg ctgttggcgg     420
ggtaggcccg aaggaggcat ctacaaatgc ccgagccctt tctgatcccc acccccccgc     480
tccctgcgtc gtccgagtga cagattctac taattgaacg gttatgggtc atccttgtaa     540
ccgttggacg acataacacc acgcttcagt tcttcatgtt ttaaatacat atttaacgga     600
tggctgcaga gccagctggg aaacacgcgg attgaaaaat aatgctccag aaggcacgag     660
actggggcga aggcgagagc gggctgggct tctagcggag accgcagagg gagacatatc     720
tcagaactag gggcaataac gtgggtttct ctttgtattt gtttattttg taactttgct     780
acttgaagac caattattta ctatgctaat ttgtttgctt gtttttaaaa ccgtacttgc     840
acagtaaaag ttccccaaca acggaagtaa cccgacgttc ctcacactcc ctaggagact     900
gtgtgcgtgt gtgcccgcgc gtgcgctcac agtgtcaagt gctagcatcc gagatctgca     960
gaaacaaatg tctgaattcg aaatgtatgg gtgtgagaaa ttcagctcgg ggaagagatt    1020
agggactggg ggagacaggt ggctgcctgt actataagga accgccaacg ccagcatctg    1080
tagtccaagc agggctgctc tgtaaaggct tagcaatttt ttctgtaggc ttgctgcaca    1140
cggtctctgg cttttcccat ctgtaaaatg ggtgaatgca tccgtacctc agctacctcc    1200
gtgaggtgct tctccagttc gggcttaatt cctcatcgtc aagagttttc aggtttcaga    1260
gccagcctgc aatcggtaaa acatgtccca acgcggtcgc gagtggttcc atctcgctgt    1320
ctggcccaca gcgtggagaa gccttgccca ggcctgaaac ttctctttgc agttccagaa    1380
agcaggcgac tgggacggaa ggctctttgc taacctttta cagcggagcc ctgcttggac    1440
tacagatgcc agcgttgccc ctgccccaag gcgtgtggtg atcacaaaga cgacactgaa    1500
aatacttact atcatccggc tcccctgcta ataaatggag gggtgtttaa ctacaggcac    1560
gaccctgccc ttgtgctagc gcggttaccg tgcggaaata actcgtccct gtacccacac    1620
catcctcaac ctaaaggaga gttgtgaatt ctttcaaaac actcttctgg agtccgtccc    1680
ctccctcctt gcccgccctc taccctcaa gtccctgccc ccagctgggg gcgctaccgg    1740
ctgccgtcgg agctgcagcc acggccatct cctagacgcg cgagtagagc accaagatag    1800
tggggacttt gtgcctgggc atcgtttaca tttggggcgc caaatgccca cgtgttgatg    1860
aaaccagtga gatgggaaca ggcggcggga aaccagacag aggaagagct agggaggaga    1920
ccccagcccc ggatcctggg tcgccagggt tttccgcgcg catcccaaaa ggtgcggctg    1980
cgtggggcat caggttagtt tgttagactc tgcagagtct ccaaaccatc ccatccccca    2040
acctgactct gtggtggccg tattttttac agaaatttga ccacgttccc tttctccctt    2100
ggtcccaagc gcgctcagcc ctccctccat cccccttgag ccgcccttct cctccccctc    2160
gcctcctcgg gtccctcctc cagtccctcc ccaagaatct cccggccacg ggcgcccatt    2220
ggttgtgcgc agggaggagg cgtgtgcccg gcctggcgag tttcattgag cggaattagc    2280
```

ccggatgaca tcagcttccc agccccccgg cgggcccagc tcattggcga ggcagcccct 2340
ccaggacacg cacattgttc cccgccccg cccccgccac cgctgccgcc gtcgccgctg 2400
ccaccgggct ataaaaaccg gccgagcccc taaaggtgcg gatgcttatt atagatcgac 2460
gcgacaccag cgcccggtgc caggttctcc cctgaggctt ttcggagcga gctcctcaaa 2520
tcgcatccag agtaagtgtc cccgccccac agcagccgca gcctagatcc cagggacaga 2580
ctctcctcaa ctcggctgtg acccagaatg ctccgataca gggggtctgg atccctactc 2640
tgcgggccat ttctccagag cgactttgct cttctgtcct ccccacactc accgctgcat 2700
ctccctcacc aaaagcgaga agtcggagcg acaacagctc tttctgccca agccccagtc 2760
agctggtgag ctccccgtgg tctccagatg cagcacatgg actctgggcc ccgcgccggc 2820
tctgggtgca tgtgcgtgtg cgtgtgtttg ctgcgtggtg tcgatggaga taaggtggat 2880
ccgtttgagg aaccaaatca ttagttctct atctagatct ccattctccc caaagaaagg 2940
ccctcacttc ccactcgttt attccagccc gggggctcag ttttcccaca cctaactgaa 3000
agcccgaagc ctctagaatg ccacccgcac cccgagggtc accaacgctc cctgaaataa 3060
cctgttgcat gagagcagag gggagataga gagagcttaa ttataggtac ccgcgtgcag 3120
ctaaaaggag ggccagagat agtagcgagg gggacgagga gccacgggcc acctgtgccg 3180
ggaccccgcg ctgtggtact gcggtgcagg cgggagcagc ttttctgtct ctcactgact 3240
cactctctct ctctctccct ctctctctct ctcattctct ctcttttctc ctcctctcct 3300
ggaagttttc gggtccgagg gaaggaggac cctgcgaaag ctgcgacgac tatcttcccc 3360
tggggccatg gactcggacg ccagcctggt gtccagccgc ccgtcgtcgc cagagcccga 3420
tgaccttttt ctgccggccc ggagtaaggg cagcagcggc agcgccttca ctgggggcac 3480
cgtgtcctcg tccaccccga gtgactgccc 3510

<210> SEQ ID NO 34
<211> LENGTH: 333
<212> TYPE: DNA
<213> ORGANISM: Homo sapiens

<400> SEQUENCE: 34
ttaattcgaa aatggcagac agagctgagc gctgccgttc ttttcaggat tgaaaatgtg 60
ccagtgggcc aggggcgctg ggacccgcgg tgcggaagac tcggaacagg aagaaatagt 120
ggcgcgctgg gtgggctgcc ccgccgccca cgccggttgc cgctggtgac agtggctgcc 180
cggccaggca cctccgagca gcaggtctga gcgtttttgg cgtcccaagc gttccgggcc 240
gcgtcttcca gagcctctgc tcccagcggg gtcgctgcgg cctggcccga aggatttgac 300
tctttgctgg gaggcgcgct gctcagggtt ctg 333

<210> SEQ ID NO 35
<211> LENGTH: 385
<212> TYPE: DNA
<213> ORGANISM: Homo sapiens

<400> SEQUENCE: 35
ccggtcccca gtttggaaaa aggcgcaaga agcgggcttt tcagggaccc cggggagaac 60
acgagggctc cgacgcggga gaaggattga agcgtgcaga ggcgccccaa attgcgacaa 120
tttactggga tccttttgtg gggaaaggag gcttagaggc tcaagctata ggctgtccta 180
gagcaactag gcgagaacct ggccccaaac tccctcctta cgccctggca caggttcccg 240
gcgactggtg ttcccaaggg agccccctga gcctaccgcc cttgcagggg gtcgtgctgc 300

```
ggcttctggg tcataaacgc cgaggtcggg ggtggcggag ctgtagaggc tgcccgcgca    360

gaaagctcca ggatcccaat atgtg                                          385


<210> SEQ ID NO 36
<211> LENGTH: 105
<212> TYPE: DNA
<213> ORGANISM: Homo sapiens

<400> SEQUENCE: 36

gcgcaggtcc ccccagtccc cgagggagtg cgccccgacgg aaacgcccct agcccgcggg    60

cctcgctttc ctctcccggg ttcctgggtc acttcccgct gtctc                    105


<210> SEQ ID NO 37
<211> LENGTH: 147
<212> TYPE: DNA
<213> ORGANISM: Homo sapiens

<400> SEQUENCE: 37

ttccctcgcg gctttggaaa gggggtgcaa atgcaccctt ctgcgggccc gctacccgct    60

gcaacacctg tgtttccttt ctgggcacct tctaggtttc tagatattgc tgtgaatacg   120

gtcctccgct gtacagttga aaacaaa                                        147


<210> SEQ ID NO 38
<211> LENGTH: 365
<212> TYPE: DNA
<213> ORGANISM: Homo sapiens

<400> SEQUENCE: 38

tgggaattta ggtcgggcac tgccgatatg tcgccttcca caaggcgggc ccgggcctct    60

gctgaccgtg caccggtcct ggggctgggt aattctgcag cagcagcgca gcccatgccg   120

gggaatttgc gggcagagga gacagtgagg cccgcgttct gtgcgggaac tcccgagctc   180

acagagccca agaccacacg gctgcatctg cttggctgac tgggccaggc ccacgcgtag   240

taacccggac gtctctctct cacagtcccc ttgcgtctgg ccagggagct gccaggctgc   300

accccgcggt ggggatcggg agaggggcag tgtcgcccat ccccggaagg ctgagcctgg   360

tgcag                                                                365


<210> SEQ ID NO 39
<211> LENGTH: 418
<212> TYPE: DNA
<213> ORGANISM: Homo sapiens

<400> SEQUENCE: 39

cggttttctc ctggaggact gtgttcagac agatactggt ttccttatcc gcaggtgtgc    60

gcggcgctcg caagtggtca gcataacgcc gggcgaattc ggaaagcccg tgcgtccgtg   120

gacgacccac ttggaaggag ttgggagaag tccttgttcc cacgcgcgga cgcttccctc   180

cgtgtgtcct tcgagccaca aaaagcccag accctaaccc gctcctttct cccgccgcgt   240

ccatgcagaa ctccgccgtt cctgggaggg gaagcccgcg aggcgtcggg agaggcacgt   300

cctccgtgag caaagagctc ctccgagcgc gcggcgggga cgctgggccg acaggggacc   360

gcgggggcag ggcggagagg acccgccctc gagtcggccc agccctaaca ctcaggac     418


<210> SEQ ID NO 40
<211> LENGTH: 906
<212> TYPE: DNA
```

<213> ORGANISM: Homo sapiens

<400> SEQUENCE: 40
agggaatcgg gctgaccagt cctaaggtcc cacgctcccc tgacctcagg gcccagagcc 60
tcgcattacc ccgagcagtg cgttggttac tctccctgga aagccgcccc cgccggggca 120
agtgggagtt gctgcactgc ggtctttgga ggcctaggtc gcccagagta ggcggagccc 180
tgtatccctc ctggagccgg cctgcggtga ggtcggtacc cagtacttag ggagggagga 240
cgcgcttggt gctcagggta ggctgggccg ctgctagctc ttgatttagt ctcatgtccg 300
cctttgtgcc ggcctctccg atttgtgggt ccttccaaga aagagtcctc tagggcagct 360
agggtcgtct cttgggtctg gcgaggcggc aggccttctt cggacctatc cccagaggtg 420
taacggagac tttctccact gcagggcggc ctggggcggg catctgccag gcgagggagc 480
tgccctgccg ccgagattgt ggggaaacgg cgtggaagac accccatcgg agggcaccca 540
atctgcctct gcactcgatt ccatcctgca acccaggaga aaccatttcc gagttccagc 600
cgcagaggca cccgcggagt tgccaaaaga gactcccgcg aggtcgctcg gaaccttgac 660
cctgacacct ggacgcgagg tctttcagga ccagtctcgg ctcggtagcc tggtccccga 720
ccaccgcgac caggagttcc ttcttccctt cctgctcacc agccggccgc cggcagcggc 780
tccaggaagg agcaccaacc cgcgctgggg gcggaggttc aggcggcagg aatggagagg 840
ctgatcctcc tctagccccg gcgcattcac ttaggtgcgg gagccctgag gttcagcctg 900
actttc 906

<210> SEQ ID NO 41
<211> LENGTH: 860
<212> TYPE: DNA
<213> ORGANISM: Homo sapiens

<400> SEQUENCE: 41
cactacggat ctgcctggac tggttcagat gcgtcgttta aaggggggggg ctggcactcc 60 agagaggagg gggcgctgca ggttaattga tagccacgga agcacctagg cgccccatgc 120
gcggagccgg agccgccagc tcagtctgac ccctgtcttt tctctcctct tccctctccc 180
acccctcact ccgggaaagc gagggccgag gtaggggcag atagatcacc agacaggcgg 240
agaaggacag gagtacagat ggagggacca ggacacagaa tgcaaaagac tggcaggtga 300
gaagaaggga gaaacagagg gagagagaaa gggagaaaca gagcagaggc ggccgccggc 360
ccggccgccc tgagtccgat ttccctcctt ccctgaccct tcagtttcac tgcaaatcca 420
cagaagcagg tttgcgagct cgaatacctt tgctccactg ccacacgcag caccgggact 480
gggcgtctgg agcttaagtc tgggggtctg agcctgggac cggcaaatcc gcgcagcgca 540
tcgcgcccag tctcggagac tgcaaccacc gccaaggagt acgcgcggca ggaaacttct 600
gcggcccaat ttcttcccca gctttggcat ctccgaaggc acgtacccgc cctcggcaca 660
agctctctcg tcttccactt cgacctcgag gtggagaaag aggctggcaa gggctgtgcg 720
cgtcgctggt gtggggaggg cagcaggctg cccctccccg cttctgcagc gagttttccc 780
agccaggaaa agggagggag ctgtttcagg aatttcagtg ccttcaccta gcgactgaca 840
caagtcgtgt gtataggaag 860

<210> SEQ ID NO 42
<211> LENGTH: 452
<212> TYPE: DNA
<213> ORGANISM: Homo sapiens

<400> SEQUENCE: 42
ggagcctgaa gtcagaaaag atggggcctc gttactcact ttctagccca gcccctggcc 60
ctgggtcccg cagagccgtc atcgcaggct cctgcccagc ctctggggtc gggtgagcaa 120
ggtgttctct tcggaagcgg gaagggctgc gggtcgggga cgtcccttgg ctgccacccc 180
tgattctgca tccttttcgc tcgaatccct gcgctaggca tcctccccga tcccccaaaa 240
gcccaagcac tgggtctggg ttgaggaagg gaacgggtgc ccaggccgga cagaggctga 300
aaggaggcct caaggttcct ctttgctaca aagtggagaa gttgctctac tctggagggc 360
agtggccttt tccaaacttt tccacttagg tccgtaagaa aagcaattca tacacgatca 420
gcgctttcgg tgcgaggatg gaaagaaact tc 452

<210> SEQ ID NO 43
<211> LENGTH: 1992
<212> TYPE: DNA
<213> ORGANISM: Homo sapiens

<400> SEQUENCE: 43
ttttcctgtt acagagctga gcccactcat gtggtgccaa gtagcgacta tctctcggcc 60
acctccaccc agagcaatgt gggcgccccc agcgggtggg agcgattgcc gagcggcgca 120
agggcgttta acgcctaacc ccctcctcct gggttgccaa gccgctaggt cgccgtttcc 180
aacgtggctg cgcgggactg aagtccgacg actcctcgtc ctcagtagga gacacacctc 240
ccactgcccc cagccacgcg agctatgggc agaatcgggg caacggtaat atctggatgg 300
ggcaggctcc cctgaggctg tgcttaagaa aaaaggaatc tggagtagcc tgagggggccc 360 cacgaggggg cctcctttgc gatcgtctcc cagccttagg ccaaggctac ggaggcaggc 420
ggccgagtgt tggcgcccag cccggccgag gactggatgg aggacgagaa gcagcctgcc 480
tctgggcgac agctgcggac gcagcctcgc cgcctcgccg cctcagcctc ggtcccagcg 540
tctctaaagc cgcgcccatt ttacagatgc agggcaggga gacaagaggc atctccgggg 600
gccgagtaga atgatggcgc gggttctccc ggcgccctga tttcgaggct gcgcccgggg 660
ccctacatgc aggcggggag gcctgggccg aaggcgtctg caaggagggg cgagtctgcc 720
cggtccgggc agggagtgag gccacagtca gttctcccta ggaggccgcg cagcgggtag 780
ggtatgggac tgggggacgc aacggggacc tggccgaatc agagccctca gcagagaacg 840
ccgaaaactc tggggccggc cgctcgcttc ccgctagtgg gaatggtttc cggtcatccg 900
ttcccagtcc agccccgggt agggagctct gatttgcaat gcacagcact tgcgaggttc 960
gaatgccccc gcaatttgca gatggaaata ctaagcctag gccgggcgtg gtggctcaag 1020
cctatcatct cagccctttg ggaggccaag ccgggaggat tgtttgagcc caagaattca 1080
aaaccagcct gagcaacata gcgaccccgt ctctacaaaa taaaataaaa taaattatcc 1140
gggcgtggtg gcacgcgcct gtggttccag ctactccgga ggctgaggtg ggaggatcgc 1200
ttgagtccgg gaggtcgagg ctacagtgag ccgtgatcgc accactgcac tccagcctgg 1260
gcgacagagt gagaccttgt ctcaaaaaag gaaaaaaaga aaaagaaagt aagcttcaaa 1320
gaagctctga taatagttct gggtcgtgca gcggtggcgg ccccgcgctc tcgcccctaa 1380
agcaagcgct ctttgtactg ggtggaggag ctttgagtag tgagggtgga gatgcagctt 1440
cggggtggcg cagccaccct gacactaggc ccggggtcgc agtgggacag aagagtctgc 1500
cgctctgact tgggctctga gttccaaggg cgcccggcac ttctagcctc ccaggcttgc 1560
gcgctggcgc ctttgccatc cgtgccgaag tggggagacc tagccgcgac caccacgagc 1620
gcagcggtga cacccagagg tcccaccggg cccctgggca gggtaacctt agcctgtccg 1680
cttcggcagc tttgcgaaga gtggcgcgca gctagggctg aggctcttgc ggacctgcgg 1740
tcgaagcagg cggctgagcc agttcgatcg ccaaggcctg ggctgccgac agtggtgcgc 1800
gctctgttcc gccgcggccg ggccaggcgc tctggaatag cgatgggggg acacggcctc 1860
caactttctg cagagaccat cgggcagctc cgggcctaag cagcgacctc accgaaggtt 1920
cctgggaacc tttgccaaaa tcccagcctc tgcctcggtc cagctaaacc gtgtgtaaac 1980
aagtgcacca ag 1992

<210> SEQ ID NO 44
<211> LENGTH: 448
<212> TYPE: DNA
<213> ORGANISM: Homo sapiens

<400> SEQUENCE: 44
ataaaggacc gggtaatttc gcggaatgcg gattttgaga caggcccaga cggcggcgga 60
ttccctgtgt cccccaactg gggcgatctc gtgaacacac ctgcgtccca ccccgatcct 120
aggttggggg gaaagggtat gggaaccctg agcccagagc gcgcccgct ctttcctttg 180 ctccccggct tccctggcca gccccctccc ggctggtttc ctcgctcact cggcgcctgg 240
cgtttcgggc gtctggagat caccgcgtgt ctggcacccc aacgtctagt ctccccgcag 300
gttgaccgcg gcgcctggag ccgggaatag gggtggggag tccggagaac caaacccgag 360
cctgaagttg ccattcgggt gactcccgag aaagcccggg agcattttgg ccaatgcggg 420
tttttacctg aacttcagca tcttcacc 448

<210> SEQ ID NO 45
<211> LENGTH: 395
<212> TYPE: DNA
<213> ORGANISM: Homo sapiens

<400> SEQUENCE: 45
aattggaaaa ccctggtatt gtgcctgttt gggggaagaa aacgtcaata aaaattaatt 60
gatgagttgg cagggcgggc ggtgcgggtt cgcggcgagg cgcagggtgt catggcaaat 120
gttacggctc agattaagcg attgttaatt aaaaagcgac ggtaattaat actcgctacg 180
ccatatgggc ccgtgaaaag gcacaaaagg tttctccgca tgtggggttc cccttctctt 240
ttctccttcc acaaaagcac cccagcccgt gggtccccc tttggcccca aggtaggtgg 300
aactcgtcac ttccggccag ggaggggatg gggcggtctc cggcgagttc caagggcgtc 360
cctcgttgcg cactcgcccg cccaggttct ttgaa 395

<210> SEQ ID NO 46
<211> LENGTH: 491
<212> TYPE: DNA
<213> ORGANISM: Homo sapiens

<400> SEQUENCE: 46
gggaagcgat cgtctcctct gtcaactcgc gcctgggcac ttagcccctc ccgtttcagg 60
gcgccgcctc cccggatggc aaacactata aagtggcggc gaataaggtt cctcctgctg 120
ctctcggttt agtccaagat cagcgatatc acgcgtcccc cggagcatcg cgtgcaggag 180
ccatggcgcg ggagctatac cacgaagagt tcgcccgggc gggcaagcag gcggggctgc 240
aggtctggag gattgagaag ctggagctgg tgcccgtgcc ccagagcgct cacggcgact 300
tctacgtcgg ggatgcctac ctggtgctgc acacggccaa gacgagccga ggcttcacct 360
accacctgca cttctggctc ggtaagggac ggcgggcggc gggaccccga cgcaccaagg 420
ccggcgaggg gagggcgtag gggtctgaga tttgcaggcg tgggagtaaa ggggaccgca 480
aactgagcta g 491

<210> SEQ ID NO 47
<211> LENGTH: 1284
<212> TYPE: DNA
<213> ORGANISM: Homo sapiens

<400> SEQUENCE: 47
ctcaggggcg ggaagtggcg ggtgggagtc acccaagcgt gactgcccga ggcccctcct 60
gccgcggcga ggaagctcca taaaagccct gtcgcgaccc gctctctgca ccccatccgc 120
tggctctcac ccctcggaga cgctcgcccg acagcatagt acttgccgcc cagccacgcc 180
cgcgcgccag ccaccgtgag tgctacgacc cgtctgtcta ggggtgggag cgaacggggc 240
gcccgcgaac ttgctagaga cgcagcctcc cgctctgtgg agccctgggg ccctgggatg 300
atcgcgctcc actccccagc ggactatgcc ggctccgcgc cccgacgcgg accagccctc 360
ttggcggcta aattccactt gttcctctgc tcccctctga ttgtccacgg cccttctccc 420
gggcccttcc cgctgggcgg ttcttctgag ttacctttta gcagatatgg agggagaacc 480
cgggaccgct atcccaaggc agctggcggt ctccctgcgg gtcgccgcct tgaggcccag 540
gaagcggtgc gcggtaggaa ggtttccccg gcagcgccat cgagtgagga atccctggag 600
ctctagagcc ccgcgccctg ccacctccct ggattcttgg gctccaaatc tctttggagc 660
aattctggcc cagggagcaa ttctctttcc ccttccccac cgcagtcgtc accccgaggt 720
gatctctgct gtcagcgttg atcccctgaa gctaggcaga ccagaagtaa cagagaagaa 780
acttttcttc ccagacaaga gtttgggcaa gaagggagaa aagtgaccca gcaggaagaa 840
cttccaattc ggttttgaat gctaaactgg cggggccccc accttgcact ctcgccgcgc 900
gcttcttggt ccctgagact tcgaacgaag ttgcgcgaag ttttcaggtg gagcagaggg 960
gcaggtcccg accggacggc gcccggagcc cgcaaggtgg tgctagccac tcctgggttc 1020
tctctgcggg actgggacga gagcggattg gggtcgcgt gtggtagcag gaggaggagc 1080
gcggggggca gaggagggag gtgctgcgcg tgggtgctct gaatccccaa gcccgtccgt 1140
tgagccttct gtgcctgcag atgctaggta acaagcgact ggggctgtcc ggactgaccc 1200
tcgccctgtc cctgctcgtg tgcctgggtg cgctggccga ggcgtacccc tccaagccgg 1260
acaacccggg cgaggacgca ccag 1284

<210> SEQ ID NO 48
<211> LENGTH: 554
<212> TYPE: DNA
<213> ORGANISM: Homo sapiens

<400> SEQUENCE: 48
tggagaacct tgggctctgt ggcctcaaag gtaggggtga tttcgagggg ccggcacctc 60
acagggcagg ttccaccgcg gaaacgcagt catcgcccag cgaccctgct cctggccctc 120
agcctccccc caggtttctt tttctcttga atcaagccga ggtgcgccaa tggccttcct 180
tgggtcggat ccggggggcc agggccagct tacctgcttt caccgagcag tggatatgtg 240
ccttggactc gtagtacacc cagtcgaagc cggcctccac cgccaggcgg gccagcatgc 300
cgtacttgct gcggtcgcgg tcagacgtgg tgatgtccac tgcgcggccc tcgtagtgca 360
gagactcctc tgagtggtgg ccatcttcgt cccagccctc ggtcacccgc agtttcactc 420
ctggccactg gttcatcacc gagatggcca aagcgttcaa cttgtcctta cacctctgcg 480
aagacaaggg gacccccacc gacggacacg ttagcctggg caaccgccac ccctcccggc 540
ccctccatca gcct 554

<210> SEQ ID NO 49
<211> LENGTH: 772
<212> TYPE: DNA
<213> ORGANISM: Homo sapiens

<400> SEQUENCE: 49
tctcacgacc catccgttaa cccaccgttc ccaggagctc cgaggcgcag cggcgacaga 60
ggttcgcccc ggcctgctag cattggcatt gcggttgact gagcttcgcc taacaggctt 120
ggggagggtg ggctgggctg ggctgggctg ggctgggtgc tgcccggctg tccgcctttc 180
gttttcctgg gaccgaggag tcttccgctc cgtatctgcc tagagtctga atccgacttt 240
ctttcctttg ggcacgcgct cgccagtgga gcacttcttg ttctggcccc gggctgatct 300
gcacgcggac ttgagcaggt gccaaggtgc cacgcagtcc cctcacggct ttcggggggt 360
cttggagtcg ggtggggagg gagacttagg tgtggtaacc tgcgcaggtg ccaaagggca 420
gaaggagcag ccttggatta tagtcacggt ctctccctct cttccctgcc atttttaggg 480
ctttctctac gtgctgttgt ctcactgggt ttttgtcgga gccccacgcc ctccggcctc 540
tgattcctgg aagaaagggt tggtcccctc agcaccccca gcatcccgga aaatggggag 600
caaggctctg ccagcgccca tcccgctcca cccgtcgctg cagctcacca attactcctt 660
cctgcaggcc gtgaacacct tcccggccac ggtggaccac ctgcagggcc tgtacggtct 720
cagcgcggta cagaccatgc acatgaacca ctggacgctg ggtatcccca at 772

<210> SEQ ID NO 50
<211> LENGTH: 1362
<212> TYPE: DNA
<213> ORGANISM: Homo sapiens

<400> SEQUENCE: 50
tggtttcctt tcgcttctcg cctcccaaac acctccagca agtcggaggg cgcgaacgcg 60
gagccagaaa cccttcccca aagtttctcc cgccaggtac ctaattgaat catccatagg 120
atgacaaatc agccagggcc aagatttcca gacacttgag tgacttcccg gtccccgagg 180
tgacttgtca gctccagtga gtaacttgga actgtcgctc ggggcaaggt gtgtgtctag 240
gagagagccg gcggctcact cacgctttcc agagagcgac ccgggccgac ttcaaaatac 300
acacagggtc atttataggg actggagccg cgcgcaggac aacgtctccg agactgagac 360
attttccaaa cagtgctgac attttgtcgg gccccataaa aaatgtaaac gcgaggtgac 420
gaacccggcg gggagggttc gtgtctggct gtgtctgcgt cctggcggcg tgggaggtta 480
tagttccaga cctggcggct gcggatcgcc gggccggtac ccgcgaggag tgtaggtacc 540
ctcagcccga ccacctcccg caatcatggg gacaccggct tggatgagac acaggcgtgg 600
aaaacagcct tcgtgaaact ccacaaacac gtggaacttg aaaagacaac tacagccccg 660
cgtgtgcgcg agagacctca cgtcacccca tcagttccca cttcgccaaa gtttcccttc 720
agtggggact ccagagtggt gcgccccatg cccgtgcgtc ctgtaacgtg ccctgattgt 780
gtacccctct gcccgctcta cttgaaatga aaacacaaaa actgttccga attagcgcaa 840

-continued ctttaaagcc ccgttatctg tcttctacac tgggcgctct taggccactg acagaaacat 900
ggtttgaacc ctaattgttg ctatcagtct cagtcagcgc aggtctctca gtgacctgtg 960
acgccgggag ttgaggtgcg cgtatcctta aacccgcgcg aacgccaccg gctcagcgta 1020
gaaaactatt tgtaatccct agtttgcgtc tctgagcttt aactccccca cactctcaag 1080
cgcccggttt ctcctcgtct ctcgcctgcg agcaaagttc ctatggcatc cacttaccag 1140
gtaaccggga tttccacaac aaagcccggc gtgcgggtcc cttcccccgg ccggccagcg 1200
cgagtgacag cgggcggccg gcgctggcga ggagtaactt ggggctccag cccttcagag 1260
cgctccgcgg gctgtgcctc cttcggaaat gaaaaccccc atccaaacgg ggggacggag 1320
cgcggaaacc cggcccaagt gccgtgtgtg cgcgcgcgtc tg 1362

<210> SEQ ID NO 51
<211> LENGTH: 476
<212> TYPE: DNA
<213> ORGANISM: Homo sapiens

<400> SEQUENCE: 51
gaaagccatc cttaccattc ccctcaccct ccgccctctg atcgcccacc cgccgaaagg 60
gtttctaaaa atagcccagg gcttcaaggc cgcgcttctg tgaagtgtgg agcgagcggg 120
cacgtagcgg tctctgccag gtggctggag ccctggaagc gagaaggcgc ttcctccctg 180
catttccacc tcaccccacc cccggctcat ttttctaaga aaaagttttt gcggttccct 240
ttgcctccta cccccgctgc cgcgcggggt ctgggtgcag acccctgcca ggttccgcag 300
tgtgcagcgg cggctgctgc gctctcccag cctcggcgag ggttaaaggc gtccggagca 360
ggcagagcgc cgcgcgccag tctattttta cttgcttccc ccgccgctcc gcgctccccc 420
ttctcagcag ttgcacatgc cagctctgct gaaggcatca atgaaaacag cagtag 476

<210> SEQ ID NO 52
<211> LENGTH: 300
<212> TYPE: DNA
<213> ORGANISM: Homo sapiens

<400> SEQUENCE: 52
atcgaaaatg tcgacatctt gctaatggtc tgcaaacttc cgccaattat gactgacctc 60
ccagactcgg ccccaggagg ctcgtattag gcagggaggc cgccgtaatt ctgggatcaa 120
aagcgggaag gtgcgaactc ctctttgtct ctgcgtgccc ggcgcgcccc cctcccggtg 180
ggtgataaac ccactctggc gccggccatg cgctgggtga ttaatttgcg aacaaacaaa 240
agcggcctgg tggccactgc attcgggtta aacattggcc agcgtgttcc gaaggcttgt 300

<210> SEQ ID NO 53
<211> LENGTH: 1246
<212> TYPE: DNA
<213> ORGANISM: Homo sapiens

<400> SEQUENCE: 53
atcaacatcg tggctttggt cttttccatc atggtgagtg aatcacggcc agaggcagcc 60
tgggaggaga gacccgggcg gctttgagcc cctgcagggg agtccgcgcg ctctctgcgg 120
ctcccttcct cacggcccgg cccgcgctag gtgttctttg tcctcgcacc tcctcctcac 180
ctttctcggg ctctcagagc tctccccgca atcatcagca cctcctctgc actcctcgtg 240
gtactcagag ccctgatcaa gcttccccca ggctagcttt cctcttcttt ccagctccca 300
gggtgcgttt cctctccaac ccggggaagt tcttccgtgg actttgctga ctcctctgac 360
cttcctaggc acttgcccgg ggcttctcaa ccctcttttc tagagcccca gtgcgcgcca 420
ccctagcgag cgcagtaagc tcataccccg agcatgcagg ctctacgttc ctttccctgc 480
cgctccgggg gctcctgctc tccagcgccc aggactgtct ctatctcagc ctgtgctccc 540
ttctctcttt gctgcgccca agggcaccgc ttccgccact ctccgggggg tccccaggcg 600
attcctgatg ccccctcctt gatcccgttt ccgcgctttg gcacggcacg ctctgtccag 660
gcaacagttt cctctcgctt cttcctacac ccaacttcct ctccttgcct ccctccggcg 720
cccccttttt aacgcgcccg aggctggctc acacccacta cctctttagg cctttcttag 780
gctccccgtg tgccccccctc accagcaaag tgggtgcgcc tctcttactc tttctaccca 840
gcgcgtcgta gttcctcccc gtttgctgcg cactggccct aacctctctt ctcttggtgt 900
cccccagagc tcccaggcgc ccctccaccg ctctgtcctg cgcccggggc tctcccggga 960
atgaactagg ggattccacg caacgtgcgg ctccgcccgc cctctgcgct cagacctccc 1020
gagctgcccg cctctctagg agtggccgct ggggcctcta gtccgccctt ccggagctca 1080
gctccctagc cctcttcaac cctggtagga acacccgagc gaaccccacc aggagggcga 1140
cgagcgcctg ctaggccctc gccttattga ctgcagcagc tggcccgggg gtggcggcgg 1200
ggtgaggttc gtaccggcac tgtcccggga caacccttgc agttgc 1246

<210> SEQ ID NO 54
<211> LENGTH: 984
<212> TYPE: DNA
<213> ORGANISM: Homo sapiens

<400> SEQUENCE: 54
acaaataaaa caccctctag cttcccctag actttgttta actggccggg tctccagaag 60
gaacgctggg gatgggatgg gtggagagag ggagcggctc aaggacttta gtgaggagca 120
ggcgagaagg agcacgttca ggcgtcaaga ccgatttctc cccctgcttc gggagacttt 180
tgaacgctcg gagaggcccg gcatctcacc actttacttg gccgtagggg cctccggcac 240
ggcaggaatg agggaggggg tccgattgga cagtgacggt ttggggccgt tcggctatgt 300
tcagggacca tatggtttgg ggacagcccc agtagttagt aggggacggg tgcgttcgcc 360
cagtccccgg atgcgtaggg aggcccagtg gcaggcagct gtcccaagca gcgggtgcgc 420
gtccctgcgc gctgtgtgtt cattttgcag agccagcctt cggggaggtg aaccagctgg 480
gaggagtgtt cgtgaacggg aggccgctgc ccaacgccat ccggcttcgc atcgtggaac 540
tggcccaact gggcatccga ccgtgtgaca tcagccgcca gctacgggtc tcgcacggct 600
gcgtcagcaa gatcctggcg cgatacaacg agacgggctc gatcttgcca ggagccatcg 660
ggggcagcaa gccccgggtc actacccccca ccgtggtgaa acacatccgg acctacaagc 720
agagagaccc cggcatcttc gcctgggaga tccgggaccg cctgctggcg gacggcgtgt 780
gcgacaagta caatgtgccc tccgtgagct ccatcagccg cattctgcgc aacaagatcg 840
gcaacttggc ccagcagggt cattacgact catacaagca gcaccagccg acgccgcagc 900
cagcgctgcc ctacaaccac atctactcgt accccagccc tatcacggcg gcggccgcca 960
aggtgcccac gccacccggg gtgc 984

<210> SEQ ID NO 55
<211> LENGTH: 545
<212> TYPE: DNA
<213> ORGANISM: Homo sapiens

<400> SEQUENCE: 55
aggaggcgca acgcgctgcc agggcggctt tatcctgccg ccacagggcg gggaccagcc 60
cggcagccgg gtgtccagcg ccgctcacgt gcctcgcctg gagcttagct ctcagactcc 120
gaagagggcg actgagactt gggcctggga gttggcttcg gggtacccaa ggcgacgaca 180
gctgagttgt accacgaagc tcaggccgag gcctcctccc ttgtctggcc ttcgaatcca 240
tactggcagc ctctcctctc aggcactccg cgggccgggc cactaggccc cctgctcctg 300
gagctgcgct atgatccggg tcttgagatg cgcgcgattc tctctgaacc ggtggagagg 360
aggctctgcc ccgcgcggag cgaggacagc ggcgcccgag cttcccgcgc ctctccaggg 420
cccaatggca agaacagcct ccgaagtgcg cggatgacag gaaaagatct tcagttcttc 480
tgccgctaga gaagtgcggg atacaagcct ctattggatc cacaacctgg agtcctgcct 540
tcgga 545

<210> SEQ ID NO 56
<211> LENGTH: 1533
<212> TYPE: DNA
<213> ORGANISM: Homo sapiens

<400> SEQUENCE: 56
atctgcgtgc ccttttctgg gcgagccctg ggagatccag ggagaactgg gcgctccaga 60
tggtgtatgt ctgtaccttc acagcaaggc ttcccttgga tttgaggctt cctattttgt 120
ctgggatcgg ggtttctcct tgtcccagtg gcagccccgc gttgcgggtt ccgggcgctg 180
cgcggagccc aaggctgcat ggcagtgtgc agcgcccgcc agtcgggctg gtgggttgtg 240
cactccgtcg gcagctgcag aaaggtggga gtgcaggtct tgcctttcct caccgggcgg 300
ttggcttcca gcaccgaggc tgacctatcg tggcaagttt gcggccccccg cagatcccca 360 gtggagaaag agggctcttc cgatgcgatc gagtgtgcgc ctccccgcaa agcaatgcag 420
accctaaatc actcaaggcc tggagctcca gtctcaaagg tggcagaaaa ggccagacct 480
aactcgagca cctactgcct tctgcttgcc ccgcagagcc ttcagggact gactgggacg 540
cccctggtgg cgggcagtcc catccgccat gagaacgccg tgcagggcag cgcagtggag 600
gtgcagacgt accagccgcc gtggaaggcg ctcagcgagt ttgccctcca gagcgacctg 660
gaccaacccg ccttccaaca gctggtgagg ccctgcccta cccgccccga cctcgggact 720
ctgcgggttg gggatttagc cacttagcct ggcagagagg ggagggggtg gccttgggct 780
gaggggctgg gtacagccct aggcggtggg ggagggggaa cagtggcggg ctctgaaacc 840
tcacctcggc ccattacgcg ccctaaacca ggtctccctg gattaaagtg ctcacaagag 900
aggtcgcagg attaaccaac ccgctccccc gccctaatcc ccccctcgtg cgcctgggga 960
cctggcctcc ttctccgcag ggcttgctct cagctggcgg ccggtcccca agggacactt 1020
tccgactcgg agcacgcggc cctggagcac cagctcgcgt gcctcttcac ctgcctcttc 1080
ccggtgtttc cgccgcccca ggtctccttc tccgagtccg gctccctagg caactcctcc 1140
ggcagcgacg tgacctccct gtcctcgcag ctcccggaca cccccaacag tatggtgccg 1200
agtcccgtgg agacgtgagg gggacccctc cctgccagcc cgcggacctc gcatgctccc 1260
tgcatgagac tcacccatgc tcaggccatt ccagttccga aagctctctc gccttcgtaa 1320
ttattctatt gttatttatg agagagtacc gagagacacg gtctggacag cccaaggcgc 1380
caggatgcaa cctgctttca ccagactgca gacccctgct ccgaggactc ttagtttttc 1440
aaaaccagaa tctgggactt accagggtta gctctgccct ctcctctcct ctctacgtgg 1500
ccgccgctct gtctctccac gccccacctg tgt 1533

<210> SEQ ID NO 57
<211> LENGTH: 702
<212> TYPE: DNA
<213> ORGANISM: Homo sapiens

<400> SEQUENCE: 57
aggtctcttc agactgccca ttctccgggc ctcgctgaat gcgggggctc tatccacagc 60
gcgcggggcc gagctcaggc aggctggggc gaagatctga ttctttcctt cccgccgcca 120
aaccgaatta atcagtttct tcaacctgag ttactaagaa agaaaggtcc ttccaaataa 180
aactgaaaat cactgcgaat gacaatacta tactacaagt tcgttttggg gccggtgggt 240
gggatggagg agaaagggca cggataatcc cggagggccg cggagtgagg aggactatgg 300
tcgcggtgga atctctgttc cgctggcaca tccgcgcagg tgcggctctg agtgctggct 360
cggggttaca gacctcggca tccggctgca ggggcagaca gagacctcct ctgctagggc 420
gtgcggtagg catcgtatgg agcccagaga ctgccgagag cactgcgcac tcaccaagtg 480
ttaggggtgc ccgtgataga ccgccaggga aggggctggt tcggagggaa ttcccgctac 540
cgggaaggtc ggaactcggg gtgatcaaac aaggaatgca tctcacctcc gtgggtgctt 600
gtgctgcgca aggaattatt accggagcgg ttgcgatggc ctttgcccgg cgacccaaga 660
agagtaagca aactaccgtc cacccagcgg atcaggtcca at 702

<210> SEQ ID NO 58
<211> LENGTH: 3180
<212> TYPE: DNA
<213> ORGANISM: Homo sapiens

<400> SEQUENCE: 58
gatgtcctgt ttctagcagc ctccagagcc aagctaggcg agaggcgtag gaggcagaga 60
gagcgggcgc gggaggccag ggtccgcctg ggggcctgag gggacttcgt ggggtcccgg 120
gagtggccta gaaacaggga gctgggaggg ccgggaagag cttgaggctg agcgggggac 180
gaacgggcag cgcaaagggg agatgaacgg aatggccgag gagccacgca ttcgccttgt 240
gtccgcggac ccttgttccc gacaggcgac caagccaagg ccctccggac tgacgcggcc 300
tgagcagcag cgagtgtgaa gtttggcacc tccggcggcg agacggcgcg ttctggcgcg 360
cggctcctgc gtccggctgg tggagctgct gcgccctatg cggcctgccg agggcgccgc 420
cgagggcccg cgagctccgt ggggtcgggg tggggggacc cgggagcgga cagcgcggcc 480
cgaggggcag gggcaggggc gcgcctggcc tggggtgtgt ctgggccccg gctccgggct 540
cttgaaggac cgcgagcagg aggcttgcgc aatcccttgg ctgagcgtcc acggagaaag 600
aaaaagagca aaagcagagc gagagtggag cgagggatgg gggcgggcaa agagccatcc 660
gggtctccac caccgccctg acacgcgacc cggctgtctg ttggggaccg cacgggggct 720
cgggcgagca ggggagggag gagcctgcgc ggggctcgtg ttcgcccagg aatcccggag 780
aagctcgaag acggtctggt gttgaacgca cacgtggact ccatttcatt accaccttgc 840
agctcttgcg ccacggaggc tgctgctgcc cggcggctgc tacccaccga gacccacgtg 900
gcccctcccc aggggtgtag gggtgacggt tgtcttctgg tgacagcaga ggtgttgggt 960
ttgcgactga tctctaacga gcttgaggcg caaacctagg attccctgag tgttggggtg 1020
cggcgggggg gcaagcaagg tgggacgacg cctgcctggt ttccctgact agttgcgggg 1080

-continued ggtgggggcc ggctctcagg ggccaccaga agctgggtgg gtgtacagga aaatattttt 1140
ctcctgccgt gtttggcttt ttcctggcat ttttgcccag ggcgaagaac tgtcgcgcgg 1200
ggcagctcca ccgcggaggg agaggggtcg cgaggctggc gcgggaagcg ctgtaggtgg 1260
cagtcatccg tccacgccgc acaggccgtc tgcgccgtcg gaccatcggg aggtctgcag 1320
caactttgtc ccggccagtc cccttgtccg ggaaggggct gagcttcccg acactctacc 1380
ctccccctct tgaaaatccc ctggaaaatc tgtttgcaat gggtgtttcc gcggcgtcca 1440
ggtctgggct gccgggggag gccgagcggc tgctgcagcc tccctgctgc caggggcgtc 1500
ggactccgct tcgctcacta cgcccaggcc cctcaggggc ccacgctcag gacttcgggg 1560
ccacacagca ggacccggtg ccccgacgac gagtttgcgc aggacccggg ctgggccagc 1620
cgcggagctg gggaggaagg ggcgggggtc ggtgcagcgg atcttttctg ttgctgcctg 1680
tgcggcggca ggaagcgtct tgaggctccc caagactacc tgaggggccg cccaagcact 1740
tcagaagccc aaggagcccc cggccacccc cgctcctggc ctttttgcca acgactttga 1800
aagtgaaatg cacaagcacc agcaattgac ttcccttccg tggttattta ttttgtcttt 1860
gtggatggtg ggcagatggg gagagaggcc cctacctaac ctcggtggct ggtccctaga 1920
ccacccctgc cagccggtgt ggggaggagc tcaggtccgc gggagagcga atgggcgcca 1980
ggaggtggga cagaatcctg ggaaggtaca gcggacgccc tggaagctcc cctgatgccc 2040
cagagggccc ttcctgggaa acctcccggg ggggtgcccc ataccatccc acccggctgt 2100
cttggcccct cccagggagc cgcaggagaa actagcccta cacctgggat tcccagagcc 2160
ttctgctggg gctcctgccc ccgacttcgg ataaccagct ccgcacaggt ccccgagaag 2220
ggccgctggc ctgcttattt gatactgccc cctcccagac aggggctggt cgagcccctg 2280
gttctgctgc cagactgaag ccttccagac gccacctcgg tttgggcccc cagggccctc 2340
aggggcccca ggagaggaga gctgctatct agctcagcca caggctcgct cctggtgggg 2400
gccaggctga aggagtggac cctggagagg tcgggaacct tttaacagcc gtgggctgga 2460
gggtggctac taagtgttcg gtctgggaag aggcatgacc cgcaccatcc cggggaaata 2520
aacgacttct taagggaatc ttctcgctga gcgggtgctc tgggccagga gattgccacc 2580
gccagcccac ggaacccaga tttgggctct gccttgagcg ggccgcctgt ggcttcccgg 2640
gtcgctcccc cgactcagaa agctctcaag ttggtatcgt tttcccggcc ctcggaggtg 2700
gattgcagat caccgagagg ggatttacca gtaaccacta cagaatctac ccgggcttta 2760
acaagcgctc atttctctcc cttgtcctta gaaaaacttc gcgctggcgt tgatcatatc 2820
gtacttgtag cggcagctta ggggcagcgg aactggtggg gttgtgcgtg caggggggagg 2880 ctgtgaggga gccctgcact ccgcccctcc acccttctgg aggagtggct ttgtttctaa 2940
gggtgccccc ccaacccccg ggtccccact tcaatgtttc tgctctttgt cccaccgccc 3000
gtgaaagctc ggctttcatt tggtcggcga agcctccgac gcccccgagt cccaccctag 3060
cgggccgcgc ggcactgcag ccgggggttc ctgcggactg gcccgacagg gtgcgcggac 3120
ggggacgcgg gccccgagca ccgcgacgcc agggtccttt ggcagggccc aagcacccct 3180

<210> SEQ ID NO 59
<211> LENGTH: 1038
<212> TYPE: DNA
<213> ORGANISM: Homo sapiens

<400> SEQUENCE: 59

```
tggcggccgg cgggcacagc cggctcattg ttctgcacta caaccactcg ggccggctgg     60

ccgggcgcgg ggggccggag gatggcggcc tgggggccct gcgggggctg tcggtggccg    120

ccagctgcct ggtggtgctg gagaacttgc tggtgctggc ggccatcacc agccacatgc    180

ggtcgcgacg ctgggtctac tattgcctgg tgaacatcac gctgagtgac ctgctcacgg    240

gcgcggccta cctggccaac gtgctgctgt cgggggcccg caccttccgt ctggcgcccg    300

cccagtggtt cctacgggag ggcctgctct tcaccgccct ggccgcctcc accttcagcc    360

tgctcttcac tgcaggggag cgctttgcca ccatggtgcg gccggtggcc gagagcgggg    420

ccaccaagac cagccgcgtc tacggcttca tcggcctctg ctggctgctg gccgcgctgc    480

tggggatgct gcctttgctg ggctggaact gcctgtgcgc ctttgaccgc tgctccagcc    540

ttctgcccct ctactccaag cgctacatcc tcttctgcct ggtgatcttc gccggcgtcc    600

tggccaccat catgggcctc tatggggcca tcttccgcct ggtgcaggcc agcgggcaga    660

aggccccacg cccagcggcc cgccgcaagg cccgccgcct gctgaagacg gtgctgatga    720

tcctgctggc cttcctggtg tgctggggcc cactcttcgg gctgctgctg gccgacgtct    780

ttggctccaa cctctgggcc caggagtacc tgcggggcat ggactggatc ctggccctgg    840

ccgtcctcaa ctcggcggtc aaccccatca tctactcctt ccgcagcagg gaggtgtgca    900

gagccgtgct cagcttcctc tgctgcgggt gtctccggct gggcatgcga gggcccgggg    960

actgcctggc ccgggccgtc gaggctcact ccggagcttc caccaccgac agctctctga   1020

ggccaaggga cagctttc                                                 1038
```

<210> SEQ ID NO 60
<211> LENGTH: 374
<212> TYPE: DNA
<213> ORGANISM: Homo sapiens

<400> SEQUENCE: 60

```
tagtaaggca ccgaggggtg gctcctctcc ctgcagcggc tgtcgcttac catcctgtag     60

accgtgacct cctcacacag cgccaggacg aggatcgcgg tgagccagca ggtgactgcg    120

atcctggagc tggtcgcagc aggccatcct gcacgcggtg gaggcgcccc ctgcaggccg    180

cagcgcatcc ccagcttctg gacgcactgt gagcggttat gcagcagcac gctcatatga    240

gatgccccgc agggtgctat gcaggcccac gtccccacaa agcccatggc aggcgcccgg    300

gtgccggagc acgcacttgg ccccatggat ctctgtgccc agggctcagc caggcatctg    360

gccgctaaag gttt                                                      374
```

<210> SEQ ID NO 61
<211> LENGTH: 246
<212> TYPE: DNA
<213> ORGANISM: Homo sapiens

<400> SEQUENCE: 61

```
tctcatctga gcgctgtctt tcaccagagc tctgtaggac tgaggcagta gcgctggccc     60

gcctgcgaga gcccgaccgt ggacgatgcg tcgcgccctt cccatcgcgg cctgggcggg    120

cccgcctgcc ctcggctgag cccggtttcc ctaccccggg gcacctcccc tcgcccgcac    180

ccggccccag tccctcccag gcttgcgggt agagcctgtc tttgcccaga aggccgtctc    240

caagct                                                               246
```

<210> SEQ ID NO 62
<211> LENGTH: 222

<212> TYPE: DNA
<213> ORGANISM: Homo sapiens

<400> SEQUENCE: 62
cagtccccga ggccctcccc ggtgactcta accagggatt tcagcgcgcg gcgcggggct 60
gcccccaggc gtgacctcac ccgtgctctc tccctgcaga atctcctacg acccggcgag 120
gtaccccagg tacctgcctg aagcctactg cctgtgccgg ggctgcctga ccgggctgtt 180
cggcgaggag gacgtgcgct tccgcagcgc ccctgtctac at 222

<210> SEQ ID NO 63
<211> LENGTH: 2209
<212> TYPE: DNA
<213> ORGANISM: Homo sapiens

<400> SEQUENCE: 63
agagagacat tttccacgga ggccgagttg tggcgcttgg ggttgtgggc gaaggacggg 60
gacacggggg tgaccgtcgt ggtggaggag aaggtctcgg aactgtggcg gcggcggccc 120
ccctgcgggt ctgcgcggat gaccttggcg ccgcggtggg ggtccggggg ctggctggcc 180
tgcaggaagg cctcgactcc cgacacctgc tccatgaggc tcagcctctt cacgcccgac 240
gtcgggctgg ccacgcgggc agcttctggc ttcggggggg ccgcgatagg ttgcggcggg 300
gtggcggcca caccaaaagc catctcggtg tagtcaccat tgtccccggt gtccgaggac 360
aacgatgagg cggcgcccgg gccctgggcg gtggcaacgg ccgaggcggg gggcaggcgg 420
tacagctccc ccggggccgg cggcggtggc ggcggctgca gagacgacga cggggacgcg 480
gacggacgcg gggcaacgg cggatacggg gaggaggcct cgggggacag gaggccgtcc 540
aaggagccca cggggtggcc gctcggggcg cccggcttag gagacttggg ggagctgaag 600
tcgaggttca tgtagtcgga gagcggagac cgctgccggc tgtcgctgct ggtgcccggg 660
gtgcctgagc ccagcgacga ggccgggctg ctggcggaca agagcgagga ggacgaggcc 720
gccgacgcca gcaggggagg cgcgggcggc gacaggcggg ccccgggctc gccaaagtcg 780
atgttgatgt actcgccggg gctcttgggc tccggtggca gtgggtactc gtgcatgctg 840
ggcaggctgg gcagcccctc cagggacagg cgcgtgggcc tcaccgcccg gccgcgctgg 900
cccaagaagc cctccgggcg gccgccgcta ggccgcacgg gcgaaggcac tacagggtga 960
gggggctgcg tggggccggc cccgaaggcg ctggccgcct ggctgggccc tggcgtggcc 1020
tgaggctcca gacgctcctc ctccaggatg cgccccacgg gggagctcat gagcacgtac 1080
tggtcgctgt ccccgccaca ggtgtagggg gccttgtagg agcggggcaa ggagctgtag 1140
cagcagccgg gaacgcccct gagcggctcc ccgccggggt gcagggctgc ggagaagaag 1200
tcgggcgggg tgcccgtggt gaccgcgtcg ctgggggaca cgttgaggta gtccccgttg 1260
ggcagcagct tgccatctgc atgctccatg gacagcttgg aaccgcacca catgcgcatg 1320
tacccactgt cctcggggga gctctcggcg ggcgagctgg ccttgtagcc gcccccgctc 1380
gccgggaatg tcctgcccgc cgcagaggtg ggtgctggcc ccgcaggccc cgcagaaggc 1440
acggcggcgg cggcggcggc ggcggccctg ggctgcaaga tctgcttggg ggcggacacg 1500
ctggcggggc tcatgggcat gtagtcgtcg ctcctgcagc tgccgctccc actgcccgcg 1560
agggccgcgc cgggcgtcat gggcatgtag ccgtcgtctg cccccaggtt gctgctggag 1620
ctcctgtggg agccgatctc gatgtctccg tagtcctctg ggtaggggtg gtaggccacc 1680
ttgggagagg acgcggggca ggacgggcag aggcggcccg cgctgcccga gaaggtggcc 1740

-continued cgcatcaggg tgtattcatc cagcgaggca gaggagggct ggggcaccgg ccgctgccgg 1800
gctggcgtgg tcagggagta ggtcctcttg cgcagccctc ggtccaggtc ctgggccgcg 1860
tcccccgaga cccggcggta ggagcggcca cagtggctca ggggcctgtc catggtcatg 1920
tacccgtaga actcaccgcc gccgccgccg tctcgggccg ggggcgtctc cgcgatggac 1980
tcgggcgtgt tgcttcggtg gctgcagaag gcgcgcaggt cgcctgggct ggagccgtac 2040
tcgtccaggg acatgaagcc ggggtcgctg gggagcccg aggcggaggc gctgccgctg 2100
gagggccgct ggccggggcc gtggtgcagc ggatgcggca gaggcgggtg cgggccgggc 2160
ggcggcgggt aggagcccga gccgtggccg ctgctggacg acagggagc 2209

<210> SEQ ID NO 64
<211> LENGTH: 149
<212> TYPE: DNA
<213> ORGANISM: Homo sapiens

<400> SEQUENCE: 64
taacctaaag aatgaagtca tgccccggcc tgcacccggg aaactgcaca cagcgaaaga 60
tcgccactga gataaagagc tgaaagctat tccccaattc agctgtttca gccgtgcggt 120
ctcacaatgg gctcacagac ggcagcatc 149

<210> SEQ ID NO 65
<211> LENGTH: 832
<212> TYPE: DNA
<213> ORGANISM: Homo sapiens

<400> SEQUENCE: 65
gtttccacaa tccacctcgt agctggggcg tgccgcttgc ctcggcttgt cccggcagaa 60
cactcttacc tttaatggcg actgaaaagt tgccacgagt tcctgatcat tgtggtaggt 120
gctgcgtgaa gctgagacgt gcgtgagcca catcccaggg ggctttgagc ccccaccgcg 180
gcggcggctg aggggaggct tgtcgtactc gcacaggagg acacagggct gcagtgttca 240
ctccagggcc tcttatcatt gggatctgag gaattttccg agaggaagtg cgaattaaca 300
atgatgaaag gtttgtgagt gagtgacagg cacgttctat tgagcactgc atggggcatt 360
atgtgccacc agagacgggg gcagaggtca agagccctcg agggctggga gagttcggag 420
gatagaagtc atcagagcac aatgaagcca gaccctgcag ccgccttccc cttcgggggc 480
ttccttagaa tgcagcattg cggggactga gctgtcccag gtgaaggggg gccgtcacgg 540
tgtgtggacg cccctcggct cagccctcta agagactcgg cagccaggat gggctcaagg 600
catgagccct caaaggaggt taggaaggag cgagggagaa aagatatgct tgtgtgacgt 660
cctggccgaa gtgagaacaa ttgtatcaga taatgagtca tgtcccattg aggggtgccg 720
acaaggactc gggaggaggc cacggagccc tgtactgagg agacgcccac agggagcctc 780
gggggcccag cgtcccggga tcactggatg gtaaagccgc cctgcctggc gt 832

<210> SEQ ID NO 66
<211> LENGTH: 256
<212> TYPE: DNA
<213> ORGANISM: Homo sapiens

<400> SEQUENCE: 66
tccagctgca gcgagggcgg ccaggccccc ttctccgacc tgcaggggta gcgcggcctc 60
ggcgccggag acccgcgcgc tgtctggggc tgcggtggcg tggggagggc gcggcccccg 120
gacgccccga ggaaggggca cctcaccgcc cccacccaga gcgcctggcc gtgcgggctg 180
cagaggaccc ctccggggca gaggcaggtt ccacggaaga ccccggcccg ctggggcttc 240
cccggagact ccagag 256

<210> SEQ ID NO 67
<211> LENGTH: 184
<212> TYPE: DNA
<213> ORGANISM: Homo sapiens

<400> SEQUENCE: 67
acttactgct tccaaaagcg ctgggcacag ccttatatga ctgaccccgc ccccgagtcc 60
caggccgccc catgcaaccg cccaaccgcc caaccgccac tccaaaggtc accaaccact 120
gctccaggcc acgggctgcc tctccccacg gctctagggc ccttcccctc caccgcaggc 180
tgac 184

<210> SEQ ID NO 68
<211> LENGTH: 118
<212> TYPE: DNA
<213> ORGANISM: Homo sapiens

<400> SEQUENCE: 68
tgccacaccc aggtaccgcc cgcccgcgcg agagccgggc aggtgggccg cggatgctcc 60
cagaggccgg cccagcagag cgatggactt ggacaggcta agatggaagt gacctgag 118

<210> SEQ ID NO 69
<211> LENGTH: 1534
<212> TYPE: DNA
<213> ORGANISM: Homo sapiens

<400> SEQUENCE: 69
tcgccagcgc agcgctggtc catgcaggtg ccacccgagg tgagcgcgga ggcaggcgac 60
gcggcagtgc tgccctgcac cttcacgcac ccgcaccgcc actacgacgg gccgctgacg 120
gccatctggc gcgcgggcga gccctatgcg ggcccgcagg tgttccgctg cgctgcggcg 180
cggggcagcg agctctgcca gacggcgctg agcctgcacg gccgcttccg gctgctgggc 240
aacccgcgcc gcaacgacct ctcgctgcgc gtcgagcgcc tcgccctggc tgacgaccgc 300
cgctacttct gccgcgtcga gttcgccggc gacgtccatg accgctacga gagccgccac 360
ggcgtccggc tgcacgtgac aggcgaggcg gcgtgggagc gggtccccgg cctcccttcc 420
cgccctcccg cctgccccgc cccaagggct acgtgggtgc caggcgctgt gctgagccag 480
gaagggcaac gagacccagc cctctcctct accccaggga tctcacacct gggggtagtt 540
taggaccacc tgggagcttg acacaaatgc agaatccagg tcccaggaag ggctgaggtg 600
ggcccgggaa taggcattgc cgtgactctc gtagagtgac tgtccccagt ggctctcaga 660
cgaagaggcg agaaagacaa gtgaatggca atcctaaata tgccaagagg tgcaatgtgg 720
tgtgtgctac cagcccggaa agacactcgc agcccctcta cccaggggtg cacagacagc 780
ccaccaagta gtgcctagca ctttgccaga ccctgatata caaagatgcc tgaaccaggg 840
tcccgtccct agagcagtgg ctctccactc tagcccccac cctgctctgc gacaataatg 900
gccacttagc atttgctagg gagccgggac ctagtccaag cacccacaag catgaatttg 960
ccaaatcttt tcagcaacct cttaaggcaa ctgctatcat gatcctcact ttacacatgg 1020
agaagcagaa gcagagatga tagaatcttt cgcccaaggc cacatctgta ttgggacggg 1080
ggcagcctgg cacccaagtg cccattcctc ccttctgacc agcccccacc cctccggctc 1140

-continued

```
tggcgtccaa agggctaagg ggaggggtgc ccttgtgaca gtcacccgcc ttctcccctg   1200

cagccgcgcc gcggatcgtc aacatctcgg tgctgcccag tccggctcac gccttccgcg   1260

cgctctgcac tgccgaaggg gagccgccgc ccgccctcgc ctggtccggc ccggccctgg   1320

gcaacagctt ggcagccgtg cggagcccgc gtgagggtca cggccaccta gtgaccgccg   1380

aactgcccgc actgacccat gacggccgct acacgtgtac ggccgccaac agcctgggcc   1440

gctccgaggc cagcgtctac ctgttccgct tccatggcgc cagcggggcc tcgacggtcg   1500

ccctcctgct cggcgctctc ggcttcaagg cgct                                1534
```

<210> SEQ ID NO 70
<211> LENGTH: 269
<212> TYPE: DNA
<213> ORGANISM: Homo sapiens

<400> SEQUENCE: 70

```
atgaacttca agggcgacat catcgtggtc tacgtcagcc agacctcgca ggagggcgcg     60

gcggcggctg cggagcccat gggccgcccg gtgcaggagg agaccctggc gcgccgagac    120

tccttcgcgg ggaacggccc gcgcttcccg gacccgtgcg gcggccccga ggggctgcgg    180

gagccggaga aggcctcgag gccggtgcag gagcaaggcg gggccaaggc ttgagcgccc    240

cccatggctg ggagcccgaa gctcggagc                                      269
```

<210> SEQ ID NO 71
<211> LENGTH: 282
<212> TYPE: DNA
<213> ORGANISM: Homo sapiens

<400> SEQUENCE: 71

```
tcagtgttat gtggggagcg ctagatcgtg cacacagtag gcgtcaggaa gtgttttccc     60

cagtaattta ttctccatgg tactttgcta aagtcatgaa ataactcaga ttttgttttc    120

caaggaagga gaaaggccca gaatttaaga gcaggcagac acacaaccgg gcacccccag    180

accctggccc ttccagcagt caggaattga cttgccttcc aaagccccag cccggagctt    240

gaggaacgga ctttcctgcg caggggggatc ggggcgcact cg                      282
```

<210> SEQ ID NO 72
<211> LENGTH: 142
<212> TYPE: DNA
<213> ORGANISM: Homo sapiens

<400> SEQUENCE: 72

```
gtggaaacac aacctgcctt ccattgtctg cgcctccaaa acacaccccc cgcgcatccg     60

tgaagctgtg tgtttctgtg ttactacagg ggccggctgt ggaaatccca cgctccagac    120

cgcgtgccgg gcaggcccag cc                                             142
```

<210> SEQ ID NO 73
<211> LENGTH: 741
<212> TYPE: DNA
<213> ORGANISM: Homo sapiens

<400> SEQUENCE: 73

```
tccacacctc gggcagtcac taggaaaagg gtcgccaact gaaaggcctg caggaaccag     60

gatgatacct gcgtcagtcc cgcggctgct gcgagtgcgc gctctcctgc caggggggacc    120

tcagaccctc ctttacagca caccgagggc cctgcagaca cgcgagcggg ccttcagttt    180

gcaaaccctg aaagcgggcg cggtccacca ggacgatctg gcagggctct gggtgaggag    240
```

gccgcgtctt tatttggggt cctcgggcag ccacgttgca gctctggggg aagactgctt 300
aaggaacccg ctctgaactg cgcgctggtg tcctctccgg ccctcgcttc cccgaccccg 360
cacaggctaa cgggagacgc gcaggcccac cccaccggct ggagaccccg gcacggcccg 420
catccgccag gattgaagca gctggcttgg acgcgcgcag ttttcctttg gcgacattgc 480
agcgtcggtg cggccacaat ccgtccactg gttgtgggaa cggttggagg tcccccaaga 540
aggagacacg cagagctctc cagaaccgcc tacatgcgca tggggcccaa acagcctccc 600
aaggagcacc caggtccatg cacccgagcc caaaatcaca gacccgctac gggcttttgc 660
acatcagctc caaacacctg agtccacgtg cacaggctct cgcacagggg actcacgcac 720
ctgagttcgc gctcacagat c 741

<210> SEQ ID NO 74
<211> LENGTH: 4498
<212> TYPE: DNA
<213> ORGANISM: Homo sapiens

<400> SEQUENCE: 74
ctgccctcgc ggatctcccc cggcctcgcc ggcctccgcc tgtcctccca ccaccctctc 60
cgggccagta ccttgaaagc gatgggcagg gtcttgttgc agcgccagtg cgtaggcagc 120
acggagcaga ggaagttggg gctgtcggtg cgcaccagct cgcccgggtg gtcggccagc 180
acctccacca tgctgcggtc gccgctcctc agcttgccgg ccagggcagc gccggcgtcc 240
ggggcgccca gcggcaacgc ctcgctcatc ttgcctgggc tcagcgcggt ggaaggcggc 300
gtgaagcggc ggctcgtgct ggcatctacg gggatacgca tcacaacaag ccgattgagt 360
taggaccctg caaacagctc ctaccagacg gcgacagggg cgcggatctt cagcaagcag 420
ctcccgggag accaacatac acgttcaggg gcctttatta ctgcgggggg tggggggggg 480
cgggggtggt taggggagga gggagactaa gttactaaca gtccaggagg ggaaaacgtt 540
ctggttctgc ggatcggcct ctgacccagg atgggctcct agcaaccgat tgcttagtgc 600
attaaaaagt ggagactatc ttccacgaat cttgcttgca gaggttaagt tctgtctttg 660
gctgttagaa aagttcctga aggcaaaatt ctcatacact tcctaaaata tttatgcgaa 720
gagtaaaacg atcagcaaac acattatttg gaagttccag tagttaatgc ctgtcagttt 780
tttgcaggtg agttttgtct aaagtcccaa cagaacacaa ttatctcccg taacaaggcc 840
acttttatca tgcaaaactg gcttcagtcc cgaaaagcaa gagctgagac ttccaaaggt 900
agtgctacta atgtatgtgc acgtatatat aaatatatac atatgctcta cttcataaaa 960
tatttacaat acaatctgtg gagaatttaa acacaacaga aatccattaa tgtacgctgc 1020
agattttttt aagtagcctt gaaaatcagc ttcagtagtt ggagcagtgc tgagctagaa 1080
gtacttgtca tgttctctgt tctctcaatg aattctgtca aaacgctcag tgcagaaaat 1140
tcagcgtttc agagatcttc agctaatctt aaaacaacaa tcataagaag gcccagtcga 1200
tgacactcag ggttctacag ctctcccaca tctgtgaact cgggtttggg gatgttggtt 1260
aagtttgtgg ctggtcctct ggtttgttgg gagttgagca gccgcagagt cacacacatg 1320
caaacacgca ctcttcggaa ggcagccact gtctacatca gctgggtgac tcagccctga 1380
ctcgggcagc agcgagacga tactcctcca ccgtcgccca gcacccgccg gttagctgct 1440
ccgaggcacg aacacccacg agcgccgcgt aaccgcagca ggtggagcgg gccttgaggg 1500
agggctccgc ggcgcagatc gaaacagatc gggcggctcg ggttacacac gcacgcacat 1560

-continued

```
cctgccacgc acactgccac gcacacgcaa cttcacggct cgcctcggac cacagagcac   1620
tttctccccc tgttgtaaaa ggaaaacaat tggggaaaag ttcgcagcca ggaaagaagt   1680
tgaaaacatc cagccaagaa gccagttaat tcaaaaggaa gaaaggggaa aaacaaaaaa   1740
aaacaacaaa aaaaggaagg tccaacgcag gccaaggaga agcagcagag gttgacttcc   1800
ttctggcgtc cctaggagcc ccggaaagaa gtgcctggcg gcgcagggcc gggcagcgtg   1860
gtgccctggc tgggtccggc cgcggggcgc ccgtcccgcc cgcgcccgct ggctctatga   1920
atgagagtgc ctggaaatga acgtgctttt actgtaagcc cggccggagg aattccattc   1980
cctcagctcg tttgcatagg ggcggccggc ggccaatcac aggcctttcc ggtatcagcc   2040
agggcgcggc tcgccgccgc cggctcctgg aattggcccg cgcgccccccg ccgccgcgcc   2100
gcgcgctact gtacgcagcc cgggcgggga gtcggaggcc acccccgcgc cccgcatcca   2160
agcctgcatg ctggcccggg gccccgcccg cgtgcggacc cctttccgca gccacacgca   2220
ggcttgtgcg gctccgcgag tggccacggt ccggagacct ggaaaaagaa agcaggcccc   2280
gccggcccga ggaggacccg gccggcgcgc cgcacccgga gaggcccggc cccgcgagcc   2340
gctgcaggca ggcgcagtgg ccgccacgag gctcccgaac cgggctgcag cccgcggacg   2400
gccccagatc ctgcgcggcc gcccagggcc aggcctccgc ttccagggcg gggtgcgat   2460
ttggccgcgg ggcccggggg agccactccg cgctcctgca ccgtccggct ggcagctgcg   2520
gcgaagcggc gctgattcct tgcatgaggc cggacggcgt ccgcgcgtgc cgtttgctct   2580
cagcgtcttc ccttgggtcg gtttctgtaa tgggtgtttt ttaccgctgc gcccgggccg   2640
cggctcgatc cctccgcgcg tctcacttgc tgcgtgcgtc agcggccagc gaagagtttc   2700
ctagtcagga aagaccccaa gaacgcgcgg ctggaaggaa agttgaaagc agccacgcgg   2760
cttgctcccg ggccttgtag cgccggcacc cgcagcagcc ggacagcctg cccgggcccc   2820
gcgtctcccc tccggctccc cggaagcggc ccccgctcct ctccccgccc ccgtgcgctc   2880
gagcggcccc aggtgcggaa cccaccccgg cttcgcgtgc gggcggccgc ttccccctgc   2940
gccggtcccc gcggtgctgc gggcattttc gcggagctcg gagggccccg cccccggtcc   3000
ggcgtgcgct gccaactccg accccgcccg gcggggctcc ctcccagcgg aggctgctcc   3060
cgtcaccatg agtccctcca cgccctccct gccgggccct gcacctcccg gggcctctca   3120
tccaccccgg ggctgcaacc cagtccccgg atcccggccc cgttccaccg cgggctgctt   3180
tgtggtcccc gcggagcccc tcaattaagc tccccggcgc gggggtccct cgccgacctc   3240
acggggcccc tgacgcccgc tcctccctcc cccagggcta gggtgctgtg gccgctgccg   3300
cgcagggact gtccccgggc gttgccgcgg gcccggacgc aggaggggc cggggttgac   3360
tggcgtggag gcctttcccg ggcgggcccg gactgcgcgg agctgtcggg acgcgccgcg   3420
ggctctggcg gacgccaggg ggcagcagcc gccctccctg gacgccgcgc gcagtccccg   3480
gagctcccgg aacgcccccg acggcgcggg gctgtgcggc ccgcctcgtg gccttcgggt   3540
cgcccgggaa gaactagcgt tcgaggataa aagacaggaa gccgccccag agcccacttg   3600
agctggaacg gccaaggcgc gtttccgagg ttccaatata gagtcgcagc cggccaggtg   3660
gggactctcg gaccaggcct ccccgctgtg cggcccggtc ggggtctctt cccgaagccc   3720
ctgttcctgg ggcttgactc gggccgctct tggctatctg tgcttcagga gcccgggctt   3780
ccgggggct aaggcgggcg gcccgcggcc tcaaccctct ccgcctccgc tccccctggg   3840
cactgccagc acccgagttc agttttgttt taatggacct ggggtctcgg aaagaaaact   3900
tactacattt ttcttttaaa atgatttttt taagcctaat tccagttgta aatccccccc   3960
```

-continued tccccccgcc caaacgtcca ctttctaact ctgtccctga gaagagtgca tcgcgcgcgc 4020
ccgcccgccc gcaggggccg cagcgccttt gcctgcgggt tcggacgcgg cccgctctag 4080
aggcaagttc tgggcaaggg aaaccttttc gcctggtctc caatgcattt ccccgagatc 4140
ccacccaggg ctcctggggc cacccccacg tgcatccccc ggaacccccg agatgcggga 4200
gggagcacga gggtgtggcg gctccaaaag taggcttttg actccagggg aaatagcaga 4260
ctcgggtgat ttgcccctcg gaaaggtcca gggaggctcc tctgggtctc gggccgcttg 4320
cctaaaaccc taaaccccgc gacgggggct gcgagtcgga ctcgggctgc ggtctcccag 4380
gagggagtca agttccttta tcgagtaagg aaagttggtc ccagccttgc atgcaccgag 4440
tttagccgtc agaggcagcg tcgtgggagc tgctcagcta ggagtttcaa ccgataaa 4498

<210> SEQ ID NO 75
<211> LENGTH: 453
<212> TYPE: DNA
<213> ORGANISM: Homo sapiens

<400> SEQUENCE: 75
ttcggaagtg agagttctct gagtcccgca cagagcgagt ctctgtcccc agcccccaag 60
gcagctgccc tggtgggtga gtcaggccag gcccggagac ttcccgagag cgagggaggg 120
acagcagcgc ctccatcaca gggaagtgtc cctgcgggag gccctggccc tgattgggcg 180
ccggggcgga gcggcctttg ctctttgcgt ggtcgcgggg gtataacagc ggcgcgcgtg 240
gctcgcagac cggggagacg ggcgggcgca cagccggcgc ggaggcccca cagccccgcc 300
gggacccgag gccaagcgag ggctgccag tgtcccggga cccaccgcgt ccgccccagc 360
cccgggtccc cgcgcccacc ccatggcgac ggacgcggcg ctacgccggc ttctgaggct 420
gcaccgcacg gagatcgcgg tggccgtgga cag 453

<210> SEQ ID NO 76
<211> LENGTH: 560
<212> TYPE: DNA
<213> ORGANISM: Homo sapiens

<400> SEQUENCE: 76
acgcacactg gggtgtgat ggaaaggggg acgcgatgga taggggtggg cgcacactgg 60
gggacgcgac ggggaggggt gagcacacac tgggggtgtg atggagaggg cgacgcaata 120
gggaggggtg ggcgcacacc agggacgcga tgatggggac gggtgggcgc acaccaggtg 180
gcatgatggg gaggagtggg tacacaccat ggggggcgtg atggggaggc gtgggcgtac 240 accgggggc gcgatgggga ggggtgggcg cacaccgggg gacgcgatgg aggcggtggg 300
tgcacacggg gcgcgatggg tgggagtagg tgcacactga gggcacgatt ggggagacac 360
gaaggagagg ggtgggcgca cactggggga cgcgatggcc gggacacgat gcggagaagt 420
gggtgaatac cggggtcgcg atgggcgccc tggaaggacg gcagtgctgc tcacaggggc 480
caggcccctc agagcgcgcc ccttgggggt aaccccagac gcttgttccc gagccgactc 540
cgtgcactcg acacaggatc 560

<210> SEQ ID NO 77
<211> LENGTH: 157
<212> TYPE: DNA
<213> ORGANISM: Homo sapiens

<400> SEQUENCE: 77
ccacagggtg gggtgcgccc acctgccctg tccatgtggc cttgggcctg cgggggagag 60
ggaatcagga cccacagggc gagccccctc cgtagcccgc ggcaccgact ggatctcagt 120
gaacacccgt cagcccatcc agaggctaga aggggga 157

<210> SEQ ID NO 78
<211> LENGTH: 114
<212> TYPE: DNA
<213> ORGANISM: Homo sapiens

<400> SEQUENCE: 78
ttgaggtctc tgtgcatgct tgtgcgtacc ctggactttg ccgtgagggg tggccagtgc 60
tctgggtgcc tttgccagac aactggtctg ccgggccgag cattcatgct ggtc 114

<210> SEQ ID NO 79
<211> LENGTH: 104
<212> TYPE: DNA
<213> ORGANISM: Homo sapiens

<400> SEQUENCE: 79
tgacgcgccc ctctccccgc agctccacct ggttgcgctc aacagccccc tgtcaggcgg 60
catgcggggc atccgcgggg ccgacttcca gtgcttccag cagg 104

<210> SEQ ID NO 80
<211> LENGTH: 659
<212> TYPE: DNA
<213> ORGANISM: Homo sapiens

<400> SEQUENCE: 80
aacacactgt ctcgcactag gtgctcgcgg aagagcgcgg cgtcgatgct gcggctcagg 60
ttgatgggcg atggcggccg cagatccagc tcgctcagcg atggcgccgg tcccacaccg 120
ttgcgggaca gtcccgggcc accctggggt ccgcgaccca acgacgcagc cgagccccag 180
gcgcctgaac tgggcgtggc cagctgccca ctctccgccg ggttgcggat gaggctcttg 240
ctgatgtcca agctgcctgc accaacgttg ctgggccctg catagcagtt attgggtcgc 300
tccggcacct cgctctttcc tgacggcgcc gggcacgcca gacgcatcag cttagcccag 360
caagcgtgct ccgtgggcgg cctgggtctc gcggcagcca ccgcggccaa cgccagggcg 420
agcgcccatg tcagctccag gaggcgcagc cagaagtgga caccccacca ggcccacgag 480
aagcggccca cgcggcctgg gcccgggtac agccagagcg cagccgccag ctgcaagccg 540
ctagccagca gccccagcgc gcccgccaca gccaacagcc gagggcccgg gctggcatcc 600
cagccccgtg ggccgtccag caggcggcga cggcacaggc agagcgtgcc cagagccac 659

<210> SEQ ID NO 81
<211> LENGTH: 813
<212> TYPE: DNA
<213> ORGANISM: Homo sapiens

<400> SEQUENCE: 81
gtctgcacga agcccgcggc ggcctgcagg gggcccagcg actcgtccag ggaaccggtg 60
cgcaggagca gccgggggcg cggcgcgccg gccgcccttg ggggactctg gggccggggg 120
cgcagctcga tctgacgctt gggcactgtc cggggcctgg cgggcgcggc gccctcctcc 180
agagccacct ccacacactc gaactgcgct ggggcggcag gacttggccc acggggccgc 240
agctctaggt aggtggccca gcgggagcca ccatcgggga cctgggactg gcgtgggacc 300
gcggcgggag acgctggccc cggcggcaag gggctgatga aggccggctc cgtgaactgt 360

```
tgttgcgcct cgcgatcgtc tgcgccggag cagccgaaca ggggtccgac gccgaagatg    420

acttccatct cccccgacgg cagcgtgcgc agctggggct ggggtggccg tgggccggaa    480

cctgggcctc gcgggaaacc cgagccgggc ccgtgccgct ggcggctatt ctgggcgctg    540

acggacaggc gaggctgcgc gcccgccccc cgcccaggag ccacccaggg ccaattcgct    600

gggcctttcg cgtccggccc aacgtccggg ggctccggag aacctggagc cgtgtagtag    660

gagcctgacg aaccggagga gtcctggcgc cgcgcggggg ccgtgggcag ctgcctcggg    720

atcccaggca gggctggcgg ggcgagcgcg gtcagcatgg tggggccgga cgccgtgcac    780

tatctccctc gcattcgcct ccgctggtgg cgc                                 813
```

```
<210> SEQ ID NO 82
<211> LENGTH: 440
<212> TYPE: DNA
<213> ORGANISM: Homo sapiens

<400> SEQUENCE: 82

ctggagagaa ctatacgggc tgtgggagtc accgggcgac tatcaccggg cctcctttcc     60

acatcctcct ccgggaaggg accccgttcc gggcctcgac cggcgcagac tgggctgacc    120

cactttcttg ggcccactga gtcacctcga aacctccagg ccggtagcgg ggaggagagg    180

aggagcaggc gggggtgcca aggtgtgggc tgcgccctgg ttagggggcg agcccggctt    240

gtttatgagg aggagcgcgg aggaggatcc agacacacag gcttgcgcgc ccagactcgc    300

ccggccagcg gctggcggcc tccgacgtca ccaaaccggt tgggtgagag ggcagagagc    360

agggggaagg gccgcagtcc cgcccgcgcc ccccggcacg caccgtacat cttgccctcg    420

tctgacagga tgatcttccg                                                440
```

```
<210> SEQ ID NO 83
<211> LENGTH: 252
<212> TYPE: DNA
<213> ORGANISM: Homo sapiens

<400> SEQUENCE: 83

gagtgcggag tgaaggggtg cactgggcac tcagcgcggc ccttgggagg cagggccgcc     60

ccagcctgcc ctcctgtctg ggaaggccgt ccagaagcag gagccccggg gaaaacaact    120

ggctggacgg ggcggccttc agtgtctctc ccagcctgag agtcgcttcc caccacctgg    180

gcacgaacct gctctgcgat ctccggcaag ttcctgcgcc tcctgtcggt aaaatgcaga    240

tcgtggcgtc tt                                                        252
```

```
<210> SEQ ID NO 84
<211> LENGTH: 1539
<212> TYPE: DNA
<213> ORGANISM: Homo sapiens

<400> SEQUENCE: 84

tcttctttcc gcccctaggg ggcacaagcg ggcatgtcca agcgcctagg agcccgtacc     60

gctggggacc tccccttccg cgaaccccga gcgggtagac ccagagcaat ccgagtgtgg    120

aaacaatgga gagggggcgt gttgagctgg ggtctccatg cctcgttggg gagagggagg    180

tgagtttgtg tcttctggaa ggcgtggggg ctgtgccctc gtgggggtag gaagtgctcc    240

cgtggggcgg ggtgcggatc ggagaggtga gtgggtgcgt ctgtccagcg gtccgcccgg    300

tgtggtcgtg cccggcccgc gtggggatgg gggtgtctct cccgctgggc aactatacca    360
```

-continued

```
gcgcaaccgg ggcgtcggcg cggcccacgc tagcggcgct gctccggcgg cgggggctgg    420

gcgtggcggt gatgctgggc gtggtggccg cgctgggcgt ggtggccgcg ctgccgccct    480

cacccgggca gccgtgctgg agaaggatgt cggcgcacag ctggcttcca gcctggcggg    540

cgtagaacag cgccgtgcgg ccctgggcgt cacgggccgc cacgtccgcg ccgtactaga    600

gggcggaaac ggccgcgtga ccgcgcgtcc ccagggcgcc cacacccggc gccgcctccc    660

ccacatggcc aagcctactt ccggggtccc tctgggaatt tcgggctttc ccgcgccagg    720

cgttttccga gatgaagcct caaagacccc ctttcctccc cccagctcac gtacccacag    780

cagcagttgc gtgatgacga cgtgggcgag ctcggccgcc aggtggagtg gggagcgcag    840

ctgtgggtcc tctacgctgg tgtcgagcgg cccgtgtcgc gcatgggcca aaagcaggag    900

aacggtagcc acgtcctggg cctgcacggc ggcccacagc tggcggccca gcggctcctc    960

cgaggtgctc agcggcgcca ggaacagtag ctgctcgtac ttggcgcgaa tccacgactc   1020

gcgctcctcc ctgcaagacc agggatcaac ggaaaaggct ctagggaccc ccagccagga   1080

cttctgcccc tacccacggg accgtctcag gttcgcacac cctcagcaac cctccccccg   1140

ctctgttccc tcacgcttac cgcgaagagt cccgcgaggg cttggcacgg cctcgcgtgt   1200

cgctttccca cacgcggttg gccgtgtcgt tgccaatagc cgtcagcacc agggtcagct   1260

cccgtggcca gtcgtccaag tccagcgagc gaacgcggga caggtgtgtg cccaggttgc   1320

ggtggatgcc agaacactcg atgcagatga gggcgcccag gttcaagctg gcccacgtgg   1380

ggtctgcgga aggagcgtag aggtcggctc ccagccgggc agcacaggca ccccggcatt   1440

cactacactc cctagcccct ccgctgcctc ctggcactca ctgggggccc cgcagtccac   1500

gcagattgaa ttccccttgg cgttccggat cgcctggat                          1539
```

<210> SEQ ID NO 85
<211> LENGTH: 2648
<212> TYPE: DNA
<213> ORGANISM: Homo sapiens

<400> SEQUENCE: 85

```
agccaggtcc agcccccgcg cctgacaccg gccggacgtt cccggggcgc cgcagctgcg     60

gcgggaactc tgggatccgg agccatctgc tcccacccgc tccggagcca aaccccgggg    120

gccgcctccg ctcccggacc cgcctcctct cccgggagtg tgagccgaac caagagtctc    180

ctgcctatct cctccagtag gaaaatagta ataataatag acaccctgcc ccccgtaaaaa    240

acactacctt ccccgtaccg cctcccaagt ctcccggggt acggattgcc tttgcagcag    300

ttccgcccca cctgactcac tccagggtca gccccgggtg ggtttcaatg cggctctggg    360

gagggggtgg gcagtggggg aagtgaggct tcctatccgc cccctctcac ttcacattta    420

aatattctgc acgttccagc ccccgcggac tcgcgtaccg cccaatccgc cttcaccgca    480

cgaaaaacat cactagcctg ctctcagccc aggggacgac tagtccctgg cgagaagctg    540

cctgcaaggt cactgtcatg ccacctgccc caagtgctca ggggaaactg aggcttcctc    600

atccccttca ccttcaacgt cgctctaaac acggcaaagc cccgtttcca tgctcccaga    660

gttcagctga ggctggaagt ggggtcctgg gcttctctgg gagcaatttt ctagtcactc    720

tgatcaagga cgttactttc ccagaaagct ctgaggctga gtccctctga aatcaagtcc    780

tttctcctgt cgcacaatgt agctactcgc cccgcttcag gactcctatt ctttgcccca    840

atccttgaca gaggggtgag cttggttcat ccgcccaccc cagagaaaag cttccctagt    900

ttcctggacc tcgctcctcc accccaagct gagcattcca ggtacccttc cctccctgtt    960
```

ctcaagccct gactcaactc actaggggaa gcgcggagct cggcgcccag cagctccctg 1020
gacccgctgc cagaagacag gctggggggt ccgggaaggg gcccggagcc aggaggccct 1080
cctgtgctct tggtgaagat gccgctgata aacttgagca tcttgcggtc acgagtggat 1140
gctcggcccc cctcccggcc ccgtttcagc cccggagctg gaggctccag agtgattgga 1200
ggtgcaggcc cggggggctg cgcggaagca gcggtgacag cagtggctgg actcggagtt 1260
ggtgggaggg ttagcggagg aggagagccg gcaggcggtc ccggatgcaa gtcactgttg 1320
tccaaggtct tactcttgcc tttccgaggg gacaacttcc ctcgggctcc agccccagcc 1380
ccgaccccac cagaggtcga agctgtagag ccccctcccc cggcggcggc ggcggtggcg 1440
gcggcagaga ccgaagctcc agtcccggcg ctgctctttg accccttgac cctgggcttg 1500
ccctcgcttt cgggccatga caggcggcta cccgcgccct tgcccccgcc ggctttggct 1560
ccactcgtgg tcacggtctt gcaaggcttg ggagccggcg gaggaggcgc caccttgagc 1620
ctccggctgc cggtgccagg gtgcggagag gatgagccag ggatgccgcc gcccgcccgg 1680
ccttcgggct ccgggccgcc ccagctcggg ctgctgagca gggggcgccg ggaggaggtg 1740
ggggcgcccc caggcttggg gtcggggctc agtcccccgg agagcggggg tcccggaggg 1800
acggcccaga gggagaggcg gcggccggga gcgggggaga ctgggcgggc cggactggcc 1860
ggagccgggg acagggctgg gggctccgcg cccccggtgc ccgcgctgct cgtgctgatc 1920
cacagcgcat cctgccggtg gaagagacgt tcgtgccgct tcttgcccgg ctcctccgcg 1980
cctcgggggc tgccaggatc cccagtctcg gagcctctgg caccggcggc gccggccgcg 2040
gccgcagacg gagaaggcgg cggcggaggc accgactcga gcttaaccag ggtcagcgag 2100
atgaggtagg tcgttgtccg gcgctgaagc gcgcccgcgc cccggctcat ggggcccgga 2160
gacccccgag ctggggaggg gaggggactc ccccggactg cctcaggggg gcccggccat 2220
ggggccgccc tgctcgctgc ccccagcccc cggacccccgc tgagcccccg gcccggctcc 2280
gctgtcgccg ccgcctccgc cgcctccgct tgcgcccccc tcccatcaca tggggcgccc 2340
cctccccatg ctccccgccc tgcgccccca ccctcttgga gccccgggac cttggtgctg 2400
ctccagggag gcgcgccgga ccgtccaccc cggcctgggt gggggcgctg agatgggtgg 2460
gggagggcgg ggaggacagt agtgggggca aatgggggag agagaggaaa agggagcaga 2520
aaaggggacc ggaggctagg ggaaacgaac ctgtgcgggg gaggcagggg cggggaattg 2580
ggactcaagg gacaggggcc gcggatgcgg tcggaaagag ggtctagagg agggtgggaa 2640
gctagtgg 2648

<210> SEQ ID NO 86
<211> LENGTH: 452
<212> TYPE: DNA
<213> ORGANISM: Homo sapiens

<400> SEQUENCE: 86
aggagcgcaa ggcttgcagg gcatgctggg agagcgcagg gaacgctggg agagcgcggg 60
aaatactggg attggctccc gagggctgtg aggagggcac gaggggacac tccgatgaag 120
gcagggcacg cggggcgagc cgggagcgtc tcctgagggc agcgaggagg gagctgaggc 180
acgcgggctc tcaatcgacg ccccacagag accaagaggc ctggccttgg ggggcagctg 240
cttgaaggag gcagagcgga agcgagggag actgctggag gccctgccgc ccacccgccc 300
tttcctcccc ctgaggagac gcctgacgca tctgcagtgc aggaggccgt gggcgttaga 360
agtgttgctt ttccagtttg taagaccatt ttcctgattc tcttccccac ggttgcggag 420
gagcaggtca gggccgccat gagggcagga tc 452

<210> SEQ ID NO 87
<211> LENGTH: 232
<212> TYPE: DNA
<213> ORGANISM: Homo sapiens

<400> SEQUENCE: 87
tcgaccgcta ctattatgaa aacagcgacc agcccattga cttaaccaag tccaagaaca 60
agccgctggt gtccagcgtg gctgattcgg tggcatcacc tctgcgggag agcgcactca 120
tggacatctc cgacatggtg aaaaacctca caggccgcct gacgcccaag tcctccacgc 180
cctccacagt ttcagagaag tccgatgctg atggcagcag ctttgaggag gc 232

<210> SEQ ID NO 88
<211> LENGTH: 221
<212> TYPE: DNA
<213> ORGANISM: Homo sapiens

<400> SEQUENCE: 88
tgtgccgtcg cacacagacg ccctcaacgt cggagagctg tgagcggggc cgtgctcttg 60
ggatgggagc ccccgggaga gctgcccgcc aacaccactc cgacgtgatc catgctggac 120
ataaagtgct cttccctccg ctagtcatcg gccgagcggg cccctcgctc ctgggtgtaa 180
gttctttctg tgcgtccttc tcccatctcc gtgcagttca g 221

<210> SEQ ID NO 89
<211> LENGTH: 477
<212> TYPE: DNA
<213> ORGANISM: Homo sapiens

<400> SEQUENCE: 89
ccatgcgccg ctgcgcgcgc gagttcgggc tgctgctgct gttcctctgc gtggccatgg 60
cgctcttcgc gccactggtg cacctggccg agcgcgagct gggcgcgcgc cgcgacttct 120
ccagcgtgcc cgccagctat tggtgggccg tcatctccat gaccaccgtg ggctacggcg 180
acatggtccc gcgcagcctg cccgggcagg tggtggcgct cagcagcatc ctcagcggca 240
tcctgctcat ggccttcccg gtcacctcca tcttccacac cttttcgcgc tcctactccg 300
agctcaagga gcagcagcag cgcgcggcca gccccgagcc ggccctgcag gaggacagca 360
cgcactcggc cacagccacc gaggacagct cgcagggccc cgacagcgcg ggcctggccg 420
acgactccgc ggatgcgctg tgggtgcggg cagggcgctg acgcctgcgc cgcccac 477

<210> SEQ ID NO 90
<211> LENGTH: 1200
<212> TYPE: DNA
<213> ORGANISM: Homo sapiens

<400> SEQUENCE: 90
gtcctaacat cccaggtggc ggcgcgctgg ctccctggag cggggcggga cgcggccgcg 60
cggactcacg tgcacaaccg cgcgggacgg ggccacgcgg actcacgtgc acaaccgcgg 120
gaccccagcg ccagcgggac cccagcgcca gcgggacccc agcgccagcg ggaccccagc 180
gccagcggga ccccagcgcc agcgggaccc cagcgccagc gggaccccag cgccagcggg 240
tctgtggccc agtggagcga gtggagcgct ggcgacctga gcggagactg cgccctggac 300
gccccagcct agacgtcaag ttacagcccg cgcagcagca gcaaagggga aggggcagga 360
gccgggcaca gttggatccg gaggtcgtga cccaggggaa agcgtgggcg gtcgacccag 420
ggcagctgcg gcggcgaggc aggtgggctc cttgctccct ggagccgccc ctccccacac 480
ctgccctcgg cgcccccagc agttttcacc ttggccctcc gcggtcactg cgggattcgg 540
cgttgccgcc agcccagtgg ggagtgaatt agcgccctcc ttcgtcctcg gcccttccga 600
cggcacgagg aactcctgtc ctgccccaca gaccttcggc ctccgccgag tgcggtactg 660
gagcctgccc cgccagggcc ctggaatcag agaaagtcgc tctttggcca cctgaagcgt 720
cggatcccta cagtgcctcc cagcctgggc gggagcggcg gctgcgtcgc tgaaggttgg 780
ggtccttggt gcgaaaggga ggcagctgca gcctcagccc caccccagaa gcggccttcg 840
catcgctgcg gtgggcgttc tcgggcttcg acttcgccag cgccgcgggg cagaggcacc 900
tggagctcgc agggcccaga cctgggttgg aaaagcttcg ctgactgcag gcaagcgtcc 960
gggaggggcg gccaggcgaa gccccggcgc tttaccacac acttccgggt cccatgccag 1020
ttgcatccgc ggtattgggc aggaaatggc agggctgagg ccgaccctag gagtataagg 1080
gagccctcca tttcctgccc acatttgtca cctccagttt tgcaacctat cccagacaca 1140
cagaaagcaa gcaggactgg tggggagacg gagcttaaca ggaatatttt ccagcagtga 1200

<210> SEQ ID NO 91
<211> LENGTH: 900
<212> TYPE: DNA
<213> ORGANISM: Homo sapiens

<400> SEQUENCE: 91
caccttcccc gaggtaatta ttttctgggg ggtaggggtg ggggttggga gggtgaagaa 60
aggaagaaaa agaaggccga tcacactggg caccggcgga ggaagcgtgg agtccattga 120
tctaggtact tgtggggagg ggagaacccg agcagcagct gcaaacggaa gggctgtgag 180
cgagcgggcg ggcgggtggc tggcagcgag gccaccagca ggggggcccc gggccgaggc 240
cgcgccacct cggcaccacg cgggcagccg gtgcggcggg gtcgccacgg ccaggggagc 300
gctgggtgcc caccatggca gttatgcaag cggtgacccc ctggtcttgc ctccccgccg 360
ccctgcactc cttcctcccc gctgccgaca cttggatctc tctagctctt tctctcccct 420
gtgttttcaa acaggaagtg cacggctgtc tataacgtgc tgccgggtct caggatggag 480
gagtgaagtc tcctgtcgcc gtggttccag cctccggagc tcgcccaagc cgcgtcccca 540
gagagcgccc tgagagaaca gggtggccgc ttggtccagg tgcgcggggt cgggtctggg 600
tccagggagc gggtcgggaa gtctgcggca cggagcactg ctagtgtcgg atctgcatct 660
ccagctctgt gctgcagctt cacttgcccg ccccccacca ctggcttctc acccggggtc 720
tctgccaaac tctggctgct gccgccctgg gttcgggccg gcggaaggcc ctgggcgtgc 780
gctgcggagc cgcctgcgag gactccacta gggcgctttc caggctggac tgccccgggc 840
tgcgctggag ctgccagtgc tcggggagtc ttcctggagt ccccagctgc cctctccacc 900

<210> SEQ ID NO 92
<211> LENGTH: 200
<212> TYPE: DNA
<213> ORGANISM: Homo sapiens

<400> SEQUENCE: 92
ctcttcccaa gttacgccac cggtcgagga cggcaggaga cccccgagtg cagagaaagc 60
tcaaaccggc agcgaagtcg gtcctagcca agctgaaaaa acgtctcgga tttcgcggac 120
agcggcctag acacagcccg atcttccagt cctagtgccc tggtcgagac ggttctatcc 180
ttttgcaaag aagccggaaa 200

<210> SEQ ID NO 93
<211> LENGTH: 400
<212> TYPE: DNA
<213> ORGANISM: Homo sapiens

<400> SEQUENCE: 93
tctcggttgc aatccccacc ctcctcaccc agcagggcag gaggcaccca acttggagga 60
gaaaggggtg ggggaggtga aacagagacc ggagagtcac gagggctggg ccgccgagag 120
caggagaata taccgtgtca cacacctcca ttctctcaca cacgttgcag acacaaatca 180
ctgacggttt ccacgtgctg cgctcgtgag cggaggtgtt caaagagggg gcagatgagt 240
tacttcccga gacggaaccg gggtcccacc gtccgccgcc ttcagtagca caaccaatct 300
ctgaacactc aaaccgcgca tctctggcgc atcaccatcc tatttaaggc cacgggctcc 360
gcccttttcc tcccctccct tcttttccac tctttttcca 400

<210> SEQ ID NO 94
<211> LENGTH: 700
<212> TYPE: DNA
<213> ORGANISM: Homo sapiens

<400> SEQUENCE: 94
ctgccagaga tgtgtctgtc ttgcgccccg catgcactgc ctgcggggct gcgctgcact 60
ccccggcggc gccacgggtc tggcccccgc gcttctacgt gttgggggga tgcatggacc 120
ttggagatcc gtagttggcc ctaaccttct cggaatctcc tctgcacgcg ctgcctgttc 180
ctcctctgca cgctctgtcc gttcctttgc aacttctgtg ggaattgtcc tggcgtggga 240
aacgcccccg cgctctttgg cacttagggt gtgagtgttg cgccccttgc cgcagcgctc 300
agggcagcat cccgctcgag gatgcagggt tctcaccaag cagtgagggg gactcacgcg 360
ccgccgggga gcggagccag gctccgagaa gggagcaggc tcgagccgct gggttttcgc 420
aagccttggg gcctctggcc gcccttccat gcctccgggc gcgggcggct cagcaggtcc 480
ccggcttcgg gaagttttgt gcgcggatcg ctggtgggga gggcgcgcgg gccagtggct 540
gagcttgcag cgaagtttcc gtgaaggaaa ctgcatgtgc ctttggaggc gactcgggac 600
tgctgtaggg tggactgggt gtctatggag ttgcgggtca gagcgagtag ggtgggtcct 660
ttcctgggac aggactggga attggggctc gaagtagggg 700

<210> SEQ ID NO 95
<211> LENGTH: 200
<212> TYPE: DNA
<213> ORGANISM: Homo sapiens

<400> SEQUENCE: 95
aggggtgtcc tccaacatct ctgaaccgcc ttcccttcct cctcactggc gccctcttgc 60
ctcagtcgtc ggagatggag aggcggctga agattggcag gcggcggcca gggtcgaggc 120
tgggagactc agagccgctg aggctgccgg agctcaggga gccgcttagg tagctgtcgc 180
ggtccgacag cgagtccggg 200

<210> SEQ ID NO 96
<211> LENGTH: 5000
<212> TYPE: DNA
<213> ORGANISM: Homo sapiens

<400> SEQUENCE: 96

```
tctgactctc gggctggagc agccgagaca gcgctcccca gcgggactac agaatcccgg     60
gtgtcggcct gggggccctg gattggcagt ggtggagtct tctgagccta acagctacta    120
ggaatgacag agttgcagat ggctttgtcg cccgcggggc ggctcaagcg tcctgggtcc    180
caggcctctg tcctacggcc aggccgccgg ctcaacgggc cgaagggaat cgggctgacc    240
agtcctaagg tcccacgctc ccctgacctc agggcccaga gcctcgcatt accccgagca    300
gtgcgttggt tactctccct ggaaagccgc ccccgccggg gcaagtggga gttgctgcac    360
tgcggtcttt ggaggcctag gtcgcccaga gtaggcggag ccctgtatcc ctcctggagc    420
cggcctgcgg tgaggtcggt acccagtact tagggaggga ggacgcgctt ggtgctcagg    480
gtaggctggg ccgctgctag ctcttgattt agtctcatgt ccgcctttgt gccggcctct    540
ccgatttgtg ggtccttcca agaaagagtc ctctagggca gctagggtcg tctcttgggt    600
ctggcgaggc ggcaggcctt cttcggacct atccccagag gtgtaacgga gactttctcc    660
actgcagggc ggcctggggc gggcatctgc caggcgaggg agctgccctg ccgccgagat    720
tgtggggaaa cggcgtggaa gacaccccat cggagggcac ccaatctgcc tctgcactcg    780
attccatcct gcaacccagg agaaaccatt tccgagttcc agccgcagag gcacccgcgg    840
agttgccaaa agagactccc gcgaggtcgc tcggaacctt gaccctgaca cctggacgcg    900
aggtctttca ggaccagtct cggctcggta gcctggtccc cgaccaccgc gaccaggagt    960
tccttcttcc cttcctgctc accagccggc cgccggcagc ggctccagga aggagcacca   1020
acccgcgctg gggcggaggg ttcaggcggc aggaatggag aggctgatcc tcctctagcc   1080
ccggcgcatt cacttaggtg cgggagccct gaggttcagc ctgactttcc cgactccgcc   1140
gggcgcttgg tgggctcctg ggcttctggg ctcaccctta cacctgtgta ctaaagggct   1200
gctaccctcc cgaggtgtac gtccgccgcc tcggcgctca tcggggtgtt ttttcaccct   1260
ctcgcggtgc acgctttttc tctcacgtca gctcacatct ttcagtacac agccactggg   1320
tctccctgcc cctccagcct ttcctaggca gctttgaggg cccagacgac tgaagtctta   1380
ctgctaggat gggaacacga tgaaaaagga aggggcccag tcaaaagtcc tctcctcttc   1440
ggtttttctt caactgtcct tcacaaaaac atttatttct gtcccagcgc cctggcggat   1500
ttcggcagat gggccctagg gggttgtgga ggccaaattc ccaggatgct ggtcctgcct   1560
ttttcattgg ccaaaactgt atttcctaca acgactaaag ataaccaaga actgagtaga   1620
ccctgttctc tcaccagatc tccctggctc tgtttaactt ttcctggtgc aatgcgatgg   1680
caccaccagc tccccaggca ggcaccactc cctcaagata ccatttgggg tagggatttg   1740
agtcctggag agggtcagcg gggcgccggg gtgggggtgg gaaggagact gacagggaca   1800
caccgcgagc tccgcatact ctcctctgcc ccctgtagcc cggggcttta atgaccccaa   1860
gcagatttcc tgtctctggt ctagccagct gcccctaggg ctggatttta tttcttcatg   1920
gggtttcacc ctaaagggcc ccctggtcat gggacctggt tgggaacaaa tgaaagatgt   1980
cttgtagcaa atgctttcag gggagcagaa aagaagattg ggcacttcca gtcacttggt   2040
cactttaggt ggctggaaca aaactggtga ctttcacgac tgctacaggg tgagggggtg   2100
aagggtggca gagaggtgac aagccactgg gaatcctatt cagtggggat gccgacaggg   2160
agtggctgta atcaactgag caacatctgt gtgaatgtta ttcacaggtc aggacagcag   2220
cttggtcttc ccaggtgagg aactgaggac tggcctgcat agatttgtgc agtaggtgag   2280
```

-continued

```
tagcttccaa atttattttc agaacttcca tgtagtacct gcctctccat ttaaatattt   2340
tttaaaattt tatttattta aatattttct tggttagctt tccaagaggg aggaaaagag   2400
gggagttgca acaagtagtg cccctatgct gggattcatt ttccagagta aagcctggga   2460
ctggcaccct gacccctacc ggcaggtgaa aactccaggc aaactgctga gatcccacct   2520
gggctggctg agatagtgcc tggggtgcat ccctcagcag ctgccacctg ggccctgggg   2580
ccatctcttt ctctggcatc aagcagccag gtgtcaaggc cttcccagca atccatgctg   2640
catggctggg tcttgttcta gcaggtcgat gggcagggac tggtagctta gccagggcac   2700
cagtgcgtgg ctgtgggttt gtgtgcttct gtggagaagc atgatgtgta tgtgtgtgtg   2760
tgggcacagg catgaggaag ggttcatttg tgcaggtatc tcccatgtat atcagtgtgg   2820
gagagtgcct gaggatgtgt ttgtgtgtct gaaaatgggc ggagggtctg ttgtgctaat   2880
gtgtgcaggg gtgaacatgt gtgtgacagt ctgtgtgttt ccctgagtgg tggctgcgtg   2940
agagggtgag gggatttggt gttgtctacc atgcccggca catagcaggc tcttaataat   3000
cttgaattta attaatgtta aatgtgtatg ttcccatcct tgtggaagtt ggtatagagc   3060
ctgttttcct gtgattgtga gactggaaaa tgggggacgg gcaggggcga gacaggatac   3120
agaggctact gttttcttcc tccctagaag taagtacata gaagagtggg ctctggcacc   3180
tcacgggaca tcaccaagtc ctgtgtggct ggctaggctg tcccaaggtg gcttcaggca   3240
tcacttgaat cttttgagac cttcaggcag tagcctgcca ttcaccctgt cagtcagcag   3300
aagttgggcc cacacaggcc atagaaacac agagcagttc ccgggaggac ctgagctgtc   3360
cctgagagca gagcttccag gagaggccgc aggaactgcc ttgaccggaa ttcctcttgg   3420
ggtgcaaagg tggagggaca catggtgcga ccccaggcag aggactgcag ccactccgtg   3480
cagtcccagc ctctggggta gccccttgac ctccaggcct gcacagatcc aaggccgagg   3540
tccaggctcc agcgccaaat tagctggcct agcagcctgc agccgctcta atctcaacta   3600
ggaaggaatc cttgcgctta gaaagtccaa gcgaaagggt attctgattt tatcccggtt   3660
ttaccagaaa atgctgaaag gaaaagcccc gagaggacac agtgctctag gaactcgggg   3720
cgccacgagc gcctcatccc ctcccttccg cccggccgcg gtgccctggt cgctgaggga   3780
cgcggtcagt acctaccgcc actgcgaccc gagaagggaa agcctcaact tcttcctctc   3840
ggagtcctgc ccactacgga tctgcctgga ctggttcaga tgcgtcgttt aaaggggggg   3900
gctggcactc cagagaggag gggcgctgc aggttaattg atagccacgg aagcacctag    3960
gcgccccatg cgcggagccg gagccgccag ctcagtctga cccctgtctt ttctctcctc   4020
ttccctctcc cacccctcac tccgggaaag cgagggccga ggtaggggca gatagatcac   4080
cagacaggcg gagaaggaca ggagtacaga tggagggacc aggacacaga atgcaaaaga   4140
ctggcaggtg agaagaaggg agaaacagag ggagagagaa agggagaaac agagcagagg   4200
cggccgccgg cccggccgcc ctgagtccga tttccctcct tccctgaccc ttcagtttca   4260
ctgcaaatcc acagaagcag gtttgcgagc tcgaatacct ttgctccact gccacacgca   4320
gcaccgggac tgggcgtctg gagcttaagt ctgggggtct gagcctggga ccggcaaatc   4380
cgcgcagcgc atcgcgccca gtctcggaga ctgcaaccac cgccaaggag tacgcgcggc   4440
aggaaacttc tgcggcccaa tttcttcccc agctttggca tctccgaagg cacgtacccg   4500
ccctcggcac aagctctctc gtcttccact tcgacctcga ggtggagaaa gaggctggca   4560
agggctgtgc gcgtcgctgg tgtggggagg gcagcaggct gcccctcccc gcttctgcag   4620
cgagttttcc cagccaggaa aagggaggga gctgtttcag gaatttcagt gccttcacct   4680
```

agcgactgac acaagtcgtg tgtataggaa ggcgtctggc tgtttcggga ctcaccagag 4740
agcatcgcca accagaacgg cccacccggg gtgtcgagtc ttggtaggga aatcagacac 4800
agctgcactc ccggcccgcg ggccttgtgg catataacca tttatatatt tatgatttct 4860
aattttatta taaaataaaa gcagaaatat ttcccgaaga acattcacat gagggcatta 4920
cggggagacg gcaagtcggc ggctcggggg gcgcgctcag ccgggagcgc tgtagtcaca 4980
gtcccgggag gaagagcgcg 5000

<210> SEQ ID NO 97
<211> LENGTH: 1500
<212> TYPE: DNA
<213> ORGANISM: Homo sapiens

<400> SEQUENCE: 97
tggaacaagt gtcagagagt aagcaaacga ctttctgagc tgtgactctg ctcctcgact 60
gcccacgtgc tctccgctgt ctgcactcct gcctcacctg ggctgactcg gactctccac 120
ctcctttgct gcttccggca tgagctaccc aggagcctaa ggcgctcctt cccgcaactc 180
cggtccccgc gccccgggac tgcaaatcct ttaaacagag gccccagagc taggggtttt 240
cccaggctct ggtgggcgtg ggctgacagt cgctgggagc cccgcaacag gggggatgtc 300
caggcaggta tgcacccagc tcccggcgtt tcccggagtc accacaatgt ttccctttct 360
ctctccccca cgtatgctgc taggggtact ccccagatag gattttcttt gtcttttctc 420
ctagtaacac cgaagccctc tcgtgcccgg ggactgcaga ggaacgccag accatccgga 480
ccttgcggga tggctcggtg tgtgtgtttt actgtgtgtc ggagtgtcgc gcatgtgtgc 540
gtgttggggc gcgttatcaa caggggccta gggcaccccc actctttctt gctctcttcc 600
cccatcactt catggacctc cgaggcgcaa agcgctcgac cctctcctgg gctcagtggc 660
ttgggtactc cgggctgagc tcagctgggg agtcccctta cccagcccgc accggcaccc 720
cgaagcttca aagttgcggc aaacagttgc ggggagcaga ggaactgagg tccaggccag 780
cgcgcccgcg gtcgctcgcc ttggggagca ggctgagccg agggtcgtgc gggtgcgcgg 840
cagaggcggt aggaggcgga ggagaggggg gagaaagagg gggcggtggg gaacagctgc 900
cggggtaggc gaggcgcaag gtggctcccc gcggccccgc gccccgcggc tctcggacgc 960
accaggcagc caatggctgc gcagaggtgt acagcagatg gcgtctgact gcgccgttcc 1020
ttcctcctcc tcctcctcct ccttctcttc ctcctcctcc ttctcttcct cctcctcctc 1080
cttcagtgct gaggagccag agtcgccgcc gggttgccag acgctggaat gggtggtctt 1140
ccgacacaca ccaccatctt tcttgcgctc gggaagctcg gggctcagcg gctcccagag 1200
gttacggcgg cggctctggc gagacgggtg agtgcaagca cgcggagccc cgagtcgggg 1260
atgccgggcc ccctggccgg ccgactgggg cgcggggtgg cagcgccggg gaagggggcg 1320
cgctgccggc gcagactttg ctctttcctc gccggacagc catcgtcgcc ccttctccca 1380
gccagacgcg ggaacttgga agcggatctt ctcggacgcc tctggcttgg ggctgcggga 1440
agcgtgggct gcccggggcg cagtgtgcgg agaccctcta ggcgggcggg gacgccccac 1500

<210> SEQ ID NO 98
<211> LENGTH: 800
<212> TYPE: DNA
<213> ORGANISM: Homo sapiens

<400> SEQUENCE: 98

-continued

```
gttattatcc acggggtcct aattaaagct tgattaaaat gcccttcttt ctctaaaaaa     60

ttacgaacta ggcaacttca tacattttga atggcgcagt gtttcctctt ccaactgttt    120

agtttgtagt atactatgta agcaacatca attatcaacc cttgcaagat gacaacatga    180

gcctgtgggg gaagcacttg aggggaggga ggagaaactt ctctttttta ataatcagcc    240

ggaaacaatg tttaacaaga atctgatgag gtcactgcag taaatatttt tcctcttaca    300

gagccaatca tcacggaggg atcccctgaa tttaaagtcc tggaggatgc atggactgtg    360

gtctccctag acaatcaaag gtgtttgctt tctgctctgt tgcttttaaa ttgtatggga    420

aaggaagatt ggtccgacgg cgcgcttgtg gcccggccgg agcttgcgtg cgcgttctga    480

cggctgggtg ctgtgttaca ggtcggcgca gttcgagcac acggttctga tcacgtcgag    540

gggcgcgcag atcctgacca aactacccca tgaggcctga ggagccgccc gaaggtcgcg    600

gtgacctggt gcctttttaa ataaattgct gaaatttggc tggagaactt ttagaagaaa    660

cagggaaatg accggtggtg cggtaacctg cgtggctcct gatagcgttt ggaagaacgc    720

gggggagact gaagagcaac tggaactcg gatctgaagc cctgctgggg tcgcgcggct    780

ttggaaaaac aaatcctggc                                                800
```

<210> SEQ ID NO 99
<211> LENGTH: 40
<212> TYPE: DNA
<213> ORGANISM: Homo sapiens

<400> SEQUENCE: 99

```
tccctgctgt gggacccgag gagaggagaa ctggttcgct                           40
```

<210> SEQ ID NO 100
<211> LENGTH: 500
<212> TYPE: DNA
<213> ORGANISM: Homo sapiens

<400> SEQUENCE: 100

```
tctctctctc tctcttgctt ggtttctgta atgaggaagt tctccgcagc tcagtttcct     60

ttccctcact gagcgcctga aacaggaagt cagtcagtta agctggtggc agcagccgag    120

gccaccaaga ggcaacgggc ggcaggttgc agtggagggg cctccgctcc cctcggtggt    180

gtgtgggtcc tgggggtgcc tgccggcccg gccgaggagg cccacgccca ccatggtccc    240

ctgctggaac catggcaaca tcacccgctc caaggcggag gagctgcttt ccaggacagg    300

caaggacggg agcttcctcg tgcgtgccag cgagtccatc tcccgggcat acgcgctctg    360

cgtgctgtga gtacaacctg ctccctcccc gggcacagat atgacagagg ggcttagagg    420

gggcccagct ttgagatggg ttgttcttat gtcacaggac agagtgatct gacatgcaca    480

cttccccgcc accctgtcat                                                500
```

<210> SEQ ID NO 101
<211> LENGTH: 500
<212> TYPE: DNA
<213> ORGANISM: Homo sapiens

<400> SEQUENCE: 101

```
tgtcctcgaa gaagggcctg agcagcagca gaggaccccca ggcgaccgtg cctgagccgg     60

gcgccgacga cgactgagca cctgatatgt ccccggcact cgcagccccg cggccggagt    120

cgctgtgggt gagcggtcgt cgagcttcac agaggccggg ctctgtgcca gggccccgac    180

agggcaggaa gcagatagag tcccacaagc acaagcccag tgcgcagaaa gggttactta    240
```

aaaaataagt tctgtgataa aatcaaacag ggtgaagggc tggaaacagg tcatgagggc 300
gcaaacaggt cgtgagggcg caaacaggtc gtgagggcgc aaacaggtcg tgagggcgca 360
aacaggtcgt gagggcgcaa acaggtcgtg agggcgcaaa cagatcgtga gggcgcaaac 420
aggtcgtgag ggcgcaaaca ggtcgtgagg gtgcaaacag gtcgtgaggg cgcaaacagg 480
tcgtgagggt gcaaacaggt 500

<210> SEQ ID NO 102
<211> LENGTH: 300
<212> TYPE: DNA
<213> ORGANISM: Homo sapiens

<400> SEQUENCE: 102
aaatgagacc tctggggaga ctgtcaaccc caggggtaaa acaaaaattc tgatcagaaa 60
ctgagtttcc caaagaaggg gctaaatgtt ttccaacact ttcggggctc agggaagatg 120
actctgtaag gacactgaga atcttcctcg cgtgccacgg ggaggaggac tgggggcgtt 180
tgaggggctc agcgcaccag aggagtgagg tggaggaggg cgttcccgcg tcctcctctt 240
caatccagag cagctcaacg acgtggctcc ctttctatgt atccctcaaa gccttcgcgt 300

<210> SEQ ID NO 103
<211> LENGTH: 600
<212> TYPE: DNA
<213> ORGANISM: Homo sapiens

<400> SEQUENCE: 103
taggctctag tggacctagc agtgggagag ctacttgggc tggtttcttt cctgacgctg 60
cagggatggg catcggcctg gaaccagaag cgcaggagct gggccacggc agagtaatta 120
agaaaataat gaaattgatg gcggatgggg gcgctagaaa tcctggggcg tctacttaaa 180
accagagatt cgcggtcggc cccacggaat cccggctctg tgtgcgccca ggttccgggg 240
cttgggcgtt gccggttctc acactaggaa ggagcctgaa gtcagaaaag atggggcctc 300
gttactcact ttctagccca gcccctggcc ctgggtcccg cagagccgtc atcgcaggct 360
cctgcccagc ctctggggtc gggtgagcaa ggtgttctct tcggaagcgg gaagggctgc 420
gggtcgggga cgtcccttgg ctgccacccc tgattctgca tccttttcgc tcgaatccct 480
gcgctaggca tcctccccga tcccccaaaa gcccaagcac tgggtctggg ttgaggaagg 540
gaacgggtgc ccaggccgga cagaggctga aaggaggcct caaggttcct ctttgctaca 600

<210> SEQ ID NO 104
<211> LENGTH: 800
<212> TYPE: DNA
<213> ORGANISM: Homo sapiens

<400> SEQUENCE: 104
gaggttgctg actcaggagc caggagctga gaaactccta ggctagcagc cgttgagcct 60
aattttattt tctggctttc tccgaaatgt ctcgtttccc tcatctttct ggtccttttc 120
gtctctctta ttttccccaa aacgtctacc tcacttcgtc ttcctttctc ctcccctccc 180
cctctctttc ctctatactc tcttcccatt tagccttgca ggcccctcct ccccggtgtt 240
ggagagctca aagacgcgcg aaactcaagg atctggccct gaccagggac gggattaggc 300
gggaagtggt gacggcctga aaaggctggg ctcgaacccg tgccttcctg aaaggactct 360
ccccgccaca agtcacaccc acccgcaggc ctgctggcca aagaaacaaa ggagtcgggc 420

```
gtggatccag gagaaacagg ttttcgctct cggatctccc tgggcaaatc agggatcctg    480

agcgctatac cccgcagtcg tacggagcct ctgggaaagg ggatttaagg gtgacttcca    540

ctttcagctt cggctacttg ttgcctgcgg tccaagcctt ctctgcttcc tcctacctcg    600

tcttaggcct ctgtagaaag tgcacgccgc gtttcccctt ccaggctctg agagggcctg    660

caggcccgtg gccgcctccg acaagatgcc ttccagtgct aggggggcca ctttggcggg    720

atgggggtcg gttggttaaa aaaaacttaa gttctggctc agtcgagtgt ggcaaaagcc    780

gagggtcggg ggttgggggg                                                800
```

<210> SEQ ID NO 105
<211> LENGTH: 2000
<212> TYPE: DNA
<213> ORGANISM: Homo sapiens

<400> SEQUENCE: 105

```
tactgacctg gtctccgcct caccggcctc ttgcggccgc tgcagaagcg cactttgctg     60

aacaccccga ggacgtgcct ctcgcacagg gagcgcccgt ctttgctggg gctggagcgg    120

cgcttggagg ccgacactcg gtcgctgttg gactccctcg cctgccgctt ctgccggatc    180

aaggagctgg ctatcgccgc agccatagct gctcagcgag ggcctcaggc cccagcctct    240

actgcgccct ccggcttgcg ctccgccggg gcgagggcag gacctgggcg gccagggaaa    300

gggcagtcgc ggggaggcag tgctaaaatt tgaggaggct gcagtatcga aaacccggcg    360

ctcacaaggt tagtcaaagt ctgggcagtg gcgacaaaat gtgtgaaaat ccagatgtaa    420

acttccccaa cctctggcgg ccggggggcg gggcggggcg gtcccaggcc ctcttgcgaa    480

gtagacgttt gcaccccaaa cttgcacccc aaggcgatcg gcgtccaagg ggcagtgggg    540

agtttagtca cactgcgttc ggggtaccaa gtggaagggg aagaacgatg cccaaaataa    600

caagacgtgc ctctgttgga gaggcgcaag cgttgtaagg tgtccaaagt atacctacac    660

atacatacat agaaaacccg tttacaaagc agagtctgga cccaggcggg tagcgcgccc    720

ccggtagaaa atactaaaaa gtgaataaaa cgttccttta gaaaacaagc caccaaccgc    780

acgagagaag gagaggaagg cagcaattta actccctgcg gcccgcggtt ctgaagatta    840

ggaggtccgt cccagcaggg tgaggtctac agaatgcatc gcgccggctg cggctttcca    900

ggggccggcc acccgagttc tggaattccg agaggcgcga agtgggagcg gttacccgga    960

gtctgggtag gggcgcgggg cgggggcagc tgtttccagc tgcggtgaga gcaactcccg   1020

gccagcagca ctgcaaagag agcgggaggc gagggagggg ggagggcgcg agggagggag   1080

ggagatcctc gagggccaag cacccctcgg ggagaaacca gcgagaggcg atctgcgggg   1140

tcccaagagt gggcgctctt tctctttccg cttgctttcc ggcacgagac gggcacagtt   1200

ggtgattatt tagggaatcc taaatctgga atgactcagt agtttaaata agccccctca   1260

aaaggcagcg atgccgaagg tgtcctctcc agctcggcgc ccacacgcct ttaactggag   1320

ctccccgcca tggtccaccc ggggccgccg caccgagctg gtctccgcac aggctcagag   1380

ggagcgaggg aagggaggga aggaaggggc gccctggcgg gctcgggatc aggtcatcgc   1440

cgcgctgctg cccgtgcccc ctaggctcgc gcgccccggc agtcagcagc tcacaggcag   1500

cagatcagat ggggattacc cgccggacgc aaggccgatc actcagtccc gcgccgccca   1560

tcccggccga ggaaggaagt gacccgcgcg ctgcgaatac ccgcgcgtcc gctcgggtgg   1620

ggcgggggct ggctgcaggc gatgttggct cgcggcggct gaggctcctg gccggagctg   1680

cccaccatgg tctggcgcca ggggcgcagg cggggcccct aggcctcctg ggctacctc    1740
```

```
gcgaggcagc cgagggcgca acccgggcgc ttggggccgg aggcggaatc aggggccggg   1800

gccaggaggc aggtgcaggc ggctgccaac tcgcccaact tgctgcgcgg gtggccgctc   1860

agagccgcgg gcttgcgggg cgccccccgc cgccgcgccg ccgcctcccc aggcccggga   1920

gggggcgctc agggtggagt cccattcatg ggctgaggct ctgggcgcgc ggagccgccg   1980

ccgcccctcc ggctggctca                                               2000
```

<210> SEQ ID NO 106
<211> LENGTH: 800
<212> TYPE: DNA
<213> ORGANISM: Homo sapiens

<400> SEQUENCE: 106

```
gggggacaca gagaggaggg gttgcgggcc tgtgagaatg aagagcacag agcggagagg     60

gggaggagga gggaaaggaa ggcgtggcag tgagagagaa gaggaagaag agaggaggag    120

tggggagggg agggagagca agacagcagc gggtctggat tcccctccga gccacatctg    180

gtcaggttct aagtaattag aagattttcc cattggttta cccaagggct ctctctctga    240

ttaattttcg aaagagttgg ccaattttaa tcatagcaaa cacgatgatc acggtgatca    300

tggcctgaac agctaaaagc agaaaataaa acccccagaa cggactatga tcttgacctt    360

tgcccgtggt caccggctgg gcccacaccc agggttctga gctgttggga gccaaggctg    420

ggtggacagg ggcttccgag gagctgtccg cagcggggcg gggaggcggg ccccgggggc    480

ccgggcactc cgcgtcaccc cccggcaggg cccagagcgg caggccggcg tgcgccccag    540

ggcctgcgca ccgtgggggc tcttccccgc ccacgaggcc taggtgctgc cgcagccacc    600

ccaggaaggg ccccaggcca cagtcgcagc gccaggagtt gtgccccaac aggacctccg    660

tcagccgggg cagagcccca aacacgtcgc caggcagggt ctccagctgg ttgtggtcga    720

gctggacgct ctccaggctg ctgagattgc ggaagagggc acggggcagg gcgcgcagcc    780

tgttgcggcg cagggacacc                                                800
```

<210> SEQ ID NO 107
<211> LENGTH: 550
<212> TYPE: DNA
<213> ORGANISM: Homo sapiens

<400> SEQUENCE: 107

```
gccccggtgc accgcgcgtc cagccggccc aactcgagct agaagcccca accactgccc     60

agtgcctgag ttgcagtctt gggtccttta gaaacctgga gatgtgcgta aaattcagat    120

gccggtattc ccgaacttcc ccaggcctca gcatatctcg gcggcctgtg gacagatggg    180

aggctaccaa tcgctccggc gtccgcagcc cgacccctgc cgccagaccc cggacgtctt    240

ccggataata aagttcccgc tctaattcat tttccctaat ctggacgccc ctaatctaca    300

gcttttattg cgcccagtta aaagtcgagg gaattcgctg tccctccgcg ctcggataat    360

taccccctaaa tggccacggc agccccttgt gtttcctgga gattagaacc ccgcagtcat    420

caatggcagg gccgagtgag ccgccaatca cctccgctca ctccctgaga gccgctggcc    480

tgggccgcag gaggagaggc cataaagcga caggcgcaga aaatggccaa gccccgaccc    540

cgcttcaggc                                                           550
```

<210> SEQ ID NO 108
<211> LENGTH: 2000
<212> TYPE: DNA

<213> ORGANISM: Homo sapiens

<400> SEQUENCE: 108

```
agggtgcctc tgttcaaatt agaaaaaggc gccccctcag ggcagactca gcccagctgc     60
caggggacaa gtcctggcta acgggagctg gagctgggtt tcacctccag gtgcctcctt    120
ggcggggcgc cccgtgcagg ctacagccta cagctgtcag cgccggtccg gagccggagc    180
gcgggaatca ctcgctgcct cagcccaagc gggttcactg ggtgcctgcg gcagctgcgc    240
aggtggagag cgcccagcct gggaggcagt agtacgggta atagtaggag ggctgcagtg    300
gcagaagcga gggtggccgc agcacttcgc cgggcaggta ttgtctctgg tcgtcgcgca    360
ccagcacctt tacggccacc ttcttggcgg cgggcgccga ggccagcagg tcggctgcca    420
tctgccggcg ctttgtcttg tagcgacggt tctggaacca gattttcacc tgcgtctcgg    480
tgagcttcag cgacgcggcc aggtctgcgc gctcgggccc ggacaggtag cgctggtggt    540
taaagcggcg ctccagctcg aagacctgcg cgtgggagaa agcggcccgc gagcgcttct    600
tgcgtggctt gggcgccgcc ggctcctcct cctcctccgc gacgcctgcc ggcccgctgc    660
cgcccccgcc gccggccccg ctgcacagcg cggacacgtg tgcacctctg gggccaacac    720
cgtcgtcctc ggtccttggg ctgcggtcgc ctgcggaccc cggtgggaac agaaacaaga    780
gactgtcagc gccacagacg aggtgaggcc gggcctcaac tgcaggggtc acgggagtgg    840
ggcggaaata cactttgatc ccactcaagc ggagcggagg tctgggaggc cctgggcccg    900
ggagaccagt cttagactct tgccccactg ggtatcccat ctaggcctct tctggggagg    960
gcggcagact cagccgctgt gtcaacgctg tgttgtcgag accagctccc caccctctct   1020
gggccccagg ctcccctcag taacttgggg cactcgaccc gagcatccgc gaaagccctc   1080
ccggctctca gcgttgagca ttgggattct agactgcatt tccgtctctc tgcttgggtt   1140
cacgcgcctc tccacactta gttcacacgc acacacgcgc gcgtcctcgc agcacacact   1200
tgtctggtgc aggtaaggga aggtggaggc ggatcctggg gccaaaggta tttagaatct   1260
ttcaccctca gccgcctggg attgctgtga gagacatgga aacaggctga gccgaggcct   1320
tagatgagag gatggactgg agagtaaaga gggagggttg cccctgcatc gagtttttgg   1380
accctgatcc cacaccagct tctcggtctc gtacccgccc ttccgaagaa ctccagcaga   1440
aaggtccagc ggtcccctgt gcttgaggcc tacagaagct tgtacccaac tagggcaggc   1500
acccgggtct tccagaccac aggacaggac aggccacggc tgaggaggcc tctctcctgc   1560
ctccaggatg aactaaagac ccaatccggg atcttcggcc tagggctgct ctcccagacc   1620
tggggtctga gaaagccaaa ccagcccttt ccccaaagct ctagttctgc agattctcag   1680
ctctggccca ctcggaggtg ttcttcacca cctatccacc tactgtgggg cccggccctg   1740
ggaccttgaa ctggcaggtc tctggtccag agctaggtca ctggctacct gaggtctctg   1800
aacccctcac ttttccgctt ccctgatttt ggggatttgg ggacagacac ggcagaaagc   1860
actggcgacg aactcaaaaa ctcccgaacg caaggggcag cggttctccc aacccagtct   1920
aatgcacatt ggcccaggat gtctcaggcc tcaccccagg acgtagggct ctgaggagct   1980
actccggtct ctcgcgggct                                               2000
```

<210> SEQ ID NO 109
<211> LENGTH: 1000
<212> TYPE: DNA
<213> ORGANISM: Homo sapiens

<400> SEQUENCE: 109
gagaagggat gtggcggggg gctcctccgg ccctggactc cctgggtgga ctagaaaagg 60
gcaaagaagt ggtcacatct gtgggccaga ctggtgcgcg atctttggag gcgcagcagc 120
aaggccgcgc cagggctgag cccagaccgc ccacgaggag gcccgccagg cccggagcag 180
cggcgcgtgc gggggcgtgc cgagcgcagg ctctagggcc cctgcttcgc cccagctgga 240
ccccgcgggc ggtcggtgca gctcgagcgt gtgggctgcg atgccctgcc tgagacttcg 300
ggctagggat gcgggcggga agtgggggtg cggcggcagc tgcagattag attccttttt 360
tttttggccg gagggacgtg caaacttcta gtgcccgggc caagagggcg accccggagg 420
tgcgtaggtg gccctccggg ttcccgcttc tcctagtgcc tctgaaaata ccgtcagggt 480
aaagggagac aggcagtaag tcttaccacc accgcccttt ccccatgtca ttggccaaaa 540
actgaacatt aagataaagc agctgtttca gtcaatggaa agcggtaggg cgaggttgta 600
cccaaaaccc ggtttagacg gccaatgaag tcctaggaaa agccgccccg ggggcacgtt 660
caggtggagc ggctgcacct cgggtcgttc taagggatgg gctgcgtggt acccacggaa 720
ttcatgggtc caaaaggtcc tggtcacctg tccaaacatc catcccctgg cgcatggcgg 780
ttgacaagat ggcccggcca cccagaggaa ggaggatccg ggacggggaa cttcgcgccg 840
ggaagctgta gcccagagct gcagctcagc attcgcaaga gattcatctt ttttttctct 900
cgtgttcgga gaaacagata aacaagacac cgcctcatca gataagaacg tctccttcga 960
tgtcacggat ttcaagaggt agctggagaa actgacgtca 1000

<210> SEQ ID NO 110
<211> LENGTH: 1300
<212> TYPE: DNA
<213> ORGANISM: Homo sapiens

<400> SEQUENCE: 110
caggtcaggc agaacttctg cccttcccgc tactggcacc ccaagcaggg atgcactggg 60
atgcgtggca ggggcgggat ctcctgggag cgtctcagcc cagcagggag tggggaagca 120
agagggaagg cttaccttcc tcggtggctg gcaggaggtg gtcgctgcta gcgagggga 180 tgcaaaggtc gttgtcctgg gggaaacggt cgcactcaag catgtcgggc caggggaagc 240
cgaaggcgga catgaccggg gcgcagcggt ccttcacctg cacgcagagc gagtggcatg 300
gctggatggt ctcgtctagg tcatcgaggc agacgggggc gaagagcgag cacaggaact 360
tcttggtgtc cgggtggcac tgcttcatga ccagcgggat ccaagcgccg gcctgctcca 420
gcacctcctt catggtctcg tggcccagca ggttgggcag ccgcatgttc tggtattcga 480
tgccgtggca cagctgcagg ttggcaggga tgggcttgca attgctgcgc ttgtaggaga 540
agtcgggctg gccaaagagg aagagcccgc gcgccgagcc caggcagcag tgcgaggcga 600
ggaagagcag cagcagcgag ccagggccct gcagcatcgt gggcgcgcga ccccgagggg 660
gcagagggag cggagccggg gaagggcgag gcggccggag ttcgagcttg tcccgggccc 720
gctctcttcg ctgggtgcga ctcggggccc cgaaaagctg gcagccggcg gctggggcgc 780
ggagaagcgg gacaccggga ggacagcgcg ggcgaggcgc tgcaagcccg cgcgcagctc 840
cggggggctc cgacccgggg gagcagaatg agccgttgct ggggcacagc cagagttttc 900
ttggcctttt ttatgcaaat ctggagggtg gggggagcaa gggaggagcc aatgaagggt 960
aatccgagga gggctggtca ctactttctg ggtctggttt tgcgttgaga atgcccctca 1020
cgcgcttgct ggaagggaat tctggctgcg ccccctcccc tagatgccgc cgctcgcccg 1080
ccctaggatt tctttaaaca acaaacagag aagcctggcc gctgcgcccc cacagtgagc 1140
gagcagggcg cgggctgcgg gagtgggggg cacgcagggc accccgcgag cggcctcgcg 1200
accaggtact ggcgggaacg cgcctagccc cgcgtgccgc cggggcccgg gcttgttttg 1260
ccccagtccg aagtttctgc tgggttgcca ggcatgagtg 1300

<210> SEQ ID NO 111
<211> LENGTH: 500
<212> TYPE: DNA
<213> ORGANISM: Homo sapiens

<400> SEQUENCE: 111
tgcgatcatt aaaatcagtt ccttccctcc tgtcctgagg gtaggggcgg gcagatttta 60
ttacttctct tttcctgata gcagaactga ggcggggttg tggaggagcg acggaggacc 120
acctctaact tcccttcact tcctggattt gaagcctcag ggccaccggc ctcagtcctg 180
ttacggtggc ggactcgcga ggttttccag cagctcattc cgggacggcg gtgtctagtc 240
cagtccaggg taactgggct ctctgagagt ccgacctcca tcggtctggg agcgagtggt 300
tcgagttcag atgctgggaa ccgtcgcttc tccccggccg ggctcgctgt tttctcctcc 360
gctcgccgtc atcaagcccg gctatgagca gggctttaaa tcctccctcc ctcacccgca 420
ggtttaccga gcagccccgg agctctcaga catgctgcgc tgcggcggcc agaggagggg 480
tgggggcatt gccctctgca 500

<210> SEQ ID NO 112
<211> LENGTH: 500
<212> TYPE: DNA
<213> ORGANISM: Homo sapiens

<400> SEQUENCE: 112
gggcttgggc cgcaggcttc cctggacttc cgcagtcccc cttctcccca ttccagaacc 60
tgccgagccc ctgctgcatc tgggacccgc cttcaccgtt tcccaatccc agcggttagc 120
ccctgcgccc cctttttggt ctccactttg ccgttcgaaa atgcctaggt tggtggatcg 180
accctccgcg gagcaaagac ggatggctgg caggagcagg ttcaggagct gggccaaggt 240
attctctgct tccgcctttg tgtccgcccc cccgcccccct gctccccgct tcccgccagc 300
atctctcctt ttctgctcag gagtgtttgg cccggcggtc caccccggct tcccgagata 360
cgctagagtt gcccccacgt cctgtccgcc gcgcccctac ccaccgggtt gccttcgggg 420
cccttcggtg ctgtgtagtc ggcgtggcgc tgtgagctag gcgaacagga acccccaggc 480
ccgccacgtc tacgctatta 500

<210> SEQ ID NO 113
<211> LENGTH: 600
<212> TYPE: DNA
<213> ORGANISM: Homo sapiens

<400> SEQUENCE: 113
ttctggggcc tggatgggtg cgagcgggac ccgggggagt gggagtcgcc aggctctgag 60
caagcaaggg ctgcacctgc acctctgccg ggcatgaaga aaggtaagga aggaaggagc 120
tcacccgggt gggagacaga gccggggcgc gcgagcttgg tgtgggggcg ccactccggg 180
gcggagggga ggggctacca gtgacttctc cgagtcggga gctagaaaga ggcttccggc 240
caggttccct tggaacaggt gtcggagttg ttgggagagg gggctgcaag aaagaggggt 300
gcagaaactg gttcattaga tggaggctct gggcggaacc gcgaggacac cctggcagcg 360

```
cgctgtgcct gcgttaggcc gggaggggag aggcctccgg acggcgaagt gtccctaggg    420

acccagacgc ctcgggagcg atccgggccg ctgcgaagcc ctgcccacca ggagtggatc    480

cccaggattc acctcccggc tgcctgctct gagctgagaa ggggatctgg ttcttcacaa    540

taccgtggat ggcggggaag gggagggagc ctggggtaaa atcccatctt ggtttcctcg    600
```

<210> SEQ ID NO 114
<211> LENGTH: 1300
<212> TYPE: DNA
<213> ORGANISM: Homo sapiens

<400> SEQUENCE: 114

```
tgtcacagaa accccagcag cgcagccacc ggactgggtt ctggaggccg agccgcagtc     60

cgtgcggcgg cgctgggaag agaaggcgcc ccggcagctc ccctgccacc ggccccgagg    120

agcggctggc tcccccagcc cagcgccgcc gccgcccggt aactccaggc gcaactgggc    180

gcaactgggg cagctgcgac accgaatccc tcacatctgc aacctgggtg ctgcggccac    240

tgagaaaatg gaggcgcaga ccaacgagcg gtgccgcgac cgagagacct cggctggcga    300

aatggtggtg ccgggagcct gcgagtgacg ccagccggcg gggttgtcaa ggacaacatt    360

cgttttgacg cagccaatgg cgccgtcacc aagaaaccat cgactctgag aaaaaagaga    420

ggttcggcca ccgagaaact ccgtacgaca agtgctgtgg cagaaaaacc gcctactccg    480

cgccacaggc aaaacagcca atggaaaccc caggtgctgc gaccgtgaca ccggcactag    540

agggtctcgg atggagaaag cggcgcacgg agaccaggaa actatgtgta gcacaactag    600

cagaaaaccg tctggtcggc catccgggag aaagcgcgga tcagaaacaa gcgacttcga    660

tgcagggaac cgcgcagcca ctgaagaaag tgacccacgt ggcagtggtg ccagcgaaac    720

actgcagttt ggacggcagc tgtggggatg ccacagagaa acatgcactg ccactgaagt    780

acatccagct ccgcggagct agtgttcata tgatcaagaa accgccagtt gggctctgct    840

agaaactttt agtcctccct taacggctat cctacccaca acagacaatg cctttaccca    900

gcacctagcg gtgctgagac ccgcctgggc cagcacagag cgcagagcag tacgggtacg    960

gagaaacgcc ggactcagtg aaaccagcct tgcctccagc ggattccccg gcttcgccgg   1020

acgccacagg cagagtgccg cggggaaacc tctggctccc taaaccgatt agattgtggg   1080

agtggggggg acactcacaa gttgtgtgga agggaaccag cggcaatggg acccggcgag   1140

cacttgcccg cagcaaatgc ctgcgctgct gcaaaaaaaa caacttttgg cgcaaagaat   1200

gttgcggcca gagagcatcc gctgtcgctg acaaaggagt agcaatggca atgagaaacc   1260

gccggcgcca cggccgaccg cggcggctca cgcctatgat                         1300
```

<210> SEQ ID NO 115
<211> LENGTH: 2100
<212> TYPE: DNA
<213> ORGANISM: Homo sapiens

<400> SEQUENCE: 115

```
caaacgctga gagacaaaaa gacaccaaca cccaccagga ctgcgtcctg ccagctcttc     60

actccgctga cctgaccttc cacgccccta gtcctcgagc ggacttgacc tgtgggggag    120

taccgaaccg tccccatgag gccctccaag cggccaggtg gcctccgcca ctctctccac    180

ccccacctcc tccacccccc agcccatcgg tccatcttcg atctgcaaaa cacgccgggt    240

cagcgacgca tcggtcccag gcttgtgacc acctctttct ctgttacttg gggagccagg    300
```

-continued cccaccgctc aggatcacag tgaggagaaa aaagacacaa acgccaggac agggcggctg 360
gggaaggaaa ctgctaggga ccgctcattg tcagcctggc gtgtcccacg gatcgcagga 420
cccgtcgagg ctttgctctc tgcgacccga atactcctgg gcctctcgac ctcctcctcg 480
gactcaggcg tccgcgtctc cggtcatcac gggagaccaa ttggtttaca aatagtgatg 540
ataaacctgg gaccgacctt ggggctgtgt aaaagtctac tgacagatgt aatggagggt 600
tgttagcagt cacaaagcct gtcggacccg tagcattagt tcaagagact attttcgtgt 660
cgcaccaaaa ttactgcgcg tgtaaaccaa tttccccgac ggaagaataa acagagattc 720
gtttgaagcg cgagatgaaa acagatgggg tatcgcaaac agttccccaa aatacaacag 780
acttctgggc caattacacg tggttagctc tgaatggcag aggaaatagt tttctttgct 840
gctaaatgtc acaaaagtca cctaaaggca cagaggaggc cgctctgttt ttgcgaaact 900
tgctaaaatt aatctgcgct gggccacttg cagaaagcag aaccacctcc cgccccccacc 960 tcgcctccag ccgccggggt tcaggcgttt gtgaaagaca gaacctttgg gctagggacc 1020
cgggcactgg tgcttcgaag tccgaatccg ccggccgaga aaacgacaag agaaagaaaa 1080
tccagcgggc gctctctcca gcgccaggcc ggtgtaggag ggcgctgggg ctcggcctgc 1140
cacccctacc cgacattggg aagcagcccc tgcgctcccg cggcgcctca gcctccggtc 1200
cccgccccga ggtgcgcgtt cctcctcccg catgcccgtc tcgggcccca cggagcaaga 1260
agatagacga tgacgaggcg cgcccatcca tccgggccga cgaggtcagg cccgcgccac 1320
aggcaaaaat tgcgcaagcc cggccgcagg gatttcgcgg gcgcctgggt cccaggtgcg 1380
cggccgaaat cctcagggaa aatcccgagg ggccaacggt ctaggccaca gggctgctgg 1440
gcccgggcct ggctcagagc gcattcgggc ggggaggccg cacgccgcac ccgggcctct 1500
cctccgagcc cgaggcaggc actgagctcc gggccagcca ggtgcctccc ggctggtgcg 1560
agaccccggg cctgctggga ggcgtgggca gggcagggca gggctgaacc ccagcgactg 1620
aatctcgaag gcaggaggcc tcggaggtca tcggcccagc tcgcctgaaa ctgtccctgc 1680
tcgtgccagg gcgcgggcag aggagaaagg acagggcgga gcaagcccac tgcagaactg 1740
cggtcggtgg ctgcgaaggg tccgggtcac cgcgctcccg gacgccggaa gccgcgctgg 1800
cggggccgcg gggagggagg ctgggtaccg gggccgtccg gccggaggaa gcggctccgg 1860
ccgcgctgtc cgcgcttggg agccgcgtgc agggttcagc cgtgtttcag ttgccctctg 1920
acctgacccc gggcgcacaa aggcctcccg ggtgcgccgc catggcccag tcttccagtc 1980
gctgccaaat taatgagccc acgtcaggtt gggtttacag ctcggccggg aagcagccga 2040
gtggaaaatg agctcggggc cgctccagag gctcccgcac aactgcagag gctgcccgcg 2100

<210> SEQ ID NO 116
<211> LENGTH: 250
<212> TYPE: DNA
<213> ORGANISM: Homo sapiens

<400> SEQUENCE: 116
tttccaagac agaaggaggg aactaggcgc cttttttcca ctccgctgac cccaacgtct 60
gggctgtgcg ttgtaacgca gttggcgggg ccttcagctt gggatgaggg cgaaggggct 120
cgggatgggt gggaaagcaa ggaccgggca acaggtgggg aggtggcgga cttttgtctc 180
ggggaaggaa atcggctgtg ctgaaagggc ggaaagcagt agcgcacaga actagtgtct 240
gcggggtccc 250

<210> SEQ ID NO 117
<211> LENGTH: 250
<212> TYPE: DNA
<213> ORGANISM: Homo sapiens

<400> SEQUENCE: 117

```
ccctcctgtg gctgcttggg cagacgcctg tggcctgtcg gatgcggccc acatcgagag     60

cctgcaggag aagtcgcagt gcgcactgga ggagtacgtg aggagccagt accccaacca    120

gcccagccgt tttggcaaac tgctgctgcg actgccctcg ctgcgcaccg tgtcctcctc    180

cgtcatcgag cagctcttct tcgtccgttt ggtaggtaaa acccccatcg aaactctcat    240

ccgcgatatg                                                           250
```

<210> SEQ ID NO 118
<211> LENGTH: 2000
<212> TYPE: DNA
<213> ORGANISM: Homo sapiens

<400> SEQUENCE: 118

```
tcctcctttg tgtatgtcaa cccagaggat ggacggatct ttgcccagcg tacctttgac     60

tatgaattgc tgcagatgct gcagattgtg gtgggggttc gagactccgg ctctccccca    120

ttgcatgcca acacatctct gcatgtgttt gtcctagacg agaatgataa tgccccagct    180

gtgctgcacc cacggccaga ctgggaacac tcagcccccc agcgtctccc tcgctctgct    240

cctcctggct ccttggtcac caaggtgaca gccgtggatg ctgatgcagg ccacaatgcg    300

tggctctcct actcactgtt gccacagtcc acagccccag gactgttcct cgtgtctaca    360

cacactggtg aggtgcgcac agcccgggcc ttactggagg atgactctga cacccagcag    420

gtggtggtcc tggtgaggga caatggtgac ccttcactct cctccacagc cacagtgctg    480

ctggttctgg aggatgagga ccctgaggaa atgcccaaat ccagtgactt cctcatacac    540

cctcctgagc gttcagacct taccctttac ctcattgtgg ctctagcgac cgtcagtctc    600

ttatccctag tcaccttcac ctttctgtca gcgaagtgcc ttcagggaaa cgcagacggg    660

gacgggggtg gagggcagtg ctgcaggcgc caggactcac cctccccgga cttctataag    720

cagtccagcc ccaacctgca ggtgagctcg gacggcacgc tcaagtacat ggaggtgacg    780

ctgcggccca cagactcgca gagccactgc tacaggacgt gcttttcacc ggcctcggac    840

ggcagtgact tcacttttct aagacccctc agcgttcagc agcccacagc tctggcgctg    900

gagcctgacg ccatccggtc ccgctctaat acgctgcggg agcggagcca ggtgaggggc    960

tcggcgccgc cccgggcgac ccctgggggc ggcactggag aagccgcccg tcctcataag   1020

ggattgaact tgcatccact cctctccggc cggcttggtc gctggctgcg ctccacccga   1080

ttctcgggat cattggaccg tttgcgcgaa accagagtgg ccgattaagg gatggggctc   1140

cgagcaccgg gggtggtggc gactgtgggc gaggggaggt gggaccgacc cccaccccta   1200

cactcaaaaa aggccggggc ctccttcgag cttccggtga atttcgggcg atttccgcgg   1260

gtgtcggggg tcccgggagg aggcagtcac agatccaccc ctgcagccag cctcctaggc   1320

gccggctccg gcacgcttcg ccggtctgta gatttcctct tcgatttctc cccagctccc   1380

agcatctgtg acttcactgt taccctccct atccccgcat cacccaaccg cacctgtctg   1440

cgggacttag gtgtgcgcgc ggggctcatg cgtgtcctcc ctgctggcca cccccacggc   1500

ccacacaagt tgcacgggct cgccacgccc cgccaacacg tgcgcggacg cacgcacgca   1560

ctcctcgcac gtgggcttac gcgaatacca gctttcactg ccactcgctc gcggccagat   1620
```

```
tcacaggcct gttccggtcc actcgcagct cccctctgcc gctccctccg ccgggctcag   1680

gagtactcgt agctgattgt gcgcgcctga gggtcccaga tcgcggccgc ccaggaccag   1740

gcgaggactc cggagcctcc tctcacctct cccacctgcg ccccgggctg ggccgggtcg   1800

cctgggggc ggcctgagcg aggcgcgggg ccaggagcgc tggagcgact gccgctctaa   1860

gtgccgggcg ggcaggactc tacgatcctt gggccagagg tccggatggt cccgggactc   1920

cgtctcaagg gtcggcgacc cctcaaccca gaagcctcga gcaggcggac aggcagagct   1980

gcccagtggc cgaggcgcgg                                               2000
```

<210> SEQ ID NO 119
<211> LENGTH: 1100
<212> TYPE: DNA
<213> ORGANISM: Homo sapiens

<400> SEQUENCE: 119

```
atttgtcgtt gtgccattgc tgccactgtt gttcttgtcc agggaaacac cggtggccaa     60

cccagatcgg atacaatggt gcggctctgg actgagcctc caaccacatt agccatgggc    120

agcattgttg ctgccgctgc tgttatttta attatgattg tacgttaacc accaccttcc    180

ttcctctgcc tcccttcagc tgcaatgatg tatgttactt tttggtaact ggatttcatt    240

aacatttatg aactctcata aagtagtaga aaaagcaatt tgtgtggaag aattttccac    300

ctcattaaac agtgttcttt tgggggtcaa gctgatattt tttttgttgt tagatttttt    360

ttataggtcc tttgtccttc cctaagccct gggggatgaa aggagagccg tccacccagc    420

gaggggcttg tgtgccctag agggcgctgg gccccgcgcg ctttcctggc tgtccccgcc    480

ggctttccac cctccccaaa gcccaggtgc ccaccgtggg tcgctgcggc ctttcccctt    540

cttggccaaa tccgattact tcgcagcctg cagatggcat cgccggctaa gggcagcctg    600

cggcaggtcc ccgagcctga gcactcctcc tatctggggc ctgagaggac gctctgggct    660

ttttcccagg cccagggtgc gcggcctgct agcgcctttc gaggcacagt cccaagatag    720

gctcttgtcc ttcgacgccc ccttggcaca agcgcactgg cgccctccgc tcaacccacc    780

ttgcctttgg ggcgggcttc aaccctggga agacaggcct gggggaagcg agaggagagg    840

cccgaataga ggttccggct caatctttcc cagacggagg cctggtgttt ccagctcagt    900

tgcatcttcc agccgcgggc tcctggccca aacagaatgt gtttgctttc acaccgggac    960

ggcaagcgga gtccgcctca gtgagcagcg agctgcgcag tccggacggg tgtcgccccc   1020

agagactcgc cagccgcccc cagacactcg ccagccgtcc ccatctctaa tccaccgtcc   1080

aggcccgggc cctgggaaga                                               1100
```

<210> SEQ ID NO 120
<211> LENGTH: 800
<212> TYPE: DNA
<213> ORGANISM: Homo sapiens

<400> SEQUENCE: 120

```
ccgtgtctcc cttaagaact ggggcctcat ctccactcca gctgcgcgtg cacgtgtgct     60

cccggcagga cgcgcgccca ggagcgcgct gggggctgcc ccgcccctct ctccctcccc    120

cgcgggtaaa ctccgggcat ccatcagtct gttaattgca ctaattagag atcgcagagg    180

tgttaattgg aaaaccctgg tattgtgcct gtttggggga agaaaacgtc aataaaaatt    240

aattgatgag ttggcagggc gggcggtgcg ggttcgcggc gaggcgcagg gtgtcatggc    300

aaatgttacg gctcagatta agcgattgtt aattaaaaag cgacggtaat taatactcgc    360
```

```
tacgccatat gggcccgtga aaaggcacaa aaggtttctc cgcatgtggg gttccccttc    420

tcttttctcc ttccacaaaa gcaccccagc ccgtgggtcc cccctttggc cccaaggtag    480

gtggaactcg tcacttccgg ccagggaggg gatggggcgg tctccggcga gttccaaggg    540

cgtccctcgt tgcgcactcg cccgcccagg ttctttgaag agccaggagc ctccggggaa    600

gtgggagccc ccagcggccc gcagactgcc tcagagcgga agaggcagcc gcggctttga    660

cccagcttcc ttccgacggc atctgcagga gcctctaggc ctgacatagg ctccgaggtg    720

ccctggctcc cccacgggga atgctgaggg ttgggccact aggtcctgcc taagtgcagg    780

acctgagcct cagacaaatc                                                 800


<210> SEQ ID NO 121
<211> LENGTH: 300
<212> TYPE: DNA
<213> ORGANISM: Homo sapiens

<400> SEQUENCE: 121

gggattgccg gctttgagaa aatatgaaga aaccgatttc tccttccact ttgccagtgc     60

actttccttc cactttcact ggtgctgggg gcggcgcact ctttacgaca tataagcgga    120

aaattctgca aaagtggccc ccggggatcc ccgcccgacc cctgtctgtc gctaatgtgg    180

gcctgtctcc ggaaattcga ggttgggcct ttgcctgaat ctgttgctat tgctcccctt    240

gctaccgctg acacttggca ccgccgcctc ctagcagcgg ccagacgcgg ggctgggggc    300


<210> SEQ ID NO 122
<211> LENGTH: 400
<212> TYPE: DNA
<213> ORGANISM: Homo sapiens

<400> SEQUENCE: 122

gttgcgagcg cggcacaggt tgctggtagc ttctggactc tggaggcttg gccttccttc     60

taagccgatg gcggggaaag aacctcgttt ccacagcttc cccgaccccc gccgcttgcc    120

atttggggac gggaagcgcg cccgggtcgc ttcacgtccc tctgggccgg agccctttcc    180

atggctggct cctctggggg cccttgggcc tgtgagcagc gtctacttcc ctcagagaag    240

aatcctttcc ttcccccatc gaagtgtccc tttctgtatc ctgaaataac ccctcctggg    300

tgaggccagt tcccctctgt cgccctcctc ccgcaggcgt ccgggagcct cgtgaggacc    360

ccgtgcagtt gagtccaggc gacaggtgcc tccccaggtg                           400


<210> SEQ ID NO 123
<211> LENGTH: 800
<212> TYPE: DNA
<213> ORGANISM: Homo sapiens

<400> SEQUENCE: 123

cagtgcgccc cttaccggag cacccatggc ctcccgcgtt accccaaatt ttgtaggcag     60

actgtcagag ttcgaagcca gctgtgtcct ctgcgggccg tgtgacccta ggctatctgg    120

gctgctcgga gccttagttt ccctagttgt gaagagggag ggtgtgacca tggcccggag    180

ctctccgaaa ggctgtgcgg attgctcggt ggcgggatgt ggagcgcgtc ttctatgatg    240

ccaggtgctg gccaagcgct cgatgcaggc tgctccagtt aggtcgatgc gatggcggga    300

agcactttcc tctgcaatgg agagacgccg acaccccgag cccgaaggct tgcaaggcgc    360

gctctcgcca ctggggtcgg ggatccgtgg gttctctatc ccgcttaccc actccatcct    420
```

tagcagctgt cgtcggtccc agacctctac cttggagaga ccaaggcggc ccagagccca 480
ggagactact gcgcggtacg ccaggatcca gaagtggatt ctgacttcta aagacccctc 540
ccaagccaac gctatcaggg tccctgcaag cggttgactg tggcggaggc agaaccaaaa 600
cctttgctct gcccgcggcg ctccagcctc tcacccagga cagtgctctg ggctccagcc 660
gctgcagtgg ggtcgggaca cagacgccga gttagaagcc ccgccgctgc aggtccctgc 720
ttggtcggcg cggtgacggt gtcgctggcg gcggcggggg ccttcctttg gctgcccggc 780
catttaatca gagctattat 800

<210> SEQ ID NO 124
<211> LENGTH: 1000
<212> TYPE: DNA
<213> ORGANISM: Homo sapiens

<400> SEQUENCE: 124
tttagtattt aaggagaaaa gcctcatttt ccagaatcga ataagcgaat taatcgcaca 60
attgtgtaga atggaactca gtctgtaaaa aatcaagacc aacgtacttt ttaatattct 120
aacatctcca agtagtagtt acaagtattg tacccatgaa gtccaggtaa ttaatttgtt 180
caatgtcaca ctgttaaaag tcaggtgggc tccaaagcac agtcctaacc agcatgctct 240
actgcctcct ctgaggcaac agccgaagtg cagaccactg ggaataaata gctgcccggt 300
cttccccact cctaaattct cccgacagac cccaaagcct ctctgagagc ctctctgacc 360
gccctgcggc ccaccccgag ttcccggcat cctctgggat ccctcttcct ggagccaaaa 420
cctacgcagg ctcctttcct ccgagctggt tgctaggtga tctccgaagg ctgtccgaag 480
tctcgcgagg gcggacccgt tgcctgatga cgagagttgg gagtgtggct ggggctgcgg 540
atctccagca gtggcgttac ttctagcggc tggataccgg gttctccgcg agatcgcgag 600
atcccgagat attctccccg cacggaagcg acgactggcc tggccagagg actcgcgtgg 660
gagcgaggtg ccggccccga caggacggtg aggtatgcag aagtaaggcg gggcgccccc 720
tgcgggaagc gagcgcgccc cggaaaatga gcgcctcccc acaccaaggt gtccaggagt 780
gagtgcggga aggaactcgg ccgcccggag ttgtggcctc atcgtgcttc ccgccaaaaa 840
cgccttggta ctgtcgggac gcggctaagc gtggacgcgc ccgcatctgc ccctcctccg 900
cagtggtgga agacacccgc ggagcgccgg tggataaggg ccgtttcctg agaccagagc 960
tgtatccgca gcaggtcagc acttcgtgcg ccctgtgtgc 1000

<210> SEQ ID NO 125
<211> LENGTH: 300
<212> TYPE: DNA
<213> ORGANISM: Homo sapiens

<400> SEQUENCE: 125
agcggcgctg ttcccgggct gggtgcagct gctaaggaca aggcccctgc tccgaagaac 60
gcggtggctc ggggataccc tgaaagggac ggccatggcg cacatgggat gccctagggt 120
tcgtgggagg gcatgcaggc gcagcccccg caggggttgg cctgccagag aaggcagggg 180
agagcactcg gggctgcaca aatggtgtgg ccggagggaa ggtgcagcct tgtgtgtgtc 240
tggatgaggg ctgggcatag gagcttggta tttgatcctg aaagctctgc gtttccaaag 300

<210> SEQ ID NO 126
<211> LENGTH: 600
<212> TYPE: DNA
<213> ORGANISM: Homo sapiens

<400> SEQUENCE: 126
gagtcatact tgtagtcaca tccttttcct ttctccaacc cactggttaa tcatgaaagg 60
ctcttctgat tggctgcctc ctggcagtag tgcctcagcg cgacggttcg ggagcaaata 120
aataattccc gctgggaagc tgtttctcag acaggagcag cgacacccct gccacgcctg 180
ccgcctggag ttgagtgggg taagcacgcc ggcctccagg aatcgacggt gccacgtggt 240
tcttcttgca cttctcttct tctccagttt caggggacac cgtggggtgt gcgagcccgg 300
gggagcgcag ggaagggcgg gttgggctgc aggtgggaat gtgcggtcct tctgcgccct 360
caacagagct tccttccttt ttgccaaggt ccccgtgccg ccttcagcgc gcctccttat 420
gcacctctac ctctgctgca gcgtacctct tccgcagccc tagcggcctc cccgaggggc 480
gccgcggcct cggctgtccc tcccctgcct ggcacgacca cctgaccccc agcgacccaa 540
gaagcaagtt gtgtttgcag acgcaaaggg gctgtcgttg gtatcggtgc actggtttga 600

<210> SEQ ID NO 127
<211> LENGTH: 1700
<212> TYPE: DNA
<213> ORGANISM: Homo sapiens

<400> SEQUENCE: 127
acactttctg tgtgggaggg cacaagacat gggctatgac atggccagag accccacctt 60
ctttacacat gtaaaaacca accaaatcaa gatgcgtcaa cggtgattct tcctcccaca 120
ttgtttccct ttttaaactg ttatttttc aatccatgga gcagttgaga aacgggtatg 180
catctctcct cccctcccct tctatcaaag cctgtaagac acataaggaa atccaaagcc 240
acagtaatag agagagagag agagagagag agagagagag agagagagag agagaaaaca 300
gaacaaaaga aatcctcctt ggcttgtttt tccagggtgg ccaggcaagg tgtgaaaatc 360
catatttccc tctgggctgg caggtagaag ttactgggaa ggctgcgctc ccttctctcc 420
caccggctct cacatccagg ctgttccctc accctcagcc tcccccagcg ccagcttcct 480
cctccgcctc tctgcagcca ggcctcccct gcaaggcgga ccttggccca ccttggttcc 540
gggccaaggc ggcgggaaag gcaccgctac ctgcagccgc acgactccac caccatgtcc 600
tcgtactgct tgtagaccac attattgccc gcgtcgatgt atagaatgct gatgggagtc 660
aatttggtgg gcacgcagca gctgggcggg gtggagccgg ggtccatgga gttcatcagc 720
gtctggatga tggcgtggtt ggtgggctcc aggtgcgagc gcagcgggaa gtcgcataca 780
ccctcgcagt gataggcctc gtactccagg ggcgcgataa tccagtcgtc ccagcccagc 840
tccttgaagt tcacgtgcag gggcttcttg ctgcagcgta gcctggactt cttgccgtgc 900
cgcttgccat ggcgactggc gaaggccgtg cgccgccgcc ggcggccggg cgagggcagc 960
caaggcctgg catccggggc gcccgacggc ggcggccacg acccctcggc gcccgcgccc 1020
gggcccgcag cctcggccga gcccagctgc tcgcgcatct ctgcgaacag gttcttgcgc 1080
tgggatctgg tgaataccac cagcagggcc cgctcctggg gaggccgcac cctccggccg 1140
aagcccagac tccgcaggtc cgggggcggc ggttgctggg gtccccgcgc gcgcgcctcg 1200
gcctccccgg cgtccagctc gccccatgcg gcccgcagct ccaagcacag ctgcttccag 1260
ggctggtggc gcaggccctg ccacacgtcg aagacttccc agccggccgg cggcgccccc 1320
tgcgggtcca gggtccgcgc gtccagcagt aggggcgaaa ggcaagggaa gagctgcacg 1380
tggagcggcc cggctggtgg cccccagggc gctgagggcg cctggcgaaa gagccgcagc 1440

-continued

```
tccgcgccca ccagctcttc tttgtctgag agcatggaca catcaaacaa atacttctgt   1500

ctccggagag gagtgtgcga gagatcgtct gcgagataaa aaataattac agtcagtttc   1560

acttaagggg gagatcagcc cggtgctctt cggccgcccc gggaggaaaa gggcggggag   1620

tgggggcagg tcggccgggc agtccagctt gcccggccca gggcctgacc accccggctc   1680

cccatctggc tggtgcatgg                                               1700
```

<210> SEQ ID NO 128
<211> LENGTH: 2000
<212> TYPE: DNA
<213> ORGANISM: Homo sapiens

<400> SEQUENCE: 128

```
gcccgctgtg aatgtaggtg aggtgatccc gggaacctgg gtctgaaatc agacctgtgt     60

tgccattggg agcacggaga gaggggaagc gccctgctta ggcccaggcc gggcgtcctg    120

gtggtgggac cgcagccgca ctcacctcca ggccaacgga caaggttcct gcaagccagc    180

agggccactc tgtgcttggc ctactgcagc tcccctgcag ctcctttcct ctccctcccc    240

ggagcgctct cctctctcct ctcccctctc ttctctctcc tctctcgtct cctggggcat    300

cccgggtgga gggatgtagg ggtcgctcct cggtgccagg ccgggaagca gctcaggcct    360

cccaagagct tggcgctcag tctgggaaaa ggggttcctc tggcctcagg gacgttctcc    420

gcccccaccc cacccccctgg gagcctgaac catctggaag ggatcttagt cgggggttgg    480

gaggagagcc cgtggatagg aggagggggc gattctaggc cgaatccagc ccctgaggtg    540

tcacttttct ttcctgcggc ccgtcaccgc tgatagatgg ggctgagggc agaggaagga    600

aaaagaaaac ctccgaggtc agtgcggggc gaggtgagcc cctcccaggg ccctctggcc    660

caggaggatg aagcgcgccg gcttcgctct tgcacgccgg cttgccatcc gggtaagcgc    720

gggaaaggcg gccacagggc gcggcggcag cgcagcgcgt gggatctcac gacccatccg    780

ttaacccacc gttcccagga gctccgaggc gcagcggcga cagaggttcg ccccggcctg    840

ctagcattgg cattgcggtt gactgagctt cgcctaacag gcttggggag ggtgggctgg    900

gctgggctgg gctgggctgg gtgctgcccg gctgtccgcc tttcgttttc ctgggaccga    960

ggagtcttcc gctccgtatc tgcctagagt ctgaatccga ctttctttcc tttgggcacg   1020

cgctcgccag tggagcactt cttgttctgg ccccgggctg atctgcacgc ggacttgagc   1080

aggtgccaag gtgccacgca gtcccctcac ggctttcggg gggtcttgga gtcgggtggg   1140

gagggagact taggtgtggt aacctgcgca ggtgccaaag ggcagaagga gcagccttgg   1200

attatagtca cggtctctcc ctctcttccc tgccattttt agggctttct ctacgtgctg   1260

ttgtctcact gggtttttgt cggagcccca cgccctccgg cctctgattc ctggaagaaa   1320

gggttggtcc cctcagcacc cccagcatcc cggaaaatgg ggagcaaggc tctgccagcg   1380

cccatcccgc tccacccgtc gctgcagctc accaattact ccttcctgca ggccgtgaac   1440

accttcccgg ccacggtgga ccacctgcag ggcctgtacg gtctcagcgc ggtacagacc   1500

atgcacatga accactggac gctggggtat cccaatgtgc acgagatcac ccgctccacc   1560

atcacggaga tggcggcggc gcagggcctc gtggacgcgc gcttcccctt cccggccctg   1620

ccttttacca cccacctatt ccaccccaag caggggggcca ttgcccacgt cctcccagcc   1680

ctgcacaagg accggccccg ttttgacttt gccaatttgg cggtggctgc cacgcaagag   1740

gatccgccta agatgggaga cctgagcaag ctgagcccag gactgggtag ccccatctcg   1800

ggcctcagta aattgactcc ggacagaaag ccctctcgag gaaggttgcc ctccaaaacg   1860
```

```
aaaaaagagt ttatctgcaa gttttgcggc agacacttta ccaaatccta caatttgctc   1920

atccatgaga ggacccacac ggacgagagg ccgtacacgt gtgacatctg ccacaaggcc   1980

ttccggaggc aagatcacct                                                2000
```

<210> SEQ ID NO 129
<211> LENGTH: 2000
<212> TYPE: DNA
<213> ORGANISM: Homo sapiens

<400> SEQUENCE: 129

```
cactcccccg ccgcctccgc ccctaaccct cggccccgtg cgcgagcgag cgagggagcg     60

aacgcagcgc aacaaaacaa actagtgccg gcttcctgtt gtgcaactcg ctcctgagtg    120

agtcgggggc cgaaagggtg ctgcggctgg gaagcccggg cgccggggac ctgcgcgcgc    180

tgcccggcct ggccggagcc tgtagcccgg gggcgccacg gccgggctcg cagtcccccc    240

acgccggccc cccggtcccc gccgagccag tgtcctcacc ctgtggtttc ctttcgcttc    300

tcgcctccca aacacctcca gcaagtcgga gggcgcgaac gcggagccag aaacccttcc    360

ccaaagtttc tcccgccagg tacctaattg aatcatccat aggatgacaa atcagccagg    420

gccaagattt ccagacactt gagtgacttc ccggtccccg aggtgacttg tcagctccag    480

tgagtaactt ggaactgtcg ctcggggcaa ggtgtgtgtc taggagagag ccggcggctc    540

actcacgctt tccagagagc gacccgggcc gacttcaaaa tacacacagg gtcatttata    600

gggactggag ccgcgcgcag gacaacgtct ccgagactga gacattttcc aaacagtgct    660

gacattttgt cgggccccat aaaaaatgta aacgcgaggt gacgaacccg gcggggaggg    720

ttcgtgtctg gctgtgtctg cgtcctggcg gcgtgggagg ttatagttcc agacctggcg    780

gctgcggatc gccgggccgg tacccgcgag gagtgtaggt accctcagcc cgaccacctc    840

ccgcaatcat ggggacaccg gcttggatga gacacaggcg tggaaaacag ccttcgtgaa    900

actccacaaa cacgtggaac ttgaaaagac aactacagcc ccgcgtgtgc gcgagagacc    960

tcacgtcacc ccatcagttc ccacttcgcc aaagtttccc ttcagtgggg actccagagt   1020

ggtgcgcccc atgcccgtgc gtcctgtaac gtgccctgat tgtgtacccc tctgcccgct   1080

ctacttgaaa tgaaaacaca aaaactgttc cgaattagcg caactttaaa gccccgttat   1140

ctgtcttcta cactgggcgc tcttaggcca ctgacagaaa catggtttga accctaattg   1200

ttgctatcag tctcagtcag cgcaggtctc tcagtgacct gtgacgccgg gagttgaggt   1260

gcgcgtatcc ttaaacccgc gcgaacgcca ccggctcagc gtagaaaact atttgtaatc   1320

cctagtttgc gtctctgagc tttaactccc ccacactctc aagcgcccgg tttctcctcg   1380

tctctcgcct gcgagcaaag ttcctatggc atccacttac caggtaaccg ggatttccac   1440

aacaaagccc ggcgtgcggg tcccttcccc cggccggcca gcgcgagtga cagcgggcgg   1500

ccggcgctgg cgaggagtaa cttggggctc cagcccttca gagcgctccg cgggctgtgc   1560

ctccttcgga aatgaaaacc cccatccaaa cggggggacg gagcgcggaa acccggccca   1620

agtgccgtgt gtgcgcgcgc gtctgcgagg gcagcggcgg cagggggagg aggaggcaga   1680

ggcggggtgg ctggaccctc ggcatcagct cattctcccc tgctacacac atacacacac   1740

aaataatgtt tctaaaaagt tcagttgcga ctttgtgcct cgcctgtcct gttcatcctc   1800

gtcctgggcc ggggaatgct tctgggggcc gaccccggga tgctggctaa ttgctgccgg   1860

cgggttccgt cgccggtgtg accctggacg gcgcggacgg cgtacagggg gtcccgggag   1920
```

-continued gggcagtggc cgcggcactc gccgccggtg cccgtgcgcg ccgcgctctg ggctgcccgg 1980
gcggcgcagt gtggacgcgg 2000

<210> SEQ ID NO 130
<211> LENGTH: 800
<212> TYPE: DNA
<213> ORGANISM: Homo sapiens

<400> SEQUENCE: 130
ctgaaaagcc gtcagggaaa ccacacatgt tcaacccctg gcggctcccc caaacctctc 60
atttccagta actgtgtgtt tccgctcgtc aacagctgaa accgagcgga acttgggggg 120
ccccaccacg cggccctgct gtgcggcacg gggctcatct gtcccccggc tgcggggagt 180
cagctctcac cgcccacctc cttcccagat agtctctgtg cccactcgac ggcccggcaa 240
gcccagcccc tgcctgccac ggccacagca gcctcagaga gctgccctct ctggccaggg 300
tcagggcctg agctgctgcc tcccgcaggg tcgagggcag gacacttgtc tgaggcttgg 360
gtggggcaat ggcacctcct cagggcctca gcccccgggc aggctcggtg accatgggcc 420
tacagcaggg aaaattctgg gccaaaagct ccagcctcct actagggcat ctgtctgcaa 480
atgcacctta acctgaccgc ttgggctgtg ggggagcctg tttcagggaa agtgagggac 540
gcgccagttt cctcctttgg acttgatgag gcacgaacgc atctctaata aagccaggtc 600
tccccgccgt ggctccctgg gcgggtgcct gtggctcggg ccatgagtca cgctgggtaa 660
ccccactacg gggaagaggg caggaagctg ggagccaccg cctctgtgcc cggttgtcat 720
ctcggcacga gggcgaccgt cggcttcgtc ctgccctcat ggctgagggc ttttgggatg 780
tggcgggaga cgggggagtc 800

<210> SEQ ID NO 131
<211> LENGTH: 500
<212> TYPE: DNA
<213> ORGANISM: Homo sapiens

<400> SEQUENCE: 131
aaatcatcag aatggctaaa atgaaaaaga cagacaacag caagtgctga caagggtgtg 60
gggcggccaa atgctcctgc actgctggca ggggacctga gaactgcagg gcattccctg 120
gcttcctgcc cctcctggga ctggggaccc cccagggaca gcctaaggga actgcattta 180
tcttcacgtc tgccaaaaga taacacgaag atgttcaaag ctaagccccc aggctggtaa 240
gagctccaag gcaccagcag tgtgtgcaga actgggggga gtctgttctc ccagggatgc 300
tcccatcacc tgctgccagc agtggggcat gccggtcccc tggggtgtgg ccaaggggct 360
gtgtctcctg cccgggctgc cggcccctct caggttcact ttcccatctc taagcccacg 420
tctcgctgca gttcaagttt gccaggccac caacgggtga cacgcccggc gcagtggggg 480
actccgcact ttctgcgcac 500

<210> SEQ ID NO 132
<211> LENGTH: 1200
<212> TYPE: DNA
<213> ORGANISM: Homo sapiens

<400> SEQUENCE: 132
accctttgtg cctgggtccc ataaacaatg tgctttttaa aggggagccc cctcccagct 60
ccggcctttt tctccagcgt gggcagccaa tcagctgcgc agagctgcat agctggaccg 120
ctttccattc tgagtagcaa caacgtacta atttgatgca cacatggatg cctcgcgcac 180

```
tctgcaaatt catcacccgc atcttgcatt agtcatctga cggactgcca agtgtttcat    240

tttctttcca tgtgacttta ttattaccac ctctctcctc tcttccaaaa acctccccaaa   300

aagggcggtg gggcgggggg cggggcaggg agagggagag aaatccagca gacatctagc    360

tctgcctttc tttcccagcc acagccaggg tagggctgat aaggcgctga tgcgttgatg    420

gcagccttgc agagctagac ctgcacttaa cttgcagctg cctcccgagc ctccaagatg    480

tccacgccct gggtgacagg cggcagggcg ctgccccgtg ctcccccggc tctgctcgac    540

agcagcacgc agtgagagcc tcgccgccgc cgaggagcaa ctcatggtgc ctccgctttg    600

ttttagttca tcaaatttct acgactcatt aggcactttg ccactgctct tcttcctcct    660

ccttccgcct ccccgctccc ccacccccac tattttttct tcctgtccct catcgtgccg    720

ccctaactct ggctcccggt tccgtttttg acagtaacgg cacagccaac aagatgaacg    780

gagctttgga tcactcagac caaccagacc cagatgccat taagatgttt gtcggacaga    840

tcccccggtc atggtcggaa aaggagctga aagaactttt tgagccttac ggagccgtct    900

accagatcaa cgtcctccgg gaccggagtc agaaccctcc gcagagtaaa ggtacagagc    960

gcggggcggg ggtcgccagg cgtccaggtg ggcgtcgcgg ggcactgggg ctgtccgagc   1020

ccccagcctg caggaggaag ggcgggtagg caggagggct ggaagcagcc ggtgctggcg   1080

gcccctgtgc tccaggggct gctcccgact cctccccgca cccccgcccg cctgcccgcc   1140

gggacaggtt ggaggcggga gagagggacc gaggcagggc gggagcgcag aggctcggtc   1200
```

<210> SEQ ID NO 133
<211> LENGTH: 800
<212> TYPE: DNA
<213> ORGANISM: Homo sapiens

<400> SEQUENCE: 133

```
taacaaataa gccgcccgtg gtccgcgctg tgggtgaccc ttggcgcctt cgaggtctgg     60

agccctaggg taaataagga aacggggcgc ctctagagtt ttaaatgaac tctgttattg    120

gaagcttcag tagggaccct gaaaacaatt aacgtcttaa ttagcatttt aatgtctcca    180

ttattacggc gcgggctcta gctcagccct ttaccttacc ttctcaccgt taacagggga    240

gggggattgt atttttagtt catctttttta tgtttttgag ttgttatcct gtctgtctga   300

ttccagcctc gagggtttga tgatgcggcc cgagcctggc tgtggtcgcc tgtcggggct    360

ggagcgggac cctcagccgg gccgggcctg ggggctaacg ttttcacagt gcgccctgag    420

tttccttggg ttactgctgg gaccgcgcag gaggaagcaa agagtttttc gagctagacc    480

aacaggaaac acattgacgg aaatgttgcc atagcccatg ggtggcttt aactggccgc     540

ccccgcgggc tgggtgtgaa atcagaggag gccgcggctc cccggccag gattggaggc     600

tcctcgcgca acctaatgcg ggtgtccggg cccgagcgct tcccgcgcag ccaggccttg    660

tcggtgcagc agccccgctc ctccccaaca cgcacacacc cggtgttcgc aagtgcggct    720

caccaaggga gatccaaggg ggcaaaaagt tatgtataaa tccgagagcc actggggaaa    780

gagggtcgtg gtattgtaag                                                800
```

<210> SEQ ID NO 134
<211> LENGTH: 500
<212> TYPE: DNA
<213> ORGANISM: Homo sapiens

<400> SEQUENCE: 134
ctaccctgtg ctatcctgag ctgtagtctt ctgaaatgat cgtttggctt cccagccaag 60
gcagggctcc cccaaagttc attcccactc ttgcagtttc acctcgggat gcttccgcag 120
aatttcagcg cctaagcaga caaggtcaaa gtaaaccgct tcaccgctgc ttctggcgca 180
ggggcccaga gcgcgtgcag ctccccagca cagaccaaca gcaggagagg ggtccgggcg 240
ggagccctgg gctgtagata agcaaaacgc acccattttc tctcctattt actccagagg 300
cacctctcct cccccactcc tggcatctct ttatcactgg ctccctctcc ctgtggcata 360
tttttgggta gtagaatgct gaggtcacag ggagcggctc tttatccaag cagtggggac 420
atcagcctgg agccctgagc atgaaccagc aagatgcaga ctctcgctct tgactttggg 480
ctccaggagc tgccccgacc 500

<210> SEQ ID NO 135
<211> LENGTH: 1100
<212> TYPE: DNA
<213> ORGANISM: Homo sapiens

<400> SEQUENCE: 135
cagtgctccg ctccgggaaa ttgcatcgtc acgacaaacg ggaccgtgat aaaacgaccc 60
tttccgtcct tatttgtaga tcactcagac gagattgaac tgcacttgtt tccccttcga 120
ggggagccgc gttttcaggg tagccgaagg cttggggctg aggggggggcc ctcaccaagg 180 cgcgggtggg ggccggagcc tcaactcgat gagaagtgac aggcgtttgg gggatctggg 240
ctccggccgg gaccagcgca agcagggact ttgcggggac accgcttctc caacagagca 300
aggcctggcc cacgtttccg gtttctccta acttcctttt attgccttcc tttgcttcgc 360
aagttccatc tacccctcca gctacagagc cccacctcta ggcacaggaa gcttcccgga 420
aaaagaaagg ctgtcccaga aagagaccga gagagacttt ccaaacttcg ggcatagcca 480
cggcaattcc cagtctgcta atgccaaggc gggcgcgtaa ggccgcctaa atctagacct 540
ccctcctcac tcatttcaaa aaataacaac gtgccagcca cctccgcaga taccgccggc 600
tggtgcttgc ccaggagacg ccagggccag agcgccactc ccagcatcga aatggcagag 660
agaaagcgca gctccaaatt ccccttcaga ggttaagcct caatcattgt gtcccttccc 720
tagggactgc tggcgctctc gcccactggc gatgattatg cgcctagaac tcgaccgcga 780
agcaactaat aggaaaacat atggtgtcaa tttggatgct ccgcgcctcg cgcacacccg 840
ggaacgagcg gcacaaagcc ctgccggccg gcccgcgacc ccgcgcccct cggggcctgc 900
cagccgggcc gcagcgacaa acgctcaggg ctgcgcgccc tggctggggc ccgcccgaga 960
gacagcctgc ggctggggag tctgagctcc aaggggagag cccagccgcc gaaggcgagc 1020
ctaccggcca agccctgggg tccggcaggt tctgcacaac tactcccgca aagctcgcca 1080
cctttgtgcc ctttcctcag 1100

<210> SEQ ID NO 136
<211> LENGTH: 500
<212> TYPE: DNA
<213> ORGANISM: Homo sapiens

<400> SEQUENCE: 136
gggccctcgc ggctcaagcg ccagcgctgg agagagagtc tgagggtacc acgggcgtgc 60
tggcctgggt gctcactccc gccctccttc atgagcggct ttcctctggg tgtgtccagg 120
gcatcacaga gctcttctgc ccaaacccgg aggcctacca gggcctgccc accttgcctc 180
cttccacact ctctgtagca gcagccgcag ccatggcggg gatgaagaca gcctccgggg 240
actacatcga ctcgtcatgg gagctgcggg tgtttgtggg agaggaggac ccagaggccg 300
agtcggtcac cctgcgggtc actggggagt cgcacatcgg cggggtgctc ctgaagattg 360
tggagcagat cagtgagtgt ccgctgcccg cttgctgaac tcggcaccat gggcggccgc 420
cacgggtgtc tctgggcact tccgggccat ccctgctgct cagctcccga taatggtgtc 480
acggtgactc aggcattagc 500

<210> SEQ ID NO 137
<211> LENGTH: 600
<212> TYPE: DNA
<213> ORGANISM: Homo sapiens

<400> SEQUENCE: 137
tgtttacgga atcgggatcg aggggccgat aagtagttta cacgccggcc agagcagagg 60
gctggaggtc ggagttgggg gctggaggaa cgggtggcgt ttttaggatt cagtaacagg 120
atcacagctt tttcttgtgg tggaagctat tggaatttgg ggagggtagc acgaggggtc 180
ctgcagctcc gcgtgtgaaa aagcgtttag gtaggcgatg aaagtagttg atctgagcca 240
tggcaggcga gccccgaatt tttgctgctt ccccctgaaa gtgtttcttt aggaggagag 300
gacttgggcc acacaggacc cggtcctaag agagcgattc cgggaagcgg acagatcgaa 360
gagaccttct gggcgaagcg gcagggcagc ctcgcggggc tgggagtgga tctgaggtcc 420
cgacccaggc ggctcggagt gctccaggag ccacctgggt ctgcgggcgc agcgcggcgg 480
ggcgggagcg gtggcccgca ggggccgcgg cctgcgatga aggccggggg gcagcgctag 540
cagcgaggtg ccacagtggg ccgaggagtc tgggctgtgg cccagggtag gaccggctca 600

<210> SEQ ID NO 138
<211> LENGTH: 150
<212> TYPE: DNA
<213> ORGANISM: Homo sapiens

<400> SEQUENCE: 138
acctaaacca agctctccct ccctgccgtc tccttccctg gcctgggtct gaaggagagg 60
aggtgcccag aagttcagag cggcataacc acagagatac tacctaatta acataccaga 120
agcataaaga actcatttgc attggagagt 150

<210> SEQ ID NO 139
<211> LENGTH: 900
<212> TYPE: DNA
<213> ORGANISM: Homo sapiens

<400> SEQUENCE: 139
ataactacgg gggtgggggt ggggaaggaa gagatccaag gaggcagaag gctgcggtca 60
aaatattttg gggtggcaga gtcacgtagg atgtggctgt gggttctggc agcccagaga 120
ttcagctccc gcctcctccc tcagagcgag tccatagcta ccctcacgtc ccccgtggcg 180
gtcctcgcca cgctccggag cgggttaccc atgagggtgc tagacctggg cagcgggaac 240
ctcgaagagg tggagattgc aggctgggac tccagatttc gggcagggat gcggggaagg 300
gaagacgcct cgctggaggc ggaatggagg gcaaggcgaa ggaggatggt gcaggaaacg 360
gcgacaaggc gcccggccag gcccgcgagc taccgagacc cgggttccaa tcctcccccc 420
ttccgcaaac gcccgggttc gaggtacctg gcgggcaagg gccgcagcgg agcgaagcgg 480
gctggccatg gggaggctgc ggggacgcgg ggctgcagag agcggcagtg gcacggagcg 540
cgcggctgga agcgaaagca ggcggtgtgg ccaagccccg gcgcacggcc catagggcgc 600
tgggtaccac gacctggggc cgcgcgccag ggccaggcgc agggtacgac gcaacccctc 660
cagcatccct tggggaggag cctccaaccg tctcgtccca gtctgtctgc agtcgctaaa 720
accgaagcgg ttgtccctgt caccggggtc gcttgcggag gcccgagaat gcgcgccacg 780
aacgagcgcc tttccaagcg cagatatttc gcgagcatcc ttgtttatta aacaacctct 840
aggtgaatgg ccgggaagcg cccctcggtc aaggctaagg aaacctcgga gaaactacat 900

<210> SEQ ID NO 140
<211> LENGTH: 600
<212> TYPE: DNA
<213> ORGANISM: Homo sapiens

<400> SEQUENCE: 140
cagtccagcc gcttgcctca cttcttcccg cttgccttat ctccccgcag acgtggttcc 60
cctgcagccc gaggtgagca gctaccggcg cgggcgcaag aaacgcgtgc cctacactaa 120
ggtgcagctg aaggagctag agaaggaata cgcggctagc aagttcatca ccaaagagaa 180
gcgccggcgc atctccgcca ccacgaacct ctctgagcgc caggtaacca tctggttcca 240
gaaccggcgg gtcaaagaga agaaggtggt cagcaaatcg aaagcgcctc atctccactc 300
cacctgacca cccacccgct gcttgcccca tctatttatg tctccgcttt gtaccataac 360
cgaacccacg gaaagacgct gcgcgggtgc agaagagtat ttaatgttaa ggaaagagaa 420
gaaccgcgcc gcccggaggc agagaggctc catggccgtg ctgctgggcc atccccaact 480
ccctatccca tccccagcct ccaccccccat ccagatggga ctcacgtggc ttcaacagct 540
ttggaaatgg gtcccgagtg ggccgtgcga ggaaggctgt cgacctctac tcctccttgc 600

<210> SEQ ID NO 141
<211> LENGTH: 1500
<212> TYPE: DNA
<213> ORGANISM: Homo sapiens

<400> SEQUENCE: 141
caagatcgac tttcttagga agggggagag gagggaactc ttcacgaagg gaggtgggag 60
tccacctcag acctctattg gaaggaaatc gagttgttcc gggggactga ggtctcttgc 120
ataaggcatg ggatccttat tattattatt attattttta aatcccccgc ggaggagctc 180
tgggcaaatg aataccgagg cgccgctcta gctggttagg cttgggatgc gataactcag 240
tgccctcttg cagacttgca tagaaataat tactgggttg tcgtggaggg gacacgagac 300
agagggagtt ctccgtaatg tgccttgcgg agagaaaggt ccaagaatgc aattcgtccc 360
agagtggccc ggcaggggcg gggtgcgagt gggtggtgga gtaggggtgg gagtggagag 420
aggtggtttc tgtagagaat aattattgta ccagggcccg ccgaggcacg aggcactcta 480
ttttgttttg taatcacgac gactattatt tttagtctga tcaatgggca caatttctaa 540
gcagcgcagt ggtggatgct cgcaaacttt tgcgcaccgc tggaaaccca ctaggttgag 600
ttgcaaaacg taccgcgtag acgcccctgg tggcgccgag agaagagcta ggcctgccca 660
gcacagagcc ggagagcgtc gggccttccg gaagggtaag ttctccgcca aggggtcccg 720
agggagctgg acgtctgaat ctggacttgc ccccagcttc ggggttcgat tctgggtttt 780
gcgcgtcccc aacccccagg gctttccgaa gcatggcctg gctccaggcc cggtcctgta 840
aggactggaa cggcagcaaa atgtgcaggg aggcagtcgg ccggcagagc tgcggcggga 900
gccaaggtca ggcccgcggg gagagcgggc agcttccagc gccggccaca agctcccagg 960
ccagctgggc cgcagacccc tttgcttcca gagagcacaa cccgcgtcct ttctctcagc 1020
caggctgcag tggctgcccc gagcttcgct ttcgtttccc aagctgttaa taacgatatg 1080
tccccaaatc cgaggctcgt gtttgctccc agatgccaag aacgcaaccc gaaatccttc 1140
tcccaaaccc taggtcgacg agatgagttc ctacttgacc tctgagccga ggtgggccgg 1200
aaaccgaggc ctaggccccg ccggggctgc aaggaaaagg ggaaactccg agcgtagcgt 1260
cttttccttg tggttccttt ctccggcatc ccggactgcg ggccctgcag ccacctggac 1320
cggcattcaa aggattctgc aagtccagct tcacagactg gctttcccag acgctccgaa 1380
gcccgcacca cgaacagaat aaaggagaga cgagagatcg caactagatt tgagaatcct 1440
cgttcttttc cccaatcgtt cgggcagtaa actccggagc cggctacagc gcgcatcctc 1500

<210> SEQ ID NO 142
<211> LENGTH: 500
<212> TYPE: DNA
<213> ORGANISM: Homo sapiens

<400> SEQUENCE: 142
actgtcctcc tccctcaatt gcctattttt tgcccatagc tctaacttaa ccctgtgatc 60
accccagatc gctacttctg acccccatct cctctcccac accaacctcc agcgcgcgaa 120
gcagagaacg agaggaaagt ttgcggggtt cgaatcgaaa atgtcgacat cttgctaatg 180
gtctgcaaac ttccgccaat tatgactgac ctcccagact cggccccagg aggctcgtat 240
taggcaggga ggccgccgta attctgggat caaaagcggg aaggtgcgaa ctcctctttg 300
tctctgcgtg cccggcgcgc ccccctcccg gtgggtgata aacccactct ggcgccggcc 360
atgcgctggg tgattaattt gcgaacaaac aaaagcggcc tggtggccac tgcattcggg 420
ttaaacattg gccagcgtgt tccgaaggct tgtgctgggc ctggcctcca ggagaaccca 480
cgaggccagc gctccccgga 500

<210> SEQ ID NO 143
<211> LENGTH: 900
<212> TYPE: DNA
<213> ORGANISM: Homo sapiens

<400> SEQUENCE: 143
ctcagggaat cacatgtccg cctggcctgg cctggtacca aatgtttata gacaggacga 60
gggtcgctgg aatcgcctcg ctcctttcag cttggcgcta aggcgcgaat ctcgatcctc 120
ctagtatttc tctggcgtct gtctctatct cagtctctgc ttttgtctct ttctccctcc 180
ctccgcccca gtctttccgt ctctttttcc tcgaatgcac gtggaattcg gaattgaaaa 240
ttgaggtcag aatctccctt tttcttccag ttatccgcgc cgctgcccca cgcctagcgg 300
cttggatctg catagacatc tatctacccg caacaagatc cgagctgcag aagcaaacct 360
aatctgtctc cgcaccatcc cctgctctgt agacccactg ccccatccca cgccacatcc 420
ttgaggttca agtagcgact ccagcggatg attcggagaa tgccctgctt tccaaaggcc 480
ccaacccgtg tttttatttt ctttttcctt tgcccgcttg accaactttg gtttctttca 540
gggcccggag gtgcctgcgc cgcgcttggc tttgctttcc gccgccccag gagacccggg 600
actgtggttt ccgctcgcca catcccagcc tggtgcgcac acaagagcct ggcgagcttc 660
cctcgcgcgc ttacagtcaa ctactttggg cctcggtttc cctgctcctt gtagatcaga 720
gaagggacgg gcgaaatgcc tgcgagggag ggttggcgaa tgggttggtt ggtggcaaga 780
ctgcagttct tgtacatgga cgggggttgg ggggtcaaca ctggaagaac tcctgcctga 840
cgccaagagc cacccgcttt ccagctcgtc ccactccgcg gatgtttacc caccttcatg 900

<210> SEQ ID NO 144
<211> LENGTH: 500
<212> TYPE: DNA
<213> ORGANISM: Homo sapiens

<400> SEQUENCE: 144
tttggggcac ccaacccttc ccaagcctcg gttttcccga tcttgtggga tccttgcggc 60
gcgaatgggg ttggaagcac cttggaagct acagagtacc gggtcgggac aatttccggc 120
actgccccag ttcagtggtt tatagaaaat ttctttctct ctctcaggtc cactaagacc 180
gagagagaga gagaagtcga ctctggcaca cccgggcgag gggctgccgg gattcgggag 240
ctggcgcggt tgatttttc cgagaatcct ccacttgggg tgacgtcggg cagcgcgcgc 300
gggccgtgag gttaatgccc aggcttttct ctaaagcgtc cgggaatgat ccggcgaata 360
aaacgggtgt ctgcaaagtt aatgaattgt acaaggaggc tgagggtggg gacttcgacc 420
cggggagcca gaggcggttc tggtggacgc ttccccgtgc gcctaggggt gcgctgggct 480
ttcccagccg aggtctgcag 500

<210> SEQ ID NO 145
<211> LENGTH: 2000
<212> TYPE: DNA
<213> ORGANISM: Homo sapiens

<400> SEQUENCE: 145
ccagacagtt aaggtaaaac gttgaagtca agaggaagta gtgagtctgt tgccaactgg 60
atagggttgg tcctgtccca tctaaatgta ttagaattaa gtggctttta aaaatgagct 120
ggtcatcttc agcccacggg ctggccaatt tggaacttaa tgggcctttg cgtcctcctt 180
ccctgagcct ccttttattc cagacttctc agtgtgagtc tgtgcgtccc tccgacgatc 240
tcagggagtg gggtgccttc atctgcctgt tccctgttcc tcaggctgac gctcccgctg 300
tcctccccgc ctcccctcac tccttttctc cctcccttcc tccttgtggg gaggctcttg 360
gccagggtcc ctgagcccgg gcgggtgctg gcagaggacg cagaaggggt gaggtcacgt 420
ctcccttgag ccccgagccg ctggcttttc agagcctcgc cacaagccgg cggccagagc 480
cccagaccac acagaccgtg cgctcctccg ccctcccggc gccgccggcc tcgcccatgt 540
ctcagtacgc ccctagcccg gacttcaaga gggctttgga cagcagtccc gaggccaaca 600
ctgaagatga caagaccgag gaggacgtgc ccatgcccaa gaactacctg tggctcacca 660
tcgtctcgtg tttttgccct gcgtacccca tcaacatcgt ggctttggtc ttttccatca 720
tggtgagtga atcacggcca gaggcagcct gggaggagag acccgggcgg ctttgagccc 780
ctgcagggga gtccgcgcgc tctctgcggc tcccttcctc acggcccggc ccgcgctagg 840
tgttctttgt cctcgcacct cctcctcacc tttctcgggc tctcagagct ctccccgcaa 900
tcatcagcac ctcctctgca ctcctcgtgg tactcagagc cctgatcaag cttcccccag 960
gctagctttc ctcttctttc cagctcccag ggtgcgtttc ctctccaacc cggggaagtt 1020
cttccgtgga ctttgctgac tcctctgacc ttcctaggca cttgcccggg gcttctcaac 1080
cctcttttct agagccccag tgcgcgccac cctagcgagc gcagtaagct cataccccga 1140
gcatgcaggc tctacgttcc tttccctgcc gctccggggg ctcctgctct ccagcgccca 1200
ggactgtctc tatctcagcc tgtgctccct tctctctttg ctgcgcccaa gggcaccgct 1260
tccgccactc tccggggggt ccccaggcga ttcctgatgc cccctccttg atcccgtttc 1320
cgcgctttgg cacggcacgc tctgtccagg caacagtttc ctctcgcttc ttcctacacc 1380
caacttcctc tccttgcctc cctccggcgc cccctttta acgcgcccga ggctggctca 1440
cacccactac ctctttaggc ctttcttagg ctccccgtgt gcccccctca ccagcaaagt 1500
gggtgcgcct ctcttactct ttctacccag cgcgtcgtag ttcctccccg tttgctgcgc 1560
actggcccta acctctcttc tcttggtgtc ccccagagct cccaggcgcc cctccaccgc 1620
tctgtcctgc gcccggggct ctcccgggaa tgaactaggg gattccacgc aacgtgcggc 1680
tccgcccgcc ctctgcgctc agacctcccg agctgcccgc ctctctagga gtggccgctg 1740
gggcctctag tccgcccttc cggagctcag ctccctagcc ctcttcaacc ctggtaggaa 1800
cacccgagcg aaccccacca ggagggcgac gagcgcctgc taggccctcg ccttattgac 1860
tgcagcagct ggcccggggg tggcggcggg gtgaggttcg taccggcact gtcccgggac 1920
aacccttgca gttgcgctcc ctcccccacc ggctcacctc gcctgcagct gggccacgga 1980
actccccggc cacagacgca 2000

<210> SEQ ID NO 146
<211> LENGTH: 600
<212> TYPE: DNA
<213> ORGANISM: Homo sapiens

<400> SEQUENCE: 146
ctctctgggc cttaggaaaa tggaaatgac acctgtacct gcccttccag gactgacagg 60
aggggctgct ccatgaaacc tcactgctgc ggtcataatg tcattatctt ttgccttaaa 120
gggatttctt ctgcaccagc acctaaagtg gcagcccctt acccttggcc atcagctgga 180
ccctggtgct ctcctggagc ccaaaacctc tgttttgtgt tgcatcctgc tgaccagcca 240
cagtccacac ccatctgagt gtctgagcag aacagcccag aggccacacc aggatggctt 300
tccaccggtc accttccccc acccactcat aaaccctgcg tctctggggg agagggtggc 360
gaggtcccct ccccacatag atggaaacac tgaggcctga ttcatggtgc cccctgtgaa 420
gcgcctcatg gccagcaccg gggggcagca ggccagggcg gggacacata cccggttctc 480
gtcgtagatg atctgcacca ggctgcggtg cttcgactcg atgggcggcg gtgacacggg 540
cttctcaggc tcgggcggct tggcagcctc ctcctccagc tgttgctgtg gggagaggca 600

<210> SEQ ID NO 147
<211> LENGTH: 400
<212> TYPE: DNA
<213> ORGANISM: Homo sapiens

<400> SEQUENCE: 147
cttgaaaact cccagccccc tttgtccaga tggggatgga ggtggccagg ctgccccgtt 60
gattgtgtgc cgaggagccc tccccgggaa ggctgtgatt tatacgcgca ggcttgtcac 120
ggggtgaaag gaagggccac tttttcattt tgatccaatg ttaggtttga aagccaccca 180
ctgctgtaaa ctcagctgga tccgcgggcc gtgattaaac acattgcccg ctttgttgcc 240
gagatggtgt ttcggaaggc gctgtgaatg cacttccctt tgcggggctc acacagacaa 300
gatgtgtgtt gcaaggatga ggcgcctgct cggcctccag cccagggccg ggaagggaga 360
aggtgctgtg cgtcgctgcc tgtgtcgccc gcggctctcc 400

<210> SEQ ID NO 148

<211> LENGTH: 1200
<212> TYPE: DNA
<213> ORGANISM: Homo sapiens

<400> SEQUENCE: 148
cgcgtcaggg ccgagctctt cactggcctg ctccgcgctc ttcaatgcca gcgccaggcg 60
ctcaccctgc agagcgtccc gcctctcaaa gaggggtgtg acccgcgagt ttagatagga 120
ggttcctgcc gtggggaaca ccccgccgcc ctcggagctt tttctgtggc gcagcttctc 180
cgcccgagcc gcgcgcggag ctgccggggg ctccttagca cccgggcgcc ggggccctcg 240
cccttccgca gccttcactc cagccctctg ctcccgcacg ccatgaagtc gccgttctac 300
cgctgccaga acaccacctc tgtggaaaaa ggcaactcgg cggtgatggg cggggtgctc 360
ttcagcaccg gcctcctggg caacctgctg gccctggggc tgctggcgcg ctcggggctg 420
gggtggtgct cgcggcgtcc actgcgcccg ctgccctcgg tcttctacat gctggtgtgt 480
ggcctgacgg tcaccgactt gctgggcaag tgcctcctaa gcccggtggt gctggctgcc 540
tacgctcaga accggagtct gcgggtgctt gcgcccgcat tggacaactc gttgtgccaa 600
gccttcgcct tcttcatgtc cttctttggg ctctcctcga cactgcaact cctggccatg 660
gcactggagt gctggctctc cctagggcac cctttcttct accgacggca catcaccctg 720
cgcctgggcg cactggtggc cccggtggtg agcgccttct ccctggcttt ctgcgcgcta 780
cctttcatgg gcttcgggaa gttcgtgcag tactgccccg gcacctggtg ctttatccag 840
atggtccacg aggagggctc gctgtcggtg ctggggtact ctgtgctcta ctccagcctc 900
atggcgctgc tggtcctcgc caccgtgctg tgcaacctcg gcgccatgcg caacctctat 960
gcgatgcacc ggcggctgca gcggcacccg cgctcctgca ccagggactg tgccgagccg 1020
cgcgcggacg ggagggaagc gtcccctcag cccctggagg agctggatca cctcctgctg 1080
ctggcgctga tgaccgtgct cttcactatg tgttctctgc ccgtaattgt gagtccccgg 1140
gccccgaggc agcagggcac tgagactgtc cggccgcgga tgcggggcgg gaagggtgga 1200

<210> SEQ ID NO 149
<211> LENGTH: 2000
<212> TYPE: DNA
<213> ORGANISM: Homo sapiens

<400> SEQUENCE: 149
cttccgccgc ggtatctgcg tgccctttc tgggcgagcc ctgggagatc cagggagaac 60
tgggcgctcc agatggtgta tgtctgtacc ttcacagcaa ggcttccctt ggatttgagg 120
cttcctattt tgtctgggat cggggtttct ccttgtccca gtggcagccc cgcgttgcgg 180
gttccgggcg ctgcgcggag cccaaggctg catggcagtg tgcagcgccc gccagtcggg 240
ctggtgggtt gtgcactccg tcggcagctg cagaaaggtg ggagtgcagg tcttgccttt 300
cctcaccggg cggttggctt ccagcaccga ggctgaccta tcgtggcaag tttgcggccc 360
ccgcagatcc ccagtggaga aagagggctc ttccgatgcg atcgagtgtg cgcctccccg 420
caaagcaatg cagaccctaa atcactcaag gcctggagct ccagtctcaa aggtggcaga 480
aaaggccaga cctaactcga gcacctactg ccttctgctt gccccgcaga gccttcaggg 540
actgactggg acgcccctgg tggcgggcag tcccatccgc catgagaacg ccgtgcaggg 600
cagcgcagtg gaggtgcaga cgtaccagcc gccgtggaag gcgctcagcg agtttgccct 660
ccagagcgac ctggaccaac ccgccttcca acagctggtg aggccctgcc ctacccgccc 720
cgacctcggg actctgcggg ttggggattt agccacttag cctggcagag aggggagggg 780
gtggccttgg gctgaggggc tgggtacagc cctaggcggt gggggagggg gaacagtggc 840
gggctctgaa acctcacctc ggcccattac gcgccctaaa ccaggtctcc ctggattaaa 900
gtgctcacaa gagaggtcgc aggattaacc aacccgctcc cccgccctaa tccccccctc 960
gtgcgcctgg ggacctggcc tccttctccg cagggcttgc tctcagctgg cggccggtcc 1020
ccaagggaca ctttccgact cggagcacgc ggccctggag caccagctcg cgtgcctctt 1080
cacctgcctc ttcccggtgt ttccgccgcc ccaggtctcc ttctccgagt ccggctccct 1140
aggcaactcc tccggcagcg acgtgacctc cctgtcctcg cagctcccgg acacccccaa 1200
cagtatggtg ccgagtcccg tggagacgtg agggggaccc ctccctgcca gcccgcggac 1260
ctcgcatgct ccctgcatga gactcaccca tgctcaggcc attccagttc cgaaagctct 1320
ctcgccttcg taattattct attgttattt atgagagagt accgagagac acggtctgga 1380
cagcccaagg cgccaggatg caacctgctt tcaccagact gcagacccct gctccgagga 1440
ctcttagttt ttcaaaacca gaatctggga cttaccaggg ttagctctgc cctctcctct 1500
cctctctacg tggccgccgc tctgtctctc cacgccccac ctgtgtcccc atctcggccg 1560
gcccggagct cgcccacgcg gaccccccgcc ctgccccagc tcagcgctcc ctggcggctt 1620
cgcccgggct cctagcgggg aaaaggaagg ggataactca gaggaacaga cactcaaact 1680
cccaaagcgc atgattgctg ggaaacagta gaaaccagac ttgccttgaa agtgtttaag 1740
ttattcgacg gaggacagag tatgtgagcc tttgccgaac aaacaaacgt aagttattgt 1800
tatttattgt gagaacagcc agttcatagt gggacttgta ttttgatctt aataaaaaat 1860
aataacccgg ggcgacgcca ctcctctgtg ctgttggcgc ggcgggaggg ccggcggagg 1920
ccagttcagg ggtcaggctg gcgtcggctg ccggggctcc gcgtgctgcg ggcggggcgg 1980
gcccggtggg gattgggcgc 2000

<210> SEQ ID NO 150
<211> LENGTH: 1000
<212> TYPE: DNA
<213> ORGANISM: Homo sapiens

<400> SEQUENCE: 150
agtttgggga gccttttctc catttgagaa aaaacaaact tacagcgagg ggtgaggggt 60
tagggtttgg gattggggaa aatgtgggtg gggagccccc ccaaggaagt gaggaggggg 120
ctgcaaggat tacacctggg catacgtttc cctagaaatc acattcattg tatttttata 180
atttattcta aatctttcat gcgaagaaag tcagtagtga gtgttagtac tggtggccct 240
cctgatcaca cttgcatctc ttgagtgtgc cttaaaggtc ttgggaatgg aaaatataaa 300
aactgcttcg tgatgcgtca tctttatccc ccactccccc acccattcca atatattttc 360
tacttccagc ctaaattcgg ggccccctac cgaggccggc catgatcttg agggcggcat 420
aggggaggcc gcgctctgtc caccccagcc tggtgatgcc gttcgcttct tgtgcccggt 480
attgtgggct acatgccttt ccggcgtacg gagctgagcg tccaggccag tgcccctcaa 540
cctctcagta atgtttaccc gaggccgtcg tgcaatgaga ctattcgcat ggcattgtca 600
acgcggcggc gcgcgcgtct cggccctccg cggcttgcca gactgtcctg caaaccacct 660
cacccgtctc tttggcgcag gagactcagg ctgtaaccgg agaaaacact tcaccctgga 720
accctaactc aggtcctggc aaaagatgcg agaggaagac ttgctctctt aataaatctc 780
ggccgcccgc acatctggcc cctagacctg ctcggtagag gactggctgg tggatgcgcg 840
gtccaggccg tgggcactcg acccacctct attttccttc ccgaggcgcc cctggattac 900
cactttcggt ttgcgcttac atccgggatg tcgaatttcc cagggaatca taattatttt 960
atctataatt tattctaacc ccaaggttcc aagaaaatct 1000

<210> SEQ ID NO 151
<211> LENGTH: 1100
<212> TYPE: DNA
<213> ORGANISM: Homo sapiens

<400> SEQUENCE: 151
acattccttc taaaatgtgg gctttctgtg tacatgggcg cgcattccca ggactcggtt 60
ccctgggtgg aattcaccca ggaatacaat cgattttctg aacctgcgta aggccacagg 120
cagctctgaa aatgaaagcg tttgctaagt gggggagatc tcaccgatcg aacgtttaaa 180
aatggctttg tcttcattca gctctcccga tttattctgt gttttacaaa tagaagctca 240
gagcttctgt cgcccagtcc ttgcatgact catggcggtg gccacacggg tttcagggat 300
aacgggatgt ttagaaaatc gctgcatatc ggagtttcct agcacgttcc atttatactg 360
aacgcaggcg gccgctgaaa atccagcctc gactcttgct aatgactggg taggaccctc 420
ggggtcctgc gacggtgctg gagggtgttc ccggctccga tgtggggagg cctgcgcggg 480
gactaggttc tcgagaggcg agcgggcgcg ccagagaacc cgagactgct gcggggccgg 540
atgcgggatc cctgggctgc ggttctacgc agaaacgcca atggccatgc ctccccagct 600
cctcccagcc ccagtcacta ggccggcgcc tggcccggag atcctcccag agccctggcg 660
gtgccatcat gccggagaag acaagctcgg ccccgctgga attcgctcca aacacagatg 720
ctcatttttg gaatattcta gaaaaataac aagatcttgt ttgtcgttat gattcacggg 780
aggtaactga tgggagggcc atttacatga gggcagacac tgtggggcga aggtgacttc 840
tggacgtagg ctttaaagta ggaacggctc caaattccca atatctccgg ccttaccggt 900
tgcaaatcgg acccctgcgg gaaaaccaga cacttctgtt tcgtggcttt cgggctgcct 960
ccagcccacg caggctcgtt tagtccccgt ggagtcagcc ccgagccttc ctagtcctgg 1020
aacaagggct ccaggtcgcg gccgcgggaa gccgccaaga gggcggggag tagggattcc 1080
ctccagctcc gcagggcatc 1100

<210> SEQ ID NO 152
<211> LENGTH: 1500
<212> TYPE: DNA
<213> ORGANISM: Homo sapiens

<400> SEQUENCE: 152
tcctcctcgg cctcagatgt cgtcccacct gcccacgagc agggaacctg gaacccactc 60
tcccggcagt ccccagcggg ttccgccacc cggcggccgc ccctgacacc gagtgggtgg 120
gaggaagagg cagctggcgg ggatgggcca ttgagacctc ttgaaaaata ttaaaagaca 180
ggatgggtag agatttctcc gggagaaagt tcgagggtgc atcgggtcgc ggctgggagg 240
agtacccgaa atgccagcag gagaaatgca acctgtttag gccacacctt caatccccga 300
ggctgtctgg agagactgcg tgcgggggac ttgccggcgt tcccacaccg cgcctgcaat 360
ccactcccgc ggctgcctgg cctctgccac tcgcggcttg aagccagtgg ctctcaagcc 420
ctcggccccg cggcggcccg cgcagccttc acccggcgcc ggcaccacga agcctggccg 480
cagtggactc cccgcagctc gctgcgccct ggcgtctccc gtcgaggagg gagggacgga 540
ggcctgagcc gggagctccc tggcggtggt cgggccgccc cccttgaggc ctgctccccc 600
ctctcggcct cgccaaatcc ctgaaagccc agtccccctt cgtcaccccg gggcttcta 660 atcactcggt atcgatttcc ctaactcttt tcatcctgtt gaagacacat cttaaaacac 720
tccagcccgg agtgtgctct gggctttatc cacactaata aaatgattta cccttctctc 780
cgcgctctcc tcacagagga aaatcgttcg agccccggct atttgtgtgt gatcagtaaa 840
tatttagtgc gctgacatcc ttagctgggc ttcggatcga ttcggggccc accgggaggt 900
gcgcacggtc cgggcggggc cgcgccgagc tcgccgaggg ggctcctccc gccctcgccg 960
ccggccgctg atttacggcc cctgcaacca gctaaggggg gcgaaagcgc gcctggaaaa 1020
ttggcttttc aaccttttac ttttgacatt cagccacttc cccaggctct aattctcgcc 1080
cgcactcctc cctcccgccc tactaagggt tgccctgtgc gccctgcgag cccttccagc 1140
agcaacgcgc ggcgctcgcg ccccctcggc ccggggacca cctatcacag ccctgagccg 1200
cgacgcgggg aggccccggc ccctgctatg gggtcgcct ccttcgagga gagatgctct 1260
ccgcccgccc acacctctga gggaggagag ggggtggaga agcccagagc tgcatctgct 1320
ggatgacgag ccgctctccc tgctaccctt tctccgaccc gtcggccttt ctcctactct 1380
ggagactgat cctcgacgtc catcgggccg gatggcgtcg ggtggaagcg ttactttcct 1440
cgcagaaaaa ctcctcctct ttcctaagat cagaaaaagc gcttagcttg gaattgttag 1500

<210> SEQ ID NO 153
<211> LENGTH: 600
<212> TYPE: DNA
<213> ORGANISM: Homo sapiens

<400> SEQUENCE: 153
cctaggcatt ctcagcccgt tttgctggag ggggcatttg aggcctggcc agcttagcca 60
gcctacaagg agtgttactg ggtgaaaac agccagcggg gaccagtctg cttgtggccc 120
gccaggtgcc tgggatgggg aagcagcaaa tgcccacctt cctgcccaac cccctcctcc 180
ctcttcatgg ggggaactgg gggtggcagc ggctgccggg tgcgagcggg ctcaggcctg 240
tggccctgcc tgacgttggt ccccatcaag ccatgtgacg agaccaggcc acaagaaaga 300
ggtttcaaca agcgttatcg tttcctggaa ctccaactcg gcgacttccc cgaagaccgg 360
ctgtgcctgg cgggcgggct gcgcacagcg gggacaaggc tgccccctc ctcctccgct 420 gcctccgcgg ccgcgtctat ctcagtctga ctacctggaa gcagcactcc accctccagc 480
ccagcggccc tcggctcagc tgccaggtca ccggcaaccc cgggagcggt ggggcagggg 540
ctgctccgcc agcctctgtg atgttcaggc cgggctgcac cagcccggga cccctaggtg 600

<210> SEQ ID NO 154
<211> LENGTH: 700
<212> TYPE: DNA
<213> ORGANISM: Homo sapiens

<400> SEQUENCE: 154
gcactggttc ccctttacct gagccaacaa cctaccagga agtttccatc aagatgtcat 60
cagtgcccca ggaaacccct catgcaacca gtcatcctgc tgttcccata acagcaaact 120
ctctaggatc ccacaccgtg acaggtggaa ccataacaac gaactctcca gaaacctcca 180
gtaggaccag tggagcccct gttaccacgg cagctagctc tctggagacc tccagaggca 240
cctctggacc ccctcttacc atggcaactg tctctctgga gacttccaaa ggcacctctg 300
gaccccctgt taccatggca actgactctc tggagacctc cactgggacc actggacccc 360

-continued ctgttaccat gacaactggc tctctggagc cctccagcgg ggccagtgga ccccaggtct 420
ctagcgtaaa actatctaca atgatgtctc caacgacctc caccaacgca agcactgtgc 480
ccttccggaa cccagatgag aactcacgag gcatgctgcc agtggctgtg cttgtggccc 540
tgctggcggt catagtcctc gtggctctgc tcctgctgtg gcgccggcgg cagaagcggc 600
ggactggggc cctcgtgctg agcagaggcg gcaagcgtaa cggggtggtg gacgcctggg 660
ctgggccagc ccaggtccct gaggaggggg ccgtgacagt 700

<210> SEQ ID NO 155
<211> LENGTH: 300
<212> TYPE: DNA
<213> ORGANISM: Homo sapiens

<400> SEQUENCE: 155
tgtccgacag gcacacagag cgccgccagg cacggccctc attcttcacc ccgagctccc 60
gcaaggtcgg cgaggaggct ggagcagcgg gtaggaagcg ggccgaggct cccccgacgc 120
tgggccgcaa ctgtcatcgc agatccctga aaaacgagct ctgtaatcgt tgccgtcagc 180
gggtgtacaa ttgcagcctt atgtttcctg ccgctgttta ccttcctgag cggcgcccag 240
agatgcacac acgctgccct gaagcgggac gtgacctctg ggcacctgtg aggtcctggg 300

<210> SEQ ID NO 156
<211> LENGTH: 500
<212> TYPE: DNA
<213> ORGANISM: Homo sapiens

<400> SEQUENCE: 156
gtcggctcct gcgctcccaa cggggtggcc gtttccttcc tcgcaccctc ttctctcccg 60
gtgcctgcgg tcccaccttc cagatacccc tcggagagtc cagctgagct ctcgccagag 120
ctttcccctt ccaacccgct cgacttgccc agatcccaag ctgggcttct ctctccatcg 180
ccccagaaag tgggtcttgg agaccgaggc aagaatttgg gcctccgctt ctgttccaga 240
ccccggaccc cttgccaaaa tgcggcagat gtgcagattg ggccgcgctt ggttcctggc 300
tgggtttatg gagcctgcgg ctgaggcagg ctccgcagac cccgagccag agtgggattt 360
aacggcggcc ggtgcgctgt gcttggtcaa ccccggtaac cgtcacgctg ctagtgatat 420
gaaaaaaacc tgccagcgtt ctgcttttct gccccgctgc agtctttagc acccgccagg 480
attctgtccg agtgtttgga 500

<210> SEQ ID NO 157
<211> LENGTH: 1000
<212> TYPE: DNA
<213> ORGANISM: Homo sapiens

<400> SEQUENCE: 157
tttagtgtgt gcataaaaca tcccagctaa tctcaaatag acttttcctg agcagaggct 60
gaaatttgca agtaatgcaa agaagactcc gggagagcgt cgccgatggt ggagcgggag 120
acgggcgtgg ggagccccac tgcagtgctg ggatcgaagt ggtgctgacc ccaagacctc 180
tcccctcctc ctcccccggg agcttctcca gggttatttg ggaaatgagg gggaactcca 240
atccctgaga aagcgctcag gggcttgctg aggtgagcgc aaatggaagc acaaggccgg 300
gctggccgtg ggctcagtaa ccagtcggct gcccggcttg cgccagcact aaatgctcga 360
tcagaaagag aaaaagaggc gcaataattc caaatttcag gaaaagtcaa atcggagagg 420
ggggacgcag gtctcttcag actgcccatt ctccgggcct cgctgaatgc gggggctcta 480

```
tccacagcgc gcggggccga gctcaggcag gctggggcga agatctgatt ctttccttcc    540

cgccgccaaa ccgaattaat cagtttcttc aacctgagtt actaagaaag aaaggtcctt    600

ccaaataaaa ctgaaaatca ctgcgaatga caatactata ctacaagttc gttttggggc    660

cggtgggtgg gatggaggag aaagggcacg gataatcccg gagggccgcg gagtgaggag    720

gactatggtc gcggtggaat ctctgttccg ctggcacatc cgcgcaggtg cggctctgag    780

tgctggctcg gggttacaga cctcggcatc cggctgcagg ggcagacaga gacctcctct    840

gctagggcgt gcggtaggca tcgtatggag cccagagact gccgagagca ctgcgcactc    900

accaagtgtt aggggtgccc gtgatagacc gccagggaag gggctggttc ggagggaatt    960

cccgctaccg ggaaggtcgg aactcggggt gatcaaacaa                         1000
```

<210> SEQ ID NO 158
<211> LENGTH: 500
<212> TYPE: DNA
<213> ORGANISM: Homo sapiens

<400> SEQUENCE: 158

```
catggtgctt caggaaggga ggggacgaga gccctgggct tgtggtgtcc acgtggacag     60

ctaatgagga gccttgccga tgaggagcat gcgttcccga cggggcggcc gaatgcggaa    120

ggagccgcca ttctctccgc cctgaccgcg ggattctctg cagcagatga gaaacggcgc    180

tgactcagca gggtccctcc caggccccga gcggtcatct ggtgaccccc gcgcttcccc    240

cacggcccag ccggagaagg gcaaagggaa gtcccggctc caaggcgcac ccagagatgc    300

ggtgcatgtg gcaggatggc ccagccccgt cggcagcccc agcttcctgc ccctggtttc    360

cttcctccca cgggctacag gcctctgatg agctttggaa agcaggaaac acacaggcta    420

gtaactatga atgggtccaa aaaacactcc ttattacttt aaactactta ggaagaagca    480

cagcgttgcc aaacgccaga                                                 500
```

<210> SEQ ID NO 159
<211> LENGTH: 1200
<212> TYPE: DNA
<213> ORGANISM: Homo sapiens

<400> SEQUENCE: 159

```
gcgcgggggg ccggaggatg gcggcctggg ggccctgcgg gggctgtcgg tggccgccag     60

ctgcctggtg gtgctggaga acttgctggt gctggcggcc atcaccagcc acatgcggtc    120

gcgacgctgg gtctactatt gcctggtgaa catcacgctg agtgacctgc tcacgggcgc    180

ggcctacctg gccaacgtgc tgctgtcggg ggcccgcacc ttccgtctgg cgcccgccca    240

gtggttccta cgggagggcc tgctcttcac cgccctggcc gcctccacct tcagcctgct    300

cttcactgca ggggagcgct ttgccaccat ggtgcggccg gtggccgaga gcggggccac    360

caagaccagc cgcgtctacg gcttcatcgg cctctgctgg ctgctggccg cgctgctggg    420

gatgctgcct ttgctgggct ggaactgcct gtgcgccttt gaccgctgct ccagccttct    480

gcccctctac tccaagcgct acatcctctt ctgcctggtg atcttcgccg gcgtcctggc    540

caccatcatg ggcctctatg gggccatctt ccgcctggtg caggccagcg ggcagaaggc    600

cccacgccca gcggcccgcc gcaaggcccg ccgcctgctg aagacggtgc tgatgatcct    660

gctggccttc ctggtgtgct ggggcccact cttcgggctg ctgctggccg acgtctttgg    720

ctccaacctc tgggcccagg agtacctgcg gggcatggac tggatcctgg ccctggccgt    780
```

-continued

```
cctcaactcg gcggtcaacc ccatcatcta ctccttccgc agcagggagg tgtgcagagc    840

cgtgctcagc ttcctctgct gcgggtgtct ccggctgggc atgcgagggc ccggggactg    900

cctggcccgg gccgtcgagg ctcactccgg agcttccacc accgacagct ctctgaggcc    960

aagggacagc tttcgcggct cccgctcgct cagctttcgg atgcgggagc ccctgtccag   1020

catctccagc gtgcggagca tctgaagttg cagtcttgcg tgtggatggt gcagccaccg   1080

ggtgcgtgcc aggcaggccc tcctggggta caggaagctg tgtgcacgca gcctcgcctg   1140

tatggggagc agggaacggg acaggccccc atggtcttcc cggtggcctc tcggggcttc   1200
```

<210> SEQ ID NO 160
<211> LENGTH: 600
<212> TYPE: DNA
<213> ORGANISM: Homo sapiens

<400> SEQUENCE: 160

```
gggcgggttg ccacactgtc ccctttctgc atgggaggaa gggggctcga gaactgagtc     60

agccacacaa aacgaggatg gacagaactc ctgagtagcg agggtgcctg ccgggcgcga    120

ggaggagggg gaagacgagg aagacgagga ggaggaatag ggagcaccac atgacagagg    180

ggctgcctca gaccacaaag cgcttcctca tcctttcctc gccctttgat gccgccggca    240

acgtgactct gcgagcagcg gggcagacgc caggtctccc tcgcaggcgg gaaaggggct    300

ccaaggcggg tgctgccttg ctcgggtcac atggctacgt gggggccttg ctcaaattca    360

cttcctgcct tcattacaaa actgtcaaag gggatcgcac gtttgcaggg tgtcacccaa    420

gcattctggt tttgcaaacg acgctgtgcg gcaggcggtc tgatacctga tgagctcggt    480

gtggcggggt cggcagcatt tcctccgggg ttttgagctc tggccacttc tccttttgtt    540

ccacccaatc tcacccactt ctgggcttcg aggccagagt gtcttaacaa gggggcacgt    600
```

<210> SEQ ID NO 161
<211> LENGTH: 500
<212> TYPE: DNA
<213> ORGANISM: Homo sapiens

<400> SEQUENCE: 161

```
gagcgagact ttgtctcaaa aaaaaaaaaa accaaataaa ttgaaagctg agaaattcag     60

agcacaagaa gacaagcgcg ccccctcttt tagctgtcaa catggcggag ccgtccctgg    120

tgacgcagcc tccaaaggcc tccctgtgcc ctcctgagac cgcaagaggg aaagtggcag    180

cgacagtgat cgtggtgtct ttgtggcggt tgtgttgacc tcactgaccc ccgaagtgcc    240

gctctagggt ctgtcctcag cggtgacccg gccgggtcga agggcagagt tccgctgtca    300

ctagccctcc acccgtcctg tgtgctggga tgccctcgcg gcgccgtcca cgccaccgcc    360

gccccctctt gtgggttctg tctcctccgt gtctaggatc ctcctgcatc cgtttttcct    420

tcctcccttc tctccctccg tctgtcttgc ccgcacctga ggttgtcgca gaggcgctga    480

gacgggccag caggagctgt                                                500
```

<210> SEQ ID NO 162
<211> LENGTH: 600
<212> TYPE: DNA
<213> ORGANISM: Homo sapiens

<400> SEQUENCE: 162

```
tgctgtcccg gtcctgtcgc agtcctcaaa gatgctagag tgacagtcct ctaggggtag     60

agatggtcgt cctcccagga gaaggtggcc cggagacttg gaggtgggat caatcctgcc    120
```

agtcctggat caggaggcct ctgtcgggcg ccgccccccct tcctcctcca tcagcaacag 180
gcggcgccgg ccagcctcat agtcagcctc atccacactg accagcaggc gaacagcctc 240
ccggcccaca gcctctcgca gggcctcagt caggaacacg ccccgcaggg cctgcagcag 300
ggcgccactc aggtagtcgc cccagaaggc gtccagatag gagagctctg agaacttgat 360
gtcacaaacc acagagccca ggtcccttga gcgcagcact gcggtggcct gcccaaacac 420
gtccagctgc cgcgccagcg cctggggccg ccgggatgcc acgccctgct ccaaggctgg 480
cccatgctcg cagtactctg ctcgaacccg gagccggatg tctgcagggg aaggagggat 540
ttgtcaggga gggggccaac actagacaca cttatgggga acgccaccct tcctccctcc 600

<210> SEQ ID NO 163
<211> LENGTH: 500
<212> TYPE: DNA
<213> ORGANISM: Homo sapiens

<400> SEQUENCE: 163
tgatgcccgg cccccagggg ggcagaggcg ccgccaccat gagcctgggc aagctctcgc 60
ctgtgggctg ggtgtccagt tcacagggaa agaggcggct gactgcagac atgatcagcc 120
acccactcgg ggacttccgc cacaccatgc atgtgggccg tggcggggat gtcttcgggg 180
acacgtcctt cctcagcaac cacggtggca gctccgggag cacccatcgc tcaccccgca 240
gcttcctggc caagaagctg cagctggtgc ggagggtggg ggcgcccccc cggaggatgg 300
catctccccc tgcaccctcc ccggctccac cggccatctc ccccatcatc aagaacgcca 360
tctccctgcc ccagctcaac caggccgcct acgacagcct cgtggttggc aagctcagct 420
tcgacagcag ccccaccagc tccacggacg gccactccag ctacggtgag ggcctgggcc 480
atcttggccc acttttcaga 500

<210> SEQ ID NO 164
<211> LENGTH: 200
<212> TYPE: DNA
<213> ORGANISM: Homo sapiens

<400> SEQUENCE: 164
ggccgggcaa aaagccgccg caacaaaaag ctgcgctgac gggcggaaaa agccgcggcg 60
gcggagccaa aaagccgggg cggcaaaaag ccacggtggc gggcgcaaac agccgcaaaa 120
agccgcggtg gtgggggcaa aatcagtggg agcaggggca aaaaaacaca aaaagccgcg 180
gcggcggggg caaaaagcca 200

<210> SEQ ID NO 165
<211> LENGTH: 400
<212> TYPE: DNA
<213> ORGANISM: Homo sapiens

<400> SEQUENCE: 165
tggctttgct ggagtgtgat gtgataggaa atgtgcagcc aaagacaaaa gaagatgtaa 60
gtaggcttga ctcattgcag ctaagaaccc agatgttacc ttgagggtat taactaataa 120
gcagtttaaa tcagaatggc acattctgat ttgtttttg tatgttcaca tttggcaggc 180
atagatactg tttgaaaaga gaaaagtcag tacatagagg taacaagctt aaatatgtgc 240
caagtctaga aacaagagac tagggggata aggacctttc gaaattaaat gcaagatttg 300
aaaactgatt ggctggggga tgaggcaaag gcaggtcttt aaggtcaatc cctgttttgc 360

-continued tttaagttgt tagcgggtgg ttttatcata tattgtagaa 400

<210> SEQ ID NO 166
<211> LENGTH: 650
<212> TYPE: DNA
<213> ORGANISM: Homo sapiens

<400> SEQUENCE: 166
ttcctgggaa tgtcagctaa cctgagccta ggggcctgag cccaagggca gactgaggct 60
cccccagcac agggaggtgc tgcctgtgac aaggggtagt gctggcacag tgcaggctac 120
tccctagaaa gatcagcttg aatatgcagg aagagcagga ccctcgggct gaggcagagg 180
tggaatggga agtgcatggt ggtaatttag ttctccagag gccagaagta ggaggagcgg 240
ttggaatgct gatggcccaa agggaaaccc tggactaccc tggcctccca caggactctc 300
atagtaattg cggctccctg cagtggtgag gccagaagga gtgttgccca atgctgtcat 360
catccagtcc accccccacc caccatcaac agatgagtat ggtcatgagt gtggtcacct 420
catcagtcat ttgctcagtt gtgaaaaaga aattgttcag agaagagcaa agtgtttttc 480
catgagccaa aggtcagcca agttatgcta atgaggagga ctggagacag cgtgtcacag 540
acaccgagaa ggagcactgg gcaagggcac ttctcccagg gcagagccca caagaagcgt 600
cctggcacca gacactcagg gaactgaagg ctggcagggg cccgcccagt 650

<210> SEQ ID NO 167
<211> LENGTH: 5000
<212> TYPE: DNA
<213> ORGANISM: Homo sapiens

<400> SEQUENCE: 167
tccccccagc tgggtataag caaactttcc tgtctatggg ccgcagagac caccatctag 60
ttcccccgcc aaaactttac atgattttaa ttctcctgat gaagatgaga ggataacagc 120
caacagagag ggcagaggat gggatgggac tcccttgctc agagacctca cctctaggtc 180
tttacctcct attgagaata agtcagttct gtagtaagaa ctctgtgtcc acggcaaccc 240
caaacagaat cctagcgctc ttgtgattct tgtagaatgg ggaatagaac gagcttggcc 300
caagactgca cagacttaaa aacatactat tctttgaaaa tggcaatcat taaaaagtca 360
ggaaacaaca ggtgctggag aggatgtgga gaaataggaa cacttttaca ctgttggtgg 420
gactgtaaac tagttcaacc atggtggaag tcagtgtggc gattcctcag ggatctagaa 480
ctagaaatac catttgaccc agccatccca ttactgggta tatacccaaa ggactataaa 540
tcatgctgct atacagacac atgcacacgt atgtttactg cagcactatt cacaatagca 600
aagacttgga accaacccaa atgtccaaca atgatagact ggattaagaa aatgtggcac 660
atatacacca tggaatacta tgcagccata aaaaatgatg agttcatgtc ctttgtaggg 720
acatggatga aattggaaat cattctcagt aaactatcgc aagaacaaaa aaccaaacac 780
tgcatattct cactcatagg tgggaactga acaatgagaa cacgtggacc caggaagggg 840
aacatcacac tctggggact gttgtggggt ggggggaggg gggagggata gcattgggag 900
atataccaaa tgctagatga ggagtttgtg ggtgcagcgc accagcatgt cacacgttta 960
catatgtaac taacctgcac attgtgcaca tgtaccctaa aacttaaagt ataataaaaa 1020
aaatactgtt ctgccataca tacagatact cattaaagat gagggagaag ggcatggggt 1080
gggggagaat gtaccaaaac caaagaccac aggataataa cctcagagca gagactatct 1140
ctctagttat tttttctttt gtatgtaatg gagaggatta ttatttactc tgatgaagaa 1200

```
gtttacatca agtgttcagc ttcctttgtg ggttacagag aataaccaga gggctcagtt   1260
atgctctctg aataactatg tttgcttagt gttttctaaa caatattaaa tttcactaaa   1320
atagacaagg ttgataggac ttgggggcat aactcattga ctcaagctat cattttatag   1380
gattgtgaga aaacaaatag atgaacattt aaaatacact catattctcg ctagaaaaga   1440
ggattttgaa tattcttaca tcaaagacat ggtaaatgtt taaggcaatg aatatgctaa   1500
ttaccatgat ttgatcatta tgcaatgtaa aatgtactga aacatcacat tgtacctcat   1560
aaatatgtac aatttattat gtgcgaatta aaattttgag tataagaaaa aataaacttc   1620
aattgtaaga aaacaaccca acttttaaaa aacgggcaaa atacgtgaac agatacttca   1680
ctaatagaga tttgcaactg gcaaataagc aaatgaaaaa ctggtcatca tcactatcta   1740
ttagagaaat gcagattaaa actacaataa gaaacaatgc tgcccgtcca gacgcattgt   1800
tttgaccgtt tccaacttgt cccagccctt cccggggcat cgctggggac cctacgccga   1860
cgtccccccct ccgcccgcgc cccaagggcc gactgggcaa attgggagac ccgccccgcg   1920
gggcgaccca acttttcgga acagcacccc accgcccacc cccgcagacc cccggacccc   1980
cgctcccggc ggagactcag ggaaccccgc accccaagcc cttctaaatc gtgcagcgtg   2040
agtgtgacgg ccaagagcgg atgcagcccg ggatcgcccg caccttcccg tgggcggaag   2100
cgcaggagcc agctggggag ggggcgccct agaggagcgg ctagaaagca gacacgggga   2160
actcaggtca tcctgggggg ggacaagaca acgagagccg ggcgcctcgg gggcggcgcg   2220
ggagcctccg caggaccggg cgggcgcccc ggctggcgcg ggcgggggc gcgcccccctt   2280
tacctgcggc tccggctcct aggccatttc ctcacgcggc ggcggccggg actgagctaa   2340
caccactcag gccggccggg tttgaatgag gaggagcggg cgcggagagg aggggacggg   2400
gagggcggag ggagggaggg aggcgtcgcg gagtttttct cggccttttg tgcggacacc   2460
tcccggattc cgcgcccgca cccggccccc caaaagacac ggggagccgc gggcgagggg   2520
ttcagccatc cgccgaggcg cctagtgcct tcgcgcctcc aagacccccc cccaacaaaa   2580
aggagcgtcc cccaccccta cccccgcccg gaggacttag ggcctgggct cacctcgggc   2640
gcggagctaa gtgtaggcgc cgggggtccc tagagccgcc ggggcgcagc gagtccggcg   2700
ctgggtaact gttgggtcag aaactgttca ggtagcagct gttgtgccct cccttggccc   2760
cgccgctcgg agacgccccg ccccctgcct tgaacggccg cccggccccg ccccagcgcc   2820
cacgtgacta gcataggcgc gcccccgttc cgcccgccgc cgcagactcc gcctccggga   2880
cgcgagcgag cggcgagcgc gcgcactacc agttcttgct cggcgactcc cgcgcacgcg   2940
cgcgccgtgc caccctcccc gcacccctcc tcccgccatc cggcttaacg tggcgggcgc   3000
gcgccgcggc agtagccgtg acaggtaccc ggcggggcgg ggggggaggg ggttggcccg   3060
cgagggtgtg cgcaggcaca gacccgggtc ctgtccccgc cgccccctcc tctgcaaggt   3120
gtgcctgggc gaggggaggg gcccgcggcc cgaacccctg ggtcaccccc gaattacaaa   3180
caaaaacctt aacgccattg ctcgcgggtt agaaggcagc tgtgcgtgct caggaaaaga   3240
agccacgcac aagagaccgc acgcggcgtg gatacagtga cacgaaacac ccaaaatctc   3300
ttttgaaagg gaaaccaggc acagtggctc atgcctataa tcccagcact ttcgggggcc   3360
aaggcgctca cctaaacccg agagttcaag accagcctgg gcaatacagc gaaaccctgt   3420
ctctacgaaa aatataaaaa ttagctgggc atagggctgg gcacggtggc tcacgcctgt   3480
aatcccagca ttttggaggc cgaggcgggc ggatcacgag gtcaggagtt ccagaccatc   3540
```

-continued

```
ctggctaaca cagtgaaacc ttctctctac taaaaataca aaaaaaatta gccgggcgtg   3600

gtggcaggtg cctgtagtcc tagctacttg ggaggttgag gcaggagaat ggcatgaatc   3660

agggagcgga ggctgcagtg agctgagatt gcgccactgc actccagcct gggggacaga   3720

gtgagactcc gtctcaaaaa aaaaaataat aattagctgg gcatggtggc tggcacacat   3780

ggtcccagct actcaggagg ctgaggtgga aggatctctt gatcccgggg aggtcaaggc   3840

tgcagtgagc caagatggca tcaccgcact ccagcctggg ccacagaccc tgtctcaaaa   3900

aaaaaagaga aagtggggaa gaaaatgtaa tacaaattaa tataccaaca gcaattagtg   3960

agtacttttt ccatggagct gggagaggga ataaatgttt gtaaaattaa aatgttctac   4020

gctagaaatc aactttcctt ctatgctttc tttacttcac cccttatagc tacttagtaa   4080

atctcacaaa tcctatcctt ctgatctctc tgaaatgtat gtaccctttc ccttctattc   4140

tcaccaccca tgtttctttg tttccttcta gcctgtgtaa taatctcata atcgcacctc   4200

ctgtacctgc cttctttcta gtccagaata cgttttccta aattccacca ataaccatcc   4260

tgctactgct ttgtgtgaaa ttctccaaaa aaaattttac ttttccaaaa taagtcaggc   4320

tccctctctt aggatacaaa accacaccat ggtcccagcc aatctttcag cctgattcac   4380

tcagtatata tttattgacc tctcctttct cccaagcact tggctagata ataattaaag   4440

agtgcggcac aaaacaaatt ggattcctcc cctcatggag cttgtatttt cacaggaagc   4500

acagacatta aataaattaa aacacaaaaa aatagacaag catataatta cagtatgtat   4560

cctagagaaa tatcactcat gcagaaagca tacacaagga tgcagcactg tttccaatag   4620

cgaaaagcta gaaacaacct acatgttcac caaaagaaaa tggccacata aactatacca   4680

tatccaaatt atccaaattt tagaatatag acaacaggtt gggcgcggtg gctcacacct   4740

gtaatcccag cactttggga agccgaggcg ggtggatcac aaggtcagga gttcaagacc   4800

agcctggcca acatggtgaa accccgtctc ctctaaaaaa acaaaaaaat cagctgggca   4860

ctgtggcagg agcctgtaat cccagctact gaggagactg aggcaggaga atcgcttgaa   4920

ccctggaggc agaggttgca gtgagccaag atcgcgccac tgcactctag cctgggtgac   4980

agagcaagac tccatctcag                                                5000
```

<210> SEQ ID NO 168
<211> LENGTH: 1500
<212> TYPE: DNA
<213> ORGANISM: Homo sapiens

<400> SEQUENCE: 168

```
tgtaggagtc ctccggtgct ggagtccaga gcacagtgag gctgggtcct cccgtgccat     60

agtgtagggc atggcgggac agggatcctg ccctgcgata gtccagtgct tgagtccgca    120

gtaaggcaat ggtcctccaa tgctggagtt cacggcgttg tggggtcggg gtcctttggt    180

gacttagtcc agggcgtacc agggcggggg tccacagttg ccatagtgag gatcttggag    240

gaaggtggtt cctgccttgc tgtagtccgg ggagcagggg gcaggggtcc tctcttgtca    300

gagtctctgg cgcggggtgg gggtggaggt gggggttttc ctatgcgata gcccacgggt    360

cggtgaagcc gggtcctccc gtgcctttgt ccagggcgca ggggggcgag ggtcttcggt    420

ggtggagtcc gcggagcggc aggacggggg tcctccagtg ccatattcca gggcgcggcg    480

gagtggggga cctgtcctgc agtggtccag ggcatgtggg agtggtggtc ctgctgtgcc    540

tcagtccagt gcgcggtggg acggcggtcc tgctgtgctg tagtgcagga cgcggtggcg    600

caggggtagt ccagagagcg ccgtggcagg gggtcctcca gtgctggaat ccagtgcaag    660
```

gcgggtcagg ggtcttaccg tgccgaagtc ggtggcaagg gtcctcccgt gccatagtct 720
agggggcgac ggggcagggt tctctagtgc aggtgtccag ggtgtggcag ggcaggagtc 780
ctcttgtgca ggagtccagg acgtagccga ggagtcctcc aatgtcagag tccagggctc 840
tgcggggccg ggttccccca tgccagagtg tagggcgcgt tcaggtgagg gtcttggcgt 900
gcagtaatcc agggtgcggt ggggcagggg tagtccagac ctccatggcg ggcgtccctc 960
tgtgcaggag cccagtgcct ggcggatcgg gggtccttct gtgctgtagt ccagggcacc 1020
gcaaggtgtg ggtcctctgg tgccctagtc cagggggcgg cgagtcagag gttctcccgt 1080
gtctcagtct agggcctggt aggactgggg tcctggagtc cacgtggtag cccaagttgc 1140
cgcaggacca ggtactctgg aaccacagtc cagggcgctg aggggcagga gtagttcagg 1200
gcgagccggg gcccaggtcc tcgggagcca gagtccaggg tgtggagggg tgggggttct 1260
gcagtggcac agtccaggac accgcggggc gggacagggc ggggatcctc ccgtgcctta 1320
gtccagggct gagccgcggg agaggtcctt cagtagcaca gtctagcgca cggcgttgca 1380
ggtgtcctcc agtgcctgag gccacggcag gtcgcgggtc ccactgtgct ctagttcagg 1440
gcggagtggg tctgaggtct tctcctgcct cagtctaggg cgctggagag cggggatcct 1500

<210> SEQ ID NO 169
<211> LENGTH: 2500
<212> TYPE: DNA
<213> ORGANISM: Homo sapiens

<400> SEQUENCE: 169
gggttggtcc tagaaagcgt gaggatcgcc gagtgcactg ccctcccagc ctagggtcca 60
ctcttccttg gcccgagccc agagctcggg gtttcaggcg ctgggccctg tgcagctgcc 120
cagaataggc tgagcggcag gttcccgccc tggcaaggga tccagcagtg gaatcctcac 180
tgctgttggc tgcgggcaag gtcagcgggg tttccatcgc tgctggtggg agccacctgg 240
cggtggtagc tgcaagtgag cgcgtggcag agactggcag ggctggtccc agacaccctg 300
agggtctctg ggtgcatcgc cctaccaccc tagggtctgc tcttccttag cctgctccca 360
ggacgcggtg tacgagggct agactctgag cagcctccag gatggggctg agcagcggat 420
tcctgccctg ctgcagctac agtctgaatt aggcgccacc gcagtatctg gccctggggt 480
acgtgctact gggtggcatg gacagagatg gggctgccca cagctgctat ggggctgagc 540
agccgattct cgccctgctg cagcgggcga ccgctgcaat ccccagcgct atgggaccga 600
ccacctgact tagatgcctt ggaggcatcc ggtcctgggg tcttgctgct ggtgtctgcg 660
ggcagggtca cggctgccac tactactgct gtgcgccatg ggcaggtgcc agctgcagct 720
gagtccgagg cagatgctgt cagggctggt ctgaggttgc ctaagggtgg ctgagtgcac 780
cacgcttcca ccccagggtc cgttattcct aggccggctc ccagattgca gggttgtggg 840
cgttggacac tgtgcagcca tgaggatctg gttgggtgca gattcccgcc ctcctgcagc 900
tgagaagcca atctcataac aggcgctgca gtgacctctg gctctgcggt ccgcgctgct 960
gctggagctg gcagagaaca gagctgccac cgctgctgct tccaggagtg tgcagctggc 1020
agctgcagct gagcccgtgg cggaggctgg aaggccttat tccagaagcc ttgagggtcc 1080
ccgaatgcac cgccctccca ccctaaggtc cagtcttcct tgcccgcgcc cagagagttg 1140
gattgcaggc gctgagcaca gtgcaggtgc tgggatgggg ctaagctgaa agtttccgcc 1200
ctctggctgc tgcggggccg acagcctgag ttatgcgccg cggcggcttt tggtcatggg 1260
atccgcactg ccggtggctt gcacagggtc gggggctgcc acagctgcta tagttcaccg 1320
tgtgcacgtg gcagccgccc ctgagcccac cgctgaggct gcagggctgg tccggtccca 1380
gacggcctga gggccatttg cccgcgccca gatccgggtg gctgcgctgg gcactgtgca 1440
gcctcccgga atccgctgaa gggcacgttc ccgctctcct acagctgtgg gccgactgcc 1500
tgattttggc cactaggtgg agtctggctc tagggtttcg aggccgctgg tgttggtggg 1560
cggagtccgg gtttgccacc gctgcgctcc atgagcaggt agcagctgca gcggagcttt 1620
agaccgaggc tggcagggct ggccccagac ggcctgaggg tcagggagtg cagggtcctc 1680
ccaccctagg tccgctcttc ctttcccctt acccagagcg ggttgtgcgg gctctgggct 1740
ctgtgccggc gctgggctct gtgcagccgc cgagatgggg ctgagcagcg gatttcctcc 1800
ctgctgcagc tggaggacga ttacctgcac tagccgctga ggcggcatct ggccctgggt 1860
tactgcagct ggtgacgcgg gcagggtcag ggttggttgc aggtggcagc tgctgctaaa 1920
cccattgcga gcctcagggt caccaagttc accgtccttt catcatagta tctgatcttt 1980
ggcccgcgcc cagagtgcgg actggcctgc gctggggact gcatagcttc tgggggccgg 2040
tcagcgccag tttcacgtcc tcctgcagct gcgtggccta aggtcttagg cgccgcggcg 2100
ctatctggcc ctgctgtcga cgctgctggt ggtggggaca gggtcaaggg ttgccactgc 2160
tgctcccgtg cgccatcggc aggtggcagt tgcagatgag cccacaattg aggctgttgg 2220
ggctgctccc aggttgttag agggtcgccg agttcaccga catgccaccc taggttacgc 2280
tcttggcccg cacccagagc gccgggttac gggtcctggg ccctgtgcag ccacggggat 2340
ggtgctgagt gcaggttccc gtcttcctga gatgcggggc gaccactgga attagcctct 2400
gtggtggtat ctgaccctag ggtccgagct gctggtggcg tgggcggggt cgaagtcgcc 2460
tctgttgctg cggcgtgcca tttgcaccgt cctctggtac 2500

<210> SEQ ID NO 170
<211> LENGTH: 1600
<212> TYPE: DNA
<213> ORGANISM: Homo sapiens

<400> SEQUENCE: 170
aaatactcta ctgaaaaaac agaaatagta aatgaataca gtaaagtttt agaatacaaa 60
atcagcatag aaaaatcagt cgcatttcta tacccaacag cataccatct gaaaaaggaa 120
tcaagaaacc aatcccattt aaaatagcta taaaaaaatg cctgggaata aactaagcca 180
aataaatatg tctaaaatga aaactataaa acattgataa aaatcaattg aaaaagatac 240
aaataaaggg aaagttatcc catttttatg aattagaagt attaatactg ttaaaatgac 300
catcatactc aaatcagtct ataggtccaa tacaatctct aacaaatttc caatgtaatt 360
cttcagagat gttaaaaaag gttttaaaaa tcgttctgcg gatgttaaaa ggatttttaa 420
aacgcttttt tcgttctgca ggcgaaggct gtggccgtgc tcccgccggc cagttcccag 480
cagcagcgca ttgcccctgc tccacgcctt cgctccaggc ccgcaggggc gcagccccgc 540
gggaatcagc actgagccgg tcccgccgcc gccccagtgt ccgggctgcg actgcgggga 600
gccgatcgcc cagcgattgg aggagggcga cgaggccttc cgccagagcg agtaccagaa 660
agcagccggg ctcttccgct ccacgctggc ccggctggcg cagcccgacc gcggtcagtg 720
cctgaggctg ggggaacgcgc tggcccgcgc cgaccgcctc ccggtggccc tgggcgcgtt 780
ctgtgtcgcc ctgcggctcg aggcgctgcg gccggaggag ctgggagagc tggcagagct 840
ggcgggcggc ctggtgtgcc ccggcctgcg cgaacggcca ctgttcacgg ggaagccggg 900

```
cggcgagctt gaggcgccag gctagggagg gccggccctg gagcccggcg cgccccgcga    960
cctgctcggc tgcccgcggc tgctgcacaa gccggtgaca ctgccctgcg ggctcacggt   1020
ctgcaagcgc tgcgtggagc cggggccgag cggccacagg cgctgcgcgt gaacgtggtg   1080
ctgagccgca agctggagag gtgcttcccg gccaagtgcc cgctgctcag gctggagggt   1140
caggcgcgga gcctgcagcg ccagcagcag cccgaggccg cgctgctcag gtgcgaccag   1200
gccctgtagc tgtgacttgg ctgtggggct ggcccgcctc cctgacccct gtcaggcgga   1260
gcagctggag ctgacccacg ggcctgggct ttcgagcgct ttgtccaggc gctaatgatg   1320
ggaaggtgaa aggtgggggt ggccacaccc tgcagtcagg gtggcaggtg tcagaggcca   1380
catgcaaccc actggttttg tcttttccag gatgctgata agtttcccgc ggcccccgga   1440
gcagctctgt aaggccctgt aattgccttt cgttcccttc tgctctattg aggagtggga   1500
agatgacaaa gtgtttttgc tcaacccgaa ggaaaatgca catgggagga cacaccgggt   1560
tactatttga gtagcccaga caggagagca gcggtctgct                         1600
```

<210> SEQ ID NO 171
<211> LENGTH: 1500
<212> TYPE: DNA
<213> ORGANISM: Homo sapiens

<400> SEQUENCE: 171

```
tgggtggatt gcttgagccc aggagttcga gaccagcctg gacaaaatgg cagaaactcc     60
atgtctacaa aaaatacaaa aattagccgg gcatgatgtt ctgcgcctgt agtcccagct    120
actcaggagg ctgaggtggg aggatcgctt gagcccagga ggcggagttt gcagtgagct    180
gagatgtcac tgcattccag cctgggagac agagccagac tctgtctcaa aagaaaaaaa    240
gaaaaaaaaa aaagaaaaga aaaaacgaaa ttgtattctg aatacatctt ctaaaacact    300
acatttactt gcactatatt aaactggttt tatcctgacc acaattgcag gtgaaagata    360
ccactgttgt tctatttttc tggtaagtag agtgagccat gtcttcccca gggaaagacg    420
cctcctaaaa atttgtagga ccacctttgg ttttcttcca gatatttttt ttgtcatcgc    480
ttttcctgcg cccaattccc atctgtctag cccttctgcc tccgctggtc tttttcgcga    540
gcctctcccc agccgcaggt attcgtctgg gctgcagccc ctcccatctc ctggggcgtg    600
accacctgtc caggccccgc ccccgtccaa cccgcggaga cccgccccct tccccggaca    660
ccgggttcag cgcccgagcg tgcgagcgcg tccccgctcg tcgcccggct cggcgtcggg    720
agcgcgctct gtgtggtcgc tgctgcagtg ttgttgtggc tgtgagaagg cggcggcggc    780
ggcggagcag cagccggacc agactcccta gtagctcagg cgctgccctg cgccggccct    840
ggcagggagc ctggtgagat ggtggaggag gaggctgtgc cgtggctggc cttgctgtgt    900
cctgctgcct ggttagaacc ccatccccgt cccccgtctc ctccgggggg tgaggaggag    960
ctggaagagg ggccggcctc tgtccggccc ggccaggcgg cagtcaccct ctgaggaggc   1020
agcgcccggg gaggggcctc ccaggcggcc gccgccgcca gggggaggcg ctgggagtgg   1080
gagtgggagc gggacctcag ctgccaagct cggcccggac cctaggtgcg ggggaggcgg   1140
ggtcccgggc tcgggctgcc tgcccggacc tggcggggat gggcccgtgc ggctccgggt   1200
gtgggacgta ccctcagagc gcccggggtt attcccactg actccaggga ggtgagtgtg   1260
cgcccttcgc tccctgccgt gtctgtgagg gtccatcgtt gccggagact ggaggtcggg   1320
ggccatggga gccccggggc gaacggtgcg gacatgggcc ttgtggaaag gaggagtgac   1380
```

-continued cgcctgagcg tgcagcagga catcttcctg acctggtaat aattaggtga gaaggatggt 1440
tgggggcggt cggcgtaact cagggaacac tggtcaggct gctccccaaa cgattacggt 1500

<210> SEQ ID NO 172
<211> LENGTH: 1700
<212> TYPE: DNA
<213> ORGANISM: Homo sapiens

<400> SEQUENCE: 172
gtctctagga caccctaaga tggcggcgag ggagacggtg aaggttggct cccgcctgtc 60
tgggctctga tcctctgtct ccccctcccc ctgcggccgg ctcatggcct ggcggaggcc 120
cgaaccaaag acctccgcac cgccgtgtac aacgccgccc gtgacggcaa gggggcagct 180
gctccagaag ctgctcagca gccggagccg ggaggaactg gacgagctga ctggctaggt 240
ggccggcggg gggacgccgc tgctcatcgc cgcctgctac ggccacctgg acgtggtgga 300
gtacctggtg gacccgtgcg gcgcgagcgt ggaggccggt ggctcggtgc acttcgatgg 360
cgagaccatg gagggtgcgc cgccgctgtg ggcgcggacc acctggacgt ggtgcggagc 420
ctgctgcgcc gcggggcctc ggtgaactgc accacgcgca ccaactccac gcccctccgc 480
gccgcctgct tcgagggcct cctggaggtg gtgcgctacc tggtcggcga gcaccaggcc 540
aacctggagg tggccaaccg gcacggccac atgtgcctca tgatctcgtg ctacaagggc 600
caccgtgaga tcgcccgcta cctgctggag cagggcgccc aggtgaactg gcgcagcgcc 660
aagggcaaca cggccctgca caactgtgcc gagaccagca gcctggagat cctgcagctg 720
ctgctggggt gcaaggccag catggaacgt gatagctacg gcatgacccc gttgctcccg 780
gccagcgtga cgggccacac caacatcgtg gagtacctca tccaggagca gcccggccag 840
gagcagctca taggggtaga ggctcagctt aggctgcccc aagaaggctc ctccaccagc 900
caggggtgtg cgcagcctca gggggctccg tgctgcatct tctcccctga ggtactgaac 960
ggggaatctt accaaagctg ctgtcccacc agccgggaag ctgccatgga agccttggaa 1020
ttgctgggat ctacctatgt ggataagaaa cgagatctgc ttggggccct taaacactgg 1080
aggcgggcca tggagctgcg tcaccagggg ggtgagtacc tgcccaaact ggagccccca 1140
cagctggtcc tggcctatga ctattccagg gaggtcaaca ccaccgagga gctggaggcg 1200
ctgatcaccg acgccgatga gatgcgtatg caggccttgt tgatccggga gcgcatcctc 1260
agtccctcgc accccgacac ttcctattgt atccgttaca ggggcgcagt gtacgccgac 1320
tcggggaata tcgagtgcta catccgcttg tggaagtacg ccctggacat gcaacagagc 1380
aacctggagc ctctgagccc catgagcgcc agcagcttcc tctccttcgc cgaactcttc 1440
tcctacgtgc tgcaggaccc ggctgccaaa ggcagcctgg gcacccagat cggctttgca 1500
gacctcatgg gggtcctcac caaaggggtc cgggaagtgg aatgggccct gcagctgctc 1560
agggagccta gagactcggc ccagttcaac aaggcgctgg ccatcatcct ccacctgctc 1620
tacctgctgg agaaagtgga gtgcaccccc agccaggagc acctgaagca ccagaccatc 1680
tatcgcctgc tcaagtgcgc 1700

<210> SEQ ID NO 173
<211> LENGTH: 300
<212> TYPE: DNA
<213> ORGANISM: Homo sapiens

<400> SEQUENCE: 173
taaaaataaa ttgtaataaa tatgccggcg gatggtagag atgccgaccc taccgaggag 60
cagatggcag aaacagagag aaacgacgag gagcagttcg aatgccagga acggctcaag 120
tgccaggtgc aggtgggggc ccccgaggag gaggaggagg acgcgggcct ggtggccaag 180
gccgaggccg tggctgcagg ctggatgctc gatttcctcc gcttctctct ttgccgagct 240
ttccgcgacg gccgctcgga ggacttctgc aggatccgca acagggcaga ggctattatt 300

<210> SEQ ID NO 174
<211> LENGTH: 600
<212> TYPE: DNA
<213> ORGANISM: Homo sapiens

<400> SEQUENCE: 174
cgccaccacg tgcgggtagc gccgcatcgc cccagccgtg ttccttggtc tccgtctccg 60
ccgcgcccgc ctggtgaact ggagcacagg gaccatagtt ctggaaattt atcctttttc 120
tctccatgga ttcagcagca gtgtctaaaa gaaaaaaatt catcaatcat ttatgtatat 180
tttaatataa aggtaaaaca ctgcgaacca gtggaaccgg atagaaagta attcagtttt 240
acagaacaca actgtttttc aggctctttt attaaatata aaagagccat atatatttct 300
gtggaattcc ccttttactt aagaattcat tatcagcgaa ttagtttaag gaggctgttt 360
tgttagaggc tgtggttgca ttcaaaaatt ggaataggaa caatgacttg taaaaattca 420
acattttatt ttatttttga gatggagtct cgctctgtcg cccaggctgt agtgcagtgg 480
cgcgatctcg gctcactgca acctcagcct cccgggttta aggaattctc tgcttcagcc 540
tcctgaatag ctgggattac aggcgcatgc caccaagccc agctaatttt ttttgtattt 600

<210> SEQ ID NO 175
<211> LENGTH: 1300
<212> TYPE: DNA
<213> ORGANISM: Homo sapiens

<400> SEQUENCE: 175
ccctgaacag tcagagttta ctgcccactt ttgctggagg agaagctcct gaacaactag 60
agagactgtg gttcccaaag agcagcctgt aggcctgagg actgctctat gaccggcgtc 120
agtccctgcc tccctccctc cgtccctcct tccctccttc cttcccaggc cttctctgac 180
taccagatcc agcagatgac ggccaacttt gtggatcagt ttggcttcaa tgatgaggag 240
tttgcagacc atgacaacaa catcaagtga gtccacttgg atgccccctg cacgaggcac 300
gactccccct cctcgctgct gaagtcccat gggggcagct cccttagtcc ttgccgggag 360
ataacaggtg tttccagttg catgagggtg ctgaggcccc cagtgagaac caggggagga 420
gcactgaggc ctcagatgag caccggggga ggagccctga ggccccagat gagcaccagg 480
ggaggagcac tgaggcccca gatgagcacc gggggaggag cgttgaagcc ccagatgagc 540
accagaggag gagagctgag gccccagatg agccccgggg gaggagctct gaggccccag 600
acgagcaccg ggggaggagc gccgaggccc cagatgagca ccgggggagg agcgccgagg 660
ccccagatga gcagtggggg aggagccccg aggcccccag atgagcagtg ggcggggcag 720
ggagcgccga ggccatcccc cttgctcttg cagcgcccca tttgacagga tcgcggagat 780
caacttcaac atcgacactg acgaggacag tgtgagcgag cggggctgtg cggggtcatg 840
caggcaccct gttcccaggc agctcaggcc gcgcccatgg ctcggtctgt ggtgggcctg 900
tgcggtgggg ctgggagagg cccctctgtg gagctaggaa cagtcgcttt tcttgaccct 960
ccccatcatg ccctccagcc catggcgccc acatcctgaa ctaagcccct ctgggagccc 1020
tgtggggaga gcgcctcctg tctcccccag accctctgga aactgacctt ggcgttttac 1080
tctgcagccc agcgcggctc tgaggcctgc tgcagcgacc gcatccagca ctttgatgag 1140
aacgaggaca tctcggagga cagcgacact tgctgtgctg cccaggtgaa ggccagagcc 1200
aggtgcgggg cctgcccatc cccccaaagc ctctgccgag gaggtgcagc ccccagaaca 1260
cccgtcagat gcccagacgc cctgctgttt gttatgccgg 1300

<210> SEQ ID NO 176
<211> LENGTH: 110
<212> TYPE: DNA
<213> ORGANISM: Homo sapiens

<400> SEQUENCE: 176
tttgggccac gaggcaagtt caaagcggga gacttttgtt ttataaaatg atggtgagca 60
gctccggttt tatgtcaaac atcagggttt cgtgcaggat ataaacattt 110

<210> SEQ ID NO 177
<211> LENGTH: 1500
<212> TYPE: DNA
<213> ORGANISM: Homo sapiens

<400> SEQUENCE: 177
attgccgtac tttgcttccc tttgtatgta tttcttgtat gctgccgagt cactgatggc 60
tagctctgtc tggcaagtaa ttcaaaaatg ctgtttatgt agaaaggaaa ggtagggact 120
ttaccacact ctgtcattaa agggagcaat tgaagaacaa aggaactgag taaataccta 180
tatattgcct tttgtgttgc gaaacactgt agcacaaaca catttgtgtt cagccaaatg 240
ttttacttcc ttttgtaata acgcatatag taggttgtct ccacatatgt acaagaatcc 300
atattttatt taaacgtata tagtcaattg ttcatattta taggctgcaa acatttctca 360
atctcaaaga cttttacata tccactccca cacagctatt tgttattatt ttaaaagttc 420
ttaaattaaa aaaaaaaata aaatatacta atatctctgt tggttgattt tattaagcaa 480
cttaggattt caacacagtt taaatcatat tgatgactca gatcctggca ggtcttacaa 540
ttcctgtgaa atgagagcac agctaataaa aatattaagc aattactttt attaaaatca 600
tagggttttt ttcattatca catagaaatg attgatctat acagattggt ctcactcatg 660
tgtcttttgg gctgcttggg agcttcatgt agaagtggaa agtccccttt gctcttcctt 720
cgaccaaggt ggggaaaatg aaggcataga atacaatcta gggctattaa agaattgctg 780
gcattacttc tctctatcac gtgtgagcct ggctgcctgc ttcctgaggt aggggatcca 840
ggatgagact gtgccggagc ctgtttccac aactgcattt ggagatccgt cttattgatt 900
agcgggggaa aggggtgggg atcaggagtg tgaggtgagg ggaggaccaa ctgacgactg 960
gctcaatgaa gcacaagaca ttttcttccg gaaagatgtc aaacaactga gaaacagcca 1020
gagaggaagt agaaaggtgg aaaaatgagg agaccctgga agaaatgaag gcatttccta 1080
tgagacagcc ttggggcttt tttcttttct ttctttttt ttgcttccat catctgacct 1140
gcaaaggcta gagtgacagc gtcatgcaaa tgctgcagtc cagcaggtct gggagagggt 1200
ggatgctaga ctgtgagtta atgttaatga tgagcgcagt gaaaatacca gccgctgcca 1260
ccccctgctc acagaagcgc tctgagtcag catcagatgc tttgcctcgc ctctcgctgt 1320
gtatctgtat gcctgtgtgc gcgcgcgtgc tcgctcgggc atccgtgtct agccgagggg 1380
agggggtggc gtgtgagtgc gtggagggta aaagccagtc agtcagtgag aagcaaaggt 1440
acgttggaga gcaactaaaa tctgactgat ttccatcttt ggagcatcag atgtattccc 1500

<210> SEQ ID NO 178
<211> LENGTH: 200
<212> TYPE: DNA
<213> ORGANISM: Homo sapiens

<400> SEQUENCE: 178
gcagcctcct cctgaaaaat gtaagccatt tccactttgt aaagctacgt ttatattcca 60
ccacgatacg atggaaaaga aaacccaagg caatttaata tacgggttgg gaagaaagtt 120
ttgctgatgg aactacatta gcctccactc cagcaaagca aacaaggaac cacactaaag 180
aaatgtactg aatcttttaa 200

<210> SEQ ID NO 179
<211> LENGTH: 800
<212> TYPE: DNA
<213> ORGANISM: Homo sapiens

<400> SEQUENCE: 179
tgcctgagcg cagagcggct gctgctgctg tgatccagga ccagggcgca ccggctcagc 60
ctctcacttg tcagaggccg gggaagagaa gcaaagcgca acggtgtggt ccaagccggg 120
gcttctgctt cgcctctagg acatacacgg gaccccctaa cttcagtccc ccaaacgcgc 180
accctcgaag tcttgaactc cagccccgca catccacgcg cggcacaggc gcggcaggcg 240
gcaggtcccg gccgaaggcg atgcgcgcag gggtcgggc agctgggctc gggcggcggg 300
agtagggccc ggcagggagg cagggaggct gcagagtcag agtcgcgggc tgcgccctgg 360
gcagaggccg ccctcgctcc acgcaacacc tgctgctgcc accgcgccgc gatgagccgc 420
gtggtctcgc tgctgctggg cgccgcgctg ctctgcggcc acggagcctt ctgccgccgc 480
gtggtcagcg gtgagtcagg ggccgtctcc ccgaagaacg agcggggaga ggggaccacg 540
gggcgcggcg ggcagcctgt tctcgggcgg aggctctccg gggcgttgga aacctgcatg 600
gtgtaaggac ccgggaggag gcggggagaa attgattgtg ctgttctcct ccctctcttc 660
tctaacacac acgcagaaaa gtttaaattt ttgtgaagcg cttgcttacg tagctgcgga 720
gcgagcctct gcttcattac gagcggcata gcctttttca ggagtgattt ccactttctt 780
tgtgagagag ttgaccacac 800

<210> SEQ ID NO 180
<211> LENGTH: 600
<212> TYPE: DNA
<213> ORGANISM: Homo sapiens

<400> SEQUENCE: 180
ttcaatttac actcgcacac gcgggtacgt gggtgttcgg ggtagggcac tgatctgggg 60
aaggtctccc ccccgcgacc caactcatct ttgcacattt gcagtcctcc ctcggtgcac 120
tcctggcggg gatctggcca gtgcagcgca ctgggaccga gggcagagcc cgcggagtga 180
ggccaggaga gacttcaggc ctctaaggac acagctgagg ctaaggctga gttgaacgca 240
gcccctcccg cggctcgtcc cctctccagt gtctctcccg taaggtgccg ctcccaacag 300
caatgggtcg agatgtagag gaaacactct gtacgttatt tttccgccca ccctttagcg 360
cctgaggaga cagacagtgt agactttagg gtacaattgc ttcccctctg tcgcggcggg 420
gtggggagcg tgggaagggg acagccgcgc aaggggccag cctgctccag gtttgagcga 480
gagagggaga aggaggtcca cggagagaca agaatctccc tcctcccacg cccaaaagga 540
ataagctgcg gggcacaccg cccgcctcca gatcccccat tcacgttgag ccggggcgcg 600

<210> SEQ ID NO 181
<211> LENGTH: 600
<212> TYPE: DNA
<213> ORGANISM: Homo sapiens

<400> SEQUENCE: 181
tcattatccg attgattttc ctggtatcac atcacttaag tttaagtagc tcttatgtta 60
cttagtaatg actgcaaaac acgagttgtg atgcgggcaa tttggataca acaaaaagaa 120
gccattaagt ttgttcgtta gttaacaggt gaaagctctc aagttattaa ggataaaaat 180
gctagtatat atatatatgg tttggaacta tactgcggat tttggatcat atccgccatg 240
gataagggag gaatactata atcaggtttg ttttaaattc catgtctaat gacttcgtta 300
tctagatcac ctgtagagct gtttttattg taggagtttt ccttggtttt aatcttttga 360
tttgtttttc atgttaatac tgaaattttt aaaaattgca tattgtactt cctatatgaa 420
aattttacta tgtattttta tttttatttt ccttttcctt taggaagaat tagtttgttc 480
cctgacagag ttagagtaag ggcaaattac ttgtctctat aaacaactca gatgttttga 540
gccggtgttg taggggttat ctttttctgg ttttgcattt tattatagga catagtgctt 600

<210> SEQ ID NO 182
<211> LENGTH: 140
<212> TYPE: DNA
<213> ORGANISM: Homo sapiens

<400> SEQUENCE: 182
agaaagaaga aatccggtaa aaggatgtgt tattgagttt gcagttggtg tttgatcttg 60
cacagatttt ctcaggggcc ttaagaccgg tgccttggaa ctgccatctg ggcatagaca 120
gaagggagca tttatacgcc 140

<210> SEQ ID NO 183
<211> LENGTH: 900
<212> TYPE: DNA
<213> ORGANISM: Homo sapiens

<400> SEQUENCE: 183
cgaagatggc ggaggtgcag gtcctggtgc tcgatggtcg aggccatctc ctggtccgcc 60
tggcggccat cgtggctaaa caggtactgc tgggccggaa agtggtggtc gtacgctgcg 120
aaggcatcaa catttctggc aatttctaca gaaacaagtt gaagtacctg ggtttcctcc 180
gcaagcggat gaacacccac ctttcccgag gtccctacca cttccgggcc ccccagccgc 240
atcttctggc ggaccgtgcg aggtatgccg ccccacaaga ccaagcgagg ccaggcttct 300
ctggaccgcc tcaaggtgtt tgaccgcatc ccaccgccct acgacaagaa aaagcggatg 360
gtgttcctgc tccctcaagg ttgtgcgtct gaagcctaca agaaagtttg cctatctggg 420
gcgcctggct cacgaggttg gctggaagta ccaggcagtg acagccaccc tggaggagaa 480
gaggaaagag aaagccaaga tccactaccg gaagaagaaa cagctcatga ggctacggaa 540
acaggccgag aagaacatgg agaagaaaat tgacaaatac acagaggtcc tcaagaccca 600
cagactcctg gtctgagccc aataaagact gttaattcct catgcgtggc ctgcccttcc 660
tccatcgtcg ccctggaatg tacgggaccc aggggcagca gcagtccagg cgccacaggc 720
agcctcggac acaggaagct gggagcaagg aaagggtctt agtcactgcc tcccgaagtt 780
gcttgaaagc actcggagaa ctgtgcaggt gtcatttatc tatgaccaat aggaagagca 840
accagttact attagtgaaa gggagccaga agactgattg gagggcccta tcttgtgagc 900

<210> SEQ ID NO 184
<211> LENGTH: 1400
<212> TYPE: DNA
<213> ORGANISM: Homo sapiens

<400> SEQUENCE: 184
gcctgaagac catttcttcc tctcttaggg acctgctggt ctccagctga ttcggtccag 60
gaggaaaaac ctcccacttg ctcctctcgg gctccctgca aggagagagt agagacactc 120
ctgccaccca gttgcaagaa gtcgccactt ccccctccag ccgactgaaa gttcgggcga 180
cgtctgggcc gtcatttgaa ggcgtttcct tttctttaag aacaaaggtt ggagcccaag 240
ccttgcggcg cggtgcagga aagtacacgg cgtgtgttga gagaaaaaaa atacacacac 300
gcaatgaccc acgagaaagg gaaaggggaa aacaccaact acccgggcgc tgggcttttt 360
cgacttttcc tttaaaaaga aaaaagtttt tcaagctgta ggttccaaga acaggcagga 420 gggggagaa gggggggggg gttgcagaaa aggcgcctgg tcggttatga gtcacaagtg 480
agttataaaa gggtcgcacg ttcgcaggcg cgggcttcct gtgcgcggcc gagcccgggc 540
ccagcgccgc ctgcagcctc gggaagggag cggatagcgg agccccgagc cgcccgcaga 600
gcaagcgcgg ggaaccaagg agacgctcct ggcactgcag gtacgccgac ttcagtctcg 660
cgctcccgcc cgcctttcct ctcttgaacg tggcagggac gccgggggac ttcggtgcga 720
gggtcaccgc cgggttaact ggcgaggcaa ggcgggggca gcgcgcacgt ggccgtggag 780
cccggcctgg tcccgcgcgc gcctgcgggt gccccctggg gactcagtgg tgtcgcctcg 840
cccgggacca gagattgcgc tggatggatt cccgcgggca gaggcagggg gaaggagggg 900
tgttcgaaac ctaatacttg agcttctttg caaagtttcc ttggatggtt ggggacgtac 960
ctgtataatg gccctggacc agcttccctg ttggagtggc cagagaagtg tgtaaaacac 1020
actagagggg cagggtggaa aaagagactg ccttcaaaac ttgtatcttt tcgatttcat 1080
tttgaaaaat aactacaaat ctattttaat tttacaaagt tagactcata gcattttaga 1140
tatcaatgtc ttcatttaac agaagtgaag atggagcaaa cgctcaatca gcgtctgtat 1200
ttattcgctc ctgttgtgcc agggtgcgtt tttgccgagc ggttgccttt ctttactcac 1260 aaaacccccct tgatgtctgt cctccacgtt ttacgaggga gagccggatc ttttgaagtt 1320
tgtatcatct aaagcaggta tattgggatg actatggata gaatttaacc tgaaaacact 1380
gaagttgaca gctgacaaag 1400

<210> SEQ ID NO 185
<211> LENGTH: 200
<212> TYPE: DNA
<213> ORGANISM: Homo sapiens

<400> SEQUENCE: 185
cataacaaga gtcattctaa tgtgattata aaggacccga agctttgctt ttaaaattca 60
atacttaggt agaaagaaaa tgataacttt ttccctttga tttttattca ctatttttat 120
aacactagca gccctgagac accggattgg aaatatctat gcctcttgat gttacctggg 180
caccactgca tcacagtcct 200

<210> SEQ ID NO 186
<211> LENGTH: 400
<212> TYPE: DNA

<213> ORGANISM: Homo sapiens

<400> SEQUENCE: 186
aatagtaatt gccaacagtc aagatatgta ctaccaccaa attccgtgtt atttgtgatc 60
aaaagatata cacagatact tgaaaactga tttctacgtt gcatatggga aaaatacctc 120
atttttctca gctgtccatt atttttgaga tattatgtgc agtgatagta agaacaagca 180
gatttggaac acatcagcaa taattttttc aatcagagtc ctgccaaaat gaaagaattt 240
gacagtatcc ggcaccctgt actcatgctt ggcttctgta gaaactgtgg cttgcaaaag 300
ggcagctggg tactgtgttt tggtacctca ttctttaaac gtataatggg aatctggttg 360
gttcaggaaa acccttgcct acttattatt actctgtttt 400

<210> SEQ ID NO 187
<211> LENGTH: 250
<212> TYPE: DNA
<213> ORGANISM: Homo sapiens

<400> SEQUENCE: 187
ggcccatact taatgtattt ttaaacgttt taacatttac taatatagaa ccttctattg 60
cctatttcct tctggtttat tccctttcct tctgtcattg aagaaatggt tctagtggta 120
gaaatactcc acgattgaga agaatgtggg aagaaaggag ggctggtggg taagaattgc 180
tcatgatgtc tccctctgaa ttctgtgctc tcacaatgac actccaatgt gtggtttgac 240
gcctggaaga 250

<210> SEQ ID NO 188
<211> LENGTH: 250
<212> TYPE: DNA
<213> ORGANISM: Homo sapiens

<400> SEQUENCE: 188
tgcttcaacc ggaaatgtgg ttgaattacc cttacagtga acctgatcag tggtaacagg 60
agatgctaga acaggaaaag acaagtttcc cctttcctcc ctatcccatc aattactttg 120
aggtgtattt tttctttgca acccctccag agaagtcggc aatgtttaac gagcatgcct 180
gccaagtggc ttgccttata cctcattatg aagtgatact cagggccact aacacatcgc 240
acagcattgc 250

<210> SEQ ID NO 189
<211> LENGTH: 500
<212> TYPE: DNA
<213> ORGANISM: Homo sapiens

<400> SEQUENCE: 189
tatgattccc tcgatttccc tcaatcttaa ccattgtgga tcacagcagg agggccagaa 60
agtgagcttc agcctggcac cgggacctca gcctctccct taaactttcc ctaatcctcg 120
gagctagtgt tactcaagtg actccacagt gttgcccgat cccttcagac atggccttga 180
tgatctccaa aactcatgct acctttgcca gcctaaagca tccactctgt gccccaaaac 240
gtgaatgtca aataccettc aaggcagaag gctatttcta tttttgtttg tttctgttta 300
aggcaacaat caccaacatt tggtacacat gagccatcct gtgaaacatc aaggcgcttc 360
gttggcagca agtcaacttc ggtttcagaa gaaagctgca ctatttcctg aggttagagg 420
tttaaaccaa aacaagacaa ccacatttta accccaaatc tgccgactga gggtaaccat 480
gatccttcct tcacagcacc 500

<210> SEQ ID NO 190
<211> LENGTH: 150
<212> TYPE: DNA
<213> ORGANISM: Homo sapiens

<400> SEQUENCE: 190
tactaaatca acccaaaccc gagaacccgg tcatggagaa ataaatgata gtaatctatg 60
ctgttcatct gttccatcac tcactcactc tcttgctgaa caagaaaggg ccacccatgt 120
agcaaaccac atgtaaagag ccgggaagac 150

<210> SEQ ID NO 191
<211> LENGTH: 300
<212> TYPE: DNA
<213> ORGANISM: Homo sapiens

<400> SEQUENCE: 191
tattattttg ttcaaagtag acgggtatac taacatctgt gggcaagttt accacacgcc 60
acttaaaaca ggctaacagg gtcatatgcc aaaacgttca ggtttgcatt tttgaaaagc 120
tcagagatct gacagatgtg ttccggccgc gatttaacat gcggctccag tgagaaggaa 180
gcagatatga caaatggttc acttatttca gaactaaaac cccagaggag cagcctgagc 240
caaaaaggga agtgatcaat ggaaaagacg gtcgaatctg ctcacaggca aggcaagggg 300

<210> SEQ ID NO 192
<211> LENGTH: 300
<212> TYPE: DNA
<213> ORGANISM: Homo sapiens

<400> SEQUENCE: 192
aagacctgga gtttccatta caccgaattg gcacttaata actgttgtcg gagcatttct 60
taagccacat tttcgtaaag tggctttaaa attgctctgc cagtaggcag gttgctaaga 120
tggtcagaga caaacttctg aacgactctt gtaaaatata cagaaatatt ttcagaactt 180
ttatcagtaa aattacaaaa cgtgttgcaa ggaaggtgct tgtgataaca ctgtccccag 240
aaccttagtg aagttaccaa ctggtggaaa attttctctt gcactcggct taaaaatcat 300

<210> SEQ ID NO 193
<211> LENGTH: 400
<212> TYPE: DNA
<213> ORGANISM: Homo sapiens

<400> SEQUENCE: 193
gcaggggtga ctggtcctct ctctctgcac ctcgcaggat ttctctggaa gatctgagcc 60
cgagcgtcgt gctgcacatg accgagaagc tgggttacaa gaacagcgac gtgatcaaca 120
ctgtgctctc caaccgcgcc tgccacatcc tggccatcta cttcctctta aacaagaaac 180
tggagcgcta tttgtcaggg gtaagtgcga ccctagaggc gatcgtctct gctgtctgtg 240
gaaaaaagag ctcctacacc caaagtgctt ctcagttgct gacacttgat ccaagctgct 300
aatttaatct aatgtgaggc tgagttttct gaatgtggga taaagtcgta gctaaacctg 360
cttctcaggg agtgcctttt atctgcaatg tttttcaaat 400

<210> SEQ ID NO 194
<211> LENGTH: 1100
<212> TYPE: DNA
<213> ORGANISM: Homo sapiens

<400> SEQUENCE: 194
aagtaacggg atcaaattaa ttattatttt ggtggccgcc tctcttctcc accccaagcc 60
aggcaagact caccctcggc cctgcccgcc ccagcatttc aaatggaata cctaggtggc 120
ccagggggac ccctgacccc tatatcctgt ttctttctgc ctgctttgct acttttctcc 180
ttgataaaag gagagagtga gagataatta acaaaaaaca tggccccagg acaatgaaac 240
aactggcctt ggccggccag aaatgtatcc tggttttcta ggtgaacttt ctcccatcaa 300
tctttccttt aacctctctg ttagtggaag caataggaac acccctcccc tcccctgagc 360
aaatgctttc ttttgactgg aaacaaaaca ggggctcggc gaaggctgag gtgaaatctg 420
ggtggcatgg gcgccgcaca atggggccgc tgttccccgg cccgggcttg tgttttacaa 480
caggggaggg gcgggcgtga atggtctgat gattggaaca atccccccga ttcaggccta 540
caaacgcatc ttctgttcca caccgagggg acagaaagga gaaaagtgac aaagaacgcg 600
gggcgggggg aattaaaaca aaatgcgctc gactaaaaaa tctctcatat cctgcatatt 660
ccagaaagcg gctctatgga gagagccttc aggaggcctc agccatatct gaatggcttt 720
ctctggcctc tgatttattg atgaagctga agcgacttgc tggagaaagg cctggagcct 780
tctttgtctc cgagatgaag tacaataggc cacagggcgg agatctcttg tgatgctctc 840
gggtcctgcc tttctcttgc cctctcctcc ctgcaaatac cagcagcggt gacaaacgat 900
tggtggtgtg cctgggagag ccggtgacaa gactgggcca cttgaggtct ccttaagagg 960
gtattatggc cagggcgacg tttgtgctgt gaagatggca cactccattt tgtcaatggc 1020
tctcatcggc ccagataatc gccccctgcc tgcctgtcag gggcgcagcc ggccgattca 1080
tggcgccctc ggagaaagta 1100

<210> SEQ ID NO 195
<211> LENGTH: 10000
<212> TYPE: DNA
<213> ORGANISM: Homo sapiens

<400> SEQUENCE: 195
gtctttcccg ccccttgtc taaactcaaa accgagtccg ggcgcgcctt gcagggcgcc 60
cgagctctgc agcggcgttg cgggctgaac ccatccggca caaactgcgg gccactggcc 120
cctcacacct gggagtttgc ggcgctggcc tgcagcccgg ggcccacgtg gcggaagctt 180
tcccgggcgc gcgctgcgca gccccgcggg gccggggaga caccgctcgg gagtcctccg 240
ctcggctgca gaatctttat cagctgcact ttaccgcagc cctggctagg acgctaggcg 300
gtggagcgcc ctatccaggt gcgccgccgc accatggatc accgcgcccg gtcccgcagt 360
cccgccatgg cctggggagg cccgaagccc ggggacagtg gccggcccat ctccggctcc 420
gcggaccccc ggctcaggcg ggagggcagg cgggtccctg caggccccca gggagcccgg 480
gagcctctct ctggcgtcat tcagtcccgg ggcaacctga agcgcggtag atattggaga 540
gggggcgtct gttgggggga cctggcgtca ttactgatgg ctagcaggga ggagggaacg 600
ggttgtcacc tcggcctcat aaggccgtga gtgagtagtc cagggcctct tcaggcattt 660
ttgaaactgg attaactagg ggggaaattg tagcactgaa gccaccgtga ctgtcttttg 720
cgctgtgtgg aaactccggt aaaactcttt gggcaacagt cttatcacca gctcttcaac 780
gtgtgcagcc cttctggtcc tgtccctgtt ctgggcccca ggaatgcaaa gcaggtccag 840
gcactgtgaa gaccctggcg gtggaggaag aggcttcccg gctgtggagg aagccagacc 900
cttacaacac aagacgagaa ccagacctgc gtgggggagc tctggatgct acaggggctc 960

```
aaggaggggt ggaggggcct tcccaggcca acccctgaac ggcttggaca agatgctcag   1020
atggacggga ggaacggcgt gtgggatggg ggagctggag gcgggtgggt ggggggggga   1080
ggatggggaa agcgctggcc cacccagtgt gggaggggta gaggaaaagc ccgcaggggc   1140
caggttggga ccccgtaggc cgggttagag ggcttggact tgatcctgac aggcgacagg   1200
gagacatatt gctacttatt atgtgcacag tggccagatc tctaaagaaa acaccatccc   1260
ccaccccccac cccccatata gtaaaccagg tggtccgccc agtgctccca gggaggtgat   1320
gggaaatccc actccatacc ctgcggtgag gggttccatg ccctccacgt gtgcaactac   1380
tccgggccca gggaaacact gggccccatc cggtaacccc cggcccagtc gggtttccca   1440
gttcacatta taaccaaacg gtcttgccag ctagacagac agacacccct gacctgttta   1500
ccctgatcct ctgctctcag gattaatcac aacttgtcga agggggtggc ttccagtggg   1560
gtggaccgct ctgtcaatgc cagcgtgtgt ctagcatctc ctggggtggg ggtgtgggga   1620
agggaggtgt aggatgaagc cctagaagcc tcaggcaatt gtgatccggt gggctggata   1680
ctgaagccca cccctgcctt gacctcaatt ttcagtatct tcatctgtaa aatgggaaca   1740
acctgccttc ctcctagccc taaaggggct gctgtcaaga ttggctgaga tagctgtttg   1800
caagctgagc tcaatgaaag ttcattgtgt ccccctcagt cctatcccaa tatcgtctca   1860
ctgcaaaggt ggggggcagc ttaacttcaa gggcacttca aggatagcca ggtggctgtc   1920
agcccagctt tccaggatgg gagcaggatc ttgacagaag ggttgactgg gaggggcagt   1980
tgctggtttg ggcttcgtta ggttgcattt ttgtttgttg tcctttcatt tccctggggc   2040
agcacccctt cctgcaagct ccaggccttc ctctggaatg ctcctagagc ccaacctctg   2100
ctggtgcctg agcttaagcc aggccagcta aggggatcct ggattcacac ggcctcacag   2160
tcactcagat tgttagcaga agacaaaaat tacaagggga gggcgtcatg tgattcttac   2220
acaccctcca aatccagcag acaccttgga agccacaggt agcttcaaga aacccatttt   2280
acggatgaga acctgagatg gagaaaggac aactggagat ctctgagtct ctgagcccac   2340
actccctacc tccctgcacc tccaggcact ctgctggcag gatcttgggc aaatgcccac   2400
agctctctga gagtcagttt tcctgtctgt aaaatgggag tcataccttc ctcctatggc   2460
cggtgagaga ctaaattaaa ctatgtctgt caagacacct gaaactcctg gcacaattta   2520
ggttgccttc aagtggtcac agttgtcatt aggtggaagt caacacccca atcattgtaa   2580
aggtgcccat ataccccaag atccagatta cagctctcac agtttattat atacagcgaa   2640
aaaacacata acacaccttt gcccacattt acatgtattt tacggaccat gtttcacatc   2700
agtccgcatg cacatctgca cgtgtgtgca ttcggcagta tttaccaagc acctgccaag   2760
tgccagggcc tgtcctccgc acccggcgtg aactgtcctg gaccagtccc gggagccgcg   2820
gttctgacca gccgtgctga ccctggacga ctccatgagc tgttttgtga gaaagacacg   2880
ccatttgttt gcagagttct gacttctgag ggtcatgta gcacatgttt ggtagccaaa   2940
cgctgtcatt cacgaccagg agcgatggct gcaatgcctt tttctttgct ttgctttccg   3000
gtgccgggag ccttgcctcc cgccgccacc cctggtcagc tctgcgcaag aacgtcgttc   3060
tgtttggcag ccaggccgag acgcagcctg aatgtgagca ggaactcgga gaagggaagg   3120
gagagaatca gaaagaaggc ccgggaggga cccgggaagc agtgggaggt ctgcgccctg   3180
gagccccgcg agagcccgcc ggtttggcac gggctcctcc cgggccgccc ggcggtccaa   3240
caaaggccgg ccccgacacg cacccggtct tttgtgggag agaaacacaa agaagaggga   3300
```

```
aaaacacgga ggaggccaac agcaccagga cgcgggggcc aaccaggaac tcccggagcc   3360
ggggcccatt agcctctgca aatgagcact ccattcccca ggaaggggcc ccagctgcgc   3420
gcgctggtgg gaaccgcagt gcctgggacc cgcccaggtc gcccaccccg ggcgccgggc   3480
gcaggacccg gacaagtcct ggggacgcct ccaggacgca ccagggcaag cttgggcacc   3540
gggatctaat ttctagttat tcctgggacg gggtggggag gcataggaga cacaccgaga   3600
ggtactcagc atccgattgg caccagggcc aagggagccc aggggcgaca cagacctccc   3660
cgacctccca agctactccg gcgacgggag gatgttgagg gaagcctgcc aggtgaagaa   3720
ggggccagca gcagcacaga gcttccgact ttgccttcca ggctctagac tcgcgccatg   3780
ccaagacggg cccctcgact ttcacccctg actcccaact ccagccactg gaccgagcgc   3840
gcaaagaacc tgagaccgct tgctctcacc gccgcaagtc ggtcgcagga cagacaccag   3900
tgggcagcaa caaaaaaaga aaccgggttc cgggacacgt gccggcggct ggactaacct   3960
cagcggctgc aaccaaggag cgcgcacgtt gcgcctgctg gtgtttatta gctacactgg   4020
caggcgcaca actccgcgcc ccgactggtg gccccacagc gcgcaccaca catggcctcg   4080
ctgctgttgg cggggtaggc ccgaaggagg catctacaaa tgcccgagcc ctttctgatc   4140
cccacccccc cgctccctgc gtcgtccgag tgacagattc tactaattga acggttatgg   4200
gtcatccttg taaccgttgg acgacataac accacgcttc agttcttcat gttttaaata   4260
catatttaac ggatggctgc agagccagct gggaaacacg cggattgaaa aataatgctc   4320
cagaaggcac gagactgggg cgaaggcgag agcgggctgg gcttctagcg gagaccgcag   4380
agggagacat atctcagaac taggggcaat aacgtgggtt tctctttgta tttgtttatt   4440
ttgtaacttt gctacttgaa gaccaattat ttactatgct aatttgtttg cttgttttta   4500
aaaccgtact tgcacagtaa aagttcccca acaacggaag taacccgacg ttcctcacac   4560
tccctaggag actgtgtgcg tgtgtgcccg cgcgtgcgct cacagtgtca agtgctagca   4620
tccgagatct gcagaaacaa atgtctgaat tcgaaatgta tgggtgtgag aaattcagct   4680
cggggaagag attagggact gggggagaca ggtggctgcc tgtactataa ggaaccgcca   4740
acgccagcat ctgtagtcca agcagggctg ctctgtaaag gcttagcaat tttttctgta   4800
ggcttgctgc acacggtctc tggcttttcc catctgtaaa atgggtgaat gcatccgtac   4860
ctcagctacc tccgtgaggt gcttctccag ttcgggctta attcctcatc gtcaagagtt   4920
ttcaggtttc agagccagcc tgcaatcggt aaaacatgtc ccaacgcggt cgcgagtggt   4980
tccatctcgc tgtctggccc acagcgtgga gaagccttgc ccaggcctga aacttctctt   5040
tgcagttcca gaaagcaggc gactgggacg gaaggctctt tgctaacctt ttacagcgga   5100
gccctgcttg gactacagat gccagcgttg cccctgcccc aaggcgtgtg gtgatcacaa   5160
agacgacact gaaaatactt actatcatcc ggctcccctg ctaataaatg gaggggtgtt   5220
taactacagg cacgaccctg cccttgtgct agcgcggtta ccgtgcggaa ataactcgtc   5280
cctgtaccca caccatcctc aacctaaagg agagttgtga attctttcaa aacactcttc   5340
tggagtccgt cccctccctc cttgcccgcc ctctacccct caagtccctg cccccagctg   5400
ggggcgctac cggctgccgt cggagctgca gccacggcca tctcctagac gcgcgagtag   5460
agcaccaaga tagtggggac tttgtgcctg ggcatcgttt acatttgggg cgccaaatgc   5520
ccacgtgttg atgaaaccag tgagatggga acaggcggcg ggaaaccaga cagaggaaga   5580
gctagggagg agaccccagc cccggatcct gggtcgccag ggttttccgc gcgcatccca   5640
aaaggtgcgg ctgcgtgggg catcaggtta gtttgttaga ctctgcagag tctccaaacc   5700
```

-continued

```
atcccatccc ccaacctgac tctgtggtgg ccgtattttt tacagaaatt tgaccacgtt   5760
ccctttctcc cttggtccca agcgcgctca gccctccctc catccccctt gagccgccct   5820
tctcctcccc ctcgcctcct cgggtccctc ctccagtccc tccccaagaa tctcccggcc   5880
acgggcgccc attggttgtg cgcagggagg aggcgtgtgc ccggcctggc gagtttcatt   5940
gagcggaatt agcccggatg acatcagctt cccagccccc cggcgggccc agctcattgg   6000
cgaggcagcc cctccaggac acgcacattg ttccccgccc ccgcccccgc caccgctgcc   6060
gccgtcgccg ctgccaccgg gctataaaaa ccggccgagc ccctaaaggt gcggatgctt   6120
attatagatc gacgcgacac cagcgcccgg tgccaggttc tcccctgagg cttttcggag   6180
cgagctcctc aaatcgcatc cagagtaagt gtccccgccc cacagcagcc gcagcctaga   6240
tcccagggac agactctcct caactcggct gtgacccaga atgctccgat acagggggtc   6300
tggatcccta ctctgcgggc catttctcca gagcgacttt gctcttctgt cctccccaca   6360
ctcaccgctg catctccctc accaaaagcg agaagtcgga gcgacaacag ctctttctgc   6420
ccaagcccca gtcagctggt gagctccccg tggtctccag atgcagcaca tggactctgg   6480
gccccgcgcc ggctctgggt gcatgtgcgt gtgcgtgtgt ttgctgcgtg gtgtcgatgg   6540
agataaggtg gatccgtttg aggaaccaaa tcattagttc tctatctaga tctccattct   6600
ccccaaagaa aggccctcac ttcccactcg tttattccag cccgggggct cagttttccc   6660
acacctaact gaaagcccga agcctctaga atgccacccg caccccgagg gtcaccaacg   6720
ctccctgaaa taacctgttg catgagagca gaggggagat agagagagct taattatagg   6780
tacccgcgtg cagctaaaag gagggccaga gatagtagcg agggggacga ggagccacgg   6840
gccacctgtg ccgggacccc gcgctgtggt actgcggtgc aggcgggagc agcttttctg   6900
tctctcactg actcactctc tctctctctc cctctctctc tctctcattc tctctctttt   6960
ctcctcctct cctggaagtt ttcgggtccg agggaaggag gaccctgcga aagctgcgac   7020
gactatcttc ccctggggcc atggactcgg acgccagcct ggtgtccagc cgcccgtcgt   7080
cgccagagcc cgatgacctt tttctgccgg cccggagtaa gggcagcagc ggcagcgcct   7140
tcactggggg caccgtgtcc tcgtccaccc cgagtgactg cccgccggag ctgagcgccg   7200
agctgcgcgg cgctatgggc tctgcgggcg cgcatcctgg ggacaagcta ggaggcagtg   7260
gcttcaagtc atcctcgtcc agcacctcgt cgtctacgtc gtcggcggct gcgtcgtcca   7320
ccaagaagga caagaagcaa atgacagagc cggagctgca gcagctgcgt ctcaagatca   7380
acagccgcga gcgcaagcgc atgcacgacc tcaacatcgc catggatggc ctccgcgagg   7440
tcatgccgta cgcacacggc ccttcggtgc gcaagctttc caagatcgcc acgctgctgc   7500
tggcgcgcaa ctacatcctc atgctcacca actcgctgga ggagatgaag cgactggtga   7560
gcgagatcta cgggggccac cacgctggct tccacccgtc ggcctgcggc ggcctggcgc   7620
actccgcgcc cctgcccgcc gccaccgcgc acccggcagc agcagcgcac gccgcacatc   7680
accccgcggt gcaccacccc atcctgccgc ccgccgccgc agcggctgct gccgccgctg   7740
cagccgcggc tgtgtccagc gcctctctgc ccggatccgg gctgccgtcg gtcggctcca   7800
tccgtccacc gcacggccta ctcaagtctc cgtctgctgc cgcggccgcc ccgctggggg   7860
gcgggggcgg cggcagtggg gcgagcgggg gcttccagca ctggggcggc atgccctgcc   7920
cctgcagcat gtgccaggtg ccgccgccgc accaccacgt gtcggctatg ggcgccggca   7980
gcctgccgcg cctcacctcc gacgccaagt gagccgactg gcgccggcgc gttctggcga   8040
```

-continued

```
caggggagcc aggggccgcg gggaagcgag gactggcctg cgctgggctc gggagctctg   8100
tcgcgaggag gggcgcagga ccatggactg ggggtggggc atggtgggga ttccagcatc   8160
tgcgaaccca agcaatgggg gcgcccacag agcagtgggg agtgagggga tgttctctcc   8220
gggacctgat cgagcgctgt ctggctttaa cctgagctgg tccagtagac atcgttttat   8280
gaaaaggtac cgctgtgtgc attcctcact agaactcatc cgacccccga cccccacctc   8340
cgggaaaaga ttctaaaaac ttctttccct gagagcgtgg cctgacttgc agactcggct   8400
tgggcagcac ttcggggggg gagggggtgt tatgggaggg ggacacattg gggccttgct   8460
cctcttcctc ctttcttggc gggtgggaga ctccgggtag ccgcactgca gaagcaacag   8520
cccgaccgcg ccctccaggg tcgtccctgg cccaaggcca ggggccacaa gttagttgga   8580
agccggcgtt cggtatcaga agcgctgatg gtcatatcca atctcaatat ctgggtcaat   8640
ccacaccctc ttagaactgt ggccgttcct ccctgtctct cgttgatttg ggagaatatg   8700
gttttctaat aaatctgtgg atgttccttc ttcaacagta tgagcaagtt tatagacatt   8760
cagagtagaa ccacttgtgg attggaataa cccaaaactg ccgatttcag ggcgggtgc    8820
attgtagtta ttattttaaa atagaaacta ccccaccgac tcatctttcc ttctctaagc   8880
acaaagtgat ttggttattt tggtacctga gaacgtaaca gaattaaaag gcagttgctg   8940
tggaaacagt ttgggttatt tgggggttct gttggctttt taaaattttc ttttttggat   9000
gtgtaaattt atcaatgatg aggtaagtgc gcaatgctaa gctgtttgct cacgtgactg   9060
ccagccccat cggagtctaa gccggctttc ctctattttg gtttattttt gccacgttta   9120
acacaaatgg taaactcctc cacgtgcttc ctgcgttccg tgcaagccgc ctcggcgctg   9180
cctgcgttgc aaactgggct ttgtagcgtc tgccgtgtaa caccccttcct ctgatcgcac   9240
cgcccctcgc agagagtgta tcatctgttt tatttttgta aaaacaaagt gctaaataat   9300
atttattact tgtttggttg caaaaacgga ataaatgact gagtgttgag attttaaata   9360
aaatttaaag taaagtcggg ggatttccat ccgtgtgcca ccccgaaaag gggttcagga   9420
cgcgatacct tgggaccgga tttggggatc gttcccccag tttggcacta gagacacaca   9480
tgcattatct ttcaaacatg ttccgggcaa atcctccggg tctttttcac aacttgcttg   9540
tccttatttt tattttctga cgcctaaccc ggaactgcct ttctcttcag ttgagtattg   9600
agctccttta taagcagaca tttccttccc ggagcatcgg actttgggac ttgcagggtg   9660
agggctgcgc ctttggctgg gggtctgggc tctcaggagt cctctactgc tcgattttta   9720
gatttttatt tcctttctgc tcagaggcgg tctcccgtca ccaccttccc cctgcgggtt   9780
tccttggctt cagctgcgga cctggattct gcggagccgt agcgttccca gcaaagcgct   9840
tggggagtgc ttggtgcaga atctactaac ccttccattc cttttcagcc atctccacta   9900
ccctccccca gcggccaccc ccgccttgag ctgcaaagga tcaggtgctc cgcacctctg   9960
gaggagcact ggcagcgctt tggcctctgt gctctttcct                        10000
```

<210> SEQ ID NO 196
<211> LENGTH: 500
<212> TYPE: DNA
<213> ORGANISM: Homo sapiens

<400> SEQUENCE: 196

```
ccggcacggc ccgcatccgc caggattgaa gcagctggct tggacgcgcg cagttttcct     60
ttggcgacat tgcagcgtcg gtgcggccac aatccgtcca ctggttgtgg gaacggttgg    120
aggtccccca agaaggagac acgcagagct ctccagaacc gcctacatgc gcatggggcc    180
```

caaacagcct cccaaggagc acccaggtcc atgcacccga gcccaaaatc acagacccgc 240
tacgggcttt tgcacatcag ctccaaacac ctgagtccac gtgcacaggc tctcgcacag 300
gggactcacg cacctgagtt cgcgctcaca gatccacgca caccggtgct tgcacacgca 360
agggcctaga actgcaaagc agcggcctct ctggaccgcc tccctccggc cctcctgagc 420
cctactgagc cctgctgagt cctggaggcc ctgtgacccg gtgtccttgg accgcaagca 480
tcctggttta ccatccctac 500

<210> SEQ ID NO 197
<211> LENGTH: 1000
<212> TYPE: DNA
<213> ORGANISM: Homo sapiens

<400> SEQUENCE: 197
ggacgcggcc cgctctagag gcaagttctg ggcaagggaa accttttcgc ctggtctcca 60
atgcatttcc ccgagatccc acccagggct cctggggcca cccccacgtg catccccccgg 120 aacccccgag atgcgggagg gagcacgagg gtgtggcggc tccaaaagta ggcttttgac 180
tccaggggaa atagcagact cgggtgattt gcccctcgga aaggtccagg gaggctcctc 240
tgggtctcgg gccgcttgcc taaaacccta aaccccgcga cgggggctgc gagtcggact 300
cgggctgcgg tctcccagga gggagtcaag ttcctttatc gagtaaggaa agttggtccc 360
agccttgcat gcaccgagtt tagccgtcag aggcagcgtc gtgggagctg ctcagctagg 420
agtttcaacc gataaacccc gagtttgaag cccgacaaaa agctgatagc aatcacagct 480
tttgctcctt gactcgatgg gatcgcggga catttgggtt tccccggagc ggcgcaggct 540
gttaactgcg cagcgcggtg ccctcttgaa aagaagaaac agaccaacct ctgcccttcc 600
ttactgagga tctaaaatga atggaaagag gcaggggctc cggggaaagg gaacccctta 660
gtcggccggg cattttacgg agcctgcact ttcaaggaca gccacagcgt gtacgaagtg 720
aggaattcct ttccaccaag agcgctcatt ttagcgacaa tacagaattc cccttccttt 780
gcctaaggga gaaaggaaag gaaacattac caggttcatt cccagtgttt ccctggagta 840
atgctagaat ttacttttgt cataatgcaa aattaaaaaa aaaaaaaata caacgaagcg 900
atacgttggg cggatgctac gtgacagatt tttccaaatt ttgttgcggg gagagggagg 960
gaggagaatt gaaaacggct cacaacagga atgaaatgta 1000

<210> SEQ ID NO 198
<211> LENGTH: 100
<212> TYPE: DNA
<213> ORGANISM: Homo sapiens

<400> SEQUENCE: 198
tttttaatgc tcagagaagt tcgtattact gattcgggaa cactgagttt ttcagctcct 60
gtaaaactat tttcaggttt attttcaagt acattcttta 100

<210> SEQ ID NO 199
<211> LENGTH: 400
<212> TYPE: DNA
<213> ORGANISM: Homo sapiens

<400> SEQUENCE: 199
caccctagag gcaaggacgg ggtctgtgtc aagaggcttc ccagagaagt gaaaactctg 60
caggtgcagc cgctgggaga gcatcaagaa gggcagggtg gaggggcagg gggcgaaggg 120

```
agggggtgaa gcccgcaccc tacccccaca tgaaactgat tccactaccc catctctgca    180

agcgtccaga ggcagagagg ccaacatttc ggggacagct tggaggcggg agatttaggc    240

agggctcctt aaacttttat gtgcatgaaa atcaggccaa tcacggggct cttgagcaaa    300

tggggacgat gattcagcag gtctgggctg aggcctcaga ttctgcactt ctaacaagtt    360

cccaggtggt agtgatgctg ccagtccaaa gaccacactg                          400
```

<210> SEQ ID NO 200
<211> LENGTH: 5000
<212> TYPE: DNA
<213> ORGANISM: Homo sapiens

<400> SEQUENCE: 200

```
tgcttcagtg gggtaaactt gaaccgctga gaagacaagc agggagtcgg tctcgctgag     60

atttttacct gtggttctag gaacgcagag gcatgtgagt gttcaggctt tgcatagacc    120

actaagccac ttctaagaac aaggctacct gagccatttt gcaaaaatat gtacgtgccg    180

aggcttttcc tccccacacc tacctcaact ctttctgccg acacactgca cttttcaagg    240

gaacccaagt ttgggttcgg caagaattgt acgttgcaca ccgtgtgtga taattccagg    300

gaatttcaat cgcatcttgt cttccttcct aagcaaattc ggtgggaacc tggtgtggtg    360

tgatagaaaa agccccgagt tctctgtggt agaccacatc aatttcatgt gccagtctct    420

cagactccgg cttgcctctc tcaaggaagg gaacaatggt ttgcttggct tcactcctct    480

ctttcccccc aatttccaca tgggtatctg gctaaaaatg agttacaggt ttccttctgt    540

gagaattgca tggactgata aagtaccatc ccaggaagaa aacaaagatg ctgtcttccc    600

tttcggctca cagttgccgt tggggaggga acacacgctg taaattatag gcagccagaa    660

gtgaccgcat tgaccactgc gagtggccca gctatggcaa caggctgaga actctggggg    720

agagccattt gttggcaggg atggtgattc ttctagcatc aagctctaag atgatgacca    780

aacggtatca aaagaaatga tattttgcta cctctccggc ttgggtgaat gatgtggaca    840

gttaacctgg acaatttaaa cctttatgtt gatggatcac ttggatgaaa ttaaccagga    900

aattgccaag atttcacttg gccctctgac atcaaatctc aatattatat taccaaatta    960

gagattctaa agaaccctga gttcctttca ctgaaaggaa ggagtggaaa aacctttcca   1020

gatgatccct tttgagtctt ggtgcgagct caggccctcc ctacactgcc tccgtgaaag   1080

ctaaccgacc cttgttccta acctagcgca ggtcagctga gtgtccatcg ggcacaggag   1140

ccctgggctt gtccgggaga tagccagact cctgctattt cctgatgtct gcatagctca   1200

gcgtgtccct caccatcttt gccgttggcc agtaaggaga gccccagggg ccagcactgc   1260

acactgaaac ccaacctatt gctcaatgga atgcttaaaa atttcctgaa tctgccttcc   1320

tgagttgata aaataggaaa caatacacgt tctgaggggg tactgaaagc agagtaaagc   1380

caggaagatc tttttttct gttattctat acaaatattg cttcctctgc ttgttagcag   1440

cccagaggaa atgcagccag ggagccgttt gcagcttttc accagtggcc ggtgtctctg   1500

tgttaccaac caaacgacgc tgcaagacta gtgactaacg cacgtctgca tgattcaact   1560

tcactaaaat tccctctgct gccagtaaag aagcacttga aaactcttta atttgaaact   1620

tgagcttggt taatgacttg ttttcttctc tttctcttta acttctctct tgccatctcc   1680

aacacacaca cacacacaca cacacacaca cacacacaca cacacacact ctctctctct   1740

ctctctctct ctctctctct ctctcatcaa gttttttaat ttcagggacc cggaaacata   1800

cagccccgtg cattcacaat agcatttgct gtgataaagt ggccggcaag ccctctgcat   1860
```

```
tcccctgctc acttagctgt atgaataaat aatgagtcac agatacaatt tgggtgctca   1920
agagagtttg tagccagaaa attaattatt ctcccatccc agcccactcc atctcagctt   1980
tgccaaacca tcaagataca ctttgcaggc actggtcaga gtgcgtgccc cgacgcacac   2040
ggcaatgcct ttgagacatt ttatgttatt atttttgttt gtttaagcac agccctcttt   2100
taccacgaaa gatacacaag acgcacatgc acacacatac tcacacactc acagctcaac   2160
cacagctttg tccatttcaa gaggctggtt tcaaaaatgg agacaggttt tccaccctgg   2220
ctgttcctat tcataagcct gtaatctaac gacttaagct gcgagaatgc ttaactcggg   2280
aaacttctct attgcccttt tccagagaga cctcggtatg ccacaatttg cttcctttct   2340
ctcttgaaag atgctggttg tctctttgca ttgaggctac aaggaaaaac acagcacagc   2400
cccatgctga tgattttaac ctaaccaagt ctgtcagtct cctgtactct ctgccttata   2460
gagacagctg ccttgccact ttggccctga agtccccagg ctggtgcaag gctatctgag   2520
agcctccgcc tcctgcccca cactggcacc agccctcctg gctggctctg tgcatgtgcc   2580
tgctaagccc cagggcaggc tgcattctgg gccacacagc atgccgagtt aaggataact   2640
cagacacagg cattccgggc aagggacagc aaaataaaac ccagggagct tcgtgcaagc   2700
ttcataatct ctaagccttt aaacaagacc agcacaactt actcgcactt gacaaagttc   2760
tcacgcaccg actgaacact ccaacagcat aactaagtat ttattaaaac atttctgaag   2820
agcttccatc tgattagtaa gtaatccaat agacttgtaa tcatatgcct cagtttgaat   2880
tcctctcaca aacaagacag ggaactggca ggcaccgagg catctctgca ccgaggtgaa   2940
acaagctgcc atttcattac aggcaaagct gagcaaaagt agatattaca agaccagcat   3000
gtactcacct ctcatgaagc actgtgggta cgaaggaaat gactcaaata tgctgtctga   3060
agccatcgct tcctcctgaa aatgcaccct cttctgaagg cgggggactc aatgatttct   3120
tttaccttcg gagcgaaaac caagacaggt cactgtttca gcctcacccc tctagcccta   3180
catctctctt tcttctcccc tctgctggat acctctggga ctccccaagc cctattaaaa   3240
aatgcacctt tgtaaaaaca aatattcaaa ttgttaaaga ttaaaaaaaa aaaaaaagcc   3300
agcgccgcct tggctgtggg ttggtgatgc tcaccacgct gcgaaaccct gtggtttgca   3360
ttcagtgtga ttcgtcctgc ctgctgacca ctatgctggg ttcagacttc tgacactgcc   3420
aggctaccca acttgtggtt ctgtggttgt ttatgaggcc caaagaagtt ttcacacaac   3480
ccaaattaca aatttaactg ttccccttc cacagcccat ctcaattggt tcttgccaat   3540
catgtgactt aagtgatgtc aattttttt tttcttttct gagcaatgcc cttccttccc   3600
tccacctgcc ctcccccagg ctgtgcaaga aaatagccga gtagactttg caagaggggg   3660
ggatgtagaa aaaagtgact cagtcactta ttatatctca atggtctttg ctgatttagt   3720
acaactcggc tcctgttgtt atttgtggtt tttggaacta ctgattattt tgataaagat   3780
ttcattgctg cttattcaat agtaattcaa cgctggcatc aagccgctgc tccgacagga   3840
tgtggatccc atcatttaaa atgctaggca tcagctccgg gagagttaag tccttggtaa   3900
cgtctatcat ggcataagtg aaactataaa agggaaaaat aaataaaaag aaatgttttg   3960
gtgagagtct gaccccctaca acgggctggc aactcacagg tattttaaag cctgggaaag   4020
ggaaagaatt ttacttttga aataaaagga ctgttttaat gaaaccaaaa ttatgtggtt   4080
ttattccccc taaatggaca actttagtat gtatctcttt cagtaaagag ataaaatcat   4140
agtacagtct taacacacac acacacacac acacacacac acacacacac acaaattagg   4200
```

-continued

```
aagctaaagg aaaacaaagc agagagaatt tctgtatttg ggacaaagca gtggttactc   4260

tgcagatgtt tatttgtatt gtcacttggg aaagctccct gtattgcctt tctctagttc   4320

aattcaaatc aataggctaa tttacacctg taggtaaaac tacactttga gcacatgagg   4380

atgccacaat agaaggggaa ccaggaggag acacttctcc tggggctgac taatgaatat   4440

tatatagcgc gtcctctacc ttagaaagac atgcctgttt gaagatgcta aaaacaggat   4500

aattttgtaa gtgggcaaac cactgtggtc acacgtattt cattttccgg ccccactggc   4560

tttacctgct gacaactaaa acgtcatttt gttttgtagt tccaagatga agaaaggctt   4620

attttcctga tttactacct tattcatttg gctctgctct gcctacatcc gccatagcac   4680

tctgcgcacg tgaaatttcg acacataggg tcaagagaac ctgtgtgatg atgggttgta   4740

aatgccagtc ctggattcta agctgcagta gccagcacag gcacttcaga aaggctgaac   4800

tcccacaaca ctccctcggt tttccctcat ccacttaatt tcacacacac aaagacccac   4860

aacgatagta gcttccatgg cacaagtctt tcaaaaggaa cagacacaat tttacttac   4920

tcctgttttg actaaagcag gaattgaaac tcaacagacc gctttctctt acacttgtga   4980

gaagttagct ggccacatgt                                                5000
```

<210> SEQ ID NO 201
<211> LENGTH: 500
<212> TYPE: DNA
<213> ORGANISM: Homo sapiens

<400> SEQUENCE: 201

```
agggaaaaga gataacgaaa gaaagaaaga aaaaaaaaag ggccggcaat ttcatgtaca     60

tttgttttgg cattcgctga attctagaga tgaaaacaat ctcctgcttt taattcagtc    120

cacgtgcaac aaagttgtac gttgggagat ctggctttta ataagaacga ttaacaagcg    180

tttttgatca caggaagttg agaagagtcg ctgcttctaa gaatacaata aacattgact    240

agcagttaga cggtccatct ttctctatca gccgtttagc agcctctact ttgatttggg    300

gcaaatgcga gatgggacca ggagagagct ccccacaccc ccaccaccac gtgggcagtg    360

gttctgttcc agagcgcctt ccttcctgtc cagggaggca ggctgctgag gccgtttctg    420

ggcaagaggc cattgtcggg atatttgctt tagatagctt gcagctgggc tgagtgggtg    480

tttcattcag actcaacaca                                                500
```

<210> SEQ ID NO 202
<211> LENGTH: 700
<212> TYPE: DNA
<213> ORGANISM: Homo sapiens

<400> SEQUENCE: 202

```
agcctggcgc acccgcccta atttgagtca gggaccctag gcgcctgcag ctccggttcg     60

ggttgagtgc ctcctgtcag gatgtgaagc tgctgtcccc cccgggggcc tccagcactg    120

ctgaggactc agcagtcagc ctctcctccc acttgggctc atttacagag agcatctcca    180

ggaatcagtc atggggaaag gggaaacgcg gagtgacaac acaacacgta gaaagttctc    240

tgccgccttg gtcaggcttg tcagcctcac agcccatcct gctcctgcgg gaggaaaagt    300

gagcagaact cagcccggag atgagccgca ggccggcagc ccctgcctct gccctgcttg    360

ttgtgactgc aatgcaaggc tctctgtagg tgcgggggat tcgggttaaa tgggtctcca    420

gtggtccagc gctcccagca aaggccgacc acaagaatta gcgggctagt tatttaccat    480

aaccatatac aaaaccacaa gcatcagcgt tccctcaaat acatccgaga cgctgtatat    540
```

ctctttatta aagcctgtca gggtttgtta ttgcacagct tggccttgaa ccccaactaa 600
accaggctgc ttgagcaaag aaccaagcaa tgcaagcatt caggcaggac cattataacc 660
ctgaggccaa aggcagaagc agggagagga gacgtcttcc 700

<210> SEQ ID NO 203
<211> LENGTH: 500
<212> TYPE: DNA
<213> ORGANISM: Homo sapiens

<400> SEQUENCE: 203
agaccagcct cggtcttcgg cctgcgggtt ctgcaaagtc aggctagctg gctctccgcc 60
tgctccgcac cccggcgagg ttccggtggg gaggggtagg gatggttcag ccccgccccg 120
ctagggcggg gcctgcgcct gcgcgctcag cggccgggcg tgtaacccac gggtgcgcgc 180
ccacgaccgc cagactcgag cagtctctgg aacacgctgc ggggctcccg ggcctgagcc 240
aggtctgttc tccacgcagg tgttccgcgc gccccgttca gccatgtcgt ccggcatcca 300
tgtagcgctg gtgactggag gcaacaaggg catcggcttg gccatcgtgc gcgacctgtg 360
ccggctgttc tcgggggacg tggtgctcac ggcgcgggac gtgacgcggg gccaggcggc 420
cgtacagcag ctgcaggcgg agggcctgag cccgcgcttc caccagctgg acatcgacga 480
tctgcagagc atccgcgccc 500

<210> SEQ ID NO 204
<211> LENGTH: 1500
<212> TYPE: DNA
<213> ORGANISM: Homo sapiens

<400> SEQUENCE: 204
aaacgtttaa aatatatttc taaacagaat gggccaattc agtcacagta actgttgatc 60
tccatagcag agcaacccac aaagacagaa ctgatttttt tcccataatc aggggtgaaa 120
aatatacaac ttgtttctga accaaaacca caatttctgc agtttaaaat gtttcactgc 180
taatatggcc ctggtagaaa ttatgtagtt tcttttcttc tttaaaaaaa aaaaaaatta 240
aaaaaatttc ctaagacact aaatgctcca tctggaatgt agattctgat cacaaagcag 300
ctcagttaac ctaaaaaata aaaaattccc atcacctgtc tcagtagggc ctgagagtag 360
tgtggggaac cccagctttg gtatggagag tcatggcccc ttgaaccaga tagagacctt 420
gaatagccat agctggtgct tctctcagga taaactctga tgtaggaagt atcaccctca 480
tgagagtgga atttggtcat ccagttgacg cagggcatat tccatgtctt cttttctgag 540
acacccaacc atccccactc catccttctg cacatccgtg taacaggcat ccccagcttc 600
tcgcgtgtga tccttcaggt cctgccagct gcctgatgga agaagtccat ttcttccata 660
aatagcatcc tctgcatctc gagggtcctc gaagcgcacg gaggcgaagg gcacaaggcc 720
gtaccggctc ttgagctcga tctcgcggat gcggctgtac ttgtagaaca ggtcctgcgg 780
ctccttctcg cgcacgtggg tcggaaggtt tccccacgta gatgcacccg tcgccctccc 840
agccgcgctc gtgtccgccc agccggacaa ccgcaccgcc cgacgctgct ggccagccgc 900
agcccgcatc cgcccgtatc gccgccgctg ccgcctcagc acggctgccc ccgcagcgtc 960
tgttttgttt tattctaaca gggtctctct ctgtcgccca ggctggagtg cagtggcgtg 1020
atcttggctc cctgcaacct ctgcctcccg ggttcaagcg attcacctgc ctcagcctcc 1080
caagtagtgg gcattatagg tgccagctaa ccatggccgg ctaatttttt ttttttttt 1140

```
tttttttttt tgagacagag tcttgctctg tcacccaggc tggagtgcag tggcgcgatc   1200
tcggctccct gcaacctccg cctcctgggt tcaagcgatt ctcctgcctc agcctcctga   1260
gtagctggga ttacagctat gtacagcgat gtctgcaaag atagggattt aacagcactc   1320
atatcttcat gttcataaaa aagtcctaca cgcgtgatgt acgtctagat ctttcctttt   1380
gtcacaggat atagcacggt agttacggat atagtctccg cagtgcctgg gtttgactca   1440
gcttccccac gtactgtcct gcgcatattt tgtgtctcag tttcctcatc tttaaggtag   1500
```

<210> SEQ ID NO 205
<211> LENGTH: 17000
<212> TYPE: DNA
<213> ORGANISM: Homo sapiens

<400> SEQUENCE: 205

```
cacgcgcccc ggcctggctg gaggggccaa cccagcgggg cccgcctgcc cgccggcctt     60
tctgtaactt tctctcttta aacttccaat gaatgaacgt gcctcttctt acggatttgt    120
ttagattagg gaatagattc ctcgctgata gcgttgcttt gcaaataaga cctcctatat    180
tattcaaacc aaacgagttt gtgtctttaa aggactatag cagccccatt ctatgttaag    240
ggttggctat tacaattatt atatgcttag ggaaaaaatg taagccccgt agtttgtgct    300
tttcttgatg tacagaaagg tttatcttag gtggataggt tttgttttgt ttcttaaatg    360
ggattttttt ggttcgtgtc tttgaagggc tgtttcgcga cgtcattaat gaactaatcg    420
gttttcagat ttcaagacgg tgtgtaattg atgtaaccac tgaggaattt cagtgcacac    480
cagactaaga ctcttccagc gcaggggatt ccagatgctt cttgggccct ctggaagcca    540
tggggatgtt tccagaccga aaggagggct ttgctgggga gcagatgtgc tgcctctccc    600
cgacccagga ttttgaggcc atgtttccgt taatctggac cgagagccct ctgggagagg    660
gaggcaggtc gtagggggcg ggggtgaggg ggagcgagat gaggtcgtcg ctggacgctg    720
ggctcccttg tcgttgtcct tttccccaga atccatggtc aggcctaggg agccacccct    780
gggtgctcga gatgagtccc caccctcact gaaggtcggt cactggatgt ttgtgtgcat    840
cgtaaggggc ccaccgaagt cccgaagcct tctcagggac cagcgagaaa gaggagcagg    900
cttgggagac agggaaggaa aatgcagggg aaagggctca cccctcgacc ccaggtaaaa    960
ttagaaggaa cgtgtggcaa cccaggtgca gctttggtcg ctcgctcaag gactttgcta   1020
gtcactacca ttaattaatt aatcactatc attaactacc aaggacaccg tttttattcc   1080
cctaaaagcg tcaccttgag gggaatggag aattgggcag cagctatgca aatcctggga   1140
caggagacac tgcctgagga ccctctctca ctcccaatcc cagaacccga agttatcccc   1200
gacaaccaag tccaagcaca tgaaccaaga cgatcagctt caggcagctc cttaccccca   1260
caagcggccc aggaggtggg cattatcccc cacccctggg atttctccat ccctccctct   1320
tctctcctgc gggagagaga gctgtggtca cccagttggg cgcgatggct ctggactaat   1380
ggggtctcta gacccagggc acaaaggcca atctgccagg ggttactgca tgtaatgaga   1440
taatcagaca tgttgaccaa cctaaaagaa aagactctcc cagggagtaa ctcccagtga   1500
aataatttat taaaaaaagc aaaaaagaga cataaatttc tctctactac ttgaggaaac   1560
agcaaacaga acgaattagg gtcttggcct ctgcaggaat aaattatttc cgacttggtc   1620
tggatacctg taattatttg taagctgtgg gtagtaatac tgtaattgtc ccccggtcct   1680
ttctggaagt agcaatgacc ccaaggacaa ttggtgacgt ctccacaggg tttacacatg   1740
gaaaggagtg aaaaatcgag gaattctttc agatagccca gaccaaaaat cctctcagcc   1800
```

```
atgaaaaggt catatatgtg atgctgggcc aagcggactt ttctggagta accatatcat   1860
aactgattgc ggatgtagac aagagcgtat aaaccaaata ggcttgaatc aacgcagtcc   1920
tggattttct gttgcctctg cttgctgggg cagtggaagt tcttaaactc cacttcagag   1980
gttggaaatt cttcccctc ccccacctcc ttagtgacaa ggtctctgat ctcctgctgc   2040
cactgcaata gcctctccca tcccgcgggg aacggccgga gttcttccct tgatctctcc   2100
cgagtcggct tccgctgggg atggatcgca ggtaggcgcc ggcgcggcct ggggaagaac   2160
agttgcggag catctgaagc ggaaaatcca agcagatgtg aggcgatccg ggcccgcctc   2220
gttcctcttg gggcctgaat ttcttccaga taagtttcct aatggaacat ttctaagagg   2280
tggggtacga ggcggcttgc tcgcacgcgc agtgggacag actgcgggtg gggacgtact   2340
gagaggtccg gacctcaatg cgtccgaccc gtctccacac cgcccttttc cagcccccag   2400
tctcctttca ttccctactc ttcaggctcc tttggggcca gtgggtgaac cgccatttag   2460
aacggtgcct cggactcggg ggtcgtgcgc tccatctctg cctccccccct ggggcccgcg   2520
aggctggtcc gggctttctg agctgggcgt tcggctttag gcccaatacc tggaccagga   2580
atttcttctc cccgcgccag aagggaaaga cataggaggt gtcccaatct gcggtcaccg   2640
ccgatgctcc tgaccactct agtgagcacc tgcccggtac ttttccattc caacagagct   2700
tccagcttca tactaactat cccacatacg gcctgtgggt attagctcta agtgtccttt   2760
tccgagggcc cgaggctccc cctccagcag ggagagctcc gggacggccc ccaccaaggg   2820
ttgggtttct tccttcacaa ttccacagag gcatccctgt ccttcctacc tgggaaacct   2880
cgaggtgcgg tgcccgtgta cttctggtac tttgcgtggt gccatcaggg accccagagc   2940
cacagctgcg tgtgtgtgtg gatgtgtgtg tgtgtgtgcg cgcgcgcgcg tgtacggcga   3000
aaggatgtgc ttgggggagc cgagtacaca acgtctgctt gggcagctgc tgggcaggcg   3060
ttgggcctgg aggtatctca cacccacgta tcttccagtc ttcaaacacg gcattgctct   3120
gcctcccgta gcgcgcttcg aacctgcctc gcggacacgt gaacagaggc tgtccctggg   3180
aagataagtg cgctttcccg taaaatccgg gaaatttgcc ttgaggaaag tttccgttct   3240
tgttacttgt cgggtttctc ccacttccac ttagccatgt ttctgcgatc tgggtaatcc   3300
ctttcaagcc caggaggaat tctcccgggt ccataattga gggtcggaag ccgtgggggt   3360
gagaaacgca ttaaatcctc ccgaagccca ggaggtgcca gagcgggctc agggggccgc   3420
ctgcggaagc tgcggcaggg gctgggtccg tagcctctaa cccccttggag ctccttctcc   3480
cagaggcccg gagccggcag ctgtcagcgc agccaggagc gggatcctgg gcgcggaggt   3540
gggtccgact cgccaggctt gggcattgga gacccgcgcc gctagcccat ggccctctgc   3600
tcaagccgct gcaacaggaa agcgctcctg gatccgaaac cccaaaggaa agcgctgtta   3660
ctctgtgcgt ccggctcgcg tggcgtcgcg gtttcggagc accaagcctg cgagccctgg   3720
ccacgatgtg gactccgcaa ggggctaggg acaggcaggg ggagagcccg ggtttgcgca   3780
caccttccag cccctggagg gagcctgctc ggcttcgaac gccttcgaac ttttgacctt   3840
caaaggagtc cctggaaaag gtcaggagcg cctgctgcag gcacggttgc cgaaggccag   3900
gccttcctgg cgcaggggag ggccagggga gggaagcgga tactcagtcg ctgtccgacg   3960
gcgagttttc ggagcagcag gctcatgatc ccgggccagt ggcgagagca gtgacaccga   4020
gaacccaaat ctccgcgccc ccatccgcgg cccggtgtcc tcccggcccc tgctgacctc   4080
caggtcacgc accccactgc tccacggctc tgcagcctgt ggcacacggc cgagagtccc   4140
```

-continued

```
cacatgatct cgacgccaag gtaaggaatt gccctgcgtc ctctgagcct gtctctggcc   4200
tggggggccg ggaaagctgc actcctggaa gaggtggggt tatgtgaccg ccgctgcagg   4260
ggtgcgcgga ggactcctgg gccgcacacc catttccagg ctgcgggagc cggacagggg   4320
agggcagagg ggggacaaaa ggactcttta ggtccaaaat gaccctgaag gagagtccag   4380
aatgcccagt ggccgcgtct gcaacggagt cttctttctc caattgcctt ctgccccatc   4440
accatgggcc ccacctgcgc cacctgcgcc caccctgtga ccctggctca gcgaccttgg   4500
cccttaatcg cccaacgccg attcctcaaa attccggctg cgctgaatcg ggctgctttt   4560
gccgccgccc cggcagttgg gccctgtttc cgccggcgcc ctgggagagg cctcaccact   4620
cggctgggct ccctggcccc tcccttcccc tggcctgagc gcccctgcgg cctcccgctc   4680
ctcctgagaa ggcgacaatc tctttgcacc ttagtgtttc gaggacagaa agggcagaag   4740
ggtcacttcg gagccactcg cgccgttttc acgtgtgtgt gtaatggggg gagggggct   4800
cccggctttc cccttttcag ctcttggacc tgcaacaccg ggagggcgag gacgcgggac   4860
cagcgcaccc tcggaaggct cgatcctccc cggcagggcg cctggccaac gagtcgcgcc   4920
gcctcctctc ggccgcgcct gctggtgacc ttcccgagag ccacaggggc ggcctcggca   4980
cccctccttc cctcgccctc cctgccgccc atcctagctc cggggtccgg cgaccggcgc   5040
tcaggagcgg gtccccgcgg cgcgccgtgt gcactcaccg cgacttcccc gaacccggga   5100
gcgcgcgggt ctctcccggg agagtccctg gaggcagcga cgcggaggcg cgcctgtgac   5160
tccagggccg cggcggggtc ggaggcaaga ttcgccgccc ccgcccccgc cgcggtccct   5220
ccccctccc gctcccccct ccgggaccca ggcggccagt gctccgcccg aaggcgggtc   5280
tgccataaac aaacgcggct cggccgcacg tggacagcgg aggtgctgcg cctagccaca   5340
catcgcgggc tccggcgctg cgtctccagg cacagggagc cgccaggaag ggcaggagag   5400
cgcgcccggg ccagggcccg gccccagccg cctgcgactc gctcccctcc gctgggctcc   5460
cgctccatgg ctccgcggcc accgccgccc ctgtcgccct ccggtccgga ggggccttgc   5520
cgcagccggt tcgagcactc gacgaaggag taagcagcgc ctccgcctcc gcgccggccg   5580
cccccacccc ccaggaaggc cgaggcagga gaggcaggag ggaggaaaca ggagcgagca   5640
ggaacggggc tccggttgct gcaggacggt ccagcccgga ggaggctgcg ctccgggcag   5700
cggcgggcgg cgccgccggg ttgctcggag ctcaggcccg gcggctgcgg ggaggcgtct   5760
cggaaccccg ggaggccccc cgcacctgcc cgcggcccac tccgcggact cacctggctc   5820
ccggctcccc cttccccatc cccgccgccg cagcccgagc ggggctccgc gggcctggag   5880
cacggccggg tctaatatgc ccggagccga ggcgcgatga aggagaagtc caagaatgcg   5940
gccaagacca ggagggagaa ggaaaatggc gagttttacg agcttgccaa gctgctcccg   6000
ctgccgtcgg ccatcacttc gcagctggac aaagcgtcca tcatccgcct caccacgagc   6060
tacctgaaga tgcgcgccgt cttccccgaa ggtgaggcct caggtgggcg gccggggacg   6120
ctggggagcc cggcggcccc ggcccaggcg ggaagcgcaa gccagcccgc ccagaggggt   6180
tgccgcggcc tggcgtccag agctggggcg tctgagggag gttgcgtgag ggtcttcggc   6240
ttcggcgctg gcttggggcg aggggccagg gccttggcgg cccaggcgac caaaccctct   6300
cctggtccag ggctgggtga gggcgaatta cgaattgttc caggggcagg cagtccccca   6360
gcccgcacgg ccagcgagtt ctttctggtt ttgttctttc tccctttcct ccttccttcc   6420
ttcgccagtg cattctggtt tggtttggat ttttttctct ctttctttcc tttctttctt   6480
tctttctctt tctttttctt tctttcttcc tctttctttc attctcccct tccttccttc   6540
```

cttggccccc tctctccctc cctccttcct tccttccttt gccaatgcat tggtttgttt 6600
tctttccttt tctgctttcc ttcctttctt tggaagttca ctctggtttt gctttctttc 6660
tttccccatc ccttcctttc tttatccctc cttcccttcc tccttttctt tctacgattc 6720
cctttatttt tccttcattc ctccctcttt ttgtctcttc tggaggaggt gaaggagggt 6780
cagcttcagg cgctgcgagt cagcggggat cacggtgagg cccaagcact gcaggctgag 6840
gccacagagc gaacacttgt gctgagccgg gccctctcgt gaggctgggg tgcgggaagt 6900
ccgggcagga gagacccgcc cccgccgttg ctgagctgag acccggctga aagagagggg 6960
tccgattaat tcgaaaatgg cagacagagc tgagcgctgc cgttcttttc aggattgaaa 7020
atgtgccagt gggccagggg cgctgggacc cgcggtgcgg aagactcgga acaggaagaa 7080
atagtggcgc gctgggtggg ctgccccgcc gcccacgccg gttgccgctg gtgacagtgg 7140
ctgcccggcc aggcacctcc gagcagcagg tctgagcgtt tttggcgtcc caagcgttcc 7200
gggccgcgtc ttccagagcc tctgctccca gcggggtcgc tgcggcctgg cccgaaggat 7260
ttgactcttt gctgggaggc gcgctgctca gggttctggt gggtcctctg ggcccaggag 7320
ctgggagggc tgcgccggcc tctggagccc cgggagccag tgccgaggta gggagacaac 7380
ttccgccgca gggcgccgga cggtcggggc agagcaggcg acaggtgtcc ctaggccgca 7440
gggcgcttcc atagcgccat ccccaccagg cactctactc gaaatcggaa agctcgacct 7500
tttgcgttcg cctctgccaa gcctgttatt tgtgctggcc gctgggtctg gagctgcgct 7560
tctcggcccc tccccggtgg agcgcagagg gctggtctgc aagcgcggcc tccagccccg 7620
cggctccccg gcccaggagc caggcgcggg ctgacccggg agcacccggc agcggagggg 7680
gctggaagcg gaccctaggc ctctcctgtg ccacccggcc ctaccgcgcg gccgcggggc 7740
gctctcctct cgggcgcagc ggtccttcag cccagggcag gttcctccct ttcctactcg 7800
gaacgtggca aagatacccc agtcccagcc cctccagctg agagctgttg cccaaggtcg 7860
tcgctacttg tccgctcaat ggtgacccct tggcagagaa ctagggatga ttccactccg 7920
gttgatgttt taggggaaat taaaagaaca ttcggttttc tgagtctcct tccggggagg 7980
cgtggtggta actggtttgc tgggaagagc cgttccttaa ccgcatgcaa caaagcaggt 8040
gtggaatccg gacgagaggg cactcactgc cttctgcccc ctttggaaat agaaaaagcc 8100
ttcgaagcag caatccaaag atcaaatgat ttgcggtcaa tgatttcaat taaaccagaa 8160
attagtaagg gagggccgag aagacacggc tgctcagaag ctgttcgctg tttgagggat 8220
ttcccggaga gcctgttaaa agatgcgaag tggtgggtgt accgctcagc cacctttaaa 8280
ccggctctgt gcgttctggc tctggaaagc aagtctccag gcatttgggc tcagaattgc 8340
tgggccccga gtttgggcgg gggtggtcct tctgggggtc aggccttgag cagcttgcac 8400
tggtggcagg tttgggagca gttgaggggc ttcctgtgtg tcttttggag ggggtgaccc 8460
tggaagttgg cactctggaa gggagctgtt tggccctaga gttttggaaa gggccctgaa 8520
cctgttcggt ccccctcgga aagggaaggg agcagtggct tagtccctcc ctcctccatt 8580
cgtgcaatgc ctggggtagg ggtagacctg gagccggtgg actcatatcc ttggaattcg 8640
tcaggacagc tgctccgggg ccttggccct cagtcagtct ggggctgagg agtagggaag 8700
ctgggaactt ggggcagagg aagaagatgc gtttagaaag acctccatta tgcaaactgg 8760
agtccattta tgcaaactgg tcacccttcc agtagctcca aagagtggca gtggagtggc 8820
atcttgattg atttaacctc ttctcagggg acctgggtct gcgagggagg atatggctgc 8880

-continued

```
ggggttggaa taggatctgt ctgagctgcc agggtcaggg tggtggccct agggaggttt   8940
tagggccagg gtggtcccgg gctgtggcag gggctctcag atcgcctcgg gctctcagct   9000
gcaaggtgaa aaataccatg aggaattgat ctgccaaggg cggtcttgtc tcaaagcaag   9060
tggattgctg gggtaaagaa tctagagacc agcttaggac tctgggagga agaaaaaaaa   9120
aaaaagaata gcatagtcct aaggaactgc aaggatcacc agattaaccc ttcatacctg   9180
gggaaattaa ggccagacat gacacaggcc tttcccaagg ctctgtagca agggcaatag   9240
caggccagtt gctgccactg cggtcctgtg gggcatgttc tcactccact gcacccagga   9300
ggctgccagc ctctgttcct tttaacatag atctcctcag ttgttaagac agaaagagga   9360
actcagaggg gtccctgtgt gcaaggcaga gggagaccac cagaaccagg gtaagcaccc   9420
cacttggtag ccagttcaag gacttgggga tgttttcaac atttacagcg aggtttgagg   9480
ccccattgtc atgcagcgct actcggcctt ggtctcctta tctgtaaaat gggcccatta   9540
gcaatgcaca gggttgctgt gatgaagggt gaggtcccac aagcaaaagc tgtgcagtga   9600
ggggggaatc ctaagcattg ttcctatgcc attcacccct tcctgtgagc tccccatatt   9660
ccctggctca aaggagtctt gaatggcagg gatggaggac tcactgcctg gactttgaag   9720
acccctgctt tctgggtgac caccttttct tccctttgac agtgaactaa tacattggag   9780
gtagatagtg ctgggaagag gacaggagac cacggctgac tttggacatg ggctcgaaat   9840
tgataacttg atgagtcttg gagggtggtt aagataagct cggggctggg gcagcgctga   9900
ggtctgatgg tcagccagcc ctccccaaag tgtggccctc cgttctggag ataggggctt   9960
tggaaactgc aaaagcgtcc tggcaggcca gctctggttg ctccctggcc atagctgctc  10020
tgactacagg cagcaggacg caggtcggcc tctgcccatc ggaggtcaga ggcagggcct  10080
ccagcaccag actcagcagt gccactgcaa acctggcaca acaggctggt cccaggactc  10140
agctcagcag tgaagttgga aaccaaggtt gagtctcccc atctcccttt ccccaacccg  10200
aaagacccaa gatgggtgtg ggtgaaagag ggagaaagaa ttgctactcc agaaactgtc  10260
atttgcccac acgaaacgag gtggggttca aggtctgaac tcttccagtg cctgggtgcc  10320
tttgggttta aattcagctg caggtgcccc catcaccact tccacctgag cacaccacga  10380
gaagccaggt tatcttagaa actgtttccc ggaatcaaag cgacttgatt tggagagttg  10440
ggtgaggaga aactcacccc tataccccte agggcgtcag agatgtgagg caattctcta  10500
cctccgctgg aaaaaatgca gatttattaa aggtcgactg tttagcagaa caacgtagat  10560
tttttacaac gctttccccg tctctgcttt gaagcctgcc aggctgcagc tggggatcca  10620
ggagggaaag cccgcaggcg cagaggggac aatccgggaa gtggtaaagg ggacacccgg  10680
gcacagggcc tgtgctttcg ttgcaggcga ggaagtggag cgcgcgctgc agattcagcg  10740
cggggctaga ggaggggacc tggatccctg aaccccgggg cggaaaggga gcctccgggc  10800
ggctgtgggt gccgcgctcc tcggagccag cagctgctgg ggcggcgtcc gaactcccca  10860
ggtctgcgca cggcaatggg ggcaccgggc cttctgtctg tcctcagaat acgtaggata  10920
cccgcgggcg acaagccggg ccaggctagg agcctccttc cctgcccctc cccatcggcc  10980
gcgggaggct ttcttggggc gtccccacga ccaccccctt ctcacccggt ccccagtttg  11040
gaaaaaggcg caagaagcgg gcttttcagg gaccccgggg agaacacgag ggctccgacg  11100
cgggagaagg attgaagcgt gcagaggcgc cccaaattgc gacaatttac tgggatcctt  11160
ttgtggggaa aggaggctta gaggctcaag ctataggctg tcctagagca actaggcgag  11220
aacctggccc caaactccct ccttacgccc tggcacaggt tcccggcgac tggtgttccc  11280
```

aagggagccc cctgagccta ccgcccttgc agggggtcgt gctgcggctt ctgggtcata 11340
aacgccgagg tcgggggtgg cggagctgta gaggctgccc gcgcagaaag ctccaggatc 11400
ccaatatgtg cttgcgtgga gcagggagcg gaagaggcag ccggtcctca ccctcctctc 11460
ccgccacgca catatccttc ttgacttcga agtggtttgc aatccgaaag tgagaccttg 11520
agtcctcaga tggccggcaa cgcgccgagg tcacgctccc cagaaacacc cctctcccct 11580
cccctacccc agctccccct ggggcgggtg gtaattgggg gaggagaggc cgcaggcagg 11640
gaaggggtgg gaaagccaga gagggaggca caaagtgatg gcagcccggc aaacactggg 11700
gcttcgggct gggccgcgct cgtttaatcc cacaaaaatc ccattttgga ggtgagaaat 11760
agaggttaga ggtcgggccc ttctggagat cagaccgagg agacgggccc agctggcgtc 11820
ttaaagcaag gagggggagt cgggaggagg tgagacccct gcacccaggt ggggctccca 11880
aaccgttctg gatttaccac actcccaggt ccgattttcc atggagggct ggggttaggg 11940
actggcacct tcttgttgtt aaccgcattt gatattcaca agaaccctgt gaggagactt 12000
tgtcaccgtt tttagatgcc tgaggttgcc ggaggggcag tgagagaatc gtctaacctg 12060
gtgttcctac cacagtccag gccctgtgtc ctgggctgga cccacagccc ctgccaccac 12120
ccagaggaag gcgcgaagct ggctgcctcc tttacgggtc tcccttaggt gccctcatga 12180
agggggacgg ccacctcaca gtgcaggaac tatctccccg tttgctccca aatagtcttc 12240
ttggtgtggt gctgtctatg gtctgtgacc tgcatctgga gttaccccca ggaccagctt 12300
cggaagagga gggatcgctt ggaggccgtg cagtgtgagg aacggcaggc agggtgtggg 12360
accaacatgc acacactcgc aggtgctggg gccagggagg aatgaggcgc tggctccctt 12420
tccctccatt tctccctggg ggtcccagca acctggccat ccctgacttc caacagcaca 12480
gcgtccccac aggtcctgca gtgctctgca ggggtgcagg gagctcccct ccccccagcc 12540
gcaacctcac cttcctcacc cccacccctc cggcaggaaa ccacaggctg ggttggggac 12600
ccctggtgct ccaagagagc agtgagtgct gggagccgct aaccccgagg cgcctagcac 12660
agactcttct caccccttat ttctgaaata aagcccttcc ttaggtccag atgaggacca 12720
cgtgctcagt gcctcacttt cgtgggagtg tatatcactt tacagtatca agacaatttt 12780
ctttcgttac aaatctttat ttagtctctg cgtttagacc aaagtagatt tttatgggct 12840
gagtgaaaaa acctcgcccg cattggtttc tgatggaaca gctggcagcg ccacggcccc 12900
gggtggggtg gcctagaggc aggggtgctt gggaggaaca tctagcaccc gaccacctcc 12960
accaggtggg aaagggacgt ttgcaccaaa tctccgccgg caaagcagag gctttgggga 13020
attacagaaa aactataatg atctaaaaga gaacaagtta tcttgaactg tgcgggtatt 13080
tgaatcatac agaaaattgt cctgtgtgcc caatgcactt ttgcatgtag agccagggcc 13140
ttcgaggaag ctttcaggag atcccgggca gcggagtctg gtctggagtt tcatttccgt 13200
aggtgcagat ttctccccaa gtcttcccgc catgggcttt gcaagaagcc agggcccaga 13260
ggccacgctc accgttaaca ctgcacaggg caaaggtggc tccaggacaa ctgcccaacc 13320
ccaggaacga cccagcagca gagaaaagga cagctgccag ggtgcctttg tcgctttttg 13380
gaaatcagaa ttcctgggtc cttagttaag tcttacttca ccaaatccca ggaccttcac 13440
attttggttc ttgccattgc taacagttgt aaatgctgcc gccacgaggc ctgggaggaa 13500
ggacccgctg gtgagagcac agggagtgct gctgtgatca cggtggtgat gcggggtgag 13560
cgcgatttcc cgggattaaa aagccaccgc tgcccccgtg gtggaggctg ggggccccccg 13620 aataatgagc tgtgattgta ttcccgggat cgtgtatgtg gaaattagcc acctcctcag 13680
ccaggataag cccctaattc cttgagccca ggaggagaaa ttaaaggtca tccctttta 13740
aattgaggaa tagtggtttt ttttaacttt ttttttttta ggtttttagt tgccgaatag 13800
ggaagggttt gcgaagccgc tgccctgggc cgaggtgcat tttacgcttc cagaggtcga 13860
ggcctccaga gaccgcgatg cccagggcgt tcccggggag gctgagagac ccagggtgct 13920
ctgggtgact gcacggcgac tcctcgggaa cccactcgtg gctgcccgct tggaagggct 13980
ttgcggcccc gggaacgatc tccaggatct ccacggctgg tcaggttccc cgtccctcgt 14040
atcccgcgct gcccgggggc tcctgccttt ggttcagtgc tcgcggcacc accgcactca 14100
ggacggcagt ggggggctgg ggctggggct gggcctggcc cagcgtgggt tggggcgggg 14160
gacgcgccag cagcgcccgc agctcgctcc gcaggggtcg cagccagggg tcgggagcta 14220
ggctcgtggg ccgggagacg ccgggcgcgt tgtcctccgg ggaggttggg gtgcaggcgg 14280
tgcaccgacc ctcgccatct ggcgctgcag ccaccagcca cggcgcttag tggagggtct 14340
gcggccaggc tcccggcgga aagattccgg ggagggctcg ggggttgtcc cagcccgcgc 14400
taagcgccgc agcctcgccc ggctttcctg cttcctcgga ctgtgcaggg gaagcctggg 14460
gtctcgcggg gcgcagcagt caggtcgagg gtgcagcagg aggggagtcc tgacgggcag 14520
gtccctcttt cccctggtgc gcaacactgg ttggtagctt ttgcggaggt ggtgaagaag 14580
ggcaggaggc ctgttgagcg gaggagtccg gggatcccta attatgtgac aggagaccct 14640
ttccagttcg gcctgtggcc catccctctc tcaccgccgg cagattggag tctgctctcg 14700
gggagccccc aggtaaaccc ctcacaggga gaaggtttcg gattggaagg aggaccgcgc 14760
tcgtggggcg cctgtgagag ctgggaagcc caaggggtag cgtgtagggg gtttttttatg 14820
cgggaggagc tgcctcctgg gcggcgggga ctttctgtct cagcctgtct gcctttggga 14880
aaacaaggag ttgccggaga agcagggaaa gaaaggaggg agggaaggag ggtccttggg 14940
ggaatatttg cgggtcaaat cgatatcccc gtttggccac gagaatggcg atttcaaagc 15000
agattagatt actttgtggc atttcaaata aaacggcaat ttcagggcca tgagcacgtg 15060
ggcgacccgc gggagctgtg ggcctggcag gctcgcacag gcgcccgggc tgccggccgc 15120
tgcggggatt tctcccccag ccttttcttt ttaacagagg gcaaaggggc gacggcgaga 15180
gcacagatgg cggctgcgga gccggggagg cggcggggag acgcgcggga ctcgtgggga 15240
gggctggcag ggtgcagggg ttccgcgtga cctgcccggc tcccaggcat cgggctgggc 15300
gctgcagttt accgatttgc tttcgtccct cgtccaggtt taggagacgc gtggggacag 15360
ccgagccgcg ccgggcccct ggacggcgtc gccaaggagc tgggatcgca cttgctgcag 15420
gtagagcggc ctcgccgggg gaggagcgca gccgccgcag gctcccttcc caccccgcca 15480
ccccagcctc caggcgtccc ttccccagga gcgccaggca gatccagagg ctgccggggg 15540
ctggggatgg ggtggtcccc actgcggagg gatggacgct tagcatgtcg gatgcggcct 15600
gcggccaacc ctaccctaac cctacgtctg cccccacacc ccgccgaagg ccccaggact 15660
ccccaggcca cctgagacct acgccagggg cgcctcccga gcgtggtcaa gtgctttcca 15720
atctcacttc cctcagcagg ttccacccag cgcttgctct gtgccaggcg ccagggctgg 15780
agcagcagaa atgattgggc tgctctgagc tctgaagcat tcggccgctg tgtgtgtgca 15840
aggggcgcaa ggacggagag acagcatcaa taatacaata ttaacaggag cacttgtcca 15900
gagcttactg caagccacat tcagttccgg accttattga cttccccctc ccatctagag 15960
tggattctgg tttttcaatt tgttttgttt tgttttttgt ttgtttgttt gtttttgaga 16020

```
cggagtctca ctctgtggcc caggctagag tgcaatggcg cgatctcggc tcactccaac  16080

ctccgcctcc cgggttcaag cgattctccc gcttcagcct cccgagtagc caggattgca  16140

ggcacccgcc atcatgcctg gctaattttt gtagagacag ggtttcaccc aggctggtct  16200

cgatctcctg acctccgatg atccgcccac ctcagccttc caaagtgttg ggattacagg  16260

cgtgagccaa cgcgtcctgc cttgattctg tttttaactc catttttag aggaggaaat  16320

tgaggcacag agaggttaaa taacatgtct aaggtcacac agcaaggggt ggagcggagt  16380

tagcccactg gcctagctct agagcccacc cggataacca gaacttggtg aggcctccgg  16440

gctcttgctt ggtttggagc caggtgctta gcgccccgag cccggggcca ttcaccctgc  16500

aggagctgca cgcgcccctg acctcggctt ttccctggca gcagaggggc tttgcgggtc  16560

ggccgggtag ccctgagcac agctcgccac ttccaggtgg gctgttggcg ctggctgggg  16620

acacatcccg atctttcaaa tgccctttac agagcctcat caacgacccg attcattccc  16680

ccctcctgtc atttgtctct gccatcgaaa aatgcctacc gagagctgct ctgcatttcc  16740

gccctctatt ttgtgtttta ctttaaaata ataataaaaa aaatgttggc tgcaggacgc  16800

catgacttag gtcagcgagt cagccgctag ctctgcattt ccaaaaagca gatcttttca  16860

caactctctt gccccaagtg ccctggtgtg gtttattttt taaaatgcat gcctgcggaa  16920

gagaagaccc ggggaatatt cgaaaccccg agcttttaca acataaagcg catggtgtgg  16980

ccgcggcgag taatggcgct                                              17000
```

```
<210> SEQ ID NO 206
<211> LENGTH: 1500
<212> TYPE: DNA
<213> ORGANISM: Homo sapiens

<400> SEQUENCE: 206

caaatcactt gaactcaagt tcaagaccag cctgggcaac atggtgaaac cacatctcta     60

caaaagtaaa gaaaattagc caggcatggt gctgtgtgcc tgtagttcca gctactcctg    120

gggaggtcga ggctgcagtg agccgcaatc acgccacttg tactccagcc tgggcgacag    180

agcaagtccc catctcaaaa aaaaaaaaaa aaaaaaaaaa aaaaggctgg gtgtggtggt    240

cccagatact cagaggctga aaagggagga ttgcttgagc ccaggagttc aaggctgcag    300

tgagctgcga tcacatcaat gcactccatc cagcctgagc aatggagtga gaccctgact    360

atatttaaaa aaaaaaaaaa taggaagaaa caactcaacc acagggctag tatgttactc    420

ggttataaaa tgataaagcc ctaaacagag aattagcccg tttccagaag aggccaagaa    480

cagatgatac agctgaactg aactcctgcc tgtacagctc gttttctaca agattccaga    540

cctggaagat gatggcatcc agcccccatt gaagcacctc gaacaagaaa aacgccgagt    600

ccgaagagcc aggccttgaa cacacgattc ctgtctataa ataactcccc ctggggaata    660

aaaagcagga tccaaggcag gaaacccgag ccgtggaatc tggtaagttc ttaggaaacc    720

cactcacggg cctgagtccc ccgtggaagc ggcgacttcg gcacctggac acccgagtcc    780

ccagagcccc gggcggccgc gcgtccctac ctgcaggcct gataccggcc gcggagcgct    840

cctggccccg ctcccgccag gctccgggac cgctgaaacg cacccagggg ggtgaaggcg    900

tagtcgccaa ggacagcgca gatggcagcg gaggcatggg agccggaacc taccgtggca    960

aagggccagg tcgggacgcc cctcggcgca gccccaaatc ctgcccgcgc cccagccccg   1020

ctcaggccgc gcccctgcca cctctggcca cacgggctga gacgtctggc tcctgcacag   1080
```

cgcacttccc gctgcccttc tccactggct gctcaggccc tgcctcgcca gcacggcatc 1140
cgcgggggat ccctacctgt cctttagggc ttgcctcata ggtcaaacgt cacctcccag 1200
ggaggtatgg cctgcccccct ggccaggtgg gccccttcca cgctcgcctg caacaccacc 1260
cacccacctt gataactgct tgtaaaggtt gtactgcttt ccccccttgag actgcaaacc 1320 ttcaagggca ggaaatgggt ctgttttcct ggcaaaataa tgaagttggc ttaaggtttt 1380
gctgaataaa atgagtgaca gacaaaagta gccaaatttg gcactcctga tgggttattt 1440
gatgaaggag gtgcaatgta tgggcttaac tagttattct ggatttcttt ccccatgtta 1500

<210> SEQ ID NO 207
<211> LENGTH: 200
<212> TYPE: DNA
<213> ORGANISM: Homo sapiens

<400> SEQUENCE: 207
caaggccggt gcacgcggac ccgaggattc ggtagatgtc cccgaagacc cgctgccgct 60
ctaaggcggt ggaagcgaga ttctccggaa acccagggaa tccgatgctc gcacaggacc 120
aaagcccgag gccgcgggga ccacagaggg acggagaagc cgggactcct cacatcccac 180
atccggcagg ggaagcccag 200

<210> SEQ ID NO 208
<211> LENGTH: 2000
<212> TYPE: DNA
<213> ORGANISM: Homo sapiens

<400> SEQUENCE: 208
ctgataataa agttttacca ttttataatt taaaaatgta aatatggagt tgggcatggt 60
ggttgggagg ctgagaccag aagatcgctt gagcccaggg gtttgagacc agcctgggca 120
acatgcagaa accctgtctc tacaaataaa aaattagcca agcgtggtag cacgcacctg 180
taatcccagc tactcgggag gctgaggcag gagaatcgct tgagcctggg aggtggaggc 240
tgcagtgagc tgagactgta ccactgcact ccagcctggg tgacagagtg aggctctgtc 300
tcaaaaaaac aaaacacaaa aaaacaaaca aaaaaaagca aatatatgta aaaataggaa 360
gtgcggtttc ccaaaatgag gtctgtaaac aactgatcta gaaaatgttc tggaaaaagt 420
aaaaaaggat caggatctga ggtcaactga cctctccctg cgctctggac aggcaaacag 480
gcaaggttcc ctctgaggcc gtagcggctt ctcgtgggcg agtccctgtt cgcaggtgac 540
gtgtggacca cgctcttccg aagcgtctgg cctgtgtgct ctcggggagg ggacgcaggt 600
cagcccacct agccgatggc taacaagtca gtttgttttc tgaacggaag cttaaaccta 660
gaaaagtaac tgggttgggg tgggggtgta gccacatgca gtaaaagcac tgcctgtctg 720
tataacaacg acctgatgaa aaaaggaacg cgtgaaatgg ggagtgttag ggcgtcacaa 780
actccagtgt ggttgaaatg aaagcagaaa gcaaatggca agctggcttc cccttccagc 840
ttttcacaac cctgccttgc tcatggtcag ccccaagcac gggcggaaga aaggactgga 900
ggggagggaa aggggtgggg agcgagggta ccagaggcgt gggaggacgg ggacaaaggg 960
gcagcaaggg accggcggaa aggaaagtcg gcgttagctg gattggaaac agtccagaca 1020
gaacgatggg ctctgctgcc tccgggtggg gcaccaagcg gggagcgggg ccacgaggca 1080
ggggacagtg aagcaccatg cagcgcccac cagccggcag cgcccaccag cctgcgctgc 1140
gctgcacatg gtacccgcgg ccccagctgg ccagtgtgtg gcggagatga gaccctcgtg 1200
aagagactaa gcggccacag cagggggaag ggttgctcac ataaccccat actgctcaca 1260
ctacgaggtt aactgccgtg agatctgcct gcagccagca gaaacccgtt ctaggaaaac 1320
gttgcccagt gacttcagtg agtgccactg acccgggcgc ctccgccccg gcgtccggca 1380
gcagcaccga ttgcgcagga ggcaccttgc aaacaacctt tcctgatccg cgctgcagtt 1440
cccaggccgg ttgcagccgt ttcacagaga ctgcgcacac aaagcgtctc cgtgccctgc 1500
cattcacctt tcgacacagc cgcaacccct cttttcagtg ttaaaacctg gcgccaaaag 1560
gaacatgcga tgtgacgtgt tacctctgcg catgcgccgg gcattcccag cgccccgaac 1620
ctgatgaacg cgcggtgggg accccaggct tccgtgcttt cgttttcctg gaagctacgt 1680
gtcctcagtc tacatattgt tacctggaaa ataaagtttt ctcctttttt cttcctttgt 1740
taacaggcag aaggtgtagg ctgcaggttt cgggcctaag agagggcatg gctggcgaca 1800
cggagtagac tcctagatga cataacggag gcgagtctgc accggggact cggcattagg 1860
aggaggcaga ggaaaagccc accaccgtgg ccgagggaga tctagcaagc agcttgcagg 1920
gggtgaagtg tgtgcaaagc aggctgagac ctgtccagta tcgaaacacg ccgcggtggt 1980
caagcaggct ttaccatgct 2000

<210> SEQ ID NO 209
<211> LENGTH: 700
<212> TYPE: DNA
<213> ORGANISM: Homo sapiens

<400> SEQUENCE: 209
tgaggctcaa aacaggtgtc tgtgagcttc acaggcggta aggccgtgtc tacatggccg 60
ggacatgcat cccggggctg cccctgccgt gctgcccgag tgcacggggg atgaggacct 120
gacaaggcca ttgatcttgc gggagcttcc tgaactactc cagcgtgaaa atcttccaga 180
aggattctcc acagggcaat gaggcaagaa atttacagct tagcctgatt aatgggccag 240
gcagttaaga gttctttgcc aagctatgag cataatttat agtcatcacg gcaggaggaa 300
aggccacata actcacatcc ttaaagggcc cttagaacaa gagacacgcc ggatcattga 360
aaacgtctcc actcctggcg ccaaaagaga tcggcacgtt tctgggtatt ctggtcaaag 420
aacagggagt ctggattaat atacacggca gaaaaaagcg aagaaaagac acacaggtca 480
tatatttctg actgatattc cgtttgttgt tttcggaggg acttggtatt tatttaacca 540
cattctcact tgacacgccc cctccccaca ccttgtaaat gccttcctct ttagccgagt 600
catttttcat cacatagaat tgaaatgttg ccaggaaggc ggtttatgag attgtagaaa 660
tggcactaga gaaagcagtg tgaaaagagg cctagaacgt 700

<210> SEQ ID NO 210
<211> LENGTH: 600
<212> TYPE: DNA
<213> ORGANISM: Homo sapiens

<400> SEQUENCE: 210
tctctacatg ctatctacta aaaacttagg caaggaaatg catcagacca aacaccccac 60
agcacagaga accgaccggc cattgctttc caatctccgc aaacctaacc attgctggaa 120
gaaatcttac tcacagtgca cagacagtag gtattttatt gaagataaac atatagtgga 180
acaaaccaaa ttacccccat ttgagttacg tgagcactca gttctcagcg tggatgtccc 240
acaaatcaag tcaacatttg cgtcccatta ccagcagcca cttgccgagt atctcttcgc 300
ttccactggg actgcctggc atccctgatg ctaaggagcc actgaagagc ctccaaatgt 360

```
ctgacattca caaacgcatc ttttgctttg acccgaccct tcaacctctc cgagtctgct    420

gccttttctc agacacacat ccaggcaccg ttagggatag ttagagaatc tgaaaattca    480

gaagcgctcc gaaaagcctt tccaaaagta atccacagca ctcaacagtg aatttagaaa    540

ccccaatttt tttctgagtt tgaagttttt aagccttgcg gatggttgga gtaggaaaaa    600
```

<210> SEQ ID NO 211
<211> LENGTH: 1100
<212> TYPE: DNA
<213> ORGANISM: Homo sapiens

<400> SEQUENCE: 211

```
tcagacaagc tctgtgcagt cggaattttt taaagatgca ctgtcacttg aggaagacag     60

gtgatcttcc tgcggcacaa atagaagcaa agagatttct cttcttctct gtagagcaac    120

acaattgata aatggccgat aatctccacc aaattggcag cagtaggctg cccgaaggca    180

gcaggcatat tcgtctttgt gaattgtttt actatgatgc tgtcacattt ccaggaataa    240

gacggttaaa atgatatatt gttgtggttt ggcatttgca gctttgctct gacttccctg    300

gtaactgcca acatctgcaa attattatgt gcttaaaaaa aaaatcaacc gccaccgcag    360

gctgccccca cggtccctgg ctgggccagg cctcctgcca ggccacaggg cagagttctt    420

ggaccaggag gcagcagggt caaaacccag gttgcctagg aagcccccaa agacagttat    480

ggatagagct gggagcccga aacacatgcg gcagtctctc agtttccagg taccggttct    540

cacatcatcc atgcatgtgt ttgaggaaaa acaaaaaaaa attgatggtt gccaaaaaca    600

aaaatgcttc catatcaaag tttatcagtg tcaatgtcaa gagacttctg gttcgtagac    660

tcattttggc ttgaggccac cagaagtgaa ctctggtttc taaatgcaga agcagaggca    720

ctggccgatc atggaagatg cagggaactg ttcaagaggc ccaagcctgg tgctcagaaa    780

cttggcagga tcaagcatct cgcccaggaa ttcatcccct gcttgtctaa gccggctggc    840

tctcgtgact gactcggaac aacagagcag atgtttgcgt gggaggcaag cctcacccaa    900

catctgtcct gcggcgggaa ggcctgggtg ttcacagata gagctggagt tccccggtgg    960

gtggcacaga caattagctg gggctgcctc acatgtaatc taattacagg ggaaacaggc   1020

tcaaacaccg ggtgataagc agcgcaactg tttcgggtga ctctgtaatt tttcctccat   1080

taattttctc cataacgcac                                               1100
```

<210> SEQ ID NO 212
<211> LENGTH: 250
<212> TYPE: DNA
<213> ORGANISM: Homo sapiens

<400> SEQUENCE: 212

```
gttgcctggg atatgcttat atcaaaaact tacgtgtcac ttacctagca tttgcatttc     60

actgggcctc ctaaattctg tgtggtaacc gactgccacc ggacatgctg tttacttctc    120

tatcctcacg cagccagttg ccacattcaa cataacactg caaatattgc cggtggatcc    180

tgacttcctc gtggacccta ctgtgtcggg aaaaacaaac aaacgaaccc tggaaggaaa    240

caccatgagt                                                           250
```

<210> SEQ ID NO 213
<211> LENGTH: 600
<212> TYPE: DNA
<213> ORGANISM: Homo sapiens

<400> SEQUENCE: 213
tcataaatat ttccaaatgt attcctattt gtctctacag agtctaacag acataaatag 60
cgaattgaag gttctgtctt aaaacccagc agaaagaaaa acaatgacca gaaaaaaaaa 120
acaattgtct ttggcttccc aagaacagca tcggatttca actggaacca cagatggtcc 180
gttgatagaa gcgactactt tttagctctg gaggacgaca aaaggaacca gcttcttcct 240
gtgggtgtca cagcgaggtc gcctggccac atcaggtacc agagcgagcg ccctcacctg 300
ataggccctg tacaacctca gccacagcac tgtcaggagg aacacgcgga actagcaacc 360
taggagggta aaggcggagt tgggagggaa cacgaggcag gcaggtcggc tggctgctga 420
gctacaggct gcactcctag gacgtctacg tgtaattgag aaaaataaga caaaaataac 480
ttactgtgca ggcaattaat tctggttggc atagcgatcc tcttaagtta aagggaatga 540
gcatgagatg aagagaagta agaggcagaa agaattatgc aagagcaaca tcagagtgga 600

<210> SEQ ID NO 214
<211> LENGTH: 2000
<212> TYPE: DNA
<213> ORGANISM: Homo sapiens

<400> SEQUENCE: 214
acgccgagcc gcctctgcag gggaaaccga agcagatgtg gtgagataat acatccaacc 60
ctgagtgcta ctctaacctg ccagaggcgg agggttctca gtgagatgaa agcattacag 120
atgcgttaga tctaagggag gggcctgcag atgcgcagct ggcagagaaa ccagggaggg 180
gctgaactgt cagtcgcgac caccagggat ctgaatcagt tcaccgacag ccttggggac 240
attcaccttg ggctccacaa cctgtcagaa atgcccccaa gcccaaaggc gtcgagagaa 300
tggccaggtt gtttcagatt gacacatatc ctaatgtaca agtcagccca cacaccccac 360
gtgcactgag cgtctcttgt tgttcacccc aaataaactc tgccggaact ggggcgggac 420
tcgcaggggc ggagaagggg ggagacgggc agagggcaga agtggatggt gagaagagcc 480
aatggagggg ccccgtgaga gtgagcaagg ctgcacccct aaccgacgtc ctggggctac 540
tgtacaaaca aagaaccaca ggctgggagg ctgaacaaca gacctgcact ctctcgcagc 600
tcggaggctg caggtctgaa atcgaggggc tgacagcgct ggtttcctct ggaggctgcg 660
agggagaaac cgtcccctgc ctctcccagg ctctggggtg agcccttcct ggcatcccgg 720
gctcattgta gatggatcac tccaatctcc atggcttctc agggcttccc tccatgcacc 780
tcaaatctct ctctccttcc ttttgtaagg atgccagtca ttggatttag gttcacctta 840
aatccaggat gatctcatct aaattacatc tgcaaaaaga cccttttttcc aagtaagttg 900 acattcacag gtacctgggg ttaggattgg acatatcttt tgcaggggtg caggggggctg 960 ccactgagcc cgctgcacag ggtgacctgg gccaagggcc cttcactttc acttcctcat 1020
tggcaagctg ccctgtgttt ggactgggtc gaggctgtca accttgctgc ccctcggagt 1080 ccccccctggt gtcccccaaa cagattctaa gctgctttcc tggggctgga ggccaggcat 1140
tgggattttt taaagagctt cccagcaggt gagcagcctt tcatgggtat caggagacct 1200
tcctggcaaa tgtggtgaag gtccttcctc ctgagcgatg ccttagaccc aggagcccag 1260
ggaggctgct cacctgatcg ttaggacagg agcagtggaa acctctggcc tcagaccccc 1320
tggaggaatc cctccctcta agactctggg actggtgcac gcaaggagct atcgtgaaca 1380
ttgctcccaa ctggccgctt gcttgtcccc cggctcccct tggccccagt ggcggctttg 1440
cctgaattag agggcgtgag agccacctgt gtctcagcac tgcaattaaa gcaggaagcc 1500

-continued

```
ctttcggaag cagccgtgtg caccagcctc ccatgggtgg agcagagcaa accacccact   1560

tctgccctct gcccttcttc ccttttctcg acaccctgcg gccccccagt ttcagcagag   1620

tttatttggg gtgaaaaaca agagatgctc agcgcctgtg ggatgtgtgg gctgactcgt   1680

acattaggat gtgtgtcaat ctgaaataac ctggccgtta tatggatgcc ttggggcttg   1740

gggggtttct ggcagtctgt cgagcccgag gtgaatgtcc ccaaggctgc tggtgaatca   1800

gatccctggc gttctccgtt ggcagttcag cccaacagtt tctctgccgg ccgtgcctct   1860

gcaggtccct cctctgatct gattggatta atatttgaat caatagactg agtcaagcag   1920

aatgtgggtg ggcctcatgc aatcagctga agccctgaaa agagcaaaag ggctgcccct   1980

tcccccgagg aggagagaac                                               2000
```

<210> SEQ ID NO 215
<211> LENGTH: 700
<212> TYPE: DNA
<213> ORGANISM: Homo sapiens

<400> SEQUENCE: 215

```
cacatttcag agctgaggtg ctggtgcggg caggtctcct gagctggggg gtcagctgtg     60

tggccagtga tggtgacgcc tcaggccgtg catggccggg gaggcggccc tgcctctgca    120

ctcttttgac tccatgacta ctggtgtctt cggacgccag agtcggggga gcaaccatgg    180

ggcaccgccc ctgcctgggg aggcagcacg aggcctgagc ccagcttaca gggggacatc    240

cacccccgct gagagcccca ccttcacggc gaggatctgt agaagaagac atttgatatt    300

actcggcaaa aaaaacaaga aacgaaaaca caaaaagagc tcctctgaag aagaaaaggt    360

atttgcgctg tggtccacct agaaataatg ttgttggcac aactagagca ttcctcagtc    420

attcaggagc actccctgcc ggtgcgtcca catgtcccaa ccccgataga tgaggcgctg    480

ttcgcccgtg gaggggtcag gttgtcgtga ccttatcttt acccttaggc cgtccatccc    540

ggggcctggg gtttcctgcg ccagtcacgg tgggctgtgt aggtggccat gtgttcggtc    600

tttccccagg aggtacgtac catgtgctgg gaggcctgga ggctgagccg ccccccgcgc    660

ctatgagttg caccctcaca gcggcggcca aacctcctgc                          700
```

<210> SEQ ID NO 216
<211> LENGTH: 200
<212> TYPE: DNA
<213> ORGANISM: Homo sapiens

<400> SEQUENCE: 216

```
caggcttgag cggtgactgg gagaccccgg gaatggaaat ggcgctcaaa tgctggtgtg     60

gtgtccgcag gggaacggcc cgcgggtgtg tggagtctgc gcccctgtgg cttcagctgc    120

gtcgggggac tgcgggaatc ttccagactc cagtttaaat cagagaggtg tgtccacgaa    180

aagagtcaaa ctaaaacatt                                                200
```

<210> SEQ ID NO 217
<211> LENGTH: 1300
<212> TYPE: DNA
<213> ORGANISM: Homo sapiens

<400> SEQUENCE: 217

```
aacgagacag tgcaaaaagc cgctgcctgg tgacctggca tgcagactcg gccctcccac     60

ttgcacggtg atccactgaa gacaacagct gcctctgtac tcacgctccc ccacactccc    120

ctccttcctg ccctggtttc tccatcccta gatgccatcc catgccccaa accatccgcc    180
```

aagcacaata acctcgcccc cacccacccc atgaggtcac tcgagttgac aaccagataa 240
cagtttttgt tttgttttgt tttgttttgt tttgtttgtt tttgagacgg ggtctcgctc 300
tgttgcccag gctggagtgc aatgacgtta tctcggctca ccacaacctc cgcctcccgg 360
gttcaagaga ttcttctgcc tcagctgcct gagtagctgg gactacaggc gcgtgccacc 420
attctcagct aacttttgta tttttagtag agacagggtt tcattatatt ggccaggctg 480
gtctcgaact cctgacctct tgatccgccc acctcagcct ctcaaagtgc agggattaca 540
ggcgtgagcc accgcgccca atagcaattt gatgacccat cccctccact gctgggaaaa 600
ggctgggcac cgcccacact ccatgcagct ctctttccct ggctcggaat cgctgcaggc 660
gccacagacc agacgcgcac tgttccccac tcctgcttat cggccgcgcg gcatcccctt 720
gtcgcagcac tccagcatcc atgcagccgc gcggcacccc gtcttcggag cactccagaa 780
tccatgcaga gcgcagcacc ccacatccag agcgctccag aatccatgaa gcacgcggca 840
ccccctcgtc agagtgctcc agaatccatg aagtgcgcag caccccttaa tcggagcgct 900
ctagaacccg tgcagcgagc agcaccccac acccggagcg ctccagaatc catgaagcca 960
gcagcacccc acacccggag tgctccagaa tccacgcagc acgtggcatc tcctcgtcat 1020
agcgttctag aatccatgca gcgagcagta ccccacaccg ggagcgctcc agaatccacg 1080
cagcgtctgg cacatcttta tcagagcgct ccagagtcca tgcagccaca gtcctccaac 1140
ggaccctgag attgtttctg caaaaggcca tgccttcata aatctgaaaa tttggaaaac 1200
atccttctac ttatatcctt acaacccacc attcaagctg tagaagcctt tctggaaccc 1260
caagcagaag gatatccaaa atgtaaaaac ggtggggcct 1300

<210> SEQ ID NO 218
<211> LENGTH: 1000
<212> TYPE: DNA
<213> ORGANISM: Homo sapiens

<400> SEQUENCE: 218
atagtgcgac tgttccgaag tctttatcac agttactggt gatgcttttt tccagatgtc 60
ctcgacgtgc acccatgaag ggctccacct gagagtgcca gggtcctccg tgggatgggg 120
ctggaggggg tgctcttgcc gtcctgggct cccaagcagc cataggaaca atagggtgat 180
ggggtcccag agatagaggc cagtgacagc agcgctttga acccctcaca cgggcacggg 240
ccctctggca gggatgggcg tcccggtcac acggagatgg gggctgctgc tgcctgcagg 300
tagaggaagg gacgtgtttg gcagtcctgt gacccctggg cacctcgcct cccccacggc 360
cggctctgct tgtaaacaga caagtgcaca agcgcagccc ggtgaaggca cagcggtccc 420
aggaggcatc tgggctgcac cccagcgagc cgcccataca cgtggagatg ccggccaagg 480
ccctgcagca cacggcagag gaaggcgcga tgggagccat gctgggcccg gaaggtgccg 540
ccgcccggag ctgtagccat cactccagct cttcttttaa gtgttcccag aaattgtgac 600
ccaccaaaat ctgagagcac ccgacagtaa gccagaggac cttgatgtga gatcccagca 660
cggtgtgggg gcggactgtg gtgggtgctg tctcggcccc cacccccttcc acaggtcggt 720 gtgcacatcc cacggcgcct gctaagctgc agtcttctcc aaaggggtca ctctccgtgg 780
gaagggagcc acccgccccc gggtgatgtc cccagtcagt gactgacgac agtccccagc 840
cgaggtgagg gaccagctcc tgcatccctc actccggggc ttgcctgtgg gccagggtgg 900
gggcgagcct cagcagagac cgcgtccccc ttgcctgtcc tgccctgcct cccctgcctc 960
ccccgcgcct ctgctgagca cgcccagagg gagctgcttg 1000

<210> SEQ ID NO 219
<211> LENGTH: 500
<212> TYPE: DNA
<213> ORGANISM: Homo sapiens

<400> SEQUENCE: 219
cacttgaaaa gcacaactca tggtgccaaa gctctgacac ggactccact ggagctgtgg 60
gcagggggtg ccaaggtacc gagttccaag ccgttgttat ttgagagcgt gcccccgcc 120 atgagagcag gtgggggac ataaagtgac acaggatgga ctggccaaag gctgaggacg 180
atcacttacc tcacaggatg atgccacccc cacggacagg caaggagctc tcaccttccc 240
caggacccca gctgccacca gagctccaga tggccctggg ggtgtctgta aagcctgtga 300
ccgtccacca ggtggagacc aggctggcca ggggagggag aggaagtgac cactggccct 360
ggcactggct ggccggctcc agcaggcccg aaggggaggg aggagcctgg gtgcaccaga 420
ctctctcaat aagcagcacc cagacactta acagatggaa agcggtggct tggaactcac 480
ttccaacgaa acaatagcac 500

<210> SEQ ID NO 220
<211> LENGTH: 1300
<212> TYPE: DNA
<213> ORGANISM: Homo sapiens

<400> SEQUENCE: 220
agcacctcct accccaccct ccccattcct gccatcccca gggtccaggg agcccagatt 60
ccagggaagg gttgcattag ctcccactcg gagtcctgat gcagcagaga cagacagagg 120
ccctgggaga agtgagcatg aattattaag acaagacaag ggtgaggccc cagagagggg 180
gtggcggaag ggtcatgttc atgcagcgag agttgcttcg agcttgaacc gcgtatccag 240
gagtcaagca gattgcaact ggcgagaggc cttcagaaat gccccgtgag agtcctgtgt 300
gcagagctcc atctcagcac acttcctgtt cttttggttc gtcgattttt gcattttcag 360
tcccctgtga tccattattt ataacagtgg agattggcct cagacactag cagtgaggaa 420
aacaaaagcg aagctacgca gaaaaatgac aagagtgatg agcacagcag tcatgacaaa 480
tgagccctgt gcggaggccc gggatccgcg cagatgccgg cgcgggggaa atgggccctg 540
aaatcccacc gtcaggccag gcagctctga gcgtgacctg gagggctgtt cagacggtct 600
gggtagccgt gtcctgcgca tgaacatcct ccgtcgggag aggaattccc cacggattat 660
cagagctgct ccctccaccc cccgccacgt cccacgcggg ccacatcaac tccctctgca 720
gcctctggcc agcggctgag ccctccgtgt ctcccctcgt taatgcctcc ttcaccatcc 780
cctcctgaag tttcccccat tgcatacacg cgctgaggcc cacccggtat caaggactcc 840
cattgcttgc gaaaaagatt ccacccctct tagaacagag accagggccg ctgtagcaaa 900
tggccataaa tgccacagct taaaacaaca gaaacggatt atctcgcagc tctggaggat 960
ggagtccaaa atctgaatcg ctgggctgaa atccaggtgt gggcagggcc gcgctccctc 1020
tagaggctcc cccggagatt cccttccttg cctcttccag ctgctggtgg ctgccagcag 1080
tttgggaatt gcggccgcat cacaccacct ttctgtttgt tgttgacatc cccgcctccc 1140
ctgcctgcgg ggtcttagat gtctctctcc ttcccactga gtttcactcc acatttgaat 1200
tggattaact catgccatgt taggcaaacg tgcccctcaa atccttccac ttaacagaca 1260
tttattgaag gttcctgtgt gcggggccca agagaaggga 1300

<210> SEQ ID NO 221
<211> LENGTH: 200
<212> TYPE: DNA
<213> ORGANISM: Homo sapiens

<400> SEQUENCE: 221
gaatgttcaa agaaagagcc ctccttgcct tcctcttctt ccacccctgc cctctgcaga 60
ctggggttct gtagaccccc aaagtaagtc cgccacaccg gaaggaagtg agttacacag 120
gggcccacat gggaaccgct ttttgtcctg tcttggtggg aaaatggcca cgaccccagc 180
ccaggctctg ccacgccaca 200

<210> SEQ ID NO 222
<211> LENGTH: 1600
<212> TYPE: DNA
<213> ORGANISM: Homo sapiens

<400> SEQUENCE: 222
ccatcttcct aggcctgcgt ttcccccaca ccggggactt gtgctggaaa gaaaagctgc 60
gttggcagcc aggagccggg gaaactgtcc agggaggcat cctctgcgat gaaggcgggg 120
cctcggcgtg gcccgttccg cgctctgtcc agccctggag aagccccacc ctcaccgagc 180
tcgaaatacc ccctccctga gagccgagac tcatggccgg gaccccttgg acagaagatg 240
cggatgctaa cccggcgctt ccaccacagc cccggcggca ctggggagcg agcgcggcca 300
tcccgcgcgt aggtggtgtt tctctgcagg cgccagtttc accgcgggcg cccaggatcc 360
tcaacggttc tgttgtgatg tgattcccct cttcgacttc gtcattcagc ctcagtccct 420
cagtccccaa ataccgaaag gcagtctttt tttttttttt ttgagacgga gtttcactct 480
tgttgcccag gctggagtgc aatggtgcga tctcggttca ctgcaacctc cgtctccctg 540
gctcaagcga ttctcccggc tcagcctccc gagtagctgg gattacaggc acctgccacc 600
acgcccggct aatttttttgt atttttagta gagacggggt ttcaccatgt tggccaggat 660
ggtctggaac tcctgatctc aggtgatcca cccgcctctg cctcccaaag tgctgggatt 720
acaggcgtga gccaccgcgc ccggcctttt tttcttttttt cttttgaagt taatgaactt 780
gaattttatt ttatttacag aatagccccc atgagatact tgaagacccg gtgccaagcg 840
acagtgttga ccccaggtgg tcagtcctgc ctggcccctt ccgagggatg cgccttcacc 900
ataaccatgt cacggacagg cgtgtgggca agggggcatc gctgtatttt tcacaactct 960
ttccactgaa cacgacaatg acatttttca ccacccgtat gcatcaacca aatgaaaaga 1020
tgagcctgtg acattcccgt gcgtagagtt acagcttttc ttttcaaaac gaaccttcag 1080
tttggagccg aagcggaagc acgtggcgtc tgacgtctcc agggagaccc gccgccctcg 1140
ctgccgcctc accgcgcttc tgttttgcag gtaatcttca gcaagtactg caactccagc 1200
gacatcatgg acctgttctg catcgccacc ggcctgcctc ggtgagtgcg cgctgcgggc 1260
tctgcccggt gacgccacgc ggcctcctcg ccttttcggg atggctggga ggggcgggaa 1320
gaggcgctga agggcccgag gcaccggcct tctacaaggg gctcttcgaa atcaatcaat 1380
gcgcagaatc ccgagggagg ctcagccgcc ctccgggcct ctctgcctcc acaggtgatg 1440
gctgtgtcca caaggaggaa accgtcgggc tgaattaaac agaaccgccc tcctaagagt 1500
gtgggttttt ctgccgggcg tggtgtctca cacctgtaat cccaacactt tgagaggccg 1560
aggtgggcag atcacctgag gtcaggagtt cgagaccagc 1600

<210> SEQ ID NO 223
<211> LENGTH: 400
<212> TYPE: DNA
<213> ORGANISM: Homo sapiens

<400> SEQUENCE: 223
aggcagcagg gttaggactt caacatacaa cttttggggg gagatgtact tcagcccata 60
acacaccacg tgggaggata acaccgattt cagagcttgc agaggaagcc gccaggaact 120
ccagtgagac atcagccccc aggtgcctgt caggcacgcc gggctgtggg gggcacctgg 180
gcccatctga gtaacggagg cgcatccgca cttcccccag gagtacattt ttagaaccca 240
cagcgccata aaccaaagac aaggagactt cctggtgccc cgtcagcttc tggaggcgac 300
gttctcggct gacagctctg gcagcctccc ctgtaggtga gagacaggta aatgggactc 360
ttgcttccaa aacggaacag ggtaaaaatt ctcaagcgtt 400

<210> SEQ ID NO 224
<211> LENGTH: 700
<212> TYPE: DNA
<213> ORGANISM: Homo sapiens

<400> SEQUENCE: 224
tgctgcaccc ccgctgccct ccctcccgct ggccggcagc accttctcca cccgggcccc 60
tctgctcaca gcgctccccg cccccgtctc cccgaggggc ggggagccag gacatggccc 120
tgaaagccta gccctggcct tgacctcccc agagcgccct ccccaccctc cgccctctgc 180
caaccctggc ccctgccctg gccccgtcct tgtcctctgc tgctggcctt ggggtcgcgc 240
cccgcagact gggctgtgcg tgggggtcct ggcggcctgt gccgtcccac gcctacgggg 300
atgggcgagg tccttcttgg ggcttctctt acccactctc cagtcacctg agggcgctgc 360
ttccctgcgg ccaccccagg tttctgtgca gccgaagcct ctgcctctgc ggccgggtga 420
tcccaagacc ccggggtcca gggaggcacg ggatctgctc ccccggtccc aaatgcaccg 480
gctgcgcctt aggagggacg gcctccaccc atggcgctgg cgcccagggg ccgctcctcg 540
gactacagca cttgctcgtc gccctgcgcc ctgtttagtt ctcatcacca gcagcctgga 600
ctagggccct ggtccttctg gcctccttcc acagcccgct gcacatctca cccacttccc 660
cgaggtgctg tcattgttta gctgggcccc tcagcctccg 700

<210> SEQ ID NO 225
<211> LENGTH: 300
<212> TYPE: DNA
<213> ORGANISM: Homo sapiens

<400> SEQUENCE: 225
ttaaagggga gtggttgtat gaagagttcc tcagtcaaag gtgtgcagct gggaagccca 60
ccccacctaa gagggaggtc tgacaaactg tccacactga accactcaga cctgcatcag 120
ggccccgttt cttccataag ccgccaagta cagccctgag tcaactgaac tcaggcctgg 180
gaggcttccc aaagctgact tgactcagct ttgaactgaa atgaccgtac catgacaacc 240
ctgatgaaaa gctaaactga gcccaattat tcaacagtaa aattcagttg gtctcactca 300

<210> SEQ ID NO 226
<211> LENGTH: 450
<212> TYPE: DNA
<213> ORGANISM: Homo sapiens

<400> SEQUENCE: 226
tgctaccagc tgcttgggct tgggcaagtc accctagctc tcagatgtca tctgtaaatg 60
atgacaatgc caatgtggca ctgttctgag agtcagacag aacgtatgtg tgcttcacat 120
atggtgctca tgaagtgcta tcattatcta aggaaaacag aaaacgaagt tcagagtctc 180
tctaaacgca tgacaccaga ccaacaggga gtttcaaaaa ataggtctga agtaaatcaa 240
ttctcctggt ctcaatacac tgaaaacaaa ctattagggg actgaccgaa cccaccttag 300
gaaccacctt acgtcacctt ctgtctctac tgcaaaaccc tcccttaata ctgttcaaat 360
acgctgacaa tccagatcca tatccaatgg aaccagcaat catgcctgtg tgccagcaat 420
gtcagggagg gaagccgatc tctgatgaat 450

<210> SEQ ID NO 227
<211> LENGTH: 1000
<212> TYPE: DNA
<213> ORGANISM: Homo sapiens

<400> SEQUENCE: 227
caggtgccgg ccaccacacc cggctaattt ttgtgttttt agtggagaca gggtttcgcc 60
atgttggccg ggctggtctc aaactcctga cctcatgtga tccacccgcc tcggccttcc 120
aaagtgctgg gattacaagt gtaagccact gcgcccggcc aagagtgaag ttctgatagc 180
tggggtaaga aaggccgtgg gaacagccgg tttcagacac gctgggtcta agacgctgcg 240
tctggcgctg ctcggcatcc aatgggagcc gtggagaagc caggcgagtg cgtagggcgg 300
agccagcgca caggaaatag gacgtgatga ggtcaaccgg ctggtccaag tgtggacgga 360
agtagaggat gcaagcaccg agccccgggg cccccagcat tggcggggag gagctcgcgg 420
tgcgggagaa gcaggggacc gcgcatcctg gagaccaggt ggagccagtg cgcccggaag 480
gggcgtggcc cgctgacagc cgcccaggag gccgggggag gcctggagcc gagggccgcg 540
cgtggcaatg tggagagaca ttttggtgga gtcatggggc cacagcctga ttggtgagaa 600
caggaaggga aattgcagat gggcctgggc cccctggctc ccgcatactc caggaccagg 660
gctgagtcat cgttcaccgt gtgtgaccag ggccccgtgt ggccggctgt cactcggtat 720
ccagttaccc tgggcagacc actggcggca ccccccagcc agaggccgca gcaacacaca 780
cgcctgcagg cgaccaggcc ggactgcatg ccccgtgggg gaactgaggg cgtttcagta 840
acagagtgtt aggggacacg ggttgggtgg cttggaaagg gcctaaggtg gggtttgttt 900
tagattgggg tggtgagggc gcaggggccc ggtaggattc tctaacaggg cagcagccac 960
tcatttagca acaggagagg cgtccagcgt ttcgtgggct 1000

<210> SEQ ID NO 228
<211> LENGTH: 3100
<212> TYPE: DNA
<213> ORGANISM: Homo sapiens

<400> SEQUENCE: 228
acccaaccac aggcctcctc tctgagccac gggtgagcgg tgcaggttct gctgttctgg 60
agggcctgag tcccacccag cacctcataa acagggtcct ccccagggct gctgcagtag 120
gcatcaacgc cagggtgcaa aatgcctcag ggagccaagg ctgagccagg ggagtgagaa 180
ggagcatgtg gaagtgcgtt ttggagaggc agctgcgcag gctgtcagca ggctccggcc 240
gcttctatag acagcatgac accaagggca gtgacctcat tccacaggct gagtccagcc 300
agccagccaa gcatcaccag ccagacgatt gaccctaacg gaccaaccaa cccgtaacga 360

-continued

```
cccctcctac cataaccagt agccagccag cccataacca gccaacttat ctataaccag    420
ccacctgacc atagccaaac aaccagccgg cccaccagta gcattcagcc cctcagctgg    480
ccctgagggt ttggagacag gtcgagggtc atgcctgtct gtccaggaga cagtcacagg    540
cccccgaaag ctctgcccca cttggtgtgt gggagaagag gccggcaggt gaccgaagca    600
tctctgttct gataaccggg acccgccctg tctctgccaa ccccagcagg gacggcaccc    660
tctgggcagc tccacatggc acgtttggat ttcaggttcg atccgaccgg gacaagttcg    720
tcatcttcct cgatgtgaag cacttctccc cggaggacct caccgtgaag gtgcaggacg    780
actttgtgga gatccacgga aagcacaacg agcgccaggt gagcccaggc actgagaggt    840
gggagagggg ggcgagttgg gcgcgaggac aagggggtca cggcgggcac gaccgggcct    900
gcacacctgc accatgcctt caaccctggg agagggacgc tctccagggg accccgaatc    960
aggcctggct tttccccaag ggagggggcg tgcccacctg agcacagcca gcccctcccg   1020
gtgacagagg tcaccattcc cgagctaatg tggctcaggg atccaggtta gggtcccttc   1080
ccgggctgca cccagccgtc gccagctcca tccctgtcac ctggatgcca gggtggtctt   1140
agaaagaacc ccaggaagtg ggagtgcccc gggtggccgc ctcctagcca gtgtacatct   1200
tcacatgaac cctacctgag gaagccagtc cccgacggca tagctgcatc cgcttggaat   1260
gctttacagg cattgacacc ttcgcctcac agcagcactt tggaaccagt gtcctcatta   1320
ttccagggca cggctgggga acaagggggt cctcagcctg ctgggtccca cagctagtac   1380
cgggcaggtg gacgggagct tctccccaca gtcaccctga tgccccgctc ttgctcggct   1440
ggaggcctcg gatctccgtg gtgttgaggg agccggggca ctggagccct ggtgacctgc   1500
atctcctggc ggagccggga agagctcatg gactgtcaca gatggacagt gccccgcggg   1560
ggctggagag cagagtgggg ctggaaggtg gaactcttag ccaaagtctt ggtttctttt   1620
ggccagggtc ctctttcaat ggctggagaa ggtggtgctg gggggtgaac gctgacctcc   1680
tcatgtgctg cccctccctc gcctgggccc ggtaaagccc ccacgtagcc ccagccagcc   1740
tggaacatgc ttcctgagct cccagctctt ggtctttgca cccagtggag gaggaggtca   1800
gcccagggag ctgagtctgc ggtttagggc gtccagggga cgtggaagca tgtgggtcgt   1860
ctggccacat taggtagggc tgcagagacc tgggctagag cagtcctgcg gggtctggaa   1920
ggggaagact ggctgaggtg cggggcctgg tctggaatga tcctgcgatt ttggagtgaa   1980
gccatggagc gggaagagac aaccccccgc ggggaatagc ccggcaagtg gccacgaggc   2040
caggctgagg tccagagaag caggggcatg aatccataaa tcccaggggg cctggccatg   2100
ggatgtgctg gctgcacccg gcccctgtga gagcccccgc aggctggccc ccttctgcag   2160
tcagtggggc tggggcagct tctctggcat ggggcgaggc agccgcctgc acagtggccc   2220
ccctgactgt gcgcccccac cctctccagg acgaccacgg ctacatttcc cgtgagttcc   2280
accgccgcta ccgcctgccg tccaacgtgg accagtcggc cctctcttgc tccctgtctg   2340
ccgatggcat gctgaccttc tgtggcccca agatccagac tggcctggat gccacccacg   2400
ccgagcgagc catccccgtg tcgcgggagg agaagcccac ctcggctccc tcgtcctaag   2460
caggcattgc ctcggctggc tcccctgcag ccctggccca tcatgggggg agcaccctga   2520
gggcggggtg tctgtcttcc tttgcttccc ttttttcctt tccaccttct cacatggaat   2580
gagggtttga gagagcagcc aggagagctt agggtctcag ggtgtcccag accccgacac   2640
cggccagtgg cggaagtgac cgcacctcac actcctttag atagcagcct ggctcccctg   2700
gggtgcaggc gcctcaactc tgctgagggt ccagaaggag ggggtgacct ccggccaggt   2760
```

gcctcctgac acacctgcag cctccctccg cggcgggccc tgcccacacc tcctggggcg 2820
cgtgaggccc gtggggccgg ggcttctgtg cacctgggct ctcgcggcct cttctctcag 2880
accgtcttcc tccaacccct ctatgtagtg ccgctcttgg ggacatgggt cgcccatgag 2940
agcgcagccc gcggcaatca ataaacagca ggtgatacaa gcaacccgcc gtctgctggt 3000
gctgtctcca tcaggggcgc gaggggcagg agggcggcgc cgggagggag gacagcgggg 3060
tctcctgctc gcgttggacc cggtggcctc ggaacgatgg 3100

<210> SEQ ID NO 229
<211> LENGTH: 1000
<212> TYPE: DNA
<213> ORGANISM: Homo sapiens

<400> SEQUENCE: 229
tttttgtgtt tttagtagag atgggatttc accatgttgg ccaggctggt ctcaaactcc 60
tggcctcatg caatcctcct gcctcagtag tagtagttgg gattacaggt gtgagctgcc 120
atgcccagct gcaggtgcgg aagctggggg cctcagagac tgtggactcc tggccggtga 180
ggagcggcat gggccgggag agctgactct tcagcgggac tgaggtggct ggagcgtgac 240
cctttcctga gggcaaacag ggagggcctt ggagcccggc gctcaggaca ggcccctgct 300
ggcccggcag cctgagcttc cacacttttc cagggcgtct cgagttcgcc cacagagctg 360
ttgtttcagg ataaaaaatg cccttgtatt ccacgttcca gttcagaggc ccgtctgttc 420
ccaagagcgg aggcgtcagc cgcatgagtc ccaccggaag ccgggttgcc gggtccccgt 480
ccctgccctg cagacgacgc attccggagc cccctggga agctgcctgg ctctcccagg 540
cctggctgcc ttcgcacgag ggctccgagg catgctcatc ctacgtgact gcccgagtgt 600
gcacacgcct ggccgtgtgt gggcgtgtgc ctggggcccg agctcaggag caaggcctgc 660
gtggacctgt tgtctgaaac aagccagtag acagctgcgt caatgcaggc aagctgaaca 720
gggctgcttt ttcagcctga caaccccagg ggctgaacag gagctggggg aggagcaagg 780
ggccgttccc ctgccccaca gcacagcaca cgaccccgcc ttggaacctg gggcccgggg 840
tgaatcgagg gtcctggagc aagaggggct gctccacagg agagcctgtc ccgccacccc 900
tcagccacca gattcggggc tgctggactt gttctcaaac ctgcacagtg agtgacagct 960
gctgagacgg aggtctcagg cagtgcaggt gaatcagcat 1000

<210> SEQ ID NO 230
<211> LENGTH: 500
<212> TYPE: DNA
<213> ORGANISM: Homo sapiens

<400> SEQUENCE: 230
tccttatttt ttagttctca agccctgtag ggtgttttcg gtcgcagttg tttgggctgt 60
ggtcctgacc ctcctgagtt ccagtggctc tgttcaggag agctgcctgg ggccgggact 120
tctgaaacac acactgagcc acaggccggc ccggcggctt gggttcaccg ccgcctcttt 180
gtgtgtgatg tcctgggata ggcccgtgca cgttcagatg acactgtaca tataaataac 240
ttgtagccga gaacaggatg gggcggggag gaggggaggg cagaacgtac cacagcagca 300
gaagtcactg tggatgcctt cgtaagttgc atggaaggtt tttaaaccta gccctgccga 360
gcagccctct cctggtccgg gagaacgatg gggagagagc tggcgttcag ctttcatcac 420
tggagccgtt ccttcttccg gccccccgag ggcctgtcca tgatcacact ttgtcttgtt 480
tcgggggtgg cccctgtgac 500

<210> SEQ ID NO 231
<211> LENGTH: 1300
<212> TYPE: DNA
<213> ORGANISM: Homo sapiens

<400> SEQUENCE: 231
caagcctgtg gtagggacca ggtcagagta aacaggaaga cagctttcgg ccaggcggtg 60
cacctcggtg ccggtgagtg tgagcgtgtg tgcgtgtgca cgtgtgcaga tgtgtgtgga 120
cgctcccttc tccgcagcag ctcctgaccc cctgcaggtg accctcagcc agccccaggg 180
ctgcccccac tctcccctgt ggacacctac ctcatttggg gtgaagtggg gggactgggg 240
tgtgaggggt gctttggggg gcacacttcg acccctctct ctgcaggcca agtcctgagg 300
ctcagtttcc tcctctgtgc cccggcgacg tggtgcaggc ctcgcgagtg acgtgagggt 360
tcatgaccca ggtgtgggca gccagccctt cacgggaggc cacccacctg gccacagtgc 420
ctgggaattt aggtcgggca ctgccgatat gtcgccttcc acaaggcggg cccgggcctc 480
tgctgaccgt gcaccggtcc tggggctggg taattctgca gcagcagcgc agcccatgcc 540
ggggaatttg cgggcagagg agacagtgag gcccgcgttc tgtgcgggaa ctcccgagct 600
cacagagccc aagaccacac ggctgcatct gcttggctga ctgggccagg cccacgcgta 660
gtaacccgga cgtctctctc tcacagtccc cttgcgtctg gccagggagc tgccaggctg 720
caccccgcgg tggggatcgg gagaggggca gtgtcgccca tccccggaag gctgagcctg 780
gtgcagccag ggagtgaggg ggcgggaagc cggggtgctg ccctgagggt gccccgacac 840
gctctcctgg ggccctgagc ggctgccacg tgcgtccagg gttctggcca cagggtgggc 900
aggggccctg tgctcctcac tggaggcccc tgaggctctg gaactgagac catccacccg 960
ccggccccct ctcgccggct ccggcacccc tgcctactgt gacttcctgc cccggactcg 1020
ctctgccagc ttggggcaaa ccacttccct ctggggtttt cacttccctc tttcccaagt 1080
ggggaaagac cacctgtccc cgacccagaa agggcccctg cccgagggca gcagcagtgc 1140
caggctggca tgtgaggctt ggggcaggcc cggcccccag aggcacaggg cgatgctctg 1200
tgggacgctg tgtcgtttct aagtacaagg tcaggagagg agccccctga ccccggaggg 1260
gaggagaggc agggcaggaa accgccacca tctcagccca 1300

<210> SEQ ID NO 232
<211> LENGTH: 200
<212> TYPE: DNA
<213> ORGANISM: Homo sapiens

<400> SEQUENCE: 232
gcccactgtg ggtgtgcccg tgtgtgtggc tgtgaggcgt gagtgcaggc gtgaagtgtc 60
tgggagtggg agcgggcatg agtgtgtgcc acgggcctgc tgttgggtcc ttggaggcca 120
cggttgcccc tgaagggact gcaagctctt ttttgatttg tagttatttg agaagtctat 180
acaggaagaa aattaaaccg 200

<210> SEQ ID NO 233
<211> LENGTH: 1000
<212> TYPE: DNA
<213> ORGANISM: Homo sapiens

<400> SEQUENCE: 233
agcgcccagc gcagggccgg gacccagagt ggactctacc gtggggctgc ctcaaagaaa 60

```
tctcagcaaa cacaggaagc cagcccaccc gtgcagccat ggggccagga agcccgccct    120
ttaccaagtc atttgggcat tttttctctg tgctaacagc ccagatggag ccatagcctc    180
aacctctgtg ttctgataac accaagctgg gacgccggag ccatgcaggg gacagtgccc    240
ggcctgaggc tgcagcctgg gtctggatgc ctttctaatt cagggcctcc tcatggcctg    300
gttccataaa tggtcaaatg cagcctgaca gcgcagcctc ctatcagcgc tgggctccgt    360
accgccacac agcccacata ccccgttccc caggagacgc ccgcaggtgg gcagcgtcac    420
tcccacccgc cgagcacacg ctgtccccgt ctcgtgtccc gaggagccgg aagcagctgc    480
ttcctcccag cctgaaagct gcacctcggg ctgcactcgg ctccccgaac ccgccctccg    540
ctgccctgca attcgccaag ggagctaccc ttcccatata aaaatttcac ctccatttcc    600
ttgtagagaa gaaacatttc tgacagcaag gaagattcta atttgaaaag caagtgattc    660
atctcccggt gccaaacagc agacgcaggc gttaccagtc tgggtggggc gcccgagctg    720
gggacctggg gtcctctggg aggggcaaga aggcagcgat gctggccccc gcctccatct    780
gcccatccca tctgcttcca cacaccgccc tgccgtagct gcttgcagcc cttctctgtc    840
agtttctcca tcttttggtt tggtgataaa tgagagttcc catcgggtgt gccaccctct    900
gtgtgacggg gagcagagaa gaccctgcgt ccaagtcctc ctgggggaag agcgaagatg    960
ctgggaccag ccccagctgt caggggggtct ccaatcccag                        1000

<210> SEQ ID NO 234
<211> LENGTH: 1300
<212> TYPE: DNA
<213> ORGANISM: Homo sapiens

<400> SEQUENCE: 234

ggaacggaga gccgccaggc ccaaacctcc cagaatttgc gcagtattct cggcctagag     60
agcgaggagt ggccttggcg aggtccctct ttggctcttc tggcttagcc ggggttttaa    120
acttgttatc tgcaaagcag aaggaaagtc agcccctgat gtaagtgtca agtaaaataa    180
atcggatggg tcctttcctg tttggcgagg aatgctacac taagggggac tgcgttcaaa    240
tgggcagtct ttgctggaaa cctcgcctcc gcgcgccttc cctcgctcgg attcaggcgc    300
ttttacgtta agggttgaat ttttgtgtca acaggcacct cgggaggtcg cctagacaac    360
tgagcggagc aactgagata acccccgcta cgtgtggagt gacctagtcc attaacttgc    420
cccagcacgc ccgctgagtc cgcaaaatat aggatggcct cgggttttag atgaacccaa    480
agctaagatt tcttccctct ctggaattag caagcagccc gccctgccca actcccctgg    540
aagcgcgcgt gctcgccagg cctcgggacg cctgcgcggg cgcccttgca ctggcaccag    600
ggctccgggg taggggcgca ccgatctgcc caagcctctg caggcactgg aggaaggcga    660
gccctccacc cgctcaacag gccccagtgc cggcctttcc ttccagtctc aactccaccc    720
gggggcccgg gggctccaca gttaaaaact ccacgccacg gagatcgcag gtaagctgct    780
ggctcaacga ggtgtgctaa atgggattaa agatcctgga ccgtggccag gcgcggcggc    840
tcaagcctgt aatcccagcg atcagggagg ccgccgcggg aggattgctt gagcccagga    900
gtttgagacc agcttgggca acatagcgag acaccgtctc tacaaaaaaa taacaaatag    960
tggggcgtga tggcgcgcgc ctgtagtctc agctacttgg gcggtcgaga tgggaggatc   1020
gatcgagtct gggaggtcga ggctgcagtg agccaggatc accgccaaga tcgcgccact   1080
gcattccagc ctgggcgaca gagggagacc ctgtctcaaa aacaaacaaa aaatcctaga   1140
```

ccgtttacaa acagccttcc gtctcttcct ggtcaagtcc taaccctggc taacctcgcc 1200
gtctacagcc tgaattttgg caaccgaaag gcagcgccgg cgccacgtgc acacgggctg 1260
ggccgctccg ccagctgcca gggccactgc cgcgctcact 1300

<210> SEQ ID NO 235
<211> LENGTH: 300
<212> TYPE: DNA
<213> ORGANISM: Homo sapiens

<400> SEQUENCE: 235
cgcacacaca gcacagacgc ctgcatcttc ccatgcgtgg tttctgctct tgcctctctg 60
ggtttttgtt tcacttcggt cgagtttttg gtggtgttga gcggatagcc ggggaagttg 120
gagtcttgtt tgtggccgcc tcgtgctcgt gtctgtatct aagatcctca ggctgctcct 180
ttttgggtaa ggtctgttgc ttctctagga acagtgacgg tggcagagcc cgtggcccct 240
ctctcctgtc ccagagccaa gctgtttcct ctccccactc ccgggcaccc tgcgggcaag 300

<210> SEQ ID NO 236
<211> LENGTH: 1000
<212> TYPE: DNA
<213> ORGANISM: Homo sapiens

<400> SEQUENCE: 236
cacagcccag cttcaagcct ggccgaccag gggtttggca tgaagacccc ggcagggctg 60
gggctgtgct ggaatccacc cggaagtttc ctgccccttg ggctgcccac caggtcccct 120
ttctgctctg atcaagctgg acaaaacgtc gtggggccac agcacagggg gccaacgcaa 180
gctgggatcg tcagacgtta ggaaatccca aggaagaaga gaaaggggac acattcggga 240
gacgtcggca cacgctcgaa gcagcggaca ggcacctctc tgtggacaag gcagactggg 300
cggccgagat tccgcataga tgcctgcttc ctccacgacc tccacgtgtg gctggcccag 360
tccgggtccc cctcacctcc tctgtctgtc ttggtggcct cacgccgtgg gctgtgatgc 420
cggctacgct gcttgggtgg ccaagggtct gagctgcaag acgcccagcc tgggtctctc 480
ccgagctctc ccacgtcctg tctgctcctc ctccgagctc ccggttgact ctcacgactg 540
caccagcctc tcccccagga aggcgtggaa acaacctcct tctcccaggc ccgctctgcc 600
tcctgcgttt caaggcaaat ccgttcctcc aggagatgat gcaaccacat cctgttggag 660
cccagagaag tgcggatgca gcccggggct ctttctttcc tagaaccctg cctgggagtg 720
gcttccctga actaaggaca gagactttgt cttcgttgcc tctcggcctg tgggcactga 780
gcatacagta ggtgctcagt aaatgcttgc aggccgatgc ccagagccat tagccctcat 840
catggtgagc tcggcagccg gtgttggggc tgggctgggc ctaggtgtgc gtgggggcgg 900
tgctggtctg ctttgctggg agccatggac accggaggaa cagggcccca tcagtgcggt 960
cagagtgcaa actcggagcg tccttctctg gaaaacgaat 1000

<210> SEQ ID NO 237
<211> LENGTH: 500
<212> TYPE: DNA
<213> ORGANISM: Homo sapiens

<400> SEQUENCE: 237
gggagggggc gtggccagca ggcagctggg tggggctgag ccagggcgat ccgaccccga 60
accggagctt ttagcacttt gagtccctgt actcagaggt ctcctgcagc cgggaatccc 120
actgtgctgt ggtccctggc agccagcacc cacccccagc ttctccgtca aggttgagga 180

-continued cggagcactc ctgcctctga ttaactggac gcaggagaag cagttgcttt aatccggagc 240
cttgagttgg gacagataat gagtcattca accagatttt ccaaggacac actaactttg 300
gtatgatgcg tgtgtgcccc tgaatccacg tggtcaggaa agcccaggga acactggcct 360
gtgactcact gagcaggttc ccttgttacc ccgaggggtg atttactcct ctgacagtga 420
cacggacact gtgcgtccat tccccgggcg ggcagaggac actcccagat gcccacgagg 480
ggcccagcaa gcactggcca 500

<210> SEQ ID NO 238
<211> LENGTH: 600
<212> TYPE: DNA
<213> ORGANISM: Homo sapiens

<400> SEQUENCE: 238
ctgcaggacc tgctcgttca cagatgttct cctagaagca gaagctgttt cttgttgcaa 60
acaaatttgc tgtgtcctgt cttaggagtc tcacctgaat ttaccaagga tgcatctgtg 120
cttggggatg gctcggtttg aggggtctga ggagcggctc ccctggatcc tttcctcccc 180
aggagcccac ctgccgagct gtcagcgtca gccccacatc tcaagatgag gaaatggagg 240
tcgaagccat gcacacgcag gcgtcctgct gacatgcagg ccaggcgggt gcctctgtat 300
tcagcagcct cagggctgtg gccagttcag gcagcagagg ggcctcatcc cggtgcttcc 360
ctgcaggcag ttgtggggcc ggcctgcagc aggggctcag acagggcctt gggagaggga 420
gggatcacag aggtgtccag tgacaggcag ggcgggcaga gcccatgggg ccttgggctc 480
ctcactcctt cggtcagtca gggtgacatc tggagccacc tccattaatg gtgggttatg 540
atttggttcc catgcagccc gtgccagctc gctgggagga ggacgaggac gcctgtgatc 600

<210> SEQ ID NO 239
<211> LENGTH: 5000
<212> TYPE: DNA
<213> ORGANISM: Homo sapiens

<400> SEQUENCE: 239
aagaggaaat tcccacctaa taaattttgg tcagaccggt tgatctcaaa accctgtctc 60
ctgataagat gttatcaatg acaatggtgc ccgaaacttc attagcaatt ttaatttcgc 120
cttggagctg tggtcctgtg atctcgccct gcctccactg gccttgtgat attctattac 180
cctgttaagt acttgctgtc tgtcacccac acctattcgc acactccttc cccttttgaa 240
actccctaat aaaaacttgc tggtttttgc ggcttgtggg gcatcacaga tcctaccaac 300
gtgtgatgtc tcccccggac gcccagcttt aaaatttctc tcttttgtac tctgtccctt 360
tatttctcaa gccagtcgat gcttaggaaa atagaaaaga acctacgtga ttatcggggc 420 aggtccccccg ataaccccca gctgcagatc gaggcctagt gcgagcacag gtccccccag 480
acccttccca gtgcccacca accggcggcc taggccaggt agaactggca gcgcctcccc 540
tgctgcaaca ccaggctctg gtagaaactt cagaaaacat gcaccggcaa aaccaaggaa 600
gggtggctgc gtcccgggtt cttccgcgca gctgtgtgta cacgcatgca cacacccaca 660
cgcacacacc cacgtgcaca cccccatgca cacgcaccca cttgcacgcc catgcacgca 720
cacacgcgcg tgcacccatg cgcacgcacc catgcacaca cacgcgcgca cacacccacg 780
tgcgcaccca catgtacaca cccacgtgca cacacccacg cgtacacacc cacgcgcaca 840
caccgctgtc cccagccgtg cagaacgatc ctccctgagt ccccggctcc gacccacacg 900

```
cagcactcgc taaacgcttc ccacgcagtc gttttgctgg gttgcgcttc acccacttct    960
cagaggggc ggccgaggca gaggtgtcgg ggatcgagca gctccgggcc tcaggggtcg   1020
ccccgccacc gttttccttt cccagatgct gggacggggg cagggagggg ctccccaggc   1080
tgaacccgac taggtcaccc tagaagcgag gcgagcttct cttctgtttt tcttcggcgc   1140
ccctgagccc ctgacagtgc ccaagctgcc catgggattg gattcgccag agcctcctac   1200
gcagacccca cccagggcca aagccaaccc caagccccac caccttggtg gtgtgggatg   1260
aaaagtgagc catcgagaga tggggtcccc ccaccccaa cccctccaag gacaaaggcg   1320
ggctgggaag cacccgcttt cacgtccgcc cctgcccggc tttcctagcg gaattggcgc   1380
cggcatcagt tgggggttgt gggatcagtg aggaatcccg tggggtcgcc tccatttatc   1440
agttgtgtgg ggttgggcga gcacccctag ccccagccca ggcgatcagg gcgcgaagcc   1500
cactggacgc ggatttggga ttaggacggg ggtgacagcc aggaggaccg cacctgccct   1560
ccccactcct gccgctccac ccctgccccc accgcaacac caaggtctcc accaggaaga   1620
tgggggtggg gaaaggacgc ggggtggggg ggggtgcggg gagagaggac acagggtcgg   1680
aagggtgagg ggtagtggca gaggcggagg ccgaggccac gcagctgcgg ggcgcaggga   1740
ggggcagagg aggggcgttc agatgggaac ctagtccaga cccgtcgggg ccctcgtgtg   1800
cggctcgtta tcctggaacc agagaggctg gagacccttg gcttgtctgg agcggaaccg   1860
tagtgtccaa tagagtgtgt ggggctcagc cctaaagcta aacattcttt atttcctgat   1920
gaccatgggg gcggagcggg ggaaaagccc tggccttata gtttagaatt ttataaaagg   1980
aaaggcgtgg ccactgacaa tttgcgcttc aggagtccca gagtgaccgc ctggctcgga   2040
gcagggaatg agggggtcct taactctgag atttgttttc tgagagacaa aggtgatggg   2100
tgaggcggct aagcctctga ttctctatag gtggcggtca ttcatttcag aacatgaatg   2160
gattcagtaa ataaacatga tagaaaaatg ccacaagccc taggcccatt ggagtggact   2220
ggacagtctg ttcccagtgt gtccctcagc ctcggtcccc caccccttccc ggagccctgg   2280
gggtcacaca catccctcct ggctgcctag cctgtgcccc ccgattcccc ccctccccgc   2340
cccgcgcgtg cacacacaca cacacacaca cacacacaca cacacacacc acacagcacg   2400
aggcgacaga gatatgagag agagcgagcg agagaggacg ggagagagag ggagtgcaag   2460
tgtgcgctgg gggtaacccg tgcatgcatg cattgggggt aacaggctgg agctcagatc   2520
cctcccccag cccccagcag gggggactgc aggctcctgg tctgagtggg gagctgggcc   2580
ccctggacag aggactgggc tgcggggtca ggaatgggca cacttcctaa ctgcaggaca   2640
ctctaagggc tttggtcatg cacacgcagc caagagaagg tgtcgctggc acacagcctt   2700
ccaggagcgg acttggagac ctcgccaagg accaggactc cccagcactc acactccctt   2760
aggcgctgaa gtccagagga cagaggttga gggcagagct cctgggagca ccagtggaag   2820
taggagggct gggctggaaa acctccccca acctcctatt gcaaagaggc tccagccagc   2880
agcctccaca ccccagtgat cttttaagat gcaaatctgc gccatcattt atttcctcag   2940
tgccttctcc agctcctggg atgcacactg cccgtcccca ggcccagaga cctgaccacc   3000
ctcattcctc cctcagccca ccctggggtc tctccaccag ctgacagcct tcctgcagtc   3060
ccctccccga atgctgctcc ctgaggccct cctggacacc tgcagggcag gcacagcccg   3120
cgggacctca cagcacttgc tccgggcaga gctgcagttt ggccaagttg ccagctccgt   3180
gtgggcaggg gccctggcct gtggctgcca catcccgggt gggggcacgg cctttcctgg   3240
cgtggatgct gagcaaacgt agggggaagg ggagtgaatg aggagagcca ggtagctcag   3300
```

-continued gggctgaggc ctcactgagc agggtcccgc gtgaccggtc cccaccgctg acggttcctg 3360
gggtaacact caggacaggg agaggcaatg gaaagagacg tggccgccct cgcatcctgc 3420
agctcccgca ctcccagcct cccagcctcc cacccagccc cccagagccc accagtgacc 3480
ccgcccactg ggtcctcaga tggctcccac gggatctcct gccttgatct cctgtccaca 3540
tggaggtgaa gtgggttgct ctgaatgagg ggtgccgagc ctagggcgca gcccactctc 3600
ctgggtccgc agcatcacgc agcccggacc acaggctcct tacaagaatc ggaagggtcc 3660
ctgcaatcgc ccttcgcact gaggcttcct actgtgtggt gtaaaaacac aggcttgtcc 3720
tcccttgctg cccacggggc tggagccgcc tgaaaatccc agcccacaac ttccccaaag 3780
cctggcagtc acttgaatag ccaaatgagt cctagaaagc gagagacgag aggggaatga 3840
gcgccgaaaa tcaaagcagg ttcccctcct gacaactcca gagaaggcgc atgggccccg 3900
tggcagaccc gaacccccag cctcgcgacc gcctgtgacc tgcgggtcaa ccacccgccg 3960
cggctccacg ccgtgggcac agactcaggg agcaggatga gaaagctgag acggcgcagc 4020
cacggcccgg tgccttcacg cgcacagcga cacagcccca gccagcgggg cccacgctaa 4080
ggcggaatcc cacagaagcc tacagagcga gcgcgcgcct gtgcttccca aaacggaatg 4140
gaaccaaggt gacttctaca gaacgatctg aagccctggc tggcccttat gctagtctct 4200
tgggagcgtt ccaaatgcag ctcaatatta cttacttgac ttttatcttt cctccctggt 4260
tcgtggtatt tataactggg tcatctttta actatttgca acgtagcttc aggggagagg 4320
gggagggctt tataaataac ctgtattatt attatgcagg ttgattctgt tccctgagct 4380
aaagggaaca tgaaaataca tgtctgtgac tcatgccccc ccacccccac tccagggtgt 4440
gctgaggagt ctctcagctg ccccggggtc ctcgagcagg ggagggagaa aggctggcgc 4500
tgcgccctcc atcgcgtgaa gccaggggat tttgctctgc gacaagctga cttggctctc 4560
gtattgtttg cagaatcacc cagttccaag gcagtccctg cgggcaggtg cagctgtgcg 4620
ggagcttcag tcctgtcccc aacacccagg cagtaatggt tccagcacgg aaggtctacc 4680
tacctcccac tgcacagccc gagggctgtc ctggaggcac agccatccgt ccctgggtgg 4740
gcaggcacgt ttatgacccc cacccccacc cccaccccc acgcgagtca gcacgttcca 4800
tactcgggtg atcgtgctca tcccctggtc atgtcatcgg gatctgagtg ccatccgagc 4860
agagagctgt ggcccggtgc cgggggtgga cttcatctat tccagggaac caaggatgca 4920
tgatttgcaa acaaaaccag aagcgcaagc catctcctcg cctcccctga tagccgtgct 4980
gcggagcctg agtgctggag 5000

<210> SEQ ID NO 240
<211> LENGTH: 600
<212> TYPE: DNA
<213> ORGANISM: Homo sapiens

<400> SEQUENCE: 240
caggaaccac gggacctgct gcctagcggc cctgttccac ccttggccgc tcgcaaaatg 60
tttaggcttc ataaggtttg cccagggtca caaatttaac tcacagcaaa caatgaaatc 120
agcgcatgat tttcgagccc tcgtggtcac cctcccttcc tcctgccctt tcctgcatgg 180
gcagcagcag ggtgaggagc tgctctcccc aggcccaggc tggagtccct cagacgacct 240
gccggccagg gtaccccccct gcccccacac agcgcctgac agagcccccc acactggggg 300
aacgtgggga cccaagcagg ggcagcggcc tcaccgggca ggcggcgacc tgcatcatgg 360

```
cgtccagccc accctcgggt gcatccaggt ttccggaaat cagctgcttc ccgacctcgg    420

tctgaaactg gttggagttg ttggtcagct tcagcacgtg cctgaaggca aacgggggct    480

ggcactcttt ctccttgttg gggcatgggt ttcgcagctt atcagggtgc gtgttcacga    540

acggcagcac ggtcttgtcc acgaaggacc cgaagcctgc agggcacatg gaggggctgg    600


<210> SEQ ID NO 241
<211> LENGTH: 400
<212> TYPE: DNA
<213> ORGANISM: Homo sapiens

<400> SEQUENCE: 241

tgcgtttagt gtaaaaatat caggtgtggc tgcacggagt gaaaaatcac aggctccacg     60

gagccgggag gcctgctgcc ctgccctctt gctttgatga ggaaatggcg accgcagaag    120

gaaatgtagc agcaccggca accggcatcc gtggggccac gccgggctgc ttcccagggc    180

cctccagcca agcagccaca ggaaagagta gatgttgatc ccaagctagg actgaggagt    240

ccgtccctaa gagccgaggg agtcaggtgg gcgaaactgg ccgcatgtct gggtacaact    300

gctcagggtt tctcatctgc tgaatcacca agctaggttc tgaagccagg cgtgagtgag    360

caggactgga gcaggattct gggaacaatc ttttccctcc                          400


<210> SEQ ID NO 242
<211> LENGTH: 2000
<212> TYPE: DNA
<213> ORGANISM: Homo sapiens

<400> SEQUENCE: 242

gctggggaac tgaaggaagg gctgtggagc ctgaagcctg ggcctggcct gtgctgcggc     60

cgcaccgctg ggtgatgcag gagccactcc acctccctgg caccccagcc tcatccggca    120

acctgggagc gtgggcctcc tgcccctcca gggaggccct ggccgtgtcc tcatggggcc    180

cctccaggtc cttgtggctc caggtcggga cagtggctgt gagatctgac cctcccgttc    240

cccctccacc aagtaggaga aaccccggag catgagccct cgtccttcac cgtcccgggg    300

acagggggac ccccagatgc tgcacggctg acaggccaac gtggcagaag ctccagcttc    360

acaggaagcc agtgaccatg agagtctgta gctgtaacga agccacagag ctgtggcttt    420

ctttcccctt cagctctagg aaaggttatc tgccctgcac agatctccgg aggcctggct    480

gggctctgag agcatcagac tgattatcgt aagaaaataa tctctgcaga cacattcctt    540

gctagaagca ggggacaaag cccagcttca aagacaattc cacacacgcc ctccctgccc    600

tgcacagctg cctgccgggt gggagcagag cccttgcagc cgggctcagg ggcctgggca    660

gggacagcgt gtggcagggg cacagctgag acaggagcct caaagcgaca ccaacccgac    720

gtgaagctac agttgaggag acacagctgc ccccattccc gggcctcatc tccacagtga    780

gacgctggac tctctccctg acccaccgtc tcttagaacc tcccctccat ccggagcagt    840

tcggcagccc cagggcagcc aggggaaccc tgccgagtgc ctctgggccg ccacagaccg    900

cagagcccgc gggagccttg ctcacacagc ctcaggtcca ctgtggtctt gggggaaagc    960

cctgtcctgg gacaggggag ccgggggtcc tggccctgga ccaccatctg gggaccacgt   1020

tgtcacgcct gcaaagctcc ctgccccacc cccatgtgcc ggctggtgtt gacacctttg   1080

tagagtggga acctgcctcc gaccccagcc tgcagccaca gggcaggtta tagaccaggt   1140

gagagggcgc cgcgcccaga accaaggagc acaagtccgc agtgcccatg agatcctcat   1200

gctggccggc gcaggagcca tcctcggcct ctgcaggtcc tcgtgggaaa ccgcgggggc   1260
```

```
acgtggggcg gctgcagggt ccgcaaagcc ggctgtttgc gaagggcgca gctccacctg   1320

gaacagccga ggccgcccac gcgcttcccg cgggatcaga gcagcctcca cggctgttgt   1380

ctcaggcacc acgggatgcc tttcttcgtt tcaatagctg tgggaaagcc tcaatcggtc   1440

ctgaaagaac ccagatgtgc agcaatgaca aggccttctc tgagactcta gaaccttctg   1500

ccatctcaga caggagggag ccgtgaggca ggcgggagat ttgcagtcag caaaggacgg   1560

gcaggtgggg cagctgcaca cccagggccc tctccacggt cttcccgggc ccacccctcc   1620

cgcggtcctg ggtcatccac ctgctggcct cactctgccc acgcggccag gtcccaccgg   1680

cccctgagct caacagacca aagctggccc gaccccaccc ccaagaagaa tgaaacaatt   1740

ttttttacc tcttgcagaa aagtaaaaga tcatttattc attctgtttc tagatagcaa   1800

aactaagtgt caaaagcacc ttctgcacac agtctgcaca cactggccgg tggtcctgtt   1860

cccgcaaggt tgagctgtgt tccagagaca tgggtcctcc gggtgatgag gagccgctgg   1920

agggccctga gctgcacgtg ctaatgatta acgccccgtc cgtgctggcc ggtttctcaa   1980

atgcctcctg acgattgcgc                                                2000
```

```
<210> SEQ ID NO 243
<211> LENGTH: 2200
<212> TYPE: DNA
<213> ORGANISM: Homo sapiens

<400> SEQUENCE: 243

ggcctgagga gtcaaacggt gcaaaccctg ccccactctg tttgggaagc acctgctgtg     60

tggcaggcgc tgcgcttggt gctggggata gaccatgggg aagaaacaca cagaacctgc    120

cctgctctca aggaacaggc cctgggggcg gccaggggca gagacccaag gcagacaccc    180

acacagtggc gtaatgacag tgcttatggt ggggacctgg ctgcacagca ggtcagcaag    240

gggatgttca ggtgacactg gggcacgga gacccagggg agagtggatt gacagagggg    300

acgctgggca aatgtcccga ggctgaggtg gagttgcggg aaggaggagg ctgccgggca    360

gaggcgcaga gagctttgca ggtgttggca gagaccagca ggccctgcga ggcctggggt    420

gtgtcctcag ctgggagggc catagaagga tctgggcttg cagatgctgg tgcagactgg    480

aggcctgggg tgtgagagtc caggcggggc tcctgccaac acccagggga gtgggcctgg    540

gccaggtgga ccgggagctg gcacggtggt caggtgcttg gaggctgcgt gccacgctgg    600

ggacctggag gtgtgtgagg aggtgtctgt tgctcctggg gctgccgcct gcagggctgg    660

gtgtgcagca gtgcggggca atgaagtggg cgggttctgg gatggtggac gttccctttg    720

ttgggaacgt gttggtgcca agctgccatt tgagtttggc tctgaggggt ctgggcaggg    780

gacacacagg gaatcacaca ggatggagtg agttcccagg gacccagggt ggcttggcct    840

gagaacagct cccactccca gatgtgtggg aagccctcgg caccaagcct cagcctctcc    900

atctgtgaaa tggagacaac gtcactggac ttgcaggctg tccatgaggg tgatgcgatc    960

agaaagggtg gagttcctga acgccccggg gtcggggtct cacagcagga gcttagctgg   1020

tgtcggcatc tcctggaccc gtcctcagct ccgagcgccc agtcctgcca cctgtgtcca   1080

agtctgcact gtgcccacga ggccctcaag gccgcagaca gccccacact tctcggacgc   1140

cgccccagca cggtccttgt gtgaggtgga cactccttct ggacgccgcc ccagcacggt   1200

ccttgtgtga ggtggacact ccttctggac gccgccccag tacggtcctt gtgtgaggtg   1260

gacactcctt ctagggaagg agtagtaact cttgggtggt cgggtagttg ccatggaaag   1320
```

```
gggcagtaat gcccaggtat tgccgtggca accgtaaact gacatggcgc actggagggc   1380

gtgcctcatg gaaagctacc tgtgcccctg ccctgtgtta gctaggcctc aatgtggtcc   1440

agtatctgag caccgcctcc tgcctcagat gttcccgtct gtcaccccat taccagggcg   1500

gcacttcggg tcctttccag ccatcattgt cctggcattg ccacagtgga cactgccaca   1560

caggcttgtg tgcttgcgcg tacccaggtc ctcacctctc tgggataaac caggcacgtg   1620

gcggccgccc cattttccac ccgccagcgg tggaggagtt gcccagcctt gcaggaaaac   1680

agctctcatg ccagcagcgg agcatcctat tcaagttttc tcagggctgc cagcacaaat   1740

gctgcatgcc gggcggcttc ctcagcagac cgttgtttct ctgcgtcctg gaggctggac   1800

gtcccaggtc cccgtgtggc aggcccggtt cctcccgcag cctctccttg gcttgtgggc   1860

ggcgtctcct ccctgggtcc tcgcagggcc acccctccgt gtgtctgtgt cctccctccc   1920

cttataagga ccccaggcag actggatcag ggcctgccct aaggactgaa ttttacctta   1980

atcacctctt taaaagctgt ctccaaatac agtcaccttc tggggtcctg gctgttaggg   2040

ctttgatgca tggatttggg ggacaccgct cagcccctaa cagcccccat cctctgcctg   2100

cctttaccat ggggctgagc ccagccctgc aggagtcccc tggtttgatg tctgctgtgg   2160

ccacggcgac cctcaggctg ctccagccgc acttgtgctt                         2200
```

<210> SEQ ID NO 244
<211> LENGTH: 1600
<212> TYPE: DNA
<213> ORGANISM: Homo sapiens

<400> SEQUENCE: 244

```
ggggagtctc caggggctgg ggctggagcc gcatcagaga ggaaaggggt gtttgaaaaa     60

ggggcagggc ctgggaccca ggaaactgtt cttccagaga cacccgtgaa gctgagcttt    120

gcctctcagg gaagctgtga ccccacgggt gctgcccaga gagatcgggc caggtggagc    180

caagatggac tggaattccc cgacggggac aaggggccgg acgaggctga cttgccctgt    240

ctgatgaatg gtcaggtttg ctttttctcc tgaaaacacg aggcagtgat cccggccagc    300

taattccagc agactggaga cgggatggtg gagaatgagg ctgtgggcgg gaagagcaga    360

tgggactcgc cagcatcctc acggcagggc cgcgctattg ccctccctcc cctcctactc    420

tctggggtcc caggagcccc agatacgcaa tgctgccagg cgatttctgg cgccccgcag    480

acccctgccc ctggagttgg gccaggtccc ggctggagca aagggggctc cttcaagccc    540

gctcctccct gtcaaacccg aggagcctga caggcgcagc gtcaccagcg tcaccgggcc    600

atagtgagcg gccaagccag cgtcaccggg ccatagtgag cggccaagcc agcgtcaccg    660

ggccatagtg agccgccaag ccagcgtcac cgggccatag tgagccgcca agccagtgtc    720

accgggccat agtgagcggc caagccttgg tctgccagag ccggccgcac cagaaggatt    780

tctgggtccc cagtcctgga ggagcacacg gtttacacca ggccttggga ggggaagagg    840

caaggcgtgg gcccagccct cactccccag gagaaaccct gtttgagcgg cagaggagac    900

tggagagacc ccagggcggg gatccctgag aggagagaaa ccccggaattc atccacggag    960

gcgttcaccc agaggagacc cggagcttct ccaggagagg ctggattgct ccaacagggg   1020

ccctgaggag ctgatggcaa gagcggaagg cagctctgac tcgtgcgtct gactccaggt   1080

gtggccgttg gggctacagt gggaccagcc tgttgtcact gaacccacaa agtgcctccg   1140

agcgcgggtg gagagagggg gacctcccac cgtctgctgg ccttgaatct tgaatctaat   1200

tcccgtctgt gctttgatgg gagaggcact gggagcgggc ggctttttca gttcctttta   1260
```

tcttgaatgg cctttggggg attttcacag attctgagtt caaagcccag ggaggtgtgg 1320
gaacgtgaca ttcctcaccg cattcctcac cgcattcctc tgtaaaccag gcggtgttgg 1380
cacccatgag cctgtgtctt ctatgacatc aggagtttta tccctcacgt cagaaatcag 1440
ggttccaggc gccttggttt ttcttggcgc cagcggcttg gctatagaag aaaaactgaa 1500
ggggccaggt gcggtggctc acacctgtaa tcccagcact ttggaaggcc aaggcgggtg 1560
gatcacgagg tcaggggttc gagaccagcc aacatggcaa 1600

<210> SEQ ID NO 245
<211> LENGTH: 7000
<212> TYPE: DNA
<213> ORGANISM: Homo sapiens

<400> SEQUENCE: 245
gctcctcagg gggaggttcg gggcctttgg tctctggact tgggcagcag aaaggaaaca 60
tccctggggg cctgtggtga cccccatcct ccccagggtg gtctggcagg ggacactgtt 120
ttccaaagca aagccagagc gccaagggct ctcgggattc acgagatcca catttatccc 180
aagttagaac agcacatctg tgcgtgcaaa cttcattctg acttcggccg gctgtccttc 240
ttgcccaaag caccgtgagg cctcatccct gcatccctgt tgcttctttc atgtgggatg 300
agaacccagg aaggggctga gtgtgactcc tctggttttt agagagcact gcccccgccc 360
cgccccctcc tgcttcccca ccttttcaca gttgcctggc tggggcgtaa gtgaattgac 420
agcatttagt ttgagtgact ttcgagttac tttttttctt tttttgagac agagtctcgc 480
tctgtcgccc agggtggact gcagtggtgt aatcttggct cactgcaacc tctacctccc 540
gggttcaagc gattctcaca tctcagcctc tggagtagct ggaattacag gcgcccgcca 600
ccacacctgg ctaatttttg tgtttttagt agagatgggg tttcaccatg ttggccaggc 660
tggtctcgaa ctcctgacct caggtgatcc gcctgccttg gcctcccaaa gtgctgggat 720
tacaggtgtg agccaccgag cctggcctgg agttattttg ggagagggca gcccctggtt 780
cagcgtggcg aggctgcgct tgctctcccg ggcgggcgtc cacaccctcc tcgccgagat 840
ggagaagccc aaacccctgc agcgctcccc catcacgtcc ggccctggaa gcccccggaa 900
accctgccac gccctgagtg ggagagcgca ggtccctttc cggccctgga agcccccaga 960
aacccttggg tgccaggcct ggccgggaca gcagcgacac tgcatgctca gcccttgcgt 1020
gagaccacgg gagtgtccgc cctctgcacg tgctgctgat tgcccacttc gtccagcagg 1080
tttgggagct tgtggctgca tcctcctgca gacacttgcc cattctgggg cctcctctct 1140
gtcttttctc ctctgttgag ggtctggga gggaggcctt ggagggtacc catgctgctg 1200
ggactgatgc tccccgcggt ggaaggagct gcctcttgaa cagcaggggg ctgagcagag 1260
gggaggggat gcgggggtgc cgtgcacaca ggtgctctca ggacgcaggg gcttctcagc 1320
cctgctgtcc cagggctgca ctccagcagg gcagactcct gaggtgcaga caccccagct 1380
tcacgctcac acttctggaa ggcgatgtct gtgcgtttgc tttctgctgc agtttaaaaa 1440
gccgggctct ctccggagcg tgtgtagggc ctggtcactg gaatatctgg actcagtgtt 1500
aatggcagcc acgctggggg ctgggcccag ctttctgttc tccgtgtggg tgccatatcc 1560
acctccatcg cagccctttc tctctcgacc ttttaaatca cagtgtcacc tccccctgct 1620
gtcctgccag tggcccctgg aggcttctcc ccacccccttt cttctggggc aattcttaag 1680
gctggcattg aatcaggagg ccagatgtgg cccctagtaa ctcaccagca gtccctgagg 1740

```
cttctggctc ccctggccca ccagcctccc atgtctgcct caggcctctt gacccgcctg   1800
gcactgacca gactgtgtgc ccgggtgccg tgcccatggg ctccgcctcc cccaggcagg   1860
ccccctcttg ctccgcggcc acccctgctc ttgacctcac acctctgcgg tgtgtctgga   1920
cacaccagca ccacggcggg cggggagcgg aattctccag gtggggtggg caggccggcg   1980
ggtgttgagg tctctgtgca tgcttgtgcg taccctggac tttgccgtga ggggtggcca   2040
gtgctctggg tgcctttgcc agacaactgg tctgccgggc cgagcattca tgctggtcgc   2100
catcacgtga ctcccatgcg ccctggccct ggggttgggt ctgcaggact gagaaccagc   2160
ggaagggggg cgaggcctcg ggaatgcgcc ggcaactggc gatgagctca ggcctgacta   2220
atgagcccag gtgactcata cacccggggc ctggatgagt ctgactgggt caggacttcc   2280
ctgcttgttc tgtcctggga gatgttgtcc ctggccctgc agagccggga ggacacgagg   2340
cctcctgggt cacagccaac gcagcctact cctgcccact gctcgcgccg gccaaggccc   2400
gtcggcacca cctcctccat gaagccttcc tgactgcccc catccctctg tgggcagctc   2460
gagtgtgcat cttgagtgct gtgcaggttg gggtccggcg ctcctgcagg caggcggcgt   2520
ctgggcctgg gggctctcag agtttgagga gcgtgtggtg agggtggcct cgggcctcaa   2580
agacgcagcg ctgtgggaac cgggagactg gctgagcccg ctctgaggaa ggtggggcca   2640
ggggcaccct cagctgaccc ggcgtgcagg ggtgaccagc caggcgtggc caaggatggg   2700
gtctctggga tcaggagact tcagtagcag ccaggaccga ggccaccagt ttccaccctg   2760
gcattttcca tcttttgaag gactggaaac gattggattc tttaactttt ttaagttgag   2820
gtgaaattca caacgcataa aattaaccat cttaaagcga acaattcggt gacatttagt   2880
acagccagaa ggctgtgcag ccatcaccac tgcccaactc tagaacattc acacgccgga   2940
gagagggagc cctgggccat cacgcagcca ccgcccggcc ccaagaacct gcgagtccac   3000
tttccacctc tggatcggcg gttctggacg ttcatgcagg tggttcccgc agtgcgaggc   3060
cttttgtttc gggctcctct cacaagcctc acgtttccag gtacgtcgtg gtgttgtgca   3120
gacccacaat tcatcccttt tcatgggtgt gtaatagtcc accatagatt ctctacgttt   3180
taaagcatgt tttatgtgcc tgaaatgtct ctgcactcga gactatagct tgctttcttt   3240
cttttctttt ttttttttta atttgagacg gagtcttgct ctgttttcag gctggagtgc   3300
agtggtgcga tctcggctca ctataacctc tgcctcccag gttcaactga ttcttttgcc   3360
tcagcctccc gagtagctgg gactataggc gcgccacccc acccggccaa tttttttgta   3420
tttttagtag agatggggtt tcatcatgtt ggccaggatg gtctcgatct tccgaccttg   3480
tgatctgccc gcctcggcct cccaaattgt tgggattaca ggcgtgagcc accgcgccca   3540
gccgagacta cagctttctt taactgcatc cctggaggga tctgagagtc tctttccctg   3600
tctcctttcc tttggaaaac atttcagcca gggctcccca agatgaaagg ccagagtccc   3660
aggcatgggc gttgcaggtg cacagttgcc acggggagct gtgggtgatg gtcgctgtca   3720
gcgatggctg ctgcaggtcc ctgtgaggaa ggggcagtgc cacagcagga ggagagggag   3780
tcagcggacg ttgattggca gtgcccgccc attccatcat tcagtcaccc actgtgcacc   3840
cagcacccag gctcggctgc atagaacatg gcccaggaag gctccacttc ctgtctcctc   3900
ttctcccctc tccagtctca tgatggggct ggaggcatct tctagttttg agttctgagc   3960
taatgaacat gctcatgagc aggcggcagg atcccaggac ggtggagctg ggagcctgac   4020
tgcgggtgac ggacaggctc tggcagcccc tgtcagcatc ctctccaggg catgtgaaag   4080
ccagtgtgtc ctcagctgcc agtgccccct ccccacctcc tctgggccca tgtgcacggg   4140
```

acctgggctc ccccaaccaa gcctgcccgc cttggttcag cagaacggct cctgtctcta 4200
cagcggtgcc aggccaggag tgctgtgtct gtgaagcggg gtcatggttt tggggccctc 4260
atctccctcg cgccctctca ttggggaccc cccgtctccc tagcgccctc tcgtcctctc 4320
ctgcatgtgc tgtgtctgtg aagcggggtc atggttttgg ggccccccgt ctccctagcg 4380
ttctctcgcc ctctccagca tgtgaagtgg ggtcatggtt tgggggcccc catctcccta 4440
gcgccctctc gttggggacc ccccgtctcc ctagcgccct ctcgccctcg cctgcatgtg 4500
ctgtgtccat gaagtggggt catggtttgg gggcccccta tctttctagc accctctcgc 4560
cctctcctgt atgtgaagtg gggtcatggt ttgggggccg ccatctttct agcgccctct 4620
cgccttctcc tgagcgtgtg gaactctgtg gtggtcagag ctaaggttct gaataggtcg 4680
aagcacctcc ccggtgcctc tcaccctgaa tgctctggga ggacacagcc ttttcatagg 4740
ctacgactga catggcagga ggggcctgcc tgccacccgg gtcctctgct gcctgctgct 4800
tgctggggag gggggctcgag actgggatcc tgggcttctg ctccagctgt gcccaaggga 4860
gctgctgagg agggaccggg tggggcatcc actctgggca ggttcagggt cattcttggt 4920
gaccccgggt ccggttacaa aggctgatgg agcgcgtggg tggctgccta agtctctgga 4980
agcccaagaa tgtggagatg gcgcgtctcg gcccggggtc tcgtggctgg tctgggagaa 5040
cttgccttta tttctaggca ggaggctgca ctgcaaggga gcgtcagtgg cccggctggc 5100
tttccccggc cctcagcccg cactcgtcca ccaaagcaag ctcctttgtg gggctgccct 5160
gggaagccgg gatcacgagg ctctgccggc cgtggtcacc ccatgaggca gggtcagctc 5220
gggagcaagg cggatcagat ggaacagaac acgtagacca cctcgcccgc ccttagtcag 5280
ctgggccatt gaaaatcaag tccgtagaaa gacctagaaa taagtcccgg ggtgcccttg 5340
cctgttgacg ggcgggccga gcaggactgt tctcaggcag gcactggtct cttggcttcc 5400
aggtggtttg tttgctggtt tgaggctggg ggtgacgctc ctgtgcggga ggaggtcgca 5460
ttccattcat agcggcttat ctgggctgtc aggcaggcct gggagggagc ctgcctctgt 5520
gctctccaag ggtgggcgac ggacagacag ggtgtcccac cccttctggg ccaaggacag 5580
agggtcagtg tttgcagaga cctggggagg cccaggtgac ctccaccgag cacctgctgt 5640
gtgcagggcc agtgctggct gcagagacag cggagcgtgt gtggacccgg cggcccaggg 5700
gaggggggca ggcaggaccc ggcggcccag gggagggggg caggcaggac ccggcggccc 5760
aggggaggtg ggcaggcagg acccggcggc ccaggggagg ggggcaggca ggacccggcg 5820
gcccagggga gggggcaggc aggacccggc ggcccagggg agggggcag gcaggactcg 5880 gcggcccagg ggaggggggc aggcaggacc aggcggccct gggggtcagg ggtggaggcc 5940
aggcctagac ggcccacagg agggtggact cattctgacc gattcctgga agcccccgga 6000
aagtggtgat gttctggagg gcccagcaga ccccaaggcc cccaagacaa tcccagctgg 6060
ctctctgcgg ctctcggtgt ctgccatttg agacaatttg ggcacaggca gggcaggccg 6120
tcgcggacgg tctaagccgc gcgcattggt gggggcagca gagcccctgc tctcagctcc 6180
tcggggtaca gcgggggtac caggcgggtg agtgggtggg tggtcactgc tcctgccaag 6240
ggcagccctg gtttggtttg cacttgctgc cctggtgacg gctgctctca ttcctgcccc 6300
attgctaaca agggtgtcat aagctacttt cccggcccac atcctattaa gcccatggag 6360
accctcccac agctgagcct gctgtgggct gcaggccctg ggcggtgccc acctcggtcc 6420
ccactggcct ccttccagca ctttagagca gacacaggtt ggagataagg aaagttccag 6480

-continued agcacagact ggaacaagcc ccaggcctct ccctgcccca gcagggcctc cctggatttg 6540
ggggacaggt gccctcatgg ggggtcctga aggtcagagc tggggctggg gctgggctgg 6600
cggaggtggc cttggcggag gccacattcc agggtctcag tgagagtctg tggcaggcag 6660
ccttgcagat gccgctgagg gaccccccac ttcatgttgt gggtgatgtg gtccattgat 6720
tgcctccagg tttaaatcag gtggatattt acctagcggc ctcctctccc tctgcacagg 6780
gcctggagtg ggatggactg gggtgctcag ctggaggctc tgcagacaca gccccctggg 6840
ctatgcaggc cctgctggga gccacattgc catttttcat cacccacttt ttgggtgaga 6900
accccctcga gtcctaacat ctgccgcatc tcagagcctg tggctccagt cagagcatct 6960
ggaccatact gctggggtca gagcgcggca ggacaatggc 7000

<210> SEQ ID NO 246
<211> LENGTH: 1500
<212> TYPE: DNA
<213> ORGANISM: Homo sapiens

<400> SEQUENCE: 246
tgccaccacc atcttcaggt agagcttctc tctcctcctt gctgggcggg gcccctccct 60
ggggaagcct gcaggaccca gacagccaag gactctcgcc cgccgcagcc gctcccagcc 120
agcagctcca acgccctgac gtccgcctgc gcacgccact tctgcacccc ctggtgatgg 180
gctccctggg caagcacgcg gccccctccg ccttctcctc tgggctcccg ggcgcactgt 240
ctcaggtcgc agtcaccact ttaaccaggg acagcggtgc ttgggtctcc cacgtggcta 300
actctgtggg gccgggtctt gctaataact ctgccctgct cggggctgac cccgaggccc 360
ccgccggtcg ctgcctgccc ctgccaccct ccctgccagt ctgcggccac ctgggcatct 420
cacgcttctg gctgcccaac cacctccacc acgagagcgg cgagcaggtg cgggccgggg 480
cacgggcgtg ggggggcctg ctgcagacgc actgccaccc cttcctcgcc tggttcttct 540
gcctgctgct ggtcccccca tgcggcagcg tcccgccgcc cgccccgcca ccctgctgcc 600
agttctgcga ggccctgcag gatgcgtgtt ggagccgcct gggcgggggc cggctgcccg 660
tcgcctgtgc ctcgctcccg acccaggagg atgggtactg tgtgctcatt gggccggctg 720
caggtaactg gccggccccg atctccccac cctttccttt ttgccttgcc aggtaagtgt 780
gggcggggct gacgtgagcc tggtacaggt tccccccaca tcgaatctct acgttcaggg 840
gcccgtggcc ctcgggaggt gggagagctg ggagtgaggc ctcctgtgtg gggaggaggc 900
cggcgtctgg acaggaagag ggctggatga accgcagccg atgtgtccag gtgccacctg 960
ggcctggagc tccctgagca ttttagcgca tttagtcctc agcacggtcc cgagataccc 1020
tgccatgccc cgagtcacag aggggaaact gaggcgtggg gcagtggcgt gactcacccc 1080
agggagccga gattcccgct caggtgtggc tgcatcgacc ttgctccggt cactaagctg 1140
cacggttcga tgcgcttcct gggagcccca gcgtgctcgg gccaagggtg ctgccgcgtg 1200
ggcagtgcag agaccctacc agcgtgggga ccagggaggt ctgcagggcc cgtcctgaga 1260
gggagccttt catgtccccc tccccatcct gaagcacaca gcctccctgc cacagtgggg 1320
gccgcttctg ggcccagggg acgttgcccc atcaccgtgt ggcctggcct tgttgctggc 1380
tggacagttg ggggcaggaa gaggagggaa agggggactc tttaacctcc tgggggcagg 1440
ggcagcccag aaaggacccc agcagatccc tcctctgtgt ccgggagtag acggggcccc 1500

<210> SEQ ID NO 247
<211> LENGTH: 2000

<212> TYPE: DNA
<213> ORGANISM: Homo sapiens

<400> SEQUENCE: 247
gggctccaca gcggcctgtc tcctcacagg gttcagccca gtctgctctc actcatttgc 60
tgattcattc tttcattcag ccagtcaata gtcatggccc ctcctgtgtg ccgggtggcc 120
atggatattg ccctgggtaa cacacagcct ggccctgtgg agcagacagt ggggacagcc 180
atgtggacag ggtgcaggtg gatggcaatg gcagctgggt caggaggggc tgagggccgt 240
ggggaaaggt gcagaatcaa taggggcatc cggactgggg tgcaggcctg ggggctggga 300
tttctagggt ggaggtcacc tctgagggag acagagcaag gccctgggag attagaaggt 360
cgaaggtcgc cgtgttgagg tcaggggccc tgaattggag ccgcggcaaa ggagagggca 420
ggtcagggca cgtggtgagt gattgctgcg gcttctgagc acggctgggt ctgtggggcc 480
tgagcagagg tgacccgcga tccggcgcca cggcaggcag gactccccac ccttgctgct 540
gcctacaccc ccagggcagc cccagagtcg ggggcgcagc tccctgcttg ccagttcaga 600
gcccagcccc tctcacccag cccagaggag gacacagatg gaggaggggc acccggaggg 660
tccccccgcc gacaggcccc acgtctccca cctgcaggac aatgaagtgg ccgccttgca 720
gccccccgtg gtgcagctgc acgacagcaa cccctacccg cggcgggagc acccccaccc 780
caccgcgcgg ccctggcggg cagatgacat cctggccagc ccccctcgcc tgcccgagcc 840
ccagccctac cccggagccc cgcaccacag ctcctacgtg cacctgcggc cggcgcgacc 900
cacaagccca cccgcccaca gccaccgcga cttccagccg gtggtgagtg ccccccccaaa 960 gtgggcttgg ctccatctag cccctcggct ctcggcagca gaagagggcc cagcccctgc 1020
agagctgctg gggtcccag gcttcggcca tgggtggggg tctggcggct cagggccact 1080
cagggcggct tggctggccc tgggacttgc cctctggtgg ccaagcagtg gtcatgaaag 1140
tccagccgct gtcacatcct tgaggaaccg gcgtacctcc gcctacagcg gcagctgggg 1200
gcacccacgt ggcccggggc tgctctgacc tggcagcgta tgggggctgc tgcctgggcc 1260
cctcagtgtg tcacttgcgc gcctcccgct cagcgcccct cggccgtgcc tgtccacaca 1320
ggtgcggggc cggggtggtg cgcccggggc ctgggtgcag gggcagcgt gggacacagc 1380 ccgtgacgcg cccctctccc cgcagctcca cctggttgcg ctcaacagcc ccctgtcagg 1440
cggcatgcgg ggcatccgcg gggccgactt ccagtgcttc cagcaggcgc gggccgtggg 1500
gctggcgggc accttccgcg ccttcctgtc ctcgcgcctg caggacctgt acagcatcgt 1560
gcgccgtgcc gaccgcgcag ccgtgcccat cgtcaacctc aaggtgggtc agtccagtcc 1620
tgagggcgcg ggctcctcgg cccccacttg acctctgggg tgaactccca gcggggagct 1680
cccctctagg gcctctggag gccaccatgt tacagacact ggcgcctagg ctggcgactt 1740
cagggcaggc tccgggtggg tcacacccct ccaggctcag gccaggcctc tgcatccctg 1800
ggcactgcca cgtcccccag ggcatcccat gaggcccccc cgtggccccc tgaccccccg 1860
ctcccccggc agtgcccctc agagggtccc atgctgctgg accaagtgtc cacacaggtg 1920
atagggctca catacaagcc tggaatcagg aaccgtcctt tgggcctcta gtgccatgcg 1980
ggctggtggc ccctctgcca 2000

<210> SEQ ID NO 248
<211> LENGTH: 2000
<212> TYPE: DNA
<213> ORGANISM: Homo sapiens -continued

<400> SEQUENCE: 248
gcctggagtg tagtcctgct gaaggccaga gaccacacac tccacccaga ctccggatct 60
ccctccccag caggggggatg gaggccctgc cgctgggagt gctggtgtta tgtggaaggg 120
ctgggcttct ccagggctcc tgggaggcct aaacatcttg caaggttttg acgttaatta 180
ctattatgat tgctttctgt gtgttactgt tttccccaca ctttagccag ctaatgtgga 240
gctacagaag gccctcgccc ctacccctcc agatgtccca gcccatgaca agcaggaagg 300
ccgggtgctg ggagacttcc tggggctgga tctgacatca ttccaagcag atgataacct 360
gccttcccga tttccaaacc cacagcaaga caccctggag ttatttataa atgcgagccc 420
ctgggtgcac ttctgacggg accagcaccc tgacggccat gagagggtgg agacagcgca 480
ccccgagctc agggaggcag gaaactctgg acctggaggc cgggcaccat gagggacacg 540
ctgcaggccc agctgctgcc gcctggggcg gggctgccct gcaggctccg ggaaaaccca 600
gaaccaggcc ggatcagcgt gtgtcaagag gcggggcgtg agagatgagc tgcttttttt 660
cttcacaggg ttggcaggaa ctgcaaataa tagaaagtct ttagggtcta acacgctgcc 720
ctgaaaacac tatcattact ttcctaatga ctaactgtgt ctttcagccg gcggggcagg 780
cagctgaggc cgcaggctcc cgcagaggac cgggggaggc tggcagcctg taatctgggg 840
gcgctgacag tgctctgccc agaccctcgc gccagctcca gctccagcac agcagccctg 900
ggtccctctg gccccctgcc cgcagagtcc aggtgtggca gaggccgccc agtatccctt 960
ctcctcctcc ttttctaaaa acagagtctc acgatgtttc ccatgcgggt ctccaacgcc 1020
tgggctcaag cgatccttct gcctcggcct cccaaagcgt tgggattaag gggcgagcca 1080
ccgcgcccgg cccaccttcc cttctggttc atttccagta aggtcctgtc cacagcgtcc 1140
ttcccagcat tcccaccagg ctgcaggcct tggcctccct cccctccatt ctcattctcc 1200
ccgaaaccgc caagcgcgtc caaagcacgg gttcgccaag cgcccccccc gccccactcc 1260
acattccctt ccccgccgac tcagcctccg tagctcgcgg acggcccctc ctcacgccag 1320
cccaggcttt tttttttttt ttttcttcta ttttaaggtt gtcttttaat gacacaagcg 1380
acatttggag acaaaaggac acatctcttc ctgacccacc tccaacccca gctgacggcc 1440
gccctgagcc tggcgtagac ggcccggaac gttccctgcg tgggttccgt ccatcccgaa 1500
cccctgtccc cgcgccggct ccgggggtgc tcggggggcc gcgtggggtc tgtgacgtcg 1560
cctcgaggct gcatcccggt gacccggcag cccctggcgc tcgcgggagg cgggcgggcg 1620
cggaccccag gctttaggc gcgattcctg cagctggctg ccggcccgag gttctggggt 1680
gtctgaggtc tcgggcgggg cgaggacgtt tctccggctc agcccccccca cctcctgccc 1740
tgccgccccc cacacccagc tccccacgga cgccaagagg cgcctcccac cccggcgagg 1800
acccgcgggg aaacggggcc caggcgcggc gactgcggag gacgcgcctc ggccccagcg 1860
ccctggtcct cggggcgtcc ggctgccctt gcccgaggcc ggggcgggcg ctcagcgccg 1920
cggaagaaac gcccgggcgg ggacgcacag cgaggcgggc tccgcgggaa gtaccgggaa 1980
aacggcgcgg agcggaacag 2000

<210> SEQ ID NO 249
<211> LENGTH: 3000
<212> TYPE: DNA
<213> ORGANISM: Homo sapiens

<400> SEQUENCE: 249
tggagcaatc ccagagaggc tgaggtgttc aggctggccc cagatgcaca cgagcgtgaa 60

-continued

```
gcctgttcag aagccagctc ctcacaccct ctcccctgcc agaggctcca gcaccccctc    120
ccctctcctc tcccctccct tccctgtggt cctcctgccc accccacccc cgtctgcatg    180
tgcaccgtca cggagatgcg tgtactaggg cggaggtcgg ggacagtcgt cagaaggaca    240
caggaaagaa gggaacagga atcccataac agaacattat ccggcaggag taattaacac    300
aggcaggact ggaggctttg ttttgttttg cttaaaaaac agtggtattt aaattaatgg    360
gcatgggaag actattcagt gaaagacatc ggtcattgag gtatctattc aaaaacacgg    420
tttagtactc tgccacacac cgaacgcaac gccacagcag ccatagaagc gtgtgtggct    480
gtttaacgtg gtctttttgg ggagggcatc ctaggcagag caggcgtgga agggaaggcg    540
gcggacggaa caaaacgcgg gcacgcaacg gctgctgcgc cggatctgag gcagggccag    600
cctgtgggag cagcaacatc gctcgcagga cagcgatgga gcccccacga atccgcgtga    660
aagcagcaac cacctagaaa tgaacgtaca gctgcttaga aacagaatac ggatgacccg    720
aaagacttcc cgatggtagt caccagcata caggacctga cacgggcgtg cgggcagggt    780
gtgccgctac ggggtccctg gcgcacctgc taccccctgct acccgcattc accgcacgcg    840
gagggtgcgg gccgtgaagg ttatacatgc aaatatcctt ccaccagcca gttctccttc    900
caggaatctg ccacccgacc cttgtgttgt gcacagacat ggtccaggtg tttgcgacgt    960
gattgtttat cagagagaga gaagggaaat ctccaggctc gctgtagctg caggagctct   1020
gggggctgcg cccatcgtgg agacggatag ctgtctctca tgaacacagg acagcaagtc   1080
cggctgcggc cacagaagac tcgccctcct ggacgcagcg tcttccttcc tcagccccac   1140
actggaggtg gccagtgcca tccacagcag aaggggccag ccgggaccag gctcacgccg   1200
tggaattctg ctctgtggta agaggaagag cgatagctgg aacccagcgc cgtcgcacac   1260
acagcgggga agagtctcag aaatgttact ttgagtcaaa aagctggaca aaaaaaggcg   1320
caagccagat ggtgctgaag aggccacagg aggctggcag ccaggggggtc tggcacctca   1380
ctcggaggcg cagtgggccc gtccggaatt agtggccata cggcaagtgc cgagtggaca   1440
tcaaaccgtc acttcagact cctgcgcttc actgcctgtc ggttatgcct gggttttgaa   1500
atcaagtcac agaacacctg gaatgtggtg tttacgcaga acaaagcggg tgcctcggag   1560
gagagagcct agggacaggg gcacctcccg gtgtgggtgc ccagggttgc agggtggctt   1620
cctctgtctg cgcggttttc agagccccag ggtcctgcct gcccggctgc ctggaggcgg   1680
cccacatcct gctctgcgcc gccgaatctc agcctgaaca gcttcgctgg tgtttgtgtt   1740
gacttatttg ttcttttttt ttttttttt ttttaaataa aggattccga tgctgttaca   1800
gtcaataaaa gccacaggtc tgggtgacct acaaatgtgt gtgtctgact ttctgcagtt   1860
taaatcgcca ctgagcctta aggcgtctgg cccgcgcatt gaggaatcca cgtgggtctc   1920
ggggtcccca tgcctgccca gctccctgct tcagcctggg cgggtctggc gggcatttct   1980
gcgagcctgt ccctgggccc gcctcctggc cagacttcca gaaacattgt ccacatcccc   2040
gttgcacgtc cccccgtcac cggaaactgc agcccacagc actgggaaga acccgggagg   2100
caggcgttag gacggggtgg ccgagacagg gaagggagcc atggcggacg tcctcaccca   2160
agccagggct tcctgcccct gtggtactga caggagcccc gcaggacgtg gggttggctt   2220
tgggcagctc ggtggacact tctctttcag atcctgccac agcaaagctc acgagactca   2280
cttcttccca ttggaattca ctaagaacaa attcaacaat tcagacgccc cagctggagg   2340
tttattttat ggattttacc tgtgcggtat ttagggttgt gtttatgaat aaaggtgtgc   2400
```

```
gttctggcaa gtagaaatac agagcttgtc tttcacccaa gtatctgtaa ctttctccaa   2460
tgcagacact aaaatgcaat aaaaacaaac caaacccatt aaacatgaat tagatgaggc   2520
aggctgatgg gaggttgtgg gattaacagg ccgtcagcgg attgaagctg cgcacatcgc   2580
tgggatgctg ctgcgggagg attcggtcta atccgggagc atctggctgg gcagtgggca   2640
gcgtctgcag tcgtggctgc ttgaaggtat gaaggttgtg gcctttgctt ccccccatca   2700
ggctgcccca ccctggaccc cacccagacc cctcgggcac cctggggtca tcttcagctc   2760
ccccttctct tccttccttc tcttccgcct gggcccctac tgtgacccga ggtcagcaga   2820
ggaccctggc aggtggctgc tccctgggac tcgactgtgc aggtgaggct tggggtgacc   2880
gctgctcctg ctcctgctcc tctcgccgtc cccaccctcc tccatcatgc tgtcaacatg   2940
catgtgggct gcagccctca gcctgcagga cgctgtcagt gcagctcctc agtggccagg   3000
```

<210> SEQ ID NO 250
<211> LENGTH: 2500
<212> TYPE: DNA
<213> ORGANISM: Homo sapiens

<400> SEQUENCE: 250

```
atcttgtctt ccttgtccca gtcctggaac cagccactgc cccagcagct cctgtgtgtg     60
gtggcatgtt ctggaagcca ggatgcatgg tgctcctggg ctgctgtggg tcctgggctg    120
ctgtgggtcc cgagctgctg tgggtcctgg gctgcacccc tgcagaacac ttccttccat    180
gttcagctcc ctatatggaa ccccagttcc agccccacag cacagggtcc cccagttctt    240
cctgcctcag gtgtgcacca cgaggaatcc aactgccagt atctgtgcgt ggcctcccgc    300
cgggaggagg ctgccggagg ctctgagctc tagccccaca gcactggcac atcctagatt    360
tccgggaaga cacggcctcc tccccagggg aaggtggtgg tgcccacacc cagagcattc    420
attcctgcag tggagacaga gggacctgcc tctccaactg tgggtgtcag gagccaaggc    480
gcatggtaaa tggggctctc tgtgaggcca ggtgcacggc cccatctcca gcagcagcgg    540
ccatgccacc cagctgcact ctgtggggga ggtgccatga ttgacggggg cccctccctg    600
tgtccagtgt cctcctccct ccacgggccc ctctgcacac cgtcctcaca gtctccctct    660
gcacaccgtc ctcacagcct ccctctgcac accatcctca tggtctccct ctgcacaccg    720
tcctcacagc ctccctctgc acaccgtcct cacagcctcc ctctgcacac cgtcctcaca    780
gcctccctct gcacaccatc ctcatggtct ccctctcctt ccacagaccc ctctgctcgc    840
catcctgacg gcctccctct ccctccacgg accccctctac acactgtcct cccagcctcc    900
ctctacacgc catcctcaca gcctccctct ccctccacgg gcccctctac acaccgtcct    960
cacggcctcc ctctccctcc acgggcccct ctgcacaccg tcctcacagc ctccctctcc   1020
ctccacgggc ccctctgcac gccgtcctca cggcctccct ctgcctccac gggcccctct   1080
gcacgccgtc ctcacggcct ccctctgcct ccacgggccc ctctgcatgc cgtcctcacg   1140
gcctccctct ctctccacgg gcccctctgc acgccgtcct cacggcctcc ctctctctcc   1200
acgggcccct ctgcacgccg tcctcacagc cttcctcttt ttccacagac ccctctgcac   1260
gccgtcctca cggcctccct ctccctccac gggcccctct gcatgccgtc ctcacagcct   1320
caccgacgtc accattgctg gccccgcttc aggtgacagg ccacagtagc acctgtcagc   1380
tctgtcccgc tgctggacag ggagatactg ggccactcag cccagcgggg aacgtgtgtc   1440
ccgaaactgc cttgggctcg ccatcagaac tgtggcagca tcttccagcg ttccttttaa   1500
caggctgccg ttggaatagg agtcacggag caattgcagt gctaagtttt ctttaagtca   1560
```

cacaattgaa ggaggcttta tttttcacac atttcttcca gagtttcctg gtagcctgag 1620
tgcatgggtg atgcccccctg agttatttat caggggcagc cagctgccct cccccggggc 1680
acttacagtc agcccatctc tgtcctggtc aggtgggcgc caaggaagac ccggctcagg 1740
gcctctgtat gggcagcctg gcttgtacac acacccctcc ccaccagcag attctgaatt 1800
ctcccttctt catgcacacc gggaaggtcc cttctgcact cataccggga aggtaggcag 1860
gtttcggtag tgtctgcctc cagtgttttc ctcctcctgc tctatgacat catctttctg 1920
tgattttttt tttcttgcag gaagttggaa gcatcatcgg gaaggtaatt attgattgaa 1980
tctctgcctc tcctggggtc tctgtaaggg gatggtgagg atggcagcct ccctgggtac 2040
taggtggcac ccagtaggtg cgcctttccc agttggtggg tggtctgtgt tccatgaaga 2100
caggacccca gaggtgtcgc ctttatgctg tatgacattg aagctggtcc ctggctctgc 2160
gtggcctgag gggaaggggt tcactccagc tggtcacctc gctgcccccct gcccgtggcc 2220 ttggtggcca gtccttcttt cccggttgaa gaccccacga agaatgattt ctcacgcctt 2280
cttcagccgg ctgtgtagtc tgggtggtct ccaggagtgc cagtggaggc agcagccccc 2340
agacaattcc tttccaaatc agggctggcc cgggggaagt aaggcccagt ttggaagcct 2400
gctgccccgg gaggccgagc agtgagggcc acctccctgt cttcatcaca ttttcaccgc 2460
ttccgggggt ccttcccctc agtcccacca tgggggcgcc 2500

<210> SEQ ID NO 251
<211> LENGTH: 6000
<212> TYPE: DNA
<213> ORGANISM: Homo sapiens

<400> SEQUENCE: 251
gctggacacc tctgagagcg tggccctgag gctgaagccc tacggggccc tcgtggacaa 60
agtcaagtcc ttcaccaagc gcttcatcga caacctgagg gacaggtagg agggacgccc 120
cgtgaccttc ctcctgtgct tctgggcctc ttggagggag gggtgggggc ccaggggaac 180
acgggtgcga cggcctcaac ctcctaaggt tgggcgagcg ttgccctgac cggggcccct 240
cccggcgccc tccagagtga ggccggggcc ctttccggcg ccctccagag tgagctggtc 300
tgagcctctc ccagcgcctt ccagagtgag ctggtttgag accctgctcg cgggggtggc 360
acctgttcag cagggccgag gtgacagtga ggctgagatg tagggaagag aggctcccgc 420
aggctgaccg agagggctca gcgcactggc ccagacacgc agtcctgcct ggtgcgcggg 480
agcccctcac taaccacctg gaccctggtt tgttccgtgg gcagtgagag cctctacctg 540
ggtcctggat cccacgttct gaaggtcccc gactcgggag ccaggagggg tgtcgctctg 600
cagccccagg gcccccaggc ttggttctgg gcttgggaca cggcaccctc tgctccacgt 660
tcctccatct gtgcgtgtgg ctgaggacag accgggggga gaggggagtc ggtcctgtgg 720
gtgcacaggg ccgctgaggg gggggcatgt agaacggggc tcccccactg agacgggtcc 780
tggcagtggg gacacagctt agccggcgta ggaacccccg tcctccttga ccctgctgac 840
tggccgctgg gccggagcct cccgccacca gaaggggcac agtcagaggc tgccggtaac 900
agcagggtgg accttccagc ccacaccgtg cccagcagga gccattggta ccaggaaccc 960
tgagcttagt ggacatggcc aggcccgtgc ggcagtgttt gggggggggt ctggctgtgg 1020
atggcaccgg ggaggggcgg ccgcgtggcc cagcgtcccc cgagtcgccc ttgttgcctt 1080
tactcagtct ccccatgact cagtttccca cctgtgaaat ggggcggagt catccccatg 1140

-continued

```
tcgctgccac tggattcctg caggcgccgt ggtcactctg ctgaatggat gggagggtgg   1200
gtggggcaga ggtgggccca ccccaggctg gggcagagca gacccctgag agcctcaggc   1260
tcaggtgctc agagggcagc gagggggctg ctcagatccc cggggtgcct ccttccccca   1320
ctgtcatgct gccccactgc aggcccaagg accccaccc agcagggcca cacactcagg    1380
gctcctggtc tgagggcctg agggatcggg gcgcaggtcg cttgctggcc acacccgcct   1440
gcacagcctt ccaggagggc cggcctcagg gccacagggc aagtccagct gtgtgtcagc   1500
cacggccagg gtggggcagc ctgtccatct gggtgacgtc gcgccctggg acgggtagcg   1560
atggcgccag gggccgcccg cctcacgccc gccgtgcctg ttcctggcag gtactaccgc   1620
tgtgaccgaa acctggtgtg gaacgcaggc gcgctgcact acagtgacga ggtggagatc   1680
atccaaggcc tcacgcgcat gcctggcggc cgcgacgcac tcaaaagcag cgtggacgcg   1740
gtcaagtact ttgggaaggg cacctacacc gactgcgcta tcaagaaggg gctggagcag   1800
ctcctcgtgg ggtgagtggc ccccagcctc ctgcccacgc cagttctcac gcgtggtacc   1860
cagcctgggc tggggttggc ctggggtccc tgtgcggctt cagctgcagc ctccctgttc   1920
tcttggaggc tgcacggcct ccctgaccca ctttgtgggc aggaaagaga cggagacaga   1980
cagagacaga gagaaacaga aacagggaga aacagacaca gagagagaca gagacagaga   2040
gagatagaga cagagacaga gagagacaga gacaaagagt gacagaggga ccaagacagg   2100
cagacagaga caaacagaga cagagacaga gacacagaga gagacacaga gagacagaga   2160
cgggaacaga gacaggcaga cagagacaga gagagacaga gacagaaaca gagacagagg   2220
gacagagaca ggcagagaga gacagagaga cagagacaga gacagacaaa cagagacaga   2280
gagacagaaa cagggacaga gacagaaaga gagagagaca gagggaaaca gagagagaca   2340
gagacagata gaaaaagaca gaggcagaga gaagcagaga cagagaaaca aagacagtca   2400
gagacagaca gagacagaga cagaaacaga gacagagaga cagagacaga ggggcagaga   2460
caggcagaca gagagacaga gacagagaca gcgaaacaga gacagaaaca tacagagaca   2520
gagagacaga gagaagcaga gacagacaga ggcagagaga cagagagaag cagagacagg   2580
gacagagaca gagacagaaa tagagagata gagacagagg gacagagaca gagagataga   2640
gacagagagg gagacagaga gatagaagca gagagagaga gacaaagaca gaggcagaga   2700
gacagagaga gaagcacaga cagagacaga cagagagaca gggacagaca gagacagaga   2760
gaccggaaac agaggcagag agactgagag actgagagag acggggtggt tttccccaca   2820
gcatcaacac caagcagggc taggatcact gaaacagact catcagaccc gaagcatgcg   2880
ctttctcggg gtttttctgg actgaggggt ttcctctcat cccagtgtcc agctgtgggg   2940
acgcaggggc cgcaagcccc ggagtgtcca gaggggaacg tggcctcccc acacccagcc   3000
cttcacgagg cctcaggatc ccagtggggg tacccgaggc tgccctgtcc agccaggcgg   3060
tgcggggggt ttggggagag cctctccccg aggtcggtct cagagggcca catggccggt   3120
gtgggccgga cattcccttt ccaatggttg tgcccacttc cctccagagt tggtgccaag   3180
ctgggacctg ggggacttgg agtctcagga agtcgtccgc tgtctgcagg gggtgcatgg   3240
gggatgtggc cacacacgtc agagtgcggc cccctgtgga agccacagac agacacgact   3300
cccctaaatg agctcgccct tctggccgag atgctcagcg tccccagcag gctgcccgac   3360
tgccctgcga tactgccctc cttcctgctg ctcccacttt ccctttcggg gggttggatt   3420
tggggcattc agggatcgcc ctgttgtttg ctcatcacac ccatttcctg caagagccac   3480
ggtgaccgag cagccttgag ttgaggcagc ttgtgggtag acgcggcggg catctcggag   3540
```

```
gggcacgctc cctgccaccc tcagcctcca ctcactggtc aggggctttg cgccccaggg   3600
caccccagga accgagcctc ctttggggtc atgggtgcct ctcctgggag ggcgtggatt   3660
ttccaaagca gtttagagaa atgagaccca caggcgttat ttcccatggt gaggttcttt   3720
tcagtaaccc ccaccgtata gccaggatca gcaaagagag gcggctcctc ccggtgagac   3780
agggaccagc acctcccgga caggcttggg tctccctcca gttcccccac ctagtctcga   3840
ggtctcacgc tgccctctcc tgtccagggg ctcccacctg aaggagaata agtacctgat   3900
tgtggtgacc gacgggcacc ccctggaggg ctacaaggaa ccctgtgggg ggctggagga   3960
tgctgtgaac gaggccaagc acctgggcgt caaagtcttc tcggtggcca tcacacccga   4020
ccacctggta ggcaccggcc ccccccggca gatgccccca accacaggga gtggcggctg   4080
caaggccccc ggcagctggg accgtctttt ggtcctcggg agggtgtggg ttctccagcc   4140
ggccaccctt gcccctgaga ggccagcccc tcctgctgag gagcctggag cgccccagcc   4200
cagcctcccc tctggccctg tgggaagcgg ccccggccgt caggggtccc agccctgctc   4260
agcccaccct gaacactgcc cccaggagcc gcgtctgagc atcatcgcca cggaccacac   4320
gtaccggcgc aacttcacgg cggctgactg gggccagagc cgcgacgcag aggaggccat   4380
cagccagacc atcgacacca tcgtggacat gatcgtgagg cccctgccca ggagacgggg   4440
aggcccgcgg cggccgcagg tggaaagtaa ttctgcgttt ccatttctct ttccagaaaa   4500
ataacgtgga gcaagtggta agagccctcc ccaccacccc cagccgtgag tctgcacacg   4560
tccacccaca cgtccacctg tgtgttcagg acgcatgtcc ctatgcatat ccgcccatgt   4620
gcccgggaca catgtcccct gcgtgtctgc ccgtgtgccc gggatgtgtg tccccctgcg   4680
tgtccacctg tgtgtctgcc catgtgcctg ggacatgtgt ccgcctgtgc gtccatccgt   4740
gtgtccgtct gcccatgtgc ctgggtcgca tgtcaccctg tgtcccagcc gtatgtccgt   4800
ggctttccca ctgactcgtc tccatgcttt ccccccacag tgctgctcct tcgaatgcca   4860
ggtgagtgtg ccccccgacc cctgaccccg cgccctgcac cctgggaacc tgagtctggg   4920
gtcctggctg accgtcccct ctgccttgca gcctgcaaga ggacctccgg ggctccgggg   4980
cgaccccggc tttgaggtga gtggtgactc ctgctcctcc catgtgttgt ggggcctggg   5040
agtgggggtg gcaggaccaa agcctcctgg gcacccaagt ccaccatgag gatccagagg   5100
ggacggcggg ggtccagatg gaggggacgg cgggggtcca gatggagggg acggcgggag   5160
tccagatgga ggggatggcg gggtccagat ggaggggacg gcggggtcca gatggagggg   5220
acggcggggt ccagatggag gggatggcgg ggtccagatg gaggggacgg cggggtccag   5280
atggagggga cggcggggtc cagatggagg ggacgtcggg gctccagatg gaggggacgg   5340
cgggagtcca gatggagggg acggcggggt ccagatggag gggacggcgg ggtccagatg   5400
gaggggacgg cggggtccag atggagggga cgtcggggct ccagatggag gggacggcgg   5460
gagtccagat ggaggggacg gcgtggtcca gatggagggg acggcggggt ccagatggag   5520
gggacgtcgg ggctccagat ggaggggacg gcgggggtcc agatggaggg gacggcgggg   5580
tccagatgga ggggacggcg gggtccagat ggaggggacg gcggggtcca gatggagggg   5640
acggcggggt ccagatggag gggacggcgg ggtccagatg gaggggacgg cgggagtcca   5700
gatggagggg acggcgtggt ccagatggag gggacggcgg ggtccagatg gaggggacgt   5760
cggggctcca gatggagggg acggcggggt ccagatggag gggatgtcgg ggtccagatg   5820
gaagggacgg cggggtccag caggcaggct ccggccgtgc agggtgtgga ctgtcccggg   5880
```

ggcgctgggg gcttctgagg gtgtctctgt ccgccctgcc ctcagccgca ctctgttcag 5940
aaggaccttt ctggaggtag gagggtgaga atgtgggtcc cctgcttctg tgtggctcac 6000

<210> SEQ ID NO 252
<211> LENGTH: 7000
<212> TYPE: DNA
<213> ORGANISM: Homo sapiens

<400> SEQUENCE: 252
ggccggggag gcggggaggc tgccccaaga gtaaaagcct ttctgacgtg cgcaggacgc 60
ggccctgact ggtctaactg actctttctc ttctcctcag cttgctgtgg tgagacccag 120
gctctagctc ctgagagaat ggatcccggg ggtcggggag cgaggcctgg gtcccacaca 180
tgtcacagga cagcacatgg cactctggtc cccgcccgca gctccctgca cctgcccgcc 240
ccctctgggg cctgctccaa gccagcaggg ttcccgggtg ttgggctggg ccccgccctc 300
tttcacccat aactgaaata accaggagca ggcttggggg ggtccctgct ccatcattct 360
ggcccacagg ccccacccta gcctggctga gcaacgccag ccctgaccag ccgccggaca 420
gagcagcctt tacggggcca tgggaggggg tgggcttttc tggggctgag acggggggac 480
cccaacgtgt caggtgagga tgtggcagcc aaggaggggc cagggcggtg gaggggaggg 540
gccagggcac tggaggggag gggcgtgctc tgctgacacc gcccccgcct gcagaatgca 600
agtgcggccc catcgacctc ctgttcgtgc tggacagctc agagagcatt ggcctgcaga 660
acttcgagat tgccaaggac ttcgtcgtca aggtcatcga ccggctgagc cgggacgagc 720
tggtcaaggt gaggcctcgc cccgcccggc tttctcaagc ccaggtgcac cccgaccctg 780
ccggccgccc ctgcccgcgc cagacctcag cctcccgagg ccaccgctgc atccctgtga 840
cttccctact catgacaagg atgccaggca cgcgccagcc cgtccaggcc tccagctcca 900
cctggcgagg ctggcccatt gtacacaggc gccccagatg agggagggtc tccccctctc 960
cttgaagggc ggtagtctgg ggtcctgagt gctgggtgtg ggcttgtccc tcgtggacag 1020
aacccaggag ggcttcatcc accaaggaag attgctttgc agggtaccca ggtcccgggg 1080
gctgtgccac cctctgggca cccggagcca atcgcagggt acccaggtcc cgggggctgt 1140
gccaccctct gtgcacccag agccaatcgc aggggaccca ggtcctgagg tcctgggggc 1200
catgccaccc tctgggcacc cgcagccaat agagtcaccc ttgggaagct tatgcggacc 1260
tggggcagca ctcgcgtcct gaccccggtg ccggtcccac agttcgagcc agggcagtcg 1320
tacgcgggtg tggtgcagta cagccacagc cagatgcagg agcacgtgag cctgcgcagc 1380
cccagcatcc ggaacgtgca ggagctcaag gagtgagtgc cccacgcggc caggaccctc 1440
ccacccctcg ccccgaccgc tgttcccacg gcaggtcggc cctgacccct gatcccaggt 1500
gggctcggcc ccgcggcagg cctggcccca accggccctt cctgcccttt gctatgcaga 1560
gccatcaaga gcctgcagtg gatggcgggc ggcaccttca cgggggaggc cctgcagtac 1620
acgcgggacc agctgctgcc gcccagcccg aacaaccgca tcgccctggt catcactgac 1680
gggcgctcag acactcagag ggacaccaca ccgctcaacg tgctctgcag ccccggcatc 1740
caggtggggt ggccaccccc aggctgcacc tgccccgcct agggcgcccc gccagccagg 1800
gtggccttgt ccccagaaag acgagggcag agcaggctgc gccacaccga tactgtctgt 1860
ccccacaggt ggtctccgtg ggcatcaaag acgtgtttga cttcatccca ggctcagacc 1920
agctcaatgt catttcttgc caaggcctgg caccatccca gggccggccc ggcctctcgc 1980
tggtcaagga gaactatgca gagctgctgg aggatgcctt cctgaagaat gtcaccgccc 2040

```
agatctgcat aggtgcgcat ggggccaccc gggcagtccc agatctgcgt aggtgcgcgc   2100
ggggccgccc gggcagtccc agatctgcgt aggtgcacgc ggggccgccc gggcagtccc   2160
agatctgcgt aggtgcacgc ggggccgccc agggccgtcc cagatctgtg taggtgcgcg   2220
caggcgccca gggctgtccc agaggcctcc tcccagctca ctgttacctc caggggcacg   2280
gccaccctgt aggtgcgcac ggggccgcct ggggctgtcc cacaggcatc ctcctcccgg   2340
ctcgctgtga cttccggggg cacggccacc cctgtgctcg gccgggaggt cctgtgacat   2400
ctccttgcgg ggttataggt ggagcagtgg gctcacactg cacggctttt ctcttttaca   2460
gacaagaagt gtccagatta cacctgcccc agtgagtacc tcggcggccg ggacacgtgg   2520
ggaggagggc accgtggttg gggcgagggc tctgagagga cggggctctg ggaggagggc   2580
ctggcggtca cgagagtagg tgcatggctc actccggtgg ctgagcacca ccgtgccgtg   2640
ccctctctgg ggagcttaga cgctctctgg ccggcccact gcggctgcat caccagggcc   2700
tcatgctaac ggctgcccac cccgccccgc agtcacgttc tcctccccgg ctgacatcac   2760
catcctgctg gacggctccg ccagcgtggg cagccacaac tttgacacca ccaagcgctt   2820
cgccaagcgc ctggccgagc gcttcctcac agcgggcagg acggaccccg cccacgacgt   2880
gcgggtggcg gtggtgcagt acagcggcac gggccagcag cgcccagagc gggcgtcgct   2940
gcagttcctg cagaactaca cggccctggc cagtgccgtc gatgccatgg actttatcaa   3000
cgacgccacc gacgtcaacg atgccctggg ctatgtgacc cgcttctacc gcgaggcctc   3060
gtccggcgct gccaagaaga ggctgctgct cttctcagat ggcaactcgc agggcgccac   3120
gcccgctgcc atcgagaagg ccgtgcagga agcccagcgg gcaggcatcg agatcttcgt   3180
ggtggtcgtg ggccgccagg tgaatgagcc ccacatccgc gtcctggtca ccggcaagac   3240
ggccgagtac gacgtggcct acggcgagag ccacctgttc cgtgtcccca gctaccaggc   3300
cctgctccgc ggtgtcttcc accagacagt ctccaggaag gtggcgctgg gctagcccac   3360
cctgcacgcc ggcaccaaac cctgtcctcc caccccctccc cactcatcac taaacagagt   3420
aaaatgtgat gcgaattttc ccgaccaacc tgattcgcta gattttttttt aaggaaaagc   3480
ttggaaagcc aggacacaac gctgctgcct gctttgtgca gggtcctccg gggctcagcc   3540
ctgagttggc atcacctgcg cagggccctc tggggctcag ccctgagcta gtgtcacctg   3600
cacagggccc tctgaggctc agccctgagc tggcgtcacc tgtgcagggc cctctggggc   3660
tcagccctga gctggcctca cctgggttcc ccaccccggg ctctcctgcc ctgccctcct   3720
gcccgccctc cctcctgcct gcgcagctcc ttccctaggc acctctgtgc tgcatcccac   3780
cagcctgagc aagacgccct ctcggggcct gtgccgcact agcctccctc tcctctgtcc   3840
ccatagctgg tttttcccac caatcctcac ctaacagtta ctttacaatt aaactcaaag   3900
caagctcttc tcctcagctt ggggcagcca ttggcctctg tctcgttttg ggaaaccaag   3960
gtcaggaggc cgttgcagac ataaatctcg gcgactcggc cccgtctcct gagggtcctg   4020
ctggtgaccg gcctggacct tggccctaca gccctggagg ccgctgctga ccagcactga   4080
ccccgacctc agagagtact cgcaggggcg ctggctgcac tcaagaccct cgagattaac   4140
ggtgctaacc ccgtctgctc ctccctcccg cagagactgg ggcctggact ggacatgaga   4200
gccccttggt gccacagagg gctgtgtctt actagaaaca acgcaaacct ctccttcctc   4260
agaatagtga tgtgttcgac gttttatcaa aggccccctt tctatgttca tgttagtttt   4320
gctccttctg tgtttttttc tgaaccatat ccatgttgct gacttttcca aataaaggtt   4380
```

-continued

```
ttcactcctc tccctgtggt tatcttcccc acaaagtaaa atcctgccgt gtgccccaaa   4440
ggagcagtca caggaggttg gggggcgtgt gcgtgcgtgc tcactcccaa cccccatcac   4500
caccagtccc aggccagaac cagggctgcc cttggctaca gctgtccatc catgcccctt   4560
atctgcgtct gcgtcggtga catggagacc atgctgcacc tgtggacaga gaggagctga   4620
gaaggcaaca ccctgggctt tggggtcggg agcagatcag gcctcagtgg gctggggccg   4680
gccacatcca ccgaggtcaa ccacagaggc cggccacagg ttctaggctt ggtactgaaa   4740
taccccctggg agctcggaag gggagttgag atactgcagg gcccatagga agaagtcttg   4800
ggaggctcca cctttggggc agaggaagaa gtcttgggag gctccacctt tggggcagag   4860
caagaagagg gcggagggca gaggcagcga gggctcatcc tcaaaagaaa gaagttagtg   4920
gcccctgaat cccagaatcc ggggtgcacg gctgttctgg gggccgctag ggactaaga   4980
ggatcggccg agggctgggc tggaggaggg cagcagggat gggcggcgag ggtgagggtg   5040
gggcttcctg aaggccttca cctgcgggga ccccggcgag cccctcaggt gccacaggca   5100
gggacacgcc tcgctcgatg cgtcacacca tgtggccacc agagctgcgg gaaaatgctg   5160
gggaccctgc atttccgttt caggtggcga acaagcgccc ctcacagaac tgcaggtaga   5220
gacgggcccg gggcagacgc agtgaggcgg tgggcggggc ccggggcaga tgcagtgagg   5280
cggtgggcgg ggcccggggc agaggcagcg agcggtgggc ggggcccggg gcagacgcag   5340
tgaggcggtg ggcggggccc ggggcagagg cagcgggtgg tggccggggc ccggggcaga   5400
cgcagtgagg cggtgggcgg ggcccggggt agtcgcagta ggtggtgggc ggggcccggg   5460
gcagacgcag tgaggtggtg ggcggggccc ggggcagacg cagtgaggcg gtgggagggg   5520
cccggggcag acgcagtgag gcggtgggcg gggcccgggt cagaggcaac gggtggtggg   5580
cggggcccgg ggcagacgca gtgaggcggt gggcggggcc cggggcagat gcagtgaggc   5640
ggtgggcggg gcccggggca gatgcagtga ggcggtggga ggggcccggg gcagacgcag   5700
tgaggcggtg ggcggggccc ggggcagacg cagtgaggcg gtgggcgggg cccggggcag   5760
acgcagtgag gcagttgcca gcctctctca gctgcctcat gggattcgca ctgcagctgc   5820
ggccctggcg cgacaagggc tggacttggc cagcgggacg gtccctcacg gcgctgaggc   5880
ccacactctg cgtggagcct ccccgtgccc aggctaccct gcaaggtcct cggagaggct   5940
tcctccagcc ccagccccca cacagctccg gcccaggccc gctcttcccc atcccagttg   6000
ctttgcgctg tatacggcca ggtgaccccg agccggccct gagccctcgt cccggcttcc   6060
tcccctgtaa gctgggtgaa ggactccatg gcacccacct gagagggttg tggcgaggcc   6120
caggccccctc gtgcccacac ggccggcggc ccatgcctgg caggggctgg gaggaggctg   6180
gggcgaccag aggggagcgg cctgtcctgg aggaggccca gggaccctgg tgagagggtc   6240
tctcccaagt gctctctatg ggaccccctt cctctgcgcc cgtccttcac ggacctctcc   6300
gggtcacccc tgggctgcac actgggttca ggggggcctt gaggtggggc ccctgttccc   6360
aagtcccggc ggggtttctc ctgaacctca acccatcctc acctgcgggc attcccatcc   6420
cccaacgcct gggtcaccag gattccaggc aggaggggcg gtgggggtta ccaaggcccg   6480
ggttgccatg cagaaccccc agccaccacg cagaccccca cggggcccag ggaagctcct   6540
ggtctcacac tgcacctcac acttcctgtg ggggcagact ccaaggtccc ggcctctcat   6600
cttgtagaaa ctgaggcaca ggagggacac acactcccac ggccggtcac cgtggccccc   6660
acacctccca ctggactgac acctggccag gctccggaca cccgtggcac agcctcagcc   6720
cctgcggccc ctgctccgtg gcccccaggc cccagctccc atgtgcacgt cctgcctcag   6780
```

-continued gcctggaggc ccctcggccc caaataatca gacaattcaa cagcaaaact actttttca 6840 ggctggcagg actctgggca accccctgca acagcccct gccctatcac agccacctt 6900 gcctcccagg cacggagacc ccaccatcag gtcccagcct tggttcatcc ccaagcaccc 6960
tgtgtgttgg gatggcgatg ctggctgagc ccctgcatcc 7000

<210> SEQ ID NO 253
<211> LENGTH: 2500
<212> TYPE: DNA
<213> ORGANISM: Homo sapiens

<400> SEQUENCE: 253
agggcgtttg ggaacacccc tcccggaggg gtgaggcggc ccagcctgcg gctgccagag 60
gacacaggtt ctgctgcgga acctgcagac atggccataa caggccacag tgctcgggcc 120
cacacagcct ggacccacat ggccctgtgt cacctcctca ggggcaggct tcagggcctc 180
gaccctagag gctgcccctc ggttctgctc catggacggc gcaggcaggc ccaggcctgt 240
gacgagttca cggaagctcc aggatgaccc ccgctctgcg ccctcctcca gcattccaga 300
ccacaaacca ctctgggcta aaacgaggca tcgccagagc atcccacttc ctcggaaagc 360
tgcggtctgg ggacgcgtct tggccctgaa gaggctccag atggctccca tcaggcctct 420
ccgcctacgt gcggccgaca tggagtgaca gagcgtcggg gacacagaat tcagagctgg 480
gcctggggct gctttgagat actgatggct gccagggggc acagagaccc gtcctgcaga 540
cagggctgtg agggccacag ggggcctcgg ggagaggcag tgggagggag gacagtgggg 600
gcctccagct gggtgagcag ctggagcgag gggggcccgg ggcttgtgat ggtgctgccg 660
accctagagg tgccggcccc acgatggaga gcacgtagtg ccccccggga gtcaggaggc 720
cgggcctgac ctcgggggct gcagccaggg gaggccggca ccccagataa cccccaaaga 780
actgcaggcc ctgaggcgag gccagagtgg gggcgggggc aggtcccagc cgaggaggtg 840
ctccgtgctg cctcagcaga acccatgatg ggctggccca aggctctgaa ggtggaaagg 900
cctcacacat tctgccccgg ctgacgcctt ccttgggcca gtgctcgggg gtgtgtaaca 960
aacgccaaga cgcattgtaa agaaggaagc ctgcgtttcc atcaccggct taatatcaaa 1020
caaaagtgca attttgaaaa tgtagtccaa ggttttctgt ggtgcggaaa tggccaggcc 1080
agacctccgt gggtggtcct tcgtgtccac gtcagcgccc tacatccaca ctgtgggcac 1140
catgacctca catgcggagc ggagcagggc cggcgcccgg agagccaggc tggtcacgaa 1200
cgaggcctag agggcgtcag gccccaaagc actcacaggc ttctcctctg tcctcggggc 1260
cttcagacac ctgcatgcgc cgattcagcc acccgcgcgc gccgattccc ctggccatgg 1320
ggtttccaaa gtgtgtgctc agaggacagt ttcctccagg atgacctgtc agtggctctc 1380
tgtgccgggg acgtcgcgtg ctgggtcccg gtctgaatgc ttcctaacga tttacccagt 1440
tccttttctc cactcaggag gcgtttgctg agaggcacag gctgagcccc cgtgctgatg 1500
ccacgaccga gggaacgggt ctccctgtcg gcgtgaactg acccggccag gcgtccactg 1560
ccactcggac tgtctcccag gcacgtggcg cccacacggg cagaacacgc cctccacaca 1620
cgcggcttcg ggcagaacac gaggcgccct ccacacacgc ggcttcgggg cttgtcatga 1680
aaaaagctga atgctggggg tgcagctttc accaacagaa tcccgtttgg aagggacgcg 1740
gtgagacatg atccacccta agttgtgatc ctgggtgagc cgccgtccac accctgctga 1800
gggtcccttc acccacttta ttctccagaa aaccctgccc atcagggctg agtcccacgc 1860
cttccctctc cgtccaggcc tggctttgac ctctggggtc gtgtggggca caggggacac 1920
cctatccagg cagaggccct acggctatct ggaggaagtg gtgggagctg ggcttctgcc 1980
tggaggatgc acccagaggg gtcacagtcc acacagagac acacgggtgc cttccagatg 2040
gctgagccag tccagcccag aagggcctgg gggttggggg ctgcacctgg cctgtcccca 2100
ccagcagggc tcagggcttc ccaaggtgtg tgggggacgg ggcagcacct ctcaaccagg 2160
tcacctgaaa cccgaactga aaggcatcct aagttaagac attaactccc attgtcaagg 2220
tgccatcgtc aattctgtct ccaaatcctt ctttgttatt tcatgtattc acagagtgac 2280
gctccgtgtt tcgttcagcc tgcaggcctg cagaagctgc atctcgggat ggccaagagc 2340
ccggccaggc cccacggctg cacccaggac gggattcatg ccccatgcct ggcttctcac 2400
gaccacagag tgcctttccc gggactggat ggaggcagag tgagagaaga gcctggagca 2460
agtgttttgg accacagtga tcaaacacgg agcccgtggg 2500

<210> SEQ ID NO 254
<211> LENGTH: 700
<212> TYPE: DNA
<213> ORGANISM: Homo sapiens

<400> SEQUENCE: 254
aagaaaggcc agaccgggca cggtggctca cgcctgtaat cccaacactt ggggaggccg 60
aggcgggcag atcacctgag gtcaggagtt cgagaccagc ctggccaaca gggtgaaacc 120
ccgtctctac taaaaataca aaaaaaaatt agccgggcgt ggtggcaggc acctgtaatc 180
ccagctaatc gggaggctga ggcaggagaa aatcacttga acctgggagg cggaggctgc 240
agtgagctga gatcgcgcca ctgcactcca gcctgggtga gggagcgaga ctgtctcaaa 300
aaaaaaaaaa aaaaaaaaaa aaaaggaaag aaaggcccgg tgagatgctt tctcttaaac 360
acggccctgc acgttgagtt gctgcctcct gtggcctatt tcacgtttat gcaaagtcgg 420
gcgcctgatg cggggctcac ccgccacaag caggggtcct ggtgctgctc atggaagggg 480
ccctacccag cccgcggggc actggctggg acggggctgc ccaggtccgc ccaggatcca 540
aacacccagc cccgcccagc ggcccttcct ggcctgcagt ggaggctgta atgggcaggg 600
gtggtgggaa tcccagctca cagggcgcct gctcttagaa gggcggcatc tgggtccaga 660
ggtcagaaac gtcagatgcc catcccagaa gtggcgggga 700

<210> SEQ ID NO 255
<211> LENGTH: 10000
<212> TYPE: DNA
<213> ORGANISM: Homo sapiens

<400> SEQUENCE: 255
gggtgaatga gtagatgtat gggtgagtag gtgggtaggt gggtagatgg atgggtgggt 60
gggcgagtgt gtggttagat gatggatggc tgaatggatg agtgggggga tggatgggtg 120
agtgggtgta tgtatggatg ggttagtggg tgggtggatg aatggatggg tgcataaagg 180
atggatggat gaatgagtta gtgggttggc agatggatgg atgggtgagt cagtggatag 240
atggatgggt gggtggatag aggatggatg gttgggtagg tgatgggtgg atgagtggat 300
agatgggtat gtgagtgagt ggggggatgg gtaggtgggt ggatggatgg ttaggtgaat 360
gagtggatgg acagacggac agtgggtgga tggatgagtg aacggatgga ccgatggatg 420
aatgggtggg tgggtagagg atggacggac aggtgagtgg gtgggtggat ggatagatgg 480
gtaagtgagt ggatagatag atgggtgggt ggacagagga tgggtggatg aatggatggg 540

```
ttagtgggtg gctgggtgga tggatgatgg atgggtgact gggtggatgg atggatgggt    600
tagtgggtgg ctgggtggat agatggatgg gtgattgggc gaatgggcga atgggtggat    660
gggtgggcgt ggagttggtg ggtacatgat aatggggtgg aatacccatg gattggaatg    720
agctgttttg gctgctattt ctgggacacc cagctctgcc aggcccctac ccctctggtg    780
ggccaggctc tgacggtggc cactcatggc ctttctagct ctggtgccag catagggaag    840
gaggaggcac agccttgtct tactccttgc acctgttagc cccccccccc gccaagggag    900
gacccgtggt tggggacagc acagggggcc ctgctgtgtg cagggactgt ccctggggcc    960
actgaagccc acctgttctt gttccttctc aggcggatcc tggtccccct ggtgagccag   1020
gccctcgggg gccaagagga gtcccaggac ccgaggtagg ttggtggcca gtccccatgc   1080
cctcccccca acctgccagg ccaacacaca cccaagcctc gtggttctgc ccacggtgga   1140
cccacgtatc agtgggcagt ggcctgggag agactcagcc acccagcctt ggccccagag   1200
tctcagcctc atccttcctt ccccagggtg agcccggccc ccctggagac ccccggtctca  1260
cggtaggtgt cacatggggc agaaccagtg tccttctcct gccaaaacta gacaccaaga   1320
gcagcagggg tgggggaagg tcagctggca cggtcagaga gcaagatcag tggaggaggt   1380
cagagggcaa ggtcagagag caagcttggt tggggaaggt cacagggcaa ggttggtggg   1440
gggaggaggg tggcagcgag gttggtaggg acaggacccg ccagcctccc cgcatggctg   1500
cctccacacg tgggctggaa tgtcccggga cccccaggcc aggaccttgc tgtggaaact   1560
cttctggggc cccgggggga ctaccctgcc tgccgtgtgc attgcaggag tgtgacgtca   1620
tgacctacgt gagggagacc tgcgggtgct gcggtgaggc actgcccacg gcagggtcgg   1680
ggcccatgca ccgggtggag ggcgggagtg cagcagggct gggtcatcgc tgggtcctgc   1740
atgtgcacgt gaccctaggg tctgaggtct ccccggtacc ccccgatgac cctgccaccc   1800
ccccagactg tgagaagcgc tgtggcgccc tggacgtggt cttcgtcatc gacagctccg   1860
agagcattgg gtacaccaac ttcacactgg agaagaactt cgtcatcaac gtggtcaaca   1920
ggctgggtgc catcgctaag gaccccaagt ccgagacagg tcagcggggc aggggcgggt   1980
gcagcattgc ggggggccgg gcggggcgtg ggaggcgatg agatgggaga agtccagacg   2040
cgtccctcca acgagggcct ctgcatggct ggggatgccc cagaccccga ggcctctggc   2100
aacgacctca cgcgtgcggc ttgcagggac gcgtgtgggc gtggtgcagt acagccacga   2160
gggcaccttt gaggccatcc agctggacga cgaacgtatc gactccctgt cgagcttcaa   2220
ggaggctgtc aagaacctcg agtggattgc gggcggcacc tggacaccct cagccctcaa   2280
gtttgcctac gaccgcctca tcaaggagag ccggcgccag aagacacgtg tgtttgcggt   2340
ggtcatcacg gacgggcgcc acgaccctcg ggacgatgac ctcaacttgc gggcgctgtg   2400
cgaccgcgac gtcacagtga cggccatcgg catcggggac atgttccacg agaagcacga   2460
gagtgaaaac ctctactcca tcgcctgcga caagccacag caggtgcgca acatgacgct   2520
gttctccgac ctggtcgctg agaagttcat cgatgacatg gaggacgtcc tctgcccggg   2580
tgagcgtgtg ggcgcggggc agtcggccga ggagcagcag gccccagccg ctgtctagcg   2640
tgagccccag ggacaccccct cacctgaggg atgaatgtgc agcccaggat cttgggctgt  2700
gggtgggaag gggtcgggcc ctctcggggc tgcagggcag aggccagctg caccctgagc   2760
ctgtctaggc agatcagtga acggccgctg agggttcgct agggactgac cctggcctgg   2820
cccggcctct ctcctctctt ccagaccctc agatcgtgtg cccagacctt ccctgccaaa   2880
```

-continued

```
caggtaatgc agggcaccct gagccaccac cccagactag caaagcagcc ctggtgtcct   2940
tcctcctcga gggccgggct gggggagggg ccgtgcaggg acccgggggg cggcggagcc   3000
actgcggagg ctgctcctta gggagatggc cccaggatgg cagcacaggg gaggaggggc   3060
ttggggaagg caggctccca ggaacgcagg aacagcatca cgaggccatg aggtgggtgc   3120
tgctagcctg gcgctgtgct cggcatgtgg ccactggtct tgaaggccca ccatgggcct   3180
tgcagtctcc ctcagctgcc gcccagctcc catgggctgg ccgtgcatgt gccactcgga   3240
ggaagccctg gattcagtga gtgaaaccat cccggggtgg aagcactgac accccccagc   3300
accagcaggt cttgctccaa ccctggcctg cctcggagct gcagctgcgg ctctcacatc   3360
tctgggagtg ggggagccca tgtcccggat gtggcccacg tgggtgtgaa gctggagctg   3420
ggggtgccgt ccaggctctg ctggacgtgg tgctgccccc atggtgcact gctgcaccgt   3480
acctgggccc acaggaggtc cccgggggcg ttaggagctg agtccccctc agtgagccgt   3540
cccctccagg agtgtgaggg tagggatgcc atggagacag ggtgggaggg tccgacctgg   3600
aggaccacag ggaggaaacc tcagggtctg cggtacgaag tcagcgcttc ctcagcacgc   3660
gggtcgcggt gtgcgttcgg gcgttccatg gggagctccc ggtgggtgag ctgggccact   3720
gagcacattc acaggccctg aggctgcccc aggggaggag ccgtggactc agagccgagg   3780
ttccccatac gtgctgcgac agagaaccta gggcttgcac ctgggtctgg ctgcccttca   3840
gcaggcgggc agcctctggc cccacaacag tgggctgtgc ttctgccgcc aaggtgcagg   3900
cgtcctcccc cagggtccac atcagcagca ggggcacctg gaccctgagg gcaggaacca   3960
gaccttggct cctccaccca ccccctcgtt cctgatgggg cagggaagtc tcgggacccc   4020
atgatgggcg acatggcgat ggtcactgtg ggtgctttgc tatcaggtgg ggggccttcc   4080
tctccactct gggtccagtg tgagtggccg ctatggcttc ccctccactc caggttctat   4140
cgtgagtggg tgggtgctgc gtctgtggat gtcacgtgac ctttcctctt tagcctatca   4200
ttgtagttgg gagttagtta gcccgttgag cgtcattgaa tttccagtgt tgagccagcc   4260
ctgcgtgccc gggataaacc cacctggccg tggtgtgtgg ccctgtttat gcacgtgggc   4320
cctgattcgc tgatgcctgc ctgagggttt gcgcttatcg gcgacatcag cctgcacttt   4380
tcttttctcg tgatctctct ggttctggcc tcagggtgac gtgggcctcg tagggtcctg   4440
tggtggctcc tccccagacg gtgacatgga gtgagcccat tctccctcct gggagtgggt   4500
cactcaggcc accagagcac cacagggaaa gcagccaggg aggacacgga ggcccttgaa   4560
gctctggcct cttctgaggc ctccaggacc tgacagtgag tgggagcagc cctggcagaa   4620
cccctcccct cctctcggcc gccctgacac ctcatccccg acactcagag ctcatcctcc   4680
ttcccagctg tttccaattt caaagtgaac tcgaccttgt ggctccagga gatgcagcag   4740
ggacagtgtt aaatcggctt tcaccagccc acacggccag gcatcctcct cggccctcct   4800
gggcactggg tggacaccac tggctgtggc ctggccctgg ccttctccag acagccctgt   4860
ccaccccaaa gcccagccac cctgggcctg cagcaggcct gtggagttct cagttgcgtg   4920
gggaccagag ggtgctggag aaacaaacca gacgcagctg aaggcagtca gggcagggcg   4980
caatcagcga taagagctgc ataggggcca cagcgtaacc tgagctccag tcggtggaaa   5040
gaaaaggcag agacgttgca gaggccaggt ctgctcaggg gaagacagtt ctgggtgtag   5100
aggactcaca tcccagagag gctgaggaag ggtttaccac cgcaagcttt ctcaggcggg   5160
ctcttgaggg gtggctgggg tcttcctggc gacgggcctg cggcactgga agccctactg   5220
gagtttggcc tgtctccggc acaggtttgg acggagctgt tttgtgctga aaggttttct   5280
```

```
cggggtccgt ggtgtccccc aaaggtgcca ccgtgcgggt ctcctagctc cctgccagct   5340
tcctgtccct gtgctcactg cccccacgcc tcctgccaag gccgagccac acacccgctc   5400
cacctgcatt tcctctaccg actcgccagc ccaaatgccg ctcttcactc tggcctcgct   5460
gagcggctgc ccgaggagga gctctaggcc gacgcccacc gcaggcctta cagtcttctc   5520
tggacgctcc cttgcagatg caccgtggcc tggcggcgag cccccggtca ccttcctccg   5580
cacggaagag gggccggacg ccaccttccc caggaccatt cccctgatcc aacagttgct   5640
aaacgccacg gagctcacgc aggacccggc cgcctactcc cagctggtgg ccgtgctggt   5700
ctacaccgcc gagcgggcca agttcgccac cggggtagag cggcaggact ggatggagct   5760
gttcattgac acctttaagc tggtgcacag ggacatcgtg gggaccccg agaccgcgct    5820
ggccctctgc taaagcccgg gcacccgccc agccgggctg ggccctccct gccacactag   5880
cttcccaggg ctgcccccga caggctggct ctcagtggag gccagagatc tggaatcggg   5940
gtcagcgggg ctacagtcct tccaggggct ctggggcagc tcccagcctc ttcccatgct   6000
ggtggccacc gtgtcccttg ctgcggctgc atcttccagt ctctcctccg tcttcctgtg   6060
gccgctctct ttataagaac cctggtcatt gaatttaagg cccaccccaa gtccagaatg   6120
acctcgcaag acccttaact cactcccgtc tgcagagtcc ttctttgctg catcaggtca   6180
ccctcacagg ctccagggtt tgggtgtgga agtctttgga ggcccttact tagcggccca   6240
gctgggctgc cgtgcgtctg ggatggggct gagggagggt gctgcccagg tgctggagga   6300
tgttccagca ccaggttcca gcggagcctc ggaaacaggc cccagaggct ggtgagcctc   6360
gctgggtgtg ggcactaatc ccgtgcatgg tgactcgtgg gcgctcacgg cccacctggt   6420
ggcaggtgaa ggcttccggt tgggcagcag atagtcctgg gggaagctgg cagtcctggc   6480
accatgacgt atctgggctg gtgtcatgca cagtagggcg aatggccaca gctgcctgcc   6540
agcagccctg atcccggggt gtctgcaccc ttccagccca acctctgggt ctccaaaagc   6600
acagtcgggg gagcatccac caggcacaac ctctgcggtc ctcagaggac tgagcagaga   6660
atcccagggt ccacaatgtt ggggagcggc agggatcacc atccaaaggg agcggccccc   6720
acggcgagct gaccccgacg ttctgactgc aggagccctc atccaggctg ggctcctgcc   6780
gggcacggct gtgaccattt ctcagggcca ggttctcgtc cccacaccca ctgcacaggg   6840
caggccaggc tggtcttccc actgtgggga tgaaggatcc tccacaggag gaggagagca   6900
gagtccacag acatcccaac agcctcagcc tccctgtgcc tggccggccc ccacagcttc   6960
cccgtctcct ccaggcccca cagacactga tgaatggaca gagaccccca aaaccagctg   7020
ccccttgcat gtctgtctcc atatgtttgg tgacagcagt gaaaatgtta ttagttttga   7080
gggggtttgg gaagcccagc ggtacctgag gagtttctgg acatttaagc cggttcctag   7140
gtgtggcctt aacagggagg ctgcccttcc tttcactgaa tgagctgcgt cactcataag   7200
ctcactgagg gaaccccatc tgccagctcg tgcgtgctca gacggcgtcc atgtctcaag   7260
cgttctgtga aggctgcggt gcagcgtgag gtcaccctgc tgtgttcaga gctttgctca   7320
ctgcctgcgg ggctggaccg ttgcacctcc agggccccca gaaaccgagt ttcgggtcag   7380
ggtcctctgt gtgcattcct gggggtccat gtaccagctg tgacgacgtc caggggttgg   7440
gctgagaagc agacaccctt ggggaaactg gctctgtccc tcccctcccc catcccagga   7500
gctgaggtct tggtgaggcc acagggccag gtccacgcaa ggactgtccg tgtcctgtcc   7560
tgtggtctct ggccccacgt gacacccaca cgtgtggtag gcagcctggc ctgggttgtg   7620
```

-continued

```
gctatggcca ggcccccaag ctgtccccga tgcccagggc tggtgaccac ccaggcaggt   7680
gggggcccca cttggtaaca gagtcatagg gcagaaccca cctgggctgc cacagaaggt   7740
ctggctgccc ctgtgcccac tgctccccac catggccaat cagaagagtc aggggctcct   7800
ggtctttccg ggagggacgt ggcccagcca gctctaggtg ttctgagcag ctctgggacc   7860
cagcgattga ggggtcaggc tgggggtgtc agagccaggg tcctccttaa gtacctccca   7920
cactacacag acagtggccc ttttgtgggc agcaaattct tgagccatga aaggatgctt   7980
tgggcccctt ccctcccagg agggcagcct gtgcagggat ggtgctcagc aggtggacag   8040
ggcctggggc ctgtgtcagg gtctcaggcc tgggagcacc agcagaggag atggcggctc   8100
ccagcagtgc cgcctgaaag tgtcttgggc taaggaccca cacccagggc tgccctgcag   8160
aaacgccccc gcagagccca gtggtctgtg aggttgcagg cagggtgcga atggaagggc   8220
acaggtgcgg ggctggcacc tgcccggtcc tgcccacctc ccctccgccc agcccgcacc   8280
tgcgtctccc cacagagctg tccgtggcac agtgcacgca gcggcccgtg gacatcgtct   8340
tcctgctgga cggctccgag cggctgggtg agcagaactt ccacaaggcc cggcgcttcg   8400
tggagcaggt ggcgcggcgg ctgacgctgg cccggaggga cgacgaccct ctcaacgcac   8460
gcgtggcgct gctgcagttt ggtggccccg gcgagcagca ggtggccttc ccgctgagcc   8520
acaacctcac ggccatccac gaggcgctgg agaccacaca atacctgaac tccttctcgc   8580
acgtgggcgc aggcgtggtg cacgccatca atgccatcgt gcgcagcccg cgtggcgggg   8640
cccggaggca cgcagagctg tccttcgtgt tcctcacgga cggcgtcacg ggcaacgaca   8700
gtctgcacga gtcggcgcac tccatgcgca agcagaacgt ggtacccacc gtgctggcct   8760
tgggcagcga cgtggacatg gacgtgctca ccacgctcag cctgggtgac cgcgccgccg   8820
tgttccacga gaaggactat gacagcctgg cgcaacccgg cttcttcgac cgcttcatcc   8880
gctggatctg ctagcgccgc cgcccgggcc ccgcagtcga gggtcgtgag cccacccccgt   8940
ccatggtgct aagcgggccc gggtcccaca cggccagcac cgctgctcac tcggacgacg   9000
ccctgggcct gcacctctcc agctcctccc acggggtccc cgtagccccg gcccccgccc   9060
agccccaggt ctccccaggc cctccgcagg ctgcccggcc tccctccccc tgcagccatc   9120
ccaaggctcc tgacctacct ggcccctgag ctctggagca agccctgacc caataaaggc   9180
tttgaaccca ttgcgtgcct gcttgcgagc ttctgtgcgc aggagagacc tcaaaggtgt   9240
cttgtggcca ggagggaaac actgcagctg tcgctcgccc accagggtca atggctcccc   9300
cgggcccagc cctgacctcc taggacatca actgcaggtg ctggctgacc ccgcctgtgc   9360
agaccccaca gccttgatca gcaaactctc cctccagccc cagccaggcc caaagtgctc   9420
taagaagtgt caccatggct gagggtcttc tgtgggtgga cgcatgatta acactagacg   9480
gggagacagc aggtgctgag cctgttgtgt tctgtgtgga gatctcagtg agtttttgct   9540
gttcagaccc cagggtcctt caggctcagc tcaggagccc cacagtgaac cagaggctcc   9600
acaggcaggt gctgacctga caggagtggg cttggtggcc atcacagggc accacagaca   9660
cagcttgaac aactaccagt atcggccaca ggcctggagg catcagccgg gccatgcttc   9720
ctctggaggg ctagaggagg actagagaag ggcctgcccc ggcctctccc cagcatccca   9780
gggttcctga tctcctggat aaggatacaa gtcaccacac tggactgggg ctcagcctgc   9840
tctagaatac ctcacctaag tcacagtgga ccaggctcag cctgctctaa ggtgagctta   9900
cccgagacac tggaccagag atcagcctat cctgggataa gctcacccga gtcacactgg   9960
accagggctc agcctattcc gggatgagct cacccgagtc                        10000
```

<210> SEQ ID NO 256
<211> LENGTH: 800
<212> TYPE: DNA
<213> ORGANISM: Homo sapiens

<400> SEQUENCE: 256
gacacttcca tgactgcagc tgaccagtcc acctgccagc ggttgaccac tcccacttcg 60
ccagcgaccg aaggggaggg gaggggcctc acctgagggc aacagcagaa cccaccacct 120
ggtcttgctt tactcagacc tgagggtgtg aaaggtgccc gtgacctccc gcatcaggga 180
gctggccgcc accctcgact cccggggagc aggcgtcccg cgacccccctc atctaccagg 240 ccatctgagc tgggcggcgc ctcacctccg ctcccggggg agccggcctc agggtaggca 300
tgcgccctgg gtgggagcag gtcgtggccg ccgccctcct ggcagctctg gctgagcagc 360
cgccgcagca tctgattctc cttcaggagg cgcacctgct tcttcaggtc cgcgttctcg 420
ctcaggagcc ggctcatcag ctcgccgcct tcagccatgg cgggtgcgtc cctccttgtc 480
cctcacggct cctgcagccc catggaggtg ggagcccaga gcccgcaggc accacagaaa 540
cagcccaggc acggagttcc gtagccacca ccgccttcca cgccttgtga tgtcactgcc 600
ctagtgatga ggtgcccagc accctgcctg cccccgcgat ggctcatggc cccgttgagg 660
cagtgaagct ggaggcccgt ggcgtgcaca ggcagccact cccacattat gaccagggcc 720
cgagaatgcc aaggacatta ggcagctacg ggatgtagcg actgtactcc aagaggggcg 780
tccaagccac tccccattga 800

<210> SEQ ID NO 257
<211> LENGTH: 293
<212> TYPE: DNA
<213> ORGANISM: Homo sapiens

<400> SEQUENCE: 257
aggtggaggt tgcagtgagc cctcctcccc tcctccccct tcccttccca cctcccatgc 60
ccccctttct tcctcccact cccctcccga ggcccccgctt attctcccgg cctgtggcgg 120
ttcgtgcact cgctgagctc aggttctggt gaaggtgccc ggagccgggt cccgccttcg 180
gcctgagcta gagccgcgcg ggcggccggc ttcccccaaa ccctgtggga ggggcatccc 240
gaggaggcga ccccagagag tggggcgcgg acaccttccc tggggagggc cag 293

<210> SEQ ID NO 258
<211> LENGTH: 474
<212> TYPE: DNA
<213> ORGANISM: Homo sapiens

<400> SEQUENCE: 258
ccttccagat gttccagaag gagaaggcgg tgctggacga gctgggccga cgcacgggga 60
cccggctgca gcccctgacc cggggcctct tcggagggag ctgagggccg cgttccttct 120
gaaagcggga cgcgggaggg gtggaggctg cggggagccg gggtcgcaca cgaataaata 180
acgaatgaac gtacgagggg aacctcctct tatttccttc acgttgcatc gggtattttt 240
cgttattgta aataaaacgg ttccgagccg tggcatcgag agggcgtctg gagttcaggg 300
aacgcgtggc ccccgcccgg gagcaccgcg cagcgctcgc ctctcgccct tcaagggggt 360
ccctgcccgg agcctgcgcc cccggagagg aaggggctcg aggggcttgg gtgccgcagc 420
gcgtccttcc gtagaaaagg cttgcgtcag tatttcctgc ttttacctcc tgag 474

<210> SEQ ID NO 259
<211> LENGTH: 346
<212> TYPE: DNA
<213> ORGANISM: Homo sapiens

<400> SEQUENCE: 259
cagtatttcc tgcttttacc tcctgagtat tggaatattc gagtaaaccc tggagtttca 60
gcgccagcgc acgcctcttc atcagggcag cgcgtcgcga gcgcgctggt tccccggggc 120
ctcccggcca cggacaccgc tctagccagg gccacggcga ggccgccgag cagcacctca 180
gagacctgcg tgagttctaa agcctggggc tactacaatt ctgctcatct gtttgtcctg 240
tgaaatgatt cagggacatg aaaatgcctt cccactgact tgcgtcctgt cttagcctgg 300
acttgtcccc ttgggaacac gggccaggcc cctctgttcc tgaagt 346

<210> SEQ ID NO 260
<211> LENGTH: 490
<212> TYPE: DNA
<213> ORGANISM: Homo sapiens

<400> SEQUENCE: 260
atgtctgcag ggaagaagca gggggaccct gaataaagtt tccgtttttc ctatttgtta 60
aagtgataga gcattatagg accagagaac aggtgtgtct gtacactgtg caggtccccg 120
gggcaggctc tgagtccgtc tgcacacggt gcgggtcccc ggggcgcgcc ctgagcccgt 180
ctgcacacgg tgcgggtccc cggggcgcgc cctgagcccg tctgcacacg gtgcgggtcc 240
ccggggcgcg ccctgagccc gtctgcacac ggtgcgggtc cccggggcgc gccctgagcc 300
cgtctgcaca cggtgcgggt ccccggggcg cgccctgagc ccgtctgcac acggtgcggg 360
tccccggggc gcgccctgag cccgtctgta cacggtgcgg gtccccgggg cgcgccctga 420
gtctctacta aaaatacaaa aattagccag gcgtggtggt tcaagcctgt aatcccagct 480
ccttgggagg 490

<210> SEQ ID NO 261
<211> LENGTH: 2000
<212> TYPE: DNA
<213> ORGANISM: Homo sapiens

<400> SEQUENCE: 261
catacatggt tattagaaaa ggcatctcat ccaaatgtgg tggctcgtgc ttgtaatccc 60
agtgcttcag gaggccaagg gaggaggatt acttgagcct aagagtttga gaccagcctg 120
ggcaacacaa caagaccttg cctctacaaa aaacttaaaa actagctggg tatgatggtg 180
cacacctgta gtcccagcta cttgggaggc ggaggcgggc agatcgcctg aggtcaggag 240
ttcgagacca gcctggccaa catgatgaaa ccccgtctct actaaaaata caaaaattag 300
ccgagtgtgg tggtgcatgc ctgtaatccc agctactcag gaggctgagg caggagaatc 360
acttgaaccc gggaggcgga ggttgccatg agccgagatc acgtcactgc actccagcct 420
gggtgacaga gcacaaaaga caggcatgac tttgtactta actgctcagc tttgtaatca 480
ctgggggccc agatgctcac ttggattcta actttgttgg catctgggcc taaaagccgt 540
gatgcaggtg agcaatgatg cagagggctc tgtgcgcctg gcgggctctg tttgcctgct 600
gggctctgtg cgcctgctgg gctctgtgcg cccgggaagg tgcggccacc ctcacgcgga 660
aggcggccag cggatcccgg tgcgcgcagc tcccagcgct ggggttccag cgccccgcct 720
cttcctatag caaccagcgg gacctgccgt cccccggggc accccgaggg gtctgcgccc 780

```
gcttctttcc gaaacgggaa ggcgctgggg gctcggcagc cagagggacg ggttcaggga    840

gcgtccggtg agcctaagac gcgcctttgc cggggttgcc gggtgtctgc ctctcactta    900

ggtattagga accgtggcac aaatctgtag gttttcctct gggggtgggc ggaggctcca    960

aaccggacgg ttttctcctg gaggactgtg ttcagacaga tactggtttc cttatccgca   1020

ggtgtgcgcg gcgctcgcaa gtggtcagca taacgccggg cgaattcgga aagcccgtgc   1080

gtccgtggac gacccacttg gaaggagttg ggagaagtcc ttgttcccac gcgcggacgc   1140

ttccctccgt gtgtccttcg agccacaaaa agcccagacc ctaacccgct cctttctccc   1200

gccgcgtcca tgcagaactc cgccgttcct gggaggggaa gcccgcgagg cgtcgggaga   1260

ggcacgtcct ccgtgagcaa agagctcctc cgagcgcgcg gcggggacgc tgggccgaca   1320

ggggaccgcg ggggcagggc ggagaggacc cgccctcgag tcggcccagc cctaacactc   1380

aggaccgcct ccagccggag gtctgcgccc ttctgaggac cctgcctggg ggagcttatt   1440

gcggttcttt tgcaaatacc cgctgcgctt ggacggagga agcgcccacg cgtcgacccc   1500

ggaaacgaag gcctccctga tgggaacgca tgcgtccagg agcctttatt tactcttaat   1560

tctgcccgat gcttgtacgt gtgtgaaatg cttcagatgc ttttgggagc gaggtgttac   1620

ataaatcatg gaaatgcctc ctggtctcac cacacccagg gtgacagctg agatgcggct   1680

tctccagggt ggagcctcct cgttttccag agctgcttgt tgaagtcttc ccagggcccc   1740

tgacttgcac tggaaactgc tcaccttggc atcgggatgt ggagcaagaa atgcttttgt   1800

tttcattcat cctagtgttc ataaaatgga aaacaaataa ggacatacaa aaacattaat   1860

aaaataaatt aatggaacta gattttttcag aaagcacaac aaacacaaaa tccaagtatt   1920

gccatgtcag caacacattc ctactttaag ttttatgaag ttaattggag tagtggagaa   1980

caaaagtgga tgtggggcag                                               2000
```

<210> SEQ ID NO 262
<211> LENGTH: 88
<212> TYPE: DNA
<213> ORGANISM: Homo sapiens

<400> SEQUENCE: 262

```
gattgacagt ttctccttcc ccagactggc caatcacagg caggaagatg aaggttctgt     60

gggctgcgtt gctggtcaca ttcctggc                                        88
```

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 263

```
acgttggatg ttgacagttt ctccttcccc                                      30
```

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
acgttggatg gaatgtgacc agcaacgcag 30

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
gcaggaagat gaaggtty 18

<210> SEQ ID NO 266
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 266
gattgacagt ttctccttcc ccagactggc caatcacagg caggaagatg aaggttttgt 60
gggctgcgtt gctggtcaca ttcctggc 88

<210> SEQ ID NO 267
<211> LENGTH: 90
<212> TYPE: DNA
<213> ORGANISM: Homo sapiens

<400> SEQUENCE: 267
gagttttgga tagtaaaata agtttcgaac tctggcacct ttcaattttg tcgcactctc 60
cttgtttttg acaatgcaat catatgcttc 90

<210> SEQ ID NO 268
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 268
acgtggatag taaaataagt ttcgaactct g 31

<210> SEQ ID NO 269
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 269
gaagcatatg attgcattgt caaaaac 27

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 270

```
atttcaattt tgtcgcacty                                              20


<210> SEQ ID NO 271
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271

gagttttgga tagtaaaata agtttcgaac tctggcacct ttcaattttg tcgcactttc     60

cttgtttttg acaatgcaat catatgcttc                                      90


<210> SEQ ID NO 272
<211> LENGTH: 97
<212> TYPE: DNA
<213> ORGANISM: Homo sapiens

<400> SEQUENCE: 272

gaactcctct ttgtctctgc gtgcccggcg cgcccccctc ccggtgggtg ataaacccac     60

tctggcgccg gccatgcgct gggtgattaa tttgcga                              97


<210> SEQ ID NO 273
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273

acgttggatg tctttgtctc tgcgtgccc                                       29


<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274

acgttggatg ttaatcaccc agcgcatggc                                      30


<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275

cccctcccgg tgggtgataa ay                                              22


<210> SEQ ID NO 276
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
```

gaactcctct ttgtctctgc gtgcccggcg cgcccccctc ccggtgggtg ataaatccac 60
tctggcgccg gccatgcgct gggtgattaa tttgcga 97

<210> SEQ ID NO 277
<211> LENGTH: 86
<212> TYPE: DNA
<213> ORGANISM: Homo sapiens

<400> SEQUENCE: 277
ccattggccg tccgccgtgg cagtgcgggc gggagcgcag ggagagaacc acagctggaa 60
tccgattccc accccaaaac ccagga 86

<210> SEQ ID NO 278
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 278
acgttggatg ccattggccg tccgccgtg 29

<210> SEQ ID NO 279
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 279
acgttggatg tcctgggttt tggggtggga a 31

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 280
ttccagctgt ggttctctc 19

<210> SEQ ID NO 281
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 281
ccattggccg tccgccgtgg cagtgcgggc gggagcgcag agagagaacc acagctggaa 60
tccgattccc accccaaaac ccagga 86

<210> SEQ ID NO 282
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 282
acgttggatg acatggtcgg ccccacggaa t 31

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 283
acgttggatg acccattggc cgtccgccgt 30

<210> SEQ ID NO 284
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 284
acgttggatg gaactcctct ttgtctctgc g 31

<210> SEQ ID NO 285
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 285
acgttggatg cgcagcaacg ggaccgctac a 31

<210> SEQ ID NO 286
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 286
acgttgcgta gcaacctgtt acatattaa 29

<210> SEQ ID NO 287
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
acgttggatg catagaggcc catgatggtg g 31

<210> SEQ ID NO 288
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
acgttggatg gtgtggtcag ctcttccctt cat 33

<210> SEQ ID NO 289
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
acgttggatg ctccttccta gtgtgagaac cg 32

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
acgttggatg ttttggggtg ggaatcggat t 31

<210> SEQ ID NO 291
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
acgttggatg tggcatggcc ggcgccaga 29

<210> SEQ ID NO 292
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
acgttggcat ctaggtaggt ctttgtagcc aa 32

<210> SEQ ID NO 293
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
acgttggatc tgagcaaagg caatcaacac cc 32

<210> SEQ ID NO 294
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
acgttggatg accttctgcc cctctactcc aa 32

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 295
acgttggccc acatgtaatg tgttgaaaaa gca 33

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 296
caggttccgg ggcttggg 18

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 297
cgcagggaga gaaccacag 19

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 298
cccctcccgg tgggtgataa a 21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 299
aaagctgtag gacaatcggg t 21

<210> SEQ ID NO 300
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 300
catttttcta catcctttgt tt 22

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 301
agaagatcac caggcagaag agg 23

<210> SEQ ID NO 302
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 302
acttggagaa caaaggacac cgtta 25

<210> SEQ ID NO 303
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 303
ggtcggcccc acggaatccc ggctctgtgt gcgcccaggt tccggggctt gggtgttgcc 60
ggttctcaca ctaggaagga g 81

<210> SEQ ID NO 304
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 304
ccattggccg tccgccgtgg cagtgcgggc gggagcgcag agagagaacc acagctggaa 60
tccgattccc accccaaaa 79

<210> SEQ ID NO 305
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 305
gaactcctct ttgtctctgc gtgcccggcg cgcccccctc ccggtgggtg ataaatccac 60
tctggcgccg gccatgc 77

<210> SEQ ID NO 306
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 306
gcagcaacgg gaccgctaca gccactggac aaagccgtag gacaatcggg taacattggc 60
tacaaagacc tacctagatg c 81

<210> SEQ ID NO 307
<211> LENGTH: 95
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 307
gcgtagcaac ctgttacata ttaaagtttt attatactac atttttctac atcctttgtt 60
tcagagtgtt gattgccttt gctcagtatc ttcag 95

<210> SEQ ID NO 308
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 308
ccttctgccc ctctactcca agcgctacac cctcttctgc ctggtgatct ttgccggcgt 60
cctggccacc atcatgggcc tctatg 86

<210> SEQ ID NO 309
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 309
gtgtggtcag ctcttccctt catcacatac ttggagaaca aaggacaccg ttatccatgc 60
tttttcaaca cattacatgt ggg 83

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 310
acgttggatg ttctgcccct ctactccaag 30

<210> SEQ ID NO 311
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 311
acgttggatg tcagctcttc ccttcatcac 30

<210> SEQ ID NO 312
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 312
acgttggatg ttgacagttt ctccttcccc 30

<210> SEQ ID NO 313
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 313
acgttggatg cggtcggccc cacggaat 28

<210> SEQ ID NO 314
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 314
acgtggatag taaaataagt ttcgaactct g 31

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 315
acgttggatg cacagctcac cgcagcaacg 30

<210> SEQ ID NO 316
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 316
acgttggatg tctttgtctc tgcgtgccc 29

<210> SEQ ID NO 317
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 317
acgttggatg gactgagccc cagaactcg 29

<210> SEQ ID NO 318
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 318
acgttggatg aagccaagtt tccctccgc 29

<210> SEQ ID NO 319
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 319
acgttagcgt agcaacctgt tacatattaa 30

<210> SEQ ID NO 320
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 320
acgttggatg catagaggcc catgatggtg 30

<210> SEQ ID NO 321
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 321
acgttggatg cctacctccc acatgtaatg t 31

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 322
acgttggatg gaatgtgacc agcaacgcag 30

<210> SEQ ID NO 323
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 323
acgttggatg ctccttccta gtgtgagaac cg 32

<210> SEQ ID NO 324

<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 324
gaagcatatg attgcattgt caaaaac 27

<210> SEQ ID NO 325
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 325
acgttggatg ctaggtaggt ctttgtagcc aa 32

<210> SEQ ID NO 326
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 326
acgttggatg ttaatcaccc agcgcatggc 30

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 327
acgttggatg gtgggtttgt gctttccacg 30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 328
acgttggatg cttttgcttt cccagccagg 30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 329
acgttggatg ctgagcaaag gcaatcaaca 30

<210> SEQ ID NO 330
<211> LENGTH: 17

<212> TYPE: DNA
<213> ORGANISM: Artificial Sequence
<220> FEATURE:
<223> OTHER INFORMATION: Description of Artificial Sequence: Synthetic
primer

<400> SEQUENCE: 330
ttctgcctgg tgatctt 17

<210> SEQ ID NO 331
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 331
aacaaaggac accgtta 17

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 332
gcaggaagat gaaggtt 17

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 333
aaggttccgg ggcttggg 18

<210> SEQ ID NO 334
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 334
atttcaattt tgtcgcact 19

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 335
agctgtagga caatcgggt 19

<210> SEQ ID NO 336
<211> LENGTH: 20
<212> TYPE: DNA

-continued

<213> ORGANISM: Artificial Sequence
<220> FEATURE:
<223> OTHER INFORMATION: Description of Artificial Sequence: Synthetic
primer

<400> SEQUENCE: 336
ccctcccggt gggtgataaa 20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 337
agggccgggg tctgcgcgtg 20

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 338
gaggcactgc ccggacaaac c 21

<210> SEQ ID NO 339
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 339
catttttcta catcctttgt tt 22

<210> SEQ ID NO 340
<211> LENGTH: 86
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 340
ccttctgccc ctctactcca agcgctacac cctcttctgc ctggtgatct ttgccggcgt 60
cctggccacc atcatgggcc tctatg 86

<210> SEQ ID NO 341
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 341
gtgtggtcag ctcttccctt catcacatac ttggagaaca aaggacaccg ttatccatgc 60
tttttcaaca cattacatgt gggaggtagg 90

<210> SEQ ID NO 342
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 342
gattgacagt ttctccttcc ccagactggc caatcacagg caggaagatg aaggttttgt 60
gggctgcgtt gctggtcaca ttcctggc 88

<210> SEQ ID NO 343
<211> LENGTH: 98
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 343
aaaaccagag attcgcggtc ggccccacgg aatcccggct ctgtgtgcgc ccaggttccg 60
gggcttgggt gttgccggtt ctcacactag gaaggagc 98

<210> SEQ ID NO 344
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 344
gagttttgga tagtaaaata agtttcgaac tctggcacct ttcaattttg tcgcactttc 60
cttgtttttg acaatgcaat catatgcttc 90

<210> SEQ ID NO 345
<211> LENGTH: 95
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 345
gcagccagct caccgcagca acgggaccgc tacagccact ggacaaagct gtaggacaat 60
cgggtgacat tggctacaaa gacctaccta gatgc 95

<210> SEQ ID NO 346
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 346
gaactcctct ttgtctctgc gtgcccggcg cgcccccctc ccggtgggtg ataaatccac 60
tctggcgccg gccatgcgct gggtgattaa tttgcga 97

<210> SEQ ID NO 347
<211> LENGTH: 86
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 347

gtgggtttgt gctttccacg cgtgcacaca cacgcgcaga ccccggccct tgccccgcct     60

acctccccga gttctggggc tcagtc                                          86


<210> SEQ ID NO 348
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348

gcgccagctt ttgctttccc agccagggcg cggtgaggtt tgtccgggca gtgcctcgag     60

caactgggaa ggccaaggcg gagggaaac                                       89


<210> SEQ ID NO 349
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349

gcgtagcaac ctgttacata ttaaagtttt attatactac atttttctac atcctttgtt     60

ttagggtgtt gattgccttt gctcagtatc ttcagc                               96


<210> SEQ ID NO 350
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350

cgcaaccact                                                            10


<210> SEQ ID NO 351
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351

cgcgaccact                                                            10
```